US008962247B2

(12) United States Patent
Ehrich et al.

(10) Patent No.: US 8,962,247 B2
(45) Date of Patent: Feb. 24, 2015

(54) PROCESSES AND COMPOSITIONS FOR METHYLATION-BASED ENRICHMENT OF FETAL NUCLEIC ACID FROM A MATERNAL SAMPLE USEFUL FOR NON INVASIVE PRENATAL DIAGNOSES

(75) Inventors: Mathias Ehrich, San Diego, CA (US); Anders Olof Herman Nygren, San Diego, CA (US); Taylor Jacob Jensen, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 710 days.

(21) Appl. No.: 12/727,198

(22) Filed: Mar. 18, 2010

(65) Prior Publication Data

US 2010/0273165 A1 Oct. 28, 2010

Related U.S. Application Data

(63) Continuation-in-part of application No. 12/561,241, filed on Sep. 16, 2009, now Pat. No. 8,476,013.

(60) Provisional application No. 61/192,264, filed on Sep. 16, 2008.

(51) Int. Cl.
*C12Q 1/68* (2006.01)
*C07H 21/02* (2006.01)
*C07H 21/04* (2006.01)

(52) U.S. Cl.
CPC ............ *C12Q 1/6869* (2013.01); *C12Q 1/6804* (2013.01); *C12Q 1/6806* (2013.01); *C12Q 1/6809* (2013.01); *C12Q 1/6888* (2013.01); *C12Q 2600/16* (2013.01)
USPC ........................................ 435/6.11; 536/23.1

(58) Field of Classification Search
None
See application file for complete search history.

(56) References Cited

U.S. PATENT DOCUMENTS

| | | | |
|---|---|---|---|
| 4,109,496 | A | 8/1978 | Allemann et al. |
| 4,179,337 | A | 12/1979 | Davis et al. |
| 4,458,066 | A | 7/1984 | Caruthers et al. |
| 4,469,863 | A | 9/1984 | Ts'o et al. |
| 4,522,811 | A | 6/1985 | Eppstein et al. |
| 4,656,127 | A | 4/1987 | Mundy |
| 4,676,980 | A | 6/1987 | Segal et al. |
| 4,683,195 | A | 7/1987 | Mullis et al. |
| 4,683,202 | A | 7/1987 | Mullis |
| 4,851,331 | A | 7/1989 | Vary et al. |
| 4,868,103 | A | 9/1989 | Stavrianopoulos et al. |
| 4,873,316 | A | 10/1989 | Meade et al. |
| 4,965,188 | A | 10/1990 | Mullis et al. |
| 5,048,530 | A | 9/1991 | Hurwitz |
| 5,075,212 | A | 12/1991 | Rotbart |
| 5,118,937 | A | 6/1992 | Hillenkamp et al. |
| 5,210,015 | A | 5/1993 | Gelfand et al. |
| 5,272,071 | A | 12/1993 | Chappel |
| 5,283,317 | A | 2/1994 | Saifer et al. |
| 5,487,972 | A | 1/1996 | Gelfand et al. |
| 5,492,806 | A | 2/1996 | Drmanac et al. |
| 5,525,464 | A | 6/1996 | Drmanac et al. |
| 5,536,821 | A | 7/1996 | Agrawal et al. |
| 5,541,306 | A | 7/1996 | Agrawal et al. |
| 5,547,835 | A | 8/1996 | Koster |
| 5,589,330 | A | 12/1996 | Shuber |
| 5,605,798 | A | 2/1997 | Koster |
| 5,614,622 | A | 3/1997 | Iyer et al. |
| 5,631,169 | A | 5/1997 | Lakowicz et al. |
| 5,637,683 | A | 6/1997 | Usher et al. |
| 5,637,684 | A | 6/1997 | Cook |
| 5,656,493 | A | 8/1997 | Mullis et al. |
| 5,679,524 | A | 10/1997 | Nikiforov et al. |
| 5,691,141 | A | 11/1997 | Koster |
| 5,695,940 | A | 12/1997 | Drmanac et al. |
| 5,700,922 | A | 12/1997 | Cook |
| 5,717,083 | A | 2/1998 | Cook et al. |
| 5,719,262 | A | 2/1998 | Buchardt et al. |
| 5,720,928 | A | 2/1998 | Schwartz |
| 5,739,308 | A | 4/1998 | Kandimalla et al. |
| 5,739,314 | A | 4/1998 | Roy et al. |
| 5,766,849 | A | 6/1998 | McDonough et al. |
| 5,773,601 | A | 6/1998 | Agrawal |
| 5,786,146 | A | 7/1998 | Herman et al. |
| 5,834,189 | A | 11/1998 | Stevens et al. |
| 5,849,483 | A | 12/1998 | Shuber |
| 5,849,497 | A | 12/1998 | Steinman |
| 5,849,542 | A | 12/1998 | Reeve et al. |
| 5,849,546 | A | 12/1998 | Sousa et al. |
| 5,851,770 | A | 12/1998 | Babon et al. |
| 5,869,242 | A | 2/1999 | Kamb |

(Continued)

FOREIGN PATENT DOCUMENTS

| | | |
|---|---|---|
| EP | 264166 | 4/1988 |
| EP | 0401384 | 12/1990 |

(Continued)

OTHER PUBLICATIONS

Uhlmann et al; (Electrophoresis, vol. 23, pp. 4072-4079).*
Office Action dated: Mar. 18, 2013 in U.S. Appl. No. 12/401,493, filed Mar. 10, 2009 and published as: 2009/0317817 on: Dec. 24, 2009.
Office Action dated: Feb. 27, 2013 in U.S. Appl. No. 12/561,241, filed Sep. 16, 2009.
Office Action dated: Apr. 5, 2013 in U.S. Appl. No. 13/495,975, filed Jun. 13, 2012.
Office Action dated: Apr. 5, 2013 in U.S. Appl. No. 13/517,532, filed Jun. 13, 2012.
Extended European Search Report dated Apr. 22, 2013 in European Application No. EP10843520 filed: Dec. 20, 2010 based on International Application No. PCT/US2010/061319.
Cell Death Detection ELISA PLUS Cat. No. 11 774 425 001 "Detection of Post-translational Modifications on Native Intact Nucleosomes by ELISA," Version 11.0, Roche, Content Version: Sep. 2010, pp. 1-19.

(Continued)

*Primary Examiner* — Jehanne Sitton
(74) *Attorney, Agent, or Firm* — Grant IP, Inc.

(57) ABSTRACT

Provided are compositions and processes that utilize genomic regions that are differentially methylated between a mother and her fetus to separate, isolate or enrich fetal nucleic acid from a maternal sample. The compositions and processes described herein are particularly useful for non-invasive prenatal diagnostics, including the detection of chromosomal aneuploidies.

16 Claims, 32 Drawing Sheets

(56) References Cited

U.S. PATENT DOCUMENTS

| | | | |
|---|---|---|---|
| 5,876,934 | A | 3/1999 | Duthie et al. |
| 5,886,165 | A | 3/1999 | Kandimalla et al. |
| 5,891,625 | A | 4/1999 | Buchardt et al. |
| 5,908,755 | A | 6/1999 | Kumar et al. |
| 5,912,118 | A | 6/1999 | Ansorge et al. |
| 5,928,906 | A | 7/1999 | Koster et al. |
| 5,929,226 | A | 7/1999 | Padmapriya et al. |
| 5,952,174 | A | 9/1999 | Nikiforov et al. |
| 5,955,599 | A | 9/1999 | Iyer et al. |
| 5,958,692 | A | 9/1999 | Cotton et al. |
| 5,962,674 | A | 10/1999 | Iyer et al. |
| 5,976,802 | A | 11/1999 | Ansorge et al. |
| 5,977,296 | A | 11/1999 | Nielsen et al. |
| 5,981,186 | A | 11/1999 | Gabe et al. |
| 5,998,143 | A | 12/1999 | Ellis et al. |
| 6,004,744 | A | 12/1999 | Goelet et al. |
| 6,013,431 | A | 1/2000 | Soderlund et al. |
| 6,013,499 | A | 1/2000 | Narumiya et al. |
| 6,017,702 | A | 1/2000 | Lee et al. |
| 6,018,041 | A | 1/2000 | Drmanac et al. |
| 6,024,925 | A | 2/2000 | Little et al. |
| 6,043,031 | A | 3/2000 | Koster et al. |
| 6,045,996 | A | 4/2000 | Cronin et al. |
| 6,046,005 | A | 4/2000 | Ju et al. |
| 6,057,134 | A | 5/2000 | Lader et al. |
| 6,087,095 | A | 7/2000 | Rosenthal et al. |
| 6,107,037 | A | 8/2000 | Sousa et al. |
| 6,110,684 | A | 8/2000 | Kemper et al. |
| 6,117,992 | A | 9/2000 | Iyer |
| 6,136,541 | A | 10/2000 | Gulati |
| 6,140,053 | A | 10/2000 | Koster |
| 6,140,054 | A | 10/2000 | Wittwer et al. |
| 6,140,482 | A | 10/2000 | Iyer et al. |
| 6,142,681 | A | 11/2000 | Gulati |
| 6,143,496 | A | 11/2000 | Brown et al. |
| 6,156,501 | A | 12/2000 | McGall et al. |
| 6,183,958 | B1 | 2/2001 | Stanton, Jr. |
| 6,194,144 | B1 | 2/2001 | Koster |
| 6,194,180 | B1 | 2/2001 | Joyce |
| 6,197,506 | B1 | 3/2001 | Fodor et al. |
| 6,210,574 | B1 | 4/2001 | Sammons et al. |
| 6,210,891 | B1 | 4/2001 | Nyren et al. |
| 6,214,556 | B1 | 4/2001 | Olek et al. |
| 6,214,560 | B1 | 4/2001 | Yguerabide et al. |
| 6,223,127 | B1 | 4/2001 | Berno |
| 6,225,625 | B1 | 5/2001 | Pirrung et al. |
| 6,229,911 | B1 | 5/2001 | Balaban et al. |
| 6,239,273 | B1 | 5/2001 | Pease et al. |
| 6,251,638 | B1 | 6/2001 | Umansky et al. |
| 6,258,538 | B1 | 7/2001 | Koster et al. |
| 6,258,540 | B1 | 7/2001 | Lo et al. |
| 6,297,028 | B1 | 10/2001 | Taniguchi et al. |
| 6,326,174 | B1 | 12/2001 | Joyce et al. |
| 6,368,834 | B1 | 4/2002 | Senapathy et al. |
| 6,440,706 | B1 | 8/2002 | Vogelstein et al. |
| 6,468,748 | B1 | 10/2002 | Monforte et al. |
| 6,610,492 | B1 | 8/2003 | Stanton, Jr. et al. |
| 6,664,056 | B2 | 12/2003 | Lo et al. |
| 6,723,513 | B2 | 4/2004 | Lexow |
| 6,759,217 | B2 | 7/2004 | Kopreski |
| 6,818,394 | B1 | 11/2004 | O'Donnell-Maloney et al. |
| 6,884,586 | B2 | 4/2005 | Van Ness et al. |
| 6,916,634 | B2 | 7/2005 | Kopreski |
| 6,927,028 | B2 | 8/2005 | Dennis et al. |
| 6,929,911 | B2 | 8/2005 | Oefner et al. |
| 7,081,339 | B2 | 7/2006 | Slepnev |
| 7,169,314 | B2 | 1/2007 | Unger et al. |
| 7,244,567 | B2 | 7/2007 | Chen et al. |
| 7,253,259 | B2 | 8/2007 | Otagiri et al. |
| 7,285,422 | B1 | 10/2007 | Little et al. |
| 7,468,249 | B2 | 12/2008 | Xie et al. |
| 7,655,399 | B2 | 2/2010 | Cantor et al. |
| 7,709,262 | B2 | 5/2010 | Cantor et al. |
| 7,785,798 | B2 | 8/2010 | Cantor et al. |
| 8,195,415 | B2 | 6/2012 | Fan et al. |
| 2001/0008615 | A1 | 7/2001 | Little et al. |
| 2001/0051341 | A1 | 12/2001 | Lo et al. |
| 2002/0006621 | A1 | 1/2002 | Bianchi |
| 2003/0022207 | A1 | 1/2003 | Balasubramanian et al. |
| 2003/0082600 | A1 | 5/2003 | Olek et al. |
| 2003/0087276 | A1 | 5/2003 | Kopreski |
| 2003/0096426 | A1 | 5/2003 | Little et al. |
| 2003/0180748 | A1 | 9/2003 | Braun et al. |
| 2003/0180779 | A1 | 9/2003 | Lofton-Day et al. |
| 2003/0211483 | A1 | 11/2003 | Schroeder et al. |
| 2003/0211522 | A1 | 11/2003 | Landes et al. |
| 2004/0014105 | A1 | 1/2004 | Schroeder et al. |
| 2004/0081993 | A1 | 4/2004 | Cantor et al. |
| 2004/0115684 | A1 | 6/2004 | Costa |
| 2004/0137470 | A1 | 7/2004 | Dhallan |
| 2004/0203037 | A1 | 10/2004 | Lo et al. |
| 2005/0009059 | A1 | 1/2005 | Shapero et al. |
| 2005/0019762 | A1 | 1/2005 | Olek |
| 2005/0037388 | A1 | 2/2005 | Antonarakis et al. |
| 2005/0059003 | A1 | 3/2005 | Enoki et al. |
| 2005/0064406 | A1 | 3/2005 | Zabarovsky et al. |
| 2005/0064428 | A1 | 3/2005 | Berlin |
| 2005/0069879 | A1 | 3/2005 | Berlin |
| 2005/0079521 | A1 | 4/2005 | Beaulieu et al. |
| 2005/0112590 | A1 | 5/2005 | Boom et al. |
| 2005/0153316 | A1 | 7/2005 | Jeddeloh et al. |
| 2005/0153347 | A1 | 7/2005 | Shapero et al. |
| 2005/0164241 | A1 | 7/2005 | Hahn et al. |
| 2005/0266473 | A1 | 12/2005 | Zhang et al. |
| 2005/0272070 | A1 | 12/2005 | Ehrich et al. |
| 2005/0287592 | A1 | 12/2005 | Kless |
| 2006/0019278 | A1 | 1/2006 | Lo et al. |
| 2006/0094039 | A1 | 5/2006 | Rosenfeld et al. |
| 2006/0136142 | A1 | 6/2006 | Berlin et al. |
| 2006/0160105 | A1 | 7/2006 | Dhallan |
| 2006/0166228 | A1 | 7/2006 | Page et al. |
| 2006/0210992 | A1 | 9/2006 | van den Boom |
| 2006/0252068 | A1 | 11/2006 | Lo et al. |
| 2006/0252071 | A1 | 11/2006 | Lo et al. |
| 2007/0048755 | A1 | 3/2007 | Di Fiore |
| 2007/0059707 | A1 | 3/2007 | Cantor et al. |
| 2007/0065823 | A1 | 3/2007 | Dressman et al. |
| 2007/0111233 | A1 | 5/2007 | Bianchi et al. |
| 2007/0202525 | A1 | 8/2007 | Quake et al. |
| 2007/0207466 | A1 | 9/2007 | Cantor et al. |
| 2007/0212689 | A1 | 9/2007 | Bianchi et al. |
| 2007/0243549 | A1 | 10/2007 | Bischoff |
| 2007/0275402 | A1 | 11/2007 | Lo et al. |
| 2008/0020390 | A1 | 1/2008 | Mitchell et al. |
| 2008/0070792 | A1 | 3/2008 | Stoughton et al. |
| 2008/0096766 | A1 | 4/2008 | Lee |
| 2008/0299562 | A1 | 12/2008 | Oeth et al. |
| 2008/0305479 | A1 | 12/2008 | VanDenBoom |
| 2009/0026082 | A1 | 1/2009 | Rothberg et al. |
| 2009/0029377 | A1 | 1/2009 | Lo et al. |
| 2009/0061425 | A1 | 3/2009 | Lo et al. |
| 2009/0111712 | A1 | 4/2009 | VanDenBoom |
| 2009/0142755 | A1 | 6/2009 | Albitar |
| 2009/0202984 | A1 | 8/2009 | Cantor et al. |
| 2009/0317818 | A1 | 12/2009 | Ehrich et al. |
| 2010/0105049 | A1 | 4/2010 | Ehrich et al. |
| 2010/0184046 | A1 | 7/2010 | Klass et al. |
| 2010/0203529 | A1 | 8/2010 | Kuslich et al. |
| 2010/0216153 | A1 | 8/2010 | Lapidus et al. |
| 2010/0227320 | A1 | 9/2010 | Fu |
| 2010/0240054 | A1 | 9/2010 | Bischoff |
| 2010/0273165 | A1 | 10/2010 | Ehrich et al. |
| 2010/0279295 | A1 | 11/2010 | Roy et al. |
| 2011/0033851 | A1 | 2/2011 | Rand |
| 2011/0105353 | A1 | 5/2011 | Lo et al. |
| 2011/0151460 | A1 | 6/2011 | Klass et al. |
| 2011/0177517 | A1 | 7/2011 | Rava et al. |
| 2011/0178719 | A1 | 7/2011 | Rabinowirz et al. |
| 2011/0201507 | A1 | 8/2011 | Rava et al. |
| 2011/0212846 | A1 | 9/2011 | Spier |
| 2011/0224087 | A1 | 9/2011 | Quake et al. |
| 2011/0276277 | A1 | 11/2011 | Lo et al. |
| 2011/0288780 | A1 | 11/2011 | Rabinowirz et al. |
| 2012/0184449 | A1 | 7/2012 | Hixson et al. |

(56) References Cited

U.S. PATENT DOCUMENTS

| | | | |
|---|---|---|---|
| 2012/0264618 | A1 | 10/2012 | Nygren |
| 2012/0276542 | A1 | 11/2012 | Nygren |
| 2012/0277119 | A1 | 11/2012 | Ehrich et al. |
| 2012/0282613 | A1 | 11/2012 | Patsalis et al. |
| 2013/0130923 | A1 | 5/2013 | Ehrich et al. |
| 2013/0143211 | A1 | 6/2013 | Ehrich et al. |
| 2013/0150249 | A1 | 6/2013 | Ehrich et al. |
| 2013/0230858 | A1 | 9/2013 | Cantor et al. |
| 2013/0295564 | A1 | 11/2013 | Ehrich et al. |
| 2013/0296180 | A1 | 11/2013 | Ehrich et al. |
| 2013/0310260 | A1 | 11/2013 | Kim et al. |
| 2014/0093873 | A1 | 4/2014 | Tynan et al. |

FOREIGN PATENT DOCUMENTS

| | | |
|---|---|---|
| EP | 1 373 561 | 2/2009 |
| EP | 1524321 | 4/2009 |
| JP | 2005-514956 | 5/2005 |
| JP | 2008-521389 | 6/2008 |
| WO | WO 91/06667 | 5/1991 |
| WO | WO 94/10300 | 5/1994 |
| WO | WO 97/12058 | 4/1997 |
| WO | WO 97/35589 | 10/1997 |
| WO | WO 97/37041 | 10/1997 |
| WO | WO 98/20020 | 5/1998 |
| WO | WO 98/22489 | 5/1998 |
| WO | WO 98/39352 | 9/1998 |
| WO | WO 98/39474 | 9/1998 |
| WO | WO 98/54364 | 12/1998 |
| WO | WO 99/57318 | 5/1999 |
| WO | WO 00/52625 | 9/2000 |
| WO | WO 00/56746 | 9/2000 |
| WO | WO 00/66771 | 11/2000 |
| WO | WO 00/75372 | 12/2000 |
| WO | WO 01/14398 | 3/2001 |
| WO | WO 01/20039 | 3/2001 |
| WO | WO 01/25485 | 4/2001 |
| WO | WO 01/27326 | 4/2001 |
| WO | WO 01/27327 | 4/2001 |
| WO | WO 01/27329 | 4/2001 |
| WO | WO 01/29259 | 4/2001 |
| WO | WO 02/18616 | 3/2002 |
| WO | WO 02/086163 | 10/2002 |
| WO | WO 03/000919 | 1/2003 |
| WO | WO 03/057909 | 7/2003 |
| WO | WO 03/062441 | 7/2003 |
| WO | WO 03/080863 | 10/2003 |
| WO | WO 2004/013284 | 2/2004 |
| WO | WO 2004/076653 | 9/2004 |
| WO | WO 2004/079011 | 9/2004 |
| WO | WO 2005/012578 | 2/2005 |
| WO | WO 2005/021793 | 3/2005 |
| WO | WO 2005/023091 | 3/2005 |
| WO | WO 2005/035725 | 4/2005 |
| WO | WO 2005/040399 | 5/2005 |
| WO | WO 2005/098050 | 10/2005 |
| WO | WO 2006/056480 | 6/2006 |
| WO | WO 2006/097049 | 9/2006 |
| WO | WO 2006/097051 | 9/2006 |
| WO | WO 2007/016668 | 2/2007 |
| WO | WO 2007/028155 | 3/2007 |
| WO | WO 2007/092473 | 8/2007 |
| WO | WO 2007/100911 | 9/2007 |
| WO | WO 2007/121276 | 10/2007 |
| WO | WO 2007/132166 | 11/2007 |
| WO | WO 2007/132167 | 11/2007 |
| WO | WO 2007/132166 | 12/2007 |
| WO | WO 2007/140417 | 12/2007 |
| WO | WO 2007/147063 | 12/2007 |
| WO | WO 2008/098142 | 8/2008 |
| WO | WO 2008/103761 | 8/2008 |
| WO | WO 2008/103763 | 8/2008 |
| WO | WO 2008/118988 | 10/2008 |
| WO | WO 2008/157264 | 12/2008 |
| WO | WO 2009/032779 | 3/2009 |
| WO | WO 2009/032781 | 3/2009 |
| WO | WO 2009/039507 | 3/2009 |
| WO | WO 2009/046445 | 4/2009 |
| WO | WO 2009/091934 | 7/2009 |
| WO | WO 2009/114543 | 9/2009 |
| WO | WO 2010/004265 | 1/2010 |
| WO | WO 2010/033639 | 3/2010 |
| WO | WO 2010/065470 | 6/2010 |
| WO | WO 2010/115016 | 10/2010 |
| WO | WO 2011/034631 | 3/2011 |
| WO | WO 2011/087760 | 7/2011 |
| WO | WO 2011/091063 | 7/2011 |
| WO | WO 2011/092592 | 8/2011 |
| WO | WO 2011/142836 | 11/2011 |
| WO | WO 2011/143659 | 11/2011 |
| WO | WO 2012/118745 | 9/2012 |
| WO | WO 2012/149339 | 11/2012 |
| WO | WO 2013/052913 | 4/2013 |
| WO | WO 2013/055817 | 4/2013 |

OTHER PUBLICATIONS

Dai et al., "Detection of Post-translational Modifications on Native Intact Nucleosomes by ELISA," Journal of Visualized Experiments, 2011, pp. 1-4.

Li et al., Dynamic Distribution of Linker Histone H1.5 in Cellular Differentiation, PLOS Genetics, vol. 8, Issue 8, e1002879, Aug. 2012, pp. 1-13.

Millipore, QIA25 Nucleosome ELISA Kit, Information Brochure, Calbiochem, Feb. 26, 2013.

Salgame et al., "An ELISA for detection of apoptosis," Nucleic Acids Research, 1997, vol. 25, No. 3, pp. 680-681.

Terme et al. "Histone H1 Variants Are Differentially Expressed and Incorporated into Chromatin during Differentiation and Reprogramming to Pluripotency," The Journal of Clinical Chemistry, vol. 286, No. 41, Oct. 14, 2011, pp. 35347-35357.

Weiss et al., "H1 variant-specific lysine methylation by G9a/KMT1C and Glp1/KMT1D," Epigenetics & Chromatin Mar. 24, 2010, 3:7, pp. 1-13.

Zhang et al., "Histone H1 Depletion Impairs Embryonic Stem Cell Differentiation," PLOS Genetics, vol. 8, Issue 5, e1002691, May 2012, pp. 1-14.

International Search Report and Written Opinion mailed on Jul. 1, 2013 in International Application No. PCT/US2013/028699, filed on Mar. 1, 2013.

Go et al., "Non-invasive aneuploidy detection using free fetal DNA and RNA in maternal plasma: recent progress and future possibilities" Human Reproduction Update (2011) 17(3):372-382.

Beaudet, "Progress toward noninvasive prenatal diagnosis" Clin. Chem. (2011) 57(6):802-804.

Office Action dated Aug. 13, 2013 in U.S. Appl. No. 13/517,508, filed Jun. 13, 2012 and published as US 2013-0143211 on Jun. 6, 2013.

Chan et al., "Hypermethylated Rassfia in Maternal Plasma: A Universal Fetal DNA Marker that Improves the Reliability of Noninvasive Prenatal Diagnosis" Clin. Chem. (2006) 52:2211-2218.

International Search Report and Written Opinion mailed on Jul. 16, 2013 in International Application No. PCT/US2013/041906, filed on May 20, 2013.

Tabor et al., "Non-Invasive Fetal Genome Sequencing: Opportunities and Challenges" American Journal of Medical genetics Part A (2012) 158A(10):2382-2384.

Kitzman et al., "Noninvasive Whole-Genome Sequencing of a Human Fetus" Science Translation Medicine (2012) 4(137-140):115-122.

International Search Report and Written Opinion mailed on Aug. 14, 2013 in International Application No. PCT/US2013/041354, filed on May 16, 2013.

Office Action dated Sep. 20, 2013 in U.S. Appl. No. 13/517,532, filed Jun. 13, 2012 and published as US 2013-0150249 on Jun. 13, 2013.

Office Action dated Sep. 24, 2013 in U.S. Appl. No. 13/495,975, filed Jun. 13, 2012 and published as US 2012-0277119 on Nov. 1, 2012.

Sayres et al., "Cell-free fetal nucleic acid testing: A review of the technology and its applications" Obstetrical and Gynecological Survey (2011) 66(7):431-442.

(56) References Cited

OTHER PUBLICATIONS

Sharma et al., "Mass spectrometric based analysis, characterization and applications of circulating cell free DNA isolated from human body fluids" International Journal of Mass Spectrometry (2011) 304:172-183.
NCBI dbSNP cluster report record for rs16139, accessed Sep. 16, 2013.
Amicucci et al., Clin. Chem. 46:301-302, 2000.
Ausubel et al., Current Protocols in Molecular Biology (Ausubel et al., eds., 1994).
Batzer et al., Nucleic Acid Res. 19:5081 (1991).
Beaucage & Caruthers, Tetrahedron Lett. 22: 1859-1862 (1981).
Braslaysky et al., PNAS 100(7): 3960-3964 (2003).
Chiu et al., Lancet 360:998-1000, 2002.
Colella et al. Biotechniques. Jul. 2003;35(1):146-50.
Costa et al., N. Engl. J. Med. 346:1502, 2002).
Costello et al., Restriction Landmark Genomic Scanning (RLGS): Analysis of CpG Islands in genomes by 2D Gel Electrophoresis, Methods in Molecular Biology, DNA Methylation, 2 Methods and Protocols, v. 507, 2nd eds., pp. 131-148 (2000).
Dear Brief Funct Genomic Proteomic 2003; 1: 397-416.
Ding C, Cantor CR (2003) A high-throughput gene expression analysis technique using competitive PCR and matrix-assisted laser desorption ionization time-of-flight MS. Proc Natl Acad Sci U S A 100:3059-3064.
Dupont JM, Tost J, Jammes H, and Gut IG. Anal Biochem, Oct. 2004; 333(1): 119-27; and Tooke N and Pettersson M. IVDT. Nov. 2004; 41.
Eads et al., Cancer Res. 59:2302-2306, 1999.
Ehrich M, et al. (2005) Quantitative high-throughput analysis of DNA methylation patterns by base specific cleavage and mass spectrometry. *Proc Natl Acad Sci U S A* 102:15785-15790.
Ehrich M, et al. (2008) Cytosine methylation profiling of cancer cell lines. *Proc Natl Acad Sci U S A* 105:4844-4848.
Frommer et al., Proc. Natl. Acad. Sci. USA 89:1827-1831, 1992.
Gebhard C, Schwarzfischer L, Pham TH, Andreesen R, Mackensen A, Rehli M (2006) Rapid and sensitive detection of CpG-methylation using methyl-binding (MB)-PCR. Nucleic Acids Res 34:e82.
Gebhard C, Schwarzfischer L, Pham TH, Schilling E, Klug M, Andreesen R, Rehli M (2006) Genomewide profiling of CpG methylation identifies novel targets of aberrant hypermethylation in myeloid leukemia. Cancer Res 66:6118-6128).
Gonzalgo & Jones, Nucleic Acids Res. 25:2529-2531, 1997.
Harris T D et al. 2008 Science, 320, 106-109.
Herman et al. Proc. Nat. Acad. Sci. USA 93:9821-9826, 1996.
Innis, et al., PCR Protocols: A Guide to Methods and Applications, Academic Press, Inc. N.Y., 1990. PCR.
Jurinke, C., Oeth, P., van den Boom, D., "MALDI-TOF mass spectrometry: a versatile tool for high-performance DNA analysis." Mol. Biotechnol. 26, 147-164 (2004).
Kalinina et al., "Nanoliter scale PCR with TaqMan detection." Nucleic Acids Research. 25; 1999-2004, (1997)).
Kriegler, Gene Transfer and Expression: A Laboratory Manual (1990).
Laird, P.W. Nature Reviews Cancer 3, 253-266 (2003).
Lee Ti, et al. (2006) Control of developmental regulators by Polycomb in human embryonic stem cells. *Cell* 125:301-313).
Lo et al., Clin. Chem. 45:1747-1751, 1999.
Lo et al., Clin. Chem. 45:184-188, 1999.
Lo et al., Lancet 350:485-487, 1997.
Lo et al., N. Engl. J. Med. 339:1734-1738, 1998).
Margulies, M. et al. 2005 Nature 437, 376-380.
Meller A. 2007 Clin Chem 53: 1996-2001.
Nakano et al., "Single-molecule PCR using water-in-oil emulsion;" Journal of Biotechnology 102: 117-124 (2003.
Needleham-VanDevanter et. al., Nucleic Acids Res. 12: 6159-6168 (1984).
Nolte, Adv. Clin. Chem. 33:201-235, 1998.
Oeth, P. et al., "iPLEX™ Assay: Increased Plexing Efficiency and Flexibility for MassARRAY® System through single base primer extension with mass-modified Terminators." SEQUENOM Application Note (2005).
Ohtsuka et al., J. Biol. Chem. 260:2605-2608 (1985).
Pearson & Reanier, J. Chrom. 255: 137-149 (1983).
Rossolini et al., Mol. Cell. Probes 8:91-98 (1994).
Sadri & Hornsby, Nucl. Acids Res. 24:5058-5059, 1996.
Saito et al., Lancet 356:1170, 2000.
Sambrook and Russell, Molecular Cloning, A Laboratory Manual (3rd ed. 2001).
Sambrook et al., Molecular Biology: A laboratory Approach, Cold Spring Harbor, N.Y. (1989).
Sekizawa et al., Clin. Chem. 47:2164-2165, 2001.
Soni and Meller, Clinical Chemistry 53(11): 1996-2001 (2007).
Takai et al., Proc. Natl. Acad. Sci. U.S.A. 99:3740-3745, 2002).
Tooke N and Pettersson M. IVDT. Nov. 2004; 41.
Toyota et al., Cancer Res. 59:2307-12, 1999.
Uhlmann, K. et al. Electrophoresis 23:4072-4079 (2002).
Venter et al., Science 291: 1304-1351 (2001.
Vogelstein and Kinzler (Digital PCR. Proc Natl Acad Sci U S A. 96; 9236-41, (1999).
Wald and Hackshaw, Prenat Diagn 17(9):821-829 (1997).
Xiong & Laird, Nucleic Acids Res. 25:2532-2534, 1997.
Yamada et al. (Genome Research 14:247-266, 2004).
Zhong et al., Am. J. Obstet. Gynecol. 184:414-419, 2001).
Zhong et al., Prenat. Diagn. 20:795-798, 2000.
Extended European Search Report dated: Apr. 19, 2012 in European Application No. EP 09815148 filed: Sep. 16, 2009.
Beckman Coulter, Introduction to Capillary Electrophoresis, Beckman Coulter 1991.
Bianchi, 'Fetal cells in the mother: from genetic diagnosis to diseases associated with fetal cell microchimerism', In: European Journal of Obstetrics & Gynecology and Reproductive Biology, Sep. 2000, vol. 92(I), pp. 103-108.
Burnier et al., "Cell-derived microparticles in haemostasis and vascular medicine," Thromb Haemost 2009, 101:439-451.
Caliper LifeSciences, Products and Contract Services, LabChip GX 2010, printed from the internet on Mar. 15, 2011 (http://www.caliperl.com/products/labchip-gx.htm).
Chu et al, "A novel approach toward the challenge of accurately quantifying fetal DNA in maternal plasma," Prenatal Diagnosis, 2010; 30:1226-1229.
Ehrich et al., "Noninvasive detection of fetal trisomy 21 by sequencing of DNA in maternal blood: a study in a clinical setting," Reports of Major Impact, American Journal of Obstetrics and Gyenocology, Mar. 2011, 205e1-205e11.
Ernani et al., Agilent's SureSelect Target Enrichment System: Bringing Cost and Process Efficiency to Next-Generation Sequencing Product Note, Agilent Technologies, Mar. 16, 2009.
Haddow, et al.,"Screening of maternal serum for fetal Down's syndrome in the first trimester", In: The New England Journal of Medicine, Apr. 2, 1998, vol. 338(14), pp. 955-961.
HiSeq 2000 Sequencing System Specification Sheet, Illumina Inc. 2010.
Hromandnikova, et al., "Quantification of Fetal and Total Circulatory DNA in Maternal Plasma Samples Before and After Size Fractionation by Agarose Gel Electrophoresis,"DNA and Cell Biology, vol. 25, No. 11, 2006, pp. 635-640.
Kristensen et al., "PCR-Based Methods for Detecting Single-Locus DNA Methylation Biomarkers in Cancer Diagnostics, Prognostics, and Response to Treatement", Clinical Chemistry, Washington DC, vol. 55, No. 8., Aug. 1, 2009, pp. 1471-1483.
Kumps et al., "RMeseuarlcthi aprtilcelex Amplicon Quantification (MAQ), a fast and efficient method for the simultaneous detection of copy number alterations in neuroblastoma," BMC Genomics 2010, 11:298, pp. 1-10.
Lee et al., Fetal Nucleic Acids in Maternal Plasma, In:Fetal and Maternal Medicine Review, 2006, vol. 17,(2), pp. 125-137.
Liu et al., "Quantification of regional DNA methylation by liquid chromatography/tandem mass spectrometry", Analytical Biochemistry, Academic Press Inc, New York, vol. 391, No. 2, Aug. 15, 2009, pp. 106-113.

(56) References Cited

OTHER PUBLICATIONS

Liu et al., "The ribosomal small-subunit protein S28 gene from *Helianthus annuus* (asteraceae) is down-regulated in response to drought, high salinity, and abscisic acid," American Journal of Botany, vol. 90, No. 4., Apr. 1, 2003, pp. 526-531.
Lun et al., "Noninvasive prenatal diagnosis of monogenic diseases by digital size selection and relative mutation dosage on DNA in maternal plasma," PNAS, vol. 105, No. 50, Dec. 16, 2008, pp. 19920-19925.
Molecular Cloning of PCR Products, Unit 15.4, Current Protocols in Molecular Biology, (2001 John Wiley & Sons, Inc.) 15.4.1-15.4.11, Supplement 56.
Mouliere et al., "High Fragmentation Characterizes Tumour-Derived Circulating DNA," PLoS One, Sep. 2011, vol. 6, Issue 9, e23438, 1-10.
Nygren et al., "Quantification of Fetal DNA by Use of Methylation-Based DNA Discrimination," Clinical Chemistry, 56:10, pp. 1627-1635.
Peters et al., "Noninvasive Prenatal Diagnosis of a Fetal Microdeletion Syndrome," New England Journal of Medicine, Nov. 10, 2011, pp. 1847-1848.
Sanchez et al, "Effects of Sulpiride on Prolactin and mRNA Levels of Steroid 5a-reductase Isozymes in Adult Rat Brain," Neurochem Res (2008) 33:820-825.
Spetzler et al, Enriching for Rare Subpopulations of Circulating Microvesicles by the Depletion of Endothelial-and Leukocyte-Derived Microvesicles, CARIS Life Sciences, Carisome Posters, Papers, Abstracts and Presentations, American Academy of Cancer Research (AACR 2011).
Strohmeier, Fred, "A New High-Performance Capillary Electrophoresis Instrument," 10-19, Hewlett-Packard Journal, Jun. 1995.
The Cancer Test, Cell Free DNA, 2007, Health Screen Inc. printed from the internet on Mar. 20, 2011 (http://www.thecancertest.com/science-of-cell-free-dna/.
Tong et al., "Noninvasive Prenatal Detection of Fetal Trisomy 18 by Epigenetic Allelic Ratio Analysis in Maternal Plasma: Theoretical and Empirical Considerations," Clinical Chemistry 52:12, pp. 2149-2202.
Tynan et al., "Fractional DNA quantification by massively parallel shotgun sequencing-implications for fetal fraction measurement in maternal plasma," (Sequenom MME) ASHG Poster, 2011.
Wilkinson, In situ Hybridization, Wilkinson ed., IRL Press, Oxford University Press, Oxford 1998.
Zahra S, et al, Plasma microparticles are not elevated in fresh plasma from patients with gynaecologicalmalignancy—An observational study, Gynecol Onco, Oct. 2011;123(1):152-156.
Zheng et al., "Nonhematopoietically Derived DNA Is Shorter than Hematopoietically Derived DNA in Plasma: A Transplantation Model," Clin Chem 58:2, Nov. 3, 2011.
Zimmermann Lecturer, et al., 'Serum parameters and nuchal translucency in first trimester screening for fetal chromosomal abnormalities', In: BJOG: An International Journal of Obstetrics & Gynaecology, 1996, vol. 103(10), pp. 1009-1014.
Extended European Search Report dated Jan. 4, 2012 in European Application No. EP10817598.5 filed: Mar. 18, 2010.
International Preliminary Report on Patentability dated: Sep. 3, 2009 in International Application No. PCT/US2008/54468 filed on Feb. 20, 2008.
International Search Report and Written Opinion dated: Sep. 23, 2008 in International Application No. PCT/US2008/54468 filed on Feb. 20, 2008.
International Preliminary Report on Patentability dated: Feb. 18, 2010 in International Application No. PCT/US2008/54470 filed on Feb. 20, 2008.
International Search Report and Written Opinion dated: Aug. 18, 2008 in International Application No. PCT/US2008/54470 filed on Feb. 20, 2008.
International Preliminary Report on Patentability dated: Dec. 30, 2009 in International Application No. PCT/US2008/066791 filed on Jun. 12, 2008.
International Search Report and Written Opinion dated: Dec. 22, 2008 in International Application No. PCT/US2008/066791 filed on Jun. 12, 2008.
International Preliminary Report on Patentability dated: Mar. 29, 2012 in International Application No. PCT/US2010/027879 filed on Mar. 18, 2010.
International Preliminary Report on Patentability dated: Jul. 5, 2012 in International Application No. PCT/US2010/061319 filed on Dec. 20, 2010.
International Search Report and Written Opinion dated: Sep. 21, 2011 in International Application No. PCT/US2010/061319 filed on Dec. 20, 2010.
International Search Report and Written Opinion dated: Jan. 10, 2012 in International Application No. PCT/US2012/035479 filed on Apr. 27, 2012.
Office Action dated: Jan. 28, 2013 in U.S. Appl. No. 13/457,978, filed Apr. 27, 2012 and published as: 2012/0276542 on: Oct. 1, 2012.
Office Action dated: Feb. 6, 2013 in U.S. Appl. No. 13/458,036, filed Apr. 27, 2012 and published as: 2012/0264618 on: Oct. 18, 2012.
Office Action dated: Feb. 5, 2013 in U.S. Appl. No. 13/458,341, filed Apr. 27, 2012.
Adinolfi et al., "Rapid detection of aneuploidies by microsatellite and the quantitative fluorescent polymerase chain reaction." Prenat Diagn. Dec. 1997;17(13):1299-311.
Agresti, Categorical Data Analysis, 2nd Ed. 2002. Wiley.
Altschul et al., "Basic local alignment search tool." J Mol Biol. Oct. 5, 1990;215(3):403-10.
Altschul et al., "Gapped BLAST and PSI-BLAST: a new generation of protein database search programs." Nucleic Acids Res. Sep. 1, 1997;25(17):3389-402.
Amir et al., Nature Genet. 23:185-88 (1999).
Anantha et al., "Porphyrin binding to quadrupled T4G4." Biochemistry. Mar. 3, 1998;37(9):2709-14.
Anders et al., Clin Chem, Oct. 2010, 56(10):1627-1635, Epub Aug. 20, 2010.
Anderson, S., "Shotgun DNA sequencing using cloned Dnase I-generated fragments," Nucl. Acids Res. 9:3015-3027 (1981.
Antonarakis et al., Am J Hum Genet. Mar. 1992;50(3):544-50.
Antonarakis et al., Nat Genet. Feb. 1993;3(2):146-50.
Aoki E. et al., "Methylation status of the pI51NK4B gene in hematopoietic progenitors and peripheral blood cells in myelodysplastic syndromes", Leukemia 14(4):586-593 (2000.
Armour et al., "Measurement of locus copy number by hybridisation with amplifiable probes." Nucleic Acids Res. Jan. 15, 2000;28(2):605-9.
Armour et al., "The detection of large deletions or duplications in genomic DNA." Hum Mutat. Nov. 2002;20(5):325-37.
Asimakopoulos FA et al., "ABL 1 methylation is a distinct molecular event associated with clonal evolution of chronic myeloid leukemia" Blood 94(7):2452-2460 (1999.
Aston et al. (1999) Methods Enzymol. 303:55-73.
Aston et al. (1999) Trends Biotechnol. 17(7):297-302.
Banerji et al., "A lymphocyte-specific cellular enhancer is located downstream of the joining region in immunoglobulin heavy chain genes." Cell. Jul. 1983;33(3):729-40.
Bartel et al., Biotechniques 14: 920-924 (1993.
Batey et al. (1992) Nucl. Acids Res. 20, 4515-4523.
Batey et al. (1996) Nucl. Acids Res. 24, 4836-4837.
Benson G. Tandem repeats finder: a program to analyze DNA sequences. Nucleic Acids Res. Jan. 15, 1999;27(2):573-80).
Bodenteich, A., Chissoe, S., Wang, Y.-F. and Roe, B. A. (1994) In Adams, M. D., Fields, C. and Venter, J. C. (eds.) Automated DNA Sequencing and Analysis. Academic Press, San Diego, CA.
Boguski et al., "Identification of a cytidine-specific ribonuclease from chicken liver." J Biol Chem. Mar. 10, 1980;255(5):2160-3.
Boom et al. (1990, J. Clin. Microbiol. 28: 495-503.
Boom et al. (1991, J. Clin. Microbiol. 29: 1804-1811.
Boyer, L.A. et al. Polycomb complexes repress developmental regulators in murine embryonic stem cells. Nature 441, 349-53 (2006).

(56) References Cited

OTHER PUBLICATIONS

Brizot et al., "Maternal serum hCG and fetal nuchal translucency thickness for the prediction of fetal trisomies in the first trimester of pregnancy." Br J Obstet Gynaecol. Feb. 1995;102(2):127-32.
Bullinger et al., "Use of gene-expression profiling to identify prognostic subclasses in adult acute myeloid leukemia." N Engl J Med. Apr. 15, 2004;350(16)1 605-16.
Burlingame et al. Anal. Chem. 70:647R-716R (1998).
Byrne et al., "Multiplex gene regulation: a two-tiered approach to transgene regulation in transgenic mice." Proc Natl Acad Sci U S A. Jul. 1989;86(14):5473-7.
Calame et al., "Transcriptional controlling elements in the immunoglobulin and T cell receptor loci." Adv Immunol. 1988;43:235-75.
Camper et al., "Postnatal repression of the alpha-fetoprotein gene is enhancer independent." Genes Dev. Apr. 1989;3(4):537-46.
Chan et al. (2004) Clin. Chem. 50:88-92.
Chan et al., Oncogene 22:924-934 (2003).
Chang et al., "LIBSVM: a library for Support Vector Machines," 2001.
Chen et al., "Fluorescence energy transfer detection as a homogeneous DNA diagnostic method." Proc Natl Acad Sci U S A. Sep. 30, 1997;94(20):10756-61.
Chen et al., "Template-directed dye-terminator incorporation (TDI) assay: a homogeneous DNA diagnostic method based on fluorescence resonance energy transfer." Nucleic Acids Res. Jan. 15, 1997;25(2):347-53.
Cheson et al, "Report of the National Cancer Institute-sponsored workshop on definitions of diagnosis and response in acute myeloid leukemia" J Clin Oncol 8:813-819, 1990.
Cheung et al. (1994, J. Clin. Microbiol. 32: 2593-2597).
Chirgwin et al. (1979, Biochem. 18: 5294-5299.
Chitty, L. Br Med Bull 54:839-856 (1998).
Chiu et al., "Effects of blood-processing protocols on fetal and total DNA quantification in maternal plasma." Clin Chem. Sep. 2001;47(9):1607-13.
Chomczynski and Mackey (1995, Anal. Biochem. 225: 163-164).
Chomczynski and Mackey (1995, Biotechniques 19: 942-945).
Chomczynski and Sacchi (1987, Analytical Biochem. 162: 156-159).
Chomczynski, (1993, Biotech. 15: 532-537).
Chow, K.C., et al., Mass Spectrometric detection of a SNP panel as an internal positive control for fetal DNA analysis in maternal plasma. Clin. Chem. 53, 141-142 (2007).
Cruikshank et al., "A lipidated anti-Tat antibody enters living cells and blocks HIV-1 viral replication," J. Acquired Immune Deficiency Syndromes and Human Retrovirology 14:193 (1997).
Current Protocols in Molecular Biology, John Wiley & Sons, N.Y. , 6.3.1-6.3.6 (1989).
D'Alton., "Prenatal diagnostic procedures." Semin Perinatol. Jun. 1994;18(3):140-62.
Das, R. et al. Proc Natl Acad Sci U S A 103, 10713-6 (2006).
Davison., "Sedimentation of deoxyribonucleic acid isolated under low hydrodynamic shear." Nature. Mar. 26, 1960;185:918-20.
Davison., "The Effect of Hydrodynamic Shear on the Deoxyribonucleic Acid From T(2) and T(4) Bacteriophages." Proc Natl Acad Sci U S A. Nov. 1959;45(11):1560-8.
Dayie et al. (1998) J. Mag. Reson. 130, 97-101 (1998).
Deininger, P. L. "Random subcloning of sonicated DNA: application to shotgun DNA sequence analysis," Anal. Biochem. 129(1):216-223 (1983).
Dembo et al., 1994, Ann. Prob. 22: 2022-2039.
Donis-Keller et al., Nucl. Acids Res. 4:2527-2537 (1977).
Donis-Keller., "Phy M: an RNase activity specific for U and A residues useful in RNA sequence analysis." Nucleic Acids Res. Jul. 25, 1980;8(14):3133-42.
Eckhardt, F. et al. Nat Genet 38, 1378-85 (2006.
Edlund et al., "Cell-specific expression of the rat insulin gene: evidence for role of two distinct 5' flanking elements." Science. Nov. 22, 1985;230(4728):912-6.
Egger et al., "Reverse transcription multiplex PCR for differentiation between polio- and enteroviruses from clinical and environmental samples." J Clin Microbiol. Jun. 1995;33(6):1442-7.
Ehrich, M., Zoll, S., Sur, S. & van den Boom, D. Nucleic Acids Res (2007).
Eiben et al., "First-trimester screening: an overview." J Histochem Cytochem. Mar. 2005;53(3):281-3.
Eva and Aaronson, Nature, 316:273-275, 1985.
Fajkusova L. et al., "Detailed Mapping of Methylcytosine Positions at the CpG Island Surrounding the Pa Promoter at the bcr-abl Locus in CML Patients and in Two Cell Lines, K562 and BV173" Blood Cells Mol. Dis. 26(3):193-204 (2000).
Fan et al., "Noninvasive diagnosis of fetal aneuploidy by shotgun sequencing DNA from maternal blood." Proc Natl Acad Sci U S A. Oct. 21, 2008;105(42):16266-71. Epub Oct. 6, 2008.
Fan et al., "Working Set Selection Using the Second Order Information for Training SVM" Journal of Machine Learning Research 6 (2005) 1889-1918.
Feinberg., "Methylation meets genomics." Nat Genet. Jan. 2001;27(1):9-10.
Ferguson-Smith, "Placental mRNA in maternal plasma: Prospects for fetal screening", PNAS vol. 100, No. 8, 4360-4362 Apr. 15, 2003.
Fournie et al. (1986 Anal. Biochem. 158: 250-256).
Futreal, P.A. et al. Nat Rev Cancer 4, 177-83 (2004).
Gardiner-Garden et al., "CpG islands in vertebrate genomes." J Mol Biol. Jul. 20, 1987;196(2):261-82.
Giles et al., "Acute myeloid leukemia." Hematology Am Soc Hematol Educ Program. 2002:73-110.
Go et al. Clin Chem. Dec. 2007;53(12):2223-4.
Goeddel, Gene Expression Technology: Methods in Enzymology 185, Academic Press, San Diego, CA (1990).
Gottesman, S., Gene Expression Technology: Methods in Enzymology, Academic Press, San Diego, California 185: 119-128 (1990).
Grompe et al., Proc. Natl. Acad. Sci. USA 86: 5855-5892 (1989.
Grompe., "The rapid detection of unknown mutations in nucleic acids." Nat Genet. Oct. 1993;5(2):111-117.
Grunau et al., "Bisulfite genomic sequencing: systematic investigation of critical experimental parameters." Nucleic Acids Res. Jul. 1, 2001;29(13):E65, 1-7.
Gupta et al., "Use of specific endonuclease cleavage in RNA sequencing." Nucleic Acids Res. Jun. 1977;4(6):1957-78.
Haase et al., Methods in Virology, pp. 189-226, 1984.
Hage & Tweed, J. Chromatogr. B Biomed. Sci. Appl. Oct. 10; 699 (1-2): 499-525 (1997.
Hahn et al., (2011) Placenta 32 Suppl: S17-S20.
Hahner et al., "Matrix-assisted laser desorption/ionization mass spectrometry (MALDI) of endonuclease digests of RNA." Nucleic Acids Res. May 15, 1997;25(10):1957-64.
Hames and Higgins eds., Nucleic Acid Hybridization: A Practical Approach, IRL Press, 1985.
Hannish, J. and M. McClelland, "Activity of DNA modification and restriction enzymes in KGB, a potassium glutamate buffer," Gene Anal. Tech 5:105 (1988.
Hart et al., J.Biol.Chem., 269:62-65, 1994.
Hasan et al., Nucl. Acids Res. 24:2150-2157 (1996.
Heegaard, J Mol. Recognit. Winter; 11(1-6): 141-8 (1998).
Hennig et al (2007) J. Am. Chem. Soc. 129, 14911-14921.
Hershey, A. D. and Burgi, E. J. Mol. Biol, 2:143-152 (1960.
Hill, Craig, "Gen-Probe Transcription-Mediated Amplification: System Principles," Jan. 1996 httl://www.gen-probe.com/pdfs/tma_whiteppr.pdf.
Homer, J. et al., Prenat Diagn 23:566-571 (2003).
Hook, E. B. Lancet 2:169-172 (1981).
Hu, D. G. et al., "Aneuploidy detection in single cells using DNA array-based comparative genomic hybridization", Mol Hum Reprod 10: 283-289, (2004).
Huang et al., "Mechanism of ribose 2'-group discrimination by an RNA polymerase." Biochemistry. Jul. 8, 1997;36(27):8231-42.
Hulten et al., "Rapid and simple prenatal diagnosis of common chromosome disorders: advantages and disadvantages of the molecular methods FISH and QF-PCR." Reproduction. Sep. 2003;126(3):279-97.

(56) References Cited

OTHER PUBLICATIONS

Hunkapiller et al., "A microchemical facility for the analysis and synthesis of genes and proteins." Nature. Jul. 12-18, 1984;310(5973)105-11.
Hyrup et al., "Peptide nucleic acids (PNA): synthesis, properties and potential applications." Bioorg Med Chem. Jan. 1996;4(1):5-23.
Imai et al. , 1992, J. Virol. Methods 36: 181-184).
Imamura et al., "Prenatal diagnosis of adrenoleukodystrophy by means of mutation analysis." Prenat Diagn. Mar. 1996;16(3):259-61.
International Preliminary Report on Patentability, mailed on Sep. 23, 2010 in International application No. PCT/US2009/036683 filed on: Mar. 10, 2009 and published as WO 09/114543 on Sep. 17, 2009.
International Search Report and Written Opinion, mailed on Feb. 24, 2010 in International application No. PCT/US2009/036683 filed on: Mar. 10, 2009 and published as WO 09/114543 on Sep. 17, 2009.
Invitation to Pay Additional Fees and Partial International Search Report mailed on: Dec. 28, 2009 in International application No. PCT/US2009/036683 filed on: Mar. 10, 2009 and published as WO 09/114543 on Sep. 17, 2009.
Issa., "CpG island methylator phenotype in cancer." Nat Rev Cancer. Dec. 2004;4(12):988-93.
Iverson et al., 1981, Prenat. Diagn. 9: 31-48.
Iwabuchi et al., Oncogene 8: 1693-1696 (1993.
Jing et al. (1998) Proc Natl Acad Sci USA. 95(14):8046-51.
Johansen et al., "An investigation of methods for enriching trophoblast from maternal blood." Prenat Diagn. Oct. 1995;15(10):921-31.
Kaneko et al., Gut 52:641-646 (2003).
Karlin et al., "Methods for assessing the statistical significance of molecular sequence features by using general scoring schemes." Proc Natl Acad Sci U S A. Mar. 1990;87(6):2264-8.
Kent, "BLAT—the BLAST-like alignment tool." Genome Res. Apr. 2002;12(4):656-64.
Kessel et al., "Murine developmental control genes." Science. Jul. 27, 1990;249(4967):374-9.
Kidd JM et al. Mapping and sequencing of structural variation from eight human genomes. Nature. May 1, 2008;453 (7191):56-64).
Kuchino et al., "Enzymatic RNA sequencing." Methods Enzymol. 1989;180:154-63.
Kuhn et al., "DNA Helicases" Cold Spring Harb Symp Quant Biol. 1979;43 Pt 1:63-7.
Kulkarmi et al., "Global DNA methylation patterns in placenta and its association with maternal hypertension in pre-eclampsia," (2011) DNA Cell Biol. 30(2):79-84.
Lai et al. (1999) Nat Genet. 23(3):309-13.
Larkin et al., "Clustal W and Clustal X version 2.0." Bioinformatics. Nov. 1, 2007;23(21):2947-8. Epub Sep. 10, 2007.
Leung et al., "An efficient algorithm for identifying matches with errors in multiple long molecular sequences." J Mol Biol. Oct. 20, 1991;221(4):1367-78.
Li et al. Nucl. Acids Res. 23:4495-4501 (1995).
Li et al., "Size separation of circulatory DNA in maternal plasma permits ready detection of fetal DNA polymorphisms." Clin Chem. Jun. 2004;50(6):1002-11. Epub Apr. 8, 2004.
Li et al., "Targeted mutation of the DNA methyltransferase gene results in embryonic lethality." Cell. Jun. 12, 1992;69(6):915-26.
Li, Y., et al., Genotyping fetal paternally inherited SNPs by MALDI-TOF MS using cell-free fetal DNA in maternal plasma: Influence of size fractionation. Electrophoresis 27, 3889-3896 (2006).
Lingbeek, M.E., Bruggeman, S.W. & van Lohuizen, M. Cell 118, 409-18 (2004).
Little, et al. Nat Med 3:1413-6 (1997.
Litz C. E. et al., "Methylation status of the major breakpoint cluster region in Philadelphia chromosome negative leukemias" Leukemia 6(1):35-41 (1992.
Lo et al. (Nat Med. Feb. 2007;13(2):218-23).
Lo et al., "Maternal Plasma DNA Sequencing Reveals the Genome-Wide Genetic and Mutational Profile of the Fetus," Prenatal Diagnosis, Science Translational Medicine, Dec. 8, 2010, vol. 2, Issue 61, 1-13.
Lo et al., "Presence of fetal DNA in maternal plasma and serum." Lancet. Aug. 16, 1997;350(9076):485-7.
Lo et al., "Quantitative analysis of fetal DNA in maternal plasma and serum: implications for noninvasive prenatal diagnosis." Am J Hum Genet. Apr. 1998;62(4):768-75.
Lo, "Recent advances in fetal nucleic acids in maternal plasma." J Histochem Cytochem. Mar. 2005;53(3):293-6.
Lun et al., "Microfluidics digital PCR reveals a higher than expected fraction of fetal DNA in maternal plasma." Clin Chem. Oct. 2008;54(10):1664-72. Epub Aug. 14, 2008.
Madura et al., J. Biol. Chem. 268: 12046-12054 (1993).
Majlessi et al., Nucleic Acids Research, 26(9):2224-2229, (1998).
Malik et al., "Polyethylene glycol (PEG)-modified granulocyte-macrophage colony-stimulating factor (GM-CSF) with conserved biological activity." Exp Hematol. Sep. 1992;20(8):1028-35.
Mann et al., "Development and implementation of a new rapid aneuploidy diagnostic service within the UK National Health Service and implications for the future of prenatal diagnosis." Lancet. Sep. 29, 2001;358(9287)1057-61.
Mann, K. Methods Mol Med 92:141-156 (2004).
Mao and Williamson (1999) Nucl. Acids Res. 27, 4059-4070.
Marais et al., EMBO J. 14: 3136-3145 (1995).
Marais et al., J. Biol. Chem. 272: 4378-4383 (1997.
Mason et al., EMBO J. 18: 2137-2148 (1999.
McClelland, M. et al., "A single buffer for all restriction endonucleases," Nucl. Acids Res. 16:364 (1988).
McConnell, H. M. et al., Science 257: 1906-1912 (1992)).
Metzker M Nature Rev 11:31-46 (2010).
Meyers & Miller, CABIOS 4:11-17 (1989).
Mito, Y., Henikoff, J.G. & Henikoff, S. Nat Genet 37, 1090-7 (2005.
Moudrianakis E. N. and Beer M. Proc Natl Acad Sci USA. Mar. 1965; 53:564-71.
Nakamaye et al., Nucl. Acids Res. 23:9947-9959(1988).
Nakano et al. "Single-molecule PCR using water-in-oil emulsion;" Journal of Biotechnology 102 (2003) 117-124.
Needleman et al., "A general method applicable to the search for similarities in the amino acid sequence of two proteins." J Mol Biol. Mar. 1970;48(3)444-453.
Ng et al. , 2003, Proc. Natl. Acad. Sci. USA 100 : 4748-4753.
Ng et al., 2002, Clin. Chem. 48: 1212-1217.
Nicolaides et al., "One-stop clinic for assessment of risk of chromosomal defects at 12 weeks of gestation." J Matern Fetal Neonatal Med. Jul. 2002;12(1):9-18.
Nicolaides, K. H. et al., Prenat Diagn 22:308-315 (2002)).
Nicolaidis et al., "Origin and mechanisms of non-disjunction in human autosomal trisomies." Hum Reprod. Feb. 1998;13(2):313-9.
Nishizuka et al., "Proteomic profiling of the NCI-60 cancer cell lines using new high-density reverse-phase lysate microarrays." Proc Natl Acad Sci U S A. Nov. 25, 2003;100(24):14229-34. Epub Nov. 17, 2003.
Nosaka, K. et al., "Increasing methylation of the CDKN2A gene is associated with the progression of adult T-cell leukemia", Cancer Res. 60(4):1043-1048 (2000).
Oefner, P. J. et al., "Efficient random subcloning of DNA sheared in a recirculating point-sink flow system," Nucl. Acids Res. 24(20):3879-3886 (1996).
Oeth et al., "Qualitative and quantitative genotyping using single base primer extension coupled with matrix-assisted laser desorption/ ionization time-of-flight mass spectrometry (MassARRAY)." Methods Mol Biol. 2009;578:307-43.
Ohm, J.E. et al. A stem cell-like chromatin pattern may predispose tumor suppressor genes to DNA hypermethylation and heritable silencing. Nat Genet 39, 237-42 (2007).
Okano et al., "DNA methyltransferases Dnmt3a and Dnmt3b are essential for de novo methylation and mammalian development." Cell. Oct. 29, 1999;99(3):247-57.
Olek et al., "A modified and improved method for bisulphite based cytosine methylation analysis." Nucleic Acids Res. Dec. 15, 1996;24(24):5064-6.
Oligonucleotides and Analogues, A Practical Approach, F. Eckstein, editor, IRL Press, Oxford, 1991.
Orita et al., Proc. Natl. Acad. Sci. U.S.A 86: 27776-2770 (1989.
Osborne, et al., Curr. Opin. Chem. Biol.1(1): 5-9 (1997.

(56) References Cited

OTHER PUBLICATIONS

Oudejans et al., 2003, Prenatal Diagnosis 23: 111-116.
Padilla et al., "Efficient synthesis of nucleic acids heavily modified with non-canonical ribose 2'-groups using a mutantT7 RNA polymerase (RNAP)." Nucleic Acids Res. Mar. 15, 1999;27(6):1561-1563.
Palomaki et al., "Maternal serum screening for Down syndrome in the United States: a 1995 survey." Am J Obstet Gynecol. May 1997;176(5):1046-51.
Pandya et al., "Screening for fetal trisomies by maternal age and fetal nuchal translucency thickness at 10 to 14 weeks of gestation." Br J Obstet Gynaecol. Dec. 1995;102(12):957-62.
Patel, D. J., Curr. Opin. Chem. Biol. Jun;1(1): 32-46 (1997).
Paulin, R. et al. in Nucleic Acids Res. 26:5009-5010, 1998.
Pearson, 1988, Proc. Natl. Acad. Sci. USA 85(5): 2444-2448.
Perry-O'Keefe et al., "Peptide nucleic acid pre-gel hybridization: an alternative to southern hybridization." Proc Natl Acad Sci U S A. Dec. 10, 1996;93(25):14670-5.
Pertl et al., "Rapid molecular method for prenatal detection of Down's syndrome." Lancet. May 14, 1994;343(8907):1197-8.
Petersen and Mikkelsen. Cytogenet Cell Genet. 2000;91(1-4):199-203.
Pinkert et al., Genes Dev. 1: 268-277 (1987).
Poon et al. , 2000, Clin. Chem. 46: 1832-1834.
Poon et al., "Differential DNA methylation between fetus and mother as a strategy for detecting fetal DNA in maternal plasma." Clin Chem. Jan. 2002;48(1):35-41.
Porter et al., Biochemistry 34: 11963-11969 (1995).
Qu et al., "Analysis of drug-DNA binding data." Methods Enzymol. 2000;321:353-69.
Queen et al., "Immunoglobulin gene transcription is activated by downstream sequence elements." Cell. Jul. 1983;33(3):741-8.
Radding., "Homologous pairing and strand exchange in genetic recombination." Annu Rev Genet. 1982;16:405-37.
Randen et al., "Prenatal genotyping of RHD and SRY using maternal blood," VOX Sanguinis, vol. 85, No. 4, Nov. 2003, pp. 300-306.
Rashtchian (1994, PCR Methods Applic. 4: S83-S91).
Rivas, G., and Minton, A. P., Trends Biochem Sci Aug;18(8): 284-7 (1993).
Robertson et al., Nature Rev. Genet. 1:11-19 (2000).
Robinson M. D. and T. P. Speed. "A comparison of Affymetrix gene expression arrays." BMC Bioinformatics 8:449 (2007).
Rojo et al., "Cusativin, a new cytidine-specific ribonuclease accumulated in seeds of *Cucumis sativus* L." Planta. 1994;194(3):328-38.
Rollins et al., "Large-scale structure of genomic methylation patterns." Genome Res. Feb. 2006;16(2):157-63. Epub Dec. 19, 2005.
Romero and Rotbard, Diagnostic Molecular Biology: Principles and Applications, pp, 401-406; Pershing et al, eds., Mayo Foundation, Rochester, Minn., 1993.
Roschke et al., "Karyotypic complexity of the NCI-60 drug-screening panel." Cancer Res. Dec. 15, 2003;63(24):8634-47.
Rosenberg, H. S. and Bendich, A. J. Am. Chem. Soc. 82:3198-3201 (1960).
Santoro, S. W. and Joyce, G. F. "A general purpose RNA-cleaving DNA enzyme," Proc. Natl. Acad. Sci. USA 94:4262-4266 (1997.
Sargent et al., Meth. Enz. 152:432 (1988)).
Schlesinger et al., "Polycomb-mediated methylation on Lys27 of histone H3 pre-marks genes for de novo methylation in cancer." Nat Genet. Feb. 2007;39(2):232-6. Epub Dec. 31, 2006.
Schouten et al., "Relative quantification of 40 nucleic acid sequences by multiplex ligation-dependent probe amplification." Nucleic Acids Res. Jun. 15, 2002;30(12):e57.
Schriefer, L. A. et al., "Low pressure DNA shearing: a method for random DNA sequence analysis," Nucl. Acids Res. 18:7455-7456 (1990.
Schuler GD, Sequence mapping by electronic PCR., Genome Res. May 1997;7(5):541-50.
Scott et al. (2004) J. Am. Chem. Soc. 126, 11776-11777.
Sheffield et al., "Identification of novel rhodopsin mutations associated with retinitis pigmentosa by GC-clamped denaturing gradient gel electrophoresis." Am J Hum Genet. Oct. 1991;49(4):699-706.
Silverman et al., "Methylation inhibitor therapy in the treatment of myelodysplastic syndrome." Nat Clin Pract Oncol. Dec. 2005;2 Suppl 1:S12-23.
Simoncsits et al., "New rapid gel sequencing method for RNA." Nature. Oct. 27, 1977;269(5631):833-6.
Singer et al., Biotechniques 4:230-250, 1986.
Sjolander & Urbaniczk, Anal. Chem. 63: 2338-2345 (1991.
Slater et al., "Rapid, high throughput prenatal detection of aneuploidy using a novel quantitative method (MLPA)." J Med Genet. Dec. 2003;40(12):907-12.
Smith et al., "Identification of common molecular subsequences." J Mol Biol. Mar. 25, 1981;147(1):195-7.
Smith et al., "Single-step purification of polypeptides expressed in *Escherichia coli* as fusions with glutathione S-transferase." Gene. Jul. 15, 1988;67(1):31-40.
Snijders et al., "Assembly of microarrays for genome-wide measurement of DNA copy number." Nat Genet. Nov. 2001;29(3):263-4.
Snijders et al., "First-trimester ultrasound screening for chromosomal defects." Ultrasound Obstet Gynecol. Mar. 1996;7(3):216-26.
Snijders et al., "UK multicentre project on assessment of risk of trisomy 21 by maternal age and fetal nuchal-translucency thickness at 10-14 weeks of gestation. Fetal Medicine Foundation First Trimester Screening Group." Lancet. Aug. 1, 1998;352(9125):343-6.
Sousa et al., "A mutant T7 RNA polymerase as a DNA polymerase." EMBO J. Sep. 15, 1995;14(18):4609-21.
Stanssens et al., "High-throughput MALDI-TOF discovery of genomic sequence polymorphisms." Genome Res. Jan. 2004;14(1):126-33.
Staunton et al., "Chemosensitivity prediction by transcriptional profiling." Proc Natl Acad Sci U S A. Sep. 11, 2001;98(19)10787-92.
Staunton, J.E. et al. Proc Natl Acad Sci U S A 98, 10787-92 (2001).
Strathdee, et al., Am. J. Pathol. 158:1121-1127 (2001).
Supplementary European Search Report dated: Jul. 14, 2011 for European Application No. EP 09720284 filed: Mar. 10, 2009 based on internation application No. PCT/US2009/036683.
Szabo et al., Curr. Opin. Struct. Biol. 5: 699-705 (1995).
Tang et al. (2002) Analytical Chemistry 74, 226-331.
Strachan, "The Human Genome," BIOS Scientific Publishers, 1992.
The World Health Organization histological typing of lung tumours, Am J Clin Pathol 1982; 77:123-136.
Thorstenson, Y.R. et al., "An Automated Hydrodynamic Process for Controlled, Unbiased DNA Shearing," Genome Research 8:848-855 (1998).
Tolbert and Williamson (1996) J. Am. Chem. Soc. 118, 7929-7940.
Tolbert and Williamson (1997) J. Am. Chem. Soc. 119, 12100-12108.
Tost et al., Nucl. Acids Res. 37:e50 (2003).
Toyota et al., "Methylation profiling in acute myeloid leukemia." Blood. May 1, 2001;97(9):2823-9.
Tungwiwat et al., "Non-invasive fetal sex determination using a conventional nested PCR analysis of fetal DNA in maternal plasma," Clinica Chimica Acta, vol. 334, No. 1-2, Aug. 2003, pp. 173-177.
Valk et al., "Prognostically useful gene-expression profiles in acute myeloid leukemia." N Engl J Med. Apr. 15, 2004;350(16)1 617-28.
Valk-Lingbeek et al., "Stem cells and cancer; the polycomb connection." Cell. Aug. 20, 2004;118(4):409-18.
Van der Schoot, C.E., et al., Real-time PCR of bi-allelic insertion/deletion polymorphisms can serve as a reliable positive control for cell-free fetal DNA in non-invasive prenatal genotyping [abstract] Blood 102, 93a (2003).
Veltman et al., "High-throughput analysis of subtelomeric chromosome rearrangements by use of array-based comparative genomic hybridization." Am J Hum Genet. May 2002;70(5):1269-76. Epub Apr. 9, 2002.
Verbeck et al. in the Journal of Biomolecular Techniques (vol. 13, Issue 2, 56-61).
Verma et al., "Rapid and simple prenatal DNA diagnosis of Down's syndrome." Lancet. Jul. 4, 1998;352(9121):9-12.
Vincenet et al., "Helicase-Dependent isothermal DNA Amplification,"EMBO reports 5(8):795-800 (2004).

(56) References Cited

OTHER PUBLICATIONS

Vire et al., "The Polycomb group protein EZH2 directly controls DNA methylation." Nature. Feb. 16, 2006;439(7078):871-4. Epub Dec. 14, 2005.
Volkerding et al. Clin Chem 55:641-658 (2009).
Vu et al. (Genomics 64(2):p. 29331-40, 1999.
Wada et al., "Codon usage tabulated from the GenBank genetic sequence data." Nucleic Acids Res. May 11, 1992;20 Suppl:21 11-8.
Wang, H. et al. BMC Genomics 7, 166 (2006.
Wapner et al., "First-trimester screening for trisomies 21 and 18." N Engl J Med. Oct. 9, 2003;349(15)1 405-13.
Waterman et al., 1980, J. Mol. Biol. 147: 195-197.
Weber et al., Oncogene 19: 169-176 (2000.
Weisenberger, D.J. et al. Nat Genet 38, 787-93 (2006.
White et al., "Detecting single base substitutions as heteroduplex polymorphisms." Genomics. Feb. 1992;12(2):301-6.
Widschwendter, M. et al. Epigenetic stem cell signature in cancer. Nat Genet 39, 157-8 (2007).
Wilkinson, In situ Hybridization, Wilkinson ed., IRL Press, Oxford University Press, Oxford.
Winoto et al., "A novel, inducible and T cell-specific enhancer located at the 3' end of the T cell receptor alpha locus." EMBO J. Mar. 1989;8(3):729-33.
Yan et al., "A novel diagnostic strategy for trisomy 21 using short tandem repeats," Electrophoresis 2006, 27,416-422.
Zervos et al., Cell 72:223-232 (1993.
Zhao et al., (2010) Pretat Diag 30(8):778-782.
Zimmermann, B. et al., Clin Chem 48:362-363 (2002).
Zuker "Mfold web server for nucleic acid folding and hybridization prediction," Nucleic Acids Res. 31(13), 3406-3415.
Office Action dated: Sep. 24, 2012 in U.S. Appl. No. 13/458,036, filed Apr. 27, 2012 and published as: 2012/0264618 on: Oct. 18, 2012.
Office Action dated: Sep. 17, 2012 in U.S. Appl. No. 13/457,978, filed Apr. 27, 2012 and published as: 2012/0276542 on: Oct. 1, 2012.
Office Action dated: Sep. 17, 2012 in U.S. Appl. No. 13/458,341, filed Apr. 27, 2012.
International Preliminary Report on Patentability mailed on: Apr. 4, 2011 in International Application No. PCT/US2009/057215 filed on Sep. 16, 2009 and published as: WO 10/033639 on Mar. 25, 2010.
International Search Report and Written Opinion mailed on: Dec. 29, 2010 in International Application No. PCT/US2009/057215 filed on Sep. 16, 2009 and published as: WO 10/033639 on Mar. 25, 2010.
International Search Report and Written Opinion mailed on: Dec. 30, 2010 in International Application No. PCT/US2010/027879 filed on Mar. 18, 2010.
Old RW, "Candidate epigenetic biomarkers for non-invasive prenatal diagnosis of Down syndrom," Reprod Biomed. Online 2007, vol. 15, No. 2, pp. 227-235.
International Search Report and Written Opinion mailed on Oct. 23, 2013 in International Application No. PCT/US2013/050145, filed on Jul. 11, 2013.
Tsui et al., "Systemic Identification of Placental Epigenetic Signatures for the Noninvasive Prenatal Detection of Edwards Syndrome" PLOS One (2010) 5(11):e15069.
Lo and Chiu, "Prenatal diagnosis: progress through plasma nucleic acids" Nature Reviews Genetics (2007) 8:71-77.
International Preliminary Report on Patentability mailed on Nov. 7, 2013 in International Application No. PCT/US2012/035479, filed on Apr. 27, 2012 and published as WO 2012/149339 on Nov. 1, 2012.
Office Action dated Nov. 22, 2013 in U.S. Appl. No. 12/401,493, filed Mar. 10, 2009 and published as US 2009-0317817 on Dec. 24, 2009.
Office Action dated Jan. 7, 2014 in U.S. Appl. No. 13/517,508, filed Jun. 13, 2012 and published as US 2013-0143211 on Jun. 6, 2013.
Office Action dated Feb. 5, 2014 in U.S. Appl. No. 13/517,508, filed Jun. 13, 2012 and published as US 2013-0143211 on Jun. 6, 2013.
Office Action dated Mar. 7, 2014 in U.S. Appl. No. 13/801,384, filed Mar. 13, 2013 and published as US 2013-0296180 on Nov. 7, 2013.
Bock et al., "CpG island methylation in human lymphocytes is highly correlated with DNA sequence, repeats, and predicted DNA structure" PLOS Genetics (2006) 2(3):e26.
Cross et al., "Purification of CpG islands using a methylated DNA binding column" Nature Genetics (1994) 6(3):236-244.
Hua et al., "Quantitative methylation analysis of multiple genes using methylation-sensitive restriction enzyme-based quantitative PCR for the detection of hepatocellular carcinoma" Experimental and Molecular Pathology (2011) 91:455-460.
Roach et al., "Association between the abnormal expression of matrix-degrading enzymes by human osteoarthritic chondrocytes and demethylation of specific CpG sites in the promoter regions" Arthritis & Rheumatism (2005) 52(10):3110-3124.
Yamada et al., "Suppressive effect of epigallocatechin gallate (EGCg) on DNA methylation in mice: Detection by methylation sensitive restriction endonuclease digestion and PCR" Journal of Food, Agriculture & Environment (2005) 3(2):73-76.
International Search Report and Written Opinion mailed on Jul. 30, 2014 in International Application No. PCT/US2014/025132, filed on Mar. 13, 2014.
Office Action dated Aug. 8, 2014 in U.S. Appl. No. 13/782,901, filed Mar. 1, 2013 and published as US 2013-0230858 on Sep. 5, 2013.
Fan et al., "Analysis of the size distributions of fetal and maternal cell-free DNA by paired-end sequencing" Clinical Chemistry (2010) 56(8):1279-1286.
Office Action dated Jun. 26, 2014 in U.S. Appl. No. 13/782,857, filed Mar. 1, 2013 and published as US 2013-0310260 on Nov. 21, 2013.
International Preliminary Report on Patentability mailed on Sep. 12, 2014 in International Application No. PCT/US2013/028699, filed on Mar. 1, 2013 and published as WO 2013/131021 on Sep. 6, 2013.
Office Action dated Nov. 7, 2014 in U.S. Appl. No. 13/791,466, filed Mar. 8, 2013 and published as US 2013-0295564 on Nov. 7, 2013.

* cited by examiner

Fractionating DNA
Based on Methylation

CORRELATION BETWEEN MICROARRAY AND EpiTYPER RESULTS

1. Assay Design

2. CCF DNA isolation

3. DNA digestion

4. Addition of primers and known amount of competitor oligonucleotide Followed by PCR

5. Primer extension

6. Analyte separation

D   C

1. Selection of differentially methylated targets for specific DNA sequence capture 2. Distribution of CCF DNA after capture 3. Distribution of CCF DNA after digestion 4. Quantification of non-digested DNA molecules

PROCESSES AND COMPOSITIONS FOR METHYLATION-BASED ENRICHMENT OF FETAL NUCLEIC ACID FROM A MATERNAL SAMPLE USEFUL FOR NON INVASIVE PRENATAL DIAGNOSES

RELATED PATENT APPLICATIONS

This patent application is a continuation-in-part of U.S. patent application Ser. No. 12/561,241, filed Sep. 16, 2009, having the same title as this application, which claims the benefit of U.S. Provisional Patent Application No. 61/192,264, filed Sep. 16, 2008. The entire content of the foregoing patent applications is incorporated by reference herein, including all text, drawings and tables.

FIELD

The technology in part relates to prenatal diagnostics and enrichment methods.

SEQUENCE LISTING

The instant application contains a Sequence Listing which has been submitted via EFS-Web and is hereby incorporated by reference in its entirety. Said ASCII copy, created on May 27, 2010, is named SEQ-6022-CP.txt and is 426,562 bytes in size.

BACKGROUND

Non-invasive prenatal testing is becoming a field of rapidly growing interest. Early detection of pregnancy-related conditions, including complications during pregnancy and genetic defects of the fetus is of crucial importance, as it allows early medical intervention necessary for the safety of both the mother and the fetus. Prenatal diagnosis has been conducted using cells isolated from the fetus through procedures such as chorionic villus sampling (CVS) or amniocentesis. However, these conventional methods are invasive and present an appreciable risk to both the mother and the fetus. The National Health Service currently cites a miscarriage rate of between 1 and 2 percent following the invasive amniocentesis and chorionic villus sampling (CVS) tests.

An alternative to these invasive approaches has been developed for prenatal screening, e.g., to detecting fetal abnormalities, following the discovery that circulating cell-free fetal nucleic acid can be detected in maternal plasma and serum (Lo et al., Lancet 350:485-487, 1997; and U.S. Pat. No. 6,258,540). Circulating cell free fetal nucleic acid (cffNA) has several advantages making it more applicable for non-invasive prenatal testing. For example, cell free nucleic acid is present at higher levels than fetal cells and at concentrations sufficient for genetic analysis. Also, cffNA is cleared from the maternal bloodstream within hours after delivery, preventing contamination from previous pregnancies.

Examples of prenatal tests performed by detecting fetal DNA in maternal plasma or serum include fetal rhesus D (RhD) genotyping (Lo et al., N. Engl. J. Med. 339:1734-1738, 1998), fetal sex determination (Costa et al., N. Engl. J. Med. 346:1502, 2002), and diagnosis of several fetal disorders (Amicucci et al., Clin. Chem. 46:301-302, 2000; Saito et al., Lancet 356:1170, 2000; and Chiu et al., Lancet 360:998-1000, 2002). In addition, quantitative abnormalities of fetal DNA in maternal plasma/serum have been reported in preeclampsia (Lo et al., Clin. Chem. 45:184-188, 1999 and Zhong et al., Am. J. Obstet. Gynecol. 184:414-419, 2001), fetal trisomy 21 (Lo et al., Clin. Chem. 45:1747-1751, 1999 and Zhong et al., Prenat. Diagn. 20:795-798, 2000) and hyperemesis gravidarum (Sekizawa et al., Clin. Chem. 47:2164-2165, 2001).

SUMMARY

The invention provides inter alio human epigenetic biomarkers that are useful for the noninvasive detection of fetal genetic traits, including, but not limited to, the presence or absence of fetal nucleic acid, the absolute or relative amount of fetal nucleic acid, fetal sex, and fetal chromosomal abnormalities such as aneuploidy. The human epigenetic biomarkers of the invention represent genomic DNA that display differential CpG methylation patterns between the fetus and mother. The compositions and processes of the invention allow for the detection and quantification of fetal nucleic acid in a maternal sample based on the methylation status of the nucleic acid in said sample. More specifically, the amount of fetal nucleic acid from a maternal sample can be determined relative to the total amount of nucleic acid present, thereby providing the percentage of fetal nucleic acid in the sample. Further, the amount of fetal nucleic acid can be determined in a sequence-specific (or locus-specific) manner and with sufficient sensitivity to allow for accurate chromosomal dosage analysis (for example, to detect the presence or absence of a fetal aneuploidy).

In the first aspect of the invention, a method is provided for enriching fetal nucleic acids from a maternal biological sample, based on differential methylation between fetal and maternal nucleic acid comprising the steps of: (a) binding a target nucleic acid, from a sample, and a control nucleic acid, from the sample, to a methylation-specific binding protein; and (b) eluting the bound nucleic acid based on methylation status, wherein differentially methylated nucleic acids elute at least partly into separate fractions. In an embodiment, the nucleic acid sequence includes one or more of the polynucleotide sequences of SEQ ID NOs: 1-261. SEQ ID NOs: 1-261 are provided in Tables 4A-4C. The invention includes the sequences of SEQ ID NOs: 1-261, and variations thereto. In an embodiment, a control nucleic acid is not included in step (a).

In a related embodiment, a method is provided for enriching fetal nucleic acid from a maternal sample, which comprises the following steps: (a) obtaining a biological sample from a woman; (b) separating fetal and maternal nucleic acid based on the methylation status of a CpG-containing genomic sequence in the sample, wherein the genomic sequence from the fetus and the genomic sequence from the woman are differentially methylated, thereby distinguishing the genomic sequence from the woman and the genomic sequence from the fetus in the sample. In an embodiment, the genomic sequence is at least 15 nucleotides in length, comprising at least one cytosine, further wherein the region consists of (1) a genomic locus selected from Tables 1A-1C; and (2) a DNA sequence of no more than 10 kb upstream and/or downstream from the locus. For this aspect and all aspects of the invention, obtaining a biological sample from a woman is not meant to limit the scope of the invention. Said obtaining can refer to actually drawing a sample from a woman (e.g., a blood draw) or to receiving a sample from elsewhere (e.g., from a clinic or hospital) and performing the remaining steps of the method.

In a related embodiment, a method is provided for enriching fetal nucleic acid from a maternal sample, which comprises the following steps: (a) obtaining a biological sample from the woman; (b) digesting or removing maternal nucleic acid based on the methylation status of a CpG-containing genomic sequence in the sample, wherein the genomic sequence from the fetus and the genomic sequence from the woman are differentially methylated, thereby enriching for the genomic sequence from the fetus in the sample. Maternal nucleic acid may be digested using one or more methylation sensitive restriction enzymes that selectively digest or cleave maternal nucleic acid based on its methylation status. In an embodiment, the genomic sequence is at least 15 nucleotides in length, comprising at least one cytosine, further wherein the region consists of (1) a genomic locus selected from Tables 1A-1C; and (2) a DNA sequence of no more than 10 kb upstream and/or downstream from the locus.

In a second aspect of the invention, a method is provided for preparing nucleic acid having a nucleotide sequence of a fetal nucleic acid, which comprises the following steps: (a) providing a sample from a pregnant female; (b) separating fetal nucleic acid from maternal nucleic acid from the sample of the pregnant female according to a different methylation state between the fetal nucleic acid and the maternal nucleic acid counterpart, wherein the nucleotide sequence of the fetal nucleic acid comprises one or more CpG sites from one or more of the polynucleotide sequences of SEQ ID NOs: 1-261 within a polynucleotide sequence from a gene or locus that contains one of the polynucleotide sequences of SEQ ID NOs: 1-261; and (c) preparing nucleic acid comprising a nucleotide sequence of the fetal nucleic acid by an amplification process in which fetal nucleic acid separated in part (b) is utilized as a template. In an embodiment, a method is provided for preparing nucleic acid having a nucleotide sequence of a fetal nucleic acid, which comprises the following steps: (a) providing a sample from a pregnant female; (b) digesting or removing maternal nucleic acid from the sample of the pregnant female according to a different methylation state between the fetal nucleic acid and the maternal nucleic acid counterpart, wherein the nucleotide sequence of the fetal nucleic acid comprises one or more CpG sites from one or more of the polynucleotide sequences of SEQ ID NOs: 1-261 within a polynucleotide sequence from a gene that contains one of the polynucleotide sequences of SEQ ID NOs: 1-261; and (c) preparing nucleic acid comprising a nucleotide sequence of the fetal nucleic acid. The preparing process of step (c) may be a hybridization process, a capture process, or an amplification process in which fetal nucleic acid separated in part (b) is utilized as a template. Also, in the above embodiment wherein maternal nucleic acid is digested, the maternal nucleic acid may be digested using one or more methylation sensitive restriction enzymes that selectively digest or cleave maternal nucleic acid based on its methylation status. In either embodiment, the polynucleotide sequences of SEQ ID NOs: 1-261 may be within a polynucleotide sequence from a CpG island that contains one of the polynucleotide sequences of SEQ ID NOs: 1-261. The polynucleotide sequences of SEQ ID NOs: 1-261 are further characterized in Tables 1-3 herein, including the identification of CpG islands that overlap with the polynucleotide sequences provided in SEQ ID NOs: 1-261. In an embodiment, the nucleic acid prepared by part (c) is in solution. In yet an embodiment, the method further comprises quantifying the fetal nucleic acid from the amplification process of step (c).

In a third aspect of the invention, a method is provided for enriching fetal nucleic acid from a sample from a pregnant female with respect to maternal nucleic acid, which comprises the following steps: (a) providing a sample from a pregnant female; and (b) separating or capturing fetal nucleic acid from maternal nucleic acid from the sample of the pregnant female according to a different methylation state between the fetal nucleic acid and the maternal nucleic acid, wherein the nucleotide sequence of the fetal nucleic acid comprises one or more CpG sites from one or more of the polynucleotide sequences of SEQ ID NOs: 1-261 within a polynucleotide sequence from a gene that contains one of the polynucleotide sequences of SEQ ID NOs: 1-261. In an embodiment, the polynucleotide sequences of SEQ ID NOs: 1-261 may be within a polynucleotide sequence from a CpG island that contains one of the polynucleotide sequences of SEQ ID NOs: 1-261. The polynucleotide sequences of SEQ ID NOs: 1-261 are characterized in Tables 1A-1C herein. In an embodiment, the nucleic acid separated by part (b) is in solution. In yet an embodiment, the method further comprises amplifying and/or quantifying the fetal nucleic acid from the separation process of step (b).

In a fourth aspect of the invention, a composition is provided comprising an isolated nucleic acid from a fetus of a pregnant female, wherein the nucleotide sequence of the nucleic acid comprises one or more of the polynucleotide sequences of SEQ ID NOs: 1-261. In one embodiment, the nucleotide sequence consists essentially of a nucleotide sequence of a gene, or portion thereof. In an embodiment, the nucleotide sequence consists essentially of a nucleotide sequence of a CpG island, or portion thereof. The polynucleotide sequences of SEQ ID NOs: 1-261 are further characterized in Tables 1A-1C. In an embodiment, the nucleic acid is in solution. In an embodiment, the nucleic acid from the fetus is enriched relative to maternal nucleic acid. In an embodiment, the composition further comprises an agent that binds to methylated nucleotides. For example, the agent may be a methyl-CpG binding protein (MBD) or fragment thereof.

In a fifth aspect of the invention, a composition is provided comprising an isolated nucleic acid from a fetus of a pregnant female, wherein the nucleotide sequence of the nucleic acid comprises one or more CpG sites from one or more of the polynucleotide sequences of SEQ ID NOs: 1-261 within a polynucleotide sequence from a gene, or portion thereof, that contains one of the polynucleotide sequences of SEQ ID NOs: 1-261. In an embodiment, the nucleotide sequence of the nucleic acid comprises one or more CpG sites from one or more of the polynucleotide sequences of SEQ ID NOs: 1-261 within a polynucleotide sequence from a CpG island, or portion thereof, that contains one of the polynucleotide sequences of SEQ ID NOs: 1-261. The polynucleotide sequences of SEQ ID NOs: 1-261 are further characterized in Tables 1A-1C. In an embodiment, the nucleic acid is in solution. In an embodiment, the nucleic acid from the fetus is enriched relative to maternal nucleic acid. Hyper- and hypomethylated nucleic acid sequences of the invention are identified in Tables 1A-1C. In an embodiment, the composition further comprises an agent that binds to methylated nucleotides. For example, the agent may be a methyl-CpG binding protein (MBD) or fragment thereof.

In some embodiments, a nucleotide sequence of the invention includes three or more of the CpG sites. In an embodiment, the nucleotide sequence includes five or more of the CpG sites. In an embodiment, the nucleotide sequence is from a gene region that comprises a PRC2 domain (see Table 3). In an embodiment, the nucleotide sequence is from a gene region involved with development. For example, SOX14—which is an epigenetic marker of the present invention (See Table 1)—is a member of the SOX (SRY-related HMG-box) family of transcription factors involved in the regulation of embryonic development and in the determination of cell fate.

In some embodiments, the genomic sequence from the woman is methylated and the genomic sequence from the fetus is unmethylated. In other embodiments, the genomic sequence from the woman is unmethylated and the genomic sequence from the fetus is methylated. In an embodiment, the genomic sequence from the fetus is hypermethylated relative to the genomic sequence from the mother. Fetal genomic sequences found to be hypermethylated relative to maternal genomic sequence are provided in SEQ ID NOs: 1-59, 90-163, 176, 179, 180, 184, 188, 189, 190, 191, 193, 195, 198, 199, 200, 201, 202, 203, 205, 206, 207, 208, 209, 210, 211, 212, 213, 214, 221, 223, 225, 226, 231, 232, 233, 235, 239, 241, 257, 258, 259, and 261. Alternatively, the genomic sequence from the fetus is hypomethylated relative to the genomic sequence from the mother. Fetal genomic sequences found to be hypomethylated relative to maternal genomic sequence are provided in SEQ ID NOs: 60-85, 164, 165, 166, 167, 168, 169, 170, 171, 172, 173, 174, 175, 177, 178, 181, 182, 183, 185, 186, 187, 192, 194, 196, 197, 204, 215, 216, 217, 218, 219, 220, 222, 224, 227, 228, 229, 230, 234, 236, 237, 238, 240, 242, 243, 244, 245, 246, 247, 248, 249, 250, 251, 252, 253, 254, 255, 256, and 260. Methylation sensitive restriction enzymes of the invention may be sensitive to hypo- or hyper-methylated nucleic acid.

In an embodiment, the fetal nucleic acid is extracellular nucleic acid. Generally the extracellular fetal nucleic acid is about 500, 400, 300, 250, 200 or 150 (or any number there between) nucleotide bases or less. In an embodiment, the digested maternal nucleic acid is less than about 90, 100, 110, 120, 130, 140 or 150 base pairs. In a related embodiment, the fetal nucleic acid is selectively amplified, captured or separated from or relative to the digested maternal nucleic acid based on size. For example, PCR primers may be designed to amplify nucleic acid greater than about 75, 80, 85, 90, 95, 100, 105, 110, 115 or 120 (or any number there between) base pairs thereby amplifying fetal nucleic acid and not digested maternal nucleic acid. In an embodiment, the nucleic acid is subjected to fragmentation prior to the methods of the invention. Examples of methods of fragmenting nucleic acid, include but are not limited to sonication and restriction enzyme digestion. In some embodiments the fetal nucleic acid is derived from the placenta. In other embodiments the fetal nucleic acid is apoptotic.

In some embodiments, the present invention provides a method in which the sample is a member selected from the following: maternal whole blood, maternal plasma or serum, amniotic fluid, a chorionic villus sample, biopsy material from a pre-implantation embryo, fetal nucleated cells or fetal cellular remnants isolated from maternal blood, maternal urine, maternal saliva, washings of the female reproductive tract and a sample obtained by celocentesis or lung lavage. In certain embodiments, the biological sample is maternal blood. In some embodiments, the biological sample is a chorionic villus sample. In certain embodiments, the maternal sample is enriched for fetal nucleic acid prior to the methods of the present invention. Examples of fetal enrichment methods are provided in PCT Publication Nos. WO/2007140417A2, WO2009/032781A2 and US Publication No. 20050164241.

In some embodiments, all nucleated and anucleated cell populations are removed from the sample prior to practicing the methods of the invention. In some embodiments, the sample is collected, stored or transported in a manner known to the person of ordinary skill in the art to minimize degradation or the quality of fetal nucleic acid present in the sample.

The sample can be from any animal, including but not limited, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may have a detectable pregnancy-associated disorder or chromosomal abnormality.

In some embodiments, the sample is treated with a reagent that differentially modifies methylated and unmethylated DNA. For example, the reagent may comprise bisulfite; or the reagent may comprise one or more enzymes that preferentially cleave methylated DNA; or the reagent may comprise one or more enzymes that preferentially cleave unmethylated DNA. Examples of methylation sensitive restriction enzymes include, but are not limited to, HhaI and HpaII.

In one embodiment, the fetal nucleic acid is separated from the maternal nucleic acid by an agent that specifically binds to methylated nucleotides in the fetal nucleic acid. In an embodiment, the fetal nucleic acid is separated or removed from the maternal nucleic acid by an agent that specifically binds to methylated nucleotides in the maternal nucleic acid counterpart. In an embodiment, the agent that binds to methylated nucleotides is a methyl-CpG binding protein (MBD) or fragment thereof.

In a sixth aspect of the invention, a method is provided for determining the amount or copy number of fetal DNA in a maternal sample that comprises differentially methylated maternal and fetal DNA. The method is performed by a) distinguishing between the maternal and fetal DNA based on differential methylation status; and b) quantifying the fetal DNA of step a). In a specific embodiment, the method comprises a) digesting the maternal DNA in a maternal sample using one or more methylation sensitive restriction enzymes thereby enriching the fetal DNA; and b) determining the amount of fetal DNA from step a). The amount of fetal DNA can be used inter alio to confirm the presence or absence of fetal nucleic acid, determine fetal sex, diagnose fetal disease or a pregnancy-associated disorder, or be used in conjunction with other fetal diagnostic methods to improve sensitivity or specificity. In one embodiment, the method for determining the amount of fetal DNA does not require the use of a polymorphic sequence. For example, an allelic ratio is not used to quantify the fetal DNA in step b). In an embodiment, the method for determining the amount of fetal DNA does not require the treatment of DNA with bisulfite to convert cytosine residues to uracil. Bisulfite is known to degrade DNA, thereby, further reducing the already limited fetal nucleic acid present in maternal samples. In one embodiment, determining the amount of fetal DNA in step b) is done by introducing one or more competitors at known concentrations. In an embodiment, determining the amount of fetal DNA in step b) is done by RT-PCR, primer extension, sequencing or counting. In a related embodiment, the amount of nucleic acid is determined using BEAMing technology as described in US Patent Publication No. US20070065823. In a another related embodiment, the amount of nucleic acid is determined using the shotgun sequencing technology described in US Patent Publication No. US20090029377 (U.S. application Ser. No. 12/178,181), or variations thereof. In an embodiment, the restriction efficiency is determined and the efficiency rate is used to further determine the amount of fetal DNA. Exemplary differentially methylated nucleic acids are provided in SEQ ID NOs: 1-261.

In a seventh aspect of the invention, a method is provided for determining the concentration of fetal DNA in a maternal sample, wherein the maternal sample comprises differentially methylated maternal and fetal DNA, comprising a) determining the total amount of DNA present in the maternal sample; b) selectively digesting the maternal DNA in a maternal sample using one or more methylation sensitive restriction enzymes thereby enriching the fetal DNA; c) determining the amount of fetal DNA from step b); and d) comparing the amount of fetal DNA from step c) to the total amount of DNA from step a), thereby determining the concentration of fetal DNA in the maternal sample. The concentration of fetal DNA can be used inter alio in conjunction with other fetal diagnostic methods to improve sensitivity or specificity. In one embodiment, the method for determining the amount of fetal DNA does not require the use of a polymorphic sequence. For example, an allelic ratio is not used to quantify the fetal DNA in step b). In an embodiment, the method for determining the amount of fetal DNA does not require the treatment of DNA with bisulfite to convert cytosine residues to uracil. In one embodiment, determining the amount of fetal DNA in step b) is done by introducing one or more competitors at known concentrations. In an embodiment, determining the amount of fetal DNA in step b) is done by RT-PCR, sequencing or counting. In an embodiment, the restriction efficiency is determined and used to further determine the amount of total DNA and fetal DNA. Exemplary differentially methylated nucleic acids are provided in SEQ ID NOs: 1-261.

In an eighth aspect of the invention, a method is provided for determining the presence or absence of a fetal aneuploidy using fetal DNA from a maternal sample, wherein the maternal sample comprises differentially methylated maternal and fetal DNA, comprising a) selectively digesting the maternal DNA in a maternal sample using one or more methylation sensitive restriction enzymes thereby enriching the fetal DNA; b) determining the amount of fetal DNA from a target chromosome; c) determining the amount of fetal DNA from a reference chromosome; and d) comparing the amount of fetal DNA from step b) to step c), wherein a biologically or statistically significant difference between the amount of target and reference fetal DNA is indicative of the presence of a fetal aneuploidy. In one embodiment, the method for determining the amount of fetal DNA does not require the use of a polymorphic sequence. For example, an allelic ratio is not used to quantify the fetal DNA in step b). In an embodiment, the method for determining the amount of fetal DNA does not require the treatment of DNA with bisulfite to convert cytosine residues to uracil. In one embodiment, determining the amount of fetal DNA in steps b) and c) is done by introducing one or more competitors at known concentrations. In an embodiment, determining the amount of fetal DNA in steps b) and c) is done by RT-PCR, sequencing or counting. In an embodiment, the amount of fetal DNA from a target chromosome determined in step b) is compared to a standard control, for example, the amount of fetal DNA from a target chromosome from euploid pregnancies. In an embodiment, the restriction efficiency is determined and used to further determine the amount of fetal DNA from a target chromosome and from a reference chromosome. Exemplary differentially methylated nucleic acids are provided in SEQ ID NOs: 1-261.

In a ninth aspect of the invention, a method is provided for detecting the presence or absence of a chromosomal abnormality by analyzing the amount or copy number of target nucleic acid and control nucleic acid from a sample of differentially methylated nucleic acids comprising the steps of: (a) enriching a target nucleic acid, from a sample, and a control nucleic acid, from the sample, based on its methylation state; (b) performing a copy number analysis of the enriched target nucleic acid in at least one of the fractions; (c) performing a copy number analysis of the enriched control nucleic acid in at least one of the fractions; (d) comparing the copy number from step (b) with the copy number from step (c); and (e) determining if a chromosomal abnormality exists based on the comparison in step (d), wherein the target nucleic acid and control nucleic acid have the same or substantially the same methylation status. In a related embodiment, a method is provided for detecting the presence or absence of a chromosomal abnormality by analyzing the amount or copy number of target nucleic acid and control nucleic acid from a sample of differentially methylated nucleic acids comprising the steps of: (a) binding a target nucleic acid, from a sample, and a control nucleic acid, from the sample, to a binding agent; (b) eluting the bound nucleic acid based on methylation status, wherein differentially methylated nucleic acids elute at least partly into separate fractions; (c) performing a copy number analysis of the eluted target nucleic acid in at least one of the fractions; (d) performing a copy number analysis of the eluted control nucleic acid in at least one of the fractions; (e) comparing the copy number from step (c) with the copy number from step (d); and (f) determining if a chromosomal abnormality exists based on the comparison in step (e), wherein the target nucleic acid and control nucleic acid have the same or substantially the same methylation status. Differentially methylated nucleic acids are provided in SEQ ID NOs: 1-261.

In a tenth aspect of the invention, a method is provided for detecting the presence or absence of a chromosomal abnormality by analyzing the allelic ratio of target nucleic acid and control nucleic acid from a sample of differentially methylated nucleic acids comprising the steps of: (a) binding a target nucleic acid, from a sample, and a control nucleic acid, from the sample, to a binding agent; (b) eluting the bound nucleic acid based on methylation status, wherein differentially methylated nucleic acids elute at least partly into separate fractions; (c) performing an allelic ratio analysis of the eluted target nucleic acid in at least one of the fractions; (d) performing an allelic ratio analysis of the eluted control nucleic acid in at least one of the fractions; (e) comparing the allelic ratio from step c with the all from step d; and (f) determining if a chromosomal abnormality exists based on the comparison in step (e), wherein the target nucleic acid and control nucleic acid have the same or substantially the same methylation status. Differentially methylated nucleic acids are provided in SEQ ID NOs: 1-261, and SNPs within the differentially methylated nucleic acids are provided in Table 2. The methods may also be useful for detecting a pregnancy-associated disorder.

In an eleventh aspect of the invention, the amount of maternal nucleic acid is determined using the methylation-based methods of the invention. For example, fetal nucleic acid can be separated (for example, digested using a methylation-sensitive enzyme) from the maternal nucleic acid in a sample, and the maternal nucleic acid can be quantified using the methods of the invention. Once the amount of maternal nucleic acid is determined, that amount can subtracted from the total amount of nucleic acid in a sample to determine the amount of fetal nucleic acid. The amount of fetal nucleic acid can be used to detect fetal traits, including fetal aneuploidy, as described herein.

For all aspects and embodiments of the invention described herein, the methods may also be useful for detecting a pregnancy-associated disorder. In some embodiments, the sample comprises fetal nucleic acid, or fetal nucleic acid and maternal nucleic acid. In the case when the sample comprises fetal and maternal nucleic acid, the fetal nucleic acid and the maternal nucleic acid may have a different methylation status. Nucleic acid species with a different methylation status can be differentiated by any method known in the art. In an embodiment, the fetal nucleic acid is enriched by the selective digestion of maternal nucleic acid by a methylation sensitive restriction enzyme. In an embodiment, the fetal nucleic acid is enriched by the selective digestion of maternal nucleic acid using two or more methylation sensitive restriction enzymes in the same assay. In an embodiment, the target nucleic acid and control nucleic acid are both from the fetus. In an embodiment, the average size of the fetal nucleic acid is about 100 bases to about 500 bases in length. In an embodiment the chromosomal abnormality is an aneuploidy, such as trisomy 21. In some embodiments, the target nucleic acid is at least a portion of a chromosome which may be abnormal and the control nucleic acid is at least a portion of a chromosome which is very rarely abnormal. For example, when the target nucleic acid is from chromosome 21, the control nucleic acid is from a chromosome other than chromosome 21—preferably another autosome. In an embodiment, the binding agent is a methylation-specific binding protein such as MBD-Fc. Also, the enriched or eluted nucleic acid is amplified and/or quantified by any method known in the art. In an embodiment, the fetal DNA is quantified using a method that does not require the use of a polymorphic sequence. For example, an allelic ratio is not used to quantify the fetal DNA. In an embodiment, the method for quantifying the amount of fetal DNA does not require the treatment of DNA with bisulfite to convert cytosine residues to uracil.

In some embodiments, the methods of the invention include the additional step of determining the amount of one or more Y-chromosome-specific sequences in a sample. In a related embodiment, the amount of fetal nucleic acid in a sample as determined by using the methylation-based methods of the invention is compared to the amount of Y-chromosome nucleic acid present.

Methods for differentiating nucleic acid based on methylation status include, but are not limited to, methylation sensitive capture, for example using, MBD2-Fc fragment; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes. Except where explicitly stated, any method for differentiating nucleic acid based on methylation status can be used with the compositions and methods of the invention.

In some embodiments, methods of the invention may further comprise an amplification step. The amplification step can be performed by PCR, such as methylation-specific PCR. In an embodiment, the amplification reaction is performed on single molecules, for example, by digital PCR, which is further described in U.S. Pat. Nos. 6,143,496 and 6,440,706, both of which are hereby incorporated by reference. In other embodiments, the method does not require amplification. For example, the amount of enriched fetal DNA may be determined by counting the fetal DNA (or sequence tags attached thereto) with a flow cytometer or by sequencing means that do not require amplification. In an embodiment, the amount of fetal DNA is determined by an amplification reaction that generates amplicons larger than the digested maternal nucleic acid, thereby further enriching the fetal nucleic acid.

In some embodiments, the fetal nucleic acid (alone or in combination with the maternal nucleic acid) comprises one or more detection moieties. In one embodiment, the detection moiety may be any one or more of a compomer, sugar, peptide, protein, antibody, chemical compound (e.g., biotin), mass tag (e.g., metal ions or chemical groups), fluorescent tag, charge tag (e.g., such as polyamines or charged dyes) and hydrophobic tag. In a related embodiment, the detection moiety is a mass-distinguishable product (MDP) or part of an MDP detected by mass spectrometry. In a specific embodiment, the detection moiety is a fluorescent tag or label that is detected by mass spectrometry. In some embodiments, the detection moiety is at the 5' end of a detector oligonucleotide, the detection moiety is attached to a non-complementary region of a detector oligonucleotide, or the detection moiety is at the 5' terminus of a non-complementary sequence. In certain embodiments, the detection moiety is incorporated into or linked to an internal nucleotide or to a nucleotide at the 3' end of a detector oligonucleotide. In some embodiments, one or more detection moieties are used either alone or in combination. See for example US Patent Applications U520080305479 and U520090111712. In certain embodiments, a detection moiety is cleaved by a restriction endonuclease, for example, as described in U.S. application Ser. No. 12/726,246. In some embodiments, a specific target chromosome is labeled with a specific detection moiety and one or more non-target chromosomes are labeled with a different detection moiety, whereby the amount target chromsome can be compared to the amount of non-target chromosome.

For embodiments that require sequence analysis, any one of the following sequencing technologies may be used: a primer extension method (e.g., iPLEX®; Sequenom, Inc.), direct DNA sequencing, restriction fragment length polymorphism (RFLP analysis), real-time PCR, for example using "STAR" (Scalable Transcription Analysis Routine) technology (see U.S. Pat. No. 7,081,339), or variations thereof, allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, fluorescence tagged dNTP/ddNTPs, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invaderm assay, hybridization using at least one probe, hybridization using at least one fluorescently labeled probe, electrophoresis, cloning and sequencing, for example as performed on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT.™.) technology of Pacific Biosciences, or nanopore-based sequencing (Soni G V and Meller A. 2007 Clin Chem 53: 1996-2001), for example, using an Ion Torrent ion sensor that measures an electrical charge associated with each individual base of DNA as each base passes through a tiny pore at the bottom of a sample well, or Oxford Nanopore device that uses a nanopore to measure the electrical charge associated with each individual unit of DNA, and combinations thereof. Nanopore-based methods may include sequencing nucleic acid using a nanopore, or counting nucleic acid molecules using a nanopore, for example, based on size wherein sequence information is not determined.

The absolute copy number of one or more nucleic acids can be determined, for example, using mass spectrometry, a system that uses a competitive PCR approach for absolute copy number measurements. See for example, Ding C, Cantor CR (2003) A high-throughput gene expression analysis technique using competitive PCR and matrix-assisted laser desorption ionization time-of-flight MS. Proc Natl Acad Sci U S A 100: 3059-3064, and U.S. patent application Ser. No. 10/655,762, which published as US Patent Publication No. 20040081993, both of which are hereby incorporated by reference.

In some embodiments, the amount of the genomic sequence is compared with a standard control, wherein an increase or decrease from the standard control indicates the presence or progression of a pregnancy-associated disorder. For example, the amount of fetal nucleic acid may be compared to the total amount of DNA present in the sample. Or when detecting the presence or absence of fetal aneuploidy, the amount of fetal nucleic acid from target chromosome may be compared to the amount of fetal nucleic acid from a reference chromosome. Preferably the reference chromosome is another autosome that has a low rate of aneuploidy. The ratio of target fetal nucleic acid to reference fetal nucleic acid may be compared to the same ratio from a normal, euploid pregnancy. For example, a control ratio may be determined from a DNA sample obtained from a female carrying a healthy fetus who does not have a chromosomal abnormality. Preferably, one uses a panel of control samples. Where certain chromosome anomalies are known, one can also have standards that are indicative of a specific disease or condition. Thus, for example, to screen for three different chromosomal aneuploidies in a maternal plasma of a pregnant female, one preferably uses a panel of control DNAs that have been isolated from mothers who are known to carry a fetus with, for example, chromosome 13, 18, or 21 trisomy, and a mother who is pregnant with a fetus who does not have a chromosomal abnormality.

In some embodiments, the present invention provides a method in which the alleles from the target nucleic acid and control nucleic acid are differentiated by sequence variation. The sequence variation may be a single nucleotide polymorphism (SNP) or an insertion/deletion polymorphism. In an embodiment, the fetal nucleic acid should comprise at least one high frequency heterozygous polymorphism (e.g., about 2%, 3%, 4%, 5%, 6%, 7%, 8%, 9%, 10%, 11%, 12%, 13%, 14%, 15%, 16%, 17%, 18%, 19%, 20%, 25% or more frequency rate), which allows the determination of the allelic-ratio of the nucleic acid in order to assess the presence or absence of the chromosomal abnormality. A list of exemplary SNPs is provided in Table 2, however, this does not represent a complete list of polymorphic alleles that can be used as part of the invention. Any SNP meeting the following criteria may also be considered: (a) the SNP has a heterozygosity frequency greater than about 2% (preferably across a range of different populations), (b) the SNP is a heterozygous locus; and (c)(i) the SNP is within nucleic acid sequence described herein, or (c)(iii) the SNP is within about 5 to about 2000 base pairs of a SNP described herein (e.g., within about 5, 10, 15, 20, 25, 30, 40, 50, 60, 70, 80, 90, 100, 200, 300, 400, 500, 600, 700, 800, 900, 1000, 1250, 1500, 1750 or 2000 base pairs of a SNP described herein).

In other embodiments, the sequence variation is a short tandem repeat (STR) polymorphism. In some embodiments, the sequence variation falls in a restriction site, whereby one allele is susceptible to digestion by a restriction enzyme and the one or more other alleles are not. In some embodiments, the sequence variation is a methylation site.

In some embodiments, performing an allelic ratio analysis comprises determining the ratio of alleles of the target nucleic acid and control nucleic acid from the fetus of a pregnant woman by obtaining an nucleic acid-containing biological sample from the pregnant woman, wherein the biological sample contains fetal nucleic acid, partially or wholly separating the fetal nucleic acid from the maternal nucleic acid based on differential methylation, discriminating the alleles from the target nucleic acid and the control nucleic acid, followed by determination of the ratio of the alleles, and detecting the presence or absence of a chromosomal disorder in the fetus based on the ratio of alleles, wherein a ratio above or below a normal, euploid ratio is indicative of a chromosomal disorder. In one embodiment, the target nucleic acid is from a suspected aneuploid chromosome (e.g., chromosome 21) and the control nucleic acid is from a euploid chromosome from the same fetus.

In some embodiments, the present invention is combined with other fetal markers to detect the presence or absence of multiple chromosomal abnormalities, wherein the chromosomal abnormalities are selected from the following: trisomy 21, trisomy 18 and trisomy 13, or combinations thereof. In some embodiments, the chromosomal disorder involves the X chromosome or the Y chromosome.

In some embodiments, the compositions or processes may be multiplexed in a single reaction. For example, the amount of fetal nucleic acid may be determined at multiple loci across the genome. Or when detecting the presence or absence of fetal aneuploidy, the amount of fetal nucleic acid may be determined at multiple loci on one or more target chromosomes (e.g., chromosomes 13, 18 or 21) and on one or more reference chromosomes. If an allelic ratio is being used, one or more alleles from Table 2 can be detected and discriminated simultaneously. When determining allelic ratios, multiplexing embodiments are particularly important when the genotype at a polymorphic locus is not known. In some instances, for example when the mother and child are homozygous at the polymorphic locus, the assay may not be informative. In one embodiment, greater than 1, 2, 3, 4, 5, 6, 7, 8, 9, 10, 11, 12, 13, 14, 15, 16, 17, 18, 19, 20, 25, 30, 35, 40, 50, 100, 200, 300 or 500, and any intermediate levels, polynucleotide sequences of the invention are enriched, separated and/or examined according the methods of the invention. When detecting a chromosomal abnormality by analyzing the copy number of target nucleic acid and control nucleic acid, less than 3, 4, 5, 6, 7, 8, 9, 10, 11, 12, 13, or 14 polynucleotide sequences may need to be analyzed to accurately detect the presence or absence of a chromosomal abnormality. In an embodiment, the compositions or processes of the invention may be used to assay samples that have been divided into 2, 3, 4, 5, 6, 7, 8, 9, 10, 11, 12, 13, 14, 15, 16, 17, 18, 19, 20, 25, 30, 35, 40, 50, 100 or more replicates, or into single molecule equivalents. Methods for analyzing fetal nucleic acids from a maternal sample in replicates, including single molecule analyses, are provided in US Application No, 11/364,294, which published as US Patent Publication No. US 2007-0207466 A1, which is hereby incorporated by reference.

In a further embodiment, the present invention provides a method wherein a comparison step shows an increased risk of a fetus having a chromosomal disorder if the ratio of the alleles or absolute copy number of the target nucleic acid is higher or lower by 1 standard deviation from the standard control sequence. In some embodiments, the comparison step shows an increased risk of a fetus having a chromosomal disorder if the ratio of the alleles or absolute copy number of the target nucleic acid is higher or lower by 2 standard deviation from the standard control sequence. In some other embodiments, the comparison step shows an increased risk of a fetus having a chromosomal disorder if the ratio of the alleles or absolute copy number of the target nucleic acid is higher or lower by 3 standard deviation from the standard control sequence. In some embodiments, the comparison step shows an increased risk of a fetus having a chromosomal disorder if the ratio of the alleles or absolute copy number of the target nucleic acid is higher or lower than a statistically significant standard deviation from the control. In one embodiment, the standard control is a maternal reference, and in an embodiment the standard control is a fetal reference chromosome (e.g., non-trisomic autosome).

In some embodiments, the methods of the invention may be combined with other methods for diagnosing a chromosomal abnormality. For example, a noninvasive diagnostic method may require confirmation of the presence or absence of fetal nucleic acid, such as a sex test for a female fetus or to confirm an RhD negative female fetus in an RhD negative mother. In an embodiment, the compositions and methods of the invention may be used to determine the percentage of fetal nucleic acid in a maternal sample in order to enable another diagnostic method that requires the percentage of fetal nucleic acid be known. For example, does a sample meet certain threshold concentration requirements? When determining an allelic ratio to diagnose a fetal aneuploidy from a maternal sample, the amount or concentration of fetal nucleic acid may be required to make a diagnose with a given sensitivity and specificity. In other embodiments, the compositions and methods of the invention for detecting a chromosomal abnormality can be combined with other known methods thereby improving the overall sensitivity and specificity of the detection method. For example, mathematical models have suggested that a combined first-trimester screening program utilizing maternal age (MA), nuchal translucency (NT) thickness, serum-free beta-hCG, and serum PAPP-A will detect more than 80% of fetuses with Down's syndrome for a 5% invasive testing rate (Wald and Hackshaw, Prenat Diagn 17(9):921-9 (1997)). However, the combination of commonly used aneuploidy detection methods combined with the non-invasive free fetal nucleic acid-based methods described herein may offer improved accuracy with a lower false positive rate. Examples of combined diagnostic methods are provided in PCT Publication Number WO2008157264A2 (assigned to the Applicant), which is hereby incorporated by reference. In some embodiments, the methods of the invention may be combined with cell-based methods, wherein fetal cells are procured invasively or non-invasively.

In certain embodiments, an increased risk for a chromosomal abnormality is based on the outcome or result(s) produced from the compositions or methods provided herein. An example of an outcome is a deviation from the euploid absolute copy number or allelic ratio, which indicates the presence of chromosomal aneuploidy. This increase or decrease in the absolute copy number or ratio from the standard control indicates an increased risk of having a fetus with a chromosomal abnormality (e.g., trisomy 21). Information pertaining to a method described herein, such as an outcome, result, or risk of trisomy or aneuploidy, for example, may be transfixed, renditioned, recorded and/or displayed in any suitable medium. For example, an outcome may be transfixed in a medium to save, store, share, communicate or otherwise analyze the outcome. A medium can be tangible (e.g., paper) or intangible (e.g., electronic medium), and examples of media include, but are not limited to, computer media, databases, charts, patient charts, records, patient records, graphs and tables, and any other medium of expression. The information sometimes is stored and/or renditioned in computer readable form and sometimes is stored and organized in a database. In certain embodiments, the information may be transferred from one location to another using a physical medium (e.g., paper) or a computer readable medium (e.g., optical and/or magnetic storage or transmission medium, floppy disk, hard disk, random access memory, computer processing unit, facsimile signal, satellite signal, transmission over an internet or transmission over the world-wide web).

In practicing the present invention within all aspects mentioned above, a CpG island may be used as the CpG-containing genomic sequence in some cases, whereas in other cases the CpG-containing genomic sequence may not be a CpG island.

In some embodiments, the present invention provides a kit for performing the methods of the invention. One component of the kit is a methylation-sensitive binding agent.

BRIEF DESCRIPTION OF THE DRAWINGS

FIG. 6 discloses SEQ ID NOS 350 and 351, respectively, in order of appearance.

In FIG. 14A, the copy number for each sample is shown. Two samples (no 25 and 26) have a significantly higher total copy number than all the other samples. A mean of approximately 1300 amplifiable copies/ml plasma was obtained (range 766-2055).

DEFINITIONS

Figure 1:
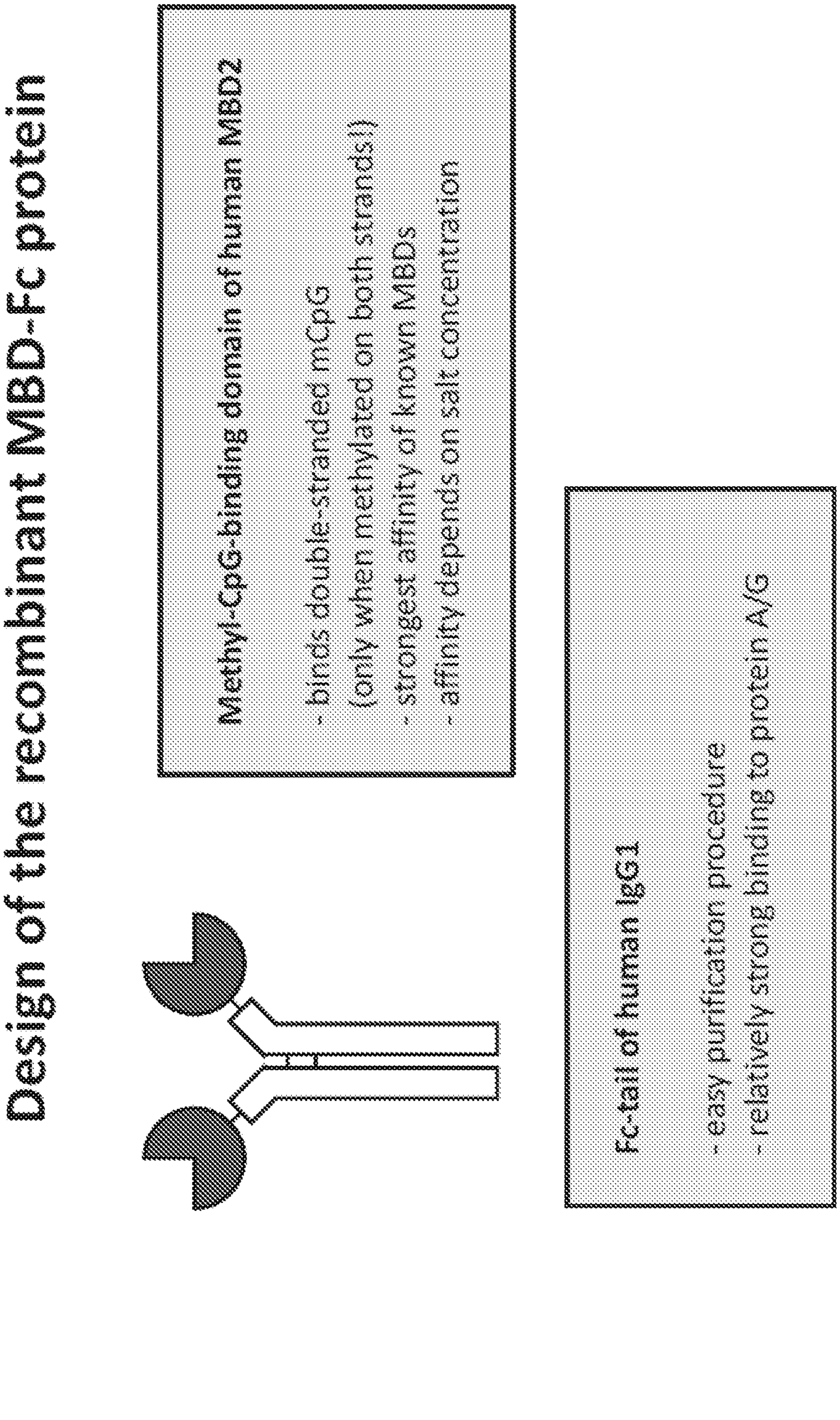
FIG. 1: Shows the design of the recombinant MBD-Fc protein used to separate differentially methylated DNA.

The term "pregnancy-associated disorder," as used in this application, refers to any condition or disease that may affect a pregnant woman, the fetus, or both the woman and the fetus. Such a condition or disease may manifest its symptoms during a limited time period, e.g., during pregnancy or delivery, or may last the entire life span of the fetus following its birth. Some examples of a pregnancy-associated disorder include ectopic pregnancy, preeclampsia, preterm labor, RhD incompatibility, fetal chromosomal abnormalities such as trisomy 21, and genetically inherited fetal disorders such as cystic fibrosis, beta-thalassemia or other monogenic disorders. The compositions and processes described herein are particularly useful for diagnosis, prognosis and monitoring of pregnancy-associated disorders associated with quantitative abnormalities of fetal DNA in maternal plasma/serum, including but not limited to, preeclampsia (Lo et al., Clin. Chem. 45:184-188, 1999 and Zhong et al., Am. J. Obstet. Gynecol. 184:414-419, 2001), fetal trisomy (Lo et al., Clin. Chem. 45:1747-1751, 1999 and Zhong et al., Prenat. Diagn. 20:795-798, 2000) and hyperemesis gravidarum (Sekizawa et al., Clin. Chem. 47:2164-2165, 2001). For example, an elevated level of fetal nucleic acid in maternal blood (as compared to a normal pregnancy or pregnancies) may be indicative of a preeclamptic pregnancy. Further, the ability to enrich fetal nucleic from a maternal sample may prove particularly useful for the non-invasive prenatal diagnosis of autosomal recessive diseases such as the case when a mother and father share an identical disease causing mutation, an occurrence previously perceived as a challenge for maternal plasma-based non-trisomy prenatal diagnosis.

The term "chromosomal abnormality" or "aneuploidy" as used herein refers to a deviation between the structure of the subject chromosome and a normal homologous chromosome. The term "normal" refers to the predominate karyotype or banding pattern found in healthy individuals of a particular species, for example, a euploid genome (in humans, 46XX or 46XY). A chromosomal abnormality can be numerical or structural, and includes but is not limited to aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. Chromosomal abnormality may also refer to a state of chromosomal abnormality where a portion of one or more chromosomes is not an exact multiple of the usual haploid number due to, for example, chromosome translocation. Chromosomal translocation (e.g. translocation between chromosome 21 and 14 where some of the 14th chromosome is replaced by extra 21st chromosome) may cause partial trisomy 21. A chromosomal abnormality can be correlated with presence of a pathological condition or with a predisposition to develop a pathological condition. A chromosomal abnormality may be detected by quantitative analysis of nucleic acid.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. For example, the nucleic acids provided in SEQ ID NOs: 1-261 (see Tables 4A-4C) can be in any form useful for conducting processes herein (e.g., linear, circular, supercoiled, single-stranded, double-stranded and the like) or may include variations (e.g., insertions, deletions or substitutions) that do not alter their utility as part of the present invention. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

A "nucleic acid comprising one or more CpG sites" or a "CpG-containing genomic sequence" as used herein refers to a segment of DNA sequence at a defined location in the genome of an individual such as a human fetus or a pregnant woman. Typically, a "CpG-containing genomic sequence" is at least 15 nucleotides in length and contains at least one cytosine. Preferably, it can be at least 30, 50, 80, 100, 150, 200, 250, or 300 nucleotides in length and contains at least 2, 5, 10, 15, 20, 25, or 30 cytosines. For anyone "CpG-containing genomic sequence" at a given location, e.g., within a region centering around a given genetic locus (see Tables 1A-1C), nucleotide sequence variations may exist from individual to individual and from allele to allele even for the same individual. Typically, such a region centering around a defined genetic locus (e.g., a CpG island) contains the locus as well as upstream and/or downstream sequences. Each of the upstream or downstream sequence (counting from the 5' or 3' boundary of the genetic locus, respectively) can be as long as 10 kb, in other cases may be as long as 5 kb, 2 kb, 1 kb, 500 bp, 200 bp, or 100 bp. Furthermore, a "CpG-containing genomic sequence" may encompass a nucleotide sequence transcribed or not transcribed for protein production, and the nucleotide sequence can be an inter-gene sequence, intra-gene sequence, protein-coding sequence, a non protein-coding sequence (such as a transcription promoter), or a combination thereof.

As used herein, a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring, however, for purposes herein, thymine is not considered a methylated nucleotide when present in DNA since thymine is a typical nucleotide base of DNA. Typical nucleoside bases for DNA are thymine, adenine, cytosine and guanine. Typical bases for RNA are uracil, adenine, cytosine and guanine. Correspondingly a "methylation site" is the location in the target gene nucleic acid region where methylation has, or has the possibility of occurring. For example a location containing CpG is a methylation site wherein the cytosine may or may not be methylated.

As used herein, a "CpG site" or "methylation site" is a nucleotide within a nucleic acid that is susceptible to methylation either by natural occurring events in vivo or by an event instituted to chemically methylate the nucleotide in vitro.

As used herein, a "methylated nucleic acid molecule" refers to a nucleic acid molecule that contains one or more methylated nucleotides that is/are methylated.

A "CpG island" as used herein describes a segment of DNA sequence that comprises a functionally or structurally deviated CpG density. For example, Yamada et al. (Genome Research 14:247-266, 2004) have described a set of standards for determining a CpG island: it must be at least 400 nucleotides in length, has a greater than 50% GC content, and an OCF/ECF ratio greater than 0.6. Others (Takai et al., Proc. Natl. Acad. Sci. U.S.A. 99:3740-3745, 2002) have defined a CpG island less stringently as a sequence at least 200 nucleotides in length, having a greater than 50% GC content, and an OCF/ECF ratio greater than 0.6.

The term "epigenetic state" or "epigenetic status" as used herein refers to any structural feature at a molecular level of a nucleic acid (e.g., DNA or RNA) other than the primary nucleotide sequence. For instance, the epigenetic state of a genomic DNA may include its secondary or tertiary structure determined or influenced by, e.g., its methylation pattern or its association with cellular proteins.

The term "methylation profile" "methylation state" or "methylation status," as used herein to describe the state of methylation of a genomic sequence, refers to the characteristics of a DNA segment at a particular genomic locus relevant to methylation. Such characteristics include, but are not limited to, whether any of the cytosine (C) residues within this DNA sequence are methylated, location of methylated C residue(s), percentage of methylated C at any particular stretch of residues, and allelic differences in methylation due to, e.g., difference in the origin of the alleles. The term "methylation" profile" or "methylation status" also refers to the relative or absolute concentration of methylated C or unmethylated C at any particular stretch of residues in a biological sample. For example, if the cytosine (C) residue(s) within a DNA sequence are methylated it may be referred to as "hypermethylated"; whereas if the cytosine (C) residue(s) within a DNA sequence are not methylated it may be referred to as "hypomethylated". Likewise, if the cytosine (C) residue(s) within a DNA sequence (e.g., fetal nucleic acid) are methylated as compared to another sequence from a different region or from a different individual (e.g., relative to maternal nucleic acid), that sequence is considered hypermethylated compared to the other sequence. Alternatively, if the cytosine (C) residue(s) within a DNA sequence are not methylated as compared to another sequence from a different region or from a different individual (e.g., the mother), that sequence is considered hypomethylated compared to the other sequence. These sequences are said to be "differentially methylated", and more specifically, when the methylation status differs between mother and fetus, the sequences are considered "differentially methylated maternal and fetal nucleic acid".

Figure 2:
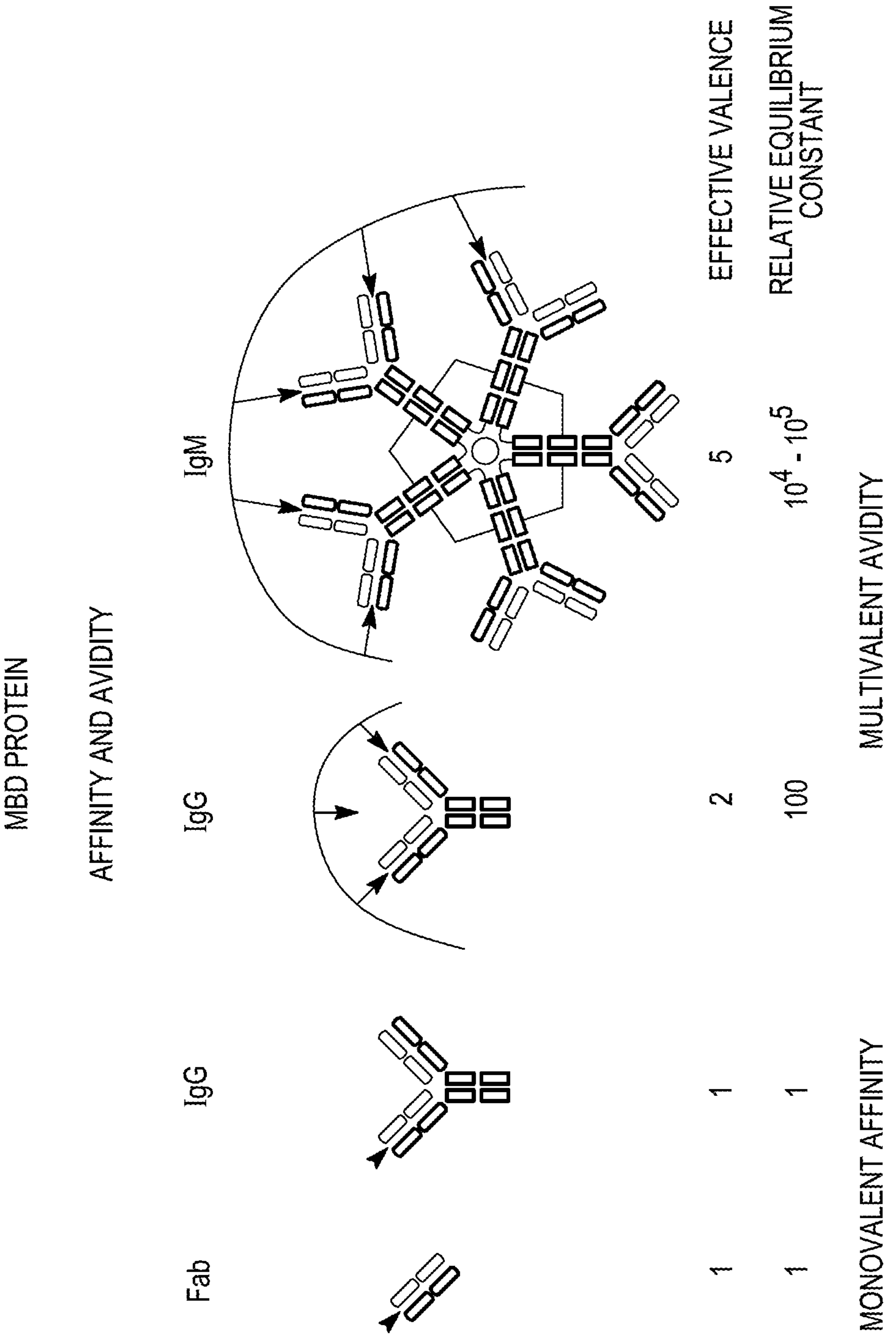
FIG. 2: Shows the methyl-CpG-binding, antibody-like protein has a high affinity and high avidity to its "antigen", which is preferably DNA that is methylated at CpG di-nucleotides.

The term "agent that binds to methylated nucleotides" as used herein refers to a substance that is capable of binding to methylated nucleic acid. The agent may be naturally-occurring or synthetic, and may be modified or unmodified. In one embodiment, the agent allows for the separation of different nucleic acid species according to their respective methylation states. An example of an agent that binds to methylated nucleotides is described in PCT Patent Application No. PCT/EP2005/012707, which published as WO06056480A2 and is hereby incorporated by reference. The described agent is a bifunctional polypeptide comprising the DNA-binding domain of a protein belonging to the family of Methyl-CpG binding proteins (MBDs) and an Fc portion of an antibody (see FIG. 1). The recombinant methyl-CpG-binding, antibody-like protein can preferably bind CpG methylated DNA in an antibody-like manner. That means, the methyl-CpG-binding, antibody-like protein has a high affinity and high avidity to its "antigen", which is preferably DNA that is methylated at CpG dinucleotides. The agent may also be a multivalent MBD (see FIG. 2).

The term "polymorphism" as used herein refers to a sequence variation within different alleles of the same genomic sequence. A sequence that contains a polymorphism is considered "polymorphic sequence". Detection of one or more polymorphisms allows differentiation of different alleles of a single genomic sequence or between two or more individuals. As used herein, the term "polymorphic marker" or "polymorphic sequence" refers to segments of genomic DNA that exhibit heritable variation in a DNA sequence between individuals. Such markers include, but are not limited to, single nucleotide polymorphisms (SNPs), restriction fragment length polymorphisms (RFLPs), short tandem repeats, such as di-, tri- or tetra-nucleotide repeats (STRs), and the like. Polymorphic markers according to the present invention can be used to specifically differentiate between a maternal and paternal allele in the enriched fetal nucleic acid sample.

The terms "single nucleotide polymorphism" or "SNP" as used herein refer to the polynucleotide sequence variation present at a single nucleotide residue within different alleles of the same genomic sequence. This variation may occur within the coding region or non-coding region (i.e., in the promoter or intronic region) of a genomic sequence, if the genomic sequence is transcribed during protein production. Detection of one or more SNP allows differentiation of different alleles of a single genomic sequence or between two or more individuals.

The term "allele" as used herein is one of several alternate forms of a gene or non-coding regions of DNA that occupy the same position on a chromosome. The term allele can be used to describe DNA from any organism including but not limited to bacteria, viruses, fungi, protozoa, molds, yeasts, plants, humans, non-humans, animals, and archeabacteria.

The terms "ratio of the alleles" or "allelic ratio" as used herein refer to the ratio of the population of one allele and the population of the other allele in a sample. In some trisomic cases, it is possible that a fetus may be tri-allelic for a particular locus. In such cases, the term "ratio of the alleles" refers to the ratio of the population of any one allele against one of the other alleles, or any one allele against the other two alleles.

The term "non-polymorphism-based quantitative method" as used herein refers to a method for determining the amount of an analyte (e.g., total nucleic acid, Y-chromosome nucleic acid, or fetal nucleic acid) that does not require the use of a polymorphic marker or sequence. Although a polymorphism may be present in the sequence, said polymorphism is not required to quantify the sequence. Examples of non-polymorphism-based quantitative methods include, but are not limited to, RT-PCR, digital PCR, array-based methods, sequencing methods, nanopore-based methods, nucleic acid-bound bead-based counting methods and competitor-based methods wherein one or more competitors are introduced at a known concentration(s) to determine the amount of one or more analytes. In some embodiments, some of the above exemplary methods (for example, sequencing) may need to be actively modified or designed such that one or more polymorphisms are not interrogated.

The terms "absolute amount" or "copy number" as used herein refers to the amount or quantity of an analyte (e.g., total nucleic acid or fetal nucleic acid). The present invention provides compositions and processes for determining the absolute amount of fetal nucleic acid in a mixed maternal sample. Absolute amount or copy number represents the number of molecules available for detection, and may be expressed as the genomic equivalents per unit. The term "concentration" refers to the amount or proportion of a substance in a mixture or solution (e.g., the amount of fetal nucleic acid in a maternal sample that comprises a mixture of maternal and fetal nucleic acid). The concentration may be expressed as a percentage, which is used to express how large/small one quantity is, relative to another quantity as a fraction of 100. Platforms for determining the quantity or amount of an analyte (e.g., target nucleic acid) include, but are not limited to, mass spectrometery, digital PCR, sequencing by synthesis platforms (e.g., pyrosequencing), fluorescence spectroscopy and flow cytometry.

The term "sample" as used herein refers to a specimen containing nucleic acid. Examples of samples include, but are not limited to, tissue, bodily fluid (for example, blood, serum, plasma, saliva, urine, tears, peritoneal fluid, ascitic fluid, vaginal secretion, breast fluid, breast milk, lymph fluid, cerebrospinal fluid or mucosa secretion), umbilical cord blood, chorionic villi, amniotic fluid, an embryo, a two-celled embryo, a four-celled embryo, an eight-celled embryo, a 16-celled embryo, a 32-celled embryo, a 64-celled embryo, a 128-celled embryo, a 256-celled embryo, a 512-celled embryo, a 1024-celled embryo, embryonic tissues, lymph fluid, cerebrospinal fluid, mucosa secretion, or other body exudate, fecal matter, an individual cell or extract of the such sources that contain the nucleic acid of the same, and subcellular structures such as mitochondria, using protocols well established within the art.

Fetal DNA can be obtained from sources including but not limited to maternal blood, maternal serum, maternal plasma, fetal cells, umbilical cord blood, chorionic villi, amniotic fluid, urine, saliva, lung lavage, cells or tissues.

The term "blood" as used herein refers to a blood sample or preparation from a pregnant woman or a woman being tested for possible pregnancy. The term encompasses whole blood or any fractions of blood, such as serum and plasma as conventionally defined.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that modifies methylated and/or unmethylated DNA in a process through which distinguishable products result from methylated and non-methylated DNA, thereby allowing the identification of the DNA methylation status. Such processes may include, but are not limited to, chemical reactions (such as a C.fwdarw.U conversion by bisulfite) and enzymatic treatment (such as cleavage by a methylation-dependent endonuclease). Thus, an enzyme that preferentially cleaves or digests methylated DNA is one capable of cleaving or digesting a DNA molecule at a much higher efficiency when the DNA is methylated, whereas an enzyme that preferentially cleaves or digests unmethylated DNA exhibits a significantly higher efficiency when the DNA is not methylated.

The terms "non-bisulfite-based method" and "non-bisulfite-based quantitative method" as used herein refer to any method for quantifying methylated or non-methylated nucleic acid that does not require the use of bisulfite. The terms also refer to methods for preparing a nucleic acid to be quantified that do not require bisulfite treatment. Examples of non-bisulfite-based methods include, but are not limited to, methods for digesting nucleic acid using one or more methylation sensitive enzymes and methods for separating nucleic acid using agents that bind nucleic acid based on methylation status.

The terms "methyl-sensitive enzymes" and "methylation sensitive restriction enzymes" are DNA restriction endonucleases that are dependent on the methylation state of their DNA recognition site for activity. For example, there are methyl-sensitive enzymes that cleave or digest at their DNA recognition sequence only if it is not methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated. As used herein, the terms "cleave", "cut" and "digest" are used interchangeably.

The term "target nucleic acid" as used herein refers to a nucleic acid examined using the methods disclosed herein to determine if the nucleic acid is part of a pregnancy-related disorder or chromosomal abnormality. For example, a target nucleic acid from chromosome 21 could be examined using the methods of the invention to detect Down's Syndrome.

The term "control nucleic acid" as used herein refers to a nucleic acid used as a reference nucleic acid according to the methods disclosed herein to determine if the nucleic acid is part of a chromosomal abnormality. For example, a control nucleic acid from a chromosome other than chromosome 21 (herein referred to as a "reference chromosome") could be as a reference sequence to detect Down's Syndrome. In some embodiments, the control sequence has a known or predetermined quantity.

The term "sequence-specific" or "locus-specific method" as used herein refers to a method that interrogates (for example, quantifies) nucleic acid at a specific location (or locus) in the genome based on the sequence composition. Sequence-specific or locus-specific methods allow for the quantification of specific regions or chromosomes.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Primers" as used herein refer to oligonucleotides that can be used in an amplification method, such as a polymerase chain reaction (PCR), to amplify a nucleotide sequence based on the polynucleotide sequence corresponding to a particular genomic sequence, e.g., one located within the CpG island CG1137, PDE9A, or CGI009 on chromosome 21, in various methylation status. At least one of the PCR primers for amplification of a polynucleotide sequence is sequence-specific for the sequence. The term "template" refers to any nucleic acid molecule that can be used for amplification in the invention. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

The term "amplification reaction" as used herein refers to a process for copying nucleic acid one or more times. In embodiments, the method of amplification includes but is not limited to polymerase chain reaction, self-sustained sequence reaction, ligase chain reaction, rapid amplification of cDNA ends, polymerase chain reaction and ligase chain reaction, O-beta phage amplification, strand displacement amplification, or splice overlap extension polymerase chain reaction. In some embodiments, a single molecule of nucleic acid is amplified, for example, by digital PCR.

The term "sensitivity" as used herein refers to the number of true positives divided by the number of true positives plus the number of false negatives, where sensitivity (sens) may be within the range of 0 sens 1. Ideally, method embodiments herein have the number of false negatives equaling zero or close to equaling zero, so that no subject is wrongly identified as not having at least one chromosome abnormality or other genetic disorder when they indeed have at least one chromosome abnormality or other genetic disorder. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of 0 spec 1. Ideally, methods embodiments herein have the number of false positives equaling zero or close to equaling zero, so that no subject wrongly identified as having at least one chromosome abnormality other genetic disorder when they do not have the chromosome abnormality other genetic disorder being assessed. Hence, a method that has sensitivity and specificity equaling one, or 100%, sometimes is selected.

One or more prediction algorithms may be used to determine significance or give meaning to the detection data collected under variable conditions that may be weighed independently of or dependently on each other. The term "variable" as used herein refers to a factor, quantity, or function of an algorithm that has a value or set of values. For example, a variable may be the design of a set of amplified nucleic acid species, the number of sets of amplified nucleic acid species, percent fetal genetic contribution tested, percent maternal genetic contribution tested, type of chromosome abnormality assayed, type of genetic disorder assayed, type of sex-linked abnormalities assayed, the age of the mother and the like. The term "independent" as used herein refers to not being influenced or not being controlled by another. The term "dependent" as used herein refers to being influenced or controlled by another. For example, a particular chromosome and a trisomy event occurring for that particular chromosome that results in a viable being are variables that are dependent upon each other.

One of skill in the art may use any type of method or prediction algorithm to give significance to the data of the present invention within an acceptable sensitivity and/or specificity. For example, prediction algorithms such as Chi-squared test, z-test, t-test, ANOVA (analysis of variance), regression analysis, neural nets, fuzzy logic, Hidden Markov Models, multiple model state estimation, and the like may be used. One or more methods or prediction algorithms may be determined to give significance to the data having different independent and/or dependent variables of the present invention. And one or more methods or prediction algorithms may be determined not to give significance to the data having different independent and/or dependent variables of the present invention. One may design or change parameters of the different variables of methods described herein based on results of one or more prediction algorithms (e.g., number of sets analyzed, types of nucleotide species in each set). For example, applying the Chi-squared test to detection data may suggest that specific ranges of maternal age are correlated to a higher likelihood of having an offspring with a specific chromosome abnormality, hence the variable of maternal age may be weighed differently verses being weighed the same as other variables.

In certain embodiments, several algorithms may be chosen to be tested. These algorithms can be trained with raw data. For each new raw data sample, the trained algorithms will assign a classification to that sample (i.e. trisomy or normal). Based on the classifications of the new raw data samples, the trained algorithms' performance may be assessed based on sensitivity and specificity. Finally, an algorithm with the highest sensitivity and/or specificity or combination thereof may be identified.

DETAILED DESCRIPTION

Introduction

The presence of fetal nucleic acid in maternal plasma was first reported in 1997 and offers the possibility for non-invasive prenatal diagnosis simply through the analysis of a maternal blood sample (Lo et al., Lancet 350:485-487, 1997). To date, numerous potential clinical applications have been developed. In particular, quantitative abnormalities of fetal nucleic acid, for example DNA, concentrations in maternal plasma have been found to be associated with a number of pregnancy-associated disorders, including preeclampsia, preterm labor, antepartum hemorrhage, invasive placentation, fetal Down syndrome, and other fetal chromosomal aneuploidies. Hence, fetal nucleic acid analysis in maternal plasma represents a powerful mechanism for the monitoring of fetomaternal well-being.

However, fetal DNA co-exists with background maternal DNA in maternal plasma. Hence, most reported applications have relied on the detection of Y-chromosome sequences as these are most conveniently distinguishable from maternal DNA. Such an approach limits the applicability of the existing assays to only 50% of all pregnancies, namely those with male fetuses. Thus, there is much need for the development of sex-independent compositions and methods for enriching and analyzing fetal nucleic acid from a maternal sample. Also, methods that rely on polymorphic markers to quantify fetal nucleic acid may be susceptible to varying heterozygosity rates across different ethnicities thereby limiting their applicability (e.g., by increasing the number of markers that are needed).

It was previously demonstrated that fetal and maternal DNA can be distinguished by their differences in methylation status (U.S. Pat. No. 6,927,028, which is hereby incorporated by reference). Methylation is an epigenetic phenomenon, which refers to processes that alter a phenotype without involving changes in the DNA sequence. By exploiting the difference in the DNA methylation status between mother and fetus, one can successfully detect and analyze fetal nucleic acid in a background of maternal nucleic acid.

The present inventors provides novel genomic polynucleotides that are differentially methylated between the fetal DNA from the fetus (e.g., from the placenta) and the maternal DNA from the mother, for example from peripheral blood cells. This discovery thus provides a new approach for distinguishing fetal and maternal genomic DNA and new methods for accurately quantifying fetal nucleic which may be used for non-invasive prenatal diagnosis.

Methodology

Practicing the invention utilizes routine techniques in the field of molecular biology. Basic texts disclosing the general methods of use in the invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, Tetrahedron Lett. 22: 1859-1862 (1981), using an automated synthesizer, as described in Van Devanter et. al., Nucleic Acids Res. 12: 6159-6168 (1984). Purification of oligonucleotides is performed using any art-recognized strategy, e.g., native acrylamide gel electrophoresis or anion-exchange high performance liquid chromatography (HPLC) as described in Pearson & Reanier, J. Chrom. 255: 137-149 (1983).

Acquisition of Blood Samples and Extraction of DNA

The present invention relates to separating, enriching and analyzing fetal DNA found in maternal blood as a non-invasive means to detect the presence and/or to monitor the progress of a pregnancy-associated condition or disorder. Thus, the first steps of practicing the invention are to obtain a blood sample from a pregnant woman and extract DNA from the sample.

A. Acquisition of Blood Samples

A blood sample is obtained from a pregnant woman at a gestational age suitable for testing using a method of the present invention. The suitable gestational age may vary depending on the disorder tested, as discussed below. Collection of blood from a woman is performed in accordance with the standard protocol hospitals or clinics generally follow. An appropriate amount of peripheral blood, e.g., typically between 5-50 ml, is collected and may be stored according to standard procedure prior to further preparation. Blood samples may be collected, stored or transported in a manner known to the person of ordinary skill in the art to minimize degradation or the quality of nucleic acid present in the sample.

B. Preparation of Blood Samples

The analysis of fetal DNA found in maternal blood according to the present invention may be performed using, e.g., the whole blood, serum, or plasma. The methods for preparing serum or plasma from maternal blood are well known among those of skill in the art. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

C. Extraction of DNA

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

In some embodiments, the sample may first be enriched or relatively enriched for fetal nucleic acid by one or more methods. For example, the discrimination of fetal and maternal DNA can be performed using the compositions and processes of the present invention alone or in combination with other discriminating factors. Examples of these factors include, but are not limited to, single nucleotide differences between chromosome X and Y, chromosome Y-specific sequences, polymorphisms located elsewhere in the genome, size differences between fetal and maternal DNA and differences in methylation pattern between maternal and fetal tissues.

Other methods for enriching a sample for a particular species of nucleic acid are described in PCT Patent Application Number PCT/U.S.07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, maternal nucleic acid is selectively removed (either partially, substantially, almost completely or completely) from the sample.

Methylation Specific Separation of Nucleic Acid

The methods provided herein offer an alternative approach for the enrichment of fetal DNA based on the methylation-specific separation of differentially methylated DNA. It has recently been discovered that many genes involved in developmental regulation are controlled through epigenetics in embryonic stem cells. Consequently, multiple genes can be expected to show differential DNA methylation between nucleic acid of fetal origin and maternal origin. Once these regions are identified, a technique to capture methylated DNA can be used to specifically enrich fetal DNA. For identification of differentially methylated regions, a novel approach was used to capture methylated DNA. This approach uses a protein, in which the methyl binding domain of MBD2 is fused to the Fc fragment of an antibody (MBD-FC) (Gebhard C, Schwarzfischer L, Pham TH, Schilling E, Klug M, Andreesen R, Rehli M (2006) Genomewide profiling of CpG methylation identifies novel targets of aberrant hypermethylation in myeloid leukemia. Cancer Res 66:6118-6128). This fusion protein has several advantages over conventional methylation specific antibodies. The MBD-FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC on the other hand binds all DNA molecules regardless of their methylation status. The strength of this protein—DNA interaction is defined by the level of DNA methylation. After binding genomic DNA, eluate solutions of increasing salt concentrations can be used to fractionate non-methylated and methylated DNA allowing for a more controlled separation (Gebhard C, Schwarzfischer L, Pham TH, Andreesen R, Mackensen A, Rehli M (2006) Rapid and sensitive detection of CpG-methylation using methyl-binding (MB)-PCR. Nucleic Acids Res 34:e82). Consequently this method, called Methyl-CpG immunoprecipitation (MCIP), cannot only enrich, but also fractionate genomic DNA according to methylation level, which is particularly helpful when the unmethylated DNA fraction should be investigated as well.

Methylation Sensitive Restriction Enzyme Digestion

The invention also provides compositions and processes for determining the amount of fetal nucleic acid from a maternal sample. The invention allows for the enrichment of fetal nucleic acid regions in a maternal sample by selectively digesting nucleic acid from said maternal sample with an enzyme that selectively and completely or substantially digests the maternal nucleic acid to enrich the sample for at least one fetal nucleic acid region. Preferably, the digestion efficiency is greater than about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Following enrichment, the amount of fetal nucleic acid can be determined by quantitative methods that do not require polymorphic sequences or bisulfite treatment, thereby, offering a solution that works equally well for female fetuses and across different ethnicities and preserves the low copy number fetal nucleic acid present in the sample.

For example, there are methyl-sensitive enzymes that preferentially or substantially cleave or digest at their DNA recognition sequence if it is non-methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated.

Methyl-sensitive enzymes that digest unmethylated DNA suitable for use in methods of the invention include, but are not limited to, HpaII, HhaI, MaeII, BstUI and AciI. An enzyme that can be used is HpaII that cuts only the unmethylated sequence CCGG. Another enzyme that can be used is HhaI that cuts only the unmethylated sequence GCGC. Both enzymes are available from New England BioLabs®, Inc. Combinations of two or more methyl-sensitive enzymes that digest only unmethylated DNA can also be used. Suitable enzymes that digest only methylated DNA include, but are not limited to, Dpnl, which cuts at a recognition sequence GATC, and McrBC, which belongs to the family of AAA-.sup.+proteins and cuts DNA containing modified cytosines and cuts at recognition site 5' . . . Pu.sup.mC(N.sub.40-3000) Pu.sup.mC . . . 3' (New England BioLabs, Inc., Beverly, Mass.).

Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al., Molecular Biology: A laboratory Approach, Cold Spring Harbor, N.Y. 1989) provide a general description of methods for using restriction enzymes and other enzymes. Enzymes often are used under conditions that will enable cleavage of the maternal DNA with about 95%-100% efficiency, preferably with about 98%-100% efficiency.

Other Methods for Methylation Analysis

Various methylation analysis procedures are known in the art, and can be used in conjunction with the present invention. These assays allow for determination of the methylation state of one or a plurality of CpG islands within a DNA sequence. In addition, the methods maybe used to quantify methylated nucleic acid. Such assays involve, among other techniques, DNA sequencing of bisulfite-treated DNA, PCR (for sequence-specific amplification), Southern blot analysis, and use of methylation-sensitive restriction enzymes.

Genomic sequencing is a technique that has been simplified for analysis of DNA methylation patterns and 5-methylcytosine distribution by using bisulfite treatment (Frommer et al., Proc. Natl. Acad. Sci. USA 89:1827-1831, 1992). Additionally, restriction enzyme digestion of PCR products amplified from bisulfite-converted DNA may be used, e.g., the method described by Sadri & Hornsby (Nucl. Acids Res. 24:5058-5059, 1996), or COBRA (Combined Bisulfite Restriction Analysis) (Xiong & Laird, Nucleic Acids Res. 25:2532-2534, 1997). COBRA analysis is a quantitative methylation assay useful for determining DNA methylation levels at specific gene loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the interested CpG islands, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

The MethyLight™ assay is a high-throughput quantitative methylation assay that utilizes fluorescence-based real-time PCR (TaqMan.®.) technology that requires no further manipulations after the PCR step (Eads et al., Cancer Res. 59:2302-2306, 1999). Briefly, the MethyLight.™. process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight process can by used with a "TaqMan" probe in the amplification process. For example, double-stranded genomic DNA is treated with sodium bisulfite and subjected to one of two sets of PCR reactions using TaqMan.®. probes; e.g., with either biased primers and TaqMan.®. probe, or unbiased primers and TaqMan.®. probe. The TaqMan.®. probe is dual-labeled with fluorescent "reporter" and "quencher" molecules, and is designed to be specific for a relatively high GC content region so that it melts out at about 10.degree. C. higher temperature in the PCR cycle than the forward or reverse primers. This allows the TaqMan.®. probe to remain fully hybridized during the PCR annealing/extension step. As the Taq polymerase enzymatically synthesizes a new strand during PCR, it will eventually reach the annealed TaqMan.®. probe. The Taq polymerase 5' to 3' endonuclease activity will then displace the TaqMan.®. probe by digesting it to release the fluorescent reporter molecule for quantitative detection of its now unquenched signal using a real-time fluorescent detection system.

Typical reagents (e.g., as might be found in a typical MethyLight.™.-based kit) for MethyLight.™. analysis may include, but are not limited to: PCR primers for specific gene (or methylation-altered DNA sequence or CpG island); TaqMan.®. probes; optimized PCR buffers and deoxynucleotides; and Taq polymerase.

The Ms-SNuPE technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997).

Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

MSP (methylation-specific PCR) allows for assessing the methylation status of virtually any group of CpG sites within a CpG island, independent of the use of methylation-sensitive restriction enzymes (Herman et al. Proc. Nat. Acad. Sci. USA 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus umethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

The MCA technique is a method that can be used to screen for altered methylation patterns in genomic DNA, and to isolate specific sequences associated with these changes (Toyota et al., Cancer Res. 59:2307-12, 1999). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Another method for analyzing methylation sites is a primer extension assay, including an optimized PCR amplification reaction that produces amplified targets for subsequent primer extension genotyping analysis using mass spectrometry. The assay can also be done in multiplex. This method (particularly as it relates to genotyping single nucleotide polymorphisms) is described in detail in PCT publication WO05012578A1 and US publication US20050079521A1. For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Four additional methods for DNA methylation analysis include restriction landmark genomic scanning (RLGS, Costello et al., 2000), methylation-sensitive-representational difference analysis (MS-RDA), methylation-specific AP-PCR (MS-AP-PCR) and methyl-CpG binding domain column/segregation of partly melted molecules (MBD/SPM).

Additional methylation analysis methods that may be used in conjunction with the present invention are described in the following papers: Laird, P. W. Nature Reviews Cancer 3, 253-266 (2003); Biotechniques; Uhlmann, K. et al. Electrophoresis 23:4072-4079 (2002)-PyroMeth; Colella et al. Biotechniques. 2003 July; 35(1):146-50; Dupont J M, Tost J, Jammes H, and Gut I G. Anal Biochem, October 2004; 333 (1): 119-27; and Tooke N and Pettersson M. IVDT. November 2004; 41.

Polynucleotide Sequence Amplification and Determination

Following separation of nucleic acid in a methylation-differential manner, the nucleic acid may be subjected to sequence-based analysis. Furthermore, once it is determined that one particular genomic sequence of fetal origin is hypermethylated or hypomethylated compared to the maternal counterpart, the amount of this fetal genomic sequence can be determined. Subsequently, this amount can be compared to a standard control value and serve as an indication for the potential of certain pregnancy-associated disorder.

A. Amplification of Nucleotide Sequences

In many instances, it is desirable to amplify a nucleic acid sequence of the invention using any of several nucleic acid amplification procedures which are well known in the art (listed above and described in greater detail below). Specifically, nucleic acid amplification is the enzymatic synthesis of nucleic acid amplicons (copies) which contain a sequence that is complementary to a nucleic acid sequence being amplified. Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., PCR Protocols: A Guide to Methods and Applications, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a polynucleotide sequence is typically used in practicing the present invention, one of skill in the art will recognize that the amplification of a genomic sequence found in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular genomic sequence of the invention, which represents a particular methylation pattern, or to quantitatively determine the amount of this particular genomic sequence in the maternal blood. For a review of branched-DNA signal amplification for direct quantitation of nucleic acid sequences in clinical samples, see Nolte, Adv. Clin. Chem. 33:201-235, 1998.

The compositions and processes of the invention are also particularly useful when practiced with digital PCR. Digital PCR was first developed by Kalinina and colleagues (Kalinina et al., "Nanoliter scale PCR with TaqMan detection." Nucleic Acids Research. 25; 1999-2004, (1997)) and further developed by Vogelstein and Kinzler (Digital PCR. Proc Natl Acad Sci USA. 96; 9236-41, (1999)). The application of digital PCR for use with fetal diagnostics was first described by Cantor et al. (PCT Patent Publication No. WO05023091A2) and subsequently described by Quake et al. (US Patent Publication No. US 20070202525), which are both hereby incorporated by reference. Digital PCR takes advantage of nucleic acid (DNA, cDNA or RNA) amplification on a single molecule level, and offers a highly sensitive method for quantifying low copy number nucleic acid. Fluidigm® Corporation offers systems for the digital analysis of nucleic acids.

B. Determination of Polynucleotide Sequences

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes in a polynucleotide sequence for practicing the methods of the present invention include but are not limited to mass spectrometry, primer extension, polynucleotide hybridization, real-time PCR, and electrophoresis.

Use of a primer extension reaction also can be applied in methods of the invention. A primer extension reaction operates, for example, by discriminating the SNP alleles by the incorporation of deoxynucleotides and/or dideoxynucleotides to a primer extension primer which hybridizes to a region adjacent to the SNP site. The primer is extended with a polymerase. The primer extended SNP can be detected physically by mass spectrometry or by a tagging moiety such as biotin. As the SNP site is only extended by a complementary deoxynucleotide or dideoxynucleotide that is either tagged by a specific label or generates a primer extension product with a specific mass, the SNP alleles can be discriminated and quantified.

Reverse transcribed and amplified nucleic acids may be modified nucleic acids. Modified nucleic acids can include nucleotide analogs, and in certain embodiments include a detectable label and/or a capture agent. Examples of detectable labels include without limitation fluorophores, radioisotopes, colormetric agents, light emitting agents, chemiluminescent agents, light scattering agents, enzymes and the like. Examples of capture agents include without limitation an agent from a binding pair selected from antibody/antigen, antibody/antibody, antibody/antibody fragment, antibody/antibody receptor, antibody/protein A or protein G, hapten/anti-hapten, biotin/avidin, biotin/streptavidin, folic acid/ folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) pairs, and the like. Modified nucleic acids having a capture agent can be immobilized to a solid support in certain embodiments Mass spectrometry is a particularly effective method for the detection of a polynucleotide of the invention, for example a PCR amplicon, a primer extension product or a detector probe that is cleaved from a target nucleic acid. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. For a review of genotyping methods using Sequenom® standard iPLEX™ assay and MassARRAY® technology, see Jurinke, C., Oeth, P., van den Boom, D., "MALDI-TOF mass spectrometry: a versatile tool for high-performance DNA analysis." Mol. Biotechnol. 26, 147-164 (2004); and Oeth, P. et al., "iPLEX™ Assay: Increased Plexing Efficiency and Flexibility for MassARRAY® System through single base primer extension with mass-modified Terminators." SEQUENOM Application Note (2005), both of which are hereby incorporated by reference. For a review of detecting and quantifying target nucleic using cleavable detector probes that are cleaved during the amplification process and detected by mass spectrometry, see U.S. patent application Ser. No. 11/950,395, which was filed Dec. 4, 2007, and is hereby incorporated by reference.

Sequencing technologies are improving in terms of throughput and cost. Sequencing technologies, such as that achievable on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT.™.) technology of Pacific Biosciences, and nanopore sequencing (Soni G V and Meller A. 2007 Clin Chem 53: 1996-2001), allow the sequencing of many nucleic acid molecules isolated from a specimen at high orders of multiplexing in a parallel fashion (Dear Brief Funct Genomic Proteomic 2003; 1: 397-416).

Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing. Nucleotide sequence species, amplification nucleic acid species and detectable products generated there from can be considered a "study nucleic acid" for purposes of analyzing a nucleotide sequence by such sequence analysis platforms.

Sequencing by ligation is a nucleic acid sequencing method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated primer, preparing the primer for another round of ligation. In some embodiments primers may be labeled with more than one fluorescent label (e.g., 1 fluorescent label, 2, 3, or 4 fluorescent labels).

An example of a system that can be used by a person of ordinary skill based on sequencing by ligation generally involves the following steps. Clonal bead populations can be prepared in emulsion microreactors containing study nucleic acid ("template"), amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes competes for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag. Such a system can be used to exponentially amplify amplification products generated by a process described herein, e.g., by ligating a heterologous nucleic acid to the first amplification product generated by a process described herein and performing emulsion amplification using the same or a different solid support originally used to generate the first amplification product. Such a system also may be used to analyze amplification products directly generated by a process described herein by bypassing an exponential amplification process and directly sorting the solid supports described herein on the glass slide.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination.

An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., "Single-molecule PCR using water-in-oil emulsion;" Journal of Biotechnology 102: 117-124 (2003)). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., U.S. Pat. No. 7,169,314; Braslaysky et al., PNAS 100(7): 3960-3964 (2003)). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer—released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer—released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known to the person of ordinary skill (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons sometimes are performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis is facilitated by sequence analysis apparatus and components known to the person of ordinary skill in the art.

Methods provided herein allow for high-throughput detection of nucleic acid species in a plurality of nucleic acids (e.g., nucleotide sequence species, amplified nucleic acid species and detectable products generated from the foregoing). Multiplexing refers to the simultaneous detection of more than one nucleic acid species. General methods for performing multiplexed reactions in conjunction with mass spectrometry, are known (see, e.g., U.S. Pat. Nos. 6,043,031, 5,547,835 and International PCT application No. WO 97/37041). Multiplexing provides an advantage that a plurality of nucleic acid species (e.g., some having different sequence variations) can be identified in as few as a single mass spectrum, as compared to having to perform a separate mass spectrometry analysis for each individual target nucleic acid species. Methods provided herein lend themselves to high-throughput, highly-automated processes for analyzing sequence variations with high speed and accuracy, in some embodiments. In some embodiments, methods herein may be multiplexed at high levels in a single reaction.

In certain embodiments, the number of nucleic acid species multiplexed include, without limitation, about 1 to about 500 (e.g., about 1-3,3-5, 5-7,7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501).

Design methods for achieving resolved mass spectra with multiplexed assays can include primer and oligonucleotide design methods and reaction design methods. See, for example, the multiplex schemes provided in Tables X and Y. For primer and oligonucleotide design in multiplexed assays, the same general guidelines for primer design applies for uniplexed reactions, such as avoiding false priming and primer dimers, only more primers are involved for multiplex reactions. For mass spectrometry applications, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. In some embodiments multiplex analysis may be adapted to mass spectrometric detection of chromosome abnormalities, for example. In certain embodiments multiplex analysis may be adapted to various single nucleotide or nanopore based sequencing methods described herein. Commercially produced micro-reaction chambers or devices or arrays or chips may be used to facilitate multiplex analysis, and are commercially available.

Detection of Fetal Aneuploidy

For the detection of fetal aneuploidies, some methods rely on measuring the ratio between maternally and paternally inherited alleles. However, the ability to quantify chromosomal changes is impaired by the maternal contribution of cell free nucleic acids, which makes it necessary to deplete the sample from maternal DNA prior to measurement. Promising approaches take advantage of the different size distribution of fetal and maternal DNA or measure RNA that is exclusively expressed by the fetus (see for example, U.S. patent application Ser. No. 11/384,128, which published as US20060252071 and is hereby incorporated by reference). Assuming fetal DNA makes up only about 5% of all cell free DNA in the maternal plasma, there is a decrease of the ratio difference from 1.6% to only about 1.2% between a trisomy sample and a healthy control. Consequently, reliable detection of allele ratio changes requires enriching the fetal fraction of cell free DNA, for example, using the compositions and methods of the present invention.

Some methods rely on measuring the ratio of maternal to paternally inherited alleles to detect fetal chromosomal aneuploidies from maternal plasma. A diploid set yields a 1:1 ratio while trisomies can be detected as a 2:1 ratio. Detection of this difference is impaired by statistical sampling due to the low abundance of fetal DNA, presence of excess maternal DNA in the plasma sample and variability of the measurement technique. The latter is addressed by using methods with high measurement precision, like digital PCR or mass spectrometry. Enriching the fetal fraction of cell free DNA in a sample is currently achieved by either depleting maternal DNA through size exclusion or focusing on fetal-specific nucleic acids, like fetal-expressed RNA. Another differentiating feature of fetal DNA is its DNA methylation pattern. Thus, provided herein are novel compositions and methods for accurately quantifying fetal nucleic acid based on differential methylation between a fetus and mother. The methods rely on sensitive absolute copy number analysis to quantify the fetal nucleic acid portion of a maternal sample, thereby allowing for the prenatal detection of fetal traits. The methods of the invention have identified approximately 3000 CpG rich regions in the genome that are differentially methylated between maternal and fetal DNA. The selected regions showed highly conserved differential methylation across all measured samples. In addition the set of regions is enriched for genes important in developmental regulation, indicating that epigenetic regulation of these areas is a biologically relevant and consistent process (see Table 3). Enrichment of fetal DNA can now be achieved by using our MBD-FC protein to capture all cell free DNA and then elute the highly methylated DNA fraction with high salt concentrations. Using the low salt eluate fractions, the MBD-FC is equally capable of enriching non-methylated fetal DNA.

The present invention provides 63 confirmed genomic regions on chromosomes 13, 18 and 21 with low maternal and high fetal methylation levels. After capturing these regions, SNPs can be used to determine the aforementioned allele ratios. When high frequency SNPs are used around 10 markers have to be measured to achieve a high confidence of finding at least one SNP where the parents have opposite homozygote genotypes and the child has a heterozygote genotype.

In an embodiment, a method for chromosomal abnormality detection is provided that utilizes absolute copy number quantification. A diploid chromosome set will show the same number of copies for differentially methylated regions across all chromosomes, but, for example, a trisomy 21 sample would show 1.5 times more copies for differentially methylated regions on chromosome 21. Normalization of the genomic DNA amounts for a diploid chromosome set can be achieved by using unaltered autosomes as reference (also provided herein—see Table 1B). Comparable to other approaches, a single marker is less likely to be sufficient for detection of this difference, because the overall copy numbers are low. Typically there are approximately 100 to 200 copies of fetal DNA from 1 ml of maternal plasma at 10 to 12 weeks of gestation. However, the methods of the present invention offer a redundancy of detectable markers that enables highly reliable discrimination of diploid versus aneuploid chromosome sets.

Data Processing and Identifying Presence or Absence of a Chromosome Abnormality

The term "detection" of a chromosome abnormality as used herein refers to identification of an imbalance of chromosomes by processing data arising from detecting sets of amplified nucleic acid species, nucleotide sequence species, or a detectable product generated from the foregoing (collectively "detectable product"). Any suitable detection device and method can be used to distinguish one or more sets of detectable products, as addressed herein. An outcome pertaining to the presence or absence of a chromosome abnormality can be expressed in any suitable form, including, without limitation, probability (e.g., odds ratio, p-value), likelihood, percentage, value over a threshold, or risk factor, associated with the presence of a chromosome abnormality for a subject or sample. An outcome may be provided with one or more of sensitivity, specificity, standard deviation, coefficient of variation (CV) and/or confidence level, or combinations of the foregoing, in certain embodiments.

Detection of a chromosome abnormality based on one or more sets of detectable products may be identified based on one or more calculated variables, including, but not limited to, sensitivity, specificity, standard deviation, coefficient of variation (CV), a threshold, confidence level, score, probability and/or a combination thereof. In some embodiments, (i) the number of sets selected for a diagnostic method, and/or (ii) the particular nucleotide sequence species of each set selected for a diagnostic method, is determined in part or in full according to one or more of such calculated variables.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome determined by an algorithm is not due to chance) in certain embodiments is expressed as a p-value, and sometimes the p-value is about 0.05 or less (e.g., about 0.05, 0.04, 0.03, 0.02 or 0.01, or less than 0.01 (e.g., about 0.001 or less, about 0.0001 or less, about 0.00001 or less, about 0.000001 or less)).

For example, scoring or a score may refer to calculating the probability that a particular chromosome abnormality is actually present or absent in a subject/sample. The value of a score may be used to determine for example the variation, difference, or ratio of amplified nucleic detectable product that may correspond to the actual chromosome abnormality. For example, calculating a positive score from detectable products can lead to an identification of a chromosome abnormality, which is particularly relevant to analysis of single samples.

In certain embodiments, simulated (or simulation) data can aid data processing for example by training an algorithm or testing an algorithm. Simulated data may for instance involve hypothetical various samples of different concentrations of fetal and maternal nucleic acid in serum, plasma and the like. Simulated data may be based on what might be expected from a real population or may be skewed to test an algorithm and/or to assign a correct classification based on a simulated data set. Simulated data also is referred to herein as "virtual" data. Fetal/maternal contributions within a sample can be simulated as a table or array of numbers (for example, as a list of peaks corresponding to the mass signals of cleavage products of a reference biomolecule or amplified nucleic acid sequence), as a mass spectrum, as a pattern of bands on a gel, or as a representation of any technique that measures mass distribution. Simulations can be performed in most instances by a computer program. One possible step in using a simulated data set is to evaluate the confidence of the identified results, i.e. how well the selected positives/negatives match the sample and whether there are additional variations. A common approach is to calculate the probability value (p-value) which estimates the probability of a random sample having better score than the selected one. As p-value calculations can be prohibitive in certain circumstances, an empirical model may be assessed, in which it is assumed that at least one sample matches a reference sample (with or without resolved variations). Alternatively other distributions such as Poisson distribution can be used to describe the probability distribution.

In certain embodiments, an algorithm can assign a confidence value to the true positives, true negatives, false positives and false negatives calculated. The assignment of a likelihood of the occurrence of a chromosome abnormality can also be based on a certain probability model.

Simulated data often is generated in an in silico process. As used herein, the term "in silico" refers to research and experiments performed using a computer. In silico methods include, but are not limited to, molecular modeling studies, karyotyping, genetic calculations, biomolecular docking experiments, and virtual representations of molecular structures and/or processes, such as molecular interactions.

As used herein, a "data processing routine" refers to a process, that can be embodied in software, that determines the biological significance of acquired data (i.e., the ultimate results of an assay). For example, a data processing routine can determine the amount of each nucleotide sequence species based upon the data collected. A data processing routine also may control an instrument and/or a data collection routine based upon results determined. A data processing routine and a data collection routine often are integrated and provide feedback to operate data acquisition by the instrument, and hence provide assay-based judging methods provided herein.

As used herein, software refers to computer readable program instructions that, when executed by a computer, perform computer operations. Typically, software is provided on a program product containing program instructions recorded on a computer readable medium, including, but not limited to, magnetic media including floppy disks, hard disks, and magnetic tape; and optical media including CD-ROM discs, DVD discs, magneto-optical discs, and other such media on which the program instructions can be recorded.

Different methods of predicting abnormality or normality can produce different types of results. For any given prediction, there are four possible types of outcomes: true positive, true negative, false positive, or false negative. The term "true positive" as used herein refers to a subject correctly diagnosed as having a chromosome abnormality. The term "false positive" as used herein refers to a subject wrongly identified as having a chromosome abnormality. The term "true negative" as used herein refers to a subject correctly identified as not having a chromosome abnormality. The term "false negative" as used herein refers to a subject wrongly identified as not having a chromosome abnormality. Two measures of performance for any given method can be calculated based on the ratios of these occurrences: (i) a sensitivity value, the fraction of predicted positives that are correctly identified as being positives (e.g., the fraction of nucleotide sequence sets correctly identified by level comparison detection/determination as indicative of chromosome abnormality, relative to all nucleotide sequence sets identified as such, correctly or incorrectly), thereby reflecting the accuracy of the results in detecting the chromosome abnormality; and (ii) a specificity value, the fraction of predicted negatives correctly identified as being negative (the fraction of nucleotide sequence sets correctly identified by level comparison detection/determination as indicative of chromosomal normality, relative to all nucleotide sequence sets identified as such, correctly or incorrectly), thereby reflecting accuracy of the results in detecting the chromosome abnormality.

EXAMPLES

The following examples are provided by way of illustration only and not by way of limitation. Those of skill in the art will readily recognize a variety of non-critical parameters that could be changed or modified to yield essentially the same or similar results.

In Example 1 below, the Applicants used a new fusion protein that captures methylated DNA in combination with CpG Island array to identify genomic regions that are differentially methylated between fetal placenta tissue and maternal blood. A stringent statistical approach was used to only select regions which show little variation between the samples, and hence suggest an underlying biological mechanism. Eighty-five differentially methylated genomic regions predominantly located on chromosomes 13, 18 and 21 were validated. For this validation, a quantitative mass spectrometry based approach was used that interrogated 261 PCR amplicons covering these 85 regions. The results are in very good concordance (95% confirmation), proving the feasibility of the approach.

Next, the Applicants provide an innovative approach for aneuploidy testing, which relies on the measurement of absolute copy numbers rather than allele ratios.

Example 1

Figure 3:
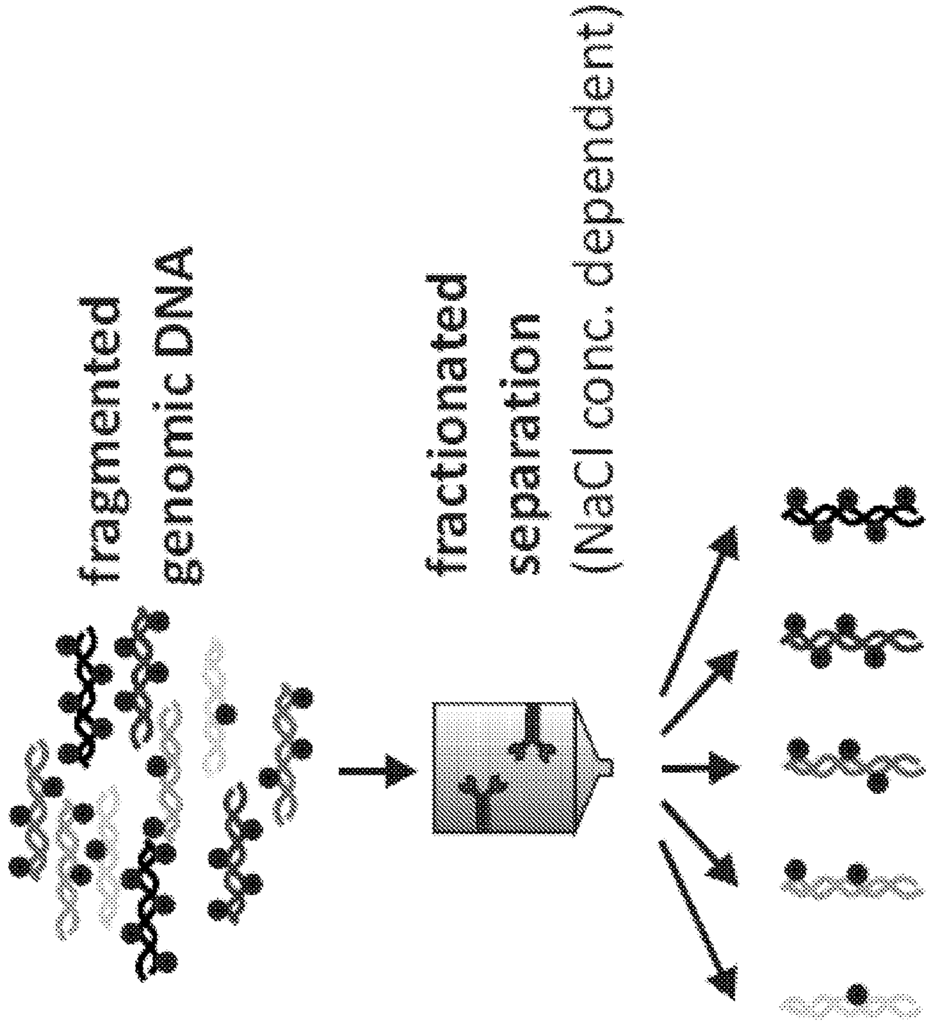
FIG. 3: Shows the methyl binding domain of MBD-FC binds all DNA molecules regardless of their methylation status. The strength of this protein/DNA interaction is defined by the level of DNA methylation. After binding genomic DNA, eluate solutions of increasing salt concentrations can be used to fractionate non-methylated and methylated DNA allowing for a controlled separation.
Figure 4:
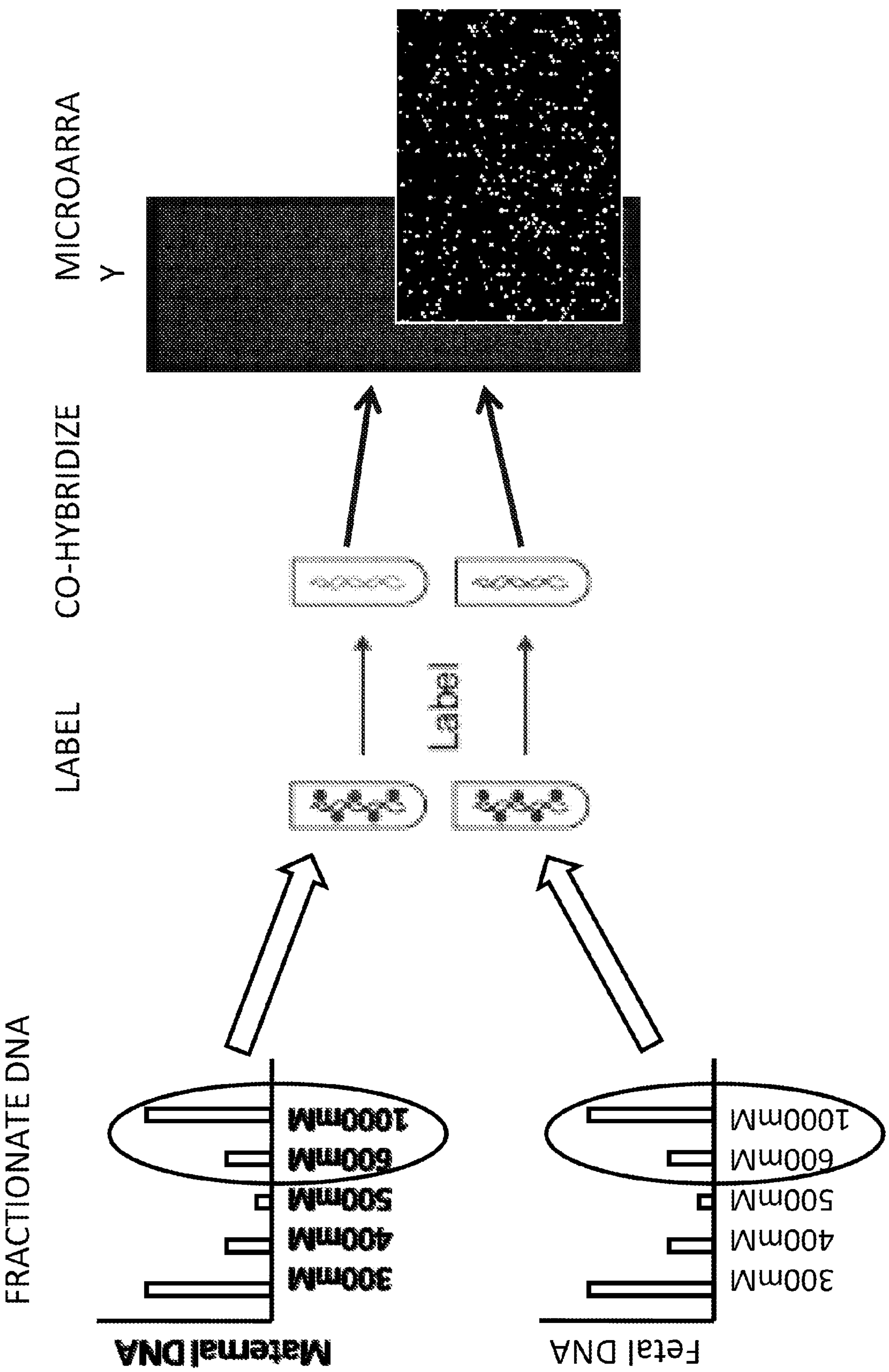
FIG. 4: Shows the experiment used to identify differentially methylated DNA from a fetus and mother using the recombinant MBD-Fc protein and a microarray.
Figure 5:
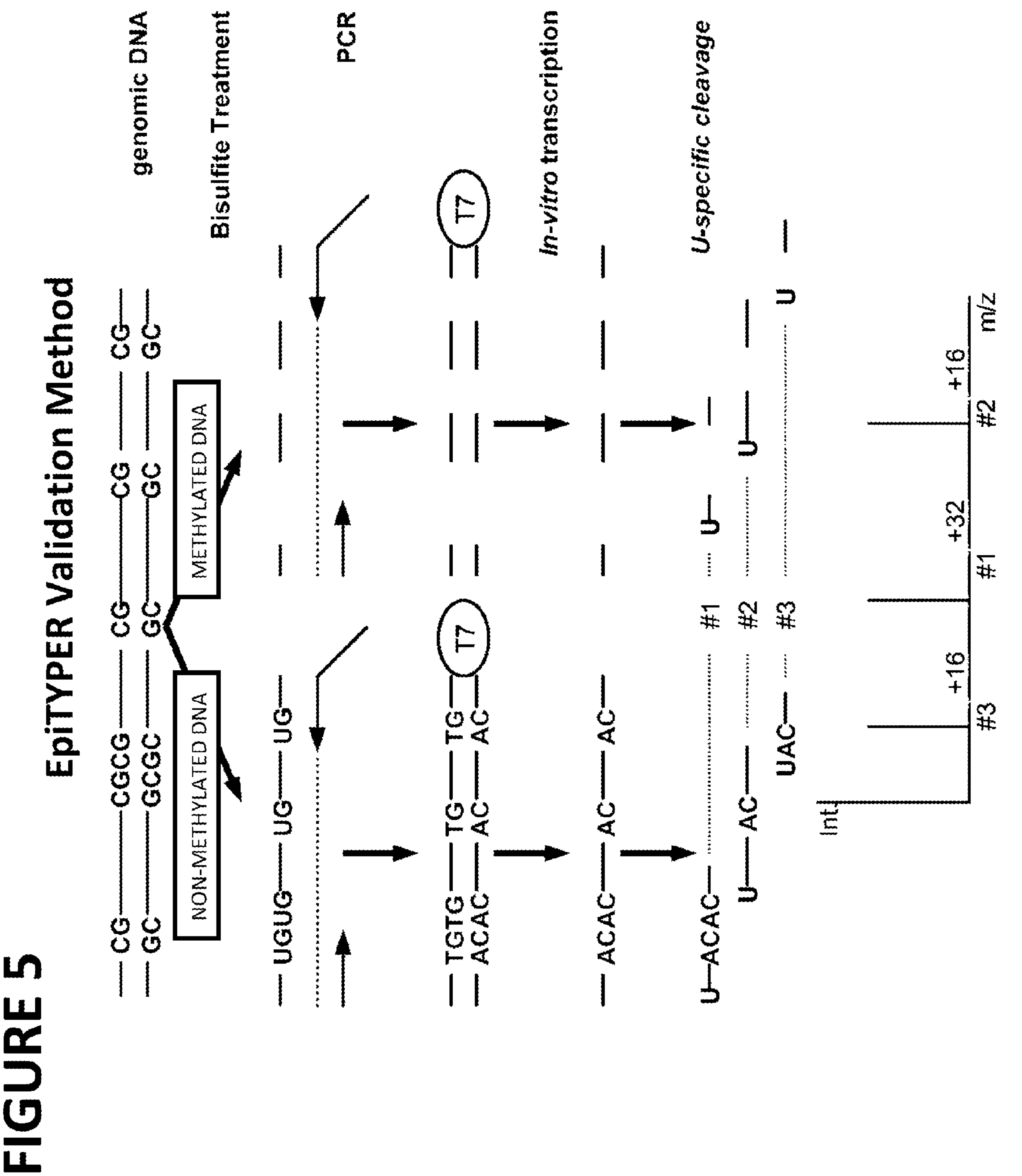
FIG. 5: Shows typical results generated by Sequenom® EpiTYPER™ method, which was used to validate the results generated from the experiment illustrated in FIG. 4.
Figure 6:
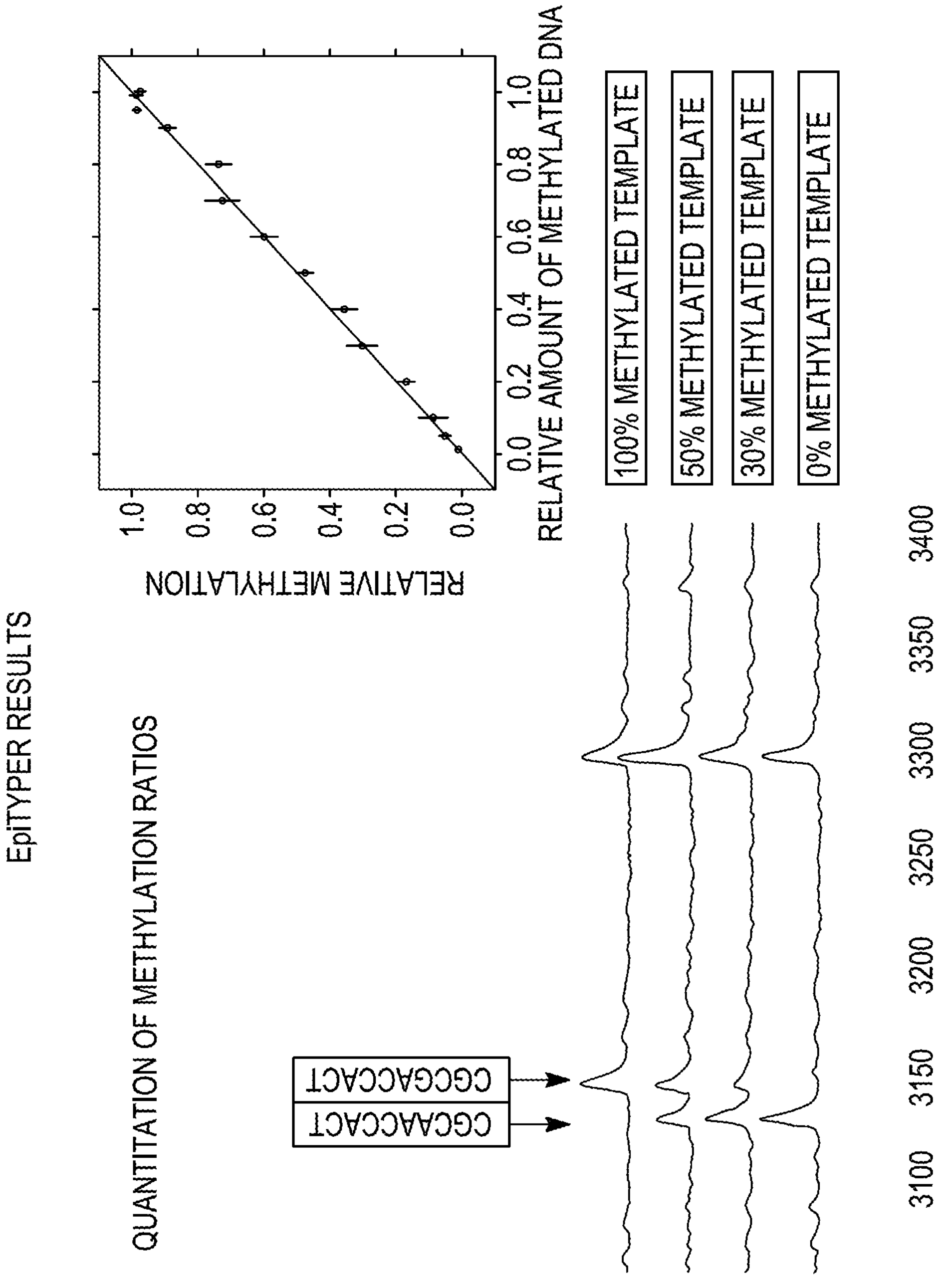
FIG. 6: Shows the correlation between the log ratios derived from microarray analysis (x axis) and methylation differences obtained by EpiTYPER analysis (y axis). Each data point represents the average for one region across all measured samples. The microarray analysis is comparative in nature because the highly methylated fraction of the maternal DNA is hybridized together with the highly methylated fraction of placenta DNA. Positive values indicate higher methylation of the placenta samples. In mass spectrometry each samples is measured individually. We first calculated difference in methylation by subtracting the maternal methylation values from the placenta methylation value. To compare the results with the microarray data we calculated the average of the differences for all maternal/placenta DNA pairs.

In the below Example, ten paired maternal and placental DNA samples were used to identify differentially methylated regions. These results were validated using a mass spectrometry-based quantitative methylation assay. First, genomic DNA from maternal buffy coat and corresponding placental tissue was first extracted. Next the MBD-FC was used to capture the methylated fraction of each DNA sample. See FIGS. 1-3. The two tissue fractions were labeled with different fluorescent dyes and hybridized to an Agilent® CpG Island microarray. See FIG. 4. This was done to identify differentially methylated regions that could be utilized for prenatal diagnoses. Therefore, two criteria were employed to select genomic regions as potential enrichment markers: the observed methylation difference had to be present in all tested sample pairs, and the region had to be more than 200 by in length.

DNA Preparation and Fragmentation

Genomic DNA (gDNA) from maternal buffy coat and placental tissue was prepared using the QIAamp DNA Mini Kit™ and QIAamp DNA Blood Mini Kit™, respectively, from Qiagen® (Hilden, Germany). For MCIp, gDNA was quantified using the Nanoprop ND 1000™ spectrophotometer (Thermo Fisher®, Waltham, Mass., USA). Ultrasonication of 2.5 μg DNA in 500 μl TE buffer to a mean fragment size of 300-500 by was carried out with the Branson Digital Sonifier 450™ (Danbury, Conn., USA) using the following settings: amplitude 20%, sonication time 110 seconds, pulse on/pulse off time 1.4/0.6 seconds. Fragment range was monitored using gel electrophoresis.

Methyl-CpG Immunoprecipitation

Per sample, 56 μg purified MBD-Fc protein and 150 μl of Protein A Sepharose 4 Fast Flow beads (Amersham Biosciences®, Piscataway, N.J., USA) were rotated in 15 ml TBS overnight at 4° C. Then, the MBD-Fc beads (150 μl/assay) were transferred and dispersed in to 2 ml Ultrafree-CL centrifugal filter devices (Millipore®, Billerica, Mass., USA) and spin-washed three times with Buffer A (20 mM Tris-HCl, pH8.0, 2 mM $MgCl_2$, 0.5 mM EDTA 300 mM NaCl, 0.1% NP-40). Sonicated DNA (2 μg) was added to the washed MBD-Fc beads in 2 ml Buffer A and rotated for 3 hours at 4° C. Beads were centrifuged to recover unbound DNA fragments (300 mM fraction) and subsequently washed twice with 600 μl of buffers containing increasing NaCl concentrations (400, 500, 550, 600, and 1000 mM). The flow through of each wash step was collected in separate tubes and desalted using a MinElute PCR Purification Kit™ (Qiagen®). In parallel, 200 ng sonicated input DNA was processed as a control using the MinElute PCR Purification Kit™ (Qiagen®).

Microarray Handling and Analysis

To generate fluorescently labeled DNA for microarray hybridization, the 600 mM and 1M NaCl fractions (enriched methylated DNA) for each sample were combined and labeled with either Alexa Fluor 555-aha-dCTP (maternal) or Alexa Fluor 647-aha-dCTP (placental) using the BioPrime Total Genomic Labeling System™ (Invitrogen®, Carlsbad, Calif., USA). The labeling reaction was carried out according to the manufacturer's manual. The differently labeled genomic DNA fragments of matched maternal/placental pairs were combined to a final volume of 80 μl, supplemented with 50 μg Cot-1 DNA (Invitrogen®), 52 μl of Agilent 10× blocking reagent (Agilent Technologies®, Santa Clara, Calif., USA), 78 μl of deionized formamide, and 260 μl Agilent 2× hybridization buffer. The samples were heated to 95° C. for 3 min, mixed, and subsequently incubated at 37° C. for 30 min. Hybridization on Agilent CpG Island Microarray Kit™ was then carried out at 67° C. for 40 hours using an Agilent SureHyb™ chamber and an Agilent hybridization oven. Slides were washed in Wash I (6×SSPE, 0.005% N-lauroylsarcosine) at room temperature for 5 min and in Wash II (0.06×SSPE) at 37° C. for an additional 5 min. Next, the slides were submerged in acetonitrile and Agilent Ozone Protection Solution™, respectively, for 30 seconds. Images were scanned immediately and analyzed using an Agilent DNA Microarray Scanner™. Microarray images were processed using Feature Extraction Software v9.5 and the standard CGH protocol.

Bisulfite Treatment

Genomic DNA sodium bisulfite conversion was performed using EZ-96 DNA Methylation Kit™ (ZymoResearch, Orange County, CA). The manufacturer's protocol was followed using 1 ug of genomic DNA and the alternative conversion protocol (a two temperature DNA denaturation).

Quantitative Methylation Analysis

Sequenom's MassARRAY® System was used to perform quantitative methylation analysis. This system utilizes matrix-assisted laser desorption ionization time-of-flight (MALDI-TOF) mass spectrometry in combination with RNA base specific cleavage (Sequenom® MassCLEAVE™). A detectable pattern is then analyzed for methylation status. PCR primers were designed using Sequenom® EpiDESIGNER™ (www.epidesigner.com). A total of 261 amplicons, covering 85 target regions, were used for validation (median amplification length=367 bp, min=108, max=500; median number of CpG's per amplicon=23, min=4, max=65). For each reverse primer, an additional T7 promoter tag for in-vivo transcription was added, as well as a 10mer tag on the forward primer to adjust for melting temperature differences. The MassCLEAVE™ biochemistry was performed as previously described (Ehrich M, et al. (2005) Quantitative high-throughput analysis of DNA methylation patterns by base specific cleavage and mass spectrometry. *Proc Natl Acad Sci USA* 102:15785-15790). Mass spectra were acquired using a MassARRAY™ Compact MALDI-TOF (Sequenom®, San Diego) and methylation ratios were generated by the EpiTYPER™ software v1.0 (Sequenom®, San Diego).

Statistical Analysis

All statistical calculations were performed using the R statistical software package (www.r-project.org). First, the array probes were grouped based on their genomic location. Subsequent probes that were less than 1000 by apart were grouped together. To identify differentially methylated regions, a control sample was used as reference. In the control sample, the methylated fraction of a blood derived control DNA was hybridized against itself. Ideally this sample should show log ratios of the two color channels around 0. However because of the variability in hybridization behavior, the probes show a mean log ratio of 0.02 and a standard deviation of 0.18. Next the log ratios observed in our samples were compared to the control sample. A two way, paired t-test was used to test the NULL hypothesis that the groups are identical. Groups that contained less than 4 probes were excluded from the analysis. For groups including four or five probes, all probes were used in a paired t-test. For Groups with six or more probes, a sliding window test consisting of five probes at a time was used, whereby the window was moved by one probe increments. Each test sample was compared to the control sample and the p-values were recorded. Genomic regions were selected as being differentially methylated if eight out of ten samples showed a p value<0.01, or if six out of ten samples showed a p value<0.001. The genomic regions were classified as being not differentially methylated when the group showed less than eight samples with a p value<0.01 and less than six samples with a p value<0.001. Samples that didn't fall in either category were excluded from the analysis. For a subset of genomic regions that have been identified as differentially methylated, the results were confirmed using quantitative methylation analysis.

The Go analysis was performed using the online GOstat tool (http://gostat.wehi.edu.au/cgibin/-goStat.pl). P values were calculated using Fisher's exact test.

Microarray-Based Marker Discovery Results

To identify differentially methylated regions a standard sample was used, in which the methylated DNA fraction of monocytes was hybridized against itself. This standard provided a reference for the variability of fluorescent measurements in a genomic region. Differentially methylated regions were then identified by comparing the log ratios of each of the ten placental/maternal samples against this standard. Because the goal of this study was to identify markers that allow the reliable separation of maternal and fetal DNA, the target selection was limited to genes that showed a stable, consistent methylation difference over a contiguous stretch of genomic DNA. This focused the analysis on genomic regions where multiple probes indicated differential methylation. The selection was also limited to target regions where all samples showed differential methylation, excluding those with strong inter-individual differences. Two of the samples showed generally lower log ratios in the microarray analysis. Because a paired test was used for target selection, this did not negatively impact the results. Based on these selection criteria, 3043 genomic regions were identified that were differentially methylated between maternal and fetal DNA. 21778 regions did not show a methylation difference. No inter-chromosomal bias in the distribution of differentially methylated regions was observed. The differentially methylated regions were located next to or within 2159 known genes. The majority of differentially methylated regions are located in the promoter area (18%) and inside the coding region (68%), while only few regions are located downstream of the gene (7%) or at the transition from promoter to coding region (7%). Regions that showed no differential methylation showed a similar distribution for promoter (13%) and downstream (5%) locations, but the fraction of regions located in the transition of promoter to coding region was higher (39%) and the fraction inside the coding region was lower (43%).

It has been shown in embryonic stem cells (ES) that genes targeted by the polycomb repressive complex 2 (PRC2) are enriched for genes regulating development (Lee T I, et al. (2006) Control of developmental regulators by Polycomb in human embryonic stem cells. *Cell* 125:301-313). It has also been shown that differentially methylated genes are enriched for genes targeted by PRC2 in many cancer types (Ehrich M, et al. (2008) Cytosine methylation profiling of cancer cell lines. *Proc Natl Acad Sci USA* 105:4844-48). The set of genes identified as differentially methylated in this study is also enriched for genes targeted by PRC2 (p-value<0.001, odds ratio=3.6, 95% CI for odds ratio=3.1-4.2). A GO analysis of the set of differentially methylated genes reveals that this set is significantly enriched for functions important during development. Six out of the ten most enriched functions include developmental or morphogenic processes [anatomical structure morphogenesis (GO:0009653, p value=0), developmental process (GO:0032502, p value=0), multicellular organismal development (GO:0007275, p value=0), developmental of an organ (GO:0048513, p value=0), system development (GO:0048731, p value=0) and development of an anatomical structure (GO:0048856, p value=0)].

Validation using Sequenom® EpiTYPER™

Figure 7:
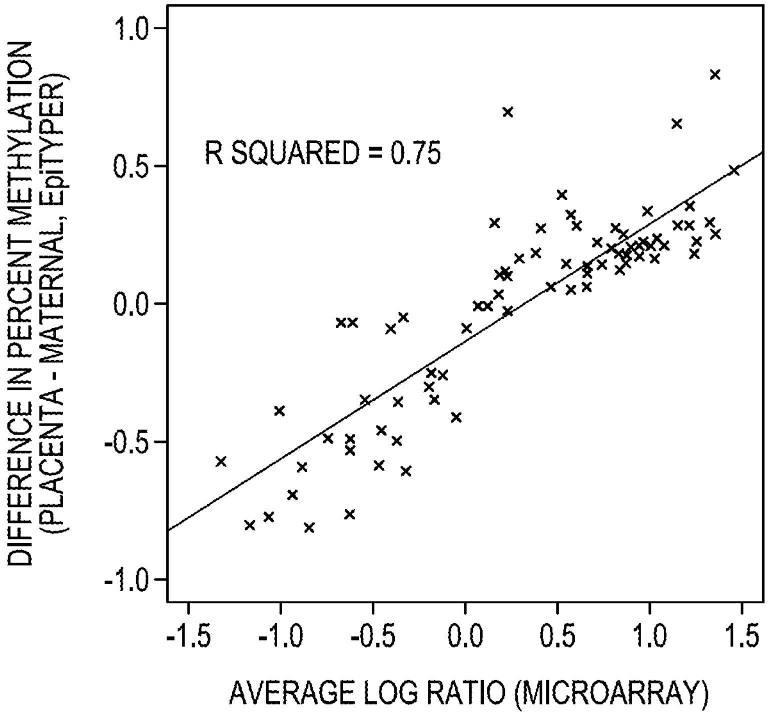
FIG. 7 shows a correlation between microarray and EpiTYPER™ results.

To validate the microarray findings, 63 regions from chromosomes 13, 18 and 21 and an additional 26 regions from other autosomes were selected for confirmation by a different technology. Sequenom EpiTYPER™ technology was used to quantitatively measure DNA methylation in maternal and placental samples. For an explanation of the EpiTYPER™ methods, see Ehrich M, Nelson M R, Stanssens P, Zabeau M, Liloglou T, Xinarianos G, Cantor C R, Field J K, van den Boom D (2005) Quantitative high-throughput analysis of DNA methylation patterns by base specific cleavage and mass spectrometry. Proc Natl Acad Sci USA 102:15785-15790). For each individual CpG site in a target region the average methylation value across all maternal DNA samples and across all placenta samples was calculated. The difference between average maternal and placenta methylation was then compared to the microarray results. The results from the two technologies were in good concordance (see FIG. 7). For 85 target regions the quantitative results confirm the microarray results (95% confirmation rate). For 4 target regions, all located on chromosome 18, the results could not be confirmed. The reason for this discrepancy is currently unclear.

In contrast to microarrays, which focus on identification of methylation differences, the quantitative measurement of DNA methylation allowed analysis of absolute methylation values. In the validation set of 85 confirmed differentially methylated regions, a subset of 26 regions is more methylated in the maternal DNA sample and 59 regions are more methylated in the placental sample (see Table 1A). Interestingly, genes that are hypomethylated in the placental samples tend to show larger methylation differences than genes that are hypermethylated in the placental sample (median methylation difference for hypomethylated genes=39%, for hypermethylated genes=20%).

Example 2

Figure 10:
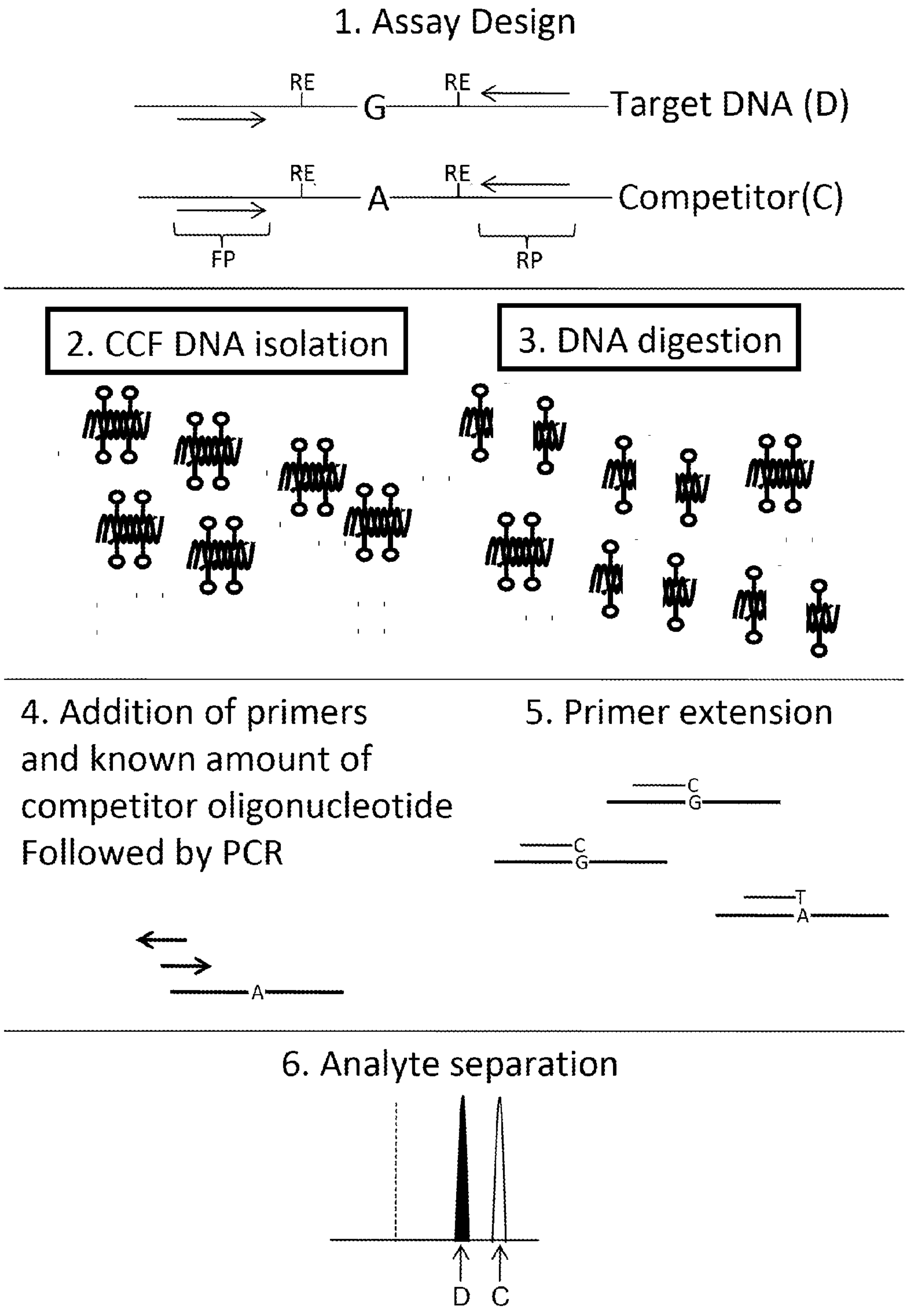
FIG. 10: Shows one embodiment of the Fetal Quantifier Method. Maternal nucleic acid is selectively digested and the remaining fetal nucleic acid is quantified using a competitor of known concentration. In this schema, the analyte is separated and quantified by a mass spectromter.
Figure 11:
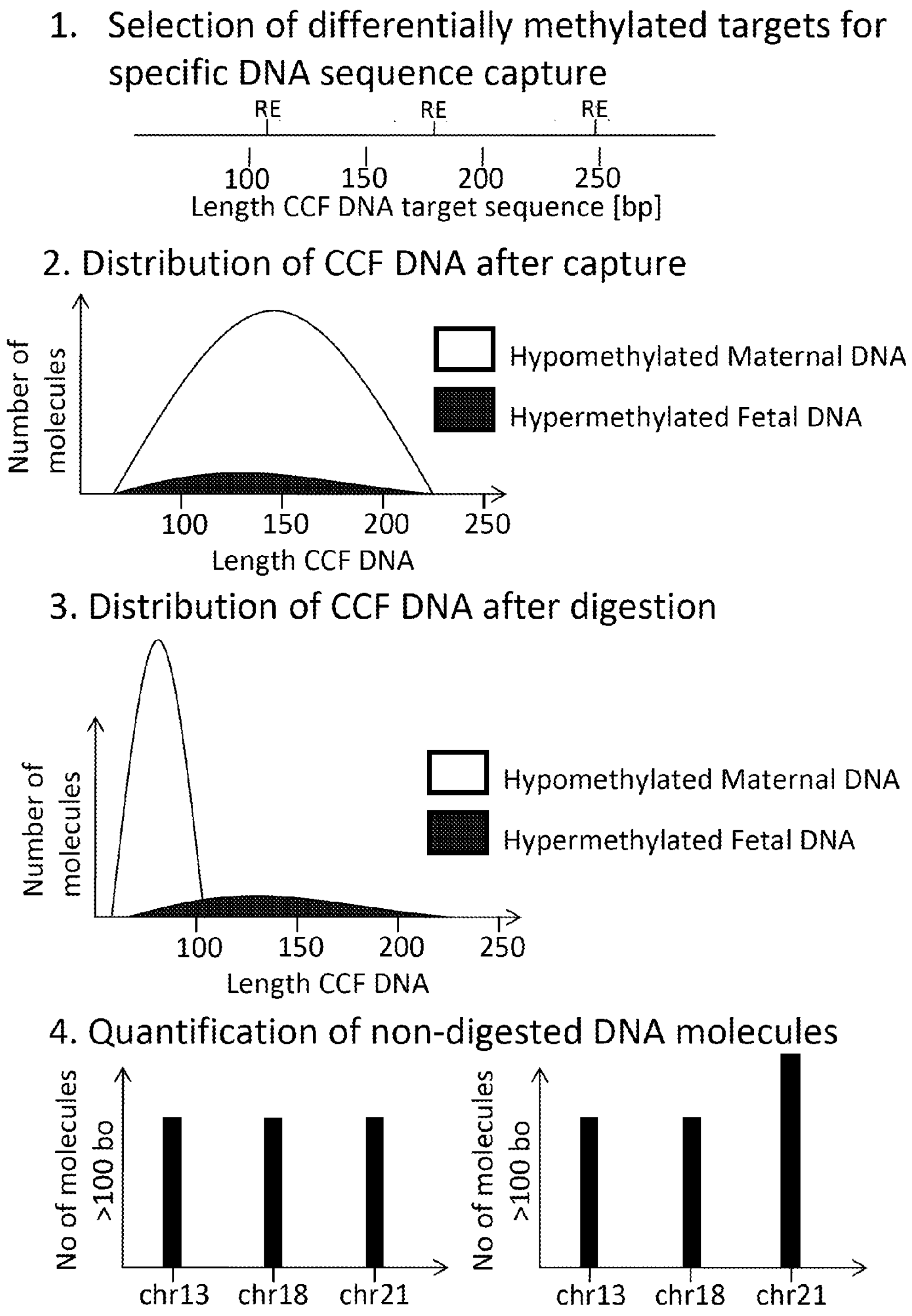
FIG. 11: Shows one embodiment of the Methylation-Based Fetal Diagnostic Method. Maternal nucleic acid is selectively digested and the remaining fetal nucleic acid is quantified for three different chromosomes (13, 18 and 21). Parts 2 and 3 of the Figure illustrate the size distribution of the nucleic acid in the sample before and after digestion. The amplification reactions can be size-specific (e.g., greater than 100 base pair amplicons) such that they favor the longer, non-digested fetal nucleic acid over the digested maternal nucleic acid, thereby further enriching the fetal nucleic acid. The spectra at the bottom of the Figure show an increased amount of chromosome 21 fetal nucleic acid indicative of trisomy 21.

Example 2 describes a non-invasive approach for detecting the amount of fetal nucleic acid present in a maternal sample (herein referred to as the "Fetal Quantifier Method"), which may be used to detect or confirm fetal traits (e.g., fetal sex of RhD compatibility), or diagnose chromosomal abnormalities such as Trisomy 21 (both of which are herein referred to as the "Methylation-Based Fetal Diagnostic Method"). FIG. 10 shows one embodiment of the Fetal Quantifier Method, and FIG. 11 shows one embodiment of the Methylation-Based Fetal Diagnostic Method. Both processes use fetal DNA obtained from a maternal sample. The sample comprises maternal and fetal nucleic acid that is differentially methylated. For example, the sample may be maternal plasma or serum. Fetal DNA comprises approximately 2-30% of the total DNA in maternal plasma. The actual amount of fetal contribution to the total nucleic acid present in a sample varies from pregnancy to pregnancy and can change based on a number of factors, including, but not limited to, gestational age, the mother's health and the fetus' health.

As described herein, the technical challenge posed by analysis of fetal DNA in maternal plasma lies in the need to be able to discriminate the fetal DNA from the co-existing background maternal DNA. The methods of the present invention exploit such differences, for example, the differential methylation that is observed between fetal and maternal DNA, as a means to enrich for the relatively small percentage of fetal DNA present in a sample from the mother. The non-invasive nature of the approach provides a major advantage over conventional methods of prenatal diagnosis such as, amniocentesis, chronic villus sampling and cordocentesis, which are associated with a small but finite risk of fetal loss. Also, because the method is not dependent on fetal cells being in any particular cell phase, the method provides a rapid detection means to determine the presence and also the nature of the chromosomal abnormality. Further, the approach is sex-independent (i.e., does not require the presence of a Y-chromosome) and polymorphic-independent (i.e., an allelic ratio is not determined). Thus, the compositions and methods of the invention represent improved universal, noninvasive approaches for accurately determining the amount of fetal nucleic acid present in a maternal sample.

Assay Design and Advantages

There is a need for accurate detection and quantification of fetal DNA isolated noninvasively from a maternal sample. The present invention takes advantage of the presence of circulating, cell free fetal nucleic acid (ccfDNA) in maternal plasma or serum. In order to be commercially and clinically practical, the methods of the invention should only consume a small portion of the limited available fetal DNA. For example, less than 50%, 40%, 30%, 25%, 20%, 15%, 10%, 5% or less of the sample. Further, the approach should preferably be developed in a multiplex assay format in which one or more (preferably all) of the following assays are included:

- Assays for the detection of total amount of genomic equivalents present in the sample, i.e., assays recognizing both maternal and fetal DNA species;
- Assays for the detection of fetal DNA isolated from a male pregnancy, i.e., sequences specific for chromosome Y;
- Assays specific for regions identified as differentially methylated between the fetus and mother; or
- Assays specific for regions known to be hypomethylated in all tissues to be investigated, which can serve as a control for restriction efficiency.

Other features of the assay may include one or more of the following:

- For each assay, a target-specific, competitor oligonucleotide that is identical, or substantially identical, to the target sequence apart from a distinguishable feature of the competitor, such as a difference in one or more nucleotides relative to the target sequence. This oligonucleotide when added into the PCR reaction will be co-amplified with the target and a ratio obtained between these two PCR amplicons will indicate the number of target specific DNA sequences (e.g., fetal DNA from a specific locus) present in the maternal sample.
- The amplicon lengths should preferably be of similar length in order not to skew the amplification towards the shorter fragments. However, as long as the amplification efficiency is about equal, different lengths may be used.
- Differentially methylated targets can be selected from Tables 1A-1C or from any other targets known to be differentially methylated between mother and fetus.

These targets can be hypomethylated in DNA isolated from non-pregnant women and hypermethylated in samples obtained from fetal samples. These assays will serve as controls for the restriction efficiency.

The results obtained from the different assays can be used to quantify one or more of the following:

Total number of amplifiable genomes present in the sample (total amount of genomic equivalents);

The fetal fraction of the amplifiable genomes (fetal concentration or percentage); or Differences in copy number between fetally-derived DNA sequences (for example, between fetal chromosome 21 and a reference chromosome such as chromosome 3).

Examples of Assays Used in the Test

Below is an outline of the reaction steps used to perform a method of the invention, for example, as provided in FIG. 10. This outline is not intended to limit the scope of the invention. Rather it provides one embodiment of the invention using the Sequenom® MassARRAY® technology.

1) DNA isolation from plasma samples.

2) Digestion of the DNA targets using methylation sensitive restriction enzymes (for example, HhaI and HpaII). For each reaction the available DNA was mixed with water to a final volume of 25 ul.

10 ul of a reaction mix consisting of 10 units HhaI, 10 units HpaII and a reaction buffer were added. The sample was incubated at an optimal temperature for the restriction enzymes. HhaI and HpaII digest non-methylated DNA (and will not digest hemi- or completely methylated DNA). Following digestion, the enzymes were denatured using a heating step.

3) Genomic Amplification—PCR was performed in a total volume of 50 ul by adding PCR reagents (Buffer, dNTPs, primers and polymerase). Exemplary PCR and extend primers are provided below. In addition, synthetic competitor oligonucleotide was added at known concentrations.

4) Replicates (optional)—Following PCR the 50 ul reaction was split into 5 ul parallel reactions (replicates) in order to minimize variation introduced during the post PCR steps of the test. Post PCR steps include SAP, primer extension (MassEXTEND® technology), resin treatment, dispensing of spectrochip and MassARRAY.

5) Quantification of the Amplifiable Genomes—Sequenom MassARRAY® technology was used to determine the amount of amplification product for each assay. Following PCR, a single base extension assay was used to interrogate the amplified regions (including the competitor oligonucleotides introduced in step 3). Specific extend primers designed to hybridize directly adjacent to the site of interest were introduced. See extend primers provided below. These DNA oligonucleotides are referred to as iPLEX® MassEXTEND® primers. In the extension reaction, the iPLEX primers were hybridized to the complementary DNA templates and extended with a DNA polymerase. Special termination mixtures that contain different combinations of deoxy- and dideoxynucleotide triphosphates along with enzyme and buffer, directed limited extension of the iPLEX primers. Primer extension occurs until a complementary dideoxynucleotide is incorporated.

The extension reaction generated primer products of varying length, each with a unique molecular weight. As a result, the primer extension products can be simultaneously separated and detected using Matrix Assisted Laser Desorption/Ionization, Time-Of-Flight (MALDI-TOF) mass spectrometry on the MassARRAY® Analyzer Compact. Following this separation and detection, SEQUENOM's proprietary software automatically analyzes the data.

Figure 18:
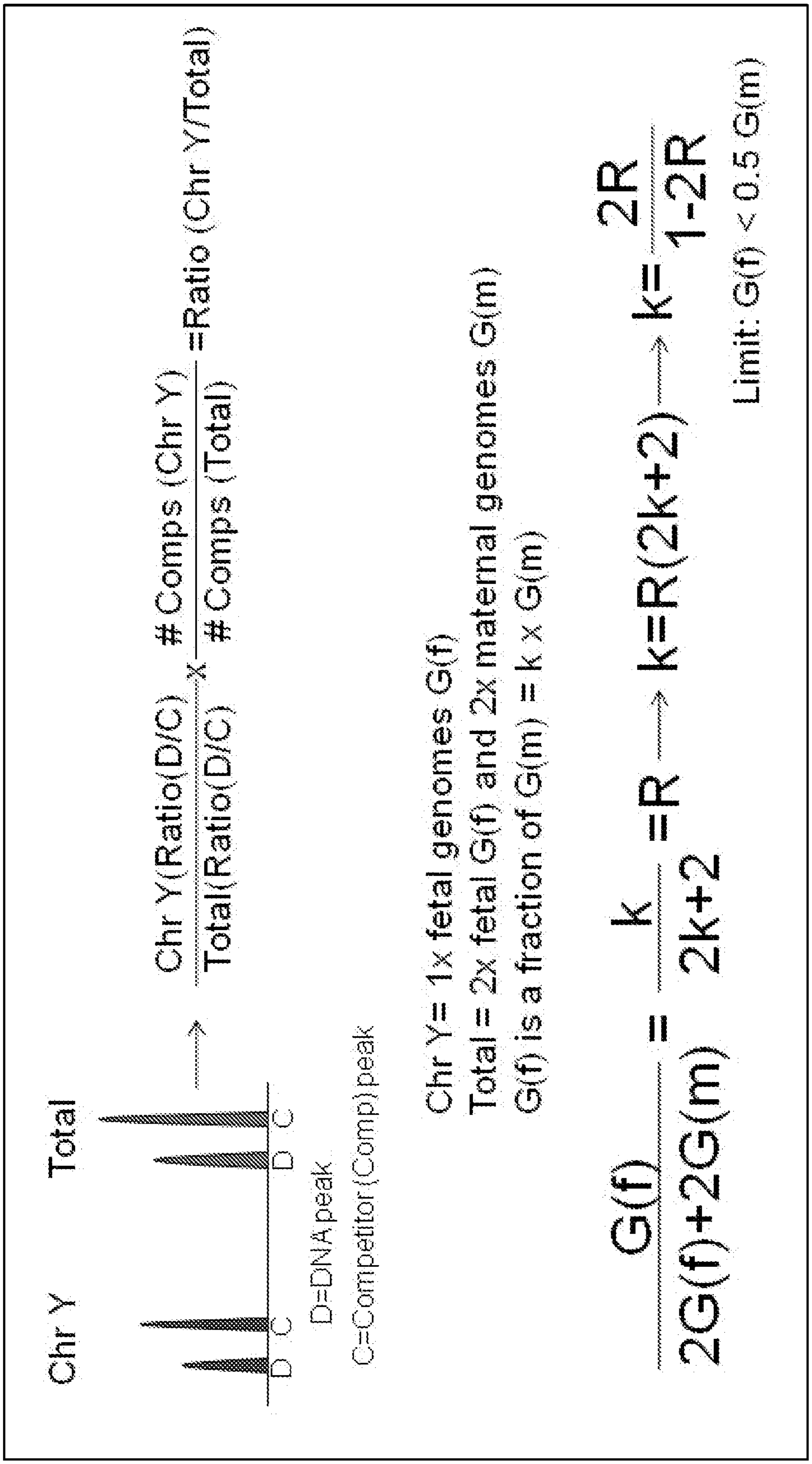
FIG. 18: Provides a specific method for calculating fetal DNA fraction (or concentration) in a sample using the Y-chromosome-specific markers for male pregnancies and the mean of the methylated fraction for all pregnancies (regardless of fetal sex).

6) Calculating the amount and concentration of fetal nucleic acid—Methods for calculating the total amount of genomic equivalents present in the sample, the amount (and concentration) of fetal nucleic acid isolated from a male pregnancy, and the amount (and concentration) of fetal nucleic based on differentially methylated targets are provided below and in FIGS. 18 and 19.

The above protocol can be used to perform one or more of the assays described below. In addition to the sequences provided immediately below, a multiplex scheme that interrogates multiple targets is provided in Table X below.

1) Assay for the Quantification of the Total Number of Amplifiable Genomic Equivalents in the Sample.

Targets were selected in housekeeping genes not located on the chromosomes 13, 18, 21, X or Y. The targets should be in a single copy gene and not contain any recognition sites for the methylation sensitive restriction enzymes.

Underlined sequences are PCR primer sites, italic is the site for the single base extend primer and bold letter (C) is the nucleotide extended on human DNA ApoE Chromosome 19:45409835-45409922 DNA target sequence with interrogated nucleotide C in bold. All of the chromosome positions provided in this section are from the February 2009 UCSC Genome Build.

GATTGACAGTTTCTCCTTCCCCAGACTGGCCAATCACAG*GCAGGAAGATGAAGGTT*CTGTGGGCTGCGTTGCT
GGTCACATTCCTGGC (SEQ ID NO: 262)

ApoE Forward Primer: 5'-ACGTTGGATG-TTGACAGTTTCTCCTTCCCC (SEQ ID NO: 263)
(Primer contains a 5' 10 bp MassTag separated by a dash)

ApoE Reverse Primer: 5'-ACGTTGGATG-GAATGTGACCAGCAACGCAG (SEQ ID NO: 264)
(Primer contains a 5' 10 bp MassTag separated by a dash)

ApoE Extension Primer: 5'-GCAGGAAGATGAAGGTT [C/T] (SEQ ID NO: 265)
Primer extends C on human DNA targets and T on synthetic DNA targets ApoE synthetic competitor oligonucleotide: 5'-
GATTGACAGTTTCTCCTTCCCCAGACTGGCCAATCACAGGCAGGAAGATGAAGGTTTTGTGGGCTGCGTTGCT
GGTCACATTCCTGGC (SEQ ID NO: 266) (Bold T at position 57 is different from human DNA)

2) Assay for the Quantification of the Total Number of Chromosome Y Sequences in the Sample.

Targets specific for the Y-chromosome were selected, with no similar or paralog sequences elsewhere in the genome. The targets should preferably be in a single copy gene and not contain any recognition sites for the methylation sensitive restriction enzyme(s).

Underlined sequences are PCR primer sites, and italic nucleotide(s) is the site for the single-base extend primer and bold letter (C) is the nucleotide extended on human DNA.

SRY on chrY: 2655628-2655717 (reverse complement)
GAGTTTTGGATAGTAAAATAAGTTTCGAACTCTGGCACC*TTTCAATTTTGTCGCACT*CTCCTTGTTTTTGACAAT
GCAATCATATGCTTC (SEQ ID NO: 267)

SRY Forward Primer: 5'-ACG-TGGATAGTAAAATAAGTTTCGAACTCTG (SEQ ID NO: 268)
(Primer contains a 5' 3 bp MassTag separated by a dash)

SRY Reverse Primer: 5'-GAAGCATATGATTGCATTGTCAAAAAC (SEQ ID NO: 269)

SRY Extension Primer: 5'-aTTTCAATTTTGTCGCACT [C/T] (SEQ ID NO: 270)
Primer extends C on human DNA targets and T on synthetic DNA targets.
5' Lower case "a" is a non-complementary nucleotide SRY synthetic competitor oligonucleotide: 5'-
GAGTTTTGGATAGTAAAATAAGTTTCGAACTCTGGCACCTTTCAATTTTGTCGCACTTTCCTTGTTTTTGACAAT
GCAATCATATGCTTC (SEQ ID NO: 271)

3) Assay for the Quantification of Fetal Methylated DNA Sequences Present in the Sample.

Targets were selected in regions known to be differentially methylated between maternal and fetal DNA. Sequences were selected to contain several restriction sites for methylation sensitive enzymes. For this study the HhaI (GCGC) and HpaII (CCGG) enzymes were used.

Underlined sequences are PCR primer sites, italic is the site for the single base extend primer and bold letter (C) is the nucleotide extended on human DNA, lower case letter are recognition sites for the methylation sensitive restriction enzymes.

TBX3 on chr12: 115124905-115125001
GAACTCCTCTTTGTCTCTGCGTGCccggcgcgc*CCCCCTCccggTGGGTGATAAA*CCCACTCTGgcgccggCCATgcgc
TGGGTGATTAATTTGCGA (SEQ ID NO: 272)

TBX3 Forward Primer: 5'-ACGTTGGATG-TCTTTGTCTCTGCGTGCCC (SEQ ID NO: 273)
(Primer contains a 5' 10 bp MassTag separated by a dash)

TBX3 Reverse Primer: 5'-ACGTTGGATG-TTAATCACCCAGCGCATGGC (SEQ ID NO: 274)
(Primer contains a 5' 10 bp MassTag separated by a dash)

TBX3 Extension Primer: 5'-CCCCTCCCGGTGGGTGATAAA [C/T] (SEQ ID NO: 275)
Primer extends C on human DNA targets and T on synthetic DNA targets.
5' Lower case "a" is a non-complementary nucleotide TBX3 synthetic competitor oligonucleotide: 5'-
GAACTCCTCTTTGTCTCTGCGTGCCCGGCGCGCCCCCCTCCCGGTGGGTGATAAATCCACTCTGGCGCCGGCC
ATGCGCTGGGTGATTAATTTGCGA (SEQ ID NO: 276)

4) Control Assay for the Enzyme Restriction Efficiency.

Targets were selected in regions known not to be methylated in any tissue to be investigated. Sequences were selected to contain no more than one site for each restriction enzyme to be used.

Underlined sequences are PCR primer sites, italic nucleotide(s) represent the site for the single-base extend primer and bold letter (G) is the reverse nucleotide extended on human DNA, lower case letter are recognition sites for the methylation sensitive restriction enzymes.

CACNA1G chr17: 48637892-48637977 (reverse complement)
CCATTGGCCGTCCGCCGTGGCAGTGCGGGCGGGAgcgcAGG*GAGAGAACCACAGCTGGAATCC*GATTCCCAC
CCCAAAACCCAGGA (SEQ ID NO: 277)

Hhal Forward Primer: 5'-ACGTTGGATG-CCATTGGCCGTCCGCCGTG (SEQ ID NO: 278)
(Primer contains a 5' 10 bp MassTag separated by a dash)

Hhal Reverse Primer: 5'-ACGTTGGATG-TCCTGGGTTTTGGGGTGGGAA (SEQ ID NO: 279)
(Primer contains a 5' 10 bp MassTag separated by a dash)

Hhal Extension Primer: 5'-TTCCAGCTGTGGTTCTCTC (SEQ ID NO: 280)

Hhal synthetic competitor oligonucleotide: 5'-
CCATTGGCCGTCCGCCGTGGCAGTGCGGGCGGGAGCGCAGA*GAGAGAACCACAGCTGGAAT*CCGATTCCCA
CCCCAAAACCCAGGA (SEQ ID NO: 281)

Validation Experiments

The sensitivity and accuracy of the present invention was measured using both a model system and clinical samples. In the different samples, a multiplex assay was run that contains 2 assays for total copy number quantification, 3 assays for methylation quantification, 1 assay specific for chromosome Y and 1 digestion control assay. See Table X. Another multiplex scheme with additional assays is provided in7 Table Y.

TABLE X

PCR Primers and Extend Primers

Table X discolses 'First Primer'as SEQ ID NOS 282-288, 'Second Primer'as SEQ ID NOS 289-295, and 'Extend Primer'as SEQ ID NOS 296-302, respectively, in order of appearance.

| Gene ID | * | First Primer | Second Primer | Extend Primer |
|---|---|---|---|---|
| SOX14 | M | ACGTTGGATGACATGGTCGGCCCCACGGAAT | ACGTTGGATGCTCCTTCCTAGTGTGAGAACCG | CAGGTTCCGGGGCTTGGG |
| Hhal_CTRL | D | ACGTTGGATGACCCATTGGCCGTCCGCCGT | ACGTTGGATGTTTTGGGGTGGGAATCGGATT | CGCAGGGAGAGAACCACAG |
| TBX3 | M | ACGTTGGATGGAACTCCTCTTTGTCTCTGCG | ACGTTGGATGTGGCATGGCCGGCGCCAGA | CCCCTCCCGGTGGGTGATAAA |
| SRY | Y | ACGTTGGATGCGCAGCAACGGGACCGCTACA | ACGTTGGCATCTAGGTAGGTCTTTGTAGCCAA | AAAGCTGTAGGACAATCGGGT |
| ALB | T | ACGTTGCGTAGCAACCTGTTACATATTAA | ACGTTGGATCTGAGCAAAGGCAATCAACACCC | CATTTTTCTACATCCTTTGTTT |
| EDG6 | M | ACGTTGGATGCATAGAGGCCCATGATGGTGG | ACGTTGGATGACCTTCTGCCCCTCTACTCCAA | agAAGATCACCAGGCAGAAGAGG |
| RNaseP | T | ACGTTGGATGGTGTGGTCAGCTCTTCCCTT CAT | ACGTTGGCCCACATGTAATGTGTTGAAAAAGCA | ACTTGGAGAACAAAGGACACCGTTA |

TABLE X

Competitor Oligonucleotide Sequence

Table X discloses SEQ ID NOS 303-309, respectively, in order of appearance.

| Gene ID | * | Competitor Oligonucleotide Sequence |
|---|---|---|
| SOX14 | M | GGTCGGCCCCACGGAATCCCGGCTCTGTGTGCGCCCAGGTTCCGGGGCTTGGGTGTTGCCGGTTCTCACACTAGGAAGGAG |
| Hhal_CTRL | D | CCATTGGCCGTCCGCCGTGGCAGTGCGGGCGGGAGCGCAGAGAGAGAACCACAGCTGGAATCCGATTCCCACCCCAAAA |
| TBX3 | M | GAACTCCTCTTTGTCTCTGCGTGCCCGGCGCGCCCCCCTCCCGGTGGGTGATAAATCCACTCTGGCGCCGGCCATGC |
| SRY | Y | GCAGCAACGGGACCGCTACAGCCACTGGACAAAGCCGTAGGACAATCGGGTAACATTGGCTACAAAGACCTACCTAGATGC |
| ALB | T | GCGTAGCAACCTGTTACATATTAAAGTTTTATTATACTACATTTTTCTACATCCTTTGTTTCAGAGTGTTGATTGCCTTTGCTCAGTATCT TCAG |
| EDG6 | M | CCTTCTGCCCCTCTACTCCAAGCGCTACACCCTCTTCTGCCTGGTGATCTTTGCCGGCGTCCTGGCCACCATCATGGGCCTCTATG |
| RNaseP | T | GTGTGGTCAGCTCTTCCCTTCATCACATACTTGGAGAACAAAGGACACCGTTATCCATGCTTTTTCAACACATTACATGTGGG |

TABLE Y

PCR Primers and Extend Primers

Table Y discolses 'First Primer'as SEQ ID NOS 310-319, 'Second Primer'as SEQ ID NOS 320-329, and 'Extend Primer'as SEQ ID NOS 330-339, respectively, in order of appearance.

| Gene ID | * | First Primer | Second Primer | Extend Primer |
|---|---|---|---|---|
| EDG6 | M | ACGTTGGATGTTCTGCCCCTCTACTCCAAG | ACGTTGGATGCATAGAGGCCCATGATGGTG | TTCTGCCTGGTGATCTT |
| RNAseP | T | ACGTTGGATGTCAGCTCTTCCCTTCATCAC | ACGTTGGATGCCTACCTCCCACATGTAATGT | AACAAAGGACACCGTTA |
| ApoE | T | ACGTTGGATGTTGACAGTTTCTCCTTCCCC | ACGTTGGATGGAATGTGACCAGCAACGCAG | GCAGGAAGATGAAGGTT |
| SOX14 | M | ACGTTGGATGCGGTCGGCCCCACGGAAT | ACGTTGGATGCTCCTTCCTAGTGTGAGAACCG | aAGGTTCCGGGGCTTGGG |
| SRY no2 | Y | ACGTGGATAGTAAAATAAGTTTCGAACTCTG | GAAGCATATGATTGCATTGTCAAAAAC | aTTTCAATTTTGTCGCACT |
| SRY no1 | Y | ACGTTGGATGCACAGCTCACCGCAGCAACG | ACGTTGGATGCTAGGTAGGTCTTTGTAGCCAA | AGCTGTAGGACAATCGGGT |
| TBX3 | M | ACGTTGGATGTCTTTGTCTCTGCGTGCCC | ACGTTGGATGTTAATCACCCAGCGCATGGC | CCCTCCCGGTGGGTGATAAA |
| CACNA1G dig CTRL 1 | D | ACGTTGGATGGACTGAGCCCCAGAACTCG | ACGTTGGATGGTGGGTTTGTGCTTTCCACG | AGGGCCGGGGTCTGCGCGTG |

TABLE Y-continued

PCR Primers and Extend Primers
Table Y discolses 'First Primer'as SEQ ID NOS 310-319, 'Second Primer'as SEQ ID NOS 320-329, and 'Extend Primer'as SEQ ID NOS 330-339, respectively, in order of appearance.

| Gene ID | * | First Primer | Second Primer | Extend Primer |
|---|---|---|---|---|
| DAPK1 dig CTRL 2 | D | ACGTTGGATGAAGCCAAGTTTCCCTCCGC | ACGTTGGATGCTTTTGCTTTCCCAGCCAGG | GAGGCACTGCCCGGACAAACC |
| ALB | T | ACGTTAGCGTAGCAACCTGTTACATATTAA | ACGTTGGATGCTGAGCAAAGGCAATCAACA | CATTTTTCTACATCCTTTGTTT |

TABLE Y

Competitor Oligonucleotide Sequence
Table Y discloses SEQ ID NOS 340-349, respectively, in order of appearance.

| Gene ID | * | Competitor |
|---|---|---|
| EDG6 | M | CCTTCTGCCCCTCTACTCCAAGCGCTACACCCTCTTCTGCCTGGTGATCTTTGCCGGCGTCCTGGCCACCATCATGGGCCTCTATG |
| RNAseP | T | GTGTGGTCAGCTCTTCCCTTCATCACATACTTGGAGAACAAAGGACACCGTTATCCATGCTTTTTCAACACATTACATGTGGGAGGTAGG |
| ApoE | T | GATTGACAGTTTCTCCTTCCCCAGACTGGCCAATCACAGGCAGGAAGATGAAGGTTTTGTGGGCTGCGTTGCTGGTCACATTCCTGGC |
| SOX14 | M | AAAACCAGAGATTCGCGGTCGGCCCCACGGAATCCCGGCTCTGTGTGCGCCCAGGTTCCGGGGCTTGGGTGTTGCCGGTTCTCACACTA GGAAGGAGC |
| SRY no2 | Y | GAGTTTTGGATAGTAAAATAAGTTTCGAACTCTGGCACCTTTCAATTTTGTCGCACTTTCCTTGTTTTTGACAATGCAATCATATGCTTC |
| SRY no1 | Y | GCAGCCAGCTCACCGCAGCAACGGGACCGCTACAGCCACTGGACAAAGCTGTAGGACAATCGGGTGACATTGGCTACAAAGACCTAC CTAGATGC |
| TBX3 | M | GAACTCCTCTTTGTCTCTGCGTGCCCGGCGCGCCCCCCTCCCGGTGGGTGATAAATCCACTCTGGCGCCGGCCATGCGCTGGGTGATTA ATTTGCGA |
| CACNA1G dig CTRL 1 | D | GTGGGTTTGTGCTTTCCACGCGTGCACACACACGCGCAGACCCCGGCCCTTGCCCCGCCTACCTCCCCGAGTTCTGGGGCT CAGTC |
| DAPK1 dig CTRL 2 | D | GCGCCAGCTTTTGCTTTCCCAGCCAGGGCGCGGTGAGGTTTGTCCGGGCAGTGCCTCGAGCAACTGGGAAGGCCAAGGCGGAG GGAAAC |
| ALB | T | GCGTAGCAACCTGTTACATATTAAAGTTTTATTATACTACATTTTTCTACATCCTTTGTTTTAGGGTGTTGATTGCCTTTGCTCAGTAT CTTCAGC |

Figure 12:
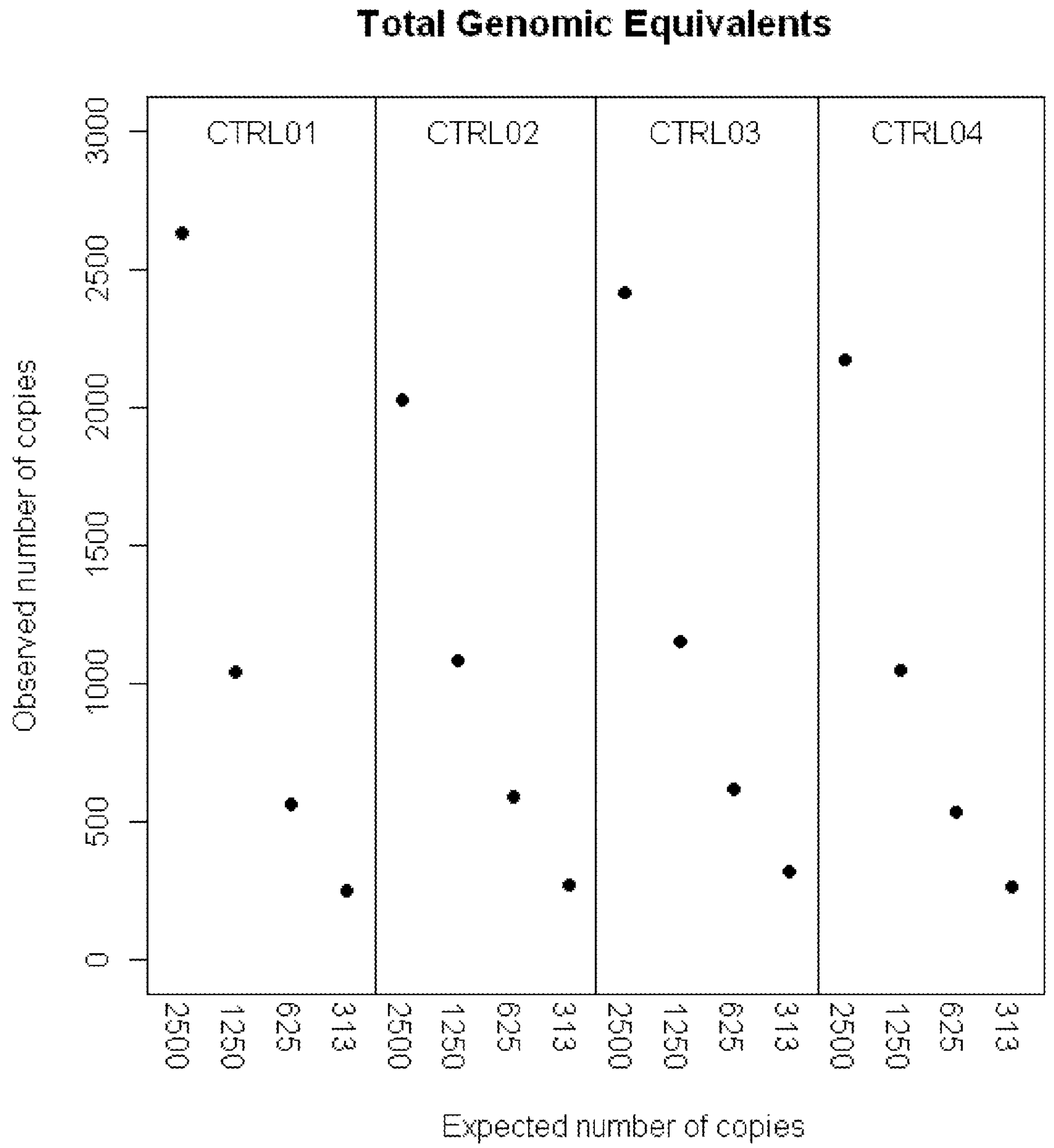
FIG. 12: Shows the total number of amplifiable genomic copies from four different DNA samples isolated from the blood of non-pregnant women. Each sample was diluted to contain approximately 2500, 1250, 625 or 313 copies per reaction. Each measurement was obtained by taking the mean DNA/competitor ratio obtained from two total copy number assays (ALB and RNAseP in Table X). As FIG. 12 shows, the total copy number is accurate and stable across the different samples, thus validating the usefulness of the competitor-based approach.

T = Assay for Total Amount
M = Assay for Methylation quantification
Y = Y-Chromosome Specific Assay
D = Digestion control Model System Using Genomic DNA In order to determine the sensitivity and accuracy of the method when determining the total number of amplifiable genomic copies in a sample, a subset of different DNA samples isolated from the blood of non-pregnant women was tested. Each sample was diluted to contain approximately 2500, 1250, 625 or 313 copies per reaction. The total number of amplifiable genomic copies was obtained by taking the mean DNA/competitor ratio obtained from the three total copy number assays. The results from the four different samples are shown in FIG. 12.

Figure 13A:
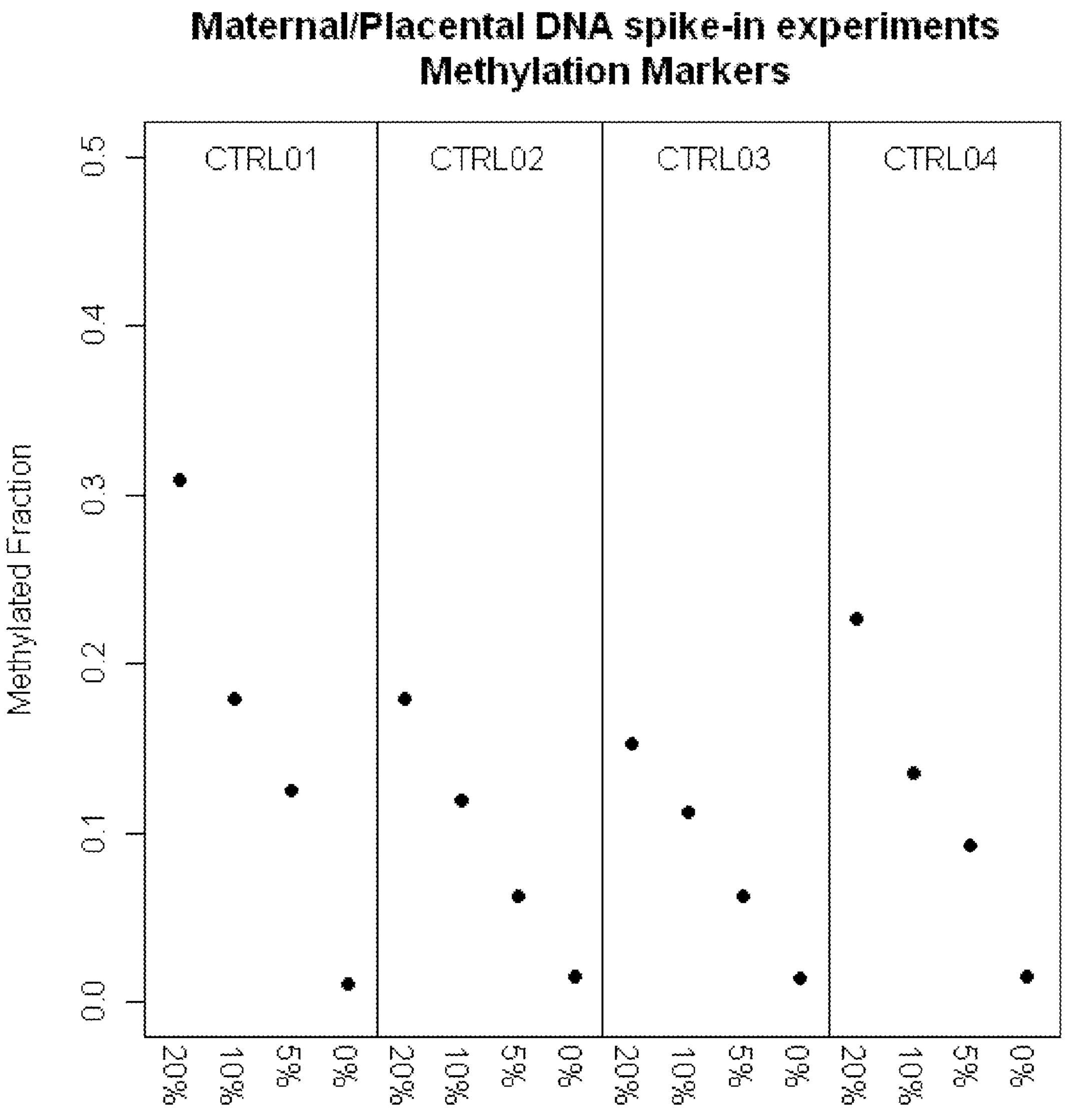
FIGS. 13A and B: A model system was created that contained a constant number of maternal non-methylated DNA with varying amounts of male placental methylated DNA spiked-in. The samples were spiked with male placental amounts ranging from approximately 0 to 25% relative to the maternal non-methylated DNA. The fraction of placental DNA was calculated using the ratios obtained from the methylation assays (FIG. 13A) and the Y-chromosome marker (FIG. 13B) as compared to the total copy number assay. The methylation and Y-chromosome markers are provided in Table X.
Figure 13B:
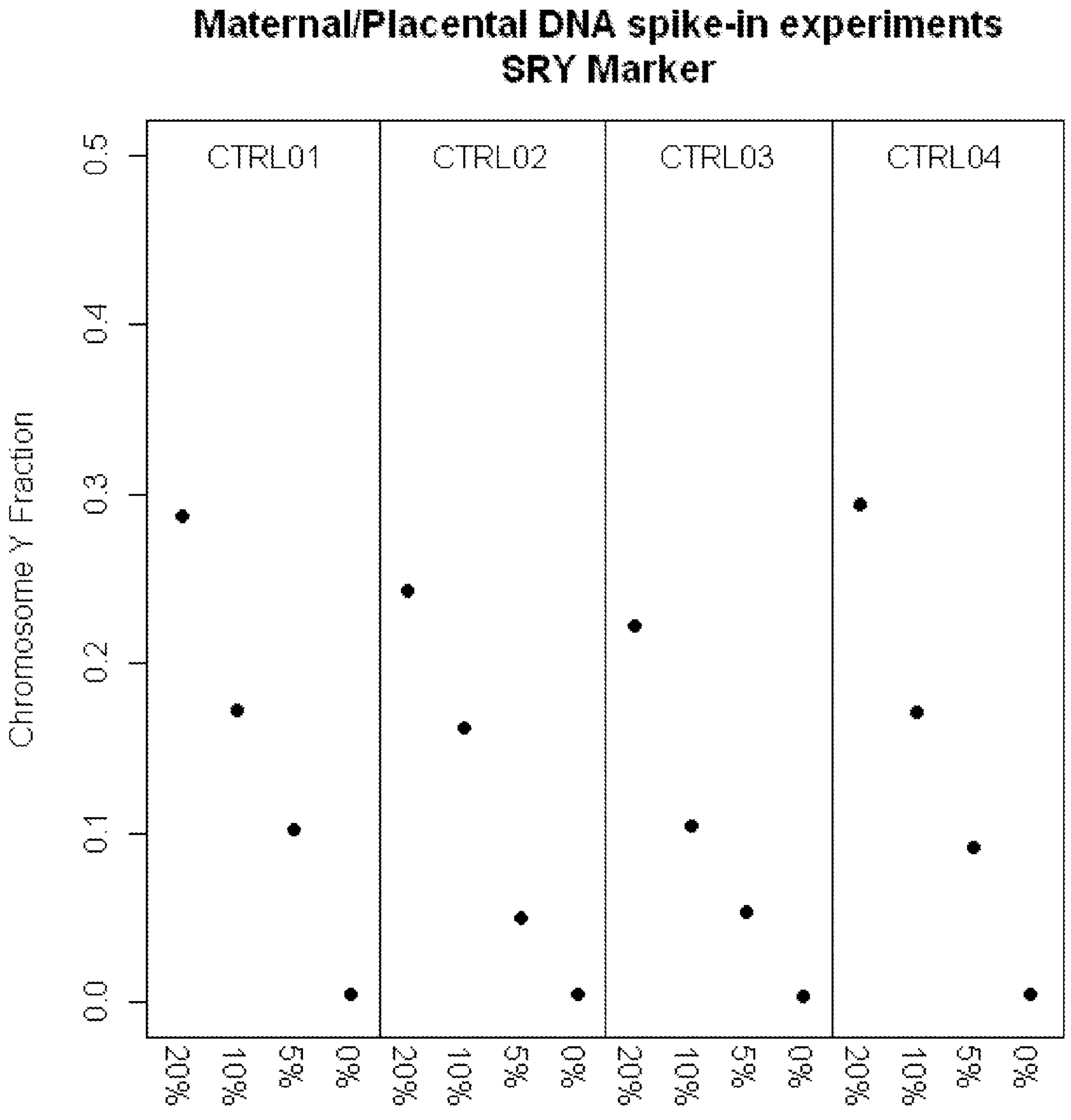

To optimize the reaction, a model system was developed to simulate DNA samples isolated from plasma. These samples contained a constant number of maternal non-methylated DNA and were spiked with different amounts of male placental methylated DNA. The samples were spiked with amounts ranging from approximately 0 to 25% relative to the maternal non-methylated DNA. The results are shown in FIGS. 13A and B. The fraction of placental DNA was calculated using the ratios obtained from the methylation assays (FIG. 13A), the SRY markers (FIG. 13B) and the total copy number assays. The primer sequences for the methylation assays (TBX), Y-chromosome assays (SRY) and total copy number (APOE) are provided above. The model system demonstrated that the methylation-based method performed equal to the Y-chromosome method (SRY markers), thus validating the methylation-based method as a sex-independent fetal quantifier.

Plasma Samples

To investigate the sensitivity and accuracy of the methods in clinical samples, 33 plasma samples obtained from women pregnant with a male fetus were investigated using the multiplex scheme from Table X. For each reaction, a quarter of the DNA obtained from a 4 ml extraction was used in order to meet the important requirement that only a portion of the total sample is used.

Total Copy Number Quantification

Figures 14A, 14B:
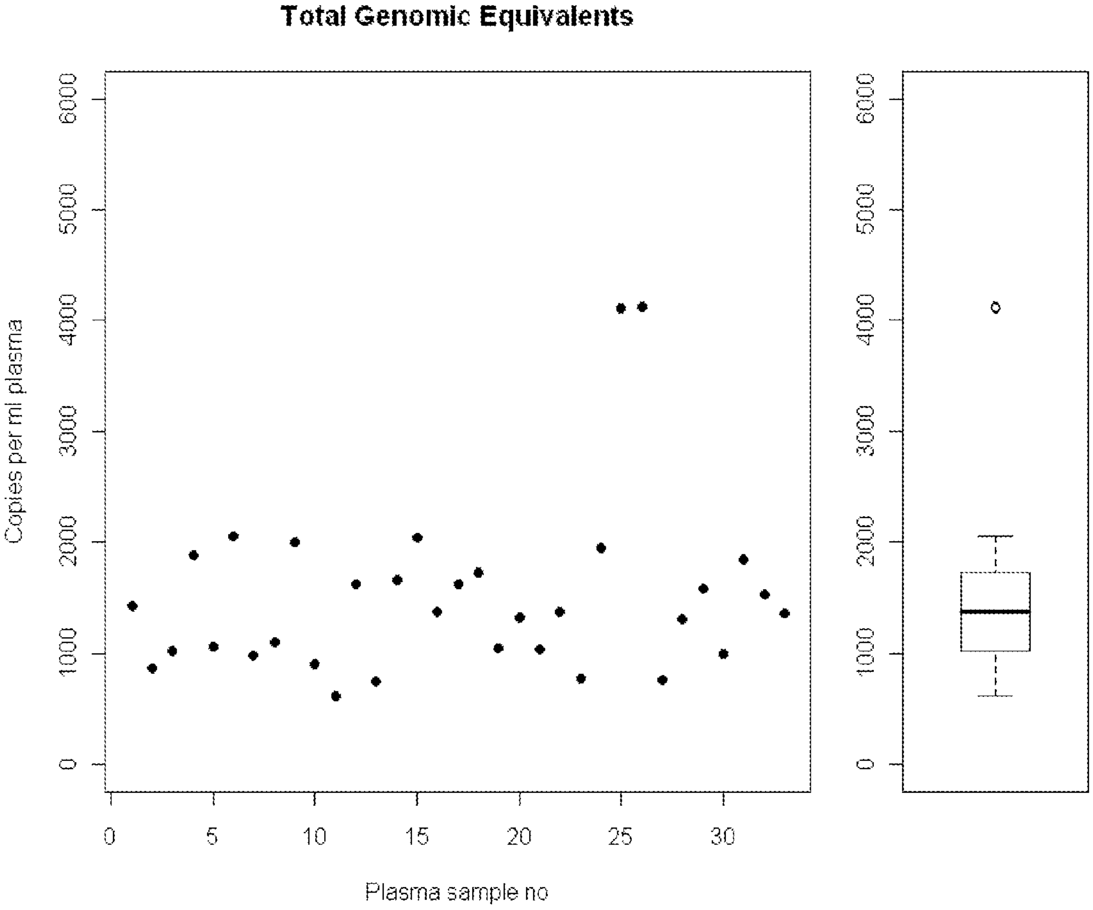
FIGS. 14A and B: Show the results of the total copy number assay from plasma samples.
FIG. 14B shows a box-and-whisker plot of the given values, summarizing the results.

The results from the total copy number quantification can be seen in FIGS. 14A and B. In FIG. 14A, the copy number for each sample is shown. Two samples (nos. 25 and 26) have a significantly higher total copy number than all the other samples. In general, a mean of approximately 1300 amplifiable copies/ml plasma was obtained (range 766-2055). FIG. 14B shows a box-and-whisker plot of the given values, summarizing the results.

Figures 15A, 15B:
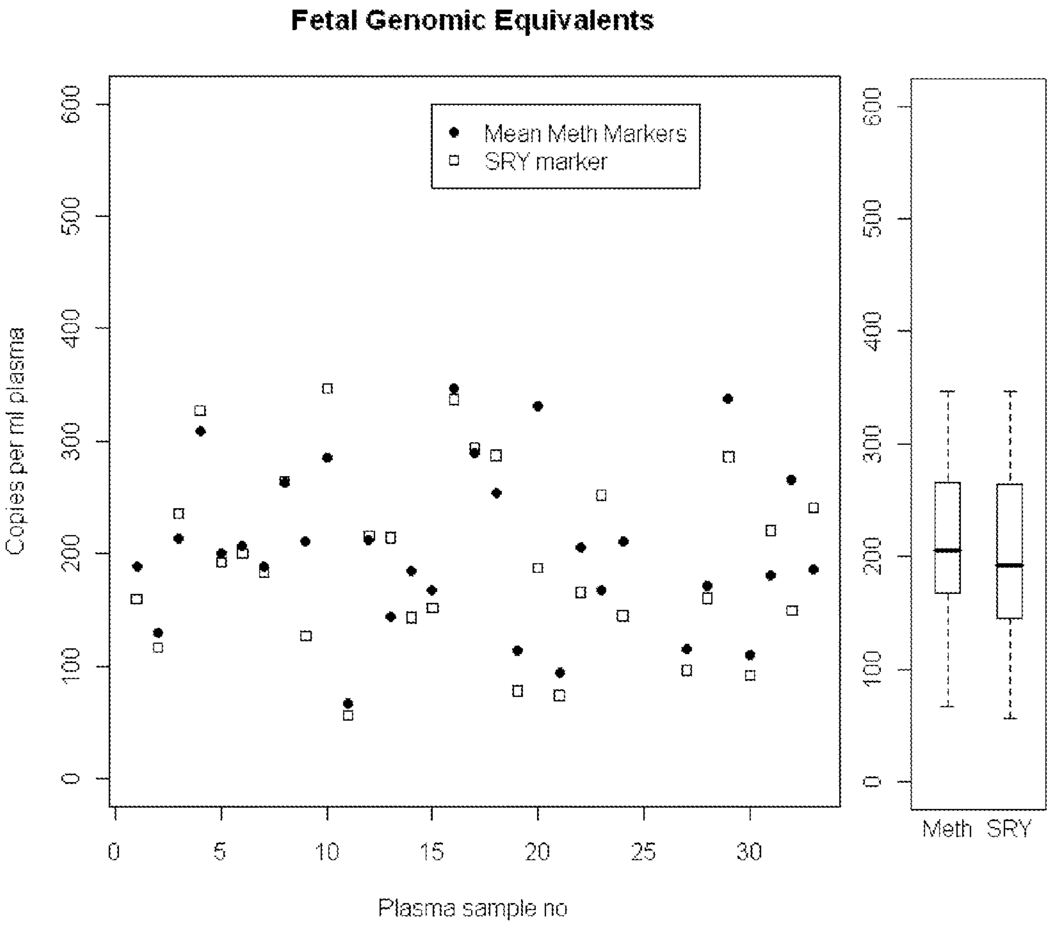
FIGS. 15A and B: The amount (or copy numbers) of fetal nucleic acid from 33 different plasma samples taken from pregnant women with male fetuses are plotted. The copy numbers obtained were calculated using the methylation markers and the Y-chromosome-specific markers using the assays provided in Table X. As can be seen in FIG. 15B, the box-and-whisker plot of the given values indicated minimal difference between the two different measurements, thus validating the accuracy and stability of the method.

Correlation Between Results Obtained from the Methylation Markers and the Y-Chromosome Marker In FIGS. 15A and B, the numbers of fetal copies for each sample are plotted. As all samples were from male pregnancies. The copy numbers obtained can be calculated using either the methylation or the Y-chromosome-specific markers. As can be seen in FIG. 15B, the box-and-whisker plot of the given values indicated minimal difference between the two different measurements.

Figure 16:
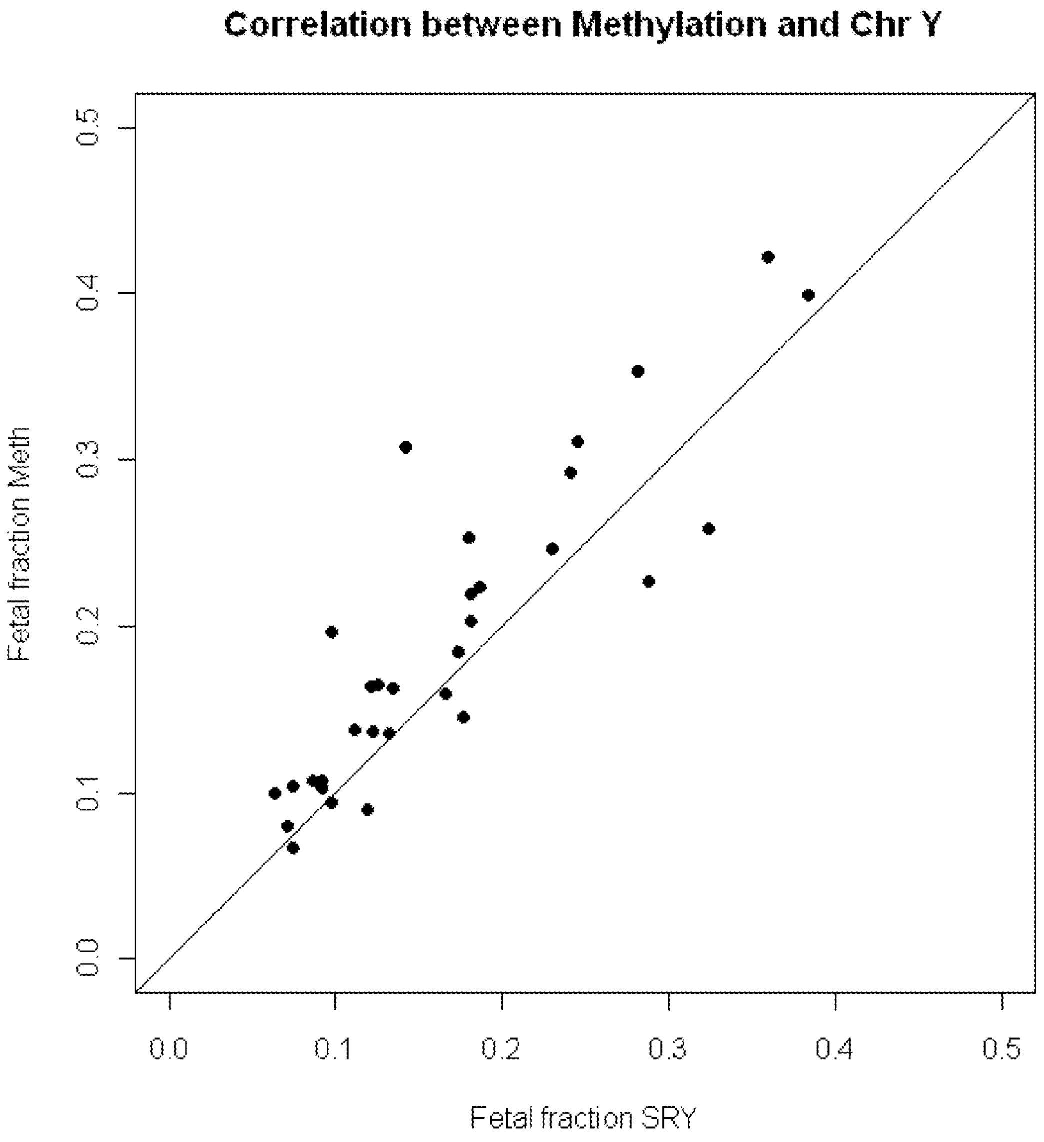
FIG. 16: Shows a paired correlation between the results obtained using the methylation markers versus the Y-chromosome marker from FIG. 15A.

The results showing the correlation between results obtained from the methylation markers and the Y-chromosome marker (SRY) is shown in FIG. 16. Again, the methylation-based method performed equal to the Y-chromosome method (SRY markers), further validating the methylation-based method as a sex-independent and polymorphism-independent fetal quantifier. The multiplexed assays disclosed in Table X were used to determine the amount fetal nucleic.

Figure 17:
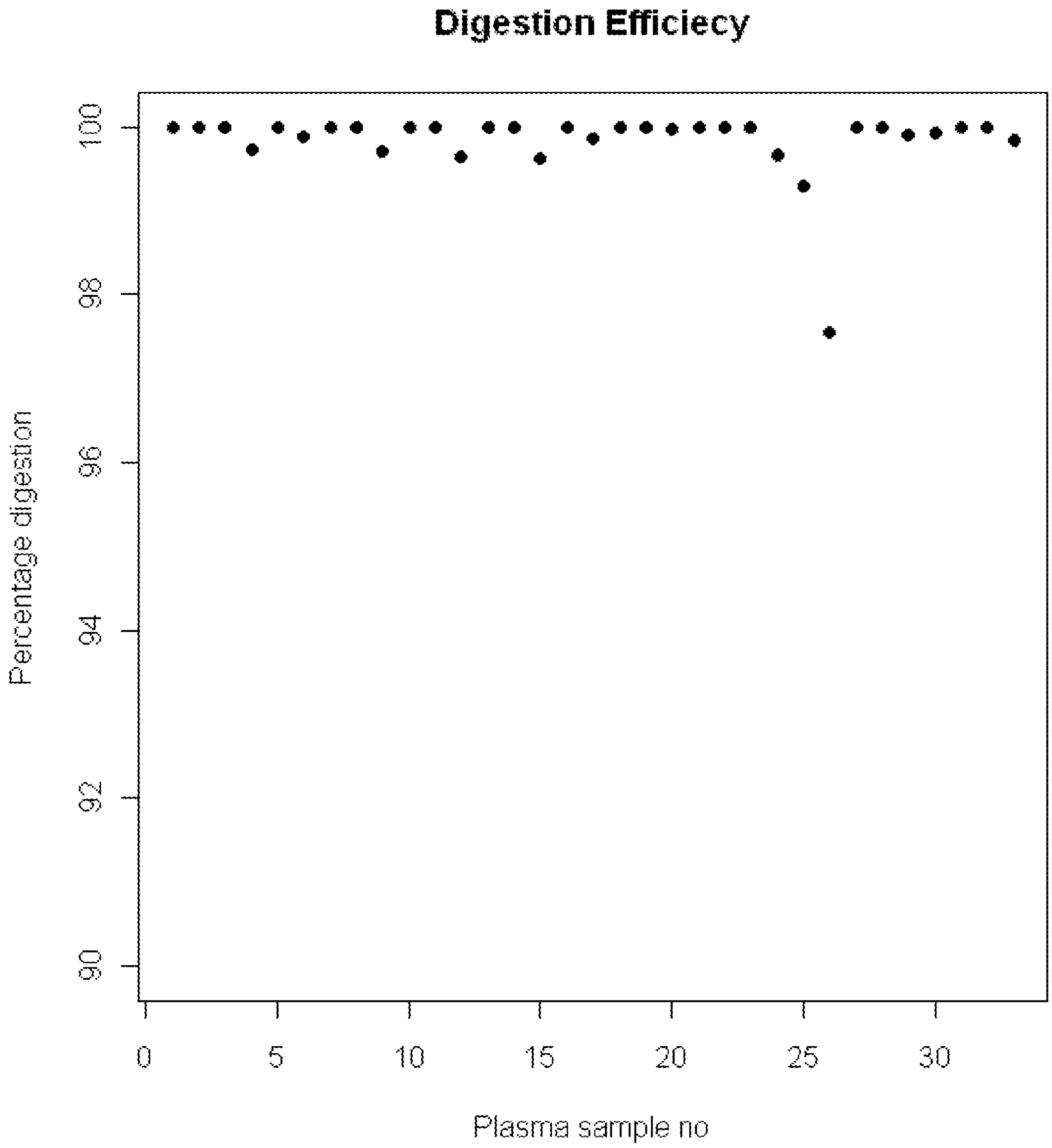
FIG. 17: Shows the digestion efficiency of the restriction enzymes using the ratio of digestion for the control versus the competitor and comparing this value to the mean total copy number assays. Apart from sample 26 all reactions indicate the efficiency to be above about 99%.

Finally, the digestion efficiency was determined by using the ratio of digestion for the control versus the competitor and comparing this value to the mean total copy number assays. See FIG. 17. Apart from sample 26 all reactions indicate the efficiency to be above 99%.

Data Analysis

Mass spectra analysis was done using Typer 4 (a Sequenom software product). The peak height (signal over noise) for each individual DNA analyte and competitor assay was determined and exported for further analysis.

The total number of molecules present for each amplicon was calculated by dividing the DNA specific peak by the competitor specific peak to give a ratio. (The "DNA" Peak in FIGS. 18 and 19 can be thought of as the analyte peak for a given assay). Since the number of competitor molecules added into the reaction is known, the total number of DNA molecules can be determined by multiplying the ratio by the number of added competitor molecules.

The fetal DNA fraction (or concentration) in each sample was calculated using the Y-chromosome-specific markers for male pregnancies and the mean of the methylated fraction for all pregnancies. In brief, for chromosome Y, the ratio was obtained by dividing the analyte (DNA) peak by the competitor peak and multiplying this ratio by the number of competitor molecules added into the reaction. This value was divided by a similar ratio obtained from the total number of amplifiable genome equivalents determination (using the Assay(s) for Total Amount). See FIG. 18. Since the total amount of nucleic acid present in a sample is a sum of maternal and fetal nucleic acid, the fetal contribution can be considered to be a fraction of the larger, background maternal contribution. Therefore, translating this into the equation shown in FIG. 18, the fetal fraction (k) of the total nucleic acid present in the sample is equal to the equation: $k=2\times R/(1-2R)$, where R is the ratio between the Y-chromosome amount and the total amount. Since the Y-chromosome is haploid and Assays for the Total Amount are determined using diploid targets, this calculation is limited to a fetal fraction smaller than 50% of the maternal fraction.

Figure 19:
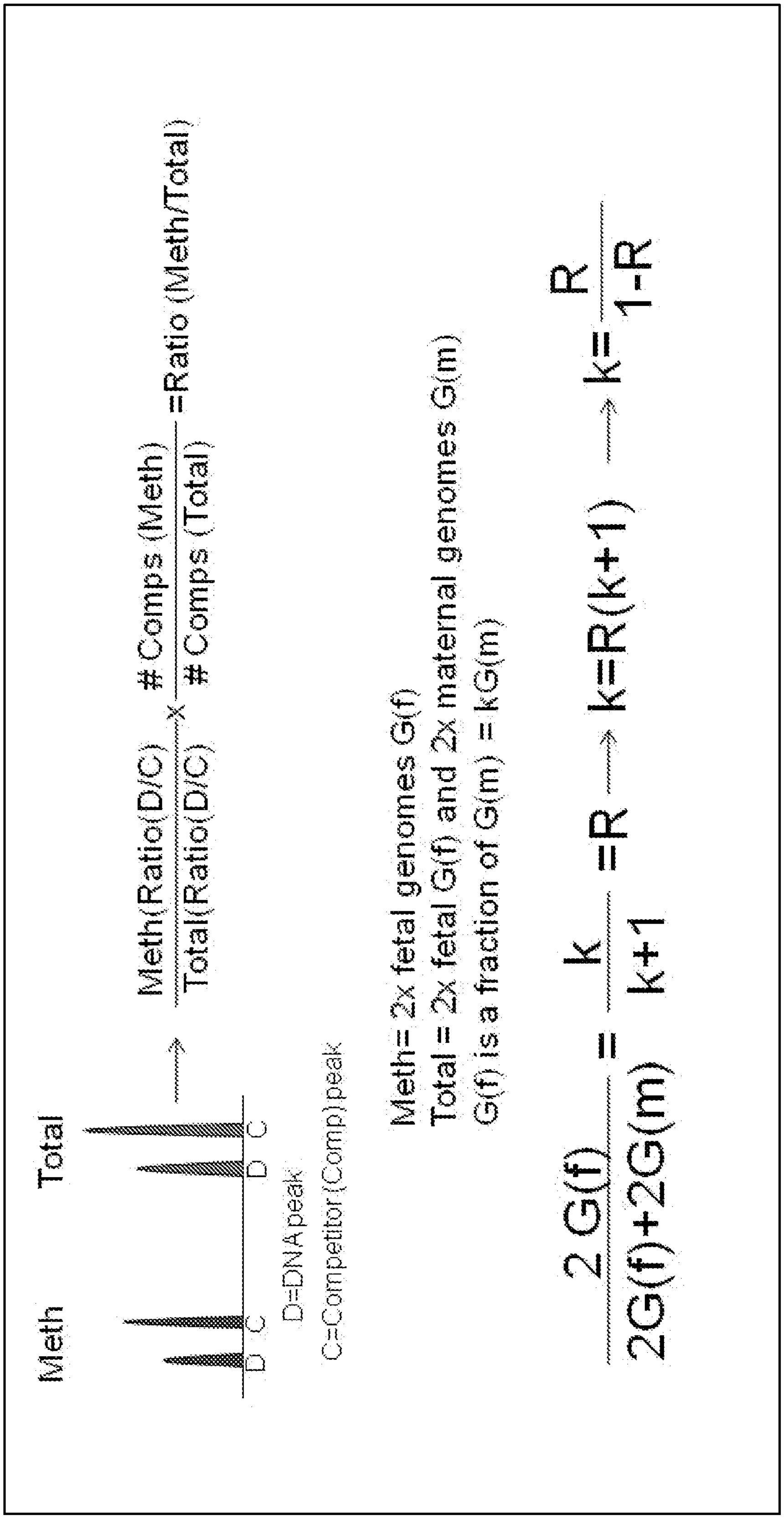
FIG. 19: Provides a specific method for calculating fetal DNA fraction (or concentration) in a sample without the Y-chromosome-specific markers. Instead, only the Assays for Methylation Quantification were used to determine the concentration of fetal DNA.

In FIG. 19, a similar calculation for the fetal concentration is shown by using the methylation specific markers (see Assays for Methylation Quantification). In contrast to Y-chromosome specific markers, these markers are from diploid targets, therefore, the limitations stated for the Y-Chromosome Specific Assay can be omitted. Thus, the fetal fraction (k) can be determined using the equation: $k=R(1-R)$, where R is the ratio between the methylation assay and the total assay.

Simulation

Figure 8:
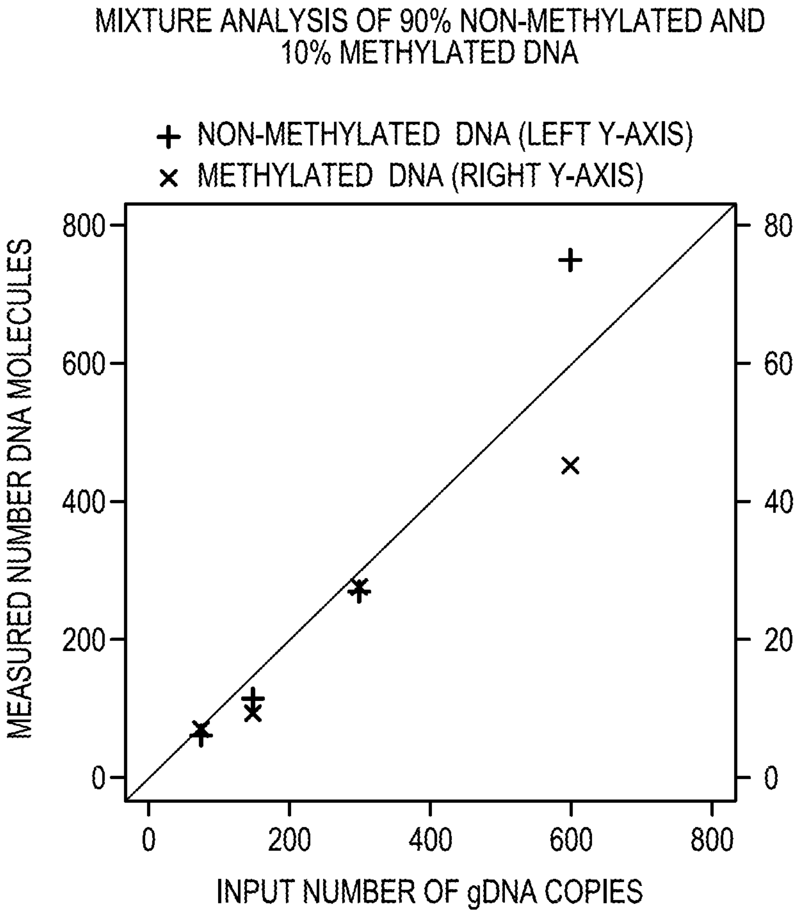
FIG. 8: Shown is the correlation between the number of gDNA molecules that were expected and the number of molecules measured by competitive PCR in combination with mass spectrometry analysis. In this experiment we used DNA derived from whole blood (black plus signs) and commercially available fully methylated DNA(red crosses) in a 90 to 10 ratio. We used the MBD-FC fusion protein to separate the non-methylated and the methylated fraction of DNA. Each fraction was subject to competitive PCR analysis with mass spectrometry readout. The method has been described earlier for the analysis of copy number variations and is commercially available for gene expression analysis. The approach allows absolute quantification of DNA molecules with the help of a synthetic oligonucleotides of know concentration. In this experiment we targeted the MGMT locus, which was not methylated in the whole blood sample used here. Using an input of 300 total gDNA copies we expect to see 270 copies of non-methylated DNA and 30 copies of methylated DNA. The measured copy numbers are largely in agreement with the expected values. The data point at 600 copies of input DNA indicates a bias in the reaction and shows that this initial proof of concept experiment needs to be followed up with more development work, before the assay can be used. However, this initial data indicates the feasibility of the approach for capturing and quantifying of a few copies of methylated DNA in the presence of an excess of unmethylated DNA species.
Figure 9A:
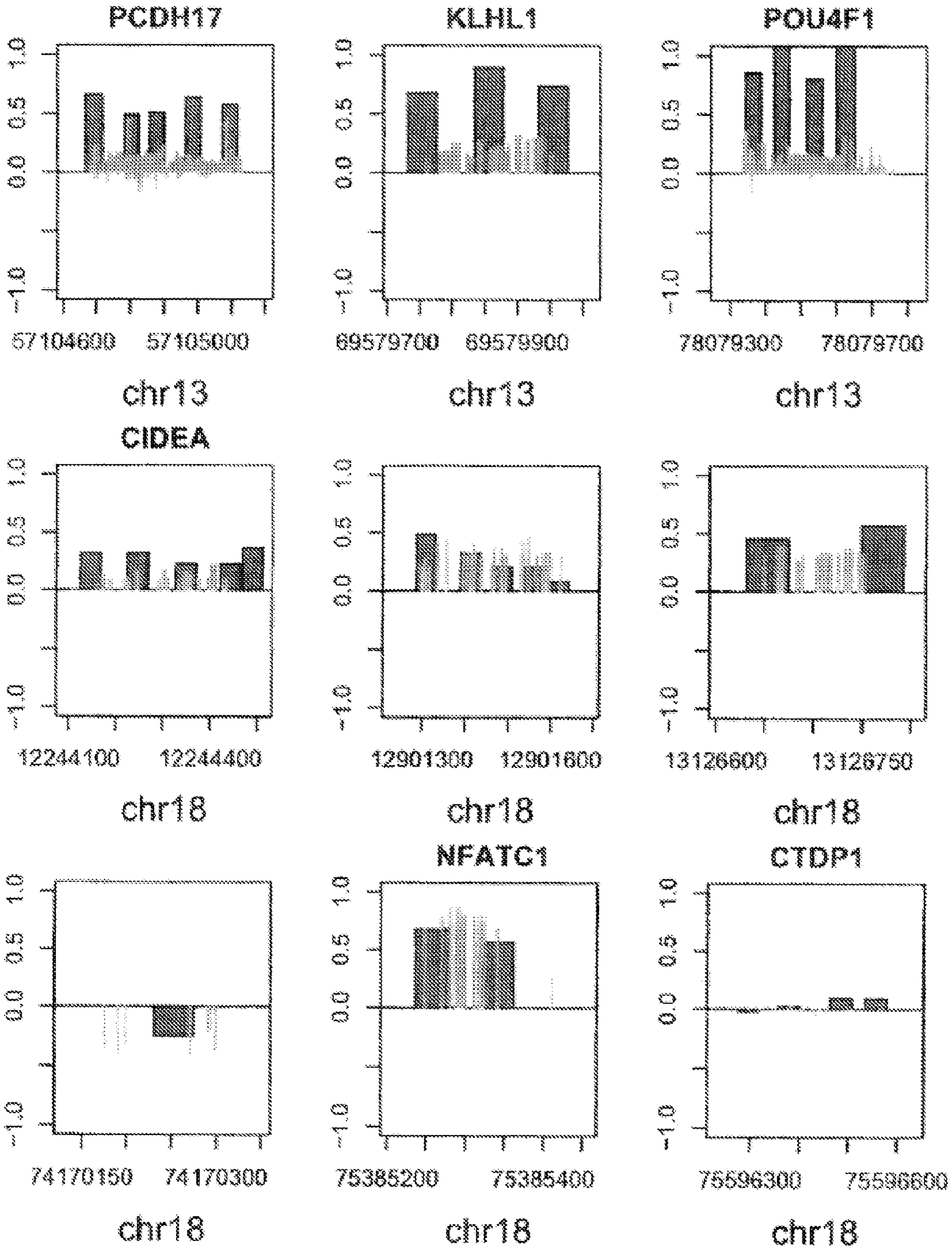
FIG. 9A-9L show bar graph plots of the methylation differences obtained from the microarray analysis (dark bars) and the mass spectrometry analysis (light grey bars) with respect to their genomic location. For each of the 85 region that were identified to be differentially methylated by microarray an individual plot is provided. The x axis for each plot shows the chromosomal position of the region. The y axis depicts the log ration (in case of the microarrays) and the methylation differences (in case of the mass spectrometry results). For the microarrays each hybridization probe in the area is shown as a single black (or dark grey) bar. For the mass spectrometry results each CpG site, is shown as a light grey bar. Bars showing values greater than zero indicate higher DNA methylation in the placenta samples compared to the maternal DNA. For some genes the differences are small (i.e. RB1 or DSCR6) but still statistically significant. Those regions would be less suitable for a fetal DNA enrichment strategy.
Figure 9B:
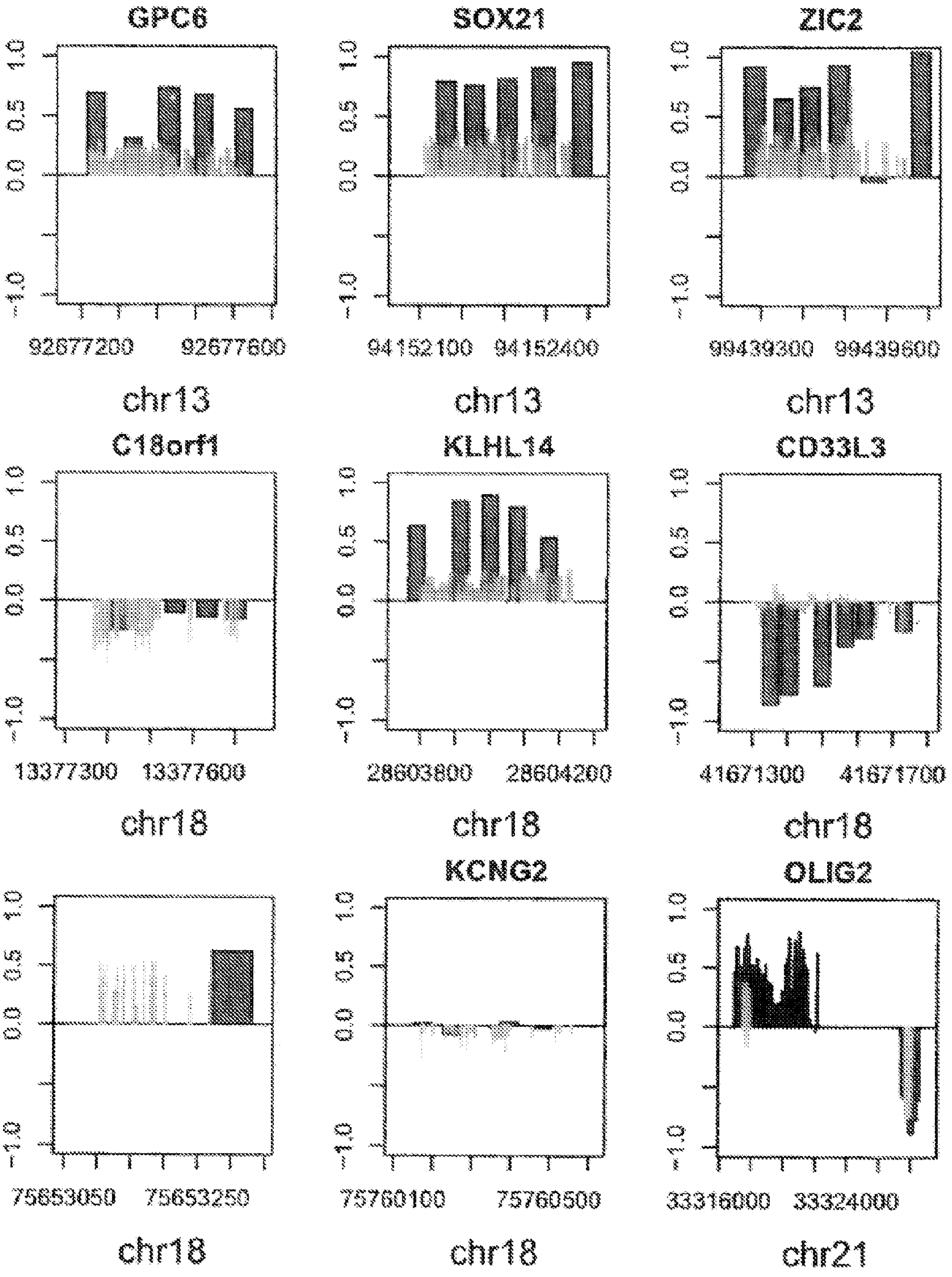
Figure 9C:
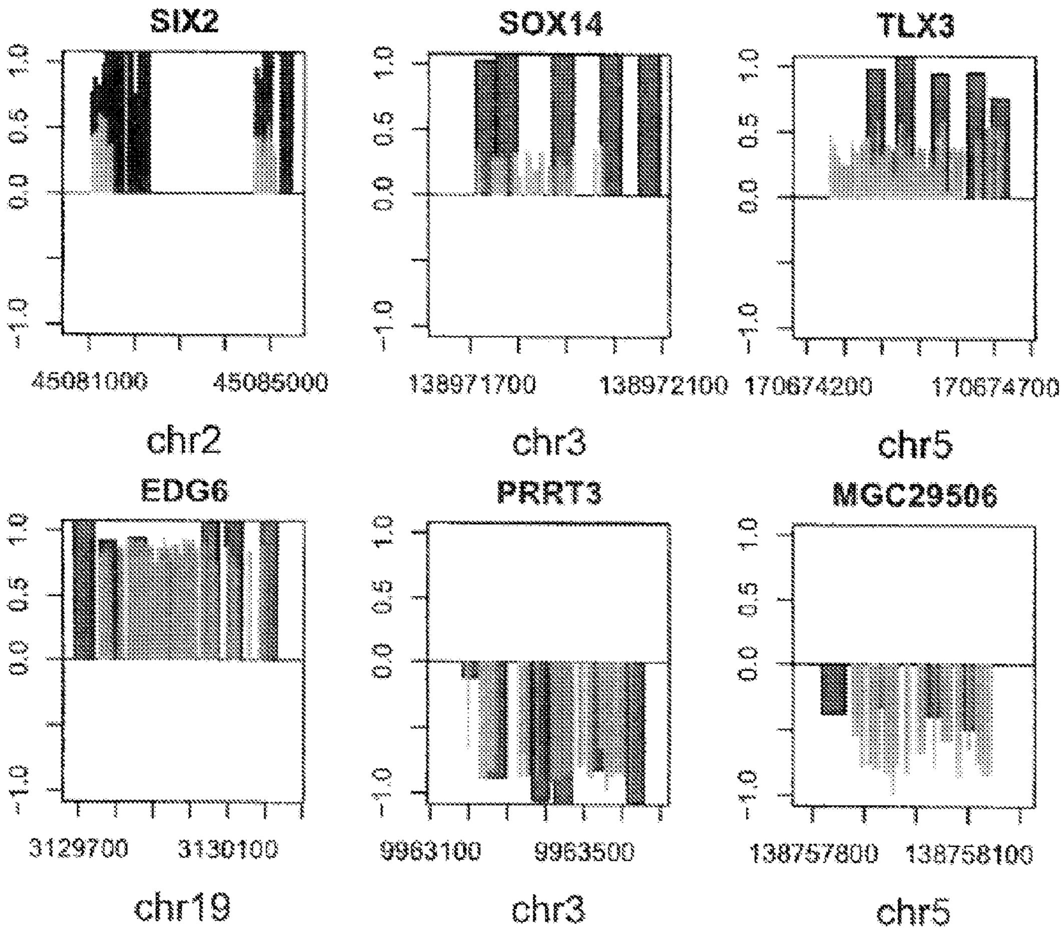
Figure 9D:
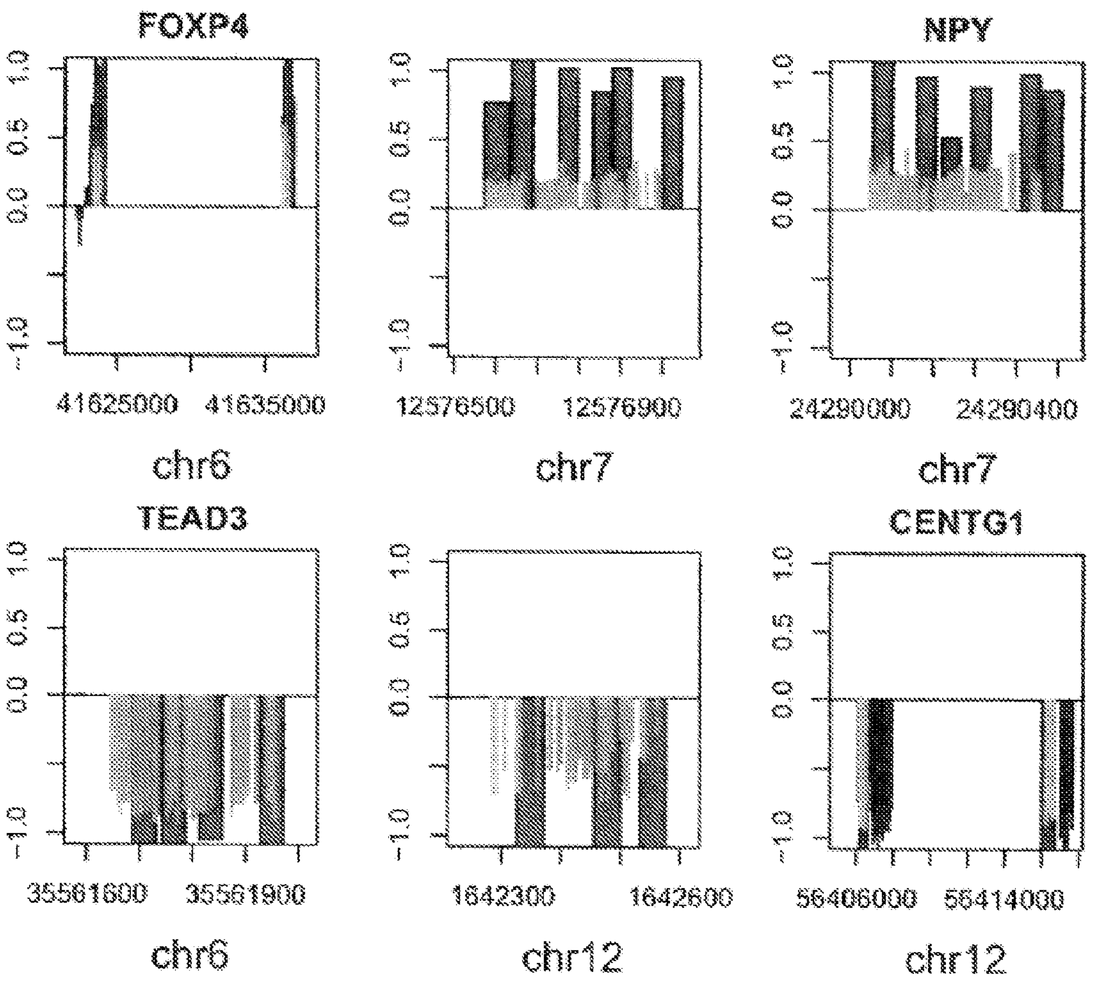
Figure 9E:
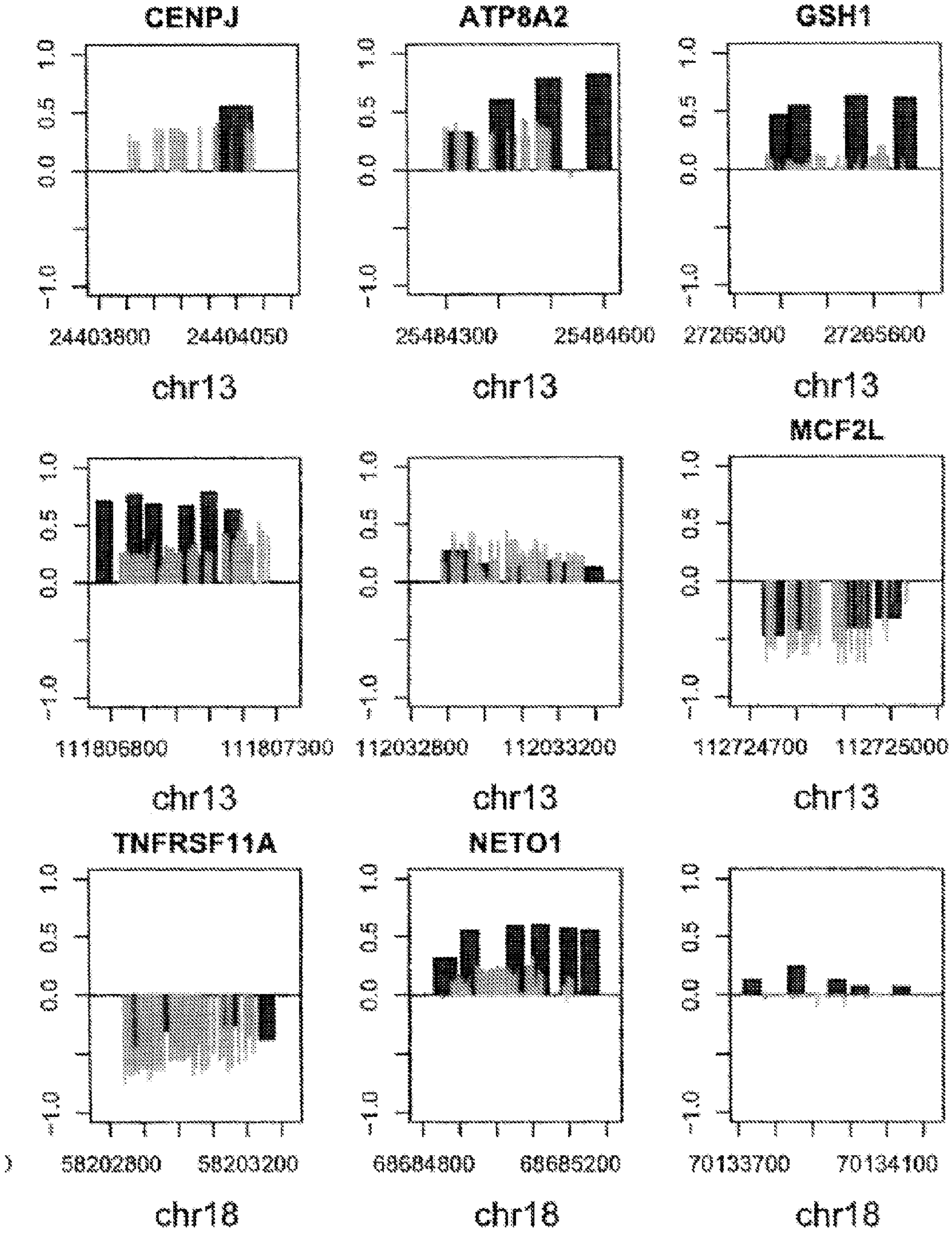
Figure 9F:
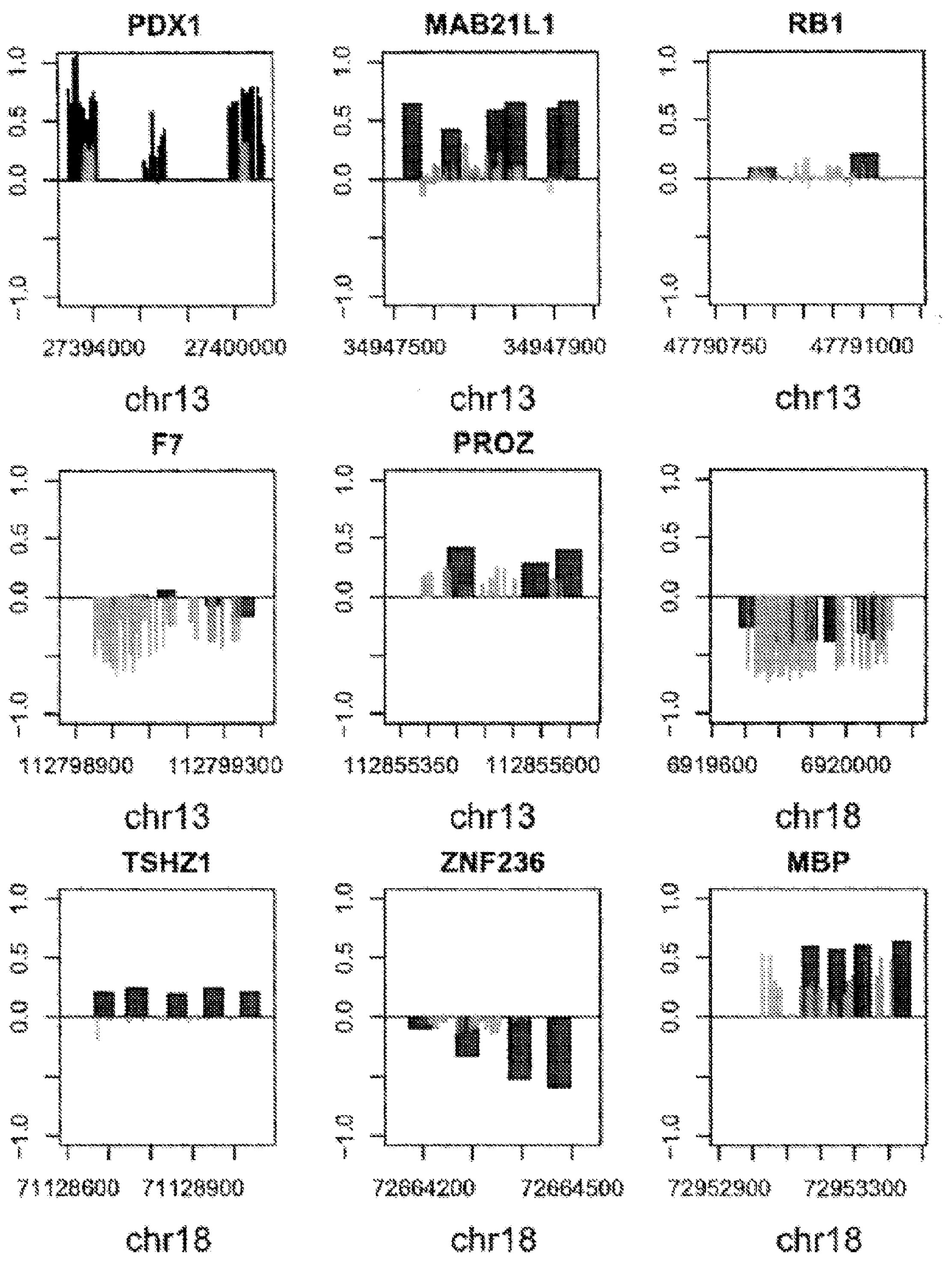
Figure 9G:
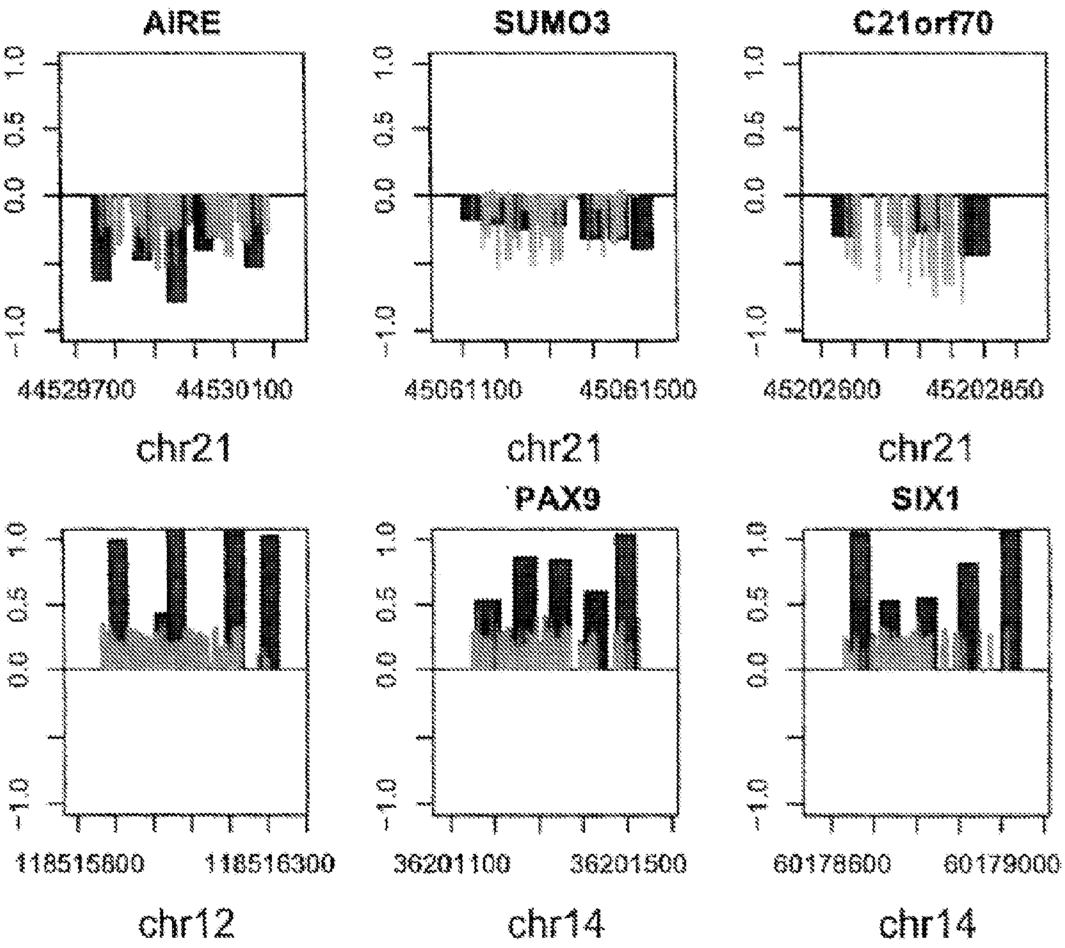
Figure 9H:
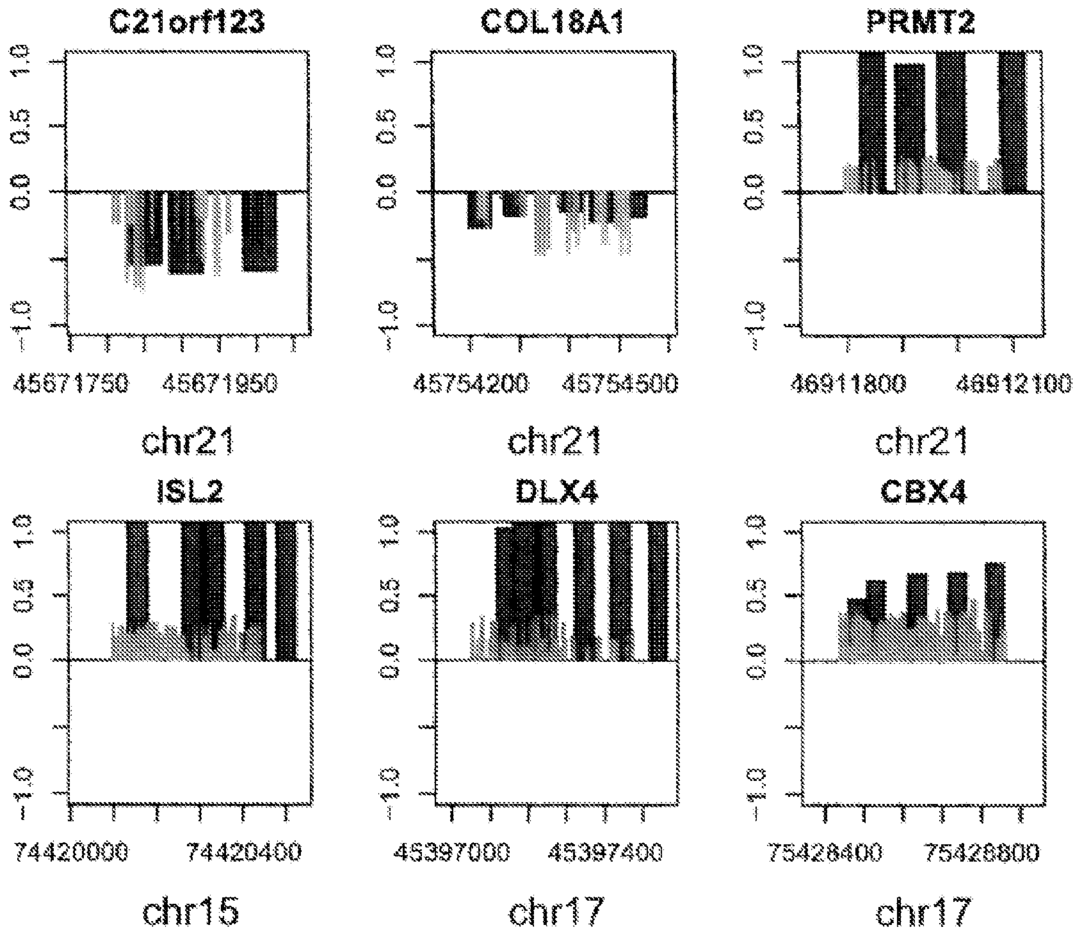
Figure 9I:
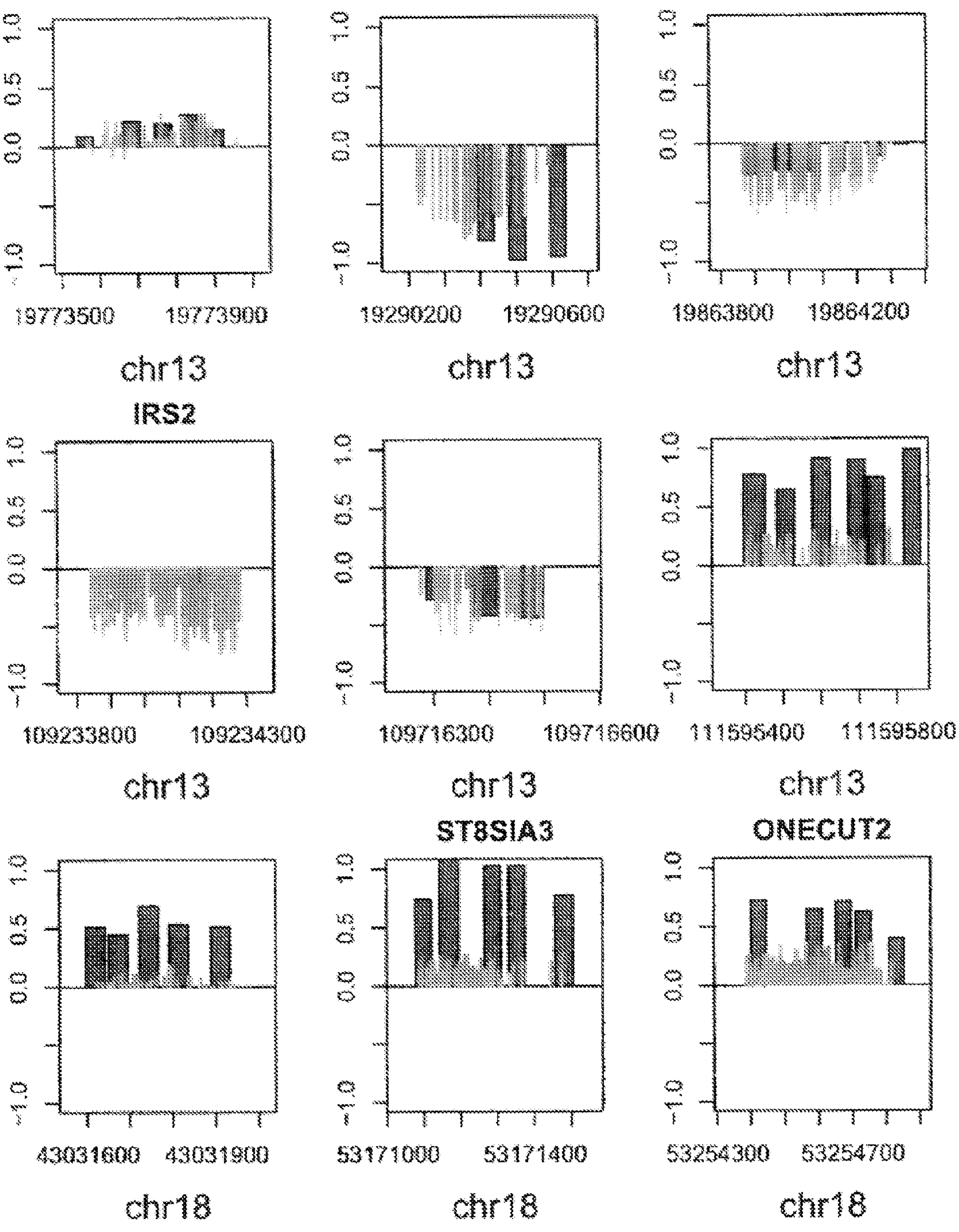
Figure 9J:
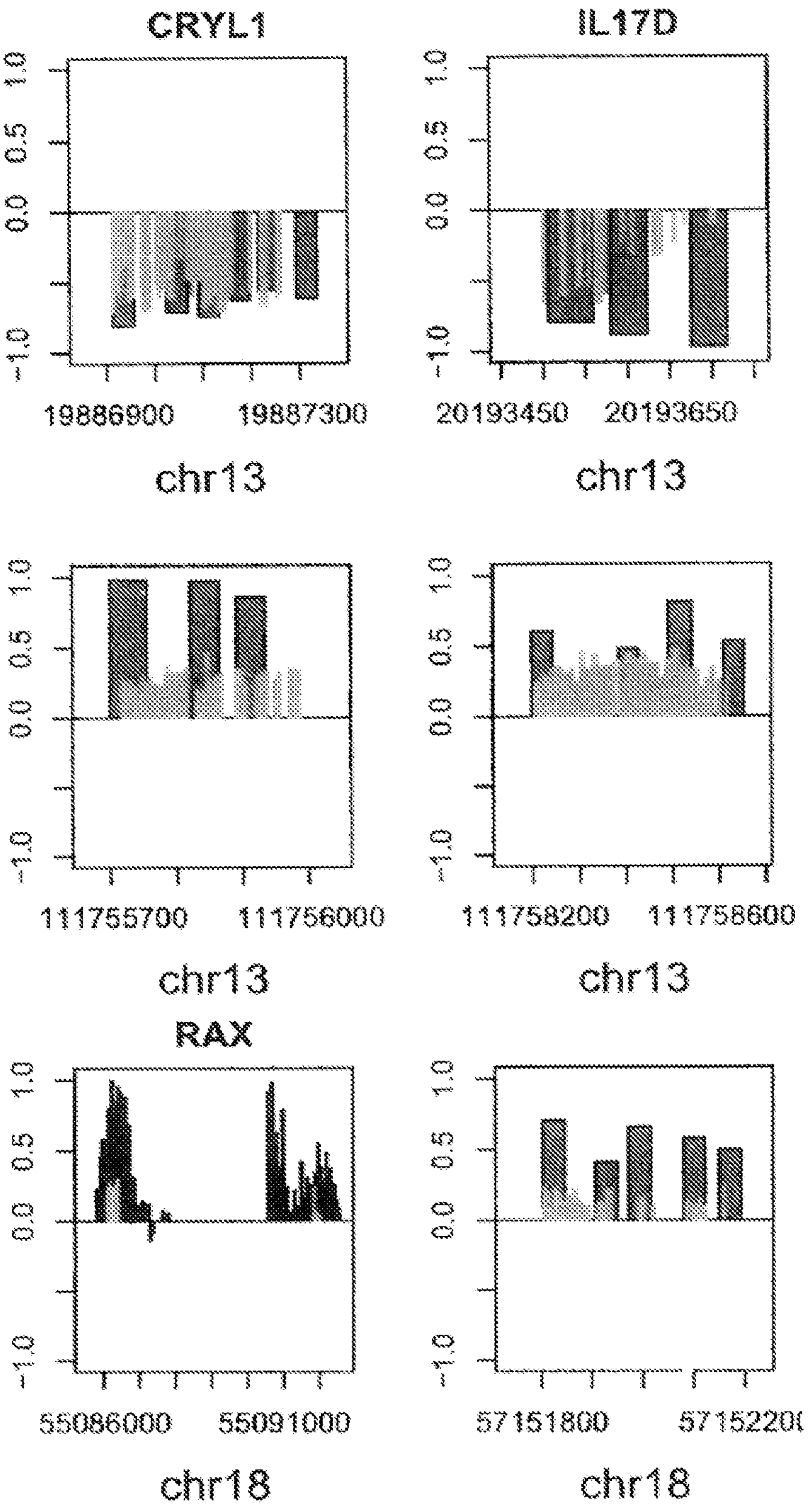
Figure 9K:
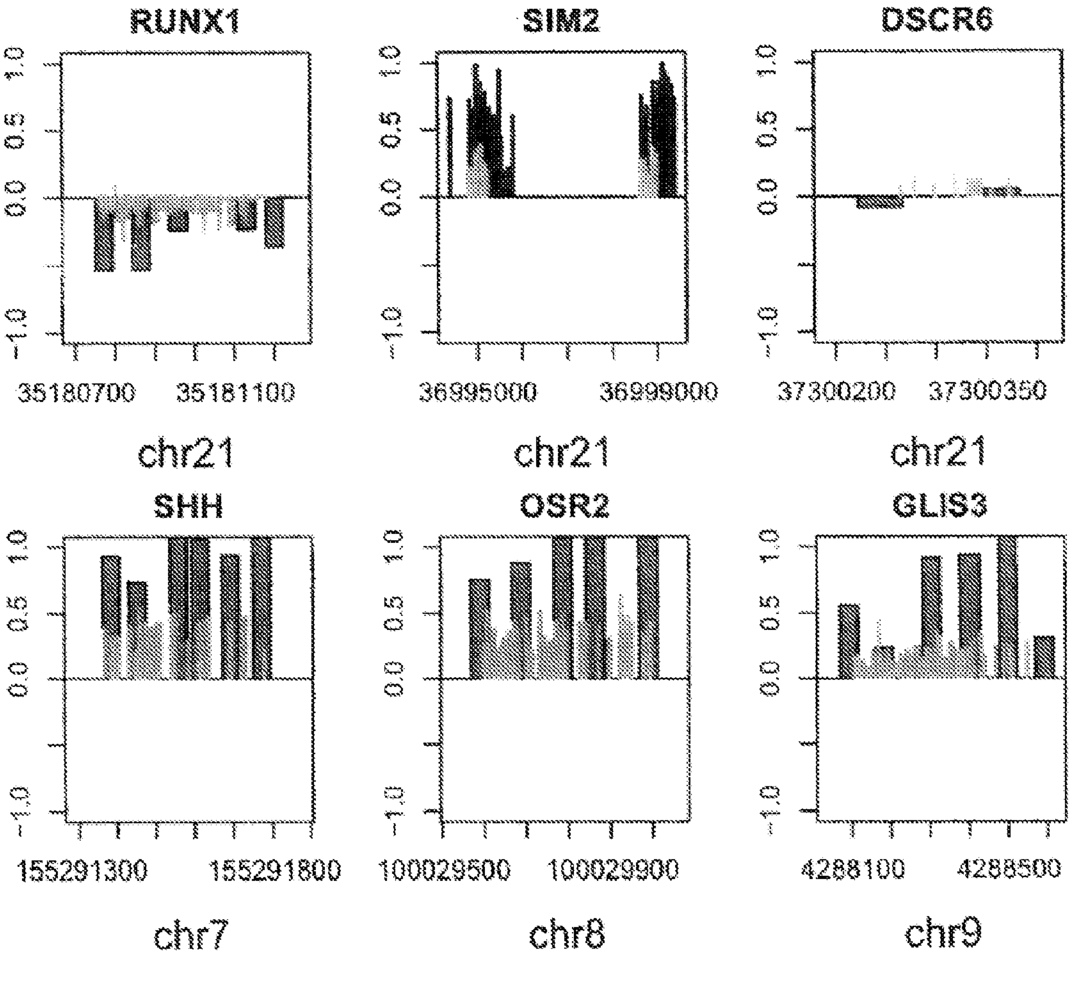
Figure 9L:
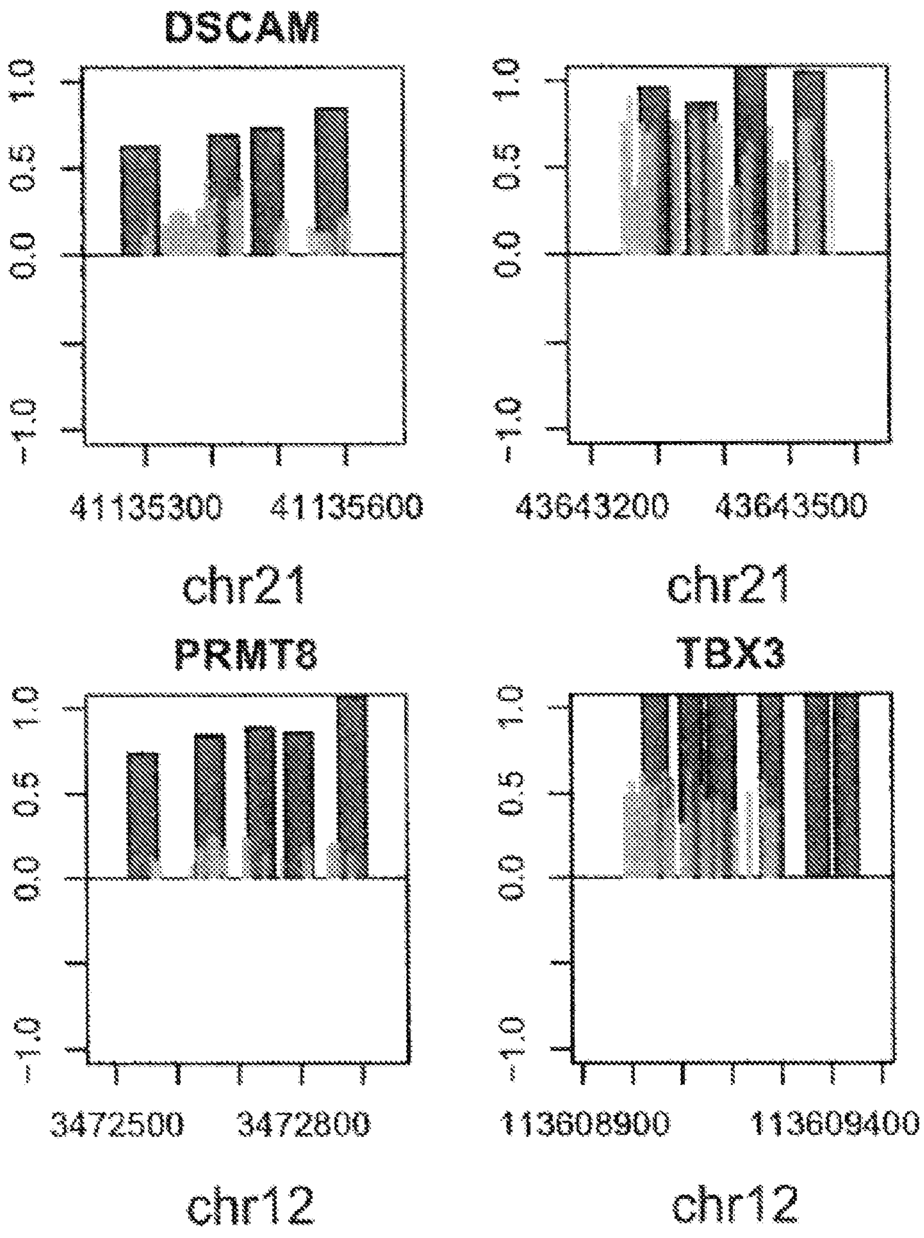

A first simple power calculation was performed that assumes a measurement system that uses 20 markers from chromosome 21, and 20 markers from one or more other autosomes. Starting with 100 copies of fetal DNA, a measurement standard deviation of 25 copies and the probability for a type I error to be lower than 0.001, it was found that the methods of the invention will be able to differentiate a diploid from a triploid chromosome set in 99.5% of all cases. The practical implementation of such an approach could for example be achieved using mass spectrometry, a system that uses a competitive PCR approach for absolute copy number measurements. The method can run 20 assays in a single reaction and has been shown to have a standard deviation in repeated measurements of around 3 to 5%. This method was used in combination with known methods for differentiating methylated and non-methylated nucleic acid, for example, using methyl-binding agents to separate nucleic acid or using methylation-sensitive enzymes to digest maternal nucleic acid. FIG. 8 shows the effectiveness of MBD-FC protein (a methyl-binding agent) for capturing and thereby separating methylated DNA in the presence of an excess of unmethylated DNA (see FIG. 8).

A second statistical power analysis was performed to assess the predictive power of an embodiment of the Methylation-Based Fetal Diagnostic Method described herein. The simulation was designed to demonstrate the likelihood of differentiating a group of trisomic chromosome 21 specific markers from a group of reference markers (for example, autosomes excluding chromosome 21). Many parameters influence the ability to discriminate the two populations of markers reliably. For the present simulation, values were chosen for each parameter that have been shown to be the most likely to occur based on experimentation. The following parameters and respective values were used:

Copy Numbers
- Maternal copy numbers=2000
- Fetal copy numbers for chromosomes other than 21, X and Y=200
- Fetal copy numbers for chromosome 21 in case of euploid fetus=200
- Fetal copy numbers for chromosome 21 in case of aneuploid T21 fetus=300

Percent fetal DNA (before methylation-based enrichment)=10% (see above)

Methylation Frequency
- Average methylation percentage in a target region for maternal DNA=10%
- Average methylation percentage in a target region for fetal DNA=80%

Average percentage of non-methylated and non-digested maternal DNA (i.e., a function of restriction efficiency (among other things)=5%

Number of assays targeting chromosome 21=10

Number of assays targeting chromosomes other than 21, X and Y=10

Figure 20:
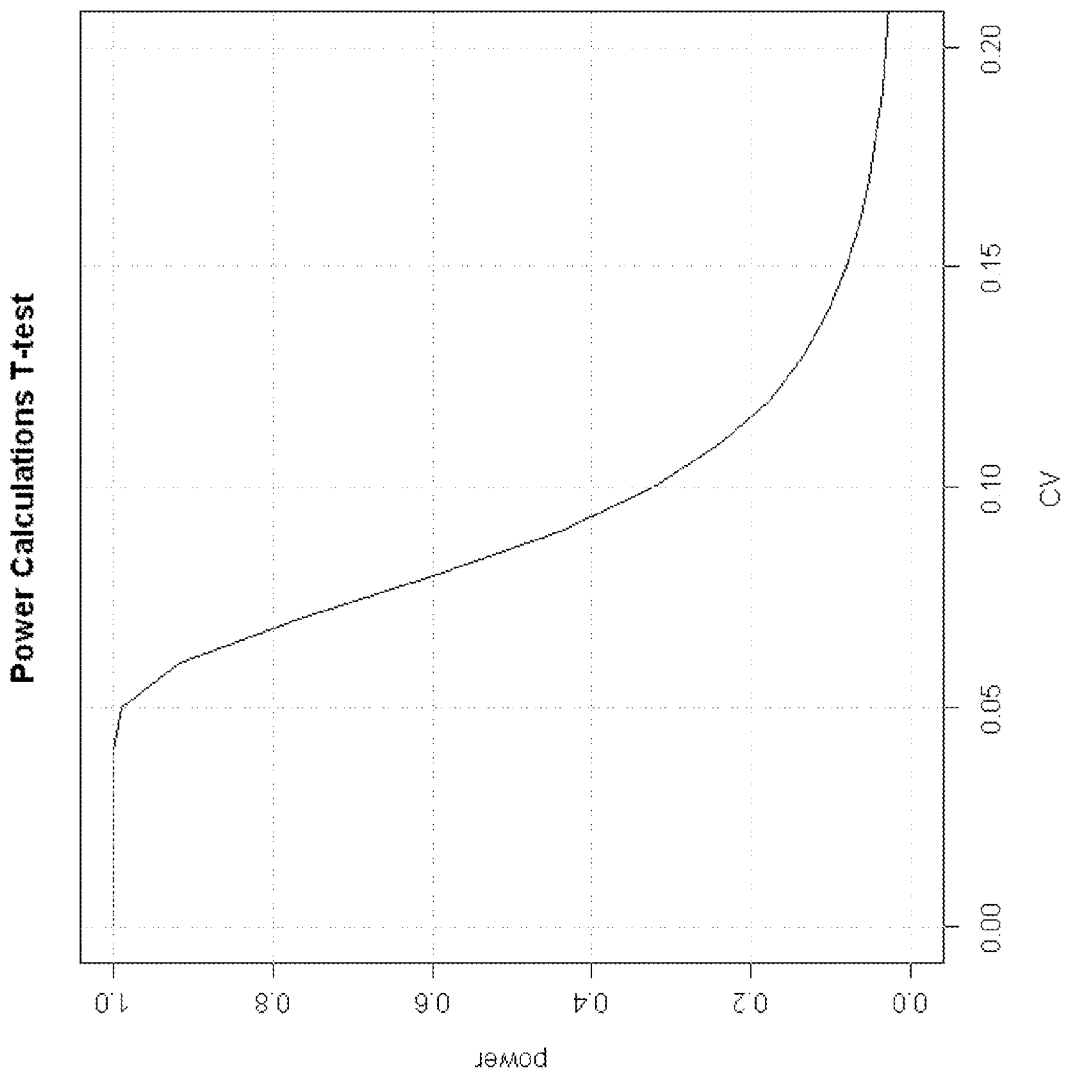
FIG. 20: Shows a power calculation t-test for a simulated trisomy 21 diagnosis using the methods of the invention. The Figure shows the relationship between the coefficient of variation (CV) on the x-axis and the power to discriminate the assay populations using a simple t-test (y-axis). The data indicates that in 99% of all cases, one can discriminate the two population (euploid vs. aneuploid) on a significance level of 0.001 provided a CV of 5% or less.

The results are displayed in FIG. 20. Shown is the relationship between the coefficient of variation (CV) on the x-axis and the power to discriminate the assay populations using a simple t-test (y-axis). The data indicates that in 99% of all cases, one can discriminate the two population (euploid vs. aneuploid) on a significance level of 0.001 provided a CV of 5% or less. Based on this simulation, the method represents a powerful noninvasive diagnostic method for the prenatal detection of fetal aneuploidy that is sex-independent and will work in all ethnicities (i.e., no allelic bias).

Example 3

Additional Differentially-Methylated Targets

Differentially-methylated Targets not Located on Chromosome 21

Additional differentially-methylated targets were selected for further analysis based upon previous microarray analysis. See Example 1 for a description of the microarray analysis. During the microarray screen, differentially methylated regions (DMRs) were defined between placenta tissue and PBMC. Regions were selected for EpiTYPER confirmation based upon being hypermethylated in placenta relative to PBMC. After directionality of the change was selected for, regions were chosen based upon statistical significance with regions designed beginning with the most significant and working downward in terms of significance. These studies were performed in eight paired samples of PBMC and placenta. Additional non-chromosome 21 targets are provided in Table 1B, along with a representative genomic sequence from each target in Table 4B.

Differentially-methylated Targets Located on Chromosome 21

The microarray screen uncovered only a subset of DMRs located on chromosome 21. The coverage of chromosome 21 by the microarray, however, was insufficient. Therefore a further analysis was completed to examine all 356 CpG islands on chromosome 21 using the standard settings of the UCSC genome browser. As shown in Table 1C below, some of these targets overlapped with those already examined in Table 1A. More specifically, CpG sites located on chromosome 21 including ~1000 bp upstream and downstream of each CpG was investigated using Sequenom's EpiTYPER® technology. See Example 1, "Validation using Sequenom® EpiTYPER™" for a description of Sequenom's EpiTYPER® technology. These studies were performed in eight paired samples of PBMC and placenta. In addition, since DMRs may also be located outside of defined CpG islands, data mining was performed on publicly available microarray data to identify potential candidate regions with the following characteristics: hypermethylated in placenta relative to maternal blood, not located in a defined CpG island, contained greater than 4 CpG dinucleotides, and contained a recognition sequence for methylation sensitive restriction enzymes. Regions that met these criteria were then examined using Sequenom's EpiTYPER® technology on eight paired PBMC and placenta samples. Additional chromosome 21 targets are provided in Table 1C, along with a representative genomic sequence from each target in Table 4C.

Tables 1B and 1C provide a description of the different targets, including their location and whether they were analyzed during the different phases of analysis, namely microarray analysis, EpiTYPER 8 analysis and EpiTYPER 73 analysis. A "YES" indicates it was analyzed and a "NO" indicates it was not analyzed. The definition of each column in Table 1B and 1C is listed below.

Region Name: Each region is named by the gene(s) residing within the area defined or nearby. Regions where no gene name is listed but rather only contain a locus have no refseq genes in near proximity.

Gene Region: For those regions contained either in close proximity to or within a gene, the gene region further explains the relationship of this region to the nearby gene.

Chrom: The chromosome on which the DMR is located using the hg18 build of the UCSC genome browser.

Start: The starting position of the DMR as designated by the hg18 build of the UCSC genome browser.

End: The ending position of the DMR as designated by the hg18 build of the UCSC genome browser.

Microarray Analysis: Describes whether this region was also/initially determined to be differentially methylated by microarray analysis. The methylated fraction of ten paired placenta and PBMC samples was isolated using the MBD-Fc protein. The two tissue fractions were then labeled with either Alexa Fluor 555-aha-dCTP(PBMC) or Alexa Fluor 647-aha-dCTP (placental) using the BioPrime Total Genomic Labeling System™ and hybridized to Agilent® CpG Island microarrays. Many regions examined in these studies were not contained on the initial microarray.

EpiTYPER 8 Samples: Describes whether this region was analyzed and determined to be differentially methylated in eight paired samples of placenta and peripheral blood mononuclear cells (PBMC) using EpiTYPER technology. Regions that were chosen for examination were based on multiple criteria. First, regions were selected based on data from the Microarray Analysis. Secondly, a comprehensive examination of all CpG islands located on chromosome 21 was undertaken. Finally, selected regions on chromosome 21 which had lower CpG frequency than those located in CpG islands were examined.

EpiTYPER 73 Samples: Describes whether this region was subsequently analyzed using EpiTYPER technology in a sample cohort consisting of 73 paired samples of placenta and PBMC. All regions selected for analysis in this second sample cohort were selected based on the results from the experimentation described in the EpiTYPER 8 column. More specifically, the regions in this additional cohort exhibited a methylation profile similar to that determined in the EpiTYPER 8 Samples analysis. For example, all of the regions listed in Tables 1B-1C exhibit different levels of DNA methylation in a significant portion of the examined CpG dinucleotides within the defined region. Differential DNA methylation of CpG sites was determined using a paired T Test with those sites considered differentially methylated if the p-value (when comparing placental tissue to PBMC) is $p<0.05$.

Previously Validated EpiTYPER: Describes whether this region or a portion of this region was validated using EpiTYPER during previous experimentation. (See Examples 1 and 2).

Relative Methylation Placenta to Maternal: Describes the direction of differential methylation.

Regions labeled as "hypermethylation" are more methylated within the designated region in placenta samples relative to PBMC and "hypomethylation" are more methylated within the designated region in PBMC samples.

TABLE 1A

| GENE NAME | CHROM | START | END | CpG ISLAND | MEAN LOG RATIO MICRO-ARRAY | MEAN MATERNAL METHYLATION EPITYPER | MEAN PLACENTA METHYLATION EPITYPER | METHYLATION DIFFERENCE PLACENTA-MATERNAL | RELATIVE METHYLATION PLACENTA TO MATERNAL |
|---|---|---|---|---|---|---|---|---|---|
| chr13 group00016 | chr13 | 19773745 | 19774050 | chr13: 19773518-19774214 | 0.19 | 0.22 | 0.32 | 0.1 | HYPERMETHYLATION |
| chr13 group00005 | chr13 | 19290394 | 19290768 | : — | −0.89 | 0.94 | 0.35 | −0.59 | HYPOMETHYLATION |
| CRYL1 | chr13 | 19887090 | 19887336 | chr13: 19887007-19887836 | −0.63 | 0.74 | 0.21 | −0.53 | HYPOMETHYLATION |
| IL17D | chr13 | 20193675 | 20193897 | chr13: 20193611-20194438 | −1.01 | 0.53 | 0.13 | −0.39 | HYPOMETHYLATION |
| CENPJ | chr13 | 24404023 | 24404359 | : — | 0.57 | 0.17 | 0.49 | 0.32 | HYPERMETHYLATION |
| ATP8A2 | chr13 | 25484475 | 25484614 | chr13: 25484287-25484761 | 0.81 | 0.16 | 0.43 | 0.27 | HYPERMETHYLATION |
| GSH1 | chr13 | 27265542 | 27265834 | chr13: 27264549-27266505 | 0.57 | 0.13 | 0.19 | 0.05 | HYPERMETHYLATION |
| PDX1 | chr13 | 27393789 | 27393979 | chr13: 27392001-27394099 | 0.55 | 0.06 | 0.2 | 0.14 | HYPERMETHYLATION |
| PDX1 | chr13 | 27400459 | 27401165 | chr13: 27400362-27400744; chr13: 27401057-27401374 | 0.73 | 0.12 | 0.26 | 0.14 | HYPERMETHYLATION |
| MAB21L1 | chr13 | 34947737 | 34948062 | chr13: 34947570-34948159 | 0.66 | 0.11 | 0.17 | 0.06 | HYPERMETHYLATION |
| RB1 | chr13 | 47790983 | 47791646 | chr13: 47790636-47791858 | 0.18 | 0.45 | 0.48 | 0.03 | HYPERMETHYLATION |
| PCDH17 | chr13 | 57104856 | 57106841 | chr13: 57104527-57106931 | 0.46 | 0.15 | 0.21 | 0.06 | HYPERMETHYLATION |
| KLHL1 | chr13 | 69579933 | 69580146 | chr13: 69579733-69580220 | 0.79 | 0.09 | 0.28 | 0.2 | HYPERMETHYLATION |
| POU4F1 | chr13 | 78079515 | 78081073 | chr13: 78079328-78079615; chr13: 78080860-78081881 | 0.66 | 0.12 | 0.23 | 0.11 | HYPERMETHYLATION |
| GPC6 | chr13 | 92677402 | 92678666 | chr13: 92677246-92678878 | 0.66 | 0.06 | 0.19 | 0.13 | HYPERMETHYLATION |
| SOX21 | chr13 | 94152286 | 94153047 | chr13: 94152190-94153185 | 0.94 | 0.16 | 0.4 | 0.25 | HYPERMETHYLATION |
| ZIC2 | chr13 | 99439660 | 99440858 | chr13: 99439335-99440189; chr13: 99440775-99441095 | 0.89 | 0.13 | 0.35 | 0.22 | HYPERMETHYLATION |
| IRS2 | chr13 | 109232856 | 109235065 | chr13: 109232467-109238181 | −0.17 | 0.73 | 0.38 | −0.35 | HYPOMETHYLATION |
| chr13 group00350 | chr13 | 109716455 | 109716604 | chr13: 109716325-109716726 | −0.37 | 0.77 | 0.41 | −0.36 | HYPOMETHYLATION |
| chr13 group00385 | chr13 | 111595578 | 111595955 | chr13: 111595459-111596131 | 0.87 | 0.06 | 0.2 | 0.14 | HYPERMETHYLATION |
| chr13 group00390 | chr13 | 111756337 | 111756593 | chr13: 111755805-111756697 | 0.71 | 0.12 | 0.34 | 0.22 | HYPERMETHYLATION |
| chr13 group00391 | chr13 | 111759856 | 111760045 | chr13: 111757885-111760666 | 0.86 | 0.11 | 0.36 | 0.25 | HYPERMETHYLATION |
| chr13 group00395 | chr13 | 111808255 | 111808962 | chr13: 111806599-111808492; chr13: 111808866-111809114 | 0.96 | 0.13 | 0.35 | 0.22 | HYPERMETHYLATION |
| chr13 group00399 | chr13 | 112033503 | 112033685 | chr13: 112032967-112033734 | 0.38 | 0.26 | 0.43 | 0.18 | HYPERMETHYLATION |
| MCF2L | chr13 | 112724910 | 112725742 | chr13: 112724782-112725121; chr13: 112725628-112725837 | −0.47 | 0.91 | 0.33 | −0.58 | HYPOMETHYLATION |
| F7 | chr13 | 112799123 | 112799379 | chr13: 112798487-112799566 | −0.05 | 0.97 | 0.55 | −0.41 | HYPOMETHYLATION |
| PROZ | chr13 | 112855566 | 112855745 | chr13: 112855289-112855866 | 0.29 | 0.15 | 0.3 | 0.16 | HYPERMETHYLATION |
| chr18 group00039 | chr18 | 6919797 | 6919981 | chr18: 6919450-6920088 | −0.38 | 0.88 | 0.39 | −0.49 | HYPOMETHYLATION |
| CIDEA | chr18 | 12244327 | 12244696 | chr18: 12244147-12245089 | 0.23 | 0.14 | 0.23 | 0.1 | HYPERMETHYLATION |
| chr18 group00091 | chr18 | 12901467 | 12901643 | chr18: 12901024-12902704 | 0.16 | 0.15 | 0.43 | 0.29 | HYPERMETHYLATION |

TABLE 1A-continued

| GENE NAME | CHROM | START | END | CpG ISLAND | MEAN LOG RATIO MICRO-ARRAY | MEAN MATERNAL METHYLATION EPITYPER | MEAN PLACENTA METHYLATION EPITYPER | METHYLATION DIFFERENCE PLACENTA-MATERNAL | RELATIVE METHYLATION PLACENTA TO MATERNAL |
|---|---|---|---|---|---|---|---|---|---|
| chr18 group00094 | chr18 | 13126819 | 13126986 | chr18: 13126596-13127564 | 0.41 | 0.07 | 0.34 | 0.27 | HYPERMETHYLATION |
| C18orf1 | chr18 | 13377536 | 13377654 | chr18: 13377385-13377686 | −0.12 | 0.95 | 0.69 | −0.26 | HYPOMETHYLATION |
| KLHL14 | chr18 | 28603978 | 28605183 | chr18: 28603688-28606300 | 0.83 | 0.07 | 0.19 | 0.12 | HYPERMETHYLATION |
| CD33L3 | chr18 | 41671477 | 41673011 | chr18: 41671386-41673101 | −0.34 | 0.49 | 0.44 | −0.05 | HYPOMETHYLATION |
| ST8SIA3 | chr18 | 53171265 | 53171309 | chr18: 53170705-53172603 | 1.02 | 0.09 | 0.25 | 0.16 | HYPERMETHYLATION |
| ONECUT2 | chr18 | 53254808 | 53259810 | chr18: 53254152-53259851 | 0.74 | 0.09 | 0.23 | 0.14 | HYPERMETHYLATION |
| RAX | chr18 | 55086286 | 55086436 | chr18: 55085813-55087807 | 0.88 | 0.11 | 0.26 | 0.16 | HYPERMETHYLATION |
| chr18 group00277 | chr18 | 57151972 | 57152311 | chr18: 57151663-57152672 | 0.58 | 0.08 | 0.21 | 0.13 | HYPERMETHYLATION |
| TNFRSF11A | chr18 | 58203013 | 58203282 | chr18: 58202849-58203367 | −0.33 | 0.88 | 0.28 | −0.6 | HYPOMETHYLATION |
| NETO1 | chr18 | 68685099 | 68687060 | chr18: 68684945-68687851 | 0.65 | 0.09 | 0.22 | 0.13 | HYPERMETHYLATION |
| chr18 group00304 | chr18 | 70133945 | 70134397 | chr18: 70133732-70134724 | 0.12 | 0.93 | 0.92 | −0.01 | NOT CONFIRMED |
| TSHZ1 | chr18 | 71128742 | 71128974 | chr18: 71128638-71129076 | 0.23 | 0.95 | 0.92 | −0.03 | NOT CONFIRMED |
| ZNF236 | chr18 | 72664454 | 72664736 | chr18: 72662797-72664893 | −0.62 | 0.17 | 0.1 | −0.07 | HYPOMETHYLATION |
| MBP | chr18 | 72953150 | 72953464 | chr18: 72953137-72953402 | 0.6 | 0.44 | 0.72 | 0.28 | HYPERMETHYLATION |
| chr18 group00342 | chr18 | 74170347 | 74170489 | chr18: 74170210-74170687 | −0.2 | 0.78 | 0.48 | −0.3 | HYPOMETHYLATION |
| NFATC1 | chr18 | 75385424 | 75386008 | chr18: 75385279-75386532 | 0.23 | 0.14 | 0.84 | 0.7 | HYPERMETHYLATION |
| CTDP1 | chr18 | 75596358 | 75596579 | chr18: 75596009-75596899 | 0.07 | 0.97 | 0.96 | −0.01 | NOT CONFIRMED |
| chr18 group00430 | chr18 | 75653272 | 75653621 | : — | 0.52 | 0.24 | 0.62 | 0.39 | HYPERMETHYLATION |
| KCNG2 | chr18 | 75760343 | 75760820 | chr18: 75759900-75760988 | 0.01 | 0.84 | 0.75 | −0.09 | NOT CONFIRMED |
| OLIG2 | chr21 | 33317673 | 33321183 | chr21: 33316998-33322115 | 0.66 | 0.11 | 0.2 | 0.09 | HYPERMETHYLATION |
| OLIG2 | chr21 | 33327593 | 33328334 | chr21: 33327447-33328408 | −0.75 | 0.77 | 0.28 | −0.49 | HYPOMETHYLATION |
| RUNX1 | chr21 | 35180938 | 35185436 | chr21: 35180822-35181342; chr21: 35182320-35185557 | −0.68 | 0.14 | 0.07 | −0.07 | HYPOMETHYLATION |
| SIM2 | chr21 | 36994965 | 36995298 | chr21: 36990063-36995761 | 0.83 | 0.08 | 0.26 | 0.18 | HYPERMETHYLATION |
| SIM2 | chr21 | 36999025 | 36999410 | chr21: 36998632-36999555 | 0.87 | 0.06 | 0.24 | 0.18 | HYPERMETHYLATION |
| DSCR6 | chr21 | 37300407 | 37300512 | chr21: 37299807-37301307 | 0.22 | 0.04 | 0.14 | 0.11 | HYPERMETHYLATION |
| DSCAM | chr21 | 41135559 | 41135706 | chr21: 41135380-41135816 | 1.03 | 0.06 | 0.29 | 0.23 | HYPERMETHYLATION |
| chr21 group00165 | chr21 | 43643421 | 43643786 | chr21: 43643322-43643874 | 1.14 | 0.16 | 0.81 | 0.65 | HYPERMETHYLATION |
| AIRE | chr21 | 44529935 | 44530388 | chr21: 44529856-44530472 | −0.55 | 0.62 | 0.27 | −0.35 | HYPOMETHYLATION |

TABLE 1A-continued

| GENE NAME | CHROM | START | END | CpG ISLAND | MEAN LOG RATIO MICRO-ARRAY | MEAN MATERNAL METHYLATION EPITYPER | MEAN PLACENTA METHYLATION EPITYPER | METHYLATION DIFFERENCE PLACENTA-MATERNAL | RELATIVE METHYLATION PLACENTA TO MATERNAL |
|---|---|---|---|---|---|---|---|---|---|
| SUMO3 | chr21 | 45061293 | 45061853 | chr21: 45061154-45063386 | −0.41 | 0.55 | 0.46 | −0.09 | HYPOMETHYLATION |
| C21orf70 | chr21 | 45202815 | 45202972 | chr21: 45202706-45203073 | −0.46 | 0.96 | 0.51 | −0.46 | HYPOMETHYLATION |
| C21orf123 | chr21 | 45671984 | 45672098 | chr21: 45671933-45672201 | −0.63 | 0.92 | 0.43 | −0.49 | HYPOMETHYLATION |
| COL18A1 | chr21 | 45754383 | 45754487 | chr21: 45753653-45754639 | −0.18 | 0.97 | 0.72 | −0.25 | HYPOMETHYLATION |
| PRMT2 | chr21 | 46911967 | 46912385 | chr21: 46911628-46912534 | 1.08 | 0.04 | 0.25 | 0.21 | HYPERMETHYLATION |
| SIX2 | chr2 | 45081223 | 45082129 | chr2: 45081148-45082287 | 1.15 | 0.08 | 0.36 | 0.28 | HYPERMETHYLATION |
| SIX2 | chr2 | 45084851 | 45085711 | chr2: 45084715-45084986; chr2: 45085285-45086054 | 1.21 | 0.07 | 0.35 | 0.28 | HYPERMETHYLATION |
| SOX14 | chr3 | 138971870 | 138972322 | chr3: 138971738-138972096; chr3: 138972281-138973691 | 1.35 | 0.08 | 0.33 | 0.25 | HYPERMETHYLATION |
| TLX3 | chr5 | 170674439 | 170676431 | chr5: 170674208-170675356; chr5: 170675783-170676712 | 0.91 | 0.11 | 0.35 | 0.24 | HYPERMETHYLATION |
| FOXP4 | chr6 | 41623666 | 41624114 | chr6: 41621630-41624167 | 1.1 | 0.07 | 0.27 | 0.2 | HYPERMETHYLATION |
| FOXP4 | chr6 | 41636384 | 41636779 | chr6: 41636244-41636878 | 1.32 | 0.04 | 0.33 | 0.29 | HYPERMETHYLATION |
| chr7 group00267 | chr7 | 12576755 | 12577246 | chr7: 12576690-12577359 | 0.94 | 0.08 | 0.26 | 0.17 | HYPERMETHYLATION |
| NPY | chr7 | 24290224 | 24291508 | chr7: 24290083-24291605 | 0.93 | 0.09 | 0.3 | 0.21 | HYPERMETHYLATION |
| SHH | chr7 | 155291537 | 155292091 | chr7: 155288453-155292175 | 0.98 | 0.19 | 0.52 | 0.33 | HYPERMETHYLATION |
| OSR2 | chr8 | 100029764 | 100030536 | chr8: 100029673-100030614 | 1.21 | 0.08 | 0.43 | 0.35 | HYPERMETHYLATION |
| GLIS3 | chr9 | 4288283 | 4289645 | chr9: 4287817-4290182 | 1.24 | 0.06 | 0.24 | 0.18 | HYPERMETHYLATION |
| PRMT8 | chr12 | 3472714 | 3473190 | chr12: 3470227-3473269 | 0.86 | 0.07 | 0.23 | 0.16 | HYPERMETHYLATION |
| TBX3 | chr12 | 113609153 | 113609453 | chr12: 113609112-113609535 | 1.45 | 0.09 | 0.56 | 0.48 | HYPERMETHYLATION |
| chr12 group00801 | chr12 | 118516189 | 118517435 | chr12: 118515877-118517595 | 1.1 | 0.06 | 0.25 | 0.19 | HYPERMETHYLATION |
| PAX9 | chr14 | 36201402 | 36202386 | chr14: 36200932-36202536 | 0.89 | 0.11 | 0.32 | 0.21 | HYPERMETHYLATION |
| SIX1 | chr14 | 60178801 | 60179346 | chr14: 60178707-60179539 | 0.95 | 0.1 | 0.33 | 0.22 | HYPERMETHYLATION |
| ISL2 | chr15 | 74420013 | 74421546 | chr15: 74419317-74422570 | 1.08 | 0.08 | 0.27 | 0.19 | HYPERMETHYLATION |
| DLX4 | chr17 | 45397228 | 45397930 | chr17: 45396281-45398063 | 1.25 | 0.1 | 0.32 | 0.22 | HYPERMETHYLATION |
| CBX4 | chr17 | 75428613 | 75431793 | chr17: 75427586-75433676 | 1 | 0.07 | 0.27 | 0.21 | HYPERMETHYLATION |
| EDG6 | chr19 | 3129836 | 3130874 | chr19: 3129741-3130986 | 1.35 | 0.04 | 0.87 | 0.83 | HYPERMETHYLATION |
| PRRT3 | chr3 | 9963364 | 9964023 | chr3: 9962895-9964619 | −0.85 | 0.9 | 0.09 | −0.81 | HYPOMETHYLATION |
| MGC29506 | chr5 | 138757911 | 138758724 | chr5: 138755609-138758810 | −0.63 | 0.93 | 0.17 | −0.76 | HYPOMETHYLATION |
| TEAD3 | chr6 | 35561812 | 35562252 | chr6: 35561754-35562413 | −1.17 | 0.92 | 0.13 | −0.8 | HYPOMETHYLATION |
| chr12 group00022 | chr12 | 1642456 | 1642708 | chr12: 1642195-1642774 | −1.33 | 0.66 | 0.09 | −0.57 | HYPOMETHYLATION |
| CENTG1 | chr12 | 56406249 | 56407788 | chr12: 56406176-56407818 | −1.07 | 0.95 | 0.19 | −0.77 | HYPOMETHYLATION |
| CENTG1 | chr12 | 56416146 | 56418794 | chr12: 56416095-56416628; chr12: 56418745-56419001 | −0.94 | 0.85 | 0.16 | −0.69 | HYPOMETHYLATION |

Information in Table 1A based on the March 2006 human reference sequence (NCBI Build 36.1), which was produced by the International Human Genome Sequencing Consortium.

TABLE 1B

Non-Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| TFAP2E | Intron | chr1 | 35815000 | 35816200 | YES | YES | NO | NO | Hypermethylation |
| LRRC8D | Intron/Exon | chr1 | 90081350 | 90082250 | YES | YES | NO | NO | Hypermethylation |
| TBX15 | Promoter | chr1 | 119333500 | 119333700 | YES | YES | NO | NO | Hypermethylation |
| C1orf51 | Upstream | chr1 | 148520900 | 148521300 | YES | YES | NO | NO | Hypermethylation |
| chr1: 179553900-179554600 | Intergenic | chr1 | 179553900 | 179554600 | YES | YES | NO | NO | Hypermethylation |
| ZFP36L2 | Exon | chr2 | 43304900 | 43305100 | YES | YES | NO | NO | Hypermethylation |
| SIX2 | Downstream | chr2 | 45081000 | 45086000 | YES | YES | NO | YES | Hypermethylation |
| chr2: 137238500-137240000 | Intergenic | chr2 | 137238500 | 137240000 | YES | YES | NO | NO | Hypermethylation |
| MAP1D | Intron/Exon | chr2 | 172652800 | 172653600 | YES | YES | NO | NO | Hypermethylation |
| WNT6 | Intron | chr2 | 219444250 | 219444290 | YES | YES | NO | NO | Hypermethylation |
| INPP5D | Promoter | chr2 | 233633200 | 233633700 | YES | YES | YES | NO | Hypermethylation |
| chr2: 241211100-241211600 | Intergenic | chr2 | 241211100 | 241211600 | YES | YES | YES | NO | Hypermethylation |
| WNT5A | Intron | chr3 | 55492550 | 55492850 | YES | YES | NO | NO | Hypermethylation |
| chr3: 138971600-138972200 | Intergenic | chr3 | 138971600 | 138972200 | YES | YES | YES | YES | Hypermethylation |
| ZIC4 | Intron | chr3 | 148598200 | 148599000 | YES | YES | NO | NO | Hypermethylation |
| FGF12 | Intron/Exon | chr3 | 193608500 | 193610500 | YES | YES | NO | NO | Hypermethylation |
| GP5 | Exon | chr3 | 195598400 | 195599200 | YES | YES | NO | NO | Hypermethylation |
| MSX1 | Upstream | chr4 | 4910550 | 4911100 | YES | YES | NO | NO | Hypermethylation |
| NKX3-2 | Intron/Exon | chr4 | 13152500 | 13154500 | YES | YES | NO | NO | Hypermethylation |
| chr4: 111752000-111753000 | Intergenic | chr4 | 111752000 | 111753000 | YES | YES | YES | NO | Hypermethylation |
| SFRP2 | Promoter | chr4 | 154928800 | 154930100 | YES | YES | NO | NO | Hypermethylation |
| chr4: 174664300-174664800 | Intergenic | chr4 | 174664300 | 174664800 | YES | YES | NO | NO | Hypermethylation |
| chr4: 174676300-174676800 | Intergenic | chr4 | 174676300 | 174676800 | YES | YES | NO | NO | Hypermethylation |
| SORBS2 | Intron | chr4 | 186796900 | 186797500 | YES | YES | NO | NO | Hypermethylation |
| chr5: 42986900-42988200 | Intergenic | chr5 | 42986900 | 42988200 | YES | YES | NO | NO | Hypermethylation |
| chr5: 72712000-72714100 | Intergenic | chr5 | 72712000 | 72714100 | YES | YES | NO | NO | Hypermethylation |
| chr5: 72767550-72767800 | Intergenic | chr5 | 72767550 | 72767800 | YES | YES | NO | NO | Hypermethylation |
| NR2F1 | Intron/Exon | chr5 | 92955000 | 92955250 | YES | YES | NO | NO | Hypermethylation |
| PCDHGA1 | Intron | chr5 | 140850500 | 140852500 | YES | YES | YES | NO | Hypermethylation |
| chr6: 10489100-10490200 | Intergenic | chr6 | 10489100 | 10490200 | YES | YES | YES | NO | Hypermethylation |
| FOXP4 | Intron | chr6 | 41636200 | 41637000 | YES | YES | NO | YES | Hypermethylation |
| chr7: 19118400-19118700 | Intergenic | chr7 | 19118400 | 19118700 | YES | YES | NO | NO | Hypermethylation |
| chr7: 27258000-27258400 | Intergenic | chr7 | 27258000 | 27258400 | YES | YES | NO | NO | Hypermethylation |
| TBX20 | Upstream | chr7 | 35267500 | 35268300 | YES | YES | NO | NO | Hypermethylation |
| AGBL3 | Promoter | chr7 | 134321300 | 134322300 | YES | YES | NO | NO | Hypermethylation |
| XPO7 | Downstream | chr8 | 21924000 | 21924300 | YES | YES | NO | NO | Hypermethylation |
| chr8: 41543400-41544000 | Intergenic | chr8 | 41543400 | 41544000 | YES | YES | NO | NO | Hypermethylation |
| GDF6 | Exon | chr8 | 97225400 | 97227100 | YES | YES | NO | NO | Hypermethylation |
| OSR2 | Intron/Exon | chr8 | 100029000 | 100031000 | YES | YES | YES | YES | Hypermethylation |
| GLIS3 | Intron/Exon | chr9 | 4288000 | 4290000 | YES | YES | NO | YES | Hypermethylation |
| NOTCH1 | Intron | chr9 | 138547600 | 138548400 | YES | YES | YES | NO | Hypermethylation |
| EGFL7 | Upstream | chr9 | 138672350 | 138672850 | YES | YES | NO | NO | Hypermethylation |
| CELF2 | Intron/Exon | chr10 | 11246700 | 11247900 | YES | YES | NO | NO | Hypermethylation |
| HHEX | Intron | chr10 | 94441000 | 94441800 | YES | YES | NO | NO | Hypermethylation |
| DOCK1/FAM196A | Intron/Exon | chr10 | 128883000 | 128883500 | YES | YES | NO | NO | Hypermethylation |
| PAX6 | Intron | chr11 | 31782400 | 31783500 | YES | YES | NO | NO | Hypermethylation |
| FERMT3 | Intron/Exon | chr11 | 63731200 | 63731700 | YES | YES | YES | NO | Hypermethylation |
| PKNOX2 | Intron | chr11 | 124541200 | 124541800 | YES | YES | NO | NO | Hypermethylation |
| KIRREL3 | Intron | chr11 | 126375150 | 126375300 | YES | YES | NO | NO | Hypermethylation |
| BCAT1 | Intron | chr12 | 24946700 | 24947600 | YES | YES | NO | NO | Hypermethylation |
| HOXC13 | Intron/Exon | chr12 | 52625000 | 52625600 | YES | YES | NO | NO | Hypermethylation |
| TBX5 | Promoter | chr12 | 113330500 | 113332000 | YES | YES | NO | NO | Hypermethylation |
| TBX3 | Upstream | chr12 | 113609000 | 113609500 | YES | YES | NO | YES | Hypermethylation |
| chr12: 113622100-113623000 | Intergenic | chr12 | 113622100 | 113623000 | YES | YES | YES | NO | Hypermethylation |

TABLE 1B-continued

Non-Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| chr12: 113657800-113658300 | Intergenic | chr12 | 113657800 | 113658300 | YES | YES | NO | NO | Hypermethylation |
| THEM233 | Promoter | chr12 | 118515500 | 118517500 | YES | YES | NO | YES | Hypermethylation |
| NCOR2 | Intron/Exon | chr12 | 123516200 | 123516800 | YES | YES | YES | NO | Hypermethylation |
| THEM132C | Intron | chr12 | 127416300 | 127416700 | YES | YES | NO | NO | Hypermethylation |
| PTGDR | Promoter | chr14 | 51804000 | 51805200 | YES | YES | NO | NO | Hypermethylation |
| ISL2 | Intron/Exon | chr15 | 74420000 | 74422000 | YES | YES | NO | YES | Hypermethylation |
| chr15: 87750000-87751000 | Intergenic | chr15 | 87750000 | 87751000 | YES | YES | NO | NO | Hypermethylation |
| chr15: 87753000-87754100 | Intergenic | chr15 | 87753000 | 87754100 | YES | YES | NO | NO | Hypermethylation |
| NR2F2 | Upstream | chr15 | 94666000 | 94667500 | YES | YES | YES | NO | Hypermethylation |
| chr16: 11234300-11234900 | Intergenic | chr16 | 11234300 | 11234900 | YES | YES | NO | NO | Hypermethylation |
| SPN | Exon | chr16 | 29582800 | 29583500 | YES | YES | YES | NO | Hypermethylation |
| chr16: 85469900-85470200 | Intergenic | chr16 | 85469900 | 85470200 | YES | YES | NO | NO | Hypermethylation |
| SLFN11 | Promoter | chr17 | 30725100 | 30725600 | YES | YES | NO | NO | Hypermethylation |
| DLX4 | Upstream | chr17 | 45396800 | 45397800 | YES | YES | NO | YES | Hypermethylation |
| SLC38A10 (MGC15523) | Intron | chr17 | 76873800 | 76874300 | YES | YES | YES | NO | Hypermethylation |
| S1PR4 | Exon | chr19 | 3129900 | 3131100 | YES | YES | YES | YES | Hypermethylation |
| MAP2K2 | Intron | chr19 | 4059700 | 4060300 | YES | YES | YES | NO | Hypermethylation |
| UHRF1 | Intron | chr19 | 4867300 | 4867800 | YES | YES | YES | NO | Hypermethylation |
| DEDD2 | Exon | chr19 | 47395300 | 47395900 | YES | YES | YES | NO | Hypermethylation |
| CDC42EP1 | Exon | chr22 | 36292300 | 36292800 | YES | YES | YES | NO | Hypermethylation |

TABLE 1C

Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| chr21: 9906600-9906800 | Intergenic | chr21 | 9906600 | 9906800 | NO | YES | NO | NO | Hypomethylation |
| chr21: 9907000-9907400 | Intergenic | chr21 | 9907000 | 9907400 | NO | YES | NO | NO | Hypomethylation |
| chr21: 9917800-9918450 | Intergenic | chr21 | 9917800 | 9918450 | NO | YES | NO | NO | Hypomethylation |
| TPTE | Promoter | chr21 | 10010000 | 10015000 | NO | YES | NO | NO | Hypomethylation |
| chr21: 13974500-13976000 | Intergenic | chr21 | 13974500 | 13976000 | NO | YES | NO | NO | Hypomethylation |
| chr21: 13989500-13992000 | Intergenic | chr21 | 13989500 | 13992000 | NO | YES | NO | NO | Hypomethylation |
| chr21: 13998500-14000100 | Intergenic | chr21 | 13998500 | 14000100 | NO | YES | NO | NO | Hypomethylation |
| chr21: 14017000-14018500 | Intergenic | chr21 | 14017000 | 14018500 | NO | YES | NO | NO | Hypomethylation |
| chr21: 14056400-14058100 | Intergenic | chr21 | 14056400 | 14058100 | NO | YES | NO | NO | Hypomethylation |
| chr21: 14070250-14070550 | Intergenic | chr21 | 14070250 | 14070550 | NO | YES | NO | NO | Hypomethylation |
| chr21: 14119800-14120400 | Intergenic | chr21 | 14119800 | 14120400 | NO | YES | NO | NO | Hypomethylation |
| chr21: 14304800-14306100 | Intergenic | chr21 | 14304800 | 14306100 | NO | YES | NO | NO | Hypomethylation |
| chr21: 15649340-15649450 | Intergenic | chr21 | 15649340 | 15649450 | NO | YES | YES | NO | Hypermethylation |
| C21orf34 | Intron | chr21 | 16881500 | 16883000 | NO | YES | NO | NO | Hypomethylation |
| BTG3 | Intron | chr21 | 17905300 | 17905500 | NO | YES | NO | NO | Hypomethylation |
| CHODL | Promoter | chr21 | 18539000 | 18539800 | NO | YES | YES | NO | Hypermethylation |
| NCAM2 | Upstream | chr21 | 21291500 | 21292100 | NO | YES | NO | NO | Hypermethylation |
| chr21: 23574000-23574600 | Intergenic | chr21 | 23574000 | 23574600 | NO | YES | NO | NO | Hypomethylation |
| chr21: 24366920-24367060 | Intergenic | chr21 | 24366920 | 24367060 | NO | YES | NO | NO | Hypomethylation |
| chr21: 25656000-25656900 | Intergenic | chr21 | 25656000 | 25656900 | NO | YES | NO | NO | Hypomethylation |
| MIR155HG | Promoter | chr21 | 25855800 | 25857200 | NO | YES | YES | NO | Hypermethylation |
| CYYR1 | Intron | chr21 | 26830750 | 26830950 | NO | YES | NO | NO | Hypomethylation |
| chr21: 26938800-26939200 | Intergenic | chr21 | 26938800 | 26939200 | NO | YES | NO | NO | Hypomethylation |
| GRIK1 | Intron | chr21 | 30176500 | 30176750 | NO | YES | NO | NO | Hypomethylation |
| chr21: 30741350-30741600 | Intergenic | chr21 | 30741350 | 30741600 | NO | YES | NO | NO | Hypermethylation |
| TIAM1 | Intron | chr21 | 31426800 | 31427300 | NO | YES | YES | NO | Hypermethylation |
| TIAM1 | Intron | chr21 | 31475300 | 31475450 | NO | YES | NO | NO | Hypermethylation |
| TIAM1 | Intron | chr21 | 31621050 | 31621350 | NO | YES | YES | NO | Hypermethylation |
| SOD1 | Intron | chr21 | 31955000 | 31955300 | NO | YES | NO | NO | Hypomethylation |
| HUNK | Intron/Exon | chr21 | 32268700 | 32269100 | NO | YES | YES | NO | Hypermethylation |
| chr21: 33272200-33273300 | Intergenic | chr21 | 33272200 | 33273300 | NO | YES | NO | NO | Hypomethylation |
| OLIG2 | Promoter | chr21 | 33314000 | 33324000 | YES | YES | NO | YES | Hypermethylation |
| OLIG2 | Downstream | chr21 | 33328000 | 33328500 | YES | YES | NO | NO | Hypomethylation |
| RUNX1 | Intron | chr21 | 35185000 | 35186000 | NO | YES | NO | NO | Hypomethylation |

TABLE 1C-continued

Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| RUNX1 | Intron | chr21 | 35320300 | 35320400 | NO | YES | NO | NO | Hypermethylation |
| RUNX1 | Intron | chr21 | 35321200 | 35321600 | NO | YES | NO | NO | Hypermethylation |
| RUNX1 | Intron/Exon | chr21 | 35340000 | 35345000 | NO | YES | YES | NO | Hypermethylation |
| chr21: 35499200-35499700 | Intergenic | chr21 | 35499200 | 35499700 | NO | YES | YES | NO | Hypermethylation |
| chr21: 35822800-35823500 | Intergenic | chr21 | 35822800 | 35823500 | NO | YES | YES | NO | Hypermethylation |
| CBR1 | Promoter | chr21 | 36364000 | 36364500 | NO | YES | NO | NO | Hypermethylation |
| DOPEY2 | Downstream | chr21 | 36589000 | 36590500 | NO | YES | NO | NO | Hypomethylation |
| SIM2 | Promoter | chr21 | 36988000 | 37005000 | YES | YES | YES | YES | Hypermethylation |
| HLCS | Intron | chr21 | 37274000 | 37275500 | YES | YES | YES | NO | Hypermethylation |
| DSCR6 | Upstream | chr21 | 37300200 | 37300400 | YES | YES | NO | YES | Hypermethylation |
| DSCR3 | Intron | chr21 | 37551000 | 37553000 | YES | YES | YES | NO | Hypermethylation |
| chr21: 37841100-37841800 | Intergenic | chr21 | 37841100 | 37841800 | NO | YES | YES | NO | Hypermethylation |
| ERG | Intron | chr21 | 38791400 | 38792000 | NO | YES | YES | NO | Hypermethylation |
| chr21: 39278700-39279800 | Intergenic | chr21 | 39278700 | 39279800 | NO | YES | YES | NO | Hypermethylation |
| C21orf129 | Exon | chr21 | 42006000 | 42006250 | NO | YES | YES | NO | Hypermethylation |
| C2CD2 | Intron | chr21 | 42188900 | 42189500 | NO | YES | YES | NO | Hypermethylation |
| UMODL1 | Upstream | chr21 | 42355500 | 42357500 | NO | YES | YES | NO | Hypermethylation |
| UMODL1/C21orf128 | Intron | chr21 | 42399200 | 42399900 | NO | YES | NO | NO | Hypomethylation |
| ABCG1 | Intron | chr21 | 42528400 | 42528600 | YES | YES | NO | NO | Hypomethylation |
| chr21: 42598300-42599600 | Intergenic | chr21 | 42598300 | 42599600 | YES | YES | NO | NO | Hypomethylation |
| chr21: 42910000-42911000 | Intergenic | chr21 | 42910000 | 42911000 | NO | YES | NO | NO | Hypomethylation |
| PDE9A | Upstream | chr21 | 42945500 | 42946000 | NO | YES | NO | NO | Hypomethylation |
| PDE9A | Intron | chr21 | 42961400 | 42962700 | NO | YES | NO | NO | Hypomethylation |
| PDE9A | Intron | chr21 | 42977400 | 42977600 | NO | YES | NO | NO | Hypermethylation |
| PDE9A | Intron/Exon | chr21 | 42978200 | 42979800 | YES | YES | NO | NO | Hypomethylation |
| PDE9A | Intron | chr21 | 43039800 | 43040200 | NO | YES | YES | NO | Hypermethylation |
| chr21: 43130800-43131500 | Intergenic | chr21 | 43130800 | 43131500 | NO | YES | NO | NO | Hypomethylation |
| U2AF1 | Intron | chr21 | 43395500 | 43395800 | NO | YES | NO | NO | Hypermethylation |
| U2AF1 | Intron | chr21 | 43398000 | 43398450 | NO | YES | YES | NO | Hypermethylation |
| chr21: 43446600-43447600 | Intergenic | chr21 | 43446600 | 43447600 | NO | YES | NO | NO | Hypomethylation |
| CRYAA | Intron/Exon | chr21 | 43463000 | 43466100 | NO | YES | NO | NO | Hypomethylation |
| chr21: 43545000-43546000 | Intergenic | chr21 | 43545000 | 43546000 | YES | YES | NO | NO | Hypomethylation |
| chr21: 43606000-43606500 | Intergenic | chr21 | 43606000 | 43606500 | NO | YES | NO | NO | Hypomethylation |
| chr21: 43643000-43644300 | Intergenic | chr21 | 43643000 | 43644300 | YES | YES | YES | YES | Hypermethylation |
| C21orf125 | Upstream | chr21 | 43689100 | 43689300 | NO | YES | NO | NO | Hypermethylation |
| C21orf125 | Downstream | chr21 | 43700700 | 43701700 | NO | YES | NO | NO | Hypermethylation |
| HSF2BP | Intron/Exon | chr21 | 43902500 | 43903800 | YES | YES | NO | NO | Hypomethylation |
| AGPAT3 | Intron | chr21 | 44161100 | 44161400 | NO | YES | YES | NO | Hypermethylation |
| chr21: 44446500-44447500 | Intergenic | chr21 | 44446500 | 44447500 | NO | YES | NO | NO | Hypomethylation |
| TRPM2 | Intron | chr21 | 44614500 | 44615000 | NO | YES | NO | NO | Hypomethylation |
| C21orf29 | Intron | chr21 | 44750400 | 44751000 | NO | YES | NO | NO | Hypomethylation |
| C21orf29 | Intron | chr21 | 44950000 | 44955000 | NO | YES | YES | NO | Hypermethylation |
| ITGB2 | Intron/Exon | chr21 | 45145500 | 45146100 | NO | YES | NO | NO | Hypomethylation |
| POFUT2 | Downstream | chr21 | 45501000 | 45503000 | NO | YES | NO | NO | Hypomethylation |
| chr21: 45571500-45573700 | Intergenic | chr21 | 45571500 | 45573700 | NO | YES | NO | NO | Hypomethylation |
| chr21: 45609000-45610600 | Intergenic | chr21 | 45609000 | 45610600 | NO | YES | NO | NO | Hypomethylation |
| COL18A1 | Intron | chr21 | 45670000 | 45677000 | YES | YES | NO | YES | Hypomethylation |
| COL18A1 | Intron/Exon | chr21 | 45700500 | 45702000 | NO | YES | NO | NO | Hypomethylation |
| COL18A1 | Intron/Exon | chr21 | 45753000 | 45755000 | YES | YES | NO | YES | Hypomethylation |
| chr21: 45885000-45887000 | Intergenic | chr21 | 45885000 | 45887000 | NO | YES | NO | NO | Hypomethylation |
| PCBP3 | Intron | chr21 | 46111000 | 46114000 | NO | YES | NO | NO | Hypomethylation |
| PCBP3 | Intron/Exon | chr21 | 46142000 | 46144500 | NO | YES | NO | NO | Hypomethylation |
| COL6A1 | Intron/Exon | chr21 | 46227000 | 46233000 | NO | YES | NO | NO | Hypomethylation |
| COL6A1 | Intron/Exon | chr21 | 46245000 | 46252000 | NO | YES | NO | NO | Hypomethylation |
| chr21: 46280500-46283000 | Intergenic | chr21 | 46280500 | 46283000 | NO | YES | NO | NO | Hypomethylation |
| COL6A2 | Intron | chr21 | 46343500 | 46344200 | NO | YES | NO | NO | Hypomethylation |
| COL6A2 | Intron/Exon | chr21 | 46368000 | 46378000 | NO | YES | NO | NO | Hypomethylation |
| C21orf56 | Intron/Exon | chr21 | 46426700 | 46427500 | NO | YES | NO | NO | Hypomethylation |
| C21orf57 | Intron | chr21 | 46541568 | 46541861 | NO | YES | NO | NO | Hypermethylation |
| C21orf57 | Exon | chr21 | 46541872 | 46542346 | NO | YES | NO | NO | Hypermethylation |
| C21orf57 | Downstream | chr21 | 46542319 | 46542665 | NO | YES | NO | NO | Hypermethylation |
| C21orf58 | Intron | chr21 | 46546914 | 46547404 | NO | YES | NO | NO | Hypomethylation |
| PRMT2 | Downstream | chr21 | 46911000 | 46913000 | YES | YES | NO | YES | Hypermethylation |
| ITGB2 | Intron | chr21 | 45170700 | 45171100 | NO | YES | YES | NO | Hypermethylation |

TABLE 2

| GENE NAME | CHROM | START | END | SNPs |
|---|---|---|---|---|
| chr13 group00016 | chr13 | 19773745 | 19774050 | rs7996310; rs12870878 |
| chr13 group00005 | chr13 | 19290394 | 19290768 | rs11304938 |
| CENPJ | chr13 | 24404023 | 24404359 | rs7326661 |
| ATP8A2 | chr13 | 25484475 | 25484614 | rs61947088 |
| PDX1 | chr13 | 27400459 | 27401165 | rs58173592; rs55836809; rs61944011 |
| RB1 | chr13 | 47790983 | 47791646 | rs2804094; rs4151432; rs4151433; rs4151434; rs4151435 |
| PCDH17 | chr13 | 57104856 | 57106841 | rs35287822; rs34642962; rs41292834; rs45500496; rs45571031; rs41292836; rs28374395; rs41292838 |
| KLHL1 | chr13 | 69579933 | 69580146 | rs3751429 |
| POU4F1 | chr13 | 78079515 | 78081073 | rs11620410; rs35794447; rs2765065 |
| GPC6 | chr13 | 92677402 | 92678666 | rs35689696; rs11839555; rs55695812; rs35259892 |
| SOX21 | chr13 | 94152286 | 94153047 | rs41277652; rs41277654; rs35276096; rs5805873; rs35109406 |
| ZIC2 | chr13 | 99439660 | 99440858 | rs9585309; rs35501321; rs9585310; rs7991728; rs1368511 |
| IRS2 | chr13 | 109232856 | 109235065 | rs61747993; rs1805097; rs9583424; rs35927012; rs1056077; rs1056078; rs34889228; rs1056080; rs1056081; rs12853546; rs4773092; rs35223808; rs35894564; rs3742210; rs34412495; rs61962699; rs45545638; rs61743905 |
| chr13 group00395 | chr13 | 111808255 | 111808962 | rs930346 |
| MCF2L | chr13 | 112724910 | 112725742 | rs35661110; rs2993304; rs1320519; rs7320418; rs58416100 |
| F7 | chr13 | 112799123 | 112799379 | rs2480951; rs2476320 |
| CIDEA | chr18 | 12244327 | 12244696 | rs60132277 |
| chr18 group00091 | chr18 | 12901467 | 12901643 | rs34568924; rs8094284; rs8094285 |
| C18orf1 | chr18 | 13377536 | 13377654 | rs9957861 |
| KLHL14 | chr18 | 28603978 | 28605183 | rs61737323; rs61737324; rs12960414 |
| CD33L3 | chr18 | 41671477 | 41673011 | rs62095363; rs2919643 |
| ONECUT2 | chr18 | 53254808 | 53259810 | rs35685953; rs61735644; rs8084084; rs35937482; rs35427632; rs7232930; rs3786486; rs34286480; rs3786485; rs28655657; rs4940717; rs4940719; rs3786484; rs34040569; rs35542747; rs33946478; rs35848049; rs7231349; rs7231354; rs34481218; rs12962172; rs3911641 |
| RAX | chr18 | 55086286 | 55086436 | rs58797899; rs45501496 |
| chr18 group00277 | chr18 | 57151972 | 57152311 | rs17062547 |
| TNFRSF11A | chr18 | 58203013 | 58203282 | rs35114461 |
| NETO1 | chr18 | 68685099 | 68687060 | rs4433898; rs34497518; rs35135773; rs6566677; rs57425572; rs36026929; rs34666288; rs10627137; rs35943684; rs9964226; rs4892054; rs9964397; rs4606820; rs12966677; rs8095606 |
| chr18 group00304 | chr18 | 70133945 | 70134397 | rs8086706; rs8086587; rs8090367; rs999332; rs17806420; rs58811193 |
| TSHZ1 | chr18 | 71128742 | 71128974 | rs61732783; rs3744910; rs1802180 |
| chr18 group00342 | chr18 | 74170347 | 74170489 | rs7226678 |
| NFATC1 | chr18 | 75385424 | 75386008 | rs28446281; rs56384153; rs4531815; rs3894049 |
| chr18 group00430 | chr18 | 75653272 | 75653621 | rs34967079; rs35465647 |
| KCNG2 | chr18 | 75760343 | 75760820 | rs3744887; rs3744886 |
| OLIG2 | chr21 | 33317673 | 33321183 | rs2236618; rs11908971; rs9975039; rs6517135; rs2009130; rs1005573; rs1122807; rs10653491; rs10653077; rs35086972; rs28588289; rs7509766; rs62216114; rs35561747; rs7509885; rs11547332 |
| OLIG2 | chr21 | 33327593 | 33328334 | rs7276788; rs7275842; rs7275962; rs7276232; rs16990069; rs13051692; rs56231743; rs35931056 |
| RUNX1 | chr21 | 35180938 | 35185436 | rs2843956; rs55941652; rs56020428; rs56251824; rs13051109; rs13051111; rs3833348; rs7510136; rs743289; rs5843690; rs33915227; rs11402829; rs2843723; rs8128138; rs8131386; rs2843957; rs57537540; rs13048584; rs7281361; rs2843965; rs2843958 |
| SIM2 | chr21 | 36994965 | 36995298 | rs2252821 |
| SIM2 | chr21 | 36999025 | 36999410 | rs58347144; rs737380 |
| DSCAM | chr21 | 41135559 | 41135706 | rs35298822 |
| AIRE | chr21 | 44529935 | 44530388 | rs35110251; rs751032; rs9978641 |
| SUMO3 | chr21 | 45061293 | 45061853 | rs9979741; rs235337; rs7282882 |
| C21orf70 | chr21 | 45202815 | 45202972 | rs61103857; rs9979028; rs881318; rs881317 |
| COL18A1 | chr21 | 45754383 | 45754487 | rs35102708; rs9980939 |
| PRMT2 | chr21 | 46911967 | 46912385 | rs35481242; rs61743122; rs8131044; rs2839379 |
| SIX2 | chr2 | 45081223 | 45082129 | rs62130902 |
| SIX2 | chr2 | 45084851 | 45085711 | rs35417092; rs57340219 |
| SOX14 | chr3 | 138971870 | 138972322 | rs57343003 |
| TLX3 | chr5 | 170674439 | 170676431 | rs11134682; rs35704956; rs2964533; rs35601828 |
| FOXP4 | chr6 | 41623666 | 41624114 | rs12203107; rs1325690 |
| FOXP4 | chr6 | 41636384 | 41636779 | rs56835416 |
| chr7 group00267 | chr7 | 12576755 | 12577246 | rs56752985; rs17149965; rs6948573; rs2240572 |
| NPY | chr7 | 24290224 | 24291508 | rs2390965; rs2390966; rs2390967; rs2390968; rs3025123; rs16146; rs16145; rs16144; rs13235842; rs13235935; rs13235938; rs13235940; rs13235944; rs36083509; rs3025122; rs16143; rs16478; rs16142; rs16141; rs16140; rs16139; rs2229966; rs1042552; rs5571; rs5572 |
| SHH | chr7 | 155291537 | 155292091 | rs9333622; rs1233554; rs9333620; rs1233555 |
| GLIS3 | chr9 | 4288283 | 4289645 | rs56728573; rs12340657; rs12350099; rs35338539; rs10974444; rs7852293 |
| PRMT8 | chr12 | 3472714 | 3473190 | rs12172776 |

TABLE 2-continued

| GENE NAME | CHROM | START | END | SNPs |
|---|---|---|---|---|
| TBX3 | chr12 | 113609153 | 113609453 | rs60114979 |
| chr12 group00801 | chr12 | 118516189 | 118517435 | rs966246; rs17407022; rs970095; rs2711748 |
| PAX9 | chr14 | 36201402 | 36202386 | rs17104893; rs12883298; rs17104895; rs35510737; rs12882923; rs12883049; rs28933970; rs28933972; rs28933971; rs28933373; rs61734510 |
| SIX1 | chr14 | 60178801 | 60179346 | rs761555 |
| ISL2 | chr15 | 74420013 | 74421546 | rs34173230; rs11854453 |
| DLX4 | chr17 | 45397228 | 45397930 | rs62059964; rs57481357; rs56888011; rs17638215; rs59056690; rs34601685; rs17551082 |
| CBX4 | chr17 | 75428613 | 75431793 | rs1285243; rs35035500; rs12949177; rs3764374; rs62075212; rs62075213; rs3764373; rs3764372; rs55973291 |
| EDG6 | chr19 | 3129836 | 3130874 | rs34728133; rs34573539; rs3826936; rs34914134; rs61731111; rs34205484 |
| MGC29506 | chr5 | 138757911 | 138758724 | rs11748963; rs7447765; rs35262202 |
| CENTG1 | chr12 | 56406249 | 56407788 | rs61935742; rs12318065; rs238519; rs238520; rs238521; rs808930; rs2640595; rs2640596; rs2640597; rs2640598; rs34772922 |
| CENTG1 | chr12 | 56416146 | 56418794 | rs11830475; rs34482618; rs2650057; rs2518686; rs12829991 |

TABLE 3

| GENE NAME | RELATIVE METHYLATION PLACENTA TO MATERNAL | PRC2 TARGET |
|---|---|---|
| PCDH17 | HYPERMETHYLATION | TRUE |
| KLHL1 | HYPERMETHYLATION | TRUE |
| POU4F1 | HYPERMETHYLATION | TRUE |
| SOX21 | HYPERMETHYLATION | TRUE |
| ZIC2 | HYPERMETHYLATION | TRUE |
| CIDEA | HYPERMETHYLATION | TRUE |
| KLHL14 | HYPERMETHYLATION | TRUE |
| ONECUT2 | HYPERMETHYLATION | TRUE |
| RAX | HYPERMETHYLATION | TRUE |
| TNFRSF11A | HYPOMETHYLATION | TRUE |
| OLIG2 | HYPERMETHYLATION | TRUE |
| OLIG2 | HYPOMETHYLATION | TRUE |
| SIM2 | HYPERMETHYLATION | TRUE |
| SIM2 | HYPERMETHYLATION | TRUE |
| CRYL1 | HYPOMETHYLATION | TRUE |
| IL17D | HYPOMETHYLATION | TRUE |
| GSH1 | HYPERMETHYLATION | TRUE |

TABLE 3-continued

| GENE NAME | RELATIVE METHYLATION PLACENTA TO MATERNAL | PRC2 TARGET |
|---|---|---|
| MAB21L1 | HYPERMETHYLATION | TRUE |
| SIX2 | HYPERMETHYLATION | TRUE |
| SIX2 | HYPERMETHYLATION | TRUE |
| SOX14 | HYPERMETHYLATION | TRUE |
| TLX3 | HYPERMETHYLATION | TRUE |
| SHH | HYPERMETHYLATION | TRUE |
| OSR2 | HYPERMETHYLATION | TRUE |
| TBX3 | HYPERMETHYLATION | TRUE |
| PAX9 | HYPERMETHYLATION | TRUE |
| SIX1 | HYPERMETHYLATION | TRUE |
| ISL2 | HYPERMETHYLATION | TRUE |
| DLX4 | HYPERMETHYLATION | TRUE |
| CBX4 | HYPERMETHYLATION | TRUE |
| CENTG1 | HYPOMETHYLATION | TRUE |
| CENTG1 | HYPOMETHYLATION | TRUE |

TABLE 4A

| SEQ ID NO | GENE NAME | SEQUENCE |
|---|---|---|
| 1 | chr13 group-00016 | CAGCAGGCGCGCTCCCGGCGAATCTGC-<br>CTGAATCGCCGTGAATGCGGTGGGGTGCAGGGCAGGGGCTGGTTTTCTCAGCCGGTCTTGGC<br>TTTTCTCTTTCTCTCCTGCTCCACCAG-<br>CAGCCCCTCCGCGGGTCCCATGGGCTCCGCGCTCAGAACAGCCCGGAACCAGGCGCCGCTCG<br>CCGCTCGCTGGGGGCCACCCGCCTCTC-<br>CCCGGAACAGCCTCCCGCGGGCCTCTTGGCCTCGCACTGGCGCCCTCACCCACACATCGTCC<br>CTTTATCCGCTCAGACGCTGCAAAGGGCCTTCTGTCTC |
| 2 | CENPJ | GCTTTGGATTTATCCTCATTG-<br>GCTAAATCCCTCCTGAAACATGAAACTGAAACAAAGCCCTGAACCCCCTCAGGCTGAAAAGACAAACC<br>CCGCCTGAGGCCGGGTCCCGCTCCCCAC-<br>CTGGAGGGACCCAATTCTGGGCGCCTTCTGGCGACGGTCCCTGCTAGGGACGCTGCGCTCT<br>CCGAGTGCGAGTTTTCGCCAAACT-<br>GATAAAGCACGCAGAACCGCAATCCCCAAACTAACACTGAACCCGGACCCGCGATCCCCAAACTG<br>ACAAGGGACCCGGAACAGCGACCCCCAAACCGACACGGGACTCGGGAACCGCTATCTCCAAAGGGCAGC |
| 3 | ATP8A2 | TTTCCACAACAGGGAGCCAGCATTGAG-<br>GCGCCCAGATGGCATCTGCTGGAAATCACGGGCCGCTGGTGAAGCACCACGCCTTACCCGAC<br>GTGGGGAGGTGATCCCCCACCTCATCCCACCCCCTTCTGTCTGTCTCCTT |
| 4 | GSH1 | GCTGGACAAGGAGCGCTCACTG-<br>TAGCTCTGCTGTGGATTGTGTTGGGGCGAAGAGATGGGTAAGAGGTCAAAGTCGTAGGATTCTGGCG<br>ACCGCCTACCAAGGGATTGGGTCCACAG-<br>CACAGAGGTCTGATCGCTTCCTTCTCTGCTCTGCCACCTCCAGACAGCAGCTCTAACCAGC<br>TGCCCAGCAGCAAGAGGATGCGCACG-<br>GCTTTCACCAGCACGCAGCTGCTAGAGCTGGAGCGCGAGTTCGCTTCTAATATGTACCTGTCC<br>CGCCTACGTCGCATCGAGATCGCGA |

TABLE 4A-continued

| SEQ ID NO | GENE NAME | SEQUENCE |
|---|---|---|
| 5 | PDX1 | TGCCTGACACTGACCCCAGGCGCAGC-<br>CAGGAGGGGCTTTGTGCGGGAGAGGGAGGGGGACCCCAGCTTGCCTGGGGTCCACGGGACTCT<br>CTTCTTCCTAGTTCACTTTCTTGCTAAG-<br>GCGAAGGTCCTGAGGCAGGACGAGGGCTGAACTGCGCTGCAATCGTCCCCACCTCCAGCGA<br>AACCCAGTTGAC |
| 6 | PDX1 | TCGGCGGAGAGACCTCGAGGAGAG-<br>TATGGGGAAAGGAATGAATGCTGCGGAGCGCCCCTCTGGGCTCCACCCAAGCCTCGGAGGCGGGA<br>CGGTGGGCTCCGTCCCGACCCCTTAG-<br>GCAGCTGGACCGATACCTCCTGGATCAGACCCCACAGGAAGACTCGCGTGGGGCCCGATATGT<br>GTACTTCAAACTCTGAGCGGCCACCCT-<br>CAGCCAACTGGCCAGTGGATGCGAATCGTGGGCCCTGAGGGGCGAGGGCGCTCGGAACTGCA<br>TGCCTGTGCACGGTGCCGGGCTCTCCA-<br>GAGTGAGGGGGCCGTAAGGAGATCTCCAAGGAAGCCGAAAAAAGCAGCCAGTTGGGCTTCGG<br>GAAAGACTTTTCTGCAAAGGAAGT-<br>GATCTGGTCCCAGAACTCCAGGGTTGACCCCAGTACCTGACTTCTCCGGGAGCTGTCAGCTCTCC<br>TCTGTTCTTCGGGCTTGGCGCGCTC-<br>CTTTCATAATGGACAGACACCAGTGGCCTTCAAAAGGTCTGGGGTGGGGGAACGGAGGAAGTGG<br>CCTTGGGTGCAGAGGAAGAGCAGAGCTC-<br>CTGCCAAAGCTGAACGCAGTTAGCCCTACCCAAGTGCGCGCTGGCTCGGCATATGCGCTCC<br>AGAGCCGGCAGGACAGCCCGGCCCTGCTCACCCCGAGGAGAAATCCAACAGCGCAGCCTCCTGCACCTCCTTGCCCCAGAGAC |
| 7 | MAB21L1 | AGATCCCGGTGCATTTAAAGGCCGGCGT-<br>GATCTGCACCACGTACCTATCTCGGATTCTCAGTTTCACTTCGCTGGTGTCTGCCACCATC<br>TTTACCACATCCCGGTAGCTA-<br>CATTTGTCTACCGCTTGAGCCACCAGCGTCTGAAACCTGGACCGGATTTTGCGCGCCGAGAGGTAGCC<br>GGAGGCGGTAATGAATTCCACCCAGAGG-<br>GACATGCTCCTCTTGCGCCCGTCGCTCAACTTCAGCACCGCGCAGCCGGGCAGTGAGCCAT<br>CGTCCACGAAGTTGAACACCCCCATTTGGTTGAGATAAAGCACCACTTCAAATTCGGT |
| 8 | RB1 | ACTATGCCTTGAGGGTCAAAACGTCTG-<br>GATTTCCTGATCGATGCTGTCGTCGCTGTCCACGGAGCTACTGTCGCCGTCAGAGCGGGAAG<br>GCACGTTCAGGGAGTAGAAGCGTGGGCT-<br>TGCAGAAAGGGACCTGTTGCTGCCTTACATGGGGGCCGGCAGGGTAGTCTTGGAAATGCCC<br>AAGATTGCTTCCGCGCGCGTCAGT-<br>TCAGCGGACGTGTCTGCCTGGCACGAGGACCGTTCTACAAACTCGTTCCTGGAAGCCGGGCTCGC<br>TGGAGGCGGAGCTTTGGTTTCCTTCGG-<br>GAGCTTGTGGGGAATGGTCAGCGTCTAGGCACCCCGGGCAAGGGTCTGTGGCCTTGGTGGCC<br>ACTGGCTTCCTCTAGCTGGGTGTTTTC-<br>CTGTGGGTCTCGCGCAAGGCACTTTTTTGTGGCGCTGCTTGTGCTGTGTGCGGGGTCAGGCG<br>TCCTCTCTCCTCCCGGCGCTGGGC-<br>CCTCTGGGGCAGGTCCCCGTTGGCCTCCTTGCGTGTTTGCCGCAGCTAGTACACCTGGATGGCCT<br>CCTCAGTGCCGTCGTTGCTGCTG-<br>GAGTCTGACGCCTCGGGCGCCTGCGCCGCACTTGTGACTTGCTTTCCCCTTCTCAGGGCGCCAGCG<br>CTCCTCTTGACCCCGCTTTTATTCTGTGGTGCTTCTGAAG |
| 9 | PCDH17 | GCAAGTCGGGTAGCTACCGGGTGCTG-<br>GAGAACTCCGCACCGCACCTGCTGGACGTGGACGCAGACAGCGGGCTCCTCTACACCAAGCAG<br>CGCATCGACCGCGAGTCCCTGTGCCGC-<br>CACAATGCCAAGTGCCAGCTGTCCCTCGAGGTGTTCGCCAACGACAAGGAGATCTGCATGAT<br>CAAGGTAGAGATCCAGGACATCAACGA-<br>CAACGCGCCCTCCTTCTCCTCGGACCAGATCGAAATGGACATCTCGGAGAACGCTGCTCCGG<br>GCACCCGCTTCCCCCTCACCAGCGCA-<br>CATGACCCCGACGCCGGCGAGAATGGGCTCCGCACCTACCTGCTCACGCGCGACGATCACGGC<br>CTCTTTGGACTGGACGTTAAGTCCCGCG-<br>GCGACGGCACCAAGTTCCCAGAACTGGTCATCCAGAAGGCTCTGGACCGCGAGCAACAGAA<br>TCACCATACGCTCGTGCTGACTGCCCTG-<br>GACGGTGGCGAGCCTCCACGTTCCGCCACCGTACAGATCAACGTGAAGGTGATTGACTCCA<br>ACGACAACAGCCCGGTCTTCGAGGCGC-<br>CATCCTACTTGGTGGAACTGCCCGAGAACGCTCCGCTGGGTACAGTGGTCATCGATCTGAAC<br>GCCACCGACGCCGATGAAGGTCCCAATG-<br>GTGAAGTGCTCTACTCTTTCAGCAGCTACGTGCCTGACCGCGTGCGGGAGCTCTTCTCCAT<br>CGACCCCAAGACCGGCCTAATCCGTGT-<br>GAAGGGCAATCTGGACTATGAGGAAAACGGGATGCTGGAGATTGACGTGCAGGCCCGAGACC<br>TGGGGCCTAACCCTATCCCAGCCCACTG-<br>CAAAGTCACGGTCAAGCTCATCGACCGCAACGACAATGCGCCGTCCATCGGTTTCGTCTCC<br>GTGCGCCAGGGGGCGCTGAGCGAGGC-<br>CGCCCCTCCCGGCACCGTCATCGCCCTGGTGCGGGTCACTGACCGGGACTCTGGCAAGAACGG<br>ACAGCTGCAGTGTCGGGTCCTAGGCG-<br>GAGGAGGGACGGGCGGCGGCGGGGGCCTGGGCGGGCCCGGGGGTTCCGTCCCCTTCAAGCTTG<br>AGGAGAACTACGACAACTTCTACACG-<br>GTGGTGACTGACCGCCCGCTGGACCGCGAGACACAAGACGAGTACAACGTGACCATCGTGGCG<br>CGGGACGGGGGCTCTCCTCCCCT-<br>CAACTCCACCAAGTCGTTCGCGATCAAGATTCTAGACGAGAACGACAACCCGCCTCGGTTCACCAA<br>AGGGCTCTACGTGCTTCAGGTGCAC-<br>GAGAACAACATCCCGGGAGAGTACCTGGGCTCTGTGCTCGCCCAGGATCCCGACCTGGGCCAGA<br>ACGGCACCGTATCCTACTCTATCCTGC-<br>CCTCGCACATCGGCGACGTGTCTATCTACACCTATGTGTCTGTGAATCCCACGAACGGGGCC<br>ATCTACGCCCTGCGCTCCTTTAACTTC-<br>GAGCAGACCAAGGCTTTTGAGTTCAAGGTGCTTGCTAAGGACTCGGGGGCGCCCGCGCACTT |

TABLE 4A-continued

| SEQ ID NO | GENE NAME | SEQUENCE |
|---|---|---|
| | | GGAGAGCAACGCCACGGTGAGGGTGA-<br>CAGTGCTAGACGTGAATGACAACGCGCCAGTGATCGTGCTCCCCACGCTGCAGAACGACACCG<br>CGGAGCTGCAGGTGCCGCGCAACGCTG-<br>GCCTGGGCTATCTGGTGAGCACTGTGCGCGCCCTAGACAGCGACTTCGGCGAGAGCGGGCGT<br>CTCACCTACGAGATCGTGGACGGCAAC-<br>GACGACCACCTGTTTGAGATCGACCCGTCCAGCGGCGAGATCCGCACGCTGCACCCTTTCTG<br>GGAGGACGTGACGCCCGTGGTGGAGCTG-<br>GTGGTGAAGGTGACCGACCACGGCAAGCCTACCCTGTCCGCAGTGGCCAAGCTCATCATCC<br>GCTCGGTGAGCGGATCCCTTC-<br>CCGAGGGGGTACCACGGGTGAATGGCGAGCAGCACCACTGGGACATGTCGCTGCCGCTCATCGTGACT<br>CTGAGCACTATCTCCATCATCCTCCTA |
| 10 | KLHL1 | ATGCGCCCTCTGCACCCCTAGAGCCA-<br>GAAGACGCTAGGTGGGCTGCGCGCTCTGCCAGGCGAAGGCTGGAGCGCAGACGGCAAAGCCGC<br>GCGTTTCAGCCGTGGTCGGGTCCGCAG-<br>GACCTGGGCGTGGGGACACCACCAGGCAGGAGCAGAGGCAGGACTGGGACGCCAAAAGCTGA<br>GAATCCTCGATGCCCGCGCGAGAGCCCCGTGTTAT |
| 11 | POU4F1 | TTCTGGAAACCGGGCCCCACTTGCAGGC-<br>CCGGCCACCTTGGGTTCTGGTGGCCGAAGCCGGAGCTGTGTTTCTCGCAGACTCGGGGAGC<br>TACATTGTGCGTAGGCAATTGTT-<br>TAGTTTGAAAGGAGGCACATTTCACCACGCAGCCAGCGCCCTGCATGCAGGAGAAGCCCCCAGGGC<br>CCAGGGTCGGCTGGCTTTAGAGGCCACT-<br>TAGGTTGTTTTAAGCACATGTGAAAGGGCAGACAGCAGGGGAGCAGGATATGGGTAAGATC<br>TTCGGGTCTCAGAACAGGGGCTGCCCT-<br>TGGGCTGTCCCGGCGCCCTGGGCTCTGACACTGAAGGGTGGAATGGAGGAAGGAATGGAGAA<br>AGGACGGTGGAACTTTCGCTTC-<br>CCCTCTGGGCCGCCTTCCCAGGGTCATGCCTGAGCTGCTTTGATCCCAGTGTCGCGCATCTTGGTCC<br>GCTACCTCCCAGGCGATAGC-<br>TACTGGGCTCCTCGCTGGCCTCACTGGGGGCCATCCCGGGCAGTGGCCTGCCCTCCGAGGCCCGCGGGA<br>CCCAGCCCAGAGCTGAGGTTGGAGT-<br>TCTCCGGGCCACGTTCCGGGTCGCTTAGGCTCGGAGATTTCCCGGAGACCGTCGTCCTCCCTTT<br>CTGCTTGGCACTGCGGAGCTCCCTCGGC-<br>CTCTCTCCTCCTCTGGTCCCTAAGGCCCGGAGTGGTTGGCGGTACTGGGGCCCGTCGTCAT<br>CTCTGCTTCTAAGGCATTCA-<br>GACTGGGCTCCAGCTGGGACCGGCAGAGGAGGTTCTCAAGGAAACTGGTGGGAAATATAGTTTTCTTTC<br>GTCTGGTCGTTTAATTTAAATGCAACT-<br>TCCCTTGGGGACATTTTCCTGGACGTTAACCAGACCACCTTGAGATGTCGTTGATGACCTAG<br>AGACCCAGATGATGCGTCCCAGGAAAGT-<br>TCACTGCTGACTATTGTCACTCTTGGCGTTATATCTATAGATATAGACCTATGTACATATC<br>TCCACCCTGATCTCTCCGTGGACAT-<br>GAAACCCACCTACCTTGTGAAAGCCCTACGGGTGACACATGACTACTACGTCTCTGTCCCAACA<br>GGGGCTGGGCCTCCCCTGCCTAATAGT-<br>TGCCAGGAGTTTCGCAGCCCAAGTGAATAATGTCTTATGGCTGAACGTGGCCAAGGACTCCT<br>GTGATTTAGGTCCCAGGAGGAGCA-<br>GAGACGTCCCCGCCCCGCCTGGGCCCTGCCGCATTCAAAGCTGGAAGAAGGCGCTGATCAGAGAA<br>GGGGCTTCCAGGTCCTGGGTTAGAACAA-<br>CAACAAACAAACGAAACTCCACAACAGACACGCCTGCCCATGACCCCACGCAAGGACATAG<br>GAAGTTCTGTCGCCTTCCTGCTCCGCG-<br>GATAGCCGCCTGCCGTCTGCTGCCACCAGAACGCACGGACGCTCGGGGTGGAGGTAGTCAAT<br>GGGCAGCAGGGGACCCCCAGCCCCCA-<br>CAAGCGCGGCTCCGAGGACCTGGAAGCGGGTGCCTGTCGCTCTCCGCAGGCTCCGCTCTGCCT<br>CCAGGAGCAAGATCCCCAAAAGGGTCTGGAAGCTGTGGAGAAAAC |
| 12 | GPC6 | TTTTTTAAACACTTCTTTTCCTTCTCT-<br>TCCTCGTTTTGATTGCACCGTTTCCATCTGGGGGCTAGAGGAGCAAGGCAGCAGCCTTCCCA<br>GCCAGCCCTTGTTGGCTTGCCATCGTC-<br>CATCTGGCTTATAAAAGTTTGCTGAGCGCAGTCCAGAGGGCTGCGCTGCTCGTCCCCTCGGC<br>TGGCAGAAGGGGGTGACGCTGGGCAGCG-<br>GCGAGGAGCGCGCCGCTGCCTCTGGCGGGCTTTCGGCTTGAGGGGCAAGGTGAAGAGCGCA<br>CCGGCCGTGGGGTTTACCGAGCTG-<br>GATTTGTATGTTGCACCATGCCTTCTTGGATCGGGGCTGTGATTCTTCCCCTCTTGGGGCTGCTG<br>CTCTCCCTCCCCGCCGGGGCGGATGT-<br>GAAGGCTCGGAGCTGCGGAGAGGTCCGCCAGGCGTACGGTGCCAAGGGATTCAGCCTGGCGGA<br>CATCCCCTACCAGGAGATCGCAGG-<br>TAAGCGCGGGCGCGCTGCAGGGGCAGGCTGCAGCCCTCGGCTGCCGCACGTCCCACTGGCCGCCC<br>GGCGTCCCCTTCCTTCCCCCTGTTGCT-<br>GAGTTGGTGCTCACTTTCTGCCACCGCTATGGGACTCCGCGTCTCCGTGTTGGGCGGCGGAT<br>GCTCCTGCGGCTTCTTCGGCGGGGGAAG-<br>GTGTGCGTCTCCGCCGCCTCATTGTGTGCACACGCGGGAGCACCCTGGCTCCCGCCTCCCG<br>CTGCTCTCGCGCCCTTCTACCCCTTAGT-<br>TGATGGCTCAGGCCCGGCTGGCCAGGGAGCCCGGGTCACTCCGGGGCGGCTGCAAGGCGCA<br>GACGGAGAGCCGAGCCGGGCGCTCACTC-<br>CGCGTTCTGGTTCGGGCAAACTTGGAAGAACTGCGACCGCAGTTTGCCCAGCGCCACAGTC<br>TGAGTGGCGCCTTCTCCACTCCCGCCCT-<br>TGCGCCGGCAGGGGCGGTGGAGAGACGCGGAGGGCTCCCCCAGCCCCTCTCTCCCCTATCC<br>GTCCTTCGGGCGACAGAGCGCCCG-<br>GCGCTCGGGCCGGGGGCGGGCAAGGCTGGGAGGGACCCTCGCCGGGGACCTGGCCTCTGGACGCC<br>GGCGTTTCAAGGCTGGTTTGGGGACT-<br>TCACGGGCTGCCTGTTTCAGATGTGGGGCGGGCTTTCCCGTTAGGGTTCCTCAGTGCTTCCCC |

TABLE 4A-continued

| SEQ ID NO | GENE NAME | SEQUENCE |
|---|---|---|
| | | AGTTGCTGTTGGCCACTCAGGGCCCGGG- GACACCCTGCCACCCGGTCTGGAGCCGGCCTCGTCTGCCAGCGAACAGCCAACTTTAGCGG GTGGCTCAGCTGGGGATT |
| 13 | SOX21 | CACTCAGTGTGTGCATATGAGAGCG- GAGAGACAGCGACCTGGAGGCCATGGGTGGGGGCGGGTGGTGAAGCTGCCGAAGCCTACACATA CACTTAGCTTTGACACTTCTCGTAGGT- TCCAAAGACGAAGACACGGTGGCTTCAGGGAGACAAGTCGCAAGGGCGACTTTTCCAAGCGG GAGATGGTGAAGTCTTTGGACGTG- TAGTGGGTAGGTGATGATCCCCGCAGCCGCCTGTAGGCCCGCAGACTTCAGAAAACAAGGGCCTT CTGTGAGCGCTGTGTCCTCCCCGGAATC- CGCGGCTTAACACATTCTTTCCAGCTGCGGGGCCAGGATCTCCACCCCGCGCATCCGTGGA CACACTTAGGGTCGCCTTTGTTTTGCG- CAGTGATTCAAGTTGGGTAACCCTTGCTCAACACTTGGGAAATGGGGAGAATCTCCCCCACC CGCAACCTCCCGCACCCCAGGTTC- CCAAAATCTGAATCTGTATCCTAGAGTGGAGGCAGCGTCTAGAAAGCAAAGAAACGGTGTCCAAA GACCCCGGAGAGTTGAGTGAGCGCA- GATCCGTGACGCCTGCGGTACGCTAGGGCATCCAGGCTAGGGTGTGTGTGTGCGGGTCGGGGGG CGCACAGAGACCGCGCTGGTTTAGGTG- GACCCGCAGTCCCGCCCGCATCTGGAACGAGCTGCTTCGCAGTTCCGGCTCCCGGCGCCCCA GAGAAGTTCGGGGAGCGGTGAGCCTAGCCGCCGCGCGCTCATGTTTATT |
| 14 | ZIC2 | AGTCACTCCAGGATCAGAGGCCGCGTCG- GTTCTGCTTGGGGCATGGGCAGAGGGAGGCTGCTGGGGCCAAGCCCCGGCTGGACGCGAGG AGGACCCGCACGCCCATACCTGGCTGTC- CCAGAGCTCTTCCCTAGGCCGGCACCTTCGCTCTTCCTCTTCCCCACCCCCTAGCCCTTTT GAAGAAACTCGTCCCGTCTCTTTTTCA- GACGGATGTTTTCAGTCTCAAGTGGTTTTATTTTCCGCACAAAACCCTGAGATCAAGGGCAG ATCACAGACTGTACCGGAG- GCTCGGGTTTCCCTGGACTCTGTGCTGTTCTGCGTCCCAGGGTTGGCTAGGAAGGAAGGCCTGGGCCGGC GAGGTGACGGGTCTCCCGCCCAGGTCG- GCAGGACGGGGGGAGGTGTGTCCCGGTAGGTCCCTGGTGAGCTCACCCGTGGCATCGGGGAC CCGCGGGAACCCACCGGGCGCCCACTA- GAGACTCGGGTCCTACCCTCCCCCACACTACTCCACCGAAATGATCGGAAGGGCGCGCTAGG CCTGCTTCCAAGGGCTCAGTGATAAAG- GCCTCAAAATCACACTCCATCAAGACTTGGTTGAAGCTTTGGGTAGGTTTGTTGTTGTTGTT GTTGTTGTTTGTTTGTTTGTTTTAGCA- GACACGTCCTGGAAAGAGGTCCTCAGAACCCAAAGGTTCAATAATGATTTGTGGATGGATTG ATTATAGTCTGATATCGCTCTGGTTCCA- CAGAAACCCGGAGCTCCTTGGCCCACTGTTACCCCAGCAGACCTAAATGGACGGTTTCTGT TTTTCACTGGCAGCTCAGAACTGGACCG- GAAGAAGTTCCCCTCCACTTCCCCCCTCCCGACACCAGATCATTGCTGGGTTTTTATTTTC GGGGGAAAAACAACAACAACAACAA- CAAAAAAAACACTAGGTCCTTCCAGACTGGATCAGGTGATCGGGCAAAAACCCTCAGGCTAGTC GCGGCTGGGTGCCCGAGCATGAAAAGGC- CTCCGTGGCCGTTTGAACAGGGTGTTGCAAATGAAACTTTTGTAAGCCATAACCAGGGCAT CCTGAGGGTCTGAGTTCACGGTCAAG- GCTGTGGGCTACTAGGTCCAGCGAGTCCAGGCCTCGCCCCGCCCCCGAGCTGCCACAGCCAAG ATCTTCGGCAGGGAATTCGAGACCAGGGTCCTCCCACTCCT |
| 15 | chr13 group- 00385 | TTTCGTGCCGCTGTTTTCAAT- GCGCTAACGAGGCACGTTATTCTTAGCCGCGTCCGGGAGGGGATCACATTCCTGCGCAGTTGCGCTGC TGGCGGAAGTGACTTGTTTTCTAACGAC- CCTCGTGACAGCCAGAGAATGTCCGTTTCTCGGAGCGCAGCACAGCCTGTCCCATCGAGAA GCCTCGGGTGAGGGGCCCGGTGGGCGC- CCGGAGGCCGCTGGAGGGCTGTGGGAGGGACGGTGGCTCCCCACTCCCGTGGCGAAGGGCAG GCAAACCAGAAGCCTCTTTTGAGAGC- CGTTTGGGATTGAGACGAGTAAGCCACAGCGAGTGGTTAGAAGTAGGTTAGGAAGAAGGGGAG GTAAGAAAGCCGAGTAGGGTT |
| 16 | chr13 group- 00390 | GTTCGGTGGACAAGGGGGCAGCGCCCA- CAGCAAGCCGGAAAGAGGGAGGCGCGGGGCCGCGCTTGGGGCCTGCCGCTGCACGCCAGCCT GGGCAAAGAGCTGCCACCTTCTGCGGGC- GAAGCGGGTCGGGACGCAGGACGGCAGCGGGGCTGGAGGCAGCTACGTGGGTCCACACCCC CATGCCCTGCAAGGCTCCTTGGCCCTGCTTCTCCTCTGTCTCGGCGGGAGAGGAGCAGCCTCGGTTTTACAGAATTTC |
| 17 | chr13 group- 00391 | TGTGCCATTTAGTGAGAGGT- GTTTTGGGCAAAGAATCAATTTAACTGTGACTGACCGACGGGCTTGACTGTATTAATTCTGCTACCGAA AAAAAAAAAAAAAAAAAGCAATGAGC- CGCAAGCCTTGGACTCGCAGAGCTGCCGGTGCCCGTCCGAGAGCCCCACCAGCGCGGCTCAC GCCTCAGTCTC |
| 18 | chr13 group- 00395 | AGAGTCCCAGTTCTGCAGGCCGCTC- CAGGGCTAGGGGTAGAGATGGTGGCAGGTGGTGCGTCAACTCTCTAGGGAAGAGGAACTTGCAT TACAAAGACTTGTCTTTCTGAGCT- GAAGTCAAAACGGGGGCGTCAAGCGCGCTCCGTTTGGCGGCGGTGGAGGGGCCGCGCGCCCGCGC TGTCCCAGCCGGAGCTGCCCTGGCTGGT- GATTGGAGGTTTAACGTCCGGAATTCAGGCGCTTCTGCAGCTCAGATTTGCCGGCCAAGGG GCCTCAGTTGCAACTTTTCAAAATGGT- GTTTCTGGAAAATAACAAATTCAGACTCAACTGGTGACAGCTTTTGGCTATAGAGAATGAAA |

TABLE 4A-continued

| SEQ ID NO | GENE NAME | SEQUENCE |
|---|---|---|
| | | CTGCTTCCCTTTGGCGGTGGAACTCT-<br>TAAACTTCGAAGAGTGAAAGAATACAATGAAATAAAATGCCATAAGATCACTGGATTTTTCAG<br>AAAAAGGAAGACCCCAAATTACTC-<br>CCAAAATGAGGCTTTGTAAATTCTTGTTAAAAATCTTTAAATCTCGAATTTCCCCCTACAACATC<br>TGATGAGTGCTTTAAGAGCAAACGAG-<br>CAAATCCCACCTCGAGAATCAACAAACCCAAGCTCTGGCCAAGGCTCTCCCCGCGTTTTCTTC<br>TCGTGACCTGGGGAATGTCCCGCCCCATCGCTCACCTGGCTCTTGTCATCTCGCTCATCTTGAAGTGACCCGTGGACAATGCTG |
| 19 | chr13 group-00399 | AGCTGCCCTCTGTGGCCATGAGCGGGT-<br>GTCCAGCCCCTTCCAAGGCTGCACCGGGGAGACGCTGGTTTTCTGCTCGCTGTGACCGAACA<br>AAGCCCCTAAGAGTCAGTGCGCGGAACA-<br>GAAGAGCCGGACCCCGACGGGCCGAGTCCCAACGTGAGGCACCCGGCAGAGAAAACACGTT<br>CACG |
| 20 | PROZ | CCTCGGCAGCACCGGCATGGCTGGAGGC-<br>CAGTACGGCCAGGTGTGGCGGGAGGGAGCGCCGTCTGGCTTGGGTCGTCCATCCTGACAGG<br>ACGCTGCAAGGGCAGGAGCCCCGCGC-<br>CCCGTGTCCTGCGCCCCCGCTCGAGGACAAGCCCCAGCCGCCGGTCTCCGCTGGGTTCCGACA<br>G |
| 21 | CIDEA | CTTTAAGAGGCTGTGCAGGCAGACAGAC-<br>CTCCAGGCCCGCTAGGGGATCCGCGCCATGGAGGCCGCCCGGGACTATGCAGGAGCCCTCA<br>TCAGGCGAGTGCCCCGCGTCCCCCTGAT-<br>TGCCGTGCGCTTCCAATCGCCTTGCGTTCGGTGGCCTCATATTCCCCTGTGCGCCTCTAGT<br>ACCGTACCCCGCTCCCTTCAGCCCCCT-<br>GCTCCCCGCATTCTCTTGCGCTCCGCGACCCCGCGCACACACCCATCCGCCCCACTGGTGCC<br>CAAGCCGTCCAGCCGCGCCCGCGGGCA-<br>GAGCCCAATCCCGTCCCGCGCCTCCTCACCCTCTTGCAGCTGGGCACAGGTACCAGGTGTGG<br>CTCTTGCGAGGTG |
| 22 | chr18 group-00091 | AGACTTGCAGAACTCGGGCCCCCTGGAG-<br>GAGACCTAACCGCCACGGTCTTGGGGAGGTTCCGGAGGGCCTCGGTTGTCTGCACTCCCAA<br>CACCAAGAAACCCCTGAGACGCGAAGCTGCCAGCGTGCTGCCCTCAGAGCAGGGCGACGCAAAGCCAGCGGACCCCGGGGTGGCGGG |
| 23 | chr18 group-00094 | TGCTCGGCTGGGGGGCTCGCTCCG-<br>CACTTTCGGTGCCAGAAAATGCCCAGAGGAGCGGGGCGGCCCCAGAGCCTCCTTTCGGGGCGCGA<br>GGCCCGGCGCGTGTGTACGGAGTCCAGTCCCCCCAGGGAGTGGGGTGCCCGCACCTTCCCCTCCGCGCTCGGAGCCAC |
| 24 | KLHL14 | TCTTGCACACCTGCTTGTAGTTCTGCAC-<br>CGAGATCTGGTCGTTGAGGAACTGCACGCAGAGCTTGGTGACCTGGGGGATGTGCAGGATC<br>TTGCTGACCGACAGCACCTCCTCCAC-<br>CGTGTCCAGGGACAGGGTCACGTTGGCCGTGTAGAGGTACTCGAGCACCAGGCGCAGCCCGAT<br>GGACGAGCAGCCCTGCAGCACCAGGT-<br>TGTTGATGGCCCGGGGGCTGGTCAGCAGCTTGTCGTCGGGGGAGGAAGAAGGAGTCCCGGGCT<br>CCTCCTGCGGCGGCGGCTGCTGCTGCT-<br>GTGACGGCTGCTGCTGCGGCGGCTGCTGCTGGTCCTTGGGGGCCCCCAGGCCGTCCTGGCCG<br>CCGACCCCTCCCCCGAGAGGGGGGTG-<br>GCTGGAGAAGAGCGATCGGAAGTACTGCGAGCAGGAGGCCAGCACGGCCTTGTGGCAATGGAA<br>GCTGCTGGCCCTGGGCCGTCAGGGT-<br>CACGTCGCAAAACAGCTGCTTCCTCCACAGCAGGTTGAGGCCGTGCAGCAGTTGTCGCTGTGGC<br>TGGGGTCGAAGGTGGAGGTCCTGTC-<br>CCCGGATCTGGACATGGCGAGCTGACTCGGTGCACCTGGCTTTAAACCCTCCTCCAACCTGGCA<br>GACAGGGGTGGGGGATGGGAGGGAGGG-<br>GAGCAGGGTGGTGGAGCGGGTGGGGTGTGGTCGGGGTGGGGAAGGGTGTGGAGGGGGAGGGGA<br>GGGCGAAGAACAAGAATCAAGGCT-<br>CAGCTTGACTCCCTCCTGGCGCGCTCCGGACCCCGACCCTAGGAGGAAAGTCCGAAGACGCTGGA<br>TCCGTGAGCGCCACCAGAAGGGCCCT-<br>GTCTGGGGTCCCGGCGCCGGTTCTGCGCCCTGCGGCTCCTCTCGCCACCTCCCACACACTTCG<br>TCCCTCACTTTCCTAAAACCAACCACCT-<br>CAGCTCGGCTGTTGGCAGCAACAGCAGTGGCAGCAGCGACGGCAAAGTGGCGGCTGAGGCC<br>GAGGCACCTCGTGGGCTCGTGTCCATGC-<br>CGGGCCAGATGAAGGGAAAGGCCGGGAAGTGGGGAGCCGGGGGTGCCCTGAAAGCTCAGAG<br>GCGACCGACGGCGAAGGTTCCAGGT-<br>CAACTTGTGCCCGAAGCTTTGCTTTTCGCAGTTGGCCCAGTTTGGGGGAGGGGGTAGGAACAGG<br>GGCCCGACCAGCGTGCGGGGTGTGCGAATCTTAGCTCTCCAAAAGCTG |
| 25 | ST8SIA3 | CCTCTGTGTTAGTGCCCTCGGGAATTTGGTTGATGGGGTGTTTG |
| 26 | ONECUT2 | TGATGTCGCACCTGAACGGCCTGCAC-<br>CACCCGGGCCACACTCAGTCTCACGGGCCGGTGCTGGCACCCAGTCGCGAGCGGCCACCCTCG<br>TCCTCATCGGGCTCGCAGGTGGC-<br>CACGTCGGGCCAGCTGGAAGAAATCAACACCAAAGAGGTGGCCCAGCGCATCACAGCGGAGCTGAA<br>GCGCTACAGTATCCCCCAGGC-<br>GATCTTTGCGCAGAGGGTGCTGTGCCGGTCTCAGGGGACTCTCTCCGACCTGCTCCGGAATCCAAAAC<br>CGTGGAGTAAACTCAAATCTGGCAGG-<br>GAGACCTTCCGCAGGATGTGGAAGTGGCTTCAGGAGCCCGAGTTCCAGCGCATGTCCGCCTTA<br>CGCCTGGCAGGTAAGGCCGGGGCTAGC-<br>CAGGGGCCAGGCTGCTGGGAAGAGGGCTCCGGGTCCGGTGCTTGTGGCCCAAGTCTGCGCGC |

TABLE 4A-continued

| SEQ ID NO | GENE NAME | SEQUENCE |
|---|---|---|
| | | CGAGTCACTTCTCTTGATTCTTTCCT-<br>TCTCTTTCCTATACACGTCCTCTTTCTTCTCGTTTTTATTTCTTCTTCCATTTTCTCTTTCTC<br>TTCCGCTCTTCCCCTACTTTCCCTTCTC-<br>CCTTTTCTTTTTCTTTCTTACTCTCTCCTTGTCCCTGAGCTTTCATTGACCGACCCCCCCC<br>CATTTCATTCGCCCTCCCCTCAATGTGC-<br>CAACCTTTGCCCTATTTCCGATCTTCCCAGGTACTGGGAGGCGGGATGGGGGTGTGCGTTT<br>TCCTCTAGGAGCCCTGTCTTTCCAAGAC-<br>CCACAGAAACCAGGACCTGCCCTTATTCAAAACCCCATGCACTTCAAGTCTCTTTTAGACA<br>ACACATTTCAATTTTCCGGGCTGAC-<br>TAGTCTCCCTGTGCAGAGGCAGTTGAGAGGCTTTGCTCTGCAGAGGGAAAAGAGCTCTCTACTC<br>TCCCACCCACCATATAGGCAAACT-<br>TATTTGGTCATTGGCTGAAGGCACAGCCTTGCCCCCGCGGGGAACCGGCGGCCAGGATACAACAG<br>CGCTCCTGGAGCCCATCTCTGGCCTTG-<br>GCGTTGGCGCAGGGACTTTCTGACCGGGCTTGAGGGGCTCGGGCCAGCTCCAATGTCACTAC<br>TCTACAGCGAGGGCAGGGTGTAAGGT-<br>TGAGAAGGTCACATTCACCGCTTTGGGAGGACGTGGGAGAAGAGACTGAGGGGAAAGCGCTTT<br>GCCTTGCTCACCGGCCGTCCTTGCCCCG-<br>GTCCCAGCGTTTGCTGGGATTTGCCAGGATTTGCCGGGGCTCCGGGAGACCCTGAGCACTC<br>GCAGGAAGAGGTGCTGAGAAAT-<br>TAAAAATTCAGGTTAGTTAATGCATCCCTGCCGCCGGCTGCAGGCTCCGCCTTTGCATTAAGCGGGC<br>GCTGATTGTGCGCGCCTGGCGAC-<br>CGCGGGGAGGACTGGCGGCCCGCGGGAGGGGACGGGTAGAGGCGCGGGTTACATTGTTCTGGAGCC<br>GGCTCGGCTCTTTGTGCCTCCTCTAGCG-<br>GCCAAGCTGCGAGGTACAGCCCTCTATTGTTCTAGGAGCACAGAAACCTCCTGTGTGGGCG<br>GCGGGTGCGCGAGCTAGAGGGAAAGATG-<br>CAGTAGTTACTGCGACTGGCACGCAGTTGCGCGCTTTTGTGCGCACGGACCCCGCGCGGTG<br>TGCGTGGCGACTGCGCTGCCCCTAGGAG-<br>CAAGCCACGGGCCCAGAGGGGCAAAATGTCCAGGTCCCCCGCTGGGAAGGACACACTATAC<br>CCTATGGCAAGCCAGGGTGGGCGACTTC-<br>CCATGGATCGGGTGGAGGGGGGTATCTTTCAGGATCGGCGGGCGGTCTAGGGGAACAATTC<br>GTGGTGGCGATGATTTGCAT-<br>AGCGCGGGTCTTGGGATGCGCGCGGTTCCGAGCCAGCCTCGCACAGCTCGCTTCCGGAGCTGCGAGCTC<br>AGGTTTCCACCCCCGATC-<br>CCCCGGGCTTTCCTCGCACCGCTGAGCCCAGCTTGTGGGGTGCACTCGACCAACGCCCGACAGGGCTGGGG<br>TAATGTGACAGGCAGCAGGTCAC-<br>CCGGGCTTGGGGAGGGGGAGTTTCCGCTTTGACAGCATTTTCCTTTGCCGTCTGCTGGTGGATTCC<br>TATTCCCAGTCGGTAATCGCCCCGCAGT-<br>GTTGATCTAAGAAGGTAAAGAAAACTAGGTTTCCCTGCAAAGAGCCTCCCCCAAATCGGCG<br>GACTCCGGATACTTTGAGTGGATTTA-<br>GAAATTTATGTAATCTTTCTCCTTTAGTTTATTTTTCATCCTCTCCTACAGTTTTCTCTGATT<br>TGCTGTTGGTTCGGGGCAAGATAAAG-<br>CAGCCAGTAGAGAGCGATAATAATAGCGGCGGGAAATGAACTGGAGACTGGCTGACAGTTCTT<br>GAACATTTTGTCATAGATCCCCCCGAAT-<br>GTCCCAGGCTGTCTCTGGTGGGTTTTAGTACCCGCCGGCTTCTTGGGCACCGGGACCAGAA<br>GGAACTTGGCAGCTGGTCTTAGGGGTA-<br>CAGTTAAAGGCAGGATGACAGCTATTCTCCTGCTCATCTCAGAGCGCTGCCGCCCCCTCATG<br>CCGGTCGCGCAAAGAACACAGCTTT-<br>TAAAAAACACGTGCCTTCTGCCCATATAGGTCTGAAAGTGATGAGGAAAGTAATGCTTCGCCTA<br>TTAGCGAGTTTCAGCTTTTAAAATGATC-<br>CCAAGCGTTGCTGAGATGAGAAAGCGTGGCATCCCGGGGGTCCTCAGCCCCACCCGCGCCC<br>ATGGTGCAAGTCTGCAGGGACAGGC-<br>CCGGGACAGCACTGCCCACGCTGCTAGATTTTCCGCAGAGGATCGCTGAAGCTGCCTTCGTGGG<br>AGACAGAATGCCTCCTCCAGCGAGTG-<br>GAAAAGGCCTGCTGAGGACCCCGCTTTGCTCGAGCATTCAAATGTGTGTCTGTTTTATTACCC<br>TGGGTTGAAAAGGGACAAGAGCTTTAGC-<br>CTTTTTATCTGGCCATTTTATCAGCAACTACAAGTGTGTTGAGTGGTTATTATTACATAGG<br>AGGCTTTTCAGTTTGGGGTCAGTAGAT-<br>CAGTCTCTTCAGACACTGATGCAGAAGCTGGGACTGGTAAGTAGGTATTATGTGCTCGGAGC<br>GCTAGGGGACAGGAGCAAATGGAGAA-<br>GAAAAGCGGAGGCTTTCTCCGCCCGGAGTATCGATCGGAATCCCCGCCGGTACGCCGCAGAGG<br>GCCCTCGCCGTTGGGCCCCGGGGGTT-<br>TAACAAGCCCAGCCGCTCCGCAGGCGGCTCGGCCGGACTCTCAGACCGGTGCCTGGAAGACAC<br>CGTCCCTGCCCCCCTCCCGCCAAACCT-<br>GCCTCTTCTCTTTCTCTCATAGGTTATAGGTTCCCTTTCTCTCTCATTTTGGCCCCGCCCCC<br>GGGTCCTGCCAAACAGCCAAGCAGGC-<br>CGGGGTTTAGGGGGCTCAGAATGAAGAGGTCTGATTTGGCCAGCGCCGGCAAAGCTCACCCTT<br>AGGCGAGGTCACAACAGAGGCAGGTCCT-<br>TCCTGCCCAGCCTGCCGGTGTAGTCACAGCCAAGGGTGGCACTTGAAAGGAAAAGGGAGAA<br>AACTTCGGAGAAATTTAGATTGC-<br>CCCAACGTTAGATTTCAGAGAAATTGACTCCAAATGCACGGATTCGTTCGGAAAGGGCGGCTAAGT<br>GGCAGGTGGTTGCAACCCCGCCCG-<br>GTCGGGCCTTCGCAGAGGTTCCCCAAGACCAGCCCTTGCAGGGCGGTTTTCAGCAACCTGACAAG<br>AGGCGGCCAAGACAAATTTCTGCGGGT-<br>TCGAGCACACACTCTCGGGCGTTGGGCCCCAGAGACCTCTAAACCAAGCACAAACAAGAAGG<br>GAGTGAGAGAACCCAGGCTAGAACTTG-<br>CACGGGCATCCCACTGAGGAAAAGCGAGGCCTCGGTGGCAGGCATGTTTTCTTCCGACGCCC<br>GAAAATCGAGCCGAGCGCCCGACTA-<br>CATTTACTGCAGAGGTTTCCGCCTCCAGTGAGCCCGGATCCCCCAGCGGCCTGCCCGGAGCTGG<br>TCTCCAGTCCCCGCCGTAGTCCGACG-<br>CACGGCCCTCTCCTGGCAGCAAGCTCCCAGCGGCCAGTCTGAAGCCAATTCTGTTCAGGCGGC<br>CGAGGGCCCTTAGCCAACCCACCATGAT-<br>GTCGCCTGGGCCACCTGATGCCCGCAGCGGCGGGACACGGCCCGGGCAGTGCGCAGTGGCT |

TABLE 4A-continued

| SEQ ID NO | GENE NAME | SEQUENCE |
|---|---|---|
| | | CCTGCTAGGGGCACCGCGTGCGTGCT-<br>TGTCTCCCGCTGCGCCGGGGACGTCCTTGGGTGACACGGGCCGCTGGGCACCTCCCAAGCCGA<br>GGAAACGGACCCCCTTCGCA-<br>GAGTCTCGCGCCCACCCCCCAACCTCCCACCTCGTTTCTCGCTGCTAGGGCTCCCGACTCAGCCCACCT<br>CTCCTGGCGGTTTAGTTAGGGATCA-<br>GAGCTGGAGAGGCTGAACGCAACCCGTGCCAGTACGGAACAGACGATATGTTTGCCTGCTAGCT<br>GCTTGGATGAATAATTGAAAAGTTCGCT-<br>GCAGTCTGTGCTTCGTCAAGTCCCGGGTGCCGGGAGAACACCTTCCCAACACGCATCAGGG<br>GTGGGCGGGAGCGGGCAGAGGAGCGG-<br>GACCCGAGGGAGGAGAGTGAACCCGAGCAGGAGAAGCAGCCCAGGCAGCCAGGCGCCCTCGAT<br>GCGAGAGGCTGGGCATTTATTTTTATTC-<br>CAGGCTTTCCACTGTGTGGTTATGTCACTTTCTCAAACAAATGTGTATATGGAGGGAGATC<br>GATGCTGATAATGTTTAGAAGATTAAAA-<br>GAGCATTAATGCTGGCAACAATAACGTAAACGTGTGGACCCAGATTTCATTGATCTGGAAC<br>TTGATCCGGCGCGTTTCCAGTAAGC-<br>CCGACGGCGCGCTCTTCCCAGCAGAGCGCTCACCAGCGCCACGGCCCCGCGGTTTTCCAGCGGT<br>GCCGCTTCGCCAGCTCTGCGCGGGT-<br>TCTCCCGTCTGACCGCAGCTCCTCCCCCGCGAGGCCCCAGCCCGCCTTACTTCCCCGAGGTTTT<br>CTCCTCCTCTCGCGGGGCTCTCTGC-<br>CCTCTGCACCCCCTCCCCCGACCTCTGCACCACCCGCCCCTGTGCGCACACACCGCTACTTGCG<br>CTTCCGGCGATCCGCCTG |
| 27 | RAX | AACCGGAGATCTGCTTGGTGAACT-<br>GAGAGGAGTCCTTAGGAGAGCGGGGACGCCAGGGGCCGGGGGACACTTCGCTCTCGCCCTAGGGA<br>AGGTGGTCTTGACGCTTTCTATTGAAGTCAAACTTGAAAATATCAGCTGCCGCTGGACTAT |
| 28 | chr18<br>group-<br>00277 | CGTGAGCAGAACGCCCGCCCTGGAG-<br>CAGTTAGGACCGAAGGTCTCCGGAGAGTCGCCGGCGGTGCCAGGTAACGCAGAGGGCTCGGGTC<br>GGGCCCCGCTTCTGGGGCTTGGGACTC-<br>CGGGCGCGCGGAGCCAGCCCTCTGGGGCGAAATCCCCGGGCGGCGTGCGCGGTCCCTCTCCG<br>CGCTGTGCTCTCCCAGCAACTCCCTGC-<br>CACCTCGACGAGCCTACCGGCCGCTCCGAGTTCGACTTCCTCGGACTTAGTGGGAGAAGGGG<br>TTGGAAATGGGCTGCCGGGACTGGGGGAGCTGCTCTCTGGAAGCAGGGAAGCTGGGGCGCACCGGGGCAGGT |
| 29 | NETO1 | TAGAAGAGGAAGACTCCTCTGGCCCCAC-<br>TAGGTATCATCCGCGCTCTCCCGCTTTCCACCTGCGCCCTCGCTTGGGCCAATCTCTGCCG<br>CACGTGTCCATCCCTGAACTGCACGC-<br>TATCCTCCACCCCCGGGGGGTTCCTGCGCACTGAAAGACCGTTCTCCGGCAGGTTTTGGGATC<br>CGGCGACGGCTGACCGCGCGCCGC-<br>CCCCACGCCCGGTTCCACGATGCTGCAATACAGAAAGTTTACGTCGGCCCCGACCCGCGCGGGAC<br>CTGCAGGGTCCGCCGGAGCGCGGCGCA-<br>GAGGCTTTTCCTGCGCGTTGGCCCCGGGAAAGGGGCGGGAGGGCTGGCTCCGGGAGCGCACG<br>TGGCGCGGCGGGGAGGGTACTCACTGT-<br>GAAGCACGCTGCGCCCATGGATCATGTCTGTGCGTACACCAGAGGCTCCGGGCTCCACTAAT<br>TCCATTTAGAGACGGGAAGACTTC-<br>CAGTGGCGGGGGGAGGACAGGGTCGAGAGGTGTTAAAGACGCAAAGCAAGAAGGAAATAAAGGGG<br>GGCCGAGAGGGAGACCGAGAGGAAGGGG-<br>GAGCTCCGAGCCCACGCTGCAGCCAGATCCGGATGAGTCCGTCCTCCGCCCCGGGCGGGCT<br>CTCGCTCTCGCTGGCCCTCAGCGCCGCG-<br>CAGCCAGCAGCATCCCCACCGTGACGCTCGCATCACACCCGGGCGCCGGCCGCCACCATCC<br>GCGCCGCCGCCGTCAGGACCCTCCTC-<br>CCGGGCATCGTCGCCGCCGCGGGGTCGGGAGGACGCGGCGCGCGGGAGGCGGCGGTCGCAGGG<br>CGAGCCCCGGGACGCCCCGAGCCGGGGC-<br>CGGGGCCGGGGAGAGGGCGCAGCGAGGTGGGGGCCAGTCCAGACCGACGGCAGCGACGGAG<br>ACGGGCGGCGGCGGCGGCGCCGGCGGCG-<br>GCGGGGTGGCTCAGTCCCCGTCTCAGACGCGCCGCGCAGCAGGTCGGAGCAGCCTCCCCGG<br>GAGGATGTCCAGCGGCAGCGCTC-<br>CTCGCTCCAGCCCTTGGGGATCTTCCGCTGAGGCATTGAAGGCAGGAAGAAGGGGTCCGTCATCGG<br>CTCGCCGGGCTGCGCGCCACCTCTGC-<br>TATCTTGCGGAAAGAGGAGCGGGTGGGTGGGCGTCTGGGAGGCGGGCTGGAGGGCGGTGCAGG<br>GGAGCGGGGCGGCCGGGGGGGGGC-<br>CGGGGGGCGGGGAAGGGAGGGAGGAGAAAGGAGCCGGAAGAGGGCAGAGTTACCAAATGGGCTC<br>CTTAGTCATGGCTTGGGGCTCCACGAC-<br>CCTCCTGGAAGCCCGGAGCCTGGGTGGGATAGCGAGGCTGCGCGCGGCCGGCGCCCCGGGGC<br>TGGTGCGCGGCAGAATGGGGCCGCGGCG-<br>GCGGCAGCAAGGACATCCCAGCCGCGCGGATCTGGGGAGGGGCGGGGAGGGGGTGAGGAC<br>CCGGCTGGGATCCGCGGCTCGGCCCGC-<br>CAGGGCGCAGAGAGAGGATGCAGCCGCAAATCCCGAGCCGGATCCTCGTGCCGGACGGAAGG<br>CGTGGAAGCGGGAGGGGCCTTCGTGT-<br>GAAAATCCCTTGTGGGGTTTGGTGTTTCACTTTTTAAAGGTTAGACCTTGCGGGCTCTCTGCC<br>TCCCACCCCTTCTTTTCCATCCGCG-<br>TAAAGGAACTGGGCGCCCCCTCTCCCTCCCTCCCTGGGGCGCAGGTTTCGCCGCGGACTCCGCG<br>CTCAGCTTGGGAGACACG-<br>GCAGGGGCGCGCCCCAGGGAAAGGCGGCCGTAAAAGTTTCGCGGTTGAGCACTGGGCCTGATGTCCAGTCC<br>CCCCACCAAATTACTCCTGCAAA-<br>GACGCGGGCTTCTTGCAATTGAGCCCCCCACCTCGAGGTATTTAAAACCACCCCAAGGCACACACG<br>GACCCCCGTTCCCCCGCGCCACTTCCTC-<br>CTACAGGCTCGCGCGGCGCGTTAAAGTCTGGGAGACACGAGTTGCGGGGAAACAGCACCGG<br>AAG |

TABLE 4A-continued

| SEQ ID NO | GENE NAME | SEQUENCE |
|---|---|---|
| 30 | MBP | AAGAAACAGCTCATTTCGGAGCTGAGGA-<br>CAAGGCGTGGGAAGAAGACGCGTTTGGTTTCACCCAGGCGGGTGGCGGCAAAGCTGTGGGA<br>TGCGCGCTGCACACTCCTTCCGTCATC-<br>CCGTTCCCACCTTCCACACACACCTGCGGGAGGTCGGACATGTCCTGATTGCGTGTTCATCA<br>CGATGGCAAACCGAACATGAG-<br>GAGAACGCCACTGACGCTGGGTGCGCCGGCTTTCCCAGCCCTCGTGCATAACGGGGAGGGAGATGCAG<br>AAGTTTTTTCCAACATCGGTGCAAAGGGGAAGCTGAGGTTTTCCTAT |
| 31 | NFATC1 | TCTGTCAGCTGCTGCCATGGGGCAGCGG-<br>GAAGGCCCTGGAGGGTGCCTGGGCTGTGTCTGGTCCCGGCCACGCGTCCCTGCAGCGTCTG<br>AGACCTTGTGGAACACACTTGACCCG-<br>GCGCTGGGACGGGGTCGGCCCACACGCACCGCCAGCCCGCAGGAGTGAGGTGCAGGCTGCCGC<br>TGGCTCCTTAGGCCTCGACAGCTCTCT-<br>TGAGGTCGGCCCTCCTCCCCTCCCGAGAGCTCAGCAGCCGCAGACCCAGGCAGAGAGAGCAA<br>AGGAGGCTGTGGTGGCCCCCGACGG-<br>GAACCTGGGTGGCCGGGGGACACACCGAGGAACTTTCCGCCCCCCGACGGGCTCTCCCACCGAG<br>TGCTCAGGTGCTCGTGGGCAGCAAGGG-<br>GAAGCCCCATGGCCATGCCGCTTCCCTTTCACCCCAGCGACGCGCCCTCCTGTGCCCGCGGG<br>GAACAAGACGGCTCTCGGCGGCCATG-<br>CAGGCGGCCTGTCCCACGAACACGATGGAGACCTCAGACGCCGTCCCCACCCTGTCACTGTCA<br>CCATCACCCATCCTGTCCCCTCACGCCTCCCCACATCCCATCATTACTAC |
| 32 | chr18<br>group-<br>00430 | GAAGTAGAATCACAGTAAATGAGGAGT-<br>TAGGGAATTTAGGGTAGAGATTAAAGTAATGAACAGAGGAGGAGGCCTGAGACAGCTGCAGA<br>GAGACCCTGTGTTCCCTGTGAGGT-<br>GAAGCGTCTGCTGTCAAAGCCGGTTGGCGCTGAGAAGAGGTACCGGGGGCAGCACCCGCCTCCTG<br>GGAGAGGGATGGGCCTGCGGGCAC-<br>CTGGGGGAACCGCACGGACACAGACGACACTATAAACGCGGGCGAGACATCAGGGACCGGGAAAC<br>AGAAGGACGCGCGTTTCGAGCAGCTGCCCAGTGGGCCACAAGCCCCGCCACGCCACAGCCTCTTCCCCTCAGCACGCAGAGA |
| 33 | OLIG2 | TACTCCGGCGACGGGAGGATGTTGAGG-<br>GAAGCCTGCCAGGTGAAGAAGGGGCCAGCAGCAGCACAGAGCTTCCGACTTTGCCTTCCAGG<br>CTCTAGACTCGCGCCATGCCAA-<br>GACGGGCCCCTCGACTTTCACCCCTGACTCCCAACTCCAGCCACTGGACCGAGCGCGCAAAGAACCT<br>GGAGACCGCTTGCTCTCACCGCCG-<br>CAAGTCGTCGCAGGACAGACACCAGTGGGCAGCAACAAAAAAAGAAACCGGGTTCCGGGACACGT<br>AGCCGGCGGCTGGACTAACCTCAGCG-<br>GCTGCAACCAAGGAGCGCGCCGTTGCGCCTGCTGGTGTTTATTAGCTACACTGGCAGGCGCAC<br>AACTCCGCGCCCCGACTGGTGGCCCCA-<br>CAGCGCGCACCACACATGGCCTCGCTGCTGTTGGCGGGGTAGGCCCGAAGGAGGCATCTACA<br>GAATGCCCGAGCCCTTTCTGATCCCCAC-<br>CCCCCCGCTCCCTGCGTCGTCCGAGTGACAGATTCTACTAATTGAACGTTATGGGTCATCC<br>TTGTAACCGTTGGACGACATAACAC-<br>CACGCTTCAGTTCTTCATGTTTTAAATACATATTTAACGGATGGCTGCAGAGCCAGCTGGGAAA<br>CACGCGGATTGAAAAATAATGCTCCA-<br>GAAGGCACGAGACTGGGGCGAAGGCGAGAGCGGGCTGGGCTTCTAGCGGAGACCGCAGAGGGA<br>GACATATCTCAGAAC-<br>TAGGGGCAATAACGTGGGTTTCTCTTTGTATTTGTTTATTTTGTAACTTTGCTACTTGAAGACCAATTATTTAC<br>TATGCTAATTTGTTTGCTTGTTTT-<br>TAAAACCGTACTTGCACAGTAAAAGTTCCCCAACAACGGAAGTAACCCGACGTTCCTCACACTCC<br>CTAGGAGACTGTGTGCGTGTGTGC-<br>CCGCGCGTGCGCTCACAGTGTCAAGTGCTAGCATCCGAGATCTGCAGAAACAAATGTCTGAATTC<br>GAAATGTATGGGTGTGAGAAAT-<br>TCAGCTCGGGGAAGAGATTAGGGACTGGGGGAGACAGGTGGCTGCCTGTACTATAAGGAACCGCCAA<br>CGCCAGCATCTGTAGTCCAAGCAGGGCT-<br>GCTCTGTAAAGGCTTAGCAATTTTTTCTGTAGGCTTGCTGCACACGGTCTCTGGCTTTTCC<br>CATCTGTAAAATGGGTGAATGCATCCG-<br>TACCTCAGCTACCTCCGTGAGGTGCTTCTCCAGTTCGGGCTTAATTCCTCATCGTCAAGAGT<br>TTTCAGGTTTCAGAGCCAGCCTG-<br>CAATCGGTAAAACATGTCCCAACGCGGTCGCGAGTGGTTCCATCTCGCTGTCTGGCCCACAGCGTG<br>CGAGAAGCCTTGCCCAGGCTGAAACT-<br>TCTCTTTGCAGTTCCAGAAAGCAGGCGACTGGGACGGAAGGCTCTTTGCTAACCTTTTACAGC<br>GGAGCCCTGCTTGGACTACAGATGC-<br>CAGCGTTGCCCCTGCCCCAAGGCGTGTGGTGATCACAAAGACGACACTGAAAATACTTACTATC<br>ATCCGGCTCCCCTGCTAATAAATG-<br>GAGGGGTGTTTAACTACAGGCACGACCCTGCCCTTGTGCTAGCGCGGTTACCGTGCGGAAATAAC<br>TCGTCCCTGTACCCACACCATCCTCAAC-<br>CTAAAGGAGAGTTGTGAATTCTTTCAAAACACTCTTCTGGAGTCCGTCCCCTCCCTCCTTG<br>CCCGCCCTCTACCCCTCAAGTCCCTGC-<br>CCCCAGCTGGGGGCGCTACCGGCTGCCGTCGGAGCTGCAGCCACGGCCATCTCCTAGACGCG<br>CGAGTAGAGCACCAAGATAGTGGG-<br>GACTTTGTGCCTGGGCATCGTTTACATTTGGGGCGCCAAATGCCCACGTGTTGATGAAACCAGTG<br>AGATGGGAACAGGCGGCGGGAAACCAGA-<br>CAGAGGAAGAGCTAGGGAGGAGACCCCAGCCCCGGATCCTGGGTCGCCAGGGTTTTCCGCG<br>CGCATCCCAAAAGGTGCGGCT-<br>GCGTGGGGCATCAGGTTAGTTTGTTAGACTCTGCAGAGTCTCCAAACCATCCCATCCCCCAACCTGAC<br>TCTGTGGTGGCCGTATTTTTTACA-<br>GAAATTTGACCACGTTCCCTTTCTCCCTTGGTCCCAAGCGCGCTCAGCCCTCCCTCCATCCCCCT<br>TGAGCCGCCCTTCTCCTCCCCCTCGC-<br>CTCCTCGGGTCCCTCCTCCAGTCCCTCCCCAAGAATCTCCCGGCCACGGGCGCCCATTGGTTG |

TABLE 4A-continued

| SEQ ID NO | GENE NAME | SEQUENCE |
|---|---|---|
| | | CTGCGCAGGGAGGAGGCGTGTGCCCGGC-<br>CTGGCGAGTTTCATTGAGCGGAATTAGCCCGGATGAATCAGCTTCCCAGCCCCCCGGCGGG<br>CCCAGCTCATTGGCGAGGCAGCCCCTC-<br>CAGGACACGCACATTGTTCCCCGCCCCCGCCCCCGCCACCGCTGCCGCCGTCGCCGCTGCCA<br>CCGGGCTATAAAAACCGGCCGAGC-<br>CCCTAAAGGTGCGGATGCTTATTATAGATCGACGCGACACCAGCGCCCGGTGCCAGGTTCTCCCC<br>TGAGGCTTTTCGGAGCGAGCTCCT-<br>CAAATCGCATCCAGAGTAAGTGTCCCCGCCCCACAGCAGCCGCAGCCTAGATCCCAGGGACAGAC<br>TCTCCTCAACTCGGCTGTGACCCAGAAT-<br>GCTCCGATACAGGGGGTCTGGATCCCTACTCTGCGGGCCATTTCTCCAGAGCGACTTTGCT<br>CTTCTGTCCTCCCCACACTCACCGCTG-<br>CATCTCCCTCACCAAAAGCGAGAAGTCGGAGCGACAACAGCTCTTTCTGCCCAAGCCCCAGT<br>CAGCTGGTGAGCTCCCCGTGGTCTCCA-<br>GATGCAGCACATGGACTCTGGGCCCCGCGCCGGCTCTGGGTGCATGTGCGTGTGCGTGTGTT<br>TGCTGCGTGGTGTCGATGGAGATAAG-<br>GTGGATCCGTTTGAGGAACCAAATCATTAGTTCTCTATCTAGATCTCCATTCTCCCCAAAGAA<br>AGGCCCTCACTTCCCACTCGTTTATTC-<br>CAGCCCGGGGGCTCAGTTTTCCCACACCTAACTGAAAGCCCGAAGCCTCTAGAATGCCACCC<br>GCACCCCGAGGGTCACCAACGCTCCCT-<br>GAAATAACCTGTTGCATGAGAGCAGAGGGGAGATAGAGAGAGCTTAATTATAGGTACCCGCG<br>TGCAGCTAAAAGGAGGGCCAGAGATAG-<br>TAGCGAGGGGGACGAGGAGCCACGGGCCACCTGTGCCGGGACCCCGCGCTGTGGTACTGCGG<br>TGCAGGCGGGAGCAGCTTTTCTGTCTCT-<br>CACTGACTCACTCTCTCTCTCTCCCTCTCTCTCTCTCATTCTCTCTCTTTTCTCCTC<br>CTCTCCTGGAAGTTTTCGGGTCCGAGG-<br>GAAGGAGGACCCTGCGAAAGCTGCGACGACTATCTTCCCCTGGGGCCATGGACTCGGACGCC<br>AGCCTGGTGTCCAGCCGCCCGTCGTCGC-<br>CAGAGCCCGATGACCTTTTTCTGCCGGCCCGGAGTAAGGGCAGCAGCGGCAGCGCCTTCAC<br>TGGGGGCACCGTGTCCTCGTCCACCCCGAGTGACTGCCC |
| 34 | SIM2 | TTAATTCGAAAATGGCAGACAGAGCT-<br>GAGCGCTGCCGTTCTTTTCAGGATTGAAAATGTGCCAGTGGGCCAGGGGCGCTGGGACCCGCG<br>GTGCGGAAGACTCGGAACAGGAAGAAAT-<br>AGTGGCGCGCTGGGTGGGCTGCCCCGCCGCCCACGCCGGTTGCCGCTGGTGACAGTGGCTG<br>CCCGGCCAGGCACCTCCGAGCAGCAG-<br>GTCTGAGCGTTTTTGGCGTCCCAAGCGTTCCGGGCCGCGTCTTCCAGAGCCTCTGCTCCCAGC<br>GGGGTCGCTGCGGCCTGGCCCGAAGGATTTGACTCTTTGCTGGGAGGCGCGCTGCTCAGGGTTCTG |
| 35 | SIM2 | CCGGTCCCCAGTTTGGAAAAAGGCGCAA-<br>GAAGCGGGCTTTTCAGGGACCCCGGGGAGAACACGAGGGCTCCGACGCGGGAGAAGGATTG<br>AAGCGTGCAGAGGCGCCCCAAATTGCGA-<br>CAATTTACTGGGATCCTTTTGTGGGGAAAGGAGGCTTAGAGGCTCAAGCTATAGGCTGTCC<br>TAGAGCAACTAGGCGAGAACCTGGC-<br>CCCAAACTCCCTCCTTACGCCCTGGCACAGGTTCCCGGCGACTGGTGTTCCCAAGGGAGCCCCC<br>TGAGCCTACCGCCCTTGCAGGGGGTCGT-<br>GCTGCGGCTTCTGGGTCATAAACGCCGAGGTCGGGGGTGGCGGAGCTGTAGAGGCTGCCCG<br>CGCAGAAAGCTCCAGGATCCCAATATGTG |
| 36 | DSCR6 | GCGCAGGTCCCCCCAGTCCCCGAGG-<br>GAGTGCGCCCGACGGAAACGCCCCTAGCCCGCGGGCCTCGCTTTCCTCTCCCGGGTTCCTGGGT<br>CACTTCCCGCTGTCTC |
| 37 | DSCAM | TTCCCTCGCGGCTTTGGAAAGGGGGTG-<br>CAAATGCACCCTTCTGCGGGCCCGCTACCCGCTGCAACACCTGTGTTTCCTTTCTGGGCACC<br>TTCTAGGTTTCTAGATATTGCTGTGAATACGGTCCTCCGCTGTACAGTTGAAAACAAA |
| 38 | chr21 group-00165 | TGGGAATTTAGGTCGGGCACTGC-<br>CGATATGTCGCCTTCCACAAGGCGGGCCCGGGCCTCTGCTGACCGTGCACCGGTCCTGGGGCTGGG<br>TAATTCTGCAGCAGCAGCGCAGCCCAT-<br>GCCGGGGAATTTGCGGGCAGAGGAGACAGTGAGGCCCGCGTTCTGTGCGGGAACTCCCGAGC<br>TCACAGAGCCCAAGACCACACGGCTG-<br>CATCTGCTTGGCTGACTGGGCCAGGCCCACGCGTAGTAACCCGGACGTCTCTCTCTCACAGTC<br>CCCTTGCGTCTGGCCAGGGAGCTGCCAG-<br>GCTGCACCCCGCGGTGGGGATCGGGAGAGGGGCAGTGTCGCCCATCCCCGGAAGGCTGAGC<br>CTGGTGCAG |
| 39 | PRMT2 | CGGTTTTCTCCTGGAGGACTGTGTTCA-<br>GACAGATACTGGTTTCCTTATCCGCAGGTGTGCGCGGCGCTCGCAAGTGGTCAGCATAACGC<br>CGGGCGAATTCGGAAAGCCCGTGCGTC-<br>CGTGGACGACCCACTTGGAAGGAGTTGGGAGAAGTCCTTGTTCCCACGCGCGGACGCTTCCC<br>TCCGTGTGTCCTTCGAGCCACAAAAAGC-<br>CCAGACCCTAACCCGCTCCTTTCTCCCGCCGCGTCCATGCAGAACTCCGCCGTTCCTGGGA<br>GGGGAAGCCCGCGAGGCGTCGGGAGAG-<br>GCACGTCCTCCGTGAGCAAAGAGCTCCTCCGAGCGCGCGGCGGGGACGCTGGGCCGACAGGG<br>GACCGCGGGGGCAGGGCGGAGAGGACCCGCCCTCGAGTCGGCCCAGCCCTAACACTCAGGAC |
| 40 | SIX2 | AGGGAATCGGGCTGACCAGTCCTAAG-<br>GTCCCACGCTCCCCTGACCTCAGGGCCCAGAGCCTCGCATTACCCCGAGCAGTGCGTTGGTTA<br>CTCTCCCTGGAAAGCCGCCCCCGC-<br>CGGGGCAAGTGGGAGTTGCTGCACTGCGGTCTTTGGAGGCCTAGGTCGCCCAGAGTAGGCGGAGC |

TABLE 4A-continued

| SEQ ID NO | GENE NAME | SEQUENCE |
|---|---|---|
| | | CCTGTATCCCTCCTGGAGCCGGCCTGCG-<br>GTGAGGTCGGTACCCAGTACTTAGGGAGGGAGGACGCGCTTGGTGCTCAGGGTAGGCTGGG<br>CCGCTGCTAGCTCTTGATTTAGTCTCAT-<br>GTCCGCCTTTGTGCCGGCCTCTCCGATTTGTGGGTCCTTCCAAGAAAGAGTCCTCTAGGGC<br>AGCTAGGGTCGTCTCTTGGGTCTGGC-<br>GAGGCGGCAGGCCTTCTTCGGACCTATCCCCAGAGGTGTAACGGAGACTTTCTCCACTGCAGG<br>GCGGCCTGGGGCGGGCATCTGCCAGGC-<br>GAGGGAGCTGCCCTGCCGCCGAGATTGTGGGGAAACGGCGTGGAAGACACCCCATCGGAGGG<br>CACCCAATCTGCCTCTGCACTCGATTC-<br>CATCCTGCAACCCAGGAGAAACCATTTCCGAGTTCCAGCCGCAGAGGCACCCGCGGAGTTGC<br>CAAAAGAGACTCCCGCGAGGTCGCTCG-<br>GAACCTTGACCCTGACACCTGGACGCGAGGTCTTTCAGGACCAGTCTCGGCTCGGTAGCCTG<br>GTCCCCGACCACCGCGACCAGGAGTTC-<br>CTTCTTCCCTTCCTGCTCACCAGCCGGCCGCCGGCAGCGGCTCCAGGAAGGAGCACCAACCC<br>GCGCTGGGGGCGGAGGTTCAGGCGGCAG-<br>GAATGGAGAGGCTGATCCTCCTCTAGCCCCGGCGCATTCACTTAGGTGCGGGAGCCCTGAG<br>GTTCAGCCTGACTTTC |
| 41 | SIX2 | CACTACGGATCTGCCTGGACTGGTTCA-<br>GATGCGTCGTTTAAAGGGGGGGGCTGGCACTCCAGAGAGGAGGGGGCGCTGCAGGTTAATTG<br>ATAGCCACGGAAGCACCTAGGCGC-<br>CCCATGCGCGGAGCCGGAGCCGCCAGCTCAGTCTGACCCCTGTCTTTTCTCTCCTCTTCCCTCTC<br>ACCACCCCTCACTCCGGGAAAGC-<br>GAGGGCCGGGTAGGGGCAGATAGATCACCAGACAGGCGGAGAAGGACAGGAGTACAGATGGAGGGA<br>CCAGGACACAGAATGCAAAAGACTG-<br>GCAGGTGAGAAGAAGGGAGAAACAGAGGGAGAGAGAAAGGGAGAAACAGAGCAGAGGCGGCCGC<br>CGGCCCGGCCGCCCTGAGTCCGATTTC-<br>CCTCCTTCCCTGACCCTTCAGTTTCACTGCAAATCCACAGAAGCAGGTTTGCGAGCTCGAAT<br>ACCTTTGCTCCACTGCCACACGCAGCAC-<br>CGGGACTGGGCGTCTGGAGCTTAAGTCTGGGGGTCTGAGCCTGGGACCGGCAAATCCGCGC<br>AGCGCATCGCGCCCAGTCTCGGAGACTG-<br>CAACCACCGCCAAGGAGTACGCGCGGCAGGAAACTTCTGCGGCCCAATTTCTTCCCCAGCT<br>TTGGCATCTCCGAAGGCACGTACCCGC-<br>CCTCGGCACAAGCTCTCTCGTCTTCCACTTCGACCTCGAGGTGGAGAAAGAGGCTGGCAAGG<br>GGCTGTGCGCGTCGCTGTGTGGG-<br>GAGGGCAGCAGGCTGCCCCTCCCCGCTTCTGCAGCGAGTTTTCCCAGCCAGGAAAAGGGAGGGAGC<br>TGTTTCAGGAATTTCAGTGCCTTCACCTAGCGACTGACACAAGTCGTGTGTATAGGAAG |
| 42 | SOX14 | GGAGCCTGAAGTCAGAAAAGATGGGGC-<br>CTCGTTACTCACTTTCTAGCCCAGCCCCTGGCCCTGGGTCCCGCAGAGCCGTCATCGCAGGC<br>TCCTGCCCAGCCTCTGGGGTCGGGTGAG-<br>CAAGGTGTTCTCTTCGGAAGCGGGAAGGGCTGCGGGTCGGGGACGTCCCTTGGCTGCCACC<br>CCTGATTCTGCATCCTTTTCGCTC-<br>GAATCCCTGCGCTAGGCATCCTCCCCGATCCCCCAAAAGCCCAAGCACTGGGTCTGGGTTGAGGA<br>AGGGAACGGGTGCCCAGGCCGGACAGAG-<br>GCTGAAAGGAGGCCTCAAGGTTCCTCTTTGCTACAAAGTGGAGAAGTTGCTCTACTCTGGA<br>GGGCAGTGGCCTTTTCCAAACTTTTC-<br>CACTTAGGTCCGTAAGAAAAGCAATTCATACACGATCAGCGCTTTCGGTGCGAGGATGGAAAG<br>AAACTTC |
| 43 | TLX3 | TTTTCCTGTTACAGAGCTGAGCCCACT-<br>CATGTGGTGCCAAGTAGCGACTATCTCTCGGCCACCTCCACCCAGAGCAATGTGGGCGCCCC<br>CAGCGGGTGGGAGCGATTGCCGAGCG-<br>GCGCAAGGGCGTTTAACGCCTAACCCCCTCCTCCTGGGTTGCCAAGCCGCTAGGTCGCCGTTT<br>CCAACGTGGCTGCGCGGGACTGAAGTC-<br>CGACGACTCCTCGTCCTCAGTAGGAGACACACCTCCCACTGCCCCCAGCCACGCGAGCTATG<br>GGCAGAATCGGGGCAACGGTAATATCTG-<br>GATGGGGCAGGCTCCCCTGAGGCTGTGCTTAAGAAAAAAGGAATCTGGAGTAGCCTGAGGG<br>GCCCCACGAGGGGGCCTCCTTTGC-<br>GATCGTCTCCCAGCCTTAGGCCAAGGCTACGGAGGCAGGCGGCCGAGTGTTGGCGCCCAGCCCGG<br>CCGAGGACTGGATGGAGGACGAGAAG-<br>CAGCCTGCCTCTGGGCGACAGCTGCGGACGCAGCCTCGCCGCCTCGCCGCCTCAGCCTCGGTC<br>CCAGCGTCTCTAAAGCCGCGCCCATTT-<br>TACAGATGCAGGGCAGGGAGACAAGAGGCATCTCCGGGGGCCGAGTAGAATGATGGCGCGGG<br>TTCTCCCGGCGCCCTGATTTCGAGGCT-<br>GCGCCCGGGGCCCTACATGCAGGCGGGGAGGCCTGGGCCGAAGGCGTCTGCAAGGAGGGGCG<br>AGTCTGCCCGGTCCGGGCAGGGAGTGAG-<br>GCCACAGTCAGTTCTCCCTAGGAGGCCGCGCAGCGGGTAGGGTATGGGACTGGGGGACGCA<br>ACGGGGACCTGGCCGAATCAGAGCCCT-<br>CAGCAGAGAACGCCGAAAACTCTGGGGCCGGCCGCTCGCTTCCCGCTAGTGGGAATGGTTTC<br>CGGTCATCCGTTCCCAGTCCAGC-<br>CCCGGGTAGGGAGCTCTGATTTGCAATGCACAGCACTTGCGAGGTTCGAATGCCCCCGCAATTTGC<br>AGATGGAAATACTAAGCCTAGGC-<br>CGGGCGTGGTGGCTCAAGCCTATCATCTCAGCCCTTTGGGAGGCCAAGCCGGGAGGATTGTTTGAG<br>CCCAAGAATTCAAAACCAGCCTGAGCAA-<br>CATAGCGACCCCGTCTCTACAAAATAAAATAAAATAAATTATCCGGGCGTGGTGGCACGCG<br>CCTGTGGTTCCAGCTACTCCGGAGGCT-<br>GAGGTGGGAGGATCGCTTGAGTCCGGGAGGTCGAGGCTACAGTGAGCCGTGATCGCACCACT<br>GCACTCCAGCCTGGGCGACAGAGT-<br>GAGACCTTGTCTCAAAAAAGGAAAAAAAGAAAAAGAAAGTAAGCTTCAAAGAAGCTCTGATAATA<br>GTTCTGGGTCGTGCAGCGGTGGCGGC-<br>CCCGCGCTCTCGCCCCTAAAGCAAGCGCTCTTTGTACTGGGTGGAGGAGCTTTGAGTAGTGAG |

TABLE 4A-continued

| SEQ ID NO | GENE NAME | SEQUENCE |
|---|---|---|
| | | GGTGGAGATGCAGCTTCGGGGTGGCG-CAGCCACCCTGACACTAGGCCCGGGGTCGCAGTGGGACAGAAGAGTCTGCCGCTCTGACTTGG GCTCTGAGTTCCAAGGGCGCCCGGCACT-TCTAGCCTCCCAGGCTTGCGCGCTGGCGCCTTTGCCATCCGTGCCGAAGTGGGGAGACCTA GCCGCGACCACCACGAGCGCAGCGGTGA-CACCCAGAGGTCCCACCGGGCCCCTGGGCAGGGTAACCTTAGCCTGTCCGCTTCGGCAGCT TTGCGAAGAGTGGCGCGCAGCTAGGGCT-GAGGCTCTTGCGGACCTGCGGTCGAAGCAGGCGGCTGAGCCAGTTCGATCGCCAAGGCCTG GGCTGCCGACAGTGGTGCGCGCTCTGT-TCCGCCGCGGCCGGGCCAGGCGCTCTGGAATAGCGATGGGGGGACACGGCCTCCAACTTTCT GCAGAGACCATCGGGCAGCTCCGGGC-CTAAGCAGCGACCTCACCGAAGGTTCCTGGGAACCTTTGCCAAAATCCCAGCCTCTGCCTCGG TCCAGCTAAACCGTGTGTAAACAAGTGCACCAAG |
| 44 | FOXP4 | ATAAAGGACCGGGTAATTTCGCGGAAT-GCGGATTTTGAGACAGGCCCAGACGGCGGCGGATTCCCTGTGTCCCCCAACTGGGGCGATCT CGTGAACACACCTGCGTCCCAC-CCCGATCCTAGGTTGGGGGGAAAGGGTATGGGAACCCTGAGCCCAGAGCGCGCCCCGCTCTTTCCTT TGCTCCCCGGCTTCCCTGGCCAGC-CCCCTCCCGGCTGGTTTCCTCGCTCACTCGGCGCCTGGCGTTTCGGGCGTCTGGAGATCACCGCG TGTCTGGCACCCCAACGTCTAGTCTC-CCCGCAGGTTGACCGCGGCGCCTGGAGCCGGGAATAGGGGTGGGGAGTCCGGAGAACCAAACC CGAGCCTGAAGTTGCCATTCGGGT-GACTCCCGAGAAAGCCCGGGAGCATTTTGGCCAATGCGGGTTTTTACCTGAACTTCAGCATCTTC ACC |
| 45 | FOXP4 | AATTGGAAAACCCTGGTATTGTGCCT-GTTTGGGGGAAGAAAACGTCAATAAAAATTAATTGATGAGTTGGCAGGGCGGGCGGTGCGGGT TCGCGGCGAGGCGCAGGGTGTCATG-GCAAATGTTACGGCTCAGATTAAGCGATTGTTAATTAAAAAGCGACGGTAATTAATACTCGCTA CGCCATATGGGCCCGTGAAAAGGCA-CAAAAGGTTTCTCCGCATGTGGGGTTCCCCTTCTCTTTTCTCCTTCCACAAAAGCACCCCAGCC CGTGGGTCCCCCCTTTGGCCCCAAGG-TAGGTGGAACTCGTCACTTCCGGCCAGGGAGGGGATGGGGCGGTCTCCGGCGAGTTCCAAGGG CGTCCCTCGTTGCGCACTCGCCCGCCCAGGTTCTTTGAA |
| 46 | chr7 group-00267 | GGGAAGCGATCGTCTCCTCTGT-CAACTCGCGCCTGGGCACTTAGCCCCTCCCGTTTCAGGGCGCCGCCTCCCCGGATGGCAAACACTAT AAAGTGGCGGCGAATAAGGTTCCTCCT-GCTGCTCTCGGTTTAGTCCAAGATCAGCGATATCACGCGTCCCCCGGAGCATCGCGTGCAGG AGCCATGGCGCGGGAGCTATACCACGAA-GAGTTCGCCCGGGCGGGCAAGCAGGCGGGGCTGCAGGTCTGGAGGATTGAGAAGCTGGAGC TGGTGCCCGTGCCCCAGAGCGCTCACG-GCGACTTCTACGTCGGGGATGCCTACCTGGTGCTGCACACGGCCAAGACGAGCCGAGGCTTC ACCTACCACCTGCACTTCTGGCTCGG-TAAGGGACGGCGGGCGGCGGGACCCCGACGCACCAAGGCCGGCGAGGGGAGGGCGTAGGGGTC TGAGATTTGCAGGCGTGGGAGTAAAGGGGACCGCAAACTGAGCTAG |
| 47 | NPY | CTCAGGGGCGGGAAGTGGCGGGTGG-GAGTCACCCAAGCGTGACTGCCCGAGGCCCCTCCTGCCGCGGCGAGGAAGCTCCATAAAAGCCC TGTCGCGACCCGCTCTCTGCACCCCATC-CGCTGGCTCTCACCCCTCGGAGACGCTCGCCCGACAGCATAGTACTTGCCGCCCAGCCACG CCCGCGCGCCAGCCACCGTGAGTGCTAC-GACCCGTCTGTCTAGGGGTGGGAGCGAACGGGGCGCCCGCGAACTTGCTAGAGACGCAGCC TCCCGCTCTGTGGAGCCCTGGGGC-CCTGGGATGATCGCGCTCCACTCCCCAGCGGACTATGCCGGCTCCGCGCCCCGACGCGGACCAGC CCTCTTGGCGGCTAAATTCCACTTGTTC-CTCTGCTCCCCTCTGATTGTCCACGGCCCTTCTCCCGGGCCCTTCCCGCTGGGCGGTTCTT CTGAGTTACCTTTTAGCAGATATGGAGG-GAGAACCCGGGACCGCTATCCCAAGGCAGCTGGCGGTCTCCCTGCGGGTCGCCGCCTTGAG GCCCAGGAAGCGGTGCGCGGTAGGAAG-GTTTCCCCGGCAGCGCCATCGAGTGAGGAATCCCTGGAGCTCTAGAGCCCCGCGCCCTGCCA CCTCCCTGGATTCTTGGGCTC-CAAATCTCTTTGGAGCAATTCTGGCCCAGGGAGCAATTCTCTTTCCCCTTCCCCACCGCAGTCGTCAC CCCGAGGTGATCTCTGCTGTCAGCGT-TGATCCCCTGAAGCTAGGCAGACCAGAAGTAACAGAGAAGAAACTTTTCTTCCCAGACAAGAG TTTGGGCAAGAAGGGAGAAAAGTGAC-CCAGCAGGAAGAACTTCCAATTCGGTTTTGAATGCTAAACTGGCGGGGCCCCCACCTTGCACT CTCGCCGCGCGCTTCTTGGTCCCT-GAGACTTCGAACGAAGTTGCGCGAAGTTTTCAGGTGGAGCAGAGGGGCAGGTCCCGACCGGACGG CGCCCGGAGCCCGCAAGGTGGTGCTAGC-CACTCCTGGGTTCTCTCTGCGGGACTGGGACGAGAGCGGATTGGGGGTCGCGTGTGGTAGC AGGAGGAGGAGCGCGGGGGGCAGAG-GAGGGAGGTGCTGCGCGTGGGTGCTCTGAATCCCCAAGCCCGTCCGTTGAGCCTTCTGTGCCTG CAGATGCTAGGTAACAAGC-GACTGGGGCTGTCCGGACTGACCCTCGCCCTGTCCCTGCTCGTGTGCCTGGGTGCGCTGGCCGAGGCGTA CCCCTCCAAGCCGGACAACCCGGGCGAGGACGCACCAG |
| 48 | SHH | TGGAGAACCTTGGGCTCTGTGGCCT-CAAAGGTAGGGGTGATTTCGAGGGGCCGGCACCTCACAGGGCAGGTTCCACCGCGGAAACGCAG |

TABLE 4A-continued

| SEQ ID NO | GENE NAME | SEQUENCE |
|---|---|---|
| | | TCATCGCCCAGCGACCCTGCTCCTGGC-<br>CCTCAGCCTCCCCCCAGGTTTCTTTTTCTCTTGAATCAAGCCGAGGTGCGCCAATGGCCTTC<br>CTTGGGTCGGATCCGGGGGGCCAGGGC-<br>CAGCTTACCTGCTTTCACCGAGCAGTGGATATGTGCCTTGGACTCGTAGTACACCCAGTCGA<br>AGCCGGCCTCCACCGCCAGGCGGGCCAG-<br>CATGCCGTACTTGCTGCGGTCGCGGTCAGACGTGGTGATGTCCACTGCGCGGCCCTCGTAG<br>TGCAGAGACTCCTCTGAGTGGTGGC-<br>CATCTTCGTCCCAGCCCTCGGTCACCCGCAGTTTCACTCCTGGCCACTGGTTCATCACCGAGAT<br>GGCCAAAGCGTTCAACTTGTCCTTACAC-<br>CTCTGCGAAGACAAGGGGACCCCCACCGACGGACACGTTAGCCTGGGCAACCGCCACCCCT<br>CCCGGCCCCTCCATCAGCCT |
| 49 | OSR2 | TCTCACGACCCATCCGTTAACCCACCGT-<br>TCCCAGGAGCTCCGAGGCGCAGCGGCGACAGAGGTTCGCCCCGGCCTGCTAGCATTGGCAT<br>TGCGGTTGACTGAGCTTCGCCTAACAG-<br>GCTTGGGGAGGGTGGGCTGGGCTGGGCTGGGCTGGGCTGGGTGCTGCCCGGCTGTCCGCCTT<br>TCGTTTTCCTGGGACCGAGGAGTCTTC-<br>CGCTCCGTATCTGCCTAGAGTCTGAATCCGACTTTCTTTCCTTTGGGCACGCGCTCGCCAGT<br>GGAGCACTTCTTGTTCTGGCCCCGGGCT-<br>GATCTGCACGCGGACTTGAGCAGGTGCCAAGGTGCCACGCAGTCCCCTCACGGCTTTCGGG<br>GGGTCTTGGAGTCGGGTGGGGAGG-<br>GAGACTTAGGTGTGGTAACCTGCGCAGGTGCCAAAGGGCAGAAGGAGCAGCCTTGGATTATAGTC<br>ACGGTCTCTCCCTCTCTTCCCTGC-<br>CATTTTTAGGGCTTTCTCTACGTGCTGTTGTCTCACTGGGTTTTTGTCGGAGCCCCACGCCCTCC<br>GGCCTCTGATTCCTGGAAGAAAGGGTTG-<br>GTCCCCTCAGCACCCCCAGCATCCCGGAAAATGGGGAGCAAGGCTCTGCCAGCGCCCATCC<br>CGCTCCACCCGTCGCTGCAGCTCAC-<br>CAATTACTCCTTCCTGCAGGCCGTGAACACCTTCCCGGCCACGGTGGACCACCTGCAGGGCCTG<br>TACGGTCTCAGCGCGGTACAGACCATGCACATGAACCACTGGACGCTGGGGTATCCCAAT |
| 50 | GLIS3 | TGGTTTCCTTTCGCTTCTCGCCTC-<br>CCAAACACCTCCAGCAAGTCGGAGGGCGCGAACGCGGAGCCAGAAACCCTTCCCCAAAGTTTCTC<br>CCGCCAGGTACCTAATTGAATCATCCAT-<br>AGGATGACAAATCAGCCAGGGCCAAGATTTCCAGACACTTGAGTGACTTCCCGGTCCCCGA<br>GGTGACTTGTCAGCTCCAGTGAGTAACT-<br>TGGAACTGTCGCTCGGGGCAAGGTGTGTGTCTAGGAGAGAGCCGGCGGCTCACTCACGCTT<br>TCCAGAGAGCGACCCGGGCCGACT-<br>TCAAAATACACACAGGGTCATTTATAGGGACTGGAGCCGCGCGCAGGACAACGTCTCCGAGACTG<br>AGACATTTTCCAAACAGTGCTGA-<br>CATTTTGTCGGGCCCCATAAAAAATGTAAACGCGAGGTGACGAACCCGGCGGGGAGGGTTCGTGTC<br>TGGCTGTGTCTGCGTCCTGGCGGCGTGG-<br>GAGGTTATAGTTCCAGACCTGGCGGCTGCGGATCGCCGGGCCGGTACCCGCGAGGAGTGTA<br>GGTACCCTCAGCCCGACCACCTCCCG-<br>CAATCATGGGGACACCGGCTTGGATGAGACACAGGCGTGGAAAACAGCCTTCGTGAAACTCCA<br>CAAACACGTGGAACTTGAAAAGACAAC-<br>TACAGCCCCGCGTGTGCGCGAGAGACCTCACGTCACCCCATCAGTTCCCACTTCGCCAAAGT<br>TTCCCTTCAGTGGGGACTCCAGAGTGGT-<br>GCGCCCCATGCCCGTGCGTCCTGTAACGTGCCCTGATTGTGTACCCCTCTGCCCGCTCTAC<br>TTGAAATGAAAACACAAAAACTGTTC-<br>CGAATTAGCGCAACTTTAAAGCCCCGTTATCTGTCTTCTACACTGGGCGCTCTTAGGCCACTG<br>ACAGAAACATGGTTTGAACCCTAATTGT-<br>TGCTATCAGTCTCAGTCAGCGCAGGTCTCTCAGTGACCTGTGACGCCGGGAGTTGAGGTGC<br>GCGTATCCTTAAACCCGCGCGAACGC-<br>CACCGGCTCAGCGTAGAAAACTATTTGTAATCCCTAGTTTGCGTCTCTGAGCTTTAACTCCCC<br>CACACTCTCAAGCGCCCGGTTTCTC-<br>CTCGTCTCTCGCCTGCGAGCAAAGTTCCTATGGCATCCACTTACCAGGTAACCGGGATTTCCAC<br>AACAAAGCCCGGCGTGCGGGTCCCTTC-<br>CCCCGGCCGGCCAGCGCGAGTGACAGCGGGCGGCCGGCGCTGGCGAGGAGTAACTTGGGGCT<br>CCAGCCCTTCAGAGCGCTCCGCGGGCT-<br>GTGCCTCCTTCGGAAATGAAAACCCCCATCCAAACGGGGGGACGGAGCGCGGAAACCCGGCC<br>CAAGTGCCGTGTGTGCGCGCGCGTCTG |
| 51 | PRMT8 | GAAAGCCATCCTTACCATTCCCCTCAC-<br>CCTCCGCCCTCTGATCGCCCACCCGCCGAAAGGGTTTCTAAAAATAGCCCAGGGCTTCAAGG<br>CCGCGCTTCTGTGAAGTGTGGAGC-<br>GAGCGGGCACGTAGCGGTCTCTGCCAGGTGGCTGGAGCCCTGGAAGCGAGAAGGCGCTTCCTCCC<br>TGCATTTCCACCTCACCCCACCCCCG-<br>GCTCATTTTTCTAAGAAAAAGTTTTTGCGGTTCCCTTTGCCTCCTACCCCCGCTGCCGCGCGG<br>GGTCTGGGTGCAGACCCCTGCCAGGTTC-<br>CGCAGTGTGCAGCGGCGGCTGCTGCGCTCTCCCAGCCTCGGCGAGGGTTAAAGGCGTCCGG<br>AGCAGGCAGAGCGCCGCGCGCCAGTC-<br>TATTTTTACTTGCTTCCCCCGCCGCTCCGCGCTCCCCCTTCTCAGCAGTTGCACATGCCAGCT<br>CTGCTGAAGGCATCAATGAAAACAGCAGTAG |
| 52 | TBX3 | ATCGAAAATGTCGACATCTTGCTAATG-<br>GTCTGCAAACTTCCGCCAATTATGACTGACCTCCCAGACTCGGCCCCAGGAGGCTCGTATTA<br>GGCAGGGAGGCCGCCGTAATTCTGGGAT-<br>CAAAAGCGGGAAGGTGCGAACTCCTCTTTGTCTCTGCGTGCCCGGCGCGCCCCCCTCCCGG<br>TGGGTGATAAACCCACTCTGGCGCCGGC-<br>CATGCGCTGGGTGATTAATTTGCGAACAAACAAAAGCGGCCTGGTGGCCACTGCATTCGGG<br>TTAAACATTGGCCAGCGTGTTCCGAAGGCTTGT |

TABLE 4A-continued

| SEQ ID NO | GENE NAME | SEQUENCE |
|---|---|---|
| 53 | chr12<br>group-<br>00801 | ATCAACATCGTGGCTTTGGTCTTTTC-<br>CATCATGGTGAGTGAATCACGGCCAGAGGCAGCCTGGGAGGAGAGACCCGGGCGGCTTTGAGC<br>CCCTGCAGGGGAGTCCGCGCGCTCTCT-<br>GCGGCTCCCTTCCTCACGGCCCGGCCCGCGCTAGGTGTTCTTTGTCCTCGCACCTCCTCCTC<br>ACCTTTCTCGGGCTCTCAGAGCTCTC-<br>CCCGCAATCATCAGCACCTCCTCTGCACTCCTCGTGGTACTCAGAGCCCTGATCAAGCTTCCC<br>CCAGGCTAGCTTTCCTCTTCTTTC-<br>CAGCTCCCAGGGTGCGTTTCCTCTCCAACCCGGGGAAGTTCTTCCGTGGACTTTGCTGACTCCTC<br>TGACCTTCCTAGGCACTTGCCCGGGGCT-<br>TCTCAACCCTCTTTTCTAGAGCCCCAGTGCGCGCCACCCTAGCGAGCGCAGTAAGCTCATA<br>CCCCGAGCATGCAGGCTCTACGTTC-<br>CTTTCCCTGCCGCTCCGGGGGCTCCTGCTCTCCAGCGCCCAGGACTGTCTCTATCTCAGCCTGT<br>GCTCCCTTCTCTCTTTGCTGCGC-<br>CCAAGGGCACCGCTTCCGCCACTCTCCGGGGGGTCCCCAGGCGATTCCTGATGCCCCCTCCTTGAT<br>CTTAACGCGCCCGAGGCTGGCTCACAC-<br>CCACTACCTCTTTAGGCCTTTCTTAGGCTCCCCGTGTGCCCCCCTCACCAGCAAAGTGGGTG<br>CGCCTCTCTTACTCTTTCTAC-<br>CCAGCGCGTCGTAGTTCCTCCCCGTTTGCTGCGCACTGGCCCTAACCTCTCTTCTCTTGGTGTCCCCC<br>AGAGCTCCCAGGCGCCCCTCCAC-<br>CGCTCTGTCCTGCGCCCGGGGCTCTCCCGGGAATGAACTAGGGGATTCCACGCAACGTGCGGCTCC<br>GCCCGCCCTCTGCGCTCAGACCTC-<br>CCGAGCTGCCCGCCTCTCTAGGAGTGGCCGCTGGGGCCTCTAGTCCGCCCTTCCGGAGCTCAGCT<br>CCCTAGCCCTCTTCAACCCTGGTAGGAA-<br>CACCCGAGCGAACCCCACCAGGAGGGCGACGAGCGCCTGCTAGGCCCTCGCCTTATTGACT<br>GCAGCAGCTGGCCCGGGGGTGGCGGCGGGGTGAGGTTCGTACCGGCACTGTCCCGGGACAACCCTTGCAGTTGC |
| 54 | PAX9 | ACAAATAAAACACCCTCTAGCTTC-<br>CCCTAGACTTTGTTTAACTGGCCGGGTCTCCAGAAGGAACGCTGGGGATGGGATGGGTGGAGAGA<br>GGGAGCGGCTCAAGGACTTTAGTGAG-<br>GAGCAGGCGAGAAGGAGCACGTTCAGGCGTCAAGACCGATTTCTCCCCCTGCTTCGGGAGACT<br>TTTGAACGCTCGGAGAGGCCCGGCATCT-<br>CACCACTTTACTTGGCCGTAGGGGCCTCCGGCACGGCAGGAATGAGGGAGGGGGTCCGATT<br>GGACAGTGACGGTTTGGGGCCGTTCGGC-<br>TATGTTCAGGGACCATATGGTTTGGGGACAGCCCCAGTAGTTAGTAGGGGACGGGTGCGTT<br>CGCCCAGTCCCCGGATGCGTAGGGAGGC-<br>CCAGTGGCAGGCAGCTGTCCCAAGCAGCGGGTGCGCGTCCCTGCGCGCTGTGTGTTCATTT<br>TGCAGAGCCAGCCTTCGGGGAGGTGAAC-<br>CAGCTGGGAGGAGTGTTCGTGAACGGGAGGCCGCTGCCCAACGCCATCCGGCTTCGCATCG<br>TGGAACTGGCCCAACTGGGCATCCGAC-<br>CGTGTGACATCAGCCGCCAGCTACGGGTCTCGCACGGCTGCGTCAGCAAGATCCTGGCGCGA<br>TACAACGAGACGGGCTCGATCTTGCCAG-<br>GAGCCATCGGGGGCAGCAAGCCCCGGGTCACTACCCCCACCGTGGTGAAACACATCCGGAC<br>CTACAAGCAGAGAGACCCCGGCATCT-<br>TCGCCTGGGAGATCCGGGACCGCCTGCTGGCGGACGGCGTGTGCGACAAGTACAATGTGCCCT<br>CCGTGAGCTCCATCAGCCGCATTCTGCG-<br>CAACAAGATCGGCAACTTGGCCCAGCAGGGTCATTACGACTCATACAAGCAGCACCAGCCG<br>ACGCCGCAGCCAGCGCTGCCCTACAAC-<br>CACATCTACTCGTACCCCAGCCCTATCACGGCGGCGGCCGCCAAGGTGCCCACGCCACCCGG<br>GGTGC |
| 55 | SIX1 | AGGAGGCGCAACGCGCTGCCAGGGCG-<br>GCTTTATCCTGCCGCCACAGGGCGGGGACCAGCCCGGCAGCCGGGTGTCCAGCGCCGCTCACG<br>TGCCTCGCCTGGAGCTTAGCTCTCA-<br>GACTCCGAAGAGGGCGACTGAGACTTGGGCCTGGGAGTTGGCTTCGGGGTACCCAAGGCGACGA<br>CAGCTGAGTTGTACCACGAAGCTCAGGC-<br>CGAGGCCTCCTCCCTTGTCTGGCCTTCGAATCCATACTGGCAGCCTCTCCTCTCAGGCACT<br>CCGCGGGCCGGGCCACTAGGCCCCCT-<br>GCTCCTGGAGCTGCGCTATGATCCGGGTCTTGAGATGCGCGCGATTCTCTCTGAACCGGTGGA<br>GAGGAGGCTCTGCCCCGCGCGGAGCGAG-<br>GACAGCGGCGCCCGAGCTTCCCGCGCCTCTCCAGGGCCCAATGGCAAGAACAGCCTCCGAA<br>GTGCGCGGATGACAGGAAAAGATCT-<br>TCAGTTCTTCTGCCGCTAGAGAAGTGCGGGATACAAGCCTCTATTGGATCCACAACCTGGAGTC<br>CTGCCTTCGGA |
| 56 | ISL2 | ATCTGCGTGCCCTTTTCTGGGCGAGC-<br>CCTGGGAGATCCAGGGAGAACTGGGCGCTCCAGATGGTGTATGTCTGTACCTTCACAGCAAGG<br>CTTCCCTTGGATTTGAGGCTTC-<br>CTATTTTGTCTGGGATCGGGGTTTCTCCTTGTCCCAGTGGCAGCCCCGCGTTGCGGGTTCCGGGCGC<br>TGCGCGGAGCCCAAGGCTGCATGGCAGT-<br>GTGCAGCGCCCGCCAGTCGGGCTGGTGGGTTGTGCACTCCGTCGGCAGCTGCAGAAAGGTG<br>GGAGTGCAGGTCTTGCCTTTCCTCAC-<br>CGGGCGGTTGGCTTCCAGCACCGAGGCTGACCTATCGTGGCAAGTTTGCGGCCCCCGCAGATC<br>CCCAGTGGAGAAAGAGGGCTCTTCCGAT-<br>GCGATCGAGTGTGCGCCTCCCCGCAAAGCAATGCAGACCCTAAATCACTCAAGGCCTGGAG<br>CTCCAGTCTCAAAGGTGGCAGAAAAGGC-<br>CAGACCTAACTCGAGCACCTACTGCCTTCTGCTTGCCCCGCAGAGCCTTCAGGGACTGACT<br>GGGACGCCCCTGGTGGCGGGCAGTC-<br>CCATCCGCCATGAGAACGCCGTGCAGGGCAGCGCAGTGGAGGTGCAGACGTACCAGCCGCCGTG<br>GAAGGCGCTCAGCGAGTTTGCCCTCCA-<br>GAGCGACCTGGACCAACCCGCCTTCCAACAGCTGGTGAGGCCCTGCCCTACCCGCCCCGACC |

TABLE 4A-continued

| SEQ ID NO | GENE NAME | SEQUENCE |
|---|---|---|
| | | TCGGGACTCTGCGGGTTGGGGATTTAGC-<br>CACTTAGCCTGGCAGAGAGGGGAGGGGGTGGCCTTGGGCTGAGGGGCTGGGTACAGCCCTA<br>GGCGGTGGGGGAGGGGGAACAGTG-<br>GCGGGCTCTGAAACCTCACCTCGGCCCATTACGCGCCCTAAACCAGGTCTCCCTGGATTAAAGTG<br>CTCACAAGAGAGGTCGCAGGATTAAC-<br>CAACCCGCTCCCCCGCCCTAATCCCCCCCTCGTGCGCCTGGGGACCTGGCCTCCTTCTCCGCA<br>GGGCTTGCTCTCAGCTGGCGGCCGGTC-<br>CCCAAGGGACACTTTCCGACTCGGAGCACGCGGCCCTGGAGCACCAGCTCGCGTGCCTCTTC<br>ACCTGCCTCTTCCCGGTGTTTCCGCCGC-<br>CCCAGGTCTCCTTCTCCGAGTCCGGCTCCCTAGGCAACTCCTCCGGCAGCGACGTGACCTC<br>CCTGTCCTCGCAGCTCCCGGACAC-<br>CCCCAACAGTATGGTGCCGAGTCCCGTGGAGACGTGAGGGGGACCCCTCCCTGCCAGCCCGCGGA<br>CCTCGCATGCTCCCTGCATGAGACTCAC-<br>CCATGCTCAGGCCATTCCAGTTCCGAAAGCTCTCTCGCCTTCGTAATTATTCTATTGTTAT<br>TTATGAGAGAGTACCGAGAGACACG-<br>GTCTGGACAGCCCAAGGCGCCAGGATGCAACCTGCTTTCACCAGACTGCAGACCCCTGCTCCGA<br>GGACTCTTAGTTTTTCAAAACCA-<br>GAATCTGGGACTTACCAGGGTTAGCTCTGCCCTCTCCTCTCCTCTCTACGTGGCCGCCGCTCTGTC<br>TCTCCACGCCCCACCTGTGT |
| 57 | DLX4 | AGGTCTCTTCAGACTGCCCATTCTC-<br>CGGGCCTCGCTGAATGCGGGGGCTCTATCCACAGCGCGCGGGGCCGAGCTCAGGCAGGCTGGGG<br>CGAAGATCTGATTCTTTCCTTCCCGC-<br>CGCCAAACCGAATTAATCAGTTTCTTCAACCTGAGTTACTAAGAAAGAAAGGTCCTTCCAAAT<br>AAAACTGAAAATCACTGCGAATGA-<br>CAATACTATACTACAAGTTCGTTTTGGGGCCGGTGGGTGGGATGGAGGAGAAAGGGCACGGATAA<br>TCCCGGAGGGCCGCGGAGTGAGGAGGAC-<br>TATGGTCGCGGTGGAATCTCTGTTCCGCTGGCACATCCGCGCAGGTGCGGCTCTGAGTGCT<br>GGCTCGGGGTTACAGACCTCGGCATCCG-<br>GCTGCAGGGGCAGACAGAGACCTCCTCTGCTAGGGCGTGCGGTAGGCATCGTATGGAGCCC<br>AGAGACTGCCGAGAGCACTGCGCACT-<br>CACCAAGTGTTAGGGGTGCCCGTGATAGACCGCCAGGGAAGGGGCTGGTTCGGAGGGAATTCC<br>CGCTACCGGGAAGGTCGGAACTCGGGGT-<br>GATCAAACAAGGAATGCATCTCACCTCCGTGGGTGCTTGTGCTGCGCAAGGAATTATTACC<br>GGAGCGGTTGCGATGGCCTTTGCCCGGCGACCCAAGAAGAGTAAGCAAACTACCGTCCACCCAGCGGATCAGGTCCAAT |
| 58 | CBX4 | GATGTCCTGTTTCTAGCAGCCTCCA-<br>GAGCCAAGCTAGGCGAGAGGCGTAGGAGGCAGAGAGAGCGGGCGCGGGAGGCCAGGGTCCGCCT<br>GGGGGCCTGAGGGGACTTCGTGGGGTC-<br>CCGGGAGTGGCCTAGAAACAGGGAGCTGGGAGGGCCGGGAAGAGCTTGAGGCTGAGCGGGGG<br>ACGAACGGGCAGCGCAAAGGGGAGAT-<br>GAACGGAATGGCCGAGGAGCCACGCATTCGCCTTGTGTCCGCGGACCCTTGTTCCCGACAGGC<br>GACCAAGCCAAGGCCCTCCGGACT-<br>GACGCGGCCTGAGCAGCAGCGAGTGTGAAGTTTGGCACCTCCGGCGGCGAGACGGCGCGTTCTGG<br>CGCGCGGCTCCTGCGTCCGGCTGGTG-<br>GAGCTGCTGCGCCCTATGCGGCCTGCCGAGGGCGCCGCCGAGGGCCCGCGAGCTCCGTGGGGT<br>CGGGGTGGGGGGACCCGGGAGCGGA-<br>CAGCGCGGCCCGAGGGGCAGGGGCAGGGGCGCGCCTGGCCTGGGGTGTGTCTGGGCCCCGGCTC<br>CGGGCTCTTGAAGGACCGCGAGCAGGAG-<br>GCTTGCGCAATCCCTTGGCTGAGCGTCCACGGAGAAAGAAAAAGAGCAAAAGCAGAGCGAG<br>AGTGGAGCGAGGGATGGGGGCGGGCAAA-<br>GAGCCATCCGGGTCTCCACCACCGCCCTGACACGCGACCCGGCTGTCTGTTGGGGACCGCA<br>CGGGGGCTCGGGCGAGCAGGGGAGGGAG-<br>GAGCCTGCGCGGGGCTCGTGTTCGCCCAGGAATCCCGGAGAAGCTCGAAGACGGTCTGGTG<br>TTGAACGCACACGTGGACTCCATTTCAT-<br>TACCACCTTGCAGCTCTTGCGCCACGGAGGCTGCTGCTGCCCGGCGGCTGCTACCCACCGA<br>GACCCACGTGGCCCCTCCCCAGGGGTG-<br>TAGGGGTGACGGTTGTCTTCTGGTGACAGCAGAGGTGTTGGGTTTGCGACTGATCTCTAACG<br>AGCTTGAGGCGCAAACCTAGGATTCCCT-<br>GAGTGTTGGGGTGCGGCGGGGGGGCAAGCAAGGTGGGACGACGCCTGCCTGGTTTCCCTGA<br>CTAGTTGCGGGGGGTGGGGGCCGGCTCT-<br>CAGGGGCCACCAGAAGCTGGGTGGGTGTACAGGAAAATATTTTTCTCCTGCCGTGTTTGGC<br>TTTTTCCTGGCATTTTTGCCCAGGGC-<br>GAAGAACTGTCGCGCGGGGCAGCTCCACCGCGGAGGGAGAGGGGTCGCGAGGCTGGCGCGGGA<br>AGCGCTGTAGGTGGCAGTCATCCGTC-<br>CACGCCGCACAGGCCGTCTGCGCCGTCGGACCATCGGGAGGTCTGCAGCAACTTTGTCCCGGC<br>CAGTCCCCTTGTCCGGGAAGGGGCT-<br>GAGCTTCCCGACACTCTACCCTCCCCCTCTTGAAAATCCCCTGGAAAATCTGTTTGCAATGGGT<br>GTTTCCGCGGCGTCCAGGTCTGGGCTGC-<br>CGGGGGAGGCCGAGCGGCTGCTGCAGCCTCCCTGCTGCCAGGGGCGTCGGACTCCGCTTCG<br>CTCACTACGCCCAGGCCCCTCAGGGGC-<br>CCACGCTCAGGACTTCGGGGCCACACAGCAGGACCCGGTGCCCCGACGACGAGTTTGCGCAG<br>GACCCGGGCTGGGCCAGCCGCG-<br>GAGCTGGGGAGGAAGGGGCGGGGGTCGGTGCAGCGGATCTTTTCTGTTGCTGCCTGTGCGGCGGCAG<br>GAAGCGTCTTGAGGCTCCCCAAGACTAC-<br>CTGAGGGGCCGCCCAAGCACTTCAGAAGCCCAAGGAGCCCCCGGCCACCCCCGCTCCTGGC<br>CTTTTTGCCAACGACTTTGAAAGT-<br>GAAATGCACAAGCACCAGCAATTGACTTCCCTTCCGTGGTTATTTATTTTGTCTTTGTGGATGGT<br>GGGCAGATGGGGAGAGAGGCCCCTAC-<br>CTAACCTCGGTGGCTGGTCCCTAGACCACCCCTGCCAGCCGGTGTGGGGAGGAGCTCAGGTCC<br>GCGGGAGAGCGAATGGGCGCCAGGAG-<br>GTGGGACAGAATCCTGGGAAGGTACAGCGGACGCCCTGGAAGCTCCCCTGATGCCCCAGAGGG |

TABLE 4A-continued

| SEQ ID NO | GENE NAME | SEQUENCE |
|---|---|---|
| | | CCCTTCCTGGGAAACCTCCCGGGGGGT-<br>GCCCCATACCATCCCACCCGGCTGTCTTGGCCCCTCCCAGGGAGCCGCAGGAGAAACTAGC<br>CCTACACCTGGGATTCCCAGAGCCTTCT-<br>GCTGGGGCTCCTGCCCCCGACTTCGGATAACCAGCTCCGCACAGGTCCCCGAGAAGGGCCG<br>CTGGCCTGCTTATTTGATACTGC-<br>CCCCTCCCAGACAGGGGCTGGTCGAGCCCCTGGTTCTGCTGCCAGACTGAAGCCTTCCAGACGCCA<br>CCTCGGTTTGGGCCCCCAGGGCCCT-<br>CAGGGGCCCCAGGAGAGGAGAGCTGCTATCTAGCTCAGCCACAGGCTCGCTCCTGGTGGGGGCC<br>AGGCTGAAGGAGTGGACCCTGGAGAG-<br>GTCGGGAACCTTTTAACAGCCGTGGGCTGGAGGGTGGCTACTAAGTGTTCGGTCTGGGAAGAG<br>GCATGACCCGCACCATCCCGGG-<br>GAAATAAACGACTTCTTAAGGGAATCTTCTCGCTGAGCGGGTGCTCTGGGCCAGGAGATTGCCACCG<br>CCAGCCCACGGAACCCA-<br>GATTTGGGCTCTGCCTTGAGCGGGCCGCCTGTGGCTTCCCGGGTCGCTCCCCCGACTCAGAAAGCTCTCAAG<br>TTGGTATCGTTTTCCCGGCCCTCGGAG-<br>GTGGATTGCAGATCACCGAGAGGGGATTTACCAGTAACCACTACAGAATCTACCCGGGCTTT<br>AACAAGCGCTCATTTCTCTCCCTTGTC-<br>CTTAGAAAAACTTCGCGCTGGCGTTGATCATATCGTACTTGTAGCGGCAGCTTAGGGGCAGC<br>GGAACTGGTGGGGTTGTGCGTGCAGGGG-<br>GAGGCTGTGAGGGAGCCCTGCACTCCGCCCCTCCACCCTTCTGGAGGAGTGGCTTTGTTTC<br>TAAGGGTGCCCCCCCAACCCCCGGGTC-<br>CCCACTTCAATGTTTCTGCTCTTTGTCCCACCGCCCGTGAAAGCTCGGCTTTCATTTGGTCG<br>GCGAAGCCTCCGACGCCCCCGAGTC-<br>CCACCCTAGCGGGCCGCGCGGCACTGCAGCCGGGGGTTCCTGCGGACTGGCCCGACAGGGTGCG<br>CGGACGGGGACGCGGGCCCCGAGCACCGCGACGCCAGGGTCCTTTGGCAGGGCCCAAGCACCCCT |
| 59 | EDG6 | TGGCGGCCGGCGGGCACAGCCGGCTCAT-<br>TGTTCTGCACTACAACCACTCGGGCCGGCTGGCCGGGCGCGGGGGGCCGGAGGATGGCGGC<br>CTGGGGGCCCTGCGGGGGCTGTCGGTG-<br>GCCGCCAGCTGCCTGGTGGTGCTGGAGAACTTGCTGGTGCTGGCGGCCATCACCAGCCACAT<br>GCGGTCGCGACGCTGGGTCTACTATTGC-<br>CTGGTGAACATCACGCTGAGTGACCTGCTCACGGGCGCGGCCTACCTGGCCAACGTGCTGC<br>TGTCGGGGGCCCGCACCTTCCGTCTG-<br>GCGCCCGCCCAGTGGTTCCTACGGGAGGGCCTGCTCTTCACCGCCCTGGCCGCCTCCACCTTC<br>AGCCTGCTCTTCACTGCAGGG-<br>GAGCGCTTTGCCACCATGGTGCGGCCGGTGGCCGAGAGCGGGGCCACCAAGACCAGCCGCGTCTACGG<br>CTTCATCGGCCTCTGCTGGCTGCTGGC-<br>CGCGCTGCTGGGGATGCTGCCTTTGCTGGGCTGGAACTGCCTGTGCGCCTTTGACCGCTGCT<br>CCAGCCTTCTGCCCCTCTACTC-<br>CAAGCGCTACATCCTCTTCTGCCTGGTGATCTTCGCCGGCGTCCTGGCCACCATCATGGGCCTCTAT<br>GGGGCCATCTTCCGCCTGGTGCAGGC-<br>CAGCGGGCAGAAGGCCCCACGCCCAGCGGCCCGCCGCAAGGCCCGCCGCCTGCTGAAGACGGT<br>GCTGATGATCCTGCTGGCCTTCCTGGT-<br>GTGCTGGGGCCCACTCTTCGGGCTGCTGCTGGCCGACGTCTTTGGCTCCAACCTCTGGGCCC<br>AGGAGTACCTGCGGGGCATGGACTG-<br>GATCCTGGCCCTGGCCGTCCTCAACTCGGCGGTCAACCCCATCATCTACTCCTTCCGCAGCAGG<br>GAGGTGTGCAGAGCCGTGCTCAGCTTC-<br>CTCTGCTGCGGGTGTCTCCGGCTGGGCATGCGAGGGCCCGGGGACTGCCTGGCCCGGGCCGT<br>CGAGGCTCACTCCGGAGCTTCCACCACCGACAGCTCTCTGAGGCCAAGGGACAGCTTTC |
| 60 | chr13<br>group-<br>00005 | TAGTAAGGCACCGAGGGGTGGCTC-<br>CTCTCCCTGCAGCGGCTGTCGCTTACCATCCTGTAGACCGTGACCTCCTCACACAGCGCCAGGAC<br>GAGGATCGCGGTGAGCCAGCAGGTGACT-<br>GCGATCCTGGAGCTGGTCGCAGCAGGCCATCCTGCACGCGGTGGAGGCGCCCCCTGCAGGC<br>CGCAGCGCATCCCCAGCTTCTGGACG-<br>CACTGTGAGCGGTTATGCAGCAGCACGCTCATATGAGATGCCCCGCAGGGTGCTATGCAGGCC<br>CACGTCCCCACAAAGCCCATGGCAG-<br>GCGCCCGGGTGCCGGAGCACGCACTTGGCCCCATGGATCTCTGTGCCCAGGGCTCAGCCAGGCA<br>TCTGGCCGCTAAAGGTTT |
| 61 | CRYL1 | TCTCATCTGAGCGCTGTCTTTCACCA-<br>GAGCTCTGTAGGACTGAGGCAGTAGCGCTGGCCCGCCTGCGAGAGCCCGACCGTGGACGATGC<br>GTCGCGCCCTTCCCATCGCGGC-<br>CTGGGCGGGCCCGCCTGCCCTCGGCTGAGCCCGGTTTCCCTACCCCGGGGCACCTCCCCTCGCCCGC<br>ACCCGGCCCCAGTCCCTCCCAGGCTTGCGGGTAGAGCCTGTCTTTGCCCAGAAGGCCGTCTCCAAGCT |
| 62 | IL17D | CAGTCCCCGAGGCCCTCCCCGGT-<br>GACTCTAACCAGGGATTTCAGCGCGCGGCGCGGGGCTGCCCCCAGGCGTGACCTCACCCGTGCTCT<br>CTCCCTGCAGAATCTCCTACGACCCGGC-<br>GAGGTACCCCAGGTACCTGCCTGAAGCCTACTGCCTGTGCCGGGGCTGCCTGACCGGGCTG<br>TTCGGCGAGGAGGACGTGCGCTTCCGCAGCGCCCCTGTCTACAT |
| 63 | IRS2 | AGAGAGACATTTTCCACGGAGGCCGAGT-<br>TGTGGCGCTTGGGGTTGTGGGCGAAGGACGGGGACACGGGGGTGACCGTCGTGGTGGAGGA<br>GAAGGTCTCGGAACTGTGGCGGCGGCG-<br>GCCCCCCTGCGGGTCTGCGCGGATGACCTTGGCGCCGCGGTGGGGGTCCGGGGGCTGGCTGG<br>CCTGCAGGAAGGCCTCGACTCCCGACAC-<br>CTGCTCCATGAGGCTCAGCCTCTTCACGCCCGACGTCGGGCTGGCCACGCGGGCAGCTTCT<br>GGCTTCGGGGGGGCCGCGATAGGTTGCG-<br>GCGGGGTGGCGGCCACACCAAAAGCCATCTCGGTGTAGTCACCATTGTCCCCGGTGTCCGA |

TABLE 4A-continued

| SEQ ID NO | GENE NAME | SEQUENCE |
|---|---|---|
| | | GGACAACGATGAGGCGGCGCCCGGGC-<br>CCTGGGCGGTGGCAACGGCCGAGGCGGGGGCAGGCGGTACAGCTCCCCCGGGGCCGGCGGCG<br>GTGGCGGCGGCTGCAGAGACGAC-<br>GACGGGGACGCGGACGGACGCGGGGGCAACGGCGGATACGGGGAGGAGGCCTCGGGGGACAGGAGG<br>CCGTCCAAGGAGCCCACGGGGTGGC-<br>CGCTCGGGGCGCCCGGCTTAGGAGACTTGGGGGAGCTGAAGTCGAGGTTCATGTAGTCGGAGAG<br>CGGAGACCGCTGCCGGCTGTCGCTGCTG-<br>GTGCCCGGGGTGCCTGAGCCCAGCGACGAGGCCGGGCTGCTGGCGGACAAGAGCGAGGAGG<br>ACGAGGCCGCCGACGCCAGCAGGGGAG-<br>GCGCGGGCGGCGACAGGCGGGCCCCGGGCTCGCCAAAGTCGATGTTGATGTACTCGCCGGGG<br>CTCTTGGGCTCCGGTGGCAGTGGG-<br>TACTCGTGCATGCTGGGCAGGCTGGGCAGCCCCTCCAGGGACAGGCGCGTGGGCCTCACCGCCCG<br>GCCGCGCTGGCCCAAGAAGCCCTC-<br>CGGGCGGCCGCCGCTAGGCCGCACGGGCGAAGGCACTACAGGGTGAGGGGGCTGCGTGGGGCCGG<br>CCCCGAAGGCGCTGGCCGCCTG-<br>GCTGGGCCCTGGCGTGGCCTGAGGCTCCAGACGCTCCTCCTCCAGGATGCGCCCCACGGGGGAGCTC<br>ATGAGCACGTACTGGTCGCTGTCCCCGC-<br>CACAGGTGTAGGGGGCCTTGTAGGAGCGGGGCAAGGAGCTGTAGCAGCAGCCGGGAACGCC<br>CCTGAGCGGCTCCCCGCCGGGGTG-<br>CAGGGCTGCGGAGAAGAAGTCGGGCGGGGTGCCCGTGGTGACCGCGTCGCTGGGGGACACGTTGA<br>GGTAGTCCCCGTTGGGCAGCAGCTTGC-<br>CATCTGCATGCTCCATGGACAGCTTGGAACCGCACCACATGCGCATGTACCCACTGTCCTCG<br>GGGGAGCTCTCGGCGGGCGAGCTGGCCT-<br>TGTAGCCGCCCCCGCTCGCCGGGAATGTCCTGCCCGCCGCAGAGGTGGGTGCTGGCCCCGC<br>AGGCCCCGCAGAAGGCACGGCGGCGGCG-<br>GCGGCGGCGGCGGCCCTGGGCTGCAAGATCTGCTTGGGGGCGGACACGCTGGCGGGGCTCA<br>TGGGCATGTAGTCGTCGCTCCTGCAGCT-<br>GCCGCTCCCACTGCCCGCGAGGGCCGCGCCGGGCGTCATGGGCATGTAGCCGTCGTCTGCC<br>CCCAGGTTGCTGCTGGAGCTCCTGTGG-<br>GAGCCGATCTCGATGTCTCCGTAGTCCTCTGGGTAGGGGTGGTAGGCCACCTTGGGAGAGGA<br>CGCGGGGCAGGACGGGCAGAGGCGGC-<br>CCGCGCTGCCCGAGAAGGTGGCCCGCATCAGGGTGTATTCATCCAGCGAGGCAGAGGAGGGCT<br>GGGGCACCGGCCGCTGCCGGGCTG-<br>GCGTGGTCAGGGAGTAGGTCCTCTTGCGCAGCCCTCGGTCCAGGTCCTGGGCCGCGTCCCCCGAG<br>ACCCGGCGGTAGGAGCGGCCACAGTG-<br>GCTCAGGGGCCTGTCCATGGTCATGTACCCGTAGAACTCACCGCCGCCGCCGCCGTCTCGGGC<br>CGGGGGCGTCTCCGCGATG-<br>GACTCGGGCGTGTTGCTTCGGTGGCTGCAGAAGGCGCGCAGGTCGCCTGGGCTGGAGCCGTACTCGTCCA<br>GGGACATGAAGCCGGGGTCGCTGGGG-<br>GAGCCCGAGGCGGAGGCGCTGCCGCTGGAGGGCCGCTGGCCGGGGCCGTGGTGCAGCGGATGC<br>GGCAGAGGCGGGTGCGGGCCGGGCGGCGGCGGGTAGGAGCCCGAGCCGTGGCCGCTGCTGGACGACAGGGAGC |
| 64 | chr13<br><br>group-<br>00350 | TAACCTAAAGAATGAAGTCATGCCCCG-<br>GCCTGCACCCGGGAAACTGCACACAGCGAAAGATCGCCACTGAGATAAAGAGCTGAAAGCTA<br>TTCCCCAATTCAGCTGTTTCAGCCGTGCGGTCTCACAATGGGCTCACAGACGGCAGCATC |
| 65 | MCF2L | GTTTCCACAATCCACCTCG-<br>TAGCTGGGGCGTGCCGCTTGCCTCGGCTTGTCCCGGCAGAACACTCTTACCTTTAATGGCGACTGAAAAG<br>TTGCCACGAGTTCCTGATCATTGTGG-<br>TAGGTGCTGCGTGAAGCTGAGACGTGCGTGAGCCACATCCCAGGGGGCTTTGAGCCCCCACCG<br>CGGCGGCGGCTGAGGGGAGGCTTGTCG-<br>TACTCGCACAGGAGGACACAGGGCTGCAGTGTTCACTCCAGGGCCTCTTATCATTGGGATCT<br>GAGGAATTTTCCGAGAGGAAGTGCGAAT-<br>TAACAATGATGAAAGGTTTGTGAGTGAGTGACAGGCACGTTCTATTGAGCACTGCATGGGG<br>CATTATGTGCCACCAGAGACGGGGGCA-<br>GAGGTCAAGAGCCCTCGAGGGCTGGGAGAGTTCGGAGGATAGAAGTCATCAGAGCACAATGA<br>AGCCAGACCCTGCAGCCGCCTTCCCCT-<br>TCGGGGGCTTCCTTAGAATGCAGCATTGCGGGGACTGAGCTGTCCCAGGTGAAGGGGGGCCG<br>TCACGGTGTGTGGACGCCCCTCGGCT-<br>CAGCCCTCTAAGAGACTCGGCAGCCAGGATGGGCTCAAGGCATGAGCCCTCAAAGGAGGTTAG<br>GAAGGAGCGAGGGAGAAAAGATATGCT-<br>TGTGTGACGTCCTGGCCGAAGTGAGAACAATTGTATCAGATAATGAGTCATGTCCCATTGAG<br>GGGTGCCGACAAGGACTCGGGAGGAGGC-<br>CACGGAGCCCTGTACTGAGGAGACGCCCACAGGGAGCCTCGGGGGCCCAGCGTCCCGGGAT<br>CACTGGATGGTAAAGCCGCCCTGCCTGGCGT |
| 66 | F7 | TCCAGCTGCAGCGAGGGCGGCCAGGC-<br>CCCCTTCTCCGACCTGCAGGGGTAGCGCGGCCTCGGCGCCGGAGACCCGCGCGCTGTCTGGGG<br>CTGCGGTGGCGTGGGGAGGGCGCGGC-<br>CCCCGGACGCCCCGAGGAAGGGGCACCTCACCGCCCCCACCCAGAGCGCCTGGCCGTGCGGGC<br>TGCAGAGGACCCCTCCGGGGCAGAGGCAGGTTCCACGGAAGACCCCGGCCCGCTGGGGCTTCCCCGGAGACTCCAGAG |
| 67 | chr18<br><br>group-<br><br>00039 | ACTTACTGCTTCCAAAAGCGCTGGGCA-<br>CAGCCTTATATGACTGACCCCGCCCCCGAGTCCCAGGCCGCCCCATGCAACCGCCCAACCGC<br>CCAACCGCCACTCCAAAGGTCACCAAC-<br>CACTGCTCCAGGCCACGGGCTGCCTCTCCCCACGGCTCTAGGGCCCTTCCCCTCCACCGCAG<br>GCTGAC |

TABLE 4A-continued

| SEQ ID NO | GENE NAME | SEQUENCE |
|---|---|---|
| 68 | C18orf1 | TGCCACACCCAGGTACCGCCCGC-<br>CCGCGCGAGAGCCGGGCAGGTGGGCCGCGGATGCTCCCAGAGGCCGGCCCAGCAGAGCGATGGACT<br>TGGACAGGCTAAGATGGAAGTGACCTGAG |
| 69 | CD33L3 | TCGCCAGCGCAGCGCTGGTCCATGCAG-<br>GTGCCACCCGAGGTGAGCGCGGAGGCAGGCGACGCGGCAGTGCTGCCCTGCACCTTCACGCA<br>CCCGCACCGCCACTACGACGGGCCGCT-<br>GACGGCCATCTGGCGCGCGGGCGAGCCCTATGCGGGCCCGCAGGTGTTCCGCTGCGCTGCGG<br>CGCGGGGCAGCGAGCTCTGCCAGACG-<br>GCGCTGAGCCTGCACGGCCGCTTCCGGCTGCTGGGCAACCCGCGCCGCAACGACCTCTCGCTG<br>CGCGTCGAGCGCCTCGCCCTGGCTGAC-<br>GACCGCCGCTACTTCTGCCGCGTCGAGTTCGCCGGCGACGTCCATGACCGCTACGAGAGCCG<br>CCACGGCGTCCGGCTGCACGTGACAGGC-<br>GAGGCGGCGTGGGAGCGGGTCCCCGGCCTCCCTTCCCGCCCTCCCGCCTGCCCCGCCCCAA<br>GGGCTACGTGGGTGCCAGGCGCTGTGCT-<br>GAGCCAGGAAGGGCAACGAGACCCAGCCCTCTCCTCTACCCCAGGGATCTCACACCTGGGG<br>GTAGTTTAGGACCACCTGGGAGCTTGA-<br>CACAAATGCAGAATCCAGGTCCCAGGAAGGGCTGAGGTGGGCCCGGGAATAGGCATTGCCGT<br>GACTCTCGTAGAGTGACTGTCCCCAGTG-<br>GCTCTCAGACGAAGAGGCGAGAAAGACAAGTGAATGGCAATCCTAAATATGCCAAGAGGTG<br>CAATGTGGTGTGTGCTACCAGCCCG-<br>GAAAGACACTCGCAGCCCCTCTACCCAGGGGTGCACAGACAGCCCACCAAGTAGTGCCTAGCAC<br>TTTGCCAGACCCTGATATACAAAGATGC-<br>CTGAACCAGGGTCCCGTCCCTAGAGCAGTGGCTCTCCACTCTAGCCCCCACCCTGCTCTGC<br>GACAATAATGGCCACTTAG-<br>CATTTGCTAGGGAGCCGGGACCTAGTCCAAGCACCCACAAGCATGAATTTGCCAAATCTTTTCAGCAACC<br>TCTTAAGGCAACTGCTATCATGATCCT-<br>CACTTTACACATGGAGAAGCAGAAGCAGAGATGATAGAATCTTTCGCCCAAGGCCACATCTG<br>TATTGGGACGGGGGCAGCCTGGCAC-<br>CCAAGTGCCCATTCCTCCCTTCTGACCAGCCCCCACCCCTCCGGCTCTGGCGTCCAAAGGGCTA<br>AGGGGAGGGGTGCCCTTGTGACAGTCAC-<br>CCGCCTTCTCCCCTGCAGCCGCGCCGCGGATCGTCAACATCTCGGTGCTGCCCAGTCCGGC<br>TCACGCCTTCCGCGCGCTCTGCACTGC-<br>CGAAGGGGAGCCGCCGCCCGCCCTCGCCTGGTCCGGCCCGGCCCTGGGCAACAGCTTGGCAG<br>CCGTGCGGAGCCCGCGTGAGGGTCACG-<br>GCCACCTAGTGACCGCCGAACTGCCCGCACTGACCCATGACGGCCGCTACACGTGTACGGCC<br>GCCAACAGCCTGGGCCGCTCCGAGGC-<br>CAGCGTCTACCTGTTCCGCTTCCATGGCGCCAGCGGGGCCTCGACGGTCGCCCTCCTGCTCGG<br>CGCTCTCGGCTTCAAGGCGCT |
| 70 | TNFRSF11A | ATGAACTTCAAGGGCGACATCATCGTG-<br>GTCTACGTCAGCCAGACCTCGCAGGAGGGCGCGGCGGCGGCTGCGGAGCCCATGGGCCGCCC<br>GGTGCAGGAGGAGACCCTGGCGCGC-<br>CGAGACTCCTTCGCGGGGAACGGCCCGCGCTTCCCGGACCCGTGCGGCGGCCCCGAGGGGCTGC<br>GGGAGCCGGAGAAGGCCTCGAGGCCGGT-<br>GCAGGAGCAAGGCGGGGCCAAGGCTTGAGCGCCCCCCATGGCTGGGAGCCCGAAGCTCGGA<br>GC |
| 71 | ZNF236 | TCAGTGTTATGTGGGGAGCGCTA-<br>GATCGTGCACACAGTAGGCGTCAGGAAGTGTTTTCCCCAGTAATTTATTCTCCATGGTACTTTGCT<br>AAAGTCATGAAATAACTCA-<br>GATTTTGTTTTCCAAGGAAGGAGAAAGGCCCAGAATTTAAGAGCAGGCAGACACACAACCGGGCACCCCC<br>AGACCCTGGCCCTTCCAGCAGTCAG-<br>GAATTGACTTGCCTTCCAAAGCCCCAGCCCGGAGCTTGAGGAACGGACTTTCCTGCGCAGGGGG<br>ATCGGGGCGCACTCG |
| 72 | chr18<br>group-<br>00342 | GTGGAAACACAACCTGCCTTCCAT-<br>TGTCTGCGCCTCCAAAACACACCCCCCGCGCATCCGTGAAGCTGTGTGTTTCTGTGTTACTACAG<br>GGGCCGGCTGTGGAAATCCCACGCTCCAGACCGCGTGCCGGGCAGGCCCAGCC |
| 73 | OLIG2 | TCCACACCTCGGGCAGTCACTAG-<br>GAAAAGGGTCGCCAACTGAAAGGCCTGCAGGAACCAGGATGATACCTGCGTCAGTCCCGCGGCTGC<br>TGCGAGTGCGCGCTCTCCTGCCAGGGG-<br>GACCTCAGACCCTCCTTTACAGCACACCGAGGGCCCTGCAGACACGCGAGCGGGCCTTCAGT<br>TTGCAAACCCTGAAAGCGGGCGCGGTC-<br>CACCAGGACGATCTGGCAGGGCTCTGGGTGAGGAGGCCGCGTCTTTATTTGGGGTCCTCGGG<br>CAGCCACGTTGCAGCTCTGGGGGAA-<br>GACTGCTTAAGGAACCCGCTCTGAACTGCGCGCTGGTGTCCTCTCCGGCCCTCGCTTCCCCGAC<br>CCCGCACAGGCTAACGGGAGACGCGCAG-<br>GCCCACCCCACCGGCTGGAGACCCCGGCACGGCCCGCATCCGCCAGGATTGAAGCAGCTGG<br>CTTGGACGCGCGCAGTTTTCCTTTGGC-<br>GACATTGCAGCGTCGGTGCGGCCACAATCCGTCCACTGGTTGTGGGAACGGTTGGAGGTCCC<br>CCAAGAAGGAGACACGCAGAGCTCTCCA-<br>GAACCGCCTACATGCGCATGGGGCCCAAACAGCCTCCCAAGGAGCACCCAGGTCCATGCAC<br>CCGAGCCCAAAATCACAGACCCGC-<br>TACGGGCTTTTGCACATCAGCTCCAAACACCTGAGTCCACGTGCACAGGCTCTCGCACAGGGGAC<br>TCACGCACCTGAGTTCGCGCTCACAGATC |

TABLE 4A-continued

| SEQ ID NO | GENE NAME | SEQUENCE |
|---|---|---|
| 74 | RUNX1 | CTGCCCTCGCGGATCTCCCCCGGC-<br>CTCGCCGGCCTCCGCCTGTCCTCCCACCACCCTCTCCGGGCCAGTACCTTGAAAGCGATGGGCAG<br>GGTCTTGTTGCAGCGCCAGTGCGTAG-<br>GCAGCACGGAGCAGAGGAAGTTGGGGCTGTCGGTGCGCACCAGCTCGCCCGGGTGGTCGGCCA<br>GCACCTCCACCATGCTGCGGTCGC-<br>CGCTCCTCAGCTTGCCGGCCAGGGCAGCGCCGGCGTCCGGGGCGCCCAGCGGCAACGCCTCGCTC<br>ATCTTGCCTGGGCTCAGCGCGGTGGAAG-<br>GCGGCGTGAAGCGGCGGCTCGTGCTGGCATCTACGGGGATACGCATCACAACAAGCCGATT<br>GAGTTAGGACCCTGCAAACAGCTCCTAC-<br>CAGACGGCGACAGGGGCGCGGATCTTCAGCAAGCAGCTCCCGGGAGACCAACATACACGTT<br>CAGGGGCCTTTATTACT-<br>GCGGGGGGTGGGGGGGGGCGGGGGTGGTTAGGGGAGGAGGGAGACTAAGTTACTAACAGTCCAGGAGGGGAA<br>AACGTTCTGGTTCTGCGGATCGGCCTCT-<br>GACCCAGGATGGGCTCCTAGCAACCGATTGCTTAGTGCATTAAAAAGTGGAGACTATCTTC<br>CACGAATCTTGCTTGCAGAGGTTAAGT-<br>TCTGTCTTTGGCTGTTAGAAAAGTTCCTGAAGGCAAAATTCTCATACACTTCCTAAAATATT<br>TATGCGAAGAGTAAAACGATCAGCAAA-<br>CACATTATTTGGAAGTTCCAGTAGTTAATGCCTGTCAGTTTTTTGCAGGTGAGTTTTGTCTA<br>AAGTCCCAACAGAACACAATTATCTC-<br>CCGTAACAAGGCCACTTTTATCATGCAAAACTGGCTTCAGTCCCGAAAAGCAAGAGCTGAGAC<br>TTCCAAAGGTAGTGCTACTAATGTATGT-<br>GCACGTATATATAAATATATACATATGCTCTACTTCATAAAATATTTACAATACAATCTGT<br>GGAGAATTTAAACACAACAGAAATCCAT-<br>TAATGTACGCTGCAGATTTTTTTAAGTAGCCTTGAAAATCAGCTTCAGTAGTTGGAGCAGT<br>GCTGAGCTAGAAGTACTTGTCATGT-<br>TCTCTGTTCTCTCAATGAATTCTGTCAAAACGCTCAGTGCAGAAAATTCAGCGTTTCAGAGATC<br>TTCAGCTAATCTTAAAACAACAATCAT-<br>AAGAAGGCCCAGTCGATGACACTCAGGGTTCTACAGCTCTCCCACATCTGTGAACTCGGGTT<br>TGGGGATGTTGGTTAAGTTTGTGGCTG-<br>GTCCTCTGGTTTGTTGGGAGTTGAGCAGCCGCAGAGTCACACACATGCAAACACGCACTCTT<br>CGGAAGGCAGCCACTGTCTACAT-<br>CAGCTGGGTGACTCAGCCCTGACTCGGGCAGCAGCGAGACGATACTCCTCCACCGTCGCCCAGCAC<br>CCGCCGGTTAGCTGCTCCGAGGCACGAA-<br>CACCCACGAGCGCCGCGTAACCGCAGCAGGTGGAGCGGGCCTTGAGGGAGGGCTCCGCGGC<br>GCAGATCGAAACAGATCGGGCG-<br>GCTCGGGTTACACACGCACGCACATCCTGCCACGCACACTGCCACGCACACGCAACTTCACGGCTCG<br>CCCTCGGACCACAGAGCACTTTCTC-<br>CCCCTGTTGTAAAAGGAAAACAATTGGGGAAAAGTTCGAGCCAGGAAAGAAGTTGAAAACATCC<br>AGCCAAGAAGCCAGTTAATTCAAAAG-<br>GAAGAAAGGGGAAAAACAAAAAAAAACAACAAAAAAAGGAAGGTCCAACGCAGGCCAAGGAGA<br>AGCAGCAGAGGTTGACTTCCTTCTG-<br>GCGTCCCTAGGAGCCCCGGAAAGAAGTGCCTGGCGGCGCAGGGCCGGGCAGCGTGGTGCCCTGG<br>CTGGGTCCGGCCGCGGGGCGCCCGTC-<br>CCGCCCGCGCCCGCTGGCTCTATGAATGAGAGTGCCTGGAAATGAACGTGCTTTTACTGTAAG<br>CCCGGCCGGAGGAATTCCATTCCCT-<br>CAGCTCGTTTGCATAGGGGCGGCCGGCGGCCAATCACAGGCCTTTCCGGTATCAGCCAGGGCGC<br>GGCTCGCCGCCGCCGGCTCCTGGAATTG-<br>GCCCGCGCGCCCCCGCCGCCGCGCCGCGCGCTACTGTACGCAGCCCGGGCGGGGAGTCGGA<br>GGCCACCCCCGCGCCCCGCATCCAAGC-<br>CTGCATGCTGGCCCGGGGCCCCGCCCGCGTGCGGACCCCTTTCCGCAGCCACACGCAGGCTT<br>GTGCGGCTCCGCGAGTGGCCACGGTCCG-<br>GAGACCTGGAAAAAGAAAGCAGGCCCCGCCGGCCCGAGGAGGACCCGGCCGGCGCGCCGCA<br>CCCGGAGAGGCCCGGCCCCGCGAGC-<br>CGCTGCAGGCAGGCGCAGTGGCCGCCACGAGGCTCCCGAACCGGGCTGCAGCCCGCGGACGGCC<br>CCAGATCCTGCGCGGCCGCCCAGGGC-<br>CAGGCCTCCGCTTCCAGGGCGGGGGTGCGATTTGGCCGCGGGGCCCGGGGGAGCCACTCCGCG<br>CTCCTGCACCGTCCGGCTGGCAGCTGCG-<br>GCGAAGCGGCGCTGATTCCTTGCATGAGGCCGGACGGCGTCCGCGCGTGCCGTTTGCTCTC<br>GAGCGTCTTCCCTTGGGTCGTTTCTG-<br>TAATGGGTGTTTTTTACCGCTGCGCCCGGGCCGCGGCTCGATCCCTCCGCGCGTCTCACTTGC<br>TGCGTGCGTCAGCGGCCAGCGAA-<br>GAGTTTCCTAGTCAGGAAAGACCCCAAGAACGCGCGGCTGGAAGGAAAGTTGAAAGCAGCCACGCG<br>GCTTGCTCCCGGGCCTTGTAGCGCCG-<br>GCACCCGCAGCAGCCGGACAGCCTGCCCGGGCCCCGCGTCTCCCCTCCGGCTCCCCGGAAGCG<br>TGCCCCCGCTCCTCTCCCCGCCCCCGT-<br>GCGCTCGAGCGGCCCCAGGTGCGGAACCCACCCCGGCTCGCGTGCGGGCGGCCGCTTCCCCC<br>TGCGCCGGTCCCCGCGGTGCT-<br>GCGGGCATTTTCGCGGAGCTCGGAGGGCCCCGCCCCCGGTCCGGCGTGCGCTGCCAACTCCGACCCCG<br>CCCGGCGGGGCTCCCTCCCAGCGGAG-<br>GCTGCTCCCGTCACCATGAGTCCCTCCACGCCCTCCCTGCCGGGCCCTGCACCTCCCGGGGCC<br>TCTCATCCACCCCGGGGCTGCAAC-<br>CCAGTCCCCGGATCCCGGCCCCGTTCCACCGCGGGCTGCTTTGTGGTCCCCGCGGAGCCCCTCAA<br>TTAAGCTCCCCGGCGCGGGGGTC-<br>CCTCGCCGACCTCACGGGGCCCCTGACGCCCGCTCCTCCCTCCCCCAGGGCTAGGGTGCTGTGGCC<br>GCTGCCGCGCAGGGACTGTCCCCGGGCGTTGCCGC<br>GGGCCCGGACGCAGGAGGGGGCCGGGGT-<br>TGACTGGCGTGGAGGCCTTTCCCGGGCGGGCCCGGACTGCGCGGAGCTGTCGGGACGCGCC<br>GCGGGCTCTGGCGGACGCCAGGGGGCAG-<br>CAGCCGCCCTCCCTGGACGCCGCGCGCAGTCCCCGGAGCTCCCGGAACGCCCCCGACGGCG<br>CGGGGCTGTGCGGCCCGCCTCGTGGCCT-<br>TCGGGTCGCCCGGGAAGAACTAGCGTTCGAGGATAAAAGACAGGAAGCCGCCCCAGAGCCC |

TABLE 4A-continued

| SEQ ID NO | GENE NAME | SEQUENCE |
|---|---|---|
| | | ACTTGAGCTGGAACGGCCAAG-<br>GCGCGTTTCCGAGGTTCCAATATAGAGTCGCAGCCGGCCAGGTGGGGACTCTCGGACCAGGCCTCCCC<br>GCTGTGCGGCCCGGTCGGGGTCTCTTC-<br>CCGAAGCCCCTGTTCCTGGGGCTTGACTCGGGCCGCTCTTGGCTATCTGTGCTTCAGGAGCC<br>CGGGCTTCCGGGGGGCTAAGGCGGGCG-<br>GCCCGCGGCCTCAACCCTCTCCGCCTCCGCTCCCCCTGGGCACTGCCAGCACCCGAGTTCAG<br>TTTTGTTTTAATGGACCTGGGGTCTCG-<br>GAAAGAAAACTTACTACATTTTTCTTTTAAAATGATTTTTTTAAGCCTAATTCCAGTTGTAA<br>ATCCCCCCCTCCCCCCGCCCAAACGTC-<br>CACTTTCTAACTCTGTCCCTGAGAAGAGTGCATCGCGCGCCCGCCCGCCCGCAGGGGCCG<br>CAGCGCCTTTGCCTGCGGGTTCG-<br>GACGCGGCCCGCTCTAGAGGCAAGTTCTGGGCAAGGGAAACCTTTTCGCCTGGTCTCCAATGCATT<br>TCCCCGAGATCCCACCCAGGGCTC-<br>CTGGGGCCACCCCCACGTGCATCCCCCGGAACCCCCGAGATGCGGGAGGGAGCACGAGGGTGTGG<br>CGGCTCCAAAAGTAGGCTTTTGACTC-<br>CAGGGGAAATAGCAGACTCGGGTGATTTGCCCCTCGGAAAGGTCCAGGGAGGCTCCTCTGGGT<br>CTCGGGCCGCTTGCCTAAAACCCTAAAC-<br>CCCGCGACGGGGGCTGCGAGTCGGACTCGGGCTGCGGTCTCCCAGGAGGGAGTCAAGTTCC<br>TTTATCGAGTAAGGAAAGTTGGTC-<br>CCAGCCTTGCATGCACCGAGTTTAGCCGTCAGAGGCAGCGTCGTGGGAGCTGCTCAGCTAGGAGT<br>TTCAACCGATAAA |
| 75 | AIRE | TTCGGAAGTGAGAGTTCTCTGAGTCCCG-<br>CACAGAGCGAGTCTCTGTCCCCAGCCCCCAAGGCAGCTGCCCTGGTGGGTGAGTCAGGCCA<br>GGCCCGGAGACTTCCCGAGAGCGAGG-<br>GAGGGACAGCAGCGCCTCCATCACAGGGAAGTGTCCCTGCGGGAGGCCCTGGCCCTGATTGGG<br>CGCCGGGGCGGAGCGGC-<br>CTTTGCTCTTTGCGTGGTCGCGGGGGTATAACAGCGGCGCGCGTGGCTCGCAGACCGGGGAGACGGGCGGGC<br>GCACAGCCGGCGCGGAGGCCCCACAGC-<br>CCCGCCGGGACCCGAGGCCAAGCGAGGGGCTGCCAGTGTCCCGGGACCCACCGCGTCCGCCC<br>CAGCCCCGGGTCCCCGCGCCCAC-<br>CCCATGGCGACGGACGCGGCGCTACGCCGGCTTCTGAGGCTGCACCGCACGGAGATCGCGGTGGCC<br>GTGGACAG |
| 76 | SUMO3 | ACGCACACTGGGGGTGTGATG-<br>GAAAGGGGGACGCGATGGATAGGGGTGGGCGCACACTGGGGGACGCGACGGGGAGGGGTGAGCACACA<br>CTGGGGGTGTGATGGAGAGGGCGACG-<br>CAATAGGGAGGGGTGGGCGCACACCAGGGACGCGATGATGGGGACGGGTGGGCGCACACCAGG<br>TGGCATGATGGGGAGGAGTGGGTACA-<br>CACCATGGGGGGCGTGATGGGGAGGCGTGGGCGTACACCGGGGGGCGCGATGGGGAGGGGTGG<br>GCGCACACCGGGGGACGCGATGGAGGCG-<br>GTGGGTGCACACGGGGCGCGATGGGTGGGAGTAGGTGCACACTGAGGGCACGATTGGGGAG<br>ACACGAAGGAGAGGGGTGGGCGCA-<br>CACTGGGGGACGCGATGGCCGGGACACGATGCGGAGAAGTGGGTGAATACCGGGGTCGCGATGGG<br>CGCCCTGGAAGGACGGCAGTGCTGCTCA-<br>CAGGGGCCAGGCCCCTCAGAGCGCGCCCCTTGGGGGTAACCCCAGACGCTTGTTCCCGAGC<br>CGACTCCGTGCACTCGACACAGGATC |
| 77 | C21orf70 | CCACAGGGTGGGGTGCGCCCACCTGC-<br>CCTGTCCATGTGGCCTTGGGCCTGCGGGGGAGAGGGAATCAGGACCCACAGGGCGAGCCCCCT<br>CCGTAGCCCGCGGCACCGACTGGATCTCAGTGAACACCCGTCAGCCCATCCAGAGGCTAGAAGGGGGA |
| 78 | C21orf123 | TTGAGGTCTCTGTGCATGCTTGTGCG-<br>TACCCTGGACTTTGCCGTGAGGGGTGGCCAGTGCTCTGGGTGCCTTTGCCAGACAACTGGTCT<br>GCCGGGCCGAGCATTCATGCTGGTC |
| 79 | COL18A1 | TGACGCGCCCCTCTCCCCGCAGCTCCAC-<br>CTGGTTGCGCTCAACAGCCCCCTGTCAGGCGGCATGCGGGGCATCCGCGGGGCCGACTTCC<br>AGTGCTTCCAGCAGG |
| 80 | PRRT3 | AACACACTGTCTCGCACTAGGT-<br>GCTCGCGGAAGAGCGCGGCGTCGATGCTGCGGCTCAGGTTGATGGGCGATGGCGGCCGCAGATCCAG<br>CTCGCTCAGCGATGGCGCCGGTCCCA-<br>CACCGTTGCGGGACAGTCCCGGGCCACCCTGGGGTCCGCGACCCAACGACGCAGCCGAGCCCC<br>AGGCGCCTGAACTGGGCGTGGCCAGCT-<br>GCCCACTCTCCGCCGGGTTGCGGATGAGGCTCTTGCTGATGTCCAAGCTGCCTGCACCAACG<br>TTGCTGGGCCCTGCATAGCAGTTAT-<br>TGGGTCGCTCCGGCACCTCGCTCTTTCCTGACGGCGCCGGGCACGCCAGACGCATCAGCTTAGC<br>CCAGCAAGCGTGCTCCGTGGGCGGC-<br>CTGGGTCTCGCGGCAGCCACCGCGGCCAACGCCAGGGCGAGCGCCCATGTCAGCTCCAGGAGGC<br>GCAGCCAGAAGTGGACACCCCACCAGGC-<br>CCACGAGAAGCGGCCCACGCGGCCTGGGCCCGGGTACAGCCAGAGCGCAGCCGCCAGCTGC<br>AAGCCGCTAGCCAGCAGCCCCAGCGCGC-<br>CCGCCACAGCCAACAGCCGAGGGCCCGGGCTGGCATCCCAGCCCCGTGGGCCGTCCAGCAG<br>GCGGCGACGGCACAGGCAGAGCGTGCCCAGAGCCAC |
| 81 | MGC29506 | GTCTGCACGAAGCCCGCGGCGGCCTG-<br>CAGGGGGCCCAGCGACTCGTCCAGGGAACCGGTGCGCAGGAGCAGCCGGGGGCGCGGCGCGCC<br>GGCCGCCCTTGGGGGACTCTGGGGC-<br>CGGGGGCGCAGCTCGATCTGACGCTTGGGCACTGTCCGGGGCCTGGCGGGCGCGGCGCCCTCCT |

TABLE 4A-continued

| SEQ ID NO | GENE NAME | SEQUENCE |
|---|---|---|
| | | CCAGAGCCACCTCCACACACTCGAACT-GCGCTGGGGCGGCAGGACTTGGCCCACGGGGCCGCAGCTCTAGGTAGGTGGCCCAGCGGGAG CCACCATCGGGGACCTGGACTG-GCGTGGGACCGCGGCGGGAGACGCTGGCCCCGGCGGCAAGGGGCTGATGAAGGCCGGCTCCGTGAA CTGTTGTTGCGCCTCGCGATCGTCT-GCGCCGGAGCAGCCGAACAGGGGTCCGACGCCGAAGATGACTTCCATCTCCCCCGACGGCAGCG TGCGCAGCTGGGGCTGGGGTGGC-CGTGGGCCGGAACCTGGGCCTCGCGGGAAACCCGAGCCGGGCCCGTGCCGCTGGCGGCTATTCTGG GCGCTGACGGACAGGCGAGGCTGCGCGC-CCGCCCCCCGCCCAGGAGCCACCCAGGGCCAATTCGCTGGGCCTTTCGCGTCCGGCCCAAC GTCCGGGGGCTCCGGAGAACCTGGAGC-CGTGTAGTAGGAGCCTGACGAACCGGAGGAGTCCTGGCGCCGCGCGGGGGCCGTGGGCAGCT GCCTCGGGATCCCAGGCAGGGCTG-GCGGGGCGAGCGCGGTCAGCATGGTGGGGCCGGACGCCGTGCACTATCTCCCTCGCATTCGCCTC CGCTGGTGGCGC |
| 82 | TEAD3 | CTGGAGAGAACTATACGGGCTGTGG-GAGTCACCGGGCGACTATCACCGGGCCTCCTTTCCACATCCTCCTCCGGGAAGGGACCCCGTTC CGGGCCTCGACCGGCGCAGACTGGGCT-GACCCACTTTCTTGGGCCCACTGAGTCACCTCGAAACCTCCAGGCCGGTAGCGGGGAGGAGA GGAGGAGCAGGCGGGGGTGCCAAGGT-GTGGGCTGCGCCCTGGTTAGGGGGCGAGCCCGGCTTGTTTATGAGGAGGAGCGCGGAGGAGGA TTCCAGACACACAGGCTTGCGCGCCCA-GACTCGCCCGGCCAGCGGCGGCGGCCTCCGACGTCACCAAACCGGTTGGGTGAGAGGGCAGA GAGCAGGGGGAAGGGCCGCAGTCCCGCCCGCGCCCCCCGGCACGCACCGTACATCTTGCCCTCGTCTGACAGGATGATCTTCCG |
| 83 | chr12 group-00022 | GAGTGCGGAGTGAAGGGGTG-CACTGGGCACTCAGCGCGGCCCTTGGGAGGCAGGGCCGCCCCAGCCTGCCCTCCTGTCTGGGAAGGCCG CCCGGGGAAAACAACTGGCTG-GACGGGGCGGCCTTCAGTGTCTCTCCCAGCCTGAGAGTCGCTTCCCACCACCTGGGCACGAACCTGCT TCCAGAAGCAGGAGCCTGCGATCTCCGGCAAGTTCCTGCGCCTCCTGTCGGTAAAATGCAGATCGTGGCGTCTT |
| 84 | CENTG1 | TCTTCTTTCCGCCCCTAGGGGGCA-CAAGCGGGCATGTCCAAGCGCCTAGGAGCCCGTACCGCTGGGGACCTCCCCTTCCGCGAACCCCG AGCGGGTAGACCCAGAGCAATCCGAGT-GTGGAAACAATGGAGAGGGGGCGTGTTGAGCTGGGGTCTCCATGCCTCGTTGGGGAGAGGGA GGTGAGTTTGTGTCTTCTGGAAG-GCGTGGGGGCTGTGCCCTCGTGGGGGTAGGAAGTGCTCCCGTGGGGCGGGGTGCGGATCGGAGAGG TGAGTGGGTGCGTCTGTCCAGCGGTC-CGCCCGGTGTGGTCGTGCCCGGCCCGCGTGGGGATGGGGGTGTCTCTCCCGCTGGGCAACTAT ACCAGCGCAACCGGGGCGTCGGCGCGGC-CCACGCTAGCGGCGCTGCTCCGGCGGCGGGGGCTGGGCGTGGCGGTGATGCTGGGCGTGGT GGCCGCGCTGGGCGTGGTGGCCGCGCT-GCCGCCCTCACCCGGGCAGCCGTGCTGGAGAAGGATGTCGGCGCACAGCTGGCTTCCAGCCT GGCGGGCGTAGAACAGCGCCGTGCGGC-CCTGGGCGTCACGGGCCGCCACGTCCGCGCCGTACTAGAGGGCGGAAACGGCCGCGTGACCG CGCGTCCCCAGGGCGCCCACACCCG-GCGCCGCCTCCCCCACATGGCCAAGCCTACTTCCGGGGTCCCTCTGGGAATTTCGGGCTTTCCC GGCGCCAGGCGTTTTCCAGATGAAGCCT-CAAAGACCCCCTTTCCTCCCCCAGCTCACGTACCCACAGCAGCAGTTGCGTGATGACGAC GTGGGCGAGCTCGGCCGCCAGGTG-GAGTGGGGAGCGCAGCTGTGGGTCCTCTACGCTGGTGTCGAGCGGCCCGTGTCGCGCATGGGCCA AAAGCAGGAGAACGGTAGCCACGTC-CTGGGCCTGCACGGCGGCCCACAGCTGGCGGCCCAGCGGCTCCTCCGAGGTGCTCAGCGGCGCC AGGAACAGTAGCTGCTCGTACTTGGCGC-GAATCCACGACTCGCGCTCCTCCCTGCAAGACCAGGGATCAACGGAAAAGGCTCTAGGGAC CCCCAGCCAGGACTTCTGCCCCTAC-CCACGGGACCGTCTCAGGTTCGCACACCCTCAGCAACCCTCCCCCGCTCTGTTCCCTCACGCT TACCGCGAAGAGTCCCGCGAGGGCTTG-GCACGGCCTCGCGTGTCGCTTTCCCACACGCGGTTGGCCGTGTCGTTGCCAATAGCCGTCAG CACCAGGGTCAGCTCCCGTGGC-CAGTCGTCCAAGTCCAGCGAGCGAACGCGGGACAGGTGTGTGCCCAGGTTGCGGTGGATGCCAGAAC ACTCGATGCAGATGAGGGCGCCCAGGT-TCAAGCTGGCCCACGTGGGGTCTGCGGAAGGAGCGTAGAGGTCGGCTCCCAGCCGGGCAGCA CAGGCACCCCGGCATTCACTACACTC-CCTAGCCCCTCCGCTGCCTCCTGGCACTCACTGGGGGCCCCGCAGTCCACGCAGATTGAATTC CCCTTGGCGTTCCGGATCGCCTGGAT |
| 85 | CENTG1 | AGCCAGGTCCAGCCCCCGCGCCTGACAC-CGGCCGGACGTTCCCGGGGCGCCGCAGCTGCGGCGGGAACTCTGGGATCCGGAGCCATCTG CTCCCACCCGCTCCGGAGCCAAAC-CCCGGGGGCCGCCTCCGCTCCCGGACCCGCCTCCTCTCCCGGGAGTGTGAGCCGAACCAAGAGTC TTCCTGCCTATCTCCTCCAGTAG-GAAAATAGAATAATAATAGACACCCTGCCCCCGTAAAAAACACTACCTTCCCCGTACCGCCTCCCA |

TABLE 4A-continued

| SEQ ID NO | GENE NAME | SEQUENCE |
|---|---|---|
| | | AGTCTCCCGGGGTACGGATTGCCTTTG-<br>CAGCAGTTCCGCCCCACCTGACTCACTCCAGGGTCAGCCCCGGGTGGGTTTCAATGCGGCTC<br>TGGGGAGGGGGTGGGCAGTGGGGGAAGT-<br>GAGGCTTCCTATCCGCCCCCTCTCACTTCACATTTAAATATTCTGCACGTTCCAGCCCCCG<br>TCGGACTCGCGTACCGCCCAATCCGCCT-<br>TCACCGCACGAAAAACATCACTAGCCTGCTCTCAGCCCAGGGGACGACAGTCCCTGGCGAG<br>AAGCTGCCTGCAAGGTCACTGTCATGC-<br>CACCTGCCCCAAGTGCTCAGGGGAAACTGAGGCTTCCTCATCCCCTTCACCTTCAACGTCGC<br>TCTAAACACGGCAAAGCCCCGTTTCCAT-<br>GCTCCCAGAGTTCAGCTGAGGCTGGAAGTGGGGTCCTGGGCTTCTCTGGGAGCAATTTTCT<br>AGTCACTCTGATCAAGGACGTTACTTTC-<br>CCAGAAAGCTCTGAGGCTGAGTCCCTCTGAAATCAAGTCCTTTCTCCTGTCGCACAATGTA<br>GCTACTCGCCCCGCTTCAGGACTCCTAT-<br>TCTTTGCCCCAATCCTTGACAGAGGGGTGAGCTTGGTTCATCCGCCCACCCCAGAGAAAAG<br>CTTCCCTAGTTTCCTGGACCTCGCTC-<br>CTCCACCCCAAGCTGAGCATTCCAGGTACCCTTCCCTCCCTGTTCTCAAGCCCTGACTCAACT<br>CACTAGGGGAAGCGCGGAGCTCGGCGC-<br>CCAGCAGCTCCCTGGACCCGCTGCCAGAAGACAGGCTGGGGGGTCCGGGAAGGGGCCCGGAG<br>CCAGGAGGCCCTCCTGTGCTCTTGGT-<br>GAAGATGCCGCTGATAAACTTGAGCATCTTGCGGTCACGAGTGGATGCTCGGCCCCCCTCCCG<br>GCCCCGTTTCAGCCCCGGAGCTGGAG-<br>GCTCCAGAGTGATTGGAGGTGCAGGCCCGGGGGGCTGCGCGGAAGCAGCGGTGACAGCAGTGG<br>CTGGACTCGGAGTTGGTGGGAGGGT-<br>TAGCGGAGGAGGAGAGCCGGCAGGCGGTCCCGGATGCAAGTCACTGTTGTCCAAGGTCTTACTC<br>TTGCCTTTCCGAGGGGACAACTTC-<br>CCTCGGGCTCCAGCCCCAGCCCCGACCCCACCAGAGGTCGAAGCTGTAGAGCCCCCTCCCCCGGC<br>GGCGGCGGCGGTGGCGGCGGCAGAGAC-<br>CGAAGCTCCAGTCCCGGCGCTGCTCTTTGACCCCTTGACCCTGGGCTTGCCCTCGCTTTCGG<br>GCCATGACAGGCGGCTACCCGCGCCCT-<br>TGCCCCCGCCGGCTTTGGCTCCACTCGTGGTCACGGTCTTGCAAGGCTTGGGAGCCGGCGGA<br>GGAGGCGCCACCTTGAGCCTCCGGCTGC-<br>CGGTGCCAGGGTGCGGAGAGGATGAGCCAGGGATGCCGCCGCCCGCCCGGCCTTCGGGCTC<br>CGGGCCGCCCCAGCTCGGGCTGCTGAG-<br>CAGGGGGCGCCGGGAGGAGGTGGGGGCGCCCCCAGGCTTGGGGTCGGGGCTCAGTCCCCCGG<br>AGAGCGGGGGTCCCGGAGGGACGGCCCA-<br>GAGGGAGAGGCGGCGGCCGGGAGCGGGGGAGACTGGGCGGGCCGGACTGGCCGGAGCCGGG<br>GACAGGGCTGGGGGCTCCGCGCCCCCG-<br>GTGCCCGCGCTGCTCGTGCTGATCCACAGCGCATCCTGCCGGTGGAAGAGACGTTCGTGCCG<br>CCTTCTTGCCCGGCTCCTCGCGC-<br>CTCGGGGGCTGCCAGGATCCCCAGTCTCGGAGCCTCTGGCACCGGCGGCGCCGGCCGCGGCCGCAG<br>ACGGAGAAGGCGGCGGCGGAGGCAC-<br>CGACTCGAGCTTAACCAGGGTCAGCGAGATGAGGTAGGTCGTTGTCCGGCGCTGAAGCGCGCCC<br>GGCGCCCCGGCTCATGGGGCCCGGAGAC-<br>CCCCGAGCTGGGGAGGGGAGGGACTCCCCCGGACTGCCTCAGGGGGGCCCGGCCATGGGGC<br>CGCCCTGCTCGCTGCCCCCAGCCCCCG-<br>GACCCCGCTGAGCCCCCGGCCCGGCTCCGCTGTCGCCGCCGCCTCCGCCGCCTCCGCTTGCG<br>CCCCCCTCCCATCACATGGGGCGC-<br>CCCCTCCCCATGCTCCCCGCCCTGCGCCCCCACCCTCTTGGAGCCCCGGGACCTTGGTGCTGCTC<br>CAGGGAGGCGCGCCGGACCGTCCAC-<br>CCCGGCCTGGGTGGGGGCGCTGAGATGGGTGGGGGAGGGCGGGGAGGACAGTAGTGGGGGCAAA<br>GTGGGGAGAGAGAGGAAAAGGGAGCA-<br>GAAAAGGGGACCGGAGGCTAGGGGAAACGAACCTGTGCGGGGGAGGCAGGGGCGGGGAATTGG<br>GACTCAAGGGACAGGGGCCGCGGATGCGGTCGGAAAGAGGGTCTAGAGGAGGGTGGGAAGCTAGTGG |
| 86 | chr18<br>group-<br>00304 | AGGAGCGCAAGGCTTGCAGGGCAT-<br>GCTGGGAGAGCGCAGGGAACGCTGGGAGAGCGCGGGAAATACTGGGATTGGCTCCCGAGGGCTGT<br>GAGGAGGGCACGAGGGGACACTCCGAT-<br>GAAGGCAGGGCACGCGGGGCGAGCCGGGAGCGTCTCCTGAGGGCAGCGAGGAGGGAGCTGAG<br>GCACGCGGGCTCTCAATCGACGCCCCA-<br>CAGAGACCAAGAGGCCTGGCCTTGGGGGGCAGCTGCTTGAAGGAGGCAGAGCGGAAGCGAGG<br>GAGACTGCTGGAGGCCCTGCCGCCCAC-<br>CCGCCCTTTCCTCCCCCTGAGGAGACGCCTGACGCATCTGCAGTGCAGGAGGCCGTGGGCGT<br>TAGAAGTGTTGCTTTTCCAGTTTGTAA-<br>GACCATTTTCCTGATTCTCTTCCCCACGGTTGCGGAGGAGCAGGTCAGGGCCGCCATGAGGG<br>CAGGATC |
| 87 | TSHZ1 | TCGACCGCTACTATTATGAAAACAGC-<br>GACCAGCCCATTGACTTAACCAAGTCCAAGAACAAGCCGCTGGTGTCCAGCGTGGCTGATTCG<br>GTGGCATCACCTCTGCGGGAGAGCG-<br>CACTCATGGACATCTCCGACATGGTGAAAAACCTCACAGGCCGCCTGACGCCCAAGTCCTCCAC<br>GCCCTCCACAGTTTCAGAGAAGTCCGATGCTGATGGCAGCAGCTTTGAGGAGGC |

TABLE 4A-continued

| SEQ ID NO | GENE NAME | SEQUENCE |
|---|---|---|
| 88 | CTDP1 | TGTGCCGTCGCACACAGACGCCCT-<br>CAACGTCGGAGAGCTGTGAGCGGGGCCGTGCTCTTGGGATGGGAGCCCCCGGGAGAGCTGCCCGC<br>CAACACCACTCCGACGTGATCCATGCTG-<br>GACATAAAGTGCTCTTCCCTCCGCTAGTCATCGGCCGAGCGGGCCCCTCGCTCCTGGGTGT<br>AAGTTCTTTCTGTGCGTCCTTCTCCCATCTCCGTGCAGTTCAG |
| 89 | KCNG2 | CCATGCGCCGCTGCGCGCGCGAGT-<br>TCGGGCTGCTGCTGCTGTTCCTCTGCGTGGCCATGGCGCTCTTCGCGCCACTGGTGCACCTGGCC<br>GAGCGCGAGCTGGGCGCGCGCCGCGACT-<br>TCTCCAGCGTGCCCGCCAGCTATTGGTGGGCCGTCATCTCCATGACCACCGTGGGCTACGG<br>CGACATGGTCCCGCGCAGCCTGC-<br>CCGGGCAGGTGGTGGCGCTCAGCAGCATCCTCAGCGGCATCCTGCTCATGGCCTTCCCGGTCACCT<br>CCATCTTCCACACCTTTTCGCGCTC-<br>CTACTCCGAGCTCAAGGAGCAGCAGCAGCGCGCGGCCAGCCCCGAGCCGGCCCTGCAGGAGGAC<br>AGCACGCACTCGGCCACAGCCACCGAG-<br>GACAGCTCGCAGGGCCCCGACAGCGCGGGCCTGGCCGACGACTCCGCGGATGCGCTGTGGGT<br>GCGGGCAGGGCGCTGACGCCTGCGCCGCCCAC |

TABLE 4B

| SEQ ID NO | GENE NAME | SEQUENCE |
|---|---|---|
| 90 | TFAP2E | GTCCTAACATCCCAGGTGGCGGCGCGCTGGCTCCCTGGAGCGGGGCGGGACGCGGCCGCGCGGACTCACGTGCACAACCGCGCGGGACGGGGCCACGCGGACTC ACGTGCACAACCGCGGGACCCCAGCGCCAGCGGGACCCCAGCGCCAGCGGGACCCCAGCGCCAGCGGGACCCCAGCGCCAGCGGGACCCCAGCGCCAGCGGGAC CCCAGCGCCAGCGGGACCCCAGCGCCAGCGGGTCTGTGGCCCAGTGGAGCGAGTGGAGCGCTGGCGACCTGAGCGGAGACTGCGCCCTGGACGCCCCAGCCTAG ACGTCAAGTTACAGCCCGCGCAGCAGCAGCAAAGGGGAAGGGGCAGGAGCCGGGCACAGTTGGATCCGGAGGTCGTGACCCAGGGGAAAGCGTGGGCGGTCGAC CCAGGGCAGCTGCGGCGGCGAGGCAGGTGGGCTCCTTGCTCCCTGGAGCCGCCCCTCCCCACACCTGCCCTCGGCGCCCCCAGCAGTTTTCACCTTGGCCCTCC GCGGTCACTGCGGGATTCGGCGTTGCCGCCAGCCCAGTGGGGAGTGAATTAGCGCCCTCCTTCGTCCTCGGCCCTTCCGACGGCACGAGGAACTCCTGTCCTGC CCCACAGACCTTCGGCCTCCGCCGAGTGCGGTACTGGAGCCTGCCCCGCCAGGGCCCTGGAATCAGAGAAAGTCGCTCTTTGGCCACCTGAAGCGTCGGATCCC TACAGTGCCTCCCAGCCTGGGCGGGAGCGGCGGCTGCGTCGCTGAAGGTTGGGGTCCTTGGTGCGAAAGGGAGGCAGCTGCAGCCTCAGCCCCACCCCAGAAGC GGCCTTCGCATCGCTGCGGTGGGCGTTCTCGGGCTTCGACTTCGCCAGCGCCGCGGGGCAGAGGCACCTGGAGCTCGCAGGGCCCAGACCTGGGTTGGAAAAGC TTCGCTGACTGCAGGCAAGCGTCCGGGAGGGGCGGCCAGGCGAAGCCCCGGCGCTTTACCACACACTTCCGGGTCCCATGCCAGTTGCATCCGCGGTATTGGGC AGGAAATGGCAGGGCTGAGGCCGACCCTAGGAGTATAAGGGAGCCCTCCATTTCCTGCCCACATTTGTCACCTCCAGTTTTGCAACCTATCCCAGACACACAGA AAGCAAGCAGGACTGGTGGGGAGACGGAGCTTAACAGGAATATTTTCCAGCAGTGA |
| 91 | LRRC8D | CACCTTCCCCGAGGTAATTATTTTCTGGGGGGTAGGGGTGGGGGTTGGGAGGGTGAAGAAAGGAAGAAAAAGAAGGCCGATCACACTGGGCACCGGCGGAGGAA GCGTGGAGTCCATTGATCTAGGTACTTGTGGGGAGGGGAGAACCCGAGCAGCAGCTGCAAACGGAAGGGCTGTGAGCGAGCGGGCGGGCGGGTGGCTGGCAGCG AGGCCACCAGCAGGGGGGGCCCGGGCCGAGGCCGCGCCACCTCGGCACCACGCGGGCAGCCGGTGCGGCGGGGTCGCCACGGCCAGGGGAGCGCTGGGTGCCCA CCATGGCAGTTATGCAAGCGGTGACCCCCTGGTCTTGCCTCCCCGCCGCCCTGCACTCCTTCCTCCCCGCTGCCGACACTTGGATCTCTCTAGCTCTTTCTCTC CCCTGTGTTTTCAAACAGGAAGTGCACGGCTGTCTATAACGTGCTGCCGGGTCTCAGGATGGAGGAGTGAAGTCTCCTGTCGCCGTGGTTCCAGCCTCCGGAGC TCGCCCAAGCCGCGTCCCCAGAGAGCGCCCTGAGAGAACAGGGTGGCCGCTTGGTCCAGGTGCGCGGGGTCGGGTCTGGGTCCAGGGAGCGGGTCGGGAAGTCT GCGGCACGGAGCACTGCTAGTGTCGGATCTGCATCTCCAGCTCTGTGCTGCAGCTTCACTTGCCCGCCCCCCACCACTGGCTTCTCACCCGGGGTCTCTGCCAA ACTCTGGCTGCTGCCGCCCTGGGTTCGGGCCGGCGGAAGGCCCTGGGCGTGCGCTGCGGAGCCGCCTGCGAGGACTCCACTAGGGCGCTTTCCAGGCTGGACTG CCCCGGGCTGCGCTGGAGCTGCCAGTGCTCGGGGAGTCTTCCTGGAGTCCCCAGCTGCCCTCTCCACC |
| 92 | TBX15 | CTCTTCCCAAGTTACGCCACCGGTCGAGGACGGCAGGAGACCCCCGAGTGCAGAGAAAGCTCAAACCGGCAGCGAAGTCGGTCCTAGCCAAGCTGAAAAAACGT CTCGGATTTCGCGGACAGCGGCCTAGACACAGCCCGATCTTCCAGTCCTAGTGCCCTGGTCGAGACGGTTCTATCCTTTTGCAAAGAAGCCGGAAA |
| 93 | C1orf51 | TCTCGGTTGCAATCCCCACCCTCCTCACCCAGCAGGGCAGGAGGCACCCAACTTGGAGGAGAAAGGGGTGGGGGAGGTGAAACAGAGACCGGAGAGTCACGAGG GCTGGGCCGCCGAGAGCAGGAGAATATACCGTGTCACACACCTCCATTCTCTCACACACGTTGCAGACACAAATCACTGACGGTTTCCACGTGCTGCGCTCGTG AGCGGAGGTGTTCAAAGAGGGGGCAGATGAGTTACTTCCCGAGACGGAACCGGGGGTCCCACGTCCGCCGCCTTCAGTAGCACAACCAATCTCTGAACACTCAA ACCGCGCATCTCTGGCGCATCACCATCCTATTTAAGGCCACGGGCTCCGCCCTTTTCCTCCCCTCCCTTCTTTTCCACTCTTTTTCCA |
| 94 | chr1: 179553900-179554600 | CTGCCAGAGATGTGTCTGTCTTGCGCCCCGCATGCACTGCCTGCGGGGCTGCGCTGCACTCCCCGGCGGCGCCACGGGTCTGGCCCCCGCGCTTCTACGTGTTG GGGGGATGCATGGACCTTGGAGATCCGTAGTTGGCCCTAACCTTCTCGGAATCTCCTCTGCACGCGCTGCCTGTTCCTCCTCTGCACGCTCTGTCCGTTCCTTT GCAACTTCTGTGGGAATTGTCCTGGCGTGGGAAACGCCCCCGCGCTCTTTGGCACTTAGGGTGTGAGTGTTGCGCCCCTTGCCGCAGCGCTCAGGGCAGCATCC CGCTCGAGGATGCAGGGTTCTCACCAAGCAGTGAGGGGGACTCACGCGCCGCCGGGGAGCGGAGCCAGGCTCCGAGAAGGGAGCAGGCTCGAGCCGCTGGGTTT TCGCAAGCCTTGGGGCCTCTGGCCGCCCTTCCATGCCTCCGGGCGCGGGCGGCTCAGCAGGTCCCCGGCTTCGGGAAGTTTTGTGCGCGGATCGCTGGTGGGGA GGGCGCGCGGGCCAGTGGCTGAGCTTGCAGCGAAGTTTCCGTGAAGGAAACTGCATGTGCCTTTGGAGGCGACTCGGGACTGCTGTAGGGTGGACTGGGTGTCT ATGGAGTTGCGGGTCAGAGCGAGTAGGGTGGGTCCTTTCCTGGGACAGGACTGGGAATTGGGGCTCGAAGTAGGGG |
| 95 | ZFP36L2 | AGGGGTGTCCTCCAACATCTCTGAACCGCCTTCCCTTCCTCCTCACTGGCGCCCTCTTGCCTCAGTCGTCGGAGATGGAGAGGCGGCTGAAGATTGGCAGGCGG CGGCCAGGGTCGAGGCTGGGAGACTCAGAGCCGCTGAGGCTGCCGGAGCTCAGGGAGCCGCTTAGGTAGCTGTCGCGGTCCGACAGCGAGTCCGGG |
| 96 | SIX2 | TCTGACTCTCGGGCTGGAGCAGCCGAGACAGCGCTCCCCAGCGGGACTACAGAATCCCGGGTGTCGGCCTGGGGGCCCTGGATTGGCAGTGGTGGAGTCTTCTG AGCCTAACAGCTACTAGGAATGACAGAGTTGCAGATGGCTTTGTCGCCCGCGGGGCGGCTCAAGCGTCCTGGGTCCCAGGCCTCTGTCCTACGGCCAGGCCGCC GGCTCAACGGGCCGAAGGGAATCGGGCTGACCAGTCCTAAGGTCCCACGCTCCCCTGACCTCAGGGCCCAGAGCCTCGCATTACCCCGAGCAGTGCGTTGGTTA CTCTCCCTGGAAAGCCGCCCCCGCCGGGGCAAGTGGGAGTTGCTGCACTGCGGTCTTTGGAGGCCTAGGTCGCCCAGAGTAGGCGGAGCCCTGTATCCCTCCTG GAGCCGGCCTGCGGTGAGGTCGGTACCCAGTACTTAGGGAGGGAGGACGCGCTTGGTGCTCAGGGTAGGCTGGGCCGCTGCTAGCTCTTGATTTAGTCTCATGT CCGCCTTTGTGCCGGCCTCTCCGATTTGTGGGTCCTTCCAAGAAAGAGTCCTCTAGGGCAGCTAGGGTCGTCTCTTGGGTCTGGCGAGGCGGCAGGCCTTCTTC |

TABLE 4B-continued

| SEQ ID NO | GENE NAME | SEQUENCE |
|---|---|---|
| | | GGACCTATCCCCAGAGGTGTAACGGAGACTTTCTCCACTGCAGGGCGGCCTGGGGCGGGCATCTGCCAGGCGAGGGAGCTGCCCTGCCGCCGAGATTGTGGGGA<br>AACGGCGTGGAAGACACCCCATCGGAGGGCACCCAATCTGCCTCTGCACTCGATTCCATCCTGCAACCCAGGAGAAACCATTTCCGAGTTCCAGCCGCAGAGGC<br>ACCCGCGGAGTTGCCAAAAGAGACTCCCGCGAGGTCGCTCGGAACCTTGACCCTGACACCTGGACGCGAGGTCTTTCAGGACCAGTCTCGGCTCGGTAGCCTGG<br>TCCCCGACCACCGCGACCAGGAGTTCCTTCTTCCCTTCCTGCTCACCAGCCGGCCGCCGGCAGCGGCTCCAGGAAGGAGCACCAACCCGCGCTGGGGGCGGAGG<br>TTCAGGCGGCAGGAATGGAGAGGCTGATCCTCCTCTAGCCCCGGCGCATTCACTTAGGTGCGGGAGCCCTGAGGTTCAGCCTGACTTTCCCGACTCCGCCGGGC<br>GCTTGGTGGGCTCCTGGGCTTCTGGGCTCACCCTTACACCTGTGTACTAAAGGGCTGCTACCCTCCCGAGGTGTACGTCCGCCGCCTCGGCGCTCATCGGGGTG<br>TTTTTTCACCCTCTCGCGGTGCACGCTTTTTCTCTCACGTCAGCTCACATCTTTCAGTACACAGCCACTGGGTCTCCCTGCCCCTCCAGCCTTTCCTAGGCAGC<br>TTTGAGGGCCCAGACGACTGAAGTCTTACTGCTAGGATGGGAACACGATGAAAAAGGAAGGGGCCCAGTCAAAAGTCCTCTCCTCTTCGGTTTTTCTTCAACTG<br>TCCTTCACAAAAACATTTATTTCTGTCCCAGCGCCCTGGCGGATTTCGGCAGATGGGCCCTAGGGGGTTGTGGAGGCCAAATTCCCAGGATGCTGGTCCTGCCT<br>TTTTCATTGGCCAAAACTGTATTTCCTACAACGACTAAAGATAACCAAGAACTGAGTAGACCCTGTTCTCTCACCAGATCTCCCTGGCTCTGTTTAACTTTTCC<br>TGGTGCAATGCGATGGCACCACCAGCTCCCCAGGCAGGCACCACTCCCTCAAGATACCATTTGGGGTAGGGATTTGAGTCCTGGAGAGGGTCAGCGGGGCGCCG<br>GGGTGGGGGTGGGAAGGAGACTGACAGGGACACACCGCGAGCTCCGCATACTCTCCTCTGCCCCCTGTAGCCCGGGGCTTTAATGACCCCAAGCAGATTTCCTG<br>TCTCTGGTCTAGCCAGCTGCCCCTAGGGCTGGATTTTATTTCTTCATGGGGTTTCACCCTAAAGGGCCCCCTGGTCATGGGACCTGGTTGGGAACAAATGAAAG<br>ATGTCTTGTAGCAAATGCTTTCAGGGGAGCAGAAAAGAAGATTGGGCACTTCCAGTCACTTGGTCACTTTAGGTGGCTGGAACAAAACTGGTGACTTTCACGAC<br>TGCTACAGGGTGAGGGGGTGAAGGGTGGCAGAGAGGTGACAAGCCACTGGGAATCCTATTCAGTGGGGATGCCGACAGGGAGTGGCTGTAATCAACTGAGCAAC<br>ATCTGTGTGAATGTTATTCACAGGTCAGGACAGCAGCTTGGTCTTCCCAGGTGAGGAACTGAGGACTGGCCTGCATAGATTTGTGCAGTAGGTGAGTAGCTTCC<br>AAATTTATTTTCAGAACTTCCATGTAGTACCTGCCTCTCCATTTAAATATTTTTTAAAATTTTATTTATTTAAATATTTTCTTGGTTAGCTTTCCAAGAGGGAG<br>GAAAAGAGGGGAGTTGCAACAAGTAGTGCCCCTATGCTGGGATTCATTTTCCAGAGTAAAGCCTGGGACTGGCACCCTGACCCCTACCGGCAGGTGAAAACTCC<br>AGGCAAACTGCTGAGATCCCACCTGGGCTGGCTGAGATAGTGCCTGGGGTGCATCCCTCAGCAGCTGCCACCTGGGCCCTGGGGCCATCTCTTTCTCTGGCATC<br>AAGCAGCCAGGTGTCAAGGCCTTCCCAGCAATCCATGCTGCATGGCTGGGTCTTGTTCTAGCAGGTCGATGGGCAGGGACTGGTAGCTTAGCCAGGGCACCAGT<br>GCGTGGCTGTGGGTTTGTGTGCTTCTGTGGAGAAGCATGATGTGTATGTGTGTGTGTGGGCACAGGCATGAGGAAGGGTTCATTTGTGCAGGTATCTCCCATGT<br>ATATCAGTGTGGGAGAGTGCCTGAGGATGTGTTTGTGTGTCTGAAAATGGGCGGAGGGTCTGTTGTGCTAATGTGTGCAGGGGTGAACATGTGTGTGACAGTCT<br>GTGTGTTTCCCTGAGTGGTGGCTGCGTGAGAGGGTGAGGGGATTTGGTGTTGTCTACCATGCCCGGCACATAGCAGGCTCTTAATAATCTTGAATTTAATTAAT<br>GTTAAATGTGTATGTTCCCATCCTTGTGGAAGTTGGTATAGAGCCTGTTTTCCTGTGATTGTGAGACTGGAAAATGGGGGACGGGCAGGGGCGAGACAGGATAC<br>AGAGGCTACTGTTTTCTTCCTCCCTAGAAGTAAGTACATAGAAGAGTGGGCTCTGGCACCTCACGGGACATCACCAAGTCCTGTGTGGCTGGCTAGGCTGTCCC<br>AAGGTGGCTTCAGGCATCACTTGAATCTTTTGAGACCTTCAGGCAGTAGCCTGCCATTCACCCTGTCAGTCAGCAGAAGTTGGGCCCACACAGGCCATAGAAAC<br>ACAGAGCAGTTCCCGGGAGGACCTGAGCTGTCCCTGAGAGCAGAGCTTCCAGGAGAGGCCGCAGGAACTGCCTTGACCGGAATTCCTCTTGGGGTGCAAAGGTG<br>GAGGGACACATGGTGCGACCCCAGGCAGAGGACTGCAGCCACTCCGTGCAGTCCCAGCCTCTGGGGTAGCCCCTTGACCTCCAGGCCTGCACAGATCCAAGGCC<br>GAGGTCCAGGCTCCAGCGCCAAATTAGCTGGCCTAGCAGCCTGCAGCCGCTCTAATCTCAACTAGGAAGGAATCCTTGCGCTTAGAAAGTCCAAGCGAAAGGGT<br>ATTCTGATTTTATCCCGGTTTTACCAGAAAATGCTGAAAGGAAAAGCCCCGAGAGGACACAGTGCTCTAGGAACTCGGGGCGCCACGAGCGCCTCATCCCCTCC<br>CTTCCGCCCGGCCGCGGTGCCCTGGTCGCTGAGGGACGCGGTCAGTACCTACCGCCACTGCGACCCGAGAAGGGAAAGCCTCAACTTCTTCCTCTCGGAGTCCT<br>GCCCACTACGGATCTGCCTGGACTGGTTCAGATGCGTCGTTTAAAGGGGGGGCTGGCACTCCAGAGAGGAGGGGGCGCTGCAGGTTAATTGATAGCCACGGAA<br>GCACCTAGGCGCCCCATGCGCGGAGCCGGAGCCGCCAGCTCAGTCTGACCCCTGTCTTTTCTCTCCTCTTCCCTCTCCCACCCCTCACTCCGGGAAAGCGAGGG<br>CCGAGGTAGGGGCAGATAGATCACCAGACAGGCGGAGAAGGACAGGAGTACAGATGGAGGGACCAGGACACAGAATGCAAAAGACTGGCAGGTGAGAAGAAGGG<br>AGAAACAGAGGGAGAGAGAAAGGGAGAAACAGAGCAGAGGCGGCCGCCGGCCCGGCCGCCCTGAGTCCGATTTCCCTCCTTCCCTGACCCTTCAGTTTCACTGC<br>AAATCCACAGAAGCAGGTTTGCGAGCTCGAATACCTTTGCTCCACTGCCACACGCAGCACCGGGACTGGGCGTCTGGAGCTTAAGTCTGGGGGTCTGAGCCTGG<br>GACCGGCAAATCCGCGCAGCGCATCGCGCCCAGTCTCGGAGACTGCAACCACCGCCAAGGAGTACGCGCGGCAGGAAACTTCTGCGGCCCAATTTCTTCCCCAG<br>CTTTGGCATCTCCGAAGGCACGTACCCGCCCTCGGCACAAGCTCTCTCGTCTTCCACTTCGACCTCGAGGTGGAGAAAGAGGCTGGCAAGGGCTGTGCGCGTCG<br>CTGGTGTGGGGAGGGCAGCAGGCTGCCCCTCCCCGCTTCTGCAGCGAGTTTTCCCAGCCAGGAAAAGGGAGGGAGCTGTTTCAGGAATTTCAGTGCCTTCACCT<br>AGCGACTGACACAAGTCGTGTGTATAGGAAGGCGTCTGGCTGTTTCGGGACTCACCAGAGAGCATCGCCAACCAGAACGGCCCACCCGGGGTGTCGAGTCTTGG<br>TAGGGAAATCAGACACAGCTGCACTCCCGGCCCGCGGGCCTTGTGGCATATAACCATTTATATATTTATGATTTCTAATTTTATTATAAAATAAAAGCAGAAAT<br>ATTTCCCGAAGAACATTCACATGAGGGCATTACGGGGAGACGGCAAGTCGGCGGCTCGGGGGGCGCGCTCAGCCGGGAGCGCTGTAGTCACAGTCCCGGGAGGA<br>AGAGCGCG |
| 97 | chr2: 137238500-137240000 | TGGAACAAGTGTCAGAGAGTAAGCAAACGACTTTCTGAGCTGTGACTCTGCTCCTCGACTGCCCACGTGCTCTCCGCTGTCTGCACTCCTGCCTCACCTGGGCT<br>GACTCGGACTCTCCACCTCCTTTGCTGCTTCCGGCATGAGCTACCCAGGAGCCTAAGGCGCTCCTTCCCGCAACTCCGGTCCCCGCGCCCCGGGACTGCAAATC<br>CTTTAAACAGAGGCCCCAGAGCTAGGGGTTTTCCCAGGCTCTGGTGGGCGTGGGCTGACAGTCGCTGGGAGCCCCGCAACAGGGGGGATGTCCAGGCAGGTATG<br>CACCCAGCTCCCGGCGTTTCCCGGAGTCACCACAATGTTTCCCTTTCTCTCTCCCCCACGTATGCTGCTAGGGGTACTCCCCAGATAGGATTTTCTTTGTCTTT<br>TCTCCTAGTAACACCGAAGCCCTCTCGTGCCCGGGGACTGCAGAGGAACGCCAGACCATCCGGACCTTGCGGGATGGCTCGGTGTGTGTGTTTTACTGTGTGTC<br>GGAGTGTCGCGCATGTGTGCGTGTTGGGGCGCGTTATCAACAGGGGCCTAGGGCACCCCCACTCTTTCTTGCTCTCTTCCCCCATCACTTCATGGACCTCCGAG |

TABLE 4B-continued

| SEQ ID NO | GENE NAME | SEQUENCE |
|---|---|---|
| | | GCGCAAAGCGCTCGACCCTCTCCTGGGCTCAGTGGCTTGGGTACTCCGGGCTGAGCTCAGCTGGGGAGTCCCCTTACCCAGCCCGCACCGGCACCCCGAAGCTT<br>CAAAGTTGCGGCAAACAGTTGCGGGGAGCAGAGGAACTGAGGTCCAGGCCAGCGCGCCCGCGGTCGCTCGCCTTGGGGAGCAGGCTGAGCCGAGGGTCGTGCGG<br>GTGCGCGGCAGAGGCGGTAGGAGGCGGAGGAGAGGGGGGAGAAAGAGGGGGCGGTGGGGAACAGCTGCCGGGGTAGGCGAGGCGCAAGGTGGCTCCCCGCGGCC<br>CCGCGCCCCGCGGCTCTCGGACGCACCAGGCAGCCAATGGCTGCGCAGAGGTGTACAGCAGATGGCGTCTGACTGCGCCGTTCCTTCCTCCTCCTCCTCCTCCT<br>CCTTCTCTTCCTCCTCCTCCTTCTCTTCCTCCTCCTCCTCCTTCAGTGCTGAGGAGCCAGAGTCGCCGCCGGGTTGCCAGACGCTGGAATGGGTGGTCTTCCGA<br>CACACACCACCATCTTTCTTGCGCTCGGGAAGCTCGGGGCTCAGCGGCTCCCAGAGGTTACGGCGGCGGCTCTGGCGAGACGGGTGAGTGCAAGCACGCGGAGC<br>CCCGAGTCGGGGATGCCGGGCCCCCTGGCCGGCCGACTGGGGCGCGGGGTGGCAGCGCCGGGGAAGGGGGCGCGCTGCCGGCGCAGACTTTGCTCTTTCCTCGC<br>CGGACAGCCATCGTCGCCCCTTCTCCCAGCCAGACGCGGGAACTTGGAAGCGGATCTTCTCGGACGCCTCTGGCTTGGGGCTGCGGGAAGCGTGGGCTGCCCGG<br>GGCGCAGTGTGCGGAGACCCTCTAGGCGGGCGGGGACGCCCCAC |
| 98 | MAP1D | GTTATTATCCACGGGGTCCTAATTAAAGCTTGATTAAAATGCCCTTCTTTCTCTAAAAAATTACGAACTAGGCAACTTCATACATTTTGAATGGCGCAGTGTTT<br>CCTCTTCCAACTGTTTAGTTTGTAGTATACTATGTAAGCAACATCAATTATCAACCCTTGCAAGATGACAACATGAGCCTGTGGGGGAAGCACTTGAGGGGAGG<br>GAGGAGAAACTTCTCTTTTTTAATAATCAGCCGGAAACAATGTTTAACAAGAATCTGATGAGGTCACTGCAGTAAATATTTTTCCTCTTACAGAGCCAATCATC<br>ACGGAGGGATCCCCTGAATTTAAAGTCCTGGAGGATGCATGGACTGTGGTCTCCCTAGACAATCAAAGGTGTTTGCTTTCTGCTCTGTTGCTTTTAAATTGTAT<br>GGGAAAGGAAGATTGGTCCGACGGCGCGCTTGTGGCCCGGCCGGAGCTTGCGTGCGCGTTCTGACGGCTGGGTGCTGTGTTACAGGTCGGCGCAGTTCGAGCAC<br>ACGGTTCTGATCACGTCGAGGGGCGCGCAGATCCTGACCAAACTACCCCATGAGGCCTGAGGAGCCGCCCGAAGGTCGCGGTGACCTGGTGCCTTTTTAAATAA<br>ATTGCTGAAATTTGGCTGGAGAACTTTTAGAAGAAACAGGGAAATGACCGGTGGTGCGGTAACCTGCGTGGCTCCTGATAGCGTTTGGAAGAACGCGGGGGAGA<br>CTGAAGAGCAACTGGGAACTCGGATCTGAAGCCCTGCTGGGGTCGCGCGGCTTTGGAAAAACAAATCCTGGC |
| 99 | WNT6 | TCCCTGCTGTGGGACCCGAGGAGAGGAGAACTGGTTCGCT |
| 100 | INPP5D | TCTCTCTCTCTCTCTTGCTTGGTTTCTGTAATGAGGAAGTTCTCCGCAGCTCAGTTTCCTTTCCCTCACTGAGCGCCTGAAACAGGAAGTCAGTCAGTTAAGCT<br>GGTGGCAGCAGCCGAGGCCACCAAGAGGCAACGGGCGGCAGGTTGCAGTGGAGGGGCCTCCGCTCCCCTCGGTGGTGTGTGGGTCCTGGGGGTGCCTGCCGGCC<br>CGGCCGAGGAGGCCCACGCCCACCATGGTCCCCTGCTGGAACCATGGCAACATCACCCGCTCCAAGGCGGAGGAGCTGCTTTCCAGGACAGGCAAGGACGGGAG<br>CTTCCTCGTGCGTGCCAGCGAGTCCATCTCCCGGGCATACGCGCTCTGCGTGCTGTGAGTACAACCTGCTCCCTCCCCGGGCACAGATATGACAGAGGGGCTTA<br>GAGGGGGCCCAGCTTTGAGATGGGTTGTTCTTATGTCACAGGACAGAGTGATCTGACATGCACACTTCCCCGCCACCCTGTCAT |
| 101 | chr2: 241211100-241211600 | TGTCCTCGAAGAAGGGCCTGAGCAGCAGCAGAGGACCCCAGGCGACCGTGCCTGAGCCGGGCGCCGACGACGACTGAGCACCTGATATGTCCCCGGCACTCGCA<br>GCCCCGCGGCCGGAGTCGCTGTGGGTGAGCGGTCGTCGAGCTTCACAGAGGCCGGGCTCTGTGCCAGGGCCCCGACAGGGCAGGAAGCAGATAGAGTCCCACAA<br>GCACAAGCCCAGTGCGCAGAAAGGGTTACTTAAAAAATAAGTTCTGTGATAAAATCAAACAGGGTGAAGGGCTGGAAACAGGTCATGAGGGCGCAAACAGGTCG<br>TGAGGGCGCAAACAGGTCGTGAGGGCGCAAACAGGTCGTGAGGGCGCAAACAGGTCGTGAGGGCGCAAACAGGTCGTGAGGGCGCAAACAGATCGTGAGGGCGC<br>AAACAGGTCGTGAGGGCGCAAACAGGTCGTGAGGGTGCAAACAGGTCGTGAGGGCGCAAACAGGTCGTGAGGGTGCAAACAGGT |
| 102 | WNT5A | AAATGAGACCTCTGGGGAGACTGTCAACCCCAGGGGTAAAACAAAAATTCTGATCAGAAACTGAGTTTCCCAAAGAAGGGGCTAAATGTTTTCCAACACTTTCG<br>GGGCTCAGGGAAGATGACTCTGTAAGGACACTGAGAATCTTCCTCGCGTGCCACGGGGAGGAGGACTGGGGGCGTTTGAGGGGCTCAGCGCACCAGAGGAGTGA<br>GGTGGAGGAGGGCGTTCCCGCGTCCTCCTCTTCAATCCAGAGCAGCTCAACGACGTGGCTCCCTTTCTATGTATCCCTCAAAGCCTTCGCGT |
| 103 | chr3: 138971600-138972200 | TAGGCTCTAGTGGACCTAGCAGTGGGAGAGCTACTTGGGCTGGTTTCTTTCCTGACGCTGCAGGGATGGGCATCGGCCTGGAACCAGAAGCGCAGGAGCTGGGC<br>CACGGCAGAGTAATTAAGAAAATAATGAAATTGATGGCGGATGGGGGCGCTAGAAATCCTGGGGCGTCTACTTAAAACCAGAGATTCGCGGTCGGCCCCACGGA<br>ATCCCGGCTCTGTGTGCGCCCAGGTTCCGGGGCTTGGGCGTTGCCGGTTCTCACACTAGGAAGGAGCCTGAAGTCAGAAAAGATGGGGCCTCGTTACTCACTTT<br>CTAGCCCAGCCCCTGGCCCTGGGTCCCGCAGAGCCGTCATCGCAGGCTCCTGCCCAGCCTCTGGGGTCGGGTGAGCAAGGTGTTCTCTTCGGAAGCGGGAAGGG<br>CTGCGGGTCGGGGACGTCCCTTGGCTGCCACCCCTGATTCTGCATCCTTTTCGCTCGAATCCCTGCGCTAGGCATCCTCCCCGATCCCCCAAAAGCCCAAGCAC<br>TGGGTCTGGGTTGAGGAAGGGAACGGGTGCCCAGGCCGGACAGAGGCTGAAAGGAGGCCTCAAGGTTCCTCTTTGCTACA |
| 104 | ZIC4 | GAGGTTGCTGACTCAGGAGCCAGGAGCTGAGAAACTCCTAGGCTAGCAGCCGTTGAGCCTAATTTTATTTTCTGGCTTTCTCCGAAATGTCTCGTTTCCCTCAT<br>CTTTCTGGTCCTTTTCGTCTCTCTTATTTCCCCAAAACGTCTACCTCACTTCGTCTTCCTTTCTCCTCCCCTCCCCCTCTCTTTCCTCTATACTCTCTTCCCA<br>TTTAGCCTTGCAGGCCCCTCCTCCCCGGTGTTGGAGAGCTCAAAGACGCGCGAAACTCAAGGATCTGGCCCTGACCAGGGACGGGATTAGGCGGGAAGTGGTGA<br>CGGCCTGAAAAGGCTGGGCTCGAACCCGTGCCTTCCTGAAAGGACTCTCCCCGCCACAAGTCACACCCACCCGCAGGCCTGCTGGCCAAAGAAACAAAGGAGTC<br>GGGCGTGGATCCAGGAGAAACAGGTTTTCGCTCTCGGATCTCCCTGGGCAAATCAGGGATCCTGAGCGCTATACCCCGCAGTCGTACGGAGCCTCTGGGAAAGG<br>GGATTTAAGGGTGACTTCCACTTTCAGCTTCGGCTACTTGTTGCCTGCGGTCCAAGCCTTCTCTGCTTCCTCCTACCTCGTCTTAGGCCTCTGTAGAAAGTGCA |

TABLE 4B-continued

| SEQ ID NO | GENE NAME | SEQUENCE |
|---|---|---|
| | | CGCCGCGTTTCCCCTTCCAGGCTCTGAGAGGGCCTGCAGGCCCGTGGCCGCCTCCGACAAGATGCCTTCCAGTGCTAGGGGGGCCACTTTGGCGGGATGGGGT |
| | | CGGTTGGTTAAAAAAAACTTAAGTTCTGGCTCAGTCGAGTGTGGCAAAAGCCGAGGGTCGGGGGTTGGGGGG |
| 105 | FGF12 | TACTGACCTGGTCTCCGCCTCACCGGCCTCTTGCGGCCGCTGCAGAAGCGCACTTTGCTGAACACCCCGAGGACGTGCCTCTCGCACAGGGAGCGCCCGTCTTT |
| | | GCTGGGGCTGGAGCGGCGCTTGGAGGCCGACACTCGGTCGCTGTTGGACTCCCTCGCCTGCCGCTTCTGCCGGATCAAGGAGCTGGCTATCGCCGCAGCCATAG |
| | | CTGCTCAGCGAGGGCCTCAGGCCCCAGCCTCTACTGCGCCCTCCGGCTTGCGCTCCGCCGGGGCGAGGGCAGGACCTGGGCGGCCAGGGAAAGGGCAGTCGCGG |
| | | GGAGGCAGTGCTAAAATTTGAGGAGGCTGCAGTATCGAAAACCCGGCGCTCACAAGGTTAGTCAAAGTCTGGGCAGTGGCGACAAAATGTGTGAAAATCCAGAT |
| | | GTAAACTTCCCCAACCTCTGGCGGCCGGGGGGCGGGGCGGGGCGGTCCCAGGCCCTCTTGCGAAGTAGACGTTTGCACCCCAAACTTGCACCCCAAGGCGATCG |
| | | GCGTCCAAGGGGCAGTGGGGAGTTTAGTCACACTGCGTTCGGGGTACCAAGTGGAAGGGGAAGAACGATGCCCAAAATAACAAGACGTGCCTCTGTTGGAGAGG |
| | | CGCAAGCGTTGTAAGGTGTCCAAAGTATACCTACACATACATACATAGAAAACCCGTTTACAAAGCAGAGTCTGGACCCAGGCGGGTAGCGCGCCCCCGGTAGA |
| | | AAATACTAAAAAGTGAATAAAACGTTCCTTTAGAAAACAAGCCACCAACCGCACGAGAGAAGGAGAGGAAGGCAGCAATTTAACTCCCTGCGGCCCGCGGTTCT |
| | | GAAGATTAGGAGGTCCGTCCCAGCAGGGTGAGGTCTACAGAATGCATCGCGCCGGCTGCGGCTTTCCAGGGGCCGGCCACCCGAGTTCTGGAATTCCGAGAGGC |
| | | GCGAAGTGGGAGCGGTTACCCGGAGTCTGGGTAGGGGCGCGGGGCGGGGGCAGCTGTTTCCAGCTGCGGTGAGAGCAACTCCCGGCCAGCAGCACTGCAAAGAG |
| | | AGCGGGAGGCGAGGGAGGGGGGAGGGCGCGAGGGAGGGAGGGAGATCCTCGAGGGCCAAGCACCCCTCGGGGAGAAACCAGCGAGAGGCGATCTGCGGGGTCCC |
| | | AAGAGTGGGCGCTCTTTCTCTTTCCGCTTGCTTTCCGGCACGAGACGGGCACAGTTGGTGATTATTTAGGGAATCCTAAATCTGGAATGACTCAGTAGTTTAAA |
| | | TAAGCCCCCTCAAAAGGCAGCGATGCCGAAGGTGTCCTCTCCAGCTCGGCGCCCACACGCCTTTAACTGGAGCTCCCCGCCATGGTCCACCCGGGGCCGCCGCA |
| | | CCGAGCTGGTCTCCGCACAGGCTCAGAGGGAGCGAGGGAAGGGAGGGAAGGAAGGGGCGCCCTGGCGGGCTCGGGATCAGGTCATCGCCGCGCTGCTGCCCGTG |
| | | CCCCCTAGGCTCGCGCGCCCCGGCAGTCAGCAGCTCACAGGCAGCAGATCAGATGGGGATTACCCGCCGGACGCAAGGCCGATCACTCAGTCCCGCGCCGCCCA |
| | | TCCCGGCCGAGGAAGGAAGTGACCCGCGCGCTGCGAATACCCGCGCGTCCGCTCGGGTGGGGCGGGGGCTGGCTGCAGGCGATGTTGGCTCGCGGCGGCTGAGG |
| | | CTCCTGGCCGGAGCTGCCCACCATGGTCTGGCGCCAGGGGCGCAGGCGGGGCCCCTAGGCCTCCTGGGGCTACCTCGCGAGGCAGCCGAGGGCGCAACCCGGGC |
| | | GCTTGGGGCCGGAGGCGGAATCAGGGGCCGGGGCCAGGAGGCAGGTGCAGGCGGCTGCCAACTCGCCCAACTTGCTGCGCGGGTGGCCGCTCAGAGCCGCGGGC |
| | | TTGCGGGGCGCCCCCCGCCGCCGCGCCGCCGCCTCCCCAGGCCCGGGAGGGGGCGCTCAGGGTGGAGTCCCATTCATGGGCTGAGGCTCTGGGCGCGCGGAGCC |
| | | GCCGCCGCCCCTCCGGCTGGCTCA |
| 106 | GP5 | GGGGGACACAGAGAGGAGGGGTTGCGGGCCTGTGAGAATGAAGAGCACAGAGCGGAGAGGGGGAGGAGGAGGGAAAGGAAGGCGTGGCAGTGAGAGAGAAGAGG |
| | | AAGAAGAGAGGAGGAGTGGGGAGGGGAGGGAGAGCAAGACAGCAGCGGGTCTGGATTCCCCTCCGAGCCACATCTGGTCAGGTTCTAAGTAATTAGAAGATTTT |
| | | CCCATTGGTTTACCCAAGGGCTCTCTCTCTGATTAATTTTCGAAAGAGTTGGCCAATTTTAATCATAGCAAACACGATGATCACGGTGATCATGGCCTGAACAG |
| | | CTAAAAGCAGAAAATAAAACCCCCAGAACGGACTATGATCTTGACCTTTGCCCGTGGTCACCGGCTGGGCCCACACCCAGGGTTCTGAGCTGTTGGGAGCCAAG |
| | | GCTGGGTGGACAGGGGCTTCCGAGGAGCTGTCCGCAGCGGGGCGGGGAGGCGGGCCCCGGGGGCCCGGGCACTCCGCGTCACCCCCCGGCAGGGCCCAGAGCGG |
| | | CAGGCCGGCGTGCGCCCCAGGGCCTGCGCACCGTGGGGGCTCTTCCCCGCCCACGAGGCCTAGGTGCTGCCGCAGCCACCCCAGGAAGGGCCCCAGGCCACAGT |
| | | CGCAGCGCCAGGAGTTGTGCCCCAACAGGACCTCCGTCAGCCGGGGCAGAGCCCCAAACACGTCGCCAGGCAGGGTCTCCAGCTGGTTGTGGTCGAGCTGGACG |
| | | CTCTCCAGGCTGCTGAGATTGCGGAAGAGGGCACGGGGCAGGGCGCGCAGCCTGTTGCGGCGCAGGGACACC |
| 107 | MSX1 | GCCCCGGTGCACCGCGCGTCCAGCCGGCCCAACTCGAGCTAGAAGCCCCAACCACTGCCCAGTGCCTGAGTTGCAGTCTTGGGTCCTTTAGAAACCTGGAGATG |
| | | TGCGTAAAATTCAGATGCCGGTATTCCCGAACTTCCCCAGGCCTCAGCATATCTCGGCGGCCTGTGGACAGATGGGAGGCTACCAATCGCTCCGGCGTCCGCAG |
| | | CCCGACCCCTGCCGCCAGACCCCGGACGTCTTCCGGATAATAAAGTTCCCGCTCTAATTCATTTTCCCTAATCTGGACGCCCCTAATCTACAGCTTTTATTGCG |
| | | CCCAGTTAAAAGTCGAGGGAATTCGCTGTCCCTCCGCGCTCGGATAATTACCCCTAAATGGCCACGGCAGCCCCTTGTGTTTCCTGGAGATTAGAACCCCGCAG |
| | | TCATCAATGGCAGGGCCGAGTGAGCCGCCAATCACCTCCGCTCACTCCCTGAGAGCCGCTGGCCTGGGCCGCAGGAGGAGAGGCCATAAAGCGACAGGCGCAGA |
| | | AAATGGCCAAGCCCCGACCCCGCTTCAGGC |
| 108 | NKX3-2 | AGGGTGCCTCTGTTCAAATTAGAAAAAGGCGCCCCCTCAGGGCAGACTCAGCCCAGCTGCCAGGGGACAAGTCCTGGCTAACGGGAGCTGGAGCTGGGTTTCAC |
| | | CTCCAGGTGCCTCCTTGGCGGGGCGCCCCGTGCAGGCTACAGCCTACAGCTGTCAGCGCCGGTCCGGAGCCGGAGCGCGGGAATCACTCGCTGCCTCAGCCCAA |
| | | GCGGGTTCACTGGGTGCCTGCGGCAGCTGCGCAGGTGGAGAGCGCCCAGCCTGGGAGGCAGTAGTACGGGTAATAGTAGGAGGGCTGCAGTGGCAGAAGCGAGG |
| | | GTGGCCGCAGCACTTCGCCGGGCAGGTATTGTCTCTGGTCGTCGCGCACCAGCACCTTTACGGCCACCTTCTTGGCGGCGGGCGCCGAGGCCAGCAGGTCGGCT |
| | | GCCATCTGCCGGCGCTTTGTCTTGTAGCGACGGTTCTGGAACCAGATTTTCACCTGCGTCTCGGTGAGCTTCAGCGACGCGGCCAGGTCTGCGCGCTCGGGCCC |
| | | GGACAGGTAGCGCTGGTGGTTAAAGCGGCGCTCCAGCTCGAAGACCTGCGCGTGGGAGAAAGCGGCCCGCGAGCGCTTCTTGCGTGGCTTGGGCGCCGCCGGCT |
| | | CCTCCTCCTCCTCCGCGACGCCTGCCGGCCCGCTGCCGCCCCCGCCGCCGGCCCCGCTGCACAGCGCGGACACGTGTGCACCTCTGGGGCCAACACCGTCGTCC |
| | | TCGGTCCTTGGGCTGCGGTCGCCTGCGGACCCCGGTGGGAACAGAAACAAGAGACTGTCAGCGCCACAGACGAGGTGAGGCCGGGCCTCAACTGCAGGGGTCAC |
| | | GGGAGTGGGGCGGAAATACACTTTGATCCCACTCAAGCGGAGCGGAGGTCTGGGAGGCCCTGGGCCCGGGAGACCAGTCTTAGACTCTTGCCCCACTGGGTATC |
| | | CCATCTAGGCCTCTTCTGGGGAGGGCGGCAGACTCAGCCGCTGTGTCAACGCTGTGTTGTCGAGACCAGCTCCCCACCCTCTCTGGGCCCCAGGCTCCCCTCAG |

TABLE 4B-continued

| SEQ ID NO | GENE NAME | SEQUENCE |
|---|---|---|
| | | TAACTTGGGGCACTCGACCCGAGCATCCGCGAAAGCCCTCCCGGCTCTCAGCGTTGAGCATTGGGATTCTAGACTGCATTTCCGTCTCTCTGCTTGGGTTCACG<br>CGCCTCTCCACACTTAGTTCACACGCACACACGCGCGCGTCCTCGCAGCACACACTTGTCTGGTGCAGGTAAGGGAAGGTGGAGGCGGATCCTGGGGCCAAAGG<br>TATTTAGAATCTTTCACCCTCAGCCGCCTGGGATTGCTGTGAGAGACATGGAAACAGGCTGAGCCGAGGCCTTAGATGAGAGGATGGACTGGAGAGTAAAGAGG<br>GAGGGTTGCCCCTGCATCGAGTTTTTGGACCCTGATCCCACACCAGCTTCTCGGTCTCGTACCCGCCCTTCCGAAGAACTCCAGCAGAAAGGTCCAGCGGTCCC<br>CTGTGCTTGAGGCCTACAGAAGCTTGTACCCAACTAGGGCAGGCACCCGGGTCTTCCAGACCACAGGACAGGACAGGCCACGGCTGAGGAGGCCTCTCTCCTGC<br>CTCCAGGATGAACTAAAGACCCAATCCGGGATCTTCGGCCTAGGGCTGCTCTCCCAGACCTGGGGTCTGAGAAAGCCAAACCAGCCCTTTCCCCAAAGCTCTAG<br>TTCTGCAGATTCTCAGCTCTGGCCCACTCGGAGGTGTTCTTCACCACCTATCCACCTACTGTGGGGCCCGGCCCTGGGACCTTGAACTGGCAGGTCTCTGGTCC<br>AGAGCTAGGTCACTGGCTACCTGAGGTCTCTGAACCCCTCACTTTTCCGCTTCCCTGATTTTGGGGATTTGGGGACAGACACGGCAGAAAGCACTGGCGACGAA<br>CTCAAAAACTCCCGAACGCAAGGGGCAGCGGTTCTCCCAACCCAGTCTAATGCACATTGGCCCAGGATGTCTCAGGCCTCACCCCAGGACGTAGGGCTCTGAGG<br>AGCTACTCCGGTCTCTCGCGGGCT |
| 109 | chr4: 111752000-111753000 | GAGAAGGGATGTGGCGGGGGGCTCCTCCGGCCCTGGACTCCCTGGGTGGACTAGAAAAGGGCAAAGAAGTGGTCACATCTGTGGGCCAGACTGGTGCGCGATCT<br>TTGGAGGCGCAGCAGCAAGGCCGCGCCAGGGCTGAGCCCAGACCGCCCACGAGGAGGCCCGCCAGGCCCGGAGCAGCGGCGCGTGCGGGGGCGTGCCGAGCGCA<br>GGCTCTAGGGCCCCTGCTTCGCCCCAGCTGGACCCCGCGGGCGGTCGGTGCAGCTCGAGCGTGTGGGCTGCGATGCCCTGCCTGAGACTTCGGGCTAGGGATGC<br>GGGCGGGAAGTGGGGGTGCGGCGGCAGCTGCAGATTAGATTCCTTTTTTTTTTGGCCGGAGGGACGTGCAAACTTCTAGTGCCCGGGCCAAGAGGGCGACCCCG<br>GAGGTGCGTAGGTGGCCCTCCGGGTTCCCGCTTCTCCTAGTGCCTCTGAAAATACCGTCAGGGTAAAGGGAGACAGGCAGTAAGTCTTACCACCACCGCCCTTT<br>CCCCATGTCATTGGCCAAAAACTGAACATTAAGATAAAGCAGCTGTTTCAGTCAATGGAAAGCGGTAGGGCGAGGTTGTACCCAAAACCCGGTTTAGACGGCCA<br>ATGAAGTCCTAGGAAAAGCCGCCCCGGGGGCACGTTCAGGTGGAGCGGCTGCACCTCGGGTCGTTCTAAGGGATGGGCTGCGTGGTACCCACGGAATTCATGGG<br>TCCAAAAGGTCCTGGTCACCTGTCCAAACATCCATCCCCTGGCGCATGGCGGTTGACAAGATGGCCCGGCCACCCAGAGGAAGGAGGATCCGGGACGGGGAACT<br>TCGCGCCGGGAAGCTGTAGCCCAGAGCTGCAGCTCAGCATTCGCAAGAGATTCATCTTTTTTTTCTCTCGTGTTCGGAGAAACAGATAAACAAGACACCGCCTC<br>ATCAGATAAGAACGTCTCCTTCGATGTCACGGATTTCAAGAGGTAGCTGGAGAAACTGACGTCA |
| 110 | SFRP2 | CAGGTCAGGCAGAACTTCTGCCCTTCCCGCTACTGGCACCCCAAGCAGGGATGCACTGGGATGCGTGGCAGGGGCGGGATCTCCTGGGAGCGTCTCAGCCCAGC<br>AGGGAGTGGGGAAGCAAGAGGGAAGGCTTACCTTCCTCGGTGGCTGGCAGGAGGTGGTCGCTGCTAGCGAGGGGGATGCAAAGGTCGTTGTCCTGGGGGAAACG<br>GTCGCACTCAAGCATGTCGGGCCAGGGGAAGCCGAAGGCGGACATGACCGGGGCGCAGCGGTCCTTCACCTGCACGCAGAGCGAGTGGCATGGCTGGATGGTCT<br>CGTCTAGGTCATCGAGGCAGACGGGGGCGAAGAGCGAGCACAGGAACTTCTTGGTGTCCGGGTGGCACTGCTTCATGACCAGCGGGATCCAAGCGCCGGCCTGC<br>TCCAGCACCTCCTTCATGGTCTCGTGGCCCAGCAGGTTGGGCAGCCGCATGTTCTGGTATTCGATGCCGTGGCACAGCTGCAGGTTGGCAGGGATGGGCTTGCA<br>ATTGCTGCGCTTGTAGGAGAAGTCGGGCTGGCCAAAGAGGAAGAGCCCGCGCGCCGAGCCCAGGCAGCAGTGCGAGGCGAGGAAGAGCAGCAGCAGCGAGCCAG<br>GGCCCTGCAGCATCGTGGGCGCGCGACCCCGAGGGGGCAGAGGGAGCGGAGCCGGGGAAGGGCGAGGCGGCCGGAGTTCGAGCTTGTCCCGGGCCCGCTCTCTT<br>CGCTGGGTGCGACTCGGGGCCCCGAAAAGCTGGCAGCCGGCGGCTGGGGCGCGGAGAAGCGGGACACCGGGAGGACAGCGCGGGCGAGGCGCTGCAAGCCCGCG<br>CGCAGCTCCGGGGGGCTCCGACCCGGGGGAGCAGAATGAGCCGTTGCTGGGGCACAGCCAGAGTTTTCTTGGCCTTTTTTATGCAAATCTGGAGGGTGGGGGGA<br>GCAAGGGAGGAGCCAATGAAGGGTAATCCGAGGAGGGCTGGTCACTACTTTCTGGGTCTGGTTTTGCGTTGAGAATGCCCCTCACGCGCTTGCTGGAAGGGAAT<br>TCTGGCTGCGCCCCCTCCCCTAGATGCCGCCGCTCGCCCGCCCTAGGATTTCTTTAAACAACAAACAGAGAAGCCTGGCCGCTGCGCCCCCACAGTGAGCGAGC<br>AGGGCGCGGGCTGCGGGAGTGGGGGGCACGCAGGGCACCCCGCGAGCGGCCTCGCGACCAGGTACTGGCGGGAACGCGCCTAGCCCCGCGTGCCGCCGGGGCCC<br>GGGCTTGTTTTGCCCCAGTCCGAAGTTTCTGCTGGGTTGCCAGGCATGAGTG |
| 111 | chr4: 174664300-174664800 | TGCGATCATTAAAATCAGTTCCTTCCCTCCTGTCCTGAGGGTAGGGGCGGGCAGATTTTATTACTTCTCTTTTCCTGATAGCAGAACTGAGGCGGGGTTGTGGA<br>GGAGCGACGGAGGACCACCTCTAACTTCCCTTCACTTCCTGGATTTGAAGCCTCAGGGCCACCGGCCTCAGTCCTGTTACGGTGGCGGACTCGCGAGGTTTTCC<br>AGCAGCTCATTCCGGGACGGCGGTGTCTAGTCCAGTCCAGGGTAACTGGGCTCTCTGAGAGTCCGACCTCCATCGGTCTGGGAGCGAGTGGTTCGAGTTCAGAT<br>GCTGGGAACCGTCGCTTCTCCCCGGCCGGGCTCGCTGTTTTCTCCTCCGCTCGCCGTCATCAAGCCCGGCTATGAGCAGGGCTTTAAATCCTCCCTCCCTCACC<br>CGCAGGTTTACCGAGCAGCCCCGGAGCTCTCAGACATGCTGCGCTGCGGCGGCCAGAGGAGGGGTGGGGGCATTGCCCTCTGCA |
| 112 | chr4: 174676300-174676800 | GGGCTTGGGCCGCAGGCTTCCCTGGACTTCCGCAGTCCCCCTTCTCCCCATTCCAGAACCTGCCGAGCCCCTGCTGCATCTGGGACCCGCCTTCACCGTTTCCC<br>AATCCCAGCGGTTAGCCCCTGCGCCCCCTTTTTGGTCTCCACTTTGCCGTTCGAAAATGCCTAGGTTGGTGGATCGACCCTCCGCGGAGCAAAGACGGATGGCT<br>GGCAGGAGCAGGTTCAGGAGCTGGGCCAAGGTATTCTCTGCTTCCGCCTTTGTGTCCGCCCCCCCGCCCCCTGCTCCCCGCTTCCCGCCAGCATCTCTCCTTTT<br>CTGCTCAGGAGTGTTTGGCCCGGCGGTCCACCCCGGCTTCCCGAGATACGCTAGAGTTGCCCCCACGTCCTGTCCGCCGCGCCCCTACCCACCGGGTTGCCTTC<br>GGGGCCCTTCGGTGCTGTGTAGTCGGCGTGGCGCTGTGAGCTAGGCGAACAGGAACCCCCAGGCCCGCCACGTCTACGCTATTA |
| 113 | SORBS2 | TTCTGGGGCCTGGATGGGTGCGAGCGGGACCCGGGGGAGTGGGAGTCGCCAGGCTCTGAGCAAGCAAGGGCTGCACCTGCACCTCTGCCGGGCATGAAGAAAGG<br>TAAGGAAGGAAGGAGCTCACCCGGGTGGGAGACAGAGCCGGGGCGCGCGAGCTTGGTGTGGGGGCGCCACTCCGGGGCGGAGGGGAGGGGCTACCAGTGACTTC |

TABLE 4B-continued

| SEQ ID NO | GENE NAME | SEQUENCE |
| --- | --- | --- |
| | | TCCGAGTCGGGAGCTAGAAAGAGGCTTCCGGCCAGGTTCCCTTGGAACAGGTGTCGGAGTTGTTGGGAGAGGGGGCTGCAAGAAAGAGGGGTGCAGAAACTGGT<br>TCATTAGATGGAGGCTCTGGGCGGAACCGCGAGGACACCCTGGCAGCGCGCTGTGCCTGCGTTAGGCCGGGAGGGGAGAGGCCTCCGGACGGCGAAGTGTCCCT<br>AGGGACCCAGACGCCTCGGGAGCGATCCGGGCCGCTGCGAAGCCCTGCCCACCAGGAGTGGATCCCCAGGATTCACCTCCCGGCTGCCTGCTCTGAGCTGAGAA<br>GGGGATCTGGTTCTTCACAATACCGTGGATGGCGGGGAAGGGGAGGGAGCCTGGGGTAAAATCCCATCTTGGTTTCCTCG |
| 114 | chr5: 42986900-42988200 | TGTCACAGAAACCCCAGCAGCGCAGCCACCGGACTGGGTTCTGGAGGCCGAGCCGCAGTCCGTGCGGCGGCGCTGGGAAGAGAAGGCGCCCCGGCAGCTCCCCT<br>GCCACCGGCCCCGAGGAGCGGCTGGCTCCCCCAGCCCAGCGCCGCCGCCGCCCGGTAACTCCAGGCGCAACTGGGCGCAACTGGGGCAGCTGCGACACCGAATC<br>CCTCACATCTGCAACCTGGGTGCTGCGGCCACTGAGAAAATGGAGGCGCAGACCAACGAGCGGTGCCGCGACCGAGAGACCTCGGCTGGCGAAATGGTGGTGCC<br>GGGAGCCTGCGAGTGACGCCAGCCGGCGGGGTTGTCAAGGACAACATTCGTTTTGACGCAGCCAATGGCGCCGTCACCAAGAAACCATCGACTCTGAGAAAAAA<br>GAGAGGTTCGGCCACCGAGAAACTCCGTACGACAAGTGCTGTGGCAGAAAAACCGCCTACTCCGCGCCACAGGCAAAACAGCCAATGGAAACCCCAGGTGCTGC<br>GACCGTGACACCGGCACTAGAGGGTCTCGGATGGAGAAAGCGGCGCACGGAGACCAGGAAACTATGTGTAGCACAACTAGCAGAAAACCGTCTGGTCGGCCATC<br>CGGGAGAAAGCGCGGATCAGAAACAAGCGACTTCGATGCAGGGAACCGCGCAGCCACTGAAGAAAGTGACCCACGTGGCAGTGGTGCCAGCGAAACACTGCAGT<br>TTGGACGGCAGCTGTGGGGATGCCACAGAGAAACATGCACTGCCACTGAAGTACATCCAGCTCCGCGGAGCTAGTGTTCATATGATCAAGAAACCGCCAGTTGG<br>GCTCTGCTAGAAACTTTTAGTCCTCCCTTAACGGCTATCCTACCCACAACAGACAATGCCTTTACCCAGCACCTAGCGGTGCTGAGACCCGCCTGGGCCAGCAC<br>AGAGCGCAGAGCAGTACGGGTACGGAGAAACGCCGGACTCAGTGAAACCAGCCTTGCCTCCAGCGGATTCCCCGGCTTCGCCGGACGCCACAGGCAGAGTGCCG<br>CGGGGAAACCTCTGGCTCCCTAAACCGATTAGATTGTGGGAGTGGGGGGGACACTCACAAGTTGTGTGGAAGGGAACCAGCGGCAATGGGACCCGGCGAGCACT<br>TGCCCGCAGCAAATGCCTGCGCTGCTGCAAAAAAAACAACTTTTGGCGCAAAGAATGTTGCGGCCAGAGAGCATCCGCTGTCGCTGACAAAGGAGTAGCAATGG<br>CAATGAGAAACCGCCGGCGCCACGGCCGACCGCGGCGGCTCACGCCTATGAT |
| 115 | chr5: 72712000-72714100 | CAAACGCTGAGAGACAAAAAGACACCAACACCCACCAGGACTGCGTCCTGCCAGCTCTTCACTCCGCTGACCTGACCTTCCACGCCCCTAGTCCTCGAGCGGAC<br>TTGACCTGTGGGGGAGTACCGAACCGTCCCCATGAGGCCCTCCAAGCGGCCAGGTGGCCTCCGCCACTCTCTCCACCCCCACCTCCTCCACCCCCCAGCCCATC<br>GGTCCATCTTCGATCTGCAAAACACGCCGGGTCAGCGACGCATCGGTCCCAGGCTTGTGACCACCTCTTTCTCTGTTACTTGGGGAGCCAGGCCCACCGCTCAG<br>GATCACAGTGAGGAGAAAAAAGACACAAACGCCAGGACAGGGCGGCTGGGGAAGGAAACTGCTAGGGACCGCTCATTGTCAGCCTGGCGTGTCCCACGGATCGC<br>AGGACCCGTCGAGGCTTTGCTCTCTGCGACCCGAATACTCCTGGGCCTCTCGACCTCCTCCTCGGACTCAGGCGTCCGCGTCTCCGGTCATCACGGGAGACCAA<br>TTGGTTTACAAATAGTGATGATAAACCTGGGACCGACCTTGGGGCTGTGTAAAAGTCTACTGACAGATGTAATGGAGGGTTGTTAGCAGTCACAAAGCCTGTCG<br>GACCCGTAGCATTAGTTCAAGAGACTATTTTCGTGTCGCACCAAAATTACTGCGCGTGTAAACCAATTTCCCCGACGGAAGAATAAACAGAGATTCGTTTGAAG<br>CGCGAGATGAAAACAGATGGGGTATCGCAAACAGTTCCCCAAAATACAACAGACTTCTGGGCCAATTACACGTGGTTAGCTCTGAATGGCAGAGGAAATAGTTT<br>TCTTTGCTGCTAAATGTCACAAAAGTCACCTAAAGGCACAGAGGAGGCCGCTCTGTTTTTGCGAAACTTGCTAAAATTAATCTGCGCTGGGCCACTTGCAGAAA<br>GCAGAACCACCTCCCGCCCCCACCTCGCCTCCAGCCGCCGGGGTTCAGGCGTTTGTGAAAGACAGAACCTTTGGGCTAGGGACCCGGGCACTGGTGCTTCGAAG<br>TCCGAATCCGCCGGCCGAGAAAACGACAAGAGAAAGAAAATCCAGCGGGCGCTCTCTCCAGCGCCAGGCCGGTGTAGGAGGGCGCTGGGGCTCGGCCTGCCACC<br>CCTACCCGACATTGGGAAGCAGCCCCTGCGCTCCCGCGGCGCCTCAGCCTCCGGTCCCCGCCCCGAGGTGCGCGTTCCTCCTCCCGCATGCCCGTCTCGGGCCC<br>CACGGAGCAAGAAGATAGACGATGACGAGGCGCGCCCATCCATCCGGGCCGACGAGGTCAGGCCCGCGCCACAGGCAAAAATTGCGCAAGCCCGGCCGCAGGGA<br>TTTCGCGGGCGCCTGGGTCCCAGGTGCGCGGCCGAAATCCTCAGGGAAAATCCCGAGGGGCCAACGGTCTAGGCCACAGGGCTGCTGGGCCCGGGCCTGGCTCA<br>GAGCGCATTCGGGCGGGGAGGCCGCACGCCGCACCCGGGCCTCTCCTCCGAGCCCGAGGCAGGCACTGAGCTCCGGGCCAGCCAGGTGCCTCCCGGCTGGTGCG<br>AGACCCCGGGCCTGCTGGGAGGCGTGGGCAGGGCAGGGCAGGGCTGAACCCCAGCGACTGAATCTCGAAGGCAGGAGGCCTCGGAGGTCATCGGCCCAGCTCGC<br>CTGAAACTGTCCCTGCTCGTGCCAGGGCGCGGGCAGAGGAGAAAGGACAGGGCGGAGCAAGCCCACTGCAGAACTGCGGTCGGTGGCTGCGAAGGGTCCGGGTC<br>ACCGCGCTCCCGGACGCCGGAAGCCGCGCTGGCGGGGCCGCGGGGAGGGAGGCTGGGTACCGGGGCCGTCCGGCCGGAGGAAGCGGCTCCGGCCGCGCTGTCCG<br>CGCTTGGGAGCCGCGTGCAGGGTTCAGCCGTGTTTCAGTTGCCCTCTGACCTGACCCCGGGCGCACAAAGGCCTCCCGGGTGCGCCGCCATGGCCCAGTCTTCC<br>AGTCGCTGCCAAATTAATGAGCCCACGTCAGGTTGGGTTTACAGCTCGGCCGGGAAGCAGCCGAGTGGAAAATGAGCTCGGGGCCGCTCCAGAGGCTCCCGCAC<br>AACTGCAGAGGCTGCCCGCG |
| 116 | chr5: 72767550-72767800 | TTTCCAAGACAGAAGGAGGGAACTAGGCGCCTTTTTTCCACTCCGCTGACCCCAACGTCTGGGCTGTGCGTTGTAACGCAGTTGGCGGGGCCTTCAGCTTGGGA<br>TGAGGGCGAAGGGGCTCGGGATGGGTGGGAAAGCAAGGACCGGGCAACAGGTGGGGAGGTGGCGGACTTTTGTCTCGGGGAAGGAAATCGGCTGTGCTGAAAGG<br>GCGGAAAGCAGTAGCGCACAGAACTAGTGTCTGCGGGGTCCC |
| 117 | NR2F1 | CCCTCCTGTGGCTGCTTGGGCAGACGCCTGTGGCCTGTCGGATGCGGCCCACATCGAGAGCCTGCAGGAGAAGTCGCAGTGCGCACTGGAGGAGTACGTGAGGA<br>GCCAGTACCCCAACCAGCCCAGCCGTTTTGGCAAACTGCTGCTGCGACTGCCCTCGCTGCGCACCGTGTCCTCCTCCGTCATCGAGCAGCTCTTCTTCGTCCGT<br>TTGGTAGGTAAAACCCCCATCGAAACTCTCATCCGCGATATG |

TABLE 4B-continued

| SEQ ID NO | GENE NAME | SEQUENCE |
|---|---|---|
| 118 | PCDHGA1 | TCCTCCTTTGTGTATGTCAACCCAGAGGATGGACGGATCTTTGCCCAGCGTACCTTTGACTATGAATTGCTGCAGATGCTGCAGATTGTGGTGGGGGTTCGAGA CTCCGGCTCTCCCCCATTGCATGCCAACACATCTCTGCATGTGTTTGTCCTAGACGAGAATGATAATGCCCCAGCTGTGCTGCACCCACGGCCAGACTGGGAAC ACTCAGCCCCCCAGCGTCTCCCTCGCTCTGCTCCTCCTGGCTCCTTGGTCACCAAGGTGACAGCCGTGGATGCTGATGCAGGCCACAATGCGTGGCTCTCCTAC TCACTGTTGCCACAGTCCACAGCCCCAGGACTGTTCCTCGTGTCTACACACACTGGTGAGGTGCGCACAGCCCGGGCCTTACTGGAGGATGACTCTGACACCCA GCAGGTGGTGGTCCTGGTGAGGGACAATGGTGACCCTTCACTCTCCTCCACAGCCACAGTGCTGCTGGTTCTGGAGGATGAGGACCCTGAGGAAATGCCCAAAT CCAGTGACTTCCTCATACACCCTCCTGAGCGTTCAGACCTTACCCTTTACCTCATTGTGGCTCTAGCGACCGTCAGTCTCTTATCCCTAGTCACCTTCACCTTT CTGTCAGCGAAGTGCCTTCAGGGAAACGCAGACGGGGACGGGGGTGGAGGGCAGTGCTGCAGGCGCCAGGACTCACCCTCCCCGGACTTCTATAAGCAGTCCAG CCCCAACCTGCAGGTGAGCTCGGACGGCACGCTCAAGTACATGGAGGTGACGCTGCGGCCCACAGACTCGCAGAGCCACTGCTACAGGACGTGCTTTTCACCGG CCTCGGACGGCAGTGACTTCACTTTTCTAAGACCCCTCAGCGTTCAGCAGCCCACAGCTCTGGCGCTGGAGCCTGACGCCATCCGGTCCCGCTCTAATACGCTG CGGGAGCGGAGCCAGGTGAGGGGCTCGGCGCCGCCCCGGGCGACCCCTGGGGGCGGCACTGGAGAAGCCGCCCGTCCTCATAAGGGATTGAACTTGCATCCACT CCTCTCCGGCCGGCTTGGTCGCTGGCTGCGCTCCACCCGATTCTCGGGATCATTGGACCGTTTGCGCGAAACCAGAGTGGCCGATTAAGGGATGGGGCTCCGAG CACCGGGGGTGGTGGCGACTGTGGGCGAGGGGAGGTGGGACCGACCCCCACCCCTACACTCAAAAAAGGCCGGGGCCTCCTTCGAGCTTCCGGTGAATTTCGGG CGATTTCCGCGGGTGTCGGGGGTCCCGGGAGGAGGCAGTCACAGATCCACCCCTGCAGCCAGCCTCCTAGGCGCCGGCTCCGGCACGCTTCGCCGGTCTGTAGA TTTCCTCTTCGATTTCTCCCCAGCTCCCAGCATCTGTGACTTCACTGTTACCCTCCCTATCCCCGCATCACCCAACCGCACCTGTCTGCGGGACTTAGGTGTGC GCGCGGGGCTCATGCGTGTCCTCCCTGCTGGCCACCCCCACGGCCCACACAAGTTGCACGGGCTCGCCACGCCCCGCCAACACGTGCGCGGACGCACGCACGCA CTCCTCGCACGTGGGCTTACGCGAATACCAGCTTTCACTGCCACTCGCTCGCGGCCAGATTCACAGGCCTGTTCCGGTCCACTCGCAGCTCCCCTCTGCCGCTC CCTCCGCCGGGCTCAGGAGTACTCGTAGCTGATTGTGCGCGCCTGAGGGTCCCAGATCGCGGCCGCCCAGGACCAGGCGAGGACTCCGGAGCCTCCTCTCACCT CTCCCACCTGCGCCCCGGGCTGGGCCGGGTCGCCTGGGGGGCGGCCTGAGCGAGGCGCGGGGCCAGGAGCGCTGGAGCGACTGCCGCTCTAAGTGCCGGGCGGG CAGGACTCTACGATCCTTGGGCCAGAGGTCCGGATGGTCCCGGGACTCCGTCTCAAGGGTCGGCGACCCCTCAACCCAGAAGCCTCGAGCAGGCGGACAGGCAG AGCTGCCCAGTGGCCGAGGCGCGG |
| 119 | chr6: 10489100-10490200 | ATTTGTCGTTGTGCCATTGCTGCCACTGTTGTTCTTGTCCAGGGAAACACCGGTGGCCAACCCAGATCGGATACAATGGTGCGGCTCTGGACTGAGCCTCCAAC CACATTAGCCATGGGCAGCATTGTTGCTGCCGCTGCTGTTATTTTAATTATGATTGTACGTTAACCACCACCTTCCTTCCTCTGCCTCCCTTCAGCTGCAATGA TGTATGTTACTTTTTGGTAACTGGATTTCATTAACATTTATGAACTCTCATAAAGTAGTAGAAAAAGCAATTTGTGTGGAAGAATTTTCCACCTCATTAAACAG TGTTCTTTTGGGGGTCAAGCTGATATTTTTTTTGTTGTTAGATTTTTTTTATAGGTCCTTTGTCCTTCCCTAAGCCCTGGGGGATGAAAGGAGAGCCGTCCACC CAGCGAGGGGCTTGTGTGCCCTAGAGGGCGCTGGGCCCCGCGCGCTTTCCTGGCTGTCCCCGCCGGCTTTCCACCCTCCCCAAAGCCCAGGTGCCCACCGTGGG TCGCTGCGGCCTTTCCCCTTCTTGGCCAAATCCGATTACTTCGCAGCCTGCAGATGGCATCGCCGGCTAAGGGCAGCCTGCGGCAGGTCCCCGAGCCTGAGCAC TCCTCCTATCTGGGGCCTGAGAGGACGCTCTGGGCTTTTTCCCAGGCCCAGGGTGCGCGGCCTGCTAGCGCCTTTCGAGGCACAGTCCCAAGATAGGCTCTTGT CCTTCGACGCCCCCTTGGCACAAGCGCACTGGCGCCCTCCGCTCAACCCACCTTGCCTTTGGGGCGGGCTTCAACCCTGGGAAGACAGGCCTGGGGGAAGCGAG AGGAGAGGCCCGAATAGAGGTTCCGGCTCAATCTTTCCCAGACGGAGGCCTGGTGTTTCCAGCTCAGTTGCATCTTCCAGCCGCGGGCTCCTGGCCCAAACAGA ATGTGTTTGCTTTCACACCGGGACGGCAAGCGGAGTCCGCCTCAGTGAGCAGCGAGCTGCGCAGTCCGGACGGGTGTCGCCCCCAGAGACTCGCCAGCCGCCCC CAGACACTCGCCAGCCGTCCCCATCTCTAATCCACCGTCCAGGCCCGGGCCCTGGGAAGA |
| 120 | FOXP4 | CCGTGTCTCCCTTAAGAACTGGGGCCTCATCTCCACTCCAGCTGCGCGTGCACGTGTGCTCCCGGCAGGACGCGCGCCCAGGAGCGCGCTGGGGGCTGCCCCGC CCCTCTCTCCCTCCCCCGCGGGTAAACTCCGGGCATCCATCAGTCTGTTAATTGCACTAATTAGAGATCGCAGAGGTGTTAATTGGAAAACCCTGGTATTGTGC CTGTTTGGGGGAAGAAAACGTCAATAAAAATTAATTGATGAGTTGGCAGGGCGGGCGGTGCGGGTTCGCGGCGAGGCGCAGGGTGTCATGGCAAATGTTACGGC TCAGATTAAGCGATTGTTAATTAAAAAGCGACGGTAATTAATACTCGCTACGCCATATGGGCCCGTGAAAAGGCACAAAAGGTTTCTCCGCATGTGGGGTTCCC CTTCTCTTTTCTCCTTCCACAAAAGCACCCCAGCCCGTGGGTCCCCCCTTTGGCCCCAAGGTAGGTGGAACTCGTCACTTCCGGCCAGGGAGGGGATGGGGCGG TCTCCGGCGAGTTCCAAGGGCGTCCCTCGTTGCGCACTCGCCCGCCCAGGTTCTTTGAAGAGCCAGGAGCCTCCGGGGAAGTGGGAGCCCCCAGCGGCCCGCAG ACTGCCTCAGAGCGGAAGAGGCAGCCGCGGCTTTGACCCAGCTTCCTTCCGACGGCATCTGCAGGAGCCTCTAGGCCTGACATAGGCTCCGAGGTGCCCTGGCT CCCCCACGGGGAATGCTGAGGGTTGGGCCACTAGGTCCTGCCTAAGTGCAGGACCTGAGCCTCAGACAAATC |
| 121 | chr7: 19118400-19118700 | GGGATTGCCGGCTTTGAGAAAATATGAAGAAACCGATTTCTCCTTCCACTTTGCCAGTGCACTTTCCTTCCACTTTCACTGGTGCTGGGGGCGGCGCACTCTTT ACGACATATAAGCGGAAAATTCTGCAAAAGTGGCCCCCGGGGATCCCCGCCCGACCCCTGTCTGTCGCTAATGTGGGCCTGTCTCCGGAAATTCGAGGTTGGGC CTTTGCCTGAATCTGTTGCTATTGCTCCCCTTGCTACCGCTGACACTTGGCACCGCCGCCTCCTAGCAGCGGCCAGACGCGGGGCTGGGGGC |

TABLE 4B-continued

| SEQ ID NO | GENE NAME | SEQUENCE |
|---|---|---|
| 122 | chr7: 27258000-27258400 | GTTGCGAGCGCGGCACAGGTTGCTGGTAGCTTCTGGACTCTGGAGGCTTGGCCTTCCTTCTAAGCCGATGGCGGGGAAAGAACCTCGTTTCCACAGCTTCCCCG<br>ACCCCCGCCGCTTGCCATTTGGGGACGGGAAGCGCGCCCGGGTCGCTTCACGTCCCTCTGGGCCGGAGCCCTTTCCATGGCTGGCTCCTCTGGGGGCCCTTGGG<br>CCTGTGAGCAGCGTCTACTTCCCTCAGAGAAGAATCCTTTCCTTCCCCCATCGAAGTGTCCCTTTCTGTATCCTGAAATAACCCCTCCTGGGTGAGGCCAGTTC<br>CCCTCTGTCGCCCTCCTCCCGCAGGCGTCCGGGAGCCTCGTGAGGACCCCGTGCAGTTGAGTCCAGGCGACAGGTGCCTCCCCAGGTG |
| 123 | TBX20 | CAGTGCGCCCCTTACCGGAGCACCCATGGCCTCCCGCGTTACCCCAAATTTTGTAGGCAGACTGTCAGAGTTCGAAGCCAGCTGTGTCCTCTGCGGGCCGTGTG<br>ACCCTAGGCTATCTGGGCTGCTCGGAGCCTTAGTTTCCCTAGTTGTGAAGAGGGAGGGTGTGACCATGGCCCGGAGCTCTCCGAAAGGCTGTGCGGATTGCTCG<br>GTGGCGGGATGTGGAGCGCGTCTTCTATGATGCCAGGTGCTGGCCAAGCGCTCGATGCAGGCTGCTCCAGTTAGGTCGATGCGATGGCGGGAAGCACTTTCCTC<br>TGCAATGGAGAGACGCCGACACCCCGAGCCCGAAGGCTTGCAAGGCGCGCTCTCGCCACTGGGGTCGGGGATCCGTGGGTTCTCTATCCCGCTTACCCACTCCA<br>TCCTTAGCAGCTGTCGTCGGTCCCAGACCTCTACCTTGGAGAGACCAAGGCGGCCCAGAGCCCAGGAGACTACTGCGCGGTACGCCAGGATCCAGAAGTGGATT<br>CTGACTTCTAAAGACCCCTCCCAAGCCAACGCTATCAGGGTCCCTGCAAGCGGTTGACTGTGGCGGAGGCAGAACCAAAACCTTTGCTCTGCCCGCGGCGCTCC<br>AGCCTCTCACCCAGGACAGTGCTCTGGGCTCCAGCCGCTGCAGTGGGGTCGGGACACAGACGCCGAGTTAGAAGCCCCGCCGCTGCAGGTCCCTGCTTGGTCGG<br>CGCGGTGACGGTGTCGCTGGCGGCGGCGGGGGCCTTCCTTTGGCTGCCCGGCCATTTAATCAGAGCTATTAT |
| 124 | AGBL3 | TTTAGTATTTAAGGAGAAAAGCCTCATTTTCCAGAATCGAATAAGCGAATTAATCGCACAATTGTGTAGAATGGAACTCAGTCTGTAAAAAAATCAAGACCAACG<br>TACTTTTTAATATTCTAACATCTCCAAGTAGTAGTTACAAGTATTGTACCCATGAAGTCCAGGTAATTAATTTGTTCAATGTCACACTGTTAAAAGTCAGGTGG<br>GCTCCAAAGCACAGTCCTAACCAGCATGCTCTACTGCCTCCTCTGAGGCAACAGCCGAAGTGCAGACCACTGGGAATAAATAGCTGCCCGGTCTTCCCCACTCC<br>TAAATTCTCCCGACAGACCCCAAAGCCTCTCTGAGAGCCTCTCTGACCGCCCTGCGGCCCACCCCGAGTTCCCGGCATCCTCTGGGATCCCTCTTCCTGGAGCC<br>AAAACCTACGCAGGCTCCTTTCCTCCGAGCTGGTTGCTAGGTGATCTCCGAAGGCTGTCCGAAGTCTCGCGAGGGCGGACCCGTTGCCTGATGACGAGAGTTGG<br>GAGTGTGGCTGGGGCTGCGGATCTCCAGCAGTGGCGTTACTTCTAGCGGCTGGATACCGGGTTCTCCGCGAGATCGCGAGATCCCGAGATATTCTCCCCGCACG<br>GAAGCGACGACTGGCCTGGCCAGAGGACTCGCGTGGGAGCGAGGTGCCGGCCCCGACAGGACGGTGAGGTATGCAGAAGTAAGGCGGGGCGCCCCCTGCGGGAA<br>GCGAGCGCGCCCCGGAAAATGAGCGCCTCCCCACACCAAGGTGTCCAGGAGTGAGTGCGGGAAGGAACTCGGCCGCCCGGAGTTGTGGCCTCATCGTGCTTCCC<br>GCCAAAAACGCCTTGGTACTGTCGGGACGCGGCTAAGCGTGGACGCGCCCGCATCTGCCCCTCCTCCGCAGTGGTGGAAGACACCCGCGGAGCGCCGGTGGATA<br>AGGGCCGTTTCCTGAGACCAGAGCTGTATCCGCAGCAGGTCAGCACTTCGTGCGCCCTGTGTGC |
| 125 | XPO7 | AGCGGCGCTGTTCCCGGGCTGGGTGCAGCTGCTAAGGACAAGGCCCCTGCTCCGAAGAACGCGGTGGCTCGGGGATACCCTGAAAGGGACGGCCATGGCGCACA<br>TGGGATGCCCTAGGGTTCGTGGGAGGGCATGCAGGCGCAGCCCCCGCAGGGGTTGGCCTGCCAGAGAAGGCAGGGGAGAGCACTCGGGGCTGCACAAATGGTGT<br>GGCCGGAGGGAAGGTGCAGCCTTGTGTGTGTCTGGATGAGGGCTGGGCATAGGAGCTTGGTATTTGATCCTGAAAGCTCTGCGTTTCCAAAG |
| 126 | chr8: 41543400-41544000 | GAGTCATACTTGTAGTCACATCCTTTTCCTTTCTCCAACCCACTGGTTAATCATGAAAGGCTCTTCTGATTGGCTGCCTCCTGGCAGTAGTGCCTCAGCGCGAC<br>GGTTCGGGAGCAAATAAATAATTCCCGCTGGGAAGCTGTTTCTCAGACAGGAGCAGCGACACCCCTGCCACGCCTGCCGCCTGGAGTTGAGTGGGGTAAGCACG<br>CCGGCCTCCAGGAATCGACGGTGCCACGTGGTTCTTCTTGCACTTCTCTTCTTCTCCAGTTTCAGGGGACACCGTGGGGTGTGCGAGCCCGGGGGAGCGCAGGG<br>AAGGGCGGGTTGGGCTGCAGGTGGGAATGTGCGGTCCTTCTGCGCCCTCAACAGAGCTTCCTTCCTTTTTGCCAAGGTCCCCGTGCCGCCTTCAGCGCGCCTCC<br>TTATGCACCTCTACCTCTGCTGCAGCGTACCTCTTCCGCAGCCCTAGCGGCCTCCCCGAGGGGCGCCGCGGCCTCGGCTGTCCCTCCCCTGCCTGGCACGACCA<br>CCTGACCCCCAGCGACCCAAGAAGCAAGTTGTGTTTGCAGACGCAAAGGGGCTGTCGTTGGTATCGGTGCACTGGTTTGA |
| 127 | GDF6 | ACACTTTCTGTGTGGGAGGGCACAAGACATGGGCTATGACATGGCCAGAGACCCCACCTTCTTTACACATGTAAAAACCAACCAAATCAAGATGCGTCAACGGT<br>GATTCTTCCTCCCACATTGTTTCCCTTTTTAAACTGTTATTTTTTCAATCCATGGAGCAGTTGAGAAACGGGTATGCATCTCTCCTCCCCTCCCCTTCTATCAA<br>AGCCTGTAAGACACATAAGGAAATCCAAAGCCACAGTAATAGAGAGAGAGAGAGAGAGAGAGAGAGAGAGAGAGAGAGAGAGAGAGAAAACAGAACAAAAGAAA<br>TCCTCCTTGGCTTGTTTTTCCAGGGTGGCCAGGCAAGGTGTGAAAATCCATATTTCCCTCTGGGCTGGCAGGTAGAAGTTACTGGGAAGGCTGCGCTCCCTTCT<br>CTCCCACCGGCTCTCACATCCAGGCTGTTCCCTCACCCTCAGCCTCCCCCAGCGCCAGCTTCCTCCTCCGCCTCTCTGCAGCCAGGCCTCCCCTGCAAGGCGGA<br>CCTTGGCCCACCTTGGTTCCGGGCCAAGGCGGCGGGAAAGGCACCGCTACCTGCAGCCGCACGACTCCACCACCATGTCCTCGTACTGCTTGTAGACCACATTA<br>TTGCCCGCGTCGATGTATAGAATGCTGATGGGAGTCAATTTGGTGGGCACGCAGCAGCTGGGCGGGGTGGAGCCGGGGTCCATGGAGTTCATCAGCGTCTGGAT<br>GATGGCGTGGTTGGTGGGCTCCAGGTGCGAGCGCAGCGGGAAGTCGCATACACCCTCGCAGTGATAGGCCTCGTACTCCAGGGGCGCGATAATCCAGTCGTCCC<br>AGCCCAGCTCCTTGAAGTTCACGTGCAGGGGCTTCTTGCTGCAGCGTAGCCTGGACTTCTTGCCGTGCCGCTTGCCATGGCGACTGGCGAAGGCCGTGCGCCGC<br>CGCCGGCGGCCGGGCGAGGGCAGCCAAGGCCTGGCATCCGGGGCGCCCGACGGCGGCGGCCACGACCCCTCGGCGCCCGCGCCCGGGCCCGCAGCCTCGGCCGA<br>GCCCAGCTGCTCGCGCATCTCTGCGAACAGGTTCTTGCGCTGGGATCTGGTGAATACCACCAGCAGGGCCCGCTCCTGGGGAGGCCGCACCCTCCGGCCGAAGC<br>CCAGACTCCGCAGGTCCGGGGGCGGCGGTTGCTGGGGTCCCCGCGCGCGCGCCTCGGCCTCCCCGGCGTCCAGCTCGCCCCATGCGGCCCGCAGCTCCAAGCAC<br>AGCTGCTTCCAGGGCTGGTGGCGCAGGCCCTGCCACACGTCGAAGACTTCCCAGCCGGCCGGCGGCGCCCCCTGCGGGTCCAGGGTCCGCGCGTCCAGCAGTAG |

TABLE 4B-continued

| SEQ ID NO | GENE NAME | SEQUENCE |
| --- | --- | --- |
| | | GGGCGAAAGGCAAGGGAAGAGCTGCACGTGGAGCGGCCCGGCTGGTGGCCCCCAGGGCGCTGAGGGCGCCTGGCGAAAGAGCCGCAGCTCCGCGCCCACCAGCT CTTCTTTGTCTGAGAGCATGGACACATCAAACAAATACTTCTGTCTCCGGAGAGGAGTGTGCGAGAGATCGTCTGCGAGATAAAAAATAATTACAGTCAGTTTC ACTTAAGGGGGAGATCAGCCCGGTGCTCTTCGGCCGCCCCGGGAGGAAAAGGGCGGGGAGTGGGGGCAGGTCGGCCGGGCAGTCCAGCTTGCCCGGCCCAGGGC CTGACCACCCCGGCTCCCCATCTGGCTGGTGCATGG |
| 128 | OSR2 | GCCCGCTGTGAATGTAGGTGAGGTGATCCCGGGAACCTGGGTCTGAAATCAGACCTGTGTTGCCATTGGGAGCACGGAGAGAGGGGAAGCGCCCTGCTTAGGCC CAGGCCGGGCGTCCTGGTGGTGGGACCGCAGCCGCACTCACCTCCAGGCCAACGGACAAGGTTCCTGCAAGCCAGCAGGGCCACTCTGTGCTTGGCCTACTGCA GCTCCCCTGCAGCTCCTTTCCTCTCCCTCCCCGGAGCGCTCTCCTCTCTCCTCTCCCCTCTCTTCTCTCTCCTCTCTCGTCTCCTGGGGCATCCCGGGTGGAGG GATGTAGGGGTCGCTCCTCGGTGCCAGGCCGGGAAGCAGCTCAGGCCTCCCAAGAGCTTGGCGCTCAGTCTGGGAAAAGGGGTTCCTCTGGCCTCAGGGACGTT CTCCGCCCCCACCCCACCCCCTGGGAGCCTGAACCATCTGGAAGGGATCTTAGTCGGGGGTTGGGAGGAGAGCCCGTGGATAGGAGGAGGGGGCGATTCTAGGC CGAATCCAGCCCCTGAGGTGTCACTTTTCTTTCCTGCGGCCCGTCACCGCTGATAGATGGGGCTGAGGGCAGAGGAAGGAAAAAGAAAACCTCCGAGGTCAGTG CGGGGCGAGGTGAGCCCCTCCCAGGGCCCTCTGGCCCAGGAGGATGAAGCGCGCCGGCTTCGCTCTTGCACGCCGGCTTGCCATCCGGGTAAGCGCGGGAAAGG CGGCCACAGGGCGCGGCGGCAGCGCAGCGCGTGGGATCTCACGACCCATCCGTTAACCCACCGTTCCCAGGAGCTCCGAGGCGCAGCGGCGACAGAGGTTCGCC CCGGCCTGCTAGCATTGGCATTGCGGTTGACTGAGCTTCGCCTAACAGGCTTGGGGAGGGTGGGCTGGGCTGGGCTGGGCTGGGCTGGGTGCTGCCCGGCTGTC CGCCTTTCGTTTTCCTGGGACCGAGGAGTCTTCCGCTCCGTATCTGCCTAGAGTCTGAATCCGACTTTCTTTCCTTTGGGCACGCGCTCGCCAGTGGAGCACTT CTTGTTCTGGCCCCGGGCTGATCTGCACGCGGACTTGAGCAGGTGCCAAGGTGCCACGCAGTCCCCTCACGGCTTTCGGGGGGTCTTGGAGTCGGGTGGGGAGG GAGACTTAGGTGTGGTAACCTGCGCAGGTGCCAAAGGGCAGAAGGAGCAGCCTTGGATTATAGTCACGGTCTCTCCCTCTCTTCCCTGCCATTTTTAGGGCTTT CTCTACGTGCTGTTGTCTCACTGGGTTTTTGTCGGAGCCCCACGCCCTCCGGCCTCTGATTCCTGGAAGAAAGGGTTGGTCCCCTCAGCACCCCCAGCATCCCG GAAAATGGGGAGCAAGGCTCTGCCAGCGCCCATCCCGCTCCACCCGTCGCTGCAGCTCACCAATTACTCCTTCCTGCAGGCCGTGAACACCTTCCCGGCCACGG TGGACCACCTGCAGGGCCTGTACGGTCTCAGCGCGGTACAGACCATGCACATGAACCACTGGACGCTGGGGTATCCCAATGTGCACGAGATCACCCGCTCCACC ATCACGGAGATGGCGGCGGCGCAGGGCCTCGTGGACGCGCGCTTCCCCTTCCCGGCCCTGCCTTTTACCACCCACCTATTCCACCCCAAGCAGGGGGCCATTGC CCACGTCCTCCCAGCCCTGCACAAGGACCGGCCCCGTTTTGACTTTGCCAATTTGGCGGTGGCTGCCACGCAAGAGGATCCGCCTAAGATGGGAGACCTGAGCA AGCTGAGCCCAGGACTGGGTAGCCCCATCTCGGGCCTCAGTAAATTGACTCCGGACAGAAAGCCCTCTCGAGGAAGGTTGCCCTCCAAAACGAAAAAAGAGTTT ATCTGCAAGTTTTGCGGCAGACACTTTACCAAATCCTACAATTTGCTCATCCATGAGAGGACCCACACGGACGAGAGGCCGTACACGTGTGACATCTGCCACAA GGCCTTCCGGAGGCAAGATCACCT |
| 129 | GLIS3 | CACTCCCCCGCCGCCTCCGCCCCTAACCCTCGGCCCCGTGCGCGAGCGAGCGAGGGAGCGAACGCAGCGCAACAAAACAAACTAGTGCCGGCTTCCTGTTGTGC AACTCGCTCCTGAGTGAGTCGGGGGCCGAAAGGGTGCTGCGGCTGGGAAGCCCGGGCGCCGGGGACCTGCGCGCGCTGCCCGGCCTGGCCGGAGCCTGTAGCCC GGGGGCGCCACGGCCGGGCTCGCAGTCCCCCCACGCCGGCCCCCCGGTCCCCGCCGAGCCAGTGTCCTCACCCTGTGGTTTCCTTTCGCTTCTCGCCTCCCAAA CACCTCCAGCAAGTCGGAGGGCGCGAACGCGGAGCCAGAAACCCTTCCCCAAAGTTTCTCCCGCCAGGTACCTAATTGAATCATCCATAGGATGACAAATCAGC CAGGGCCAAGATTTCCAGACACTTGAGTGACTTCCCGGTCCCCGAGGTGACTTGTCAGCTCCAGTGAGTAACTTGGAACTGTCGCTCGGGGCAAGGTGTGTGTC TAGGAGAGAGCCGGCGGCTCACTCACGCTTTCCAGAGAGCGACCCGGGCCGACTTCAAAATACACACAGGGTCATTTATAGGGACTGGAGCCGCGCGCAGGACA ACGTCTCCGAGACTGAGACATTTTCCAAACAGTGCTGACATTTTGTCGGGCCCCATAAAAAATGTAAACGCGAGGTGACGAACCCGGCGGGGAGGGTTCGTGTC TGGCTGTGTCTGCGTCCTGGCGGCGTGGGAGGTTATAGTTCCAGACCTGGCGGCTGCGGATCGCCGGGCCGGTACCCGCGAGGAGTGTAGGTACCCTCAGCCCG ACCACCTCCCGCAATCATGGGGACACCGGCTTGGATGAGACACAGGCGTGGAAAACAGCCTTCGTGAAACTCCACAAACACGTGGAACTTGAAAAGACAACTAC AGCCCCGCGTGTGCGCGAGAGACCTCACGTCACCCCATCAGTTCCCACTTCGCCAAAGTTTCCCTTCAGTGGGGACTCCAGAGTGGTGCGCCCCATGCCCGTGC GTCCTGTAACGTGCCCTGATTGTGTACCCCTCTGCCCGCTCTACTTGAAATGAAAACACAAAAACTGTTCCGAATTAGCGCAACTTTAAAGCCCCGTTATCTGT CTTCTACACTGGGCGCTCTTAGGCCACTGACAGAAACATGGTTTGAACCCTAATTGTTGCTATCAGTCTCAGTCAGCGCAGGTCTCTCAGTGACCTGTGACGCC GGGAGTTGAGGTGCGCGTATCCTTAAACCCGCGCGAACGCCACCGGCTCAGCGTAGAAAACTATTTGTAATCCCTAGTTTGCGTCTCTGAGCTTTAACTCCCCC ACACTCTCAAGCGCCCGGTTTCTCCTCGTCTCTCGCCTGCGAGCAAAGTTCCTATGGCATCCACTTACCAGGTAACCGGGATTTCCACAACAAAGCCCGGCGTG CGGGTCCCTTCCCCCGGCCGGCCAGCGCGAGTGACAGCGGGCGGCCGGCGCTGGCGAGGAGTAACTTGGGGCTCCAGCCCTTCAGAGCGCTCCGCGGGCTGTGC CTCCTTCGGAAATGAAAACCCCCATCCAAACGGGGGGACGGAGCGCGGAAACCCGGCCCAAGTGCCGTGTGTGCGCGCGCGTCTGCGAGGGCAGCGGCGGCAGG GGGAGGAGGAGGCAGAGGCGGGGTGGCTGGACCCTCGGCATCAGCTCATTCTCCCCTGCTACACACATACACACACAAATAATGTTTCTAAAAAGTTCAGTTGC GACTTTGTGCCTCGCCTGTCCTGTTCATCCTCGTCCTGGGCCGGGGAATGCTTCTGGGGGCCGACCCCGGGATGCTGGCTAATTGCTGCCGGCGGGTTCCGTCG CCGGTGTGACCCTGGACGGCGCGGACGGCGTACAGGGGGTCCCGGGAGGGGCAGTGGCCGCGGCACTCGCCGCCGGTGCCCGTGCGCGCCGCGCTCTGGGCTGC CCGGGCGGCGCAGTGTGGACGCGG |
| 130 | NOTCH1 | CTGAAAAGCCGTCAGGGAAACCACACATGTTCAACCCCTGGCGGCTCCCCCAAACCTCTCATTTCCAGTAACTGTGTGTTTCCGCTCGTCAACAGCTGAAACCG AGCGGAACTTGGGGGGCCCCACCACGCGGCCCTGCTGTGCGGCACGGGGCTCATCTGTCCCCCGGCTGCGGGGAGTCAGCTCTCACCGCCCACCTCCTTCCCAG ATAGTCTCTGTGCCCACTCGACGGCCCGGCAAGCCCAGCCCCTGCCTGCCACGGCCACAGCAGCCTCAGAGAGCTGCCCTCTCTGGCCAGGGTCAGGGCCTGAG |

TABLE 4B-continued

| SEQ ID NO | GENE NAME | SEQUENCE |
|---|---|---|
| | | CTGCTGCCTCCCGCAGGGTCGAGGGCAGGACACTTGTCTGAGGCTTGGGTGGGGCAATGGCACCTCCTCAGGGCCTCAGCCCCCGGGCAGGCTCGGTGACCATG GGCCTACAGCAGGGAAAATTCTGGGCCAAAAGCTCCAGCCTCCTACTAGGGCATCTGTCTGCAAATGCACCTTAACCTGACCGCTTGGGCTGTGGGGGAGCCTG TTTCAGGGAAAGTGAGGGACGCGCCAGTTTCCTCCTTTGGACTTGATGAGGCACGAACGCATCTCTAATAAAGCCAGGTCTCCCCGCCGTGGCTCCCTGGGCGG GTGCCTGTGGCTCGGGCCATGAGTCACGCTGGGTAACCCCACTACGGGGAAGAGGGCAGGAAGCTGGGAGCCACCGCCTCTGTGCCCGGTTGTCATCTCGGCAC GAGGGCGACCGTCGGCTTCGTCCTGCCCTCATGGCTGAGGGCTTTTGGGATGTGGCGGGAGACGGGGGAGTC |
| 131 | EGFL7 | AAATCATCAGAATGGCTAAAATGAAAAAGACAGACAACAGCAAGTGCTGACAAGGGTGTGGGGCGGCCAAATGCTCCTGCACTGCTGGCAGGGGACCTGAGAAC TGCAGGGCATTCCCTGGCTTCCTGCCCCTCCTGGGACTGGGGACCCCCCAGGGACAGCCTAAGGGAACTGCATTTATCTTCACGTCTGCCAAAAGATAACACGA AGATGTTCAAAGCTAAGCCCCCAGGCTGGTAAGAGCTCCAAGGCACCAGCAGTGTGTGCAGAACTGGGGGGAGTCTGTTCTCCCAGGGATGCTCCCATCACCTG CTGCCAGCAGTGGGGCATGCCGGTCCCCTGGGGTGTGGCCAAGGGGCTGTGTCTCCTGCCCGGGCTGCCGGCCCCTCTCAGGTTCACTTTCCCATCTCTAAGCC CACGTCTCGCTGCAGTTCAAGTTTGCCAGGCCACCAACGGGTGACACGCCCGGCGCAGTGGGGGACTCCGCACTTTCTGCGCAC |
| 132 | CELF2 | ACCCTTTGTGCCTGGGTCCCATAAACAATGTGCTTTTTAAAGGGGAGCCCCCTCCCAGCTCCGGCCTTTTTCTCCAGCGTGGGCAGCCAATCAGCTGCGCAGAG CTGCATAGCTGGACCGCTTTCCATTCTGAGTAGCAACAACGTACTAATTTGATGCACACATGGATGCCTCGCGCACTCTGCAAATTCATCACCCGCATCTTGCA TTAGTCATCTGACGGACTGCCAAGTGTTTCATTTTCTTTCCATGTGACTTTATTATTACCACCTCTCTCCTCTCTTCCAAAAACCTCCCAAAAAGGGCGGTGGG GCGGGGGGCGGGGCAGGGAGAGGGAGAGAAATCCAGCAGACATCTAGCTCTGCCTTTCTTTCCCAGCCACAGCCAGGGTAGGGCTGATAAGGCGCTGATGCGTT GATGGCAGCCTTGCAGAGCTAGACCTGCACTTAACTTGCAGCTGCCTCCCGAGCCTCCAAGATGTCCACGCCCTGGGTGACAGGCGGCAGGGCGCTGCCCCGTG CTCCCCCGGCTCTGCTCGACAGCAGCACGCAGTGAGAGCCTCGCCGCCGCCGAGGAGCAACTCATGGTGCCTCCGCTTTGTTTTAGTTCATCAAATTTCTACGA CTCATTAGGCACTTTGCCACTGCTCTTCTTCCTCCTCCTTCCGCCTCCCCGCTCCCCCACCCCCACTATTTTTTCTTCCTGTCCCTCATCGTGCCGCCCTAACT CTGGCTCCCGGTTCCGTTTTTGACAGTAACGGCACAGCCAACAAGATGAACGGAGCTTTGGATCACTCAGACCAACCAGACCCAGATGCCATTAAGATGTTTGT CGGACAGATCCCCCGGTCATGGTCGGAAAAGGAGCTGAAAGAACTTTTTGAGCCTTACGGAGCCGTCTACCAGATCAACGTCCTCCGGGACCGGAGTCAGAACC CTCCGCAGAGTAAAGGTACAGAGCGCGGGGCGGGGGTCGCCAGGCGTCCAGGTGGGCGTCGCGGGGCACTGGGGCTGTCCGAGCCCCCAGCCTGCAGGAGGAAG GGCGGGTAGGCAGGAGGGCTGGAAGCAGCCGGTGCTGGCGGCCCCTGTGCTCCAGGGGCTGCTCCCGACTCCTCCCCGCACCCCCGCCCGCCTGCCCGCCGGGA CAGGTTGGAGGCGGGAGAGAGGGACCGAGGCAGGGCGGGAGCGCAGAGGCTCGGTC |
| 133 | HHEX | TAACAAATAAGCCGCCCGTGGTCCGCGCTGTGGGTGACCCTTGGCGCCTTCGAGGTCTGGAGCCCTAGGGTAAATAAGGAAACGGGGCGCCTCTAGAGTTTTAA ATGAACTCTGTTATTGGAAGCTTCAGTAGGGACCCTGAAAACAATTAACGTCTTAATTAGCATTTTAATGTCTCCATTATTACGGCGCGGGCTCTAGCTCAGCC CTTTACCTTACCTTCTCACCGTTAACAGGGGAGGGGGATTGTATTTTTAGTTCATCTTTTTATGTTTTTGAGTTGTTATCCTGTCTGTCTGATTCCAGCCTCGA GGGTTTGATGATGCGGCCCGAGCCTGGCTGTGGTCGCCTGTCGGGGCTGGAGCGGGACCCTCAGCCGGGCCGGGCCTGGGGGCTAACGTTTTCACAGTGCGCCC TGAGTTTCCTTGGGTTACTGCTGGGACCGCGCAGGAGGAAGCAAAGAGTTTTTCGAGCTAGACCAACAGGAAACACATTGACGGAAATGTTGCCATAGCCCATG GGGTGGCTTTAACTGGCCGCCCCCGCGGGCTGGGTGTGAAATCAGAGGAGGCCGCGGCTCCCCCGGCCAGGATTGGAGGCTCCTCGCGCAACCTAATGCGGGTG TCCGGGCCCGAGCGCTTCCCGCGCAGCCAGGCCTTGTCGGTGCAGCAGCCCCGCTCCTCCCCAACACGCACACACCCGGTGTTCGCAAGTGCGGCTCACCAAGG GAGATCCAAGGGGGCAAAAAGTTATGTATAAATCCGAGAGCCACTGGGGAAAGAGGGTCGTGGTATTGTAAG |
| 134 | DOCK1/ FAM196A | CTACCCTGTGCTATCCTGAGCTGTAGTCTTCTGAAATGATCGTTTGGCTTCCCAGCCAAGGCAGGGCTCCCCCAAAGTTCATTCCCACTCTTGCAGTTTCACCT CGGGATGCTTCCGCAGAATTTCAGCGCCTAAGCAGACAAGGTCAAAGTAAACCGCTTCACCGCTGCTTCTGGCGCAGGGGCCCAGAGCGCGTGCAGCTCCCCAG CACAGACCAACAGCAGGAGAGGGGTCCGGGCGGGAGCCCTGGGCTGTAGATAAGCAAAACGCACCCATTTTCTCTCCTATTTACTCCAGAGGCACCTCTCCTCC CCCACTCCTGGCATCTCTTTATCACTGGCTCCCTCTCCCTGTGGCATATTTTTGGGTAGTAGAATGCTGAGGTCACAGGGAGCGGCTCTTTATCCAAGCAGTGG GGACATCAGCCTGGAGCCCTGAGCATGAACCAGCAAGATGCAGACTCTCGCTCTTGACTTTGGGCTCCAGGAGCTGCCCCGACC |
| 135 | PAX6 | CAGTGCTCCGCTCCGGGAAATTGCATCGTCACGACAAACGGGACCGTGATAAAACGACCCTTTCCGTCCTTATTTGTAGATCACTCAGACGAGATTGAACTGCA CTTGTTTCCCCTTCGAGGGGAGCCGCGTTTTCAGGGTAGCCGAAGGCTTGGGGCTGAGGGGGGGCCCTCACCAAGGCGCGGGTGGGGGCCGGAGCCTCAACTCG ATGAGAAGTGACAGGCGTTTGGGGGATCTGGGCTCCGGCCGGGACCAGCGCAAGCAGGGACTTTGCGGGGACACCGCTTCTCCAACAGAGCAAGGCCTGGCCCA CGTTTCCGGTTTCTCCTAACTTCCTTTTATTGCCTTCCTTTGCTTCGCAAGTTCCATCTACCCCTCCAGCTACAGAGCCCCACCTCTAGGCACAGGAAGCTTCC CGGAAAAAGAAAGGCTGTCCCAGAAAGAGACCGAGAGAGACTTTCCAAACTTCGGGCATAGCCACGGCAATTCCCAGTCTGCTAATGCCAAGGCGGGCGCGTAA GGCCGCCTAAATCTAGACCTCCCTCCTCACTCATTTCAAAAAATAACAACGTGCCAGCCACCTCCGCAGATACCGCCGGCTGGTGCTTGCCCAGGAGACGCCAG GGCCAGAGCGCCACTCCCAGCATCGAAATGGCAGAGAGAAAGCGCAGCTCCAAATTCCCCTTCAGAGGTTAAGCCTCAATCATTGTGTCCCTTCCCTAGGGACT GCTGGCGCTCTCGCCCACTGGCGATGATTATGCGCCTAGAACTCGACCGCGAAGCAACTAATAGGAAAACATATGGTGTCAATTTGGATGCTCCGCGCCTCGCG CACACCCGGGAACGAGCGGCACAAAGCCCTGCCGGCCGGCCCGCGACCCCGCGCCCCTCGGGGCCTGCCAGCCGGGCCGCAGCGACAAACGCTCAGGGCTGCGC |

TABLE 4B-continued

| SEQ ID NO | GENE NAME | SEQUENCE |
| --- | --- | --- |
| | | GCCCTGGCTGGGGCCCGCCCGAGAGACAGCCTGCGGCTGGGGAGTCTGAGCTCCAAGGGGAGAGCCCAGCCGCCGAAGGCGAGCCTACCGGCCAAGCCCTGGGGTCCGGCAGGTTCTGCACAACTACTCCCGCAAAGCTCGCCACCTTTGTGCCCTTTCCTCAG |
| 136 | FERMT3 | GGGCCCTCGCGGCTCAAGCGCCAGCGCTGGAGAGAGAGTCTGAGGGTACCACGGGCGTGCTGGCCTGGGTGCTCACTCCCGCCCTCCTTCATGAGCGGCTTTCCTCTGGGTGTGTCCAGGGCATCACAGAGCTCTTCTGCCCAAACCCGGAGGCCTACCAGGGCCTGCCCACCTTGCCTCCTTCCACACTCTCTGTAGCAGCAGCCGCAGCCATGGCGGGGATGAAGACAGCCTCCGGGGACTACATCGACTCGTCATGGGAGCTGCGGGTGTTTGTGGGAGAGGAGGACCCAGAGGCCGAGTCGGTCACCCTGCGGGTCACTGGGGAGTCGCACATCGGCGGGGTGCTCCTGAAGATTGTGGAGCAGATCAGTGAGTGTCCGCTGCCCGCTTGCTGAACTCGGCACCATGGGCGGCCGCCACGGGTGTCTCTGGGCACTTCCGGGCCATCCCTGCTGCTCAGCTCCCGATAATGGTGTCACGGTGACTCAGGCATTAGC |
| 137 | PKNOX2 | TGTTTACGGAATCGGGATCGAGGGGCCGATAAGTAGTTTACACGCCGGCCAGAGCAGAGGGCTGGAGGTCGGAGTTGGGGGCTGGAGGAACGGGTGGCGTTTTTAGGATTCAGTAACAGGATCACAGCTTTTTCTTGTGGTGGAAGCTATTGGAATTTGGGGAGGGTAGCACGAGGGGTCCTGCAGCTCCGCGTGTGAAAAAGCGTTTAGGTAGGCGATGAAAGTAGTTGATCTGAGCCATGGCAGGCGAGCCCCGAATTTTTGCTGCTTCCCCCTGAAAGTGTTTCTTTAGGAGGAGAGGACTTGGGCCACACAGGACCCGGTCCTAAGAGAGCGATTCCGGGAAGCGGACAGATCGAAGAGACCTTCTGGGCGAAGCGGCAGGGCAGCCTCGCGGGGCTGGGAGTGGATCTGAGGTCCCGACCCAGGCGGCTCGGAGTGCTCCAGGAGCCACCTGGGTCTGCGGGCGCAGCGCGGCGGGGCGGGAGCGGTGGCCCGCAGGGGCCGCGGCCTGCGATGAAGGCCGGGGGGCAGCGCTAGCAGCGAGGTGCCACAGTGGGCCGAGGAGTCTGGGCTGTGGCCCAGGGTAGGACCGGCTCA |
| 138 | KIRREL3 | ACCTAAACCAAGCTCTCCCTCCCTGCCGTCTCCTTCCCTGGCCTGGGTCTGAAGGAGAGGAGGTGCCCAGAAGTTCAGAGCGGCATAACCACAGAGATACTACCTAATTAACATACCAGAAGCATAAAGAACTCATTTGCATTGGAGAGT |
| 139 | BCAT1 | ATAACTACGGGGGTGGGGGTGGGGAAGGAAGAGATCCAAGGAGGCAGAAGGCTGCGGTCAAAATATTTTGGGGTGGCAGAGTCACGTAGGATGTGGCTGTGGGTTCTGGCAGCCCAGAGATTCAGCTCCCGCCTCCTCCCTCAGAGCGAGTCCATAGCTACCCTCACGTCCCCCGTGGCGGTCCTCGCCACGCTCCGGAGCGGGTTACCCATGAGGGTGCTAGACCTGGGCAGCGGGAACCTCGAAGAGGTGGAGATTGCAGGCTGGGACTCCAGATTTCGGGCAGGGATGCGGGGAAGGGAAGACGCCTCGCTGGAGGCGGAATGGAGGGCAAGGCGAAGGAGGATGGTGCAGGAAACGGCGACAAGGCGCCCGGCCAGGCCCGCGAGCTACCGAGACCCGGGTTCCAATCCTCCCCCCTTCCGCAAACGCCCGGGTTCGAGGTACCTGGCGGGCAAGGGCCGCAGCGGAGCGAAGCGGGCTGGCCATGGGGAGGCTGCGGGGACGCGGGGCTGCAGAGAGCGGCAGTGGCACGGAGCGCGCGGCTGGAAGCGAAAGCAGGCGGTGTGGCCAAGCCCCGGCGCACGGCCCATAGGGCGCTGGGTACCACGACCTGGGGCCGCGCGCCAGGGCCAGGCGCAGGGTACGACGCAACCCCTCCAGCATCCCTTGGGGAGGAGCCTCCAACCGTCTCGTCCCAGTCTGTCTGCAGTCGCTAAAACCGAAGCGGTTGTCCCTGTCACCGGGGTCGCTTGCGGAGGCCCGAGAATGCGCGCCACGAACGAGCGCCTTTCCAAGCGCAGATATTTCGCGAGCATCCTTGTTTATTAAACAACCTCTAGGTGAATGGCCGGGAAGCGCCCCTCGGTCAAGGCTAAGGAAACCTCGGAGAAACTACAT |
| 140 | HOXC13 | CAGTCCAGCCGCTTGCCTCACTTCTTCCCGCTTGCCTTATCTCCCCGCAGACGTGGTTCCCCTGCAGCCCGAGGTGAGCAGCTACCGGCGCGGGCGCAAGAAACGCGTGCCCTACACTAAGGTGCAGCTGAAGGAGCTAGAGAAGGAATACGCGGCTAGCAAGTTCATCACCAAAGAGAAGCGCCGGCGCATCTCCGCCACCACGAACCTCTCTGAGCGCCAGGTAACCATCTGGTTCCAGAACCGGCGGGTCAAAGAGAAGAAGGTGGTCAGCAAATCGAAAGCGCCTCATCTCCACTCCACCTGACCACCCACCCGCTGCTTGCCCCATCTATTTATGTCTCCGCTTTGTACCATAACCGAACCCACGGAAAGACGCTGCGCGGGTGCAGAAGAGTATTTAATGTTAAGGAAAGAGAAGAACCGCGCCGCCCGGAGGCAGAGAGGCTCCATGGCCGTGCTGCTGGGCCATCCCCAACTCCCTATCCCATCCCCAGCCTCCACCCCCATCCAGATGGGACTCACGTGGCTTCAACAGCTTTGGAAATGGGTCCCGAGTGGGCCGTGCGAGGAAGGCTGTCGACCTCTACTCCTCCTTGC |
| 141 | TBX5 | CAAGATCGACTTTCTTAGGAAGGGGGAGAGGAGGGAACTCTTCACGAAGGGAGGTGGGAGTCCACCTCAGACCTCTATTGGAAGGAAATCGAGTTGTTCCGGGGGACTGAGGTCTCTTGCATAAGGCATGGGATCCTTATTATTATTATTATTATTTTTAAATCCCCCGCGGAGGAGCTCTGGGCAAATGAATACCGAGGCGCCGCTCTAGCTGGTTAGGCTTGGGATGCGATAACTCAGTGCCCTCTTGCAGACTTGCATAGAAATAATTACTGGGTTGTCGTGGAGGGGACACGAGACAGAGGGAGTTCTCCGTAATGTGCCTTGCGGAGAGAAAGGTCCAAGAATGCAATTCGTCCCAGAGTGGCCCGGCAGGGGCGGGGTGCGAGTGGGTGGTGGAGTAGGGGTGGGAGTGGAGAGAGGTGGTTTCTGTAGAGAATAATTATTGTACCAGGGCCCGCCGAGGCACGAGGCACTCTATTTTGTTTTGTAATCACGACGACTATTATTTTTAGTCTGATCAATGGGCACAATTTCTAAGCAGCGCAGTGGTGGATGCTCGCAAACTTTTGCGCACCGCTGGAAACCCACTAGGTTGAGTTGCAAAACGTACCGCGTAGACGCCCCTGGTGGCGCCGAGAGAAGAGCTAGGCCTGCCCAGCACAGAGCCGGAGAGCGTCGGGCCTTCCGGAAGGGTAAGTTCTCCGCCAAGGGGTCCCGAGGGAGCTGGACGTCTGAATCTGGACTTGCCCCCAGCTTCGGGGTTCGATTCTGGGTTTTGCGCGTCCCCAACCCCCAGGGCTTTCCGAAGCATGGCCTGGCTCCAGGCCCGGTCCTGTAAGGACTGGAACGGCAGCAAAATGTGCAGGGAGGCAGTCGGCCGGCAGAGCTGCGGCGGGAGCCAAGGTCAGGCCCGCGGGGAGAGCGGGCAGCTTCCAGCGCCGGCCACAAGCTCCCAGGCCAGCTGGGCCGCAGACCCCTTTGCTTCCAGAGAGCACAACCCGCGTCCTTTCTCTCAGCCAGGCTGCAGTGGCTGCCCCGAGCTTCGCTTTCGTTTCCCAAGCTGTTAATAACGATATGTCCCCAAATCCGAGGCTCGTGTTTGCTCCCAGATGCCAAGAACGCAACCCGAAATCCTTCTCCCAAACCCTAGGTCGACGAGATGAGTTCCTACTTGACCTCTGAGCCGAGGTGGGCCGGAAACCGAGGCCTAGGCCCCGCCGGGGCTGCAAGGAAAAGGGGAAACTCCGAGCGTAGCGTCTTTTCCTTGTGGTTCCTTTCTCCGGCATCCCGGACTGCGGGCCCTGCAGCCACCTGGACCGGCATTCAAAGGATTCTGCAAGTCCAGCTTC |

TABLE 4B-continued

| SEQ ID NO | GENE NAME | SEQUENCE |
|---|---|---|
| | | ACAGACTGGCTTTCCCAGACGCTCCGAAGCCCGCACCACGAACAGAATAAAGGAGAGACGAGAGATCGCAACTAGATTTGAGAATCCTCGTTCTTTTCCCCAAT CGTTCGGGCAGTAAACTCCGGAGCCGGCTACAGCGCGCATCCTC |
| 142 | TBX3 | ACTGTCCTCCTCCCTCAATTGCCTATTTTTTGCCCATAGCTCTAACTTAACCCTGTGATCACCCCAGATCGCTACTTCTGACCCCCATCTCCTCTCCCACACCA ACCTCCAGCGCGCGAAGCAGAGAACGAGAGGAAAGTTTGCGGGGTTCGAATCGAAAATGTCGACATCTTGCTAATGGTCTGCAAACTTCCGCCAATTATGACTG ACCTCCCAGACTCGGCCCCAGGAGGCTCGTATTAGGCAGGGAGGCCGCCGTAATTCTGGGATCAAAAGCGGGAAGGTGCGAACTCCTCTTTGTCTCTGCGTGCC CGGCGCGCCCCCCTCCCGGTGGGTGATAAACCCACTCTGGCGCCGGCCATGCGCTGGGTGATTAATTTGCGAACAAACAAAAGCGGCCTGGTGGCCACTGCATT CGGGTTAAACATTGGCCAGCGTGTTCCGAAGGCTTGTGCTGGGCCTGGCCTCCAGGAGAACCCACGAGGCCAGCGCTCCCCGGA |
| 143 | chr12: 113622100-113623000 | CTCAGGGAATCACATGTCCGCCTGGCCTGGCCTGGTACCAAATGTTTATAGACAGGACGAGGGTCGCTGGAATCGCCTCGCTCCTTTCAGCTTGGCGCTAAGGC GCGAATCTCGATCCTCCTAGTATTTCTCTGGCGTCTGTCTCTATCTCAGTCTCTGCTTTTGTCTCTTTCTCCCTCCCTCCGCCCCAGTCTTTCCGTCTCTTTTT CCTCGAATGCACGTGGAATTCGGAATTGAAAATTGAGGTCAGAATCTCCCTTTTTCTTCCAGTTATCCGCGCCGCTGCCCCACGCCTAGCGGCTTGGATCTGCA TAGACATCTATCTACCCGCAACAAGATCCGAGCTGCAGAAGCAAACCTAATCTGTCTCCGCACCATCCCCTGCTCTGTAGACCCACTGCCCCATCCCACGCCAC ATCCTTGAGGTTCAAGTAGCGACTCCAGCGGATGATTCGGAGAATGCCCTGCTTTCCAAAGGCCCCAACCCGTGTTTTTATTTCTTTTTCCTTTGCCCGCTTG ACCAACTTTGGTTTCTTTCAGGGCCCGGAGGTGCCTGCGCCGCGCTTGGCTTTGCTTTCCGCCGCCCCAGGAGACCCGGGACTGTGGTTTCCGCTCGCCACATC CCAGCCTGGTGCGCACACAAGAGCCTGGCGAGCTTCCCTCGCGCGCTTACAGTCAACTACTTTGGGCCTCGGTTTCCCTGCTCCTTGTAGATCAGAGAAGGGAC GGGCGAAATGCCTGCGAGGGAGGGTTGGCGAATGGGTTGGTTGGTGGCAAGACTGCAGTTCTTGTACATGGACGGGGGTTGGGGGGTCAACACTGGAAGAACTC CTGCCTGACGCCAAGAGCCACCCGCTTTCCAGCTCGTCCCACTCCGCGGATGTTTACCCACCTTCATG |
| 144 | chr12: 113657800-113658300 | TTTGGGGCACCCAACCCTTCCCAAGCCTCGGTTTTCCCGATCTTGTGGGATCCTTGCGGCGCGAATGGGGTTGGAAGCACCTTGGAAGCTACAGAGTACCGGGT CGGGACAATTTCCGGCACTGCCCCAGTTCAGTGGTTTATAGAAAATTTCTTTCTCTCTCTCAGGTCCACTAAGACCGAGAGAGAGAGAGAAGTCGACTCTGGCA CACCCGGGCGAGGGGCTGCCGGGATTCGGGAGCTGGCGCGGTTGATTTTTTCCGAGAATCCTCCACTTGGGGTGACGTCGGGCAGCGCGCGCGGGCCGTGAGGT TAATGCCCAGGCTTTTCTCTAAAGCGTCCGGGAATGATCCGGCGAATAAAACGGGTGTCTGCAAAGTTAATGAATTGTACAAGGAGGCTGAGGGTGGGGACTTC GACCCGGGGAGCCAGAGGCGGTTCTGGTGGACGCTTCCCCGTGCGCCTAGGGGTGCGCTGGGCTTTCCCAGCCGAGGTCTGCAG |
| 145 | THEM233 | CCAGACAGTTAAGGTAAAACGTTGAAGTCAAGAGGAAGTAGTGAGTCTGTTGCCAACTGGATAGGGTTGGTCCTGTCCCATCTAAATGTATTAGAATTAAGTGG CTTTTAAAAATGAGCTGGTCATCTTCAGCCCACGGGCTGGCCAATTTGGAACTTAATGGGCCTTTGCGTCCTCCTTCCCTGAGCCTCCTTTTATTCCAGACTTC TCAGTGTGAGTCTGTGCGTCCCTCCGACGATCTCAGGGAGTGGGGTGCCTTCATCTGCCTGTTCCCTGTTCCTCAGGCTGACGCTCCCGCTGTCCTCCCCGCCT CCCCTCACTCCTTTTCTCCCTCCCTTCCTCCTTGTGGGGAGGCTCTTGGCCAGGGTCCCTGAGCCCGGGCGGGTGCTGGCAGAGGACGCAGAAGGGGTGAGGTC ACGTCTCCCTTGAGCCCCGAGCCGCTGGCTTTTCAGAGCCTCGCCACAAGCCGGCGGCCAGAGCCCCAGACCACACAGACCGTGCGCTCCTCCGCCCTCCCGGC GCCGCCGGCCTCGCCCATGTCTCAGTACGCCCCTAGCCCGGACTTCAAGAGGGCTTTGGACAGCAGTCCCGAGGCCAACACTGAAGATGACAAGACCGAGGAGG ACGTGCCCATGCCCAAGAACTACCTGTGGCTCACCATCGTCTCGTGTTTTTGCCCTGCGTACCCCATCAACATCGTGGCTTTGGTCTTTTCCATCATGGTGAGT GAATCACGGCCAGAGGCAGCCTGGGAGGAGAGACCCGGGCGGCTTTGAGCCCCTGCAGGGGAGTCCGCGCGCTCTCTGCGGCTCCCTTCCTCACGGCCCGGCCC GCGCTAGGTGTTCTTTGTCCTCGCACCTCCTCCTCACCTTTCTCGGGCTCTCAGAGCTCTCCCCGCAATCATCAGCACCTCCTCTGCACTCCTCGTGGTACTCA GAGCCCTGATCAAGCTTCCCCCAGGCTAGCTTTCCTCTTCTTTCCAGCTCCCAGGGTGCGTTTCCTCTCCAACCCGGGGAAGTTCTTCCGTGGACTTTGCTGAC TCCTCTGACCTTCCTAGGCACTTGCCCGGGGCTTCTCAACCCTCTTTTCTAGAGCCCCAGTGCGCGCCACCCTAGCGAGCGCAGTAAGCTCATACCCCGAGCAT GCAGGCTCTACGTTCCTTTCCCTGCCGCTCCGGGGGCTCCTGCTCTCCAGCGCCCAGGACTGTCTCTATCTCAGCCTGTGCTCCCTTCTCTCTTTGCTGCGCCC AAGGGCACCGCTTCCGCCACTCTCCGGGGGGTCCCCAGGCGATTCCTGATGCCCCCTCCTTGATCCCGTTTCCGCGCTTTGGCACGGCACGCTCTGTCCAGGCA ACAGTTTCCTCTCGCTTCTTCCTACACCCAACTTCCTCTCCTTGCCTCCCTCCGGCGCCCCCTTTTTAACGCGCCCGAGGCTGGCTCACACCCACTACCTCTTT AGGCCTTTCTTAGGCTCCCCGTGTGCCCCCCTCACCAGCAAAGTGGGTGCGCCTCTCTTACTCTTTCTACCCAGCGCGTCGTAGTTCCTCCCCGTTTGCTGCGC ACTGGCCCTAACCTCTCTTCTCTTGGTGTCCCCCAGAGCTCCCAGGCGCCCCTCCACCGCTCTGTCCTGCGCCCGGGGCTCTCCCGGGAATGAACTAGGGGATT CCACGCAACGTGCGGCTCCGCCCGCCCTCTGCGCTCAGACCTCCCGAGCTGCCCGCCTCTCTAGGAGTGGCCGCTGGGGCCTCTAGTCCGCCCTTCCGGAGCTC AGCTCCCTAGCCCTCTTCAACCCTGGTAGGAACACCCGAGCGAACCCCACCAGGAGGGCGACGAGCGCCTGCTAGGCCCTCGCCTTATTGACTGCAGCAGCTGG CCCGGGGGTGGCGGCGGGGTGAGGTTCGTACCGGCACTGTCCCGGGACAACCCTTGCAGTTGCGCTCCCTCCCCCACCGGCTCACCTCGCCTGCAGCTGGGCCA CGGAACTCCCCGGCCACAGACGCA |
| 146 | NCOR2 | CTCTCTGGGCCTTAGGAAAATGGAAATGACACCTGTACCTGCCCTTCCAGGACTGACAGGAGGGGCTGCTCCATGAAACCTCACTGCTGCGGTCATAATGTCAT TATCTTTTGCCTTAAAGGGATTTCTTCTGCACCAGCACCTAAAGTGGCAGCCCCTTACCCTTGGCCATCAGCTGGACCCTGGTGCTCTCCTGGAGCCCAAAACC TCTGTTTTGTGTTGCATCCTGCTGACCAGCCACAGTCCACACCCATCTGAGTGTCTGAGCAGAACAGCCCAGAGGCCACACCAGGATGGCTTTCCACCGGTCAC CTTCCCCCACCCACTCATAAACCCTGCGTCTCTGGGGGAGAGGGTGGCGAGGTCCCCTCCCCACATAGATGGAAACACTGAGGCCTGATTCATGGTGCCCCCTG |

TABLE 4B-continued

| SEQ ID NO | GENE NAME | SEQUENCE |
|---|---|---|
| | | TGAAGCGCCTCATGGCCAGCACCGGGGGGCAGCAGGCCAGGGCGGGGACACATACCCGGTTCTCGTCGTAGATGATCTGCACCAGGCTGCGGTGCTTCGACTCG<br>ATGGGCGGCGGTGACACGGGCTTCTCAGGCTCGGGCGGCTTGGCAGCCTCCTCCTCCAGCTGTTGCTGTGGGGAGAGGCA |
| 147 | THEM132C | CTTGAAAACTCCCAGCCCCCTTTGTCCAGATGGGGATGGAGGTGGCCAGGCTGCCCCGTTGATTGTGTGCCGAGGAGCCCTCCCCGGGAAGGCTGTGATTTATA<br>CGCGCAGGCTTGTCACGGGGTGAAAGGAAGGGCCACTTTTTCATTTTGATCCAATGTTAGGTTTGAAAGCCACCCACTGCTGTAAACTCAGCTGGATCCGCGGG<br>CCGTGATTAAACACATTGCCCGCTTTGTTGCCGAGATGGTGTTTCGGAAGGCGCTGTGAATGCACTTCCCTTTGCGGGGCTCACACAGACAAGATGTGTGTTGC<br>AAGGATGAGGCGCCTGCTCGGCCTCCAGCCCAGGGCCGGGAAGGGAGAAGGTGCTGTGCGTCGCTGCCTGTGTCGCCCGCGGCTCTCC |
| 148 | PTGDR | CGCGTCAGGGCCGAGCTCTTCACTGGCCTGCTCCGCGCTCTTCAATGCCAGCGCCAGGCGCTCACCCTGCAGAGCGTCCCGCCTCTCAAAGAGGGGTGTGACCC<br>GCGAGTTTAGATAGGAGGTTCCTGCCGTGGGGAACACCCCGCCGCCCTCGGAGCTTTTTCTGTGGCGCAGCTTCTCCGCCCGAGCCGCGCGCGGAGCTGCCGGG<br>GGCTCCTTAGCACCCGGGCGCCGGGGCCCTCGCCCTTCCGCAGCCTTCACTCCAGCCCTCTGCTCCCGCACGCCATGAAGTCGCCGTTCTACCGCTGCCAGAAC<br>ACCACCTCTGTGGAAAAAGGCAACTCGGCGGTGATGGGCGGGGTGCTCTTCAGCACCGGCCTCCTGGGCAACCTGCTGGCCCTGGGGCTGCTGGCGCGCTCGGG<br>GCTGGGGTGGTGCTCGCGGCGTCCACTGCGCCCGCTGCCCTCGGTCTTCTACATGCTGGTGTGTGGCCTGACGGTCACCGACTTGCTGGGCAAGTGCCTCCTAA<br>GCCCGGTGGTGCTGGCTGCCTACGCTCAGAACCGGAGTCTGCGGGTGCTTGCGCCCGCATTGGACAACTCGTTGTGCCAAGCCTTCGCCTTCTTCATGTCCTTC<br>TTTGGGCTCTCCTCGACACTGCAACTCCTGGCCATGGCACTGGAGTGCTGGCTCTCCCTAGGGCACCCTTTCTTCTACCGACGGCACATCACCCTGCGCCTGGG<br>CGCACTGGTGGCCCCGGTGGTGAGCGCCTTCTCCCTGGCTTTCTGCGCGCTACCTTTCATGGGCTTCGGGAAGTTCGTGCAGTACTGCCCCGGCACCTGGTGCT<br>TTATCCAGATGGTCCACGAGGAGGGCTCGCTGTCGGTGCTGGGGTACTCTGTGCTCTACTCCAGCCTCATGGCGCTGCTGGTCCTCGCCACCGTGCTGTGCAAC<br>CTCGGCGCCATGCGCAACCTCTATGCGATGCACCGGCGGCTGCAGCGGCACCCGCGCTCCTGCACCAGGGACTGTGCCGAGCCGCGCGCGGACGGAGGGAAGC<br>GTCCCCTCAGCCCCTGGAGGAGCTGGATCACCTCCTGCTGCTGGCGCTGATGACCGTGCTCTTCACTATGTGTTCTCTGCCCGTAATTGTGAGTCCCCGGGCCC<br>CGAGGCAGCAGGGCACTGAGACTGTCCGGCCGCGGATGCGGGGCGGGAAGGGTGGA |
| 149 | ISL2 | CTTCCGCCGCGGTATCTGCGTGCCCTTTTCTGGGCGAGCCCTGGGAGATCCAGGGAGAACTGGGCGCTCCAGATGGTGTATGTCTGTACCTTCACAGCAAGGCT<br>TCCCTTGGATTTGAGGCTTCCTATTTTGTCTGGGATCGGGGTTTCTCCTTGTCCCAGTGGCAGCCCCGCGTTGCGGGTTCCGGGCGCTGCGCGGAGCCCAAGGC<br>TGCATGGCAGTGTGCAGCGCCCGCCAGTCGGGCTGGTGGGTTGTGCACTCCGTCGGCAGCTGCAGAAAGGTGGGAGTGCAGGTCTTGCCTTTCCTCACCGGGCG<br>GTTGGCTTCCAGCACCGAGGCTGACCTATCGTGGCAAGTTTGCGGCCCCCGCAGATCCCCAGTGGAGAAAGAGGGCTCTTCCGATGCGATCGAGTGTGCGCCTC<br>CCCGCAAAGCAATGCAGACCCTAAATCACTCAAGGCCTGGAGCTCCAGTCTCAAAGGTGGCAGAAAAGGCCAGACCTAACTCGAGCACCTACTGCCTTCTGCTT<br>GCCCCGCAGAGCCTTCAGGGACTGACTGGGACGCCCCTGGTGGCGGGCAGTCCCATCCGCCATGAGAACGCCGTGCAGGGCAGCGCAGTGGAGGTGCAGACGTA<br>CCAGCCGCCGTGGAAGGCGCTCAGCGAGTTTGCCCTCCAGAGCGACCTGGACCAACCCGCCTTCCAACAGCTGGTGAGGCCCTGCCCTACCCGCCCCGACCTCG<br>GGACTCTGCGGGTTGGGGATTTAGCCACTTAGCCTGGCAGAGAGGGGAGGGGGTGGCCTTGGGCTGAGGGGCTGGGTACAGCCCTAGGCGGTGGGGGAGGGGGA<br>ACAGTGGCGGGCTCTGAAACCTCACCTCGGCCCATTACGCGCCCTAAACCAGGTCTCCCTGGATTAAAGTGCTCACAAGAGAGGTCGCAGGATTAACCAACCCG<br>CTCCCCCGCCCTAATCCCCCCCTCGTGCGCCTGGGGACCTGGCCTCCTTCTCCGCAGGGCTTGCTCTCAGCTGGCGGCCGGTCCCCAAGGGACACTTTCCGACT<br>CGGAGCACGCGGCCCTGGAGCACCAGCTCGCGTGCCTCTTCACCTGCCTCTTCCCGGTGTTTCCGCCGCCCCAGGTCTCCTTCTCCGAGTCCGGCTCCCTAGGC<br>AACTCCTCCGGCAGCGACGTGACCTCCCTGTCCTCGCAGCTCCCGGACACCCCCAACAGTATGGTGCCGAGTCCCGTGGAGACGTGAGGGGGACCCCTCCCTGC<br>CAGCCCGCGGACCTCGCATGCTCCCTGCATGAGACTCACCCATGCTCAGGCCATTCCAGTTCCGAAAGCTCTCTCGCCTTCGTAATTATTCTATTGTTATTTAT<br>GAGAGAGTACCGAGAGACACGGTCTGGACAGCCCAAGGCGCCAGGATGCAACCTGCTTTCACCAGACTGCAGACCCCTGCTCCGAGGACTCTTAGTTTTTCAAA<br>ACCAGAATCTGGGACTTACCAGGGTTAGCTCTGCCCTCTCCTCTCCTCTCTACGTGGCCGCCGCTCTGTCTCTCCACGCCCCACCTGTGTCCCCATCTCGGCCG<br>GCCCGGAGCTCGCCCACGCGGACCCCCGCCCTGCCCCAGCTCAGCGCTCCCTGGCGGCTTCGCCCGGGCTCCTAGCGGGGAAAAGGAAGGGGATAACTCAGAGG<br>AACAGACACTCAAACTCCCAAAGCGCATGATTGCTGGGAAACAGTAGAAACCAGACTTGCCTTGAAAGTGTTTAAGTTATTCGACGGAGGACAGAGTATGTGAG<br>CCTTTGCCGAACAAACAAACGTAAGTTATTGTTATTTATTGTGAGAACAGCCAGTTCATAGTGGGACTTGTATTTTGATCTTAATAAAAAATAATAACCCGGGG<br>CGACGCCACTCCTCTGTGCTGTTGGCGCGGCGGGAGGGCCGGCGGAGGCCAGTTCAGGGGTCAGGCTGGCGTCGGCTGCCGGGGCTCCGCGTGCTGCGGGCGGG<br>GCGGGCCCGGTGGGGATTGGGCGC |
| 150 | chr15: 87750000-87751000 | AGTTTGGGGAGCCTTTTCTCCATTTGAGAAAAAACAAACTTACAGCGAGGGGTGAGGGGTTAGGGTTTGGGATTGGGGAAAATGTGGGTGGGGAGCCCCCCCAA<br>GGAAGTGAGGAGGGGGCTGCAAGGATTACACCTGGGCATACGTTTCCCTAGAAATCACATTCATTGTATTTTTATAATTTATTCTAAATCTTTCATGCGAAGAA<br>AGTCAGTAGTGAGTGTTAGTACTGGTGGCCCTCCTGATCACACTTGCATCTCTTGAGTGTGCCTTAAAGGTCTTGGGAATGGAAAATATAAAAACTGCTTCGTG<br>ATGCGTCATCTTTATCCCCCACTCCCCCACCCATTCCAATATATTTTCTACTTCCAGCCTAAATTCGGGGCCCCCTACCGAGGCCGGCCATGATCTTGAGGGCG<br>GCATAGGGGAGGCCGCGCTCTGTCCACCCCAGCCTGGTGATGCCGTTCGCTTCTTGTGCCCGGTATTGTGGGCTACATGCCTTTCCGGCGTACGGAGCTGAGCG<br>TCCAGGCCAGTGCCCCTCAACCTCTCAGTAATGTTTACCCGAGGCCGTCGTGCAATGAGACTATTCGCATGGCATTGTCAACGCGGCGGCGCGCGCGTCTCGGC<br>CCTCCGCGGCTTGCCAGACTGTCCTGCAAACCACCTCACCCGTCTCTTTGGCGCAGGAGACTCAGGCTGTAACCGGAGAAAACACTTCACCCTGGAACCCTAAC<br>TCAGGTCCTGGCAAAAGATGCGAGAGGAAGACTTGCTCTCTTAATAAATCTCGGCCGCCCGCACATCTGGCCCCTAGACCTGCTCGGTAGAGGACTGGCTGGTG |

TABLE 4B-continued

| SEQ ID NO | GENE NAME | SEQUENCE |
|---|---|---|
| | | GATGCGCGGTCCAGGCCGTGGGCACTCGACCCACCTCTATTTTCCTTCCCGAGGCGCCCCTGGATTACCACTTTCGGTTTGCGCTTACATCCGGGATGTCGAATTTCCCAGGGAATCATAATTATTTTATCTATAATTTATTCTAACCCCAAGGTTCCAAGAAAATCT |
| 151 | chr15: 87753000-87754100 | ACATTCCTTCTAAAATGTGGGCTTTCTGTGTACATGGGCGCGCATTCCCAGGACTCGGTTCCCTGGGTGGAATTCACCCAGGAATACAATCGATTTTCTGAACCTGCGTAAGGCCACAGGCAGCTCTGAAAATGAAAGCGTTTGCTAAGTGGGGGAGATCTCACCGATCGAACGTTTAAAAATGGCTTTGTCTTCATTCAGCTCTCCCGATTTATTCTGTGTTTTACAAATAGAAGCTCAGAGCTTCTGTCGCCCAGTCCTTGCATGACTCATGGCGGTGGCCACACGGGTTTCAGGGATAACGGGATGTTTAGAAAATCGCTGCATATCGGAGTTTCCTAGCACGTTCCATTTATACTGAACGCAGGCGGCCGCTGAAAATCCAGCCTCGACTCTTGCTAATGACTGGGTAGGACCCTCGGGGTCCTGCGACGGTGCTGGAGGGTGTTCCCGGCTCCGATGTGGGGAGGCCTGCGCGGGGACTAGGTTCTCGAGAGGCGAGCGGGCGCGCCAGAGAACCCGAGACTGCTGCGGGGCCGGATGCGGGATCCCTGGGCTGCGGTTCTACGCAGAAACGCCAATGGCCATGCCTCCCCAGCTCCTCCCAGCCCCAGTCACTAGGCCGGCGCCTGGCCCGGAGATCCTCCCAGAGCCCTGGCGGTGCCATCATGCCGGAGAAGACAAGCTCGGCCCCGCTGGAATTCGCTCCAAACACAGATGCTCATTTTTGGAATATTCTAGAAAAATAACAAGATCTTGTTTGTCGTTATGATTCACGGGAGGTAACTGATGGGAGGGCCATTTACATGAGGGCAGACACTGTGGGGCGAAGGTGACTTCTGGACGTAGGCTTTAAAGTAGGAACGGCTCCAAATTCCCAATATCTCCGGCCTTACCGGTTGCAAATCGGACCCCTGCGGGAAAACCAGACACTTCTGTTTCGTGGCTTTCGGGCTGCCTCCAGCCCACGCAGGCTCGTTTAGTCCCCGTGGAGTCAGCCCCGAGCCTTCCTAGTCCTGGAACAAGGGCTCCAGGTCGCGGCCGCGGGAAGCCGCCAAGAGGGCGGGGAGTAGGGATTCCCTCCAGCTCCGCAGGGCATC |
| 152 | NR2F2 | TCCTCCTCGGCCTCAGATGTCGTCCCACCTGCCCACGAGCAGGGAACCTGGAACCCACTCTCCCGGCAGTCCCCAGCGGGTTCCGCCACCCGGCGGCCGCCCCTGACACCGAGTGGGTGGGAGGAAGAGGCAGCTGGCGGGGATGGGCCATTGAGACCTCTTGAAAAATATTAAAAGACAGGATGGGTAGAGATTTCTCCGGGAGAAAGTTCGAGGGTGCATCGGGTCGCGGCTGGGAGGAGTACCCGAAATGCCAGCAGGAGAAATGCAACCTGTTTAGGCCACACCTTCAATCCCCGAGGCTGTCTGGAGAGACTGCGTGCGGGGGACTTGCCGGCGTTCCCACACCGCGCCTGCAATCCACTCCCGCGGCTGCCTGGCCTCTGCCACTCGCGGCTTGAAGCCAGTGGCTCTCAAGCCCTCGGCCCCGCGGCGGCCCGCGCAGCCTTCACCCGGCGCCGGCACCACGAAGCCTGGCCGCAGTGGACTCCCCGCAGCTCGCTGCGCCCTGGCGTCTCCCGTCGAGGAGGGAGGGACGGAGGCCTGAGCCGGGAGCTCCCTGGCGGTGGTCGGGCCGCCCCCCTTGAGGCCTGCTCCCCCCTCTCGGCCTCGCCAAATCCCTGAAAGCCCAGTCCCCCTTCGTCACCCCGGGGGCTTCTAATCACTCGGTATCGATTTCCCTAACTCTTTTCATCCTGTTGAAGACACATCTTAAAACACTCCAGCCCGGAGTGTGCTCTGGGCTTTATCCACACTAATAAAATGATTTACCCTTCTCTCCGCGCTCTCCTCACAGAGGAAAATCGTTCGAGCCCCGGCTATTTGTGTGTGATCAGTAAATATTTAGTGCGCTGACATCCTTAGCTGGGCTTCGGATCGATTCGGGGCCCACCGGGAGGTGCGCACGGTCCGGGCGGGGCCGCGCCGAGCTCGCCGAGGGGGCTCCTCCCGCCCTCGCCGCCGGCCGCTGATTTACGGCCCCTGCAACCAGCTAAGGGGGGCGAAAGCGCGCCTGGAAAATTGGCTTTTCAACCTTTTACTTTTGACATTCAGCCACTTCCCCAGGCTCTAATTCTCGCCCGCACTCCTCCCTCCCGCCCTACTAAGGGTTGCCCTGTGCGCCCTGCGAGCCCTTCCAGCAGCAACGCGCGGCGCTCGCGCCCCCTCGGCCCGGGGACCACCTATCACAGCCCTGAGCCGCGACGCGGGGAGGCCCCGGCCCCTGCTATGGGGGTCGCCTCCTTCGAGGAGAGATGCTCTCCGCCCGCCCACACCTCTGAGGGAGGAGAGGGGGTGGAGAAGCCCAGAGCTGCATCTGCTGGATGACGAGCCGCTCTCCCTGCTACCCTTTCTCCGACCCGTCGGCCTTTCTCCTACTCTGGAGACTGATCCTCGACGTCCATCGGGCCGGATGGCGTCGGGTGGAAGCGTTACTTTCCTCGCAGAAAAACTCCTCCTCTTTCCTAAGATCAGAAAAAGCGCTTAGCTTGGAATTGTTAG |
| 153 | chr16: 11234300-11234900 | CCTAGGCATTCTCAGCCCGTTTTGCTGGAGGGGGCATTTGAGGCCTGGCCAGCTTAGCCAGCCTACAAGGAGTGTTACTGGGGTGAAAACAGCCAGCGGGGACCAGTCTGCTTGTGGCCCGCCAGGTGCCTGGGATGGGGAAGCAGCAAATGCCCACCTTCCTGCCCAACCCCCTCCTCCCTCTTCATGGGGGGAACTGGGGGTGGCAGCGGCTGCCGGGTGCGAGCGGGCTCAGGCCTGTGGCCCTGCCTGACGTTGGTCCCCATCAAGCCATGTGACGAGACCAGGCCACAAGAAAGAGGTTTCAACAAGCGTTATCGTTTCCTGGAACTCCAACTCGGCGACTTCCCCGAAGACCGGCTGTGCCTGGCGGGCGGGCTGCGCACAGCGGGGACAAGGCTGCCCCCTTCCTCCTCCGCTGCCTCCGCGGCCGCGTCTATCTCAGTCTGACTACCTGGAAGCAGCACTCCACCCTCCAGCCCAGCGGCCCTCGGCTCAGCTGCCAGGTCACCGGCAACCCCGGGAGCGGTGGGGCAGGGGCTGCTCCGCCAGCCTCTGTGATGTTCAGGCCGGGCTGCACCAGCCCGGGACCCCTAGGTG |
| 154 | SPN | GCACTGGTTCCCCTTTACCTGAGCCAACAACCTACCAGGAAGTTTCCATCAAGATGTCATCAGTGCCCCAGGAAACCCCTCATGCAACCAGTCATCCTGCTGTTCCCATAACAGCAAACTCTCTAGGATCCCACACCGTGACAGGTGGAACCATAACAACGAACTCTCCAGAAACCTCCAGTAGGACCAGTGGAGCCCCTGTTACCACGGCAGCTAGCTCTCTGGAGACCTCCAGAGGCACCTCTGGACCCCCTCTTACCATGGCAACTGTCTCTCTGGAGACTTCCAAAGGCACCTCTGGACCCCCTGTTACCATGGCAACTGACTCTCTGGAGACCTCCACTGGGACCACTGGACCCCCTGTTACCATGACAACTGGCTCTCTGGAGCCCTCCAGCGGGGCCAGTGGACCCCAGGTCTCTAGCGTAAAACTATCTACAATGATGTCTCCAACGACCTCCACCAACGCAAGCACTGTGCCCTTCCGGAACCCAGATGAGAACTCACGAGGCATGCTGCCAGTGGCTGTGCTTGTGGCCCTGCTGGCGGTCATAGTCCTCGTGGCTCTGCTCCTGCTGTGGCGCCGGCGGCAGAAGCGGCGGACTGGGGCCCTCGTGCTGAGCAGAGGCGGCAAGCGTAACGGGGTGGTGGACGCCTGGGCTGGGCCAGCCCAGGTCCCTGAGGAGGGGGCCGTGACAGT |
| 155 | chr16: 85469900-85470200 | TGTCCGACAGGCACACAGAGCGCCGCCAGGCACGGCCCTCATTCTTCACCCCGAGCTCCCGCAAGGTCGGCGAGGAGGCTGGAGCAGCGGGTAGGAAGCGGGCCGAGGCTCCCCCGACGCTGGGCCGCAACTGTCATCGCAGATCCCTGAAAAACGAGCTCTGTAATCGTTGCCGTCAGCGGGTGTACAATTGCAGCCTTATGTTTCCTGCCGCTGTTTACCTTCCTGAGCGGCGCCCAGAGATGCACACACGCTGCCCTGAAGCGGGACGTGACCTCTGGGCACCTGTGAGGTCCTGGG |

TABLE 4B-continued

| SEQ ID NO | GENE NAME | SEQUENCE |
|---|---|---|
| 156 | SLFN11 | GTCGGCTCCTGCGCTCCCAACGGGGTGGCCGTTTCCTTCCTCGCACCCTCTTCTCTCCCGGTGCCTGCGGTCCCACCTTCCAGATACCCCTCGGAGAGTCCAGC<br>TGAGCTCTCGCCAGAGCTTTCCCCTTCCAACCCGCTCGACTTGCCCAGATCCCAAGCTGGGCTTCTCTCTCCATCGCCCCAGAAAGTGGGTCTTGGAGACCGAG<br>GCAAGAATTTGGGCCTCCGCTTCTGTTCCAGACCCCGGACCCCTTGCCAAAATGCGGCAGATGTGCAGATTGGGCCGCGCTTGGTTCCTGGCTGGGTTTATGGA<br>GCCTGCGGCTGAGGCAGGCTCCGCAGACCCCGAGCCAGAGTGGGATTTAACGGCGGCCGGTGCGCTGTGCTTGGTCAACCCCGGTAACCGTCACGCTGCTAGTG<br>ATATGAAAAAAACCTGCCAGCGTTCTGCTTTTCTGCCCCGCTGCAGTCTTTAGCACCCGCCAGGATTCTGTCCGAGTGTTTGGA |
| 157 | DLX4 | TTTAGTGTGTGCATAAAACATCCCAGCTAATCTCAAATAGACTTTTCCTGAGCAGAGGCTGAAATTTGCAAGTAATGCAAAGAAGACTCCGGGAGAGCGTCGCC<br>GATGGTGGAGCGGGAGACGGGCGTGGGGAGCCCCACTGCAGTGCTGGGATCGAAGTGGTGCTGACCCCAAGACCTCTCCCCTCCTCCTCCCCCGGGAGCTTCTC<br>CAGGGTTATTTGGGAAATGAGGGGGAACTCCAATCCCTGAGAAAGCGCTCAGGGGCTTGCTGAGGTGAGCGCAAATGGAAGCACAAGGCCGGGCTGGCCGTGGG<br>CTCAGTAACCAGTCGGCTGCCCGGCTTGCGCCAGCACTAAATGCTCGATCAGAAAGAGAAAAAGAGGCGCAATAATTCCAAATTTCAGGAAAAGTCAAATCGGA<br>GAGGGGGGACGCAGGTCTCTTCAGACTGCCCATTCTCCGGGCCTCGCTGAATGCGGGGGCTCTATCCACAGCGCGCGGGGCCGAGCTCAGGCAGGCTGGGGCGA<br>AGATCTGATTCTTTCCTTCCCGCCGCCAAACCGAATTAATCAGTTTCTTCAACCTGAGTTACTAAGAAAGAAAGGTCCTTCCAAATAAAACTGAAAATCACTGC<br>GAATGACAATACTATACTACAAGTTCGTTTTGGGGCCGGTGGGTGGGATGGAGGAGAAAGGGCACGGATAATCCCGGAGGGCCGCGGAGTGAGGAGGACTATGG<br>TCGCGGTGGAATCTCTGTTCCGCTGGCACATCCGCGCAGGTGCGGCTCTGAGTGCTGGCTCGGGGTTACAGACCTCGGCATCCGGCTGCAGGGGCAGACAGAGA<br>CCTCCTCTGCTAGGGCGTGCGGTAGGCATCGTATGGAGCCCAGAGACTGCCGAGAGCACTGCGCACTCACCAAGTGTTAGGGGTGCCCGTGATAGACCGCCAGG<br>GAAGGGGCTGGTTCGGAGGGAATTCCCGCTACCGGGAAGGTCGGAACTCGGGGTGATCAAACAA |
| 158 | SLC38A10 | CATGGTGCTTCAGGAAGGGAGGGGACGAGAGCCCTGGGCTTGTGGTGTCCACGTGGACAGCTAATGAGGAGCCTTGCCGATGAGGAGCATGCGTTCCCGACGGG<br>GCGGCCGAATGCGGAAGGAGCCGCCATTCTCTCCGCCCTGACCGCGGGATTCTCTGCAGCAGATGAGAAACGGCGCTGACTCAGCAGGGTCCCTCCCAGGCCCC<br>GAGCGGTCATCTGGTGACCCCCGCGCTTCCCCCACGGCCCAGCCGGAGAAGGGCAAAGGGAAGTCCCGGCTCCAAGGCGCACCCAGAGATGCGGTGCATGTGGC<br>AGGATGGCCCAGCCCCGTCGGCAGCCCCAGCTTCCTGCCCCTGGTTTCCTTCCTCCCACGGGCTACAGGCCTCTGATGAGCTTTGGAAAGCAGGAAACACACAG<br>GCTAGTAACTATGAATGGGTCCAAAAAACACTCCTTATTACTTTAAACTACTTAGGAAGAAGCACAGCGTTGCCAAACGCCAGA |
| 159 | S1PR4 | GCGCGGGGGGCCGGAGGATGGCGGCCTGGGGGCCCTGCGGGGGCTGTCGGTGGCCGCCAGCTGCCTGGTGGTGCTGGAGAACTTGCTGGTGCTGGCGGCCATCA<br>CCAGCCACATGCGGTCGCGACGCTGGGTCTACTATTGCCTGGTGAACATCACGCTGAGTGACCTGCTCACGGGCGCGGCCTACCTGGCCAACGTGCTGCTGTCG<br>GGGGCCCGCACCTTCCGTCTGGCGCCCGCCCAGTGGTTCCTACGGGAGGGCCTGCTCTTCACCGCCCTGGCCGCCTCCACCTTCAGCCTGCTCTTCACTGCAGG<br>GGAGCGCTTTGCCACCATGGTGCGGCCGGTGGCCGAGAGCGGGGCCACCAAGACCAGCCGCGTCTACGGCTTCATCGGCCTCTGCTGGCTGCTGGCCGCGCTGC<br>TGGGGATGCTGCCTTTGCTGGGCTGGAACTGCCTGTGCGCCTTTGACCGCTGCTCCAGCCTTCTGCCCCTCTACTCCAAGCGCTACATCCTCTTCTGCCTGGTG<br>ATCTTCGCCGGCGTCCTGGCCACCATCATGGGCCTCTATGGGGCCATCTTCCGCCTGGTGCAGGCCAGCGGGCAGAAGGCCCCACGCCCAGCGGCCCGCCGCAA<br>GGCCCGCCGCCTGCTGAAGACGGTGCTGATGATCCTGCTGGCCTTCCTGGTGTGCTGGGGCCCACTCTTCGGGCTGCTGCTGGCCGACGTCTTTGGCTCCAACC<br>TCTGGGCCCAGGAGTACCTGCGGGGCATGGACTGGATCCTGGCCCTGGCCGTCCTCAACTCGGCGGTCAACCCCATCATCTACTCCTTCCGCAGCAGGGAGGTG<br>TGCAGAGCCGTGCTCAGCTTCCTCTGCTGCGGGTGTCTCCGGCTGGGCATGCGAGGGCCCGGGGACTGCCTGGCCCGGGCCGTCGAGGCTCACTCCGGAGCTTC<br>CACCACCGACAGCTCTCTGAGGCCAAGGGACAGCTTTCGCGGCTCCCGCTCGCTCAGCTTTCGGATGCGGGAGCCCCTGTCCAGCATCTCCAGCGTGCGGAGCA<br>TCTGAAGTTGCAGTCTTGCGTGTGGATGGTGCAGCCACCGGGTGCGTGCCAGGCAGGCCCTCCTGGGGTACAGGAAGCTGTGTGCACGCAGCCTCGCCTGTATG<br>GGGAGCAGGGAACGGGACAGGCCCCCATGGTCTTCCCGGTGGCCTCTCGGGGCTTC |

TABLE 4B-continued

| SEQ ID NO | GENE NAME | SEQUENCE |
|---|---|---|
| 160 | MAP2K2 | GGGCGGGTTGCCACACTGTCCCCTTTCTGCATGGGAGGAAGGGGGCTCGAGAACTGAGTCAGCCACACAAAACGAGGATGGACAGAACTCCTGAGTAGCGAGGG TGCCTGCCGGGCGCGAGGAGGAGGGGGAAGACGAGGAAGACGAGGAGGAGGAATAGGGAGCACCACATGACAGAGGGGCTGCCTCAGACCACAAAGCGCTTCCT CATCCTTTCCTCGCCCTTTGATGCCGCCGGCAACGTGACTCTGCGAGCAGCGGGGCAGACGCCAGGTCTCCCTCGCAGGCGGGAAAGGGGCTCCAAGGCGGGTG CTGCCTTGCTCGGGTCACATGGCTACGTGGGGGCCTTGCTCAAATTCACTTCCTGCCTTCATTACAAAACTGTCAAAGGGGATCGCACGTTTGCAGGGTGTCAC CCAAGCATTCTGGTTTTGCAAACGACGCTGTGCGGCAGGCGGTCTGATACCTGATGAGCTCGGTGTGGCGGGGTCGGCAGCATTTCCTCCGGGGTTTTGAGCTC TGGCCACTTCTCCTTTTGTTCCACCCAATCTCACCCACTTCTGGGCTTCGAGGCCAGAGTGTCTTAACAAGGGGGCACGT |
| 161 | UHRF1 | GAGCGAGACTTTGTCTCAAAAAAAAAAAAAAACCAAATAAATTGAAAGCTGAGAAATTCAGAGCACAAGAAGACAAGCGCGCCCCCTCTTTTAGCTGTCAACATG GCGGAGCCGTCCCTGGTGACGCAGCCTCCAAAGGCCTCCCTGTGCCCTCCTGAGACCGCAAGAGGGAAAGTGGCAGCGACAGTGATCGTGGTGTCTTTGTGGCG GTTGTGTTGACCTCACTGACCCCCGAAGTGCCGCTCTAGGGTCTGTCCTCAGCGGTGACCCGGCCGGGTCGAAGGGCAGAGTTCCGCTGTCACTAGCCCTCCAC CCGTCCTGTGTGCTGGGATGCCCTCGCGGCGCCGTCCACGCCACCGCCGCCCCCTCTTGTGGGTTCTGTCTCCTCCGTGTCTAGGATCCTCCTGCATCCGTTTT TCCTTCCTCCCTTCTCTCCCTCCGTCTGTCTTGCCCGCACCTGAGGTTGTCGCAGAGGCGCTGAGACGGGCCAGCAGGAGCTGT |
| 162 | DEDD2 | TGCTGTCCCGGTCCTGTCGCAGTCCTCAAAGATGCTAGAGTGACAGTCCTCTAGGGGTAGAGATGGTCGTCCTCCCAGGAGAAGGTGGCCCGGAGACTTGGAGG TGGGATCAATCCTGCCAGTCCTGGATCAGGAGGCCTCTGTCGGGCGCCGCCCCCCTTCCTCCTCCATCAGCAACAGGCGGCGCCGGCCAGCCTCATAGTCAGCC TCATCCACACTGACCAGCAGGCGAACAGCCTCCCGGCCCACAGCCTCTCGCAGGGCCTCAGTCAGGAACACGCCCCGCAGGGCCTGCAGCAGGGCGCCACTCAG GTAGTCGCCCCAGAAGGCGTCCAGATAGGAGAGCTCTGAGAACTTGATGTCACAAACCACAGAGCCCAGGTCCCTTGAGCGCAGCACTGCGGTGGCCTGCCCAA ACACGTCCAGCTGCCGCGCCAGCGCCTGGGGCCGCCGGGATGCCACGCCCTGCTCCAAGGCTGGCCCATGCTCGCAGTACTCTGCTCGAACCCGGAGCCGGATG TCTGCAGGGGAAGGAGGGATTTGTCAGGGAGGGGGCCAACACTAGACACACTTATGGGGAACGCCACCCTTCCTCCCTCC |
| 163 | CDC42EP1 | TGATGCCCGGCCCCCAGGGGGGCAGAGGCGCCGCCACCATGAGCCTGGGCAAGCTCTCGCCTGTGGGCTGGGTGTCCAGTTCACAGGGAAAGAGGCGGCTGACT GCAGACATGATCAGCCACCCACTCGGGGACTTCCGCCACACCATGCATGTGGGCCGTGGCGGGGATGTCTTCGGGGACACGTCCTTCCTCAGCAACCACGGTGG CAGCTCCGGGAGCACCCATCGCTCACCCCGCAGCTTCCTGGCCAAGAAGCTGCAGCTGGTGCGGAGGGTGGGGGCGCCCCCCCGGAGGATGGCATCTCCCCCTG CACCCTCCCCGGCTCCACCGGCCATCTCCCCCATCATCAAGAACGCCATCTCCCTGCCCCAGCTCAACCAGGCCGCCTACGACAGCCTCGTGGTTGGCAAGCTC AGCTTCGACAGCAGCCCCACCAGCTCCACGGACGGCCACTCCAGCTACGGTGAGGGCCTGGGCCATCTTGGCCCACTTTTCAGA |

TABLE 4C

| SEQ ID NO | GENE NAME | SEQUENCE |
|---|---|---|
| 164 | chr21: 9906600-9906800 | GGCCGGGCAAAAAGCCGCCGCAACAAAAAGCTGCGCTGACGGGCGGAAAAAGCCGCGGCGGCGGAGCCAAAAAGCCGGGGCGGCAAAAAGCCACGGTGGCGGG<br>CGCAAACAGCCGCAAAAAGCCGCGGTGGTGGGGGCAAAATCAGTGGGAGCAGGGGCAAAAAAACACAAAAAGCCGCGGCGGCGGGGGCAAAAAGCCA |
| 165 | chr21: 9907000-9907400 | TGGCTTTGCTGGAGTGTGATGTGATAGGAAATGTGCAGCCAAAGACAAAAGAAGATGTAAGTAGGCTTGACTCATTGCAGCTAAGAACCCAGATGTTACCTTG<br>AGGGTATTAACTAATAAGCAGTTTAAATCAGAATGGCACATTCTGATTTGTTTTTTGTATGTTCACATTTGGCAGGCATAGATACTGTTTGAAAAGAGAAAAG<br>TCAGTACATAGAGGTAACAAGCTTAAATATGTGCCAAGTCTAGAAACAAGAGACTAGGGGGATAAGGACCTTTCGAAATTAAATGCAAGATTTGAAAACTGAT<br>TGGCTGGGGGATGAGGCAAAGGCAGGTCTTTAAGGTCAATCCCTGTTTTGCTTTAAGTTGTTAGCGGGTGGTTTTATCATATATTGTAGAA |
| 166 | chr21: 9917800-9918450 | TTCCTGGGAATGTCAGCTAACCTGAGCCTAGGGGCCTGAGCCCAAGGGCAGACTGAGGCTCCCCCAGCACAGGGAGGTGCTGCCTGTGACAAGGGGTAGTGCT<br>GGCACAGTGCAGGCTACTCCCTAGAAAGATCAGCTTGAATATGCAGGAAGAGCAGGACCCTCGGGCTGAGGCAGAGGTGGAATGGGAAGTGCATGGTGGTAAT<br>TTAGTTCTCCAGAGGCCAGAAGTAGGAGGAGCGGTTGGAATGCTGATGGCCCAAAGGGAAACCCTGGACTACCCTGGCCTCCCACAGGACTCTCATAGTAATT<br>GCGGCTCCCTGCAGTGGTGAGGCCAGAAGGAGTGTTGCCCAATGCTGTCATCATCCAGTCCACCCCCCACCCACCATCAACAGATGAGTATGGTCATGAGTGT<br>GGTCACCTCATCAGTCATTTGCTCAGTTGTGAAAAAGAAATTGTTCAGAGAAGAGCAAAGTGTTTTTCCATGAGCCAAAGGTCAGCCAAGTTATGCTAATGAG<br>GAGGACTGGAGACAGCGTGTCACAGACACCGAGAAGGAGCACTGGGCAAGGGCACTTCTCCCAGGGCAGAGCCCACAAGAAGCGTCCTGGCACCAGACACTCAGGG<br>AACTGAAGGCTGGCAGGGGCCCGCCCAGT |
| 167 | TPTE | TCCCCCCAGCTGGGTATAAGCAAACTTTCCTGTCTATGGGCCGCAGAGACCACCATCTAGTTCCCCCGCCAAAACTTTACATGATTTTAATTCTCCTGATGAA<br>GATGAGAGGATAACAGCCAACAGAGAGGGCAGAGGATGGGATGGGACTCCCTTGCTCAGAGACCTCACCTCTAGGTCTTTACCTCCTATTGAGAATAAGTCAG<br>TTCTGTAGTAAGAACTCTGTGTCCACGGCAACCCCAAACAGAATCCTAGCGCTCTTGTGATTCTTGTAGAATGGGGAATAGAACGAGCTTGGCCCAAGACTGC<br>ACAGACTTAAAAACATACTATTCTTTGAAAATGGCAATCATTAAAAAGTCAGGAAACAACAGGTGCTGGAGAGGATGTGGAGAAATAGGAACACTTTTACACT<br>GTTGGTGGGACTGTAAACTAGTTCAACCATGGTGGAAGTCAGTGTGGCGATTCCTCAGGGATCTAGAACTAGAAATACCATTTGACCCAGCCATCCCATTACT<br>GGGTATATACCCAAAGGACTATAAATCATGCTGCTATACAGACACATGCACACGTATGTTTACTGCAGCACTATTCACAATAGCAAAGACTTGGAACCAACCC<br>AAATGTCCAACAATGATAGACTGGATTAAGAAAATGTGGCACATATACACCATGGAATACTATGCAGCCATAAAAAATGATGAGTTCATGTCCTTTGTAGGGA<br>CATGGATGAAATTGGAAATCATTCTCAGTAAACTATCGCAAGAACAAAAAACCAAACACTGCATATTCTCACTCATAGGTGGGAACTGAACAATGAGAACACG<br>TGGACCCAGGAAGGGGAACATCACACTCTGGGGACTGTTGTGGGGTGGGGGGAGGGGGGAGGGATAGCATTGGGAGATATACCAAATGCTAGATGAGGAGTTT<br>GTGGGTGCAGCGCACCAGCATGTCACACGTTTACATATGTAACTAACCTGCACATTGTGCACATGTACCCTAAAACTTAAAGTATAATAAAAAAAATACTGTT<br>CTGCCATACATACAGATACTCATTAAAGATGAGGGAGAAGGGCATGGGGTGGGGGAGAATGTACCAAAACCAAAGACCACAGGATAATAACCTCAGAGCAGAG<br>ACTATCTCTCTAGTTATTTTTTCTTTTGTATGTAATGGAGAGGATTATTATTTACTCTGATGAAGAAGTTTACATCAAGTGTTCAGCTTCCTTTGTGGGTTAC<br>AGAGAATAACCAGAGGGCTCAGTTATGCTCTCTGAATAACTATGTTTGCTTAGTGTTTTCTAAACAATATTAAATTTCACTAAAATAGACAAGGTTGATAGGA<br>CTTGGGGGCATAACTCATTGACTCAAGCTATCATTTTATAGGATTGTGAGAAAACAAATAGATGAACATTTAAAATACACTCATATTCTCGCTAGAAAAGAGG<br>ATTTTGAATATTCTTACATCAAAGACATGGTAAATGTTTAAGGCAATGAATATGCTAATTACCATGATTTGATCATTATGCAATGTAAAATGTACTGAAACAT<br>CACATTGTACCTCATAAATATGTACAATTTATTATGTGCGAATTAAAATTTTGAGTATAAGAAAAAATAAACTTCAATTGTAAGAAAACAACCCAACTTTTAA<br>AAAACGGGCAAAATACGTGAACAGATACTTCACTAATAGAGATTTGCAACTGGCAAATAAGCAAATGAAAAACTGGTCATCATCACTATCTATTAGAGAAATG<br>CAGATTAAAACTACAATAAGAAACAATGCTGCCCGTCCAGACGCATTGTTTTGACCGTTTCCAACTTGTCCCAGCCCTTCCCGGGGCATCGCTGGGGACCCTA<br>CGCCGACGTCCCCCCTCCGCCCGCGCCCCAAGGGCCGACTGGGCAAATTGGGAGACCCGCCCCGCGGGGCGACCCAACTTTTCGGAACAGCACCCCACCGCCC<br>ACCCCCGCAGACCCCCGGACCCCCGCTCCCGGCGGAGACTCAGGGAACCCCGCACCCCAAGCCCTTCTAAATCGTGCAGCGTGAGTGTGACGGCCAAGAGCGG<br>ATGCAGCCCGGGATCGCCCGCACCTTCCCGTGGGCGGAAGCGCAGGAGCCAGCTGGGGAGGGGGCGCCCTAGAGGAGCGGCTAGAAAGCAGACACGGGGAACT<br>CAGGTCATCCTGGGGGGGGACAAGACAACGAGAGCCGGGCGCCTCGGGGGCGGCGCGGGAGCCTCCGCAGGACCGGGCGGGCGCCCCGGCTGGCGCGGGCGGG<br>GGGCGCGCCCCCTTTACCTGCGGCTCCGGCTCCTAGGCCATTTCCTCACGCGGCGGCGGCCGGGACTGAGCTAACACCACTCAGGCCGGCCGGGTTTGAATGA<br>GGAGGAGCGGGCGCGGAGAGGAGGGGACGGGGAGGGCGGAGGGAGGGAGGGAGGCGTCGCGGAGTTTTTCTCGGCCTTTTGTGCGGACACCTCCCGGATTCCG<br>CGCCCGCACCCGGCCCCCCAAAAGACACGGGGAGCCGCGGGCGAGGGGTTCAGCCATCCGCCGAGGCGCCTAGTGCCTTCGCGCCTCCAAGACCCCCCCCCAA<br>CAAAAAGGAGCGTCCCCCACCCCTACCCCCGCCCGGAGGACTTAGGGCCTGGGCTCACCTCGGGCGCGGAGCTAAGTGTAGGCGCCGGGGGTCCCTAGAGCCG<br>CCGGGGCGCAGCGAGTCCGGCGCTGGGTAACTGTTGGGTCAGAAACTGTTCAGGTAGCAGCTGTTGTGCCCTCCCTTGGCCCCGCCGCTCGGAGACGCCCCGC<br>CCCCTGCCTTGAACGGCCGCCCGGCCCCGCCCCAGCGCCCACGTGACTAGCATAGGCGCGCCCCCGTTCCGCCCGCCGCCGCAGACTCCGCCTCCGGGACGCG<br>AGCGAGCGGCGAGCGCGCGCACTACCAGTTCTTGCTCGGCGACTCCCGCGCACGCGCGCGCCGTGCCACCCTCCCCGCACCCCTCCTCCCGCCATCCGGCTTA<br>ACGTGGCGGGCGCGCGCCGCGGCAGTAGCCGTGACAGGTACCCGGCGGGGCGGGGGGGGAGGGGGTTGGCCCGCGAGGGTGTGCGCAGGCACAGACCCGGGTC<br>CTGTCCCCGCCGCCCCCTCCTCTGCAAGGTGTGCCTGGGCGAGGGGAGGGGCCCGCGGCCCGAACCCCTGGGTCACCCCCGAATTACAAACAAAAACCTTAAC<br>GCCATTGCTCGCGGGTTAGAAGGCAGCTGTGCGTGCTCAGGAAAAGAAGCCACGCACAAGAGACCGCACGCGGCGTGGATACAGTGACACGAAACACCCAAAA |

TABLE 4C-continued

| SEQ ID NO | GENE NAME | SEQUENCE |
|---|---|---|
| | | TCTCTTTTGAAAGGGAAACCAGGCACAGTGGCTCATGCCTATAATCCCAGCACTTTCGGGGGCCAAGGCGCTCACCTAAACCCGAGAGTTCAAGACCAGCCTG GGCAATACAGCGAAACCCTGTCTCTACGAAAAATATAAAAATTAGCTGGGCATAGGGCTGGGCACGGTGGCTCACGCCTGTAATCCCAGCATTTTGGAGGCCG AGGCGGGCGGATCACGAGGTCAGGAGTTCCAGACCATCCTGGCTAACACAGTGAAACCTTCTCTCTACTAAAAATACAAAAAAAATTAGCCGGGCGTGGTGGC AGGTGCCTGTAGTCCTAGCTACTTGGGAGGTTGAGGCAGGAGAATGGCATGAATCAGGGAGCGGAGGCTGCAGTGAGCTGAGATTGCGCCACTGCACTCCAGC CTGGGGGACAGAGTGAGACTCCGTCTCAAAAAAAAAAAATAATAATTAGCTGGGCATGGTGGCTGGCACACATGGTCCCAGCTACTCAGGAGGCTGAGGTGGAA GGATCTCTTGATCCCGGGGAGGTCAAGGCTGCAGTGAGCCAAGATGGCATCACCGCACTCCAGCCTGGGCCACAGACCCTGTCTCAAAAAAAAAAGAGAAAGT GGGGAAGAAAATGTAATACAAATTAATATACCAACAGCAATTAGTGAGTACTTTTTCCATGGAGCTGGGAGAGGGAATAAATGTTTGTAAAATTAAAATGTTC TACGCTAGAAATCAACTTTCCTTCTATGCTTTCTTTACTTCACCCCTTATAGCTACTTAGTAAATCTCACAAATCCTATCCTTCTGATCTCTCTGAAATGTAT GTACCCTTTCCCTTCTATTCTCACCACCCATGTTTCTTTGTTTCCTTCTAGCCTGTGTAATAATCTCATAATCGCACCTCCTGTACCTGCCTTCTTTCTAGTC CAGAATACGTTTTCCTAAATTCCACCAATAACCATCCTGCTACTGCTTTGTGTGAAATTCTCCAAAAAAAATTTTACTTTTCCAAAATAAGTCAGGCTCCCTC TCTTAGGATACAAAACCACACCATGGTCCCAGCCAATCTTTCAGCCTGATTCACTCAGTATATATTTATTGACCTCTCCTTTCTCCCAAGCACTTGGCTAGAT AATAATTAAAGAGTGCGGCACAAAACAAATTGGATTCCTCCCCTCATGGAGCTTGTATTTTCACAGGAAGCACAGACATTAAATAAATTAAAACACAAAAAAA TAGACAAGCATATAATTACAGTATGTATCCTAGAGAAATATCACTCATGCAGAAAGCATACACAAGGATGCAGCACTGTTTCCAATAGCGAAAAGCTAGAAAC AACCTACATGTTCACCAAAAGAAAATGGCCACATAAACTATACCATATCCAAATTATCCAAATTTTAGAATATAGACAACAGGTTGGGCGCGGTGGCTCACAC CTGTAATCCCAGCACTTTGGGAAGCCGAGGCGGGTGGATCACAAGGTCAGGAGTTCAAGACCAGCCTGGCCAACATGGTGAAACCCCGTCTCCTCTAAAAAAA CAAAAAAATCAGCTGGGCACTGTGGCAGGAGCCTGTAATCCCAGCTACTGAGGAGACTGAGGCAGGAGAATCGCTTGAACCCTGGAGGCAGAGGTTGCAGTGA GCCAAGATCGCGCCACTGCACTCTAGCCTGGGTGACAGAGCAAGACTCCATCTCAG |
| 168 | chr21: 13974500-13976000 | TGTAGGAGTCCTCCGGTGCTGGAGTCCAGAGCACAGTGAGGCTGGGTCCTCCCGTGCCATAGTGTAGGGCATGGCGGGACAGGGATCCTGCCCTGCGATAGTC CAGTGCTTGAGTCCGCAGTAAGGCAATGGTCCTCCAATGCTGGAGTTCACGGCGTTGTGGGGTCGGGGTCCTTTGGTGACTTAGTCCAGGGCGTACCAGGGCG GGGGTCCACAGTTGCCATAGTGAGGATCTTGGAGGAAGGTGGTTCCTGCCTTGCTGTAGTCCGGGGAGCAGGGGGCAGGGGTCCTCTCTTGTCAGAGTCTCTG GCGCGGGGTGGGGGTGGAGGTGGGGGTTTTCCTATGCGATAGCCCACGGGTCGGTGAAGCCGGGTCCTCCCGTGCCTTTGTCCAGGGCGCAGGGGGGCGAGGG TCTTCGGTGGTGGAGTCCGCGGAGCGGCAGGACGGGGGTCCTCCAGTGCCATATTCCAGGGCGCGGCGGAGTGGGGGACCTGTCCTGCAGTGGTCCAGGGCAT GTGGGAGTGGTGGTCCTGCTGTGCCTCAGTCCAGTGCGCGGTGGGACGGCGGTCCTGCTGTGCTGTAGTGCAGGACGCGGTGGCGCAGGGGTAGTCCAGAGAG CGCCGTGGCAGGGGGTCCTCCAGTGCTGGAATCCAGTGCAAGGCGGGTCAGGGGTCTTACCGTGCCGAAGTCGGTGGCAAGGGTCCTCCCGTGCCATAGTCTA GGGGGCGACGGGGCAGGGTTCTCTAGTGCAGGTGTCCAGGGTGTGGCAGGGCAGGAGTCCTCTTGTGCAGGAGTCCAGGACGTAGCCGAGGAGTCCTCCAATG TCAGAGTCCAGGGCTCTGCGGGGCCGGGTTCCCCCATGCCAGAGTGTAGGGCGCGTTCAGGTGAGGGTCTTGGCGTGCAGTAATCCAGGGTGCGGTGGGGCAG GGGTAGTCCAGACCTCCATGGCGGGCGTCCCTCTGTGCAGGAGCCCAGTGCCTGGCGGATCGGGGGTCCTTCTGTGCTGTAGTCCAGGGCACCGCAAGGTGTG GGTCCTCTGGTGCCCTAGTCCAGGGGGCGGCGAGTCAGAGGTTCTCCCGTGTCTCAGTCTAGGGCCTGGTAGGACTGGGGTCCTGGAGTCCACGTGGTAGCCC AAGTTGCCGCAGGACCAGGTACTCTGGAACCACAGTCCAGGGCGCTGAGGGGCAGGAGTAGTTCAGGGCGAGCCGGGGCCCAGGTCCTCGGGAGCCAGAGTCC AGGGTGTGGAGGGGTGGGGGTTCTGCAGTGGCACAGTCCAGGACACCGCGGGGCGGGACAGGGCGGGGATCCTCCCGTGCCTTAGTCCAGGGCTGAGCCGCGG GAGAGGTCCTTCAGTAGCACAGTCTAGCGCACGGCGTTGCAGGTGTCCTCCAGTGCCTGAGGCCACGGCAGGTCGCGGGTCCCACTGTGCTCTAGTTCAGGGC GGAGTGGGTCTGAGGTCTTCTCCTGCCTCAGTCTAGGGCGCTGGAGAGCGGGGATCCT |
| 169 | chr21: 13989500-13992000 | GGGTTGGTCCTAGAAAGCGTGAGGATCGCCGAGTGCACTGCCCTCCCAGCCTAGGGTCCACTCTTCCTTGGCCCGAGCCCAGAGCTCGGGGTTTCAGGCGCTG GGCCCTGTGCAGCTGCCCAGAATAGGCTGAGCGGCAGGTTCCCGCCCTGGCAAGGGATCCAGCAGTGGAATCCTCACTGCTGTTGGCTGCGGGCAAGGTCAGC GGGGTTTCCATCGCTGCTGGTGGGAGCCACCTGGCGGTGGTAGCTGCAAGTGAGCGCGTGGCAGAGACTGGCAGGGCTGGTCCCAGACACCCTGAGGGTCTCT GGGTGCATCGCCCTACCACCCTAGGGTCTGCTCTTCCTTAGCCTGCTCCCAGGACGCGGTGTACGAGGGCTAGACTCTGAGCAGCCTCCAGGATGGGGCTGAG CAGCGGATTCCTGCCCTGCTGCAGCTACAGTCTGAATTAGGCGCCACCGCAGTATCTGGCCCTGGGGTACGTGCTACTGGGTGGCATGGACAGAGATGGGGGC TGCCACAGCTGCTATGGGGCTGAGCAGCCGATTCTCGCCCTGCTGCAGCGGGCGACCGCTGCAATCCCCAGCGCTATGGGACCGACCACCTGACTTAGATGCC TTGGAGGCATCCGGTCCTGGGGTCTTGCTGCTGGTGTCTGCGGGCAGGGTCACGGCTGCCACTACTACTGCTGTGCGCCATGGGCAGGTGCCAGCTGCAGCTG AGTCCGAGGCAGATGCTGTCAGGGCTGGTCTGAGGTTGCCTAAGGGTGGCTGAGTGCACCACGCTTCCACCCCAGGGTCCGTTATTCCTAGGCCGGCTCCCAG ATTGCAGGGTTGTGGGCGTTGGACACTGTGCAGCCATGAGGATCTGGTTGGGTGCAGATTCCCGCCCTCCTGCAGCTGAGAAGCCAATCTCATAACAGGCGCT GCAGTGACCTCTGGCTCTGCGGTCCGCGCTGCTGCTGGAGCTGGCAGAGAACAGAGCTGCCACCGCTGCTGCTTCCAGGAGTGTGCAGCTGGCAGCTGCAGCT GAGCCCGTGGCGGAGGCTGGAAGGCCTTATTCCAGAAGCCTTGAGGGTCCCCGAATGCACCGCCCTCCCACCCTAAGGTCCAGTCTTCCTTGCCCGCGCCCAG AGAGTTGGATTGCAGGCGCTGAGCACAGTGCAGGTGCTGGGATGGGGCTAAGCTGAAAGTTTCCGCCCTCTGGCTGCTGCGGGGCCGACAGCCTGAGTTATGC GCCGCGGCGGCTTTTGGTCATGGGATCCGCACTGCCGGTGGCTTGCACAGGGTCGGGGGCTGCCACAGCTGCTATAGTTCACCGTGTGCACGTGGCAGCCGCC CCTGAGCCCACCGCTGAGGCTGCAGGGCTGGTCCGGTCCCAGACGGCCTGAGGGCCATTTGCCCGCGCCCAGATCCGGGTGGCTGCGCTGGGCACTGTGCAGC CTCCCGGAATCCGCTGAAGGGCACGTTCCCGCTCTCCTACAGCTGTGGGCCGACTGCCTGATTTTGGCCACTAGGTGGAGTCTGGCTCTAGGGTTTCGAGGCC GCTGGTGTTGGTGGGCGGAGTCCGGGTTTGCCACCGCTGCGCTCCATGAGCAGGTAGCAGCTGCAGCGGAGCTTTAGACCGAGGCTGGCAGGGCTGGCCCCAG |

TABLE 4C-continued

| SEQ ID NO | GENE NAME | SEQUENCE |
|---|---|---|
| | | ACGGCCTGAGGGTCAGGGAGTGCAGGGTCCTCCCACCCTAGGTCCGCTCTTCCTTTCCCCTTACCCAGAGCGGGTTGTGCGGGCTCTGGGCTCTGTGCCGGCG<br>CTGGGCTCTGTGCAGCCGCCGAGATGGGGCTGAGCAGCGGATTTCCTCCCTGCTGCAGCTGGAGGACGATTACCTGCACTAGCCGCTGAGGCGGCATCTGGCC<br>CTGGGTTACTGCAGCTGGTGACGCGGGCAGGGTCAGGGTTGGTTGCAGGTGGCAGCTGCTGCTAAACCCATTGCGAGCCTCAGGGTCACCAAGTTCACCGTCC<br>TTTCATCATAGTATCTGATCTTTGGCCCGCGCCCAGAGTGCGGACTGGCCTGCGCTGGGGACTGCATAGCTTCTGGGGGCCGGTCAGCGCCAGTTTCACGTCC<br>TCCTGCAGCTGCGTGGCCTAAGGTCTTAGGCGCCGCGGCGCTATCTGGCCCTGCTGTCGACGCTGCTGGTGGTGGGGACAGGGTCAAGGGTTGCCACTGCTGC<br>TCCCGTGCGCCATCGGCAGGTGGCAGTTGCAGATGAGCCCACAATTGAGGCTGTTGGGGCTGCTCCCAGGTTGTTAGAGGGTCGCCGAGTTCACCGACATGCC<br>ACCCTAGGTTACGCTCTTGGCCCGCACCCAGAGCGCCGGGTTACGGGTCCTGGGCCCTGTGCAGCCACGGGGATGGTGCTGAGTGCAGGTTCCCGTCTTCCTG<br>AGATGCGGGGCGACCACTGGAATTAGCCTCTGTGGTGGTATCTGACCCTAGGGTCCGAGCTGCTGGTGGCGTGGGCGGGGTCGAAGTCGCCTCTGTTGCTGCGGCGTGC<br>CATTTGCACCGTCCTCTGGTAC |
| 170 | chr21: 13998500-14000100 | AAATACTCTACTGAAAAAACAGAAATAGTAAATGAATACAGTAAAGTTTTAGAATACAAAATCAGCATAGAAAAATCAGTCGCATTTCTATACCCAACAGCAT<br>ACCATCTGAAAAAGGAATCAAGAAACCAATCCCATTTAAAATAGCTATAAAAAAATGCCTGGGAATAAACTAAGCCAAATAAATATGTCTAAAATGAAAACTA<br>TAAAACATTGATAAAAATCAATTGAAAAAGATACAAATAAAGGGAAAGTTATCCCATTTTTATGAATTAGAAGTATTAATACTGTTAAAATGACCATCATACT<br>CAAATCAGTCTATAGGTCCAATACAATCTCTAACAAATTTCCAATGTAATTCTTCAGAGATGTTAAAAAAGGTTTAAAAATCGTTCTGCGGATGTTAAAAGG<br>ATTTTTAAAACGCTTTTTTCGTTCTGCAGGCGAAGGCTGTGGCCGTGCTCCCGCCGGCCAGTTCCCAGCAGCAGCGCATTGCCCCTGCTCCACGCCTTCGCTC<br>CAGGCCCGCAGGGGCGCAGCCCCGCGGGAATCAGCACTGAGCCGGTCCCGCCGCCGCCCCAGTGTCCGGGCTGCGACTGCGGGGAGCCGATCGCCCAGCGATT<br>GGAGGAGGGCGACGAGGCCTTCCGCCAGAGCGAGTACCAGAAAGCAGCCGGGCTCTTCCGCTCCACGCTGGCCCGGCTGGCGCAGCCCGACCGCGGTCAGTGC<br>CTGAGGCTGGGGAACGCGCTGGCCCGCGCCGACCGCCTCCCGGTGGCCCTGGGCGCGTTCTGTGTCGCCCTGCGGCTCGAGGCGCTGCGGCCGGAGGAGCTGG<br>GAGAGCTGGCAGAGCTGGCGGGCGGCCTGGTGTGCCCCGGCCTGCGCGAACGGCCACTGTTCACGGGGAAGCCGGGCGGCGAGCTTGAGGCGCCAGGCTAGGG<br>AGGGCCGGCCCTGGAGCCCGGCGCGCCCCGCGACCTGCTCGGCTGCCCGCGGCTGCTGCACAAGCCGGTGACACTGCCCTGCGGGCTCACGGTCTGCAAGCGC<br>TGCGTGGAGCCGGGGCCGAGCGGCCACAGGCGCTGCGCGTGAACGTGGTGCTGAGCCGCAAGCTGGAGAGGTGCTTCCCGGCCAAGTGCCCGCTGCTCAGGCT<br>GGAGGGTCAGGCGCGGAGCCTGCAGCGCCAGCAGCAGCCCGAGGCCGCGCTGCTCAGGTGCGACCAGGCCCTGTAGCTGTGACTTGGCTGTGGGGCTGGCCCG<br>CCTCCCTGACCCCTGTCAGGCGGAGCAGCTGGAGCTGACCCACGGGCCTGGGCTTTCGAGCGCTTTGTCCAGGCGCTAATGATGGGAAGGTGAAAGGTGGGGG<br>TGGCCACACCCTGCAGTCAGGGTGGCAGGTGTCAGAGGCCACATGCAACCCACTGGTTTTGTCTTTTCCAGGATGCTGATAAGTTTCCCGCGGCCCCCGGAGC<br>AGCTCTGTAAGGCCCTGTAATTGCCTTTCGTTCCCTTCTGCTCTATTGAGGAGTGGGAAGATGACAAAGTGTTTTTGCTCAACCCGAAGGAAAATGCACATGG<br>GAGGACACACCGGGTTACTATTTGAGTAGCCCAGACAGGAGAGCAGCGGTCTGCT |
| 171 | chr21: 14017000-14018500 | TGGGTGGATTGCTTGAGCCCAGGAGTTCGAGACCAGCCTGGACAAAATGGCAGAAACTCCATGTCTACAAAAAATACAAAAATTAGCCGGGCATGATGTTCTG<br>CGCCTGTAGTCCCAGCTACTCAGGAGGCTGAGGTGGGAGGATCGCTTGAGCCCAGGAGGCGGAGTTTGCAGTGAGCTGAGATGTCACTGCATTCCAGCCTGGG<br>AGACAGAGCCAGACTCTGTCTCAAAAGAAAAAAAGAAAAAAAAAAAAGAAAAGAAAAAACGAAATTGTATTCTGAATACATCTTCTAAAACACTACATTTACT<br>TGCACTATATTAAACTGGTTTTATCCTGACCACAATTGCAGGTGAAAGATACCACTGTTGTTCTATTTTTCTGGTAAGTAGAGTGAGCCATGTCTTCCCCAGG<br>GAAAGACGCCTCCTAAAAATTTGTAGGACCACCTTTGGTTTTCTTCCAGATATTTTTTTTGTCATCGCTTTTCCTGCGCCCAATTCCCATCTGTCTAGCCCTT<br>CTGCCTCCGCTGGTCTTTTTCGCGAGCCTCTCCCCAGCCGCAGGTATTCGTCTGGGCTGCAGCCCCTCCCATCTCCTGGGGCGTGACCACCTGTCCAGGCCCC<br>GCCCCCGTCCAACCCGCGGAGACCCGCCCCCTTCCCCGGACACCGGGTTCAGCGCCCGAGCGTGCGAGCGCGTCCCCGCTCGTCGCCCGGCTCGGCGTCGGGA<br>GCGCGCTCTGTGTGGTCGCTGCTGCAGTGTTGTTGTGGCTGTGAGAAGGCGGCGGCGGCGGCGGAGCAGCAGCCGGACCAGACTCCCTAGTAGCTCAGGCGCT<br>GCCCTGCGCCGGCCCTGGCAGGGAGCCTGGTGAGATGGTGGAGGAGGAGGCTGTGCCGTGGCTGGCCTTGCTGTGTCCTGCTGCCTGGTTAGAACCCCATCCC<br>CGTCCCCCGTCTCCTCCGGGGGGTGAGGAGGAGCTGGAAGAGGGGCCGGCCTCTGTCCGGCCCGGCCAGGCGGCAGTCACCCTCTGAGGAGGCAGCGCCCGGG<br>GAGGGGCCTCCCAGGCGGCCGCCGCCGCCAGGGGGAGGCGCTGGGAGTGGGAGTGGGAGCGGGACCTCAGCTGCCAAGCTCGGCCCGGACCCTAGGTGCGGGG<br>GAGGCGGGGTCCCGGGCTCGGGCTGCCTGCCCGGACCTGGCGGGGATGGGCCCGTGCGGCTCCGGGTGTGGGACGTACCCTCAGAGCGCCCGGGGTTATTCCC<br>ACTGACTCCAGGGAGGTGAGTGTGCGCCCTTCGCTCCCTGCCGTGTCTGTGAGGGTCCATCGTTGCCGGAGACTGGAGGTCGGGGGCCATGGGAGCCCCGGGG<br>CGAACGGTGCGGACATGGGCCTTGTGGAAAGGAGGAGTGACCGCCTGAGCGTGCAGCAGGACATCTTCCTGACCTGGTAATAATTAGGTGAGAAGGATGGTTG<br>GGGGCGGTCGGCGTAACTCAGGGAACACTGGTCAGGCTGCTCCCCAAACGATTACGGT |
| 172 | chr21: 14056400-14058100 | GTCTCTAGGACACCCTAAGATGGCGGCGAGGGAGACGGTGAAGGTTGGCTCCCGCCTGTCTGGGCTCTGATCCTCTGTCTCCCCCTCCCCCTGCGGCCGGCTC<br>ATGGCCTGGCGGAGGCCCGAACCAAAGACCTCCGCACCGCCGTGTACAACGCCGCCCGTGACGGCAAGGGGGCAGCTGCTCCAGAAGCTGCTCAGCAGCCGGA<br>GCCGGGAGGAACTGGACGAGCTGACTGGCTAGGTGGCCGGCGGGGGACGCCGCTGCTCATCGCCGCCTGCTACGGCCACCTGGACGTGGTGGAGTACCTGGT<br>GGACCCGTGCGGCGCGAGCGTGGAGGCCGGTGGCTCGGTGCACTTCGATGGCGAGACCATGGAGGGTGCGCCGCCGCTGTGGGCGCGGACCACCTGGACGTGG<br>TGCGGAGCCTGCTGCGCCGCGGGGCCTCGGTGAACTGCACCACGCGCACCAACTCCACGCCCCTCCGCGCCGCCTGCTTCGAGGGCCTCCTGGAGGTGGTGCG<br>CTACCTGGTCGGCGAGCACCAGGCCAACCTGGAGGTGGCCAACCGGCACGGCCACATGTGCCTCATGATCTCGTGCTACAAGGGCCACCGTGAGATCGCCCGC<br>TACCTGCTGGAGCAGGGCGCCCAGGTGAACTGGCGCAGCGCCAAGGGCAACACGGCCCTGCACAACTGTGCCGAGACCAGCAGCCTGGAGATCCTGCAGCTGC |

TABLE 4C-continued

| SEQ ID NO | GENE NAME | SEQUENCE |
|---|---|---|
| | | TGCTGGGGTGCAAGGCCAGCATGGAACGTGATAGCTACGGCATGACCCCGTTGCTCCCGGCCAGCGTGACGGGCCACACCAACATCGTGGAGTACCTCATCCA<br>GGAGCAGCCCGGCCAGGAGCAGCTCATAGGGGTAGAGGCTCAGCTTAGGCTGCCCCAAGAAGGCTCCTCCACCAGCCAGGGGTGTGCGCAGCCTCAGGGGGCT<br>CCGTGCTGCATCTTCTCCCCTGAGGTACTGAACGGGGAATCTTACCAAAGCTGCTGTCCCACCAGCCGGGAAGCTGCCATGGAAGCCTTGGAATTGCTGGGAT<br>CTACCTATGTGGATAAGAAACGAGATCTGCTTGGGGCCCTTAAACACTGGAGGCGGGCCATGGAGCTGCGTCACCAGGGGGGTGAGTACCTGCCCAAACTGGA<br>GCCCCCACAGCTGGTCCTGGCCTATGACTATTCCAGGGAGGTCAACACCACCGAGGAGCTGGAGGCGCTGATCACCGACGCCGATGAGATGCGTATGCAGGCC<br>TTGTTGATCCGGGAGCGCATCCTCAGTCCCTCGCACCCCGACACTTCCTATTGTATCCGTTACAGGGGCGCAGTGTACGCCGACTCGGGGAATATCGAGTGCT<br>ACATCCGCTTGTGGAAGTACGCCCTGGACATGCAACAGAGCAACCTGGAGCCTCTGAGCCCCATGAGCGCCAGCAGCTTCCTCTCCTTCGCCGAACTCTTCTC<br>CTACGTGCTGCAGGACCCGGCTGCCAAAGGCAGCCTGGGCACCCAGATCGGCTTTGCAGACCTCATGGGGGTCCTCACCAAAGGGGTCCGGGAAGTGGAATGG<br>GCCCTGCAGCTGCTCAGGGAGCCTAGAGACTCGGCCCAGTTCAACAAGGCGCTGGCCATCATCCTCCACCTGCTCTACCTGCTGGAGAAAGTGGAGTGCACCC<br>CCAGCCAGGAGCACCTGAAGCACCAGACCATCTATCGCCTGCTCAAGTGCGC |
| 173 | chr21: 14070250-14070550 | TAAAAATAAATTGTAATAAATATGCCGGCGGATGGTAGAGATGCCGACCCTACCGAGGAGCAGATGGCAGAAACAGAGAGAAACGACGAGGAGCAGTTCGAAT<br>GCCAGGAACGGCTCAAGTGCCAGGTGCAGGTGGGGGCCCCCGAGGAGGAGGAGGAGGACGCGGGCCTGGTGGCCAAGGCCGAGGCCGTGGCTGCAGGCTGGAT<br>GCTCGATTTCCTCCGCTTCTCTCTTTGCCGAGCTTTCCGCGACGGCCGCTCGGAGGACTTCTGCAGGATCCGCAACAGGGCAGAGGCTATTATT |
| 174 | chr21: 14119800-14120400 | CGCCACCACGTGCGGGTAGCGCCGCATCGCCCCAGCCGTGTTCCTTGGTCTCCGTCTCCGCCGCGCCCGCCTGGTGAACTGGAGCACAGGGACCATAGTTCTG<br>GAAATTTATCCTTTTTCTCTCCATGGATTCAGCAGCAGTGTCTAAAAGAAAAAAATTCATCAATCATTTATGTATATTTTAATATAAAGGTAAAACACTGCGA<br>ACCAGTGGAACCGGATAGAAAGTAATTCAGTTTTACAGAACACAACTGTTTTTCAGGCTCTTTTATTAAATATAAAAGAGCCATATATATTTCTGTGGAATTC<br>CCCTTTTACTTAAGAATTCATTATCAGCGAATTAGTTTAAGGAGGCTGTTTTGTTAGAGGCTGTGGTTGCATTCAAAAATTGGAATAGGAACAATGACTTGTA<br>AAAATTCAACATTTTATTTTATTTTTGAGATGGAGTCTCGCTCTGTCGCCCAGGCTGTAGTGCAGTGGCGCGATCTCGGCTCACTGCAACCTCAGCCTCCCGG<br>GTTTAAGGAATTCTCTGCTTCAGCCTCCTGAATAGCTGGGATTACAGGCGCATGCCACCAAGCCCAGCTAATTTTTTTTGTATTT |
| 175 | chr21: 14304800-14306100 | CCCTGAACAGTCAGAGTTTACTGCCCACTTTTGCTGGAGGAGAAGCTCCTGAACAACTAGAGAGACTGTGGTTCCCAAAGAGCAGCCTGTAGGCCTGAGGACT<br>GCTCTATGACCGGCGTCAGTCCCTGCCTCCCTCCCTCCGTCCCTCCTTCCCTCCTTCCTTCCCAGGCCTTCTCTGACTACCAGATCCAGCAGATGACGGCCAA<br>CTTTGTGGATCAGTTTGGCTTCAATGATGAGGAGTTTGCAGACCATGACAACAACATCAAGTGAGTCCACTTGGATGCCCCCTGCACGAGGCACGACTCCCCC<br>TCCTCGCTGCTGAAGTCCCATGGGGGCAGCTCCCTTAGTCCTTGCCGGGAGATAACAGGTGTTTCCAGTTGCATGAGGGTGCTGAGGCCCCCAGTGAGAACCA<br>GGGGAGGAGCACTGAGGCCTCAGATGAGCACCGGGGGAGGAGCCCTGAGGCCCCAGATGAGCACCAGGGGAGGAGCACTGAGGCCCCAGATGAGCACCGGGGG<br>AGGAGCGTTGAAGCCCCAGATGAGCACCAGAGGAGGAGAGCTGAGGCCCCAGATGAGCCCCGGGGGAGGAGCTCTGAGGCCCCAGACGAGCACCGGGGGAGGA<br>GCGCCGAGGCCCCAGATGAGCACCGGGGGAGGAGCGCCGAGGCCCCAGATGAGCAGTGGGGGAGGAGCCCCGAGGCCCCCAGATGAGCAGTGGGCGGGGCAGG<br>GAGCGCCGAGGCCATCCCCCTTGCTCTTGCAGCGCCCCATTTGACAGGATCGCGGAGATCAACTTCAACATCGACACTGACGAGGACAGTGTGAGCGAGCGGG<br>GCTGTGCGGGGTCATGCAGGCACCCTGTTCCCAGGCAGCTCAGGCCGCGCCCATGGCTCGGTCTGTGGTGGGCCTGTGCGGTGGGGCTGGGAGAGGCCCCTCT<br>GTGGAGCTAGGAACAGTCGCTTTTCTTGACCCTCCCCATCATGCCCTCCAGCCCATGGCGCCCACATCCTGAACTAAGCCCCTCTGGGAGCCCTGTGGGGAGA<br>GCGCCTCCTGTCTCCCCCAGACCCTCTGGAAACTGACCTTGGCGTTTTACTCTGCAGCCCAGCGCGGCTCTGAGGCCTGCTGCAGCGACCGCATCCAGCACTT<br>TGATGAGAACGAGGACATCTCGGAGGACAGCGACACTTGCTGTGCTGCCCAGGTGAAGGCCAGAGCCAGGTGCGGGGCCTGCCCATCCCCCCAAAGCCTCTGC<br>CGAGGAGGTGCAGCCCCCAGAACACCCGTCAGATGCCCAGACGCCCTGCTGTTTGTTATGCCGG |
| 176 | chr21: 15649340-15649450 | TTTGGGCCACGAGGCAAGTTCAAAGCGGGAGACTTTTGTTTTATAAAATGATGGTGAGCAGCTCCGGTTTTATGTCAAACATCAGGGTTTCGTGCAGGATATA<br>AACATTT |
| 177 | C21orf34 | ATTGCCGTACTTTGCTTCCCTTTGTATGTATTTCTTGTATGCTGCCGAGTCACTGATGGCTAGCTCTGTCTGGCAAGTAATTCAAAAATGCTGTTTATGTAGA<br>AAGGAAAGGTAGGGACTTTACCACACTCTGTCATTAAAGGGAGCAATTGAAGAACAAAGGAACTGAGTAAATACCTATATATTGCCTTTTGTGTTGCGAAACA<br>CTGTAGCACAAACACATTTGTGTTCAGCCAAATGTTTTACTTCCTTTTGTAATAACGCATATAGTAGGTTGTCTCCACATATGTACAAGAATCCATATTTTAT<br>TTAAACGTATATAGTCAATTGTTCATATTTATAGGCTGCAAACATTTCTCAATCTCAAAGACTTTTACATATCCACTCCCACACAGCTATTTGTTATTATTTT<br>AAAAGTTCTTAAATTAAAAAAAAAAATAAAATATACTAATATCTCTGTTGGTTGATTTTATTAAGCAACTTAGGATTTCAACACAGTTTAAATCATATTGATG<br>ACTCAGATCCTGGCAGGTCTTACAATTCCTGTGAAATGAGAGCACAGCTAATAAAAATATTAAGCAATTACTTTTATTAAAATCATAGGGTTTTTTTCATTAT<br>CACATAGAAATGATTGATCTATACAGATTGGTCTCACTCATGTGTCTTTTGGGCTGCTTGGGAGCTTCATGTAGAAGTGGAAAGTCCCCTTTGCTCTTCCTTC<br>GACCAAGGTGGGGAAAATGAAGGCATAGAATACAATCTAGGGCTATTAAAGAATTGCTGGCATTACTTCTCTCTATCACGTGTGAGCCTGGCTGCCTGCTTCC<br>TGAGGTAGGGGATCCAGGATGAGACTGTGCCGGAGCCTGTTTCCACAACTGCATTTGGAGATCCGTCTTATTGATTAGCGGGGGAAAGGGGTGGGGATCAGGA<br>GTGTGAGGTGAGGGGAGGACCAACTGACGACTGGCTCAATGAAGCACAAGACATTTTCTTCCGGAAAGATGTCAAACAACTGAGAAACAGCCAGAGAGGAAGT<br>AGAAAGGTGGAAAAATGAGGAGACCCTGGAAGAAATGAAGGCATTTCCTATGAGACAGCCTTGGGGCTTTTTTCTTTTCTTTCTTTTTTTTTGCTTCCATCAT |

TABLE 4C-continued

| SEQ ID NO | GENE NAME | SEQUENCE |
|---|---|---|
| | | CTGACCTGCAAAGGCTAGAGTGACAGCGTCATGCAAATGCTGCAGTCCAGCAGGTCTGGGAGAGGGTGGATGCTAGACTGTGAGTTAATGTTAATGATGAGCG CAGTGAAAATACCAGCCGCTGCCACCCCCTGCTCACAGAAGCGCTCTGAGTCAGCATCAGATGCTTTGCCTCGCCTCTCGCTGTGTATCTGTATGCCTGTGTG CGCGCGCGTGCTCGCTCGGGCATCCGTGTCTAGCCGAGGGGAGGGGGTGGCGTGTGAGTGCGTGGAGGGTAAAAGCCAGTCAGTCAGTGAGAAGCAAAGGTAC GTTGGAGAGCAACTAAAATCTGACTGATTTCCATCTTTGGAGCATCAGATGTATTCCC |
| 178 | BTG3 | GCAGCCTCCTCCTGAAAAATGTAAGCCATTTCCACTTTGTAAAGCTACGTTTATATTCCACCACGATACGATGGAAAAGAAAACCCAAGGCAATTTAATATAC GGGTTGGGAAGAAAGTTTTGCTGATGGAACTACATTAGCCTCCACTCCAGCAAAGCAAACAAGGAACCACACTAAAGAAATGTACTGAATCTTTTAA |
| 179 | CHODL | TGCCTGAGCGCAGAGCGGCTGCTGCTGCTGTGATCCAGGACCAGGGCGCACCGGCTCAGCCTCTCACTTGTCAGAGGCCGGGGAAGAGAAGCAAAGCGCAACG GTGTGGTCCAAGCCGGGGCTTCTGCTTCGCCTCTAGGACATACACGGGACCCCCTAACTTCAGTCCCCCAAACGCGCACCCTCGAAGTCTTGAACTCCAGCCC CGCACATCCACGCGCGGCACAGGCGCGGCAGGCGGCAGGTCCCGGCCGAAGGCGATGCGCGCAGGGGGTCGGGCAGCTGGGCTCGGGCGGCGGGAGTAGGGCC CGGCAGGGAGGCAGGGAGGCTGCAGAGTCAGAGTCGCGGGCTGCGCCCTGGGCAGAGGCCGCCCTCGCTCCACGCAACACCTGCTGCTGCCACCGCGCCGCGA TGAGCCGCGTGGTCTCGCTGCTGCTGGGCGCCGCGCTGCTCTGCGGCCACGGAGCCTTCTGCCGCCGCGTGGTCAGCGGTGAGTCAGGGGCCGTCTCCCCGAA GAACGAGCGGGGAGAGGGGACCACGGGGCGCGGCGGGCAGCCTGTTCTCGGGCGGAGGCTCTCCGGGGCGTTGGAAACCTGCATGGTGTAAGGACCCGGGAGG AGGCGGGGAGAAATTGATTGTGCTGTTCTCCTCCCTCTCTTCTCTAACACACACGCAGAAAAGTTTAAATTTTTGTGAAGCGCTTGCTTACGTAGCTGCGGAG CGAGCCTCTGCTTCATTACGAGCGGCATAGCCTTTTTCAGGAGTGATTTCCACTTTCTTTGTGAGAGAGTTGACCACAC |
| 180 | NCAM2 | TTCAATTTACACTCGCACACGCGGGTACGTGGGTGTTCGGGGTAGGGCACTGATCTGGGGAAGGTCTCCCCCCCGCGACCCAACTCATCTTTGCACATTTGCA GTCCTCCCTCGGTGCACTCCTGGCGGGGATCTGGCCAGTGCAGCGCACTGGGACCGAGGGCAGAGCCCGCGGAGTGAGGCCAGGAGAGACTTCAGGCCTCTAA GGACACAGCTGAGGCTAAGGCTGAGTTGAACGCAGCCCCTCCCGCGGCTCGTCCCCTCTCCAGTGTCTCTCCCGTAAGGTGCCGCTCCCAACAGCAATGGGTC GAGATGTAGAGGAAACACTCTGTACGTTATTTTTCCGCCCACCCTTTAGCGCCTGAGGAGACAGACAGTGTAGACTTTAGGGTACAATTGCTTCCCCTCTGTC GCGGCGGGGTGGGGAGCGTGGGAAGGGGACAGCCGCGCAAGGGGCCAGCCTGCTCCAGGTTTGAGCGAGAGAGGGAGAAGGAGGTCCACGGAGAGACAAGAAT CTCCCTCCTCCCACGCCCAAAAGGAATAAGCTGCGGGGCACACCGCCCGCCTCCAGATCCCCCATTCACGTTGAGCCGGGGCGCG |
| 181 | chr21: 23574000-23574600 | TCATTATCCGATTGATTTTCCTGGTATCACATCACTTAAGTTTAAGTAGCTCTTATGTTACTTAGTAATGACTGCAAAACACGAGTTGTGATGCGGGCAATTT GGATACAACAAAAAGAAGCCATTAAGTTTGTTCGTTAGTTAACAGGTGAAAGCTCTCAAGTTATTAAGGATAAAAATGCTAGTATATATATATATGGTTTGGA ACTATACTGCGGATTTTGGATCATATCCGCCATGGATAAGGGAGGAATACTATAATCAGGTTTGTTTTAAATTCCATGTCTAATGACTTCGTTATCTAGATCA CCTGTAGAGCTGTTTTTATTGTAGGAGTTTTCCTTGGTTTTAATCTTTTGATTTGTTTTTCATGTTAATACTGAAATTTTTAAAAATTGCATATTGTACTTCC TATATGAAAATTTTACTATGTATTTTTATTTTTATTTTCCTTTTCCTTTAGGAAGAATTAGTTTGTTCCCTGACAGAGTTAGAGTAAGGGCAAATTACTTGTC TCTATAAACAACTCAGATGTTTTGAGCCGGTGTTGTAGGGGTTATCTTTTTCTGGTTTTGCATTTTATTATAGGACATAGTGCTT |
| 182 | chr21: 24366920-24367060 | AGAAAGAAGAAATCCGGTAAAAGGATGTGTTATTGAGTTTGCAGTTGGTGTTTGATCTTGCACAGATTTTCTCAGGGGCCTTAAGACCGGTGCCTTGGAACTG CCATCTGGGCATAGACAGAAGGGAGCATTTATACGCC |
| 183 | chr21: 25656000-25656900 | CGAAGATGGCGGAGGTGCAGGTCCTGGTGCTCGATGGTCGAGGCCATCTCCTGGTCCGCCTGGCGGCCATCGTGGCTAAACAGGTACTGCTGGGCCGGAAAGT GGTGGTCGTACGCTGCGAAGGCATCAACATTTCTGGCAATTTCTACAGAAACAAGTTGAAGTACCTGGGTTTCCTCCGCAAGCGGATGAACACCCACCTTTCC CGAGGTCCCTACCACTTCCGGGCCCCCCAGCCGCATCTTCTGGCGGACCGTGCGAGGTATGCCGCCCCACAAGACCAAGCGAGGCCAGGCTTCTCTGGACCGC CTCAAGGTGTTTGACCGCATCCCACCGCCCTACGACAAGAAAAAGCGGATGGTGTTCCTGCTCCCTCAAGGTTGTGCGTCTGAAGCCTACAAGAAAGTTTGCC TATCTGGGGCGCCTGGCTCACGAGGTTGGCTGGAAGTACCAGGCAGTGACAGCCACCCTGGAGGAGAAGAGGAAAGAGAAAGCCAAGATCCACTACCGGAAGA AGAAACAGCTCATGAGGCTACGGAAACAGGCCGAGAAGAACATGGAGAAGAAAATTGACAAATACACAGAGGTCCTCAAGACCCACAGACTCCTGGTCTGAGC CCAATAAAGACTGTTAATTCCTCATGCGTGGCCTGCCCTTCCTCCATCGTCGCCCTGGAATGTACGGGACCCAGGGGCAGCAGCAGTCCAGGCGCCACAGGCA GCCTCGGACACAGGAAGCTGGGAGCAAGGAAAGGGTCTTAGTCACTGCCTCCCGAAGTTGCTTGAAAGCACTCGGAGAACTGTGCAGGTGTCATTTATCTATG ACCAATAGGAAGAGCAACCAGTTACTATTAGTGAAAGGGAGCCAGAAGACTGATTGGAGGGCCCTATCTTGTGAGC |
| 184 | MIR155HG | GCCTGAAGACCATTTCTTCCTCTCTTAGGGACCTGCTGGTCTCCAGCTGATTCGGTCCAGGAGGAAAAACCTCCCACTTGCTCCTCTCGGGCTCCCTGCAAGG AGAGAGTAGAGACACTCCTGCCACCCAGTTGCAAGAAGTCGCCACTTCCCCCTCCAGCCGACTGAAAGTTCGGGCGACGTCTGGGCCGTCATTTGAAGGCGTT TCCTTTTCTTTAAGAACAAAGGTTGGAGCCCAAGCCTTGCGGCGCGGTGCAGGAAAGTACACGGCGTGTGTTGAGAGAAAAAAAATACACACACGCAATGACC CACGAGAAAGGGAAAGGGGAAAACACCAACTACCCGGGCGCTGGGCTTTTTCGACTTTTCCTTTAAAAAGAAAAAAGTTTTTCAAGCTGTAGGTTCCAAGAAC AGGCAGGAGGGGGGAGAAGGGGGGGGGGGTTGCAGAAAAGGCGCCTGGTCGGTTATGAGTCACAAGTGAGTTATAAAAGGGTCGCACGTTCGCAGGCGCGGGC TTCCTGTGCGCGGCCGAGCCCGGGCCCAGCGCCGCCTGCAGCCTCGGGAAGGGAGCGGATAGCGGAGCCCCGAGCCGCCCGCAGAGCAAGCGCGGGGAACCAA |

TABLE 4C-continued

| SEQ ID NO | GENE NAME | SEQUENCE |
|---|---|---|
| | | GGAGACGCTCCTGGCACTGCAGGTACGCCGACTTCAGTCTCGCGCTCCCGCCCGCCTTTCCTCTCTTGAACGTGGCAGGGACGCCGGGGGACTTCGGTGCGAG<br>GGTCACCGCCGGGTTAACTGGCGAGGCAAGGCGGGGGCAGCGCGCACGTGGCCGTGGAGCCCGGCCTGGTCCCGCGCGCGCCTGCGGGTGCCCCCTGGGGACT<br>CAGTGGTGTCGCCTCGCCCGGGACCAGAGATTGCGCTGGATGGATTCCCGCGGGCAGAGGCAGGGGGAAGGAGGGGTGTTCGAAACCTAATACTTGAGCTTCT<br>TTGCAAAGTTTCCTTGGATGGTTGGGGACGTACCTGTATAATGGCCCTGGACCAGCTTCCCTGTTGGAGTGGCCAGAGAAGTGTGTAAAACACACTAGAGGGG<br>CAGGGTGGAAAAAGAGACTGCCTTCAAAACTTGTATCTTTTCGATTTCATTTTGAAAAATAACTACAAATCTATTTTAATTTTACAAAGTTAGACTCATAGCA<br>TTTTAGATATCAATGTCTTCATTTAACAGAAGTGAAGATGGAGCAAACGCTCAATCAGCGTCTGTATTTATTCGCTCCTGTTGTGCCAGGGTGCGTTTTTGCC<br>GAGCGGTTGCCTTTCTTTACTCACAAAACCCCCTTGATGTCTGTCCTCCACGTTTTACGAGGGAGAGCCGGATCTTTTGAAGTTTGTATCATCTAAAGCAGGT<br>ATATTGGGATGACTATGGATAGAATTTAACCTGAAAACACTGAAGTTGACAGCTGACAAAG |
| 185 | CYYR1 | CATAACAAGAGTCATTCTAATGTGATTATAAAGGACCCGAAGCTTTGCTTTTAAAATTCAATACTTAGGTAGAAAGAAAATGATAACTTTTTCCCTTTGATTT<br>TTATTCACTATTTTTATAACACTAGCAGCCCTGAGACACCGGATTGGAAATATCTATGCCTCTTGATGTTACCTGGGCACCACTGCATCACAGTCCT |
| 186 | chr21: 26938800-26939200 | AATAGTAATTGCCAACAGTCAAGATATGTACTACCACCAAATTCCGTGTTATTTGTGATCAAAAGATATACACAGATACTTGAAAACTGATTTCTACGTTGCA<br>TATGGGAAAAATACCTCATTTTTCTCAGCTGTCCATTATTTTTGAGATATTATGTGCAGTGATAGTAAGAACAAGCAGATTTGGAACACATCAGCAATAATTT<br>TTTCAATCAGAGTCCTGCCAAAATGAAAGAATTTGACAGTATCCGGCACCCTGTACTCATGCTTGGCTTCTGTAGAAACTGTGGCTTGCAAAAGGGCAGCTGG<br>GTACTGTGTTTTGGTACCTCATTCTTTAAACGTATAATGGGAATCTGGTTGGTTCAGGAAAACCCTTGCCTACTTATTATTACTCTGTTTT |
| 187 | GRIK1 | GGCCCATACTTAATGTATTTTTAAACGTTTTAACATTTACTAATATAGAACCTTCTATTGCCTATTTCCTTCTGGTTTATTCCCTTTCCTTCTGTCATTGAAG<br>AAATGGTTCTAGTGGTAGAAATACTCCACGATTGAGAAGAATGTGGGAAGAAAGGAGGGCTGGTGGGTAAGAATTGCTCATGATGTCTCCCTCTGAATTCTGT<br>GCTCTCACAATGACACTCCAATGTGTGGTTTGACGCCTGGAAGA |
| 188 | chr21: 30741350-30741600 | TGCTTCAACCGGAAATGTGGTTGAATTACCCTTACAGTGAACCTGATCAGTGGTAACAGGAGATGCTAGAACAGGAAAAGACAAGTTTCCCCTTTCCTCCCTA<br>TCCCATCAATTACTTTGAGGTGTATTTTTTCTTTGCAACCCCTCCAGAGAAGTCGGCAATGTTTAACGAGCATGCCTGCCAAGTGGCTTGCCTTATACCTCAT<br>TATGAAGTGATACTCAGGGCCACTAACACATCGCACAGCATTGC |
| 189 | TIAM1 | TATGATTCCCTCGATTTCCCTCAATCTTAACCATTGTGGATCACAGCAGGAGGGCCAGAAAGTGAGCTTCAGCCTGGCACCGGGACCTCAGCCTCTCCCTTAA<br>ACTTTCCCTAATCCTCGGAGCTAGTGTTACTCAAGTGACTCCACAGTGTTGCCCGATCCCTTCAGACATGGCCTTGATGATCTCCAAAACTCATGCTACCTTT<br>GCCAGCCTAAAGCATCCACTCTGTGCCCCAAAACGTGAATGTCAAATACCCTTCAAGGCAGAAGGCTATTTCTATTTTTGTTTGTTTCTGTTTAAGGCAACAA<br>TCACCAACATTTGGTACACATGAGCCATCCTGTGAAACATCAAGGCGCTTCGTTGGCAGCAAGTCAACTTCGGTTTCAGAAGAAAGCTGCACTATTTCCTGAG<br>GTTAGAGGTTTAAACCAAAACAAGACAACCACATTTTAACCCCAAATCTGCCGACTGAGGGTAACCATGATCCTTCCTTCACAGCACC |
| 190 | TIAM1 | TACTAAATCAACCCAAACCCGAGAACCCGGTCATGGAGAAATAAATGATAGTAATCTATGCTGTTCATCTGTTCCATCACTCACTCACTCTCTTGCTGAACAA<br>GAAAGGGCCACCCATGTAGCAAACCACATGTAAAGAGCCGGGAAGAC |
| 191 | TIAM1 | TATTATTTTGTTCAAAGTAGACGGGTATACTAACATCTGTGGGCAAGTTTACCACACGCCACTTAAAACAGGCTAACAGGGTCATATGCCAAAACGTTCAGGT<br>TTGCATTTTTGAAAAGCTCAGAGATCTGACAGATGTGTTCCGGCCGCGATTTAACATGCGGCTCCAGTGAGAAGGAAGCAGATATGACAAATGGTTCACTTAT<br>TTCAGAACTAAAACCCCAGAGGAGCAGCCTGAGCCAAAAAGGGAAGTGATCAATGGAAAAGACGGTCGAATCTGCTCACAGGCAAGGCAAGGGG |
| 192 | SOD1 | AAGACCTGGAGTTTCCATTACACCGAATTGGCACTTAATAACTGTTGTCGGAGCATTTCTTAAGCCACATTTTCGTAAAGTGGCTTTAAAATTGCTCTGCCAG<br>TAGGCAGGTTGCTAAGATGGTCAGAGACAAACTTCTGAACGACTCTTGTAAAATATACAGAAATATTTTCAGAACTTTTATCAGTAAAATTACAAAACGTGTT<br>GCAAGGAAGGTGCTTGTGATAACACTGTCCCCAGAACCTTAGTGAAGTTACCAACTGGTGGAAAATTTTCTCTTGCACTCGGCTTAAAAATCAT |
| 193 | HUNK | GCAGGGGTGACTGGTCCTCTCTCTCTGCACCTCGCAGGATTTCTCTGGAAGATCTGAGCCCGAGCGTCGTGCTGCACATGACCGAGAAGCTGGGTTACAAGAA<br>CAGCGACGTGATCAACACTGTGCTCTCCAACCGCGCCTGCCACATCCTGGCCATCTACTTCCTCTTAAACAAGAAACTGGAGCGCTATTTGTCAGGGGTAAGT<br>GCGACCCTAGAGGCGATCGTCTCTGCTGTCTGTGGAAAAAAGAGCTCCTACACCCAAAGTGCTTCTCAGTTGCTGACACTTGATCCAAGCTGCTAATTTAATC<br>TAATGTGAGGCTGAGTTTTCTGAATGTGGGATAAAGTCGTAGCTAAACCTGCTTCTCAGGGAGTGCCTTTTATCTGCAATGTTTTTCAAAT |
| 194 | chr21: 3372200-33273300 | AAGTAACGGGATCAAATTAATTATTATTTTGGTGGCCGCCTCTCTTCTCCACCCCAAGCCAGGCAAGACTCACCCTCGGCCCTGCCCGCCCCAGCATTTCAAA<br>TGGAATACCTAGGTGGCCCAGGGGGACCCCTGACCCCTATATCCTGTTTCTTTCTGCCTGCTTTGCTACTTTTCTCCTTGATAAAAGGAGAGAGTGAGAGATA<br>ATTAACAAAAAACATGGCCCCAGGACAATGAAACAACTGGCCTTGGCCGGCCAGAAATGTATCCTGGTTTTCTAGGTGAACTTTCTCCCATCAATCTTTCCTT |

TABLE 4C-continued

| SEQ ID NO | GENE NAME | SEQUENCE |
|---|---|---|
| | | TAACCTCTCTGTTAGTGGAAGCAATAGGAACACCCCTCCCCTCCCCTGAGCAAATGCTTTCTTTTGACTGGAAACAAAACAGGGGCTCGGCGAAGGCTGAGGT GAAATCTGGGTGGCATGGGCGCCGCACAATGGGGCCGCTGTTCCCCGGCCCGGGCTTGTGTTTTACAACAGGGGAGGGGCGGGCGTGAATGGTCTGATGATTG GAACAATCCCCCCGATTCAGGCCTACAAACGCATCTTCTGTTCCACACCGAGGGGACAGAAAGGAGAAAAGTGACAAAGAACGCGGGGCGGGGGGAATTAAAA CAAAATGCGCTCGACTAAAAAATCTCTCATATCCTGCATATTCCAGAAAGCGGCTCTATGGAGAGAGCCTTCAGGAGGCCTCAGCCATATCTGAATGGCTTTC TCTGGCCTCTGATTTATTGATGAAGCTGAAGCGACTTGCTGGAGAAAGGCCTGGAGCCTTCTTTGTCTCCGAGATGAAGTACAATAGGCCACAGGGCGGAGAT CTCTTGTGATGCTCTCGGGTCCTGCCTTTCTCTTGCCCTCTCCTCCCTGCAAATACCAGCAGCGGTGACAAACGATTGGTGGTGTGCCTGGGAGAGCCGGTGA CAAGACTGGGCCACTTGAGGTCTCCTTAAGAGGGTATTATGGCCAGGGCGACGTTTGTGCTGTGAAGATGGCACACTCCATTTTGTCAATGGCTCTCATCGGCCCAGATA ATCGCCCCCTGCCTGCCTGTCAGGGGCGCAGCCGGCCGATTCATGGCGCCCTCGGAGAAAGTA |
| 195 | OLIG2 | GTCTTTCCCGCCCCCTTGTCTAAACTCAAAACCGAGTCCGGGCGCGCCTTGCAGGGCGCCCGAGCTCTGCAGCGGCGTTGCGGGCTGAACCCATCCGGCACAA ACTGCGGGCCACTGGCCCCTCACACCTGGGAGTTTGCGGCGCTGGCCTGCAGCCCGGGGCCCACGTGGCGGAAGCTTTCCCGGGCGCGCGCTGCGCAGCCCCG CGGGGCCGGGGAGACACCGCTCGGGAGTCCTCCGCTCGGCTGCAGAATCTTTATCAGCTGCACTTTACCGCAGCCCTGGCTAGGACGCTAGGCGGTGGAGCGC CCTATCCAGGTGCGCCGCCGCACCATGGATCACCGCGCCCGGTCCCGCAGTCCCGCCATGGCCTGGGGAGGCCCGAAGCCCGGGGACAGTGGCCGGCCCATCT CCGGCTCCGCGGACCCCCGGCTCAGGCGGGAGGGCAGGCGGGTCCCTGCAGGCCCCCAGGGAGCCCGGGAGCCTCTCTCTGGCGTCATTCAGTCCCGGGGCAA CCTGAAGCGCGGTAGATATTGGAGAGGGGGCGTCTGTTGGGGGGACCTGGCGTCATTACTGATGGCTAGCAGGGAGGAGGGAACGGGTTGTCACCTCGGCCTC ATAAGGCCGTGAGTGAGTAGTCCAGGGCCTCTTCAGGCATTTTTGAAACTGGATTAACTAGGGGGGAAATTGTAGCACTGAAGCCACCGTGACTGTCTTTTGC GCTGTGTGGAAACTCCGGTAAAACTCTTTGGGCAACAGTCTTATCACCAGCTCTTCAACGTGTGCAGCCCTTCTGGTCCTGTCCCTGTTCTGGGCCCCAGGAA TGCAAAGCAGGTCCAGGCACTGTGAAGACCCTGGCGGTGGAGGAAGAGGCTTCCCGGCTGTGGAGGAAGCCAGACCCTTACAACACAAGACGAGAACCAGACC TGCGTGGGGGAGCTCTGGATGCTACAGGGGCTCAAGGAGGGGTGGAGGGGCCTTCCCAGGCCAACCCCTGAACGGCTTGGACAAGATGCTCAGATGGACGGGA GGAACGGCGTGTGGGATGGGGGAGCTGGAGGCGGGTGGGTGGGGGGGGGAGGATGGGGAAAGCGCTGGCCCACCCAGTGTGGGAGGGGTAGAGGAAAAGCCCG CAGGGGCCAGGTTGGGACCCCGTAGGCCGGGTTAGAGGGCTTGGACTTGATCCTGACAGGCGACAGGGAGACATATTGCTACTTATTATGTGCACAGTGGCCA GATCTCTAAAGAAAACACCATCCCCCACCCCCACCCCCCATATAGTAAACCAGGTGGTCCGCCCAGTGCTCCCAGGGAGGTGATGGGAAATCCCACTCCATAC CCTGCGGTGAGGGGTTCCATGCCCTCCACGTGTGCAACTACTCCGGGCCCAGGGAAACACTGGGCCCCATCCGGTAACCCCCGGCCCAGTCGGGTTTCCCAGT TCACATTATAACCAAACGGTCTTGCCAGCTAGACAGACAGACACCCCTGACCTGTTTACCCTGATCCTCTGCTCTCAGGATTAATCACAACTTGTCGAAGGGG GTGGCTTCCAGTGGGGTGGACCGCTCTGTCAATGCCAGCGTGTGTCTAGCATCTCCTGGGGTGGGGGTGTGGGGAAGGGAGGTGTAGGATGAAGCCCTAGAAG CCTCAGGCAATTGTGATCCGGTGGGCTGGATACTGAAGCCCACCCCTGCCTTGACCTCAATTTTCAGTATCTTCATCTGTAAAATGGGAACAACCTGCCTTCC TCCTAGCCCTAAAGGGGCTGCTGTCAAGATTGGCTGAGATAGCTGTTTGCAAGCTGAGCTCAATGAAAGTTCATTGTGTCCCCCTCAGTCCTATCCCAATATC GTCTCACTGCAAAGGTGGGGGGCAGCTTAACTTCAAGGGCACTTCAAGGATAGCCAGGTGGCTGTCAGCCCAGCTTTCCAGGATGGGAGCAGGATCTTGACAG AAGGGTTGACTGGGAGGGGCAGTTGCTGGTTTGGGCTTCGTTAGGTTGCATTTTTGTTTGTTGTCCTTTCATTTCCCTGGGGCAGCACCCCTTCCTGCAAGCT CCAGGCCTTCCTCTGGAATGCTCCTAGAGCCCAACCTCTGCTGGTGCCTGAGCTTAAGCCAGGCCAGCTAAGGGGATCCTGGATTCACACGGCCTCACAGTCA CTCAGATTGTTAGCAGAAGACAAAAATTACAAGGGGAGGGCGTCATGTGATTCTTACACACCCTCCAAATCCAGCAGACACCTTGGAAGCCACAGGTAGCTTC AAGAAACCCATTTTACGGATGAGAACCTGAGATGGAGAAAGGACAACTGGAGATCTCTGAGTCTCTGAGCCCACACTCCCTACCTCCCTGCACCTCCAGGCAC TCTGCTGGCAGGATCTTGGGCAAATGCCCACAGCTCTCTGAGAGTCAGTTTTCCTGTCTGTAAAATGGGAGTCATACCTTCCTCCTATGGCCGGTGAGAGACT AAATTAAACTATGTCTGTCAAGACACCTGAAACTCCTGGCACAATTTAGGTTGCCTTCAAGTGGTCACAGTTGTCATTAGGTGGAAGTCAACACCCCAATCAT TGTAAAGGTGCCCATATACCCCAAGATCCAGATTACAGCTCTCACAGTTTATTATATACAGCGAAAAAACACATAACACACCTTTGCCCACATTTACATGTAT TTTACGGACCATGTTTCACATCAGTCCGCATGCACATCTGCACGTGTGTGCATTCGGCAGTATTTACCAAGCACCTGCCAAGTGCCAGGGCCTGTCCTCCGCA CCCGGCGTGAACTGTCCTGGACCAGTCCCGGGAGCCGCGGTTCTGACCAGCCGTGCTGACCCTGGACGACTCCATGAGCTGTTTTGTGAGAAAGACACGCCAT TTGTTTGCAGAGTTCTGACTTCTGAGGGGTCATGTAGCACATGTTTGGTAGCCAAACGCTGTCATTCACGACCAGGAGCGATGGCTGCAATGCCTTTTTCTTT GCTTTGCTTTCCGGTGCCGGGAGCCTTGCCTCCCGCCGCCACCCCTGGTCAGCTCTGCGCAAGAACGTCGTTCTGTTTGGCAGCCAGGCCGAGACGCAGCCTG AATGTGAGCAGGAACTCGGAGAAGGGAAGGGAGAGAATCAGAAAGAAGGCCCGGGAGGGACCCGGGAAGCAGTGGGAGGTCTGCGCCCTGGAGCCCCGCGAGA GCCCGCCGGTTTGGCACGGGCTCCTCCCGGGCCGCCCGGCGGTCCAACAAAGGCCGGCCCCGACACGCACCCGGTCTTTTGTGGGAGAGAAACACAAAGAAGA GGGAAAAACACGGAGGAGGCCAACAGCACCAGGACGCGGGGGCCAACCAGGAACTCCCGGAGCCGGGGCCCATTAGCCTCTGCAAATGAGCACTCCATTCCCC AGGAAGGGGCCCCAGCTGCGCGCGCTGGTGGGAACCGCAGTGCCTGGGACCCGCCCAGGTCGCCCACCCCGGGCGCCGGGCGCAGGACCCGGACAAGTCCTGG GGACGCCTCCAGGACGCACCAGGGCAAGCTTGGGCACCGGGATCTAATTTCTAGTTATTCCTGGGACGGGGTGGGGAGGCATAGGAGACACACCGAGAGGTAC TCAGCATCCGATTGGCACCAGGGCCAAGGGAGCCCAGGGGCGACACAGACCTCCCCGACCTCCCAAGCTACTCCGGCGACGGGAGGATGTTGAGGGAAGCCTG CCAGGTGAAGAAGGGGCCAGCAGCAGCACAGAGCTTCCGACTTTGCCTTCCAGGCTCTAGACTCGCGCCATGCCAAGACGGGCCCCTCGACTTTCACCCCTGA CTCCCAACTCCAGCCACTGGACCGAGCGCGCAAAGAACCTGAGACCGCTTGCTCTCACCGCCGCAAGTCGGTCGCAGGACAGACACCAGTGGGCAGCAACAAA AAAAGAAACCGGGTTCCGGGACACGTGCCGGCGGCTGGACTAACCTCAGCGGCTGCAACCAAGGAGCGCGCACGTTGCGCCTGCTGGTGTTTATTAGCTACAC TGGCAGGCGCACAACTCCGCGCCCCGACTGGTGGCCCCACAGCGCGCACCACACATGGCCTCGCTGCTGTTGGCGGGGTAGGCCCGAAGGAGGCATCTACAAA TGCCCGAGCCCTTTCTGATCCCCACCCCCCCGCTCCCTGCGTCGTCCGAGTGACAGATTCTACTAATTGAACGGTTATGGGTCATCCTTGTAACCGTTGGACG |

TABLE 4C-continued

| SEQ ID NO | GENE NAME | SEQUENCE |
|---|---|---|
| | | ACATAACACCACGCTTCAGTTCTTCATGTTTTAAATACATATTTAACGGATGGCTGCAGAGCCAGCTGGGAAACACGCGGATTGAAAAATAATGCTCCAGAAG<br>GCACGAGACTGGGGCGAAGGCGAGAGCGGGCTGGGCTTCTAGCGGAGACCGCAGAGGGAGACATATCTCAGAACTAGGGGCAATAACGTGGGTTTCTCTTTGT<br>ATTTGTTTATTTTGTAACTTTGCTACTTGAAGACCAATTATTTACTATGCTAATTTGTTTGCTTGTTTTTAAAACCGTACTTGCACAGTAAAAGTTCCCCAAC<br>AACGGAAGTAACCCGACGTTCCTCACACTCCCTAGGAGACTGTGTGCGTGTGTGCCCGCGCGTGCGCTCACAGTGTCAAGTGCTAGCATCCGAGATCTGCAGA<br>AACAAATGTCTGAATTCGAAATGTATGGGTGTGAGAAATTCAGCTCGGGGAAGAGATTAGGGACTGGGGGAGACAGGTGGCTGCCTGTACTATAAGGAACCGC<br>CAACGCCAGCATCTGTAGTCCAAGCAGGGCTGCTCTGTAAAGGCTTAGCAATTTTTTCTGTAGGCTTGCTGCACACGGTCTCTGGCTTTTCCCATCTGTAAAA<br>TGGGTGAATGCATCCGTACCTCAGCTACCTCCGTGAGGTGCTTCTCCAGTTCGGGCTTAATTCCTCATCGTCAAGAGTTTTCAGGTTTCAGAGCCAGCCTGCA<br>ATCGGTAAAACATGTCCCAACGCGGTCGCGAGTGGTTCCATCTCGCTGTCTGGCCCACAGCGTGGAGAAGCCTTGCCCAGGCCTGAAACTTCTCTTTGCAGTT<br>CCAGAAAGCAGGCGACTGGGACGGAAGGCTCTTTGCTAACCTTTTACAGCGGAGCCCTGCTTGGACTACAGATGCCAGCGTTGCCCCTGCCCCAAGGCGTGTG<br>GTGATCACAAAGACGACACTGAAAATACTTACTATCATCCGGCTCCCCTGCTAATAAATGGAGGGGTGTTTAACTACAGGCACGACCCTGCCCTTGTGCTAGC<br>GCGGTTACCGTGCGGAAATAACTCGTCCCTGTACCCACACCATCCTCAACCTAAAGGAGAGTTGTGAATTCTTTCAAAACACTCTTCTGGAGTCCGTCCCCTC<br>CCTCCTTGCCCGCCCTCTACCCCTCAAGTCCCTGCCCCCAGCTGGGGGCGCTACCGGCTGCCGTCGGAGCTGCAGCCACGGCCATCTCCTAGACGCGCGAGTA<br>GAGCACCAAGATAGTGGGGACTTTGTGCCTGGGCATCGTTTACATTTGGGGCGCCAAATGCCCACGTGTTGATGAAACCAGTGAGATGGGAACAGGCGGCGGG<br>AAACCAGACAGAGGAAGAGCTAGGGAGGAGACCCCAGCCCCGGATCCTGGGTCGCCAGGGTTTTCCGCGCGCATCCCAAAAGGTGCGGCTGCGTGGGGCATCA<br>GGTTAGTTTGTTAGACTCTGCAGAGTCTCCAAACCATCCCATCCCCCAACCTGACTCTGTGGTGGCCGTATTTTTTACAGAAATTTGACCACGTTCCCTTTCT<br>CCCTTGGTCCCAAGCGCGCTCAGCCCTCCCTCCATCCCCCTTGAGCCGCCCTTCTCCTCCCCCTCGCCTCCTCGGGTCCCTCCTCCAGTCCCTCCCCAAGAAT<br>CTCCCGGCCACGGGCGCCCATTGGTTGTGCGCAGGGAGGAGGCGTGTGCCCGGCCTGGCGAGTTTCATTGAGCGGAATTAGCCCGGATGACATCAGCTTCCCA<br>GCCCCCCGGCGGGCCCAGCTCATTGGCGAGGCAGCCCCTCCAGGACACGCACATTGTTCCCCGCCCCCGCCCCCGCCACCGCTGCCGCCGTCGCCGCTGCCAC<br>CGGGCTATAAAAACCGGCCGAGCCCCTAAAGGTGCGGATGCTTATTATAGATCGACGCGACACCAGCGCCCGGTGCCAGGTTCTCCCCTGAGGCTTTTCGGAG<br>CGAGCTCCTCAAATCGCATCCAGAGTAAGTGTCCCCGCCCCACAGCAGCCGCAGCCTAGATCCCAGGGACAGACTCTCCTCAACTCGGCTGTGACCCAGAATG<br>CTCCGATACAGGGGGTCTGGATCCCTACTCTGCGGGCCATTTCTCCAGAGCGACTTTGCTCTTCTGTCCTCCCCACACTCACCGCTGCATCTCCCTCACCAAA<br>AGCGAGAAGTCGGAGCGACAACAGCTCTTTCTGCCCAAGCCCCAGTCAGCTGGTGAGCTCCCCGTGGTCTCCAGATGCAGCACATGGACTCTGGGCCCCGCGC<br>CGGCTCTGGGTGCATGTGCGTGTGCGTGTGTTTGCTGCGTGGTGTCGATGGAGATAAGGTGGATCCGTTTGAGGAACCAAATCATTAGTTCTCTATCTAGATC<br>TCCATTCTCCCCAAAGAAAGGCCCTCACTTCCCACTCGTTTATTCCAGCCCGGGGGCTCAGTTTTCCCACACCTAACTGAAAGCCCGAAGCCTCTAGAATGCC<br>ACCCGCACCCCGAGGGTCACCAACGCTCCCTGAAATAACCTGTTGCATGAGAGCAGAGGGGAGATAGAGAGAGCTTAATTATAGGTACCCGCGTGCAGCTAAA<br>AGGAGGGCCAGAGATAGTAGCGAGGGGGACGAGGAGCCACGGGCCACCTGTGCCGGGACCCCGCGCTGTGGTACTGCGGTGCAGGCGGGAGCAGCTTTTCTGT<br>CTCTCACTGACTCACTCTCTCTCTCTCTCCCTCTCTCTCTCTCTCATTCTCTCTCTTTTCTCCTCCTCTCCTGGAAGTTTTCGGGTCCGAGGGAAGGAGGACC<br>CTGCGAAAGCTGCGACGACTATCTTCCCCTGGGGCCATGGACTCGGACGCCAGCCTGGTGTCCAGCCGCCCGTCGTCGCCAGAGCCCGATGACCTTTTTCTGC<br>CGGCCCGGAGTAAGGGCAGCAGCGGCAGCGCCTTCACTGGGGGCACCGTGTCCTCGTCCACCCCGAGTGACTGCCCGCCGGAGCTGAGCGCCGAGCTGCGCGG<br>CGCTATGGGCTCTGCGGGCGCGCATCCTGGGGACAAGCTAGGAGGCAGTGGCTTCAAGTCATCCTCGTCCAGCACCTCGTCGTCTACGTCGTCGGCGGCTGCG<br>TCGTCCACCAAGAAGGACAAGAAGCAAATGACAGAGCCGGAGCTGCAGCAGCTGCGTCTCAAGATCAACAGCCGCGAGCGCAAGCGCATGCACGACCTCAACA<br>TCGCCATGGATGGCCTCCGCGAGGTCATGCCGTACGCACACGGCCCTTCGGTGCGCAAGCTTTCCAAGATCGCCACGCTGCTGCTGGCGCGCAACTACATCCT<br>CATGCTCACCAACTCGCTGGAGGAGATGAAGCGACTGGTGAGCGAGATCTACGGGGGCCACCACGCTGGCTTCCACCCGTCGGCCTGCGGCGGCCTGGCGCAC<br>TCCGCGCCCCTGCCCGCCGCCACCGCGCACCCGGCAGCAGCAGCGCACGCCGCACATCACCCCGCGGTGCACCACCCCATCCTGCCGCCCGCCGCCGCAGCGG<br>CTGCTGCCGCCGCTGCAGCCGCGGCTGTGTCCAGCGCCTCTCTGCCCGGATCCGGGCTGCCGTCGGTCGGCTCCATCCGTCCACCGCACGGCCTACTCAAGTC<br>TCCGTCTGCTGCCGCGGCCGCCCCGCTGGGGGGCGGGGGCGGCGGCAGTGGGGCGAGCGGGGGCTTCCAGCACTGGGGCGGCATGCCCTGCCCCTGCAGCATG<br>TGCCAGGTGCCGCCGCCGCACCACCACGTGTCGGCTATGGGCGCCGGCAGCCTGCCGCGCCTCACCTCCGACGCCAAGTGAGCCGACTGGCGCCGGCGCGTTC<br>TGGCGACAGGGGAGCCAGGGGCCGCGGGGAAGCGAGGACTGGCCTGCGCTGGGCTCGGGAGCTCTGTCGCGAGGAGGGGCGCAGGACCATGGACTGGGGGTGG<br>GGCATGGTGGGGATTCCAGCATCTGCGAACCCAAGCAATGGGGGCGCCCACAGAGCAGTGGGGAGTGAGGGGATGTTCTCTCCGGGACCTGATCGAGCGCTGT<br>CTGGCTTTAACCTGAGCTGGTCCAGTAGACATCGTTTTATGAAAAGGTACCGCTGTGTGCATTCCTCACTAGAACTCATCCGACCCCCGACCCCCACCTCCGG<br>GAAAAGATTCTAAAAACTTCTTTCCCTGAGAGCGTGGCCTGACTTGCAGACTCGGCTTGGGCAGCACTTCGGGGGGGGAGGGGGTGTTATGGAGGGGGACAC<br>ATTGGGGCCTTGCTCCTCTTCCTCCTTTCTTGGCGGGTGGGAGACTCCGGGTAGCCGCACTGCAGAAGCAACAGCCCGACCGCGCCCTCCAGGGTCGTCCCTG<br>GCCCAAGGCCAGGGGCCACAAGTTAGTTGGAAGCCGGCGTTCGGTATCAGAAGCGCTGATGGTCATATCCAATCTCAATATCTGGGTCAATCCACACCCTCTT<br>AGAACTGTGGCCGTTCCTCCCTGTCTCTCGTTGATTTGGGAGAATATGGTTTTCTAATAAATCTGTGGATGTTCCTTCTTCAACAGTATGAGCAAGTTTATAG<br>ACATTCAGAGTAGAACCACTTGTGGATTGGAATAACCCAAAACTGCCGATTTCAGGGGCGGGTGCATTGTAGTTATTATTTTAAAATAGAAACTACCCCACCG<br>ACTCATCTTTCCTTCTCTAAGCACAAAGTGATTTGGTTATTTTGGTACCTGAGAACGTAACAGAATTAAAAGGCAGTTGCTGTGGAAACAGTTTGGGTTATTT<br>GGGGGTTCTGTTGGCTTTTTAAAATTTTCTTTTTTGGATGTGTAAATTTATCAATGATGAGGTAAGTGCGCAATGCTAAGCTGTTTGCTCACGTGACTGCCAG<br>CCCCATCGGAGTCTAAGCCGGCTTTCCTCTATTTTGGTTTATTTTTGCCACGTTTAACACAAATGGTAAACTCCTCCACGTGCTTCCTGCGTTCCGTGCAAGC<br>CGCCTCGGCGCTGCCTGCGTTGCAAACTGGGCTTTGTAGCGTCTGCCGTGTAACACCCTTCCTCTGATCGCACCGCCCCTCGCAGAGAGTGTATCATCTGTTT<br>TATTTTTGTAAAAACAAAGTGCTAAATAATATTTATTACTTGTTTGGTTGCAAAAACGGAATAAATGACTGAGTGTTGAGATTTTAAATAAAATTTAAAGTAA |

TABLE 4C-continued

| SEQ ID NO | GENE NAME | SEQUENCE |
|---|---|---|
| | | AGTCGGGGGATTTCCATCCGTGTGCCACCCCGAAAAGGGGTTCAGGACGCGATACCTTGGGACCGGATTTGGGGATCGTTCCCCCAGTTTGGCACTAGAGACA<br>CACATGCATTATCTTTCAAACATGTTCCGGGCAAATCCTCCGGGTCTTTTTCACAACTTGCTTGTCCTTATTTTTATTTTCTGACGCCTAACCCGGAACTGCC<br>TTTCTCTTCAGTTGAGTATTGAGCTCCTTTATAAGCAGACATTTCCTTCCCGGAGCATCGGACTTTGGGACTTGCAGGGTGAGGGCTGCGCCTTTGGCTGGGG<br>GTCTGGGCTCTCAGGAGTCCTCTACTGCTCGATTTTTAGATTTTTATTTCCTTTCTGCTCAGAGGCGGTCTCCCGTCACCACCTTCCCCCTGCGGGTTTCCTT<br>GGCTTCAGCTGCGGACCTGGATTCTGCGGAGCCGTAGCGTTCCCAGCAAAGCGCTTGGGGAGTGCTTGGTGCAGAATCTACTAACCCTTCCATTCCTTTTCAG<br>CCATCTCCACTACCCTCCCCCAGCGGCCACCCCCGCCTTGAGCTGCAAAGGATCAGGTGCTCCGCACCTCTGGAGGAGCACTGGCAGCGCTTTGGCCTCTGTGCTCTTT<br>CCT |
| 196 | OLIG2 | CCGGCACGGCCCGCATCCGCCAGGATTGAAGCAGCTGGCTTGGACGCGCGCAGTTTTCCTTTGGCGACATTGCAGCGTCGGTGCGGCCACAATCCGTCCACTG<br>GTTGTGGGAACGGTTGGAGGTCCCCCAAGAAGGAGACACGCAGAGCTCTCCAGAACCGCCTACATGCGCATGGGGCCCAAACAGCCTCCCAAGGAGCACCCAG<br>GTCCATGCACCCGAGCCCAAAATCACAGACCCGCTACGGGCTTTTGCACATCAGCTCCAAACACCTGAGTCCACGTGCACAGGCTCTCGCACAGGGGACTCAC<br>GCACCTGAGTTCGCGCTCACAGATCCACGCACACCGGTGCTTGCACACGCAAGGGCCTAGAACTGCAAAGCAGCGGCCTCTCTGGACCGCCTCCCTCCGGCCC<br>TCCTGAGCCCTACTGAGCCCTGCTGAGTCCTGGAGGCCCTGTGACCCGGTGTCCTTGGACCGCAAGCATCCTGGTTTACCATCCCTAC |
| 197 | RUNX1 | GGACGCGGCCCGCTCTAGAGGCAAGTTCTGGGCAAGGGAAACCTTTTCGCCTGGTCTCCAATGCATTTCCCCGAGATCCCACCCAGGGCTCCTGGGGCCACCC<br>CCACGTGCATCCCCCGGAACCCCCGAGATGCGGGAGGGAGCACGAGGGTGTGGCGGCTCCAAAAGTAGGCTTTTGACTCCAGGGGAAATAGCAGACTCGGGTG<br>ATTTGCCCCTCGGAAAGGTCCAGGGAGGCTCCTCTGGGTCTCGGGCCGCTTGCCTAAAACCCTAAACCCCGCGACGGGGGCTGCGAGTCGGACTCGGGCTGCG<br>GTCTCCCAGGAGGGAGTCAAGTTCCTTTATCGAGTAAGGAAAGTTGGTCCCAGCCTTGCATGCACCGAGTTTAGCCGTCAGAGGCAGCGTCGTGGGAGCTGCT<br>CAGCTAGGAGTTTCAACCGATAAACCCCGAGTTTGAAGCCCGACAAAAAGCTGATAGCAATCACAGCTTTTGCTCCTTGACTCGATGGGATCGCGGGACATTT<br>GGGTTTCCCCGGAGCGGCGCAGGCTGTTAACTGCGCAGCGCGGTGCCCTCTTGAAAAGAAGAAACAGACCAACCTCTGCCCTTCCTTACTGAGGATCTAAAAT<br>GAATGGAAAGAGGCAGGGGCTCCGGGGAAAGGGAACCCCTTAGTCGGCCGGGCATTTTACGGAGCCTGCACTTTCAAGGACAGCCACAGCGTGTACGAAGTGA<br>GGAATTCCTTTCCACCAAGAGCGCTCATTTTAGCGACAATACAGAATTCCCCTTCCTTTGCCTAAGGGAGAAAGGAAAGGAAACATTACCAGGTTCATTCCCA<br>GTGTTTCCCTGGAGTAATGCTAGAATTTACTTTTGTCATAATGCAAAATTAAAAAAAAAAAAAATACAACGAAGCGATACGTTGGGCGGATGCTACGTGACAGATTTTT<br>CCAAATTTTGTTGCGGGGAGAGGGAGGGAGGAGAATTGAAAACGGCTCACAACAGGAATGAAATGTA |
| 198 | RUNX1 | TTTTTAATGCTCAGAGAAGTTCGTATTACTGATTCGGGAACACTGAGTTTTTCAGCTCCTGTAAAACTATTTTCAGGTTTATTTTCAAGTACATTCTTTA |
| 199 | RUNX1 | CACCCTAGAGGCAAGGACGGGGTCTGTGTCAAGAGGCTTCCCAGAGAAGTGAAAACTCTGCAGGTGCAGCCGCTGGGAGAGCATCAAGAAGGGCAGGGTGGAG<br>GGGCAGGGGGCGAAGGGAGGGGGTGAAGCCCGCACCCTACCCCCACATGAAACTGATTCCACTACCCCATCTCTGCAAGCGTCCAGAGGCAGAGAGGCCAACA<br>TTTCGGGGACAGCTTGGAGGCGGGAGATTTAGGCAGGGCTCCTTAAACTTTTATGTGCATGAAAATCAGGCCAATCACGGGGCTCTTGAGCAAATGGGGACGA<br>TGATTCAGCAGGTCTGGGCTGAGGCCTCAGATTCTGCACTTCTAACAAGTTCCCAGGTGGTAGTGATGCTGCCAGTCCAAAGACCACACTG |
| 200 | RUNX1 | TGCTTCAGTGGGGTAAACTTGAACCGCTGAGAAGACAAGCAGGGAGTCGGTCTCGCTGAGATTTTTACCTGTGGTTCTAGGAACGCAGAGGCATGTGAGTGTT<br>CAGGCTTTGCATAGACCACTAAGCCACTTCTAAGAACAAGGCTACCTGAGCCATTTTGCAAAAATATGTACGTGCCGAGGCTTTTCCTCCCCACACCTACCTC<br>AACTCTTTCTGCCGACACACTGCACTTTTCAAGGGAACCCAAGTTTGGGTTCGGCAAGAATTGTACGTTGCACACCGTGTGTGATAATTCCAGGGAATTTCAA<br>TCGCATCTTGTCTTCCTTCCTAAGCAAATTCGGTGGGAACCTGGTGTGGTGTGATAGAAAAAGCCCCGAGTTCTCTGTGGTAGACCACATCAATTTCATGTGC<br>CAGTCTCTCAGACTCCGGCTTGCCTCTCTCAAGGAAGGGAACAATGGTTTGCTTGGCTTCACTCCTCTCTTTCCCCCCAATTTCCACATGGGTATCTGGCTAA<br>AAATGAGTTACAGGTTTCCTTCTGTGAGAATTGCATGGACTGATAAAGTACCATCCCAGGAAGAAAACAAAGATGCTGTCTTCCCTTTCGGCTCACAGTTGCC<br>GTTGGGGAGGGAACACACGCTGTAAATTATAGGCAGCCAGAAGTGACCGCATTGACCACTGCGAGTGGCCCAGCTATGGCAACAGGCTGAGAACTCTGGGGGA<br>GAGCCATTTGTTGGCAGGGATGGTGATTCTTCTAGCATCAAGCTCTAAGATGATGACCAAACGGTATCAAAAGAAATGATATTTTGCTACCTCTCCGGCTTGG<br>GTGAATGATGTGGACAGTTAACCTGGACAATTTAAACCTTTATGTTGATGGATCACTTGGATGAAATTAACCAGGAAATTGCCAAGATTTCACTTGGCCCTCT<br>GACATCAAATCTCAATATTATATTACCAAATTAGAGATTCTAAAGAACCCTGAGTTCCTTTCACTGAAAGGAAGGAGTGGAAAAACCTTTCCAGATGATCCCT<br>TTTGAGTCTTGGTGCGAGCTCAGGCCCTCCCTACACTGCCTCCGTGAAAGCTAACCGACCCTTGTTCCTAACCTAGCGCAGGTCAGCTGAGTGTCCATCGGGC<br>ACAGGAGCCCTGGGCTTGTCCGGGAGATAGCCAGACTCCTGCTATTTCCTGATGTCTGCATAGCTCAGCGTGTCCCTCACCATCTTTGCCGTTGGCCAGTAAG<br>GAGAGCCCCAGGGGCCAGCACTGCACACTGAAACCCAACCTATTGCTCAATGGAATGCTTAAAAATTTCCTGAATCTGCCTTCCTGAGTTGATAAAATAGGAA<br>ACAATACACGTTCTGAGGGGGTACTGAAAGCAGAGTAAAGCCAGGAAGATCTTTTTTTTCTGTTATTCTATACAAATATTGCTTCCTCTGCTTGTTAGCAGCC<br>CAGAGGAAATGCAGCCAGGGAGCCGTTTGCAGCTTTTCACCAGTGGCCGGTGTCTCTGTGTTACCAACCAAACGACGCTGCAAGACTAGTGACTAACGCACGT<br>CTGCATGATTCAACTTCACTAAAATTCCCTCTGCTGCCAGTAAAGAAGCACTTGAAAACTCTTTAATTTGAAACTTGAGCTTGGTTAATGACTTGTTTTCTTC<br>TCTTTCTCTTTAACTTCTCTCTTGCCATCTCCAACACACACACACACACACACACACACACACACACACACACACACACACTCTCTCTCTCTCTCTCTCTCTC<br>TCTCTCTCTCTCTCATCAAGTTTTTTAATTTCAGGGACCCGGAAACATACAGCCCCGTGCATTCACAATAGCATTTGCTGTGATAAAGTGGCCGGCAAGCCCT |

TABLE 4C-continued

| SEQ ID NO | GENE NAME | SEQUENCE |
|---|---|---|
| | | CTGCATTCCCCTGCTCACTTAGCTGTATGAATAAATAATGAGTCACAGATACAATTTGGGTGCTCAAGAGAGTTTGTAGCCAGAAAATTAATTATTCTCCCAT<br>CCCAGCCCACTCCATCTCAGCTTTGCCAAACCATCAAGATACACTTTGCAGGCACTGGTCAGAGTGCGTGCCCCGACGCACACGGCAATGCCTTTGAGACATT<br>TTATGTTATTATTTTTGTTTGTTTAAGCACAGCCCTCTTTTACCACGAAAGATACACAAGACGCACATGCACACACATACTCACACACTCACAGCTCAACCAC<br>AGCTTTGTCCATTTCAAGAGGCTGGTTTCAAAAATGGAGACAGGTTTTCCACCCTGGCTGTTCCTATTCATAAGCCTGTAATCTAACGACTTAAGCTGCGAGA<br>ATGCTTAACTCGGGAAACTTCTCTATTGCCCTTTTCCAGAGAGACCTCGGTATGCCACAATTTGCTTCCTTTCTCTCTTGAAAGATGCTGGTTGTCTCTTTGC<br>ATTGAGGCTACAAGGAAAAACACAGCACAGCCCCATGCTGATGATTTTAACCTAACCAAGTCTGTCAGTCTCCTGTACTCTCTGCCTTATAGAGACAGCTGCC<br>TTGCCACTTTGGCCCTGAAGTCCCCAGGCTGGTGCAAGGCTATCTGAGAGCCTCCGCCTCCTGCCCCACACTGGCACCAGCCCTCCTGGCTGGCTCTGTGCAT<br>GTGCCTGCTAAGCCCCAGGGCAGGCTGCATTCTGGGCCACACAGCATGCCGAGTTAAGGATAACTCAGACACAGGCATTCCGGGCAAGGGACAGCAAAATAAA<br>ACCCAGGGAGCTTCGTGCAAGCTTCATAATCTCTAAGCCTTTAAACAAGACCAGCACAACTTACTCGCACTTGACAAAGTTCTCACGCACCGACTGAACACTC<br>CAACAGCATAACTAAGTATTTATTAAAACATTTCTGAAGAGCTTCCATCTGATTAGTAAGTAATCCAATAGACTTGTAATCATATGCCTCAGTTTGAATTCCT<br>CTCACAAACAAGACAGGGAACTGGCAGGCACCGAGGCATCTCTGCACCGAGGTGAAACAAGCTGCCATTTCATTACAGGCAAAGCTGAGCAAAAGTAGATATT<br>ACAAGACCAGCATGTACTCACCTCTCATGAAGCACTGTGGGTACGAAGGAAATGACTCAAATATGCTGTCTGAAGCCATCGCTTCCTCCTGAAAATGCACCCT<br>CTTCTGAAGGCGGGGGACTCAATGATTTCTTTTACCTTCGGAGCGAAAACCAAGACAGGTCACTGTTTCAGCCTCACCCCTCTAGCCCTACATCTCTCTTTCT<br>TCTCCCCTCTGCTGGATACCTCTGGGACTCCCCAAGCCCTATTAAAAAATGCACCTTTGTAAAAACAAATATTCAAATTGTTAAAGATTAAAAAAAAAAAAAA<br>AGCCAGCGCCGCCTTGGCTGTGGGTTGGTGATGCTCACCACGCTGCGAAACCCTGTGGTTTGCATTCAGTGTGATTCGTCCTGCCTGCTGACCACTATGCTGG<br>GTTCAGACTTCTGACACTGCCAGGCTACCCAACTTGTGGTTCTGTGGTTGTTTATGAGGCCCAAAGAAGTTTTCACACAACCCAAATTACAAATTTAACTGTT<br>CCCCTTTCCACAGCCCATCTCAATTGGTTCTTGCCAATCATGTGACTTAAGTGATGTCAATTTTTTTTTTTCTTTTCTGAGCAATGCCCTTCCTTCCCTCCAC<br>CTGCCCTCCCCCAGGCTGTGCAAGAAAATAGCCGAGTAGACTTTGCAAGAGGGGGGGATGTAGAAAAAAGTGACTCAGTCACTTATTATATCTCAATGGTCTT<br>TGCTGATTTAGTACAACTCGGCTCCTGTTGTTATTTGTGGTTTTTGGAACTACTGATTATTTTGATAAAGATTTCATTGCTGCTTATTCAATAGTAATTCAAC<br>GCTGGCATCAAGCCGCTGCTCCGACAGGATGTGGATCCCATCATTTAAAATGCTAGGCATCAGCTCCGGGAGAGTTAAGTCCTTGGTAACGTCTATCATGGCA<br>TAAGTGAAACTATAAAAGGGAAAAATAAATAAAAAGAAATGTTTTGGTGAGAGTCTGACCCCTACAACGGGCTGGCAACTCACAGGTATTTTAAAGCCTGGGA<br>AAGGGAAAGAATTTTACTTTTGAAATAAAAGGACTGTTTTAATGAAACCAAAATTATGTGGTTTTATTCCCCCTAAATGGACAACTTTAGTATGTATCTCTTT<br>CAGTAAAGAGATAAAATCATAGTACAGTCTTAACACACACACACACACACACACACACACACACACACACACACAAATTAGGAAGCTAAAGGAAAACAAAGCAGA<br>GAGAATTTCTGTATTTGGGACAAAGCAGTGGTTACTCTGCAGATGTTTATTTGTATTGTCACTTGGGAAAGCTCCCTGTATTGCCTTTCTCTAGTTCAATTCA<br>AATCAATAGGCTAATTTACACCTGTAGGTAAAACTACACTTTGAGCACATGAGGATGCCACAATAGAAGGGGAACCAGGAGGAGACACTTCTCCTGGGGCTGA<br>CTAATGAATATTATATAGCGCGTCCTCTACCTTAGAAAGACATGCCTGTTTGAAGATGCTAAAAACAGGATAATTTTGTAAGTGGGCAAACCACTGTGGTCAC<br>ACGTATTTCATTTTCCGGCCCCACTGGCTTTACCTGCTGACAACTAAAACGTCATTTTGTTTTGTAGTTCCAAGATGAAGAAAGGCTTATTTTCCTGATTTAC<br>TACCTTATTCATTTGGCTCTGCTCTGCCTACATCCGCCATAGCACTCTGCGCACGTGAAATTTCGACACATAGGGTCAAGAGAACCTGTGTGATGATGGGTTG<br>TAAATGCCAGTCCTGGATTCTAAGCTGCAGTAGCCAGCACAGGCACTTCAGAAAGGCTGAACTCCCACAACACTCCCTCGGTTTTCCCTCATCCACTTAATTT<br>CACACACACAAAGACCCACAACGATAGTAGCTTCCATGGCACAAGTCTTTCAAAAGGAACAGACACAATTTTTACTTACTCCTGTTTTGACTAAAGCAGGAATTGAAACT<br>CAACAGACCGCTTTCTCTTACACTTGTGAGAAGTTAGCTGGCCACATGT |
| 201 | chr21: 35499200-35499700 | AGGGAAAAGAGATAACGAAAGAAAGAAAGAAAAAAAAAAAGGGCCGGCAATTTCATGTACATTTGTTTTGGCATTCGCTGAATTCTAGAGATGAAAACAATCTC<br>CTGCTTTTAATTCAGTCCACGTGCAACAAAGTTGTACGTTGGGAGATCTGGCTTTTAATAAGAACGATTAACAAGCGTTTTTGATCACAGGAAGTTGAGAAGA<br>GTCGCTGCTTCTAAGAATACAATAAACATTGACTAGCAGTTAGACGGTCCATCTTTCTCTATCAGCCGTTTAGCAGCCTCTACTTTGATTTGGGGCAAATGCG<br>AGATGGGACCAGGAGAGAGCTCCCCACACCCCCACCACCACGTGGGCAGTGGTTCTGTTCCAGAGCGCCTTCCTTCCTGTCCAGGGAGGCAGGCTGCTGAGGC<br>CGTTTCTGGGCAAGAGGCCATTGTCGGGATATTTGCTTTAGATAGCTTGCAGCTGGGCTGAGTGGGTGTTTCATTCAGACTCAACACA |
| 202 | chr21: 35822800-35823500 | AGCCTGGCGCACCCGCCCTAATTTGAGTCAGGGACCCTAGGCGCCTGCAGCTCCGGTTCGGGTTGAGTGCCTCCTGTCAGGATGTGAAGCTGCTGTCCCCCCC<br>GGGGGCCTCCAGCACTGCTGAGGACTCAGCAGTCAGCCTCTCCTCCCACTTGGGCTCATTTACAGAGAGCATCTCCAGGAATCAGTCATGGGGAAAGGGGAAA<br>CGCGGAGTGACAACACAACACGTAGAAAGTTCTCTGCCGCCTTGGTCAGGCTTGTCAGCCTCACAGCCCATCCTGCTCCTGCGGGAGGAAAAGTGAGCAGAAC<br>TCAGCCCGGAGATGAGCCGCAGGCCGGCAGCCCCTGCCTCTGCCCTGCTTGTTGTGACTGCAATGCAAGGCTCTCTGTAGGTGCGGGGGATTCGGGTTAAATG<br>GGTCTCCAGTGGTCCAGCGCTCCCAGCAAAGGCCGACCACAAGAATTAGCGGGCTAGTTATTTACCATAACCATATACAAAACCACAAGCATCAGCGTTCCCT<br>CAAATACATCCGAGACGCTGTATATCTCTTTATTAAAGCCTGTCAGGGTTTGTTATTGCACAGCTTGGCCTTGAACCCCAACTAAACCAGGCTGCTTGAGCAA<br>AGAACCAAGCAATGCAAGCATTCAGGCAGGACCATTATAACCCTGAGGCCAAAGGCAGAAGCAGGGAGAGGAGACGTCTTCC |
| 203 | CBR1 | AGACCAGCCTCGGTCTTCGGCCTGCGGGTTCTGCAAAGTCAGGCTAGCTGGCTCTCCGCCTGCTCCGCACCCCGGCGAGGTTCCGGTGGGGAGGGGTAGGGAT<br>GGTTCAGCCCCGCCCCGCTAGGGCGGGGCCTGCGCCTGCGCGCTCAGCGGCCGGGCGTGTAACCCACGGGTGCGCGCCCACGACCGCCAGACTCGAGCAGTCT<br>CTGGAACACGCTGCGGGGCTCCCGGGCCTGAGCCAGGTCTGTTCTCCACGCAGGTGTTCCGCGCGCCCCGTTCAGCCATGTCGTCCGGCATCCATGTAGCGCT |

TABLE 4C-continued

| SEQ ID NO | GENE NAME | SEQUENCE |
|---|---|---|
| | | GGTGACTGGAGGCAACAAGGGCATCGGCTTGGCCATCGTGCGCGACCTGTGCCGGCTGTTCTCGGGGGACGTGGTGCTCACGGCGCGGGACGTGACGCGGGGC<br>CAGGCGGCCGTACAGCAGCTGCAGGCGGAGGGCCTGAGCCCGCGCTTCCACCAGCTGGACATCGACGATCTGCAGAGCATCCGCGCCC |
| 204 | DOPEY2 | AAACGTTTAAAATATATTTCTAAACAGAATGGGCCAATTCAGTCACAGTAACTGTTGATCTCCATAGCAGAGCAACCCACAAAGACAGAACTGATTTTTTTCC<br>CATAATCAGGGGTGAAAAATATACAACTTGTTTCTGAACCAAAACCACAATTTCTGCAGTTTAAAATGTTTCACTGCTAATATGGCCCTGGTAGAAATTATGT<br>AGTTTCTTTTCTTCTTTAAAAAAAAAAAAAATTAAAAAAATTTCCTAAGACACTAAATGCTCCATCTGGAATGTAGATTCTGATCACAAAGCAGCTCAGTTAA<br>CCTAAAAAATAAAAAATTCCCATCACCTGTCTCAGTAGGGCCTGAGAGTAGTGTGGGGAACCCCAGCTTTGGTATGGAGAGTCATGGCCCCTTGAACCAGATA<br>GAGACCTTGAATAGCCATAGCTGGTGCTTCTCTCAGGATAAACTCTGATGTAGGAAGTATCACCCTCATGAGAGTGGAATTTGGTCATCCAGTTGACGCAGGG<br>CATATTCCATGTCTTCTTTTCTGAGACACCCAACCATCCCCACTCCATCCTTCTGCACATCCGTGTAACAGGCATCCCCAGCTTCTCGCGTGTGATCCTTCAG<br>GTCCTGCCAGCTGCCTGATGGAAGAAGTCCATTTCTTCCATAAATAGCATCCTCTGCATCTCGAGGGTCCTCGAAGCGCACGGAGGCGAAGGGCACAAGGCCG<br>TACCGGCTCTTGAGCTCGATCTCGCGGATGCGGCTGTACTTGTAGAACAGGTCCTGCGGCTCCTTCTCGCGCACGTGGGTCGGAAGGTTTCCCCACGTAGATG<br>CACCCGTCGCCCTCCCAGCCGCGCTCGTGTCCGCCCAGCCGGACAACCGCACCGCCCGACGCTGCTGGCCAGCCGCAGCCCGCATCCGCCCGTATCGCCGCCG<br>CTGCCGCCTCAGCACGGCTGCCCCCGCAGCGTCTGTTTTGTTTTATTCTAACAGGGTCTCTCTCTGTCGCCCAGGCTGGAGTGCAGTGGCGTGATCTTGGCTC<br>CCTGCAACCTCTGCCTCCCGGGTTCAAGCGATTCACCTGCCTCAGCCTCCCAAGTAGTGGGCATTATAGGTGCCAGCTAACCATGGCCGGCTAATTTTTTTTT<br>TTTTTTTTTTTTTTTTTGAGACAGAGTCTTGCTCTGTCACCCAGGCTGGAGTGCAGTGGCGCGATCTCGGCTCCCTGCAACCTCCGCCTCCTGGGTTCAAGC<br>GATTCTCCTGCCTCAGCCTCCTGAGTAGCTGGGATTACAGCTATGTACAGCGATGTCTGCAAAGATAGGGATTTAACAGCACTCATATCTTCATGTTCATAAA<br>AAAGTCCTACACGCGTGATGTACGTCTAGATCTTTCCTTTTGTCACAGGATATAGCACGGTAGTTACGGATATAGTCTCCGCAGTGCCTGGGTTTGACTCAGC<br>TTCCCCACGTACTGTCCTGCGCATATTTTGTGTCTCAGTTTCCTCATCTTTAAGGTAG |
| 205 | SIM2 | CACGCGCCCCGGCCTGGCTGGAGGGGCCAACCCAGCGGGGCCCGCCTGCCCGCCGGCCTTTCTGTAACTTTCTCTCTTTAAACTTCCAATGAATGAACGTGCC<br>TCTTCTTACGGATTTGTTTAGATTAGGGAATAGATTCCTCGCTGATAGCGTTGCTTTGCAAATAAGACCTCCTATATTATTCAAACCAAACGAGTTTGTGTCT<br>TTAAAGGACTATAGCAGCCCCATTCTATGTTAAGGGTTGGCTATTACAATTATTATATGCTTAGGGAAAAAATGTAAGCCCCGTAGTTTGTGCTTTTCTTGAT<br>GTACAGAAAGGTTTATCTTAGGTGGATAGGTTTTGTTTTGTTTCTTAAATGGGATTTTTTTGGTTCGTGTCTTTGAAGGGCTGTTTCGCGACGTCATTAATGA<br>ACTAATCGGTTTTCAGATTTCAAGACGGTGTGTAATTGATGTAACCACTGAGGAATTTCAGTGCACACCAGACTAAGACTCTTCCAGCGCAGGGGATTCCAGA<br>TGCTTCTTGGGCCCTCTGGAAGCCATGGGGATGTTTCCAGACCGAAAGGAGGGCTTTGCTGGGGAGCAGATGTGCTGCCTCTCCCCGACCCAGGATTTTGAGG<br>CCATGTTTCCGTTAATCTGGACCGAGAGCCCTCTGGGAGAGGGAGGCAGGTCGTAGGGGGCGGGGGTGAGGGGGAGCGAGATGAGGTCGTCGCTGGACGCTGG<br>GCTCCCTTGTCGTTGTCCTTTTCCCCAGAATCCATGGTCAGGCCTAGGGAGCCACCCCTGGGTGCTCGAGATGAGTCCCCACCCTCACTGAAGGTCGGTCACT<br>GGATGTTTGTGTGCATCGTAAGGGGCCCACCGAAGTCCCGAAGCCTTCTCAGGGACCAGCGAGAAAGAGGAGCAGGCTTGGGAGACAGGGAAGGAAAATGCAG<br>GGGAAAGGGCTCACCCCTCGACCCCAGGTAAAATTAGAAGGAACGTGTGGCAACCCAGGTGCAGCTTTGGTCGCTCGCTCAAGGACTTTGCTAGTCACTACCA<br>TTAATTAATTAATCACTATCATTAACTACCAAGGACACCGTTTTTATTCCCCTAAAAGCGTCACCTTGAGGGGAATGGAGAATTGGGCAGCAGCTATGCAAAT<br>CCTGGGACAGGAGACACTGCCTGAGGACCCTCTCTCACTCCCAATCCCAGAACCCGAAGTTATCCCCGACAACCAAGTCCAAGCACATGAACCAAGACGATCA<br>GCTTCAGGCAGCTCCTTACCCCCACAAGCGGCCCAGGAGGTGGGCATTATCCCCCACCCCTGGGATTTCTCCATCCCTCCCTCTTCTCTCCTGCGGGAGAGAG<br>AGCTGTGGTCACCCAGTTGGGCGCGATGGCTCTGGACTAATGGGGTCTCTAGACCCAGGGCACAAAGGCCAATCTGCCAGGGGTTACTGCATGTAATGAGATA<br>ATCAGACATGTTGACCAACCTAAAAGAAAAGACTCTCCCAGGGAGTAACTCCCAGTGAAATAATTTATTAAAAAAAGCAAAAAAGAGACATAAATTTCTCTCT<br>ACTACTTGAGGAAACAGCAAACAGAACGAATTAGGGTCTTGGCCTCTGCAGGAATAAATTATTTCCGACTTGGTCTGGATACCTGTAATTATTTGTAAGCTGT<br>GGGTAGTAATACTGTAATTGTCCCCCGGTCCTTTCTGGAAGTAGCAATGACCCCAAGGACAATTGGTGACGTCTCCACAGGGTTTACACATGGAAAGGAGTGA<br>AAAATCGAGGAATTCTTTCAGATAGCCCAGACCAAAAATCCTCTCAGCCATGAAAAGGTCATATATGTGATGCTGGGCCAAGCGGACTTTTCTGGAGTAACCA<br>TATCATAACTGATTGCGGATGTAGACAAGAGCGTATAAACCAAATAGGCTTGAATCAACGCAGTCCTGGATTTTCTGTTGCCTCTGCTTGCTGGGGCAGTGGA<br>AGTTCTTAAACTCCACTTCAGAGGTTGGAAATTCTTCCCCCTCCCCCACCTCCTTAGTGACAAGGTCTCTGATCTCCTGCTGCCACTGCAATAGCCTCTCCCA<br>TCCCGCGGGGAACGGCCGGAGTTCTTCCCTTGATCTCTCCCGAGTCGGCTTCCGCTGGGGATGGATCGCAGGTAGGCGCCGGCGCGGCCTGGGGAAGAACAGT<br>TGCGGAGCATCTGAAGCGGAAAATCCAAGCAGATGTGAGGCGATCCGGGCCCGCCTCGTTCCTCTTGGGGCCTGAATTTCTTCCAGATAAGTTTCCTAATGGA<br>ACATTTCTAAGAGGTGGGGTACGAGGCGGCTTGCTCGCACGCGCAGTGGGACAGACTGCGGGTGGGGACGTACTGAGAGGTCCGGACCTCAATGCGTCCGACC<br>CGTCTCCACACCGCCCTTTTCCAGCCCCCAGTCTCCTTTCATTCCCTACTCTTCAGGCTCCTTTGGGGCCAGTGGGTGAACCGCCATTTAGAACGGTGCCTCG<br>GACTCGGGGGTCGTGCGCTCCATCTCTGCCTCCCCCCTGGGGCCCGCGAGGCTGGTCCGGGCTTTCTGAGCTGGGCGTTCGGCTTTAGGCCCAATACCTGGAC<br>CAGGAATTTCTTCTCCCCGCGCCAGAAGGGAAAGACATAGGAGGTGTCCCAATCTGCGGTCACCGCCGATGCTCCTGACCACTCTAGTGAGCACCTGCCCGGT<br>ACTTTTCCATTCCAACAGAGCTTCCAGCTTCATACTAACTATCCCACATACGGCCTGTGGGTATTAGCTCTAAGTGTCCTTTTCCGAGGGCCCGAGGCTCCCC<br>CTCCAGCAGGGAGAGCTCCGGGACGGCCCCCACCAAGGGTTGGGTTTCTTCCTTCACAATTCCACAGAGGCATCCCTGTCCTTCCTACCTGGGAAACCTCGAG<br>GTGCGGTGCCCGTGTACTTCTGGTACTTTGCGTGGTGCCATCAGGGACCCCAGAGCCACAGCTGCGTGTGTGTGTGGATGTGTGTGTGTGTGTGCGCGCGCGC<br>GCGTGTACGGCGAAAGGATGTGCTTGGGGGAGCCGAGTACACAACGTCTGCTTGGGCAGCTGCTGGGCAGGCGTTGGGCCTGGAGGTATCTCACACCCACGTA<br>TCTTCCAGTCTTCAAACACGGCATTGCTCTGCCTCCCGTAGCGCGCTTCGAACCTGCCTCGCGGACACGTGAACAGAGGCTGTCCCTGGGAAGATAAGTGCGC |

TABLE 4C-continued

| SEQ ID NO | GENE NAME | SEQUENCE |
|---|---|---|
| | | TTTCCCGTAAAATCCGGGAAATTTGCCTTGAGGAAAGTTTCCGTTCTTGTTACTTGTCGGGTTTCTCCCACTTCCACTTAGCCATGTTTCTGCGATCTGGGTA<br>ATCCCTTTCAAGCCCAGGAGGAATTCTCCCGGGTCCATAATTGAGGGTCGGAAGCCGTGGGGGTGAGAAACGCATTAAATCCTCCCGAAGCCCAGGAGGTGCC<br>AGAGCGGGCTCAGGGGGCCGCCTGCGGAAGCTGCGGCAGGGGCTGGGTCCGTAGCCTCTAACCCCTTGGAGCTCCTTCTCCCAGAGGCCCGGAGCCGGCAGCT<br>GTCAGCGCAGCCAGGAGCGGGATCCTGGGCGCGGAGGTGGGTCCGACTCGCCAGGCTTGGGCATTGGAGACCCGCGCCGCTAGCCCATGGCCCTCTGCTCAAG<br>CCGCTGCAACAGGAAAGCGCTCCTGGATCCGAAACCCCAAAGGAAAGCGCTGTTACTCTGTGCGTCCGGCTCGCGTGGCGTCGCGGTTTCGGAGCACCAAGCC<br>TGCGAGCCCTGGCCACGATGTGGACTCCGCAAGGGGCTAGGGACAGGCAGGGGGAGAGCCCGGGTTTGCGCACACCTTCCAGCCCCTGGAGGGAGCCTGCTCG<br>GCTTCGAACGCCTTCGAACTTTTGACCTTCAAAGGAGTCCCTGGAAAAGGTCAGGAGCGCCTGCTGCAGGCACGGTTGCCGAAGGCCAGGCCTTCCTGGCGCA<br>GGGGAGGGCCAGGGGAGGGAAGCGGATACTCAGTCGCTGTCCGACGGCGAGTTTTCGGAGCAGCAGGCTCATGATCCCGGGCCAGTGGCGAGAGCAGTGACAC<br>CGAGAACCCAAATCTCCGCGCCCCCATCCGCGGCCCGGTGTCCTCCCGGCCCCTGCTGACCTCCAGGTCACGCACCCCACTGCTCCACGGCTCTGCAGCCTGT<br>GGCACACGGCCGAGAGTCCCCACATGATCTCGACGCCAAGGTAAGGAATTGCCCTGCGTCCTCTGAGCCTGTCTCTGGCCTGGGGGGCCGGGAAAGCTGCACT<br>CCTGGAAGAGGTGGGGTTATGTGACCGCCGCTGCAGGGGTGCGCGGAGGACTCCTGGGCCGCACACCCATTTCCAGGCTGCGGGAGCCGGACAGGGGAGGGCA<br>GAGGGGGGACAAAAGGACTCTTTAGGTCCAAAATGACCCTGAAGGAGAGTCCAGAATGCCCAGTGGCCGCGTCTGCAACGGAGTCTTCTTTCTCCAATTGCCT<br>TCTGCCCCATCACCATGGGCCCCACCTGCGCCACCTGCGCCCACCCTGTGACCCTGGCTCAGCGACCTTGGCCCTTAATCGCCCAACGCCGATTCCTCAAAAT<br>TCCGGCTGCGCTGAATCGGGCTGCTTTTGCCGCCGCCCCGGCAGTTGGGCCCTGTTTCCGCCGGCGCCCTGGGAGAGGCCTCACCACTCGGCTGGGCTCCCTG<br>GCCCCTCCCTTCCCCTGGCCTGAGCGCCCCTGCGGCCTCCCGCTCCTCCTGAGAAGGCGACAATCTCTTTGCACCTTAGTGTTTCGAGGACAGAAAGGGCAGA<br>AGGGTCACTTCGGAGCCACTCGCGCCGTTTTCACGTGTGTGTGTAATGGGGGGAGGGGGGCTCCCGGCTTTCCCCTTTTCAGCTCTTGGACCTGCAACACCGG<br>GAGGGCGAGGACGCGGGACCAGCGCACCCTCGGAAGGCTCGATCCTCCCCGGCAGGGCGCCTGGCCAACGAGTCGCGCCGCCTCCTCTCGGCCGCGCCTGCTG<br>GTGACCTTCCCGAGAGCCACAGGGGCGGCCTCGGCACCCCTCCTTCCCTCGCCCTCCCTGCCGCCCATCCTAGCTCCGGGGTCCGGCGACCGGCGCTCAGGAG<br>CGGGTCCCCGCGGCGCGCCGTGTGCACTCACCGCGACTTCCCCGAACCCGGGAGCGCGCGGGTCTCTCCCGGGAGAGTCCCTGGAGGCAGCGACGCGGAGGCG<br>CGCCTGTGACTCCAGGGCCGCGGCGGGGTCGGAGGCAAGATTCGCCGCCCCCGCCCCCGCCGCGGTCCCTCCCCCCTCCCGCTCCCCCCTCCGGGACCCAGGC<br>GGCCAGTGCTCCGCCCGAAGGCGGGTCTGCCATAAACAAACGCGGCTCGGCCGCACGTGGACAGCGGAGGTGCTGCGCCTAGCCACACATCGCGGGCTCCGGC<br>GCTGCGTCTCCAGGCACAGGGAGCCGCCAGGAAGGGCAGGAGAGCGCGCCCGGGCCAGGGCCCGGCCCCAGCCGCCTGCGACTCGCTCCCCTCCGCTGGGCTC<br>CCGCTCCATGGCTCCGCGGCCACCGCCGCCCCTGTCGCCCTCCGGTCCGGAGGGGCCTTGCCGCAGCCGGTTCGAGCACTCGACGAAGGAGTAAGCAGCGCCT<br>CCGCCTCCGCGCCGGCCGCCCCCACCCCCCAGGAAGGCCGAGGCAGGAGAGGCAGGAGGGAGGAAACAGGAGCGAGCAGGAACGGGGCTCCGGTTGCTGCAGG<br>ACGGTCCAGCCCGGAGGAGGCTGCGCTCCGGGCAGCGGCGGGCGGCGCCGCCGGGTTGCTCGGAGCTCAGGCCCGGCGGCTGCGGGGAGGCGTCTCGGAACCC<br>CGGGAGGCCCCCCGCACCTGCCCGCGGCCCACTCCGCGGACTCACCTGGCTCCCGGCTCCCCCTTCCCCATCCCCGCCGCCGCAGCCCGAGCGGGGCTCCGCG<br>GGCCTGGAGCACGGCCGGGTCTAATATGCCCGGAGCCGAGGCGCGATGAAGGAGAAGTCCAAGAATGCGGCCAAGACCAGGAGGGAGAAGGAAAATGGCGAGT<br>TTTACGAGCTTGCCAAGCTGCTCCCGCTGCCGTCGGCCATCACTTCGCAGCTGGACAAAGCGTCCATCATCCGCCTCACCACGAGCTACCTGAAGATGCGCGC<br>CGTCTTCCCCGAAGGTGAGGCCTCAGGTGGGCGGCCGGGGACGCTGGGGAGCCCGGCGGCCCCGGCCCAGGCGGGAAGCGCAAGCCAGCCCGCCCAGAGGGGT<br>TGCCGCGGCCTGGCGTCCAGAGCTGGGGCGTCTGAGGGAGGTTGCGTGAGGGTCTTCGGCTTCGGCGCTGGCTTGGGGCGAGGGGCCAGGGCCTTGGCGGCCC<br>AGGCGACCAAACCCTCTCCTGGTCCAGGGCTGGGTGAGGGCGAATTACGAATTGTTCCAGGGGCAGGCAGTCCCCCAGCCCGCACGGCCAGCGAGTTCTTTCT<br>GGTTTTGTTCTTTCTCCCTTTCCTCCTTCCTTCCTTCGCCAGTGCATTCTGGTTTGGTTTGGATTTTTTTCTCTCTTTCTTTCCTTTCTTTCTTTCTTTCTCT<br>TTCTTTTTCTTTCTTTCTTCCTCTTTCTTTCATTCTCCCCTTCCTTCCTTCCTTGGCCCCCTCTCTCCCTCCCTCCTTCCTTCCTTCCTTTGCCAATGCATTG<br>GTTTGTTTTCTTTCCTTTTCTGCTTTCCTTCCTTTCTTTGGAAGTTCACTCTGGTTTTGCTTTCTTTCTTTCCCCATCCCTTCCTTTCTTTATCCCTCCTTCC<br>CTTCCTCCTTTTCTTTCTACGATTCCCTTTATTTTTCCTTCATTCCTCCCTCTTTTTGTCTCTTCTGGAGGAGGTGAAGGAGGGTCAGCTTCAGGCGCTGCGA<br>GTCAGCGGGGATCACGGTGAGGCCCAAGCACTGCAGGCTGAGGCCACAGAGCGAACACTTGTGCTGAGCCGGGCCCTCTCGTGAGGCTGGGGTGCGGGAAGTC<br>CGGGCAGGAGAGACCCGCCCCCGCCGTTGCTGAGCTGAGACCCGGCTGAAAGAGAGGGGTCCGATTAATTCGAAAATGGCAGACAGAGCTGAGCGCTGCCGTT<br>CTTTTCAGGATTGAAAATGTGCCAGTGGGCCAGGGGCGCTGGGACCCGCGGTGCGGAAGACTCGGAACAGGAAGAAATAGTGGCGCGCTGGGTGGGCTGCCCC<br>GCCGCCCACGCCGGTTGCCGCTGGTGACAGTGGCTGCCCGGCCAGGCACCTCCGAGCAGCAGGTCTGAGCGTTTTTGGCGTCCCAAGCGTTCCGGGCCGCGTC<br>TTCCAGAGCCTCTGCTCCCAGCGGGGTCGCTGCGGCCTGGCCCGAAGGATTTGACTCTTTGCTGGGAGGCGCGCTGCTCAGGGTTCTGGTGGGTCCTCTGGGC<br>CCAGGAGCTGGGAGGGCTGCGCCGGCCTCTGGAGCCCCGGGAGCCAGTGCCGAGGTAGGGAGACAACTTCCGCCGCAGGGCGCCGGACGGTCGGGGCAGAGCA<br>GGCGACAGGTGTCCCTAGGCCGCAGGGCGCTTCCATAGCGCCATCCCCACCAGGCACTCTACTCGAAATCGGAAAGCTCGACCTTTTGCGTTCGCCTCTGCCA<br>AGCCTGTTATTTGTGCTGGCCGCTGGGTCTGGAGCTGCGCTTCTCGGCCCCTCCCCGGTGGAGCGCAGAGGGCTGGTCTGCAAGCGCGGCCTCCAGCCCCGCG<br>GCTCCCCGGCCCAGGAGCCAGGCGCGGGCTGACCCGGGAGCACCCGGCAGCGGAGGGGGCTGGAAGCGGACCCTAGGCCTCTCCTGTGCCACCCGGCCCTACC<br>GCGCGGCCGCGGGGCGCTCTCCTCTCGGGCGCAGCGGTCCTTCAGCCCAGGGCAGGTTCCTCCCTTTCCTACTCGGAACGTGGCAAAGATACCCCAGTCCCAG<br>CCCCTCCAGCTGAGAGCTGTTGCCCAAGGTCGTCGCTACTTGTCCGCTCAATGGTGACCCCTTGGCAGAGAACTAGGGATGATTCCACTCCGGTTGATGTTTT<br>AGGGGAAATTAAAAGAACATTCGGTTTTCTGAGTCTCCTTCCGGGGAGGCGTGGTGGTAACTGGTTTGCTGGGAAGAGCCGTTCCTTAACCGCATGCAACAAA<br>GCAGGTGTGGAATCCGGACGAGAGGGCACTCACTGCCTTCTGCCCCCTTTGGAAATAGAAAAAGCCTTCGAAGCAGCAATCCAAAGATCAAATGATTTGCGGT<br>CAATGATTTCAATTAAACCAGAAATTAGTAAGGGAGGGCCGAGAAGACACGGCTGCTCAGAAGCTGTTCGCTGTTTGAGGGATTTCCCGGAGAGCCTGTTAAA<br>AGATGCGAAGTGGTGGGTGTACCGCTCAGCCACCTTTAAACCGGCTCTGTGCGTTCTGGCTCTGGAAAGCAAGTCTCCAGGCATTTGGGCTCAGAATTGCTGG |

TABLE 4C-continued

| SEQ ID NO | GENE NAME | SEQUENCE |
|---|---|---|
| | | GCCCCGAGTTTGGGCGGGGGTGGTCCTTCTGGGGGTCAGGCCTTGAGCAGCTTGCACTGGTGGCAGGTTTGGGAGCAGTTGAGGGGCTTCCTGTGTGTCTTTT<br>GGAGGGGGTGACCCTGGAAGTTGGCACTCTGGAAGGGAGCTGTTTGGCCCTAGAGTTTTGGAAAGGGCCCTGAACCTGTTCGGTCCCCCTCGGAAAGGGAAGG<br>GAGCAGTGGCTTAGTCCCTCCCTCCTCCATTCGTGCAATGCCTGGGGTAGGGGTAGACCTGGAGCCGGTGGACTCATATCCTTGGAATTCGTCAGGACAGCTG<br>CTCCGGGGCCTTGGCCCTCAGTCAGTCTGGGGCTGAGGAGTAGGGAAGCTGGGAACTTGGGGCAGAGGAAGAAGATGCGTTTAGAAAGACCTCCATTATGCAA<br>ACTGGAGTCCATTTATGCAAACTGGTCACCCTTCCAGTAGCTCCAAAGAGTGGCAGTGGAGTGGCATCTTGATTGATTTAACCTCTTCTCAGGGGACCTGGGT<br>CTGCGAGGGAGGATATGGCTGCGGGGTTGGAATAGGATCTGTCTGAGCTGCCAGGGTCAGGGTGGTGGCCCTAGGGAGGTTTTAGGGCCAGGGTGGTCCCGGG<br>CTGTGGCAGGGGCTCTCAGATCGCCTCGGGCTCTCAGCTGCAAGGTGAAAAATACCATGAGGAATTGATCTGCCAAGGGCGGTCTTGTCTCAAAGCAAGTGGA<br>TTGCTGGGGTAAAGAATCTAGAGACCAGCTTAGGACTCTGGGAGGAAGAAAAAAAAAAAAAAGAATAGCATAGTCCTAAGGAACTGCAAGGATCACCAGATTAA<br>CCCTTCATACCTGGGGAAATTAAGGCCAGACATGACACAGGCCTTTCCCAAGGCTCTGTAGCAAGGGCAATAGCAGGCCAGTTGCTGCCACTGCGGTCCTGTG<br>GGGCATGTTCTCACTCCACTGCACCCAGGAGGCTGCCAGCCTCTGTTCCTTTTAACATAGATCTCCTCAGTTGTTAAGACAGAAAGAGGAACTCAGAGGGGTC<br>CCTGTGTGCAAGGCAGAGGGAGACCACCAGAACCAGGGTAAGCACCCCACTTGGTAGCCAGTTCAAGGACTTGGGGATGTTTTCAACATTTACAGCGAGGTTT<br>GAGGCCCCATTGTCATGCAGCGCTACTCGGCCTTGGTCTCCTTATCTGTAAAATGGGCCCATTAGCAATGCACAGGGTTGCTGTGATGAAGGGTGAGGTCCCA<br>CAAGCAAAAGCTGTGCAGTGAGGGGGGAATCCTAAGCATTGTTCCTATGCCATTCACCCCTTCCTGTGAGCTCCCCATATTCCCTGGCTCAAAGGAGTCTTGA<br>ATGGCAGGGATGGAGGACTCACTGCCTGGACTTTGAAGACCCCTGCTTTCTGGGTGACCACCTTTTCTTCCCTTTGACAGTGAACTAATACATTGGAGGTAGA<br>TAGTGCTGGGAAGAGGACAGGAGACCACGGCTGACTTTGGACATGGGCTCGAAATTGATAACTTGATGAGTCTTGGAGGGTGGTTAAGATAAGCTCGGGGCTG<br>GGGCAGCGCTGAGGTCTGATGGTCAGCCAGCCCTCCCCAAAGTGTGGCCCTCCGTTCTGGAGATAGGGGCTTTGGAAACTGCAAAAGCGTCCTGGCAGGCCAG<br>CTCTGGTTGCTCCCTGGCCATAGCTGCTCTGACTACAGGCAGCAGGACGCAGGTCGGCCTCTGCCCATCGGAGGTCAGAGGCAGGGCCTCCAGCACCAGACTC<br>AGCAGTGCCACTGCAAACCTGGCACAACAGGCTGGTCCCAGGACTCAGCTCAGCAGTGAAGTTGGAAACCAAGGTTGAGTCTCCCCATCTCCCTTTCCCCAAC<br>CCGAAAGACCCAAGATGGGTGTGGGTGAAAGAGGGAGAAAGAATTGCTACTCCAGAAACTGTCATTTGCCCACACGAAACGAGGTGGGGTTCAAGGTCTGAAC<br>TCTTCCAGTGCCTGGGTGCCTTTGGGTTTAAATTCAGCTGCAGGTGCCCCCATCACCACTTCCACCTGAGCACACCACGAGAAGCCAGGTTATCTTAGAAACT<br>GTTTCCCGGAATCAAAGCGACTTGATTTGGAGAGTTGGGTGAGGAGAAACTCACCCCTATACCCCTCAGGGCGTCAGAGATGTGAGGCAATTCTCTACCTCCG<br>CTGGAAAAAATGCAGATTTATTAAAGGTCGACTGTTTAGCAGAACAACGTAGATTTTTTACAACGCTTTCCCCGTCTCTGCTTTGAAGCCTGCCAGGCTGCAG<br>CTGGGGATCCAGGAGGGAAAGCCCGCAGGCGCAGAGGGGACAATCCGGGAAGTGGTAAAGGGGACACCCGGGCACAGGGCCTGTGCTTTCGTTGCAGGCGAGG<br>AAGTGGAGCGCGCGCTGCAGATTCAGCGCGGGGCTAGAGGAGGGGACCTGGATCCCTGAACCCCGGGGCGGAAAGGGAGCCTCCGGGCGGCTGTGGGTGCCGC<br>GCTCCTCGGAGCCAGCAGCTGCTGGGGCGGCGTCCGAACTCCCCAGGTCTGCGCACGGCAATGGGGGCACCGGGCCTTCTGTCTGTCCTCAGAATACGTAGGA<br>TACCCGCGGGCGACAAGCCGGGCCAGGCTAGGAGCCTCCTTCCCTGCCCCTCCCCATCGGCCGCGGGAGGCTTTCTTGGGGCGTCCCCACGACCACCCCCTTC<br>TCACCCGGTCCCCAGTTTGGAAAAAGGCGCAAGAAGCGGGCTTTTCAGGGACCCCGGGGAGAACACGAGGGCTCCGACGCGGGAGAAGGATTGAAGCGTGCAG<br>AGGCGCCCCAAATTGCGACAATTTACTGGGATCCTTTTGTGGGGAAAGGAGGCTTAGAGGCTCAAGCTATAGGCTGTCCTAGAGCAACTAGGCGAGAACCTGG<br>CCCCAAACTCCCTCCTTACGCCCTGGCACAGGTTCCCGGCGACTGGTGTTCCCAAGGGAGCCCCCTGAGCCTACCGCCCTTGCAGGGGGTCGTGCTGCGGCTT<br>CTGGGTCATAAACGCCGAGGTCGGGGGTGGCGGAGCTGTAGAGGCTGCCCGCGCAGAAAGCTCCAGGATCCCAATATGTGCTTGCGTGGAGCAGGGAGCGGAA<br>GAGGCAGCCGGTCCTCACCCTCCTCTCCCGCCACGCACATATCCTTCTTGACTTCGAAGTGGTTTGCAATCCGAAAGTGAGACCTTGAGTCCTCAGATGGCCG<br>GCAACGCGCCGAGGTCACGCTCCCCAGAAACACCCCTCTCCCCTCCCCTACCCCAGCTCCCCCTGGGGCGGGTGGTAATTGGGGGAGGAGAGGCCGCAGGCAG<br>GGAAGGGGTGGGAAAGCCAGAGAGGGAGGCACAAAGTGATGGCAGCCCGGCAAACACTGGGGCTTCGGGCTGGGCCGCGCTCGTTTAATCCCACAAAAATCCC<br>ATTTTGGAGGTGAGAAATAGAGGTTAGAGGTCGGGCCCTTCTGGAGATCAGACCGAGGAGACGGGCCCAGCTGGCGTCTTAAAGCAAGGAGGGGGAGTCGGGA<br>GGAGGTGAGACCCCTGCACCCAGGTGGGGCTCCCAAACCGTTCTGGATTTACCACACTCCCAGGTCCGATTTTCCATGGAGGGCTGGGGTTAGGGACTGGCAC<br>CTTCTTGTTGTTAACCGCATTTGATATTCACAAGAACCCTGTGAGGAGACTTTGTCACCGTTTTTAGATGCCTGAGGTTGCCGGAGGGGCAGTGAGAGAATCG<br>TCTAACCTGGTGTTCCTACCACAGTCCAGGCCCTGTGTCCTGGGCTGGACCCACAGCCCCTGCCACCACCCAGAGGAAGGCGCGAAGCTGGCTGCCTCCTTTA<br>CGGGTCTCCCTTAGGTGCCCTCATGAAGGGGGACGGCCACCTCACAGTGCAGGAACTATCTCCCCGTTTGCTCCCAAATAGTCTTCTTGGTGTGGTGCTGTCT<br>ATGGTCTGTGACCTGCATCTGGAGTTACCCCCAGGACCAGCTTCGGAAGAGGAGGGATCGCTTGGAGGCCGTGCAGTGTGAGGAACGGCAGGCAGGGTGTGGG<br>ACCAACATGCACACACTCGCAGGTGCTGGGGCCAGGGAGGAATGAGGCGCTGGCTCCCTTTCCCTCCATTTCTCCCTGGGGGTCCCAGCAACCTGGCCATCCC<br>TGACTTCCAACAGCACAGCGTCCCCACAGGTCCTGCAGTGCTCTGCAGGGGTGCAGGGAGCTCCCCTCCCCCCAGCCGCAACCTCACCTTCCTCACCCCCACC<br>CCTCCGGCAGGAAACCACAGGCTGGGTTGGGGACCCCTGGTGCTCCAAGAGAGCAGTGAGTGCTGGGAGCCGCTAACCCCGAGGCGCCTAGCACAGACTCTTC<br>TCACCCCTTATTTCTGAAATAAAGCCCTTCCTTAGGTCCAGATGAGGACCACGTGCTCAGTGCCTCACTTTCGTGGGAGTGTATATCACTTTACAGTATCAAG<br>ACAATTTTCTTTCGTTACAAATCTTTATTTAGTCTCTGCGTTTAGACCAAAGTAGATTTTTATGGGCTGAGTGAAAAAACCTCGCCCGCATTGGTTTCTGATG<br>GAACAGCTGGCAGCGCCACGGCCCCGGGTGGGGTGGCCTAGAGGCAGGGGTGCTTGGGAGGAACATCTAGCACCCGACCACCTCCACCAGGTGGGAAAGGGAC<br>GTTTGCACCAAATCTCCGCCGGCAAAGCAGAGGCTTTGGGGAATTACAGAAAAACTATAATGATCTAAAAGAGAACAAGTTATCTTGAACTGTGCGGGTATTT<br>GAATCATACAGAAAATTGTCCTGTGTGCCCAATGCACTTTTGCATGTAGAGCCAGGGCCTTCGAGGAAGCTTTCAGGAGATCCCGGGCAGCGGAGTCTGGTCT<br>GGAGTTTCATTTCCGTAGGTGCAGATTTCTCCCCAAGTCTTCCCGCCATGGGCTTTGCAAGAAGCCAGGGCCCAGAGGCCACGCTCACCGTTAACACTGCACA<br>GGGCAAAGGTGGCTCCAGGACAACTGCCCAACCCCAGGAACGACCCAGCAGCAGAGAAAAGGACAGCTGCCAGGGTGCCTTTGTCGCTTTTTGGAAATCAGAA<br>TTCCTGGGTCCTTAGTTAAGTCTTACTTCACCAAATCCCAGGACCTTCACATTTTGGTTCTTGCCATTGCTAACAGTTGTAAATGCTGCCGCCACGAGGCCTG |

TABLE 4C-continued

| SEQ ID NO | GENE NAME | SEQUENCE |
|---|---|---|
| | | GGAGGAAGGACCCGCTGGTGAGAGCACAGGGAGTGCTGCTGTGATCACGGTGGTGATGCGGGGTGAGCGCGATTTCCCGGGATTAAAAAGCCACCGCTGCCCC |
| | | CGTGGTGGAGGCTGGGGGCCCCCGAATAATGAGCTGTGATTGTATTCCCGGGATCGTGTATGTGGAAATTAGCCACCTCCTCAGCCAGGATAAGCCCCTAATT |
| | | CCTTGAGCCCAGGAGGAGAAATTAAAGGTCATCCCTTTTTAAATTGAGGAATAGTGGTTTTTTTTAACTTTTTTTTTTTTAGGTTTTTAGTTGCCGAATAGGG |
| | | AAGGGTTTGCGAAGCCGCTGCCCTGGGCCGAGGTGCATTTTACGCTTCCAGAGGTCGAGGCCTCCAGAGACCGCGATGCCCAGGGCGTTCCCGGGGAGGCTGA |
| | | GAGACCCAGGGTGCTCTGGGTGACTGCACGGCGACTCCTCGGGAACCCACTCGTGGCTGCCCGCTTGGAAGGGCTTTGCGGCCCCGGGAACGATCTCCAGGAT |
| | | CTCCACGGCTGGTCAGGTTCCCCGTCCCTCGTATCCCGCGCTGCCCGGGGGCTCCTGCCTTTGGTTCAGTGCTCGCGGCACCACCGCACTCAGGACGGCAGTG |
| | | GGGGGCTGGGGCTGGGGCTGGGCCTGGCCCAGCGTGGGTTGGGGCGGGGGACGCGCCAGCAGCGCCCGCAGCTCGCTCCGCAGGGGTCGCAGCCAGGGGTCGG |
| | | GAGCTAGGCTCGTGGGCCGGGAGACGCCGGGCGCGTTGTCCTCCGGGGAGGTTGGGGTGCAGGCGGTGCACCGACCCTCGCCATCTGGCGCTGCAGCCACCAG |
| | | CCACGGCGCTTAGTGGAGGGTCTGCGGCCAGGCTCCCGGCGGAAAGATTCCGGGGAGGGCTCGGGGGTTGTCCCAGCCCGCGCTAAGCGCCGCAGCCTCGCCC |
| | | GGCTTTCCTGCTTCCTCGGACTGTGCAGGGGAAGCCTGGGGTCTCGCGGGGCGCAGCAGTCAGGTCGAGGGTGCAGCAGGAGGGGAGTCCTGACGGGCAGGTC |
| | | CCTCTTTCCCCTGGTGCGCAACACTGGTTGGTAGCTTTTGCGGAGGTGGTGAAGAAGGGCAGGAGGCCTGTTGAGCGGAGGAGTCCGGGGATCCCTAATTATG |
| | | TGACAGGAGACCCTTTCCAGTTCGGCCTGTGGCCCATCCCTCTCTCACCGCCGGCAGATTGGAGTCTGCTCTCGGGGAGCCCCCAGGTAAACCCCTCACAGGG |
| | | AGAAGGTTTCGGATTGGAAGGAGGACCGCGCTCGTGGGGCGCCTGTGAGAGCTGGGGAAGCCCAAGGGGTAGCGTGTAGGGGGTTTTTTATGCGGGAGGAGCTG |
| | | CCTCCTGGGCGGCGGGGACTTTCTGTCTCAGCCTGTCTGCCTTTGGGAAAACAAGGAGTTGCCGGAGAAGCAGGGAAAGAAAGGAGGGAGGGAAGGAGGGTCC |
| | | TTGGGGGAATATTTGCGGGTCAAATCGATATCCCCGTTTGGCCACGAGAATGGCGATTTCAAAGCAGATTAGATTACTTTGTGGCATTTCAAATAAAACGGCA |
| | | ATTTCAGGGCCATGAGCACGTGGGCGACCCGCGGGAGCTGTGGGCCTGGCAGGCTCGCACAGGCGCCCGGGCTGCCGGCCGCTGCGGGGATTTCTCCCCCAGC |
| | | CTTTTCTTTTTAACAGAGGGCAAAGGGGCGACGGCGAGAGCACAGATGGCGGCTGCGGAGCCGGGGAGGCGGCGGGGAGACGCGCGGGACTCGTGGGGAGGGC |
| | | TGGCAGGGTGCAGGGGTTCCGCGTGACCTGCCCGGCTCCCAGGCATCGGGCTGGGCGCTGCAGTTTACCGATTTGCTTTCGTCCCTCGTCCAGGTTTAGGAGA |
| | | CGCGTGGGGACAGCCGAGCCGCGCCGGGCCCCTGGACGGCGTCGCCAAGGAGCTGGGATCGCACTTGCTGCAGGTAGAGCGGCCTCGCCGGGGGAGGAGCGCA |
| | | GCCGCCGCAGGCTCCCTTCCCACCCCGCCACCCCAGCCTCCAGGCGTCCCTTCCCCAGGAGCGCCAGGCAGATCCAGAGGCTGCCGGGGGCTGGGGATGGGGT |
| | | GGTCCCCACTGCGGAGGGATGGACGCTTAGCATGTCGGATGCGGCCTGCGGCCAACCCTACCCTAACCCTACGTCTGCCCCCACACCCCGCCGAAGGCCCCAG |
| | | GACTCCCCAGGCCACCTGAGACCTACGCCAGGGGCGCCTCCCGAGCGTGGTCAAGTGCTTTCCAATCTCACTTCCCTCAGCAGGTTCCACCCAGCGCTTGCTC |
| | | TGTGCCAGGCGCCAGGGCTGGAGCAGCAGAAATGATTGGGCTGCTCTGAGCTCTGAAGCATTCGGCCGCTGTGTGTGTGCAAGGGGCGCAAGGACGGAGAGAC |
| | | AGCATCAATAATACAATATTAACAGGAGCACTTGTCCAGAGCTTACTGCAAGCCACATTCAGTTCCGGACCTTATTGACTTCCCCCTCCCATCTAGAGTGGAT |
| | | TCTGGTTTTTCAATTTGTTTTGTTTTGTTTTTTGTTTGTTTGTTTGTTTTTGAGACGGAGTCTCACTCTGTGGCCCAGGCTAGAGTGCAATGGCGCGATCTCG |
| | | GCTCACTCCAACCTCCGCCTCCCGGGTTCAAGCGATTCTCCCGCTTCAGCCTCCCGAGTAGCCAGGATTGCAGGCACCCGCCATCATGCCTGGCTAATTTTTG |
| | | TAGAGACAGGGTTTCACCCAGGCTGGTCTCGATCTCCTGACCTCCGATGATCCGCCCACCTCAGCCTTCCAAAGTGTTGGGATTACAGGCGTGAGCCAACGCG |
| | | TCCTGCCTTGATTCTGTTTTTAACTCCATTTTTTAGAGGAGGAAATTGAGGCACAGAGAGGTTAAATAACATGTCTAAGGTCACACAGCAAGGGGTGGAGCGG |
| | | AGTTAGCCCACTGGCCTAGCTCTAGAGCCCACCCGGATAACCAGAACTTGGTGAGGCCTCCGGGCTCTTGCTTGGTTTGGAGCCAGGTGCTTAGCGCCCCGAG |
| | | CCCGGGGCCATTCACCCTGCAGGAGCTGCACGCGCCCCTGACCTCGGCTTTTCCCTGGCAGCAGAGGGGCTTTGCGGGTCGGCCGGGTAGCCCTGAGCACAGC |
| | | TCGCCACTTCCAGGTGGGCTGTTGGCGCTGGCTGGGGACACATCCCGATCTTTCAAATGCCCTTTACAGAGCCTCATCAACGACCCGATTCATTCCCCCCTCC |
| | | TGTCATTTGTCTCTGCCATCGAAAAATGCCTACCGAGAGCTGCTCTGCATTTCCGCCCTCTATTTTGTGTTTTACTTTAAAATAATAATAAAAAAAATGTTGG |
| | | CTGCAGGACGCCATGACTTAGGTCAGCGAGTCAGCCGCTAGCTCTGCATTTCCAAAAAGCAGATCTTTTCACAACTCTCTTGCCCCAAGTGCCCTGGTGTGGT |
| | | TTATTTTTTAAAATGCATGCCTGCGGAAGAGAAGACCCGGGGAATATTCGAAACCCCGAGCTTTTACAACATAAAGCGCATGGTGTGGCCGCGGCGAGTAATG |
| | | GCGCT |
| 206 | HLCS | CAAATCACTTGAACTCAAGTTCAAGACCAGCCTGGGCAACATGGTGAAACCACATCTCTACAAAAGTAAAGAAAATTAGCCAGGCATGGTGCTGTGTGCCTGT |
| | | AGTTCCAGCTACTCCTGGGGAGGTCGAGGCTGCAGTGAGCCGCAATCACGCCACTTGTACTCCAGCCTGGGCGACAGAGCAAGTCCCCATCTCAAAAAAAAAA |
| | | AAAAAAAAAAAAAAAAAAGGCTGGGTGTGGTGGTCCCAGATACTCAGAGGCTGAAAAGGGAGGATTGCTTGAGCCCAGGAGTTCAAGGCTGCAGTGAGCTGCG |
| | | ATCACATCAATGCACTCCATCCAGCCTGAGCAATGGAGTGAGACCCTGACTATATTTAAAAAAAAAAAAAATAGGAAGAAACAACTCAACCACAGGGCTAGTA |
| | | TGTTACTCGGTTATAAAATGATAAAGCCCTAAACAGAGAATTAGCCCGTTTCCAGAAGAGGCCAAGAACAGATGATACAGCTGAACTGAACTCCTGCCTGTAC |
| | | AGCTCGTTTTCTACAAGATTCCAGACCTGGAAGATGATGGCATCCAGCCCCCATTGAAGCACCTCGAACAAGAAAAACGCCGAGTCCGAAGAGCCAGGCCTTG |
| | | AACACACGATTCCTGTCTATAAATAACTCCCCCTGGGGAATAAAAAGCAGGATCCAAGGCAGGAAACCCGAGCCGTGGAATCTGGTAAGTTCTTAGGAAACCC |
| | | ACTCACGGGCCTGAGTCCCCCGTGGAAGCGGCGACTTCGGCACCTGGACACCCGAGTCCCCAGAGCCCCGGGCGGCCGCGCGTCCCTACCTGCAGGCCTGATA |
| | | CCGGCCGCGGAGCGCTCCTGGCCCCGCTCCCGCCAGGCTCCGGGACCGCTGAAACGCACCCAGGGGGGTGAAGGCGTAGTCGCCAAGGACAGCGCAGATGGCA |
| | | GCGGAGGCATGGGAGCCGGAACCTACCGTGGCAAAGGGCCAGGTCGGGACGCCCCTCGGCGCAGCCCCAAATCCTGCCCGCGCCCCAGCCCCGCTCAGGCCGC |
| | | GCCCCTGCCACCTCTGGCCACACGGGCTGAGACGTCTGGCTCCTGCACAGCGCACTTCCCGCTGCCCTTCTCCACTGGCTGCTCAGGCCCTGCCTCGCCAGCA |
| | | CGGCATCCGCGGGGGATCCCTACCTGTCCTTTAGGGCTTGCCTCATAGGTCAAACGTCACCTCCCAGGGAGGTATGGCTGCCCCCTGGCCAGGTGGGCCCCT |
| | | TCCACGCTCGCCTGCAACACCACCCACCCACCTTGATAACTGCTTGTAAAGGTTGTACTGCTTTCCCCCTTGAGACTGCAAACCTTCAAGGGCAGGAAATGGG |

TABLE 4C-continued

| SEQ ID NO | GENE NAME | SEQUENCE |
|---|---|---|
| | | TCTGTTTTCCTGGCAAAATAATGAAGTTGGCTTAAGGTTTTGCTGAATAAAATGAGTGACAGACAAAAGTAGCCAAATTTGGCACTCCTGATGGGTTATTTGA<br>TGAAGGAGGTGCAATGTATGGGCTTAACTAGTTATTCTGGATTTCTTTCCCCATGTTA |
| 207 | DSCR6 | CAAGGCCGGTGCACGCGGACCCGAGGATTCGGTAGATGTCCCCGAAGACCCGCTGCCGCTCTAAGGCGGTGGAAGCGAGATTCTCCGGAAACCCAGGGAATCC<br>GATGCTCGCACAGGACCAAAGCCCGAGGCCGCGGGGACCACAGAGGGACGGAGAAGCCGGGACTCCTCACATCCCACATCCGGCAGGGGAAGCCCAG |
| 208 | DSCR3 | CTGATAATAAAGTTTTACCATTTTATAATTTAAAAATGTAAATATGGAGTTGGGCATGGTGGTTGGGAGGCTGAGACCAGAAGATCGCTTGAGCCCAGGGGTT<br>TGAGACCAGCCTGGGCAACATGCAGAAACCCTGTCTCTACAAATAAAAAATTAGCCAAGCGTGGTAGCACGCACCTGTAATCCCAGCTACTCGGGAGGCTGAG<br>GCAGGAGAATCGCTTGAGCCTGGGAGGTGGAGGCTGCAGTGAGCTGAGACTGTACCACTGCACTCCAGCCTGGGTGACAGAGTGAGGCTCTGTCTCAAAAAAA<br>CAAAACACAAAAAAACAAACAAAAAAAAGCAAATATATGTAAAAATAGGAAGTGCGGTTTCCCAAAATGAGGTCTGTAAACAACTGATCTAGAAAATGTTCTG<br>GAAAAAGTAAAAAAGGATCAGGATCTGAGGTCAACTGACCTCTCCCTGCGCTCTGGACAGGCAAACAGGCAAGGTTCCCTCTGAGGCCGTAGCGGCTTCTCGT<br>GGGCGAGTCCCTGTTCGCAGGTGACGTGTGGACCACGCTCTTCCGAAGCGTCTGGCCTGTGTGCTCTCGGGGAGGGGACGCAGGTCAGCCCACCTAGCCGATG<br>GCTAACAAGTCAGTTTGTTTTCTGAACGGAAGCTTAAACCTAGAAAAGTAACTGGGTTGGGGTGGGGGTGTAGCCACATGCAGTAAAAGCACTGCCTGTCTGT<br>ATAACAACGACCTGATGAAAAAAGGAACGCGTGAAATGGGGAGTGTTAGGGCGTCACAAACTCCAGTGTGGTTGAAATGAAAGCAGAAAGCAAATGGCAAGCT<br>GGCTTCCCCTTCCAGCTTTTCACAACCCTGCCTTGCTCATGGTCAGCCCCAAGCACGGGCGGAAGAAAGGACTGGAGGGGAGGGAAAGGGGTGGGGAGCGAGG<br>GTACCAGAGGCGTGGGAGGACGGGGACAAAGGGGCAGCAAGGGACCGGCGGAAAGGAAAGTCGGCGTTAGCTGGATTGGAAACAGTCCAGACAGAACGATGGG<br>CTCTGCTGCCTCCGGGTGGGGCACCAAGCGGGGAGCGGGGCCACGAGGCAGGGGACAGTGAAGCACCATGCAGCGCCCACCAGCCGGCAGCGCCCACCAGCCT<br>GCGCTGCGCTGCACATGGTACCCGCGGCCCCAGCTGGCCAGTGTGTGGCGGAGATGAGACCCTCGTGAAGAGACTAAGCGGCCACAGCAGGGGGAAGGGTTGC<br>TCACATAACCCCATACTGCTCACACTACGAGGTTAACTGCCGTGAGATCTGCCTGCAGCCAGCAGAAACCCGTTCTAGGAAAACGTTGCCCAGTGACTTCAGT<br>GAGTGCCACTGACCCGGGCGCCTCCGCCCCGGCGTCCGGCAGCAGCACCGATTGCGCAGGAGGCACCTTGCAAACAACCTTTCCTGATCCGCGCTGCAGTTCC<br>CAGGCCGGTTGCAGCCGTTTCACAGAGACTGCGCACACAAAGCGTCTCCGTGCCCTGCCATTCACCTTTCGACACAGCCGCAACCCCTCTTTTCAGTGTTAAA<br>ACCTGGCGCCAAAAGGAACATGCGATGTGACGTGTTACCTCTGCGCATGCGCCGGGCATTCCCAGCGCCCCGAACCTGATGAACGCGCGGTGGGGACCCCAGG<br>CTTCCGTGCTTTCGTTTTCCTGGAAGCTACGTGTCCTCAGTCTACATATTGTTACCTGGAAAATAAAGTTTTCTCCTTTTTTCTTCCTTTGTTAACAGGCAGA<br>AGGTGTAGGCTGCAGGTTTCGGGCCTAAGAGAGGGCATGGCTGGCGACACGGAGTAGACTCCTAGATGACATAACGGAGGCGAGTCTGCACCGGGGACTCGGC<br>ATTAGGAGGAGGCAGAGGAAAAGCCCACCACCGTGGCCGAGGGAGATCTAGCAAGCAGCTTGCAGGGGGTGAAGTGTGTGCAAAGCAGGCTGAGACCTGTCCA<br>GTATCGAAACACGCCGCGGTGGTCAAGCAGGCTTTACCATGCT |
| 209 | chr21: 37841100-37841800 | TGAGGCTCAAAACAGGTGTCTGTGAGCTTCACAGGCGGTAAGGCCGTGTCTACATGGCCGGGACATGCATCCCGGGGCTGCCCCTGCCGTGCTGCCCGAGTGC<br>ACGGGGGATGAGGACCTGACAAGGCCATTGATCTTGCGGGAGCTTCCTGAACTACTCCAGCGTGAAAATCTTCCAGAAGGATTCTCCACAGGGCAATGAGGCA<br>AGAAATTTACAGCTTAGCCTGATTAATGGGCCAGGCAGTTAAGAGTTCTTTGCCAAGCTATGAGCATAATTTATAGTCATCACGGCAGGAGGAAAGGCCACAT<br>AACTCACATCCTTAAAGGGCCCTTAGAACAAGAGACACGCCGGATCATTGAAAACGTCTCCACTCCTGGCGCCAAAAGAGATCGGCACGTTTCTGGGTATTCT<br>GGTCAAAGAACAGGGAGTCTGGATTAATATACACGGCAGAAAAAAGCGAAGAAAAGACACACAGGTCATATATTTCTGACTGATATTCCGTTTGTTGTTTTCG<br>GAGGGACTTGGTATTTATTTAACCACATTCTCACTTGACACGCCCCCTCCCCACACCTTGTAAATGCCTTCCTCTTTAGCCGAGTCATTTTTCATCACATAGA<br>ATTGAAATGTTGCCAGGAAGGCGGTTTATGAGATTGTAGAAATGGCACTAGAGAAAGCAGTGTGAAAAGAGGCCTAGAACGT |
| 210 | ERG | TCTCTACATGCTATCTACTAAAAACTTAGGCAAGGAAATGCATCAGACCAAACACCCCACAGCACAGAGAACCGACCGGCCATTGCTTTCCAATCTCCGCAAA<br>CCTAACCATTGCTGGAAGAAATCTTACTCACAGTGCACAGACAGTAGGTATTTTATTGAAGATAAACATATAGTGGAACAAACCAAATTACCCCCATTTGAGT<br>TACGTGAGCACTCAGTTCTCAGCGTGGATGTCCCACAAATCAAGTCAACATTTGCGTCCCATTACCAGCAGCCACTTGCCGAGTATCTCTTCGCTTCCACTGG<br>GACTGCCTGGCATCCCTGATGCTAAGGAGCCACTGAAGAGCCTCCAAATGTCTGACATTCACAAACGCATCTTTTGCTTTGACCCGACCCTTCAACCTCTCCG<br>AGTCTGCTGCCTTTTCTCAGACACACATCCAGGCACCGTTAGGGATAGTTAGAGAATCTGAAAATTCAGAAGCGCTCCGAAAAGCCTTTCCAAAAGTAATCCA<br>CAGCACTCAACAGTGAATTTAGAAACCCCAATTTTTTTCTGAGTTTGAAGTTTTTAAGCCTTGCGGATGGTTGGAGTAGGAAAAA |
| 211 | chr21: 39278700-39279800 | TCAGACAAGCTCTGTGCAGTCGGAATTTTTTAAAGATGCACTGTCACTTGAGGAAGACAGGTGATCTTCCTGCGGCACAAATAGAAGCAAAGAGATTTCTCTT<br>CTTCTCTGTAGAGCAACACAATTGATAAATGGCCGATAATCTCCACCAAATTGGCAGCAGTAGGCTGCCCGAAGGCAGCAGGCATATTCGTCTTTGTGAATTG<br>TTTTACTATGATGCTGTCACATTTCCAGGAATAAGACGGTTAAAATGATATATTGTTGTGGTTTGGCATTTGCAGCTTTGCTCTGACTTCCCTGGTAACTGCC<br>AACATCTGCAAATTATTATGTGCTTAAAAAAAAAATCAACCGCCACCGCAGGCTGCCCCCACGGTCCCTGGCTGGGCCAGGCCTCCTGCCAGGCCACAGGGCA<br>GAGTTCTTGGACCAGGAGGCAGCAGGGTCAAAACCCAGGTTGCCTAGGAAGCCCCCAAAGACAGTTATGGATAGAGCTGGGAGCCCGAAACACATGCGGCAGT<br>CTCTCAGTTTCCAGGTACCGGTTCTCACATCATCCATGCATGTGTTTGAGGAAAAACAAAAAAAAATTGATGGTTGCCAAAAACAAAAATGCTTCCATATCAA<br>AGTTTATCAGTGTCAATGTCAAGAGACTTCTGGTTCGTAGACTCATTTTGGCTTGAGGCCACCAGAAGTGAACTCTGGTTTCTAAATGCAGAAGCAGAGGCAC<br>TGGCCGATCATGGAAGATGCAGGGAACTGTTCAAGAGGCCCAAGCCTGGTGCTCAGAAACTTGGCAGGATCAAGCATCTCGCCCAGGAATTCATCCCCTGCTT |

TABLE 4C-continued

| SEQ ID NO | GENE NAME | SEQUENCE |
|---|---|---|
| | | GTCTAAGCCGGCTGGCTCTCGTGACTGACTCGGAACAACAGAGCAGATGTTTGCGTGGGAGGCAAGCCTCACCCAACATCTGTCCTGCGGCGGGAAGGCCTGG GTGTTCACAGATAGAGCTGGAGTTCCCCGGTGGGTGGCACAGACAATTAGCTGGGGCTGCCTCACATGTAATCTAATTACAGGGGAAACAGGCTCAAACACCG GGTGATAAGCAGCGCAACTGTTTCGGGTGACTCTGTAATTTTTCCTCCATTAATTTTCTCCATAACGCAC |
| 212 | C21orf129 | GTTGCCTGGGATATGCTTATATCAAAAACTTACGTGTCACTTACCTAGCATTTGCATTTCACTGGGCCTCCTAAATTCTGTGTGGTAACCGACTGCCACCGGA CATGCTGTTTACTTCTCTATCCTCACGCAGCCAGTTGCCACATTCAACATAACACTGCAAATATTGCCGGTGGATCCTGACTTCCTCGTGGACCCTACTGTGT CGGGAAAAACAAACAAACGAACCCTGGAAGGAAACACCATGAGT |
| 213 | C2CD2 | TCATAAATATTTCCAAATGTATTCCTATTTGTCTCTACAGAGTCTAACAGACATAAATAGCGAATTGAAGGTTCTGTCTTAAAACCCAGCAGAAAGAAAAACA ATGACCAGAAAAAAAAAACAATTGTCTTTGGCTTCCCAAGAACAGCATCGGATTTCAACTGGAACCACAGATGGTCCGTTGATAGAAGCGACTACTTTTTAGC TCTGGAGGACGACAAAAGGAACCAGCTTCTTCCTGTGGGTGTCACAGCGAGGTCGCCTGGCCACATCAGGTACCAGAGCGAGCGCCCTCACCTGATAGGCCCT GTACAACCTCAGCCACAGCACTGTCAGGAGGAACACGCGGAACTAGCAACCTAGGAGGGTAAAGGCGGAGTTGGGAGGGAACACGAGGCAGGCAGGTCGGCTG GCTGCTGAGCTACAGGCTGCACTCCTAGGACGTCTACGTGTAATTGAGAAAAATAAGACAAAAATAACTTACTGTGCAGGCAATTAATTCTGGTTGGCATAGC GATCCTCTTAAGTTAAAGGGAATGAGCATGAGATGAAGAGAAGTAAGAGGCAGAAAGAATTATGCAAGAGCAACATCAGAGTGGA |
| 214 | UMODL1 | ACGCCGAGCCGCCTCTGCAGGGGAAACCGAAGCAGATGTGGTGAGATAATACATCCAACCCTGAGTGCTACTCTAACCTGCCAGAGGCGGAGGGTTCTCAGTG AGATGAAAGCATTACAGATGCGTTAGATCTAAGGGAGGGGCCTGCAGATGCGCAGCTGGCAGAGAAACCAGGGAGGGGCTGAACTGTCAGTCGCGACCACCAG GGATCTGAATCAGTTCACCGACAGCCTTGGGGACATTCACCTTGGGCTCCACAACCTGTCAGAAATGCCCCCAAGCCCAAAGGCGTCGAGAGAATGGCCAGGT TGTTTCAGATTGACACATATCCTAATGTACAAGTCAGCCCACACACCCCACGTGCACTGAGCGTCTCTTGTTGTTCACCCCAAATAAACTCTGCCGGAACTGG GGCGGGACTCGCAGGGGCGGAGAAGGGGGGAGACGGGCAGAGGGCAGAAGTGGATGGTGAGAAGAGCCAATGGAGGGGCCCCGTGAGAGTGAGCAAGGCTGCA CCCCTAACCGACGTCCTGGGGCTACTGTACAAACAAAGAACCACAGGCTGGGAGGCTGAACAACAGACCTGCACTCTCTCGCAGCTCGGAGGCTGCAGGTCTG AAATCGAGGGGCTGACAGCGCTGGTTTCCTCTGGAGGCTGCGAGGGAGAAACCGTCCCCTGCCTCTCCCAGGCTCTGGGGTGAGCCCTTCCTGGCATCCCGGG CTCATTGTAGATGGATCACTCCAATCTCCATGGCTTCTCAGGGCTTCCCTCCATGCACCTCAAATCTCTCTCTCCTTCCTTTTGTAAGGATGCCAGTCATTGG ATTTAGGTTCACCTTAAATCCAGGATGATCTCATCTAAATTACATCTGCAAAAAGACCCTTTTTCCAAGTAAGTTGACATTCACAGGTACCTGGGGTTAGGAT TGGACATATCTTTTGCAGGGGTGCAGGGGGCTGCCACTGAGCCCGCTGCACAGGGTGACCTGGGCCAAGGGCCCTTCACTTTCACTTCCTCATTGGCAAGCTG CCCTGTGTTTGGACTGGGTCGAGGCTGTCAACCTTGCTGCCCCTCGGAGTCCCCCCTGGTGTCCCCCAAACAGATTCTAAGCTGCTTTCCTGGGGCTGGAGGC CAGGCATTGGGATTTTTTAAAGAGCTTCCCAGCAGGTGAGCAGCCTTTCATGGGTATCAGGAGACCTTCCTGGCAAATGTGGTGAAGGTCCTTCCTCCTGAGC GATGCCTTAGACCCAGGAGCCCAGGGAGGCTGCTCACCTGATCGTTAGGACAGGAGCAGTGGAAACCTCTGGCCTCAGACCCCCTGGAGGAATCCCTCCCTCT AAGACTCTGGGACTGGTGCACGCAAGGAGCTATCGTGAACATTGCTCCCAACTGGCCGCTTGCTTGTCCCCCGGCTCCCCTTGGCCCCAGTGGCGGCTTTGCC TGAATTAGAGGGCGTGAGAGCCACCTGTGTCTCAGCACTGCAATTAAAGCAGGAAGCCCTTTCGGAAGCAGCCGTGTGCACCAGCCTCCCATGGGTGGAGCAG AGCAAACCACCCACTTCTGCCCTCTGCCCTTCTTCCCTTTTCTCGACACCCTGCGGCCCCCCAGTTTCAGCAGAGTTTATTTGGGGTGAAAAACAAGAGATGC TCAGCGCCTGTGGGATGTGTGGGCTGACTCGTACATTAGGATGTGTGTCAATCTGAAATAACCTGGCCGTTATATGGATGCCTTGGGGCTTGGGGGGTTTCTG GCAGTCTGTCGAGCCCGAGGTGAATGTCCCCAAGGCTGCTGGTGAATCAGATCCCTGGCGTTCTCCGTTGGCAGTTCAGCCCAACAGTTTCTCTGCCGGCCGT GCCTCTGCAGGTCCCTCCTCTGATCTGATTGGATTAATATTTGAATCAATAGACTGAGTCAAGCAGAATGTGGGTGGGCCTCATGCAATCAGCTGAAGCCCTG AAAAGAGCAAAAGGGCTGCCCCTTCCCCCGAGGAGGAGAGAAC |
| 215 | UMODL1/C21orf128 | CACATTTCAGAGCTGAGGTGCTGGTGCGGGCAGGTCTCCTGAGCTGGGGGGTCAGCTGTGTGGCCAGTGATGGTGACGCCTCAGGCCGTGCATGGCCGGGGAG GCGGCCCTGCCTCTGCACTCTTTTGACTCCATGACTACTGGTGTCTTCGGACGCCAGAGTCGGGGGAGCAACCATGGGGCACCGCCCCTGCCTGGGGAGGCAG CACGAGGCCTGAGCCCAGCTTACAGGGGGACATCCACCCCCGCTGAGAGCCCCACCTTCACGGCGAGGATCTGTAGAAGAAGACATTTGATATTACTCGGCAA AAAAAACAAGAAACGAAAACACAAAAAGAGCTCCTCTGAAGAAGAAAAGGTATTTGCGCTGTGGTCCACCTAGAAATAATGTTGTTGGCACAACTAGAGCATT CCTCAGTCATTCAGGAGCACTCCCTGCCGGTGCGTCCACATGTCCCAACCCCGATAGATGAGGCGCTGTTCGCCCGTGGAGGGGTCAGGTTGTCGTGACCTTA TCTTTACCCTTAGGCCGTCCATCCCGGGGCCTGGGGTTTCCTGCGCCAGTCACGGTGGGCTGTGTAGGTGGCCATGTGTTCGGTCTTTCCCCAGGAGGTACGT ACCATGTGCTGGGAGGCCTGGAGGCTGAGCCGCCCCCCGCGCCTATGAGTTGCACCCTCACAGCGGCGGCCAAACCTCCTGC |
| 216 | ABCG1 | CAGGCTTGAGCGGTGACTGGGAGACCCCGGGAATGGAAATGGCGCTCAAATGCTGGTGTGGTGTCCGCAGGGGAACGGCCCGCGGGTGTGTGGAGTCTGCGCC CCTGTGGCTTCAGCTGCGTCGGGGGACTGCGGGAATCTTCCAGACTCCAGTTTAAATCAGAGAGGTGTGTCCACGAAAAGAGTCAAACTAAAACATT |
| 217 | chr21: 42598300-42599600 | AACGAGACAGTGCAAAAAGCCGCTGCCTGGTGACCTGGCATGCAGACTCGGCCCTCCCACTTGCACGGTGATCCACTGAAGACAACAGCTGCCTCTGTACTCA CGCTCCCCCACACTCCCCTCCTTCCTGCCCTGGTTTCTCCATCCCTAGATGCCATCCCATGCCCCAAACCATCCGCCAAGCACAATAACCTCGCCCCCACCCA CCCCATGAGGTCACTCGAGTTGACAACCAGATAACAGTTTTTGTTTTGTTTTGTTTTGTTTTGTTTTGTTTGTTTTTGAGACGGGGTCTCGCTCTGTTGCCCA |

TABLE 4C-continued

| SEQ ID NO | GENE NAME | SEQUENCE |
|---|---|---|
| | | GGCTGGAGTGCAATGACGTTATCTCGGCTCACCACAACCTCCGCCTCCCGGGTTCAAGAGATTCTTCTGCCTCAGCTGCCTGAGTAGCTGGGACTACAGGCGC<br>GTGCCACCATTCTCAGCTAACTTTTGTATTTTTAGTAGAGACAGGGTTTCATTATATTGGCCAGGCTGGTCTCGAACTCCTGACCTCTTGATCCGCCCACCTC<br>AGCCTCTCAAAGTGCAGGGATTACAGGCGTGAGCCACCGCGCCCAATAGCAATTTGATGACCCATCCCCTCCACTGCTGGGAAAAGGCTGGGCACCGCCCACA<br>CTCCATGCAGCTCTCTTTCCCTGGCTCGGAATCGCTGCAGGCGCCACAGACCAGACGCGCACTGTTCCCCACTCCTGCTTATCGGCCGCGCGGCATCCCCTTG<br>TCGCAGCACTCCAGCATCCATGCAGCCGCGCGGCACCCCGTCTTCGGAGCACTCCAGAATCCATGCAGAGCGCAGCACCCCACATCCAGAGCGCTCCAGAATC<br>CATGAAGCACGCGGCACCCCCTCGTCAGAGTGCTCCAGAATCCATGAAGTGCGCAGCACCCCTTAATCGGAGCGCTCTAGAACCCGTGCAGCGAGCAGCACCC<br>CACACCCGGAGCGCTCCAGAATCCATGAAGCCAGCAGCACCCCACACCCGGAGTGCTCCAGAATCCACGCAGCACGTGGCATCTCCTCGTCATAGCGTTCTAG<br>AATCCATGCAGCGAGCAGTACCCCACACCGGGAGCGCTCCAGAATCCACGCAGCGTCTGGCACATCTTTATCAGAGCGCTCCAGAGTCCATGCAGCCACAGTC<br>CTCCAACGGACCCTGAGATTGTTTCTGCAAAAGGCCATGCCTTCATAAATCTGAAAATTTGGAAAACATCCTTCTACTTATATCCTTACAACCCACCATTCAA<br>GCTGTAGAAGCCTTTCTGGAACCCCAAGCAGAAGGATATCCAAAATGTAAAAACGGTGGGGCCT |
| 218 | chr21: 42910000-42911000 | ATAGTGCGACTGTTCCGAAGTCTTTATCACAGTTACTGGTGATGCTTTTTTCCAGATGTCCTCGACGTGCACCCATGAAGGGCTCCACCTGAGAGTGCCAGGG<br>TCCTCCGTGGGATGGGGCTGGAGGGGGTGCTCTTGCCGTCCTGGGCTCCCAAGCAGCCATAGGAACAATAGGGTGATGGGGTCCCAGAGATAGAGGCCAGTGA<br>CAGCAGCGCTTTGAACCCCTCACACGGGCACGGGCCCTCTGGCAGGGATGGGCGTCCCGGTCACACGGAGATGGGGGCTGCTGCTGCCTGCAGGTAGAGGAAG<br>GGACGTGTTTGGCAGTCCTGTGACCCCTGGGCACCTCGCCTCCCCCACGGCCGGCTCTGCTTGTAAACAGACAAGTGCACAAGCGCAGCCCGGTGAAGGCACA<br>GCGGTCCCAGGAGGCATCTGGGCTGCACCCCAGCGAGCCGCCCATACACGTGGAGATGCCGGCCAAGGCCCTGCAGCACACGGCAGAGGAAGGCGCGATGGGA<br>GCCATGCTGGGCCCGGAAGGTGCCGCCGCCCGGAGCTGTAGCCATCACTCCAGCTCTTCTTTTAAGTGTTCCCAGAAATTGTGACCCACCAAAATCTGAGAGC<br>ACCCGACAGTAAGCCAGAGGACCTTGATGTGAGATCCCAGCACGGTGTGGGGGCGGACTGTGGTGGGTGCTGTCTCGGCCCCCACCCCTTCCACAGGTCGGTG<br>TGCACATCCCACGGCGCCTGCTAAGCTGCAGTCTTCTCCAAAGGGGTCACTCTCCGTGGGAAGGGAGCCACCCGCCCCCGGGTGATGTCCCCAGTCAGTGACT<br>GACGACAGTCCCCAGCCGAGGTGAGGGACCAGCTCCTGCATCCCTCACTCCGGGGCTTGCCTGTGGGCCAGGGTGGGGGCGAGCCTCAGCAGAGACCGCGTCC<br>CCCTTGCCTGTCCTGCCCTGCCTCCCCTGCCTCCCCCGCGCCTCTGCTGAGCACGCCCAGAGGGAGCTGCTTG |
| 219 | PDE9A | CACTTGAAAAGCACAACTCATGGTGCCAAAGCTCTGACACGGACTCCACTGGAGCTGTGGGCAGGGGGTGCCAAGGTACCGAGTTCCAAGCCGTTGTTATTTG<br>AGAGCGTGCCCCCCGCCATGAGAGCAGGTGGGGGGACATAAAGTGACACAGGATGGACTGGCCAAAGGCTGAGGACGATCACTTACCTCACAGGATGATGCCA<br>CCCCCACGGACAGGCAAGGAGCTCTCACCTTCCCCAGGACCCCAGCTGCCACCAGAGCTCCAGATGGCCCTGGGGGTGTCTGTAAAGCCTGTGACCGTCCACC<br>AGGTGGAGACCAGGCTGGCCAGGGGAGGGAGAGGAAGTGACCACTGGCCCTGGCACTGGCTGGCCGGCTCCAGCAGGCCCGAAGGGGAGGGAGGAGCCTGGGT<br>GCACCAGACTCTCTCAATAAGCAGCACCCAGACACTTAACAGATGGAAAGCGGTGGCTTGGAACTCACTTCCAACGAAACAATAGCAC |
| 220 | PDE9A | AGCACCTCCTACCCCACCCTCCCCATTCCTGCCATCCCCAGGGTCCAGGGAGCCCAGATTCCAGGGAAGGGTTGCATTAGCTCCCACTCGGAGTCCTGATGCA<br>GCAGAGACAGACAGAGGCCCTGGGAGAAGTGAGCATGAATTATTAAGACAAGACAAGGGTGAGGCCCCAGAGAGGGGGTGGCGGAAGGGTCATGTTCATGCAG<br>CGAGAGTTGCTTCGAGCTTGAACCGCGTATCCAGGAGTCAAGCAGATTGCAACTGGCGAGAGGCCTTCAGAAATGCCCCGTGAGAGTCCTGTGTGCAGAGCTC<br>CATCTCAGCACACTTCCTGTTCTTTTGGTTCGTCGATTTTTGCATTTTCAGTCCCCTGTGATCCATTATTTATAACAGTGGAGATTGGCCTCAGACACTAGCA<br>GTGAGGAAAACAAAAGCGAAGCTACGCAGAAAAATGACAAGAGTGATGAGCACAGCAGTCATGACAAATGAGCCCTGTGCGGAGGCCCGGGATCCGCGCAGAT<br>GCCGGCGCGGGGGAAATGGGCCCTGAAATCCCACCGTCAGGCCAGGCAGCTCTGAGCGTGACCTGGAGGGCTGTTCAGACGGTCTGGGTAGCCGTGTCCTGCG<br>CATGAACATCCTCCGTCGGGAGAGGAATTCCCCACGGATTATCAGAGCTGCTCCCTCCACCCCCCGCCACGTCCCACGCGGGCCACATCAACTCCCTCTGCAG<br>CCTCTGGCCAGCGGCTGAGCCCTCCGTGTCTCCCCTCGTTAATGCCTCCTTCACCATCCCCTCCTGAAGTTTCCCCCATTGCATACACGCGCTGAGGCCCACC<br>CGGTATCAAGGACTCCCATTGCTTGCGAAAAAGATTCCACCCCTCTTAGAACAGAGACCAGGGCCGCTGTAGCAAATGGCCATAAATGCCACAGCTTAAAACA<br>ACAGAAACGGATTATCTCGCAGCTCTGGAGGATGGAGTCCAAAATCTGAATCGCTGGGCTGAAATCCAGGTGTGGGCAGGGCCGCGCTCCCTCTAGAGGCTCC<br>CCCGGAGATTCCCTTCCTTGCCTCTTCCAGCTGCTGGTGGCTGCCAGCAGTTTGGGAATTGCGGCCGCATCACACCACCTTTCTGTTTGTTGTTGACATCCCC<br>GCCTCCCCTGCCTGCGGGGTCTTAGATGTCTCTCTCCTTCCCACTGAGTTTCACTCCACATTTGAATTGGATTAACTCATGCCATGTTAGGCAAACGTGCCCC<br>TCAAATCCTTCCACTTAACAGACATTTATTGAAGGTTCCTGTGTGCGGGGCCCAAGAGAAGGGA |
| 221 | PDE9A | GAATGTTCAAAGAAAGAGCCCTCCTTGCCTTCCTCTTCTTCCACCCCTGCCCTCTGCAGACTGGGGTTCTGTAGACCCCCAAAGTAAGTCCGCCACACCGGAA<br>GGAAGTGAGTTACACAGGGGCCCACATGGGAACCGCTTTTTGTCCTGTCTTGGTGGGAAAATGGCCACGACCCCAGCCCAGGCTCTGCCACGCCACA |
| 222 | PDE9A | CCATCTTCCTAGGCCTGCGTTTCCCCCACACCGGGGACTTGTGCTGGAAAGAAAAGCTGCGTTGGCAGCCAGGAGCCGGGGAAACTGTCCAGGGAGGCATCCT<br>CTGCGATGAAGGCGGGGCCTCGGCGTGGCCCGTTCCGCGCTCTGTCCAGCCCTGGAGAAGCCCCACCCTCACCGAGCTCGAAATACCCCCTCCCTGAGAGCCG<br>AGACTCATGGCCGGGACCCCTTGGACAGAAGATGCGGATGCTAACCCGGCGCTTCCACCACAGCCCCGGCGGCACTGGGGAGCGAGCGCGGCCATCCCGCGCG<br>TAGGTGGTGTTTCTCTGCAGGCGCCAGTTTCACCGCGGGCGCCCAGGATCCTCAACGGTTCTGTTGTGATGTGATTCCCCTCTTCGACTTCGTCATTCAGCCT<br>CAGTCCCTCAGTCCCCAAATACCGAAAGGCAGTCTTTTTTTTTTTTTTTGAGACGGAGTTTCACTCTTGTTGCCCAGGCTGGAGTGCAATGGTGCGATCTCG |

TABLE 4C-continued

| SEQ ID NO | GENE NAME | SEQUENCE |
|---|---|---|
| | | GTTCACTGCAACCTCCGTCTCCCTGGCTCAAGCGATTCTCCCGGCTCAGCCTCCCGAGTAGCTGGGATTACAGGCACCTGCCACCACGCCCGGCTAATTTTTT<br>GTATTTTTAGTAGAGACGGGGTTTCACCATGTTGGCCAGGATGGTCTGGAACTCCTGATCTCAGGTGATCCACCCGCCTCTGCCTCCCAAAGTGCTGGGATTA<br>CAGGCGTGAGCCACCGCGCCCGGCCTTTTTTTCTTTTTTCTTTTGAAGTTAATGAACTTGAATTTTATTTTATTTACAGAATAGCCCCCATGAGATACTTGAA<br>GACCCGGTGCCAAGCGACAGTGTTGACCCCAGGTGGTCAGTCCTGCCTGGCCCCTTCCGAGGGATGCGCCTTCACCATAACCATGTCACGGACAGGCGTGTGG<br>GCAAGGGGGCATCGCTGTATTTTTCACAACTCTTTCCACTGAACACGACAATGACATTTTTCACCACCCGTATGCATCAACCAAATGAAAAGATGAGCCTGTG<br>ACATTCCCGTGCGTAGAGTTACAGCTTTTCTTTTCAAAACGAACCTTCAGTTTGGAGCCGAAGCGGAAGCACGTGGCGTCTGACGTCTCCAGGGAGACCCGCC<br>GCCCTCGCTGCCGCCTCACCGCGCTTCTGTTTTGCAGGTAATCTTCAGCAAGTACTGCAACTCCAGCGACATCATGGACCTGTTCTGCATCGCCACCGGCCTG<br>CCTCGGTGAGTGCGCGCTGCGGGCTCTGCCCGGTGACGCCACGCGGCCTCCTCGCCTTTTCGGGATGGCTGGGAGGGGCGGAAGAGGCGCTGAAGGGCCCGA<br>GGCACCGGCCTTCTACAAGGGGCTCTTCGAAATCAATCAATGCGCAGAATCCCGAGGGAGGCTCAGCCGCCCTCCGGGCCTCTCTGCCTCCACAGGTGATGGC<br>TGTGTCCACAAGGAGGAAACCGTCGGGCTGAATTAAACAGAACCGCCCTCCTAAGAGTGTGGGTTTTTCTGCCGGGCGTGGTGTCTCACACCTGTAATCCCAA<br>CACTTTGAGAGGCCGAGGTGGGCAGATCACCTGAGGTCAGGAGTTCGAGACCAGC |
| 223 | PDE9A | AGGCAGCAGGGTTAGGACTTCAACATACAACTTTTGGGGGGAGATGTACTTCAGCCCATAACACACCACGTGGGAGGATAACACCGATTTCAGAGCTTGCAGA<br>GGAAGCCGCCAGGAACTCCAGTGAGACATCAGCCCCCAGGTGCCTGTCAGGCACGCCGGGCTGTGGGGGGCACCTGGGCCCATCTGAGTAACGGAGGCGCATC<br>CGCACTTCCCCCAGGAGTACATTTTTAGAACCCACAGCGCCATAAACCAAAGACAAGGAGACTTCCTGGTGCCCCGTCAGCTTCTGGAGGCGACGTTCTCGGC<br>TGACAGCTCTGGCAGCCTCCCCTGTAGGTGAGAGACAGGTAAATGGGACTCTTGCTTCCAAAACGGAACAGGGTAAAAATTCTCAAGCGTT |
| 224 | chr21: 43130800-43131500 | TGCTGCACCCCCGCTGCCCTCCCTCCCGCTGGCCGGCAGCACCTTCTCCACCCGGGCCCCTCTGCTCACAGCGCTCCCCGCCCCCGTCTCCCCGAGGGGCGGG<br>GAGCCAGGACATGGCCCTGAAAGCCTAGCCCTGGCCTTGACCTCCCCAGAGCGCCCTCCCCACCCTCCGCCCTCTGCCAACCCTGGCCCCTGCCCTGGCCCCG<br>TCCTTGTCCTCTGCTGCTGGCCTTGGGGTCGCGCCCCGCAGACTGGGCTGTGCGTGGGGGTCCTGGCGGCCTGTGCCGTCCCACGCCTACGGGGATGGGCGAG<br>GTCCTTCTTGGGGCTTCTCTTACCCACTCTCCAGTCACCTGAGGGCGCTGCTTCCCTGCGGCCACCCCAGGTTTCTGTGCAGCCGAAGCCTCTGCCTCTGCGG<br>CCGGGTGATCCCAAGACCCCGGGGTCCAGGGAGGCACGGGATCTGCTCCCCCGGTCCCAAATGCACCGGCTGCGCCTTAGGAGGGACGGCCTCCACCCATGGC<br>GCTGGCGCCCAGGGGCCGCTCCTCGGACTACAGCACTTGCTCGTCGCCCTGCGCCCTGTTTAGTTCTCATCACCAGCAGCCTGGACTAGGGCCCTGGTCCTTC<br>TGGCCTCCTTCCACAGCCCGCTGCACATCTCACCCACTTCCCCGAGGTGCTGTCATTGTTTAGCTGGGCCCCTCAGCCTCCG |
| 225 | U2AF1 | TTAAAGGGGAGTGGTTGTATGAAGAGTTCCTCAGTCAAAGGTGTGCAGCTGGGAAGCCCACCCCACCTAAGAGGGAGGTCTGACAAACTGTCCACACTGAACC<br>ACTCAGACCTGCATCAGGGCCCCGTTTCTTCCATAAGCCGCCAAGTACAGCCCTGAGTCAACTGAACTCAGGCCTGGGAGGCTTCCCAAAGCTGACTTGACTC<br>AGCTTTGAACTGAAATGACCGTACCATGACAACCCTGATGAAAAGCTAAACTGAGCCCAATTATTCAACAGTAAAATTCAGTTGGTCTCACTCA |
| 226 | U2AF1 | TGCTACCAGCTGCTTGGGCTTGGGCAAGTCACCCTAGCTCTCAGATGTCATCTGTAAATGATGACAATGCCAATGTGGCACTGTTCTGAGAGTCAGACAGAAC<br>GTATGTGTGCTTCACATATGGTGCTCATGAAGTGCTATCATTATCTAAGGAAAACAGAAAACGAAGTTCAGAGTCTCTCTAAACGCATGACACCAGACCAACA<br>GGGAGTTTCAAAAAATAGGTCTGAAGTAAATCAATTCTCCTGGTCTCAATACACTGAAAACAAACTATTAGGGGACTGACCGAACCCACCTTAGGAACCACCT<br>TACGTCACCTTCTGTCTCTACTGCAAAACCCTCCCTTAATACTGTTCAAATACGCTGACAATCCAGATCCATATCCAATGGAACCAGCAATCATGCCTGTGTG<br>CCAGCAATGTCAGGGAGGGAAGCCGATCTCTGATGAAT |
| 227 | chr21: 43446600-43447600 | CAGGTGCCGGCCACCACACCCGGCTAATTTTTGTGTTTTTAGTGGAGACAGGGTTTCGCCATGTTGGCCGGGCTGGTCTCAAACTCCTGACCTCATGTGATCC<br>ACCCGCCTCGGCCTTCCAAAGTGCTGGGATTACAAGTGTAAGCCACTGCGCCCGGCCAAGAGTGAAGTTCTGATAGCTGGGGTAAGAAAGGCCGTGGGAACAG<br>CCGGTTTCAGACACGCTGGGTCTAAGACGCTGCGTCTGGCGCTGCTCGGCATCCAATGGGAGCCGTGGAGAAGCCAGGCGAGTGCGTAGGGCGGAGCCAGCGC<br>ACAGGAAATAGGACGTGATGAGGTCAACCGGCTGGTCCAAGTGTGGACGGAAGTAGAGGATGCAAGCACCGAGCCCCGGGGCCCCCAGCATTGGCGGGGAGGA<br>GCTCGCGGTGCGGGAGAAGCAGGGGACCGCGCATCCTGGAGACCAGGTGGAGCCAGTGCGCCCGGAAGGGGCGTGGCCCGCTGACAGCCGCCCAGGAGGCCGG<br>GGGAGGCCTGGAGCCGAGGGCCGCGCGTGGCAATGTGGAGAGACATTTTGGTGGAGTCATGGGGCCACAGCCTGATTGGTGAGAACAGGAAGGGAAATTGCAG<br>ATGGGCCTGGGCCCCCTGGCTCCCGCATACTCCAGGACCAGGGCTGAGTCATCGTTCACCGTGTGTGACCAGGGCCCCGTGTGGCCGGCTGTCACTCGGTATC<br>CAGTTACCCTGGGCAGACCACTGGCGGCACCCCCCAGCCAGAGGCCGCAGCAACACACACGCCTGCAGGCGACCAGGCCGGACTGCATGCCCCGTGGGGGAAC<br>TGAGGGCGTTTCAGTAACAGAGTGTTAGGGGACACGGGTTGGGTGGCTTGGAAAGGGCCTAAGGTGGGGTTTGTTTTAGATTGGGGTGGTGAGGGCGCAGGGG<br>CCCGGTAGGATTCTCTAACAGGGCAGCAGCCACTCATTTAGCAACAGGAGAGGCGTCCAGCGTTTCGTGGGCT |
| 228 | CRYAA | ACCCAACCACAGGCCTCCTCTCTGAGCCACGGGTGAGCGGTGCAGGTTCTGCTGTTCTGGAGGGCCTGAGTCCCACCCAGCACCTCATAAACAGGGTCCTCCC<br>CAGGGCTGCTGCAGTAGGCATCAACGCCAGGGTGCAAAATGCCTCAGGGAGCCAAGGCTGAGCCAGGGGAGTGAGAAGGAGCATGTGGAAGTGCGTTTTGGAG<br>AGGCAGCTGCGCAGGCTGTCAGCAGGCTCCGGCCGCTTCTATAGACAGCATGACACCAAGGGCAGTGACCTCATTCCACAGGCTGAGTCCAGCCAGCCAGCCA<br>AGCATCACCAGCCAGACGATTGACCCTAACGGACCAACCAACCCGTAACGACCCCTCCTACCATAACCAGTAGCCAGCCAGCCCATAACCAGCCAACTTATCT |

TABLE 4C-continued

| SEQ ID NO | GENE NAME | SEQUENCE |
|---|---|---|
| | | ATAACCAGCCACCTGACCATAGCCAAACAACCAGCCGGCCCACCAGTAGCATTCAGCCCCTCAGCTGGCCCTGAGGGTTTGGAGACAGGTCGAGGGTCATGCC<br>TGTCTGTCCAGGAGACAGTCACAGGCCCCCGAAAGCTCTGCCCCACTTGGTGTGTGGGAGAAGAGGCCGGCAGGTGACCGAAGCATCTCTGTTCTGATAACCG<br>GGACCCGCCCTGTCTCTGCCAACCCCAGCAGGGACGGCACCCTCTGGGCAGCTCCACATGGCACGTTTGGATTTCAGGTTCGATCCGACCGGGACAAGTTCGT<br>CATCTTCCTCGATGTGAAGCACTTCTCCCCGGAGGACCTCACCGTGAAGGTGCAGGACGACTTTGTGGAGATCCACGGAAAGCACAACGAGCGCCAGGTGAGC<br>CCAGGCACTGAGAGGTGGGAGAGGGGGGCGAGTTGGGCGCGAGGACAAGGGGGTCACGGCGGGCACGACCGGGCCTGCACACCTGCACCATGCCTTCAACCCT<br>GGGAGAGGGACGCTCTCCAGGGGACCCCGAATCAGGCCTGGCTTTTCCCCAAGGGAGGGGCCGTGCCCACCTGAGCACAGCCAGCCCCTCCCGGTGACAGAGG<br>TCACCATTCCCGAGCTAATGTGGCTCAGGGATCCAGGTTAGGGTCCCTTCCCGGGCTGCACCCAGCCGTCGCCAGCTCCATCCCTGTCACCTGGATGCCAGGG<br>TGGTCTTAGAAAGAACCCCAGGAAGTGGGAGTGCCCCGGGTGGCCGCCTCCTAGCCAGTGTACATCTTCACATGAACCCTACCTGAGGAAGCCAGTCCCCGAC<br>GGCATAGCTGCATCCGCTTGGAATGCTTTACAGGCATTGACACCTTCGCCTCACAGCAGCACTTTGGAACCAGTGTCCTCATTATTCCAGGGCACGGCTGGGG<br>AACAAGGGGGTCCTCAGCCTGCTGGGTCCCACAGCTAGTACCGGGCAGGTGGACGGGAGCTTCTCCCCACAGTCACCCTGATGCCCCGCTCTTGCTCGGCTGG<br>AGGCCTCGGATCTCCGTGGTGTTGAGGGAGCCGGGGCACTGGAGCCCTGGTGACCTGCATCTCCTGGCGGAGCCGGGAAGAGCTCATGGACTGTCACAGATGG<br>ACAGTGCCCCGCGGGGGCTGGAGAGCAGAGTGGGGCTGGAAGGTGGAACTCTTAGCCAAAGTCTTGGTTTCTTTTGGCCAGGGTCCTCTTTCAATGGCTGGAG<br>AAGGTGGTGCTGGGGGGTGAACGCTGACCTCCTCATGTGCTGCCCCTCCCTCGCCTGGGCCCGGTAAAGCCCCCACGTAGCCCCAGCCAGCCTGGAACATGCT<br>TCCTGAGCTCCCAGCTCTTGGTCTTTGCACCCAGTGGAGGAGGAGGTCAGCCCAGGGAGCTGAGTCTGCGGTTTAGGGCGTCCAGGGGACGTGGAAGCATGTG<br>GGTCGTCTGGCCACATTAGGTAGGGCTGCAGAGACCTGGGCTAGAGCAGTCCTGCGGGGTCTGGAAGGGGAAGACTGGCTGAGGTGCGGGGCCTGGTCTGGAA<br>TGATCCTGCGATTTTGGAGTGAAGCCATGGAGCGGGAAGAGACAACCCCCCGCGGGGAATAGCCCGGCAAGTGGCCACGAGGCCAGGCTGAGGTCCAGAGAAG<br>CAGGGGCATGAATCCATAAATCCCAGGGGGCCTGGCCATGGGATGTGCTGGCTGCACCCGGCCCCTGTGAGAGCCCCCGCAGGCTGGCCCCCTTCTGCAGTCA<br>GTGGGGCTGGGGCAGCTTCTCTGGCATGGGGCGAGGCAGCCGCCTGCACAGTGGCCCCCCTGACTGTGCGCCCCCACCCTCTCCAGGACGACCACGGCTACAT<br>TTCCCGTGAGTTCCACCGCCGCTACCGCCTGCCGTCCAACGTGGACCAGTCGGCCCTCTCTTGCTCCCTGTCTGCCGATGGCATGCTGACCTTCTGTGGCCCC<br>AAGATCCAGACTGGCCTGGATGCCACCCACGCCGAGCGAGCCATCCCCGTGTCGCGGGAGGAGAAGCCCACCTCGGCTCCCTCGTCCTAAGCAGGCATTGCCT<br>CGGCTGGCTCCCCTGCAGCCCTGGCCCATCATGGGGGGAGCACCCTGAGGGCGGGGTGTCTGTCTTCCTTTGCTTCCCTTTTTTCCTTTCCACCTTCTCACAT<br>GGAATGAGGGTTTGAGAGAGCAGCCAGGAGAGCTTAGGGTCTCAGGGTGTCCCAGACCCCGACACCGGCCAGTGGCGGAAGTGACCGCACCTCACACTCCTTT<br>AGATAGCAGCCTGGCTCCCCTGGGGTGCAGGCGCCTCAACTCTGCTGAGGGTCCAGAAGGAGGGGGTGACCTCCGGCCAGGTGCCTCCTGACACACCTGCAGC<br>CTCCCTCCGCGGCGGGCCCTGCCCACACCTCCTGGGGCGCGTGAGGCCCGTGGGGCCGGGGCTTCTGTGCACCTGGGCTCTCGCGGCCTCTTCTCTCAGACCG<br>TCTTCCTCCAACCCCTCTATGTAGTGCCGCTCTTGGGGACATGGGTCGCCCATGAGAGCGCAGCCCGCGGCAATCAATAAACAGCAGGTGATACAAGCAACCC<br>GCCGTCTGCTGGTGCTGTCTCCATCAGGGGCGCGAGGGGCAGGAGGGCGGCGCCGGGAGGGAGGACAGCGGGGTCTCCTGCTCGCGTTGGACCCGGTGGCCTC<br>GGAACGATGG |
| 229 | chr21: 43545000-43546000 | TTTTGTGTTTTTAGTAGAGATGGGATTTCACCATGTTGGCCAGGCTGGTCTCAAACTCCTGGCCTCATGCAATCCTCCTGCCTCAGTAGTAGTAGTTGGGAT<br>TACAGGTGTGAGCTGCCATGCCCAGCTGCAGGTGCGGAAGCTGGGGGCCTCAGAGACTGTGGACTCCTGGCCGGTGAGGAGCGGCATGGGCCGGGAGAGCTGA<br>CTCTTCAGCGGGACTGAGGTGGCTGGAGCGTGACCCTTTCCTGAGGGCAAACAGGGAGGGCCTTGGAGCCCGGCGCTCAGGACAGGCCCCTGCTGGCCCGGCA<br>GCCTGAGCTTCCACACTTTTCCAGGGCGTCTCGAGTTCGCCCACAGAGCTGTTGTTTCAGGATAAAAAATGCCCTTGTATTCCACGTTCCAGTTCAGAGGCCC<br>GTCTGTTCCCAAGAGCGGAGGCGTCAGCCGCATGAGTCCCACCGGAAGCCGGGTTGCCGGGTCCCCGTCCCTGCCCTGCAGACGACGCATTCCGGAGCCCCCT<br>TGGGAAGCTGCCTGGCTCTCCCAGGCCTGGCTGCCTTCGCACGAGGGCTCCGAGGCATGCTCATCCTACGTGACTGCCCGAGTGTGCACACGCCTGGCCGTGT<br>GTGGGCGTGTGCCTGGGGCCCGAGCTCAGGAGCAAGGCCTGCGTGGACCTGTTGTCTGAAACAAGCCAGTAGACAGCTGCGTCAATGCAGGCAAGCTGAACAG<br>GGCTGCTTTTTCAGCCTGACAACCCCAGGGGCTGAACAGGAGCTGGGGGAGGAGCAAGGGGCCGTTCCCCTGCCCCACAGCACAGCACACGACCCCGCCTTGG<br>AACCTGGGGCCCGGGGTGAATCGAGGGTCCTGGAGCAAGAGGGGCTGCTCCACAGGAGAGCCTGTCCCGCCACCCCTCAGCCACCAGATTCGGGGCTGCTGGA<br>CTTGTTCTCAAACCTGCACAGTGAGTGACAGCTGCTGAGACGGAGGTCTCAGGCAGTGCAGGTGAATCAGCAT |
| 230 | chr21: 43606000-43606500 | TCCTTATTTTTTAGTTCTCAAGCCCTGTAGGGTGTTTTCGGTCGCAGTTGTTTGGGCTGTGGTCCTGACCCTCCTGAGTTCCAGTGGCTCTGTTCAGGAGAGC<br>TGCCTGGGGCCGGGACTTCTGAAACACACACTGAGCCACAGGCCGGCCCGGCGGCTTGGGTTCACCGCCGCCTCTTTGTGTGTGATGTCCTGGGATAGGCCCG<br>TGCACGTTCAGATGACACTGTACATATAAATAACTTGTAGCCGAGAACAGGATGGGGCGGGGAGGAGGGGAGGGCAGAACGTACCACAGCAGCAGAAGTCACT<br>GTGGATGCCTTCGTAAGTTGCATGGAAGGTTTTTAAACCTAGCCCTGCCGAGCAGCCCTCTCCTGGTCCGGGAGAACGATGGGGAGAGAGCTGGCGTTCAGCT<br>TTCATCACTGGAGCCGTTCCTTCTTCCGGCCCCCCGAGGGCCTGTCCATGATCACACTTTGTCTTGTTTCGGGGGTGGCCCCTGTGAC |
| 231 | chr21: 43643000-43644300 | CAAGCCTGTGGTAGGGACCAGGTCAGAGTAAACAGGAAGACAGCTTTCGGCCAGGCGGTGCACCTCGGTGCCGGTGAGTGTGAGCGTGTGTGCGTGTGCACGT<br>GTGCAGATGTGTGTGGACGCTCCCTTCTCCGCAGCAGCTCCTGACCCCCTGCAGGTGACCCTCAGCCAGCCCCAGGGCTGCCCCCACTCTCCCCTGTGGACAC<br>CTACCTCATTTGGGGTGAAGTGGGGGGACTGGGGTGTGAGGGGTGCTTTGGGGGGCACACTTCGACCCCTCTCTCTGCAGGCCAAGTCCTGAGGCTCAGTTTC<br>CTCCTCTGTGCCCCGGCGACGTGGTGCAGGCCTCGCGAGTGACGTGAGGGTTCATGACCCAGGTGTGGGCAGCCAGCCCTTCACGGGAGGCCACCCACCTGGC<br>CACAGTGCCTGGGAATTTAGGTCGGGCACTGCCGATATGTCGCCTTCCACAAGGCGGGCCCGGGCCTCTGCTGACCGTGCACCGGTCCTGGGGCTGGGTAATT |

TABLE 4C-continued

| SEQ ID NO | GENE NAME | SEQUENCE |
|---|---|---|
| | | CTGCAGCAGCAGCGCAGCCCATGCCGGGGAATTTGCGGGCAGAGGAGACAGTGAGGCCCGCGTTCTGTGCGGGAACTCCCGAGCTCACAGAGCCCAAGACCAC<br>ACGGCTGCATCTGCTTGGCTGACTGGGCCAGGCCCACGCGTAGTAACCCGGACGTCTCTCTCTCACAGTCCCCTTGCGTCTGGCCAGGGAGCTGCCAGGCTGC<br>ACCCCGCGGTGGGGATCGGGAGAGGGGCAGTGTCGCCCATCCCCGGAAGGCTGAGCCTGGTGCAGCCAGGGAGTGAGGGGGCGGGAAGCCGGGGTGCTGCCCT<br>GAGGGTGCCCCGACACGCTCTCCTGGGGCCCTGAGCGGCTGCCACGTGCGTCCAGGGTTCTGGCCACAGGGTGGGCAGGGGCCCTGTGCTCCTCACTGGAGGC<br>CCCTGAGGCTCTGGAACTGAGACCATCCACCCGCCGGCCCCCTCTCGCCGGCTCCGGCACCCCTGCCTACTGTGACTTCCTGCCCCGGACTCGCTCTGCCAGC<br>TTGGGGCAAACCACTTCCCTCTGGGGTTTTCACTTCCCTCTTTCCCAAGTGGGGAAAGACCACCTGTCCCCGACCCAGAAAGGGCCCCTGCCCGAGGGCAGCA<br>GCAGTGCCAGGCTGGCATGTGAGGCTTGGGGCAGGCCCGGCCCCCAGAGGCACAGGGCGATGCTCTGTGGGACGCTGTGTCGTTTCTAAGTACAAGGTCAGGA<br>GAGGAGCCCCCTGACCCCGGAGGGGAGGAGAGGCAGGGCAGGAAACCGCCACCATCTCAGCCCA |
| 232 | C21orf125 | GCCCACTGTGGGTGTGCCCGTGTGTGTGGCTGTGAGGCGTGAGTGCAGGCGTGAAGTGTCTGGGAGTGGGAGCGGGCATGAGTGTGTGCCACGGGCCTGCTGT<br>TGGGTCCTTGGAGGCCACGGTTGCCCCTGAAGGGACTGCAAGCTCTTTTTTGATTTGTAGTTATTTGAGAAGTCTATACAGGAAGAAAATTAAACCG |
| 233 | C21orf125 | AGCGCCCAGCGCAGGGCCGGGACCCAGAGTGGACTCTACCGTGGGGCTGCCTCAAAGAAATCTCAGCAAACACAGGAAGCCAGCCCACCCGTGCAGCCATGGG<br>GCCAGGAAGCCCGCCCTTTACCAAGTCATTTGGGCATTTTTTCTCTGTGCTAACAGCCCAGATGGAGCCATAGCCTCAACCTCTGTGTTCTGATAACACCAAG<br>CTGGGACGCCGGAGCCATGCAGGGGACAGTGCCCGGCCTGAGGCTGCAGCCTGGGTCTGGATGCCTTTCTAATTCAGGGCCTCCTCATGGCCTGGTTCCATAA<br>ATGGTCAAATGCAGCCTGACAGCGCAGCCTCCTATCAGCGCTGGGCTCCGTACCGCCACACAGCCCACATACCCCGTTCCCCAGGAGACGCCCGCAGGTGGGC<br>AGCGTCACTCCCACCCGCCGAGCACACGCTGTCCCCGTCTCGTGTCCCGAGGAGCCGGAAGCAGCTGCTTCCTCCCAGCCTGAAAGCTGCACCTCGGGCTGCA<br>CTCGGCTCCCCGAACCCGCCCTCCGCTGCCCTGCAATTCGCCAAGGGAGCTACCCTTCCCATATAAAAATTTCACCTCCATTTCCTTGTAGAGAAGAAACATT<br>TCTGACAGCAAGGAAGATTCTAATTTGAAAAGCAAGTGATTCATCTCCCGGTGCCAAACAGCAGACGCAGGCGTTACCAGTCTGGGTGGGGCGCCCGAGCTGG<br>GGACCTGGGGTCCTCTGGGAGGGGCAAGAAGGCAGCGATGCTGGCCCCCGCCTCCATCTGCCCATCCCATCTGCTTCCACACACCGCCCTGCCGTAGCTGCTT<br>GCAGCCCTTCTCTGTCAGTTTCTCCATCTTTTGGTTTGGTGATAAATGAGAGTTCCCATCGGGTGTGCCACCCTCTGTGTGACGGGGAGCAGAGAAGACCCTG<br>CGTCCAAGTCCTCCTGGGGGAAGAGCGAAGATGCTGGGACCAGCCCCAGCTGTCAGGGGGTCTCCAATCCCAG |
| 234 | HSF2BP | GGAACGGAGAGCCGCCAGGCCCAAACCTCCCAGAATTTGCGCAGTATTCTCGGCCTAGAGAGCGAGGAGTGGCCTTGGCGAGGTCCCTCTTTGGCTCTTCTGG<br>CTTAGCCGGGGTTTTAAACTTGTTATCTGCAAAGCAGAAGGAAAGTCAGCCCCTGATGTAAGTGTCAAGTAAAATAAATCGGATGGGTCCTTTCCTGTTTGGC<br>GAGGAATGCTACACTAAGGGGGACTGCGTTCAAATGGGCAGTCTTTGCTGGAAACCTCGCCTCCGCGCGCCTTCCCTCGCTCGGATTCAGGCGCTTTTACGTT<br>AAGGGTTGAATTTTTGTGTCAACAGGCACCTCGGGAGGTCGCCTAGACAACTGAGCGGAGCAACTGAGATAACCCCCGCTACGTGTGGAGTGACCTAGTCCAT<br>TAACTTGCCCCAGCACGCCCGCTGAGTCCGCAAAATATAGGATGGCCTCGGGTTTTAGATGAACCCAAAGCTAAGATTTCTTCCCTCTCTGGAATTAGCAAGC<br>AGCCCGCCCTGCCCAACTCCCCTGGAAGCGCGCGTGCTCGCCAGGCCTCGGGACGCCTGCGCGGGCGCCCTTGCACTGGCACCAGGGCTCCGGGGTAGGGGCG<br>CACCGATCTGCCCAAGCCTCTGCAGGCACTGGAGGAAGGCGAGCCCTCCACCCGCTCAACAGGCCCCAGTGCCGGCCTTTCCTTCCAGTCTCAACTCCACCCG<br>GGGGCCCGGGGGCTCCACAGTTAAAAACTCCACGCCACGGAGATCGCAGGTAAGCTGCTGGCTCAACGAGGTGTGCTAAATGGGATTAAAGATCCTGGACCGT<br>GGCCAGGCGCGGCGGCTCAAGCCTGTAATCCCAGCGATCAGGGAGGCCGCCGCGGGAGGATTGCTTGAGCCCAGGAGTTTGAGACCAGCTTGGGCAACATAGC<br>GAGACACCGTCTCTACAAAAAAATAACAAATAGTGGGGCGTGATGGCGCGCGCCTGTAGTCTCAGCTACTTGGGCGGTCGAGATGGGAGGATCGATCGAGTCT<br>GGGAGGTCGAGGCTGCAGTGAGCCAGGATCACCGCCAAGATCGCGCCACTGCATTCCAGCCTGGGCGACAGAGGGAGACCCTGTCTCAAAAACAAACAAAAAA<br>TCCTAGACCGTTTACAAACAGCCTTCCGTCTCTTCCTGGTCAAGTCCTAACCCTGGCTAACCTCGCCGTCTACAGCCTGAATTTTGGCAACCGAAAGGCAGCG<br>CCGGCGCCACGTGCACACGGGCTGGGCCGCTCCGCCAGCTGCCAGGGCCACTGCCGCGCTCACT |
| 235 | AGPAT3 | CGCACACACAGCACAGACGCCTGCATCTTCCCATGCGTGGTTTCTGCTCTTGCCTCTCTGGGTTTTTGTTTCACTTCGGTCGAGTTTTTGGTGGTGTTGAGCG<br>GATAGCCGGGGAAGTTGGAGTCTTGTTTGTGGCCGCCTCGTGCTCGTGTCTGTATCTAAGATCCTCAGGCTGCTCCTTTTTGGGTAAGGTCTGTTGCTTCTCT<br>AGGAACAGTGACGGTGGCAGAGCCCGTGGCCCCTCTCTCCTGTCCCAGAGCCAAGCTGTTTCCTCTCCCCACTCCCGGGCACCCTGCGGGCAAG |
| 236 | chr21: 44446500-44447500 | CACAGCCCAGCTTCAAGCCTGGCCGACCAGGGGTTTGGCATGAAGACCCCGGCAGGGCTGGGGCTGTGCTGGAATCCACCCGGAAGTTTCCTGCCCCTTGGGC<br>TGCCCACCAGGTCCCCTTTCTGCTCTGATCAAGCTGGACAAAACGTCGTGGGGCCACAGCACAGGGGGCCAACGCAAGCTGGGATCGTCAGACGTTAGGAAAT<br>CCCAAGGAAGAAGAGAAAGGGGACACATTCGGGAGACGTCGGCACACGCTCGAAGCAGCGGACAGGCACCTCTCTGTGGACAAGGCAGACTGGGCGGCCGAGA<br>TTCCGCATAGATGCCTGCTTCCTCCACGACCTCCACGTGTGGCTGGCCCAGTCCGGGTCCCCCTCACCTCCTCTGTCTGTCTTGGTGGCCTCACGCCGTGGGC<br>TGTGATGCCGGCTACGCTGCTTGGGTGGCCAAGGGTCTGAGCTGCAAGACGCCCAGCCTGGGTCTCTCCCGAGCTCTCCCACGTCCTGTCTGCTCCTCCTCCG<br>AGCTCCCGGTTGACTCTCACGACTGCACCAGCCTCTCCCCCAGGAAGGCGTGGAAACAACCTCCTTCTCCCAGGCCCGCTCTGCCTCCTGCGTTTCAAGGCAA<br>ATCCGTTCCTCCAGGAGATGATGCAACCACATCCTGTTGGAGCCCAGAGAAGTGCGGATGCAGCCCGGGGCTCTTTCTTTCCTAGAACCCTGCCTGGGAGTGG<br>CTTCCCTGAACTAAGGACAGAGACTTTGTCTTCGTTGCCTCTCGGCCTGTGGGCACTGAGCATACAGTAGGTGCTCAGTAAATGCTTGCAGGCCGATGCCCAG |

TABLE 4C-continued

| SEQ ID NO | GENE NAME | SEQUENCE |
|---|---|---|
| | | AGCCATTAGCCCTCATCATGGTGAGCTCGGCAGCCGGTGTTGGGGCTGGGCTGGGCCTAGGTGTGCGTGGGGGCGGTGCTGGTCTGCTTTGCTGGGAGCCATG<br>GACACCGGAGGAACAGGGCCCCATCAGTGCGGTCAGAGTGCAAACTCGGAGCGTCCTTCTCTGGAAAACGAAT |
| 237 | TRPM2 | GGGAGGGGGCGTGGCCAGCAGGCAGCTGGGTGGGGCTGAGCCAGGGCGATCCGACCCCGAACCGGAGCTTTTAGCACTTTGAGTCCCTGTACTCAGAGGTCTC<br>CTGCAGCCGGGAATCCCACTGTGCTGTGGTCCCTGGCAGCCAGCACCCACCCCCAGCTTCTCCGTCAAGGTTGAGGACGGAGCACTCCTGCCTCTGATTAACT<br>GGACGCAGGAGAAGCAGTTGCTTTAATCCGGAGCCTTGAGTTGGGACAGATAATGAGTCATTCAACCAGATTTTCCAAGGACACACTAACTTTGGTATGATGC<br>GTGTGTGCCCCTGAATCCACGTGGTCAGGAAAGCCCAGGGAACACTGGCCTGTGACTCACTGAGCAGGTTCCCTTGTTACCCCGAGGGGTGATTTACTCCTCT<br>GACAGTGACACGGACACTGTGCGTCCATTCCCCGGGCGGGCAGAGGACACTCCCAGATGCCCACGAGGGGCCCAGCAAGCACTGGCCA |
| 238 | C21orf29 | CTGCAGGACCTGCTCGTTCACAGATGTTCTCCTAGAAGCAGAAGCTGTTTCTTGTTGCAAACAAATTTGCTGTGTCCTGTCTTAGGAGTCTCACCTGAATTTA<br>CCAAGGATGCATCTGTGCTTGGGGATGGCTCGGTTTGAGGGGTCTGAGGAGCGGCTCCCCTGGATCCTTTCCTCCCCAGGAGCCCACCTGCCGAGCTGTCAGC<br>GTCAGCCCCACATCTCAAGATGAGGAAATGGAGGTCGAAGCCATGCACACGCAGGCGTCCTGCTGACATGCAGGCCAGGCGGGTGCCTCTGTATTCAGCAGCC<br>TCAGGGCTGTGGCCAGTTCAGGCAGCAGAGGGGCCTCATCCCGGTGCTTCCCTGCAGGCAGTTGTGGGGCCGGCCTGCAGCAGGGGCTCAGACAGGGCCTTGG<br>GAGAGGGAGGGATCACAGAGGTGTCCAGTGACAGGCAGGGCGGGCAGAGCCCATGGGGCCTTGGGCTCCTCACTCCTTCGGTCAGTCAGGGTGACATCTGGAG<br>CCACCTCCATTAATGGTGGGTTATGATTTGGTTCCCATGCAGCCCGTGCCAGCTCGCTGGGAGGAGGACGAGGACGCCTGTGATC |
| 239 | C21orf29 | AAGAGGAAATTCCCACCTAATAAATTTTGGTCAGACCGGTTGATCTCAAAACCCTGTCTCCTGATAAGATGTTATCAATGACAATGGTGCCCGAAACTTCATT<br>AGCAATTTTAATTTCGCCTTGGAGCTGTGGTCCTGTGATCTCGCCCTGCCTCCACTGGCCTTGTGATATTCTATTACCCTGTTAAGTACTTGCTGTCTGTCAC<br>CCACACCTATTCGCACACTCCTTCCCCTTTTGAAACTCCCTAATAAAAACTTGCTGGTTTTTGCGGCTTGTGGGGCATCACAGATCCTACCAACGTGTGATGT<br>CTCCCCCGGACGCCCAGCTTTAAAATTTCTCTCTTTTGTACTCTGTCCCTTTATTTCTCAAGCCAGTCGATGCTTAGGAAAATAGAAAAGAACCTACGTGATT<br>ATCGGGGCAGGTCCCCCGATAACCCCCAGCTGCAGATCGAGGCCTAGTGCGAGCACAGGTCCCCCCAGACCCTTCCCAGTGCCCACCAACCGGCGGCCTAGGC<br>CAGGTAGAACTGGCAGCGCCTCCCCTGCTGCAACACCAGGCTCTGGTAGAAACTTCAGAAAACATGCACCGGCAAAACCAAGGAAGGGTGGCTGCGTCCCGGG<br>TTCTTCCGCGCAGCTGTGTGTACACGCATGCACACACCCACACGCACACACCCACGTGCACACCCCCATGCACACGCACCCACTTGCACGCCCATGCACGCAC<br>ACACGCGCGTGCACCCATGCGCACGCACCCATGCACACACACGCGCGCACACACCCACGTGCGCACCCACATGTACACACCCACGTGCACACACCCACGCGTA<br>CACACCCACGCGCACACACCGCTGTCCCCAGCCGTGCAGAACGATCCTCCCTGAGTCCCCGGCTCCGACCCACACGCAGCACTCGCTAAACGCTTCCCACGCA<br>GTCGTTTTGCTGGGTTGCGCTTCACCCACTTCTCAGAGGGGGCGGCCGAGGCAGAGGTGTCGGGGATCGAGCAGCTCCGGGCCTCAGGGGTCGCCCCGCCACC<br>GTTTTCCTTTCCCAGATGCTGGGACGGGGGCAGGGAGGGGCTCCCCAGGCTGAACCCGACTAGGTCACCCTAGAAGCGAGGCGAGCTTCTCTTCTGTTTTTCT<br>TCGGCGCCCCTGAGCCCCTGACAGTGCCCAAGCTGCCCATGGGATTGGATTCGCCAGAGCCTCCTACGCAGACCCCACCCAGGGCCAAAGCCAACCCCAAGCC<br>CCACCACCTTGGTGGTGTGGGATGAAAAGTGAGCCATCGAGAGATGGGGTCCCCCCACCCCCAACCCCTCCAAGGACAAAGGCGGGCTGGGAAGCACCCGCTT<br>TCACGTCCGCCCCTGCCCGGCTTTCCTAGCGGAATTGGCGCCGGCATCAGTTGGGGGTTGTGGGATCAGTGAGGAATCCCGTGGGGTCGCCTCCATTTATCAG<br>TTGTGTGGGGTTGGGCGAGCACCCCTAGCCCCAGCCCAGGCGATCAGGGCGCGAAGCCCACTGGACGCGGATTTGGGATTAGGACGGGGGTGACAGCCAGGAG<br>GACCGCACCTGCCCTCCCCACTCCTGCCGCTCCACCCCTGCCCCCACCGCAACACCAAGGTCTCCACCAGGAAGATGGGGGTGGGGAAAGGACGCGGGGTGGG<br>GGGGGGTGCGGGGAGAGAGGACACAGGGTCGGAAGGGTGAGGGGTAGTGGCAGAGGCGGAGGCCGAGGCCACGCAGCTGCGGGGCGCAGGGAGGGGCAGAGGA<br>GGGGCGTTCAGATGGGAACCTAGTCCAGACCCGTCGGGGCCCTCGTGTGCGGCTCGTTATCCTGGAACCAGAGAGGCTGGAGACCCTTGGCTTGTCTGGAGCG<br>GAACCGTAGTGTCCAATAGAGTGTGTGGGGCTCAGCCCTAAAGCTAAACATTCTTTATTTCCTGATGACCATGGGGGCGGAGCGGGGGAAAAGCCCTGGCCTT<br>ATAGTTTAGAATTTTATAAAAGGAAAGGCGTGGCCACTGACAATTTGCGCTTCAGGAGTCCCAGAGTGACCGCCTGGCTCGGAGCAGGGAATGAGGGGGTCCT<br>TAACTCTGAGATTTGTTTTCTGAGAGACAAAGGTGATGGGTGAGGCGGCTAAGCCTCTGATTCTCTATAGGTGGCGGTCATTCATTTCAGAACATGAATGGAT<br>TCAGTAAATAAACATGATAGAAAAATGCCACAAGCCCTAGGCCCATTGGAGTGGACTGGACAGTCTGTTCCCAGTGTGTCCCTCAGCCTCGGTCCCCCACCCT<br>TCCCGGAGCCCTGGGGGTCACACACATCCCTCCTGGCTGCCTAGCCTGTGCCCCCCGATTCCCCCCCTCCCCGCCCCGCGCGTGCACACACACACACACACAC<br>ACACACACACACACACACACCACACAGCACGAGGCGACAGAGATATGAGAGAGAGCGAGCGAGAGAGGACGGGAGAGAGAGGGAGTGCAAGTGTGCGCTGGGG<br>GTAACCCGTGCATGCATGCATTGGGGGTAACAGGCTGGAGCTCAGATCCCTCCCCCAGCCCCCAGCAGGGGGGACTGCAGGCTCCTGGTCTGAGTGGGGAGCT<br>GGGCCCCCTGGACAGAGGACTGGGCTGCGGGGTCAGGAATGGGCACACTTCCTAACTGCAGGACACTCTAAGGGCTTTGGTCATGCACACGCAGCCAAGAGAA<br>GGTGTCGCTGGCACACAGCCTTCCAGGAGCGGACTTGGAGACCTCGCCAAGGACCAGGACTCCCCAGCACTCACACTCCCTTAGGCGCTGAAGTCCAGAGGAC<br>AGAGGTTGAGGGCAGAGCTCCTGGGAGCACCAGTGGAAGTAGGAGGGCTGGGCTGGAAAACCTCCCCCAACCTCCTATTGCAAAGAGGCTCCAGCCAGCAGCC<br>TCCACACCCCAGTGATCTTTTAAGATGCAAATCTGCGCCATCATTTATTTCCTCAGTGCCTTCTCCAGCTCCTGGGATGCACACTGCCCGTCCCCAGGCCCAG<br>AGACCTGACCACCCTCATTCCTCCCTCAGCCCACCCTGGGGTCTCTCCACCAGCTGACAGCCTTCCTGCAGTCCCCTCCCCGAATGCTGCTCCCTGAGGCCCT<br>CCTGGACACCTGCAGGGCAGGCACAGCCCGCGGGACCTCACAGCACTTGCTCCGGGCAGAGCTGCAGTTTGGCCAAGTTGCCAGCTCCGTGTGGGCAGGGGCC<br>CTGGCCTGTGGCTGCCACATCCCGGGTGGGGGCACGGCCTTTCCTGGCGTGGATGCTGAGCAAACGTAGGGGGAAGGGGAGTGAATGAGGAGAGCCAGGTAGC<br>TCAGGGGCTGAGGCCTCACTGAGCAGGGTCCCGCGTGACCGGTCCCCACCGCTGACGGTTCCTGGGGTAACACTCAGGACAGGGAGAGGCAATGGAAAGAGAC<br>GTGGCCGCCCTCGCATCCTGCAGCTCCCGCACTCCCAGCCTCCCAGCCTCCCACCCAGCCCCCCAGAGCCCACCAGTGACCCCGCCCACTGGGTCCTCAGATG |

TABLE 4C-continued

| SEQ ID NO | GENE NAME | SEQUENCE |
|---|---|---|
| | | GCTCCCACGGGATCTCCTGCCTTGATCTCCTGTCCACATGGAGGTGAAGTGGGTTGCTCTGAATGAGGGGTGCCGAGCCTAGGGCGCAGCCCACTCTCCTGGG<br>TCCGCAGCATCACGCAGCCCGGACCACAGGCTCCTTACAAGAATCGGAAGGGTCCCTGCAATCGCCCTTCGCACTGAGGCTTCCTACTGTGTGGTGTAAAAAC<br>ACAGGCTTGTCCTCCCTTGCTGCCCACGGGGCTGGAGCCGCCTGAAAATCCCAGCCCACAACTTCCCCAAAGCCTGGCAGTCACTTGAATAGCCAAATGAGTC<br>CTAGAAAGCGAGAGACGAGAGGGGAATGAGCGCCGAAAATCAAAGCAGGTTCCCCTCCTGACAACTCCAGAGAAGGCGCATGGGCCCCGTGGCAGACCCGAAC<br>CCCCAGCCTCGCGACCGCCTGTGACCTGCGGGTCAACCACCCGCCGCGGCTCCACGCCGTGGGCACAGACTCAGGGAGCAGGATGAGAAAGCTGAGACGGCGC<br>AGCCACGGCCCGGTGCCTTCACGCGCACAGCGACACAGCCCCAGCCAGCGGGGCCCACGCTAAGGCGGAATCCCACAGAAGCCTACAGAGCGAGCGCGCGCCT<br>GTGCTTCCCAAAACGGAATGGAACCAAGGTGACTTCTACAGAACGATCTGAAGCCCTGGCTGGCCCTTATGCTAGTCTCTTGGGAGCGTTCCAAATGCAGCTC<br>AATATTACTTACTTGACTTTTATCTTTCCTCCCTGGTTCGTGGTATTTATAACTGGGTCATCTTTTAACTATTTGCAACGTAGCTTCAGGGGAGAGGGGGAGG<br>GCTTTATAAATAACCTGTATTATTATTATGCAGGTTGATTCTGTTCCCTGAGCTAAAGGGAACATGAAAATACATGTCTGTGACTCATGCCCCCCCACCCCCA<br>CTCCAGGGTGTGCTGAGGAGTCTCTCAGCTGCCCCGGGGTCCTCGAGCAGGGGAGGGAGAAAGGCTGGCGCTGCGCCCTCCATCGCGTGAAGCCAGGGGATTT<br>TGCTCTGCGACAAGCTGACTTGGCTCTCGTATTGTTTGCAGAATCACCCAGTTCCAAGGCAGTCCCTGCGGGCAGGTGCAGCTGTGCGGGAGCTTCAGTCCTG<br>TCCCCAACACCCAGGCAGTAATGGTTCCAGCACGGAAGGTCTACCTACCTCCCACTGCACAGCCCGAGGGCTGTCCTGGAGGCACAGCCATCCGTCCCTGGGT<br>GGGCAGGCACGTTTATGACCCCCACCCCCACCCCCACCCCCCACGCGAGTCAGCACGTTCCATACTCGGGTGATCGTGCTCATCCCCTGGTCATGTCATCGGG<br>ATCTGAGTGCCATCCGAGCAGAGAGCTGTGGCCCGGTGCCGGGGGTGGACTTCATCTATTCCAGGGAACCAAGGATGCATGATTTGCAAACAAAACCAGAAGC<br>GCAAGCCATCTCCTCGCCTCCCCTGATAGCCGTGCTGCGGAGCCTGAGTGCTGGAG |
| 240 | ITGB2 | CAGGAACCACGGGACCTGCTGCCTAGCGGCCCTGTTCCACCCTTGGCCGCTCGCAAAATGTTTAGGCTTCATAAGGTTTGCCCAGGGTCACAAATTTAACTCA<br>CAGCAAACAATGAAATCAGCGCATGATTTTCGAGCCCTCGTGGTCACCCTCCCTTCCTCCTGCCCTTTCCTGCATGGGCAGCAGCAGGGTGAGGAGCTGCTCT<br>CCCCAGGCCCAGGCTGGAGTCCCTCAGACGACCTGCCGGCCAGGGTACCCCCCTGCCCCCACACAGCGCCTGACAGAGCCCCCCACACTGGGGGAACGTGGGG<br>ACCCAAGCAGGGGCAGCGGCCTCACCGGGCAGGCGGCGACCTGCATCATGGCGTCCAGCCCACCCTCGGGTGCATCCAGGTTTCCGGAAATCAGCTGCTTCCC<br>GACCTCGGTCTGAAACTGGTTGGAGTTGTTGGTCAGCTTCAGCACGTGCCTGAAGGCAAACGGGGGCTGGCACTCTTTCTCCTTGTTGGGGCATGGGTTTCGC<br>AGCTTATCAGGGTGCGTGTTCACGAACGGCAGCACGGTCTTGTCCACGAAGGACCCGAAGCCTGCAGGGCACATGGAGGGGCTGG |
| 241 | ITGB2 | TGCGTTTAGTGTAAAAATATCAGGTGTGGCTGCACGGAGTGAAAAATCACAGGCTCCACGGAGCCGGGAGGCCTGCTGCCCTGCCCTCTTGCTTTGATGAGGA<br>AATGGCGACCGCAGAAGGAAATGTAGCAGCACCGGCAACCGGCATCCGTGGGGCCACGCCGGGCTGCTTCCCAGGGCCCTCCAGCCAAGCAGCCACAGGAAAG<br>AGTAGATGTTGATCCCAAGCTAGGACTGAGGAGTCCGTCCCTAAGAGCCGAGGGAGTCAGGTGGGCGAAACTGGCCGCATGTCTGGGTACAACTGCTCAGGGT<br>TTCTCATCTGCTGAATCACCAAGCTAGGTTCTGAAGCCAGGCGTGAGTGAGCAGGACTGGAGCAGGATTCTGGGAACAATCTTTTCCCTCC |
| 242 | POFUT2 | GCTGGGGAACTGAAGGAAGGGCTGTGGAGCCTGAAGCCTGGGCCTGGCTGTGCTGCGGCCGCACCGCTGGGTGATGCAGGAGCCACTCCACCTCCCTGGCAC<br>CCCAGCCTCATCCGGCAACCTGGGAGCGTGGGCCTCCTGCCCCTCCAGGGAGGCCCTGGCCGTGTCCTCATGGGGCCCCTCCAGGTCCTTGTGGCTCCAGGTC<br>GGGACAGTGGCTGTGAGATCTGACCCTCCCGTTCCCCCTCCACCAAGTAGGAGAAACCCCGGAGCATGAGCCCTCGTCCTTCACCGTCCCGGGGACAGGGGGA<br>CCCCCAGATGCTGCACGGCTGACAGGCCAACGTGGCAGAAGCTCCAGCTTCACAGGAAGCCAGTGACCATGAGAGTCTGTAGCTGTAACGAAGCCACAGAGCT<br>GTGGCTTTCTTTCCCCTTCAGCTCTAGGAAAGGTTATCTGCCCTGCACAGATCTCCGGAGGCCTGGCTGGGCTCTGAGAGCATCAGACTGATTATCGTAAGAA<br>AATAATCTCTGCAGACACATTCCTTGCTAGAAGCAGGGGACAAAGCCCAGCTTCAAAGACAATTCCACACACGCCCTCCCTGCCCTGCACAGCTGCCTGCCGG<br>GTGGGAGCAGAGCCCTTGCAGCCGGGCTCAGGGGCCTGGGCAGGGACAGCGTGTGGCAGGGGCACAGCTGAGACAGGAGCCTCAAAGCGACACCAACCCGACG<br>TGAAGCTACAGTTGAGGAGACACAGCTGCCCCATTCCCGGGCTCATCTCCACAGTGAGACGCTGGACTCTCTCCCTGACCCACCGTCTCTTAGAACCTCCC<br>CTCCATCCGGAGCAGTTCGGCAGCCCCAGGGCAGCCAGGGGAACCCTGCCGAGTGCCTCTGGGCCGCCACAGACCGCAGAGCCCGCGGGAGCCTTGCTCACAC<br>AGCCTCAGGTCCACTGTGGTCTTGGGGGAAAGCCCTGTCCTGGGACAGGGGAGCCGGGGGTCCTGGCCCTGGACCACCATCTGGGGACCACGTTGTCACGCCT<br>GCAAAGCTCCCTGCCCCACCCCCATGTGCCGGCTGGTGTTGACACCTTTGTAGAGTGGGAACCTGCCTCCGACCCCAGCCTGCAGCCACAGGGCAGGTTATAG<br>ACCAGGTGAGAGGGCGCCGCGCCCAGAACCAAGGAGCACAAGTCCGCAGTGCCCATGAGATCCTCATGCTGGCCGGCGCAGGAGCCATCCTCGGCCTCTGCAG<br>GTCCTCGTGGGAAACCGCGGGGGCACGTGGGGCGGCTGCAGGGTCCGCAAAGCCGGCTGTTTGCGAAGGGCGCAGCTCCACCTGGAACAGCCGAGGCCGCCCA<br>CGCGCTTCCCGCGGGATCAGAGCAGCCTCCACGGCTGTTGTCTCAGGCACCACGGGATGCCTTTCTTCGTTTCAATAGCTGTGGGAAAGCCTCAATCGGTCCT<br>GAAAGAACCCAGATGTGCAGCAATGACAAGGCCTTCTCTGAGACTCTAGAACCTTCTGCCATCTCAGACAGGAGGGAGCCGTGAGGCAGGCGGGAGATTTGCA<br>GTCAGCAAAGGACGGGCAGGTGGGGCAGCTGCACACCCAGGGCCCTCTCCACGGTCTTCCCGGGCCCACCCCTCCCGCGGTCCTGGGTCATCCACCTGCTGGC<br>CTCACTCTGCCCACGCGGCCAGGTCCCACCGGCCCCTGAGCTCAACAGACCAAAGCTGGCCCGACCCCACCCCCAAGAAGAATGAAACAATTTTTTTTACCT<br>CTTGCAGAAAAGTAAAAGATCATTTATTCATTCTGTTTCTAGATAGCAAAACTAAGTGTCAAAAGCACCTTCTGCACACAGTCTGCACACACTGGCCGGTGGT<br>CCTGTTCCCGCAAGGTTGAGCTGTGTTCCAGAGACATGGGTCCTCCGGGTGATGAGGAGCCGCTGGAGGGCCCTGAGCTGCACGTGCTAATGATTAACGCCCC<br>GTCCGTGCTGGCCGGTTTCTCAAATGCCTCCTGACGATTGCGC |

TABLE 4C-continued

| SEQ ID NO | GENE NAME | SEQUENCE |
|---|---|---|
| 243 | chr21: 45571500-45573700 | GGCCTGAGGAGTCAAACGGTGCAAACCCTGCCCCACTCTGTTTGGGAAGCACCTGCTGTGTGGCAGGCGCTGCGCTTGGTGCTGGGGATAGACCATGGGGAAG<br>AAACACACAGAACCTGCCCTGCTCTCAAGGAACAGGCCCTGGGGGCGGCCAGGGGCAGAGACCCAAGGCAGACACCCACACAGTGGCGTAATGACAGTGCTTA<br>TGGTGGGGACCTGGCTGCACAGCAGGTCAGCAAGGGGATGTTCAGGTGACACTGGGGGCACGGAGACCCAGGGGAGAGTGGATTGACAGAGGGGACGCTGGGC<br>AAATGTCCCGAGGCTGAGGTGGAGTTGCGGGAAGGAGGAGGCTGCCGGGCAGAGGCGCAGAGAGCTTTGCAGGTGTTGGCAGAGACCAGCAGGCCCTGCGAGG<br>CCTGGGGTGTGTCCTCAGCTGGGAGGGCCATAGAAGGATCTGGGCTTGCAGATGCTGGTGCAGACTGGAGGCCTGGGGTGTGAGAGTCCAGGCGGGGCTCCTG<br>CCAACACCCAGGGGAGTGGGCCTGGGCCAGGTGGACCGGGAGCTGGCACGGTGGTCAGGTGCTTGGAGGCTGCGTGCCACGCTGGGGACCTGGAGGTGTGTGA<br>GGAGGTGTCTGTTGCTCCTGGGGCTGCCGCCTGCAGGGCTGGGTGTGCAGCAGTGCGGGGCAATGAAGTGGGCGGGTTCTGGGATGGTGGACGTTCCCTTTGT<br>TGGGAACGTGTTGGTGCCAAGCTGCCATTTGAGTTTGGCTCTGAGGGGTCTGGGCAGGGGACACACAGGGAATCACACAGGATGGAGTGAGTTCCCAGGGACC<br>CAGGGTGGCTTGGCCTGAGAACAGCTCCCACTCCCAGATGTGTGGGAAGCCCTCGGCACCAAGCCTCAGCCTCTCCATCTGTGAAATGGAGACAACGTCACTG<br>GACTTGCAGGCTGTCCATGAGGGTGATGCGATCAGAAAGGGTGGAGTTCCTGAACGCCCCGGGGTCGGGGTCTCACAGCAGGAGCTTAGCTGGTGTCGGCATC<br>TCCTGGACCCGTCCTCAGCTCCGAGCGCCCAGTCCTGCCACCTGTGTCCAAGTCTGCACTGTGCCCACGAGGCCCTCAAGGCCGCAGACAGCCCCACACTTCT<br>CGGACGCCGCCCCAGCACGGTCCTTGTGTGAGGTGGACACTCCTTCTGGACGCCGCCCCAGCACGGTCCTTGTGTGAGGTGGACACTCCTTCTGGACGCCGCC<br>CCAGTACGGTCCTTGTGTGAGGTGGACACTCCTTCTAGGGAAGGAGTAGTAACTCTTGGGTGGTCGGGTAGTTGCCATGGAAAGGGGCAGTAATGCCCAGGTA<br>TTGCCGTGGCAACCGTAAACTGACATGGCGCACTGGAGGGCGTGCCTCATGGAAAGCTACCTGTGCCCCTGCCCTGTGTTAGCTAGGCCTCAATGTGGTCCAG<br>TATCTGAGCACCGCCTCCTGCCTCAGATGTTCCCGTCTGTCACCCCATTACCAGGGCGGCACTTCGGGTCCTTTCCAGCCATCATTGTCCTGGCATTGCCACA<br>GTGGACACTGCCACACAGGCTTGTGTGCTTGCGCGTACCCAGGTCCTCACCTCTCTGGGATAAACCAGGCACGTGGCGGCCGCCCCATTTTCCACCCGCCAGC<br>GGTGGAGGAGTTGCCCAGCCTTGCAGGAAAACAGCTCTCATGCCAGCAGCGGAGCATCCTATTCAAGTTTTCTCAGGGCTGCCAGCACAAATGCTGCATGCCG<br>GGCGGCTTCCTCAGCAGACCGTTGTTTCTCTGCGTCCTGGAGGCTGGACGTCCCAGGTCCCCGTGTGGCAGGCCCGGTTCCTCCCGCAGCCTCTCCTTGGCTT<br>GTGGGCGGCGTCTCCTCCCTGGGTCCTCGCAGGGCCACCCCTCCGTGTGTCTGTGTCCTCCCTCCCCTTATAAGGACCCCAGGCAGACTGGATCAGGGCCTGC<br>CCTAAGGACTGAATTTTACCTTAATCACCTCTTTAAAAGCTGTCTCCAAATACAGTCACCTTCTGGGGTCCTGGCTGTTAGGGCTTTGATGCATGGATTTGGG<br>GGACACCGCTCAGCCCCTAACAGCCCCCATCCTCTGCCTGCCTTTACCATGGGGCTGAGCCCAGCCCTGCAGGAGTCCCCTGGTTTGATGTCTGCTGTGGCCA<br>CGGCGACCCTCAGGCTGCTCCAGCCGCACTTGTGCTT |
| 244 | chr21: 45609000-45610600 | GGGGAGTCTCCAGGGGCTGGGGCTGGAGCCGCATCAGAGAGGAAAGGGGTGTTTGAAAAAGGGGCAGGGCCTGGGACCCAGGAAACTGTTCTTCCAGAGACAC<br>CCGTGAAGCTGAGCTTTGCCTCTCAGGGAAGCTGTGACCCCACGGGTGCTGCCCAGAGAGATCGGGCCAGGTGGAGCCAAGATGGACTGGAATTCCCCGACGG<br>GGACAAGGGGCCGGACGAGGCTGACTTGCCCTGTCTGATGAATGGTCAGGTTTGCTTTTTCTCCTGAAAACACGAGGCAGTGATCCCGGCCAGCTAATTCCAG<br>CAGACTGGAGACGGGATGGTGGAGAATGAGGCTGTGGGCGGGAAGAGCAGATGGGACTCGCCAGCATCCTCACGGCAGGGCCGCGCTATTGCCCTCCCTCCCC<br>TCCTACTCTCTGGGGTCCCAGGAGCCCCAGATACGCAATGCTGCCAGGCGATTTCTGGCGCCCCGCAGACCCCTGCCCCTGGAGTTGGGCCAGGTCCCGGCTG<br>GAGCAAAGGGGGCTCCTTCAAGCCCGCTCCTCCCTGTCAAACCCGAGGAGCCTGACAGGCGCAGCGTCACCAGCGTCACCGGGCCATAGTGAGCGGCCAAGCC<br>AGCGTCACCGGGCCATAGTGAGCGGCCAAGCCAGCGTCACCGGGCCATAGTGAGCCGCCAAGCCAGCGTCACCGGGCCATAGTGAGCCGCCAAGCCAGTGTCA<br>CCGGGCCATAGTGAGCGGCCAAGCCTTGGTCTGCCAGAGCCGGCCGCACCAGAAGGATTTCTGGGTCCCCAGTCCTGGAGGAGCACACGGTTTACACCAGGCC<br>TTGGGAGGGGAAGAGGCAAGGCGTGGGCCCAGCCCTCACTCCCCAGGAGAAACCCTGTTTGAGCGGCAGAGGAGACTGGAGAGACCCCAGGGCGGGGATCCCT<br>GAGAGGAGAGAAACCCGGAATTCATCCACGGAGGCGTTCACCCAGAGGAGACCCGGAGCTTCTCCAGGAGAGGCTGGATTGCTCCAACAGGGGCCCTGAGGAG<br>CTGATGGCAAGAGCGGAAGGCAGCTCTGACTCGTGCGTCTGACTCCAGGTGTGGCCGTTGGGGCTACAGTGGGACCAGCCTGTTGTCACTGAACCCACAAAGT<br>GCCTCCGAGCGCGGGTGGAGAGAGGGGGACCTCCCACCGTCTGCTGGCCTTGAATCTTGAATCTAATTCCCGTCTGTGCTTTGATGGGAGAGGCACTGGGAGC<br>GGGCGGCTTTTTCAGTTCCTTTTATCTTGAATGGCCTTTGGGGGATTTTCACAGATTCTGAGTTCAAAGCCCAGGGAGGTGTGGGAACGTGACATTCCTCACC<br>GCATTCCTCACCGCATTCCTCTGTAAACCAGGCGGTGTTGGCACCCATGAGCCTGTGTCTTCTATGACATCAGGAGTTTTATCCCTCACGTCAGAAATCAGGG<br>TTCCAGGCGCCTTGGTTTTTCTTGGCGCCAGCGGCTTGGCTATAGAAGAAAAACTGAAGGGGCCAGGTGCGGTGGCTCACACCTGTAATCCCAGCACTTTGGA<br>AGGCCAAGGCGGGTGGATCACGAGGTCAGGGGTTCGAGACCAGCCAACATGGCAA |
| 245 | COL18A1 | GCTCCTCAGGGGGAGGTTCGGGGCCTTTGGTCTCTGGACTTGGGCAGCAGAAAGGAAACATCCCTGGGGGCCTGTGGTGACCCCCATCCTCCCCAGGGTGGTC<br>TGGCAGGGGACACTGTTTTCCAAAGCAAAGCCAGAGCGCCAAGGGCTCTCGGGATTCACGAGATCCACATTTATCCCAAGTTAGAACAGCACATCTGTGCGTG<br>CAAACTTCATTCTGACTTCGGCCGGCTGTCCTTCTTGCCCAAAGCACCGTGAGGCCTCATCCCTGCATCCCTGTTGCTTCTTTCATGTGGGATGAGAACCCAG<br>GAAGGGGCTGAGTGTGACTCCTCTGGTTTTTAGAGAGCACTGCCCCCGCCCCGCCCCCTCCTGCTTCCCCACCTTTTCACAGTTGCCTGGCTGGGGCGTAAGT<br>GAATTGACAGCATTTAGTTTGAGTGACTTTCGAGTTACTTTTTTTCTTTTTTTGAGACAGAGTCTCGCTCTGTCGCCCAGGGTGGACTGCAGTGGTGTAATCT<br>TGGCTCACTGCAACCTCTACCTCCCGGGTTCAAGCGATTCTCACATCTCAGCCTCTGGAGTAGCTGGAATTACAGGCGCCCGCCACCACACCTGGCTAATTTT<br>TGTGTTTTTAGTAGAGATGGGGTTTCACCATGTTGGCCAGGCTGGTCTCGAACTCCTGACCTCAGGTGATCCGCCTGCCTTGGCCTCCCAAAGTGCTGGGATT<br>ACAGGTGTGAGCCACCGAGCCTGGCCTGGAGTTATTTGGGAGAGGGCAGCCCCTGGTTCAGCGTGGCGAGGCTGCGCTTGCTCTCCCGGGCGGGCGTCCACA<br>CCCTCCTCGCCGAGATGGAGAAGCCCAAACCCCTGCAGCGCTCCCCCATCACGTCCGGCCCTGGAAGCCCCCGGAAACCCTGCCACGCCCTGAGTGGGAGAGC |

TABLE 4C-continued

| SEQ ID NO | GENE NAME | SEQUENCE |
|---|---|---|
| | | GCAGGTCCCTTTCCGGCCCTGGAAGCCCCCAGAAACCCTTGGGTGCCAGGCCTGGCCGGGACAGCAGCGACACTGCATGCTCAGCCCTTGCGTGAGACCACGG |
| | | GAGTGTCCGCCCTCTGCACGTGCTGCTGATTGCCCACTTCGTCCAGCAGGTTTGGGAGCTTGTGGCTGCATCCTCCTGCAGACACTTGCCCATTCTGGGGCCT |
| | | CCTCTCTGTCTTTTCTCCTCTGTTGAGGGGTCTGGGAGGGAGGCCTTGGAGGGTACCCATGCTGCTGGGACTGATGCTCCCCGCGGTGGAAGGAGCTGCCTCT |
| | | TGAACAGCAGGGGGCTGAGCAGAGGGGAGGGGATGCGGGGGTGCCGTGCACACAGGTGCTCTCAGGACGCAGGGGCTTCTCAGCCCTGCTGTCCCAGGGCTGC |
| | | ACTCCAGCAGGGCAGACTCCTGAGGTGCAGACACCCCAGCTTCACGCTCACACTTCTGGAAGGCGATGTCTGTGCGTTTGCTTTCTGCTGCAGTTTAAAAAGC |
| | | CGGGCTCTCTCCGGAGCGTGTGTAGGGCCTGGTCACTGGAATATCTGGACTCAGTGTTAATGGCAGCCACGCTGGGGGCTGGGCCCAGCTTTCTGTTCTCCGT |
| | | GTGGGTGCCATATCCACCTCCATCGCAGCCCTTTCTCTCTCGACCTTTTAAATCACAGTGTCACCTCCCCCTGCTGTCCTGCCAGTGGCCCCTGGAGGCTTCT |
| | | CCCCACCCCTTTCTTCTGGGGCAATTCTTAAGGCTGGCATTGAATCAGGAGGCCAGATGTGGCCCCTAGTAACTCACCAGCAGTCCCTGAGGCTTCTGGCTCC |
| | | CCTGGCCCACCAGCCTCCCATGTCTGCCTCAGGCCTCTTGACCCGCCTGGCACTGACCAGACTGTGTGCCCGGGTGCCGTGCCCATGGGCTCCGCCTCCCCCA |
| | | GGCAGGCCCCCTCTTGCTCCGCGGCCACCCCTGCTCTTGACCTCACACCTCTGCGGTGTGTCTGGACACACCAGCACCACGGCGGGCGGGGAGCGGAATTCTC |
| | | CAGGTGGGGTGGGCAGGCCGGCGGGTGTTGAGGTCTCTGTGCATGCTTGTGCGTACCCTGGACTTTGCCGTGAGGGGTGGCCAGTGCTCTGGGTGCCTTTGCC |
| | | AGACAACTGGTCTGCCGGGCCGAGCATTCATGCTGGTCGCCATCACGTGACTCCCATGCGCCCTGGCCCTGGGGTTGGGTCTGCAGGACTGAGAACCAGCGGA |
| | | AGGGGGGCGAGGCCTCGGGAATGCGCCGGCAACTGGCGATGAGCTCAGGCCTGACTAATGAGCCCAGGTGACTCATACACCCGGGGCCTGGATGAGTCTGACT |
| | | GGGTCAGGACTTCCCTGCTTGTTCTGTCCTGGGAGATGTTGTCCCTGGCCCTGCAGAGCCGGGAGGACACGAGGCCTCCTGGGTCACAGCCAACGCAGCCTAC |
| | | TCCTGCCCACTGCTCGCGCCGGCCAAGGCCCGTCGGCACCACCTCCTCCATGAAGCCTTCCTGACTGCCCCCATCCCTCTGTGGGCAGCTCGAGTGTGCATCT |
| | | TGAGTGCTGTGCAGGTTGGGGTCCGGCGCTCCTGCAGGCAGGCGGCGTCTGGGCCTGGGGGCTCTCAGAGTTTGAGGAGCGTGTGGTGAGGGTGGCCTCGGGC |
| | | CTCAAAGACGCAGCGCTGTGGGAACCGGGAGACTGGCTGAGCCCGCTCTGAGGAAGGTGGGGCCAGGGGCACCCTCAGCTGACCCGGCGTGCAGGGGTGACCA |
| | | GCCAGGCGTGGCCAAGGATGGGGTCTCTGGGATCAGGAGACTTCAGTAGCAGCCAGGACCGAGGCCACCAGTTTCCACCCTGGCATTTTCCATCTTTTGAAGG |
| | | ACTGGAAACGATTGGATTCTTTAACTTTTTTAAGTTGAGGTGAAATTCACAACGCATAAAATTAACCATCTTAAAGCGAACAATTCGGTGACATTTAGTACAG |
| | | CCAGAAGGCTGTGCAGCCATCACCACTGCCCAACTCTAGAACATTCACACGCCGGAGAGAGGGAGCCCTGGGCCATCACGCAGCCACCGCCCGGCCCCAAGAA |
| | | CCTGCGAGTCCACTTTCCACCTCTGGATCGGCGGTTCTGGACGTTCATGCAGGTGGTTCCCGCAGTGCGAGGCCTTTTGTTTCGGGCTCCTCTCACAAGCCTC |
| | | ACGTTTCCAGGTACGTCGTGGTGTTGTGCAGACCCACAATTCATCCCTTTTCATGGGTGTGTAATAGTCCACCATAGATTCTCTACGTTTTAAAGCATGTTTT |
| | | ATGTGCCTGAAATGTCTCTGCACTCGAGACTATAGCTTGCTTTCTTTCTTTTCTTTTTTTTTTTTTAATTTGAGACGGAGTCTTGCTCTGTTTTCAGGCTGGA |
| | | GTGCAGTGGTGCGATCTCGGCTCACTATAACCTCTGCCTCCCAGGTTCAACTGATTCTTTTGCCTCAGCCTCCCGAGTAGCTGGGACTATAGGCGCGCCACCC |
| | | CACCCGGCCAATTTTTTTGTATTTTTAGTAGAGATGGGGTTTCATCATGTTGGCCAGGATGGTCTCGATCTTCCGACCTTGTGATCTGCCCGCCTCGGCCTCC |
| | | CAAATTGTTGGGATTACAGGCGTGAGCCACCGCGCCCAGCCGAGACTACAGCTTTCTTTAACTGCATCCCTGGAGGGATCTGAGAGTCTCTTTCCCTGTCTCC |
| | | TTTCCTTTGGAAAACATTTCAGCCAGGGCTCCCCAAGATGAAAGGCCAGAGTCCCAGGCATGGGCGTTGCAGGTGCACAGTTGCCACGGGGAGCTGTGGGTGA |
| | | TGGTCGCTGTCAGCGATGGCTGCTGCAGGTCCCTGTGAGGAAGGGGCAGTGCCACAGCAGGAGGAGAGGGAGTCAGCGGACGTTGATTGGCAGTGCCCGCCCA |
| | | TTCCATCATTCAGTCACCCACTGTGCACCCAGCACCCAGGCTCGGCTGCATAGAACATGGCCCAGGAAGGCTCCACTTCCTGTCTCCTCTTCTCCCCTCTCCA |
| | | GTCTCATGATGGGGCTGGAGGCATCTTCTAGTTTTGAGTTCTGAGCTAATGAACATGCTCATGAGCAGGCGGCAGGATCCCAGGACGGTGGAGCTGGGAGCCT |
| | | GACTGCGGGTGACGGACAGGCTCTGGCAGCCCCTGTCAGCATCCTCTCCAGGGCATGTGAAAGCCAGTGTGTCCTCAGCTGCCAGTGCCCCCTCCCCACCTCC |
| | | TCTGGGCCCATGTGCACGGGACCTGGGCTCCCCCAACCAAGCCTGCCCGCCTTGGTTCAGCAGAACGGCTCCTGTCTCTACAGCGGTGCCAGGCCAGGAGTGC |
| | | TGTGTCTGTGAAGCGGGGTCATGGTTTTGGGGCCCTCATCTCCCTCGCGCCCTCTCATTGGGGACCCCCCGTCTCCCTAGCGCCCTCTCGTCCTCTCCTGCAT |
| | | GTGCTGTGTCTGTGAAGCGGGGTCATGGTTTTGGGGCCCCCCGTCTCCCTAGCGTTCTCTCGCCCTCTCCAGCATGTGAAGTGGGGTCATGGTTTGGGGGCCC |
| | | CCATCTCCCTAGCGCCCTCTCGTTGGGGACCCCCCGTCTCCCTAGCGCCCTCTCGCCCTCGCCTGCATGTGCTGTGTCCATGAAGTGGGGTCATGGTTTGGGG |
| | | GCCCCCTATCTTTCTAGCACCCTCTCGCCCTCTCCTGTATGTGAAGTGGGGTCATGGTTTGGGGGCCGCCATCTTTCTAGCGCCCTCTCGCCTTCTCCTGAGC |
| | | GTGTGGAACTCTGTGGTGGTCAGAGCTAAGGTTCTGAATAGGTCGAAGCACCTCCCCGGTGCCTCTCACCCTGAATGCTCTGGGAGGACACAGCCTTTTCATA |
| | | GGCTACGACTGACATGGCAGGAGGGGCCTGCCTGCCACCCGGGTCCTCTGCTGCCTGCTGCTTGCTGGGGAGGGGGCTCGAGACTGGGATCCTGGGCTTCTGC |
| | | TCCAGCTGTGCCCAAGGGAGCTGCTGAGGAGGGACCGGGTGGGGCATCCACTCTGGGCAGGTTCAGGGTCATTCTTGGTGACCCCGGGTCCGGTTACAAAGGC |
| | | TGATGGAGCGCGTGGGTGGCTGCCTAAGTCTCTGGAAGCCCAAGAATGTGGAGATGGCGCGTCTCGGCCCGGGGTCTCGTGGCTGGTCTGGGAGAACTTGCCT |
| | | TTATTTCTAGGCAGGAGGCTGCACTGCAAGGGAGCGTCAGTGGCCCGGCTGGCTTTCCCCGGCCCTCAGCCCGCACTCGTCCACCAAAGCAAGCTCCTTTGTG |
| | | GGGCTGCCCTGGGAAGCCGGGATCACGAGGCTCTGCCGGCCGTGGTCACCCCATGAGGCAGGGTCAGCTCGGGAGCAAGGCGGATCAGATGGAACAGAACACG |
| | | TAGACCACCTCGCCCGCCCTTAGTCAGCTGGGCCATTGAAAATCAAGTCCGTAGAAAGACCTAGAAATAAGTCCCGGGGTGCCCTTGCCTGTTGACGGGCGGG |
| | | CCGAGCAGGACTGTTCTCAGGCAGGCACTGGTCTCTTGGCTTCCAGGTGGTTTGTTTGCTGGTTTGAGGCTGGGGGTGACGCTCCTGTGCGGGAGGAGGTCGC |
| | | ATTCCATTCATAGCGGCTTATCTGGGCTGTCAGGCAGGCCTGGGAGGGAGCCTGCCTCTGTGCTCTCCAAGGGTGGGCGACGGACAGACAGGGTGTCCCACCC |
| | | CTTCTGGGCCAAGGACAGAGGGTCAGTGTTTGCAGAGACCTGGGGAGGCCCAGGTGACCTCCACCGAGCACCTGCTGTGTGCAGGGCCAGTGCTGGCTGCAGA |
| | | GACAGCGGAGCGTGTGTGGACCCGGCGGCCCAGGGGAGGGGGGCAGGCAGGACCCGGCGGCCCAGGGGAGGGGGGCAGGCAGGACCCGGCGGCCCAGGGGAGG |
| | | TGGGCAGGCAGGACCCGGCGGCCCAGGGGAGGGGGGCAGGCAGGACCCGGCGGCCCAGGGGAGGGGGGCAGGCAGGACCCGGCGGCCCAGGGGAGGGGGGCAGG |
| | | CAGGACTCGGCGGCCCAGGGGAGGGGGGCAGGCAGGACCAGGCGGCCCTGGGGGTCAGGGGTGGAGGCCAGGCCTAGACGGCCCACAGGAGGGTGGACTCATT |
| | | CTGACCGATTCCTGGAAGCCCCCGGAAAGTGGTGATGTTCTGGAGGGCCCAGCAGACCCCAAGGCCCCCAAGACAATCCCAGCTGGCTCTCTGCGGCTCTCGG |

TABLE 4C-continued

| SEQ ID NO | GENE NAME | SEQUENCE |
|---|---|---|
| | | TGTCTGCCATTTGAGACAATTTGGGCACAGGCAGGGCAGGCCGTCGCGGACGGTCTAAGCCGCGCGCATTGGTGGGGGCAGCAGAGCCCCTGCTCTCAGCTCC<br>TCGGGGTACAGCGGGGGTACCAGGCGGGTGAGTGGGTGGGTGGTCACTGCTCCTGCCAAGGGCAGCCCTGGTTTGGTTTGCACTTGCTGCCCTGGTGACGGCT<br>GCTCTCATTCCTGCCCCATTGCTAACAAGGGTGTCATAAGCTACTTTCCCGGCCCACATCCTATTAAGCCCATGGAGACCCTCCCACAGCTGAGCCTGCTGTG<br>GGCTGCAGGCCCTGGGCGGTGCCCACCTCGGTCCCCACTGGCCTCCTTCCAGCACTTTAGAGCAGACACAGGTTGGAGATAAGGAAAGTTCCAGAGCACAGAC<br>TGGAACAAGCCCCAGGCCTCTCCCTGCCCCAGCAGGGCCTCCCTGGATTTGGGGGACAGGTGCCCTCATGGGGGGTCCTGAAGGTCAGAGCTGGGGCTGGGGC<br>TGGGCTGGCGGAGGTGGCCTTGGCGGAGGCCACATTCCAGGGTCTCAGTGAGAGTCTGTGGCAGGCAGCCTTGCAGATGCCGCTGAGGGACCCCCCACTTCAT<br>GTTGTGGGTGATGTGGTCCATTGATTGCCTCCAGGTTTAAATCAGGTGGATATTTACCTAGCGGCCTCCTCTCCCTCTGCACAGGGCCTGGAGTGGGATGGAC<br>TGGGGTGCTCAGCTGGAGGCTCTGCAGACACAGCCCCCTGGGCTATGCAGGCCCTGCTGGGAGCCACATTGCCATTTTTCATCACCCACTTTTTGGGTGAGAA<br>CCCCCTCGAGTCCTAACATCTGCCGCATCTCAGAGCCTGTGGCTCCAGTCAGAGCATCTGGACCATACTGCTGGGGTCAGAGCGCGGCAGGACAATGGC |
| 246 | COL18A1 | TGCCACCACCATCTTCAGGTAGAGCTTCTCTCTCCTCCTTGCTGGGCGGGGCCCCTCCCTGGGGAAGCCTGCAGGACCCAGACAGCCAAGGACTCTCGCCCGC<br>CGCAGCCGCTCCCAGCCAGCAGCTCCAACGCCCTGACGTCCGCCTGCGCACGCCACTTCTGCACCCCCTGGTGATGGGCTCCCTGGGCAAGCACGCGGCCCCC<br>TCCGCCTTCTCCTCTGGGCTCCCGGGCGCACTGTCTCAGGTCGCAGTCACCACTTTAACCAGGGACAGCGGTGCTTGGGTCTCCCACGTGGCTAACTCTGTGG<br>GGCCGGGTCTTGCTAATAACTCTGCCCTGCTCGGGGCTGACCCCGAGGCCCCCGCCGGTCGCTGCCTGCCCCTGCCACCCTCCCTGCCAGTCTGCGGCCACCT<br>GGGCATCTCACGCTTCTGGCTGCCCAACCACCTCCACCACGAGAGCGGCGAGCAGGTGCGGGCCGGGGCACGGGCGTGGGGGGGCCTGCTGCAGACGCACTGC<br>CACCCCTTCCTCGCCTGGTTCTTCTGCCTGCTGCTGGTCCCCCCATGCGGCAGCGTCCCGCCGCCCGCCCCGCCACCCTGCTGCCAGTTCTGCGAGGCCCTGC<br>AGGATGCGTGTTGGAGCCGCCTGGGCGGGGGCCGGCTGCCCGTCGCCTGTGCCTCGCTCCCGACCCAGGAGGATGGGTACTGTGTGCTCATTGGGCCGGCTGC<br>AGGTAACTGGCCGGCCCCGATCTCCCCACCCTTTCCTTTTTGCCTTGCCAGGTAAGTGTGGGCGGGGCTGACGTGAGCCTGGTACAGGTTCCCCCCACATCGA<br>ATCTCTACGTTCAGGGGCCCGTGGCCCTCGGGAGGTGGGAGAGCTGGGAGTGAGGCCTCCTGTGTGGGGAGGAGGCCGGCGTCTGGACAGGAAGAGGGCTGGA<br>TGAACCGCAGCCGATGTGTCCAGGTGCCACCTGGGCCTGGAGCTCCCTGAGCATTTTAGCGCATTTAGTCCTCAGCACGGTCCCGAGATACCCTGCCATGCCC<br>CGAGTCACAGAGGGGAAACTGAGGCGTGGGGCAGTGGCGTGACTCACCCCAGGGAGCCGAGATTCCCGCTCAGGTGTGGCTGCATCGACCTTGCTCCGGTCAC<br>TAAGCTGCACGGTTCGATGCGCTTCCTGGGAGCCCCAGCGTGCTCGGGCCAAGGGTGCTGCCGCGTGGGCAGTGCAGAGACCCTACCAGCGTGGGGACCAGGG<br>AGGTCTGCAGGGCCCGTCCTGAGAGGGAGCCTTTCATGTCCCCCTCCCCATCCTGAAGCACACAGCCTCCCTGCCACAGTGGGGGCCGCTTCTGGGCCCAGGG<br>GACGTTGCCCCATCACCGTGTGGCCTGGCCTTGTTGCTGGCTGGACAGTTGGGGGCAGGAAGAGGAGGGAAAGGGGGACTCTTTAACCTCCTGGGGGCAGGGG<br>CAGCCCAGAAAGGACCCCAGCAGATCCCTCCTCTGTGTCCGGGAGTAGACGGGGCCCC |
| 247 | COL18A1 | GGGCTCCACAGCGGCCTGTCTCCTCACAGGGTTCAGCCCAGTCTGCTCTCACTCATTTGCTGATTCATTCTTTCATTCAGCCAGTCAATAGTCATGGCCCCTC<br>CTGTGTGCCGGGTGGCCATGGATATTGCCCTGGGTAACACACAGCCTGGCCCTGTGGAGCAGACAGTGGGGACAGCCATGTGGACAGGGTGCAGGTGGATGGC<br>AATGGCAGCTGGGTCAGGAGGGGCTGAGGGCCGTGGGGAAAGGTGCAGAATCAATAGGGGCATCCGGACTGGGGTGCAGGCCTGGGGGCTGGGATTTCTAGGG<br>TGGAGGTCACCTCTGAGGGAGACAGAGCAAGGCCCTGGGAGATTAGAAGGTCGAAGGTCGCCGTGTTGAGGTCAGGGGCCCTGAATTGGAGCCGCGGCAAAGG<br>AGAGGGCAGGTCAGGGCACGTGGTGAGTGATTGCTGCGGCTTCTGAGCACGGCTGGGTCTGTGGGGCCTGAGCAGAGGTGACCCGCGATCCGGCGCCACGGCA<br>GGCAGGACTCCCCACCCTTGCTGCTGCCTACACCCCCAGGGCAGCCCCAGAGTCGGGGGCGCAGCTCCCTGCTTGCCAGTTCAGAGCCCAGCCCCTCTCACCC<br>AGCCCAGAGGAGGACACAGATGGAGGAGGGGCACCCGGAGGGTCCCCCCGCCGACAGGCCCCACGTCTCCCACCTGCAGGACAATGAAGTGGCCGCCTTGCAG<br>CCCCCCGTGGTGCAGCTGCACGACAGCAACCCCTACCCGCGGCGGGAGCACCCCCACCCCACCGCGCGGCCCTGGCGGGCAGATGACATCCTGGCCAGCCCCC<br>CTCGCCTGCCCGAGCCCCAGCCCTACCCCGGAGCCCCGCACCACAGCTCCTACGTGCACCTGCGGCCGGCGCGACCCACAAGCCCACCCGCCCACAGCCACCG<br>CGACTTCCAGCCGGTGGTGAGTGCCCCCCCAAAGTGGGCTTGGCTCCATCTAGCCCCTCGGCTCTCGGCAGCAGAAGAGGGCCCAGCCCCTGCAGAGCTGCTG<br>GGGGTCCCAGGCTTCGGCCATGGGTGGGGGTCTGGCGGCTCAGGGCCACTCAGGGCGGCTTGGCTGGCCCTGGGACTTGCCCTCTGGTGGCCAAGCAGTGGTC<br>ATGAAAGTCCAGCCGCTGTCACATCCTTGAGGAACCGGCGTACCTCCGCCTACAGCGGCAGCTGGGGGCACCCACGTGGCCCGGGGCTGCTCTGACCTGGCAG<br>CGTATGGGGGCTGCTGCCTGGGCCCCTCAGTGTGTCACTTGCGCGCCTCCCGCTCAGCGCCCCTCGGCCGTGCCTGTCCACACAGGTGCGGGGCCGGGGTGGT<br>GCGCCCGGGGCCTGGGTGCAGGGGGCAGCGTGGGACACAGCCCGTGACGCGCCCCTCTCCCCGCAGCTCCACCTGGTTGCGCTCAACAGCCCCCTGTCAGGCG<br>GCATGCGGGGCATCCGCGGGGCCGACTTCCAGTGCTTCCAGCAGGCGCGGGCCGTGGGGCTGGCGGGCACCTTCCGCGCCTTCCTGTCCTCGCGCCTGCAGGA<br>CCTGTACAGCATCGTGCGCCGTGCCGACCGCGCAGCCGTGCCCATCGTCAACCTCAAGGTGGGTCAGTCCAGTCCTGAGGGCGCGGGCTCCTCGGCCCCCACT<br>TGACCTCTGGGGTGAACTCCCAGCGGGGAGCTCCCCTCTAGGGCCTCTGGAGGCCACCATGTTACAGACACTGGCGCCTAGGCTGGCGACTTCAGGGCAGGCT<br>CCGGGTGGGTCACACCCCTCCAGGCTCAGGCCAGGCCTCTGCATCCCTGGGCACTGCCACGTCCCCCAGGGCATCCCATGAGGCCCCCCCGTGGCCCCCTGAC<br>CCCCCGCTCCCCCGGCAGTGCCCCTCAGAGGGTCCCATGCTGCTGGACCAAGTGTCCACACAGGTGATAGGGCTCACATACAAGCCTGGAATCAGGAACCGTC<br>CTTTGGGCCTCTAGTGCCATGCGGGCTGGTGGCCCCTCTGCCA |
| 248 | chr21: 45885000-45887000 | GCCTGGAGTGTAGTCCTGCTGAAGGCCAGAGACCACACACTCCACCCAGACTCCGGATCTCCCTCCCCAGCAGGGGGATGGAGGCCCTGCCGCTGGGAGTGCT<br>GGTGTTATGTGGAAGGGCTGGGCTTCTCCAGGGCTCCTGGGAGGCCTAAACATCTTGCAAGGTTTTGACGTTAATTACTATTATGATTGCTTTCTGTGTGTTA<br>CTGTTTTCCCCACACTTTAGCCAGCTAATGTGGAGCTACAGAAGGCCCTCGCCCCTACCCCTCCAGATGTCCCAGCCCATGACAAGCAGGAAGGCCGGGTGCT |

TABLE 4C-continued

| SEQ ID NO | GENE NAME | SEQUENCE |
|---|---|---|
| | | GGGAGACTTCCTGGGGCTGGATCTGACATCATTCCAAGCAGATGATAACCTGCCTTCCCGATTTCCAAACCCACAGCAAGACACCCTGGAGTTATTTATAAAT<br>GCGAGCCCCTGGGTGCACTTCTGACGGGACCAGCACCCTGACGGCCATGAGAGGGTGGAGACAGCGCACCCCGAGCTCAGGGAGGCAGGAAACTCTGGACCTG<br>GAGGCCGGGCACCATGAGGGACACGCTGCAGGCCCAGCTGCTGCCGCCTGGGGCGGGGCTGCCCTGCAGGCTCCGGGAAAACCCAGAACCAGGCCGGATCAGC<br>GTGTGTCAAGAGGCGGGGCGTGAGAGATGAGCTGCTTTTTTTCTTCACAGGGTTGGCAGGAACTGCAAATAATAGAAAGTCTTTAGGGTCTAACACGCTGCCC<br>TGAAAACACTATCATTACTTTCCTAATGACTAACTGTGTCTTTCAGCCGGCGGGGCAGGCAGCTGAGGCCGCAGGCTCCCGCAGAGGACCGGGGGAGGCTGGC<br>AGCCTGTAATCTGGGGGCGCTGACAGTGCTCTGCCCAGACCCTCGCGCCAGCTCCAGCTCCAGCACAGCAGCCCTGGGTCCCTCTGGCCCCCTGCCCGCAGAG<br>TCCAGGTGTGGCAGAGGCCGCCCAGTATCCCTTCTCCTCCTCCTTTTCTAAAAACAGAGTCTCACGATGTTTCCCATGCGGGTCTCCAACGCCTGGGCTCAAG<br>CGATCCTTCTGCCTCGGCCTCCCAAAGCGTTGGGATTAAGGGGCGAGCCACCGCGCCCGGCCCACCTTCCCTTCTGGTTCATTTCCAGTAAGGTCCTGTCCAC<br>AGCGTCCTTCCCAGCATTCCCACCAGGCTGCAGGCCTTGGCCTCCCTCCCCTCCATTCTCATTCTCCCCGAAACCGCCAAGCGCGTCCAAAGCACGGGTTCGC<br>CAAGCGCCCCCCCCGCCCCACTCCACATTCCCTTCCCCGCCGACTCAGCCTCCGTAGCTCGCGGACGGCCCCTCCTCACGCCAGCCCAGGCTTTTTTTTTTT<br>TTTTTCTTCTATTTTAAGGTTGTCTTTTAATGACACAAGCGACATTTGGAGACAAAAGGACACATCTCTTCCTGACCCACCTCCAACCCCAGCTGACGGCCGC<br>CCTGAGCCTGGCGTAGACGGCCCGGAACGTTCCCTGCGTGGGTTCCGTCCATCCCGAACCCCTGTCCCCGCGCCGGCTCCGGGGGTGCTCGGGGGGCCGCGTG<br>GGGTCTGTGACGTCGCCTCGAGGCTGCATCCCGGTGACCCGGCAGCCCCTGGCGCTCGCGGAGGCGGGCGGGCGCGGACCCCAGGCTTTAGGGCGCGATTCC<br>TGCAGCTGGCTGCCGGCCCGAGGTTCTGGGGTGTCTGAGGTCTCGGGCGGGGCGAGGACGTTTCTCCGGCTCAGCCCCCCCACCTCCTGCCCTGCCGCCCCCC<br>ACACCCAGCTCCCCACGGACGCCAAGAGGCGCCTCCCACCCCGGCGAGGACCCGCGGGGAAACGGGGCCCAGGCGCGGCGACTGCGGAGGACGCGCCTCGGCC<br>CCAGCGCCCTGGTCCTCGGGGCGTCCGGCTGCCCTTGCCCGAGGCCGGGGCGGGCGCTCAGCGCCGCGGAAGAAACGCCCGGGCGGGGACGCACAGCGAGGCG<br>GGCTCCGCGGGAAGTACCGGGAAAACGGCGCGGAGCGGAACAG |
| 249 | PCBP3 | TGGAGCAATCCCAGAGAGGCTGAGGTGTTCAGGCTGGCCCCAGATGCACACGAGCGTGAAGCCTGTTCAGAAGCCAGCTCCTCACACCCTCTCCCCTGCCAGA<br>GGCTCCAGCACCCCCTCCCCTCTCCTCTCCCCTCCCTTCCCTGTGGTCCTCCTGCCCACCCCACCCCCGTCTGCATGTGCACCGTCACGGAGATGCGTGTACT<br>AGGGCGGAGGTCGGGGACAGTCGTCAGAAGGACACAGGAAAGAAGGGAACAGGAATCCCATAACAGAACATTATCCGGCAGGAGTAATTAACACAGGCAGGAC<br>TGGAGGCTTTGTTTTGTTTTGCTTAAAAAACAGTGGTATTTAAATTAATGGGCATGGGAAGACTATTCAGTGAAAGACATCGGTCATTGAGGTATCTATTCAA<br>AAACACGGTTTAGTACTCTGCCACACACCGAACGCAACGCCACAGCAGCCATAGAAGCGTGTGTGGCTGTTTAACGTGGTCTTTTTGGGGAGGGCATCCTAGG<br>CAGAGCAGGCGTGGAAGGGAAGGCGGCGGACGGAACAAAACGCGGGCACGCAACGGCTGCTGCGCCGGATCTGAGGCAGGGCCAGCCTGTGGGAGCAGCAACA<br>TCGCTCGCAGGACAGCGATGGAGCCCCCACGAATCCGCGTGAAAGCAGCAACCACCTAGAAATGAACGTACAGCTGCTTAGAAACAGAATACGGATGACCCGA<br>AAGACTTCCCGATGGTAGTCACCAGCATACAGGACCTGACACGGGCGTGCGGGCAGGGTGTGCCGCTACGGGGTCCCTGGCGCACCTGCTACCCCTGCTACCC<br>GCATTCACCGCACGCGGAGGGTGCGGGCCGTGAAGGTTATACATGCAAATATCCTTCCACCAGCCAGTTCTCCTTCCAGGAATCTGCCACCCGACCCTTGTGT<br>TGTGCACAGACATGGTCCAGGTGTTTGCGACGTGATTGTTTATCAGAGAGAGAGAAGGGAAATCTCCAGGCTCGCTGTAGCTGCAGGAGCTCTGGGGGCTGCG<br>CCCATCGTGGAGACGGATAGCTGTCTCTCATGAACACAGGACAGCAAGTCCGGCTGCGGCCACAGAAGACTCGCCCTCCTGGACGCAGCGTCTTCCTTCCTCA<br>GCCCCACACTGGAGGTGGCCAGTGCCATCCACAGCAGAAGGGGCCAGCCGGGACCAGGCTCACGCCGTGGAATTCTGCTCTGTGGTAAGAGGAAGAGCGATAG<br>CTGGAACCCAGCGCCGTCGCACACACAGCGGGGAAGAGTCTCAGAAATGTTACTTTGAGTCAAAAAGCTGGACAAAAAAAGGCGCAAGCCAGATGGTGCTGAA<br>GAGGCCACAGGAGGCTGGCAGCCAGGGGGTCTGGCACCTCACTCGGAGGCGCAGTGGGCCCGTCCGGAATTAGTGGCCATACGGCAAGTGCCGAGTGGACATC<br>AAACCGTCACTTCAGACTCCTGCGCTTCACTGCCTGTCGGTTATGCCTGGGTTTTGAAATCAAGTCACAGAACACCTGGAATGTGGTGTTTACGCAGAACAAA<br>GCGGGTGCCTCGGAGGAGAGAGCCTAGGGACAGGGGCACCTCCCGGTGTGGGTGCCCAGGGTTGCAGGGTGGCTTCCTCTGTCTGCGCGGTTTTCAGAGCCCC<br>AGGGTCCTGCCTGCCCGGCTGCCTGGAGGCGGCCCACATCCTGCTCTGCGCCGCCGAATCTCAGCCTGAACAGCTTCGCTGGTGTTTGTGTTGACTTATTTGT<br>TCTTTTTTTTTTTTTTTTTTTTAAATAAAGGATTCCGATGCTGTTACAGTCAATAAAAGCCACAGGTCTGGGTGACCTACAAATGTGTGTGTCTGACTTTCT<br>GCAGTTTAAATCGCCACTGAGCCTTAAGGCGTCTGGCCCGCGCATTGAGGAATCCACGTGGGTCTCGGGGTCCCCATGCCTGCCCAGCTCCCTGCTTCAGCCT<br>GGGCGGGTCTGGCGGGCATTTCTGCGAGCCTGTCCCTGGGCCCGCCTCCTGGCCAGACTTCCAGAAACATTGTCCACATCCCCGTTGCACGTCCCCCCGTCAC<br>CGGAAACTGCAGCCCACAGCACTGGGAAGAACCCGGGAGGCAGGCGTTAGGACGGGGTGGCCGAGACAGGGAAGGGAGCCATGGCGGACGTCCTCACCCAAGC<br>CAGGGCTTCCTGCCCCTGTGGTACTGACAGGAGCCCCGCAGGACGTGGGGTTGGCTTTGGGCAGCTCGGTGGACACTTCTCTTTCAGATCCTGCCACAGCAAA<br>GCTCACGAGACTCACTTCTTCCCATTGGAATTCACTAAGAACAAATTCAACAATTCAGACGCCCCAGCTGGAGGTTTATTTTATGGATTTTACCTGTGCGGTA<br>TTTAGGGTTGTGTTTATGAATAAAGGTGTGCGTTCTGGCAAGTAGAAATACAGAGCTTGTCTTTCACCCAAGTATCTGTAACTTTCTCCAATGCAGACACTAA<br>AATGCAATAAAAACAAACCAAACCCATTAAACATGAATTAGATGAGGCAGGCTGATGGGAGGTTGTGGGATTAACAGGCCGTCAGCGGATTGAAGCTGCGCAC<br>ATCGCTGGGATGCTGCTGCGGGAGGATTCGGTCTAATCCGGGAGCATCTGGCTGGGCAGTGGGCAGCGTCTGCAGTCGTGGCTGCTTGAAGGTATGAAGGTTG<br>TGGCCTTTGCTTCCCCCCATCAGGCTGCCCCACCCTGGACCCCACCCAGACCCCTCGGGCACCCTGGGGTCATCTTCAGCTCCCCCTTCTCTTCCTTCCTTCT<br>CTTCCGCCTGGGCCCCTACTGTGACCCGAGGTCAGCAGAGGACCCTGGCAGGTGGCTGCTCCCTGGGACTCGACTGTGCAGGTGAGGCTTGGGGTGACCGCTG<br>CTCCTGCTCCTGCTCCTCTCGCCGTCCCCACCCTCCTCCATCATGCTGTCAACATGCATGTGGGCTGCAGCCCTCAGCCTGCAGGACGCTGTCAGTGCAGCTC<br>CTCAGTGGCCAGG |

TABLE 4C-continued

| SEQ ID NO | GENE NAME | SEQUENCE |
|---|---|---|
| 250 | PCBP3 | ATCTTGTCTTCCTTGTCCCAGTCCTGGAACCAGCCACTGCCCCAGCAGCTCCTGTGTGTGGTGGCATGTTCTGGAAGCCAGGATGCATGGTGCTCCTGGGCTG<br>CTGTGGGTCCTGGGCTGCTGTGGGTCCCGAGCTGCTGTGGGTCCTGGGCTGCACCCCTGCAGAACACTTCCTTCCATGTTCAGCTCCCTATATGGAACCCCAG<br>TTCCAGCCCCACAGCACAGGGTCCCCCAGTTCTTCCTGCCTCAGGTGTGCACCACGAGGAATCCAACTGCCAGTATCTGTGCGTGGCCTCCCGCCGGGAGGAG<br>GCTGCCGGAGGCTCTGAGCTCTAGCCCCACAGCACTGGCACATCCTAGATTTCCGGGAAGACACGGCCTCCTCCCCAGGGGAAGGTGGTGGTGCCCACACCCA<br>GAGCATTCATTCCTGCAGTGGAGACAGAGGGACCTGCCTCTCCAACTGTGGGTGTCAGGAGCCAAGGCGCATGGTAAATGGGGCTCTCTGTGAGGCCAGGTGC<br>ACGGCCCCATCTCCAGCAGCAGCGGCCATGCCACCCAGCTGCACTCTGTGGGGGAGGTGCCATGATTGACGGGGGCCCCTCCCTGTGTCCAGTGTCCTCCTCC<br>CTCCACGGGCCCCTCTGCACACCGTCCTCACAGTCTCCCTCTGCACACCGTCCTCACAGCCTCCCTCTGCACACCATCCTCATGGTCTCCCTCTGCACACCGT<br>CCTCACAGCCTCCCTCTGCACACCGTCCTCACAGCCTCCCTCTGCACACCGTCCTCACAGCCTCCCTCTGCACACCATCCTCATGGTCTCCCTCTCCTTCCAC<br>AGACCCCTCTGCTCGCCATCCTGACGGCCTCCCTCTCCCTCCACGGACCCCTCTACACACTGTCCTCCCAGCCTCCCTCTACACGCCATCCTCACAGCCTCCC<br>TCTCCCTCCACGGGCCCCTCTACACACCGTCCTCACGGCCTCCCTCTCCCTCCACGGGCCCCTCTGCACACCGTCCTCACAGCCTCCCTCTCCCTCCACGGGC<br>CCCTCTGCACGCCGTCCTCACGGCCTCCCTCTGCCTCCACGGGCCCCTCTGCACGCCGTCCTCACGGCCTCCCTCTGCCTCCACGGGCCCCTCTGCATGCCGT<br>CCTCACGGCCTCCCTCTCTCTCCACGGGCCCCTCTGCACGCCGTCCTCACGGCCTCCCTCTCTCTCCACGGGCCCCTCTGCACGCCGTCCTCACAGCCTTCCT<br>CTTTTTCCACAGACCCCTCTGCACGCCGTCCTCACGGCCTCCCTCTCCCTCCACGGGCCCCTCTGCATGCCGTCCTCACAGCCTCACCGACGTCACCATTGCT<br>GGCCCCGCTTCAGGTGACAGGCCACAGTAGCACCTGTCAGCTCTGTCCCGCTGCTGGACAGGGAGATACTGGGCCACTCAGCCCAGCGGGGAACGTGTGTCCC<br>GAAACTGCCTTGGGCTCGCCATCAGAACTGTGGCAGCATCTTCCAGCGTTCCTTTTAACAGGCTGCCGTTGGAATAGGAGTCACGGAGCAATTGCAGTGCTAA<br>GTTTTCTTTAAGTCACACAATTGAAGGAGGCTTTATTTTTCACACATTTCTTCCAGAGTTTCCTGGTAGCCTGAGTGCATGGGTGATGCCCCCTGAGTTATTT<br>ATCAGGGGCAGCCAGCTGCCCTCCCCCGGGGCACTTACAGTCAGCCCATCTCTGTCCTGGTCAGGTGGGCGCCAAGGAAGACCCGGCTCAGGGCCTCTGTATG<br>GGCAGCCTGGCTTGTACACACACCCCTCCCCACCAGCAGATTCTGAATTCTCCCTTCTTCATGCACACCGGGAAGGTCCCTTCTGCACTCATACCGGGAAGGT<br>AGGCAGGTTTCGGTAGTGTCTGCCTCCAGTGTTTTCCTCCTCCTGCTCTATGACATCATCTTTCTGTGATTTTTTTTTTCTTGCAGGAAGTTGGAAGCATCAT<br>CGGGAAGGTAATTATTGATTGAATCTCTGCCTCTCCTGGGGTCTCTGTAAGGGGATGGTGAGGATGGCAGCCTCCCTGGGTACTAGGTGGCACCCAGTAGGTG<br>CGCCTTTCCCAGTTGGTGGGTGGTCTGTGTTCCATGAAGACAGGACCCCAGAGGTGTCGCCTTTATGCTGTATGACATTGAAGCTGGTCCCTGGCTCTGCGTG<br>GCCTGAGGGGAAGGGGTTCACTCCAGCTGGTCACCTCGCTGCCCCCTGCCCGTGGCCTTGGTGGCCAGTCCTTCTTTCCCGGTTGAAGACCCCACGAAGAATG<br>ATTTCTCACGCCTTCTTCAGCCGGCTGTGTAGTCTGGGTGGTCTCCAGGAGTGCCAGTGGAGGCAGCAGCCCCCAGACAATTCCTTTCCAAATCAGGGCTGGC<br>CCGGGGGAAGTAAGGCCCAGTTTGGAAGCCTGCTGCCCCGGGAGGCCGAGCAGTGAGGGCCACCTCCCTGTCTTCATCACATTTTCACCGCTTCCGGGGGTCC<br>TTCCCCTCAGTCCCACCATGGGGGCGCC |
| 251 | COL6A1 | GCTGGACACCTCTGAGAGCGTGGCCCTGAGGCTGAAGCCCTACGGGGCCCTCGTGGACAAAGTCAAGTCCTTCACCAAGCGCTTCATCGACAACCTGAGGGAC<br>AGGTAGGAGGGACGCCCCGTGACCTTCCTCCTGTGCTTCTGGGCCTCTTGGAGGGAGGGGTGGGGGCCCAGGGGAACACGGGTGCGACGGCCTCAACCTCCTA<br>AGGTTGGGCGAGCGTTGCCCTGACCGGGGCCCCTCCCGGCGCCCTCCAGAGTGAGGCCGGGGCCCTTTCCGGCGCCCTCCAGAGTGAGCTGGTCTGAGCCTCT<br>CCCAGCGCCTTCCAGAGTGAGCTGGTTTGAGACCCTGCTCGCGGGGGTGGCACCTGTTCAGCAGGGCCGAGGTGACAGTGAGGCTGAGATGTAGGGAAGAGAG<br>GCTCCCGCAGGCTGACCGAGAGGGCTCAGCGCACTGGCCCAGACACGCAGTCCTGCCTGGTGCGCGGGAGCCCCTCACTAACCACCTGGACCCTGGTTTGTTC<br>CGTGGGCAGTGAGAGCCTCTACCTGGGTCCTGGATCCCACGTTCTGAAGGTCCCCGACTCGGGAGCCAGGAGGGGTGTCGCTCTGCAGCCCCAGGGCCCCCAG<br>GCTTGGTTCTGGGCTTGGGACACGGCACCCTCTGCTCCACGTTCCTCCATCTGTGCGTGTGGCTGAGGACAGACCGGGGGGAGAGGGGAGTCGGTCCTGTGGG<br>TGCACAGGGCCGCTGAGGGGGGGGCATGTAGAACGGGGCTCCCCCACTGAGACGGGTCCTGGCAGTGGGGACACAGCTTAGCCGGCGTAGGAACCCCCGTCCT<br>CCTTGACCCTGCTGACTGGCCGCTGGGCCGGAGCCTCCCGCCACCAGAAGGGGCACAGTCAGAGGCTGCCGGTAACAGCAGGGTGGACCTTCCAGCCCACACC<br>GTGCCCAGCAGGAGCCATTGGTACCAGGAACCCTGAGCTTAGTGGACATGGCCAGGCCCGTGCGGCAGTGTTTGGGGGGGGGTCTGGCTGTGGATGGCACCGG<br>GGAGGGGCGGCCGCGTGGCCCAGCGTCCCCCGAGTCGCCCTTGTTGCCTTTACTCAGTCTCCCCATGACTCAGTTTCCCACCTGTGAAATGGGGCGGAGTCAT<br>CCCCATGTCGCTGCCACTGGATTCCTGCAGGCGCCGTGGTCACTCTGCTGAATGGATGGGAGGGTGGGTGGGGCAGAGGTGGGCCCACCCCAGGCTGGGGCAG<br>AGCAGACCCCTGAGAGCCTCAGGCTCAGGTGCTCAGAGGGCAGCGAGGGGGCTGCTCAGATCCCCGGGGTGCCTCCTTCCCCCACTGTCATGCTGCCCCACTG<br>CAGGCCCAAGGACCCCACCCCAGCAGGGCCACACACTCAGGGCTCCTGGTCTGAGGGCCTGAGGGATCGGGGCGCAGGTCGCTTGCTGGCCACACCCGCCTGC<br>ACAGCCTTCCAGGAGGGCCGGCCTCAGGGCCACAGGGCAAGTCCAGCTGTGTGTCAGCCACGGCCAGGGTGGGGCAGCCTGTCCATCTGGGTGACGTCGCGCC<br>CTGGGACGGGTAGCGATGGCGCCAGGGGCCGCCCGCCTCACGCCCGCCGTGCCTGTTCCTGGCAGGTACTACCGCTGTGACCGAAACCTGGTGTGGAACGCAG<br>GCGCGCTGCACTACAGTGACGAGGTGGAGATCATCCAAGGCCTCACGCGCATGCCTGGCGGCCGCGACGCACTCAAAAGCAGCGTGGACGCGGTCAAGTACTT<br>TGGGAAGGGCACCTACACCGACTGCGCTATCAAGAAGGGGCTGGAGCAGCTCCTCGTGGGGTGAGTGGCCCCCAGCCTCCTGCCCACGCCAGTTCTCACGCGT<br>GGTACCCAGCCTGGGCTGGGGTTGGCCTGGGGTCCCTGTGCGGCTTCAGCTGCAGCCTCCCTGTTCTCTTGGAGGCTGCACGGCCTCCCTGACCCACTTTGTG<br>GGCAGGAAAGAGACGGAGACAGACAGAGACAGAGAGAAACAGAAACAGGGAGAAACAGACACAGAGAGAGACAGAGACAGAGAGAGATAGAGACAGAGACAGA<br>GAGAGACAGAGACAAAGAGTGACAGAGGGACCAAGACAGGCAGACAGAGACAAACAGAGACAGAGACAGAGACACAGAGAGAGACACAGAGAGACAGAGACGG<br>GAACAGAGACAGGCAGACAGAGACAGAGAGAGACAGAGACAGAAACAGAGACAGAGGGACAGAGACAGGCAGAGAGAGACAGAGAGACAGAGACAGAGACAGA<br>CAAACAGAGACAGAGAGACAGAAACAGGGACAGAGACAGAAAGAGAGAGAGACAGAGGGAAACAGAGAGAGACAGAGACAGATAGAAAAAGACAGAGGCAGAG |

TABLE 4C-continued

| SEQ ID NO | GENE NAME | SEQUENCE |
|---|---|---|
| | | AGAAGCAGAGACAGAGAAACAAAGACAGTCAGAGACAGACAGAGACAGAGACAGAAACAGAGACAGAGAGACAGAGACAGAGGGGCAGAGACAGGCAGACAGA |
| | | GAGACAGAGACAGAGACAGCGAAACAGAGACAGAAACATACAGAGACAGAGAGACAGAGAGAAGCAGAGACAGACAGAGGCAGAGAGACAGAGAGAAGCAGAG |
| | | ACAGGGACAGAGACAGAGACAGAAATAGAGAGATAGAGACAGAGGGACAGAGACAGAGAGATAGAGACAGAGAGGGAGACAGAGAGATAGAAGCAGAGAGAGA |
| | | GAGACAAAGACAGAGGCAGAGAGACAGAGAGAGAAGCACAGACAGAGACAGACAGAGAGACAGGGACAGACAGAGACAGAGAGACCGGAAACAGAGGCAGAGA |
| | | GACTGAGAGACTGAGAGAGACGGGGTGGTTTTCCCCACAGCATCAACACCAAGCAGGGCTAGGATCACTGAAACAGACTCATCAGACCCGAAGCATGCGCTTT |
| | | CTCGGGGTTTTTCTGGACTGAGGGGTTTCCTCTCATCCCAGTGTCCAGCTGTGGGGACGCAGGGGCCGCAAGCCCCGGAGTGTCCAGAGGGGAACGTGGCCTC |
| | | CCCACACCCAGCCCTTCACGAGGCCTCAGGATCCCAGTGGGGGTACCCGAGGCTGCCCTGTCCAGCCAGGCGGTGCGGGGGGTTTGGGGAGAGCCTCTCCCCG |
| | | AGGTCGGTCTCAGAGGGCCACATGGCCGGTGTGGGCCGGACATTCCCTTTCCAATGGTTGTGCCCACTTCCCTCCAGAGTTGGTGCCAAGCTGGGACCTGGGG |
| | | GACTTGGAGTCTCAGGAAGTCGTCCGCTGTCTGCAGGGGGTGCATGGGGGATGTGGCCACACACGTCAGAGTGCGGCCCCCTGTGGAAGCCACAGACAGACAC |
| | | GACTCCCCTAAATGAGCTCGCCCTTCTGGCCGAGATGCTCAGCGTCCCCAGCAGGCTGCCCGACTGCCCTGCGATACTGCCCTCCTTCCTGCTGCTCCCACTT |
| | | TCCCTTTCGGGGGGTTGGATTTGGGGCATTCAGGGATCGCCCTGTTGTTTGCTCATCACACCCATTTCCTGCAAGAGCCACGGTGACCGAGCAGCCTTGAGTT |
| | | GAGGCAGCTTGTGGGTAGACGCGGCGGGCATCTCGGAGGGGCACGCTCCCTGCCACCCTCAGCCTCCACTCACTGGTCAGGGGCTTTGCGCCCCAGGGCACCC |
| | | CAGGAACCGAGCCTCCTTTGGGGTCATGGGTGCCTCTCCTGGGAGGGCGTGGATTTTCCAAAGCAGTTTAGAGAAATGAGACCCACAGGCGTTATTTCCCATG |
| | | GTGAGGTTCTTTTCAGTAACCCCCACCGTATAGCCAGGATCAGCAAAGAGAGGCGGCTCCTCCCGGTGAGACAGGGACCAGCACCTCCCGGACAGGCTTGGGT |
| | | CTCCCTCCAGTTCCCCCACCTAGTCTCGAGGTCTCACGCTGCCCTCTCCTGTCCAGGGGCTCCCACCTGAAGGAGAATAAGTACCTGATTGTGGTGACCGACG |
| | | GGCACCCCCTGGAGGGCTACAAGGAACCCTGTGGGGGGCTGGAGGATGCTGTGAACGAGGCCAAGCACCTGGGCGTCAAAGTCTTCTCGGTGGCCATCACACC |
| | | CGACCACCTGGTAGGCACCGGCCCCCCCCGGCAGATGCCCCCAACCACAGGGAGTGGCGGCTGCAAGGCCCCCGGCAGCTGGGACCGTCTTTTGGTCCTCGGG |
| | | AGGGTGTGGGTTCTCCAGCCGGCCACCCTTGCCCCTGAGAGGCCAGCCCCTCCTGCTGAGGAGCCTGGAGCGCCCCAGCCCAGCCTCCCCTCTGGCCCTGTGG |
| | | GAAGCGGCCCCGGCCGTCAGGGGTCCCAGCCCTGCTCAGCCCACCCTGAACACTGCCCCCAGGAGCCGCGTCTGAGCATCATCGCCACGGACCACACGTACCG |
| | | GCGCAACTTCACGGCGGCTGACTGGGGCCAGAGCCGCGACGCAGAGGAGGCCATCAGCCAGACCATCGACACCATCGTGGACATGATCGTGAGGCCCCTGCCC |
| | | AGGAGACGGGGAGGCCCGCGGCGGCCGCAGGTGGAAAGTAATTCTGCGTTTCCATTTCTCTTTCCAGAAAAATAACGTGGAGCAAGTGGTAAGAGCCCTCCCC |
| | | ACCACCCCCAGCCGTGAGTCTGCACACGTCCACCCACACGTCCACCTGTGTGTTCAGGACGCATGTCCCTATGCATATCCGCCCATGTGCCCGGGACACATGT |
| | | CCCCTGCGTGTCTGCCCGTGTGCCCGGGATGTGTGTCCCCCTGCGTGTCCACCTGTGTGTCTGCCCATGTGCCTGGGACATGTGTCCGCCTGTGCGTCCATCC |
| | | GTGTGTCCGTCTGCCCATGTGCCTGGGTCGCATGTCACCCTGTGTCCCAGCCGTATGTCCGTGGCTTTCCCACTGACTCGTCTCCATGCTTTCCCCCCACAGT |
| | | GCTGCTCCTTCGAATGCCAGGTGAGTGTGCCCCCCGACCCCTGACCCCGCGCCCTGCACCCTGGGAACCTGAGTCTGGGGTCCTGGCTGACCGTCCCCTCTGC |
| | | CTTGCAGCCTGCAAGAGGACCTCCGGGGCTCCGGGGCGACCCCGGCTTTGAGGTGAGTGGTGACTCCTGCTCCTCCCATGTGTTGTGGGGCCTGGGAGTGGGG |
| | | GTGGCAGGACCAAAGCCTCCTGGGCACCCAAGTCCACCATGAGGATCCAGAGGGGACGGCGGGGGTCCAGATGGAGGGGACGGCGGGGGTCCAGATGGAGGGG |
| | | ACGGCGGGAGTCCAGATGGAGGGGATGGCGGGGTCCAGATGGAGGGGACGGCGGGGTCCAGATGGAGGGGACGGCGGGGTCCAGATGGAGGGGATGGCGGGGT |
| | | CCAGATGGAGGGGACGGCGGGGTCCAGATGGAGGGGACGGCGGGGTCCAGATGGAGGGGACGTCGGGGCTCCAGATGGAGGGGACGGCGGGAGTCCAGATGGA |
| | | GGGGACGGCGGGGTCCAGATGGAGGGGACGGCGGGGTCCAGATGGAGGGGACGGCGGGGTCCAGATGGAGGGGACGTCGGGGCTCCAGATGGAGGGGACGGCG |
| | | GGAGTCCAGATGGAGGGGACGGCGTGGTCCAGATGGAGGGGACGGCGGGGTCCAGATGGAGGGGACGTCGGGGCTCCAGATGGAGGGGACGGCGGGGGTCCAG |
| | | ATGGAGGGGACGGCGGGGTCCAGATGGAGGGGACGGCGGGGTCCAGATGGAGGGGACGGCGGGGTCCAGATGGAGGGGACGGCGGGGTCCAGATGGAGGGGAC |
| | | GGCGGGGTCCAGATGGAGGGGACGGCGGGAGTCCAGATGGAGGGGACGGCGTGGTCCAGATGGAGGGGACGGCGGGGTCCAGATGGAGGGGACGTCGGGGCTC |
| | | CAGATGGAGGGGACGGCGGGGTCCAGATGGAGGGGATGTCGGGGTCCAGATGGAAGGGACGGCGGGGTCCAGCAGGCAGGCTCCGGCCGTGCAGGGTGTGGAC |
| | | TGTCCCGGGGGCGCTGGGGGCTTCTGAGGGTGTCTCTGTCCGCCCTGCCCTCAGCCGCACTCTGTTCAGAAGGACCTTTCTGGAGGTAGGAGGGTGAGAATGT |
| | | GGGTCCCCTGCTTCTGTGTGGCTCAC |
| 252 | COL6A1 | GGCCGGGGAGGCGGGGAGGCTGCCCCAAGAGTAAAAGCCTTTCTGACGTGCGCAGGACGCGGCCCTGACTGGTCTAACTGACTCTTTCTCTTCTCCTCAGCTT |
| | | GCTGTGGTGAGACCCAGGCTCTAGCTCCTGAGAGAATGGATCCCGGGGGTCGGGGAGCGAGGCCTGGGTCCCACACATGTCACAGGACAGCACATGGCACTCT |
| | | GGTCCCCGCCCGCAGCTCCCTGCACCTGCCCGCCCCCTCTGGGGCCTGCTCCAAGCCAGCAGGGTTCCCGGGTGTTGGGCTGGGCCCCGCCCTCTTTCACCCA |
| | | TAACTGAAATAACCAGGAGCAGGCTTGGGGGGGTCCCTGCTCCATCATTCTGGCCCACAGGCCCCACCCTAGCCTGGCTGAGCAACGCCAGCCCTGACCAGCC |
| | | GCCGGACAGAGCAGCCTTTACGGGGCCATGGGAGGGGGTGGGCTTTTCTGGGGCTGAGACGGGGGACCCCAACGTGTCAGGTGAGGATGTGGCAGCCAAGGA |
| | | GGGGCCAGGGCGGTGGAGGGGAGGGGCCAGGGCACTGGAGGGGAGGGGCGTGCTCTGCTGACACCGCCCCCGCCTGCAGAATGCAAGTGCGGCCCCATCGACC |
| | | TCCTGTTCGTGCTGGACAGCTCAGAGAGCATTGGCCTGCAGAACTTCGAGATTGCCAAGGACTTCGTCGTCAAGGTCATCGACCGGCTGAGCCGGGACGAGCT |
| | | GGTCAAGGTGAGGCCTCGCCCCGCCCGGCTTTCTCAAGCCCAGGTGCACCCCGACCCTGCCGGCCGCCCCTGCCCGCGCCAGACCTCAGCCTCCCGAGGCCAC |
| | | CGCTGCATCCCTGTGACTTCCCTACTCATGACAAGGATGCCAGGCACGCGCCAGCCCGTCCAGGCCTCCAGCTCCACCTGGCGAGGCTGGCCCATTGTACACA |
| | | GGCGCCCCAGATGAGGGAGGGTCTCCCCCTCTCCTTGAAGGGCGGTAGTCTGGGGTCCTGAGTGCTGGGTGTGGGCTTGTCCCTCGTGGACAGAACCCAGGAG |
| | | GGCTTCATCCACCAAGGAAGATTGCTTTGCAGGGTACCCAGGTCCCGGGGGCTGTGCCACCCTCTGGGCACCCGGAGCCAATCGCAGGGTACCCAGGTCCCGG |
| | | GGGCTGTGCCACCCTCTGTGCACCCAGAGCCAATCGCAGGGGACCCAGGTCCTGAGGTCCTGGGGGCCATGCCACCCTCTGGGCACCCGCAGCCAATAGAGTC |
| | | ACCCTTGGGAAGCTTATGCGGACCTGGGGCAGCACTCGCGTCCTGACCCCGGTGCCGGTCCCACAGTTCGAGCCAGGGCAGTCGTACGCGGGTGTGGTGCAGT |

TABLE 4C-continued

| SEQ ID NO | GENE NAME | SEQUENCE |
|---|---|---|
| | | ACAGCCACAGCCAGATGCAGGAGCACGTGAGCCTGCGCAGCCCCAGCATCCGGAACGTGCAGGAGCTCAAGGAGTGAGTGCCCCACGCGGCCAGGACCCTCCC |
| | | ACCCCTCGCCCCGACCGCTGTTCCCACGGCAGGTCGGCCCTGACCCCTGATCCCAGGTGGGCTCGGCCCCGCGGCAGGCCTGGCCCCAACCGGCCCTTCCTGC |
| | | CCTTTGCTATGCAGAGCCATCAAGAGCCTGCAGTGGATGGCGGGCGGCACCTTCACGGGGGAGGCCCTGCAGTACACGCGGGACCAGCTGCTGCCGCCCAGCC |
| | | CGAACAACCGCATCGCCCTGGTCATCACTGACGGGCGCTCAGACACTCAGAGGGACACCACACCGCTCAACGTGCTCTGCAGCCCCGGCATCCAGGTGGGGTG |
| | | GCCACCCCCAGGCTGCACCTGCCCCGCCTAGGGCGCCCCGCCAGCCAGGGTGGCCTTGTCCCCAGAAAGACGAGGGCAGAGCAGGCTGCGCCACACCGATACT |
| | | GTCTGTCCCCACAGGTGGTCTCCGTGGGCATCAAAGACGTGTTTGACTTCATCCCAGGCTCAGACCAGCTCAATGTCATTTCTTGCCAAGGCCTGGCACCATC |
| | | CCAGGGCCGGCCCGGCCTCTCGCTGGTCAAGGAGAACTATGCAGAGCTGCTGGAGGATGCCTTCCTGAAGAATGTCACCGCCCAGATCTGCATAGGTGCGCAT |
| | | GGGGCCACCCGGGCAGTCCCAGATCTGCGTAGGTGCGCGCGGGGCCGCCCGGGCAGTCCCAGATCTGCGTAGGTGCACGCGGGGCCGCCCGGGCAGTCCCAGA |
| | | TCTGCGTAGGTGCACGCGGGGCCGCCCAGGGCCGTCCCAGATCTGTGTAGGTGCGCGCAGGCGCCCAGGGCTGTCCCAGAGGCCTCCTCCCAGCTCACTGTTA |
| | | CCTCCAGGGGCACGGCCACCCTGTAGGTGCGCACGGGGCCGCCTGGGGCTGTCCCACAGGCATCCTCCTCCCGGCTCGCTGTGACTTCCGGGGGCACGGCCAC |
| | | CCCTGTGCTCGGCCGGGAGGTCCTGTGACATCTCCTTGCGGGGTTATAGGTGGAGCAGTGGGCTCACACTGCACGGCTTTTCTCTTTTACAGACAAGAAGTGT |
| | | CCAGATTACACCTGCCCCAGTGAGTACCTCGGCGGCCGGGACACGTGGGGAGGAGGGCACCGTGGTTGGGGCGAGGGCTCTGAGAGGACGGGGCTCTGGGAGG |
| | | AGGGCCTGGCGGTCACGAGAGTAGGTGCATGGCTCACTCCGGTGGCTGAGCACCACCGTGCCGTGCCCTCTCTGGGGAGCTTAGACGCTCTCTGGCCGGCCCA |
| | | CTGCGGCTGCATCACCAGGGCCTCATGCTAACGGCTGCCCACCCCGCCCCGCAGTCACGTTCTCCTCCCCGGCTGACATCACCATCCTGCTGGACGGCTCCGC |
| | | CAGCGTGGGCAGCCACAACTTTGACACCACCAAGCGCTTCGCCAAGCGCCTGGCCGAGCGCTTCCTCACAGCGGGCAGGACGGACCCCGCCCACGACGTGCGG |
| | | GTGGCGGTGGTGCAGTACAGCGGCACGGGCCAGCAGCGCCCAGAGCGGGCGTCGCTGCAGTTCCTGCAGAACTACACGGCCCTGGCCAGTGCCGTCGATGCCA |
| | | TGGACTTTATCAACGACGCCACCGACGTCAACGATGCCCTGGGCTATGTGACCCGCTTCTACCGCGAGGCCTCGTCCGGCGCTGCCAAGAAGAGGCTGCTGCT |
| | | CTTCTCAGATGGCAACTCGCAGGGCGCCACGCCCGCTGCCATCGAGAAGGCCGTGCAGGAAGCCCAGCGGGCAGGCATCGAGATCTTCGTGGTGGTCGTGGGC |
| | | CGCCAGGTGAATGAGCCCCACATCCGCGTCCTGGTCACCGGCAAGACGGCCGAGTACGACGTGGCCTACGGCGAGAGCCACCTGTTCCGTGTCCCCAGCTACC |
| | | AGGCCCTGCTCCGCGGTGTCTTCCACCAGACAGTCTCCAGGAAGGTGGCGCTGGGCTAGCCCACCCTGCACGCCGGCACCAAACCCTGTCCTCCCACCCCTCC |
| | | CCACTCATCACTAAACAGAGTAAAATGTGATGCGAATTTTCCCGACCAACCTGATTCGCTAGATTTTTTTAAGGAAAAGCTTGGAAAGCCAGGACACAACGC |
| | | TGCTGCCTGCTTTGTGCAGGGTCCTCCGGGGCTCAGCCCTGAGTTGGCATCACCTGCGCAGGGCCCTCTGGGGCTCAGCCCTGAGCTAGTGTCACCTGCACAG |
| | | GGCCCTCTGAGGCTCAGCCCTGAGCTGGCGTCACCTGTGCAGGGCCCTCTGGGGCTCAGCCCTGAGCTGGCCTCACCTGGGTTCCCCACCCCGGGCTCTCCTG |
| | | CCCTGCCCTCCTGCCCGCCCTCCCTCCTGCCTGCGCAGCTCCTTCCCTAGGCACCTCTGTGCTGCATCCCACCAGCCTGAGCAAGACGCCCTCTCGGGGCCTG |
| | | TGCCGCACTAGCCTCCCTCTCCTCTGTCCCCATAGCTGGTTTTTCCCACCAATCCTCACCTAACAGTTACTTTACAATTAAACTCAAAGCAAGCTCTTCTCCT |
| | | CAGCTTGGGGCAGCCATTGGCCTCTGTCTCGTTTTGGGAAACCAAGGTCAGGAGGCCGTTGCAGACATAAATCTCGGCGACTCGGCCCCGTCTCCTGAGGGTC |
| | | CTGCTGGTGACCGGCCTGGACCTTGGCCCTACAGCCCTGGAGGCCGCTGCTGACCAGCACTGACCCCGACCTCAGAGAGTACTCGCAGGGGCGCTGGCTGCAC |
| | | TCAAGACCCTCGAGATTAACGGTGCTAACCCCGTCTGCTCCTCCCTCCCGCAGAGACTGGGGCCTGGACTGGACATGAGAGCCCCTTGGTGCCACAGAGGGCT |
| | | GTGTCTTACTAGAAACAACGCAAACCTCTCCTTCCTCAGAATAGTGATGTGTTCGACGTTTTATCAAAGGCCCCCTTTCTATGTTCATGTTAGTTTTGCTCCT |
| | | TCTGTGTTTTTTTCTGAACCATATCCATGTTGCTGACTTTTCCAAATAAAGGTTTTCACTCCTCTCCCTGTGGTTATCTTCCCCACAAAGTAAAATCCTGCCG |
| | | TGTGCCCCAAAGGAGCAGTCACAGGAGGTTGGGGGGCGTGTGCGTGCGTGCTCACTCCCAACCCCCATCACCACCAGTCCCAGGCCAGAACCAGGGCTGCCCT |
| | | TGGCTACAGCTGTCCATCCATGCCCCTTATCTGCGTCTGCGTCGGTGACATGGAGACCATGCTGCACCTGTGGACAGAGAGGAGCTGAGAAGGCAACACCCTG |
| | | GGCTTTGGGGTCGGGAGCAGATCAGGCCTCAGTGGGCTGGGGCCGGCCACATCCACCGAGGTCAACCACAGAGGCCGGCCACAGGTTCTAGGCTTGGTACTGA |
| | | AATACCCCTGGGAGCTCGGAAGGGGAGTTGAGATACTGCAGGGCCCATAGGAAGAAGTCTTGGGAGGCTCCACCTTTGGGGCAGAGGAAGAAGTCTTGGGAGG |
| | | CTCCACCTTTGGGGCAGAGCAAGAAGAGGGCGGAGGGCAGAGGCAGCGAGGGCTCATCCTCAAAAGAAAGAAGTTAGTGGCCCCTGAATCCCAGAATCCGGGG |
| | | TGCACGGCTGTTCTGGGGGCCGCTAGGGGACTAAGAGGATCGGCCGAGGGCTGGGCTGGAGGAGGGCAGCAGGGATGGGCGGCGAGGGTGAGGGTGGGGCTTC |
| | | CTGAAGGCCTTCACCTGCGGGGACCCCGGCGAGCCCCTCAGGTGCCACAGGCAGGGACACGCCTCGCTCGATGCGTCACACCATGTGGCCACCAGAGCTGCGG |
| | | GAAAATGCTGGGGACCCTGCATTTCCGTTTCAGGTGGCGAACAAGCGCCCCTCACAGAACTGCAGGTAGAGACGGGCCCGGGGCAGACGCAGTGAGGCGGTGG |
| | | GCGGGGCCCGGGGCAGATGCAGTGAGGCGGTGGGCGGGGCCCGGGGCAGAGGCAGCGAGCGGTGGGCGGGGCCCGGGGCAGACGCAGTGAGGCGGTGGGCGGG |
| | | GCCCGGGGCAGAGGCAGCGGGTGGTGGCCGGGGCCCGGGGCAGACGCAGTGAGGCGGTGGGCGGGGCCCGGGGTAGTCGCAGTAGGTGGTGGGCGGGGCCCGG |
| | | GGCAGACGCAGTGAGGTGGTGGGCGGGGCCCGGGGCAGACGCAGTGAGGCGGTGGGAGGGGCCCGGGGCAGACGCAGTGAGGCGGTGGGCGGGGCCCGGGTCA |
| | | GAGGCAACGGGTGGTGGGCGGGGCCCGGGGCAGACGCAGTGAGGCGGTGGGCGGGGCCCGGGGCAGATGCAGTGAGGCGGTGGGCGGGGCCCGGGGCAGATGC |
| | | AGTGAGGCGGTGGGAGGGGCCCGGGGCAGACGCAGTGAGGCGGTGGGCGGGGCCCGGGGCAGACGCAGTGAGGCGGTGGGCGGGGCCCGGGGCAGACGCAGTG |
| | | AGGCAGTTGCCAGCCTCTCTCAGCTGCCTCATGGGATTCGCACTGCAGCTGCGGCCCTGGCGCGACAAGGGCTGGACTTGGCCAGCGGGACGGTCCCTCACGG |
| | | CGCTGAGGCCCACACTCTGCGTGGAGCCTCCCCGTGCCCAGGCTACCCTGCAAGGTCCTCGGAGAGGCTTCCTCCAGCCCCAGCCCCCACACAGCTCCGGCCC |
| | | AGGCCCGCTCTTCCCCATCCCAGTTGCTTTGCGCTGTATACGGCCAGGTGACCCCGAGCCGGCCCTGAGCCCTCGTCCCGGCTTCCTCCCCTGTAAGCTGGGT |
| | | GAAGGACTCCATGGCACCCACCTGAGAGGGTTGTGGCGAGGCCCAGGCCCCTCGTGCCCACACGGCCGGCGGCCCATGCCTGGCAGGGGCTGGGAGGAGGCTG |
| | | GGGCGACCAGAGGGGAGCGGCCTGTCCTGGAGGAGGCCCAGGGACCCTGGTGAGAGGGTCTCTCCCAAGTGCTCTCTATGGGACCCCCTTCCTCTGCGCCCGT |
| | | CCTTCACGGACCTCTCCGGGTCACCCCTGGGCTGCACACTGGGTTCAGGGGGGCCTTGAGGTGGGGCCCCTGTTCCCAAGTCCCGGCGGGGTTTCTCCTGAAC |
| | | CTCAACCCATCCTCACCTGCGGGCATTCCCATCCCCCAACGCCTGGGTCACCAGGATTCCAGGCAGGAGGGGCGGTGGGGGTTACCAAGGCCCGGGTTGCCAT |

TABLE 4C-continued

| SEQ ID NO | GENE NAME | SEQUENCE |
| --- | --- | --- |
| | | GCAGAACCCCCAGCCACCACGCAGACCCCCACGGGGCCCAGGGAAGCTCCTGGTCTCACACTGCACCTCACACTTCCTGTGGGGGCAGACTCCAAGGTCCCGG<br>CCTCTCATCTTGTAGAAACTGAGGCACAGGAGGGACACACACTCCCACGGCCGGTCACCGTGGCCCCCACACCTCCCACTGGACTGACACCTGGCCAGGCTCC<br>GGACACCCGTGGCACAGCCTCAGCCCCTGCGGCCCCTGCTCCGTGGCCCCCAGGCCCCAGCTCCCATGTGCACGTCCTGCCTCAGGCCTGGAGGCCCCTCGGC<br>CCCAAATAATCAGACAATTCAACAGCAAAACTACTTTTTTCAGGCTGGCAGGACTCTGGGCAACCCCCTGCAACAGCCCCCTGCCCTATCACAGCCACCCTTG<br>CCTCCCAGGCACGGAGACCCCACCATCAGGTCCCAGCCTTGGTTCATCCCCAAGCACCCTGTGTGTTGGGATGGCGATGCTGGCTGAGCCCCTGCATCC |
| 253 | chr21: 46280500-46283000 | AGGGCGTTTGGGAACACCCCTCCCGGAGGGGTGAGGCGGCCCAGCCTGCGGCTGCCAGAGGACACAGGTTCTGCTGCGGAACCTGCAGACATGGCCATAACAG<br>GCCACAGTGCTCGGGCCCACACAGCCTGGACCCACATGGCCCTGTGTCACCTCCTCAGGGGCAGGCTTCAGGGCCTCGACCCTAGAGGCTGCCCCTCGGTTCT<br>GCTCCATGGACGGCGCAGGCAGGCCCAGGCCTGTGACGAGTTCACGGAAGCTCCAGGATGACCCCCGCTCTGCGCCCTCCTCCAGCATTCCAGACCACAAACC<br>ACTCTGGGCTAAAACGAGGCATCGCCAGAGCATCCCACTTCCTCGGAAAGCTGCGGTCTGGGGACGCGTCTTGGCCCTGAAGAGGCTCCAGATGGCTCCCATC<br>AGGCCTCTCCGCCTACGTGCGGCCGACATGGAGTGACAGAGCGTCGGGGACACAGAATTCAGAGCTGGGCCTGGGGCTGCTTTGAGATACTGATGGCTGCCAG<br>GGGGCACAGAGACCCGTCCTGCAGACAGGGCTGTGAGGGCCACAGGGGGCCTCGGGGAGAGGCAGTGGGAGGGAGGACAGTGGGGGCCTCCAGCTGGGTGAGC<br>AGCTGGAGCGAGGGGGGCCCGGGGCTTGTGATGGTGCTGCCGACCCTAGAGGTGCCGGCCCCACGATGGAGAGCACGTAGTGCCCCCCGGGAGTCAGGAGGCC<br>GGGCCTGACCTCGGGGGCTGCAGCCAGGGGAGGCCGGCACCCCAGATAACCCCCAAAGAACTGCAGGCCCTGAGGCGAGGCCAGAGTGGGGGCGGGGGCAGGT<br>CCCAGCCGAGGAGGTGCTCCGTGCTGCCTCAGCAGAACCCATGATGGGCTGGCCCAAGGCTCTGAAGGTGGAAAGGCCTCACACATTCTGCCCCGGCTGACGC<br>CTTCCTTGGGCCAGTGCTCGGGGGTGTGTAACAAACGCCAAGACGCATTGTAAAGAAGGAAGCCTGCGTTTCCATCACCGGCTTAATATCAAACAAAAGTGCA<br>ATTTTGAAAATGTAGTCCAAGGTTTTCTGTGGTGCGGAAATGGCCAGGCCAGACCTCCGTGGGTGGTCCTTCGTGTCCACGTCAGCGCCCTACATCCACACTG<br>TGGGCACCATGACCTCACATGCGGAGCGGAGCAGGGCCGGCGCCCGGAGAGCCAGGCTGGTCACGAACGAGGCCTAGAGGGCGTCAGGCCCCAAAGCACTCAC<br>AGGCTTCTCCTCTGTCCTCGGGGCCTTCAGACACCTGCATGCGCCGATTCAGCCACCCGCGCGCGCCGATTCCCCTGGCCATGGGGTTTCCAAAGTGTGTGCT<br>CAGAGGACAGTTTCCTCCAGGATGACCTGTCAGTGGCTCTCTGTGCCGGGGACGTCGCGTGCTGGGTCCCGGTCTGAATGCTTCCTAACGATTTACCCAGTTC<br>CTTTTCTCCACTCAGGAGGCGTTTGCTGAGAGGCACAGGCTGAGCCCCCGTGCTGATGCCACGACCGAGGGAACGGGTCTCCCTGTCGGCGTGAACTGACCCG<br>GCCAGGCGTCCACTGCCACTCGGACTGTCTCCCAGGCACGTGGCGCCCACACGGGCAGAACACGCCCTCCACACACGCGGCTTCGGGCAGAACACGAGGCGCC<br>CTCCACACACGCGGCTTCGGGGCTTGTCATGAAAAAAGCTGAATGCTGGGGGTGCAGCTTTCACCAACAGAATCCCGTTTGGAAGGGACGCGGTGAGACATGA<br>TCCACCCTAAGTTGTGATCCTGGGTGAGCCGCCGTCCACACCCTGCTGAGGGTCCCTTCACCCACTTTATTCTCCAGAAAACCCTGCCCATCAGGGCTGAGTC<br>CCACGCCTTCCCTCTCCGTCCAGGCCTGGCTTTGACCTCTGGGGTCGTGTGGGGCACAGGGGACACCCTATCCAGGCAGAGGCCCTACGGCTATCTGGAGGAA<br>GTGGTGGGAGCTGGGCTTCTGCCTGGAGGATGCACCCAGAGGGGTCACAGTCCACACAGAGACACACGGGTGCCTTCCAGATGGCTGAGCCAGTCCAGCCCAG<br>AAGGGCCTGGGGGTTGGGGGCTGCACCTGGCCTGTCCCCACCAGCAGGGCTCAGGGCTTCCCAAGGTGTGTGGGGGACGGGGCAGCACCTCTCAACCAGGTCA<br>CCTGAAACCCGAACTGAAAGGCATCCTAAGTTAAGACATTAACTCCCATTGTCAAGGTGCCATCGTCAATTCTGTCTCCAAATCCTTCTTTGTTATTTCATGT<br>ATTCACAGAGTGACGCTCCGTGTTTCGTTCAGCCTGCAGGCCTGCAGAAGCTGCATCTCGGGATGGCCAAGAGCCCGGCCAGGCCCCACGGCTGCACCCAGGA<br>CGGGATTCATGCCCCATGCCTGGCTTCTCACGACCACAGAGTGCCTTTCCCGGGACTGGATGGAGGCAGAGTGAGAGAAGAGCCTGGAGCAAGTGTTTTGGAC<br>CACAGTGATCAAACACGGAGCCCGTGGG |
| 254 | COL6A2 | AAGAAAGGCCAGACCGGGCACGGTGGCTCACGCCTGTAATCCCAACACTTGGGGAGGCCGAGGCGGGCAGATCACCTGAGGTCAGGAGTTCGAGACCAGCCTG<br>GCCAACAGGGTGAAACCCCGTCTCTACTAAAAATACAAAAAAAAATTAGCCGGGCGTGGTGGCAGGCACCTGTAATCCCAGCTAATCGGGAGGCTGAGGCAGG<br>AGAAAATCACTTGAACCTGGGAGGCGGAGGCTGCAGTGAGCTGAGATCGCGCCACTGCACTCCAGCCTGGGTGAGGGAGCGAGACTGTCTCAAAAAAAAAAAA<br>AAAAAAAAAAAAAAAAGGAAAGAAAGGCCCGGTGAGATGCTTTCTCTTAAACACGGCCCTGCACGTTGAGTTGCTGCCTCCTGTGGCCTATTTCACGTTTATGC<br>AAAGTCGGGCGCCTGATGCGGGGCTCACCCGCCACAAGCAGGGGTCCTGGTGCTGCTCATGGAAGGGGCCCTACCCAGCCCGCGGGGCACTGGCTGGGACGGG<br>GCTGCCCAGGTCCGCCCAGGATCCAAACACCCAGCCCCGCCCAGCGGCCCTTCCTGGCCTGCAGTGGAGGCTGTAATGGGCAGGGGTGGTGGGAATCCCAGCT<br>CACAGGGCGCCTGCTCTTAGAAGGGCGGCATCTGGGTCCAGAGGTCAGAAACGTCAGATGCCCATCCCAGAAGTGGCGGGGA |
| 255 | COL6A2 | GGGTGAATGAGTAGATGTATGGGTGAGTAGGTGGGTAGGTGGGTAGATGGATGGGTGGGTGGGCGAGTGTGTGGTTAGATGATGGATGGCTGAATGGATGAGT<br>GGGGGGATGGATGGGTGAGTGGGTGTATGTATGGATGGGTTAGTGGGTGGGTGGATGAATGGATGGGTGCATAAAGGATGGATGGATGAATGAGTTAGTGGGT<br>TGGCAGATGGATGGATGGGTGAGTCAGTGGATAGATGGATGGGTGGGTGGATAGAGGATGGATGGTTGGGTAGGTGATGGGTGGATGAGTGGATAGATGGGTA<br>TGTGAGTGAGTGGGGGGATGGGTAGGTGGGTGGATGGATGGTTAGGTGAATGAGTGGATGGACAGACGGACAGTGGGTGGATGGATGAGTGAACGGATGGACC<br>GATGGATGAATGGGTGGGTGGGTAGAGGATGGACGGACAGGTGAGTGGGTGGGTGGATGGATAGATGGGTAAGTGAGTGGATAGATAGATGGGTGGGTGGACA<br>GAGGATGGGTGGATGAATGGATGGGTTAGTGGGTGGCTGGGTGGATGGATGATGGATGGGTGACTGGGTGGATGGATGGATGGGTTAGTGGGTGGCTGGGTGG<br>ATAGATGGATGGGTGATTGGGCGAATGGGCGAATGGGTGGATGGGTGGGCGTGGAGTTGGTGGGTACATGATAATGGGGTGGAATACCCATGGATTGGAATGA<br>GCTGTTTTGGCTGCTATTTCTGGGACACCCAGCTCTGCCAGGCCCCTACCCCTCTGGTGGGCCAGGCTCTGACGGTGGCCACTCATGGCCTTTCTAGCTCTGG<br>TGCCAGCATAGGGAAGGAGGAGGCACAGCCTTGTCTTACTCCTTGCACCTGTTAGCCCCCCCCCCCGCCAAGGGAGGACCCGTGGTTGGGGACAGCACAGGGG<br>GCCCTGCTGTGTGCAGGGACTGTCCCTGGGGCCACTGAAGCCCACCTGTTCTTGTTCCTTCTCAGGCGGATCCTGGTCCCCCTGGTGAGCCAGGCCCTCGGGG |

TABLE 4C-continued

| SEQ ID NO | GENE NAME | SEQUENCE |
|---|---|---|
| | | GCCAAGAGGAGTCCCAGGACCCGAGGTAGGTTGGTGGCCAGTCCCCATGCCCTCCCCCCAACCTGCCAGGCCAACACACACCCAAGCCTCGTGGTTCTGCCCA<br>CGGTGGACCCACGTATCAGTGGGCAGTGGCCTGGGAGAGACTCAGCCACCCAGCCTTGGCCCCAGAGTCTCAGCCTCATCCTTCCTTCCCCAGGGTGAGCCCG<br>GCCCCCCTGGAGACCCCGGTCTCACGGTAGGTGTCACATGGGGCAGAACCAGTGTCCTTCTCCTGCCAAAACTAGACACCAAGAGCAGCAGGGGTGGGGGAAG<br>GTCAGCTGGCACGGTCAGAGAGCAAGATCAGTGGAGGAGGTCAGAGGGCAAGGTCAGAGAGCAAGCTTGGTTGGGGAAGGTCACAGGGCAAGGTTGGTGGGGG<br>GAGGAGGGTGGCAGCGAGGTTGGTAGGGACAGGACCCGCCAGCCTCCCCGCATGGCTGCCTCCACACGTGGGCTGGAATGTCCCGGGACCCCCAGGCCAGGAC<br>CTTGCTGTGGAAACTCTTCTGGGGCCCCGGGGGGACTACCCTGCCTGCCGTGTGCATTGCAGGAGTGTGACGTCATGACCTACGTGAGGGAGACCTGCGGGTG<br>CTGCGGTGAGGCACTGCCCACGGCAGGGTCGGGGCCCATGCACCGGGTGGAGGGCGGGAGTGCAGCAGGGCTGGGTCATCGCTGGGTCCTGCATGTGCACGTG<br>ACCCTAGGGTCTGAGGTCTCCCCGGTACCCCCCGATGACCCTGCCACCCCCCCAGACTGTGAGAAGCGCTGTGGCGCCCTGGACGTGGTCTTCGTCATCGACA<br>GCTCCGAGAGCATTGGGTACACCAACTTCACACTGGAGAAGAACTTCGTCATCAACGTGGTCAACAGGCTGGGTGCCATCGCTAAGGACCCCAAGTCCGAGAC<br>AGGTCAGCGGGGCAGGGGCGGGTGCAGCATTGCGGGGGGCCGGGCGGGGCGTGGGAGGCGATGAGATGGGAGAAGTCCAGACGCGTCCCTCCAACGAGGGCCT<br>CTGCATGGCTGGGGATGCCCCAGACCCCGAGGCCTCTGGCAACGACCTCACGCGTGCGGCTTGCAGGGACGCGTGTGGGCGTGGTGCAGTACAGCCACGAGGG<br>CACCTTTGAGGCCATCCAGCTGGACGACGAACGTATCGACTCCCTGTCGAGCTTCAAGGAGGCTGTCAAGAACCTCGAGTGGATTGCGGGCGGCACCTGGACA<br>CCCTCAGCCCTCAAGTTTGCCTACGACCGCCTCATCAAGGAGAGCCGGCGCCAGAAGACACGTGTGTTTGCGGTGGTCATCACGGACGGGCGCCACGACCCTC<br>GGGACGATGACCTCAACTTGCGGGCGCTGTGCGACCGCGACGTCACAGTGACGGCCATCGGCATCGGGGACATGTTCCACGAGAAGCACGAGAGTGAAAACCT<br>CTACTCCATCGCCTGCGACAAGCCACAGCAGGTGCGCAACATGACGCTGTTCTCCGACCTGGTCGCTGAGAAGTTCATCGATGACATGGAGGACGTCCTCTGC<br>CCGGGTGAGCGTGTGGGCGCGGGGCAGTCGGCCGAGGAGCAGCAGGCCCCAGCCGCTGTCTAGCGTGAGCCCCAGGGACACCCCTCACCTGAGGGATGAATGT<br>GCAGCCCAGGATCTTGGGCTGTGGGTGGGAAGGGGTCGGGCCCTCTCGGGGCTGCAGGGCAGAGGCCAGCTGCACCCTGAGCCTGTCTAGGCAGATCAGTGAA<br>CGGCCGCTGAGGGTTCGCTAGGGACTGACCCTGGCCTGGCCCGGCCTCTCTCCTCTCTTCCAGACCCTCAGATCGTGTGCCCAGACCTTCCCTGCCAAACAGG<br>TAATGCAGGGCACCCTGAGCCACCACCCCAGACTAGCAAAGCAGCCCTGGTGTCCTTCCTCCTCGAGGGCCGGGCTGGGGGAGGGGCCGTGCAGGGACCCGGG<br>GGGCGGCGGAGCCACTGCGGAGGCTGCTCCTTAGGGAGATGGCCCCAGGATGGCAGCACAGGGGAGGAGGGGCTTGGGGAAGGCAGGCTCCCAGGAACGCAGG<br>AACAGCATCACGAGGCCATGAGGTGGGTGCTGCTAGCCTGGCGCTGTGCTCGGCATGTGGCCACTGGTCTTGAAGGCCCACCATGGGCCTTGCAGTCTCCCTC<br>AGCTGCCGCCCAGCTCCCATGGGCTGGCCGTGCATGTGCCACTCGGAGGAAGCCCTGGATTCAGTGAGTGAAACCATCCCGGGGTGGAAGCACTGACACCCCC<br>CAGCACCAGCAGGTCTTGCTCCAACCCTGGCCTGCCTCGGAGCTGCAGCTGCGGCTCTCACATCTCTGGGAGTGGGGGAGCCCATGTCCCGGATGTGGCCCAC<br>GTGGGTGTGAAGCTGGAGCTGGGGGTGCCGTCCAGGCTCTGCTGGACGTGGTGCTGCCCCCATGGTGCACTGCTGCACCGTACCTGGGCCCACAGGAGGTCCC<br>CGGGGGCGTTAGGAGCTGAGTCCCCCTCAGTGAGCCGTCCCCTCCAGGAGTGTGAGGGTAGGGATGCCATGGAGACAGGGTGGGAGGGTCCGACCTGGAGGAC<br>CACAGGGAGGAAACCTCAGGGTCTGCGGTACGAAGTCAGCGCTTCCTCAGCACGCGGGTCGCGGTGTGCGTTCGGGCGTTCCATGGGGAGCTCCCGGTGGGTG<br>AGCTGGGCCACTGAGCACATTCACAGGCCCTGAGGCTGCCCCAGGGGAGGAGCCGTGGACTCAGAGCCGAGGTTCCCCATACGTGCTGCGACAGAGAACCTAG<br>GGCTTGCACCTGGGTCTGGCTGCCCTTCAGCAGGCGGGCAGCCTCTGGCCCCACAACAGTGGGCTGTGCTTCTGCCGCCAAGGTGCAGGCGTCCTCCCCCAGG<br>GTCCACATCAGCAGCAGGGGCACCTGGACCCTGAGGGCAGGAACCAGACCTTGGCTCCTCCACCCACCCCCTCGTTCCTGATGGGGCAGGGAAGTCTCGGGAC<br>CCCATGATGGGCGACATGGCGATGGTCACTGTGGGTGCTTTGCTATCAGGTGGGGGGCCTTCCTCTCCACTCTGGGTCCAGTGTGAGTGGCCGCTATGGCTTC<br>CCCTCCACTCCAGGTTCTATCGTGAGTGGGTGGGTGCTGCGTCTGTGGATGTCACGTGACCTTTCCTCTTTAGCCTATCATTGTAGTTGGGAGTTAGTTAGCC<br>CGTTGAGCGTCATTGAATTTCCAGTGTTGAGCCAGCCCTGCGTGCCCGGGATAAACCCACCTGGCCGTGGTGTGTGGCCCTGTTTATGCACGTGGGCCCTGAT<br>TCGCTGATGCCTGCCTGAGGGTTTGCGCTTATCGGCGACATCAGCCTGCACTTTTCTTTTCTCGTGATCTCTCTGGTTCTGGCCTCAGGGTGACGTGGGCCTC<br>GTAGGGTCCTGTGGTGGCTCCTCCCCAGACGGTGACATGGAGTGAGCCCATTCTCCCTCCTGGGAGTGGGTCACTCAGGCCACCAGAGCACCACAGGGAAAGC<br>AGCCAGGGAGGACACGGAGGCCCTTGAAGCTCTGGCCTCTTCTGAGGCCTCCAGGACCTGACAGTGAGTGGGAGCAGCCCTGGCAGAACCCCTCCCCTCCTCT<br>CGGCCGCCCTGACACCTCATCCCCGACACTCAGAGCTCATCCTCCTTCCCAGCTGTTTCCAATTTCAAAGTGAACTCGACCTTGTGGCTCCAGGAGATGCAGC<br>AGGGACAGTGTTAAATCGGCTTTCACCAGCCCACACGGCCAGGCATCCTCCTCGGCCCTCCTGGGCACTGGGTGGACACCACTGGCTGTGGCCTGGCCCTGGC<br>CTTCTCCAGACAGCCCTGTCCACCCCAAAGCCCAGCCACCCTGGGCCTGCAGCAGGCCTGTGGAGTTCTCAGTTGCGTGGGGACCAGAGGGTGCTGGAGAAAC<br>AAACCAGACGCAGCTGAAGGCAGTCAGGGCAGGGCGCAATCAGCGATAAGAGCTGCATAGGGGCCACAGCGTAACCTGAGCTCCAGTCGGTGGAAAGAAAAGG<br>CAGAGACGTTGCAGAGGCCAGGTCTGCTCAGGGGAAGACAGTTCTGGGTGTAGAGGACTCACATCCCAGAGAGGCTGAGGAAGGGTTTACCACCGCAAGCTTT<br>CTCAGGCGGGCTCTTGAGGGGTGGCTGGGGTCTTCCTGGCGACGGGCCTGCGGCACTGGAAGCCCTACTGGAGTTTGGCCTGTCTCCGGCACAGGTTTGGACG<br>GAGCTGTTTTGTGCTGAAAGGTTTTCTCGGGGTCCGTGGTGTCCCCCAAAGGTGCCACCGTGCGGGTCTCCTAGCTCCCTGCCAGCTTCCTGTCCCTGTGCTC<br>ACTGCCCCCACGCCTCCTGCCAAGGCCGAGCCACACACCCGCTCCACCTGCATTTCCTCTACCGACTCGCCAGCCCAAATGCCGCTCTTCACTCTGGCCTCGC<br>TGAGCGGCTGCCCGAGGAGGAGCTCTAGGCCGACGCCCACCGCAGGCCTTACAGTCTTCTCTGGACGCTCCCTTGCAGATGCACCGTGGCCTGGCGGCGAGCC<br>CCCGGTCACCTTCCTCCGCACGGAAGAGGGGCCGGACGCCACCTTCCCCAGGACCATTCCCCTGATCCAACAGTTGCTAAACGCCACGGAGCTCACGCAGGAC<br>CCGGCCGCCTACTCCCAGCTGGTGGCCGTGCTGGTCTACACCGCCGAGCGGGCCAAGTTCGCCACCGGGGTAGAGCGGCAGGACTGGATGGAGCTGTTCATTG<br>ACACCTTTAAGCTGGTGCACAGGGACATCGTGGGGGACCCCGAGACCGCGCTGGCCCTCTGCTAAAGCCCGGGCACCCGCCCAGCCGGGCTGGGCCCTCCCTG<br>CCACACTAGCTTCCCAGGGCTGCCCCCGACAGGCTGGCTCTCAGTGGAGGCCAGAGATCTGGAATCGGGGTCAGCGGGGCTACAGTCCTTCCAGGGGCTCTGG<br>GGCAGCTCCCAGCCTCTTCCCATGCTGGTGGCCACCGTGTCCCTTGCTGCGGCTGCATCTTCCAGTCTCTCCTCCGTCTTCCTGTGGCCGCTCTCTTTATAAG<br>AACCCTGGTCATTGAATTTAAGGCCCACCCCAAGTCCAGAATGACCTCGCAAGACCCTTAACTCACTCCCGTCTGCAGAGTCCTTCTTTGCTGCATCAGGTCA |

TABLE 4C-continued

| SEQ ID NO | GENE NAME | SEQUENCE |
|---|---|---|
| | | CCCTCACAGGCTCCAGGGTTTGGGTGTGGAAGTCTTTGGAGGCCCTTACTTAGCGGCCCAGCTGGGCTGCCGTGCGTCTGGGATGGGGCTGAGGGAGGGTGCT<br>GCCCAGGTGCTGGAGGATGTTCCAGCACCAGGTTCCAGCGGAGCCTCGGAAACAGGCCCCAGAGGCTGGTGAGCCTCGCTGGGTGTGGGCACTAATCCCGTGC<br>ATGGTGACTCGTGGGCGCTCACGGCCCACCTGGTGGCAGGTGAAGGCTTCCGGTTGGGCAGCAGATAGTCCTGGGGGAAGCTGGCAGTCCTGGCACCATGACG<br>TATCTGGGCTGGTGTCATGCACAGTAGGGCGAATGGCCACAGCTGCCTGCCAGCAGCCCTGATCCCGGGGTGTCTGCACCCTTCCAGCCCAACCTCTGGGTCT<br>CCAAAAGCACAGTCGGGGGAGCATCCACCAGGCACAACCTCTGCGGTCCTCAGAGGACTGAGCAGAGAATCCCAGGGTCCACAATGTTGGGGAGCGGCAGGGA<br>TCACCATCCAAAGGGAGCGGCCCCCACGGCGAGCTGACCCCGACGTTCTGACTGCAGGAGCCCTCATCCAGGCTGGGCTCCTGCCGGGCACGGCTGTGACCAT<br>TTCTCAGGGCCAGGTTCTCGTCCCCACACCCACTGCACAGGGCAGGCCAGGCTGGTCTTCCCACTGTGGGGATGAAGGATCCTCCACAGGAGGAGGAGAGCAG<br>AGTCCACAGACATCCCAACAGCCTCAGCCTCCCTGTGCCTGGCCGGCCCCCACAGCTTCCCCGTCTCCTCCAGGCCCCACAGACACTGATGAATGGACAGAGA<br>CCCCCAAAACCAGCTGCCCCTTGCATGTCTGTCTCCATATGTTTGGTGACAGCAGTGAAAATGTTATTAGTTTTGAGGGGGTTTGGGAAGCCCAGCGGTACCT<br>GAGGAGTTTCTGGACATTTAAGCCGGTTCCTAGGTGTGGCCTTAACAGGGAGGCTGCCCTTCCTTTCACTGAATGAGCTGCGTCACTCATAAGCTCACTGAGG<br>GAACCCCATCTGCCAGCTCGTGCGTGCTCAGACGGCGTCCATGTCTCAAGCGTTCTGTGAAGGCTGCGGTGCAGCGTGAGGTCACCCTGCTGTGTTCAGAGCT<br>TTGCTCACTGCCTGCGGGGCTGGACCGTTGCACCTCCAGGGCCCCCAGAAACCGAGTTTCGGGTCAGGGTCCTCTGTGTGCATTCCTGGGGGTCCATGTACCA<br>GCTGTGACGACGTCCAGGGGTTGGGCTGAGAAGCAGACACCCTTGGGGAAACTGGCTCTGTCCCTCCCCTCCCCCATCCCAGGAGCTGAGGTCTTGGTGAGGC<br>CACAGGGCCAGGTCCACGCAAGGACTGTCCGTGTCCTGTCCTGTGGTCTCTGGCCCCACGTGACACCCACACGTGTGGTAGGCAGCCTGGCCTGGGTTGTGGC<br>TATGGCCAGGCCCCCAAGCTGTCCCCGATGCCCAGGGCTGGTGACCACCCAGGCAGGTGGGGGCCCCACTTGGTAACAGAGTCATAGGGCAGAACCCACCTGG<br>GCTGCCACAGAAGGTCTGGCTGCCCCTGTGCCCACTGCTCCCCACCATGGCCAATCAGAAGAGTCAGGGGCTCCTGGTCTTTCCGGGAGGGACGTGGCCCAGC<br>CAGCTCTAGGTGTTCTGAGCAGCTCTGGGACCCAGCGATTGAGGGGTCAGGCTGGGGGTGTCAGAGCCAGGGTCCTCCTTAAGTACCTCCCACACTACACAGA<br>CAGTGGCCCTTTTGTGGGCAGCAAATTCTTGAGCCATGAAAGGATGCTTTGGGCCCCTTCCCTCCCAGGAGGGCAGCCTGTGCAGGGATGGTGCTCAGCAGGT<br>GGACAGGGCCTGGGGCCTGTGTCAGGGTCTCAGGCCTGGGAGCACCAGCAGAGGAGATGGCGGCTCCCAGCAGTGCCGCCTGAAAGTGTCTTGGGCTAAGGAC<br>CCACACCCAGGGCTGCCCTGCAGAAACGCCCCCGCAGAGCCCAGTGGTCTGTGAGGTTGCAGGCAGGGTGCGAATGGAAGGGCACAGGTGCGGGGCTGGCACC<br>TGCCCGGTCCTGCCCACCTCCCCTCCGCCCAGCCCGCACCTGCGTCTCCCCACAGAGCTGTCCGTGGCACAGTGCACGCAGCGGCCCGTGGACATCGTCTTCC<br>TGCTGGACGGCTCCGAGCGGCTGGGTGAGCAGAACTTCCACAAGGCCCGGCGCTTCGTGGAGCAGGTGGCGCGGCGGCTGACGCTGGCCCGGAGGGACGACGA<br>CCCTCTCAACGCACGCGTGGCGCTGCTGCAGTTTGGTGGCCCCGGCGAGCAGCAGGTGGCCTTCCCGCTGAGCCACAACCTCACGGCCATCCACGAGGCGCTG<br>GAGACCACACAATACCTGAACTCCTTCTCGCACGTGGGCGCAGGCGTGGTGCACGCCATCAATGCCATCGTGCGCAGCCCGCGTGGCGGGGCCCGGAGGCACG<br>CAGAGCTGTCCTTCGTGTTCCTCACGGACGGCGTCACGGGCAACGACAGTCTGCACGAGTCGGCGCACTCCATGCGCAAGCAGAACGTGGTACCCACCGTGCT<br>GGCCTTGGGCAGCGACGTGGACATGGACGTGCTCACCACGCTCAGCCTGGGTGACCGCGCCGCCGTGTTCCACGAGAAGGACTATGACAGCCTGGCGCAACCC<br>GGCTTCTTCGACCGCTTCATCCGCTGGATCTGCTAGCGCCGCCGCCCGGGCCCCGCAGTCGAGGGTCGTGAGCCCACCCCGTCCATGGTGCTAAGCGGGCCCG<br>GGTCCCACACGGCCAGCACCGCTGCTCACTCGGACGACGCCCTGGGCCTGCACCTCTCCAGCTCCTCCCACGGGGTCCCCGTAGCCCCGGCCCCCGCCCAGCC<br>CCAGGTCTCCCCAGGCCCTCCGCAGGCTGCCCGGCCTCCCTCCCCCTGCAGCCATCCCAAGGCTCCTGACCTACCTGGCCCCTGAGCTCTGGAGCAAGCCCTG<br>ACCCAATAAAGGCTTTGAACCCATTGCGTGCCTGCTTGCGAGCTTCTGTGCGCAGGAGAGACCTCAAAGGTGTCTTGTGGCCAGGAGGGAAACACTGCAGCTG<br>TCGCTCGCCCACCAGGGTCAATGGCTCCCCCGGGCCCAGCCCTGACCTCCTAGGACATCAACTGCAGGTGCTGGCTGACCCCGCCTGTGCAGACCCCACAGCC<br>TTGATCAGCAAACTCTCCCTCCAGCCCCAGCCAGGCCCAAAGTGCTCTAAGAAGTGTCACCATGGCTGAGGGTCTTCTGTGGGTGGACGCATGATTAACACTA<br>GACGGGGAGACAGCAGGTGCTGAGCCTGTTGTGTTCTGTGTGGAGATCTCAGTGAGTTTTTGCTGTTCAGACCCCAGGGTCCTTCAGGCTCAGCTCAGGAGCC<br>CCACAGTGAACCAGAGGCTCCACAGGCAGGTGCTGACCTGACAGGAGTGGGCTTGGTGGCCATCACAGGGCACCACAGACACAGCTTGAACAACTACCAGTAT<br>CGGCCACAGGCCTGGAGGCATCAGCCGGGCCATGCTTCCTCTGGAGGGCTAGAGGAGGACTAGAGAAGGGCCTGCCCCGGCCTCTCCCCAGCATCCCAGGGTT<br>CCTGATCTCCTGGATAAGGATACAAGTCACCACACTGGACTGGGGCTCAGCCTGCTCTAGAATACCTCACCTAAGTCACAGTGGACCAGGCTCAGCCTGCTCT<br>AAGGTGAGCTTACCCGAGACACTGGACCAGAGATCAGCCTATCCTGGGATAAGCTCACCCGAGTCACACTGGACCAGGGCTCAGCCTATTCCGGGATGAGCTC<br>ACCCGAGTC |
| 256 | C21orf56 | GACACTTCCATGACTGCAGCTGACCAGTCCACCTGCCAGCGGTTGACCACTCCCACTTCGCCAGCGACCGAAGGGGAGGGGAGGGGCCTCACCTGAGGGCAAC<br>AGCAGAACCCACCACCTGGTCTTGCTTTACTCAGACCTGAGGGTGTGAAAGGTGCCCGTGACCTCCCGCATCAGGGAGCTGGCCGCCACCCTCGACTCCCGGG<br>GAGCAGGCGTCCCGCGACCCCCTCATCTACCAGGCCATCTGAGCTGGGCGGCGCCTCACCTCCGCTCCCGGGGGAGCCGGCCTCAGGGTAGGCATGCGCCCTG<br>GGTGGGAGCAGGTCGTGGCCGCCGCCCTCCTGGCAGCTCTGGCTGAGCAGCCGCCGCAGCATCTGATTCTCCTTCAGGAGGCGCACCTGCTTCTTCAGGTCCG<br>CGTTCTCGCTCAGGAGCCGGCTCATCAGCTCGCCGCCTTCAGCCATGGCGGGTGCGTCCCTCCTTGTCCCTCACGGCTCCTGCAGCCCCATGGAGGTGGGAGC<br>CCAGAGCCCGCAGGCACCACAGAAACAGCCCAGGCACGGAGTTCCGTAGCCACCACCGCCTTCCACGCCTTGTGATGTCACTGCCCTAGTGATGAGGTGCCCA<br>GCACCCTGCCTGCCCCCGCGATGGCTCATGGCCCCGTTGAGGCAGTGAAGCTGGAGGCCCGTGGCGTGCACAGGCAGCCACTCCCACATTATGACCAGGGCCC<br>GAGAATGCCAAGGACATTAGGCAGCTACGGGATGTAGCGACTGTACTCCAAGAGGGGCGTCCAAGCCACTCCCCATTGA |

TABLE 4C-continued

| SEQ ID NO | GENE NAME | SEQUENCE |
|---|---|---|
| 257 | C21orf57 | AGGTGGAGGTTGCAGTGAGCCCTCCTCCCCTCCTCCCCCTTCCCTTCCCACCTCCCATGCCCCCCTTTCTTCCTCCCACTCCCCTCCCGAGGCCCCGCTTATT<br>CTCCCGGCCTGTGGCGGTTCGTGCACTCGCTGAGCTCAGGTTCTGGTGAAGGTGCCCGGAGCCGGGTCCCGCCTTCGGCCTGAGCTAGAGCCGCGCGGGCGGC<br>CGGCTTCCCCCAAACCCTGTGGGAGGGGCATCCCGAGGAGGCGACCCCAGAGAGTGGGGCGCGGACACCTTCCCTGGGGAGGGCCAG |
| 258 | C21orf57 | CCTTCCAGATGTTCCAGAAGGAGAAGGCGGTGCTGGACGAGCTGGGCCGACGCACGGGGACCCGGCTGCAGCCCCTGACCCGGGGCCTCTTCGGAGGGAGCTG<br>AGGGCCGCGTTCCTTCTGAAAGCGGGACGCGGGAGGGGTGGAGGCTGCGGGGAGCCGGGGTCGCACACGAATAAATAACGAATGAACGTACGAGGGGAACCTC<br>CTCTTATTTCCTTCACGTTGCATCGGGTATTTTTCGTTATTGTAAATAAAACGGTTCCGAGCCGTGGCATCGAGAGGGCGTCTGGAGTTCAGGGAACGCGTGG<br>CCCCCGCCCGGGAGCACCGCGCAGCGCTCGCCTCTCGCCCTTCAAGGGGGTCCCTGCCCGGAGCCTGCGCCCCCGGAGAGGAAGGGGCTCGAGGGGCTTGGGT<br>GCCGCAGCGCGTCCTTCCGTAGAAAAGGCTTGCGTCAGTATTTCCTGCTTTTACCTCCTGAG |
| 259 | C21orf57 | CAGTATTTCCTGCTTTTACCTCCTGAGTATTGGAATATTCGAGTAAACCCTGGAGTTTCAGCGCCAGCGCACGCCTCTTCATCAGGGCAGCGCGTCGCGAGCG<br>CGCTGGTTCCCCGGGGCCTCCCGGCCACGGACACCGCTCTAGCCAGGGCCACGGCGAGGCCGCCGAGCAGCACCTCAGAGACCTGCGTGAGTTCTAAAGCCTG<br>GGGCTACTACAATTCTGCTCATCTGTTTGTCCTGTGAAATGATTCAGGGACATGAAAATGCCTTCCCACTGACTTGCGTCCTGTCTTAGCCTGGACTTGTCCC<br>CTTGGGAACACGGGCCAGGCCCCTCTGTTCCTGAAGT |
| 260 | C21orf58 | ATGTCTGCAGGGAAGAAGCAGGGGGACCCTGAATAAAGTTTCCGTTTTTCCTATTTGTTAAAGTGATAGAGCATTATAGGACCAGAGAACAGGTGTGTCTGTA<br>CACTGTGCAGGTCCCCGGGGCAGGCTCTGAGTCCGTCTGCACACGGTGCGGGTCCCCGGGGCGCGCCCTGAGCCCGTCTGCACACGGTGCGGGTCCCCGGGGC<br>GCGCCCTGAGCCCGTCTGCACACGGTGCGGGTCCCCGGGGCGCGCCCTGAGCCCGTCTGCACACGGTGCGGGTCCCCGGGGCGCGCCCTGAGCCCGTCTGCAC<br>ACGGTGCGGGTCCCCGGGGCGCGCCCTGAGCCCGTCTGCACACGGTGCGGGTCCCCGGGGCGCGCCCTGAGCCCGTCTGTACACGGTGCGGGTCCCCGGGGCG<br>CGCCCTGAGTCTCTACTAAAAATACAAAAATTAGCCAGGCGTGGTGGTTCAAGCCTGTAATCCCAGCTCCTTGGGAGG |
| 261 | PRMT2 | CATACATGGTTATTAGAAAAGGCATCTCATCCAAATGTGGTGGCTCGTGCTTGTAATCCCAGTGCTTCAGGAGGCCAAGGGAGGAGGATTACTTGAGCCTAAG<br>AGTTTGAGACCAGCCTGGGCAACACAACAAGACCTTGCCTCTACAAAAAACTTAAAAACTAGCTGGGTATGATGGTGCACACCTGTAGTCCCAGCTACTTGGG<br>AGGCGGAGGCGGGCAGATCGCCTGAGGTCAGGAGTTCGAGACCAGCCTGGCCAACATGATGAAACCCCGTCTCTACTAAAAATACAAAAATTAGCCGAGTGTG<br>GTGGTGCATGCCTGTAATCCCAGCTACTCAGGAGGCTGAGGCAGGAGAATCACTTGAACCCGGGAGGCGGAGGTTGCCATGAGCCGAGATCACGTCACTGCAC<br>TCCAGCCTGGGTGACAGAGCACAAAAGACAGGCATGACTTTGTACTTAACTGCTCAGCTTTGTAATCACTGGGGGCCCAGATGCTCACTTGGATTCTAACTTT<br>GTTGGCATCTGGGCCTAAAAGCCGTGATGCAGGTGAGCAATGATGCAGAGGGCTCTGTGCGCCTGGCGGGCTCTGTTTGCCTGCTGGGCTCTGTGCGCCTGCT<br>GGGCTCTGTGCGCCCGGGAAGGTGCGGCCACCCTCACGCGGAAGGCGGCCAGCGGATCCCGGTGCGCGCAGCTCCCAGCGCTGGGGTTCCAGCGCCCCGCCTC<br>TTCCTATAGCAACCAGCGGGACCTGCCGTCCCCCGGGGCACCCCGAGGGGTCTGCGCCCGCTTCTTTCCGAAACGGGAAGGCGCTGGGGGCTCGGCAGCCAGA<br>GGGACGGGTTCAGGGAGCGTCCGGTGAGCCTAAGACGCGCCTTTGCCGGGGTTGCCGGGTGTCTGCCTCTCACTTAGGTATTAGGAACCGTGGCACAAATCTG<br>TAGGTTTTCCTCTGGGGGTGGGCGGAGGCTCCAAACCGGACGGTTTTCTCCTGGAGGACTGTGTTCAGACAGATACTGGTTTCCTTATCCGCAGGTGTGCGCG<br>GCGCTCGCAAGTGGTCAGCATAACGCCGGGCGAATTCGGAAAGCCCGTGCGTCCGTGGACGACCCACTTGGAAGGAGTTGGGAGAAGTCCTTGTTCCCACGCG<br>CGGACGCTTCCCTCCGTGTGTCCTTCGAGCCACAAAAAGCCCAGACCCTAACCCGCTCCTTTCTCCCGCCGCGTCCATGCAGAACTCCGCCGTTCCTGGGAGG<br>GGAAGCCCGCGAGGCGTCGGGAGAGGCACGTCCTCCGTGAGCAAAGAGCTCCTCCGAGCGCGCGGCGGGGACGCTGGGCCGACAGGGGACCGCGGGGGCAGGG<br>CGGAGAGGACCCGCCCTCGAGTCGGCCCAGCCCTAACACTCAGGACCGCCTCCAGCCGGAGGTCTGCGCCCTTCTGAGGACCCTGCCTGGGGGAGCTTATTGC<br>GGTTCTTTTGCAAATACCCGCTGCGCTTGGACGGAGGAAGCGCCCACGCGTCGACCCCGGAAACGAAGGCCTCCCTGATGGGAACGCATGCGTCCAGGAGCCT<br>TTATTTACTCTTAATTCTGCCCGATGCTTGTACGTGTGTGAAATGCTTCAGATGCTTTTGGGAGCGAGGTGTTACATAAATCATGGAAATGCCTCCTGGTCTC<br>ACCACACCCAGGGTGACAGCTGAGATGCGGCTTCTCCAGGGTGGAGCCTCCTCGTTTTCCAGAGCTGCTTGTTGAAGTCTTCCCAGGGCCCCTGACTTGCACT<br>GGAAACTGCTCACCTTGGCATCGGGATGTGGAGCAAGAAATGCTTTTGTTTTCATTCATCCTAGTGTTCATAAAATGGAAAACAAATAAGGACATACAAAAAC<br>ATTAATAAAATAAATTAATGGAACTAGATTTTTCAGAAAGCACAACAAACACAAAATCCAAGTATTGCCATGTCAGCAACACATTCCTACTTTAAGTTTTATG<br>AAGTTAATTGGAGTAGTGGAGAACAAAAGTGGATGTGGGGCAG |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claims that follow.

What is claimed is:

1. A method for determining the presence or absence of a fetal aneuploidy, comprising:

a) contacting nucleic acid from a pregnant female, which nucleic acid comprises fetal nucleic acid and maternal nucleic acid, with a methylation sensitive restriction enzyme that digests the maternal nucleic acid at a plurality of loci, wherein the plurality of loci comprises loci that are hypermethylated in fetal nucleic acid, thereby enriching the fetal nucleic acid;

b) amplifying the loci, or portion thereof, not digested in (a) in an amplification reaction, thereby generating amplification products;

c) sequencing the amplification products of (b), thereby generating sequencing products;

d)determining from the sequencing products of (c) the amount of fetal nucleic acid for a plurality of loci of a target chromosome comprising a locus comprising SEQ ID NO: 211;

e) determining the amount of fetal nucleic acid from a reference chromosome; and f) comparing the amount of fetal nucleic acid for the plurality of loci of the target chromosome to the amount of fetal nucleic acid for the reference chromosome, whereby a statistically significant difference between the amount of fetal nucleic acid for the plurality of loci of the target chromosome and the amount of fetal nucleic acid for the reference chromosome determines the presence of a fetal aneuploidy.

2. The method of claim 1, wherein the plurality of loci comprises one or more loci selected from loci of SEQ ID NOs: 90-163, 176, 179, 180, 184, 188, 189, 190, 191, 193, 195, 198, 199, 200, 201, 202, 203, 205, 206, 207, 208, 209, 210, 212, 213, 214, 221, 223, 225, 226, 231, 232, 233, 235, 239, 241, 257, 258, 259, and 261.

3. The method of claim 1, wherein the plurality of loci comprises one or more loci selected from loci of SEQ ID NOs: 176, 179, 180, 184, 188, 189, 190, 191, 193, 195, 198, 199, 200, 201, 202, 203, 205, 206, 207, 208, 209, 210, 212, 213, 214, 221, 223, 225, 226, 231, 232, 233, 235, 239, 241, 257, 258, 259, and 261.

4. The method of claim 1, wherein the plurality of loci comprises one or more loci selected from loci of SEQ ID NOs: 193, 200, 208, 209, 213, 214, 231, 232, 235, and 241.

5. The method of claim 1, wherein the plurality of loci comprises the locus of SEQ ID NO:213.

6. The method of claim 1, wherein the plurality of loci comprises one or more loci selected from loci of SEQ ID NOs: 200, 208, 231, 232, and 241.

7. The method of claim 1, wherein the plurality of loci comprises the locus of SEQ ID NO:209.

8. The method of claim 1, wherein the plurality of loci comprises the locus of SEQ ID NO:214.

9. The method of claim 1 wherein the amount of fetal nucleic acid at between 3 and 15 loci on each of the target chromosome and the reference chromosome is determined.

10. The method of claim 1, wherein the amount of fetal nucleic acid at about 16 or more loci on each of the target chromosome and the reference chromosome is determined.

11. The method of claim 1, wherein determining the amount of fetal nucleic acid for the target chromosome and the reference chromosome comprises use of a competitor-based amplification method.

12. The method of claim 1, further comprising:

i) determining the amount of total nucleic acid;

ii) determining the digestion efficiency of the methylation sensitive restriction enzyme; and iii) determining the presence or absence of Y-chromosome nucleic acid in the nucleic acid.

13. The method of claim 12, wherein the amount of Y-chromosome nucleic acid present in the nucleic acid is determined for a male fetus.

14. The method of claim 13, wherein the amount of fetal nucleic acid is compared to the amount of Y-chromosome nucleic acid.

15. The method of claim 13, wherein two or more assays are used to determine the total amount of nucleic acid, one or more assays are used to determine the amount of Y-chromosome nucleic acid for a male fetus, and one or more assays are used to determine the digestion efficiency of the methylation sensitive restriction enzyme.

16. The method of claim 1, wherein the sequencing method comprises sequencing by synthesis.

* * * * *

SEQUENCE LISTING

```
<160> NUMBER OF SEQ ID NOS: 351

<210> SEQ ID NO 1
<211> LENGTH: 305
<212> TYPE: DNA
<213> ORGANISM: Homo sapiens

<400> SEQUENCE: 1

cagcaggcgc gctcccggcg aatctgcctg aatcgccgtg aatgcggtgg ggtgcagggc     60

aggggctggt tttctcagcc ggtcttggct tttctctttc tctcctgctc caccagcagc    120

ccctccgcgg gtcccatggg ctccgcgctc agaacagccc ggaaccaggc gccgctcgcc    180

gctcgctggg ggccacccgc ctctccccgg aacagcctcc cgcgggcctc ttggcctcgc    240

actggcgccc tcacccacac atcgtccctt tatccgctca gacgctgcaa agggccttct    300

gtctc                                                                305


<210> SEQ ID NO 2
<211> LENGTH: 336
<212> TYPE: DNA
<213> ORGANISM: Homo sapiens

<400> SEQUENCE: 2

gctttggatt tatcctcatt ggctaaatcc ctcctgaaac atgaaactga aacaaagccc     60

tgaaccccct caggctgaaa agacaaaccc cgcctgaggc cgggtcccgc tccccacctg    120

gagggaccca attctgggcg ccttctggcg acggtccctg ctagggacgc tgcgctctcc    180

gagtgcgagt tttcgccaaa ctgataaagc acgcagaacc gcaatcccca aactaacact    240

gaacccggac ccgcgatccc caaactgaca agggacccgg aacagcgacc cccaaaccga    300

cacgggactc gggaaccgct atctccaaag ggcagc                              336


<210> SEQ ID NO 3
<211> LENGTH: 139
<212> TYPE: DNA
<213> ORGANISM: Homo sapiens
```

<400> SEQUENCE: 3
tttccacaac agggagccag cattgaggcg cccagatggc atctgctgga aatcacgggc 60
cgctggtgaa gcaccacgcc ttacccgacg tggggaggtg atccccccacc tcatcccacc 120 cccttctgtc tgtctcctt 139

<210> SEQ ID NO 4
<211> LENGTH: 292
<212> TYPE: DNA
<213> ORGANISM: Homo sapiens

<400> SEQUENCE: 4
gctggacaag gagcgctcac tgtagctctg ctgtggattg tgttggggcg aagagatggg 60
taagaggtca aagtcgtagg attctggcga ccgcctacca agggattggg tccacagcac 120
agaggtctga tcgcttcctt ctctgctctg ccacctccag acagcagctc taaccagctg 180
cccagcagca agaggatgcg cacggctttc accagcacgc agctgctaga gctggagcgc 240
gagttcgctt ctaatatgta cctgtcccgc ctacgtcgca tcgagatcgc ga 292

<210> SEQ ID NO 5
<211> LENGTH: 190
<212> TYPE: DNA
<213> ORGANISM: Homo sapiens

<400> SEQUENCE: 5
tgcctgacac tgaccccagg cgcagccagg aggggctttg tgcgggagag ggagggggac 60
cccagcttgc ctggggtcca cgggactctc ttcttcctag ttcactttct tgctaaggcg 120
aaggtcctga ggcaggacga gggctgaact gcgctgcaat cgtccccacc tccagcgaaa 180
cccagttgac 190

<210> SEQ ID NO 6
<211> LENGTH: 706
<212> TYPE: DNA
<213> ORGANISM: Homo sapiens

<400> SEQUENCE: 6
tcggcggaga gacctcgagg agagtatggg gaaaggaatg aatgctgcgg agcgcccctc 60
tgggctccac ccaagcctcg gaggcgggac ggtgggctcc gtcccgaccc cttaggcagc 120
tggaccgata cctcctggat cagaccccac aggaagactc gcgtggggcc cgatatgtgt 180
acttcaaact ctgagcggcc accctcagcc aactggccag tggatgcgaa tcgtgggccc 240
tgaggggcga gggcgctcgg aactgcatgc ctgtgcacgg tgccgggctc tccagagtga 300
gggggccgta aggagatctc caaggaagcc gaaaaaagca gccagttggg cttcgggaaa 360
gacttttctg caaaggaagt gatctggtcc cagaactcca gggttgaccc cagtacctga 420
cttctccggg agctgtcagc tctcctctgt tcttcgggct tggcgcgctc ctttcataat 480
ggacagacac cagtggcctt caaaaggtct ggggtggggg aacggaggaa gtggccttgg 540
gtgcagagga agagcagagc tcctgccaaa gctgaacgca gttagcccta cccaagtgcg 600
cgctggctcg gcatatgcgc tccagagccg gcaggacagc ccggccctgc tcaccccgag 660
gagaaatcca acagcgcagc ctcctgcacc tccttgcccc agagac 706

<210> SEQ ID NO 7
<211> LENGTH: 325
<212> TYPE: DNA
<213> ORGANISM: Homo sapiens

<400> SEQUENCE: 7
agatcccggt gcatttaaag gccggcgtga tctgcaccac gtacctatct cggattctca 60
gtttcacttc gctggtgtct gccaccatct ttaccacatc ccggtagcta catttgtcta 120
ccgcttgagc caccagcgtc tgaaacctgg accggatttt gcgcgccgag aggtagccgg 180
aggcggtaat gaattccacc cagagggaca tgctcctctt gcgcccgtcg ctcaacttca 240
gcaccgcgca gccgggcagt gagccatcgt ccacgaagtt gaacaccccc atttggttga 300
gataaagcac cacttcaaat tcggt 325

<210> SEQ ID NO 8
<211> LENGTH: 663
<212> TYPE: DNA
<213> ORGANISM: Homo sapiens

<400> SEQUENCE: 8
actatgcctt gagggtcaaa acgtctggat ttcctgatcg atgctgtcgt cgctgtccac 60
ggagctactg tcgccgtcag agcgggaagg cacgttcagg gagtagaagc gtgggcttgc 120
agaaagggac ctgttgctgc cttacatggg ggccggcagg gtagtcttgg aaatgcccaa 180
gattgcttcc gcgcgcgtca gttcagcgga cgtgtctgcc tggcacgagg accgttctac 240
aaactcgttc ctggaagccg ggctcgctgg aggcggagct ttggtttcct tcgggagctt 300
gtggggaatg gtcagcgtct aggcaccccg ggcaagggtc tgtggccttg gtggccactg 360
gcttcctcta gctgggtgtt ttcctgtggg tctcgcgcaa ggcacttttt tgtggcgctg 420
cttgtgctgt gtgcggggtc aggcgtcctc tctcctcccg gcgctgggcc ctctggggca 480
ggtccccgtt ggcctccttg cgtgtttgcc gcagctagta cacctggatg gcctcctcag 540
tgccgtcgtt gctgctggag tctgacgcct cgggcgcctg cgccgcactt gtgacttgct 600
ttccccttct cagggcgcca gcgctcctct tgaccccgct tttattctgt ggtgcttctg 660
aag 663

<210> SEQ ID NO 9
<211> LENGTH: 1985
<212> TYPE: DNA
<213> ORGANISM: Homo sapiens

<400> SEQUENCE: 9
gcaagtcggg tagctaccgg gtgctggaga actccgcacc gcacctgctg gacgtggacg 60
cagacagcgg gctcctctac accaagcagc gcatcgaccg cgagtccctg tgccgccaca 120
atgccaagtg ccagctgtcc ctcgaggtgt tcgccaacga caaggagatc tgcatgatca 180
aggtagagat ccaggacatc aacgacaacg cgccctcctt ctcctcggac cagatcgaaa 240
tggacatctc ggagaacgct gctccgggca cccgcttccc cctcaccagc gcacatgacc 300
ccgacgccgg cgagaatggg ctccgcacct acctgctcac gcgcgacgat cacggcctct 360
ttggactgga cgttaagtcc cgcggcgacg gcaccaagtt cccagaactg gtcatccaga 420
aggctctgga ccgcgagcaa cagaatcacc atacgctcgt gctgactgcc ctggacggtg 480
gcgagcctcc acgttccgcc accgtacaga tcaacgtgaa ggtgattgac tccaacgaca 540
acagcccggt cttcgaggcg ccatcctact tggtggaact gcccgagaac gctccgctgg 600
gtacagtggt catcgatctg aacgccaccg acgccgatga aggtcccaat ggtgaagtgc 660
tctactcttt cagcagctac gtgcctgacc gcgtgcggga gctcttctcc atcgacccca 720

-continued

```
agaccggcct aatccgtgtg aagggcaatc tggactatga ggaaaacggg atgctggaga    780

ttgacgtgca ggcccgagac ctggggccta accctatccc agcccactgc aaagtcacgg    840

tcaagctcat cgaccgcaac gacaatgcgc cgtccatcgg tttcgtctcc gtgcgccagg    900

gggcgctgag cgaggccgcc cctcccggca ccgtcatcgc cctggtgcgg gtcactgacc    960

gggactctgg caagaacgga cagctgcagt gtcgggtcct aggcggagga gggacgggcg   1020

gcggcggggg cctgggcggg cccgggggtt ccgtcccctt caagcttgag gagaactacg   1080

acaacttcta cacggtggtg actgaccgcc cgctggaccg cgagacacaa gacgagtaca   1140

acgtgaccat cgtggcgcgg gacgggggct ctcctcccct caactccacc aagtcgttcg   1200

cgatcaagat tctagacgag aacgacaacc cgcctcggtt caccaaaggg ctctacgtgc   1260

ttcaggtgca cgagaacaac atcccgggag agtacctggg ctctgtgctc gcccaggatc   1320

ccgacctggg ccagaacggc accgtatcct actctatcct gccctcgcac atcggcgacg   1380

tgtctatcta cacctatgtg tctgtgaatc ccacgaacgg ggccatctac gccctgcgct   1440

cctttaactt cgagcagacc aaggcttttg agttcaaggt gcttgctaag gactcggggg   1500

cgcccgcgca cttggagagc aacgccacgg tgagggtgac agtgctagac gtgaatgaca   1560

acgcgccagt gatcgtgctc cccacgctgc agaacgacac cgcggagctg caggtgccgc   1620

gcaacgctgg cctgggctat ctggtgagca ctgtgcgcgc cctagacagc gacttcggcg   1680

agagcgggcg tctcacctac gagatcgtgg acggcaacga cgaccacctg tttgagatcg   1740

acccgtccag cggcgagatc cgcacgctgc acccttttctg ggaggacgtg acgcccgtgg   1800

tggagctggt ggtgaaggtg accgaccacg gcaagcctac cctgtccgca gtggccaagc   1860

tcatcatccg ctcggtgagc ggatcccttc ccgagggggt accacgggtg aatggcgagc   1920

agcaccactg ggacatgtcg ctgccgctca tcgtgactct gagcactatc tccatcatcc   1980

tccta                                                               1985
```

```
<210> SEQ ID NO 10
<211> LENGTH: 213
<212> TYPE: DNA
<213> ORGANISM: Homo sapiens

<400> SEQUENCE: 10

atgcgccctc tgcaccccta gagccagaag acgctaggtg ggctgcgcgc tctgccaggc     60

gaaggctgga gcgcagacgg caaagccgcg cgtttcagcc gtggtcgggt ccgcaggacc    120

tgggcgtggg gacaccacca ggcaggagca gaggcaggac tgggacgcca aaagctgaga    180

atcctcgatg cccgcgcgag agccccgtgt tat                                 213
```

```
<210> SEQ ID NO 11
<211> LENGTH: 1558
<212> TYPE: DNA
<213> ORGANISM: Homo sapiens

<400> SEQUENCE: 11

ttctggaaac cgggccccac ttgcaggccc ggccaccttg ggttctggtg gccgaagccg     60

gagctgtgtt tctcgcagac tcggggagct acattgtgcg taggcaattg tttagtttga    120

aaggaggcac atttcaccac gcagccagcg ccctgcatgc aggagaagcc cccagggccc    180

agggtcggct ggctttagag gccacttagg ttgttttaag cacatgtgaa agggcagaca    240

gcaggggagc aggatatggg taagatcttc gggtctcaga acaggggctg cccttgggct    300

gtcccggcgc cctgggctct gacactgaag ggtggaatgg aggaaggaat ggagaaagga    360
```

-continued

```
cggtggaact ttcgcttccc ctctgggccg ccttcccagg gtcatgcctg agctgctttg    420

atcccagtgt cgcgcatctt ggtccgctac ctcccaggcg atagctactg ggctcctcgc    480

tggcctcact gggggccatc ccgggcagtg gcctgccctc cgaggcccgc gggacccagc    540

ccagagctga ggttggagtt ctccgggcca cgttccgggt cgcttaggct cggagatttc    600

ccggagaccg tcgtcctccc tttctgcttg gcactgcgga gctccctcgg cctctctcct    660

cctctggtcc ctaaggcccg gagtggttgg cggtactggg gcccgtcgtc atctctgctt    720

ctaaggcatt cagactgggc tccagctggg accggcagag gaggttctca aggaaactgg    780

tgggaaatat agttttcttt cgtctggtcg tttaatttaa atgcaacttc ccttggggac    840

attttcctgg acgttaacca gaccaccttg agatgtcgtt gatgacctag agacccagat    900

gatgcgtccc aggaaagttc actgctgact attgtcactc ttggcgttat atctatagat    960

atagacctat gtacatatct ccaccctgat ctctccgtgg acatgaaacc cacctacctt   1020

gtgaaagccc tacgggtgac acatgactac tacgtctctg tcccaacagg ggctgggcct   1080

cccctgccta atagttgcca ggagtttcgc agcccaagtg aataatgtct tatggctgaa   1140

cgtggccaag gactcctgtg atttaggtcc caggaggagc agagacgtcc ccgccccgcc   1200

tgggccctgc cgcattcaaa gctggaagaa ggcgctgatc agagaagggg cttccaggtc   1260

ctgggttaga acaacaacaa acaaacgaaa ctccacaaca gacacgcctg cccatgaccc   1320

cacgcaagga cataggaagt tctgtcgcct tcctgctccg cggatagccg cctgccgtct   1380

gctgccacca gaacgcacgg acgctcgggg tggaggtagt caatgggcag caggggaccc   1440

ccagccccca caagcgcggc tccgaggacc tggaagcggg tgcctgtcgc tctccgcagg   1500

ctccgctctg cctccaggag caagatcccc aaaagggtct ggaagctgtg gagaaaac     1558
```

```
<210> SEQ ID NO 12
<211> LENGTH: 1264
<212> TYPE: DNA
<213> ORGANISM: Homo sapiens

<400> SEQUENCE: 12
```

```
tttttaaac acttcttttc cttctcttcc tcgttttgat tgcaccgttt ccatctgggg     60

gctagaggag caaggcagca gccttcccag ccagcccttg ttggcttgcc atcgtccatc    120

tggcttataa aagtttgctg agcgcagtcc agagggctgc gctgctcgtc ccctcggctg    180

gcagaagggg gtgacgctgg gcagcggcga ggagcgcgcc gctgcctctg gcgggctttc    240

ggcttgaggg gcaaggtgaa gagcgcaccg gccgtggggt ttaccgagct ggatttgtat    300

gttgcaccat gccttcttgg atcggggctg tgattcttcc cctcttgggg ctgctgctct    360

ccctccccgc cggggcggat gtgaaggctc ggagctgcgg agaggtccgc caggcgtacg    420

gtgccaaggg attcagcctg gcggacatcc cctaccagga gatcgcaggt aagcgcgggc    480

gcgctgcagg ggcaggctgc agccctcggc tgccgcacgt cccactggcc gcccggcgtc    540

cccttccttc cccctgttgc tgagttggtg ctcactttct gccaccgcta tgggactccg    600

cgtctccgtg ttgggcggcg gatgctcctg cggcttcttc ggcgggggaa ggtgtgcgtc    660

tccgccgcct cattgtgtgc acacgcggga gcaccctggc tcccgcctcc cgctgctctc    720

gcgcccttct accccttagt tgatggctca ggcccggctg gccagggagc ccgggtcact    780

ccggggcggc tgcaaggcgc agacggagag ccgagccggg cgctcactcc gcgttctggt    840

tcgggcaaac ttggaagaac tgcgaccgca gtttgcccag cgccacagtc tgagtggcgc    900
```

cttctccact cccgcccttg cgccggcagg ggcggtggag agacgcggag ggctccccca 960
gcccctctct cccctatccg tccttcgggc gacagagcgc ccggcgctcg ggccgggggc 1020
gggcaaggct gggagggacc ctcgccgggg acctggcctc tggacgccgg cgtttcaagg 1080
ctggtttggg gacttcacgg gctgcctgtt tcagatgtgg ggcgggcttt cccgttaggg 1140
ttcctcagtg cttccccagt tgctgttggc cactcagggc ccggggacac cctgccaccc 1200
ggtctggagc cggcctcgtc tgccagcgaa cagccaactt tagcgggtgg ctcagctggg 1260
gatt 1264

<210> SEQ ID NO 13
<211> LENGTH: 761
<212> TYPE: DNA
<213> ORGANISM: Homo sapiens

<400> SEQUENCE: 13
cactcagtgt gtgcatatga gagcggagag acagcgacct ggaggccatg ggtgggggcg 60
ggtggtgaag ctgccgaagc ctacacatac acttagcttt gacacttctc gtaggttcca 120
aagacgaaga cacggtggct tcagggagac aagtcgcaag ggcgactttt ccaagcggga 180
gatggtgaag tctttggacg tgtagtgggt aggtgatgat ccccgcagcc gcctgtaggc 240
ccgcagactt cagaaaacaa gggccttctg tgagcgctgt gtcctccccg gaatccgcgg 300
cttaacacat tctttccagc tgcggggcca ggatctccac cccgcgcatc cgtggacaca 360
cttagggtcg cctttgtttt gcgcagtgat tcaagttggg taacccttgc tcaacacttg 420
ggaaatgggg agaatctccc ccacccgcaa cctcccgcac cccaggttcc caaaatctga 480
atctgtatcc tagagtggag gcagcgtcta gaaagcaaag aaacggtgtc caaagacccc 540
ggagagttga gtgagcgcag atccgtgacg cctgcggtac gctagggcat ccaggctagg 600
gtgtgtgtgt gcgggtcggg gggcgcacag agaccgcgct ggtttaggtg gacccgcagt 660
cccgcccgca tctggaacga gctgcttcgc agttccggct cccggcgccc cagagaagtt 720
cggggagcgg tgagcctagc cgccgcgcgc tcatgtttat t 761

<210> SEQ ID NO 14
<211> LENGTH: 1198
<212> TYPE: DNA
<213> ORGANISM: Homo sapiens

<400> SEQUENCE: 14
agtcactcca ggatcagagg ccgcgtcggt tctgcttggg gcatgggcag agggaggctg 60
ctggggccaa gccccggctg gacgcgaggg aagaaactcg tcccaggacc cgcacgccca 120
tacctggctg tcccagagct cttccctagg ccggcacctt cgctcttcct cttccccacc 180
ccctagccct tttgtctctt tttcagacgg atgttttcag tctcaagtgg ttttattttc 240
cgcacaaaac cctgagatca agggcagatc acagactgta ccggaggctc gggtttccct 300
ggactctgtg ctgttctgcg tcccagggtt ggctaggaag gaaggcctgg gccggcgagg 360
tgacgggtct cccgcccagg tcggcaggac ggggggaggt gtgtcccggt aggtccctgg 420
tgagctcacc cgtggcatcg gggacccgcg ggaacccacc gggcgcccac tagagactcg 480
ggtcctaccc tcccccacac tactccaccg aaatgatcgg aagggcgcgc taggcctgct 540
tccaagggct cagtgataaa ggcctcaaaa tcacactcca tcaagacttg gttgaagctt 600
tgggtaggtt tgttgttgtt gttgttgttg tttgtttgtt tgttttagca gacacgtcct 660
ggaaagaggt cctcagaacc caaaggttca ataatgattt gtggatggat tgattatagt 720

```
ctgatatcgc tctggttcca cagaaacccg gagctccttg gcccactgtt accccagcag    780

acctaaatgg acggtttctg tttttcactg gcagctcaga actggaccgg aagaagttcc    840

cctccacttc ccccctcccg acaccagatc attgctgggt tttattttc ggggaaaaa    900

caacaacaac aacaacaaaa aaaacactag gtccttccag actggatcag gtgatcgggc    960

aaaaaccctc aggctagtcc ggctgggtgc ccgagcatga aaaggcctcc gtggccgttt   1020

gaacagggtg ttgcaaatga gaacttttgt aagccataac cagggcatcc tgagggtctg   1080

agttcacggt caaggctgtg ggctactagg tccagcgagt ccaggcctcg ccccgccccc   1140

gagctgccac agccaagatc ttcggcaggg aattcgagac cagggtcctc ccactcct     1198
```

<210> SEQ ID NO 15
<211> LENGTH: 377
<212> TYPE: DNA
<213> ORGANISM: Homo sapiens

<400> SEQUENCE: 15

```
tttcgtgccg ctgttttcaa tgcgctaacg aggcacgtta ttcttagccg cgtccgggag     60

gggatcacat tcctgcgcag ttgcgctgct ggcggaagtg acttgttttc taacgaccct    120

cgtgacagcc agagaatgtc cgtttctcgg agcgcagcac agcctgtccc atcgagaagc    180

ctcgggtgag gggcccggtg ggcgcccgga ggccgctgga gggctgtggg agggacggtg    240

gctccccact cccgtggcga agggcaggca aaccagaagc ctcttttgag agccgtttgg    300

gattgagacg agtaagccac agcgagtggt tagaagtagg ttaggaagaa ggggaggtaa    360

gaaagccgag tagggtt                                                   377
```

<210> SEQ ID NO 16
<211> LENGTH: 256
<212> TYPE: DNA
<213> ORGANISM: Homo sapiens

<400> SEQUENCE: 16

```
gttcggtgga caagggggca gcgcccacag caagccggaa agagggaggc gcggggccgc     60

gcttggggcc tgccgctgca cgccagcctg ggcaaagagc tgccaccttc tgcgggcgaa    120

gcgggtcggg acgcaggacg gcagcggggc tggaggcagc tacgtgggtc cacaccccca    180

tgccctgcaa ggctccttgg ccctgcttct cctctgtctc ggcgggagag gagcagcctc    240

ggttttacag aatttc                                                    256
```

<210> SEQ ID NO 17
<211> LENGTH: 189
<212> TYPE: DNA
<213> ORGANISM: Homo sapiens

<400> SEQUENCE: 17

```
tgtgccattt agtgagaggt gttttgggca aagaatcaat ttaactgtga ctgaccgacg     60

ggcttgactg tattaattct gctaccgaaa aaaaaaaaaa aaaaaaagca atgagccgca    120

agccttggac tcgcagagct gccggtgccc gtccgagagc cccaccagcg cggctcacgc    180

ctcagtctc                                                            189
```

<210> SEQ ID NO 18
<211> LENGTH: 707
<212> TYPE: DNA
<213> ORGANISM: Homo sapiens

<400> SEQUENCE: 18
agagtcccag ttctgcaggc cgctccaggg ctaggggtag agatggtggc aggtggtgcg 60
tcaactctct agggaagagg aacttgcatt acaaagactt gtctttctga gctgaagtca 120
aaacgggggc gtcaagcgcg ctccgtttgg cggcggtgga ggggccgcgc gcccgcgctg 180
tcccagccgg agctgccctg gctggtgatt ggaggtttaa cgtccggaat tcaggcgctt 240
ctgcagctca gatttgccgg ccaaggggcc tcagttgcaa cttttcaaaa tggtgtttct 300
ggaaaataac aaattcagac tcaactggtg acagcttttg gctatagaga atgaaactgc 360
ttccctttgg cggtggaact cttaaacttc gaagagtgaa agaatacaat gaaataaaat 420
gccataagat cactggattt ttcagaaaaa ggaagacccc aaattactcc caaaatgagg 480
ctttgtaaat tcttgttaaa aatctttaaa tctcgaattt cccccctacaa catctgatga 540 gtgctttaag agcaaacgag caaatcccac ctcgagaatc aacaaaccca agctctggcc 600
aaggctctcc ccgcgttttc ttctcgtgac ctggggaatg tcccgcccca tcgctcacct 660
ggctcttgtc atctcgctca tcttgaagtg acccgtggac aatgctg 707

<210> SEQ ID NO 19
<211> LENGTH: 182
<212> TYPE: DNA
<213> ORGANISM: Homo sapiens

<400> SEQUENCE: 19
agctgccctc tgtggccatg agcgggtgtc cagccccttc caaggctgca ccggggagac 60
gctggttttc tgctcgctgt gaccgaacaa agcccctaag agtcagtgcg cggaacagaa 120
gagccggacc ccgacgggcc gagtcccaac gtgaggcacc cggcagagaa aacacgttca 180
cg 182

<210> SEQ ID NO 20
<211> LENGTH: 179
<212> TYPE: DNA
<213> ORGANISM: Homo sapiens

<400> SEQUENCE: 20
cctcggcagc accggcatgg ctggaggcca gtacggccag gtgtggcggg agggagcgcc 60
gtctggcttg ggtcgtccat cctgacagga cgctgcaagg gcaggagccc cgcgccccgt 120
gtcctgcgcc cccgctcgag gacaagcccc agccgccggt ctccgctggg ttccgacag 179

<210> SEQ ID NO 21
<211> LENGTH: 369
<212> TYPE: DNA
<213> ORGANISM: Homo sapiens

<400> SEQUENCE: 21
ctttaagagg ctgtgcaggc agacagacct ccaggcccgc taggggatcc gcgccatgga 60
ggccgcccgg gactatgcag gagccctcat caggcgagtg ccccgcgtcc ccctgattgc 120
cgtgcgcttc caatcgcctt gcgttcggtg gcctcatatt cccctgtgcg cctctagtac 180
cgtaccccgc tcccttcagc cccctgctcc ccgcattctc ttgcgctccg cgaccccgcg 240
cacacaccca tccgccccac tggtgcccaa gccgtccagc cgcgcccgcg ggcagagccc 300
aatcccgtcc cgcgcctcct caccctcttg cagctgggca caggtaccag gtgtggctct 360
tgcgaggtg 369

<210> SEQ ID NO 22
<211> LENGTH: 176
<212> TYPE: DNA
<213> ORGANISM: Homo sapiens

<400> SEQUENCE: 22
agacttgcag aactcgggcc ccctggagga gacctaaccg ccacggtctt ggggaggttc 60
cggagggcct cggttgtctg cactcccaac accaagaaac ccctgagacg cgaagctgcc 120
agcgtgctgc cctcagagca gggcgacgca aagccagcgg accccggggt ggcggg 176

<210> SEQ ID NO 23
<211> LENGTH: 167
<212> TYPE: DNA
<213> ORGANISM: Homo sapiens

<400> SEQUENCE: 23
tgctcggctg gggggctcgc tccgcacttt cggtgccaga aaatgcccag aggagcgggg 60
cggccccaga gcctcctttc ggggcgcgag gcccggcgcg tgtgtacgga gtccagtccc 120
cccagggagt ggggtgcccg caccttcccc tccgcgctcg gagccac 167

<210> SEQ ID NO 24
<211> LENGTH: 1205
<212> TYPE: DNA
<213> ORGANISM: Homo sapiens

<400> SEQUENCE: 24
tcttgcacac ctgcttgtag ttctgcaccg agatctggtc gttgaggaac tgcacgcaga 60
gcttggtgac ctgggggatg tgcaggatct tgctgaccga cagcacctcc tccaccgtgt 120
ccagggacag ggtcacgttg gccgtgtaga ggtactcgag caccaggcgc agcccgatgg 180
acgagcagcc ctgcagcacc aggttgttga tggcccgggg gctggtcagc agcttgtcgt 240
cgggggagga agaaggagtc ccgggctcct cctgcggcgg cggctgctgc tgctgtgacg 300
gctgctgctg cggcggctgc tgctggtcct tgggggcccc caggccgtcc tggccgccga 360
cccctccccc gagagggggg tggctggaga agagcgatcg gaagtactgc gagcaggagg 420
ccagcacggc cttgtggcaa tggaactgct ggccctgggc cgtcagggtc acgtcgcaaa 480
acagctgctt cctccacagc aggttgaggc cgtgcagcag gttgtcgctg tggctggggt 540
cgaaggtgga ggtcctgtcc ccggatctgg acatggcgag ctgactcggt gcacctggct 600
ttaaaccctc ctccaacctg gcagacaggg gtgggggatg ggagggaggg gagcagggtg 660
gtggagcggg tggggtgtgg tcggggtggg gaagggtgtg gaggggaggg gagggcgaag 720
aacaagaatc aaggctcagc ttgactccct cctggcgcgc tccggacccc gaccctagga 780
ggaaagtccg aagacgctgg atccgtgagc gccaccagaa gggccctgtc tggggtcccg 840
gcgccggttc tgcgccctgc ggctcctctc gccacctccc acacacttcg tccctcactt 900
tcctaaaacc aaccacctca gctcggctgt tggcagcaac agcagtggca gcagcgacgg 960
caaagtggcg gctgaggccg aggcacctcg tgggctcgtg tccatgccgg gccagatgaa 1020
gggaaaggcc gggaagtggg gagccggggg tgccctgaaa gctcagaggc gaccgacggc 1080
gaaggttcca ggtcaacttg tgcccgaagc tttgcttttc gcagttggcc cagtttgggg 1140
gagggggtag gaacaggggc ccgaccagcg tgcggggtgt gcgaatctta gctctccaaa 1200
agctg 1205

<210> SEQ ID NO 25

<211> LENGTH: 44
<212> TYPE: DNA
<213> ORGANISM: Homo sapiens

<400> SEQUENCE: 25
cctctgtgtt agtgccctcg ggaatttggt tgatggggtg tttg 44

<210> SEQ ID NO 26
<211> LENGTH: 5002
<212> TYPE: DNA
<213> ORGANISM: Homo sapiens

<400> SEQUENCE: 26
tgatgtcgca cctgaacggc ctgcaccacc cgggccacac tcagtctcac gggccggtgc 60
tggcacccag tcgcgagcgg ccaccctcgt cctcatcggg ctcgcaggtg gccacgtcgg 120
gccagctgga agaaatcaac accaaagagg tggcccagcg catcacagcg gagctgaagc 180
gctacagtat cccccaggcg atctttgcgc agagggtgct gtgccggtct caggggactc 240
tctccgacct gctccggaat ccaaaaccgt ggagtaaact caaatctggc agggagacct 300
tccgcaggat gtggaagtgg cttcaggagc ccgagttcca gcgcatgtcc gccttacgcc 360
tggcaggtaa ggccggggct agccaggggc caggctgctg ggaagagggc tccgggtccg 420
gtgcttgtgg cccaagtctg cgcgccgagt cacttctctt gattctttcc ttctctttcc 480
tatacacgtc ctctttcttc tcgtttttat ttcttcttcc attttctctt tctcttccgc 540
tcttccccta ctttcccttc tcccttttct ttttctttct tactctctcc ttgtccctga 600
gctttcattg accgaccccc ccccatttca ttcgccctcc cctcaatgtg ccaacctttg 660
ccctatttcc gatcttccca ggtactggga ggcgggatgg gggtgtgcgt tttcctctag 720
gagccctgtc tttccaagac ccacagaaac caggacctgc ccttattcaa aaccccatgc 780
acttcaagtc tcttttagac aacacatttc aattttccgg gctgactagt ctccctgtgc 840
agaggcagtt gagaggcttt gctctgcaga gggaaaagag ctctctactc tcccacccac 900
catataggca aacttatttg gtcattggct gaaggcacag ccttgccccc gcggggaacc 960
ggcggccagg atacaacagc gctcctggag cccatctctg gccttggcgt tggcgcaggg 1020
actttctgac cgggcttgag ggctcgggc cagctccaat gtcactacct acagcgaggg 1080
cagggtgtaa ggttgagaag gtcacattca ccgctttggg aggacgtggg agaagagact 1140
gaggtggaaa gcgctttgcc ttgctcaccg gccgtccttg ccccggtccc agcgtttgct 1200
gggatttgcc aggatttgcc ggggctccgg gagaccctga gcactcgcag gaagaggtgc 1260
tgagaaatta aaaattcagg ttagttaatg catccctgcc gccggctgca ggctccgcct 1320
ttgcattaag cgggcgctga ttgtgcgcgc ctggcgaccg cggggaggac tggcggcccg 1380
cgggagggga cgggtagagg cgcgggttac attgttctgg agccggctcg gctctttgtg 1440
cctcctctag cggccaagct gcgaggtaca gccctctatt gttctaggag cacagaaacc 1500
tcctgtgtgg gcggcgggtg cgcgagctag agggaaagat gcagtagtta ctgcgactgg 1560
cacgcagttg cgcgcttttg tgcgcacgga ccccgcgcgg tgtgcgtggc gactgcgctg 1620
cccctaggag caagccacgg gcccagaggg gcaaaatgtc caggtccccc gctgggaagg 1680
acacactata ccctatggca agccagggtg ggcgacttcc catggatcgg gtggaggggg 1740
gtatctttca ggatcggcgg gcggtctagg ggaacaattc gtggtggcga tgatttgcat 1800
agcgcgggtc ttgggatgcg cgcggttccg agccagcctc gcacagctcg cttccggagc 1860
tgcgagctca ggtttccacc cccgatcccc cgggctttcc tcgcaccgct gagcccagct 1920

-continued

```
tgtggggtgc actcgaccaa cgcccgacag ggctggggaa tgtgacaggc agcaggttca   1980
cccgggcttg gggaggggga gtttccgctt tgacagcatt ttcctttgcc gtctgctggt   2040
ggattcctat tcccagtcgg taatcgcccc gcagtgttga tctaagaagg taaagaaaac   2100
taggtttccc tgcaaagagc ctcccccaaa tcggcggact ccggatactt tgagtggatt   2160
tagaaattta tgtaatcttt ctcctttagt ttatttttca tcctctccta cagttttctc   2220
tgatttgctg ttggttcggg gcaagataaa gcagccagta gagagcgata ataatagcgg   2280
cgggaaatga actggagact ggctgacagt tcttaacatt ttgtcataga tccccccgaa   2340
tgtcccaggc tgtctctggt gggttttagt acccgccggc ttcttgggca ccggggacca   2400
gaaggaactt ggcagctggt cttaggggta cagttaaagg caggatgaca gctattctcc   2460
tgctcatctc agagcgctgc cgccccctca tgccggtcgc gcaaagaaca cagcttttaa   2520
aaaacacgtg ccttctgccc atataggtct gaaagtgatg aggaaagtaa tgcttcgcct   2580
attagcgagt ttcagctttt aaaatgatcc caagcgttgc tgagatgaga aagcgtggca   2640
tcccgggggt cctcagcccc acccgcgccc atggtgcaag tctgcaggga caggcccggg   2700
acagcactgc ccacgctgct agattttccg cagaggatcg ctgaagctgc cttcgtggga   2760
gacagaatgc ctcctccagc gagtggaaaa ggcctgctga ggaccccgct ttgctcgagc   2820
attcaaatgt gtgtctgttt tattaccctg ggttgaaaag ggacaagagc tttagccttt   2880
ttatctggcc attttatcag caactacaag tgtgttgagt ggttattatt acataggagg   2940
cttttcagtt tggggtcagt agatcagtct cttcagacac tgatgcagaa gctgggactg   3000
gtaagtaggt attatgtgct cggagcgcta ggggacagga gcaaatggag aagaaaagcg   3060
gaggctttct ccgcccggag tatcgatcgg aatccccgcc ggtacgccgc agagggccct   3120
cgccgttggg ccccgggggt ttaacaagcc cagccgctcc gcaggcggct cggccggact   3180
ctcagaccgg tgcctggaag acaccgtccc tgccccccctc ccgccaaacc tgcctcttct   3240
ctttctctca taggttatag gttccctttc tctctcattt tggccccgcc cccgggtcct   3300
gccaaacagc caagcaggcc ggggtttagg gggctcagaa tgaagaggtc tgatttggcc   3360
agcgccggca aagctcaccc ttaggcgagg tcacaacaga ggcaggtcct tcctgcccag   3420
cctgccggtg tagtcacagc caagggtggc acttgaaagg aaaagggaga aaacttcgga   3480
gaaatttaga ttgccccaac gttagatttc agagaaattg actccaaatg cacggattcg   3540
ttcggaaagg gcggctaagt ggcaggtggt tgcaaccccg cccggtcggg ccttcgcaga   3600
ggttccccaa gaccagccct tgcagggcgg ttttcagcaa cctgacaaga ggcggccaag   3660
acaaatttct gcgggttcga gcacacactc tcgggcgttg ggccccagag acctctaaac   3720
caagcacaaa caagaaggga gtgagagaac ccaggctaga acttgcacgg gcatcccact   3780
gaggaaaagc gaggcctcgg tggcaggcat gttttcttcc gacgcccgaa aatcgagccg   3840
agcgcccgac tacatttact gcagaggttt ccgcctccag tgagcccgga tcccccagcg   3900
gcctgcccgg agctggtctc cagtccccgc cgtagtccga cgcacggccc tctcctggca   3960
gcaagctccc agcggccagt ctgaagccaa ttctgttcag gcggccgagg gcccttagcc   4020
aacccaccat gatgtcgcct gggccacctg atgcccgcag cggcgggaca cggcccgggc   4080
agtgcgcagt ggctcctgct aggggcaccg cgtgcgtgct tgtctcccgc tgcgccgggg   4140
acgtccttgg gtgacacggg ccgctgggca cctcccaagc cgaggaaacg gaccccccttc   4200
gcagagtctc gcgcccaccc cccaacctcc cacctcgttt ctcgctgcta gggctcccga   4260
```

-continued ctcagcccac ctctcctggc ggtttagtta gggatcagag ctggagaggc tgaacgcaac 4320
ccgtgccagt acggaacaga cgatatgttt gcctgctagc tgcttggatg aataattgaa 4380
aagttcgctg cagtctgtgc ttcgtcaagt cccgggtgcc gggagaacac cttcccaaca 4440
cgcatcaggg tgggcgggag cgggcagagg aggcgggacc cgagggagga gagtgaaccc 4500
gagcaggaga agcagcccag gcagccaggc gccctcgatg cgagaggctg ggcatttatt 4560
tttattccag gctttccact gtgtggttat gtcactttct caaacaaatg tgtatatgga 4620
gggagatcga tgctgataat gtttagaaga ttaaaagagc attaatgctg gcaacaataa 4680
cgtaaacgtg tggacccaga tttcattgat ctggaacttg atccggcgcg tttccagtaa 4740
gcccgacggc gcgctcttcc cagcagagcg ctcaccagcg ccacggcccc gcggttttcc 4800
agcggtgccg cttcgccagc tctgcgcggg ttctcccgtc tgaccgcagc tcctcccccg 4860
cgaggcccca gcccgcctta cttccccgag gttttctcct cctctcgcgg ggctctctgc 4920
cctctgcacc ccctcccccg acctctgcac cacccgcccc tgtgcgcaca caccgctact 4980
tgcgcttccg gcgatccgcc tg 5002

<210> SEQ ID NO 27
<211> LENGTH: 150
<212> TYPE: DNA
<213> ORGANISM: Homo sapiens

<400> SEQUENCE: 27
aaccggagat ctgcttggtg aactgagagg agtccttagg agagcgggga cgccaggggc 60
cgggggacac ttcgctctcg ccctagggaa ggtggtcttg acgctttcta ttgaagtcaa 120
acttgaaaat atcagctgcc gctggactat 150

<210> SEQ ID NO 28
<211> LENGTH: 339
<212> TYPE: DNA
<213> ORGANISM: Homo sapiens

<400> SEQUENCE: 28
cgtgagcaga acgcccgccc tggagcagtt aggaccgaag gtctccggag agtcgccggc 60
ggtgccaggt aacgcagagg gctcgggtcg ggccccgctt ctggggcttg ggactccggg 120
cgcgcggagc cagccctctg gggcgaaatc cccgggcggc gtgcgcggtc cctctccgcg 180
ctgtgctctc ccagcaactc cctgccacct cgacgagcct accggccgct ccgagttcga 240
cttcctcgga cttagtggga gaaggggttg gaaatgggct gccgggactg ggggagctgc 300
tctctggaag cagggaagct ggggcgcacc ggggcaggt 339

<210> SEQ ID NO 29
<211> LENGTH: 1961
<212> TYPE: DNA
<213> ORGANISM: Homo sapiens

<400> SEQUENCE: 29
tagaagagga agactcctct ggccccacta ggtatcatcc gcgctctccc gctttccacc 60
tgcgccctcg cttgggccaa tctctgccgc acgtgtccat ccctgaactg cacgctatcc 120
tccacccccg gggggttcct gcgcactgaa agaccgttct ccggcaggtt ttgggatccg 180
gcgacggctg accgcgcgcc gcccccacgc ccggttccac gatgctgcaa tacagaaagt 240
ttacgtcggc cccgacccgc gcgggactgc agggtccgcc ggagcgcggc gcagaggctt 300
ttcctgcgcg ttcggccccg ggaaaggggc gggagggctg gctccgggag cgcacgggcg 360
cggcggggag ggtactcact gtgaagcacg ctgcgcccat ggatcatgtc tgtgcgttac 420
accagaggct ccgggctcca ctaattccat ttagagacgg gaagacttcc agtggcgggg 480
ggaggacagg gtcgagaggt gttaaagacg caaagcaaga aggaaataaa ggggggccga 540
gagggagacc gagaggaagg gggagctccg agcccacgct gcagccagat ccggatgagt 600
ccgtcctccg ccccgggcgg gctctcgctc tcgctggccc tcagcgccgc gcagccagca 660
gcatccccac cgtgacgctc gcatcacacc cgggcgccgg ccgccaccat ccgcgccgcc 720
gccgtcagga ccctcctccc gggcatcgtc gccgccgcgg ggtcgggagg acgcggcgcg 780
cgggaggcgg cggtcgcagg gcgagccccg ggacgccccg agccggggcc ggggccgggg 840
agagggcgca gcgaggtggg ggccagtcca gaccgacggc agcgacggag cgggcggcgg 900
cggcggcgcc ggcggcggcg gggtggctca gtccccagtc tcagacgcgc cgcgcagcag 960
gtcggagcag cctccccggg aggatgtcca gcggcagcgc tcctcgctcc agcccttggg 1020
gatcttccgc tgaggcattg aaggcaggaa gaaggggtcc gtcatcggct cgccgggctg 1080
cgcgccacct ctgctatctt gcggaaagag gagcgggtgg gtgggcgtct gggaggcggg 1140
ctggagggcg gtgcagggga gcggggcggc cggggggggg gccggggggc ggggaaggga 1200
gggaggagaa aggagccgga agagggcaga gttaccaaat gggctcctta gtcatggctt 1260
ggggctccac gaccctcctg gaagcccgga gcctgggtgg gatagcgagg ctgcgcgcgg 1320
ccggcgcccc ggggctggtg cgcggcagaa tggggccgcg gcggcggcag caaggacatc 1380
ccagccgcgc ggatctgggg gaggggcggg gagggggtga ggacccggct gggatccgcg 1440
gctcggcccg ccagggcgca gagagaggat gcagccgcaa atcccgagcc ggatcctcgt 1500
gccggacgga aggcgtggaa gcgggagggg ccttcgtgtg aaaatccctt gtggggtttg 1560
gtgtttcact ttttaaaggt tagaccttgc gggctctctg cctcccaccc cttcttttcc 1620
atccgcgtaa aggaactggg cgccccctct ccctccctcc ctggggcgca ggtttcgccg 1680
cggactccgc gctcagcttg ggagacacgg caggggcgcg ccccagggaa aggcggccgt 1740
aaaagtttcg cggttgagca ctgggcctga tgtccagtcc ccccaccaaa ttactcctgc 1800
aaagacgcgg gcttcttgca attgagcccc ccacctcgag gtatttaaaa ccaccccaag 1860
gcacacacgg acccccgttc ccccgcgcca cttcctccta caggctcgcg cggcgcgtta 1920
aagtctggga gacacgagtt gcggggaaac agcaccggaa g 1961

<210> SEQ ID NO 30
<211> LENGTH: 314
<212> TYPE: DNA
<213> ORGANISM: Homo sapiens

<400> SEQUENCE: 30
aagaaacagc tcatttcgga gctgaggaca aggcgtggga agaagacgcg tttggtttca 60
cccaggcggg tggcggcaaa gctgtgggat gcgcgctgca cactccttcc gtcatcccgt 120
tcccaccttc cacacacacc tgcgggaggt cggacatgtc ctgattgcgt gttcatcacg 180
atggcaaacc gaacatgagg agaacgccac tgacgctggg tgcgccggct ttcccagccc 240
tcgtgcataa cggggaggga gatgcagaag ttttttccaa catcggtgca aaggggaagc 300
tgaggttttc ctat 314

<210> SEQ ID NO 31
<211> LENGTH: 584
<212> TYPE: DNA

<213> ORGANISM: Homo sapiens

<400> SEQUENCE: 31
tctgtcagct gctgccatgg ggcagcggga aggccctgga gggtgcctgg gctgtgtctg 60
gtcccggcca cgcgtccctg cagcgtctga gaccttgtgg aacacacttg acccggcgct 120
gggacggggt cggcccacac gcaccgccag cccgcaggag tgaggtgcag gctgccgctg 180
gctccttagg cctcgacagc tctcttgagg tcggccctcc tcccctcccg agagctcagc 240
agccgcagac ccaggcagag agagcaaagg aggctgtggt ggcccccgac gggaacctgg 300
gtggccgggg gacacaccga ggaactttcc gccccccgac gggctctccc accgaggctc 360
aggtgctcgt gggcagcaag gggaagcccc atggccatgc cgcttccctt tcaccctcag 420
cgacgcgccc tcctgtgccc gcggggaaca agacggctct cggcggccat gcaggcggcc 480
tgtcccacga acacgatgga gacctcagac gccgtcccca ccctgtcact gtcaccatca 540
cccatcctgt cccctcacgc ctccccacat cccatcatta ctac 584

<210> SEQ ID NO 32
<211> LENGTH: 349
<212> TYPE: DNA
<213> ORGANISM: Homo sapiens

<400> SEQUENCE: 32
gaagtagaat cacagtaaat gaggagttag ggaatttagg gtagagatta aagtaatgaa 60
cagaggagga ggcctgagac agctgcagag agaccctgtg ttccctgtga ggtgaagcgt 120
ctgctgtcaa agccggttgg cgctgagaag aggtaccggg ggcagcaccc gcctcctggg 180
agagggatgg gcctgcgggc acctggggga accgcacgga cacagacgac actataaacg 240
cgggcgagac atcagggacc gggaaacaga aggacgcgcg tttcgagcag ctgcccagtg 300
ggccacaagc cccgccacgc cacagcctct tcccctcagc acgcagaga 349

<210> SEQ ID NO 33
<211> LENGTH: 3510
<212> TYPE: DNA
<213> ORGANISM: Homo sapiens

<400> SEQUENCE: 33
tactccggcg acgggaggat gttgagggaa gcctgccagg tgaagaaggg gccagcagca 60
gcacagagct tccgactttg ccttccaggc tctagactcg cgccatgcca agacgggccc 120
ctcgactttc acccctgact cccaactcca gccactggac cgagcgcgca aagaacctga 180
gaccgcttgc tctcaccgcc gcaagtcggt cgcaggacag acaccagtgg gcagcaacaa 240
aaaaagaaac cgggttccgg gacacgtgcc ggcggctgga ctaacctcag cggctgcaac 300
caaggagcgc gcacgttgcg cctgctggtg tttattagct acactggcag gcgcacaact 360
ccgcgccccg actggtggcc ccacagcgcg caccacacat ggcctcgctg ctgttggcgg 420
ggtaggcccg aaggaggcat ctacaaatgc ccgagccctt tctgatcccc accccccgc 480 tccctgcgtc gtccgagtga cagattctac taattgaacg gttatgggtc atccttgtaa 540
ccgttggacg acataacacc acgcttcagt tcttcatgtt ttaaatacat atttaacgga 600
tggctgcaga gccagctggg aaacacgcgg attgaaaaat aatgctccag aaggcacgag 660
actggggcga aggcgagagc gggctgggct tctagcggag accgcagagg gagacatatc 720
tcagaactag gggcaataac gtgggtttct ctttgtattt gtttattttg taactttgct 780
acttgaagac caattattta ctatgctaat ttgtttgctt gtttttaaaa ccgtacttgc 840

-continued

```
acagtaaaag ttccccaaca acggaagtaa cccgacgttc ctcacactcc ctaggagact    900
gtgtgcgtgt gtgcccgcgc gtgcgctcac agtgtcaagt gctagcatcc gagatctgca    960
gaaacaaatg tctgaattcg aaatgtatgg gtgtgagaaa ttcagctcgg ggaagagatt   1020
agggactggg ggagacaggt ggctgcctgt actataagga accgccaacg ccagcatctg   1080
tagtccaagc agggctgctc tgtaaaggct tagcaatttt ttctgtaggc ttgctgcaca   1140
cggtctctgg cttttcccat ctgtaaaatg ggtgaatgca tccgtacctc agctacctcc   1200
gtgaggtgct tctccagttc gggcttaatt cctcatcgtc aagagttttc aggtttcaga   1260
gccagcctgc aatcggtaaa acatgtccca acgcggtcgc gagtggttcc atctcgctgt   1320
ctggcccaca gcgtggagaa gccttgccca ggcctgaaac ttctctttgc agttccagaa   1380
agcaggcgac tgggacggaa ggctctttgc taacctttta cagcggagcc ctgcttggac   1440
tacagatgcc agcgttgccc ctgccccaag gcgtgtggtg atcacaaaga cgacactgaa   1500
aatacttact atcatccggc tcccctgcta ataaatggag gggtgtttaa ctacaggcac   1560
gaccctgccc ttgtgctagc gcggttaccg tgcggaaata actcgtccct gtacccacac   1620
catcctcaac ctaaaggaga gttgtgaatt ctttcaaaac actcttctgg agtccgtccc   1680
ctccctcctt gcccgccctc taccccctcaa gtccctgccc ccagctgggg gcgctaccgg   1740
ctgccgtcgg agctgcagcc acggccatct cctagacgcg cgagtagagc accaagatag   1800
tggggacttt gtgcctgggc atcgtttaca tttggggcgc caaatgccca cgtgttgatg   1860
aaaccagtga gatgggaaca ggcggcggga aaccagacag aggaagagct agggaggaga   1920
ccccagcccc ggatcctggg tcgccagggt tttccgcgcg catcccaaaa ggtgcggctg   1980
cgtggggcat caggttagtt tgttagactc tgcagagtct ccaaaccatc ccatccccca   2040
acctgactct gtggtggccg tattttttac agaaatttga ccacgttccc tttctccctt   2100
ggtcccaagc gcgctcagcc ctccctccat ccccccttgag ccgcccttct cctccccctc   2160
gcctcctcgg gtccctcctc cagtccctcc ccaagaatct cccggccacg ggcgcccatt   2220
ggttgtgcgc agggaggagg cgtgtgcccg gcctggcgag tttcattgag cggaattagc   2280
ccggatgaca tcagcttccc agcccccccgg cgggcccagc tcattggcga ggcagcccct   2340
ccaggacacg cacattgttc cccgccccccg cccccgccac cgctgccgcc gtcgccgctg   2400
ccaccgggct ataaaaaccg gccgagcccc taaaggtgcg gatgcttatt atagatcgac   2460
gcgacaccag cgcccggtgc caggttctcc cctgaggctt ttcggagcga gctcctcaaa   2520
tcgcatccag agtaagtgtc cccgccccac agcagccgca gcctagatcc cagggacaga   2580
ctctcctcaa ctcggctgtg acccagaatg ctccgataca gggggtctgg atccctactc   2640
tgcgggccat ttctccagag cgactttgct cttctgtcct ccccacactc accgctgcat   2700
ctccctcacc aaaagcgaga agtcggagcg acaacagctc tttctgccca agccccagtc   2760
agctggtgag ctccccgtgg tctccagatg cagcacatgg actctgggcc ccgcgccggc   2820
tctgggtgca tgtgcgtgtg cgtgtgtttg ctgcgtggtg tcgatggaga taaggtggat   2880
ccgtttgagg aaccaaatca ttagttctct atctagatct ccattctccc caaagaaagg   2940
ccctcacttc ccactcgttt attccagccc gggggctcag ttttcccaca cctaactgaa   3000
agcccgaagc ctctagaatg ccacccgcac cccgagggtc accaacgctc cctgaaataa   3060
cctgttgcat gagagcagag gggagataga gagagcttaa ttataggtac ccgcgtgcag   3120
ctaaaaggag ggccagagat agtagcgagg gggacgagga gccacgggcc acctgtgccg   3180
```

ggaccccgcg ctgtggtact gcggtgcagg cgggagcagc ttttctgtct ctcactgact 3240
cactctctct ctctctccct ctctctctct ctcattctct ctcttttctc ctcctctcct 3300
ggaagttttc gggtccgagg gaaggaggac cctgcgaaag ctgcgacgac tatcttcccc 3360
tggggccatg gactcggacg ccagcctggt gtccagccgc ccgtcgtcgc cagagcccga 3420
tgaccttttt ctgccggccc ggagtaaggg cagcagcggc agcgccttca ctgggggcac 3480
cgtgtcctcg tccaccccga gtgactgccc 3510

<210> SEQ ID NO 34
<211> LENGTH: 333
<212> TYPE: DNA
<213> ORGANISM: Homo sapiens

<400> SEQUENCE: 34
ttaattcgaa aatggcagac agagctgagc gctgccgttc ttttcaggat tgaaaatgtg 60
ccagtgggcc aggggcgctg ggacccgcgg tgcggaagac tcggaacagg aagaaatagt 120
ggcgcgctgg gtgggctgcc ccgccgccca cgccggttgc cgctggtgac agtggctgcc 180
cggccaggca cctccgagca gcaggtctga gcgtttttgg cgtcccaagc gttccgggcc 240
gcgtcttcca gagcctctgc tcccagcggg gtcgctgcgg cctggcccga aggatttgac 300
tctttgctgg gaggcgcgct gctcagggtt ctg 333

<210> SEQ ID NO 35
<211> LENGTH: 385
<212> TYPE: DNA
<213> ORGANISM: Homo sapiens

<400> SEQUENCE: 35
ccggtcccca gtttggaaaa aggcgcaaga agcgggcttt tcagggaccc cggggagaac 60
acgagggctc cgacgcggga gaaggattga agcgtgcaga ggcgccccaa attgcgacaa 120
tttactggga tccttttgtg gggaaaggag gcttagaggc tcaagctata ggctgtccta 180
gagcaactag gcgagaacct ggccccaaac tccctcctta cgccctggca caggttcccg 240
gcgactggtg ttcccaaggg agccccctga gcctaccgcc cttgcagggg gtcgtgctgc 300
ggcttctggg tcataaacgc cgaggtcggg ggtggcggag ctgtagaggc tgcccgcgca 360
gaaagctcca ggatcccaat atgtg 385

<210> SEQ ID NO 36
<211> LENGTH: 105
<212> TYPE: DNA
<213> ORGANISM: Homo sapiens

<400> SEQUENCE: 36
gcgcaggtcc ccccagtccc cgagggagtg cgcccgacgg aaacgcccct agcccgcggg 60
cctcgctttc ctctcccggg ttcctgggtc acttcccgct gtctc 105

<210> SEQ ID NO 37
<211> LENGTH: 147
<212> TYPE: DNA
<213> ORGANISM: Homo sapiens

<400> SEQUENCE: 37
ttccctcgcg gctttggaaa gggggtgcaa atgcaccctt ctgcgggccc gctacccgct 60
gcaacacctg tgtttccttt ctgggcacct tctaggtttc tagatattgc tgtgaatacg 120
gtcctccgct gtacagttga aaacaaa 147

<210> SEQ ID NO 38
<211> LENGTH: 365
<212> TYPE: DNA
<213> ORGANISM: Homo sapiens

<400> SEQUENCE: 38
tgggaattta ggtcgggcac tgccgatatg tcgccttcca caaggcgggc ccgggcctct 60
gctgaccgtg caccggtcct ggggctgggt aattctgcag cagcagcgca gcccatgccg 120
gggaatttgc gggcagagga gacagtgagg cccgcgttct gtgcgggaac tcccgagctc 180
acagagccca agaccacacg gctgcatctg cttggctgac tgggccaggc ccacgcgtag 240
taacccggac gtctctctct cacagtcccc ttgcgtctgg ccagggagct gccaggctgc 300
accccgcggt ggggatcggg agaggggcag tgtcgcccat ccccggaagg ctgagcctgg 360
tgcag 365

<210> SEQ ID NO 39
<211> LENGTH: 418
<212> TYPE: DNA
<213> ORGANISM: Homo sapiens

<400> SEQUENCE: 39
cggttttctc ctggaggact gtgttcagac agatactggt ttccttatcc gcaggtgtgc 60
gcggcgctcg caagtggtca gcataacgcc gggcgaattc ggaaagcccg tgcgtccgtg 120
gacgacccac ttggaaggag ttgggagaag tccttgttcc cacgcgcgga cgcttccctc 180
cgtgtgtcct tcgagccaca aaaagcccag accctaaccc gctcctttct cccgccgcgt 240
ccatgcagaa ctccgccgtt cctgggaggg gaagcccgcg aggcgtcggg agaggcacgt 300
cctccgtgag caaagagctc ctccgagcgc gcggcgggga cgctgggccg acaggggacc 360
gcgggggcag ggcggagagg acccgccctc gagtcggccc agccctaaca ctcaggac 418

<210> SEQ ID NO 40
<211> LENGTH: 906
<212> TYPE: DNA
<213> ORGANISM: Homo sapiens

<400> SEQUENCE: 40
agggaatcgg gctgaccagt cctaaggtcc cacgctcccc tgacctcagg gcccagagcc 60
tcgcattacc ccgagcagtg cgttggttac tctccctgga aagccgcccc cgccggggca 120
agtgggagtt gctgcactgc ggtctttgga ggcctaggtc gcccagagta ggcggagccc 180
tgtatccctc ctggagccgg cctgcggtga ggtcggtacc cagtacttag ggagggagga 240
cgcgcttggt gctcagggta ggctgggccg ctgctagctc ttgatttagt ctcatgtccg 300
cctttgtgcc ggcctctccg atttgtgggt ccttccaaga aagagtcctc tagggcagct 360
agggtcgtct cttgggtctg gcgaggcggc aggccttctt cggacctatc cccagaggtg 420
taacggagac tttctccact gcagggcggc ctggggcggg catctgccag gcgagggagc 480
tgccctgccg ccgagattgt ggggaaacgg cgtggaagac accccatcgg agggcaccca 540
atctgcctct gcactcgatt ccatcctgca acccaggaga aaccatttcc gagttccagc 600
cgcagaggca cccgcggagt tgccaaaaga gactcccgcg aggtcgctcg gaaccttgac 660
cctgacacct ggacgcgagg tctttcagga ccagtctcgg ctcggtagcc tggtccccga 720
ccaccgcgac caggagttcc ttcttccctt cctgctcacc agccggccgc cggcagcggc 780
tccaggaagg agcaccaacc cgcgctgggg gcggaggttc aggcggcagg aatggagagg 840
ctgatcctcc tctagccccg gcgcattcac ttaggtgcgg gagccctgag gttcagcctg 900
actttc 906

<210> SEQ ID NO 41
<211> LENGTH: 860
<212> TYPE: DNA
<213> ORGANISM: Homo sapiens

<400> SEQUENCE: 41
cactacggat ctgcctggac tggttcagat gcgtcgttta aagggggggg ctggcactcc 60
agagaggagg gggcgctgca ggttaattga tagccacgga agcacctagg cgccccatgc 120
gcggagccgg agccgccagc tcagtctgac ccctgtcttt tctctcctct tccctctccc 180
acccctcact ccgggaaagc gagggccgag gtaggggcag atagatcacc agacaggcgg 240
agaaggacag gagtacagat ggagggacca ggacacagaa tgcaaaagac tggcaggtga 300
gaagaaggga gaaacagagg gagagagaaa gggagaaaca gagcagaggc ggccgccggc 360
ccggccgccc tgagtccgat ttccctcctt ccctgaccct tcagtttcac tgcaaatcca 420
cagaagcagg tttgcgagct cgaatacctt tgctccactg ccacacgcag caccgggact 480
gggcgtctgg agcttaagtc tgggggtctg agcctgggac cggcaaatcc gcgcagcgca 540
tcgcgcccag tctcggagac tgcaaccacc gccaaggagt acgcgcggca ggaaacttct 600
gcggcccaat ttcttcccca gctttggcat ctccgaaggc acgtacccgc cctcggcaca 660
agctctctcg tcttccactt cgacctcgag gtggagaaag aggctggcaa gggctgtgcg 720
cgtcgctggt gtggggaggg cagcaggctg cccctccccg cttctgcagc gagttttccc 780
agccaggaaa agggagggag ctgtttcagg aatttcagtg ccttcaccta gcgactgaca 840
caagtcgtgt gtataggaag 860

<210> SEQ ID NO 42
<211> LENGTH: 452
<212> TYPE: DNA
<213> ORGANISM: Homo sapiens

<400> SEQUENCE: 42
ggagcctgaa gtcagaaaag atggggcctc gttactcact ttctagccca gcccctggcc 60
ctgggtcccg cagagccgtc atcgcaggct cctgcccagc ctctggggtc gggtgagcaa 120
ggtgttctct tcggaagcgg gaagggctgc gggtcgggga cgtcccttgg ctgccacccc 180
tgattctgca tccttttcgc tcgaatccct gcgctaggca tcctccccga tcccccaaaa 240
gcccaagcac tgggtctggg ttgaggaagg gaacgggtgc ccaggccgga cagaggctga 300
aaggaggcct caaggttcct ctttgctaca aagtggagaa gttgctctac tctggagggc 360
agtggccttt tccaaacttt tccacttagg tccgtaagaa aagcaattca tacacgatca 420
gcgctttcgg tgcgaggatg gaaagaaact tc 452

<210> SEQ ID NO 43
<211> LENGTH: 1992
<212> TYPE: DNA
<213> ORGANISM: Homo sapiens

<400> SEQUENCE: 43
ttttcctgtt acagagctga gcccactcat gtggtgccaa gtagcgacta tctctcggcc 60
acctccaccc agagcaatgt gggcgccccc agcgggtggg agcgattgcc gagcggcgca 120
agggcgttta acgcctaacc ccctcctcct gggttgccaa gccgctaggt cgccgtttcc 180
aacgtggctg cgcgggactg aagtccgacg actcctcgtc ctcagtagga gacacacctc 240
ccactgcccc cagccacgcg agctatgggc agaatcgggg caacggtaat atctggatgg 300
ggcaggctcc cctgaggctg tgcttaagaa aaaaggaatc tggagtagcc tgaggggccc 360
cacgaggggg cctcctttgc gatcgtctcc cagccttagg ccaaggctac ggaggcaggc 420
ggccgagtgt tggcgcccag cccggccgag gactggatgg aggacgagaa gcagcctgcc 480
tctgggcgac agctgcggac gcagcctcgc cgcctcgccg cctcagcctc ggtcccagcg 540
tctctaaagc cgcgcccatt ttacagatgc agggcaggga gacaagaggc atctccgggg 600
gccgagtaga atgatggcgc gggttctccc ggcgccctga tttcgaggct gcgcccgggg 660
ccctacatgc aggcggggag gcctgggccg aaggcgtctg caaggagggg cgagtctgcc 720
cggtccgggc agggagtgag gccacagtca gttctcccta ggaggccgcg cagcgggtag 780
ggtatgggac tgggggacgc aacggggacc tggccgaatc agagccctca gcagagaacg 840
ccgaaaactc tggggccggc cgctcgcttc ccgctagtgg gaatggtttc cggtcatccg 900
ttcccagtcc agccccgggt agggagctct gatttgcaat gcacagcact tgcgaggttc 960
gaatgccccc gcaatttgca gatggaaata ctaagcctag gccgggcgtg gtggctcaag 1020
cctatcatct cagccctttg ggaggccaag ccgggaggat tgtttgagcc caagaattca 1080
aaaccagcct gagcaacata gcgaccccgt ctctacaaaa taaaataaaa taaattatcc 1140
gggcgtggtg gcacgcgcct gtggttccag ctactccgga ggctgaggtg ggaggatcgc 1200
ttgagtccgg gaggtcgagg ctacagtgag ccgtgatcgc accactgcac tccagcctgg 1260
gcgacagagt gagaccttgt ctcaaaaaag gaaaaaaaga aaaagaaagt aagcttcaaa 1320
gaagctctga taatagttct gggtcgtgca gcggtggcgg ccccgcgctc tcgcccctaa 1380
agcaagcgct ctttgtactg ggtggaggag ctttgagtag tgagggtgga gatgcagctt 1440
cggggtggcg cagccaccct gacactaggc ccggggtcgc agtgggacag aagagtctgc 1500
cgctctgact tgggctctga gttccaaggg cgcccggcac ttctagcctc ccaggcttgc 1560
gcgctggcgc ctttgccatc cgtgccgaag tggggagacc tagccgcgac caccacgagc 1620
gcagcggtga cacccagagg tcccaccggg cccctgggca gggtaacctt agcctgtccg 1680
cttcggcagc tttgcgaaga gtggcgcgca gctagggctg aggctcttgc ggacctgcgg 1740
tcgaagcagg cggctgagcc agttcgatcg ccaaggcctg ggctgccgac agtggtgcgc 1800
gctctgttcc gccgcggccg ggccaggcgc tctggaatag cgatgggggg acacggcctc 1860
caactttctg cagagaccat cgggcagctc cgggcctaag cagcgacctc accgaaggtt 1920
cctgggaacc tttgccaaaa tcccagcctc tgcctcggtc cagctaaacc gtgtgtaaac 1980
aagtgcacca ag 1992

<210> SEQ ID NO 44
<211> LENGTH: 448
<212> TYPE: DNA
<213> ORGANISM: Homo sapiens

<400> SEQUENCE: 44
ataaaggacc gggtaatttc gcggaatgcg gattttgaga caggcccaga cggcggcgga 60
ttccctgtgt cccccaactg gggcgatctc gtgaacacac ctgcgtccca ccccgatcct 120
aggttggggg gaaagggtat gggaaccctg agcccagagc gcgccccgct ctttcctttg 180

-continued ctccccggct tccctggcca gccccctccc ggctggtttc ctcgctcact cggcgcctgg 240
cgtttcgggc gtctggagat caccgcgtgt ctggcacccc aacgtctagt ctccccgcag 300
gttgaccgcg gcgcctggag ccgggaatag gggtggggag tccggagaac caaacccgag 360
cctgaagttg ccattcgggt gactcccgag aaagcccggg agcattttgg ccaatgcggg 420
tttttacctg aacttcagca tcttcacc 448

<210> SEQ ID NO 45
<211> LENGTH: 395
<212> TYPE: DNA
<213> ORGANISM: Homo sapiens

<400> SEQUENCE: 45
aattggaaaa ccctggtatt gtgcctgttt gggggaagaa aacgtcaata aaaattaatt 60
gatgagttgg cagggcgggc ggtgcgggtt cgcggcgagg cgcagggtgt catggcaaat 120
gttacggctc agattaagcg attgttaatt aaaaagcgac ggtaattaat actcgctacg 180
ccatatgggc ccgtgaaaag gcacaaaagg tttctccgca tgtggggttc cccttctctt 240
ttctccttcc acaaaagcac cccagcccgt gggtcccccc tttggcccca aggtaggtgg 300
aactcgtcac ttccggccag ggaggggatg gggcggtctc cggcgagttc caagggcgtc 360
cctcgttgcg cactcgcccg cccaggttct ttgaa 395

<210> SEQ ID NO 46
<211> LENGTH: 491
<212> TYPE: DNA
<213> ORGANISM: Homo sapiens

<400> SEQUENCE: 46
gggaagcgat cgtctcctct gtcaactcgc gcctgggcac ttagcccctc ccgtttcagg 60
gcgccgcctc cccggatggc aaacactata aagtggcggc gaataaggtt cctcctgctg 120
ctctcggttt agtccaagat cagcgatatc acgcgtcccc cggagcatcg cgtgcaggag 180
ccatggcgcg ggagctatac cacgaagagt tcgcccgggc gggcaagcag gcggggctgc 240
aggtctggag gattgagaag ctggagctgg tgcccgtgcc ccagagcgct cacggcgact 300
tctacgtcgg ggatgcctac ctggtgctgc acacggccaa gacgagccga ggcttcacct 360
accacctgca cttctggctc ggtaagggac ggcgggcggc gggaccccga cgcaccaagg 420
ccggcgaggg gagggcgtag gggtctgaga tttgcaggcg tgggagtaaa ggggaccgca 480
aactgagcta g 491

<210> SEQ ID NO 47
<211> LENGTH: 1284
<212> TYPE: DNA
<213> ORGANISM: Homo sapiens

<400> SEQUENCE: 47
ctcaggggcg ggaagtggcg ggtgggagtc acccaagcgt gactgcccga ggcccctcct 60
gccgcggcga ggaagctcca taaaagccct gtcgcgaccc gctctctgca ccccatccgc 120
tggctctcac ccctcggaga cgctcgcccg acagcatagt acttgccgcc cagccacgcc 180
cgcgcgccag ccaccgtgag tgctacgacc cgtctgtcta ggggtgggag cgaacggggc 240
gcccgcgaac ttgctagaga cgcagcctcc cgctctgtgg agccctgggg ccctgggatg 300
atcgcgctcc actccccagc ggactatgcc ggctccgcgc cccgacgcgg accagccctc 360
ttggcggcta aattccactt gttcctctgc tcccctctga ttgtccacgg cccttctccc 420
gggcccttcc cgctgggcgg ttcttctgag ttacctttta gcagatatgg agggagaacc 480
cgggaccgct atcccaaggc agctggcggt ctccctgcgg gtcgccgcct tgaggcccag 540
gaagcggtgc gcggtaggaa ggtttccccg gcagcgccat cgagtgagga atccctggag 600
ctctagagcc ccgcgccctg ccacctccct ggattcttgg gctccaaatc tctttggagc 660
aattctggcc cagggagcaa ttctctttcc ccttccccac cgcagtcgtc accccgaggt 720
gatctctgct gtcagcgttg atcccctgaa gctaggcaga ccagaagtaa cagagaagaa 780
acttttcttc ccagacaaga gtttgggcaa gaagggagaa aagtgaccca gcaggaagaa 840
cttccaattc ggttttgaat gctaaactgg cggggccccc accttgcact ctcgccgcgc 900
gcttcttggt ccctgagact tcgaacgaag ttgcgcgaag ttttcaggtg gagcagaggg 960
gcaggtcccg accggacggc gcccggagcc cgcaaggtgg tgctagccac tcctgggttc 1020
tctctgcggg actgggacga gagcggattg gggtcgcgt gtggtagcag gaggaggagc 1080
gcggggggca gaggagggag gtgctgcgcg tgggtgctct gaatccccaa gcccgtccgt 1140
tgagccttct gtgcctgcag atgctaggta acaagcgact ggggctgtcc ggactgaccc 1200
tcgccctgtc cctgctcgtg tgcctgggtg cgctggccga ggcgtacccc tccaagccgg 1260
acaacccggg cgaggacgca ccag 1284

<210> SEQ ID NO 48
<211> LENGTH: 554
<212> TYPE: DNA
<213> ORGANISM: Homo sapiens

<400> SEQUENCE: 48
tggagaacct tgggctctgt ggcctcaaag gtaggggtga tttcgagggg ccggcacctc 60
acagggcagg ttccaccgcg gaaacgcagt catcgcccag cgaccctgct cctggccctc 120
agcctccccc caggtttctt tttctcttga atcaagccga ggtgcgccaa tggccttcct 180
tgggtcggat ccggggggcc agggccagct tacctgcttt caccgagcag tggatatgtg 240
ccttggactc gtagtacacc cagtcgaagc cggcctccac cgccaggcgg gccagcatgc 300
cgtacttgct gcggtcgcgg tcagacgtgg tgatgtccac tgcgcggccc tcgtagtgca 360
gagactcctc tgagtggtgg ccatcttcgt cccagccctc ggtcacccgc agtttcactc 420
ctggccactg gttcatcacc gagatggcca aagcgttcaa cttgtcctta cacctctgcg 480
aagacaaggg gacccccacc gacggacacg ttagcctggg caaccgccac ccctcccggc 540
ccctccatca gcct 554

<210> SEQ ID NO 49
<211> LENGTH: 772
<212> TYPE: DNA
<213> ORGANISM: Homo sapiens

<400> SEQUENCE: 49
tctcacgacc catccgttaa cccaccgttc ccaggagctc cgaggcgcag cggcgacaga 60
ggttcgcccc ggcctgctag cattggcatt gcggttgact gagcttcgcc taacaggctt 120
ggggagggtg ggctgggctg ggctgggctg ggctgggtgc tgcccggctg tccgcctttc 180
gttttcctgg gaccgaggag tcttccgctc cgtatctgcc tagagtctga atccgacttt 240
ctttcctttg ggcacgcgct cgccagtgga gcacttcttg ttctggcccc gggctgatct 300
gcacgcggac ttgagcaggt gccaaggtgc cacgcagtcc cctcacggct ttcgggggt 360 cttggagtcg ggtggggagg gagacttagg tgtggtaacc tgcgcaggtg ccaaagggca 420
gaaggagcag ccttggatta tagtcacggt ctctccctct cttccctgcc atttttaggg 480
ctttctctac gtgctgttgt ctcactgggt ttttgtcgga gccccacgcc ctccggcctc 540
tgattcctgg aagaaagggt tggtcccctc agcaccccca gcatcccgga aaatggggag 600
caaggctctg ccagcgccca tcccgctcca cccgtcgctg cagctcacca attactcctt 660
cctgcaggcc gtgaacacct tcccggccac ggtggaccac ctgcagggcc tgtacggtct 720
cagcgcggta cagaccatgc acatgaacca ctggacgctg gggtatccca at 772

<210> SEQ ID NO 50
<211> LENGTH: 1362
<212> TYPE: DNA
<213> ORGANISM: Homo sapiens

<400> SEQUENCE: 50
tggtttcctt tcgcttctcg cctcccaaac acctccagca agtcggaggg cgcgaacgcg 60
gagccagaaa cccttcccca aagtttctcc cgccaggtac ctaattgaat catccatagg 120
atgacaaatc agccagggcc aagatttcca gacacttgag tgacttcccg gtccccgagg 180
tgacttgtca gctccagtga gtaacttgga actgtcgctc ggggcaaggt gtgtgtctag 240
gagagagccg gcggctcact cacgctttcc agagagcgac ccgggccgac ttcaaaatac 300
acacagggtc atttataggg actggagccg cgcgcaggac aacgtctccg agactgagac 360
attttccaaa cagtgctgac attttgtcgg gccccataaa aaatgtaaac gcgaggtgac 420
gaacccggcg gggagggttc gtgtctggct gtgtctgcgt cctggcggcg tgggaggtta 480
tagttccaga cctggcggct gcggatcgcc gggccggtac ccgcgaggag tgtaggtacc 540
ctcagcccga ccacctcccg caatcatggg gacaccggct tggatgagac acaggcgtgg 600
aaaacagcct tcgtgaaact ccacaaacac gtggaacttg aaaagacaac tacagccccg 660
cgtgtgcgcg agagacctca cgtcacccca tcagttccca cttcgccaaa gtttcccttc 720
agtggggact ccagagtggt gcgccccatg cccgtgcgtc ctgtaacgtg ccctgattgt 780
gtacccctct gcccgctcta cttgaaatga aaacacaaaa actgttccga attagcgcaa 840
ctttaaagcc ccgttatctg tcttctacac tgggcgctct taggccactg acagaaacat 900
ggtttgaacc ctaattgttg ctatcagtct cagtcagcgc aggtctctca gtgacctgtg 960
acgccgggag ttgaggtgcg cgtatcctta aacccgcgcg aacgccaccg gctcagcgta 1020
gaaaactatt tgtaatccct agtttgcgtc tctgagcttt aactccccca cactctcaag 1080
cgcccggttt ctcctcgtct ctcgcctgcg agcaaagttc ctatggcatc cacttaccag 1140
gtaaccggga tttccacaac aaagcccggc gtgcgggtcc cttcccccgg ccggccagcg 1200
cgagtgacag cgggcggccg gcgctggcga ggagtaactt ggggctccag cccttcagag 1260
cgctccgcgg gctgtgcctc cttcggaaat gaaaaccccc atccaaacgg ggggacggag 1320
cgcggaaacc cggcccaagt gccgtgtgtg cgcgcgcgtc tg 1362

<210> SEQ ID NO 51
<211> LENGTH: 476
<212> TYPE: DNA
<213> ORGANISM: Homo sapiens

<400> SEQUENCE: 51
gaaagccatc cttaccattc ccctcaccct ccgccctctg atcgcccacc cgccgaaagg 60
gtttctaaaa atagcccagg gcttcaaggc cgcgcttctg tgaagtgtgg agcgagcggg 120

```
cacgtagcgg tctctgccag gtggctggag ccctggaagc gagaaggcgc ttcctccctg    180

catttccacc tcaccccacc cccggctcat ttttctaaga aaaagttttt gcggttccct    240

ttgcctccta cccccgctgc cgcgcggggt ctgggtgcag acccctgcca ggttccgcag    300

tgtgcagcgg cggctgctgc gctctcccag cctcggcgag ggttaaaggc gtccggagca    360

ggcagagcgc cgcgcgccag tctattttta cttgcttccc ccgccgctcc gcgctccccc    420

ttctcagcag ttgcacatgc cagctctgct gaaggcatca atgaaaacag cagtag        476
```

<210> SEQ ID NO 52
<211> LENGTH: 300
<212> TYPE: DNA
<213> ORGANISM: Homo sapiens

<400> SEQUENCE: 52

```
atcgaaaatg tcgacatctt gctaatggtc tgcaaacttc cgccaattat gactgacctc     60

ccagactcgg ccccaggagg ctcgtattag gcagggaggc cgccgtaatt ctgggatcaa    120

aagcgggaag gtgcgaactc ctctttgtct ctgcgtgccc ggcgcgcccc cctcccggtg    180

ggtgataaac ccactctggc gccggccatg cgctgggtga ttaatttgcg aacaaacaaa    240

agcggcctgg tggccactgc attcgggtta aacattggcc agcgtgttcc gaaggcttgt    300
```

<210> SEQ ID NO 53
<211> LENGTH: 1246
<212> TYPE: DNA
<213> ORGANISM: Homo sapiens

<400> SEQUENCE: 53

```
atcaacatcg tggctttggt cttttccatc atggtgagtg aatcacggcc agaggcagcc     60

tgggaggaga gacccgggcg gctttgagcc cctgcagggg agtccgcgcg ctctctgcgg    120

ctcccttcct cacggcccgg cccgcgctag gtgttctttg tcctcgcacc tcctcctcac    180

ctttctcggg ctctcagagc tctccccgca atcatcagca cctcctctgc actcctcgtg    240

gtactcagag ccctgatcaa gcttccccca ggctagcttt cctcttcttt ccagctccca    300

gggtgcgttt cctctccaac ccggggaagt tcttccgtgg actttgctga ctcctctgac    360

cttcctaggc acttgcccgg ggcttctcaa ccctcttttc tagagcccca gtgcgcgcca    420

ccctagcgag cgcagtaagc tcataccccg agcatgcagg ctctacgttc ctttccctgc    480

cgctccgggg gctcctgctc tccagcgccc aggactgtct ctatctcagc ctgtgctccc    540

ttctctcttt gctgcgccca agggcaccgc ttccgccact ctccgggggg tccccaggcg    600

attcctgatg ccccctcctt gatcccgttt ccgcgctttg gcacggcacg ctctgtccag    660

gcaacagttt cctctcgctt cttcctacac ccaacttcct ctccttgcct ccctccggcg    720

ccccctttttt aacgcgcccg aggctggctc acacccacta cctctttagg cctttcttag    780

gctccccgtg tgccccccctc accagcaaag tgggtgcgcc tctcttactc tttctaccca    840

gcgcgtcgta gttcctcccc gtttgctgcg cactggccct aacctctctt ctcttggtgt    900

cccccagagc tcccaggcgc ccctccaccg ctctgtcctg cgcccggggc tctcccggga    960

atgaactagg ggattccacg caacgtgcgg ctccgcccgc cctctgcgct cagacctccc   1020

gagctgcccg cctctctagg agtggccgct ggggcctcta gtccgccctt ccggagctca   1080

gctccctagc cctcttcaac cctggtagga acacccgagc gaaccccacc aggagggcga   1140

cgagcgcctg ctaggccctc gccttattga ctgcagcagc tggcccgggg gtggcggcgg   1200
```

ggtgaggttc gtaccggcac tgtcccggga caacccttgc agttgc 1246

<210> SEQ ID NO 54
<211> LENGTH: 984
<212> TYPE: DNA
<213> ORGANISM: Homo sapiens

<400> SEQUENCE: 54
acaaataaaa caccctctag cttcccctag actttgttta actggccggg tctccagaag 60
gaacgctggg gatgggatgg gtggagagag ggagcggctc aaggacttta gtgaggagca 120
ggcgagaagg agcacgttca ggcgtcaaga ccgatttctc cccctgcttc gggagacttt 180
tgaacgctcg gagaggcccg gcatctcacc actttacttg gccgtagggg cctccggcac 240
ggcaggaatg agggaggggg tccgattgga cagtgacggt ttggggccgt tcggctatgt 300
tcagggacca tatggtttgg ggacagcccc agtagttagt aggggacggg tgcgttcgcc 360
cagtccccgg atgcgtaggg aggcccagtg gcaggcagct gtcccaagca gcgggtgcgc 420
gtccctgcgc gctgtgtgtt cattttgcag agccagcctt cggggaggtg aaccagctgg 480
gaggagtgtt cgtgaacggg aggccgctgc ccaacgccat ccggcttcgc atcgtggaac 540
tggcccaact gggcatccga ccgtgtgaca tcagccgcca gctacgggtc tcgcacggct 600
gcgtcagcaa gatcctggcg cgatacaacg agacgggctc gatcttgcca ggagccatcg 660
ggggcagcaa gccccgggtc actaccccca ccgtggtgaa acacatccgg acctacaagc 720
agagagaccc cggcatcttc gcctgggaga tccgggaccg cctgctggcg gacggcgtgt 780
gcgacaagta caatgtgccc tccgtgagct ccatcagccg cattctgcgc aacaagatcg 840
gcaacttggc ccagcagggt cattacgact catacaagca gcaccagccg acgccgcagc 900
cagcgctgcc ctacaaccac atctactcgt accccagccc tatcacggcg gcggccgcca 960
aggtgcccac gccacccggg gtgc 984

<210> SEQ ID NO 55
<211> LENGTH: 545
<212> TYPE: DNA
<213> ORGANISM: Homo sapiens

<400> SEQUENCE: 55
aggaggcgca acgcgctgcc agggcggctt tatcctgccg ccacagggcg gggaccagcc 60
cggcagccgg gtgtccagcg ccgctcacgt gcctcgcctg gagcttagct ctcagactcc 120
gaagagggcg actgagactt gggcctggga gttggcttcg gggtacccaa ggcgacgaca 180
gctgagttgt accacgaagc tcaggccgag gcctcctccc ttgtctggcc ttcgaatcca 240
tactggcagc ctctcctctc aggcactccg cgggccgggc cactaggccc cctgctcctg 300
gagctgcgct atgatccggg tcttgagatg cgcgcgattc tctctgaacc ggtggagagg 360
aggctctgcc ccgcgcggag cgaggacagc ggcgcccgag cttcccgcgc ctctccaggg 420
cccaatggca agaacagcct ccgaagtgcg cggatgacag gaaaagatct tcagttcttc 480
tgccgctaga gaagtgcggg atacaagcct ctattggatc cacaacctgg agtcctgcct 540
tcgga 545

<210> SEQ ID NO 56
<211> LENGTH: 1533
<212> TYPE: DNA
<213> ORGANISM: Homo sapiens

<400> SEQUENCE: 56
atctgcgtgc ccttttctgg gcgagccctg ggagatccag ggagaactgg gcgctccaga 60
tggtgtatgt ctgtaccttc acagcaaggc ttcccttgga tttgaggctt cctattttgt 120
ctgggatcgg ggtttctcct tgtcccagtg gcagccccgc gttgcgggtt ccgggcgctg 180
cgcggagccc aaggctgcat ggcagtgtgc agcgcccgcc agtcgggctg gtgggttgtg 240
cactccgtcg gcagctgcag aaaggtggga gtgcaggtct tgcctttcct caccgggcgg 300
ttggcttcca gcaccgaggc tgacctatcg tggcaagttt gcggcccccg cagatcccca 360
gtggagaaag agggctcttc cgatgcgatc gagtgtgcgc ctccccgcaa agcaatgcag 420
accctaaatc actcaaggcc tggagctcca gtctcaaagg tggcagaaaa ggccagacct 480
aactcgagca cctactgcct tctgcttgcc ccgcagagcc ttcagggact gactgggacg 540
cccctggtgg cgggcagtcc catccgccat gagaacgccg tgcagggcag cgcagtggag 600
gtgcagacgt accagccgcc gtggaaggcg ctcagcgagt ttgccctcca gagcgacctg 660
gaccaacccg ccttccaaca gctggtgagg ccctgcccta cccgccccga cctcgggact 720
ctgcgggttg gggatttagc cacttagcct ggcagagagg ggagggggtg gccttgggct 780
gaggggctgg gtacagccct aggcggtggg ggagggggaa cagtggcggg ctctgaaacc 840
tcacctcggc ccattacgcg ccctaaacca ggtctccctg gattaaagtg ctcacaagag 900
aggtcgcagg attaaccaac ccgctccccc gccctaatcc ccccctcgtg cgcctgggga 960
cctggcctcc ttctccgcag ggcttgctct cagctggcgg ccggtcccca agggacactt 1020
tccgactcgg agcacgcggc cctggagcac cagctcgcgt gcctcttcac ctgcctcttc 1080
ccggtgtttc cgccgcccca ggtctccttc tccgagtccg gctccctagg caactcctcc 1140
ggcagcgacg tgacctccct gtcctcgcag ctcccggaca cccccaacag tatggtgccg 1200
agtcccgtgg agacgtgagg gggacccctc cctgccagcc cgcggacctc gcatgctccc 1260
tgcatgagac tcacccatgc tcaggccatt ccagttccga aagctctctc gccttcgtaa 1320
ttattctatt gttatttatg agagagtacc gagagacacg gtctggacag cccaaggcgc 1380
caggatgcaa cctgctttca ccagactgca gacccctgct ccgaggactc ttagtttttc 1440
aaaaccagaa tctgggactt accagggtta gctctgccct ctcctctcct ctctacgtgg 1500
ccgccgctct gtctctccac gccccacctg tgt 1533

<210> SEQ ID NO 57
<211> LENGTH: 702
<212> TYPE: DNA
<213> ORGANISM: Homo sapiens

<400> SEQUENCE: 57
aggtctcttc agactgccca ttctccgggc ctcgctgaat gcgggggctc tatccacagc 60
gcgcggggcc gagctcaggc aggctggggc gaagatctga ttctttcctt cccgccgcca 120
aaccgaatta atcagtttct tcaacctgag ttactaagaa agaaaggtcc ttccaaataa 180
aactgaaaat cactgcgaat gacaatacta tactacaagt tcgttttggg gccggtgggt 240
gggatggagg agaaagggca cggataatcc cggagggccg cggagtgagg aggactatgg 300
tcgcggtgga atctctgttc cgctggcaca tccgcgcagg tgcggctctg agtgctggct 360
cggggttaca gacctcggca tccggctgca ggggcagaca gagacctcct ctgctagggc 420
gtgcggtagg catcgtatgg agcccagaga ctgccgagag cactgcgcac tcaccaagtg 480
ttaggggtgc ccgtgataga ccgccaggga aggggctggt tcggagggaa ttcccgctac 540

-continued

```
cgggaaggtc ggaactcggg gtgatcaaac aaggaatgca tctcacctcc gtgggtgctt    600

gtgctgcgca aggaattatt accggagcgg ttgcgatggc ctttgcccgg cgacccaaga    660

agagtaagca aactaccgtc cacccagcgg atcaggtcca at                       702


<210> SEQ ID NO 58
<211> LENGTH: 3180
<212> TYPE: DNA
<213> ORGANISM: Homo sapiens

<400> SEQUENCE: 58

gatgtcctgt ttctagcagc ctccagagcc aagctaggcg agaggcgtag gaggcagaga     60

gagcgggcgc gggaggccag ggtccgcctg ggggcctgag gggacttcgt ggggtcccgg    120

gagtggccta gaaacaggga gctgggaggg ccgggaagag cttgaggctg agcgggggac    180

gaacgggcag cgcaaagggg agatgaacgg aatggccgag gagccacgca ttcgccttgt    240

gtccgcggac ccttgttccc gacaggcgac caagccaagg ccctccggac tgacgcggcc    300

tgagcagcag cgagtgtgaa gtttggcacc tccggcggcg agacggcgcg ttctggcgcg    360

cggctcctgc gtccggctgg tggagctgct gcgccctatg cggcctgccg agggcgccgc    420

cgagggcccg cgagctccgt ggggtcgggg tggggggacc cgggagcgga cagcgcggcc    480

cgaggggcag gggcaggggc gcgcctggcc tggggtgtgt ctgggccccg gctccgggct    540

cttgaaggac cgcgagcagg aggcttgcgc aatcccttgg ctgagcgtcc acggagaaag    600

aaaaagagca aaagcagagc gagagtggag cgagggatgg gggcgggcaa agagccatcc    660

gggtctccac caccgccctg acacgcgacc cggctgtctg ttggggaccg cacgggggct    720

cgggcgagca ggggagggag gagcctgcgc ggggctcgtg ttcgcccagg aatcccggag    780

aagctcgaag acggtctggt gttgaacgca cacgtggact ccatttcatt accaccttgc    840

agctcttgcg ccacggaggc tgctgctgcc cggcggctgc tacccaccga gacccacgtg    900

gcccctcccc aggggtgtag gggtgacggt tgtcttctgg tgacagcaga ggtgttgggt    960

ttgcgactga tctctaacga gcttgaggcg caaacctagg attccctgag tgttggggtg   1020

cggcgggggg gcaagcaagg tgggacgacg cctgcctggt ttccctgact agttgcgggg   1080

ggtgggggcc ggctctcagg ggccaccaga agctgggtgg gtgtacagga aaatattttt   1140

ctcctgccgt gtttggcttt ttcctggcat ttttgcccag ggcgaagaac tgtcgcgcgg   1200

ggcagctcca ccgcggaggg agaggggtcg cgaggctggc gcgggaagcg ctgtaggtgg   1260

cagtcatccg tccacgccgc acaggccgtc tgcgccgtcg gaccatcggg aggtctgcag   1320

caactttgtc ccggccagtc cccttgtccg ggaaggggct gagcttcccg acactctacc   1380

ctccccctct tgaaaatccc ctggaaaatc tgtttgcaat gggtgtttcc gcggcgtcca   1440

ggtctgggct gccgggggag gccgagcggc tgctgcagcc tccctgctgc caggggcgtc   1500

ggactccgct tcgctcacta cgcccaggcc cctcaggggc ccacgctcag gacttcgggg   1560

ccacacagca ggacccggtg ccccgacgac gagtttgcgc aggacccggg ctgggccagc   1620

cgcggagctg gggaggaagg ggcgggggtc ggtgcagcgg atcttttctg ttgctgcctg   1680

tgcggcggca ggaagcgtct tgaggctccc caagactacc tgaggggccg cccaagcact   1740

tcagaagccc aaggagcccc cggccacccc cgctcctggc ctttttgcca acgactttga   1800

aagtgaaatg cacaagcacc agcaattgac ttcccttccg tggttattta ttttgtcttt   1860

gtggatggtg ggcagatggg gagagaggcc cctacctaac ctcggtggct ggtccctaga   1920

ccacccctgc cagccggtgt ggggaggagc tcaggtccgc gggagagcga atgggcgcca   1980
```

-continued

```
ggaggtggga cagaatcctg ggaaggtaca gcggacgccc tggaagctcc cctgatgccc   2040

cagagggccc ttcctgggaa acctcccggg ggggtgcccc ataccatccc acccggctgt   2100

cttggcccct cccagggagc cgcaggagaa actagcccta cacctgggat tcccagagcc   2160

ttctgctggg gctcctgccc ccgacttcgg ataaccagct ccgcacaggt ccccgagaag   2220

ggccgctggc ctgcttattt gatactgccc cctcccagac aggggctggt cgagcccctg   2280

gttctgctgc cagactgaag ccttccagac gccacctcgg tttgggcccc cagggccctc   2340

aggggcccca ggagaggaga gctgctatct agctcagcca caggctcgct cctggtgggg   2400

gccaggctga aggagtggac cctggagagg tcgggaacct tttaacagcc gtgggctgga   2460

gggtggctac taagtgttcg gtctgggaag aggcatgacc cgcaccatcc cggggaaata   2520

aacgacttct taagggaatc ttctcgctga gcgggtgctc tgggccagga gattgccacc   2580

gccagcccac ggaacccaga tttgggctct gccttgagcg ggccgcctgt ggcttcccgg   2640

gtcgctcccc cgactcagaa agctctcaag ttggtatcgt tttcccggcc ctcggaggtg   2700

gattgcagat caccgagagg ggatttacca gtaaccacta cagaatctac ccgggcttta   2760

acaagcgctc atttctctcc cttgtcctta gaaaaacttc gcgctggcgt tgatcatatc   2820

gtacttgtag cggcagctta ggggcagcgg aactggtggg gttgtgcgtg caggggggagg  2880

ctgtgaggga gccctgcact ccgcccctcc acccttctgg aggagtggct ttgtttctaa   2940

gggtgccccc ccaacccccg ggtccccact tcaatgtttc tgctctttgt cccaccgccc   3000

gtgaaagctc ggctttcatt tggtcggcga agcctccgac gcccccgagt cccaccctag   3060

cgggccgcgc ggcactgcag ccgggggttc ctgcggactg gcccgacagg gtgcgcggac   3120

ggggacgcgg gccccgagca ccgcgacgcc agggtccttt ggcagggccc aagcacccct   3180
```

```
<210> SEQ ID NO 59
<211> LENGTH: 1038
<212> TYPE: DNA
<213> ORGANISM: Homo sapiens

<400> SEQUENCE: 59

tggcggccgg cgggcacagc cggctcattg ttctgcacta caaccactcg ggccggctgg     60

ccgggcgcgg ggggccggag gatggcggcc tgggggccct gcgggggctg tcggtggccg    120

ccagctgcct ggtggtgctg gagaacttgc tggtgctggc ggccatcacc agccacatgc    180

ggtcgcgacg ctgggtctac tattgcctgg tgaacatcac gctgagtgac ctgctcacgg    240

gcgcggccta cctggccaac gtgctgctgt cgggggcccg caccttccgt ctggcgcccg    300

cccagtggtt cctacgggag ggcctgctct tcaccgccct ggccgcctcc accttcagcc    360

tgctcttcac tgcaggggag cgctttgcca ccatggtgcg gccggtggcc gagagcgggg    420

ccaccaagac cagccgcgtc tacggcttca tcggcctctg ctggctgctg gccgcgctgc    480

tggggatgct gcctttgctg ggctggaact gcctgtgcgc ctttgaccgc tgctccagcc    540

ttctgcccct ctactccaag cgctacatcc tcttctgcct ggtgatcttc gccggcgtcc    600

tggccaccat catgggcctc tatggggcca tcttccgcct ggtgcaggcc agcgggcaga    660

aggccccacg cccagcggcc cgccgcaagg cccgccgcct gctgaagacg gtgctgatga    720

tcctgctggc cttcctggtg tgctggggcc cactcttcgg gctgctgctg gccgacgtct    780

ttggctccaa cctctgggcc caggagtacc tgcggggcat ggactggatc ctggccctgg    840

ccgtcctcaa ctcggcggtc aaccccatca tctactcctt ccgcagcagg gaggtgtgca    900
```

```
gagccgtgct cagcttcctc tgctgcgggt gtctccggct gggcatgcga gggcccgggg    960

actgcctggc ccgggccgtc gaggctcact ccggagcttc caccaccgac agctctctga   1020

ggccaaggga cagctttc                                                 1038


<210> SEQ ID NO 60
<211> LENGTH: 374
<212> TYPE: DNA
<213> ORGANISM: Homo sapiens

<400> SEQUENCE: 60

tagtaaggca ccgaggggtg gctcctctcc ctgcagcggc tgtcgcttac catcctgtag     60

accgtgacct cctcacacag cgccaggacg aggatcgcgg tgagccagca ggtgactgcg    120

atcctggagc tggtcgcagc aggccatcct gcacgcggtg gaggcgcccc ctgcaggccg    180

cagcgcatcc ccagcttctg gacgcactgt gagcggttat gcagcagcac gctcatatga    240

gatgccccgc agggtgctat gcaggcccac gtccccacaa agcccatggc aggcgcccgg    300

gtgccggagc acgcacttgg ccccatggat ctctgtgccc agggctcagc caggcatctg    360

gccgctaaag gttt                                                      374


<210> SEQ ID NO 61
<211> LENGTH: 246
<212> TYPE: DNA
<213> ORGANISM: Homo sapiens

<400> SEQUENCE: 61

tctcatctga gcgctgtctt tcaccagagc tctgtaggac tgaggcagta gcgctggccc     60

gcctgcgaga gcccgaccgt ggacgatgcg tcgcgccctt cccatcgcgg cctgggcggg    120

cccgcctgcc ctcggctgag cccggtttcc ctaccccggg gcacctcccc tcgcccgcac    180

ccggccccag tccctcccag gcttgcgggt agagcctgtc tttgcccaga aggccgtctc    240

caagct                                                               246


<210> SEQ ID NO 62
<211> LENGTH: 222
<212> TYPE: DNA
<213> ORGANISM: Homo sapiens

<400> SEQUENCE: 62

cagtccccga ggccctcccc ggtgactcta accagggatt tcagcgcgcg gcgcggggct     60

gcccccaggc gtgacctcac ccgtgctctc tccctgcaga atctcctacg acccggcgag    120

gtaccccagg tacctgcctg aagcctactg cctgtgccgg ggctgcctga ccgggctgtt    180

cggcgaggag gacgtgcgct tccgcagcgc ccctgtctac at                       222


<210> SEQ ID NO 63
<211> LENGTH: 2209
<212> TYPE: DNA
<213> ORGANISM: Homo sapiens

<400> SEQUENCE: 63

agagagacat tttccacgga ggccgagttg tggcgcttgg ggttgtgggc gaaggacggg     60

gacacggggg tgaccgtcgt ggtggaggag aaggtctcgg aactgtggcg gcggcggccc    120

ccctgcgggt ctgcgcggat gaccttggcg ccgcggtggg ggtccggggg ctggctggcc    180

tgcaggaagg cctcgactcc cgacacctgc tccatgaggc tcagcctctt cacgcccgac    240

gtcgggctgg ccacgcgggc agcttctggc ttcggggggg ccgcgatagg ttgcggcggg    300
```

gtggcggcca caccaaaagc catctcggtg tagtcaccat tgtccccggt gtccgaggac 360
aacgatgagg cggcgcccgg gccctgggcg gtggcaacgg ccgaggcggg gggcaggcgg 420
tacagctccc ccggggccgg cggcggtggc ggcggctgca gagacgacga cggggacgcg 480
gacggacgcg ggggcaacgg cggatacggg gaggaggcct cgggggacag gaggccgtcc 540
aaggagccca cggggtggcc gctcggggcg cccggcttag gagacttggg ggagctgaag 600
tcgaggttca tgtagtcgga gagcggagac cgctgccggc tgtcgctgct ggtgcccggg 660
gtgcctgagc ccagcgacga ggccgggctg ctggcggaca agagcgagga ggacgaggcc 720
gccgacgcca gcaggggagg cgcgggcggc gacaggcggg ccccgggctc gccaaagtcg 780
atgttgatgt actcgccggg gctcttgggc tccggtggca gtgggtactc gtgcatgctg 840
ggcaggctgg gcagcccctc cagggacagg cgcgtgggcc tcaccgcccg gccgcgctgg 900
cccaagaagc cctccgggcg gccgccgcta ggccgcacgg gcgaaggcac tacagggtga 960
gggggctgcg tggggccggc cccgaaggcg ctggccgcct ggctgggccc tggcgtggcc 1020
tgaggctcca gacgctcctc ctccaggatg cgccccacgg gggagctcat gagcacgtac 1080
tggtcgctgt ccccgccaca ggtgtagggg gccttgtagg agcggggcaa ggagctgtag 1140
cagcagccgg gaacgcccct gagcggctcc ccgccggggt gcagggctgc ggagaagaag 1200
tcgggcgggg tgcccgtggt gaccgcgtcg ctgggggaca cgttgaggta gtccccgttg 1260
ggcagcagct tgccatctgc atgctccatg gacagcttgg aaccgcacca catgcgcatg 1320
tacccactgt cctcggggga gctctcggcg ggcgagctgg ccttgtagcc gcccccgctc 1380
gccgggaatg tcctgcccgc cgcagaggtg ggtgctggcc ccgcaggccc cgcagaaggc 1440
acggcggcgg cggcggcggc ggcggccctg ggctgcaaga tctgcttggg ggcggacacg 1500
ctggcggggc tcatgggcat gtagtcgtcg ctcctgcagc tgccgctccc actgcccgcg 1560
agggccgcgc cgggcgtcat gggcatgtag ccgtcgtctg cccccaggtt gctgctggag 1620
ctcctgtggg agccgatctc gatgtctccg tagtcctctg ggtaggggtg gtaggccacc 1680
ttgggagagg acgcggggca ggacgggcag aggcggcccg cgctgcccga gaaggtggcc 1740
cgcatcaggg tgtattcatc cagcgaggca gaggagggct ggggcaccgg ccgctgccgg 1800
gctggcgtgg tcagggagta ggtcctcttg cgcagccctc ggtccaggtc ctgggccgcg 1860
tcccccgaga cccggcggta ggagcggcca cagtggctca ggggcctgtc catggtcatg 1920
tacccgtaga actcaccgcc gccgccgccg tctcgggccg ggggcgtctc cgcgatggac 1980
tcgggcgtgt tgcttcggtg gctgcagaag gcgcgcaggt cgcctgggct ggagccgtac 2040
tcgtccaggg acatgaagcc ggggtcgctg ggggagcccg aggcggaggc gctgccgctg 2100
gagggccgct ggccggggcc gtggtgcagc ggatgcggca gaggcgggtg cgggccgggc 2160
ggcggcgggt aggagcccga gccgtggccg ctgctggacg acagggagc 2209

<210> SEQ ID NO 64
<211> LENGTH: 149
<212> TYPE: DNA
<213> ORGANISM: Homo sapiens

<400> SEQUENCE: 64
taacctaaag aatgaagtca tgccccggcc tgcacccggg aaactgcaca cagcgaaaga 60
tcgccactga gataaagagc tgaaagctat tccccaattc agctgtttca gccgtgcggt 120
ctcacaatgg gctcacagac ggcagcatc 149

<210> SEQ ID NO 65
<211> LENGTH: 832
<212> TYPE: DNA
<213> ORGANISM: Homo sapiens

<400> SEQUENCE: 65
gtttccacaa tccacctcgt agctggggcg tgccgcttgc ctcggcttgt cccggcagaa 60
cactcttacc tttaatggcg actgaaaagt tgccacgagt tcctgatcat tgtggtaggt 120
gctgcgtgaa gctgagacgt gcgtgagcca catcccaggg ggctttgagc ccccaccgcg 180
gcggcggctg aggggaggct tgtcgtactc gcacaggagg acacagggct gcagtgttca 240
ctccagggcc tcttatcatt gggatctgag gaattttccg agaggaagtg cgaattaaca 300
atgatgaaag gtttgtgagt gagtgacagg cacgttctat tgagcactgc atggggcatt 360
atgtgccacc agagacgggg gcagaggtca agagccctcg agggctggga gagttcggag 420
gatagaagtc atcagagcac aatgaagcca gaccctgcag ccgccttccc cttcgggggc 480
ttccttagaa tgcagcattg cggggactga gctgtcccag gtgaaggggg gccgtcacgg 540
tgtgtggacg cccctcggct cagccctcta agagactcgg cagccaggat gggctcaagg 600
catgagccct caaaggaggt taggaaggag cgagggagaa aagatatgct tgtgtgacgt 660
cctggccgaa gtgagaacaa ttgtatcaga taatgagtca tgtcccattg aggggtgccg 720
acaaggactc gggaggaggc cacggagccc tgtactgagg agacgcccac agggagcctc 780
gggggcccag cgtcccggga tcactggatg gtaaagccgc cctgcctggc gt 832

<210> SEQ ID NO 66
<211> LENGTH: 256
<212> TYPE: DNA
<213> ORGANISM: Homo sapiens

<400> SEQUENCE: 66
tccagctgca gcgagggcgg ccaggccccc ttctccgacc tgcaggggta gcgcggcctc 60
ggcgccggag acccgcgcgc tgtctggggc tgcggtggcg tggggagggc gcggcccccg 120
gacgccccga ggaaggggca cctcaccgcc cccacccaga gcgcctggcc gtgcgggctg 180
cagaggaccc ctccggggca gaggcaggtt ccacggaaga ccccggcccg ctggggcttc 240
cccggagact ccagag 256

<210> SEQ ID NO 67
<211> LENGTH: 184
<212> TYPE: DNA
<213> ORGANISM: Homo sapiens

<400> SEQUENCE: 67
acttactgct tccaaaagcg ctgggcacag ccttatatga ctgaccccgc ccccgagtcc 60
caggccgccc catgcaaccg cccaaccgcc caaccgccac tccaaaggtc accaaccact 120
gctccaggcc acgggctgcc tctccccacg gctctagggc ccttcccctc caccgcaggc 180
tgac 184

<210> SEQ ID NO 68
<211> LENGTH: 118
<212> TYPE: DNA
<213> ORGANISM: Homo sapiens

<400> SEQUENCE: 68
tgccacaccc aggtaccgcc cgcccgcgcg agagccgggc aggtgggccg cggatgctcc 60
cagaggccgg cccagcagag cgatggactt ggacaggcta agatggaagt gacctgag 118

<210> SEQ ID NO 69
<211> LENGTH: 1534
<212> TYPE: DNA
<213> ORGANISM: Homo sapiens

<400> SEQUENCE: 69
tcgccagcgc agcgctggtc catgcaggtg ccacccgagg tgagcgcgga ggcaggcgac 60
gcggcagtgc tgccctgcac cttcacgcac ccgcaccgcc actacgacgg gccgctgacg 120
gccatctggc gcgcgggcga gccctatgcg ggcccgcagg tgttccgctg cgctgcggcg 180
cggggcagcg agctctgcca gacggcgctg agcctgcacg gccgcttccg gctgctgggc 240
aacccgcgcc gcaacgacct ctcgctgcgc gtcgagcgcc tcgccctggc tgacgaccgc 300
cgctacttct gccgcgtcga gttcgccggc gacgtccatg accgctacga gagccgccac 360
ggcgtccggc tgcacgtgac aggcgaggcg gcgtgggagc gggtccccgg cctcccttcc 420
cgccctcccg cctgccccgc cccaagggct acgtgggtgc caggcgctgt gctgagccag 480
gaagggcaac gagacccagc cctctcctct accccaggga tctcacacct gggggtagtt 540
taggaccacc tgggagcttg acacaaatgc agaatccagg tcccaggaag ggctgaggtg 600
ggcccgggaa taggcattgc cgtgactctc gtagagtgac tgtccccagt ggctctcaga 660
cgaagaggcg agaaagacaa gtgaatggca atcctaaata tgccaagagg tgcaatgtgg 720
tgtgtgctac cagcccggaa agacactcgc agcccctcta cccaggggtg cacagacagc 780
ccaccaagta gtgcctagca ctttgccaga ccctgatata caaagatgcc tgaaccaggg 840
tcccgtccct agagcagtgg ctctccactc tagcccccac cctgctctgc gacaataatg 900
gccacttagc atttgctagg gagccgggac ctagtccaag cacccacaag catgaatttg 960
ccaaatcttt tcagcaacct cttaaggcaa ctgctatcat gatcctcact ttacacatgg 1020
agaagcagaa gcagagatga tagaatcttt cgcccaaggc cacatctgta ttgggacggg 1080
ggcagcctgg cacccaagtg cccattcctc ccttctgacc agcccccacc cctccggctc 1140
tggcgtccaa agggctaagg ggaggggtgc ccttgtgaca gtcacccgcc ttctcccctg 1200
cagccgcgcc gcggatcgtc aacatctcgg tgctgcccag tccggctcac gccttccgcg 1260
cgctctgcac tgccgaaggg gagccgccgc ccgccctcgc ctggtccggc ccggccctgg 1320
gcaacagctt ggcagccgtg cggagcccgc gtgagggtca cggccaccta gtgaccgccg 1380
aactgcccgc actgacccat gacggccgct acacgtgtac ggccgccaac agcctgggcc 1440
gctccgaggc cagcgtctac ctgttccgct tccatggcgc cagcggggcc tcgacggtcg 1500
ccctcctgct cggcgctctc ggcttcaagg cgct 1534

<210> SEQ ID NO 70
<211> LENGTH: 269
<212> TYPE: DNA
<213> ORGANISM: Homo sapiens

<400> SEQUENCE: 70
atgaacttca agggcgacat catcgtggtc tacgtcagcc agacctcgca ggagggcgcg 60
gcggcggctg cggagcccat gggccgcccg gtgcaggagg agaccctggc gcgccgagac 120
tccttcgcgg ggaacggccc gcgcttcccg gacccgtgcg gcggccccga ggggctgcgg 180
gagccggaga aggcctcgag gccggtgcag gagcaaggcg gggccaaggc ttgagcgccc 240

-continued

```
cccatggctg ggagcccgaa gctcggagc                                      269


<210> SEQ ID NO 71
<211> LENGTH: 282
<212> TYPE: DNA
<213> ORGANISM: Homo sapiens

<400> SEQUENCE: 71

tcagtgttat gtggggagcg ctagatcgtg cacacagtag gcgtcaggaa gtgttttccc     60

cagtaattta ttctccatgg tactttgcta aagtcatgaa ataactcaga ttttgttttc    120

caaggaagga gaaaggccca gaatttaaga gcaggcagac acacaaccgg gcaccccccag   180

accctggccc ttccagcagt caggaattga cttgccttcc aaagccccag cccggagctt    240

gaggaacgga ctttcctgcg caggggggatc ggggcgcact cg                       282


<210> SEQ ID NO 72
<211> LENGTH: 142
<212> TYPE: DNA
<213> ORGANISM: Homo sapiens

<400> SEQUENCE: 72

gtggaaacac aacctgcctt ccattgtctg cgcctccaaa acacaccccc cgcgcatccg     60

tgaagctgtg tgtttctgtg ttactacagg ggccggctgt ggaaatccca cgctccagac    120

cgcgtgccgg gcaggcccag cc                                             142


<210> SEQ ID NO 73
<211> LENGTH: 741
<212> TYPE: DNA
<213> ORGANISM: Homo sapiens

<400> SEQUENCE: 73

tccacacctc gggcagtcac taggaaaagg gtcgccaact gaaaggcctg caggaaccag     60

gatgatacct gcgtcagtcc cgcggctgct gcgagtgcgc gctctcctgc caggggggacc   120

tcagaccctc ctttacagca caccgagggc cctgcagaca cgcgagcggg ccttcagttt    180

gcaaaccctg aaagcgggcg cggtccacca ggacgatctg gcagggctct gggtgaggag    240

gccgcgtctt tatttggggt cctcgggcag ccacgttgca gctctggggg aagactgctt    300

aaggaacccg ctctgaactg cgcgctggtg tcctctccgg ccctcgcttc cccgaccccg    360

cacaggctaa cgggagacgc gcaggcccac ccccaccggct ggagaccccg gcacggcccg   420

catccgccag gattgaagca gctggcttgg acgcgcgcag ttttcctttg gcgacattgc    480

agcgtcggtg cggccacaat ccgtccactg gttgtgggaa cggttggagg tcccccaaga    540

aggagacacg cagagctctc cagaaccgcc tacatgcgca tggggcccaa acagcctccc    600

aaggagcacc caggtccatg cacccgagcc caaaatcaca gacccgctac gggcttttgc    660

acatcagctc caaacacctg agtccacgtg cacaggctct cgcacagggg actcacgcac    720

ctgagttcgc gctcacagat c                                              741


<210> SEQ ID NO 74
<211> LENGTH: 4498
<212> TYPE: DNA
<213> ORGANISM: Homo sapiens

<400> SEQUENCE: 74

ctgccctcgc ggatctcccc cggcctcgcc ggcctccgcc tgtcctccca ccaccctctc     60

cgggccagta ccttgaaagc gatgggcagg gtcttgttgc agcgccagtg cgtaggcagc    120
```

-continued

```
acggagcaga ggaagttggg gctgtcggtg cgcaccagct cgcccgggtg gtcggccagc    180
acctccacca tgctgcggtc gccgctcctc agcttgccgg ccagggcagc gccggcgtcc    240
ggggcgccca gcggcaacgc ctcgctcatc ttgcctgggc tcagcgcggt ggaaggcggc    300
gtgaagcggc ggctcgtgct ggcatctacg gggatacgca tcacaacaag ccgattgagt    360
taggaccctg caaacagctc ctaccagacg gcgacagggg cgcggatctt cagcaagcag    420
ctcccgggag accaacatac acgttcaggg gcctttatta ctgcgggggg tggggggggg    480
cgggggtggt taggggagga gggagactaa gttactaaca gtccaggagg ggaaaacgtt    540
ctggttctgc ggatcggcct ctgacccagg atgggctcct agcaaccgat tgcttagtgc    600
attaaaaagt ggagactatc ttccacgaat cttgcttgca gaggttaagt tctgtctttg    660
gctgttagaa aagttcctga aggcaaaatt ctcatacact tcctaaaata tttatgcgaa    720
gagtaaaacg atcagcaaac acattatttg gaagttccag tagttaatgc ctgtcagttt    780
tttgcaggtg agttttgtct aaagtcccaa cagaacacaa ttatctcccg taacaaggcc    840
acttttatca tgcaaaactg gcttcagtcc cgaaaagcaa gagctgagac ttccaaaggt    900
agtgctacta atgtatgtgc acgtatatat aaatatatac atatgctcta cttcataaaa    960
tatttacaat acaatctgtg gagaatttaa acacaacaga aatccattaa tgtacgctgc   1020
agattttttt aagtagcctt gaaaatcagc ttcagtagtt ggagcagtgc tgagctagaa   1080
gtacttgtca tgttctctgt tctctcaatg aattctgtca aaacgctcag tgcagaaaat   1140
tcagcgtttc agagatcttc agctaatctt aaaacaacaa tcataagaag gcccagtcga   1200
tgacactcag ggttctacag ctctcccaca tctgtgaact cgggtttggg gatgttggtt   1260
aagtttgtgg ctggtcctct ggtttgttgg gagttgagca gccgcagagt cacacacatg   1320
caaacacgca ctcttcggaa ggcagccact gtctacatca gctgggtgac tcagccctga   1380
ctcgggcagc agcgagacga tactcctcca ccgtcgccca gcacccgccg gttagctgct   1440
ccgaggcacg aacacccacg agcgccgcgt aaccgcagca ggtggagcgg gccttgaggg   1500
agggctccgc ggcgcagatc gaaacagatc gggcggctcg ggttacacac gcacgcacat   1560
cctgccacgc acactgccac gcacacgcaa cttcacggct cgcctcggac cacagagcac   1620
tttctccccc tgttgtaaaa ggaaaacaat tggggaaaag ttcgcagcca ggaaagaagt   1680
tgaaaacatc cagccaagaa gccagttaat tcaaaaggaa gaaaggggaa aaacaaaaaa   1740
aaacaacaaa aaaaggaagg tccaacgcag gccaaggaga agcagcagag gttgacttcc   1800
ttctggcgtc cctaggagcc ccggaaagaa gtgcctggcg gcgcagggcc gggcagcgtg   1860
gtgccctggc tgggtccggc cgcggggcgc ccgtcccgcc cgcgcccgct ggctctatga   1920
atgagagtgc ctggaaatga acgtgctttt actgtaagcc cggccggagg aattccattc   1980
cctcagctcg tttgcatagg ggcggccggc ggccaatcac aggcctttcc ggtatcagcc   2040
agggcgcggc tcgccgccgc cggctcctgg aattggcccg cgcgccccg ccgccgcgcc    2100
gcgcgctact gtacgcagcc cgggcgggga gtcggaggcc acccccgcgc cccgcatcca   2160
agcctgcatg ctggcccggg gccccgcccg cgtgcggacc cctttccgca gccacacgca   2220
ggcttgtgcg gctccgcgag tggccacggt ccggagacct ggaaaaagaa agcaggcccc   2280
gccggcccga ggaggacccg gccggcgcgc cgcacccgga gaggcccggc cccgcgagcc   2340
gctgcaggca ggcgcagtgg ccgccacgag gctcccgaac cgggctgcag cccgcggacg   2400
gccccagatc ctgcgcggcc gcccagggcc aggcctccgc ttccagggcg gggtgcgat    2460
```

-continued

```
ttggccgcgg ggcccggggg agccactccg cgctcctgca ccgtccggct ggcagctgcg   2520

gcgaagcggc gctgattcct tgcatgaggc cggacggcgt ccgcgcgtgc cgtttgctct   2580

cagcgtcttc ccttgggtcg gtttctgtaa tgggtgtttt ttaccgctgc gcccgggccg   2640

cggctcgatc cctccgcgcg tctcacttgc tgcgtgcgtc agcggccagc gaagagtttc   2700

ctagtcagga aagaccccaa gaacgcgcgg ctggaaggaa agttgaaagc agccacgcgg   2760

cttgctcccg ggccttgtag cgccggcacc cgcagcagcc ggacagcctg cccgggcccc   2820

gcgtctcccc tccggctccc cggaagcggc ccccgctcct ctccccgccc ccgtgcgctc   2880

gagcggcccc aggtgcggaa cccaccccgg cttcgcgtgc gggcggccgc ttccccctgc   2940

gccggtcccc gcggtgctgc gggcattttc gcggagctcg gagggccccg cccccggtcc   3000

ggcgtgcgct gccaactccg accccgcccg gcggggctcc ctcccagcgg aggctgctcc   3060

cgtcaccatg agtccctcca cgccctccct gccgggccct gcacctcccg gggcctctca   3120

tccaccccgg ggctgcaacc cagtccccgg atcccggccc cgttccaccg cgggctgctt   3180

tgtggtcccc gcggagcccc tcaattaagc tccccggcgc ggggtccct cgccgacctc    3240

acggggcccc tgacgcccgc tcctccctcc cccagggcta gggtgctgtg gccgctgccg   3300

cgcagggact gtccccgggc gttgccgcgg gcccggacgc aggagggggc cggggttgac   3360

tggcgtggag gcctttcccg ggcgggcccg gactgcgcgg agctgtcggg acgcgccgcg   3420

ggctctggcg gacgccaggg ggcagcagcc gccctccctg gacgccgcgc gcagtccccg   3480

gagctcccgg aacgcccccg acggcgcggg gctgtgcggc ccgcctcgtg gccttcgggt   3540

cgcccgggaa gaactagcgt tcgaggataa aagacaggaa gccgccccag agcccacttg   3600

agctggaacg gccaaggcgc gtttccgagg ttccaatata gagtcgcagc cggccaggtg   3660

gggactctcg gaccaggcct ccccgctgtg cggcccggtc ggggtctctt cccgaagccc   3720

ctgttcctgg ggcttgactc gggccgctct tggctatctg tgcttcagga gcccgggctt   3780

ccgggggct aaggcgggcg gcccgcggcc tcaaccctct ccgcctccgc tccccctggg    3840

cactgccagc acccgagttc agttttgttt taatggacct ggggtctcgg aaagaaaact   3900

tactacattt ttcttttaaa atgatttttt taagcctaat tccagttgta aatccccccc   3960

tccccccgcc caaacgtcca ctttctaact ctgtccctga gaagagtgca tcgcgcgcgc   4020

ccgcccgccc gcaggggccg cagcgccttt gcctgcgggt tcggacgcgg cccgctctag   4080

aggcaagttc tgggcaaggg aaaccttttc gcctggtctc caatgcattt ccccgagatc   4140

ccacccaggg ctcctggggc cacccccacg tgcatccccc ggaacccccg agatgcggga   4200

gggagcacga gggtgtggcg gctccaaaag taggcttttg actccagggg aaatagcaga   4260

ctcgggtgat ttgcccctcg gaaaggtcca gggaggctcc tctgggtctc gggccgcttg   4320

cctaaaaccc taaaccccgc gacgggggct gcgagtcgga ctcgggctgc ggtctcccag   4380

gagggagtca agttccttta tcgagtaagg aaagttggtc ccagccttgc atgcaccgag   4440

tttagccgtc agaggcagcg tcgtgggagc tgctcagcta ggagtttcaa ccgataaa     4498
```

```
<210> SEQ ID NO 75
<211> LENGTH: 453
<212> TYPE: DNA
<213> ORGANISM: Homo sapiens

<400> SEQUENCE: 75

ttcggaagtg agagttctct gagtcccgca cagagcgagt ctctgtcccc agcccccaag     60

gcagctgccc tggtgggtga gtcaggccag gcccggagac ttcccgagag cgagggaggg    120
```

-continued

```
acagcagcgc ctccatcaca gggaagtgtc cctgcgggag gccctggccc tgattgggcg    180

ccggggcgga gcggcctttg ctctttgcgt ggtcgcgggg gtataacagc ggcgcgcgtg    240

gctcgcagac cggggagacg ggcgggcgca cagccggcgc ggaggcccca cagccccgcc    300

gggacccgag gccaagcgag gggctgccag tgtcccggga cccaccgcgt ccgccccagc    360

cccgggtccc cgcgcccacc ccatggcgac ggacgcggcg ctacgccggc ttctgaggct    420

gcaccgcacg gagatcgcgg tggccgtgga cag                                 453
```

<210> SEQ ID NO 76
<211> LENGTH: 560
<212> TYPE: DNA
<213> ORGANISM: Homo sapiens

<400> SEQUENCE: 76

```
acgcacactg ggggtgtgat ggaaaggggg acgcgatgga taggggtggg cgcacactgg     60

gggacgcgac ggggaggggt gagcacacac tgggggtgtg atggagaggg cgacgcaata    120

gggaggggtg ggcgcacacc agggacgcga tgatggggac gggtgggcgc acaccaggtg    180

gcatgatggg gaggagtggg tacacaccat ggggggcgtg atggggaggc gtgggcgtac    240

accgggggc gcgatgggga ggggtgggcg cacaccgggg gacgcgatgg aggcggtggg    300

tgcacacggg gcgcgatggg tgggagtagg tgcacactga gggcacgatt ggggagacac    360

gaaggagagg ggtgggcgca cactggggga cgcgatggcc gggacacgat gcggagaagt    420

gggtgaatac cggggtcgcg atgggcgccc tggaaggacg gcagtgctgc tcacaggggc    480

caggcccctc agagcgcgcc ccttgggggt aaccccagac gcttgttccc gagccgactc    540

cgtgcactcg acacaggatc                                                560
```

<210> SEQ ID NO 77
<211> LENGTH: 157
<212> TYPE: DNA
<213> ORGANISM: Homo sapiens

<400> SEQUENCE: 77

```
ccacagggtg gggtgcgccc acctgccctg tccatgtggc cttgggcctg cgggggagag     60

ggaatcagga cccacagggc gagccccctc cgtagcccgc ggcaccgact ggatctcagt    120

gaacacccgt cagcccatcc agaggctaga aggggga                             157
```

<210> SEQ ID NO 78
<211> LENGTH: 114
<212> TYPE: DNA
<213> ORGANISM: Homo sapiens

<400> SEQUENCE: 78

```
ttgaggtctc tgtgcatgct tgtgcgtacc ctggactttg ccgtgagggg tggccagtgc     60

tctgggtgcc tttgccagac aactggtctg ccgggccgag cattcatgct ggtc          114
```

<210> SEQ ID NO 79
<211> LENGTH: 104
<212> TYPE: DNA
<213> ORGANISM: Homo sapiens

<400> SEQUENCE: 79

```
tgacgcgccc ctctccccgc agctccacct ggttgcgctc aacagccccc tgtcaggcgg     60

catgcggggc atccgcgggg ccgacttcca gtgcttccag cagg                     104
```

<210> SEQ ID NO 80
<211> LENGTH: 659
<212> TYPE: DNA
<213> ORGANISM: Homo sapiens

<400> SEQUENCE: 80
aacacactgt ctcgcactag gtgctcgcgg aagagcgcgg cgtcgatgct gcggctcagg 60
ttgatgggcg atggcggccg cagatccagc tcgctcagcg atggcgccgg tcccacaccg 120
ttgcgggaca gtcccgggcc accctggggt ccgcgaccca acgacgcagc cgagccccag 180
gcgcctgaac tgggcgtggc cagctgccca ctctccgccg ggttgcggat gaggctcttg 240
ctgatgtcca agctgcctgc accaacgttg ctgggccctg catagcagtt attgggtcgc 300
tccggcacct cgctctttcc tgacggcgcc gggcacgcca gacgcatcag cttagcccag 360
caagcgtgct ccgtgggcgg cctgggtctc gcggcagcca ccgcggccaa cgccagggcg 420
agcgcccatg tcagctccag gaggcgcagc cagaagtgga caccccacca ggcccacgag 480
aagcggccca cgcggcctgg gcccgggtac agccagagcg cagccgccag ctgcaagccg 540
ctagccagca gccccagcgc gcccgccaca gccaacagcc gagggcccgg gctggcatcc 600
cagccccgtg ggccgtccag caggcggcga cggcacaggc agagcgtgcc cagagccac 659

<210> SEQ ID NO 81
<211> LENGTH: 813
<212> TYPE: DNA
<213> ORGANISM: Homo sapiens

<400> SEQUENCE: 81
gtctgcacga agcccgcggc ggcctgcagg gggcccagcg actcgtccag ggaaccggtg 60
cgcaggagca gccgggggcg cggcgcgccg gccgcccttg ggggactctg gggccggggg 120
cgcagctcga tctgacgctt gggcactgtc cggggcctgg cgggcgcggc gccctcctcc 180
agagccacct ccacacactc gaactgcgct ggggcggcag gacttggccc acggggccgc 240
agctctaggt aggtggccca gcgggagcca ccatcgggga cctgggactg gcgtgggacc 300
gcggcgggag acgctggccc cggcggcaag gggctgatga aggccggctc cgtgaactgt 360
tgttgcgcct cgcgatcgtc tgcgccggag cagccgaaca ggggtccgac gccgaagatg 420
acttccatct cccccgacgg cagcgtgcgc agctggggct ggggtggccg tgggccggaa 480
cctgggcctc gcgggaaacc cgagccgggc ccgtgccgct ggcggctatt ctgggcgctg 540
acggacaggc gaggctgcgc gcccgccccc cgcccaggag ccacccaggg ccaattcgct 600
gggcctttcg cgtccggccc aacgtccggg ggctccggag aacctggagc cgtgtagtag 660
gagcctgacg aaccggagga gtcctggcgc cgcgcggggg ccgtgggcag ctgcctcggg 720
atcccaggca gggctggcgg ggcgagcgcg gtcagcatgg tggggccgga cgccgtgcac 780
tatctccctc gcattcgcct ccgctggtgg cgc 813

<210> SEQ ID NO 82
<211> LENGTH: 440
<212> TYPE: DNA
<213> ORGANISM: Homo sapiens

<400> SEQUENCE: 82
ctggagagaa ctatacgggc tgtgggagtc accgggcgac tatcaccggg cctcctttcc 60
acatcctcct ccgggaaggg accccgttcc gggcctcgac cggcgcagac tgggctgacc 120
cactttcttg ggcccactga gtcacctcga aacctccagg ccggtagcgg ggaggagagg 180
aggagcaggc gggggtgcca aggtgtgggc tgcgccctgg ttagggggcg agcccggctt 240
gtttatgagg aggagcgcgg aggaggatcc agacacacag gcttgcgcgc ccagactcgc 300
ccggccagcg gctggcggcc tccgacgtca ccaaaccggt tgggtgagag ggcagagagc 360
agggggaagg gccgcagtcc cgcccgcgcc ccccggcacg caccgtacat cttgccctcg 420
tctgacagga tgatcttccg 440

<210> SEQ ID NO 83
<211> LENGTH: 252
<212> TYPE: DNA
<213> ORGANISM: Homo sapiens

<400> SEQUENCE: 83
gagtgcggag tgaaggggtg cactgggcac tcagcgcggc ccttgggagg cagggccgcc 60
ccagcctgcc ctcctgtctg ggaaggccgt ccagaagcag gagccccggg gaaaacaact 120
ggctggacgg ggcggccttc agtgtctctc ccagcctgag agtcgcttcc caccacctgg 180
gcacgaacct gctctgcgat ctccggcaag ttcctgcgcc tcctgtcggt aaaatgcaga 240
tcgtggcgtc tt 252

<210> SEQ ID NO 84
<211> LENGTH: 1539
<212> TYPE: DNA
<213> ORGANISM: Homo sapiens

<400> SEQUENCE: 84
tcttctttcc gcccctaggg ggcacaagcg ggcatgtcca agcgcctagg agcccgtacc 60
gctggggacc tccccttccg cgaaccccga gcgggtagac ccagagcaat ccgagtgtgg 120
aaacaatgga gagggggcgt gttgagctgg ggtctccatg cctcgttggg gagagggagg 180
tgagtttgtg tcttctggaa ggcgtggggg ctgtgccctc gtgggggtag gaagtgctcc 240
cgtggggcgg ggtgcggatc ggagaggtga gtgggtgcgt ctgtccagcg gtccgcccgg 300
tgtggtcgtg cccggcccgc gtggggatgg gggtgtctct cccgctgggc aactatacca 360
gcgcaaccgg ggcgtcggcg cggcccacgc tagcggcgct gctccggcgg cgggggctgg 420
gcgtggcggt gatgctgggc gtggtggccg cgctgggcgt ggtggccgcg ctgccgccct 480
cacccgggca gccgtgctgg agaaggatgt cggcgcacag ctggcttcca gcctggcggg 540
cgtagaacag cgccgtgcgg ccctgggcgt cacgggccgc cacgtccgcg ccgtactaga 600
gggcggaaac ggccgcgtga ccgcgcgtcc ccagggcgcc cacacccggc gccgcctccc 660
ccacatggcc aagcctactt ccggggtccc tctgggaatt tcgggctttc ccgcgccagg 720
cgttttccga gatgaagcct caaagacccc ctttcctccc cccagctcac gtacccacag 780
cagcagttgc gtgatgacga cgtgggcgag ctcggccgcc aggtggagtg gggagcgcag 840
ctgtgggtcc tctacgctgg tgtcgagcgg cccgtgtcgc gcatgggcca aaagcaggag 900
aacggtagcc acgtcctggg cctgcacggc ggcccacagc tggcggccca gcggctcctc 960
cgaggtgctc agcggcgcca ggaacagtag ctgctcgtac ttggcgcgaa tccacgactc 1020
gcgctcctcc ctgcaagacc agggatcaac ggaaaaggct ctagggaccc ccagccagga 1080
cttctgcccc tacccacggg accgtctcag gttcgcacac cctcagcaac cctccccccg 1140
ctctgttccc tcacgcttac cgcgaagagt cccgcgaggg cttggcacgg cctcgcgtgt 1200
cgctttccca cacgcggttg gccgtgtcgt tgccaatagc cgtcagcacc agggtcagct 1260

```
cccgtggcca gtcgtccaag tccagcgagc gaacgcggga caggtgtgtg cccaggttgc   1320

ggtggatgcc agaacactcg atgcagatga gggcgcccag gttcaagctg gcccacgtgg   1380

ggtctgcgga aggagcgtag aggtcggctc ccagccgggc agcacaggca ccccggcatt   1440

cactacactc cctagcccct ccgctgcctc ctggcactca ctgggggccc cgcagtccac   1500

gcagattgaa ttccccttgg cgttccggat cgcctggat                          1539
```

<210> SEQ ID NO 85
<211> LENGTH: 2648
<212> TYPE: DNA
<213> ORGANISM: Homo sapiens

<400> SEQUENCE: 85

```
agccaggtcc agcccccgcg cctgacaccg gccggacgtt cccggggcgc cgcagctgcg     60

gcgggaactc tgggatccgg agccatctgc tcccacccgc tccggagcca aaccccgggg    120

gccgcctccg ctcccggacc cgcctcctct cccgggagtg tgagccgaac caagagtctc    180

ctgcctatct cctccagtag gaaaatagta ataataatag acaccctgcc cccgtaaaaa    240

acactacctt ccccgtaccg cctcccaagt ctcccggggt acggattgcc tttgcagcag    300

ttccgcccca cctgactcac tccagggtca gccccgggtg ggtttcaatg cggctctggg    360

gagggggtgg gcagtggggg aagtgaggct tcctatccgc cccctctcac ttcacattta    420

aatattctgc acgttccagc ccccgcggac tcgcgtaccg cccaatccgc cttcaccgca    480

cgaaaaacat cactagcctg ctctcagccc aggggacgac tagtccctgg cgagaagctg    540

cctgcaaggt cactgtcatg ccacctgccc caagtgctca ggggaaactg aggcttcctc    600

atccccttca ccttcaacgt cgctctaaac acggcaaagc ccgtttccca tgctcccaga    660

gttcagctga ggctggaagt ggggtcctgg gcttctctgg gagcaatttt ctagtcactc    720

tgatcaagga cgttactttc ccagaaagct ctgaggctga gtccctctga aatcaagtcc    780

tttctcctgt cgcacaatgt agctactcgc cccgcttcag gactcctatt ctttgcccca    840

atccttgaca gaggggtgag cttggttcat ccgcccaccc cagagaaaag cttccctagt    900

ttcctggacc tcgctcctcc accccaagct gagcattcca ggtacccttc cctccctgtt    960

ctcaagccct gactcaactc actaggggaa gcgcggagct cggcgcccag cagctccctg   1020

gacccgctgc cagaagacag gctgggggt ccgggaaggg gcccggagcc aggaggccct    1080

cctgtgctct tggtgaagat gccgctgata aacttgagca tcttgcggtc acgagtggat   1140

gctcggcccc cctcccggcc ccgtttcagc cccggagctg gaggctccag agtgattgga   1200

ggtgcaggcc cgggggctg cgcggaagca gcggtgacag cagtggctgg actcggagtt    1260

ggtgggaggg ttagcggagg aggagagccg gcaggcggtc ccggatgcaa gtcactgttg   1320

tccaaggtct tactcttgcc tttccgaggg gacaacttcc ctcgggctcc agccccagcc   1380

ccgaccccac cagaggtcga agctgtagag ccccctcccc cggcggcggc ggcggtggcg   1440

gcggcagaga ccgaagctcc agtcccggcg ctgctctttg accccttgac cctgggcttg   1500

ccctcgcttt cgggccatga caggcggcta cccgcgccct tgcccccgcc ggctttggct   1560

ccactcgtgg tcacggtctt gcaaggcttg ggagccggcg gaggaggcgc caccttgagc   1620

ctccggctgc cggtgccagg gtgcggagag gatgagccag ggatgccgcc gcccgcccgg   1680

ccttcgggct ccgggccgcc ccagctcggg ctgctgagca gggggcgccg ggaggaggtg   1740

ggggcgcccc caggcttggg gtcggggctc agtcccccgg agagcggggg tcccggaggg   1800

acggcccaga gggagaggcg gcggccggga gcgggggaga ctgggcgggc cggactggcc   1860
```

ggagccgggg acagggctgg gggctccgcg cccccggtgc ccgcgctgct cgtgctgatc 1920
cacagcgcat cctgccggtg gaagagacgt tcgtgccgct tcttgcccgg ctcctccgcg 1980
cctcgggggc tgccaggatc cccagtctcg gagcctctgg caccggcggc gccggccgcg 2040
gccgcagacg gagaaggcgg cggcggaggc accgactcga gcttaaccag ggtcagcgag 2100
atgaggtagg tcgttgtccg gcgctgaagc gcgcccgcgc cccggctcat ggggcccgga 2160
gacccccgag ctggggaggg gaggggactc ccccggactg cctcaggggg gcccggccat 2220
ggggccgccc tgctcgctgc cccccagcccc cggaccccgc tgagccccccg gcccggctcc 2280 gctgtcgccg ccgcctccgc cgcctccgct tgcgcccccc tcccatcaca tggggcgccc 2340
cctccccatg ctccccgccc tgcgccccca ccctcttgga gccccgggac cttggtgctg 2400
ctccagggag gcgcgccgga ccgtccaccc cggcctgggt gggggcgctg agatgggtgg 2460
gggagggcgg ggaggacagt agtgggggca aatgggggag agagaggaaa agggagcaga 2520
aaaggggacc ggaggctagg ggaaacgaac ctgtgcgggg gaggcagggg cggggaattg 2580
ggactcaagg gacaggggcc gcggatgcgg tcggaaagag ggtctagagg agggtgggaa 2640
gctagtgg 2648

<210> SEQ ID NO 86
<211> LENGTH: 452
<212> TYPE: DNA
<213> ORGANISM: Homo sapiens

<400> SEQUENCE: 86
aggagcgcaa ggcttgcagg gcatgctggg agagcgcagg gaacgctggg agagcgcggg 60
aaatactggg attggctccc gagggctgtg aggagggcac gaggggacac tccgatgaag 120
gcagggcacg cggggcgagc cgggagcgtc tcctgagggc agcgaggagg gagctgaggc 180
acgcgggctc tcaatcgacg ccccacagag accaagaggc ctggccttgg ggggcagctg 240
cttgaaggag gcagagcgga agcgagggag actgctggag gccctgccgc ccacccgccc 300
tttcctcccc ctgaggagac gcctgacgca tctgcagtgc aggaggccgt gggcgttaga 360
agtgttgctt ttccagtttg taagaccatt ttcctgattc tcttccccac ggttgcggag 420
gagcaggtca gggccgccat gagggcagga tc 452

<210> SEQ ID NO 87
<211> LENGTH: 232
<212> TYPE: DNA
<213> ORGANISM: Homo sapiens

<400> SEQUENCE: 87
tcgaccgcta ctattatgaa aacagcgacc agcccattga cttaaccaag tccaagaaca 60
agccgctggt gtccagcgtg gctgattcgg tggcatcacc tctgcgggag agcgcactca 120
tggacatctc cgacatggtg aaaaacctca caggccgcct gacgcccaag tcctccacgc 180
cctccacagt ttcagagaag tccgatgctg atggcagcag ctttgaggag gc 232

<210> SEQ ID NO 88
<211> LENGTH: 221
<212> TYPE: DNA
<213> ORGANISM: Homo sapiens

<400> SEQUENCE: 88
tgtgccgtcg cacacagacg ccctcaacgt cggagagctg tgagcggggc cgtgctcttg 60
ggatgggagc ccccgggaga gctgcccgcc aacaccactc cgacgtgatc catgctggac 120
ataaagtgct cttccctccg ctagtcatcg gccgagcggg cccctcgctc ctgggtgtaa 180
gttctttctg tgcgtccttc tcccatctcc gtgcagttca g 221

<210> SEQ ID NO 89
<211> LENGTH: 477
<212> TYPE: DNA
<213> ORGANISM: Homo sapiens

<400> SEQUENCE: 89
ccatgcgccg ctgcgcgcgc gagttcgggc tgctgctgct gttcctctgc gtggccatgg 60
cgctcttcgc gccactggtg cacctggccg agcgcgagct gggcgcgcgc cgcgacttct 120
ccagcgtgcc cgccagctat tggtgggccg tcatctccat gaccaccgtg ggctacggcg 180
acatggtccc gcgcagcctg cccgggcagg tggtggcgct cagcagcatc ctcagcggca 240
tcctgctcat ggccttcccg gtcacctcca tcttccacac cttttcgcgc tcctactccg 300
agctcaagga gcagcagcag cgcgcggcca gccccgagcc ggccctgcag gaggacagca 360
cgcactcggc cacagccacc gaggacagct cgcagggccc cgacagcgcg ggcctggccg 420
acgactccgc ggatgcgctg tgggtgcggg cagggcgctg acgcctgcgc cgcccac 477

<210> SEQ ID NO 90
<211> LENGTH: 1200
<212> TYPE: DNA
<213> ORGANISM: Homo sapiens

<400> SEQUENCE: 90
gtcctaacat cccaggtggc ggcgcgctgg ctccctggag cggggcggga cgcggccgcg 60
cggactcacg tgcacaaccg cgcgggacgg ggccacgcgg actcacgtgc acaaccgcgg 120
gaccccagcg ccagcgggac cccagcgcca gcgggacccc agcgccagcg ggaccccagc 180
gccagcggga ccccagcgcc agcgggaccc cagcgccagc gggaccccag cgccagcggg 240
tctgtggccc agtggagcga gtggagcgct ggcgacctga gcggagactg cgccctggac 300
gccccagcct agacgtcaag ttacagcccg cgcagcagca gcaaagggga aggggcagga 360
gccgggcaca gttggatccg gaggtcgtga cccaggggaa agcgtgggcg gtcgacccag 420
ggcagctgcg gcggcgaggc aggtgggctc cttgctccct ggagccgccc ctccccacac 480
ctgccctcgg cgcccccagc agttttcacc ttggccctcc gcggtcactg cgggattcgg 540
cgttgccgcc agcccagtgg ggagtgaatt agcgccctcc ttcgtcctcg gcccttccga 600
cggcacgagg aactcctgtc ctgccccaca gaccttcggc ctccgccgag tgcggtactg 660
gagcctgccc cgccagggcc ctggaatcag agaaagtcgc tctttggcca cctgaagcgt 720
cggatcccta cagtgcctcc cagcctgggc gggagcggcg gctgcgtcgc tgaaggttgg 780
ggtccttggt gcgaaaggga ggcagctgca gcctcagccc caccccagaa gcggccttcg 840
catcgctgcg gtgggcgttc tcgggcttcg acttcgccag cgccgcgggg cagaggcacc 900
tggagctcgc agggcccaga cctgggttgg aaaagcttcg ctgactgcag gcaagcgtcc 960
gggaggggcg gccaggcgaa gccccggcgc tttaccacac acttccgggt cccatgccag 1020
ttgcatccgc ggtattgggc aggaaatggc agggctgagg ccgaccctag gagtataagg 1080
gagccctcca tttcctgccc acatttgtca cctccagttt tgcaacctat cccagacaca 1140
cagaaagcaa gcaggactgg tggggagacg gagcttaaca ggaatatttt ccagcagtga 1200

<210> SEQ ID NO 91
<211> LENGTH: 900
<212> TYPE: DNA
<213> ORGANISM: Homo sapiens

<400> SEQUENCE: 91
caccttcccc gaggtaatta ttttctgggg ggtaggggtg ggggttggga gggtgaagaa 60
aggaagaaaa agaaggccga tcacactggg caccggcgga ggaagcgtgg agtccattga 120
tctaggtact tgtggggagg ggagaacccg agcagcagct gcaaacggaa gggctgtgag 180
cgagcgggcg ggcgggtggc tggcagcgag gccaccagca ggggggcccc gggccgaggc 240
cgcgccacct cggcaccacg cgggcagccg gtgcggcggg gtcgccacgg ccaggggagc 300
gctgggtgcc caccatggca gttatgcaag cggtgacccc ctggtcttgc ctccccgccg 360
ccctgcactc cttcctcccc gctgccgaca cttggatctc tctagctctt tctctcccct 420
gtgttttcaa acaggaagtg cacggctgtc tataacgtgc tgccgggtct caggatggag 480
gagtgaagtc tcctgtcgcc gtggttccag cctccggagc tcgcccaagc cgcgtcccca 540
gagagcgccc tgagagaaca gggtggccgc ttggtccagg tgcgcggggt cgggtctggg 600
tccagggagc gggtcgggaa gtctgcggca cggagcactg ctagtgtcgg atctgcatct 660
ccagctctgt gctgcagctt cacttgcccg ccccccacca ctggcttctc acccggggtc 720
tctgccaaac tctggctgct gccgccctgg gttcgggccg gcggaaggcc ctgggcgtgc 780
gctgcggagc cgcctgcgag gactccacta gggcgctttc caggctggac tgccccgggc 840
tgcgctggag ctgccagtgc tcggggagtc ttcctggagt ccccagctgc cctctccacc 900

<210> SEQ ID NO 92
<211> LENGTH: 200
<212> TYPE: DNA
<213> ORGANISM: Homo sapiens

<400> SEQUENCE: 92
ctcttcccaa gttacgccac cggtcgagga cggcaggaga cccccgagtg cagagaaagc 60
tcaaaccggc agcgaagtcg gtcctagcca agctgaaaaa acgtctcgga tttcgcggac 120
agcggcctag acacagcccg atcttccagt cctagtgccc tggtcgagac ggttctatcc 180
ttttgcaaag aagccggaaa 200

<210> SEQ ID NO 93
<211> LENGTH: 400
<212> TYPE: DNA
<213> ORGANISM: Homo sapiens

<400> SEQUENCE: 93
tctcggttgc aatccccacc ctcctcaccc agcagggcag gaggcaccca acttggagga 60
gaaaggggtg ggggaggtga aacagagacc ggagagtcac gagggctggg ccgccgagag 120
caggagaata taccgtgtca cacacctcca ttctctcaca cacgttgcag acacaaatca 180
ctgacggttt ccacgtgctg cgctcgtgag cggaggtgtt caaagagggg gcagatgagt 240
tacttcccga gacggaaccg ggggtcccac gtccgccgcc ttcagtagca caaccaatct 300
ctgaacactc aaaccgcgca tctctggcgc atcaccatcc tatttaaggc cacgggctcc 360
gcccttttcc tcccctccct tcttttccac tctttttcca 400

<210> SEQ ID NO 94
<211> LENGTH: 700
<212> TYPE: DNA

<213> ORGANISM: Homo sapiens

<400> SEQUENCE: 94
ctgccagaga tgtgtctgtc ttgcgccccg catgcactgc ctgcggggct gcgctgcact 60
ccccggcggc gccacgggtc tggcccccgc gcttctacgt gttgggggga tgcatggacc 120
ttggagatcc gtagttggcc ctaaccttct cggaatctcc tctgcacgcg ctgcctgttc 180
ctcctctgca cgctctgtcc gttcctttgc aacttctgtg ggaattgtcc tggcgtggga 240
aacgcccccg cgctctttgg cacttagggt gtgagtgttg cgccccttgc cgcagcgctc 300
agggcagcat cccgctcgag gatgcagggt tctcaccaag cagtgagggg gactcacgcg 360
ccgccgggga gcggagccag gctccgagaa gggagcaggc tcgagccgct gggttttcgc 420
aagccttggg gcctctggcc gcccttccat gcctccgggc gcgggcggct cagcaggtcc 480
ccggcttcgg gaagttttgt gcgcggatcg ctggtgggga gggcgcgcgg gccagtggct 540
gagcttgcag cgaagtttcc gtgaaggaaa ctgcatgtgc ctttggaggc gactcgggac 600
tgctgtaggg tggactgggt gtctatggag ttgcgggtca gagcgagtag ggtgggtcct 660
ttcctgggac aggactggga attggggctc gaagtagggg 700

<210> SEQ ID NO 95
<211> LENGTH: 200
<212> TYPE: DNA
<213> ORGANISM: Homo sapiens

<400> SEQUENCE: 95
aggggtgtcc tccaacatct ctgaaccgcc ttcccttcct cctcactggc gccctcttgc 60
ctcagtcgtc ggagatggag aggcggctga agattggcag gcggcggcca gggtcgaggc 120
tgggagactc agagccgctg aggctgccgg agctcaggga gccgcttagg tagctgtcgc 180
ggtccgacag cgagtccggg 200

<210> SEQ ID NO 96
<211> LENGTH: 5000
<212> TYPE: DNA
<213> ORGANISM: Homo sapiens

<400> SEQUENCE: 96
tctgactctc gggctggagc agccgagaca gcgctcccca gcgggactac agaatcccgg 60
gtgtcggcct gggggccctg gattggcagt ggtggagtct tctgagccta acagctacta 120
ggaatgacag agttgcagat ggctttgtcg cccgcggggc ggctcaagcg tcctgggtcc 180
caggcctctg tcctacggcc aggccgccgg ctcaacgggc cgaagggaat cgggctgacc 240
agtcctaagg tcccacgctc ccctgacctc agggcccaga gcctcgcatt accccgagca 300
gtgcgttggt tactctccct ggaaagccgc ccccgccggg gcaagtggga gttgctgcac 360
tgcggtcttt ggaggcctag gtcgcccaga gtaggcggag ccctgtatcc ctcctggagc 420
cggcctgcgg tgaggtcggt acccagtact tagggaggga ggacgcgctt ggtgctcagg 480
gtaggctggg ccgctgctag ctcttgattt agtctcatgt ccgcctttgt gccggcctct 540
ccgatttgtg ggtccttcca agaaagagtc ctctagggca gctagggtcg tctcttgggt 600
ctggcgaggc ggcaggcctt cttcggacct atccccagag gtgtaacgga gactttctcc 660
actgcagggc ggcctggggc gggcatctgc caggcgaggg agctgccctg ccgccgagat 720
tgtggggaaa cggcgtggaa gacaccccat cggagggcac ccaatctgcc tctgcactcg 780
attccatcct gcaacccagg agaaaccatt tccgagttcc agccgcagag gcacccgcgg 840
agttgccaaa agagactccc gcgaggtcgc tcggaacctt gaccctgaca cctggacgcg 900
aggtctttca ggaccagtct cggctcggta gcctggtccc cgaccaccgc gaccaggagt 960
tccttcttcc cttcctgctc accagccggc cgccggcagc ggctccagga aggagcacca 1020
acccgcgctg gggcggaggg ttcaggcggc aggaatggag aggctgatcc tcctctagcc 1080
ccggcgcatt cacttaggtg cgggagccct gaggttcagc ctgactttcc cgactccgcc 1140
gggcgcttgg tgggctcctg ggcttctggg ctcaccctta cacctgtgta ctaaagggct 1200
gctaccctcc cgaggtgtac gtccgccgcc tcggcgctca tcggggtgtt ttttcaccct 1260
ctcgcggtgc acgctttttc tctcacgtca gctcacatct ttcagtacac agccactggg 1320
tctccctgcc cctccagcct ttcctaggca gctttgaggg cccagacgac tgaagtctta 1380
ctgctaggat gggaacacga tgaaaaagga aggggcccag tcaaaagtcc tctcctcttc 1440
ggtttttctt caactgtcct tcacaaaaac atttatttct gtcccagcgc cctggcggat 1500
ttcggcagat gggccctagg gggttgtgga ggccaaattc ccaggatgct ggtcctgcct 1560
ttttcattgg ccaaaactgt atttcctaca acgactaaag ataaccaaga actgagtaga 1620
ccctgttctc tcaccagatc tccctggctc tgtttaactt ttcctggtgc aatgcgatgg 1680
caccaccagc tccccaggca ggcaccactc cctcaagata ccatttgggg tagggatttg 1740
agtcctggag agggtcagcg gggcgccggg gtgggggtgg gaaggagact gacagggaca 1800
caccgcgagc tccgcatact ctcctctgcc ccctgtagcc cggggcttta atgaccccaa 1860
gcagatttcc tgtctctggt ctagccagct gcccctaggg ctggatttta tttcttcatg 1920
gggtttcacc ctaaagggcc ccctggtcat gggacctggt tgggaacaaa tgaaagatgt 1980
cttgtagcaa atgctttcag gggagcagaa aagaagattg ggcacttcca gtcacttggt 2040
cactttaggt ggctggaaca aaactggtga ctttcacgac tgctacaggg tgagggggtg 2100
aagggtggca gagaggtgac aagccactgg gaatcctatt cagtggggat gccgacaggg 2160
agtggctgta atcaactgag caacatctgt gtgaatgtta ttcacaggtc aggacagcag 2220
cttggtcttc ccaggtgagg aactgaggac tggcctgcat agatttgtgc agtaggtgag 2280
tagcttccaa atttattttc agaacttcca tgtagtacct gcctctccat ttaaatattt 2340
tttaaaattt tatttattta aatattttct tggttagctt tccaagaggg aggaaaagag 2400
gggagttgca acaagtagtg cccctatgct gggattcatt ttccagagta aagcctggga 2460
ctggcaccct gacccctacc ggcaggtgaa aactccaggc aaactgctga gatcccacct 2520
gggctggctg agatagtgcc tggggtgcat ccctcagcag ctgccacctg ggccctgggg 2580
ccatctcttt ctctggcatc aagcagccag gtgtcaaggc cttcccagca atccatgctg 2640
catggctggg tcttgttcta gcaggtcgat gggcagggac tggtagctta gccagggcac 2700
cagtgcgtgg ctgtgggttt gtgtgcttct gtggagaagc atgatgtgta tgtgtgtgtg 2760
tgggcacagg catgaggaag ggttcatttg tgcaggtatc tcccatgtat atcagtgtgg 2820
gagagtgcct gaggatgtgt ttgtgtgtct gaaaatgggc ggagggtctg ttgtgctaat 2880
gtgtgcaggg gtgaacatgt gtgtgacagt ctgtgtgttt ccctgagtgg tggctgcgtg 2940
agagggtgag gggatttggt gttgtctacc atgcccggca catagcaggc tcttaataat 3000
cttgaattta attaatgtta aatgtgtatg ttcccatcct tgtggaagtt ggtatagagc 3060
ctgttttcct gtgattgtga gactggaaaa tgggggacgg gcaggggcga gacaggatac 3120
agaggctact gttttcttcc tccctagaag taagtacata gaagagtggg ctctggcacc 3180
tcacgggaca tcaccaagtc ctgtgtggct ggctaggctg tcccaaggtg gcttcaggca 3240
tcacttgaat cttttgagac cttcaggcag tagcctgcca ttcaccctgt cagtcagcag 3300
aagttgggcc cacacaggcc atagaaacac agagcagttc ccgggaggac ctgagctgtc 3360
cctgagagca gagcttccag gagaggccgc aggaactgcc ttgaccggaa ttcctcttgg 3420
ggtgcaaagg tggagggaca catggtgcga ccccaggcag aggactgcag ccactccgtg 3480
cagtcccagc ctctggggta gccccttgac ctccaggcct gcacagatcc aaggccgagg 3540
tccaggctcc agcgccaaat tagctggcct agcagcctgc agccgctcta atctcaacta 3600
ggaaggaatc cttgcgctta gaaagtccaa gcgaaagggt attctgattt tatcccggtt 3660
ttaccagaaa atgctgaaag gaaaagcccc gagaggacac agtgctctag gaactcgggg 3720
cgccacgagc gcctcatccc ctcccttccg cccggccgcg gtgccctggt cgctgaggga 3780
cgcggtcagt acctaccgcc actgcgaccc gagaagggaa agcctcaact tcttcctctc 3840
ggagtcctgc ccactacgga tctgcctgga ctggttcaga tgcgtcgttt aaaggggggg 3900
gctggcactc cagagaggag ggggcgctgc aggttaattg atagccacgg aagcacctag 3960
gcgccccatg cgcggagccg gagccgccag ctcagtctga cccctgtctt ttctctcctc 4020
ttccctctcc cacccctcac tccgggaaag cgagggccga ggtaggggca gatagatcac 4080
cagacaggcg gagaaggaca ggagtacaga tggagggacc aggacacaga atgcaaaaga 4140
ctggcaggtg agaagaaggg agaaacagag ggagagagaa agggagaaac agagcagagg 4200
cggccgccgg cccggccgcc ctgagtccga tttccctcct tccctgaccc ttcagtttca 4260
ctgcaaatcc acagaagcag gtttgcgagc tcgaatacct ttgctccact gccacacgca 4320
gcaccgggac tgggcgtctg gagcttaagt ctgggggtct gagcctggga ccggcaaatc 4380
cgcgcagcgc atcgcgccca gtctcggaga ctgcaaccac cgccaaggag tacgcgcggc 4440
aggaaacttc tgcggcccaa tttcttcccc agctttggca tctccgaagg cacgtacccg 4500
ccctcggcac aagctctctc gtcttccact tcgacctcga ggtggagaaa gaggctggca 4560
agggctgtgc gcgtcgctgg tgtggggagg gcagcaggct gcccctcccc gcttctgcag 4620
cgagttttcc cagccaggaa aagggaggga gctgtttcag gaatttcagt gccttcacct 4680
agcgactgac acaagtcgtg tgtataggaa ggcgtctggc tgtttcggga ctcaccagag 4740
agcatcgcca accagaacgg cccacccggg gtgtcgagtc ttggtaggga aatcagacac 4800
agctgcactc ccggcccgcg ggccttgtgg catataacca tttatatatt tatgatttct 4860
aattttatta taaaataaaa gcagaaatat ttcccgaaga acattcacat gagggcatta 4920
cggggagacg gcaagtcggc ggctcggggg gcgcgctcag ccgggagcgc tgtagtcaca 4980
gtcccgggag gaagagcgcg 5000

<210> SEQ ID NO 97
<211> LENGTH: 1500
<212> TYPE: DNA
<213> ORGANISM: Homo sapiens

<400> SEQUENCE: 97
tggaacaagt gtcagagagt aagcaaacga ctttctgagc tgtgactctg ctcctcgact 60
gcccacgtgc tctccgctgt ctgcactcct gcctcacctg ggctgactcg gactctccac 120
ctcctttgct gcttccggca tgagctaccc aggagcctaa ggcgctcctt cccgcaactc 180
cggtccccgc gccccgggac tgcaaatcct ttaaacagag gccccagagc taggggtttt 240
cccaggctct ggtgggcgtg ggctgacagt cgctgggagc cccgcaacag gggggatgtc 300

-continued caggcaggta tgcacccagc tcccggcgtt tcccggagtc accacaatgt ttccctttct 360
ctctccccca cgtatgctgc taggggtact ccccagatag gattttcttt gtcttttctc 420
ctagtaacac cgaagccctc tcgtgcccgg ggactgcaga ggaacgccag accatccgga 480
ccttgcggga tggctcggtg tgtgtgtttt actgtgtgtc ggagtgtcgc gcatgtgtgc 540
gtgttggggc gcgttatcaa caggggccta gggcaccccc actctttctt gctctcttcc 600
cccatcactt catggacctc cgaggcgcaa agcgctcgac cctctcctgg gctcagtggc 660
ttgggtactc cgggctgagc tcagctgggg agtcccctta cccagcccgc accggcaccc 720
cgaagcttca aagttgcggc aaacagttgc ggggagcaga ggaactgagg tccaggccag 780
cgcgcccgcg gtcgctcgcc ttggggagca ggctgagccg agggtcgtgc gggtgcgcgg 840
cagaggcggt aggaggcgga ggagaggggg gagaaagagg gggcggtggg gaacagctgc 900
cggggtaggc gaggcgcaag gtggctcccc gcggccccgc gccccgcggc tctcggacgc 960
accaggcagc caatggctgc gcagaggtgt acagcagatg gcgtctgact gcgccgttcc 1020
ttcctcctcc tcctcctcct ccttctcttc ctcctcctcc ttctcttcct cctcctcctc 1080
cttcagtgct gaggagccag agtcgccgcc gggttgccag acgctggaat gggtggtctt 1140
ccgacacaca ccaccatctt tcttgcgctc gggaagctcg gggctcagcg gctcccagag 1200
gttacggcgg cggctctggc gagacgggtg agtgcaagca cgcggagccc cgagtcgggg 1260
atgccgggcc ccctggccgg ccgactgggg cgcggggtgg cagcgccggg gaagggggcg 1320
cgctgccggc gcagactttg ctctttcctc gccggacagc catcgtcgcc ccttctccca 1380
gccagacgcg ggaacttgga agcggatctt ctcggacgcc tctggcttgg ggctgcggga 1440
agcgtgggct gcccggggcg cagtgtgcgg agaccctcta ggcgggcggg gacgccccac 1500

<210> SEQ ID NO 98
<211> LENGTH: 800
<212> TYPE: DNA
<213> ORGANISM: Homo sapiens

<400> SEQUENCE: 98
gttattatcc acggggtcct aattaaagct tgattaaaat gcccttcttt ctctaaaaaa 60
ttacgaacta ggcaacttca tacattttga atggcgcagt gtttcctctt ccaactgttt 120
agtttgtagt atactatgta agcaacatca attatcaacc cttgcaagat gacaacatga 180
gcctgtgggg gaagcacttg aggggaggga ggagaaactt ctcttttta ataatcagcc 240 ggaaacaatg tttaacaaga atctgatgag gtcactgcag taaatatttt tcctcttaca 300
gagccaatca tcacggaggg atcccctgaa tttaaagtcc tggaggatgc atggactgtg 360
gtctccctag acaatcaaag gtgtttgctt tctgctctgt tgcttttaaa ttgtatggga 420
aaggaagatt ggtccgacgg cgcgcttgtg gcccggccgg agcttgcgtg cgcgttctga 480
cggctgggtg ctgtgttaca ggtcggcgca gttcgagcac acggttctga tcacgtcgag 540
gggcgcgcag atcctgacca aactacccca tgaggcctga ggagccgccc gaaggtcgcg 600
gtgacctggt gcctttttaa ataaattgct gaaatttggc tggagaactt ttagaagaaa 660
cagggaaatg accggtggtg cggtaacctg cgtggctcct gatagcgttt ggaagaacgc 720
gggggagact gaagagcaac tgggaactcg gatctgaagc cctgctgggg tcgcgcggct 780
ttggaaaaac aaatcctggc 800

<210> SEQ ID NO 99

<211> LENGTH: 40
<212> TYPE: DNA
<213> ORGANISM: Homo sapiens

<400> SEQUENCE: 99
tccctgctgt gggacccgag gagaggagaa ctggttcgct 40

<210> SEQ ID NO 100
<211> LENGTH: 500
<212> TYPE: DNA
<213> ORGANISM: Homo sapiens

<400> SEQUENCE: 100
tctctctctc tctcttgctt ggtttctgta atgaggaagt tctccgcagc tcagtttcct 60
ttccctcact gagcgcctga aacaggaagt cagtcagtta agctggtggc agcagccgag 120
gccaccaaga ggcaacgggc ggcaggttgc agtggagggg cctccgctcc cctcggtggt 180
gtgtgggtcc tgggggtgcc tgccggcccg gccgaggagg cccacgccca ccatggtccc 240
ctgctggaac catggcaaca tcacccgctc caaggcggag gagctgcttt ccaggacagg 300
caaggacggg agcttcctcg tgcgtgccag cgagtccatc tcccgggcat acgcgctctg 360
cgtgctgtga gtacaacctg ctccctcccc gggcacagat atgacagagg ggcttagagg 420
gggcccagct ttgagatggg ttgttcttat gtcacaggac agagtgatct gacatgcaca 480
cttccccgcc accctgtcat 500

<210> SEQ ID NO 101
<211> LENGTH: 500
<212> TYPE: DNA
<213> ORGANISM: Homo sapiens

<400> SEQUENCE: 101
tgtcctcgaa gaagggcctg agcagcagca gaggacccca ggcgaccgtg cctgagccgg 60
gcgccgacga cgactgagca cctgatatgt ccccggcact cgcagccccg cggccggagt 120
cgctgtgggt gagcggtcgt cgagcttcac agaggccggg ctctgtgcca gggccccgac 180
agggcaggaa gcagatagag tcccacaagc acaagcccag tgcgcagaaa gggttactta 240
aaaaataagt tctgtgataa aatcaaacag ggtgaagggc tggaaacagg tcatgagggc 300
gcaaacaggt cgtgagggcg caaacaggtc gtgagggcgc aaacaggtcg tgagggcgca 360
aacaggtcgt gagggcgcaa acaggtcgtg agggcgcaaa cagatcgtga gggcgcaaac 420
aggtcgtgag ggcgcaaaca ggtcgtgagg gtgcaaacag gtcgtgaggg cgcaaacagg 480
tcgtgagggt gcaaacaggt 500

<210> SEQ ID NO 102
<211> LENGTH: 300
<212> TYPE: DNA
<213> ORGANISM: Homo sapiens

<400> SEQUENCE: 102
aaatgagacc tctggggaga ctgtcaaccc caggggtaaa acaaaaattc tgatcagaaa 60
ctgagtttcc caaagaaggg gctaaatgtt ttccaacact ttcggggctc agggaagatg 120
actctgtaag gacactgaga atcttcctcg cgtgccacgg ggaggaggac tgggggcgtt 180
tgaggggctc agcgcaccag aggagtgagg tggaggaggg cgttcccgcg tcctcctctt 240
caatccagag cagctcaacg acgtggctcc ctttctatgt atccctcaaa gccttcgcgt 300

-continued

<210> SEQ ID NO 103
<211> LENGTH: 600
<212> TYPE: DNA
<213> ORGANISM: Homo sapiens

<400> SEQUENCE: 103
taggctctag tggacctagc agtgggagag ctacttgggc tggtttcttt cctgacgctg 60
cagggatggg catcggcctg gaaccagaag cgcaggagct gggccacggc agagtaatta 120
agaaaataat gaaattgatg gcggatgggg gcgctagaaa tcctggggcg tctacttaaa 180
accagagatt cgcggtcggc cccacggaat cccggctctg tgtgcgccca ggttccgggg 240
cttgggcgtt gccggttctc acactaggaa ggagcctgaa gtcagaaaag atggggcctc 300
gttactcact ttctagccca gcccctggcc ctgggtcccg cagagccgtc atcgcaggct 360
cctgcccagc ctctggggtc gggtgagcaa ggtgttctct tcggaagcgg gaagggctgc 420
gggtcgggga cgtcccttgg ctgccacccc tgattctgca tccttttcgc tcgaatccct 480
gcgctaggca tcctccccga tcccccaaaa gcccaagcac tgggtctggg ttgaggaagg 540
gaacgggtgc ccaggccgga cagaggctga aaggaggcct caaggttcct ctttgctaca 600

<210> SEQ ID NO 104
<211> LENGTH: 800
<212> TYPE: DNA
<213> ORGANISM: Homo sapiens

<400> SEQUENCE: 104
gaggttgctg actcaggagc caggagctga gaaactccta ggctagcagc cgttgagcct 60
aattttattt tctggctttc tccgaaatgt ctcgtttccc tcatctttct ggtccttttc 120
gtctctctta ttttccccaa aacgtctacc tcacttcgtc ttcctttctc ctcccctccc 180
cctctctttc ctctatactc tcttcccatt tagccttgca ggcccctcct ccccggtgtt 240
ggagagctca aagacgcgcg aaactcaagg atctggccct gaccagggac gggattaggc 300
gggaagtggt gacggcctga aaaggctggg ctcgaacccg tgccttcctg aaaggactct 360
ccccgccaca agtcacaccc acccgcaggc ctgctggcca aagaaacaaa ggagtcgggc 420
gtggatccag gagaaacagg ttttcgctct cggatctccc tgggcaaatc agggatcctg 480
agcgctatac cccgcagtcg tacggagcct ctgggaaagg ggatttaagg gtgacttcca 540
ctttcagctt cggctacttg ttgcctgcgg tccaagcctt ctctgcttcc tcctacctcg 600
tcttaggcct ctgtagaaag tgcacgccgc gtttcccctt ccaggctctg agagggcctg 660
caggcccgtg gccgcctccg acaagatgcc ttccagtgct agggggggcca ctttggcggg 720 atgggggtcg gttggttaaa aaaaacttaa gttctggctc agtcgagtgt ggcaaaagcc 780
gagggtcggg ggttgggggg 800

<210> SEQ ID NO 105
<211> LENGTH: 2000
<212> TYPE: DNA
<213> ORGANISM: Homo sapiens

<400> SEQUENCE: 105
tactgacctg gtctccgcct caccggcctc ttgcggccgc tgcagaagcg cactttgctg 60
aacaccccga ggacgtgcct ctcgcacagg gagcgcccgt ctttgctggg gctggagcgg 120
cgcttggagg ccgacactcg gtcgctgttg gactccctcg cctgccgctt ctgccggatc 180
aaggagctgg ctatcgccgc agccatagct gctcagcgag ggcctcaggc cccagcctct 240

```
actgcgccct ccggcttgcg ctccgccggg gcgagggcag gacctgggcg gccagggaaa    300
gggcagtcgc ggggaggcag tgctaaaatt tgaggaggct gcagtatcga aaacccggcg    360
ctcacaaggt tagtcaaagt ctgggcagtg gcgacaaaat gtgtgaaaat ccagatgtaa    420
acttccccaa cctctggcgg ccggggggcg gggcggggcg gtcccaggcc ctcttgcgaa    480
gtagacgttt gcaccccaaa cttgcacccc aaggcgatcg gcgtccaagg ggcagtgggg    540
agtttagtca cactgcgttc ggggtaccaa gtggaagggg aagaacgatg cccaaaataa    600
caagacgtgc ctctgttgga gaggcgcaag cgttgtaagg tgtccaaagt atacctacac    660
atacatacat agaaaacccg tttacaaagc agagtctgga cccaggcggg tagcgcgccc    720
ccggtagaaa atactaaaaa gtgaataaaa cgttccttta gaaaacaagc caccaaccgc    780
acgagagaag gagaggaagg cagcaattta actccctgcg gcccgcggtt ctgaagatta    840
ggaggtccgt cccagcaggg tgaggtctac agaatgcatc gcgccggctg cggctttcca    900
ggggccggcc acccgagttc tggaattccg agaggcgcga agtgggagcg gttacccgga    960
gtctgggtag gggcgcgggg cgggggcagc tgtttccagc tgcggtgaga gcaactcccg   1020
gccagcagca ctgcaaagag agcgggaggc gagggagggg ggagggcgcg agggagggag   1080
ggagatcctc gagggccaag cacccctcgg ggagaaacca gcgagaggcg atctgcgggg   1140
tcccaagagt gggcgctctt tctctttccg cttgctttcc ggcacgagac gggcacagtt   1200
ggtgattatt tagggaatcc taaatctgga atgactcagt agtttaaata agccccctca   1260
aaaggcagcg atgccgaagg tgtcctctcc agctcggcgc ccacacgcct ttaactggag   1320
ctccccgcca tggtccaccc ggggccgccg caccgagctg gtctccgcac aggctcagag   1380
ggagcgaggg aagggaggga aggaagggc gccctggcgg gctcgggatc aggtcatcgc   1440
cgcgctgctg cccgtgcccc ctaggctcgc gcgccccggc agtcagcagc tcacaggcag   1500
cagatcagat ggggattacc cgccggacgc aaggccgatc actcagtccc gcgccgccca   1560
tcccggccga ggaaggaagt gacccgcgcg ctgcgaatac ccgcgcgtcc gctcgggtgg   1620
ggcgggggct ggctgcaggc gatgttggct cgcggcggct gaggctcctg gccggagctg   1680
cccaccatgg tctggcgcca ggggcgcagg cggggcccct aggcctcctg ggctacctc    1740
gcgaggcagc cgagggcgca acccgggcgc ttggggccgg aggcggaatc aggggccggg   1800
gccaggaggc aggtgcaggc ggctgccaac tcgcccaact tgctgcgcgg gtggccgctc   1860
agagccgcgg gcttgcgggg cgccccccgc cgccgcgccg ccgcctcccc aggcccggga   1920
gggggcgctc agggtggagt cccattcatg ggctgaggct ctgggcgcgc ggagccgccg   1980
ccgcccctcc ggctggctca                                                2000
```

<210> SEQ ID NO 106
<211> LENGTH: 800
<212> TYPE: DNA
<213> ORGANISM: Homo sapiens

<400> SEQUENCE: 106

```
gggggacaca gagaggaggg gttgcgggcc tgtgagaatg aagagcacag agcggagagg     60
gggaggagga gggaaaggaa ggcgtggcag tgagagagaa gaggaagaag agaggaggag    120
tggggagggg agggagagca agacagcagc gggtctggat tcccctccga gccacatctg    180
gtcaggttct aagtaattag aagattttcc cattggttta cccaagggct ctctctctga    240
ttaattttcg aaagagttgg ccaattttaa tcatagcaaa cacgatgatc acggtgatca    300
tggcctgaac agctaaaagc agaaaataaa acccccagaa cggactatga tcttgacctt    360
```

-continued

```
tgcccgtggt caccggctgg gcccacaccc agggttctga gctgttggga gccaaggctg    420

ggtggacagg ggcttccgag gagctgtccg cagcggggcg gggaggcggg ccccgggggc    480

ccgggcactc cgcgtcaccc cccggcaggg cccagagcgg caggccggcg tgcgccccag    540

ggcctgcgca ccgtgggggc tcttccccgc ccacgaggcc taggtgctgc cgcagccacc    600

ccaggaaggg ccccaggcca cagtcgcagc gccaggagtt gtgccccaac aggacctccg    660

tcagccgggg cagagcccca aacacgtcgc caggcagggt ctccagctgg ttgtggtcga    720

gctggacgct ctccaggctg ctgagattgc ggaagagggc acggggcagg gcgcgcagcc    780

tgttgcggcg cagggacacc                                                 800
```

<210> SEQ ID NO 107
<211> LENGTH: 550
<212> TYPE: DNA
<213> ORGANISM: Homo sapiens

<400> SEQUENCE: 107

```
gccccggtgc accgcgcgtc cagccggccc aactcgagct agaagcccca accactgccc     60

agtgcctgag ttgcagtctt gggtccttta gaaacctgga gatgtgcgta aaattcagat    120

gccggtattc ccgaacttcc ccaggcctca gcatatctcg gcggcctgtg gacagatggg    180

aggctaccaa tcgctccggc gtccgcagcc cgacccctgc cgccagaccc cggacgtctt    240

ccggataata aagttcccgc tctaattcat tttccctaat ctggacgccc ctaatctaca    300

gcttttattg cgcccagtta aaagtcgagg gaattcgctg tccctccgcg ctcggataat    360

taccccctaaa tggccacggc agccccttgt gtttcctgga gattagaacc ccgcagtcat    420

caatggcagg gccgagtgag ccgccaatca cctccgctca ctccctgaga gccgctggcc    480

tgggccgcag gaggagaggc cataaagcga caggcgcaga aaatggccaa gccccgaccc    540

cgcttcaggc                                                            550
```

<210> SEQ ID NO 108
<211> LENGTH: 2000
<212> TYPE: DNA
<213> ORGANISM: Homo sapiens

<400> SEQUENCE: 108

```
agggtgcctc tgttcaaatt agaaaaaggc gccccctcag ggcagactca gcccagctgc     60

caggggacaa gtcctggcta acgggagctg gagctgggtt tcacctccag gtgcctcctt    120

ggcggggcgc cccgtgcagg ctacagccta cagctgtcag cgccggtccg gagccggagc    180

gcgggaatca ctcgctgcct cagcccaagc gggttcactg ggtgcctgcg gcagctgcgc    240

aggtggagag cgcccagcct gggaggcagt agtacgggta atagtaggag ggctgcagtg    300

gcagaagcga gggtggccgc agcacttcgc cgggcaggta ttgtctctgg tcgtcgcgca    360

ccagcacctt tacggccacc ttcttggcgg cgggcgccga ggccagcagg tcggctgcca    420

tctgccggcg ctttgtcttg tagcgacggt tctggaacca gattttcacc tgcgtctcgg    480

tgagcttcag cgacgcggcc aggtctgcgc gctcgggccc ggacaggtag cgctggtggt    540

taaagcggcg ctccagctcg aagacctgcg cgtgggagaa agcggcccgc gagcgcttct    600

tgcgtggctt gggcgccgcc ggctcctcct cctcctccgc gacgcctgcc ggcccgctgc    660

cgcccccgcc gccggccccg ctgcacagcg cggacacgtg tgcacctctg ggccaacac    720

cgtcgtcctc ggtccttggg ctgcggtcgc ctgcggaccc cggtgggaac agaaacaaga    780
```

-continued

```
gactgtcagc gccacagacg aggtgaggcc gggcctcaac tgcaggggtc acgggagtgg    840

ggcggaaata cactttgatc ccactcaagc ggagcggagg tctgggaggc cctgggcccg    900

ggagaccagt cttagactct tgccccactg ggtatcccat ctaggcctct tctggggagg    960

gcggcagact cagccgctgt gtcaacgctg tgttgtcgag accagctccc caccctctct   1020

gggccccagg ctcccctcag taacttgggg cactcgaccc gagcatccgc gaaagccctc   1080

ccggctctca gcgttgagca ttgggattct agactgcatt tccgtctctc tgcttgggtt   1140

cacgcgcctc tccacactta gttcacacgc acacacgcgc gcgtcctcgc agcacacact   1200

tgtctggtgc aggtaaggga aggtggaggc ggatcctggg gccaaaggta tttagaatct   1260

ttcaccctca gccgcctggg attgctgtga gagacatgga aacaggctga gccgaggcct   1320

tagatgagag gatggactgg agagtaaaga gggagggttg cccctgcatc gagtttttgg   1380

accctgatcc cacaccagct tctcggtctc gtacccgccc ttccgaagaa ctccagcaga   1440

aaggtccagc ggtcccctgt gcttgaggcc tacagaagct tgtacccaac tagggcaggc   1500

acccgggtct tccagaccac aggacaggac aggccacggc tgaggaggcc tctctcctgc   1560

ctccaggatg aactaaagac ccaatccggg atcttcggcc tagggctgct ctcccagacc   1620

tggggtctga gaaagccaaa ccagcccttt ccccaaagct ctagttctgc agattctcag   1680

ctctggccca ctcggaggtg ttcttcacca cctatccacc tactgtgggg cccggccctg   1740

ggaccttgaa ctggcaggtc tctggtccag agctaggtca ctggctacct gaggtctctg   1800

aacccctcac ttttccgctt ccctgatttt ggggatttgg ggacagacac ggcagaaagc   1860

actggcgacg aactcaaaaa ctcccgaacg caaggggcag cggttctccc aacccagtct   1920

aatgcacatt ggcccaggat gtctcaggcc tcaccccagg acgtagggct ctgaggagct   1980

actccggtct ctcgcgggct                                               2000
```

```
<210> SEQ ID NO 109
<211> LENGTH: 1000
<212> TYPE: DNA
<213> ORGANISM: Homo sapiens

<400> SEQUENCE: 109

gagaagggat gtggcggggg gctcctccgg ccctggactc cctgggtgga ctagaaaagg     60

gcaaagaagt ggtcacatct gtgggccaga ctggtgcgcg atctttggag gcgcagcagc    120

aaggccgcgc cagggctgag cccagaccgc ccacgaggag gcccgccagg cccggagcag    180

cggcgcgtgc gggggcgtgc cgagcgcagg ctctagggcc cctgcttcgc cccagctgga    240

ccccgcgggc ggtcggtgca gctcgagcgt gtgggctgcg atgccctgcc tgagacttcg    300

ggctagggat gcgggcggga agtgggggtg cggcggcagc tgcagattag attccttttt    360

tttttggccg gagggacgtg caaacttcta gtgcccgggc caagagggcg accccggagg    420

tgcgtaggtg gccctccggg ttcccgcttc tcctagtgcc tctgaaaata ccgtcagggt    480

aaagggagac aggcagtaag tcttaccacc accgcccttt ccccatgtca ttggccaaaa    540

actgaacatt aagataaagc agctgtttca gtcaatggaa agcggtaggg cgaggttgta    600

cccaaaaccc ggtttagacg gccaatgaag tcctaggaaa agccgccccg ggggcacgtt    660

caggtggagc ggctgcacct cgggtcgttc taagggatgg gctgcgtggt acccacggaa    720

ttcatgggtc caaaaggtcc tggtcacctg tccaaacatc catcccctgg cgcatggcgg    780

ttgacaagat ggcccggcca cccagaggaa ggaggatccg ggacggggaa cttcgcgccg    840

ggaagctgta gcccagagct gcagctcagc attcgcaaga gattcatctt ttttttctct    900
```

cgtgttcgga gaaacagata aacaagacac cgcctcatca gataagaacg tctccttcga 960
tgtcacggat ttcaagaggt agctggagaa actgacgtca 1000

<210> SEQ ID NO 110
<211> LENGTH: 1300
<212> TYPE: DNA
<213> ORGANISM: Homo sapiens

<400> SEQUENCE: 110
caggtcaggc agaacttctg cccttcccgc tactggcacc ccaagcaggg atgcactggg 60
atgcgtggca ggggcgggat ctcctgggag cgtctcagcc cagcagggag tggggaagca 120
agagggaagg cttaccttcc tcggtggctg gcaggaggtg gtcgctgcta gcgagggggga 180 tgcaaaggtc gttgtcctgg gggaaacggt cgcactcaag catgtcgggc caggggaagc 240
cgaaggcgga catgaccggg gcgcagcggt ccttcacctg cacgcagagc gagtggcatg 300
gctggatggt ctcgtctagg tcatcgaggc agacgggggc gaagagcgag cacaggaact 360
tcttggtgtc cgggtggcac tgcttcatga ccagcgggat ccaagcgccg gcctgctcca 420
gcacctcctt catggtctcg tggcccagca ggttgggcag ccgcatgttc tggtattcga 480
tgccgtggca cagctgcagg ttggcaggga tgggcttgca attgctgcgc ttgtaggaga 540
agtcgggctg gccaaagagg aagagcccgc gcgccgagcc caggcagcag tgcgaggcga 600
ggaagagcag cagcagcgag ccagggccct gcagcatcgt gggcgcgcga ccccgagggg 660
gcagagggag cggagccggg gaagggcgag gcggccggag ttcgagcttg tcccgggccc 720
gctctcttcg ctgggtgcga ctcggggccc cgaaaagctg gcagccggcg gctggggcgc 780
ggagaagcgg gacaccggga ggacagcgcg ggcgaggcgc tgcaagcccg cgcgcagctc 840
cggggggctc cgacccgggg gagcagaatg agccgttgct ggggcacagc cagagttttc 900
ttggcctttt ttatgcaaat ctggagggtg gggggagcaa gggaggagcc aatgaagggt 960
aatccgagga gggctggtca ctactttctg ggtctggttt tgcgttgaga atgcccctca 1020
cgcgcttgct ggaagggaat tctggctgcg ccccctcccc tagatgccgc cgctcgcccg 1080
ccctaggatt tctttaaaca acaaacagag aagcctggcc gctgcgcccc cacagtgagc 1140
gagcagggcg cgggctgcgg gagtgggggg cacgcagggc accccgcgag cggcctcgcg 1200
accaggtact ggcgggaacg cgcctagccc cgcgtgccgc cggggcccgg gcttgttttg 1260
ccccagtccg aagtttctgc tgggttgcca ggcatgagtg 1300

<210> SEQ ID NO 111
<211> LENGTH: 500
<212> TYPE: DNA
<213> ORGANISM: Homo sapiens

<400> SEQUENCE: 111
tgcgatcatt aaaatcagtt ccttccctcc tgtcctgagg gtaggggcgg gcagatttta 60
ttacttctct tttcctgata gcagaactga ggcggggttg tggaggagcg acggaggacc 120
acctctaact tcccttcact tcctggattt gaagcctcag ggccaccggc ctcagtcctg 180
ttacggtggc ggactcgcga ggttttccag cagctcattc cgggacggcg gtgtctagtc 240
cagtccaggg taactgggct ctctgagagt ccgacctcca tcggtctggg agcgagtggt 300
tcgagttcag atgctgggaa ccgtcgcttc tccccggccg ggctcgctgt tttctcctcc 360
gctcgccgtc atcaagcccg gctatgagca gggctttaaa tcctccctcc ctcacccgca 420
ggtttaccga gcagccccgg agctctcaga catgctgcgc tgcggcggcc agaggagggg 480
tgggggcatt gccctctgca 500

<210> SEQ ID NO 112
<211> LENGTH: 500
<212> TYPE: DNA
<213> ORGANISM: Homo sapiens

<400> SEQUENCE: 112
gggcttgggc cgcaggcttc cctggacttc cgcagtcccc cttctcccca ttccagaacc 60
tgccgagccc ctgctgcatc tgggacccgc cttcaccgtt tcccaatccc agcggttagc 120
ccctgcgccc cctttttggt ctccactttg ccgttcgaaa atgcctaggt tggtggatcg 180
accctccgcg gagcaaagac ggatggctgg caggagcagg ttcaggagct gggccaaggt 240
attctctgct tccgcctttg tgtccgcccc cccgccccct gctccccgct tcccgccagc 300
atctctcctt ttctgctcag gagtgtttgg cccggcggtc caccccggct tcccgagata 360
cgctagagtt gcccccacgt cctgtccgcc gcgcccctac ccaccgggtt gccttcgggg 420
cccttcggtg ctgtgtagtc ggcgtggcgc tgtgagctag gcgaacagga acccccaggc 480
ccgccacgtc tacgctatta 500

<210> SEQ ID NO 113
<211> LENGTH: 600
<212> TYPE: DNA
<213> ORGANISM: Homo sapiens

<400> SEQUENCE: 113
ttctggggcc tggatgggtg cgagcgggac ccgggggagt gggagtcgcc aggctctgag 60
caagcaaggg ctgcacctgc acctctgccg ggcatgaaga aaggtaagga aggaaggagc 120
tcacccgggt gggagacaga gccggggcgc gcgagcttgg tgtgggggcg ccactccggg 180
gcggagggga ggggctacca gtgacttctc cgagtcggga gctagaaaga ggcttccggc 240
caggttccct tggaacaggt gtcggagttg ttgggagagg gggctgcaag aaagaggggt 300
gcagaaactg gttcattaga tggaggctct gggcggaacc gcgaggacac cctggcagcg 360
cgctgtgcct gcgttaggcc gggaggggag aggcctccgg acggcgaagt gtccctaggg 420
acccagacgc ctcgggagcg atccgggccg ctgcgaagcc ctgcccacca ggagtggatc 480
cccaggattc acctcccggc tgcctgctct gagctgagaa ggggatctgg ttcttcacaa 540
taccgtggat ggcggggaag gggagggagc ctggggtaaa atcccatctt ggtttcctcg 600

<210> SEQ ID NO 114
<211> LENGTH: 1300
<212> TYPE: DNA
<213> ORGANISM: Homo sapiens

<400> SEQUENCE: 114
tgtcacagaa accccagcag cgcagccacc ggactgggtt ctggaggccg agccgcagtc 60
cgtgcggcgg cgctgggaag agaaggcgcc ccggcagctc ccctgccacc ggccccgagg 120
agcggctggc tcccccagcc cagcgccgcc gccgcccggt aactccaggc gcaactgggc 180
gcaactgggg cagctgcgac accgaatccc tcacatctgc aacctgggtg ctgcggccac 240
tgagaaaatg gaggcgcaga ccaacgagcg gtgccgcgac cgagagacct cggctggcga 300
aatggtggtg ccgggagcct gcgagtgacg ccagccggcg gggttgtcaa ggacaacatt 360
cgttttgacg cagccaatgg cgccgtcacc aagaaaccat cgactctgag aaaaaagaga 420

```
ggttcggcca ccgagaaact ccgtacgaca agtgctgtgg cagaaaaacc gcctactccg    480
cgccacaggc aaaacagcca atggaaaccc caggtgctgc gaccgtgaca ccggcactag    540
agggtctcgg atggagaaag cggcgcacgg agaccaggaa actatgtgta gcacaactag    600
cagaaaaccg tctggtcggc catccgggag aaagcgcgga tcagaaacaa gcgacttcga    660
tgcagggaac cgcgcagcca ctgaagaaag tgacccacgt ggcagtggtg ccagcgaaac    720
actgcagttt ggacggcagc tgtggggatg ccacagagaa acatgcactg ccactgaagt    780
acatccagct ccgcggagct agtgttcata tgatcaagaa accgccagtt gggctctgct    840
agaaactttt agtcctccct taacggctat cctacccaca acagacaatg cctttaccca    900
gcacctagcg gtgctgagac ccgcctgggc cagcacagag cgcagagcag tacgggtacg    960
gagaaacgcc ggactcagtg aaaccagcct tgcctccagc ggattccccg gcttcgccgg   1020
acgccacagg cagagtgccg cggggaaacc tctggctccc taaaccgatt agattgtggg   1080
agtggggggg acactcacaa gttgtgtgga agggaaccag cggcaatggg acccggcgag   1140
cacttgcccg cagcaaatgc ctgcgctgct gcaaaaaaaa caacttttgg cgcaaagaat   1200
gttgcggcca gagagcatcc gctgtcgctg acaaaggagt agcaatggca atgagaaacc   1260
gccggcgcca cggccgaccg cggcggctca cgcctatgat                         1300
```

<210> SEQ ID NO 115
<211> LENGTH: 2100
<212> TYPE: DNA
<213> ORGANISM: Homo sapiens

<400> SEQUENCE: 115

```
caaacgctga gagacaaaaa gacaccaaca cccaccagga ctgcgtcctg ccagctcttc     60
actccgctga cctgaccttc cacgccccta gtcctcgagc ggacttgacc tgtgggggag    120
taccgaaccg tccccatgag gccctccaag cggccaggtg gcctccgcca ctctctccac    180
ccccacctcc tccacccccc agcccatcgg tccatcttcg atctgcaaaa cacgccgggt    240
cagcgacgca tcggtcccag gcttgtgacc acctctttct ctgttacttg gggagccagg    300
cccaccgctc aggatcacag tgaggagaaa aaagacacaa acgccaggac agggcggctg    360
gggaaggaaa ctgctaggga ccgctcattg tcagcctggc gtgtcccacg gatcgcagga    420
cccgtcgagg ctttgctctc tgcgacccga atactcctgg gcctctcgac ctcctcctcg    480
gactcaggcg tccgcgtctc cggtcatcac gggagaccaa ttggtttaca aatagtgatg    540
ataaacctgg gaccgacctt ggggctgtgt aaaagtctac tgacagatgt aatggagggt    600
tgttagcagt cacaaagcct gtcggacccg tagcattagt tcaagagact attttcgtgt    660
cgcaccaaaa ttactgcgcg tgtaaaccaa tttccccgac ggaagaataa acagagattc    720
gtttgaagcg cgagatgaaa acagatgggg tatcgcaaac agttccccaa aatacaacag    780
acttctgggc caattacacg tggttagctc tgaatggcag aggaaatagt tttctttgct    840
gctaaatgtc acaaaagtca cctaaaggca cagaggaggc cgctctgttt ttgcgaaact    900
tgctaaaatt aatctgcgct gggccacttg cagaaagcag aaccacctcc cgccccccacc   960
tcgcctccag ccgccggggt tcaggcgttt gtgaaagaca gaacctttgg gctagggacc   1020
cgggcactgg tgcttcgaag tccgaatccg ccggccgaga aaacgacaag agaaagaaaa   1080
tccagcgggc gctctctcca gcgccaggcc ggtgtaggag ggcgctgggg ctcggcctgc   1140
cacccctacc cgacattggg aagcagcccc tgcgctcccg cggcgcctca gcctccggtc   1200
```

cccgccccga ggtgcgcgtt cctcctcccg catgcccgtc tcgggcccca cggagcaaga 1260
agatagacga tgacgaggcg cgcccatcca tccgggccga cgaggtcagg cccgcgccac 1320
aggcaaaaat tgcgcaagcc cggccgcagg gatttcgcgg gcgcctgggt cccaggtgcg 1380
cggccgaaat cctcagggaa aatcccgagg ggccaacggt ctaggccaca gggctgctgg 1440
gcccgggcct ggctcagagc gcattcgggc ggggaggccg cacgccgcac ccgggcctct 1500
cctccgagcc cgaggcaggc actgagctcc gggccagcca ggtgcctccc ggctggtgcg 1560
agaccccggg cctgctggga ggcgtgggca gggcagggca gggctgaacc ccagcgactg 1620
aatctcgaag gcaggaggcc tcggaggtca tcggcccagc tcgcctgaaa ctgtccctgc 1680
tcgtgccagg gcgcgggcag aggagaaagg acagggcgga gcaagcccac tgcagaactg 1740
cggtcggtgg ctgcgaaggg tccgggtcac cgcgctcccg gacgccggaa gccgcgctgg 1800
cggggccgcg gggagggagg ctgggtaccg gggccgtccg gccggaggaa gcggctccgg 1860
ccgcgctgtc cgcgcttggg agccgcgtgc agggttcagc cgtgtttcag ttgccctctg 1920
acctgacccc gggcgcacaa aggcctcccg ggtgcgccgc catggcccag tcttccagtc 1980
gctgccaaat taatgagccc acgtcaggtt gggtttacag ctcggccggg aagcagccga 2040
gtggaaaatg agctcggggc cgctccagag gctcccgcac aactgcagag gctgcccgcg 2100

<210> SEQ ID NO 116
<211> LENGTH: 250
<212> TYPE: DNA
<213> ORGANISM: Homo sapiens

<400> SEQUENCE: 116
tttccaagac agaaggaggg aactaggcgc ctttttttcca ctccgctgac cccaacgtct 60
gggctgtgcg ttgtaacgca gttggcgggg ccttcagctt gggatgaggg cgaaggggct 120
cgggatgggt gggaaagcaa ggaccgggca acaggtgggg aggtggcgga cttttgtctc 180
ggggaaggaa atcggctgtg ctgaaagggc ggaaagcagt agcgcacaga actagtgtct 240
gcggggtccc 250

<210> SEQ ID NO 117
<211> LENGTH: 250
<212> TYPE: DNA
<213> ORGANISM: Homo sapiens

<400> SEQUENCE: 117
ccctcctgtg gctgcttggg cagacgcctg tggcctgtcg gatgcggccc acatcgagag 60
cctgcaggag aagtcgcagt gcgcactgga ggagtacgtg aggagccagt accccaacca 120
gcccagccgt tttggcaaac tgctgctgcg actgccctcg ctgcgcaccg tgtcctcctc 180
cgtcatcgag cagctcttct tcgtccgttt ggtaggtaaa acccccatcg aaactctcat 240
ccgcgatatg 250

<210> SEQ ID NO 118
<211> LENGTH: 2000
<212> TYPE: DNA
<213> ORGANISM: Homo sapiens

<400> SEQUENCE: 118
tcctcctttg tgtatgtcaa cccagaggat ggacggatct ttgcccagcg tacctttgac 60
tatgaattgc tgcagatgct gcagattgtg gtgggggttc gagactccgg ctctcccca 120 ttgcatgcca acacatctct gcatgtgttt gtcctagacg agaatgataa tgccccagct 180

```
gtgctgcacc cacggccaga ctgggaacac tcagcccccc agcgtctccc tcgctctgct    240
cctcctggct ccttggtcac caaggtgaca gccgtggatg ctgatgcagg ccacaatgcg    300
tggctctcct actcactgtt gccacagtcc acagccccag gactgttcct cgtgtctaca    360
cacactggtg aggtgcgcac agcccgggcc ttactggagg atgactctga cacccagcag    420
gtggtggtcc tggtgaggga caatggtgac ccttcactct cctccacagc cacagtgctg    480
ctggttctgg aggatgagga ccctgaggaa atgcccaaat ccagtgactt cctcatacac    540
cctcctgagc gttcagacct taccctttac ctcattgtgg ctctagcgac cgtcagtctc    600
ttatccctag tcaccttcac ctttctgtca gcgaagtgcc ttcagggaaa cgcagacggg    660
gacgggggtg gagggcagtg ctgcaggcgc caggactcac cctccccgga cttctataag    720
cagtccagcc ccaacctgca ggtgagctcg gacggcacgc tcaagtacat ggaggtgacg    780
ctgcggccca cagactcgca gagccactgc tacaggacgt gcttttcacc ggcctcggac    840
ggcagtgact tcacttttct aagacccctc agcgttcagc agcccacagc tctggcgctg    900
gagcctgacg ccatccggtc ccgctctaat acgctgcggg agcggagcca ggtgaggggc    960
tcggcgccgc cccgggcgac ccctgggggc ggcactggag aagccgcccg tcctcataag   1020
ggattgaact tgcatccact cctctccggc cggcttggtc gctggctgcg ctccacccga   1080
ttctcgggat cattggaccg tttgcgcgaa accagagtgg ccgattaagg gatggggctc   1140
cgagcaccgg gggtggtggc gactgtgggc gaggggaggt gggaccgacc cccacccccta  1200
cactcaaaaa aggccggggc ctccttcgag cttccggtga atttcgggcg atttccgcgg   1260
gtgtcggggg tcccgggagg aggcagtcac agatccaccc ctgcagccag cctcctaggc   1320
gccggctccg gcacgcttcg ccggtctgta gatttcctct tcgatttctc cccagctccc   1380
agcatctgtg acttcactgt taccctccct atccccgcat cacccaaccg cacctgtctg   1440
cgggacttag gtgtgcgcgc ggggctcatg cgtgtcctcc ctgctggcca cccccacggc   1500
ccacacaagt tgcacgggct cgccacgccc cgccaacacg tgcgcggacg cacgcacgca   1560
ctcctcgcac gtgggcttac gcgaatacca gctttcactg ccactcgctc gcggccagat   1620
tcacaggcct gttccggtcc actcgcagct cccctctgcc gctccctccg ccgggctcag   1680
gagtactcgt agctgattgt gcgcgcctga gggtcccaga tcgcggccgc ccaggaccag   1740
gcgaggactc cggagcctcc tctcacctct cccacctgcg ccccgggctg ggccgggtcg   1800
cctgggggc ggcctgagcg aggcgcgggg ccaggagcgc tggagcgact gccgctctaa    1860
gtgccgggcg ggcaggactc tacgatcctt gggccagagg tccggatggt cccgggactc   1920
cgtctcaagg gtcggcgacc cctcaaccca gaagcctcga gcaggcggac aggcagagct   1980
gcccagtggc cgaggcgcgg                                               2000
```

<210> SEQ ID NO 119
<211> LENGTH: 1100
<212> TYPE: DNA
<213> ORGANISM: Homo sapiens

<400> SEQUENCE: 119

```
atttgtcgtt gtgccattgc tgccactgtt gttcttgtcc agggaaacac cggtggccaa     60
cccagatcgg atacaatggt gcggctctgg actgagcctc caaccacatt agccatgggc    120
agcattgttg ctgccgctgc tgttatttta attatgattg tacgttaacc accaccttcc    180
ttcctctgcc tcccttcagc tgcaatgatg tatgttactt tttggtaact ggatttcatt    240
```

-continued

```
aacatttatg aactctcata aagtagtaga aaaagcaatt tgtgtggaag aattttccac    300

ctcattaaac agtgttcttt tgggggtcaa gctgatattt tttttgttgt tagatttttt    360

ttataggtcc tttgtccttc cctaagccct gggggatgaa aggagagccg tccacccagc    420

gaggggcttg tgtgccctag agggcgctgg gccccgcgcg ctttcctggc tgtccccgcc    480

ggctttccac cctccccaaa gcccaggtgc ccaccgtggg tcgctgcggc ctttcccctt    540

cttggccaaa tccgattact tcgcagcctg cagatggcat cgccggctaa gggcagcctg    600

cggcaggtcc ccgagcctga gcactcctcc tatctggggc ctgagaggac gctctgggct    660

ttttcccagg cccagggtgc gcggcctgct agcgcctttc gaggcacagt cccaagatag    720

gctcttgtcc ttcgacgccc ccttggcaca agcgcactgg cgccctccgc tcaacccacc    780

ttgcctttgg ggcgggcttc aaccctggga agacaggcct gggggaagcg agaggagagg    840

cccgaataga ggttccggct caatctttcc cagacggagg cctggtgttt ccagctcagt    900

tgcatcttcc agccgcgggc tcctggccca aacagaatgt gtttgctttc acaccgggac    960

ggcaagcgga gtccgcctca gtgagcagcg agctgcgcag tccggacggg tgtcgccccc   1020

agagactcgc cagccgcccc cagacactcg ccagccgtcc ccatctctaa tccaccgtcc   1080

aggcccgggc cctgggaaga                                               1100
```

<210> SEQ ID NO 120
<211> LENGTH: 800
<212> TYPE: DNA
<213> ORGANISM: Homo sapiens

<400> SEQUENCE: 120

```
ccgtgtctcc cttaagaact ggggcctcat ctccactcca gctgcgcgtg cacgtgtgct     60

cccggcagga cgcgcgccca ggagcgcgct gggggctgcc ccgcccctct ctccctcccc    120

cgcgggtaaa ctccgggcat ccatcagtct gttaattgca ctaattagag atcgcagagg    180

tgttaattgg aaaaccctgg tattgtgcct gtttggggga agaaaacgtc aataaaaatt    240

aattgatgag ttggcagggc gggcggtgcg ggttcgcggc gaggcgcagg gtgtcatggc    300

aaatgttacg gctcagatta agcgattgtt aattaaaaag cgacggtaat taatactcgc    360

tacgccatat gggcccgtga aaaggcacaa aaggtttctc cgcatgtggg gttccccttc    420

tcttttctcc ttccacaaaa gcaccccagc ccgtgggtcc cccctttggc cccaaggtag    480

gtggaactcg tcacttccgg ccagggaggg gatggggcgg tctccggcga gttccaaggg    540

cgtccctcgt tgcgcactcg cccgcccagg ttctttgaag agccaggagc ctccggggaa    600

gtgggagccc ccagcggccc gcagactgcc tcagagcgga agaggcagcc gcggctttga    660

cccagcttcc ttccgacggc atctgcagga gcctctaggc ctgacatagg ctccgaggtg    720

ccctggctcc cccacgggga atgctgaggg ttgggccact aggtcctgcc taagtgcagg    780

acctgagcct cagacaaatc                                                800
```

<210> SEQ ID NO 121
<211> LENGTH: 300
<212> TYPE: DNA
<213> ORGANISM: Homo sapiens

<400> SEQUENCE: 121

```
gggattgccg gctttgagaa aatatgaaga aaccgatttc tccttccact ttgccagtgc     60

actttccttc cactttcact ggtgctgggg gcggcgcact ctttacgaca tataagcgga    120

aaattctgca aaagtggccc ccggggatcc ccgcccgacc cctgtctgtc gctaatgtgg    180
```

gcctgtctcc ggaaattcga ggttgggcct ttgcctgaat ctgttgctat tgctcccctt 240
gctaccgctg acacttggca ccgccgcctc ctagcagcgg ccagacgcgg ggctgggggc 300

<210> SEQ ID NO 122
<211> LENGTH: 400
<212> TYPE: DNA
<213> ORGANISM: Homo sapiens

<400> SEQUENCE: 122
gttgcgagcg cggcacaggt tgctggtagc ttctggactc tggaggcttg gccttccttc 60
taagccgatg gcggggaaag aacctcgttt ccacagcttc cccgaccccc gccgcttgcc 120
atttggggac gggaagcgcg cccgggtcgc ttcacgtccc tctgggccgg agccctttcc 180
atggctggct cctctggggg cccttgggcc tgtgagcagc gtctacttcc ctcagagaag 240
aatcctttcc ttcccccatc gaagtgtccc tttctgtatc ctgaaataac ccctcctggg 300
tgaggccagt tcccctctgt cgccctcctc ccgcaggcgt ccgggagcct cgtgaggacc 360
ccgtgcagtt gagtccaggc gacaggtgcc tccccaggtg 400

<210> SEQ ID NO 123
<211> LENGTH: 800
<212> TYPE: DNA
<213> ORGANISM: Homo sapiens

<400> SEQUENCE: 123
cagtgcgccc cttaccggag cacccatggc ctcccgcgtt accccaaatt ttgtaggcag 60
actgtcagag ttcgaagcca gctgtgtcct ctgcgggccg tgtgacccta ggctatctgg 120
gctgctcgga gccttagttt ccctagttgt gaagagggag ggtgtgacca tggcccggag 180
ctctccgaaa ggctgtgcgg attgctcggt ggcgggatgt ggagcgcgtc ttctatgatg 240
ccaggtgctg gccaagcgct cgatgcaggc tgctccagtt aggtcgatgc gatggcggga 300
agcactttcc tctgcaatgg agagacgccg acaccccgag cccgaaggct tgcaaggcgc 360
gctctcgcca ctggggtcgg ggatccgtgg gttctctatc ccgcttaccc actccatcct 420
tagcagctgt cgtcggtccc agacctctac cttggagaga ccaaggcggc ccagagccca 480
ggagactact gcgcggtacg ccaggatcca gaagtggatt ctgacttcta aagacccctc 540
ccaagccaac gctatcaggg tccctgcaag cggttgactg tggcggaggc agaaccaaaa 600
cctttgctct gcccgcggcg ctccagcctc tcacccagga cagtgctctg ggctccagcc 660
gctgcagtgg ggtcgggaca cagacgccga gttagaagcc ccgccgctgc aggtccctgc 720
ttggtcggcg cggtgacggt gtcgctggcg gcggcggggg ccttcctttg gctgcccggc 780
catttaatca gagctattat 800

<210> SEQ ID NO 124
<211> LENGTH: 1000
<212> TYPE: DNA
<213> ORGANISM: Homo sapiens

<400> SEQUENCE: 124
tttagtattt aaggagaaaa gcctcatttt ccagaatcga ataagcgaat taatcgcaca 60
attgtgtaga atggaactca gtctgtaaaa aatcaagacc aacgtacttt ttaatattct 120
aacatctcca agtagtagtt acaagtattg tacccatgaa gtccaggtaa ttaatttgtt 180
caatgtcaca ctgttaaaag tcaggtgggc tccaaagcac agtcctaacc agcatgctct 240

-continued

```
actgcctcct ctgaggcaac agccgaagtg cagaccactg ggaataaata gctgcccggt    300

cttccccact cctaaattct cccgacagac cccaaagcct ctctgagagc ctctctgacc    360

gccctgcggc ccaccccgag ttcccggcat cctctgggat ccctcttcct ggagccaaaa    420

cctacgcagg ctcctttcct ccgagctggt tgctaggtga tctccgaagg ctgtccgaag    480

tctcgcgagg gcggacccgt tgcctgatga cgagagttgg gagtgtggct ggggctgcgg    540

atctccagca gtggcgttac ttctagcggc tggataccgg gttctccgcg agatcgcgag    600

atcccgagat attctccccg cacggaagcg acgactggcc tggccagagg actcgcgtgg    660

gagcgaggtg ccggccccga caggacggtg aggtatgcag aagtaaggcg gggcgccccc    720

tgcgggaagc gagcgcgccc cggaaaatga gcgcctcccc acaccaaggt gtccaggagt    780

gagtgcggga aggaactcgg ccgcccggag ttgtggcctc atcgtgcttc ccgccaaaaa    840

cgccttggta ctgtcgggac gcggctaagc gtggacgcgc ccgcatctgc ccctcctccg    900

cagtggtgga agacacccgc ggagcgccgg tggataaggg ccgtttcctg agaccagagc    960

tgtatccgca gcaggtcagc acttcgtgcg ccctgtgtgc                         1000


<210> SEQ ID NO 125
<211> LENGTH: 300
<212> TYPE: DNA
<213> ORGANISM: Homo sapiens

<400> SEQUENCE: 125

agcggcgctg ttcccgggct gggtgcagct gctaaggaca aggcccctgc tccgaagaac     60

gcggtggctc ggggataccc tgaaagggac ggccatggcg cacatgggat gccctagggt    120

tcgtgggagg gcatgcaggc gcagcccccg caggggttgg cctgccagag aaggcagggg    180

agagcactcg ggctgcacaa aatggtgtgg ccggagggaa ggtgcagcct tgtgtgtgtc    240

tggatgaggg ctgggcatag gagcttggta tttgatcctg aaagctctgc gtttccaaag    300


<210> SEQ ID NO 126
<211> LENGTH: 600
<212> TYPE: DNA
<213> ORGANISM: Homo sapiens

<400> SEQUENCE: 126

gagtcatact tgtagtcaca tccttttcct ttctccaacc cactggttaa tcatgaaagg     60

ctcttctgat tggctgcctc ctggcagtag tgcctcagcg cgacggttcg ggagcaaata    120

aataattccc gctgggaagc tgtttctcag acaggagcag cgacacccct gccacgcctg    180

ccgcctggag ttgagtgggg taagcacgcc ggcctccagg aatcgacggt gccacgtggt    240

tcttcttgca cttctcttct tctccagttt caggggacac cgtggggtgt gcgagcccgg    300

gggagcgcag ggaagggcgg gttgggctgc aggtgggaat gtgcggtcct tctgcgccct    360

caacagagct tccttccttt ttgccaaggt ccccgtgccg ccttcagcgc gcctccttat    420

gcacctctac ctctgctgca gcgtacctct tccgcagccc tagcggcctc cccgaggggc    480

gccgcggcct cggctgtccc tcccctgcct ggcacgacca cctgaccccc agcgacccaa    540

gaagcaagtt gtgtttgcag acgcaaaggg gctgtcgttg gtatcggtgc actggtttga    600


<210> SEQ ID NO 127
<211> LENGTH: 1700
<212> TYPE: DNA
<213> ORGANISM: Homo sapiens

<400> SEQUENCE: 127
```

acactttctg tgtgggaggg cacaagacat gggctatgac atggccagag accccacctt 60
ctttacacat gtaaaaacca accaaatcaa gatgcgtcaa cggtgattct tcctcccaca 120
ttgtttccct ttttaaactg ttattttttc aatccatgga gcagttgaga aacgggtatg 180
catctctcct cccctcccct tctatcaaag cctgtaagac acataaggaa atccaaagcc 240
acagtaatag agagagagag agagagagag agagagagag agagagagag agagaaaaca 300
gaacaaaaga aatcctcctt ggcttgtttt tccagggtgg ccaggcaagg tgtgaaaatc 360
catatttccc tctgggctgg caggtagaag ttactgggaa ggctgcgctc ccttctctcc 420
caccggctct cacatccagg ctgttccctc accctcagcc tcccccagcg ccagcttcct 480
cctccgcctc tctgcagcca ggcctcccct gcaaggcgga ccttggccca ccttggttcc 540
gggccaaggc ggcgggaaag gcaccgctac ctgcagccgc acgactccac caccatgtcc 600
tcgtactgct tgtagaccac attattgccc gcgtcgatgt atagaatgct gatgggagtc 660
aatttggtgg gcacgcagca gctgggcggg gtggagccgg ggtccatgga gttcatcagc 720
gtctggatga tggcgtggtt ggtgggctcc aggtgcgagc gcagcgggaa gtcgcataca 780
ccctcgcagt gataggcctc gtactccagg ggcgcgataa tccagtcgtc ccagcccagc 840
tccttgaagt tcacgtgcag gggcttcttg ctgcagcgta gcctggactt cttgccgtgc 900
cgcttgccat ggcgactggc gaaggccgtg cgccgccgcc ggcggccggg cgagggcagc 960
caaggcctgg catccggggc gcccgacggc ggcggccacg acccctcggc gcccgcgccc 1020
gggcccgcag cctcggccga gcccagctgc tcgcgcatct ctgcgaacag gttcttgcgc 1080
tgggatctgg tgaataccac cagcagggcc cgctcctggg gaggccgcac cctccggccg 1140
aagcccagac tccgcaggtc cgggggcggc ggttgctggg gtccccgcgc gcgcgcctcg 1200
gcctccccgg cgtccagctc gccccatgcg gcccgcagct ccaagcacag ctgcttccag 1260
ggctggtggc gcaggccctg ccacacgtcg aagacttccc agccggccgg cggcgccccc 1320
tgcgggtcca gggtccgcgc gtccagcagt aggggcgaaa ggcaagggaa gagctgcacg 1380
tggagcggcc cggctggtgg cccccagggc gctgagggcg cctggcgaaa gagccgcagc 1440
tccgcgccca ccagctcttc tttgtctgag agcatggaca catcaaacaa atacttctgt 1500
ctccggagag gagtgtgcga gagatcgtct gcgagataaa aaataattac agtcagtttc 1560
acttaagggg gagatcagcc cggtgctctt cggccgcccc gggaggaaaa gggcggggag 1620
tgggggcagg tcggccgggc agtccagctt gcccggccca gggcctgacc accccggctc 1680
cccatctggc tggtgcatgg 1700

<210> SEQ ID NO 128
<211> LENGTH: 2000
<212> TYPE: DNA
<213> ORGANISM: Homo sapiens

<400> SEQUENCE: 128
gcccgctgtg aatgtaggtg aggtgatccc gggaacctgg gtctgaaatc agacctgtgt 60
tgccattggg agcacggaga gaggggaagc gccctgctta ggcccaggcc gggcgtcctg 120
gtggtgggac cgcagccgca ctcacctcca ggccaacgga caaggttcct gcaagccagc 180
agggccactc tgtgcttggc ctactgcagc tcccctgcag ctcctttcct ctccctcccc 240
ggagcgctct cctctctcct ctcccctctc ttctctctcc tctctcgtct cctggggcat 300
cccgggtgga gggatgtagg ggtcgctcct cggtgccagg ccgggaagca gctcaggcct 360

-continued

```
cccaagagct tggcgctcag tctgggaaaa ggggttcctc tggcctcagg gacgttctcc    420

gcccccaccc cacccccctgg gagcctgaac catctggaag ggatcttagt cgggggttgg    480

gaggagagcc cgtggatagg aggagggggc gattctaggc cgaatccagc ccctgaggtg    540

tcacttttct ttcctgcggc ccgtcaccgc tgatagatgg ggctgagggc agaggaagga    600

aaaagaaaac ctccgaggtc agtgcggggc gaggtgagcc cctcccaggg ccctctggcc    660

caggaggatg aagcgcgccg gcttcgctct tgcacgccgg cttgccatcc gggtaagcgc    720

gggaaaggcg gccacagggc gcggcggcag cgcagcgcgt gggatctcac gacccatccg    780

ttaacccacc gttcccagga gctccgaggc gcagcggcga cagaggttcg ccccggcctg    840

ctagcattgg cattgcggtt gactgagctt cgcctaacag gcttggggag ggtgggctgg    900

gctgggctgg gctgggctgg gtgctgcccg gctgtccgcc tttcgttttc ctgggaccga    960

ggagtcttcc gctccgtatc tgcctagagt ctgaatccga ctttctttcc tttgggcacg   1020

cgctcgccag tggagcactt cttgttctgg ccccgggctg atctgcacgc ggacttgagc   1080

aggtgccaag gtgccacgca gtcccctcac ggctttcggg gggtcttgga gtcgggtggg   1140

gagggagact taggtgtggt aacctgcgca ggtgccaaag ggcagaagga gcagccttgg   1200

attatagtca cggtctctcc ctctcttccc tgccattttt agggctttct ctacgtgctg   1260

ttgtctcact gggtttttgt cggagcccca cgccctccgg cctctgattc ctggaagaaa   1320

gggttggtcc cctcagcacc cccagcatcc cggaaaatgg ggagcaaggc tctgccagcg   1380

cccatcccgc tccacccgtc gctgcagctc accaattact ccttcctgca ggccgtgaac   1440

accttcccgg ccacggtgga ccacctgcag ggcctgtacg gtctcagcgc ggtacagacc   1500

atgcacatga accactggac gctggggtat cccaatgtgc acgagatcac ccgctccacc   1560

atcacggaga tggcggcggc gcagggcctc gtggacgcgc gcttcccctt cccggccctg   1620

ccttttacca cccacctatt ccaccccaag cagggggcca ttgcccacgt cctcccagcc   1680

ctgcacaagg accggccccg ttttgacttt gccaatttgg cggtggctgc cacgcaagag   1740

gatccgccta agatgggaga cctgagcaag ctgagcccag gactgggtag ccccatctcg   1800

ggcctcagta aattgactcc ggacagaaag ccctctcgag gaaggttgcc ctccaaaacg   1860

aaaaaagagt ttatctgcaa gttttgcggc agacacttta ccaaatccta caatttgctc   1920

atccatgaga ggacccacac ggacgagagg ccgtacacgt gtgacatctg ccacaaggcc   1980

ttccggaggc aagatcacct                                                2000
```

<210> SEQ ID NO 129
<211> LENGTH: 2000
<212> TYPE: DNA
<213> ORGANISM: Homo sapiens

<400> SEQUENCE: 129

```
cactcccccg ccgcctccgc ccctaaccct cggccccgtg cgcgagcgag cgagggagcg      60

aacgcagcgc aacaaaacaa actagtgccg gcttcctgtt gtgcaactcg ctcctgagtg    120

agtcgggggc cgaaagggtg ctgcggctgg gaagcccggg cgccggggac ctgcgcgcgc    180

tgcccggcct ggccggagcc tgtagcccgg gggcgccacg gccgggctcg cagtcccccc    240

acgccggccc cccggtcccc gccgagccag tgtcctcacc ctgtggtttc ctttcgcttc    300

tcgcctccca aacacctcca gcaagtcgga gggcgcgaac gcggagccag aaacccttcc    360

ccaaagtttc tcccgccagg tacctaattg aatcatccat aggatgacaa atcagccagg    420

gccaagattt ccagacactt gagtgacttc ccggtccccg aggtgacttg tcagctccag    480
```

```
tgagtaactt ggaactgtcg ctcggggcaa ggtgtgtgtc taggagagag ccggcggctc    540

actcacgctt tccagagagc gacccgggcc gacttcaaaa tacacacagg gtcatttata    600

gggactggag ccgcgcgcag gacaacgtct ccgagactga gacattttcc aaacagtgct    660

gacattttgt cgggccccat aaaaaatgta aacgcgaggt gacgaacccg gcggggaggg    720

ttcgtgtctg gctgtgtctg cgtcctggcg gcgtgggagg ttatagttcc agacctggcg    780

gctgcggatc gccgggccgg tacccgcgag gagtgtaggt accctcagcc cgaccacctc    840

ccgcaatcat ggggacaccg gcttggatga gacacaggcg tggaaaacag ccttcgtgaa    900

actccacaaa cacgtggaac ttgaaaagac aactacagcc ccgcgtgtgc gcgagagacc    960

tcacgtcacc ccatcagttc ccacttcgcc aaagtttccc ttcagtgggg actccagagt   1020

ggtgcgcccc atgcccgtgc gtcctgtaac gtgccctgat tgtgtacccc tctgcccgct   1080

ctacttgaaa tgaaaacaca aaaactgttc cgaattagcg caactttaaa gccccgttat   1140

ctgtcttcta cactgggcgc tcttaggcca ctgacagaaa catggtttga accctaattg   1200

ttgctatcag tctcagtcag cgcaggtctc tcagtgacct gtgacgccgg gagttgaggt   1260

gcgcgtatcc ttaaacccgc gcgaacgcca ccggctcagc gtagaaaact atttgtaatc   1320

cctagtttgc gtctctgagc tttaactccc ccacactctc aagcgcccgg tttctcctcg   1380

tctctcgcct gcgagcaaag ttcctatggc atccacttac caggtaaccg ggatttccac   1440

aacaaagccc ggcgtgcggg tcccttcccc cggccggcca gcgcgagtga cagcgggcgg   1500

ccggcgctgg cgaggagtaa cttggggctc cagcccttca gagcgctccg cgggctgtgc   1560

ctccttcgga aatgaaaacc cccatccaaa cggggggacg gagcgcggaa acccggccca   1620

agtgccgtgt gtgcgcgcgc gtctgcgagg gcagcggcgg caggggggagg aggaggcaga   1680

ggcggggtgg ctggaccctc ggcatcagct cattctcccc tgctacacac atacacacac   1740

aaataatgtt tctaaaaagt tcagttgcga ctttgtgcct cgcctgtcct gttcatcctc   1800

gtcctgggcc ggggaatgct tctgggggcc gaccccggga tgctggctaa ttgctgccgg   1860

cgggttccgt cgccggtgtg accctggacg gcgcggacgg cgtacagggg gtcccgggag   1920

gggcagtggc cgcggcactc gccgccggtg cccgtgcgcg ccgcgctctg ggctgcccgg   1980

gcggcgcagt gtggacgcgg                                               2000
```

<210> SEQ ID NO 130
<211> LENGTH: 800
<212> TYPE: DNA
<213> ORGANISM: Homo sapiens

<400> SEQUENCE: 130

```
ctgaaaagcc gtcagggaaa ccacacatgt tcaacccctg gcggctcccc caaacctctc     60

atttccagta actgtgtgtt tccgctcgtc aacagctgaa accgagcgga acttgggggg    120

ccccaccacg cggccctgct gtgcggcacg gggctcatct gtcccccggc tgcggggagt    180

cagctctcac cgcccacctc cttcccagat agtctctgtg cccactcgac ggcccggcaa    240

gcccagcccc tgcctgccac ggccacagca gcctcagaga gctgccctct ctggccaggg    300

tcagggcctg agctgctgcc tcccgcaggg tcgagggcag gacacttgtc tgaggcttgg    360

gtggggcaat ggcacctcct cagggcctca gcccccgggc aggctcggtg accatgggcc    420

tacagcaggg aaaattctgg gccaaaagct ccagcctcct actagggcat ctgtctgcaa    480

atgcacctta acctgaccgc ttgggctgtg ggggagcctg tttcagggaa agtgagggac    540
```

gcgccagttt cctcctttgg acttgatgag gcacgaacgc atctctaata aagccaggtc 600
tccccgccgt ggctccctgg gcgggtgcct gtggctcggg ccatgagtca cgctgggtaa 660
ccccactacg gggaagaggg caggaagctg ggagccaccg cctctgtgcc cggttgtcat 720
ctcggcacga gggcgaccgt cggcttcgtc ctgccctcat ggctgagggc ttttgggatg 780
tggcgggaga cgggggagtc 800

<210> SEQ ID NO 131
<211> LENGTH: 500
<212> TYPE: DNA
<213> ORGANISM: Homo sapiens

<400> SEQUENCE: 131
aaatcatcag aatggctaaa atgaaaaaga cagacaacag caagtgctga caagggtgtg 60
gggcggccaa atgctcctgc actgctggca ggggacctga gaactgcagg gcattccctg 120
gcttcctgcc cctcctggga ctggggaccc cccagggaca gcctaaggga actgcattta 180
tcttcacgtc tgccaaaaga taacacgaag atgttcaaag ctaagccccc aggctggtaa 240
gagctccaag gcaccagcag tgtgtgcaga actgggggga gtctgttctc ccagggatgc 300
tcccatcacc tgctgccagc agtggggcat gccggtcccc tggggtgtgg ccaaggggct 360
gtgtctcctg cccgggctgc cggcccctct caggttcact ttcccatctc taagcccacg 420
tctcgctgca gttcaagttt gccaggccac caacgggtga cacgcccggc gcagtggggg 480
actccgcact ttctgcgcac 500

<210> SEQ ID NO 132
<211> LENGTH: 1200
<212> TYPE: DNA
<213> ORGANISM: Homo sapiens

<400> SEQUENCE: 132
accctttgtg cctgggtccc ataaacaatg tgctttttaa aggggagccc cctcccagct 60
ccggcctttt tctccagcgt gggcagccaa tcagctgcgc agagctgcat agctggaccg 120
ctttccattc tgagtagcaa caacgtacta atttgatgca cacatggatg cctcgcgcac 180
tctgcaaatt catcacccgc atcttgcatt agtcatctga cggactgcca agtgtttcat 240
tttctttcca tgtgacttta ttattaccac ctctctcctc tcttccaaaa acctcccaaa 300
aagggcggtg gggcgggggg cggggcaggg agagggagag aaatccagca gacatctagc 360
tctgcctttc tttcccagcc acagccaggg tagggctgat aaggcgctga tgcgttgatg 420
gcagccttgc agagctagac ctgcacttaa cttgcagctg cctcccgagc ctccaagatg 480
tccacgccct gggtgacagg cggcagggcg ctgccccgtg ctcccccggc tctgctcgac 540
agcagcacgc agtgagagcc tcgccgccgc cgaggagcaa ctcatggtgc ctccgctttg 600
ttttagttca tcaaatttct acgactcatt aggcactttg ccactgctct tcttcctcct 660
ccttccgcct ccccgctccc ccaccccac tattttttct tcctgtccct catcgtgccg 720
ccctaactct ggctcccggt tccgtttttg acagtaacgg cacagccaac aagatgaacg 780
gagctttgga tcactcagac caaccagacc cagatgccat taagatgttt gtcggacaga 840
tcccccggtc atggtcggaa aaggagctga aagaactttt tgagccttac ggagccgtct 900
accagatcaa cgtcctccgg gaccggagtc agaaccctcc gcagagtaaa ggtacagagc 960
gcggggcggg ggtcgccagg cgtccaggtg ggcgtcgcgg ggcactgggg ctgtccgagc 1020
ccccagcctg caggaggaag ggcgggtagg caggagggct ggaagcagcc ggtgctggcg 1080
gcccctgtgc tccaggggct gctcccgact cctccccgca cccccgcccg cctgcccgcc 1140
gggacaggtt ggaggcggga gagagggacc gaggcagggc gggagcgcag aggctcggtc 1200

<210> SEQ ID NO 133
<211> LENGTH: 800
<212> TYPE: DNA
<213> ORGANISM: Homo sapiens

<400> SEQUENCE: 133
taacaaataa gccgcccgtg gtccgcgctg tgggtgaccc ttggcgcctt cgaggtctgg 60
agccctaggg taaataagga aacggggcgc ctctagagtt ttaaatgaac tctgttattg 120
gaagcttcag tagggaccct gaaaacaatt aacgtcttaa ttagcatttt aatgtctcca 180
ttattacggc gcgggctcta gctcagccct ttaccttacc ttctcaccgt taacagggga 240
gggggattgt atttttagtt catcttttta tgtttttgag ttgttatcct gtctgtctga 300
ttccagcctc gagggtttga tgatgcggcc cgagcctggc tgtggtcgcc tgtcggggct 360
ggagcgggac cctcagccgg gccgggcctg gggctaacg ttttcacagt gcgccctgag 420
tttccttggg ttactgctgg gaccgcgcag gaggaagcaa agagtttttc gagctagacc 480
aacaggaaac acattgacgg aaatgttgcc atagcccatg ggtggcttt aactggccgc 540 ccccgcgggc tgggtgtgaa atcagaggag gccgcggctc ccccggccag gattggaggc 600
tcctcgcgca acctaatgcg ggtgtccggg cccgagcgct tcccgcgcag ccaggccttg 660
tcggtgcagc agccccgctc ctccccaaca cgcacacacc cggtgttcgc aagtgcggct 720
caccaaggga gatccaaggg ggcaaaaagt tatgtataaa tccgagagcc actggggaaa 780
gagggtcgtg gtattgtaag 800

<210> SEQ ID NO 134
<211> LENGTH: 500
<212> TYPE: DNA
<213> ORGANISM: Homo sapiens

<400> SEQUENCE: 134
ctaccctgtg ctatcctgag ctgtagtctt ctgaaatgat cgtttggctt cccagccaag 60
gcagggctcc cccaaagttc attcccactc ttgcagtttc acctcgggat gcttccgcag 120
aatttcagcg cctaagcaga caaggtcaaa gtaaaccgct tcaccgctgc ttctggcgca 180
ggggcccaga gcgcgtgcag ctccccagca cagaccaaca gcaggagagg ggtccgggcg 240
ggagccctgg gctgtagata agcaaaacgc acccattttc tctcctattt actccagagg 300
cacctctcct cccccactcc tggcatctct ttatcactgg ctccctctcc ctgtggcata 360
tttttgggta gtagaatgct gaggtcacag ggagcggctc tttatccaag cagtggggac 420
atcagcctgg agccctgagc atgaaccagc aagatgcaga ctctcgctct tgactttggg 480
ctccaggagc tgccccgacc 500

<210> SEQ ID NO 135
<211> LENGTH: 1100
<212> TYPE: DNA
<213> ORGANISM: Homo sapiens

<400> SEQUENCE: 135
cagtgctccg ctccgggaaa ttgcatcgtc acgacaaacg ggaccgtgat aaaacgaccc 60
tttccgtcct tatttgtaga tcactcagac gagattgaac tgcacttgtt tccccttcga 120

```
ggggagccgc gttttcaggg tagccgaagg cttggggctg aggggggggcc ctcaccaagg    180

cgcgggtggg ggccggagcc tcaactcgat gagaagtgac aggcgtttgg gggatctggg    240

ctccggccgg gaccagcgca agcagggact ttgcggggac accgcttctc caacagagca    300

aggcctggcc cacgtttccg gtttctccta acttcctttt attgccttcc tttgcttcgc    360

aagttccatc taccccctcca gctacagagc cccacctcta ggcacaggaa gcttcccgga    420

aaaagaaagg ctgtcccaga aagagaccga gagagacttt ccaaacttcg ggcatagcca    480

cggcaattcc cagtctgcta atgccaaggc gggcgcgtaa ggccgcctaa atctagacct    540

ccctcctcac tcatttcaaa aaataacaac gtgccagcca cctccgcaga taccgccggc    600

tggtgcttgc ccaggagacg ccagggccag agcgccactc ccagcatcga aatggcagag    660

agaaagcgca gctccaaatt ccccttcaga ggttaagcct caatcattgt gtcccttccc    720

tagggactgc tggcgctctc gcccactggc gatgattatg cgcctagaac tcgaccgcga    780

agcaactaat aggaaaacat atggtgtcaa tttggatgct ccgcgcctcg cgcacacccg    840

ggaacgagcg gcacaaagcc ctgccggccg gcccgcgacc ccgcgcccct cggggcctgc    900

cagccgggcc gcagcgacaa acgctcaggg ctgcgcgccc tggctggggc ccgcccgaga    960

gacagcctgc ggctggggag tctgagctcc aaggggagag cccagccgcc gaaggcgagc   1020

ctaccggcca agccctgggg tccggcaggt tctgcacaac tactcccgca aagctcgcca   1080

cctttgtgcc ctttcctcag                                               1100
```

<210> SEQ ID NO 136
<211> LENGTH: 500
<212> TYPE: DNA
<213> ORGANISM: Homo sapiens

<400> SEQUENCE: 136

```
gggccctcgc ggctcaagcg ccagcgctgg agagagagtc tgagggtacc acgggcgtgc     60

tggcctgggt gctcactccc gccctccttc atgagcggct ttcctctggg tgtgtccagg    120

gcatcacaga gctcttctgc ccaaacccgg aggcctacca gggcctgccc accttgcctc    180

cttccacact ctctgtagca gcagccgcag ccatggcggg gatgaagaca gcctccgggg    240

actacatcga ctcgtcatgg gagctgcggg tgtttgtggg agaggaggac ccagaggccg    300

agtcggtcac cctgcgggtc actggggagt cgcacatcgg cggggtgctc ctgaagattg    360

tggagcagat cagtgagtgt ccgctgcccg cttgctgaac tcggcaccat gggcggccgc    420

cacgggtgtc tctgggcact tccgggccat ccctgctgct cagctcccga taatggtgtc    480

acggtgactc aggcattagc                                                500
```

<210> SEQ ID NO 137
<211> LENGTH: 600
<212> TYPE: DNA
<213> ORGANISM: Homo sapiens

<400> SEQUENCE: 137

```
tgtttacgga atcgggatcg aggggccgat aagtagttta cacgccggcc agagcagagg     60

gctggaggtc ggagttgggg gctggaggaa cgggtggcgt ttttaggatt cagtaacagg    120

atcacagctt tttcttgtgg tggaagctat tggaatttgg ggagggtagc acgaggggtc    180

ctgcagctcc gcgtgtgaaa aagcgtttag gtaggcgatg aaagtagttg atctgagcca    240

tggcaggcga gccccgaatt tttgctgctt ccccctgaaa gtgtttcttt aggaggagag    300

gacttgggcc acacaggacc cggtcctaag agagcgattc cgggaagcgg acagatcgaa    360
```

gagaccttct gggcgaagcg gcagggcagc ctcgcggggc tgggagtgga tctgaggtcc 420
cgacccaggc ggctcggagt gctccaggag ccacctgggt ctgcgggcgc agcgcggcgg 480
ggcgggagcg gtggcccgca ggggccgcgg cctgcgatga aggccggggg gcagcgctag 540
cagcgaggtg ccacagtggg ccgaggagtc tgggctgtgg cccagggtag gaccggctca 600

<210> SEQ ID NO 138
<211> LENGTH: 150
<212> TYPE: DNA
<213> ORGANISM: Homo sapiens

<400> SEQUENCE: 138
acctaaacca agctctccct ccctgccgtc tccttccctg gcctgggtct gaaggagagg 60
aggtgcccag aagttcagag cggcataacc acagagatac tacctaatta acataccaga 120
agcataaaga actcatttgc attggagagt 150

<210> SEQ ID NO 139
<211> LENGTH: 900
<212> TYPE: DNA
<213> ORGANISM: Homo sapiens

<400> SEQUENCE: 139
ataactacgg gggtgggggt ggggaaggaa gagatccaag gaggcagaag gctgcggtca 60
aaatattttg ggtggcagga gtcacgtagg atgtggctgt gggttctggc agcccagaga 120
ttcagctccc gcctcctccc tcagagcgag tccatagcta ccctcacgtc ccccgtggcg 180
gtcctcgcca cgctccggag cgggttaccc atgagggtgc tagacctggg cagcgggaac 240
ctcgaagagg tggagattgc aggctgggac tccagatttc gggcagggat gcggggaagg 300
gaagacgcct cgctggaggc ggaatggagg gcaaggcgaa ggaggatggt gcaggaaacg 360
gcgacaaggc gcccggccag gcccgcgagc taccgagacc cgggttccaa tcctcccccc 420
ttccgcaaac gcccgggttc gaggtacctg gcgggcaagg gccgcagcgg agcgaagcgg 480
gctggccatg gggaggctgc ggggacgcgg ggctgcagag agcggcagtg gcacggagcg 540
cgcggctgga agcgaaagca ggcggtgtgg ccaagccccg gcgcacggcc catagggcgc 600
tgggtaccac gacctggggc cgcgcgccag ggccaggcgc agggtacgac gcaacccctc 660
cagcatccct tggggaggag cctccaaccg tctcgtccca gtctgtctgc agtcgctaaa 720
accgaagcgg ttgtccctgt caccggggtc gcttgcggag gcccgagaat gcgcgccacg 780
aacgagcgcc tttccaagcg cagatatttc gcgagcatcc ttgtttatta aacaacctct 840
aggtgaatgg ccgggaagcg cccctcggtc aaggctaagg aaacctcgga gaaactacat 900

<210> SEQ ID NO 140
<211> LENGTH: 600
<212> TYPE: DNA
<213> ORGANISM: Homo sapiens

<400> SEQUENCE: 140
cagtccagcc gcttgcctca cttcttcccg cttgccttat ctccccgcag acgtggttcc 60
cctgcagccc gaggtgagca gctaccggcg cgggcgcaag aaacgcgtgc cctacactaa 120
ggtgcagctg aaggagctag agaaggaata cgcggctagc aagttcatca ccaaagagaa 180
gcgccggcgc atctccgcca ccacgaacct ctctgagcgc caggtaacca tctggttcca 240
gaaccggcgg gtcaaagaga agaaggtggt cagcaaatcg aaagcgcctc atctccactc 300
cacctgacca cccacccgct gcttgcccca tctatttatg tctccgcttt gtaccataac 360
cgaacccacg gaaagacgct gcgcgggtgc agaagagtat ttaatgttaa ggaaagagaa 420
gaaccgcgcc gcccggaggc agagaggctc catggccgtg ctgctgggcc atccccaact 480
ccctatccca tccccagcct ccaccccat ccagatggga ctcacgtggc ttcaacagct 540
ttggaaatgg gtcccgagtg ggccgtgcga ggaaggctgt cgacctctac tcctccttgc 600

<210> SEQ ID NO 141
<211> LENGTH: 1500
<212> TYPE: DNA
<213> ORGANISM: Homo sapiens

<400> SEQUENCE: 141
caagatcgac tttcttagga agggggagag gagggaactc ttcacgaagg gaggtgggag 60
tccacctcag acctctattg gaaggaaatc gagttgttcc gggggactga ggtctcttgc 120
ataaggcatg ggatccttat tattattatt attattttta aatcccccgc ggaggagctc 180
tgggcaaatg aataccgagg cgccgctcta gctggttagg cttgggatgc gataactcag 240
tgccctcttg cagacttgca tagaaataat tactgggttg tcgtggaggg gacacgagac 300
agagggagtt ctccgtaatg tgccttgcgg agagaaaggt ccaagaatgc aattcgtccc 360
agagtggccc ggcaggggcg gggtgcgagt gggtggtgga gtaggggtgg gagtggagag 420
aggtggtttc tgtagagaat aattattgta ccagggcccg ccgaggcacg aggcactcta 480
ttttgttttg taatcacgac gactattatt tttagtctga tcaatgggca caatttctaa 540
gcagcgcagt ggtggatgct cgcaaacttt tgcgcaccgc tggaaaccca ctaggttgag 600
ttgcaaaacg taccgcgtag acgcccctgg tggcgccgag agaagagcta ggcctgccca 660
gcacagagcc ggagagcgtc gggccttccg gaagggtaag ttctccgcca aggggtcccg 720
agggagctgg acgtctgaat ctggacttgc cccccagcttc ggggttcgat tctgggtttt 780
gcgcgtcccc aacccccagg gctttccgaa gcatggcctg gctccaggcc cggtcctgta 840
aggactggaa cggcagcaaa atgtgcaggg aggcagtcgg ccggcagagc tgcggcggga 900
gccaaggtca ggcccgcggg gagagcgggc agcttccagc gccggccaca agctcccagg 960
ccagctgggc cgcagacccc tttgcttcca gagagcacaa cccgcgtcct ttctctcagc 1020
caggctgcag tggctgcccc gagcttcgct ttcgtttccc aagctgttaa taacgatatg 1080
tccccaaatc cgaggctcgt gtttgctccc agatgccaag aacgcaaccc gaaatccttc 1140
tcccaaaccc taggtcgacg agatgagttc ctacttgacc tctgagccga ggtgggccgg 1200
aaaccgaggc ctaggccccg ccggggctgc aaggaaaagg ggaaactccg agcgtagcgt 1260
cttttccttg tggttccttt ctccggcatc ccggactgcg ggccctgcag ccacctggac 1320
cggcattcaa aggattctgc aagtccagct tcacagactg gctttcccag acgctccgaa 1380
gcccgcacca cgaacagaat aaaggagaga cgagagatcg caactagatt tgagaatcct 1440
cgttcttttc cccaatcgtt cgggcagtaa actccggagc cggctacagc gcgcatcctc 1500

<210> SEQ ID NO 142
<211> LENGTH: 500
<212> TYPE: DNA
<213> ORGANISM: Homo sapiens

<400> SEQUENCE: 142
actgtcctcc tccctcaatt gcctattttt tgcccatagc tctaacttaa ccctgtgatc 60
accccagatc gctacttctg acccccatct cctctcccac accaacctcc agcgcgcgaa 120
gcagagaacg agaggaaagt ttgcggggtt cgaatcgaaa atgtcgacat cttgctaatg 180
gtctgcaaac ttccgccaat tatgactgac ctcccagact cggccccagg aggctcgtat 240
taggcaggga ggccgccgta attctgggat caaaagcggg aaggtgcgaa ctcctctttg 300
tctctgcgtg cccggcgcgc ccccctcccg gtgggtgata aacccactct ggcgccggcc 360
atgcgctggg tgattaattt gcgaacaaac aaaagcggcc tggtggccac tgcattcggg 420
ttaaacattg gccagcgtgt tccgaaggct tgtgctgggc ctggcctcca ggagaaccca 480
cgaggccagc gctccccgga 500

<210> SEQ ID NO 143
<211> LENGTH: 900
<212> TYPE: DNA
<213> ORGANISM: Homo sapiens

<400> SEQUENCE: 143
ctcagggaat cacatgtccg cctggcctgg cctggtacca aatgtttata gacaggacga 60
gggtcgctgg aatcgcctcg ctcctttcag cttggcgcta aggcgcgaat ctcgatcctc 120
ctagtatttc tctggcgtct gtctctatct cagtctctgc ttttgtctct ttctccctcc 180
ctccgcccca gtctttccgt ctctttttcc tcgaatgcac gtggaattcg gaattgaaaa 240
ttgaggtcag aatctccctt tttcttccag ttatccgcgc cgctgcccca cgcctagcgg 300
cttggatctg catagacatc tatctacccg caacaagatc cgagctgcag aagcaaacct 360
aatctgtctc cgcaccatcc cctgctctgt agacccactg ccccatccca cgccacatcc 420
ttgaggttca agtagcgact ccagcggatg attcggagaa tgccctgctt tccaaaggcc 480
ccaacccgtg tttttatttt ctttttcctt tgcccgcttg accaactttg gtttctttca 540
gggcccggag gtgcctgcgc cgcgcttggc tttgctttcc gccgccccag gagacccggg 600
actgtggttt ccgctcgcca catcccagcc tggtgcgcac acaagagcct ggcgagcttc 660
cctcgcgcgc ttacagtcaa ctactttggg cctcggtttc cctgctcctt gtagatcaga 720
gaagggacgg gcgaaatgcc tgcgagggag ggttggcgaa tgggttggtt ggtggcaaga 780
ctgcagttct tgtacatgga cgggggttgg ggggtcaaca ctggaagaac tcctgcctga 840
cgccaagagc cacccgcttt ccagctcgtc ccactccgcg gatgtttacc caccttcatg 900

<210> SEQ ID NO 144
<211> LENGTH: 500
<212> TYPE: DNA
<213> ORGANISM: Homo sapiens

<400> SEQUENCE: 144
tttggggcac ccaacccttc ccaagcctcg gttttcccga tcttgtggga tccttgcggc 60
gcgaatgggg ttggaagcac cttggaagct acagagtacc gggtcgggac aatttccggc 120
actgccccag ttcagtggtt tatagaaaat ttctttctct ctctcaggtc cactaagacc 180
gagagagaga gagaagtcga ctctggcaca cccgggcgag gggctgccgg gattcgggag 240
ctggcgcggt tgatttttc cgagaatcct ccacttgggg tgacgtcggg cagcgcgcgc 300
gggccgtgag gttaatgccc aggcttttct ctaaagcgtc cgggaatgat ccggcgaata 360
aaacgggtgt ctgcaaagtt aatgaattgt acaaggaggc tgagggtggg gacttcgacc 420
cggggagcca gaggcggttc tggtggacgc ttccccgtgc gcctaggggt gcgctgggct 480
ttcccagccg aggtctgcag 500

<210> SEQ ID NO 145
<211> LENGTH: 2000
<212> TYPE: DNA
<213> ORGANISM: Homo sapiens

<400> SEQUENCE: 145
ccagacagtt aaggtaaaac gttgaagtca agaggaagta gtgagtctgt tgccaactgg 60
atagggttgg tcctgtccca tctaaatgta ttagaattaa gtggctttta aaaatgagct 120
ggtcatcttc agcccacggg ctggccaatt tggaacttaa tgggcctttg cgtcctcctt 180
ccctgagcct ccttttattc cagacttctc agtgtgagtc tgtgcgtccc tccgacgatc 240
tcagggagtg gggtgccttc atctgcctgt tccctgttcc tcaggctgac gctcccgctg 300
tcctccccgc ctcccctcac tccttttctc cctcccttcc tccttgtggg gaggctcttg 360
gccagggtcc ctgagcccgg gcgggtgctg gcagaggacg cagaaggggt gaggtcacgt 420
ctcccttgag ccccgagccg ctggcttttc agagcctcgc cacaagccgg cggccagagc 480
cccagaccac acagaccgtg cgctcctccg ccctcccggc gccgccggcc tcgcccatgt 540
ctcagtacgc ccctagcccg gacttcaaga gggctttgga cagcagtccc gaggccaaca 600
ctgaagatga caagaccgag gaggacgtgc ccatgcccaa gaactacctg tggctcacca 660
tcgtctcgtg tttttgccct gcgtacccca tcaacatcgt ggctttggtc ttttccatca 720
tggtgagtga atcacggcca gaggcagcct gggaggagag acccgggcgg ctttgagccc 780
ctgcagggga gtccgcgcgc tctctgcggc tcccttcctc acggcccggc ccgcgctagg 840
tgttctttgt cctcgcacct cctcctcacc tttctcgggc tctcagagct ctccccgcaa 900
tcatcagcac ctcctctgca ctcctcgtgg tactcagagc cctgatcaag cttcccccag 960
gctagctttc ctcttctttc cagctcccag ggtgcgtttc ctctccaacc cggggaagtt 1020
cttccgtgga ctttgctgac tcctctgacc ttcctaggca cttgcccggg gcttctcaac 1080
cctcttttct agagccccag tgcgcgccac cctagcgagc gcagtaagct cataccccga 1140
gcatgcaggc tctacgttcc tttccctgcc gctccggggg ctcctgctct ccagcgccca 1200
ggactgtctc tatctcagcc tgtgctccct tctctctttg ctgcgcccaa gggcaccgct 1260
tccgccactc tccgggggt ccccaggcga ttcctgatgc cccctccttg atcccgtttc 1320
cgcgctttgg cacggcacgc tctgtccagg caacagtttc ctctcgcttc ttcctacacc 1380
caacttcctc tccttgcctc cctccggcgc cccctttta acgcgcccga ggctggctca 1440
cacccactac ctctttaggc ctttcttagg ctccccgtgt gcccccctca ccagcaaagt 1500
gggtgcgcct ctcttactct ttctacccag cgcgtcgtag ttcctccccg tttgctgcgc 1560
actggcccta acctctcttc tcttggtgtc ccccagagct cccaggcgcc cctccaccgc 1620
tctgtcctgc gcccggggct ctcccgggaa tgaactaggg gattccacgc aacgtgcggc 1680
tccgcccgcc ctctgcgctc agacctcccg agctgcccgc ctctctagga gtggccgctg 1740
gggcctctag tccgcccttc cggagctcag ctccctagcc ctcttcaacc ctggtaggaa 1800
cacccgagcg aaccccacca ggagggcgac gagcgcctgc taggccctcg ccttattgac 1860
tgcagcagct ggcccggggg tggcggcggg gtgaggttcg taccggcact gtcccgggac 1920
aacccttgca gttgcgctcc ctcccccacc ggctcacctc gcctgcagct gggccacgga 1980
actccccggc cacagacgca 2000

<210> SEQ ID NO 146
<211> LENGTH: 600

<212> TYPE: DNA
<213> ORGANISM: Homo sapiens

<400> SEQUENCE: 146
ctctctgggc cttaggaaaa tggaaatgac acctgtacct gcccttccag gactgacagg 60
aggggctgct ccatgaaacc tcactgctgc ggtcataatg tcattatctt ttgccttaaa 120
gggatttctt ctgcaccagc acctaaagtg gcagcccctt acccttggcc atcagctgga 180
ccctggtgct ctcctggagc ccaaaacctc tgttttgtgt tgcatcctgc tgaccagcca 240
cagtccacac ccatctgagt gtctgagcag aacagcccag aggccacacc aggatggctt 300
tccaccggtc accttccccc acccactcat aaaccctgcg tctctggggg agagggtggc 360
gaggtcccct ccccacatag atggaaacac tgaggcctga ttcatggtgc cccctgtgaa 420
gcgcctcatg gccagcaccg gggggcagca ggccagggcg gggacacata cccggttctc 480
gtcgtagatg atctgcacca ggctgcggtg cttcgactcg atgggcggcg gtgacacggg 540
cttctcaggc tcgggcggct tggcagcctc ctcctccagc tgttgctgtg gggagaggca 600

<210> SEQ ID NO 147
<211> LENGTH: 400
<212> TYPE: DNA
<213> ORGANISM: Homo sapiens

<400> SEQUENCE: 147
cttgaaaact cccagccccc tttgtccaga tggggatgga ggtggccagg ctgccccgtt 60
gattgtgtgc cgaggagccc tccccgggaa ggctgtgatt tatacgcgca ggcttgtcac 120
ggggtgaaag gaagggccac tttttcattt tgatccaatg ttaggtttga aagccaccca 180
ctgctgtaaa ctcagctgga tccgcgggcc gtgattaaac acattgcccg ctttgttgcc 240
gagatggtgt ttcggaaggc gctgtgaatg cacttccctt tgcggggctc acacagacaa 300
gatgtgtgtt gcaaggatga ggcgcctgct cggcctccag cccagggccg ggaagggaga 360
aggtgctgtg cgtcgctgcc tgtgtcgccc gcggctctcc 400

<210> SEQ ID NO 148
<211> LENGTH: 1200
<212> TYPE: DNA
<213> ORGANISM: Homo sapiens

<400> SEQUENCE: 148
cgcgtcaggg ccgagctctt cactggcctg ctccgcgctc ttcaatgcca gcgccaggcg 60
ctcaccctgc agagcgtccc gcctctcaaa gaggggtgtg acccgcgagt ttagatagga 120
ggttcctgcc gtggggaaca ccccgccgcc ctcggagctt tttctgtggc gcagcttctc 180
cgcccgagcc gcgcgcggag ctgccggggg ctccttagca cccgggcgcc ggggccctcg 240
cccttccgca gccttcactc cagccctctg ctcccgcacg ccatgaagtc gccgttctac 300
cgctgccaga acaccacctc tgtggaaaaa ggcaactcgg cggtgatggg cggggtgctc 360
ttcagcaccg gcctcctggg caacctgctg gccctggggc tgctggcgcg ctcggggctg 420
gggtggtgct cgcggcgtcc actgcgcccg ctgccctcgg tcttctacat gctggtgtgt 480
ggcctgacgg tcaccgactt gctgggcaag tgcctcctaa gcccggtggt gctggctgcc 540
tacgctcaga accggagtct gcgggtgctt gcgcccgcat tggacaactc gttgtgccaa 600
gccttcgcct tcttcatgtc cttctttggg ctctcctcga cactgcaact cctggccatg 660
gcactggagt gctggctctc cctagggcac cctttcttct accgacggca catcaccctg 720
cgcctgggcg cactggtggc cccggtggtg agcgccttct ccctggcttt ctgcgcgcta 780
cctttcatgg gcttcgggaa gttcgtgcag tactgccccg gcacctggtg ctttatccag 840
atggtccacg aggagggctc gctgtcggtg ctggggtact ctgtgctcta ctccagcctc 900
atggcgctgc tggtcctcgc caccgtgctg tgcaacctcg gcgccatgcg caacctctat 960
gcgatgcacc ggcggctgca gcggcacccg cgctcctgca ccagggactg tgccgagccg 1020
cgcgcggacg ggagggaagc gtcccctcag cccctggagg agctggatca cctcctgctg 1080
ctggcgctga tgaccgtgct cttcactatg tgttctctgc ccgtaattgt gagtccccgg 1140
gccccgaggc agcagggcac tgagactgtc cggccgcgga tgcggggcgg gaagggtgga 1200

<210> SEQ ID NO 149
<211> LENGTH: 2000
<212> TYPE: DNA
<213> ORGANISM: Homo sapiens

<400> SEQUENCE: 149
cttccgccgc ggtatctgcg tgccctttc tgggcgagcc ctgggagatc cagggagaac 60
tgggcgctcc agatggtgta tgtctgtacc ttcacagcaa ggcttccctt ggatttgagg 120
cttcctattt tgtctgggat cggggtttct ccttgtccca gtggcagccc cgcgttgcgg 180
gttccgggcg ctgcgcggag cccaaggctg catggcagtg tgcagcgccc gccagtcggg 240
ctggtgggtt gtgcactccg tcggcagctg cagaaaggtg ggagtgcagg tcttgccttt 300
cctcaccggg cggttggctt ccagcaccga ggctgaccta tcgtggcaag tttgcggccc 360
ccgcagatcc ccagtggaga aagagggctc ttccgatgcg atcgagtgtg cgcctccccg 420
caaagcaatg cagaccctaa atcactcaag gcctggagct ccagtctcaa aggtggcaga 480
aaaggccaga cctaactcga gcacctactg ccttctgctt gccccgcaga gccttcaggg 540
actgactggg acgcccctgg tggcgggcag tcccatccgc catgagaacg ccgtgcaggg 600
cagcgcagtg gaggtgcaga cgtaccagcc gccgtggaag gcgctcagcg agtttgccct 660
ccagagcgac ctggaccaac ccgccttcca acagctggtg aggccctgcc ctacccgccc 720
cgacctcggg actctgcggg ttggggattt agccacttag cctggcagag aggggagggg 780
gtggccttgg gctgaggggc tgggtacagc cctaggcggt gggggagggg gaacagtggc 840
gggctctgaa acctcacctc ggcccattac gcgccctaaa ccaggtctcc ctggattaaa 900
gtgctcacaa gagaggtcgc aggattaacc aacccgctcc cccgccctaa tcccccccctc 960 gtgcgcctgg ggacctggcc tccttctccg cagggcttgc tctcagctgg cggccggtcc 1020
ccaagggaca ctttccgact cggagcacgc ggccctggag caccagctcg cgtgcctctt 1080
cacctgcctc ttcccggtgt ttccgccgcc ccaggtctcc ttctccgagt ccggctccct 1140
aggcaactcc tccggcagcg acgtgacctc cctgtcctcg cagctcccgg acacccccaa 1200
cagtatggtg ccgagtcccg tggagacgtg agggggaccc ctccctgcca gcccgcggac 1260
ctcgcatgct ccctgcatga gactcaccca tgctcaggcc attccagttc cgaaagctct 1320
ctcgccttcg taattattct attgttattt atgagagagt accgagagac acggtctgga 1380
cagcccaagg cgccaggatg caacctgctt tcaccagact gcagacccct gctccgagga 1440
ctcttagttt ttcaaaacca gaatctggga cttaccaggg ttagctctgc cctctcctct 1500
cctctctacg tggccgccgc tctgtctctc cacgccccac ctgtgtcccc atctcggccg 1560
gcccggagct cgcccacgcg gacccccgcc ctgccccagc tcagcgctcc ctggcggctt 1620
cgcccgggct cctagcgggg aaaaggaagg ggataactca gaggaacaga cactcaaact 1680

-continued cccaaagcgc atgattgctg ggaaacagta gaaaccagac ttgccttgaa agtgtttaag 1740
ttattcgacg gaggacagag tatgtgagcc tttgccgaac aaacaaacgt aagttattgt 1800
tatttattgt gagaacagcc agttcatagt gggacttgta ttttgatctt aataaaaaat 1860
aataacccgg ggcgacgcca ctcctctgtg ctgttggcgc ggcgggaggg ccggcggagg 1920
ccagttcagg ggtcaggctg gcgtcggctg ccggggctcc gcgtgctgcg ggcggggcgg 1980
gcccggtggg gattgggcgc 2000

<210> SEQ ID NO 150
<211> LENGTH: 1000
<212> TYPE: DNA
<213> ORGANISM: Homo sapiens

<400> SEQUENCE: 150
agtttgggga gccttttctc catttgagaa aaaacaaact tacagcgagg ggtgaggggt 60
tagggtttgg gattggggaa aatgtgggtg gggagccccc ccaaggaagt gaggaggggg 120
ctgcaaggat tacacctggg catacgtttc cctagaaatc acattcattg tatttttata 180
atttattcta aatctttcat gcgaagaaag tcagtagtga gtgttagtac tggtggccct 240
cctgatcaca cttgcatctc ttgagtgtgc cttaaaggtc ttgggaatgg aaaatataaa 300
aactgcttcg tgatgcgtca tctttatccc ccactccccc acccattcca atatattttc 360
tacttccagc ctaaattcgg ggccccctac cgaggccggc catgatcttg agggcggcat 420
aggggaggcc gcgctctgtc caccccagcc tggtgatgcc gttcgcttct tgtgcccggt 480
attgtgggct acatgccttt ccggcgtacg gagctgagcg tccaggccag tgcccctcaa 540
cctctcagta atgtttaccc gaggccgtcg tgcaatgaga ctattcgcat ggcattgtca 600
acgcggcggc gcgcgcgtct cggccctccg cggcttgcca gactgtcctg caaaccacct 660
cacccgtctc tttggcgcag gagactcagg ctgtaaccgg agaaaacact tcaccctgga 720
accctaactc aggtcctggc aaaagatgcg agaggaagac ttgctctctt aataaatctc 780
ggccgcccgc acatctggcc cctagacctg ctcggtagag gactggctgg tggatgcgcg 840
gtccaggccg tgggcactcg acccacctct attttccttc ccgaggcgcc cctggattac 900
cactttcggt ttgcgcttac atccgggatg tcgaatttcc cagggaatca taattatttt 960
atctataatt tattctaacc ccaaggttcc aagaaaatct 1000

<210> SEQ ID NO 151
<211> LENGTH: 1100
<212> TYPE: DNA
<213> ORGANISM: Homo sapiens

<400> SEQUENCE: 151
acattccttc taaaatgtgg gctttctgtg tacatgggcg cgcattccca ggactcggtt 60
ccctgggtgg aattcaccca ggaatacaat cgattttctg aacctgcgta aggccacagg 120
cagctctgaa aatgaaagcg tttgctaagt gggggagatc tcaccgatcg aacgtttaaa 180
aatggctttg tcttcattca gctctcccga tttattctgt gttttacaaa tagaagctca 240
gagcttctgt cgcccagtcc ttgcatgact catggcggtg gccacacggg tttcagggat 300
aacgggatgt ttagaaaatc gctgcatatc ggagtttcct agcacgttcc atttatactg 360
aacgcaggcg gccgctgaaa atccagcctc gactcttgct aatgactggg taggaccctc 420
ggggtcctgc gacggtgctg gagggtgttc ccggctccga tgtggggagg cctgcgcggg 480

```
gactaggttc tcgagaggcg agcgggcgcg ccagagaacc cgagactgct gcggggccgg    540

atgcgggatc cctgggctgc ggttctacgc agaaacgcca atggccatgc ctccccagct    600

cctcccagcc ccagtcacta ggccggcgcc tggcccggag atcctcccag agccctggcg    660

gtgccatcat gccggagaag acaagctcgg ccccgctgga attcgctcca aacacagatg    720

ctcatttttg gaatattcta gaaaaataac aagatcttgt ttgtcgttat gattcacggg    780

aggtaactga tgggagggcc atttacatga gggcagacac tgtggggcga aggtgacttc    840

tggacgtagg ctttaaagta ggaacggctc caaattccca atatctccgg ccttaccggt    900

tgcaaatcgg accccctgcgg gaaaaccaga cacttctgtt tcgtggcttt cgggctgcct    960

ccagcccacg caggctcgtt tagtccccgt ggagtcagcc ccgagccttc ctagtcctgg   1020

aacaagggct ccaggtcgcg gccgcgggaa gccgccaaga gggcggggag tagggattcc   1080

ctccagctcc gcagggcatc                                               1100
```

<210> SEQ ID NO 152
<211> LENGTH: 1500
<212> TYPE: DNA
<213> ORGANISM: Homo sapiens

<400> SEQUENCE: 152

```
tcctcctcgg cctcagatgt cgtcccacct gcccacgagc agggaacctg gaacccactc     60

tcccggcagt ccccagcggg ttccgccacc cggcggccgc ccctgacacc gagtgggtgg    120

gaggaagagg cagctggcgg ggatgggcca ttgagacctc ttgaaaaata ttaaaagaca    180

ggatgggtag agatttctcc gggagaaagt tcgagggtgc atcgggtcgc ggctgggagg    240

agtacccgaa atgccagcag gagaaatgca acctgtttag gccacacctt caatccccga    300

ggctgtctgg agagactgcg tgcgggggac ttgccggcgt tcccacaccg cgcctgcaat    360

ccactcccgc ggctgcctgg cctctgccac tcgcggcttg aagccagtgg ctctcaagcc    420

ctcggccccg cggcggcccg cgcagccttc acccggcgcc ggcaccacga agcctggccg    480

cagtggactc cccgcagctc gctgcgccct ggcgtctccc gtcgaggagg gagggacgga    540

ggcctgagcc gggagctccc tggcggtggt cgggccgccc cccttgaggc ctgctccccc    600

ctctcggcct cgccaaatcc ctgaaagccc agtccccctt cgtcaccccg ggggcttcta    660

atcactcggt atcgatttcc ctaactcttt tcatcctgtt gaagacacat cttaaaacac    720

tccagcccgg agtgtgctct gggctttatc cacactaata aaatgattta cccttctctc    780

cgcgctctcc tcacagagga aaatcgttcg agccccggct atttgtgtgt gatcagtaaa    840

tatttagtgc gctgacatcc ttagctgggc ttcggatcga ttcggggccc accgggaggt    900

gcgcacggtc cgggcggggc cgcgccgagc tcgccgaggg ggctcctccc gccctcgccg    960

ccggccgctg atttacggcc cctgcaacca gctaaggggg gcgaaagcgc gcctggaaaa   1020

ttggcttttc aacctttttac ttttgacatt cagccacttc cccaggctct aattctcgcc   1080

cgcactcctc cctcccgccc tactaagggt tgccctgtgc gccctgcgag cccttccagc   1140

agcaacgcgc ggcgctcgcg ccccctcggc ccggggacca cctatcacag ccctgagccg   1200

cgacgcgggg aggccccggc ccctgctatg ggggtcgcct ccttcgagga gagatgctct   1260

ccgcccgccc acacctctga gggaggagag ggggtggaga agcccagagc tgcatctgct   1320

ggatgacgag ccgctctccc tgctaccctt tctccgaccc gtcggccttt ctcctactct   1380

ggagactgat cctcgacgtc catcgggccg gatggcgtcg ggtggaagcg ttactttcct   1440

cgcagaaaaa ctcctcctct ttcctaagat cagaaaaagc gcttagcttg gaattgttag   1500
```

<210> SEQ ID NO 153
<211> LENGTH: 600
<212> TYPE: DNA
<213> ORGANISM: Homo sapiens

<400> SEQUENCE: 153
cctaggcatt ctcagcccgt tttgctggag ggggcatttg aggcctggcc agcttagcca 60
gcctacaagg agtgttactg ggtgaaaaac agccagcggg gaccagtctg cttgtggccc 120
gccaggtgcc tgggatgggg aagcagcaaa tgcccacctt cctgcccaac cccctcctcc 180
ctcttcatgg ggggaactgg gggtggcagc ggctgccggg tgcgagcggg ctcaggcctg 240
tggccctgcc tgacgttggt ccccatcaag ccatgtgacg agaccaggcc acaagaaaga 300
ggtttcaaca agcgttatcg tttcctggaa ctccaactcg gcgacttccc cgaagaccgg 360
ctgtgcctgg cgggcgggct gcgcacagcg gggacaaggc tgccccccttc ctcctccgct 420 gcctccgcgg ccgcgtctat ctcagtctga ctacctggaa gcagcactcc accctccagc 480
ccagcggccc tcggctcagc tgccaggtca ccggcaaccc cgggagcggt ggggcagggg 540
ctgctccgcc agcctctgtg atgttcaggc cgggctgcac cagcccggga cccctaggtg 600

<210> SEQ ID NO 154
<211> LENGTH: 700
<212> TYPE: DNA
<213> ORGANISM: Homo sapiens

<400> SEQUENCE: 154
gcactggttc ccctttacct gagccaacaa cctaccagga agtttccatc aagatgtcat 60
cagtgcccca ggaaacccct catgcaacca gtcatcctgc tgttcccata acagcaaact 120
ctctaggatc ccacaccgtg acaggtggaa ccataacaac gaactctcca gaaacctcca 180
gtaggaccag tggagcccct gttaccacgg cagctagctc tctggagacc tccagaggca 240
cctctggacc ccctcttacc atggcaactg tctctctgga gacttccaaa ggcacctctg 300 gacccccctgt taccatggca actgactctc tggagacctc cactgggacc actggacccc 360
ctgttaccat gacaactggc tctctggagc cctccagcgg ggccagtgga ccccaggtct 420
ctagcgtaaa actatctaca atgatgtctc caacgacctc caccaacgca agcactgtgc 480
ccttccggaa cccagatgag aactcacgag gcatgctgcc agtggctgtg cttgtggccc 540
tgctggcggt catagtcctc gtggctctgc tcctgctgtg gcgccggcgg cagaagcggc 600
ggactggggc cctcgtgctg agcagaggcg gcaagcgtaa cggggtggtg gacgcctggg 660
ctgggccagc ccaggtccct gaggaggggg ccgtgacagt 700

<210> SEQ ID NO 155
<211> LENGTH: 300
<212> TYPE: DNA
<213> ORGANISM: Homo sapiens

<400> SEQUENCE: 155
tgtccgacag gcacacagag cgccgccagg cacggccctc attcttcacc ccgagctccc 60
gcaaggtcgg cgaggaggct ggagcagcgg gtaggaagcg ggccgaggct cccccgacgc 120
tgggccgcaa ctgtcatcgc agatccctga aaaacgagct ctgtaatcgt tgccgtcagc 180
gggtgtacaa ttgcagcctt atgtttcctg ccgctgttta ccttcctgag cggcgcccag 240
agatgcacac acgctgccct gaagcgggac gtgacctctg ggcacctgtg aggtcctggg 300

<210> SEQ ID NO 156
<211> LENGTH: 500
<212> TYPE: DNA
<213> ORGANISM: Homo sapiens

<400> SEQUENCE: 156
gtcggctcct gcgctcccaa cggggtggcc gtttccttcc tcgcaccctc ttctctcccg 60
gtgcctgcgg tcccaccttc cagatacccc tcggagagtc cagctgagct ctcgccagag 120
ctttcccctt ccaacccgct cgacttgccc agatcccaag ctgggcttct ctctccatcg 180
ccccagaaag tgggtcttgg agaccgaggc aagaatttgg gcctccgctt ctgttccaga 240
ccccggaccc cttgccaaaa tgcggcagat gtgcagattg ggccgcgctt ggttcctggc 300
tgggtttatg gagcctgcgg ctgaggcagg ctccgcagac cccgagccag agtgggattt 360
aacggcggcc ggtgcgctgt gcttggtcaa ccccggtaac cgtcacgctg ctagtgatat 420
gaaaaaaacc tgccagcgtt ctgcttttct gccccgctgc agtctttagc acccgccagg 480
attctgtccg agtgtttgga 500

<210> SEQ ID NO 157
<211> LENGTH: 1000
<212> TYPE: DNA
<213> ORGANISM: Homo sapiens

<400> SEQUENCE: 157
tttagtgtgt gcataaaaca tcccagctaa tctcaaatag acttttcctg agcagaggct 60
gaaatttgca agtaatgcaa agaagactcc gggagagcgt cgccgatggt ggagcgggag 120
acgggcgtgg ggagccccac tgcagtgctg ggatcgaagt ggtgctgacc ccaagacctc 180
tcccctcctc ctcccccggg agcttctcca gggttatttg ggaaatgagg gggaactcca 240
atccctgaga aagcgctcag gggcttgctg aggtgagcgc aaatggaagc acaaggccgg 300
gctggccgtg ggctcagtaa ccagtcggct gcccggcttg cgccagcact aaatgctcga 360
tcagaaagag aaaaagaggc gcaataattc caaatttcag gaaaagtcaa atcggagagg 420
ggggacgcag gtctcttcag actgcccatt ctccgggcct cgctgaatgc gggggctcta 480
tccacagcgc gcggggccga gctcaggcag gctggggcga agatctgatt ctttccttcc 540
cgccgccaaa ccgaattaat cagtttcttc aacctgagtt actaagaaag aaaggtcctt 600
ccaaataaaa ctgaaaatca ctgcgaatga caatactata ctacaagttc gttttggggc 660
cggtgggtgg gatggaggag aaagggcacg gataatcccg gagggccgcg gagtgaggag 720
gactatggtc gcggtggaat ctctgttccg ctggcacatc cgcgcaggtg cggctctgag 780
tgctggctcg gggttacaga cctcggcatc cggctgcagg ggcagacaga gacctcctct 840
gctagggcgt gcggtaggca tcgtatggag cccagagact gccgagagca ctgcgcactc 900
accaagtgtt aggggtgccc gtgatagacc gccagggaag gggctggttc ggagggaatt 960
cccgctaccg ggaaggtcgg aactcggggt gatcaaacaa 1000

<210> SEQ ID NO 158
<211> LENGTH: 500
<212> TYPE: DNA
<213> ORGANISM: Homo sapiens

<400> SEQUENCE: 158
catggtgctt caggaaggga ggggacgaga gccctgggct tgtggtgtcc acgtggacag 60
ctaatgagga gccttgccga tgaggagcat gcgttcccga cggggcggcc gaatgcggaa 120
ggagccgcca ttctctccgc cctgaccgcg ggattctctg cagcagatga gaaacggcgc 180
tgactcagca gggtccctcc caggccccga gcggtcatct ggtgaccccc gcgcttcccc 240
cacggcccag ccggagaagg gcaaagggaa gtcccggctc caaggcgcac ccagagatgc 300
ggtgcatgtg gcaggatggc ccagccccgt cggcagcccc agcttcctgc ccctggtttc 360
cttcctccca cgggctacag gcctctgatg agctttggaa agcaggaaac acacaggcta 420
gtaactatga atgggtccaa aaaacactcc ttattacttt aaactactta ggaagaagca 480
cagcgttgcc aaacgccaga 500

<210> SEQ ID NO 159
<211> LENGTH: 1200
<212> TYPE: DNA
<213> ORGANISM: Homo sapiens

<400> SEQUENCE: 159
gcgcgggggg ccggaggatg gcggcctggg ggccctgcgg gggctgtcgg tggccgccag 60
ctgcctggtg gtgctggaga acttgctggt gctggcggcc atcaccagcc acatgcggtc 120
gcgacgctgg gtctactatt gcctggtgaa catcacgctg agtgacctgc tcacgggcgc 180
ggcctacctg gccaacgtgc tgctgtcggg ggcccgcacc ttccgtctgg cgcccgccca 240
gtggttccta cgggagggcc tgctcttcac cgccctggcc gcctccacct tcagcctgct 300
cttcactgca ggggagcgct ttgccaccat ggtgcggccg gtggccgaga gcggggccac 360
caagaccagc cgcgtctacg gcttcatcgg cctctgctgg ctgctggccg cgctgctggg 420
gatgctgcct ttgctgggct ggaactgcct gtgcgccttt gaccgctgct ccagccttct 480
gcccctctac tccaagcgct acatcctctt ctgcctggtg atcttcgccg gcgtcctggc 540
caccatcatg ggcctctatg gggccatctt ccgcctggtg caggccagcg ggcagaaggc 600
cccacgccca gcggcccgcc gcaaggcccg ccgcctgctg aagacggtgc tgatgatcct 660
gctggccttc ctggtgtgct ggggcccact cttcgggctg ctgctggccg acgtctttgg 720
ctccaacctc tgggcccagg agtacctgcg gggcatggac tggatcctgg ccctggccgt 780
cctcaactcg gcggtcaacc ccatcatcta ctccttccgc agcagggagg tgtgcagagc 840
cgtgctcagc ttcctctgct gcgggtgtct ccggctgggc atgcgagggc ccggggactg 900
cctggcccgg gccgtcgagg ctcactccgg agcttccacc accgacagct ctctgaggcc 960
aagggacagc tttcgcggct cccgctcgct cagctttcgg atgcgggagc ccctgtccag 1020
catctccagc gtgcggagca tctgaagttg cagtcttgcg tgtggatggt gcagccaccg 1080
ggtgcgtgcc aggcaggccc tcctggggta caggaagctg tgtgcacgca gcctcgcctg 1140
tatggggagc agggaacggg acaggccccc atggtcttcc cggtggcctc tcggggcttc 1200

<210> SEQ ID NO 160
<211> LENGTH: 600
<212> TYPE: DNA
<213> ORGANISM: Homo sapiens

<400> SEQUENCE: 160
gggcgggttg ccacactgtc ccctttctgc atgggaggaa gggggctcga gaactgagtc 60
agccacacaa aacgaggatg gacagaactc ctgagtagcg agggtgcctg ccgggcgcga 120
ggaggagggg gaagacgagg aagacgagga ggaggaatag ggagcaccac atgacagagg 180
ggctgcctca gaccacaaag cgcttcctca tcctttcctc gccctttgat gccgccggca 240
acgtgactct gcgagcagcg gggcagacgc caggtctccc tcgcaggcgg gaaaggggct 300
ccaaggcggg tgctgccttg ctcgggtcac atggctacgt gggggccttg ctcaaattca 360
cttcctgcct tcattacaaa actgtcaaag gggatcgcac gtttgcaggg tgtcacccaa 420
gcattctggt tttgcaaacg acgctgtgcg gcaggcggtc tgatacctga tgagctcggt 480
gtggcggggt cggcagcatt tcctccgggg ttttgagctc tggccacttc tccttttgtt 540
ccacccaatc tcacccactt ctgggcttcg aggccagagt gtcttaacaa gggggcacgt 600

<210> SEQ ID NO 161
<211> LENGTH: 500
<212> TYPE: DNA
<213> ORGANISM: Homo sapiens

<400> SEQUENCE: 161
gagcgagact ttgtctcaaa aaaaaaaaaa accaaataaa ttgaaagctg agaaattcag 60
agcacaagaa gacaagcgcg ccccctcttt tagctgtcaa catggcggag ccgtccctgg 120
tgacgcagcc tccaaaggcc tccctgtgcc ctcctgagac cgcaagaggg aaagtggcag 180
cgacagtgat cgtggtgtct ttgtggcggt tgtgttgacc tcactgaccc ccgaagtgcc 240
gctctagggt ctgtcctcag cggtgacccg gccgggtcga agggcagagt tccgctgtca 300
ctagccctcc acccgtcctg tgtgctggga tgccctcgcg gcgccgtcca cgccaccgcc 360
gccccctctt gtgggttctg tctcctccgt gtctaggatc ctcctgcatc cgtttttcct 420
tcctcccttc tctccctccg tctgtcttgc ccgcacctga ggttgtcgca gaggcgctga 480
gacgggccag caggagctgt 500

<210> SEQ ID NO 162
<211> LENGTH: 600
<212> TYPE: DNA
<213> ORGANISM: Homo sapiens

<400> SEQUENCE: 162
tgctgtcccg gtcctgtcgc agtcctcaaa gatgctagag tgacagtcct ctaggggtag 60
agatggtcgt cctcccagga gaaggtggcc cggagacttg gaggtgggat caatcctgcc 120
agtcctggat caggaggcct ctgtcgggcg ccgccccccct tcctcctcca tcagcaacag 180
gcggcgccgg ccagcctcat agtcagcctc atccacactg accagcaggc gaacagcctc 240
ccggcccaca gcctctcgca gggcctcagt caggaacacg ccccgcaggg cctgcagcag 300
ggcgccactc aggtagtcgc cccagaaggc gtccagatag gagagctctg agaacttgat 360
gtcacaaacc acagagccca ggtcccttga gcgcagcact gcggtggcct gcccaaacac 420
gtccagctgc cgcgccagcg cctggggccg ccgggatgcc acgccctgct ccaaggctgg 480
cccatgctcg cagtactctg ctcgaacccg gagccggatg tctgcagggg aaggagggat 540
ttgtcaggga gggggccaac actagacaca cttatgggga acgccaccct tcctccctcc 600

<210> SEQ ID NO 163
<211> LENGTH: 500
<212> TYPE: DNA
<213> ORGANISM: Homo sapiens

<400> SEQUENCE: 163
tgatgcccgg cccccagggg ggcagaggcg ccgccaccat gagcctgggc aagctctcgc 60
ctgtgggctg ggtgtccagt tcacagggaa agaggcggct gactgcagac atgatcagcc 120
acccactcgg ggacttccgc cacaccatgc atgtgggccg tggcggggat gtcttcgggg 180
acacgtcctt cctcagcaac cacggtggca gctccgggag cacccatcgc tcaccccgca 240
gcttcctggc caagaagctg cagctggtgc ggagggtggg ggcgcccccc cggaggatgg 300
catctccccc tgcaccctcc ccggctccac cggccatctc ccccatcatc aagaacgcca 360
tctccctgcc ccagctcaac caggccgcct acgacagcct cgtggttggc aagctcagct 420
tcgacagcag ccccaccagc tccacggacg gccactccag ctacggtgag ggcctgggcc 480
atcttggccc acttttcaga 500

<210> SEQ ID NO 164
<211> LENGTH: 200
<212> TYPE: DNA
<213> ORGANISM: Homo sapiens

<400> SEQUENCE: 164
ggccgggcaa aaagccgccg caacaaaaag ctgcgctgac gggcggaaaa agccgcggcg 60
gcggagccaa aaagccgggg cggcaaaaag ccacggtggc gggcgcaaac agccgcaaaa 120
agccgcggtg gtgggggcaa aatcagtggg agcaggggca aaaaaacaca aaaagccgcg 180
gcggcggggg caaaaagcca 200

<210> SEQ ID NO 165
<211> LENGTH: 400
<212> TYPE: DNA
<213> ORGANISM: Homo sapiens

<400> SEQUENCE: 165
tggctttgct ggagtgtgat gtgataggaa atgtgcagcc aaagacaaaa gaagatgtaa 60
gtaggcttga ctcattgcag ctaagaaccc agatgttacc ttgagggtat taactaataa 120
gcagtttaaa tcagaatggc acattctgat ttgtttttg tatgttcaca tttggcaggc 180
atagatactg tttgaaaaga gaaaagtcag tacatagagg taacaagctt aaatatgtgc 240
caagtctaga aacaagagac tagggggata aggacctttc gaaattaaat gcaagatttg 300
aaaactgatt ggctggggga tgaggcaaag gcaggtcttt aaggtcaatc cctgttttgc 360
tttaagttgt tagcgggtgg ttttatcata tattgtagaa 400

<210> SEQ ID NO 166
<211> LENGTH: 650
<212> TYPE: DNA
<213> ORGANISM: Homo sapiens

<400> SEQUENCE: 166
ttcctgggaa tgtcagctaa cctgagccta ggggcctgag cccaagggca gactgaggct 60
cccccagcac agggaggtgc tgcctgtgac aaggggtagt gctggcacag tgcaggctac 120
tccctagaaa gatcagcttg aatatgcagg aagagcagga ccctcgggct gaggcagagg 180
tggaatggga agtgcatggt ggtaatttag ttctccagag gccagaagta ggaggagcgg 240
ttggaatgct gatggcccaa agggaaaccc tggactaccc tggcctccca caggactctc 300
atagtaattg cggctccctg cagtggtgag gccagaagga gtgttgccca atgctgtcat 360
catccagtcc accccccacc caccatcaac agatgagtat ggtcatgagt gtggtcacct 420
catcagtcat ttgctcagtt gtgaaaaaga aattgttcag agaagagcaa agtgtttttc 480
catgagccaa aggtcagcca agttatgcta atgaggagga ctggagacag cgtgtcacag 540
acaccgagaa ggagcactgg gcaagggcac ttctcccagg gcagagccca caagaagcgt 600
cctggcacca gacactcagg gaactgaagg ctggcagggg cccgcccagt 650

<210> SEQ ID NO 167
<211> LENGTH: 5000
<212> TYPE: DNA
<213> ORGANISM: Homo sapiens

<400> SEQUENCE: 167
tccccccagc tgggtataag caaactttcc tgtctatggg ccgcagagac caccatctag 60
ttcccccgcc aaaactttac atgattttaa ttctcctgat gaagatgaga ggataacagc 120
caacagagag ggcagaggat gggatgggac tcccttgctc agagacctca cctctaggtc 180
tttacctcct attgagaata agtcagttct gtagtaagaa ctctgtgtcc acggcaaccc 240
caaacagaat cctagcgctc ttgtgattct tgtagaatgg ggaatagaac gagcttggcc 300
caagactgca cagacttaaa aacatactat tctttgaaaa tggcaatcat taaaaagtca 360
ggaaacaaca ggtgctggag aggatgtgga gaaataggaa cacttttaca ctgttggtgg 420
gactgtaaac tagttcaacc atggtggaag tcagtgtggc gattcctcag ggatctagaa 480
ctagaaatac catttgaccc agccatccca ttactgggta tatacccaaa ggactataaa 540
tcatgctgct atacagacac atgcacacgt atgtttactg cagcactatt cacaatagca 600
aagacttgga accaacccaa atgtccaaca atgatagact ggattaagaa aatgtggcac 660
atatacacca tggaatacta tgcagccata aaaaatgatg agttcatgtc ctttgtaggg 720
acatggatga aattggaaat cattctcagt aaactatcgc aagaacaaaa aaccaaacac 780
tgcatattct cactcatagg tgggaactga acaatgagaa cacgtggacc caggaagggg 840
aacatcacac tctggggact gttgtggggt ggggggaggg gggagggata gcattgggag 900
atataccaaa tgctagatga ggagtttgtg ggtgcagcgc accagcatgt cacacgttta 960
catatgtaac taacctgcac attgtgcaca tgtaccctaa aacttaaagt ataataaaaa 1020
aaatactgtt ctgccataca tacagatact cattaaagat gagggagaag ggcatggggt 1080
gggggagaat gtaccaaaac caaagaccac aggataataa cctcagagca gagactatct 1140
ctctagttat tttttctttt gtatgtaatg gagaggatta ttatttactc tgatgaagaa 1200
gtttacatca agtgttcagc ttcctttgtg ggttacagag aataaccaga gggctcagtt 1260
atgctctctg aataactatg tttgcttagt gttttctaaa caatattaaa tttcactaaa 1320
atagacaagg ttgataggac ttgggggcat aactcattga ctcaagctat cattttatag 1380
gattgtgaga aaacaaatag atgaacattt aaaatacact catattctcg ctagaaaaga 1440
ggattttgaa tattcttaca tcaaagacat ggtaaatgtt taaggcaatg aatatgctaa 1500
ttaccatgat ttgatcatta tgcaatgtaa aatgtactga aacatcacat tgtacctcat 1560
aaatatgtac aatttattat gtgcgaatta aaattttgag tataagaaaa aataaacttc 1620
aattgtaaga aaacaaccca acttttaaaa aacgggcaaa atacgtgaac agatacttca 1680
ctaatagaga tttgcaactg gcaaataagc aaatgaaaaa ctggtcatca tcactatcta 1740
ttagagaaat gcagattaaa actacaataa gaaacaatgc tgcccgtcca gacgcattgt 1800
tttgaccgtt tccaacttgt cccagccctt cccggggcat cgctggggac cctacgccga 1860
cgtcccccct ccgcccgcgc cccaagggcc gactgggcaa attgggagac ccgccccgcg 1920
gggcgaccca acttttcgga acagcacccc accgcccacc cccgcagacc cccggacccc 1980
cgctcccggc ggagactcag ggaaccccgc accccaagcc cttctaaatc gtgcagcgtg 2040
agtgtgacgg ccaagagcgg atgcagcccg ggatcgcccg caccttcccg tgggcggaag 2100
cgcaggagcc agctggggag ggggcgccct agaggagcgg ctagaaagca gacacgggga 2160
actcaggtca tcctgggggg ggacaagaca acgagagccg ggcgcctcgg gggcggcgcg 2220
ggagcctccg caggaccggg cgggcgcccc ggctggcgcg ggcggggggc gcgcccctt 2280 tacctgcggc tccggctcct aggccatttc ctcacgcggc ggcggccggg actgagctaa 2340
caccactcag gccggccggg tttgaatgag gaggagcggg cgcggagagg aggggacggg 2400
gagggcggag ggagggaggg aggcgtcgcg gagtttttct cggccttttg tgcggacacc 2460
tcccggattc cgcgcccgca cccggccccc caaaagacac ggggagccgc gggcgagggg 2520
ttcagccatc cgccgaggcg cctagtgcct tcgcgcctcc aagacccccc cccaacaaaa 2580
aggagcgtcc cccacccta cccccgcccg gaggacttag ggcctgggct cacctcgggc 2640
gcggagctaa gtgtaggcgc cgggggtccc tagagccgcc ggggcgcagc gagtccggcg 2700
ctgggtaact gttgggtcag aaactgttca ggtagcagct gttgtgccct ccccttggccc 2760 cgccgctcgg agacgccccg ccccctgcct tgaacggccg cccggccccg ccccagcgcc 2820
cacgtgacta gcataggcgc gcccccgttc cgcccgccgc cgcagactcc gcctccggga 2880
cgcgagcgag cggcgagcgc gcgcactacc agttcttgct cggcgactcc cgcgcacgcg 2940
cgcgccgtgc caccctcccc gcacccctcc tcccgccatc cggcttaacg tggcgggcgc 3000
gcgccgcggc agtagccgtg acaggtaccc ggcggggcgg gggggagggg ggttggcccg 3060
cgagggtgtg cgcaggcaca gacccgggtc ctgtccccgc cgccccctcc tctgcaaggt 3120
gtgcctgggc gaggggaggg gcccgcggcc cgaacccctg ggtcaccccc gaattacaaa 3180
caaaaacctt aacgccattg ctcgcgggtt agaaggcagc tgtgcgtgct caggaaaaga 3240
agccacgcac aagagaccgc acgcggcgtg gatacagtga cacgaaacac ccaaaatctc 3300
ttttgaaagg gaaaccaggc acagtggctc atgcctataa tcccagcact ttcgggggcc 3360
aaggcgctca cctaaacccg agagttcaag accagcctgg gcaatacagc gaaaccctgt 3420
ctctacgaaa aatataaaaa ttagctgggc atagggctgg gcacggtggc tcacgcctgt 3480
aatcccagca ttttggaggc cgaggcgggc ggatcacgag gtcaggagtt ccagaccatc 3540
ctggctaaca cagtgaaacc ttctctctac taaaaataca aaaaaaatta gccgggcgtg 3600
gtggcaggtg cctgtagtcc tagctacttg ggaggttgag gcaggagaat ggcatgaatc 3660
agggagcgga ggctgcagtg agctgagatt gcgccactgc actccagcct gggggacaga 3720
gtgagactcc gtctcaaaaa aaaaaataat aattagctgg gcatggtggc tggcacacat 3780
ggtcccagct actcaggagg ctgaggtgga aggatctctt gatcccgggg aggtcaaggc 3840
tgcagtgagc caagatggca tcaccgcact ccagcctggg ccacagaccc tgtctcaaaa 3900
aaaaaagaga aagtggggaa gaaaatgtaa tacaaattaa tataccaaca gcaattagtg 3960
agtacttttt ccatggagct gggagaggga ataaatgttt gtaaaattaa aatgttctac 4020
gctagaaatc aactttcctt ctatgctttc tttacttcac cccttatagc tacttagtaa 4080
atctcacaaa tcctatcctt ctgatctctc tgaaatgtat gtaccctttc ccttctattc 4140
tcaccaccca tgtttctttg tttccttcta gcctgtgtaa taatctcata atcgcacctc 4200
ctgtacctgc cttctttcta gtccagaata cgttttccta aattccacca ataaccatcc 4260
tgctactgct ttgtgtgaaa ttctccaaaa aaaattttac ttttccaaaa taagtcaggc 4320
tccctctctt aggatacaaa accacaccat ggtcccagcc aatctttcag cctgattcac 4380
tcagtatata tttattgacc tctcctttct cccaagcact tggctagata ataattaaag 4440
agtgcggcac aaaacaaatt ggattcctcc cctcatggag cttgtatttt cacaggaagc 4500
acagacatta aataaattaa aacacaaaaa aatagacaag catataatta cagtatgtat 4560
cctagagaaa tatcactcat gcagaaagca tacacaagga tgcagcactg tttccaatag 4620
cgaaaagcta gaaacaacct acatgttcac caaaagaaaa tggccacata aactatacca 4680
tatccaaatt atccaaattt tagaatatag acaacaggtt gggcgcggtg gctcacacct 4740
gtaatcccag cactttggga agccgaggcg ggtggatcac aaggtcagga gttcaagacc 4800
agcctggcca acatggtgaa accccgtctc ctctaaaaaa acaaaaaaat cagctgggca 4860
ctgtggcagg agcctgtaat cccagctact gaggagactg aggcaggaga atcgcttgaa 4920
ccctggaggc agaggttgca gtgagccaag atcgcgccac tgcactctag cctgggtgac 4980
agagcaagac tccatctcag 5000

<210> SEQ ID NO 168
<211> LENGTH: 1500
<212> TYPE: DNA
<213> ORGANISM: Homo sapiens

<400> SEQUENCE: 168
tgtaggagtc ctccggtgct ggagtccaga gcacagtgag gctgggtcct cccgtgccat 60
agtgtagggc atggcgggac agggatcctg ccctgcgata gtccagtgct tgagtccgca 120
gtaaggcaat ggtcctccaa tgctggagtt cacggcgttg tggggtcggg gtcctttggt 180
gacttagtcc agggcgtacc agggcggggg tccacagttg ccatagtgag gatcttggag 240
gaaggtggtt cctgccttgc tgtagtccgg ggagcagggg gcaggggtcc tctcttgtca 300
gagtctctgg cgcggggtgg gggtggaggt gggggttttc ctatgcgata gcccacgggt 360
cggtgaagcc gggtcctccc gtgcctttgt ccagggcgca ggggggcgag ggtcttcggt 420
ggtggagtcc gcggagcggc aggacggggg tcctccagtg ccatattcca gggcgcggcg 480
gagtggggga cctgtcctgc agtggtccag ggcatgtggg agtggtggtc ctgctgtgcc 540
tcagtccagt gcgcggtggg acggcggtcc tgctgtgctg tagtgcagga cgcggtggcg 600
caggggtagt ccagagagcg ccgtggcagg gggtcctcca gtgctggaat ccagtgcaag 660
gcgggtcagg ggtcttaccg tgccgaagtc ggtggcaagg gtcctcccgt gccatagtct 720
agggggcgac ggggcagggt tctctagtgc aggtgtccag ggtgtggcag ggcaggagtc 780
ctcttgtgca ggagtccagg acgtagccga ggagtcctcc aatgtcagag tccagggctc 840
tgcggggccg ggttccccca tgccagagtg tagggcgcgt tcaggtgagg gtcttggcgt 900
gcagtaatcc agggtgcggt ggggcagggg tagtccagac ctccatggcg ggcgtccctc 960
tgtgcaggag cccagtgcct ggcggatcgg gggtccttct gtgctgtagt ccagggcacc 1020
gcaaggtgtg ggtcctctgg tgccctagtc caggggggcgg cgagtcagag gttctcccgt 1080
gtctcagtct agggcctggt aggactgggg tcctggagtc cacgtggtag cccaagttgc 1140
cgcaggacca ggtactctgg aaccacagtc cagggcgctg aggggcagga gtagttcagg 1200
gcgagccggg gcccaggtcc tcgggagcca gagtccaggg tgtggagggg tgggggttct 1260
gcagtggcac agtccaggac accgcggggc gggacagggc ggggatcctc ccgtgcctta 1320
gtccagggct gagccgcggg agaggtcctt cagtagcaca gtctagcgca cggcgttgca 1380
ggtgtcctcc agtgcctgag gccacggcag gtcgcgggtc ccactgtgct ctagttcagg 1440
gcggagtggg tctgaggtct tctcctgcct cagtctaggg cgctggagag cggggatcct 1500

<210> SEQ ID NO 169
<211> LENGTH: 2500
<212> TYPE: DNA
<213> ORGANISM: Homo sapiens

<400> SEQUENCE: 169
gggttggtcc tagaaagcgt gaggatcgcc gagtgcactg ccctcccagc ctagggtcca 60
ctcttccttg gcccgagccc agagctcggg gtttcaggcg ctgggccctg tgcagctgcc 120
cagaataggc tgagcggcag gttcccgccc tggcaaggga tccagcagtg gaatcctcac 180
tgctgttggc tgcgggcaag gtcagcgggg tttccatcgc tgctggtggg agccacctgg 240
cggtggtagc tgcaagtgag cgcgtggcag agactggcag ggctggtccc agacaccctg 300
agggtctctg ggtgcatcgc cctaccaccc tagggtctgc tcttccttag cctgctccca 360
ggacgcggtg tacgagggct agactctgag cagcctccag gatggggctg agcagcggat 420
tcctgccctg ctgcagctac agtctgaatt aggcgccacc gcagtatctg gccctggggt 480
acgtgctact gggtggcatg gacagagatg gggctgccca cagctgctat ggggctgagc 540
agccgattct cgccctgctg cagcgggcga ccgctgcaat ccccagcgct atgggaccga 600
ccacctgact tagatgcctt ggaggcatcc ggtcctgggg tcttgctgct ggtgtctgcg 660
ggcagggtca cggctgccac tactactgct gtgcgccatg ggcaggtgcc agctgcagct 720
gagtccgagg cagatgctgt cagggctggt ctgaggttgc ctaagggtgg ctgagtgcac 780
cacgcttcca ccccagggtc cgttattcct aggccggctc ccagattgca gggttgtggg 840
cgttggacac tgtgcagcca tgaggatctg gttgggtgca gattcccgcc ctcctgcagc 900
tgagaagcca atctcataac aggcgctgca gtgacctctg gctctgcggt ccgcgctgct 960
gctggagctg gcagagaaca gagctgccac cgctgctgct tccaggagtg tgcagctggc 1020
agctgcagct gagcccgtgg cggaggctgg aaggccttat tccagaagcc ttgagggtcc 1080
ccgaatgcac cgccctccca ccctaaggtc cagtcttcct tgcccgcgcc cagagagttg 1140
gattgcaggc gctgagcaca gtgcaggtgc tgggatgggg ctaagctgaa agtttccgcc 1200
ctctggctgc tgcggggccg acagcctgag ttatgcgccg cggcggcttt tggtcatggg 1260
atccgcactg ccggtggctt gcacagggtc gggggctgcc acagctgcta tagttcaccg 1320
tgtgcacgtg gcagccgccc ctgagcccac cgctgaggct gcagggctgg tccggtccca 1380
gacggcctga gggccatttg cccgcgccca gatccgggtg gctgcgctgg gcactgtgca 1440
gcctcccgga atccgctgaa gggcacgttc ccgctctcct acagctgtgg gccgactgcc 1500
tgattttggc cactaggtgg agtctggctc tagggtttcg aggccgctgg tgttggtggg 1560
cggagtccgg gtttgccacc gctgcgctcc atgagcaggt agcagctgca gcggagcttt 1620
agaccgaggc tggcagggct ggccccagac ggcctgaggg tcagggagtg caggggtcctc 1680 ccaccctagg tccgctcttc ctttcccctt acccagagcg ggttgtgcgg gctctgggct 1740
ctgtgccggc gctgggctct gtgcagccgc cgagatgggg ctgagcagcg gatttcctcc 1800
ctgctgcagc tggaggacga ttacctgcac tagccgctga ggcggcatct ggccctgggt 1860
tactgcagct ggtgacgcgg gcagggtcag ggttggttgc aggtggcagc tgctgctaaa 1920
cccattgcga gcctcagggt caccaagttc accgtccttt catcatagta tctgatcttt 1980
ggcccgcgcc cagagtgcgg actggcctgc gctggggact gcatagcttc tgggggccgg 2040
tcagcgccag tttcacgtcc tcctgcagct gcgtggccta aggtcttagg cgccgcggcg 2100
ctatctggcc ctgctgtcga cgctgctggt ggtggggaca gggtcaaggg ttgccactgc 2160

```
tgctcccgtg cgccatcggc aggtggcagt tgcagatgag cccacaattg aggctgttgg   2220

ggctgctccc aggttgttag agggtcgccg agttcaccga catgccaccc taggttacgc   2280

tcttggcccg cacccagagc gccgggttac gggtcctggg ccctgtgcag ccacggggat   2340

ggtgctgagt gcaggttccc gtcttcctga gatgcggggc gaccactgga attagcctct   2400

gtggtggtat ctgaccctag ggtccgagct gctggtggcg tgggcggggt cgaagtcgcc   2460

tctgttgctg cggcgtgcca tttgcaccgt cctctggtac                         2500
```

<210> SEQ ID NO 170
<211> LENGTH: 1600
<212> TYPE: DNA
<213> ORGANISM: Homo sapiens

<400> SEQUENCE: 170

```
aaatactcta ctgaaaaaac agaaatagta aatgaataca gtaaagtttt agaatacaaa     60

atcagcatag aaaaatcagt cgcatttcta tacccaacag cataccatct gaaaaaggaa    120

tcaagaaacc aatcccattt aaaatagcta taaaaaaatg cctgggaata aactaagcca    180

aataaatatg tctaaaatga aaactataaa acattgataa aaatcaattg aaaaagatac    240

aaataaaggg aaagttatcc catttttatg aattagaagt attaatactg ttaaaatgac    300

catcatactc aaatcagtct ataggtccaa tacaatctct aacaaatttc caatgtaatt    360

cttcagagat gttaaaaaag gttttaaaaa tcgttctgcg gatgttaaaa ggatttttaa    420

aacgcttttt tcgttctgca ggcgaaggct gtggccgtgc tcccgccggc cagttcccag    480

cagcagcgca ttgcccctgc tccacgcctt cgctccaggc ccgcaggggc gcagccccgc    540

gggaatcagc actgagccgg tcccgccgcc gccccagtgt ccgggctgcg actgcgggga    600

gccgatcgcc cagcgattgg aggagggcga cgaggccttc cgccagagcg agtaccagaa    660

agcagccggg ctcttccgct ccacgctggc ccggctggcg cagcccgacc gcggtcagtg    720

cctgaggctg gggaacgcgc tggcccgcgc cgaccgcctc ccggtggccc tgggcgcgtt    780

ctgtgtcgcc ctgcggctcg aggcgctgcg gccggaggag ctgggagagc tggcagagct    840

ggcgggcggc ctggtgtgcc ccggcctgcg cgaacggcca ctgttcacgg ggaagccggg    900

cggcgagctt gaggcgccag gctagggagg gccggccctg gagcccggcg cgccccgcga    960

cctgctcggc tgcccgcggc tgctgcacaa gccggtgaca ctgccctgcg ggctcacggt   1020

ctgcaagcgc tgcgtggagc cggggccgag cggccacagg cgctgcgcgt gaacgtggtg   1080

ctgagccgca agctggagag gtgcttcccg gccaagtgcc cgctgctcag gctggagggt   1140

caggcgcgga gcctgcagcg ccagcagcag cccgaggccg cgctgctcag gtgcgaccag   1200

gccctgtagc tgtgacttgg ctgtggggct ggcccgcctc cctgacccct gtcaggcgga   1260

gcagctggag ctgacccacg ggcctgggct ttcgagcgct ttgtccaggc gctaatgatg   1320

ggaaggtgaa aggtgggggt ggccacaccc tgcagtcagg gtggcaggtg tcagaggcca   1380

catgcaaccc actggttttg tcttttccag gatgctgata agtttcccgc ggccccccgga  1440

gcagctctgt aaggccctgt aattgccttt cgttcccttc tgctctattg aggagtggga   1500

agatgacaaa gtgtttttgc tcaacccgaa ggaaaatgca catgggagga cacaccgggt   1560

tactatttga gtagcccaga caggagagca gcggtctgct                         1600
```

<210> SEQ ID NO 171
<211> LENGTH: 1500
<212> TYPE: DNA
<213> ORGANISM: Homo sapiens

<400> SEQUENCE: 171

```
tgggtggatt gcttgagccc aggagttcga gaccagcctg gacaaaatgg cagaaactcc      60
atgtctacaa aaaatacaaa aattagccgg gcatgatgtt ctgcgcctgt agtcccagct     120
actcaggagg ctgaggtggg aggatcgctt gagcccagga ggcggagttt gcagtgagct     180
gagatgtcac tgcattccag cctgggagac agagccagac tctgtctcaa aagaaaaaaa     240
gaaaaaaaaa aaagaaaaga aaaaacgaaa ttgtattctg aatacatctt ctaaaacact     300
acatttactt gcactatatt aaactggttt tatcctgacc acaattgcag gtgaaagata     360
ccactgttgt tctatttttc tggtaagtag agtgagccat gtcttcccca gggaaagacg     420
cctcctaaaa atttgtagga ccacctttgg ttttcttcca gatatttttt ttgtcatcgc     480
ttttcctgcg cccaattccc atctgtctag cccttctgcc tccgctggtc tttttcgcga     540
gcctctcccc agccgcaggt attcgtctgg gctgcagccc ctcccatctc ctggggcgtg     600
accacctgtc caggccccgc ccccgtccaa cccgcggaga cccgcccccct tccccggaca     660
ccgggttcag cgcccgagcg tgcgagcgcg tccccgctcg tcgcccggct cggcgtcggg     720
agcgcgctct gtgtggtcgc tgctgcagtg ttgttgtggc tgtgagaagg cggcggcggc     780
ggcggagcag cagccggacc agactcccta gtagctcagg cgctgccctg cgccggccct     840
ggcagggagc ctggtgagat ggtggaggag gaggctgtgc cgtggctggc cttgctgtgt     900
cctgctgcct ggttagaacc ccatccccgt cccccgtctc ctccgggggg tgaggaggag     960
ctggaagagg ggccggcctc tgtccggccc ggccaggcgg cagtcaccct ctgaggaggc    1020
agcgcccggg gaggggcctc ccaggcggcc gccgccgcca gggggaggcg ctgggagtgg    1080
gagtgggagc gggacctcag ctgccaagct cggcccggac cctaggtgcg ggggaggcgg    1140
ggtcccgggc tcgggctgcc tgcccggacc tggcggggat gggcccgtgc ggctccgggt    1200
gtgggacgta ccctcagagc gcccggggtt attcccactg actccaggga ggtgagtgtg    1260
cgcccttcgc tccctgccgt gtctgtgagg gtccatcgtt gccggagact ggaggtcggg    1320
ggccatggga gccccggggc gaacggtgcg gacatgggcc ttgtggaaag gaggagtgac    1380
cgcctgagcg tgcagcagga catcttcctg acctggtaat aattaggtga gaaggatggt    1440
tgggggcggt cggcgtaact cagggaacac tggtcaggct gctccccaaa cgattacggt    1500
```

<210> SEQ ID NO 172
<211> LENGTH: 1700
<212> TYPE: DNA
<213> ORGANISM: Homo sapiens

<400> SEQUENCE: 172

```
gtctctagga caccctaaga tggcggcgag ggagacggtg aaggttggct cccgcctgtc      60
tgggctctga tcctctgtct ccccctcccc ctgcggccgg ctcatggcct ggcggaggcc     120
cgaaccaaag acctccgcac cgccgtgtac aacgccgccc gtgacggcaa gggggcagct     180
gctccagaag ctgctcagca gccggagccg ggaggaactg gacgagctga ctggctaggt     240
ggccggcggg gggacgccgc tgctcatcgc cgcctgctac ggccacctgg acgtggtgga     300
gtacctggtg gacccgtgcg gcgcgagcgt ggaggccggt ggctcggtgc acttcgatgg     360
cgagaccatg gagggtgcgc cgccgctgtg ggcgcggacc acctggacgt ggtgcggagc     420
ctgctgcgcc gcggggcctc ggtgaactgc accacgcgca ccaactccac gcccctccgc     480
gccgcctgct tcgagggcct cctggaggtg gtgcgctacc tggtcggcga gcaccaggcc     540
```

-continued aacctggagg tggccaaccg gcacggccac atgtgcctca tgatctcgtg ctacaagggc 600
caccgtgaga tcgcccgcta cctgctggag cagggcgccc aggtgaactg gcgcagcgcc 660
aagggcaaca cggccctgca caactgtgcc gagaccagca gcctggagat cctgcagctg 720
ctgctggggt gcaaggccag catggaacgt gatagctacg gcatgacccc gttgctcccg 780
gccagcgtga cgggccacac caacatcgtg gagtacctca tccaggagca gcccggccag 840
gagcagctca taggggtaga ggctcagctt aggctgcccc aagaaggctc ctccaccagc 900
caggggtgtg cgcagcctca gggggctccg tgctgcatct tctcccctga ggtactgaac 960
ggggaatctt accaaagctg ctgtcccacc agccgggaag ctgccatgga agccttggaa 1020
ttgctgggat ctacctatgt ggataagaaa cgagatctgc ttggggccct taaacactgg 1080
aggcgggcca tggagctgcg tcaccagggg ggtgagtacc tgcccaaact ggagccccca 1140
cagctggtcc tggcctatga ctattccagg gaggtcaaca ccaccgagga gctggaggcg 1200
ctgatcaccg acgccgatga gatgcgtatg caggccttgt tgatccggga gcgcatcctc 1260
agtccctcgc accccgacac ttcctattgt atccgttaca ggggcgcagt gtacgccgac 1320
tcggggaata tcgagtgcta catccgcttg tggaagtacg ccctggacat gcaacagagc 1380
aacctggagc ctctgagccc catgagcgcc agcagcttcc tctccttcgc cgaactcttc 1440
tcctacgtgc tgcaggaccc ggctgccaaa ggcagcctgg gcacccagat cggctttgca 1500
gacctcatgg gggtcctcac caaaggggtc cgggaagtgg aatgggccct gcagctgctc 1560
agggagccta gagactcggc ccagttcaac aaggcgctgg ccatcatcct ccacctgctc 1620
tacctgctgg agaaagtgga gtgcaccccc agccaggagc acctgaagca ccagaccatc 1680
tatcgcctgc tcaagtgcgc 1700

<210> SEQ ID NO 173
<211> LENGTH: 300
<212> TYPE: DNA
<213> ORGANISM: Homo sapiens

<400> SEQUENCE: 173
taaaaataaa ttgtaataaa tatgccggcg gatggtagag atgccgaccc taccgaggag 60
cagatggcag aaacagagag aaacgacgag gagcagttcg aatgccagga acggctcaag 120
tgccaggtgc aggtgggggc ccccgaggag gaggaggagg acgcgggcct ggtggccaag 180
gccgaggccg tggctgcagg ctggatgctc gatttcctcc gcttctctct ttgccgagct 240
ttccgcgacg gccgctcgga ggacttctgc aggatccgca acagggcaga ggctattatt 300

<210> SEQ ID NO 174
<211> LENGTH: 600
<212> TYPE: DNA
<213> ORGANISM: Homo sapiens

<400> SEQUENCE: 174
cgccaccacg tgcgggtagc gccgcatcgc cccagccgtg ttccttggtc tccgtctccg 60
ccgcgcccgc ctggtgaact ggagcacagg gaccatagtt ctggaaattt atccttttc 120 tctccatgga ttcagcagca gtgtctaaaa gaaaaaaatt catcaatcat ttatgtatat 180
tttaatataa aggtaaaaca ctgcgaacca gtggaaccgg atagaaagta attcagtttt 240
acagaacaca actgtttttc aggctctttt attaaatata aaagagccat atatatttct 300
gtggaattcc ccttttactt aagaattcat tatcagcgaa ttagtttaag gaggctgttt 360
tgttagaggc tgtggttgca ttcaaaaatt ggaataggaa caatgacttg taaaaattca 420
acattttatt ttatttttga gatggagtct cgctctgtcg cccaggctgt agtgcagtgg 480
cgcgatctcg gctcactgca acctcagcct cccgggttta aggaattctc tgcttcagcc 540
tcctgaatag ctgggattac aggcgcatgc caccaagccc agctaatttt ttttgtattt 600

<210> SEQ ID NO 175
<211> LENGTH: 1300
<212> TYPE: DNA
<213> ORGANISM: Homo sapiens

<400> SEQUENCE: 175
ccctgaacag tcagagttta ctgcccactt ttgctggagg agaagctcct gaacaactag 60
agagactgtg gttcccaaag agcagcctgt aggcctgagg actgctctat gaccggcgtc 120
agtccctgcc tccctccctc cgtccctcct tccctccttc cttcccaggc cttctctgac 180
taccagatcc agcagatgac ggccaacttt gtggatcagt ttggcttcaa tgatgaggag 240
tttgcagacc atgacaacaa catcaagtga gtccacttgg atgccccctg cacgaggcac 300
gactccccct cctcgctgct gaagtcccat gggggcagct cccttagtcc ttgccgggag 360
ataacaggtg tttccagttg catgagggtg ctgaggcccc cagtgagaac caggggagga 420
gcactgaggc ctcagatgag caccggggga ggagccctga ggccccagat gagcaccagg 480
ggaggagcac tgaggcccca gatgagcacc gggggaggag cgttgaagcc ccagatgagc 540
accagaggag gagagctgag gccccagatg agccccgggg gaggagctct gaggccccag 600
acgagcaccg gggaggagc gccgaggccc cagatgagca ccgggggagg agcgccgagg 660
ccccagatga gcagtggggg aggagccccg aggcccccag atgagcagtg ggcggggcag 720
ggagcgccga ggccatcccc cttgctcttg cagcgcccca tttgacagga tcgcggagat 780
caacttcaac atcgacactg acgaggacag tgtgagcgag cggggctgtg cggggtcatg 840
caggcaccct gttcccaggc agctcaggcc gcgcccatgg ctcggtctgt ggtgggcctg 900
tgcggtgggg ctgggagagg cccctctgtg gagctaggaa cagtcgcttt tcttgaccct 960
ccccatcatg ccctccagcc catggcgccc acatcctgaa ctaagcccct ctgggagccc 1020
tgtggggaga gcgcctcctg tctcccccag accctctgga aactgacctt ggcgttttac 1080
tctgcagccc agcgcggctc tgaggcctgc tgcagcgacc gcatccagca ctttgatgag 1140
aacgaggaca tctcggagga cagcgacact tgctgtgctg cccaggtgaa ggccagagcc 1200
aggtgcgggg cctgcccatc cccccaaagc ctctgccgag gaggtgcagc ccccagaaca 1260
cccgtcagat gcccagacgc cctgctgttt gttatgccgg 1300

<210> SEQ ID NO 176
<211> LENGTH: 110
<212> TYPE: DNA
<213> ORGANISM: Homo sapiens

<400> SEQUENCE: 176
tttgggccac gaggcaagtt caaagcggga gacttttgtt ttataaaatg atggtgagca 60
gctccggttt tatgtcaaac atcagggttt cgtgcaggat ataaacattt 110

<210> SEQ ID NO 177
<211> LENGTH: 1500
<212> TYPE: DNA
<213> ORGANISM: Homo sapiens

<400> SEQUENCE: 177

-continued

```
attgccgtac tttgcttccc tttgtatgta tttcttgtat gctgccgagt cactgatggc     60

tagctctgtc tggcaagtaa ttcaaaaatg ctgtttatgt agaaaggaaa ggtagggact    120

ttaccacact ctgtcattaa agggagcaat tgaagaacaa aggaactgag taaataccta    180

tatattgcct tttgtgttgc gaaacactgt agcacaaaca catttgtgtt cagccaaatg    240

ttttacttcc ttttgtaata acgcatatag taggttgtct ccacatatgt acaagaatcc    300

atattttatt taaacgtata tagtcaattg ttcatattta taggctgcaa acatttctca    360

atctcaaaga cttttacata tccactccca cacagctatt tgttattatt ttaaaagttc    420

ttaaattaaa aaaaaaaata aaatatacta atatctctgt tggttgattt tattaagcaa    480

cttaggattt caacacagtt taaatcatat tgatgactca gatcctggca ggtcttacaa    540

ttcctgtgaa atgagagcac agctaataaa aatattaagc aattactttt attaaaatca    600

tagggttttt ttcattatca catagaaatg attgatctat acagattggt ctcactcatg    660

tgtcttttgg gctgcttggg agcttcatgt agaagtggaa agtccccttt gctcttcctt    720

cgaccaaggt ggggaaaatg aaggcataga atacaatcta gggctattaa agaattgctg    780

gcattacttc tctctatcac gtgtgagcct ggctgcctgc ttcctgaggt aggggatcca    840

ggatgagact gtgccggagc ctgtttccac aactgcattt ggagatccgt cttattgatt    900

agcgggggaa aggggtgggg atcaggagtg tgaggtgagg ggaggaccaa ctgacgactg    960

gctcaatgaa gcacaagaca ttttcttccg gaaagatgtc aaacaactga gaaacagcca   1020

gagaggaagt agaaaggtgg aaaaatgagg agaccctgga agaaatgaag gcatttccta   1080

tgagacagcc ttggggcttt tttcttttct ttcttttttt ttgcttccat catctgacct   1140

gcaaaggcta gagtgacagc gtcatgcaaa tgctgcagtc cagcaggtct gggagagggt   1200

ggatgctaga ctgtgagtta atgttaatga tgagcgcagt gaaaatacca gccgctgcca   1260

ccccctgctc acagaagcgc tctgagtcag catcagatgc tttgcctcgc ctctcgctgt   1320

gtatctgtat gcctgtgtgc gcgcgcgtgc tcgctcgggc atccgtgtct agccgagggg   1380

agggggtggc gtgtgagtgc gtggagggta aaagccagtc agtcagtgag aagcaaaggt   1440

acgttggaga gcaactaaaa tctgactgat ttccatcttt ggagcatcag atgtattccc   1500
```

<210> SEQ ID NO 178
<211> LENGTH: 200
<212> TYPE: DNA
<213> ORGANISM: Homo sapiens

<400> SEQUENCE: 178

```
gcagcctcct cctgaaaaat gtaagccatt tccactttgt aaagctacgt ttatattcca     60

ccacgatacg atggaaaaga aaacccaagg caatttaata tacgggttgg gaagaaagtt    120

ttgctgatgg aactacatta gcctccactc cagcaaagca aacaaggaac cacactaaag    180

aaatgtactg aatcttttaa                                                200
```

<210> SEQ ID NO 179
<211> LENGTH: 800
<212> TYPE: DNA
<213> ORGANISM: Homo sapiens

<400> SEQUENCE: 179

```
tgcctgagcg cagagcggct gctgctgctg tgatccagga ccagggcgca ccggctcagc     60

ctctcacttg tcagaggccg gggaagagaa gcaaagcgca acggtgtggt ccaagccggg    120

gcttctgctt cgcctctagg acatacacgg gacccctaa cttcagtccc ccaaacgcgc    180
```

```
accctcgaag tcttgaactc cagccccgca catccacgcg cggcacaggc gcggcaggcg    240

gcaggtcccg gccgaaggcg atgcgcgcag ggggtcgggc agctgggctc gggcggcggg    300

agtagggccc ggcagggagg cagggaggct gcagagtcag agtcgcgggc tgcgccctgg    360

gcagaggccg ccctcgctcc acgcaacacc tgctgctgcc accgcgccgc gatgagccgc    420

gtggtctcgc tgctgctggg cgccgcgctg ctctgcggcc acggagcctt ctgccgccgc    480

gtggtcagcg gtgagtcagg ggccgtctcc ccgaagaacg agcggggaga ggggaccacg    540

gggcgcggcg ggcagcctgt tctcgggcgg aggctctccg gggcgttgga aacctgcatg    600

gtgtaaggac ccgggaggag gcggggagaa attgattgtg ctgttctcct ccctctcttc    660

tctaacacac acgcagaaaa gtttaaattt ttgtgaagcg cttgcttacg tagctgcgga    720

gcgagcctct gcttcattac gagcggcata gcctttttca ggagtgattt ccactttctt    780

tgtgagagag ttgaccacac                                                800
```

<210> SEQ ID NO 180
<211> LENGTH: 600
<212> TYPE: DNA
<213> ORGANISM: Homo sapiens

<400> SEQUENCE: 180

```
ttcaatttac actcgcacac gcgggtacgt gggtgttcgg ggtagggcac tgatctgggg     60

aaggtctccc ccccgcgacc caactcatct ttgcacattt gcagtcctcc ctcggtgcac    120

tcctggcggg gatctggcca gtgcagcgca ctgggaccga gggcagagcc cgcggagtga    180

ggccaggaga gacttcaggc ctctaaggac acagctgagg ctaaggctga gttgaacgca    240

gcccctcccg cggctcgtcc cctctccagt gtctctcccg taaggtgccg ctcccaacag    300

caatgggtcg agatgtagag gaaacactct gtacgttatt tttccgccca ccctttagcg    360

cctgaggaga cagacagtgt agactttagg gtacaattgc ttcccctctg tcgcggcggg    420

gtggggagcg tgggaagggg acagccgcgc aaggggccag cctgctccag gtttgagcga    480

gagagggaga aggaggtcca cggagagaca agaatctccc tcctcccacg cccaaaagga    540

ataagctgcg gggcacaccg cccgcctcca gatcccccat tcacgttgag ccggggcgcg    600
```

<210> SEQ ID NO 181
<211> LENGTH: 600
<212> TYPE: DNA
<213> ORGANISM: Homo sapiens

<400> SEQUENCE: 181

```
tcattatccg attgattttc ctggtatcac atcacttaag tttaagtagc tcttatgtta     60

cttagtaatg actgcaaaac acgagttgtg atgcgggcaa tttggataca acaaaaagaa    120

gccattaagt ttgttcgtta gttaacaggt gaaagctctc aagttattaa ggataaaaat    180

gctagtatat atatatatgg tttggaacta tactgcggat tttggatcat atccgccatg    240

gataagggag gaatactata atcaggtttg ttttaaattc catgtctaat gacttcgtta    300

tctagatcac ctgtagagct gtttttattg taggagtttt ccttggtttt aatcttttga    360

tttgtttttc atgttaatac tgaaattttt aaaaattgca tattgtactt cctatatgaa    420

aattttacta tgtattttta tttttatttt ccttttcctt taggaagaat tagtttgttc    480

cctgacagag ttagagtaag ggcaaattac ttgtctctat aaacaactca gatgttttga    540

gccggtgttg taggggttat ctttttctgg ttttgcattt tattatagga catagtgctt    600
```

<210> SEQ ID NO 182
<211> LENGTH: 140
<212> TYPE: DNA
<213> ORGANISM: Homo sapiens

<400> SEQUENCE: 182
agaaagaaga aatccggtaa aaggatgtgt tattgagttt gcagttggtg tttgatcttg 60
cacagatttt ctcaggggcc ttaagaccgg tgccttggaa ctgccatctg ggcatagaca 120
gaagggagca tttatacgcc 140

<210> SEQ ID NO 183
<211> LENGTH: 900
<212> TYPE: DNA
<213> ORGANISM: Homo sapiens

<400> SEQUENCE: 183
cgaagatggc ggaggtgcag gtcctggtgc tcgatggtcg aggccatctc ctggtccgcc 60
tggcggccat cgtggctaaa caggtactgc tgggccggaa agtggtggtc gtacgctgcg 120
aaggcatcaa catttctggc aatttctaca gaaacaagtt gaagtacctg ggtttcctcc 180
gcaagcggat gaacacccac ctttcccgag gtccctacca cttccgggcc ccccagccgc 240
atcttctggc ggaccgtgcg aggtatgccg ccccacaaga ccaagcgagg ccaggcttct 300
ctggaccgcc tcaaggtgtt tgaccgcatc ccaccgccct acgacaagaa aaagcggatg 360
gtgttcctgc tccctcaagg ttgtgcgtct gaagcctaca agaaagtttg cctatctggg 420
gcgcctggct cacgaggttg gctggaagta ccaggcagtg acagccaccc tggaggagaa 480
gaggaaagag aaagccaaga tccactaccg gaagaagaaa cagctcatga ggctacggaa 540
acaggccgag aagaacatgg agaagaaaat tgacaaatac acagaggtcc tcaagaccca 600
cagactcctg gtctgagccc aataaagact gttaattcct catgcgtggc ctgcccttcc 660
tccatcgtcg ccctggaatg tacgggaccc aggggcagca gcagtccagg cgccacaggc 720
agcctcggac acaggaagct gggagcaagg aaagggtctt agtcactgcc tcccgaagtt 780
gcttgaaagc actcggagaa ctgtgcaggt gtcatttatc tatgaccaat aggaagagca 840
accagttact attagtgaaa gggagccaga agactgattg gagggcccta tcttgtgagc 900

<210> SEQ ID NO 184
<211> LENGTH: 1400
<212> TYPE: DNA
<213> ORGANISM: Homo sapiens

<400> SEQUENCE: 184
gcctgaagac catttcttcc tctcttaggg acctgctggt ctccagctga ttcggtccag 60
gaggaaaaac ctcccacttg ctcctctcgg gctccctgca aggagagagt agagacactc 120
ctgccaccca gttgcaagaa gtcgccactt ccccctccag ccgactgaaa gttcgggcga 180
cgtctgggcc gtcatttgaa ggcgtttcct tttctttaag aacaaaggtt ggagcccaag 240
ccttgcggcg cggtgcagga aagtacacgg cgtgtgttga gagaaaaaaa atacacacac 300
gcaatgaccc acgagaaagg gaaaggggaa aacaccaact acccgggcgc tgggcttttt 360
cgacttttcc tttaaaaaga aaaaagtttt tcaagctgta ggttccaaga acaggcagga 420
ggggggagaa gggggggggg gttgcagaaa aggcgcctgg tcggttatga gtcacaagtg 480
agttataaaa gggtcgcacg ttcgcaggcg cgggcttcct gtgcgcggcc gagcccgggc 540
ccagcgccgc ctgcagcctc gggaagggag cggatagcgg agccccgagc cgcccgcaga 600
gcaagcgcgg ggaaccaagg agacgctcct ggcactgcag gtacgccgac ttcagtctcg 660
cgctcccgcc cgcctttcct ctcttgaacg tggcagggac gccgggggac ttcggtgcga 720
gggtcaccgc cgggttaact ggcgaggcaa ggcgggggca gcgcgcacgt ggccgtggag 780
cccggcctgg tcccgcgcgc gcctgcgggt gccccctggg gactcagtgg tgtcgcctcg 840
cccgggacca gagattgcgc tggatggatt cccgcgggca gaggcagggg gaaggagggg 900
tgttcgaaac ctaatacttg agcttctttg caaagtttcc ttggatggtt ggggacgtac 960
ctgtataatg gccctggacc agcttccctg ttggagtggc cagagaagtg tgtaaaacac 1020
actagagggg cagggtggaa aaagagactg ccttcaaaac ttgtatcttt tcgatttcat 1080
tttgaaaaat aactacaaat ctattttaat tttacaaagt tagactcata gcattttaga 1140
tatcaatgtc ttcatttaac agaagtgaag atggagcaaa cgctcaatca gcgtctgtat 1200
ttattcgctc ctgttgtgcc agggtgcgtt tttgccgagc ggttgccttt ctttactcac 1260 aaaacccccct tgatgtctgt cctccacgtt ttacgaggga gagccggatc ttttgaagtt 1320
tgtatcatct aaagcaggta tattgggatg actatggata gaatttaacc tgaaaacact 1380
gaagttgaca gctgacaaag 1400

<210> SEQ ID NO 185
<211> LENGTH: 200
<212> TYPE: DNA
<213> ORGANISM: Homo sapiens

<400> SEQUENCE: 185
cataacaaga gtcattctaa tgtgattata aaggacccga agctttgctt ttaaaattca 60
atacttaggt agaaagaaaa tgataacttt ttccctttga tttttattca ctatttttat 120
aacactagca gccctgagac accggattgg aaatatctat gcctcttgat gttacctggg 180
caccactgca tcacagtcct 200

<210> SEQ ID NO 186
<211> LENGTH: 400
<212> TYPE: DNA
<213> ORGANISM: Homo sapiens

<400> SEQUENCE: 186
aatagtaatt gccaacagtc aagatatgta ctaccaccaa attccgtgtt atttgtgatc 60
aaaagatata cacagatact tgaaaactga tttctacgtt gcatatggga aaaatacctc 120
atttttctca gctgtccatt atttttgaga tattatgtgc agtgatagta agaacaagca 180
gatttggaac acatcagcaa taattttttc aatcagagtc ctgccaaaat gaaagaattt 240
gacagtatcc ggcaccctgt actcatgctt ggcttctgta gaaactgtgg cttgcaaaag 300
ggcagctggg tactgtgttt tggtacctca ttctttaaac gtataatggg aatctggttg 360
gttcaggaaa acccttgcct acttattatt actctgtttt 400

<210> SEQ ID NO 187
<211> LENGTH: 250
<212> TYPE: DNA
<213> ORGANISM: Homo sapiens

<400> SEQUENCE: 187
ggcccatact taatgtattt ttaaacgttt taacatttac taatatagaa ccttctattg 60
cctatttcct tctggtttat tccctttcct tctgtcattg aagaaatggt tctagtggta 120
gaaatactcc acgattgaga agaatgtggg aagaaaggag ggctggtggg taagaattgc 180
tcatgatgtc tccctctgaa ttctgtgctc tcacaatgac actccaatgt gtggtttgac 240
gcctggaaga 250

<210> SEQ ID NO 188
<211> LENGTH: 250
<212> TYPE: DNA
<213> ORGANISM: Homo sapiens

<400> SEQUENCE: 188
tgcttcaacc ggaaatgtgg ttgaattacc cttacagtga acctgatcag tggtaacagg 60
agatgctaga acaggaaaag acaagtttcc cctttcctcc ctatcccatc aattactttg 120
aggtgtattt tttctttgca acccctccag agaagtcggc aatgtttaac gagcatgcct 180
gccaagtggc ttgccttata cctcattatg aagtgatact cagggccact aacacatcgc 240
acagcattgc 250

<210> SEQ ID NO 189
<211> LENGTH: 500
<212> TYPE: DNA
<213> ORGANISM: Homo sapiens

<400> SEQUENCE: 189
tatgattccc tcgatttccc tcaatcttaa ccattgtgga tcacagcagg agggccagaa 60
agtgagcttc agcctggcac cgggacctca gcctctccct taaactttcc ctaatcctcg 120
gagctagtgt tactcaagtg actccacagt gttgcccgat cccttcagac atggccttga 180
tgatctccaa aactcatgct acctttgcca gcctaaagca tccactctgt gccccaaaac 240
gtgaatgtca aataccettc aaggcagaag gctatttcta tttttgtttg tttctgttta 300
aggcaacaat caccaacatt tggtacacat gagccatcct gtgaaacatc aaggcgcttc 360
gttggcagca agtcaacttc ggtttcagaa gaaagctgca ctatttcctg aggttagagg 420
tttaaaccaa aacaagacaa ccacatttta accccaaatc tgccgactga gggtaaccat 480
gatccttcct tcacagcacc 500

<210> SEQ ID NO 190
<211> LENGTH: 150
<212> TYPE: DNA
<213> ORGANISM: Homo sapiens

<400> SEQUENCE: 190
tactaaatca acccaaaccc gagaacccgg tcatggagaa ataaatgata gtaatctatg 60
ctgttcatct gttccatcac tcactcactc tcttgctgaa caagaaaggg ccacccatgt 120
agcaaaccac atgtaaagag ccgggaagac 150

<210> SEQ ID NO 191
<211> LENGTH: 300
<212> TYPE: DNA
<213> ORGANISM: Homo sapiens

<400> SEQUENCE: 191
tattattttg ttcaaagtag acgggtatac taacatctgt gggcaagttt accacacgcc 60
acttaaaaca ggctaacagg gtcatatgcc aaaacgttca ggtttgcatt tttgaaaagc 120
tcagagatct gacagatgtg ttccggccgc gatttaacat gcggctccag tgagaaggaa 180
gcagatatga caaatggttc acttatttca gaactaaaac cccagaggag cagcctgagc 240
caaaaaggga agtgatcaat ggaaaagacg gtcgaatctg ctcacaggca aggcaagggg 300

<210> SEQ ID NO 192
<211> LENGTH: 300
<212> TYPE: DNA
<213> ORGANISM: Homo sapiens

<400> SEQUENCE: 192
aagacctgga gtttccatta caccgaattg gcacttaata actgttgtcg gagcatttct 60
taagccacat tttcgtaaag tggctttaaa attgctctgc cagtaggcag gttgctaaga 120
tggtcagaga caaacttctg aacgactctt gtaaaatata cagaaatatt ttcagaactt 180
ttatcagtaa aattacaaaa cgtgttgcaa ggaaggtgct tgtgataaca ctgtccccag 240
aaccttagtg aagttaccaa ctggtggaaa attttctctt gcactcggct taaaaatcat 300

<210> SEQ ID NO 193
<211> LENGTH: 400
<212> TYPE: DNA
<213> ORGANISM: Homo sapiens

<400> SEQUENCE: 193
gcaggggtga ctggtcctct ctctctgcac ctcgcaggat ttctctggaa gatctgagcc 60
cgagcgtcgt gctgcacatg accgagaagc tgggttacaa gaacagcgac gtgatcaaca 120
ctgtgctctc caaccgcgcc tgccacatcc tggccatcta cttcctctta aacaagaaac 180
tggagcgcta tttgtcaggg gtaagtgcga ccctagaggc gatcgtctct gctgtctgtg 240
gaaaaaagag ctcctacacc caaagtgctt ctcagttgct gacacttgat ccaagctgct 300
aatttaatct aatgtgaggc tgagttttct gaatgtggga taaagtcgta gctaaacctg 360
cttctcaggg agtgcctttt atctgcaatg tttttcaaat 400

<210> SEQ ID NO 194
<211> LENGTH: 1100
<212> TYPE: DNA
<213> ORGANISM: Homo sapiens

<400> SEQUENCE: 194
aagtaacggg atcaaattaa ttattatttt ggtggccgcc tctcttctcc accccaagcc 60
aggcaagact caccctcggc cctgcccgcc ccagcatttc aaatggaata cctaggtggc 120
ccagggggac ccctgacccc tatatcctgt ttctttctgc ctgctttgct acttttctcc 180
ttgataaaag gagagagtga gagataatta acaaaaaaca tggccccagg acaatgaaac 240
aactggcctt ggccggccag aaatgtatcc tggttttcta ggtgaacttt ctcccatcaa 300
tctttccttt aacctctctg ttagtggaag caataggaac acccctcccc tcccctgagc 360
aaatgctttc ttttgactgg aaacaaaaca ggggctcggc gaaggctgag gtgaaatctg 420
ggtggcatgg gcgccgcaca atggggccgc tgttccccgg cccgggcttg tgttttacaa 480
caggggaggg gcgggcgtga atggtctgat gattggaaca atccccccga ttcaggccta 540
caaacgcatc ttctgttcca caccgagggg acagaaagga gaaaagtgac aaagaacgcg 600
gggcgggggg aattaaaaca aaatgcgctc gactaaaaaa tctctcatat cctgcatatt 660
ccagaaagcg gctctatgga gagagccttc aggaggcctc agccatatct gaatggcttt 720
ctctggcctc tgatttattg atgaagctga agcgacttgc tggagaaagg cctggagcct 780
tctttgtctc cgagatgaag tacaataggc cacagggcgg agatctcttg tgatgctctc 840

```
gggtcctgcc tttctcttgc cctctcctcc ctgcaaatac cagcagcggt gacaaacgat    900

tggtggtgtg cctgggagag ccggtgacaa gactgggcca cttgaggtct ccttaagagg    960

gtattatggc cagggcgacg tttgtgctgt gaagatggca cactccattt tgtcaatggc   1020

tctcatcggc ccagataatc gccccctgcc tgcctgtcag gggcgcagcc ggccgattca   1080

tggcgccctc ggagaaagta                                               1100


<210> SEQ ID NO 195
<211> LENGTH: 10000
<212> TYPE: DNA
<213> ORGANISM: Homo sapiens

<400> SEQUENCE: 195

gtctttcccg ccccttgtc taaactcaaa accgagtccg ggcgcgcctt gcagggcgcc     60

cgagctctgc agcggcgttg cgggctgaac ccatccggca caaactgcgg gccactggcc    120

cctcacacct gggagtttgc ggcgctggcc tgcagcccgg ggcccacgtg gcggaagctt    180

tcccgggcgc gcgctgcgca gccccgcggg gccggggaga caccgctcgg gagtcctccg    240

ctcggctgca gaatctttat cagctgcact ttaccgcagc cctggctagg acgctaggcg    300

gtggagcgcc ctatccaggt gcgccgccgc accatggatc accgcgcccg gtcccgcagt    360

cccgccatgg cctggggagg cccgaagccc ggggacagtg gccggcccat ctccggctcc    420

gcggaccccc ggctcaggcg ggagggcagg cgggtccctg caggccccca gggagcccgg    480

gagcctctct ctggcgtcat tcagtcccgg ggcaacctga agcgcggtag atattggaga    540

gggggcgtct gttgggggga cctggcgtca ttactgatgg ctagcaggga ggagggaacg    600

ggttgtcacc tcggcctcat aaggccgtga gtgagtagtc cagggcctct tcaggcattt    660

ttgaaactgg attaactagg ggggaaattg tagcactgaa gccaccgtga ctgtcttttg    720

cgctgtgtgg aaactccggt aaaactcttt gggcaacagt cttatcacca gctcttcaac    780

gtgtgcagcc cttctggtcc tgtccctgtt ctgggcccca ggaatgcaaa gcaggtccag    840

gcactgtgaa gaccctggcg gtggaggaag aggcttcccg gctgtggagg aagccagacc    900

cttacaacac aagacgagaa ccagacctgc gtgggggagc tctggatgct acaggggctc    960

aaggaggggt ggaggggcct tcccaggcca acccctgaac ggcttggaca agatgctcag   1020

atggacggga ggaacggcgt gtgggatggg ggagctggag gcgggtgggt gggggggga   1080

ggatggggaa agcgctggcc cacccagtgt gggaggggta gaggaaaagc ccgcaggggc   1140

caggttggga ccccgtaggc cgggttagag ggcttggact tgatcctgac aggcgacagg   1200

gagacatatt gctacttatt atgtgcacag tggccagatc tctaaagaaa acaccatccc   1260

ccaccccac cccccatata gtaaaccagg tggtccgccc agtgctccca gggaggtgat    1320

gggaaatccc actccatacc ctgcggtgag gggttccatg ccctccacgt gtgcaactac   1380

tccgggccca gggaaacact gggccccatc cggtaacccc cggcccagtc gggtttccca   1440

gttcacatta taaccaaacg gtcttgccag ctagacagac agacacccct gacctgttta   1500

ccctgatcct ctgctctcag gattaatcac aacttgtcga agggggtggc ttccagtggg   1560

gtggaccgct ctgtcaatgc cagcgtgtgt ctagcatctc ctggggtggg ggtgtgggga   1620

agggaggtgt aggatgaagc cctagaagcc tcaggcaatt gtgatccggt gggctggata   1680

ctgaagccca cccctgcctt gacctcaatt ttcagtatct tcatctgtaa aatgggaaca   1740

acctgccttc ctcctagccc taaaggggct gctgtcaaga ttggctgaga tagctgtttg   1800

caagctgagc tcaatgaaag ttcattgtgt ccccctcagt cctatcccaa tatcgtctca   1860
```

-continued

```
ctgcaaaggt ggggggcagc ttaacttcaa gggcacttca aggatagcca ggtggctgtc   1920
agcccagctt tccaggatgg gagcaggatc ttgacagaag ggttgactgg gaggggcagt   1980
tgctggtttg ggcttcgtta ggttgcattt ttgtttgttg tcctttcatt tccctggggc   2040
agcacccctt cctgcaagct ccaggccttc ctctggaatg ctcctagagc ccaacctctg   2100
ctggtgcctg agcttaagcc aggccagcta aggggatcct ggattcacac ggcctcacag   2160
tcactcagat tgttagcaga agacaaaaat tacaagggga gggcgtcatg tgattcttac   2220
acaccctcca aatccagcag acaccttgga agccacaggt agcttcaaga aacccatttt   2280
acggatgaga acctgagatg gagaaaggac aactggagat ctctgagtct ctgagcccac   2340
actccctacc tccctgcacc tccaggcact ctgctggcag gatcttgggc aaatgcccac   2400
agctctctga gagtcagttt tcctgtctgt aaaatgggag tcataccttc ctcctatggc   2460
cggtgagaga ctaaattaaa ctatgtctgt caagacacct gaaactcctg gcacaattta   2520
ggttgccttc aagtggtcac agttgtcatt aggtggaagt caacacccca atcattgtaa   2580
aggtgcccat ataccccaag atccagatta cagctctcac agtttattat atacagcgaa   2640
aaaacacata acacaccttt gcccacattt acatgtattt tacggaccat gtttcacatc   2700
agtccgcatg cacatctgca cgtgtgtgca ttcggcagta tttaccaagc acctgccaag   2760
tgccagggcc tgtcctccgc acccggcgtg aactgtcctg gaccagtccc gggagccgcg   2820
gttctgacca gccgtgctga ccctggacga ctccatgagc tgttttgtga gaaagacacg   2880
ccatttgttt gcagagttct gacttctgag ggtcatgta gcacatgttt ggtagccaaa   2940
cgctgtcatt cacgaccagg agcgatggct gcaatgcctt tttctttgct ttgctttccg   3000
gtgccgggag ccttgcctcc cgccgccacc cctggtcagc tctgcgcaag aacgtcgttc   3060
tgtttggcag ccaggccgag acgcagcctg aatgtgagca ggaactcgga gaagggaagg   3120
gagagaatca gaaagaaggc ccgggaggga cccgggaagc agtgggaggt ctgcgccctg   3180
gagccccgcg agagcccgcc ggtttggcac gggctcctcc cgggccgccc ggcggtccaa   3240
caaaggccgg ccccgacacg cacccggtct tttgtgggag agaaacacaa agaagaggga   3300
aaaacacgga ggaggccaac agcaccagga cgcgggggcc aaccaggaac tcccggagcc   3360
ggggcccatt agcctctgca aatgagcact ccattcccca ggaaggggcc ccagctgcgc   3420
gcgctggtgg gaaccgcagt gcctgggacc cgcccaggtc gcccaccccg ggcgccgggc   3480
gcaggacccg gacaagtcct ggggacgcct ccaggacgca ccagggcaag cttgggcacc   3540
gggatctaat ttctagttat tcctgggacg gggtggggag gcataggaga cacaccgaga   3600
ggtactcagc atccgattgg caccagggcc aagggagccc aggggcgaca cagacctccc   3660
cgacctccca agctactccg gcgacgggag gatgttgagg gaagcctgcc aggtgaagaa   3720
ggggccagca gcagcacaga gcttccgact ttgccttcca ggctctagac tcgcgccatg   3780
ccaagacggg cccctcgact ttcacccctg actcccaact ccagccactg gaccgagcgc   3840
gcaaagaacc tgagaccgct tgctctcacc gccgcaagtc ggtcgcagga cagacaccag   3900
tgggcagcaa caaaaaaaga aaccgggttc cgggacacgt gccggcggct ggactaacct   3960
cagcggctgc aaccaaggag cgcgcacgtt gcgcctgctg gtgtttatta gctacactgg   4020
caggcgcaca actccgcgcc ccgactggtg gccccacagc gcgcaccaca catggcctcg   4080
ctgctgttgg cggggtaggc ccgaaggagg catctacaaa tgcccgagcc ctttctgatc   4140
cccacccccc cgctccctgc gtcgtccgag tgacagattc tactaattga acggttatgg   4200
```

-continued

```
gtcatccttg taaccgttgg acgacataac accacgcttc agttcttcat gttttaaata   4260
catatttaac ggatggctgc agagccagct gggaaacacg cggattgaaa aataatgctc   4320
cagaaggcac gagactgggg cgaaggcgag agcgggctgg gcttctagcg gagaccgcag   4380
agggagacat atctcagaac taggggcaat aacgtgggtt tctctttgta tttgtttatt   4440
ttgtaacttt gctacttgaa gaccaattat ttactatgct aatttgtttg cttgtttttta  4500
aaaccgtact tgcacagtaa aagttcccca acaacggaag taacccgacg ttcctcacac   4560
tccctaggag actgtgtgcg tgtgtgcccg cgcgtgcgct cacagtgtca agtgctagca   4620
tccgagatct gcagaaacaa atgtctgaat tcgaaatgta tgggtgtgag aaattcagct   4680
cggggaagag attagggact gggggagaca ggtggctgcc tgtactataa ggaaccgcca   4740
acgccagcat ctgtagtcca agcagggctg ctctgtaaag gcttagcaat tttttctgta   4800
ggcttgctgc acacggtctc tggcttttcc catctgtaaa atgggtgaat gcatccgtac   4860
ctcagctacc tccgtgaggt gcttctccag ttcgggctta attcctcatc gtcaagagtt   4920
ttcaggtttc agagccagcc tgcaatcggt aaaacatgtc ccaacgcggt cgcgagtggt   4980
tccatctcgc tgtctggccc acagcgtgga gaagccttgc ccaggcctga aacttctctt   5040
tgcagttcca gaaagcaggc gactgggacg gaaggctctt tgctaacctt ttacagcgga   5100
gccctgcttg gactacagat gccagcgttg cccctgcccc aaggcgtgtg gtgatcacaa   5160
agacgacact gaaaatactt actatcatcc ggctcccctg ctaataaatg gaggggtgtt   5220
taactacagg cacgaccctg cccttgtgct agcgcggtta ccgtgcggaa ataactcgtc   5280
cctgtaccca caccatcctc aacctaaagg agagttgtga attctttcaa aacactcttc   5340
tggagtccgt cccctccctc cttgcccgcc ctctacccct caagtccctg cccccagctg   5400
ggggcgctac cggctgccgt cggagctgca gccacggcca tctcctagac gcgcgagtag   5460
agcaccaaga tagtggggac tttgtgcctg ggcatcgttt acatttgggg cgccaaatgc   5520
ccacgtgttg atgaaaccag tgagatggga acaggcggcg ggaaaccaga cagaggaaga   5580
gctagggagg agaccccagc cccggatcct gggtcgccag ggttttccgc gcgcatccca   5640
aaaggtgcgg ctgcgtgggg catcaggtta gtttgttaga ctctgcagag tctccaaacc   5700
atcccatccc ccaacctgac tctgtggtgg ccgtattttt tacagaaatt tgaccacgtt   5760
ccctttctcc cttggtccca agcgcgctca gccctccctc catccccctt gagccgccct   5820
tctcctcccc ctcgcctcct cgggtccctc ctccagtccc tccccaagaa tctcccggcc   5880
acgggcgccc attggttgtg cgcagggagg aggcgtgtgc ccggcctggc gagtttcatt   5940
gagcggaatt agcccggatg acatcagctt cccagccccc cggcgggccc agctcattgg   6000
cgaggcagcc cctccaggac acgcacattg ttccccgccc ccgcccccgc caccgctgcc   6060
gccgtcgccg ctgccaccgg gctataaaaa ccggccgagc ccctaaaggt gcggatgctt   6120
attatagatc gacgcgacac cagcgcccgg tgccaggttc tcccctgagg cttttcggag   6180
cgagctcctc aaatcgcatc cagagtaagt gtccccgccc cacagcagcc gcagcctaga   6240
tcccagggac agactctcct caactcggct gtgacccaga atgctccgat acagggggtc   6300
tggatcccta ctctgcgggc catttctcca gagcgacttt gctcttctgt cctccccaca   6360
ctcaccgctg catctccctc accaaaagcg agaagtcgga gcgacaacag ctctttctgc   6420
ccaagcccca gtcagctggt gagctccccg tggtctccag atgcagcaca tggactctgg   6480
gccccgcgcc ggctctgggt gcatgtgcgt gtgcgtgtgt ttgctgcgtg gtgtcgatgg   6540
agataaggtg gatccgtttg aggaaccaaa tcattagttc tctatctaga tctccattct   6600
```

-continued ccccaaagaa aggccctcac ttcccactcg tttattccag cccgggggct cagttttccc 6660
acacctaact gaaagcccga agcctctaga atgccacccg caccccgagg gtcaccaacg 6720
ctccctgaaa taacctgttg catgagagca gaggggagat agagagagct taattatagg 6780
tacccgcgtg cagctaaaag gagggccaga gatagtagcg agggggacga ggagccacgg 6840
gccacctgtg ccgggacccc gcgctgtggt actgcggtgc aggcgggagc agcttttctg 6900
tctctcactg actcactctc tctctctctc cctctctctc tctctcattc tctctctttt 6960
ctcctcctct cctggaagtt ttcgggtccg agggaaggag gaccctgcga aagctgcgac 7020
gactatcttc ccctggggcc atggactcgg acgccagcct ggtgtccagc cgcccgtcgt 7080
cgccagagcc cgatgacctt tttctgccgg cccggagtaa gggcagcagc ggcagcgcct 7140
tcactggggg caccgtgtcc tcgtccaccc cgagtgactg cccgccggag ctgagcgccg 7200
agctgcgcgg cgctatgggc tctgcgggcg cgcatcctgg ggacaagcta ggaggcagtg 7260
gcttcaagtc atcctcgtcc agcacctcgt cgtctacgtc gtcggcggct gcgtcgtcca 7320
ccaagaagga caagaagcaa atgacagagc cggagctgca gcagctgcgt ctcaagatca 7380
acagccgcga gcgcaagcgc atgcacgacc tcaacatcgc catggatggc ctccgcgagg 7440
tcatgccgta cgcacacggc ccttcggtgc gcaagctttc caagatcgcc acgctgctgc 7500
tggcgcgcaa ctacatcctc atgctcacca actcgctgga ggagatgaag cgactggtga 7560
gcgagatcta cgggggccac cacgctggct tccacccgtc ggcctgcggc ggcctggcgc 7620
actccgcgcc cctgcccgcc gccaccgcgc acccggcagc agcagcgcac gccgcacatc 7680
accccgcggt gcaccacccc atcctgccgc ccgccgccgc agcggctgct gccgccgctg 7740
cagccgcggc tgtgtccagc gcctctctgc ccggatccgg gctgccgtcg gtcggctcca 7800
tccgtccacc gcacggccta ctcaagtctc cgtctgctgc cgcggccgcc ccgctggggg 7860
gcgggggcgg cggcagtggg gcgagcgggg gcttccagca ctggggcggc atgccctgcc 7920
cctgcagcat gtgccaggtg ccgccgccgc accaccacgt gtcggctatg ggcgccggca 7980
gcctgccgcg cctcacctcc gacgccaagt gagccgactg gcgccggcgc gttctggcga 8040
caggggagcc aggggccgcg gggaagcgag gactggcctg cgctgggctc gggagctctg 8100
tcgcgaggag gggcgcagga ccatggactg ggggtggggc atggtgggga ttccagcatc 8160
tgcgaaccca agcaatgggg gcgcccacag agcagtgggg agtgagggga tgttctctcc 8220
gggacctgat cgagcgctgt ctggctttaa cctgagctgg tccagtagac atcgttttat 8280
gaaaaggtac cgctgtgtgc attcctcact agaactcatc cgacccccga cccccacctc 8340
cgggaaaaga ttctaaaaac ttctttccct gagagcgtgg cctgacttgc agactcggct 8400
tgggcagcac ttcggggggg gagggggtgt tatgggaggg ggacacattg gggccttgct 8460
cctcttcctc ctttcttggc gggtgggaga ctccgggtag ccgcactgca gaagcaacag 8520
cccgaccgcg ccctccaggg tcgtccctgg cccaaggcca ggggccacaa gttagttgga 8580
agccggcgtt cggtatcaga agcgctgatg gtcatatcca atctcaatat ctgggtcaat 8640
ccacaccctc ttagaactgt ggccgttcct ccctgtctct cgttgatttg ggagaatatg 8700
gttttctaat aaatctgtgg atgttccttc ttcaacagta tgagcaagtt tatagacatt 8760
cagagtagaa ccacttgtgg attggaataa cccaaaactg ccgatttcag gggcgggtgc 8820
attgtagtta ttattttaaa atagaaacta ccccaccgac tcatctttcc ttctctaagc 8880
acaaagtgat ttggttattt tggtacctga gaacgtaaca gaattaaaag gcagttgctg 8940
tggaaacagt ttgggttatt tgggggttct gttggctttt taaaattttc ttttttggat 9000
gtgtaaattt atcaatgatg aggtaagtgc gcaatgctaa gctgtttgct cacgtgactg 9060
ccagccccat cggagtctaa gccggctttc ctctattttg gtttattttt gccacgttta 9120
acacaaatgg taaactcctc cacgtgcttc ctgcgttccg tgcaagccgc ctcggcgctg 9180
cctgcgttgc aaactgggct ttgtagcgtc tgccgtgtaa caccccttcct ctgatcgcac 9240 cgcccctcgc agagagtgta tcatctgttt tatttttgta aaaacaaagt gctaaataat 9300
atttattact tgtttggttg caaaaacgga ataaatgact gagtgttgag attttaaata 9360
aaatttaaag taaagtcggg ggatttccat ccgtgtgcca ccccgaaaag ggttcagga 9420 cgcgatacct tgggaccgga tttggggatc gttcccccag tttggcacta gagacacaca 9480
tgcattatct ttcaaacatg ttccgggcaa atcctccggg tctttttcac aacttgcttg 9540
tccttatttt tattttctga cgcctaaccc ggaactgcct ttctcttcag ttgagtattg 9600
agctccttta taagcagaca tttccttccc ggagcatcgg actttgggac ttgcagggtg 9660
agggctgcgc ctttggctgg gggtctgggc tctcaggagt cctctactgc tcgattttta 9720
gatttttatt tcctttctgc tcagaggcgg tctcccgtca ccaccttccc cctgcgggtt 9780
tccttggctt cagctgcgga cctggattct gcggagccgt agcgttccca gcaaagcgct 9840
tggggagtgc ttggtgcaga atctactaac ccttccattc cttttcagcc atctccacta 9900
ccctccccca gcggccaccc ccgccttgag ctgcaaagga tcaggtgctc cgcacctctg 9960
gaggagcact ggcagcgctt tggcctctgt gctctttcct 10000

<210> SEQ ID NO 196
<211> LENGTH: 500
<212> TYPE: DNA
<213> ORGANISM: Homo sapiens

<400> SEQUENCE: 196
ccggcacggc ccgcatccgc caggattgaa gcagctggct tggacgcgcg cagttttcct 60
ttggcgacat tgcagcgtcg gtgcggccac aatccgtcca ctggttgtgg gaacggttgg 120
aggtccccca agaaggagac acgcagagct ctccagaacc gcctacatgc gcatggggcc 180
caaacagcct cccaaggagc acccaggtcc atgcacccga gcccaaaatc acagacccgc 240
tacgggcttt tgcacatcag ctccaaacac ctgagtccac gtgcacaggc tctcgcacag 300
gggactcacg cacctgagtt cgcgctcaca gatccacgca caccggtgct tgcacacgca 360
agggcctaga actgcaaagc agcggcctct ctggaccgcc tccctccggc cctcctgagc 420
cctactgagc cctgctgagt cctggaggcc ctgtgacccg gtgtccttgg accgcaagca 480
tcctggttta ccatccctac 500

<210> SEQ ID NO 197
<211> LENGTH: 1000
<212> TYPE: DNA
<213> ORGANISM: Homo sapiens

<400> SEQUENCE: 197
ggacgcggcc cgctctagag gcaagttctg ggcaagggaa accttttcgc ctggtctcca 60
atgcatttcc ccgagatccc acccaggct cctggggcca cccccacgtg catccccccgg 120 aacccccgag atgcgggagg gagcacgagg gtgtggcggc tccaaaagta ggcttttgac 180
tccaggggaa atagcagact cgggtgattt gcccctcgga aaggtccagg gaggctcctc 240
tgggtctcgg gccgcttgcc taaaacccta aaccccgcga cgggggctgc gagtcggact 300
cgggctgcgg tctcccagga gggagtcaag ttcctttatc gagtaaggaa agttggtccc 360
agccttgcat gcaccgagtt tagccgtcag aggcagcgtc gtgggagctg ctcagctagg 420
agtttcaacc gataaacccc gagtttgaag cccgacaaaa agctgatagc aatcacagct 480
tttgctcctt gactcgatgg gatcgcggga catttgggtt tccccggagc ggcgcaggct 540
gttaactgcg cagcgcggtg ccctcttgaa aagaagaaac agaccaacct ctgcccttcc 600
ttactgagga tctaaaatga atggaaagag gcaggggctc cggggaaagg gaacccctta 660
gtcggccggg cattttacgg agcctgcact ttcaaggaca gccacagcgt gtacgaagtg 720
aggaattcct ttccaccaag agcgctcatt ttagcgacaa tacagaattc cccttccttt 780
gcctaaggga gaaaggaaag gaaacattac caggttcatt cccagtgttt ccctggagta 840
atgctagaat ttacttttgt cataatgcaa aattaaaaaa aaaaaaaata caacgaagcg 900
atacgttggg cggatgctac gtgacagatt tttccaaatt ttgttgcggg gagagggagg 960
gaggagaatt gaaaacggct cacaacagga atgaaatgta 1000

<210> SEQ ID NO 198
<211> LENGTH: 100
<212> TYPE: DNA
<213> ORGANISM: Homo sapiens

<400> SEQUENCE: 198
tttttaatgc tcagagaagt tcgtattact gattcgggaa cactgagttt ttcagctcct 60
gtaaaactat tttcaggttt attttcaagt acattcttta 100

<210> SEQ ID NO 199
<211> LENGTH: 400
<212> TYPE: DNA
<213> ORGANISM: Homo sapiens

<400> SEQUENCE: 199
caccctagag gcaaggacgg ggtctgtgtc aagaggcttc ccagagaagt gaaaactctg 60
caggtgcagc cgctgggaga gcatcaagaa gggcagggtg gaggggcagg gggcgaaggg 120
agggggtgaa gcccgcaccc tacccccaca tgaaactgat tccactaccc catctctgca 180
agcgtccaga ggcagagagg ccaacatttc ggggacagct tggaggcggg agatttaggc 240
agggctcctt aaacttttat gtgcatgaaa atcaggccaa tcacggggct cttgagcaaa 300
tggggacgat gattcagcag gtctgggctg aggcctcaga ttctgcactt ctaacaagtt 360
cccaggtggt agtgatgctg ccagtccaaa gaccacactg 400

<210> SEQ ID NO 200
<211> LENGTH: 5000
<212> TYPE: DNA
<213> ORGANISM: Homo sapiens

<400> SEQUENCE: 200
tgcttcagtg gggtaaactt gaaccgctga gaagacaagc agggagtcgg tctcgctgag 60
atttttacct gtggttctag gaacgcagag gcatgtgagt gttcaggctt tgcatagacc 120
actaagccac ttctaagaac aaggctacct gagccatttt gcaaaaaatat gtacgtgccg 180 aggcttttcc tccccacacc tacctcaact ctttctgccg acacactgca cttttcaagg 240
gaacccaagt ttgggttcgg caagaattgt acgttgcaca ccgtgtgtga taattccagg 300
gaatttcaat cgcatcttgt cttccttcct aagcaaattc ggtgggaacc tggtgtggtg 360

-continued

```
tgatagaaaa agccccgagt tctctgtggt agaccacatc aatttcatgt gccagtctct    420
cagactccgg cttgcctctc tcaaggaagg gaacaatggt ttgcttggct tcactcctct    480
ctttcccccc aatttccaca tgggtatctg gctaaaaatg agttacaggt ttccttctgt    540
gagaattgca tggactgata aagtaccatc ccaggaagaa aacaaagatg ctgtcttccc    600
tttcggctca cagttgccgt tggggaggga acacacgctg taaattatag gcagccagaa    660
gtgaccgcat tgaccactgc gagtggccca gctatggcaa caggctgaga actctggggg    720
agagccattt gttggcaggg atggtgattc ttctagcatc aagctctaag atgatgacca    780
aacggtatca aaagaaatga tattttgcta cctctccggc ttgggtgaat gatgtggaca    840
gttaacctgg acaatttaaa cctttatgtt gatggatcac ttggatgaaa ttaaccagga    900
aattgccaag atttcacttg gccctctgac atcaaatctc aatattatat taccaaatta    960
gagattctaa agaaccctga gttcctttca ctgaaaggaa ggagtggaaa aacctttcca   1020
gatgatccct tttgagtctt ggtgcgagct caggccctcc ctacactgcc tccgtgaaag   1080
ctaaccgacc cttgttccta acctagcgca ggtcagctga gtgtccatcg ggcacaggag   1140
ccctgggctt gtccgggaga tagccagact cctgctattt cctgatgtct gcatagctca   1200
gcgtgtccct caccatcttt gccgttggcc agtaaggaga gccccagggg ccagcactgc   1260
acactgaaac ccaacctatt gctcaatgga atgcttaaaa atttcctgaa tctgccttcc   1320
tgagttgata aaataggaaa caatacacgt tctgaggggg tactgaaagc agagtaaagc   1380
caggaagatc ttttttttct gttattctat acaaatattg cttcctctgc ttgttagcag   1440
cccagaggaa atgcagccag ggagccgttt gcagcttttc accagtggcc ggtgtctctg   1500
tgttaccaac caaacgacgc tgcaagacta gtgactaacg cacgtctgca tgattcaact   1560
tcactaaaat tccctctgct gccagtaaag aagcacttga aaactcttta atttgaaact   1620
tgagcttggt taatgacttg ttttcttctc tttctcttta acttctctct tgccatctcc   1680
aacacacaca cacacacaca cacacacaca cacacacaca cacacacact ctctctctct   1740
ctctctctct ctctctctct ctctcatcaa gttttttaat ttcagggacc cggaaacata   1800
cagccccgtg cattcacaat agcatttgct gtgataaagt ggccggcaag ccctctgcat   1860
tcccctgctc acttagctgt atgaataaat aatgagtcac agatacaatt tgggtgctca   1920
agagagtttg tagccagaaa attaattatt ctcccatccc agcccactcc atctcagctt   1980
tgccaaacca tcaagataca ctttgcaggc actggtcaga gtgcgtgccc cgacgcacac   2040
ggcaatgcct ttgagacatt ttatgttatt atttttgttt gtttaagcac agccctcttt   2100
taccacgaaa gatacacaag acgcacatgc acacacatac tcacacactc acagctcaac   2160
cacagctttg tccatttcaa gaggctggtt tcaaaaatgg agacaggttt tccaccctgg   2220
ctgttcctat tcataagcct gtaatctaac gacttaagct gcgagaatgc ttaactcggg   2280
aaacttctct attgcccttt tccagagaga cctcggtatg ccacaatttg cttcctttct   2340
ctcttgaaag atgctggttg tctctttgca ttgaggctac aaggaaaaac acagcacagc   2400
cccatgctga tgattttaac ctaaccaagt ctgtcagtct cctgtactct ctgccttata   2460
gagacagctg ccttgccact ttggccctga agtccccagg ctggtgcaag gctatctgag   2520
agcctccgcc tcctgcccca cactggcacc agccctcctg gctggctctg tgcatgtgcc   2580
tgctaagccc cagggcaggc tgcattctgg gccacacagc atgccgagtt aaggataact   2640
cagacacagg cattccgggc aagggacagc aaaataaaac ccagggagct tcgtgcaagc   2700
ttcataatct ctaagccttt aaacaagacc agcacaactt actcgcactt gacaaagttc   2760
```

```
tcacgcaccg actgaacact ccaacagcat aactaagtat ttattaaaac atttctgaag   2820
agcttccatc tgattagtaa gtaatccaat agacttgtaa tcatatgcct cagtttgaat   2880
tcctctcaca aacaagacag ggaactggca ggcaccgagg catctctgca ccgaggtgaa   2940
acaagctgcc atttcattac aggcaaagct gagcaaaagt agatattaca agaccagcat   3000
gtactcacct ctcatgaagc actgtgggta cgaaggaaat gactcaaata tgctgtctga   3060
agccatcgct tcctcctgaa aatgcaccct cttctgaagg cgggggactc aatgatttct   3120
tttaccttcg gagcgaaaac caagacaggt cactgtttca gcctcacccc tctagcccta   3180
catctctctt tcttctcccc tctgctggat acctctggga ctccccaagc cctattaaaa   3240
aatgcacctt tgtaaaaaca aatattcaaa ttgttaaaga ttaaaaaaaa aaaaaaagcc   3300
agcgccgcct tggctgtggg ttggtgatgc tcaccacgct gcgaaaccct gtggtttgca   3360
ttcagtgtga ttcgtcctgc ctgctgacca ctatgctggg ttcagacttc tgacactgcc   3420
aggctaccca acttgtggtt ctgtggttgt ttatgaggcc caaagaagtt ttcacacaac   3480
ccaaattaca aatttaactg ttcccctttc cacagcccat ctcaattggt tcttgccaat   3540
catgtgactt aagtgatgtc aatttttttt tttcttttct gagcaatgcc cttccttccc   3600
tccacctgcc ctcccccagg ctgtgcaaga aaatagccga gtagactttg caagaggggg   3660
ggatgtagaa aaaagtgact cagtcactta ttatatctca atggtctttg ctgatttagt   3720
acaactcggc tcctgttgtt atttgtggtt tttggaacta ctgattattt tgataaagat   3780
ttcattgctg cttattcaat agtaattcaa cgctggcatc aagccgctgc tccgacagga   3840
tgtggatccc atcatttaaa atgctaggca tcagctccgg gagagttaag tccttggtaa   3900
cgtctatcat ggcataagtg aaactataaa agggaaaaat aaataaaaag aaatgttttg   3960
gtgagagtct gacccctaca acgggctggc aactcacagg tattttaaag cctgggaaag   4020
ggaaagaatt ttacttttga aataaaagga ctgttttaat gaaaccaaaa ttatgtggtt   4080
ttattccccc taaatggaca actttagtat gtatctcttt cagtaaagag ataaaatcat   4140
agtacagtct taacacacac acacacacac acacacacac acacacacac acaaattagg   4200
aagctaaagg aaaacaaagc agagagaatt tctgtatttg ggacaaagca gtggttactc   4260
tgcagatgtt tatttgtatt gtcacttggg aaagctccct gtattgcctt tctctagttc   4320
aattcaaatc aataggctaa tttacacctg taggtaaaac tacactttga gcacatgagg   4380
atgccacaat agaaggggaa ccaggaggag acacttctcc tggggctgac taatgaatat   4440
tatatagcgc gtcctctacc ttagaaagac atgcctgttt gaagatgcta aaaacaggat   4500
aattttgtaa gtgggcaaac cactgtggtc acacgtattt cattttccgg ccccactggc   4560
tttacctgct gacaactaaa acgtcatttt gttttgtagt tccaagatga agaaaggctt   4620
attttcctga tttactacct tattcatttg gctctgctct gcctacatcc gccatagcac   4680
tctgcgcacg tgaaatttcg acacataggg tcaagagaac ctgtgtgatg atgggttgta   4740
aatgccagtc ctggattcta agctgcagta gccagcacag gcacttcaga aaggctgaac   4800
tcccacaaca ctccctcggt tttccctcat ccacttaatt tcacacacac aaagacccac   4860
aacgatagta gcttccatgg cacaagtctt tcaaaaggaa cagacacaat ttttacttac   4920
tcctgttttg actaaagcag gaattgaaac tcaacagacc gctttctctt acacttgtga   4980
gaagttagct ggccacatgt                                                5000
```

<210> SEQ ID NO 201

<211> LENGTH: 500
<212> TYPE: DNA
<213> ORGANISM: Homo sapiens

<400> SEQUENCE: 201
agggaaaaga gataacgaaa gaaagaaaga aaaaaaaaag ggccggcaat ttcatgtaca 60
tttgttttgg cattcgctga attctagaga tgaaaacaat ctcctgcttt taattcagtc 120
cacgtgcaac aaagttgtac gttgggagat ctggctttta ataagaacga ttaacaagcg 180
tttttgatca caggaagttg agaagagtcg ctgcttctaa gaatacaata aacattgact 240
agcagttaga cggtccatct ttctctatca gccgtttagc agcctctact ttgatttggg 300
gcaaatgcga gatgggacca ggagagagct ccccacaccc ccaccaccac gtgggcagtg 360
gttctgttcc agagcgcctt ccttcctgtc cagggaggca ggctgctgag gccgtttctg 420
ggcaagaggc cattgtcggg atatttgctt tagatagctt gcagctgggc tgagtgggtg 480
tttcattcag actcaacaca 500

<210> SEQ ID NO 202
<211> LENGTH: 700
<212> TYPE: DNA
<213> ORGANISM: Homo sapiens

<400> SEQUENCE: 202
agcctggcgc acccgcccta atttgagtca gggaccctag gcgcctgcag ctccggttcg 60
ggttgagtgc ctcctgtcag gatgtgaagc tgctgtcccc cccgggggcc tccagcactg 120
ctgaggactc agcagtcagc ctctcctccc acttgggctc atttacagag agcatctcca 180
ggaatcagtc atggggaaag gggaaacgcg gagtgacaac acaacacgta gaaagttctc 240
tgccgccttg gtcaggcttg tcagcctcac agcccatcct gctcctgcgg gaggaaaagt 300
gagcagaact cagcccggag atgagccgca ggccggcagc ccctgcctct gccctgcttg 360
ttgtgactgc aatgcaaggc tctctgtagg tgcgggggat tcgggttaaa tgggtctcca 420
gtggtccagc gctcccagca aaggccgacc acaagaatta gcgggctagt tatttaccat 480
aaccatatac aaaaccacaa gcatcagcgt tccctcaaat acatccgaga cgctgtatat 540
ctctttatta aagcctgtca gggtttgtta ttgcacagct tggccttgaa ccccaactaa 600
accaggctgc ttgagcaaag aaccaagcaa tgcaagcatt caggcaggac cattataacc 660
ctgaggccaa aggcagaagc agggagagga gacgtcttcc 700

<210> SEQ ID NO 203
<211> LENGTH: 500
<212> TYPE: DNA
<213> ORGANISM: Homo sapiens

<400> SEQUENCE: 203
agaccagcct cggtcttcgg cctgcgggtt ctgcaaagtc aggctagctg gctctccgcc 60
tgctccgcac cccggcgagg ttccggtggg gaggggtagg gatggttcag ccccgccccg 120
ctagggcggg gcctgcgcct gcgcgctcag cggccgggcg tgtaacccac gggtgcgcgc 180
ccacgaccgc cagactcgag cagtctctgg aacacgctgc ggggctcccg ggcctgagcc 240
aggtctgttc tccacgcagg tgttccgcgc gccccgttca gccatgtcgt ccggcatcca 300
tgtagcgctg gtgactggag gcaacaaggg catcggcttg gccatcgtgc gcgacctgtg 360
ccggctgttc tcgggggacg tggtgctcac ggcgcgggac gtgacgcggg gccaggcggc 420
cgtacagcag ctgcaggcgg agggcctgag cccgcgcttc caccagctgg acatcgacga 480
tctgcagagc atccgcgccc 500

<210> SEQ ID NO 204
<211> LENGTH: 1500
<212> TYPE: DNA
<213> ORGANISM: Homo sapiens

<400> SEQUENCE: 204
aaacgtttaa aatatatttc taaacagaat gggccaattc agtcacagta actgttgatc 60
tccatagcag agcaacccac aaagacagaa ctgatttttt tcccataatc aggggtgaaa 120
aatatacaac ttgtttctga accaaaacca caatttctgc agtttaaaat gtttcactgc 180
taatatggcc ctggtagaaa ttatgtagtt tcttttcttc tttaaaaaaa aaaaaaatta 240
aaaaaatttc ctaagacact aaatgctcca tctggaatgt agattctgat cacaaagcag 300
ctcagttaac ctaaaaaata aaaaattccc atcacctgtc tcagtagggc ctgagagtag 360
tgtggggaac cccagctttg gtatggagag tcatggcccc ttgaaccaga tagagacctt 420
gaatagccat agctggtgct tctctcagga taaactctga tgtaggaagt atcaccctca 480
tgagagtgga atttggtcat ccagttgacg cagggcatat tccatgtctt cttttctgag 540
acacccaacc atccccactc catccttctg cacatccgtg taacaggcat ccccagcttc 600
tcgcgtgtga tccttcaggt cctgccagct gcctgatgga agaagtccat ttcttccata 660
aatagcatcc tctgcatctc gagggtcctc gaagcgcacg gaggcgaagg gcacaaggcc 720
gtaccggctc ttgagctcga tctcgcggat gcggctgtac ttgtagaaca ggtcctgcgg 780
ctccttctcg cgcacgtggg tcggaaggtt tccccacgta gatgcacccg tcgccctccc 840
agccgcgctc gtgtccgccc agccggacaa ccgcaccgcc cgacgctgct ggccagccgc 900
agcccgcatc cgcccgtatc gccgccgctg ccgcctcagc acggctgccc ccgcagcgtc 960
tgttttgttt tattctaaca gggtctctct ctgtcgccca ggctggagtg cagtggcgtg 1020
atcttggctc cctgcaacct ctgcctcccg ggttcaagcg attcacctgc ctcagcctcc 1080
caagtagtgg gcattatagg tgccagctaa ccatggccgg ctaatttttt tttttttttt 1140
tttttttttt tgagacagag tcttgctctg tcacccaggc tggagtgcag tggcgcgatc 1200
tcggctccct gcaacctccg cctcctgggt tcaagcgatt ctcctgcctc agcctcctga 1260
gtagctggga ttacagctat gtacagcgat gtctgcaaag atagggattt aacagcactc 1320
atatcttcat gttcataaaa aagtcctaca cgcgtgatgt acgtctagat ctttcctttt 1380
gtcacaggat atagcacggt agttacggat atagtctccg cagtgcctgg gtttgactca 1440
gcttccccac gtactgtcct gcgcatattt tgtgtctcag tttcctcatc tttaaggtag 1500

<210> SEQ ID NO 205
<211> LENGTH: 17000
<212> TYPE: DNA
<213> ORGANISM: Homo sapiens

<400> SEQUENCE: 205
cacgcgcccc ggcctggctg gaggggccaa cccagcgggg cccgcctgcc cgccggcctt 60
tctgtaactt tctctcttta aacttccaat gaatgaacgt gcctcttctt acggatttgt 120
ttagattagg gaatagattc ctcgctgata gcgttgcttt gcaaataaga cctcctatat 180
tattcaaacc aaacgagttt gtgtctttaa aggactatag cagccccatt ctatgttaag 240
ggttggctat tacaattatt atatgcttag ggaaaaaatg taagccccgt agtttgtgct 300

-continued

```
tttcttgatg tacagaaagg tttatcttag gtggataggt tttgttttgt ttcttaaatg    360
ggattttttt ggttcgtgtc tttgaagggc tgtttcgcga cgtcattaat gaactaatcg    420
gttttcagat ttcaagacgg tgtgtaattg atgtaaccac tgaggaattt cagtgcacac    480
cagactaaga ctcttccagc gcaggggatt ccagatgctt cttgggccct ctggaagcca    540
tggggatgtt tccagaccga aaggagggct ttgctgggga gcagatgtgc tgcctctccc    600
cgacccagga ttttgaggcc atgtttccgt taatctggac cgagagccct ctgggagagg    660
gaggcaggtc gtagggggcg ggggtgaggg ggagcgagat gaggtcgtcg ctggacgctg    720
ggctcccttg tcgttgtcct tttccccaga atccatggtc aggcctaggg agccacccct    780
gggtgctcga gatgagtccc caccctcact gaaggtcggt cactggatgt ttgtgtgcat    840
cgtaaggggc ccaccgaagt cccgaagcct tctcagggac cagcgagaaa gaggagcagg    900
cttgggagac agggaaggaa aatgcagggg aaagggctca cccctcgacc ccaggtaaaa    960
ttagaaggaa cgtgtggcaa cccaggtgca gctttggtcg ctcgctcaag gactttgcta   1020
gtcactacca ttaattaatt aatcactatc attaactacc aaggacaccg tttttattcc   1080
cctaaaagcg tcaccttgag gggaatggag aattgggcag cagctatgca aatcctggga   1140
caggagacac tgcctgagga ccctctctca ctcccaatcc cagaacccga agttatcccc   1200
gacaaccaag tccaagcaca tgaaccaaga cgatcagctt caggcagctc cttacccccca  1260
caagcggccc aggaggtggg cattatcccc caccccctggg atttctccat ccctccctct  1320
tctctcctgc gggagagaga gctgtggtca cccagttggg cgcgatggct ctggactaat   1380
ggggtctcta gacccagggc acaaaggcca atctgccagg ggttactgca tgtaatgaga   1440
taatcagaca tgttgaccaa cctaaaagaa aagactctcc cagggagtaa ctcccagtga   1500
aataatttat taaaaaaagc aaaaaagaga cataaatttc tctctactac ttgaggaaac   1560
agcaaacaga acgaattagg gtcttggcct ctgcaggaat aaattatttc cgacttggtc   1620
tggatacctg taattatttg taagctgtgg gtagtaatac tgtaattgtc ccccggtcct   1680
ttctggaagt agcaatgacc ccaaggacaa ttggtgacgt ctccacaggg tttacacatg   1740
gaaaggagtg aaaaatcgag gaattctttc agatagccca gaccaaaaat cctctcagcc   1800
atgaaaaggt catatatgtg atgctgggcc aagcggactt ttctggagta accatatcat   1860
aactgattgc ggatgtagac aagagcgtat aaaccaaata ggcttgaatc aacgcagtcc   1920
tggattttct gttgcctctg cttgctgggg cagtggaagt tcttaaactc cacttcagag   1980
gttggaaatt cttcccctc ccccacctcc ttagtgacaa ggtctctgat ctcctgctgc    2040
cactgcaata gcctctccca tcccgcgggg aacggccgga gttcttccct tgatctctcc   2100
cgagtcggct tccgctgggg atggatcgca ggtaggcgcc ggcgcggcct ggggaagaac   2160
agttgcggag catctgaagc ggaaaatcca agcagatgtg aggcgatccg ggcccgcctc   2220
gttcctcttg gggcctgaat ttcttccaga taagtttcct aatggaacat ttctaagagg   2280
tggggtacga ggcggcttgc tcgcacgcgc agtgggacag actgcgggtg gggacgtact   2340
gagaggtccg gacctcaatg cgtccgaccc gtctccacac cgccctttc cagcccccag    2400
tctcctttca ttccctactc ttcaggctcc tttggggcca gtgggtgaac cgccatttag   2460
aacggtgcct cggactcggg ggtcgtgcgc tccatctctg cctcccccct ggggcccgcg   2520
aggctggtcc gggctttctg agctgggcgt tcggctttag gcccaatacc tggaccagga   2580
atttcttctc cccgcgccag aagggaaaga cataggaggt gtcccaatct gcggtcaccg   2640
ccgatgctcc tgaccactct agtgagcacc tgcccggtac ttttccattc caacagagct   2700
```

```
tccagcttca tactaactat cccacatacg gcctgtgggt attagctcta agtgtccttt   2760
tccgagggcc cgaggctccc cctccagcag ggagagctcc gggacggccc ccaccaaggg   2820
ttgggtttct tccttcacaa ttccacagag gcatccctgt ccttcctacc tgggaaacct   2880
cgaggtgcgg tgcccgtgta cttctggtac tttgcgtggt gccatcaggg accccagagc   2940
cacagctgcg tgtgtgtgtg gatgtgtgtg tgtgtgtgcg cgcgcgcgcg tgtacggcga   3000
aaggatgtgc ttgggggagc cgagtacaca acgtctgctt gggcagctgc tgggcaggcg   3060
ttgggcctgg aggtatctca cacccacgta tcttccagtc ttcaaacacg gcattgctct   3120
gcctcccgta gcgcgcttcg aacctgcctc gcggacacgt gaacagaggc tgtccctggg   3180
aagataagtg cgctttcccg taaaatccgg gaaatttgcc ttgaggaaag tttccgttct   3240
tgttacttgt cgggtttctc ccacttccac ttagccatgt ttctgcgatc tgggtaatcc   3300
ctttcaagcc caggaggaat tctcccgggt ccataattga gggtcggaag ccgtgggggt   3360
gagaaacgca ttaaatcctc ccgaagccca ggaggtgcca gagcgggctc agggggccgc   3420
ctgcggaagc tgcggcaggg gctgggtccg tagcctctaa ccccttggag ctccttctcc   3480
cagaggcccg gagccggcag ctgtcagcgc agccaggagc gggatcctgg gcgcggaggt   3540
gggtccgact cgccaggctt gggcattgga gacccgcgcc gctagcccat ggccctctgc   3600
tcaagccgct gcaacaggaa agcgctcctg gatccgaaac cccaaaggaa agcgctgtta   3660
ctctgtgcgt ccggctcgcg tggcgtcgcg gtttcggagc accaagcctg cgagccctgg   3720
ccacgatgtg gactccgcaa ggggctaggg acaggcaggg ggagagcccg ggtttgcgca   3780
caccttccag cccctggagg gagcctgctc ggcttcgaac gccttcgaac ttttgacctt   3840
caaaggagtc cctggaaaag gtcaggagcg cctgctgcag gcacggttgc cgaaggccag   3900
gccttcctgg cgcaggggag ggccagggga gggaagcgga tactcagtcg ctgtccgacg   3960
gcgagttttc ggagcagcag gctcatgatc ccgggccagt ggcgagagca gtgacaccga   4020
gaacccaaat ctccgcgccc ccatccgcgg cccggtgtcc tcccggcccc tgctgacctc   4080
caggtcacgc accccactgc tccacggctc tgcagcctgt ggcacacggc cgagagtccc   4140
cacatgatct cgacgccaag gtaaggaatt gccctgcgtc ctctgagcct gtctctggcc   4200
tggggggccg ggaaagctgc actcctggaa gaggtggggt tatgtgaccg ccgctgcagg   4260
ggtgcgcgga ggactcctgg gccgcacacc catttccagg ctgcgggagc cggacagggg   4320
agggcagagg ggggacaaaa ggactcttta ggtccaaaat gaccctgaag gagagtccag   4380
aatgcccagt ggccgcgtct gcaacggagt cttctttctc caattgcctt ctgccccatc   4440
accatgggcc ccacctgcgc cacctgcgcc caccctgtga ccctggctca gcgaccttgg   4500
cccttaatcg cccaacgccg attcctcaaa attccggctg cgctgaatcg ggctgctttt   4560
gccgccgccc cggcagttgg gccctgtttc cgccggcgcc ctgggagagg cctcaccact   4620
cggctgggct ccctggcccc tcccttcccc tggcctgagc gcccctgcgg cctcccgctc   4680
ctcctgagaa ggcgacaatc tctttgcacc ttagtgtttc gaggacagaa agggcagaag   4740
ggtcacttcg gagccactcg cgccgttttc acgtgtgtgt gtaatggggg gagggggggct  4800
cccggctttc cccttttcag ctcttggacc tgcaacaccg ggagggcgag gacgcgggac   4860
cagcgcaccc tcggaaggct cgatcctccc cggcagggcg cctggccaac gagtcgcgcc   4920
gcctcctctc ggccgcgcct gctggtgacc ttcccgagag ccacaggggc ggcctcggca   4980
cccctccttc cctcgccctc cctgccgccc atcctagctc cggggtccgg cgaccggcgc   5040
```

-continued

```
tcaggagcgg gtccccgcgg cgcgccgtgt gcactcaccg cgacttcccc gaacccggga   5100
gcgcgcgggt ctctcccggg agagtccctg gaggcagcga cgcggaggcg cgcctgtgac   5160
tccagggccg cggcggggtc ggaggcaaga ttcgccgccc ccgccccccgc cgcggtccct   5220
ccccccctccc gctccccct ccgggaccca ggcggccagt gctccgcccg aaggcgggtc   5280
tgccataaac aaacgcggct cggccgcacg tggacagcgg aggtgctgcg cctagccaca   5340
catcgcgggc tccggcgctg cgtctccagg cacagggagc cgccaggaag ggcaggagag   5400
cgcgcccggg ccagggcccg gccccagccg cctgcgactc gctcccctcc gctgggctcc   5460
cgctccatgg ctccgcggcc accgccgccc ctgtcgccct ccggtccgga ggggccttgc   5520
cgcagccggt tcgagcactc gacgaaggag taagcagcgc ctccgcctcc gcgccggccg   5580
cccccacccc ccaggaaggc cgaggcagga gaggcaggag ggaggaaaca ggagcgagca   5640
ggaacggggc tccggttgct gcaggacggt ccagcccgga ggaggctgcg ctccgggcag   5700
cggcgggcgg cgccgccggg ttgctcggag ctcaggcccg gcggctgcgg ggaggcgtct   5760
cggaaccccg ggaggccccc cgcacctgcc cgcggcccac tccgcggact cacctggctc   5820
ccggctcccc cttccccatc cccgccgccg cagcccgagc ggggctccgc gggcctggag   5880
cacggccggg tctaatatgc ccggagccga ggcgcgatga aggagaagtc caagaatgcg   5940
gccaagacca ggagggagaa ggaaaatggc gagttttacg agcttgccaa gctgctcccg   6000
ctgccgtcgg ccatcacttc gcagctggac aaagcgtcca tcatccgcct caccacgagc   6060
tacctgaaga tgcgcgccgt cttccccgaa ggtgaggcct caggtgggcg gccggggacg   6120
ctggggagcc cggcggcccc ggcccaggcg ggaagcgcaa gccagcccgc ccagaggggt   6180
tgccgcggcc tggcgtccag agctggggcg tctgagggag gttgcgtgag ggtcttcggc   6240
ttcggcgctg gcttggggcg aggggccagg gccttggcgg cccaggcgac caaaccctct   6300
cctggtccag ggctgggtga gggcgaatta cgaattgttc caggggcagg cagtccccca   6360
gcccgcacgg ccagcgagtt ctttctggtt ttgttctttc tccctttcct ccttccttcc   6420
ttcgccagtg cattctggtt tggtttggat ttttttctct ctttctttcc tttctttctt   6480
tctttctctt tctttttctt tctttcttcc tctttctttc attctcccct tccttccttc   6540
cttggccccc tctctccctc cctccttcct tccttccttt gccaatgcat tggtttgttt   6600
tctttccttt tctgctttcc ttcctttctt tggaagttca ctctggtttt gctttctttc   6660
tttccccatc ccttcctttc tttatccctc cttcccttcc tccttttctt tctacgattc   6720
cctttatttt tccttcattc ctccctcttt ttgtctcttc tggaggaggt gaaggagggt   6780
cagcttcagg cgctgcgagt cagcggggat cacggtgagg cccaagcact gcaggctgag   6840
gccacagagc gaacacttgt gctgagccgg gccctctcgt gaggctgggg tgcgggaagt   6900
ccgggcagga gagacccgcc cccgccgttg ctgagctgag acccggctga aagagagggg   6960
tccgattaat tcgaaaatgg cagacagagc tgagcgctgc cgttcttttc aggattgaaa   7020
atgtgccagt gggccagggg cgctgggacc cgcggtgcgg aagactcgga acaggaagaa   7080
atagtggcgc gctgggtggg ctgccccgcc gcccacgccg gttgccgctg gtgacagtgg   7140
ctgcccggcc aggcacctcc gagcagcagg tctgagcgtt tttggcgtcc caagcgttcc   7200
gggccgcgtc ttccagagcc tctgctccca gcggggtcgc tgcggcctgg cccgaaggat   7260
ttgactcttt gctgggaggc gcgctgctca gggttctggt gggtcctctg ggcccaggag   7320
ctgggagggc tgcgccggcc tctggagccc cgggagccag tgccgaggta gggagacaac   7380
ttccgccgca gggcgccgga cggtcggggc agagcaggcg acaggtgtcc ctaggccgca   7440
```

-continued gggcgcttcc atagcgccat ccccaccagg cactctactc gaaatcggaa agctcgacct 7500
tttgcgttcg cctctgccaa gcctgttatt tgtgctggcc gctgggtctg gagctgcgct 7560
tctcggcccc tccccggtgg agcgcagagg gctggtctgc aagcgcggcc tccagccccg 7620
cggctccccg gcccaggagc caggcgcggg ctgacccggg agcacccggc agcggagggg 7680
gctggaagcg gaccctaggc ctctcctgtg ccacccggcc ctaccgcgcg gccgcggggc 7740
gctctcctct cgggcgcagc ggtccttcag cccagggcag gttcctccct ttcctactcg 7800
gaacgtggca aagataccc agtcccagcc cctccagctg agagctgttg cccaaggtcg 7860
tcgctacttg tccgctcaat ggtgacccct tggcagagaa ctagggatga ttccactccg 7920
gttgatgttt taggggaaat taaaagaaca ttcggttttc tgagtctcct tccggggagg 7980
cgtggtggta actggtttgc tgggaagagc cgttccttaa ccgcatgcaa caaagcaggt 8040
gtggaatccg gacgagaggg cactcactgc cttctgcccc ctttggaaat agaaaaagcc 8100
ttcgaagcag caatccaaag atcaaatgat ttgcggtcaa tgatttcaat taaaccagaa 8160
attagtaagg gagggccgag aagacacggc tgctcagaag ctgttcgctg tttgagggat 8220
ttcccggaga gcctgttaaa agatgcgaag tggtgggtgt accgctcagc cacctttaaa 8280
ccggctctgt gcgttctggc tctggaaagc aagtctccag gcatttgggc tcagaattgc 8340
tgggccccga gtttgggcgg gggtggtcct tctgggggtc aggccttgag cagcttgcac 8400
tggtggcagg tttgggagca gttgagggc ttcctgtgtg tcttttggag gggtgaccc 8460
tggaagttgg cactctggaa gggagctgtt tggccctaga gttttggaaa gggccctgaa 8520
cctgttcggt cccccctcgga aagggaaggg agcagtggct tagtccctcc ctcctccatt 8580
cgtgcaatgc ctggggtagg ggtagacctg gagccggtgg actcatatcc ttggaattcg 8640
tcaggacagc tgctccgggg ccttggccct cagtcagtct ggggctgagg agtagggaag 8700
ctgggaactt ggggcagagg aagaagatgc gtttagaaag acctccatta tgcaaactgg 8760
agtccattta tgcaaactgg tcacccttcc agtagctcca aagagtggca gtggagtggc 8820
atcttgattg atttaacctc ttctcagggg acctgggtct gcgagggagg atatggctgc 8880
ggggttggaa taggatctgt ctgagctgcc agggtcaggg tggtggccct agggaggttt 8940
tagggccagg gtggtcccgg gctgtggcag gggctctcag atcgcctcgg gctctcagct 9000
gcaaggtgaa aaataccatg aggaattgat ctgccaaggg cggtcttgtc tcaaagcaag 9060
tggattgctg gggtaaagaa tctagagacc agcttaggac tctgggagga agaaaaaaaa 9120
aaaaagaata gcatagtcct aaggaactgc aaggatcacc agattaaccc ttcatacctg 9180
gggaaattaa ggccagacat gacacaggcc tttcccaagg ctctgtagca agggcaatag 9240
caggccagtt gctgccactg cggtcctgtg gggcatgttc tcactccact gcacccagga 9300
ggctgccagc ctctgttcct tttaacatag atctcctcag ttgttaagac agaaagagga 9360
actcagaggg gtccctgtgt gcaaggcaga gggagaccac cagaaccagg gtaagcaccc 9420
cacttggtag ccagttcaag gacttgggga tgttttcaac atttacagcg aggtttgagg 9480
ccccattgtc atgcagcgct actcggcctt ggtctcctta tctgtaaaat gggcccatta 9540
gcaatgcaca gggttgctgt gatgaagggt gaggtcccac aagcaaaagc tgtgcagtga 9600
ggggggaatc ctaagcattg ttcctatgcc attcacccct tcctgtgagc tccccatatt 9660
ccctggctca aaggagtctt gaatggcagg gatggaggac tcactgcctg gactttgaag 9720
acccctgctt tctgggtgac cacctttctt tccctttgac agtgaactaa tacattggag 9780

-continued

```
gtagatagtg ctgggaagag gacaggagac cacggctgac tttggacatg ggctcgaaat   9840
tgataacttg atgagtcttg gagggtggtt aagataagct cggggctggg gcagcgctga   9900
ggtctgatgg tcagccagcc ctccccaaag tgtggccctc cgttctggag ataggggctt   9960
tggaaactgc aaaagcgtcc tggcaggcca gctctggttg ctccctggcc atagctgctc  10020
tgactacagg cagcaggacg caggtcggcc tctgcccatc ggaggtcaga ggcagggcct  10080
ccagcaccag actcagcagt gccactgcaa acctggcaca acaggctggt cccaggactc  10140
agctcagcag tgaagttgga aaccaaggtt gagtctcccc atctcccttt ccccaacccg  10200
aaagacccaa gatgggtgtg ggtgaaagag ggagaaagaa ttgctactcc agaaactgtc  10260
atttgcccac acgaaacgag gtggggttca aggtctgaac tcttccagtg cctgggtgcc  10320
tttgggttta aattcagctg caggtgcccc catcaccact tccacctgag cacaccacga  10380
gaagccaggt tatcttagaa actgtttccc ggaatcaaag cgacttgatt tggagagttg  10440
ggtgaggaga aactcacccc tataccccctc agggcgtcag agatgtgagg caattctcta  10500
cctccgctgg aaaaaatgca gatttattaa aggtcgactg tttagcagaa caacgtagat  10560
tttttacaac gctttccccg tctctgcttt gaagcctgcc aggctgcagc tggggatcca  10620
ggagggaaag cccgcaggcg cagaggggac aatccgggaa gtggtaaagg ggacacccgg  10680
gcacagggcc tgtgctttcg ttgcaggcga ggaagtggag cgcgcgctgc agattcagcg  10740
cggggctaga ggaggggacc tggatccctg aaccccgggg cggaaaggga gcctccgggc  10800
ggctgtgggt gccgcgctcc tcggagccag cagctgctgg ggcggcgtcc gaactcccca  10860
ggtctgcgca cggcaatggg ggcaccgggc cttctgtctg tcctcagaat acgtaggata  10920
cccgcgggcg acaagccggg ccaggctagg agcctccttc cctgcccctc cccatcggcc  10980
gcgggaggct ttcttggggc gtccccacga ccacccccctt ctcacccggt ccccagtttg  11040
gaaaaaggcg caagaagcgg gcttttcagg gaccccgggg agaacacgag ggctccgacg  11100
cgggagaagg attgaagcgt gcagaggcgc cccaaattgc gacaatttac tgggatcctt  11160
ttgtggggaa aggaggctta gaggctcaag ctataggctg tcctagagca actaggcgag  11220
aacctggccc caaactccct ccttacgccc tggcacaggt tcccggcgac tggtgttccc  11280
aagggagccc cctgagccta ccgcccttgc agggggtcgt gctgcggctt ctgggtcata  11340
aacgccgagg tcgggggtgg cggagctgta gaggctgccc gcgcagaaag ctccaggatc  11400
ccaatatgtg cttgcgtgga gcagggagcg gaagaggcag ccggtcctca ccctcctctc  11460
ccgccacgca catatccttc ttgacttcga agtggtttgc aatccgaaag tgagaccttg  11520
agtcctcaga tggccggcaa cgcgccgagg tcacgctccc cagaaacacc cctctcccct  11580
cccctacccc agctccccct ggggcgggtg gtaattgggg gaggagaggc cgcaggcagg  11640
gaaggggtgg gaaagccaga gagggaggca caaagtgatg gcagcccggc aaacactggg  11700
gcttcgggct gggccgcgct cgtttaatcc cacaaaaatc ccattttgga ggtgagaaat  11760
agaggttaga ggtcgggccc ttctggagat cagaccgagg agacgggccc agctggcgtc  11820
ttaaagcaag gagggggagt cgggaggagg tgagacccct gcacccaggt ggggctccca  11880
aaccgttctg gatttaccac actcccaggt ccgattttcc atggagggct ggggttaggg  11940
actggcacct tcttgttgtt aaccgcattt gatattcaca agaaccctgt gaggagactt  12000
tgtcaccgtt tttagatgcc tgaggttgcc ggaggggcag tgagagaatc gtctaacctg  12060
gtgttcctac cacagtccag gccctgtgtc ctgggctgga cccacagccc ctgccaccac  12120
ccagaggaag gcgcgaagct ggctgcctcc tttacgggtc tcccttaggt gccctcatga  12180
```

agggggacgg ccacctcaca gtgcaggaac tatctccccg tttgctccca aatagtcttc 12240
ttggtgtggt gctgtctatg gtctgtgacc tgcatctgga gttaccccca ggaccagctt 12300
cggaagagga gggatcgctt ggaggccgtg cagtgtgagg aacggcaggc agggtgtggg 12360
accaacatgc acacactcgc aggtgctggg gccagggagg aatgaggcgc tggctccctt 12420
tccctccatt tctccctggg ggtcccagca acctggccat ccctgacttc caacagcaca 12480
gcgtccccac aggtcctgca gtgctctgca ggggtgcagg gagctcccct ccccccagcc 12540
gcaacctcac cttcctcacc cccacccctc cggcaggaaa ccacaggctg ggttggggac 12600
ccctggtgct ccaagagagc agtgagtgct gggagccgct aaccccgagg cgcctagcac 12660
agactcttct caccccttat ttctgaaata aagcccttcc ttaggtccag atgaggacca 12720
cgtgctcagt gcctcacttt cgtgggagtg tatatcactt tacagtatca agacaatttt 12780
ctttcgttac aaatctttat ttagtctctg cgtttagacc aaagtagatt tttatgggct 12840
gagtgaaaaa acctcgcccg cattggtttc tgatggaaca gctggcagcg ccacggcccc 12900
gggtggggtg gcctagaggc aggggtgctt gggaggaaca tctagcaccc gaccacctcc 12960
accaggtggg aaagggacgt ttgcaccaaa tctccgccgg caaagcagag gctttgggga 13020
attacagaaa aactataatg atctaaaaga gaacaagtta tcttgaactg tgcgggtatt 13080
tgaatcatac agaaaattgt cctgtgtgcc caatgcactt ttgcatgtag agccagggcc 13140
ttcgaggaag ctttcaggag atcccgggca gcggagtctg gtctggagtt tcatttccgt 13200
aggtgcagat ttctccccaa gtcttcccgc catgggcttt gcaagaagcc agggcccaga 13260
ggccacgctc accgttaaca ctgcacaggg caaaggtggc tccaggacaa ctgcccaacc 13320
ccaggaacga cccagcagca gagaaaagga cagctgccag ggtgcctttg tcgctttttg 13380
gaaatcagaa ttcctgggtc cttagttaag tcttacttca ccaaatccca ggaccttcac 13440
attttggttc ttgccattgc taacagttgt aaatgctgcc gccacgaggc ctgggaggaa 13500
ggacccgctg gtgagagcac agggagtgct gctgtgatca cggtggtgat gcggggtgag 13560
cgcgatttcc cgggattaaa aagccaccgc tgcccccgtg gtggaggctg ggggcccccg 13620
aataatgagc tgtgattgta ttcccgggat cgtgtatgtg gaaattagcc acctcctcag 13680
ccaggataag cccctaattc cttgagccca ggaggagaaa ttaaaggtca tccctttttta 13740
aattgaggaa tagtggtttt ttttaacttt ttttttttta ggtttttagt tgccgaatag 13800
ggaagggttt gcgaagccgc tgccctgggc cgaggtgcat tttacgcttc cagaggtcga 13860
ggcctccaga gaccgcgatg cccagggcgt tcccggggag gctgagagac ccagggtgct 13920
ctgggtgact gcacggcgac tcctcgggaa cccactcgtg gctgcccgct tggaagggct 13980
ttgcggcccc gggaacgatc tccaggatct ccacggctgg tcaggttccc cgtccctcgt 14040
atcccgcgct gcccgggggc tcctgccttt ggttcagtgc tcgcggcacc accgcactca 14100
ggacggcagt ggggggctgg ggctggggct gggcctggcc cagcgtgggt tggggcgggg 14160
gacgcgccag cagcgcccgc agctcgctcc gcaggggtcg cagccagggg tcgggagcta 14220
ggctcgtggg ccgggagacg ccgggcgcgt tgtcctccgg ggaggttggg gtgcaggcgg 14280
tgcaccgacc ctcgccatct ggcgctgcag ccaccagcca cggcgcttag tggagggtct 14340
gcggccaggc tcccggcgga aagattccgg ggagggctcg ggggttgtcc cagcccgcgc 14400
taagcgccgc agcctcgccc ggctttcctg cttcctcgga ctgtgcaggg gaagcctggg 14460
gtctcgcggg gcgcagcagt caggtcgagg gtgcagcagg aggggagtcc tgacgggcag 14520

-continued

```
gtccctcttt cccctggtgc gcaacactgg ttggtagctt ttgcggaggt ggtgaagaag  14580
ggcaggaggc ctgttgagcg gaggagtccg gggatcccta attatgtgac aggagaccct  14640
ttccagttcg gcctgtggcc catccctctc tcaccgccgg cagattggag tctgctctcg  14700
gggagccccc aggtaaaccc ctcacaggga gaaggtttcg gattggaagg aggaccgcgc  14760
tcgtggggcg cctgtgagag ctgggaagcc caaggggtag cgtgtagggg gttttttatg  14820
cgggaggagc tgcctcctgg gcggcgggga ctttctgtct cagcctgtct gcctttggga  14880
aaacaaggag ttgccggaga agcagggaaa gaaaggaggg agggaaggag ggtccttggg  14940
ggaatatttg cgggtcaaat cgatatcccc gtttggccac gagaatggcg atttcaaagc  15000
agattagatt actttgtggc atttcaaata aaacggcaat ttcagggcca tgagcacgtg  15060
ggcgacccgc gggagctgtg ggcctggcag gctcgcacag gcgcccgggc tgccggccgc  15120
tgcggggatt tctcccccag ccttttcttt ttaacagagg gcaaaggggc gacggcgaga  15180
gcacagatgg cggctgcgga gccggggagg cggcggggag acgcgcggga ctcgtgggga  15240
gggctggcag ggtgcagggg ttccgcgtga cctgcccggc tcccaggcat cgggctgggc  15300
gctgcagttt accgatttgc tttcgtccct cgtccaggtt taggagacgc gtggggacag  15360
ccgagccgcg ccgggcccct ggacggcgtc gccaaggagc tgggatcgca cttgctgcag  15420
gtagagcggc ctcgccgggg gaggagcgca gccgccgcag gctcccttcc caccccgcca  15480
ccccagcctc caggcgtccc ttccccagga gcgccaggca gatccagagg ctgccggggg  15540
ctggggatgg ggtggtcccc actgcggagg gatggacgct tagcatgtcg gatgcggcct  15600
gcggccaacc ctaccctaac cctacgtctg cccccacacc ccgccgaagg ccccaggact  15660
ccccaggcca cctgagacct acgccagggg cgcctcccga gcgtggtcaa gtgctttcca  15720
atctcacttc cctcagcagg ttccacccag cgcttgctct gtgccaggcg ccagggctgg  15780
agcagcagaa atgattgggc tgctctgagc tctgaagcat tcggccgctg tgtgtgtgca  15840
aggggcgcaa ggacggagag acagcatcaa taatacaata ttaacaggag cacttgtcca  15900
gagcttactg caagccacat tcagttccgg accttattga cttccccctc ccatctagag  15960
tggattctgg tttttcaatt tgttttgttt tgtttttttgt ttgtttgttt gtttttgaga  16020
cggagtctca ctctgtggcc caggctagag tgcaatggcg cgatctcggc tcactccaac  16080
ctccgcctcc cgggttcaag cgattctccc gcttcagcct cccgagtagc caggattgca  16140
ggcacccgcc atcatgcctg gctaattttt gtagagacag ggtttcaccc aggctggtct  16200
cgatctcctg acctccgatg atccgcccac ctcagccttc caaagtgttg ggattacagg  16260
cgtgagccaa cgcgtcctgc cttgattctg tttttaactc cattttttag aggaggaaat  16320
tgaggcacag agaggttaaa taacatgtct aaggtcacac agcaaggggt ggagcggagt  16380
tagcccactg gcctagctct agagcccacc cggataacca gaacttggtg aggcctccgg  16440
gctcttgctt ggtttggagc caggtgctta gcgccccgag cccggggcca ttcaccctgc  16500
aggagctgca cgcgcccctg acctcggctt ttccctggca gcagaggggc tttgcgggtc  16560
ggccgggtag ccctgagcac agctcgccac ttccaggtgg gctgttggcg ctggctgggg  16620
acacatcccg atctttcaaa tgccctttac agagcctcat caacgacccg attcattccc  16680
ccctcctgtc atttgtctct gccatcgaaa aatgcctacc gagagctgct ctgcatttcc  16740
gccctctatt ttgtgtttta ctttaaaata ataataaaaa aaatgttggc tgcaggacgc  16800
catgacttag gtcagcgagt cagccgctag ctctgcattt ccaaaaagca gatcttttca  16860
caactctctt gccccaagtg ccctggtgtg gtttattttt taaaatgcat gcctgcggaa  16920
```

gagaagaccc ggggaatatt cgaaaccccg agcttttaca acataaagcg catggtgtgg 16980
ccgcggcgag taatggcgct 17000

<210> SEQ ID NO 206
<211> LENGTH: 1500
<212> TYPE: DNA
<213> ORGANISM: Homo sapiens

<400> SEQUENCE: 206
caaatcactt gaactcaagt tcaagaccag cctgggcaac atggtgaaac cacatctcta 60
caaaagtaaa gaaaattagc caggcatggt gctgtgtgcc tgtagttcca gctactcctg 120
gggaggtcga ggctgcagtg agccgcaatc acgccacttg tactccagcc tgggcgacag 180
agcaagtccc catctcaaaa aaaaaaaaaa aaaaaaaaaa aaaaggctgg gtgtggtggt 240
cccagatact cagaggctga aaagggagga ttgcttgagc ccaggagttc aaggctgcag 300
tgagctgcga tcacatcaat gcactccatc cagcctgagc aatggagtga gaccctgact 360
atatttaaaa aaaaaaaaaa taggaagaaa caactcaacc acagggctag tatgttactc 420
ggttataaaa tgataaagcc ctaaacagag aattagcccg tttccagaag aggccaagaa 480
cagatgatac agctgaactg aactcctgcc tgtacagctc gttttctaca agattccaga 540
cctggaagat gatggcatcc agccccccatt gaagcacctc gaacaagaaa aacgccgagt 600
ccgaagagcc aggccttgaa cacacgattc ctgtctataa ataactcccc ctggggaata 660
aaaagcagga tccaaggcag gaaacccgag ccgtggaatc tggtaagttc ttaggaaacc 720
cactcacggg cctgagtccc ccgtggaagc ggcgacttcg gcacctggac acccgagtcc 780
ccagagcccc gggcggccgc gcgtccctac ctgcaggcct gataccggcc gcggagcgct 840
cctggccccg ctcccgccag gctccgggac cgctgaaacg cacccagggg ggtgaaggcg 900
tagtcgccaa ggacagcgca gatggcagcg gaggcatggg agccggaacc taccgtggca 960
aagggccagg tcgggacgcc cctcggcgca gccccaaatc ctgcccgcgc cccagccccg 1020
ctcaggccgc gcccctgcca cctctggcca cacgggctga gacgtctggc tcctgcacag 1080
cgcacttccc gctgcccttc tccactggct gctcaggccc tgcctcgcca gcacggcatc 1140
cgcgggggat ccctacctgt cctttagggc ttgcctcata ggtcaaacgt cacctcccag 1200
ggaggtatgg cctgcccccct ggccaggtgg gcccccttcca cgctcgcctg caacaccacc 1260
cacccacctt gataactgct tgtaaaggtt gtactgcttt ccccccttgag actgcaaacc 1320 ttcaagggca ggaaatgggt ctgttttcct ggcaaaataa tgaagttggc ttaaggtttt 1380
gctgaataaa atgagtgaca gacaaaagta gccaaatttg gcactcctga tgggttattt 1440
gatgaaggag gtgcaatgta tgggcttaac tagttattct ggatttcttt ccccatgtta 1500

<210> SEQ ID NO 207
<211> LENGTH: 200
<212> TYPE: DNA
<213> ORGANISM: Homo sapiens

<400> SEQUENCE: 207
caaggccggt gcacgcggac ccgaggattc ggtagatgtc cccgaagacc cgctgccgct 60
ctaaggcggt ggaagcgaga ttctccggaa acccagggaa tccgatgctc gcacaggacc 120
aaagcccgag gccgcgggga ccacagaggg acggagaagc cgggactcct cacatcccac 180
atccggcagg ggaagcccag 200

<210> SEQ ID NO 208
<211> LENGTH: 2000
<212> TYPE: DNA
<213> ORGANISM: Homo sapiens

<400> SEQUENCE: 208
ctgataataa agttttacca ttttataatt taaaaatgta aatatggagt tgggcatggt 60
ggttgggagg ctgagaccag aagatcgctt gagcccaggg gtttgagacc agcctgggca 120
acatgcagaa accctgtctc tacaaataaa aaattagcca agcgtggtag cacgcacctg 180
taatcccagc tactcgggag gctgaggcag gagaatcgct tgagcctggg aggtggaggc 240
tgcagtgagc tgagactgta ccactgcact ccagcctggg tgacagagtg aggctctgtc 300
tcaaaaaaac aaaacacaaa aaaacaaaca aaaaaaagca aatatatgta aaaataggaa 360
gtgcggtttc ccaaaatgag gtctgtaaac aactgatcta gaaaatgttc tggaaaaagt 420
aaaaaaggat caggatctga ggtcaactga cctctccctg cgctctggac aggcaaacag 480
gcaaggttcc ctctgaggcc gtagcggctt ctcgtgggcg agtccctgtt cgcaggtgac 540
gtgtggacca cgctcttccg aagcgtctgg cctgtgtgct ctcggggagg ggacgcaggt 600
cagcccacct agccgatggc taacaagtca gtttgttttc tgaacggaag cttaaaccta 660
gaaaagtaac tgggttgggg tgggggtgta gccacatgca gtaaaagcac tgcctgtctg 720
tataacaacg acctgatgaa aaaaggaacg cgtgaaatgg ggagtgttag ggcgtcacaa 780
actccagtgt ggttgaaatg aaagcagaaa gcaaatggca agctggcttc cccttccagc 840
ttttcacaac cctgccttgc tcatggtcag ccccaagcac gggcggaaga aaggactgga 900
ggggagggaa aggggtgggg agcgagggta ccagaggcgt gggaggacgg ggacaaaggg 960
gcagcaaggg accggcggaa aggaaagtcg gcgttagctg gattggaaac agtccagaca 1020
gaacgatggg ctctgctgcc tccgggtggg gcaccaagcg gggagcgggg ccacgaggca 1080
ggggacagtg aagcaccatg cagcgcccac cagccggcag cgcccaccag cctgcgctgc 1140
gctgcacatg gtacccgcgg ccccagctgg ccagtgtgtg gcggagatga gaccctcgtg 1200
aagagactaa gcggccacag caggggga ag ggttgctcac ataaccccat actgctcaca 1260
ctacgaggtt aactgccgtg agatctgcct gcagccagca gaaacccgtt ctaggaaaac 1320
gttgcccagt gacttcagtg agtgccactg acccgggcgc ctccgccccg gcgtccggca 1380
gcagcaccga ttgcgcagga ggcaccttgc aaacaacctt tcctgatccg cgctgcagtt 1440
cccaggccgg ttgcagccgt ttcacagaga ctgcgcacac aaagcgtctc cgtgccctgc 1500
cattcacctt tcgacacagc cgcaacccct cttttcagtg ttaaaacctg gcgccaaaag 1560
gaacatgcga tgtgacgtgt tacctctgcg catgcgccgg gcattcccag cgccccgaac 1620
ctgatgaacg cgcggtgggg accccaggct tccgtgcttt cgttttcctg gaagctacgt 1680
gtcctcagtc tacatattgt tacctggaaa ataaagtttt ctcctttttt cttcctttgt 1740
taacaggcag aaggtgtagg ctgcaggttt cgggcctaag agagggcatg gctggcgaca 1800
cggagtagac tcctagatga cataacggag gcgagtctgc accggggact cggcattagg 1860
aggaggcaga ggaaaagccc accaccgtgg ccgagggaga tctagcaagc agcttgcagg 1920
gggtgaagtg tgtgcaaagc aggctgagac ctgtccagta tcgaaacacg ccgcggtggt 1980
caagcaggct ttaccatgct 2000

<210> SEQ ID NO 209
<211> LENGTH: 700

<212> TYPE: DNA
<213> ORGANISM: Homo sapiens

<400> SEQUENCE: 209
tgaggctcaa aacaggtgtc tgtgagcttc acaggcggta aggccgtgtc tacatggccg 60
ggacatgcat cccggggctg cccctgccgt gctgcccgag tgcacggggg atgaggacct 120
gacaaggcca ttgatcttgc gggagcttcc tgaactactc cagcgtgaaa atcttccaga 180
aggattctcc acagggcaat gaggcaagaa atttacagct tagcctgatt aatgggccag 240
gcagttaaga gttctttgcc aagctatgag cataatttat agtcatcacg gcaggaggaa 300
aggccacata actcacatcc ttaaagggcc cttagaacaa gagacacgcc ggatcattga 360
aaacgtctcc actcctggcg ccaaaagaga tcggcacgtt tctgggtatt ctggtcaaag 420
aacagggagt ctggattaat atacacggca gaaaaaagcg aagaaaagac acacaggtca 480
tatatttctg actgatattc cgtttgttgt tttcggaggg acttggtatt tatttaacca 540
cattctcact tgacacgccc cctccccaca ccttgtaaat gccttcctct ttagccgagt 600
catttttcat cacatagaat tgaaatgttg ccaggaaggc ggtttatgag attgtagaaa 660
tggcactaga gaaagcagtg tgaaaagagg cctagaacgt 700

<210> SEQ ID NO 210
<211> LENGTH: 600
<212> TYPE: DNA
<213> ORGANISM: Homo sapiens

<400> SEQUENCE: 210
tctctacatg ctatctacta aaaacttagg caaggaaatg catcagacca aacaccccac 60
agcacagaga accgaccggc cattgctttc caatctccgc aaacctaacc attgctggaa 120
gaaatcttac tcacagtgca cagacagtag gtattttatt gaagataaac atatagtgga 180
acaaaccaaa ttacccccat ttgagttacg tgagcactca gttctcagcg tggatgtccc 240
acaaatcaag tcaacatttg cgtcccatta ccagcagcca cttgccgagt atctcttcgc 300
ttccactggg actgcctggc atccctgatg ctaaggagcc actgaagagc ctccaaatgt 360
ctgacattca caaacgcatc ttttgctttg acccgaccct tcaacctctc cgagtctgct 420
gccttttctc agacacacat ccaggcaccg ttagggatag ttagagaatc tgaaaattca 480
gaagcgctcc gaaaagcctt tccaaaagta atccacagca ctcaacagtg aatttagaaa 540
ccccaatttt tttctgagtt tgaagttttt aagccttgcg gatggttgga gtaggaaaaa 600

<210> SEQ ID NO 211
<211> LENGTH: 1100
<212> TYPE: DNA
<213> ORGANISM: Homo sapiens

<400> SEQUENCE: 211
tcagacaagc tctgtgcagt cggaattttt taaagatgca ctgtcacttg aggaagacag 60
gtgatcttcc tgcggcacaa atagaagcaa agagatttct cttcttctct gtagagcaac 120
acaattgata aatggccgat aatctccacc aaattggcag cagtaggctg cccgaaggca 180
gcaggcatat tcgtctttgt gaattgtttt actatgatgc tgtcacattt ccaggaataa 240
gacggttaaa atgatatatt gttgtggttt ggcatttgca gctttgctct gacttccctg 300
gtaactgcca acatctgcaa attattatgt gcttaaaaaa aaaatcaacc gccaccgcag 360
gctgccccca cggtccctgg ctgggccagg cctcctgcca ggccacaggg cagagttctt 420
ggaccaggag gcagcagggt caaaacccag gttgcctagg aagcccccaa agacagttat 480
ggatagagct gggagcccga aacacatgcg gcagtctctc agtttccagg taccggttct 540
cacatcatcc atgcatgtgt ttgaggaaaa acaaaaaaaa attgatggtt gccaaaaaca 600
aaaatgcttc catatcaaag tttatcagtg tcaatgtcaa gagacttctg gttcgtagac 660
tcattttggc ttgaggccac cagaagtgaa ctctggtttc taaatgcaga agcagaggca 720
ctggccgatc atggaagatg cagggaactg ttcaagaggc ccaagcctgg tgctcagaaa 780
cttggcagga tcaagcatct cgcccaggaa ttcatcccct gcttgtctaa gccggctggc 840
tctcgtgact gactcggaac aacagagcag atgtttgcgt gggaggcaag cctcacccaa 900
catctgtcct gcggcgggaa ggcctgggtg ttcacagata gagctggagt tccccggtgg 960
gtggcacaga caattagctg ggctgcctc acatgtaatc taattacagg ggaaacaggc 1020
tcaaacaccg ggtgataagc agcgcaactg tttcgggtga ctctgtaatt tttcctccat 1080
taattttctc cataacgcac 1100

<210> SEQ ID NO 212
<211> LENGTH: 250
<212> TYPE: DNA
<213> ORGANISM: Homo sapiens

<400> SEQUENCE: 212
gttgcctggg atatgcttat atcaaaaact tacgtgtcac ttacctagca tttgcatttc 60
actgggcctc ctaaattctg tgtggtaacc gactgccacc ggacatgctg tttacttctc 120
tatcctcacg cagccagttg ccacattcaa cataacactg caaatattgc cggtggatcc 180
tgacttcctc gtggacccta ctgtgtcggg aaaaacaaac aaacgaaccc tggaaggaaa 240
caccatgagt 250

<210> SEQ ID NO 213
<211> LENGTH: 600
<212> TYPE: DNA
<213> ORGANISM: Homo sapiens

<400> SEQUENCE: 213
tcataaatat ttccaaatgt attcctattt gtctctacag agtctaacag acataaatag 60
cgaattgaag gttctgtctt aaaacccagc agaaagaaaa acaatgacca gaaaaaaaaa 120
acaattgtct ttggcttccc aagaacagca tcggatttca actggaacca cagatggtcc 180
gttgatagaa gcgactactt tttagctctg gaggacgaca aaaggaacca gcttcttcct 240
gtgggtgtca cagcgaggtc gcctggccac atcaggtacc agagcgagcg ccctcacctg 300
ataggccctg tacaacctca gccacagcac tgtcaggagg aacacgcgga actagcaacc 360
taggagggta aaggcggagt tgggagggaa cacgaggcag gcaggtcggc tggctgctga 420
gctacaggct gcactcctag gacgtctacg tgtaattgag aaaaataaga caaaaataac 480
ttactgtgca ggcaattaat tctggttggc atagcgatcc tcttaagtta aagggaatga 540
gcatgagatg aagagaagta agaggcagaa agaattatgc aagagcaaca tcagagtgga 600

<210> SEQ ID NO 214
<211> LENGTH: 2000
<212> TYPE: DNA
<213> ORGANISM: Homo sapiens

<400> SEQUENCE: 214
acgccgagcc gcctctgcag ggggaaaccga agcagatgtg gtgagataat acatccaacc 60
ctgagtgcta ctctaacctg ccagaggcgg agggttctca gtgagatgaa agcattacag 120
atgcgttaga tctaagggag gggcctgcag atgcgcagct ggcagagaaa ccagggaggg 180
gctgaactgt cagtcgcgac caccagggat ctgaatcagt tcaccgacag ccttggggac 240
attcaccttg ggctccacaa cctgtcagaa atgcccccaa gcccaaaggc gtcgagagaa 300
tggccaggtt gtttcagatt gacacatatc ctaatgtaca agtcagccca cacaccccac 360
gtgcactgag cgtctcttgt tgttcacccc aaataaactc tgccggaact ggggcgggac 420
tcgcaggggc ggagaagggg ggagacgggc agagggcaga agtggatggt gagaagagcc 480
aatggagggg ccccgtgaga gtgagcaagg ctgcacccct aaccgacgtc ctggggctac 540
tgtacaaaca aagaaccaca ggctgggagg ctgaacaaca gacctgcact ctctcgcagc 600
tcggaggctg caggtctgaa atcgaggggc tgacagcgct ggtttcctct ggaggctgcg 660
agggagaaac cgtcccctgc ctctcccagg ctctggggtg agcccttcct ggcatcccgg 720
gctcattgta gatggatcac tccaatctcc atggcttctc agggcttccc tccatgcacc 780
tcaaatctct ctctccttcc ttttgtaagg atgccagtca ttggatttag gttcacctta 840
aatccaggat gatctcatct aaattacatc tgcaaaaaga cccttttttcc aagtaagttg 900 acattcacag gtacctgggg ttaggattgg acatatcttt tgcaggggtg caggggggctg 960 ccactgagcc cgctgcacag ggtgacctgg gccaagggcc cttcactttc acttcctcat 1020
tggcaagctg ccctgtgttt ggactgggtc gaggctgtca accttgctgc ccctcggagt 1080 ccccccctggt gtcccccaaa cagattctaa gctgctttcc tggggctgga ggccaggcat 1140
tgggattttt taaagagctt cccagcaggt gagcagcctt tcatgggtat caggagacct 1200
tcctggcaaa tgtggtgaag gtccttcctc ctgagcgatg ccttagaccc aggagcccag 1260
ggaggctgct cacctgatcg ttaggacagg agcagtggaa acctctggcc tcagaccccc 1320
tggaggaatc cctccctcta agactctggg actggtgcac gcaaggagct atcgtgaaca 1380
ttgctcccaa ctggccgctt gcttgtcccc cggctcccct tggccccagt ggcggctttg 1440
cctgaattag agggcgtgag agccacctgt gtctcagcac tgcaattaaa gcaggaagcc 1500
ctttcggaag cagccgtgtg caccagcctc ccatgggtgg agcagagcaa accacccact 1560
tctgccctct gcccttcttc ccttttctcg acaccctgcg gccccccagt ttcagcagag 1620
tttatttggg gtgaaaaaca agagatgctc agcgcctgtg ggatgtgtgg gctgactcgt 1680
acattaggat gtgtgtcaat ctgaaataac ctggccgtta tatggatgcc ttggggcttg 1740
gggggtttct ggcagtctgt cgagcccgag gtgaatgtcc ccaaggctgc tggtgaatca 1800
gatccctggc gttctccgtt ggcagttcag cccaacagtt tctctgccgg ccgtgcctct 1860
gcaggtccct cctctgatct gattggatta atatttgaat caatagactg agtcaagcag 1920
aatgtgggtg ggcctcatgc aatcagctga agccctgaaa agagcaaaag ggctgcccct 1980
tcccccgagg aggagagaac 2000

<210> SEQ ID NO 215
<211> LENGTH: 700
<212> TYPE: DNA
<213> ORGANISM: Homo sapiens

<400> SEQUENCE: 215
cacatttcag agctgaggtg ctggtgcggg caggtctcct gagctggggg gtcagctgtg 60
tggccagtga tggtgacgcc tcaggccgtg catggccggg gaggcggccc tgcctctgca 120

-continued

```
ctcttttgac tccatgacta ctggtgtctt cggacgccag agtcggggga gcaaccatgg    180

ggcaccgccc ctgcctgggg aggcagcacg aggcctgagc ccagcttaca gggggacatc    240

caccccccgct gagagcccca ccttcacggc gaggatctgt agaagaagac atttgatatt    300

actcggcaaa aaaaacaaga aacgaaaaca caaaaagagc tcctctgaag aagaaaaggt    360

atttgcgctg tggtccacct agaaataatg ttgttggcac aactagagca ttcctcagtc    420

attcaggagc actccctgcc ggtgcgtcca catgtcccaa ccccgataga tgaggcgctg    480

ttcgcccgtg gaggggtcag gttgtcgtga ccttatcttt acccttaggc cgtccatccc    540

ggggcctggg gtttcctgcg ccagtcacgg tgggctgtgt aggtggccat gtgttcggtc    600

tttccccagg aggtacgtac catgtgctgg gaggcctgga ggctgagccg ccccccgcgc    660

ctatgagttg caccctcaca gcggcggcca aacctcctgc                          700
```

<210> SEQ ID NO 216
<211> LENGTH: 200
<212> TYPE: DNA
<213> ORGANISM: Homo sapiens

<400> SEQUENCE: 216

```
caggcttgag cggtgactgg gagaccccgg gaatggaaat ggcgctcaaa tgctggtgtg     60

gtgtccgcag gggaacggcc cgcgggtgtg tggagtctgc gcccctgtgg cttcagctgc    120

gtcgggggac tgcgggaatc ttccagactc cagtttaaat cagagaggtg tgtccacgaa    180

aagagtcaaa ctaaaacatt                                                200
```

<210> SEQ ID NO 217
<211> LENGTH: 1300
<212> TYPE: DNA
<213> ORGANISM: Homo sapiens

<400> SEQUENCE: 217

```
aacgagacag tgcaaaaagc cgctgcctgg tgacctggca tgcagactcg gccctcccac     60

ttgcacggtg atccactgaa gacaacagct gcctctgtac tcacgctccc ccacactccc    120

ctccttcctg ccctggtttc tccatcccta gatgccatcc catgccccaa accatccgcc    180

aagcacaata acctcgcccc cacccacccc atgaggtcac tcgagttgac aaccagataa    240

cagtttttgt tttgttttgt tttgttttgt tttgtttgtt tttgagacgg ggtctcgctc    300

tgttgcccag gctggagtgc aatgacgtta tctcggctca ccacaacctc cgcctcccgg    360

gttcaagaga ttcttctgcc tcagctgcct gagtagctgg gactacaggc gcgtgccacc    420

attctcagct aacttttgta tttttagtag agacagggtt tcattatatt ggccaggctg    480

gtctcgaact cctgacctct tgatccgccc acctcagcct ctcaaagtgc agggattaca    540

ggcgtgagcc accgcgccca atagcaattt gatgacccat cccctccact gctgggaaaa    600

ggctgggcac cgcccacact ccatgcagct ctctttccct ggctcggaat cgctgcaggc    660

gccacagacc agacgcgcac tgttccccac tcctgcttat cggccgcgcg gcatcccctt    720

gtcgcagcac tccagcatcc atgcagccgc gcggcacccc gtcttcggag cactccagaa    780

tccatgcaga gcgcagcacc ccacatccag agcgctccag aatccatgaa gcacgcggca    840

ccccctcgtc agagtgctcc agaatccatg aagtgcgcag caccccttaa tcggagcgct    900

ctagaacccg tgcagcgagc agcaccccac acccggagcg ctccagaatc catgaagcca    960

gcagcacccc acacccggag tgctccagaa tccacgcagc acgtggcatc tcctcgtcat   1020

agcgttctag aatccatgca gcgagcagta ccccacaccg ggagcgctcc agaatccacg   1080
```

cagcgtctgg cacatcttta tcagagcgct ccagagtcca tgcagccaca gtcctccaac 1140
ggaccctgag attgtttctg caaaaggcca tgccttcata aatctgaaaa tttggaaaac 1200
atccttctac ttatatcctt acaacccacc attcaagctg tagaagcctt tctggaaccc 1260
caagcagaag gatatccaaa atgtaaaaac ggtggggcct 1300

<210> SEQ ID NO 218
<211> LENGTH: 1000
<212> TYPE: DNA
<213> ORGANISM: Homo sapiens

<400> SEQUENCE: 218
atagtgcgac tgttccgaag tctttatcac agttactggt gatgcttttt tccagatgtc 60
ctcgacgtgc acccatgaag ggctccacct gagagtgcca gggtcctccg tgggatgggg 120
ctggaggggg tgctcttgcc gtcctgggct cccaagcagc cataggaaca atagggtgat 180
ggggtcccag agatagaggc cagtgacagc agcgctttga acccctcaca cgggcacggg 240
ccctctggca gggatgggcg tcccggtcac acggagatgg gggctgctgc tgcctgcagg 300
tagaggaagg gacgtgtttg gcagtcctgt gacccctggg cacctcgcct cccccacggc 360
cggctctgct tgtaaacaga caagtgcaca agcgcagccc ggtgaaggca cagcggtccc 420
aggaggcatc tgggctgcac cccagcgagc cgcccataca cgtggagatg ccggccaagg 480
ccctgcagca cacggcagag gaaggcgcga tgggagccat gctgggcccg gaaggtgccg 540
ccgcccggag ctgtagccat cactccagct cttcttttaa gtgttcccag aaattgtgac 600
ccaccaaaat ctgagagcac ccgacagtaa gccagaggac cttgatgtga gatcccagca 660
cggtgtgggg gcggactgtg gtgggtgctg tctcggcccc cacccccttcc acaggtcggt 720 gtgcacatcc cacggcgcct gctaagctgc agtcttctcc aaaggggtca ctctccgtgg 780
gaagggagcc acccgccccc gggtgatgtc cccagtcagt gactgacgac agtccccagc 840
cgaggtgagg gaccagctcc tgcatccctc actccggggc ttgcctgtgg gccagggtgg 900
gggcgagcct cagcagagac cgcgtccccc ttgcctgtcc tgccctgcct cccctgcctc 960
ccccgcgcct ctgctgagca cgcccagagg gagctgcttg 1000

<210> SEQ ID NO 219
<211> LENGTH: 500
<212> TYPE: DNA
<213> ORGANISM: Homo sapiens

<400> SEQUENCE: 219
cacttgaaaa gcacaactca tggtgccaaa gctctgacac ggactccact ggagctgtgg 60
gcagggggtg ccaaggtacc gagttccaag ccgttgttat ttgagagcgt gccccccgcc 120
atgagagcag gtggggggac ataaagtgac acaggatgga ctggccaaag gctgaggacg 180
atcacttacc tcacaggatg atgccacccc cacggacagg caaggagctc tcaccttccc 240
caggacccca gctgccacca gagctccaga tggccctggg ggtgtctgta aagcctgtga 300
ccgtccacca ggtggagacc aggctggcca ggggagggag aggaagtgac cactggccct 360
ggcactggct ggccggctcc agcaggcccg aaggggaggg aggagcctgg gtgcaccaga 420
ctctctcaat aagcagcacc cagacactta acagatggaa agcggtggct tggaactcac 480
ttccaacgaa acaatagcac 500

<210> SEQ ID NO 220

<211> LENGTH: 1300
<212> TYPE: DNA
<213> ORGANISM: Homo sapiens

<400> SEQUENCE: 220

```
agcacctcct accccaccct ccccattcct gccatcccca gggtccaggg agcccagatt     60
ccagggaagg gttgcattag ctcccactcg gagtcctgat gcagcagaga cagacagagg    120
ccctgggaga agtgagcatg aattattaag acaagacaag ggtgaggccc cagagagggg    180
gtggcggaag ggtcatgttc atgcagcgag agttgcttcg agcttgaacc gcgtatccag    240
gagtcaagca gattgcaact ggcgagaggc cttcagaaat gccccgtgag agtcctgtgt    300
gcagagctcc atctcagcac acttcctgtt cttttggttc gtcgattttt gcattttcag    360
tcccctgtga tccattattt ataacagtgg agattggcct cagacactag cagtgaggaa    420
aacaaaagcg aagctacgca gaaaaatgac aagagtgatg agcacagcag tcatgacaaa    480
tgagccctgt gcggaggccc gggatccgcg cagatgccgg cgcgggggaa atgggccctg    540
aaatcccacc gtcaggccag gcagctctga gcgtgacctg gagggctgtt cagacggtct    600
gggtagccgt gtcctgcgca tgaacatcct ccgtcgggag aggaattccc cacggattat    660
cagagctgct ccctccaccc cccgccacgt cccacgcggg ccacatcaac tccctctgca    720
gcctctggcc agcggctgag ccctccgtgt ctcccctcgt taatgcctcc ttcaccatcc    780
cctcctgaag tttcccccat tgcatacacg cgctgaggcc cacccggtat caaggactcc    840
cattgcttgc gaaaaagatt ccacccctct tagaacagag accagggccg ctgtagcaaa    900
tggccataaa tgccacagct taaaacaaca gaaacggatt atctcgcagc tctggaggat    960
ggagtccaaa atctgaatcg ctgggctgaa atccaggtgt gggcagggcc gcgctccctc   1020
tagaggctcc cccggagatt cccttccttg cctcttccag ctgctggtgg ctgccagcag   1080
tttgggaatt gcggccgcat cacaccacct ttctgtttgt tgttgacatc cccgcctccc   1140
ctgcctgcgg ggtcttagat gtctctctcc ttcccactga gtttcactcc acatttgaat   1200
tggattaact catgccatgt taggcaaacg tgcccctcaa atccttccac ttaacagaca   1260
tttattgaag gttcctgtgt gcggggccca agagaaggga                         1300
```

<210> SEQ ID NO 221
<211> LENGTH: 200
<212> TYPE: DNA
<213> ORGANISM: Homo sapiens

<400> SEQUENCE: 221

```
gaatgttcaa agaaagagcc ctccttgcct tcctcttctt ccacccctgc cctctgcaga     60
ctggggttct gtagaccccc aaagtaagtc cgccacaccg gaaggaagtg agttacacag    120
gggcccacat gggaaccgct ttttgtcctg tcttggtggg aaaatggcca cgaccccagc    180
ccaggctctg ccacgccaca                                                200
```

<210> SEQ ID NO 222
<211> LENGTH: 1600
<212> TYPE: DNA
<213> ORGANISM: Homo sapiens

<400> SEQUENCE: 222

```
ccatcttcct aggcctgcgt ttcccccaca ccggggactt gtgctggaaa gaaaagctgc     60
gttggcagcc aggagccggg gaaactgtcc agggaggcat cctctgcgat gaaggcgggg    120
cctcggcgtg gcccgttccg cgctctgtcc agccctggag aagccccacc ctcaccgagc    180
```

```
tcgaaatacc ccctccctga gagccgagac tcatggccgg gacccccttgg acagaagatg    240
cggatgctaa cccggcgctt ccaccacagc cccggcggca ctggggagcg agcgcggcca    300
tcccgcgcgt aggtggtgtt tctctgcagg cgccagtttc accgcgggcg cccaggatcc    360
tcaacggttc tgttgtgatg tgattcccct cttcgacttc gtcattcagc ctcagtccct    420
cagtccccaa ataccgaaag gcagtctttt tttttttttt ttgagacgga gtttcactct    480
tgttgcccag gctggagtgc aatggtgcga tctcggttca ctgcaacctc cgtctccctg    540
gctcaagcga ttctcccggc tcagcctccc gagtagctgg gattacaggc acctgccacc    600
acgcccggct aattttttgt atttttagta gagacggggt ttcaccatgt tggccaggat    660
ggtctggaac tcctgatctc aggtgatcca cccgcctctg cctcccaaag tgctgggatt    720
acaggcgtga gccaccgcgc ccggcctttt tttcttttttt cttttgaagt taatgaactt    780
gaattttatt ttatttacag aatagccccc atgagatact tgaagacccg gtgccaagcg    840
acagtgttga ccccaggtgg tcagtcctgc ctggcccctt ccgagggatg cgccttcacc    900
ataaccatgt cacggacagg cgtgtgggca agggggcatc gctgtatttt tcacaactct    960
ttccactgaa cacgacaatg acatttttca ccacccgtat gcatcaacca aatgaaaaga   1020
tgagcctgtg acattcccgt gcgtagagtt acagcttttc ttttcaaaac gaaccttcag   1080
tttggagccg aagcggaagc acgtggcgtc tgacgtctcc agggagaccc gccgccctcg   1140
ctgccgcctc accgcgcttc tgttttgcag gtaatcttca gcaagtactg caactccagc   1200
gacatcatgg acctgttctg catcgccacc ggcctgcctc ggtgagtgcg cgctgcgggc   1260
tctgcccggt gacgccacgc ggcctcctcg ccttttcggg atggctggga ggggcgggaa   1320
gaggcgctga agggcccgag gcaccggcct tctacaaggg gctcttcgaa atcaatcaat   1380
gcgcagaatc ccgagggagg ctcagccgcc ctccgggcct ctctgcctcc acaggtgatg   1440
gctgtgtcca caaggaggaa accgtcgggc tgaattaaac agaaccgccc tcctaagagt   1500
gtgggttttt ctgccgggcg tggtgtctca cacctgtaat cccaacactt tgagaggccg   1560
aggtgggcag atcacctgag gtcaggagtt cgagaccagc                         1600
```

<210> SEQ ID NO 223
<211> LENGTH: 400
<212> TYPE: DNA
<213> ORGANISM: Homo sapiens

<400> SEQUENCE: 223

```
aggcagcagg gttaggactt caacatacaa cttttggggg gagatgtact tcagcccata     60
acacaccacg tgggaggata acaccgattt cagagcttgc agaggaagcc gccaggaact    120
ccagtgagac atcagccccc aggtgcctgt caggcacgcc gggctgtggg gggcacctgg    180
gcccatctga gtaacggagg cgcatccgca cttcccccag gagtacattt ttagaaccca    240
cagcgccata aaccaaagac aaggagactt cctggtgccc cgtcagcttc tggaggcgac    300
gttctcggct gacagctctg gcagcctccc ctgtaggtga gagacaggta aatgggactc    360
ttgcttccaa aacggaacag ggtaaaaatt ctcaagcgtt                          400
```

<210> SEQ ID NO 224
<211> LENGTH: 700
<212> TYPE: DNA
<213> ORGANISM: Homo sapiens

<400> SEQUENCE: 224

```
tgctgcaccc ccgctgccct ccctcccgct ggccggcagc accttctcca cccgggcccc     60

tctgctcaca gcgctccccg cccccgtctc cccgaggggc ggggagccag gacatggccc    120

tgaaagccta gccctggcct tgacctcccc agagcgccct ccccaccctc cgccctctgc    180

caaccctggc ccctgccctg gccccgtcct tgtcctctgc tgctggcctt ggggtcgcgc    240

cccgcagact gggctgtgcg tgggggtcct ggcggcctgt gccgtcccac gcctacgggg    300

atgggcgagg tccttcttgg ggcttctctt acccactctc cagtcacctg agggcgctgc    360

ttccctgcgg ccaccccagg tttctgtgca gccgaagcct ctgcctctgc ggccgggtga    420

tcccaagacc ccggggtcca gggaggcacg ggatctgctc ccccggtccc aaatgcaccg    480

gctgcgcctt aggagggacg gcctccaccc atggcgctgg cgcccagggg ccgctcctcg    540

gactacagca cttgctcgtc gccctgcgcc ctgtttagtt ctcatcacca gcagcctgga    600

ctagggccct ggtccttctg gcctccttcc acagcccgct gcacatctca cccacttccc    660

cgaggtgctg tcattgttta gctgggcccc tcagcctccg                          700
```

<210> SEQ ID NO 225
<211> LENGTH: 300
<212> TYPE: DNA
<213> ORGANISM: Homo sapiens

<400> SEQUENCE: 225

```
ttaaagggga gtggttgtat gaagagttcc tcagtcaaag gtgtgcagct gggaagccca     60

ccccacctaa gagggaggtc tgacaaactg tccacactga accactcaga cctgcatcag    120

ggccccgttt cttccataag ccgccaagta cagccctgag tcaactgaac tcaggcctgg    180

gaggcttccc aaagctgact tgactcagct ttgaactgaa atgaccgtac catgacaacc    240

ctgatgaaaa gctaaactga gcccaattat tcaacagtaa aattcagttg gtctcactca    300
```

<210> SEQ ID NO 226
<211> LENGTH: 450
<212> TYPE: DNA
<213> ORGANISM: Homo sapiens

<400> SEQUENCE: 226

```
tgctaccagc tgcttgggct tgggcaagtc accctagctc tcagatgtca tctgtaaatg     60

atgacaatgc caatgtggca ctgttctgag agtcagacag aacgtatgtg tgcttcacat    120

atggtgctca tgaagtgcta tcattatcta aggaaaacag aaaacgaagt tcagagtctc    180

tctaaacgca tgacaccaga ccaacaggga gtttcaaaaa ataggtctga agtaaatcaa    240

ttctcctggt ctcaatacac tgaaaacaaa ctattagggg actgaccgaa cccaccttag    300

gaaccacctt acgtcacctt ctgtctctac tgcaaaaccc tcccttaata ctgttcaaat    360

acgctgacaa tccagatcca tatccaatgg aaccagcaat catgcctgtg tgccagcaat    420

gtcagggagg gaagccgatc tctgatgaat                                     450
```

<210> SEQ ID NO 227
<211> LENGTH: 1000
<212> TYPE: DNA
<213> ORGANISM: Homo sapiens

<400> SEQUENCE: 227

```
caggtgccgg ccaccacacc cggctaattt ttgtgttttt agtggagaca gggtttcgcc     60

atgttggccg ggctggtctc aaactcctga cctcatgtga tccacccgcc tcggccttcc    120

aaagtgctgg gattacaagt gtaagccact gcgcccggcc aagagtgaag ttctgatagc    180
```

tggggtaaga aaggccgtgg gaacagccgg tttcagacac gctgggtcta agacgctgcg 240
tctggcgctg ctcggcatcc aatgggagcc gtggagaagc caggcgagtg cgtagggcgg 300
agccagcgca caggaaatag gacgtgatga ggtcaaccgg ctggtccaag tgtggacgga 360
agtagaggat gcaagcaccg agccccgggg cccccagcat tggcggggag gagctcgcgg 420
tgcgggagaa gcaggggacc gcgcatcctg gagaccaggt ggagccagtg cgcccggaag 480
gggcgtggcc cgctgacagc cgcccaggag gccgggggag gcctggagcc gagggccgcg 540
cgtggcaatg tggagagaca ttttggtgga gtcatggggc cacagcctga ttggtgagaa 600
caggaaggga aattgcagat gggcctgggc cccctggctc ccgcatactc caggaccagg 660
gctgagtcat cgttcaccgt gtgtgaccag ggccccgtgt ggccggctgt cactcggtat 720
ccagttaccc tgggcagacc actggcggca ccccccagcc agaggccgca gcaacacaca 780
cgcctgcagg cgaccaggcc ggactgcatg ccccgtgggg gaactgaggg cgtttcagta 840
acagagtgtt aggggacacg ggttgggtgg cttggaaagg gcctaaggtg gggtttgttt 900
tagattgggg tggtgagggc gcaggggccc ggtaggattc tctaacaggg cagcagccac 960
tcatttagca acaggagagg cgtccagcgt ttcgtgggct 1000

<210> SEQ ID NO 228
<211> LENGTH: 3100
<212> TYPE: DNA
<213> ORGANISM: Homo sapiens

<400> SEQUENCE: 228
acccaaccac aggcctcctc tctgagccac gggtgagcgg tgcaggttct gctgttctgg 60
agggcctgag tcccacccag cacctcataa acagggtcct ccccagggct gctgcagtag 120
gcatcaacgc cagggtgcaa aatgcctcag ggagccaagg ctgagccagg ggagtgagaa 180
ggagcatgtg gaagtgcgtt ttggagaggc agctgcgcag gctgtcagca ggctccggcc 240
gcttctatag acagcatgac accaagggca gtgacctcat tccacaggct gagtccagcc 300
agccagccaa gcatcaccag ccagacgatt gaccctaacg gaccaaccaa cccgtaacga 360
cccctcctac cataaccagt agccagccag cccataacca gccaacttat ctataaccag 420
ccacctgacc atagccaaac aaccagccgg cccaccagta gcattcagcc cctcagctgg 480
ccctgagggt ttggagacag gtcgagggtc atgcctgtct gtccaggaga cagtcacagg 540
cccccgaaag ctctgcccca cttggtgtgt gggagaagag gccggcaggt gaccgaagca 600
tctctgttct gataaccggg acccgccctg tctctgccaa ccccagcagg gacggcaccc 660
tctgggcagc tccacatggc acgtttggat ttcaggttcg atccgaccgg gacaagttcg 720
tcatcttcct cgatgtgaag cacttctccc cggaggacct caccgtgaag gtgcaggacg 780
actttgtgga gatccacgga aagcacaacg agcgccaggt gagcccaggc actgagaggt 840
gggagagggg ggcgagttgg gcgcgaggac aagggggtca cggcgggcac gaccgggcct 900
gcacacctgc accatgcctt caaccctggg agagggacgc tctccagggg accccgaatc 960
aggcctggct tttccccaag ggaggggccg tgcccacctg agcacagcca gcccctcccg 1020
gtgacagagg tcaccattcc cgagctaatg tggctcaggg atccaggtta gggtcccttc 1080
ccgggctgca cccagccgtc gccagctcca tccctgtcac ctggatgcca gggtggtctt 1140
agaaagaacc ccaggaagtg ggagtgcccc gggtggccgc ctcctagcca gtgtacatct 1200
tcacatgaac cctacctgag gaagccagtc cccgacggca tagctgcatc cgcttggaat 1260

```
gctttacagg cattgacacc ttcgcctcac agcagcactt tggaaccagt gtcctcatta   1320
ttccagggca cggctgggga acaaggggggt cctcagcctg ctgggtccca cagctagtac   1380
cgggcaggtg gacgggagct tctccccaca gtcaccctga tgccccgctc ttgctcggct   1440
ggaggcctcg gatctccgtg gtgttgaggg agccggggca ctggagccct ggtgacctgc   1500
atctcctggc ggagccggga agagctcatg gactgtcaca gatggacagt gccccgcggg   1560
ggctggagag cagagtgggg ctggaaggtg gaactcttag ccaaagtctt ggtttctttt   1620
ggccagggtc ctctttcaat ggctggagaa ggtggtgctg gggggtgaac gctgacctcc   1680
tcatgtgctg cccctccctc gcctgggccc ggtaaagccc ccacgtagcc ccagccagcc   1740
tggaacatgc ttcctgagct cccagctctt ggtctttgca cccagtggag gaggaggtca   1800
gcccagggag ctgagtctgc ggtttagggc gtccagggga cgtggaagca tgtgggtcgt   1860
ctggccacat taggtagggc tgcagagacc tgggctagag cagtcctgcg gggtctggaa   1920
ggggaagact ggctgaggtg cggggcctgg tctggaatga tcctgcgatt ttggagtgaa   1980
gccatggagc gggaagagac aaccccccgc ggggaatagc ccggcaagtg gccacgaggc   2040
caggctgagg tccagagaag caggggcatg aatccataaa tcccaggggg cctggccatg   2100
ggatgtgctg gctgcacccg gcccctgtga gagcccccgc aggctggccc ccttctgcag   2160
tcagtggggc tggggcagct tctctggcat ggggcgaggc agccgcctgc acagtggccc   2220
ccctgactgt gcgcccccac cctctccagg acgaccacgg ctacatttcc cgtgagttcc   2280
accgccgcta ccgcctgccg tccaacgtgg accagtcggc cctctcttgc tccctgtctg   2340
ccgatggcat gctgaccttc tgtggcccca agatccagac tggcctggat gccacccacg   2400
ccgagcgagc catccccgtg tcgcgggagg agaagcccac ctcggctccc tcgtcctaag   2460
caggcattgc ctcggctggc tcccctgcag ccctggccca tcatgggggg agcaccctga   2520
gggcggggtg tctgtcttcc tttgcttccc ttttttcctt tccaccttct cacatggaat   2580
gagggtttga gagagcagcc aggagagctt agggtctcag ggtgtcccag accccgacac   2640
cggccagtgg cggaagtgac cgcacctcac actcctttag atagcagcct ggctcccctg   2700
gggtgcaggc gcctcaactc tgctgagggt ccagaaggag ggggtgacct ccggccaggt   2760
gcctcctgac acacctgcag cctccctccg cggcgggccc tgcccacacc tcctggggcg   2820
cgtgaggccc gtggggccgg ggcttctgtg cacctgggct ctcgcggcct cttctctcag   2880
accgtcttcc tccaacccct ctatgtagtg ccgctcttgg ggacatgggt cgcccatgag   2940
agcgcagccc gcggcaatca ataaacagca ggtgatacaa gcaacccgcc gtctgctggt   3000
gctgtctcca tcaggggcgc gaggggcagg agggcggcgc cgggagggag gacagcgggg   3060
tctcctgctc gcgttggacc cggtggcctc ggaacgatgg                          3100
```

<210> SEQ ID NO 229
<211> LENGTH: 1000
<212> TYPE: DNA
<213> ORGANISM: Homo sapiens

<400> SEQUENCE: 229

```
tttttgtgtt tttagtagag atgggatttc accatgttgg ccaggctggt ctcaaactcc     60
tggcctcatg caatcctcct gcctcagtag tagtagttgg gattacaggt gtgagctgcc    120
atgcccagct gcaggtgcgg aagctggggg cctcagagac tgtggactcc tggccggtga    180
ggagcggcat gggccgggag agctgactct tcagcgggac tgaggtggct ggagcgtgac    240
cctttcctga gggcaaacag ggagggcctt ggagcccggc gctcaggaca ggcccctgct    300
```

ggcccggcag cctgagcttc cacacttttc cagggcgtct cgagttcgcc cacagagctg 360
ttgtttcagg ataaaaaatg cccttgtatt ccacgttcca gttcagaggc ccgtctgttc 420
ccaagagcgg aggcgtcagc cgcatgagtc ccaccggaag ccgggttgcc gggtccccgt 480
ccctgccctg cagacgacgc attccggagc ccccttggga agctgcctgg ctctcccagg 540
cctggctgcc ttcgcacgag ggctccgagg catgctcatc ctacgtgact gcccgagtgt 600
gcacacgcct ggccgtgtgt gggcgtgtgc ctggggcccg agctcaggag caaggcctgc 660
gtggacctgt tgtctgaaac aagccagtag acagctgcgt caatgcaggc aagctgaaca 720
gggctgcttt ttcagcctga caaccccagg ggctgaacag gagctggggg aggagcaagg 780
ggccgttccc ctgccccaca gcacagcaca cgaccccgcc ttggaacctg gggcccgggg 840
tgaatcgagg gtcctggagc aagaggggct gctccacagg agagcctgtc ccgccacccc 900
tcagccacca gattcggggc tgctggactt gttctcaaac ctgcacagtg agtgacagct 960
gctgagacgg aggtctcagg cagtgcaggt gaatcagcat 1000

<210> SEQ ID NO 230
<211> LENGTH: 500
<212> TYPE: DNA
<213> ORGANISM: Homo sapiens

<400> SEQUENCE: 230
tccttatttt ttagttctca agccctgtag ggtgttttcg gtcgcagttg tttgggctgt 60
ggtcctgacc ctcctgagtt ccagtggctc tgttcaggag agctgcctgg ggccgggact 120
tctgaaacac acactgagcc acaggccggc ccggcggctt gggttcaccg ccgcctcttt 180
gtgtgtgatg tcctgggata ggcccgtgca cgttcagatg acactgtaca tataaataac 240
ttgtagccga gaacaggatg gggcggggag gaggggaggg cagaacgtac cacagcagca 300
gaagtcactg tggatgcctt cgtaagttgc atggaaggtt tttaaaccta gccctgccga 360
gcagccctct cctggtccgg gagaacgatg gggagagagc tggcgttcag ctttcatcac 420
tggagccgtt ccttcttccg gccccccgag ggcctgtcca tgatcacact ttgtcttgtt 480
tcgggggtgg cccctgtgac 500

<210> SEQ ID NO 231
<211> LENGTH: 1300
<212> TYPE: DNA
<213> ORGANISM: Homo sapiens

<400> SEQUENCE: 231
caagcctgtg gtagggacca ggtcagagta aacaggaaga cagctttcgg ccaggcggtg 60
cacctcggtg ccggtgagtg tgagcgtgtg tgcgtgtgca cgtgtgcaga tgtgtgtgga 120
cgctcccttc tccgcagcag ctcctgaccc cctgcaggtg accctcagcc agccccaggg 180
ctgcccccac tctcccctgt ggacacctac ctcatttggg gtgaagtggg gggactgggg 240
tgtgaggggt gctttggggg gcacacttcg acccctctct ctgcaggcca agtcctgagg 300
ctcagtttcc tcctctgtgc cccggcgacg tggtgcaggc ctcgcgagtg acgtgagggt 360
tcatgaccca ggtgtgggca gccagccctt cacgggaggc cacccacctg gccacagtgc 420
ctgggaattt aggtcgggca ctgccgatat gtcgccttcc acaaggcggg cccgggcctc 480
tgctgaccgt gcaccggtcc tggggctggg taattctgca gcagcagcgc agcccatgcc 540
ggggaatttg cgggcagagg agacagtgag gcccgcgttc tgtgcgggaa ctcccgagct 600

-continued

```
cacagagccc aagaccacac ggctgcatct gcttggctga ctgggccagg cccacgcgta    660

gtaacccgga cgtctctctc tcacagtccc cttgcgtctg gccagggagc tgccaggctg    720

caccccgcgg tggggatcgg gagaggggca gtgtcgccca tccccggaag gctgagcctg    780

gtgcagccag ggagtgaggg ggcgggaagc cggggtgctg ccctgagggt gccccgacac    840

gctctcctgg ggccctgagc ggctgccacg tgcgtccagg gttctggcca cagggtgggc    900

aggggccctg tgctcctcac tggaggcccc tgaggctctg gaactgagac catccacccg    960

ccggcccccct ctcgccggct ccggcacccc tgcctactgt gacttcctgc cccggactcg   1020

ctctgccagc ttggggcaaa ccacttccct ctggggtttt cacttccctc tttcccaagt   1080

ggggaaagac cacctgtccc cgacccagaa agggcccctg cccgagggca gcagcagtgc   1140

caggctggca tgtgaggctt ggggcaggcc cggcccccag aggcacaggg cgatgctctg   1200

tgggacgctg tgtcgtttct aagtacaagg tcaggagagg agccccctga ccccggaggg   1260

gaggagaggc agggcaggaa accgccacca tctcagccca                          1300
```

<210> SEQ ID NO 232
<211> LENGTH: 200
<212> TYPE: DNA
<213> ORGANISM: Homo sapiens

<400> SEQUENCE: 232

```
gcccactgtg ggtgtgcccg tgtgtgtggc tgtgaggcgt gagtgcaggc gtgaagtgtc     60

tgggagtggg agcgggcatg agtgtgtgcc acgggcctgc tgttgggtcc ttggaggcca    120

cggttgcccc tgaagggact gcaagctctt ttttgatttg tagttatttg agaagtctat    180

acaggaagaa aattaaaccg                                                200
```

<210> SEQ ID NO 233
<211> LENGTH: 1000
<212> TYPE: DNA
<213> ORGANISM: Homo sapiens

<400> SEQUENCE: 233

```
agcgcccagc gcagggccgg gacccagagt ggactctacc gtggggctgc ctcaaagaaa     60

tctcagcaaa cacaggaagc cagcccaccc gtgcagccat ggggccagga agcccgccct    120

ttaccaagtc atttgggcat tttttctctg tgctaacagc ccagatggag ccatagcctc    180

aacctctgtg ttctgataac accaagctgg gacgccggag ccatgcaggg gacagtgccc    240

ggcctgaggc tgcagcctgg gtctggatgc ctttctaatt cagggcctcc tcatggcctg    300

gttccataaa tggtcaaatg cagcctgaca gcgcagcctc ctatcagcgc tgggctccgt    360

accgccacac agcccacata ccccgttccc caggagacgc ccgcaggtgg gcagcgtcac    420

tcccacccgc cgagcacacg ctgtccccgt ctcgtgtccc gaggagccgg aagcagctgc    480

ttcctcccag cctgaaagct gcacctcggg ctgcactcgg ctccccgaac ccgccctccg    540

ctgccctgca attcgccaag ggagctaccc ttcccatata aaaatttcac ctccatttcc    600

ttgtagagaa gaaacatttc tgacagcaag gaagattcta atttgaaaag caagtgattc    660

atctcccggt gccaaacagc agacgcaggc gttaccagtc tgggtggggc gcccgagctg    720

gggacctggg gtcctctggg aggggcaaga aggcagcgat gctggccccc gcctccatct    780

gcccatccca tctgcttcca cacaccgccc tgccgtagct gcttgcagcc cttctctgtc    840

agtttctcca tcttttggtt tggtgataaa tgagagttcc catcgggtgt gccaccctct    900

gtgtgacggg gagcagagaa gaccctgcgt ccaagtcctc ctgggggaag agcgaagatg    960
```

ctgggaccag ccccagctgt cagggggtct ccaatcccag 1000

<210> SEQ ID NO 234
<211> LENGTH: 1300
<212> TYPE: DNA
<213> ORGANISM: Homo sapiens

<400> SEQUENCE: 234
ggaacggaga gccgccaggc ccaaacctcc cagaatttgc gcagtattct cggcctagag 60
agcgaggagt ggccttggcg aggtccctct ttggctcttc tggcttagcc ggggttttaa 120
acttgttatc tgcaaagcag aaggaaagtc agcccctgat gtaagtgtca agtaaaataa 180
atcggatggg tcctttcctg tttggcgagg aatgctacac taagggggac tgcgttcaaa 240
tgggcagtct ttgctggaaa cctcgcctcc gcgcgccttc cctcgctcgg attcaggcgc 300
ttttacgtta agggttgaat ttttgtgtca acaggcacct cgggaggtcg cctagacaac 360
tgagcggagc aactgagata acccccgcta cgtgtggagt gacctagtcc attaacttgc 420
cccagcacgc ccgctgagtc cgcaaaatat aggatggcct cgggttttag atgaacccaa 480
agctaagatt tcttccctct ctggaattag caagcagccc gccctgccca actcccctgg 540
aagcgcgcgt gctcgccagg cctcgggacg cctgcgcggg cgcccttgca ctggcaccag 600
ggctccgggg taggggcgca ccgatctgcc caagcctctg caggcactgg aggaaggcga 660
gccctccacc cgctcaacag gccccagtgc cggcctttcc ttccagtctc aactccaccc 720
gggggcccgg gggctccaca gttaaaaact ccacgccacg gagatcgcag gtaagctgct 780
ggctcaacga ggtgtgctaa atgggattaa agatcctgga ccgtggccag gcgcggcggc 840
tcaagcctgt aatcccagcg atcagggagg ccgccgcggg aggattgctt gagcccagga 900
gtttgagacc agcttgggca acatagcgag acaccgtctc tacaaaaaaa taacaaatag 960
tggggcgtga tggcgcgcgc ctgtagtctc agctacttgg gcggtcgaga tgggaggatc 1020
gatcgagtct gggaggtcga ggctgcagtg agccaggatc accgccaaga tcgcgccact 1080
gcattccagc ctgggcgaca gagggagacc ctgtctcaaa aacaaacaaa aaatcctaga 1140
ccgtttacaa acagccttcc gtctcttcct ggtcaagtcc taaccctggc taacctcgcc 1200
gtctacagcc tgaattttgg caaccgaaag gcagcgccgg cgccacgtgc acacgggctg 1260
ggccgctccg ccagctgcca gggccactgc cgcgctcact 1300

<210> SEQ ID NO 235
<211> LENGTH: 300
<212> TYPE: DNA
<213> ORGANISM: Homo sapiens

<400> SEQUENCE: 235
cgcacacaca gcacagacgc ctgcatcttc ccatgcgtgg tttctgctct tgcctctctg 60
ggtttttgtt tcacttcggt cgagtttttg gtggtgttga gcggatagcc ggggaagttg 120
gagtcttgtt tgtggccgcc tcgtgctcgt gtctgtatct aagatcctca ggctgctcct 180
ttttgggtaa ggtctgttgc ttctctagga acagtgacgg tggcagagcc cgtggcccct 240
ctctcctgtc ccagagccaa gctgtttcct ctccccactc ccgggcaccc tgcgggcaag 300

<210> SEQ ID NO 236
<211> LENGTH: 1000
<212> TYPE: DNA
<213> ORGANISM: Homo sapiens

<400> SEQUENCE: 236

```
cacagcccag cttcaagcct ggccgaccag gggtttggca tgaagacccc ggcagggctg     60
gggctgtgct ggaatccacc cggaagtttc ctgccccttg ggctgcccac caggtcccct    120
ttctgctctg atcaagctgg acaaaacgtc gtggggccac agcacagggg gccaacgcaa    180
gctgggatcg tcagacgtta ggaaatccca aggaagaaga gaaaggggac acattcggga    240
gacgtcggca cacgctcgaa gcagcggaca ggcacctctc tgtggacaag gcagactggg    300
cggccgagat tccgcataga tgcctgcttc ctccacgacc tccacgtgtg gctggcccag    360
tccgggtccc cctcacctcc tctgtctgtc ttggtggcct cacgccgtgg gctgtgatgc    420
cggctacgct gcttgggtgg ccaagggtct gagctgcaag acgcccagcc tgggtctctc    480
ccgagctctc ccacgtcctg tctgctcctc ctccgagctc ccggttgact ctcacgactg    540
caccagcctc tcccccagga aggcgtggaa acaacctcct tctcccaggc ccgctctgcc    600
tcctgcgttt caaggcaaat ccgttcctcc aggagatgat gcaaccacat cctgttggag    660
cccagagaag tgcggatgca gcccggggct ctttctttcc tagaaccctg cctgggagtg    720
gcttccctga actaaggaca gagactttgt cttcgttgcc tctcggcctg tgggcactga    780
gcatacagta ggtgctcagt aaatgcttgc aggccgatgc ccagagccat tagccctcat    840
catggtgagc tcggcagccg gtgttggggc tgggctgggc ctaggtgtgc gtgggggcgg    900
tgctggtctg ctttgctggg agccatggac accggaggaa cagggcccca tcagtgcggt    960
cagagtgcaa actcggagcg tccttctctg gaaaacgaat                         1000
```

<210> SEQ ID NO 237
<211> LENGTH: 500
<212> TYPE: DNA
<213> ORGANISM: Homo sapiens

<400> SEQUENCE: 237

```
gggagggggc gtggccagca ggcagctggg tggggctgag ccagggcgat ccgaccccga     60
accggagctt ttagcacttt gagtccctgt actcagaggt ctcctgcagc cgggaatccc    120
actgtgctgt ggtccctggc agccagcacc cacccccagc ttctccgtca aggttgagga    180
cggagcactc ctgcctctga ttaactggac gcaggagaag cagttgcttt aatccggagc    240
cttgagttgg gacagataat gagtcattca accagatttt ccaaggacac actaactttg    300
gtatgatgcg tgtgtgcccc tgaatccacg tggtcaggaa agcccaggga acactggcct    360
gtgactcact gagcaggttc ccttgttacc ccgaggggtg atttactcct ctgacagtga    420
cacggacact gtgcgtccat tccccgggcg ggcagaggac actcccagat gcccacgagg    480
ggcccagcaa gcactggcca                                                500
```

<210> SEQ ID NO 238
<211> LENGTH: 600
<212> TYPE: DNA
<213> ORGANISM: Homo sapiens

<400> SEQUENCE: 238

```
ctgcaggacc tgctcgttca cagatgttct cctagaagca gaagctgttt cttgttgcaa     60
acaaatttgc tgtgtcctgt cttaggagtc tcacctgaat ttaccaagga tgcatctgtg    120
cttggggatg gctcggtttg aggggtctga ggagcggctc ccctggatcc tttcctcccc    180
aggagcccac ctgccgagct gtcagcgtca gccccacatc tcaagatgag gaaatggagg    240
tcgaagccat gcacacgcag gcgtcctgct gacatgcagg ccaggcgggt gcctctgtat    300
```

tcagcagcct cagggctgtg gccagttcag gcagcagagg ggcctcatcc cggtgcttcc 360
ctgcaggcag ttgtggggcc ggcctgcagc aggggctcag acagggcctt gggagaggga 420
gggatcacag aggtgtccag tgacaggcag ggcgggcaga gcccatgggg ccttgggctc 480
ctcactcctt cggtcagtca gggtgacatc tggagccacc tccattaatg gtgggttatg 540
atttggttcc catgcagccc gtgccagctc gctgggagga ggacgaggac gcctgtgatc 600

<210> SEQ ID NO 239
<211> LENGTH: 5000
<212> TYPE: DNA
<213> ORGANISM: Homo sapiens

<400> SEQUENCE: 239
aagaggaaat tcccacctaa taaattttgg tcagaccggt tgatctcaaa accctgtctc 60
ctgataagat gttatcaatg acaatggtgc ccgaaacttc attagcaatt ttaatttcgc 120
cttggagctg tggtcctgtg atctcgccct gcctccactg gccttgtgat attctattac 180
cctgttaagt acttgctgtc tgtcacccac acctattcgc acactccttc cccttttgaa 240
actccctaat aaaaacttgc tggtttttgc ggcttgtggg gcatcacaga tcctaccaac 300
gtgtgatgtc tcccccggac gcccagcttt aaaatttctc tcttttgtac tctgtccctt 360
tatttctcaa gccagtcgat gcttaggaaa atagaaaaga acctacgtga ttatcggggc 420
aggtcccccg ataaccccca gctgcagatc gaggcctagt gcgagcacag gtcccccccag 480 acccttccca gtgcccacca accggcggcc taggccaggt agaactggca gcgcctcccc 540
tgctgcaaca ccaggctctg gtagaaactt cagaaaacat gcaccggcaa aaccaaggaa 600
gggtggctgc gtcccgggtt cttccgcgca gctgtgtgta cacgcatgca cacacccaca 660
cgcacacacc cacgtgcaca cccccatgca cacgcaccca cttgcacgcc catgcacgca 720
cacacgcgcg tgcacccatg cgcacgcacc catgcacaca cacgcgcgca cacacccacg 780
tgcgcaccca catgtacaca cccacgtgca cacacccacg cgtacacacc cacgcgcaca 840
caccgctgtc cccagccgtg cagaacgatc ctccctgagt ccccggctcc gacccacacg 900
cagcactcgc taaacgcttc ccacgcagtc gttttgctgg gttgcgcttc acccacttct 960
cagagggggc ggccgaggca gaggtgtcgg ggatcgagca gctccgggcc tcaggggtcg 1020
ccccgccacc gttttccttt cccagatgct gggacggggg cagggagggg ctccccaggc 1080
tgaacccgac taggtcaccc tagaagcgag gcgagcttct cttctgtttt tcttcggcgc 1140
ccctgagccc ctgacagtgc ccaagctgcc catgggattg gattcgccag agcctcctac 1200
gcagacccca cccagggcca aagccaaccc caagccccac caccttggtg gtgtgggatg 1260
aaaagtgagc catcgagaga tggggtcccc ccacccccaa cccctccaag gacaaaggcg 1320
ggctgggaag cacccgcttt cacgtccgcc cctgcccggc tttcctagcg gaattggcgc 1380
cggcatcagt tgggggttgt gggatcagtg aggaatcccg tggggtcgcc tccatttatc 1440
agttgtgtgg ggttgggcga gcacccctag ccccagccca ggcgatcagg gcgcgaagcc 1500
cactggacgc ggatttggga ttaggacggg ggtgacagcc aggaggaccg cacctgccct 1560
ccccactcct gccgctccac ccctgccccc accgcaacac caaggtctcc accaggaaga 1620
tgggggtggg gaaaggacgc ggggtggggg ggggtgcggg gagagaggac acagggtcgg 1680
aagggtgagg ggtagtggca gaggcggagg ccgaggccac gcagctgcgg ggcgcaggga 1740
ggggcagagg aggggcgttc agatgggaac ctagtccaga cccgtcgggg ccctcgtgtg 1800

-continued

```
cggctcgtta tcctggaacc agagaggctg gagacccttg gcttgtctgg agcggaaccg   1860
tagtgtccaa tagagtgtgt ggggctcagc cctaaagcta aacattcttt atttcctgat   1920
gaccatgggg gcggagcggg ggaaaagccc tggccttata gtttagaatt ttataaaagg   1980
aaaggcgtgg ccactgacaa tttgcgcttc aggagtccca gagtgaccgc ctggctcgga   2040
gcagggaatg agggggtcct taactctgag atttgttttc tgagagacaa aggtgatggg   2100
tgaggcggct aagcctctga ttctctatag gtggcggtca ttcatttcag aacatgaatg   2160
gattcagtaa ataaacatga tagaaaaatg ccacaagccc taggcccatt ggagtggact   2220
ggacagtctg ttcccagtgt gtccctcagc ctcggtcccc caccettccc ggagccctgg   2280
gggtcacaca catccctcct ggctgcctag cctgtgcccc ccgattcccc ccctccccgc   2340
cccgcgcgtg cacacacaca cacacacaca cacacacaca cacacacacc acacagcacg   2400
aggcgacaga gatatgagag agagcgagcg agagaggacg ggagagagag ggagtgcaag   2460
tgtgcgctgg gggtaacccg tgcatgcatg cattgggggt aacaggctgg agctcagatc   2520
cctcccccag cccccagcag gggggactgc aggctcctgg tctgagtggg gagctgggcc   2580
ccctggacag aggactgggc tgcggggtca ggaatgggca cacttcctaa ctgcaggaca   2640
ctctaagggc tttggtcatg cacacgcagc caagagaagg tgtcgctggc acacagcctt   2700
ccaggagcgg acttggagac ctcgccaagg accaggactc cccagcactc acactccctt   2760
aggcgctgaa gtccagagga cagaggttga gggcagagct cctgggagca ccagtggaag   2820
taggagggct gggctggaaa acctccccca acctcctatt gcaaagaggc tccagccagc   2880
agcctccaca ccccagtgat cttttaagat gcaaatctgc gccatcattt atttcctcag   2940
tgccttctcc agctcctggg atgcacactg cccgtcccca ggcccagaga cctgaccacc   3000
ctcattcctc cctcagccca ccctggggtc tctccaccag ctgacagcct tcctgcagtc   3060
ccctccccga atgctgctcc ctgaggccct cctggacacc tgcagggcag gcacagcccg   3120
cgggacctca cagcacttgc tccgggcaga gctgcagttt ggccaagttg ccagctccgt   3180
gtgggcaggg gccctggcct gtggctgcca catcccgggt gggggcacgg cctttcctgg   3240
cgtggatgct gagcaaacgt agggggaagg ggagtgaatg aggagagcca ggtagctcag   3300
gggctgaggc ctcactgagc agggtcccgc gtgaccggtc cccaccgctg acggttcctg   3360
gggtaacact caggacaggg agaggcaatg gaaagagacg tggccgccct cgcatcctgc   3420
agctcccgca ctcccagcct cccagcctcc cacccagccc cccagagccc accagtgacc   3480
ccgcccactg ggtcctcaga tggctcccac gggatctcct gccttgatct cctgtccaca   3540
tggaggtgaa gtgggttgct ctgaatgagg ggtgccgagc ctagggcgca gcccactctc   3600
ctgggtccgc agcatcacgc agcccggacc acaggctcct tacaagaatc ggaagggtcc   3660
ctgcaatcgc ccttcgcact gaggcttcct actgtgtggt gtaaaaacac aggcttgtcc   3720
tcccttgctg cccacggggc tggagccgcc tgaaaatccc agcccacaac ttccccaaag   3780
cctggcagtc acttgaatag ccaaatgagt cctagaaagc gagagacgag aggggaatga   3840
gcgccgaaaa tcaaagcagg ttcccctcct gacaactcca gagaaggcgc atgggccccg   3900
tggcagaccc gaacccccag cctcgcgacc gcctgtgacc tgcgggtcaa ccacccgccg   3960
cggctccacg ccgtgggcac agactcaggg agcaggatga gaaagctgag acggcgcagc   4020
cacggcccgg tgccttcacg cgcacagcga cacagcccca gccagcgggg cccacgctaa   4080
ggcggaatcc cacagaagcc tacagagcga gcgcgcgcct gtgcttccca aaacggaatg   4140
gaaccaaggt gacttctaca gaacgatctg aagccctggc tggcccttat gctagtctct   4200
```

tgggagcgtt ccaaatgcag ctcaatatta cttacttgac ttttatcttt cctccctggt 4260
tcgtggtatt tataactggg tcatctttta actatttgca acgtagcttc aggggagagg 4320
gggagggctt tataaataac ctgtattatt attatgcagg ttgattctgt tccctgagct 4380
aaagggaaca tgaaaataca tgtctgtgac tcatgccccc ccaccccac tccagggtgt 4440 gctgaggagt ctctcagctg ccccggggtc ctcgagcagg ggagggagaa aggctggcgc 4500
tgcgccctcc atcgcgtgaa gccaggggat tttgctctgc gacaagctga cttggctctc 4560
gtattgtttg cagaatcacc cagttccaag gcagtccctg cgggcaggtg cagctgtgcg 4620
ggagcttcag tcctgtcccc aacacccagg cagtaatggt tccagcacgg aaggtctacc 4680
tacctcccac tgcacagccc gagggctgtc ctggaggcac agccatccgt ccctgggtgg 4740
gcaggcacgt ttatgacccc cacccccacc cccacccccc acgcgagtca gcacgttcca 4800
tactcgggtg atcgtgctca tcccctggtc atgtcatcgg gatctgagtg ccatccgagc 4860
agagagctgt ggcccggtgc cgggggtgga cttcatctat tccagggaac caaggatgca 4920
tgatttgcaa acaaaaccag aagcgcaagc catctcctcg cctcccctga tagccgtgct 4980
gcggagcctg agtgctggag 5000

<210> SEQ ID NO 240
<211> LENGTH: 600
<212> TYPE: DNA
<213> ORGANISM: Homo sapiens

<400> SEQUENCE: 240
caggaaccac gggacctgct gcctagcggc cctgttccac ccttggccgc tcgcaaaatg 60
tttaggcttc ataaggtttg cccagggtca caaatttaac tcacagcaaa caatgaaatc 120
agcgcatgat tttcgagccc tcgtggtcac cctcccttcc tcctgccctt tcctgcatgg 180
gcagcagcag ggtgaggagc tgctctcccc aggcccaggc tggagtccct cagacgacct 240
gccggccagg gtacccccct gcccccacac agcgcctgac agagcccccc acactggggg 300
aacgtgggga cccaagcagg ggcagcggcc tcaccgggca ggcggcgacc tgcatcatgg 360
cgtccagccc accctcgggt gcatccaggt ttccggaaat cagctgcttc ccgacctcgg 420
tctgaaactg gttggagttg ttggtcagct tcagcacgtg cctgaaggca aacgggggct 480
ggcactcttt ctccttgttg gggcatgggt ttcgcagctt atcagggtgc gtgttcacga 540
acggcagcac ggtcttgtcc acgaaggacc cgaagcctgc agggcacatg gaggggctgg 600

<210> SEQ ID NO 241
<211> LENGTH: 400
<212> TYPE: DNA
<213> ORGANISM: Homo sapiens

<400> SEQUENCE: 241
tgcgtttagt gtaaaaatat caggtgtggc tgcacggagt gaaaaatcac aggctccacg 60
gagccgggag gcctgctgcc ctgccctctt gctttgatga ggaaatggcg accgcagaag 120
gaaatgtagc agcaccggca accggcatcc gtggggccac gccgggctgc ttcccagggc 180
cctccagcca agcagccaca ggaaagagta gatgttgatc ccaagctagg actgaggagt 240
ccgtccctaa gagccgaggg agtcaggtgg gcgaaactgg ccgcatgtct gggtacaact 300
gctcagggtt tctcatctgc tgaatcacca agctaggttc tgaagccagg cgtgagtgag 360
caggactgga gcaggattct gggaacaatc ttttccctcc 400

<210> SEQ ID NO 242
<211> LENGTH: 2000
<212> TYPE: DNA
<213> ORGANISM: Homo sapiens

<400> SEQUENCE: 242
gctggggaac tgaaggaagg gctgtggagc ctgaagcctg ggcctggcct gtgctgcggc 60
cgcaccgctg ggtgatgcag gagccactcc acctccctgg caccccagcc tcatccggca 120
acctgggagc gtgggcctcc tgcccctcca gggaggccct ggccgtgtcc tcatggggcc 180
cctccaggtc cttgtggctc caggtcggga cagtggctgt gagatctgac cctcccgttc 240
cccctccacc aagtaggaga aaccccggag catgagccct cgtccttcac cgtcccgggg 300
acagggggac ccccagatgc tgcacggctg acaggccaac gtggcagaag ctccagcttc 360
acaggaagcc agtgaccatg agagtctgta gctgtaacga agccacagag ctgtggcttt 420
ctttcccctt cagctctagg aaaggttatc tgccctgcac agatctccgg aggcctggct 480
gggctctgag agcatcagac tgattatcgt aagaaaataa tctctgcaga cacattcctt 540
gctagaagca ggggacaaag cccagcttca aagacaattc cacacacgcc ctccctgccc 600
tgcacagctg cctgccgggt gggagcagag cccttgcagc cgggctcagg ggcctgggca 660
gggacagcgt gtggcagggg cacagctgag acaggagcct caaagcgaca ccaacccgac 720
gtgaagctac agttgaggag acacagctgc ccccattccc gggcctcatc tccacagtga 780
gacgctggac tctctccctg acccaccgtc tcttagaacc tcccctccat ccggagcagt 840
tcggcagccc cagggcagcc aggggaaccc tgccgagtgc ctctgggccg ccacagaccg 900
cagagcccgc gggagccttg ctcacacagc ctcaggtcca ctgtggtctt gggggaaagc 960
cctgtcctgg gacaggggag ccgggggtcc tggccctgga ccaccatctg gggaccacgt 1020
tgtcacgcct gcaaagctcc ctgccccacc cccatgtgcc ggctggtgtt gacacctttg 1080
tagagtggga acctgcctcc gaccccagcc tgcagccaca gggcaggtta tagaccaggt 1140
gagagggcgc cgcgcccaga accaaggagc acaagtccgc agtgcccatg agatcctcat 1200
gctggccggc gcaggagcca tcctcggcct ctgcaggtcc tcgtgggaaa ccgcgggggc 1260
acgtggggcg gctgcagggt ccgcaaagcc ggctgtttgc gaagggcgca gctccacctg 1320
gaacagccga ggccgcccac gcgcttcccg cgggatcaga gcagcctcca cggctgttgt 1380
ctcaggcacc acgggatgcc tttcttcgtt tcaatagctg tgggaaagcc tcaatcggtc 1440
ctgaaagaac ccagatgtgc agcaatgaca aggccttctc tgagactcta gaaccttctg 1500
ccatctcaga caggagggag ccgtgaggca ggcgggagat ttgcagtcag caaaggacgg 1560
gcaggtgggg cagctgcaca cccagggccc tctccacggt cttcccgggc ccacccctcc 1620
cgcggtcctg ggtcatccac ctgctggcct cactctgccc acgcggccag gtcccaccgg 1680
cccctgagct caacagacca aagctggccc gaccccaccc ccaagaagaa tgaaacaatt 1740 ttttttacc tcttgcagaa aagtaaaaga tcatttattc attctgtttc tagatagcaa 1800
aactaagtgt caaaagcacc ttctgcacac agtctgcaca cactggccgg tggtcctgtt 1860
cccgcaaggt tgagctgtgt tccagagaca tgggtcctcc gggtgatgag gagccgctgg 1920
agggccctga gctgcacgtg ctaatgatta acgccccgtc cgtgctggcc ggtttctcaa 1980
atgcctcctg acgattgcgc 2000

<210> SEQ ID NO 243
<211> LENGTH: 2200

<212> TYPE: DNA
<213> ORGANISM: Homo sapiens

<400> SEQUENCE: 243
ggcctgagga gtcaaacggt gcaaaccctg ccccactctg tttgggaagc acctgctgtg 60
tggcaggcgc tgcgcttggt gctggggata gaccatgggg aagaaacaca cagaacctgc 120
cctgctctca aggaacaggc cctgggggcg gccaggggca gagacccaag gcagacaccc 180
acacagtggc gtaatgacag tgcttatggt ggggacctgg ctgcacagca ggtcagcaag 240
gggatgttca ggtgacactg gggcacgga gacccagggg agagtggatt gacagagggg 300
acgctgggca aatgtcccga ggctgaggtg gagttgcggg aaggaggagg ctgccgggca 360
gaggcgcaga gagctttgca ggtgttggca gagaccagca ggccctgcga ggcctggggt 420
gtgtcctcag ctgggagggc catagaagga tctgggcttg cagatgctgg tgcagactgg 480
aggcctgggg tgtgagagtc caggcggggc tcctgccaac acccagggga gtgggcctgg 540
gccaggtgga ccgggagctg gcacggtggt caggtgcttg gaggctgcgt gccacgctgg 600
ggacctggag gtgtgtgagg aggtgtctgt tgctcctggg gctgccgcct gcagggctgg 660
gtgtgcagca gtgcggggca atgaagtggg cgggttctgg gatggtggac gttccctttg 720
ttgggaacgt gttggtgcca agctgccatt tgagtttggc tctgaggggt ctgggcaggg 780
gacacacagg gaatcacaca ggatggagtg agttcccagg gacccagggt ggcttggcct 840
gagaacagct cccactccca gatgtgtggg aagccctcgg caccaagcct cagcctctcc 900
atctgtgaaa tggagacaac gtcactggac ttgcaggctg tccatgaggg tgatgcgatc 960
agaaagggtg gagttcctga acgccccggg gtcggggtct cacagcagga gcttagctgg 1020
tgtcggcatc tcctggaccc gtcctcagct ccgagcgccc agtcctgcca cctgtgtcca 1080
agtctgcact gtgcccacga ggccctcaag gccgcagaca gccccacact tctcggacgc 1140
cgccccagca cggtccttgt gtgaggtgga cactccttct ggacgccgcc ccagcacggt 1200
ccttgtgtga ggtggacact ccttctggac gccgccccag tacggtcctt gtgtgaggtg 1260
gacactcctt ctagggaagg agtagtaact cttgggtggt cgggtagttg ccatggaaag 1320
gggcagtaat gcccaggtat tgccgtggca accgtaaact gacatggcgc actggagggc 1380
gtgcctcatg gaaagctacc tgtgcccctg ccctgtgtta gctaggcctc aatgtggtcc 1440
agtatctgag caccgcctcc tgcctcagat gttcccgtct gtcaccccat taccagggcg 1500
gcacttcggg tcctttccag ccatcattgt cctggcattg ccacagtgga cactgccaca 1560
caggcttgtg tgcttgcgcg tacccaggtc ctcacctctc tgggataaac caggcacgtg 1620
gcggccgccc cattttccac ccgccagcgg tggaggagtt gcccagcctt gcaggaaaac 1680
agctctcatg ccagcagcgg agcatcctat tcaagttttc tcagggctgc cagcacaaat 1740
gctgcatgcc gggcggcttc ctcagcagac cgttgtttct ctgcgtcctg gaggctggac 1800
gtcccaggtc cccgtgtggc aggcccggtt cctcccgcag cctctccttg gcttgtgggc 1860
ggcgtctcct ccctgggtcc tcgcagggcc acccctccgt gtgtctgtgt cctccctccc 1920
cttataagga ccccaggcag actggatcag ggcctgccct aaggactgaa ttttacctta 1980
atcacctctt taaaagctgt ctccaaatac agtcaccttc tggggtcctg gctgttaggg 2040
ctttgatgca tggatttggg ggacaccgct cagcccctaa cagcccccat cctctgcctg 2100
cctttaccat ggggctgagc ccagccctgc aggagtcccc tggtttgatg tctgctgtgg 2160
ccacggcgac cctcaggctg ctccagccgc acttgtgctt 2200

<210> SEQ ID NO 244
<211> LENGTH: 1600
<212> TYPE: DNA
<213> ORGANISM: Homo sapiens

<400> SEQUENCE: 244
ggggagtctc caggggctgg ggctggagcc gcatcagaga ggaaaggggt gtttgaaaaa 60
ggggcagggc ctgggaccca ggaaactgtt cttccagaga cacccgtgaa gctgagcttt 120
gcctctcagg gaagctgtga ccccacgggt gctgcccaga gagatcgggc caggtggagc 180
caagatggac tggaattccc cgacggggac aaggggccgg acgaggctga cttgccctgt 240
ctgatgaatg gtcaggtttg ctttttctcc tgaaaacacg aggcagtgat cccggccagc 300
taattccagc agactggaga cgggatggtg gagaatgagg ctgtgggcgg gaagagcaga 360
tgggactcgc cagcatcctc acggcagggc cgcgctattg ccctccctcc cctcctactc 420
tctggggtcc caggagcccc agatacgcaa tgctgccagg cgatttctgg cgccccgcag 480
acccctgccc ctggagttgg gccaggtccc ggctggagca aagggggctc cttcaagccc 540
gctcctccct gtcaaacccg aggagcctga caggcgcagc gtcaccagcg tcaccgggcc 600
atagtgagcg gccaagccag cgtcaccggg ccatagtgag cggccaagcc agcgtcaccg 660
ggccatagtg agccgccaag ccagcgtcac cgggccatag tgagccgcca agccagtgtc 720
accgggccat agtgagcggc caagccttgg tctgccagag ccggccgcac cagaaggatt 780
tctgggtccc cagtcctgga ggagcacacg gtttacacca ggccttggga ggggaagagg 840
caaggcgtgg gcccagccct cactccccag gagaaaccct gtttgagcgg cagaggagac 900
tggagagacc ccagggcggg gatccctgag aggagagaaa cccggaattc atccacggag 960
gcgttcaccc agaggagacc cggagcttct ccaggagagg ctggattgct ccaacagggg 1020
ccctgaggag ctgatggcaa gagcggaagg cagctctgac tcgtgcgtct gactccaggt 1080
gtggccgttg gggctacagt gggaccagcc tgttgtcact gaacccacaa agtgcctccg 1140
agcgcgggtg gagagagggg gacctcccac cgtctgctgg ccttgaatct tgaatctaat 1200
tcccgtctgt gctttgatgg gagaggcact gggagcgggc ggctttttca gttcctttta 1260
tcttgaatgg cctttggggg attttcacag attctgagtt caaagcccag ggaggtgtgg 1320
gaacgtgaca ttcctcaccg cattcctcac cgcattcctc tgtaaaccag gcggtgttgg 1380
cacccatgag cctgtgtctt ctatgacatc aggagtttta tccctcacgt cagaaatcag 1440
ggttccaggc gccttggttt ttcttggcgc cagcggcttg gctatagaag aaaaactgaa 1500
ggggccaggt gcggtggctc acacctgtaa tcccagcact ttggaaggcc aaggcgggtg 1560
gatcacgagg tcaggggttc gagaccagcc aacatggcaa 1600

<210> SEQ ID NO 245
<211> LENGTH: 7000
<212> TYPE: DNA
<213> ORGANISM: Homo sapiens

<400> SEQUENCE: 245
gctcctcagg gggaggttcg gggcctttgg tctctggact tgggcagcag aaaggaaaca 60
tccctggggg cctgtggtga cccccatcct ccccagggtg gtctggcagg ggacactgtt 120
ttccaaagca aagccagagc gccaagggct ctcgggattc acgagatcca catttatccc 180
aagttagaac agcacatctg tgcgtgcaaa cttcattctg acttcggccg gctgtccttc 240
ttgcccaaag caccgtgagg cctcatccct gcatccctgt tgcttctttc atgtgggatg 300

-continued

```
agaacccagg aaggggctga gtgtgactcc tctggttttt agagagcact gcccccgccc    360
cgccccctcc tgcttcccca ccttttcaca gttgcctggc tggggcgtaa gtgaattgac    420
agcatttagt ttgagtgact ttcgagttac tttttttctt tttttgagac agagtctcgc    480
tctgtcgccc agggtggact gcagtggtgt aatcttggct cactgcaacc tctacctccc    540
gggttcaagc gattctcaca tctcagcctc tggagtagct ggaattacag gcgcccgcca    600
ccacacctgg ctaatttttg tgtttttagt agagatgggg tttcaccatg ttggccaggc    660
tggtctcgaa ctcctgacct caggtgatcc gcctgccttg gcctcccaaa gtgctgggat    720
tacaggtgtg agccaccgag cctggcctgg agttattttg ggagagggca gcccctggtt    780
cagcgtggcg aggctgcgct tgctctcccg ggcgggcgtc cacaccctcc tcgccgagat    840
ggagaagccc aaacccctgc agcgctcccc catcacgtcc ggccctggaa gcccccggaa    900
accctgccac gccctgagtg ggagagcgca ggtccctttc cggccctgga agcccccaga    960
aacccttggg tgccaggcct ggccgggaca gcagcgacac tgcatgctca gcccttgcgt   1020
gagaccacgg gagtgtccgc cctctgcacg tgctgctgat tgcccacttc gtccagcagg   1080
tttgggagct tgtggctgca tcctcctgca gacacttgcc cattctgggg cctcctctct   1140
gtcttttctc ctctgttgag gggtctggga gggaggcctt ggagggtacc catgctgctg   1200
ggactgatgc tccccgcggt ggaaggagct gcctcttgaa cagcaggggg ctgagcagag   1260
gggaggggat gcgggggtgc cgtgcacaca ggtgctctca ggacgcaggg gcttctcagc   1320
cctgctgtcc cagggctgca ctccagcagg gcagactcct gaggtgcaga caccccagct   1380
tcacgctcac acttctggaa ggcgatgtct gtgcgtttgc tttctgctgc agtttaaaaa   1440
gccgggctct ctccggagcg tgtgtagggc ctggtcactg gaatatctgg actcagtgtt   1500
aatggcagcc acgctggggg ctgggcccag ctttctgttc tccgtgtggg tgccatatcc   1560
acctccatcg cagccctttc tctctcgacc ttttaaatca cagtgtcacc tccccctgct   1620
gtcctgccag tggcccctgg aggcttctcc ccacccctttt cttctggggc aattcttaag   1680
gctggcattg aatcaggagg ccagatgtgg cccctagtaa ctcaccagca gtccctgagg   1740
cttctggctc ccctggccca ccagcctccc atgtctgcct caggcctctt gacccgcctg   1800
gcactgacca gactgtgtgc ccgggtgccg tgcccatggg ctccgcctcc cccaggcagg   1860
ccccctcttg ctccgcggcc accccctgctc ttgacctcac acctctgcgg tgtgtctgga   1920
cacaccagca ccacggcggg cggggagcgg aattctccag gtggggtggg caggccggcg   1980
ggtgttgagg tctctgtgca tgcttgtgcg taccctggac tttgccgtga ggggtggcca   2040
gtgctctggg tgcctttgcc agacaactgg tctgccgggc cgagcattca tgctggtcgc   2100
catcacgtga ctcccatgcg ccctggccct ggggttgggt ctgcaggact gagaaccagc   2160
ggaagggggg cgaggcctcg ggaatgcgcc ggcaactggc gatgagctca ggcctgacta   2220
atgagcccag gtgactcata cacccggggc ctggatgagt ctgactgggt caggacttcc   2280
ctgcttgttc tgtcctggga gatgttgtcc ctggccctgc agagccggga ggacacgagg   2340
cctcctgggt cacagccaac gcagcctact cctgcccact gctcgcgccg gccaaggccc   2400
gtcggcacca cctcctccat gaagccttcc tgactgcccc catccctctg tgggcagctc   2460
gagtgtgcat cttgagtgct gtgcaggttg gggtccggcg ctcctgcagg caggcggcgt   2520
ctgggcctgg gggctctcag agtttgagga gcgtgtggtg agggtggcct cgggcctcaa   2580
agacgcagcg ctgtgggaac cgggagactg gctgagcccg ctctgaggaa ggtggggcca   2640
```

-continued

```
ggggcaccct cagctgaccc ggcgtgcagg ggtgaccagc caggcgtggc caaggatggg   2700
gtctctggga tcaggagact tcagtagcag ccaggaccga ggccaccagt ttccaccctg   2760
gcattttcca tcttttgaag gactggaaac gattggattc tttaactttt ttaagttgag   2820
gtgaaattca caacgcataa aattaaccat cttaaagcga acaattcggt gacatttagt   2880
acagccagaa ggctgtgcag ccatcaccac tgcccaactc tagaacattc acacgccgga   2940
gagagggagc cctgggccat cacgcagcca ccgcccggcc ccaagaacct gcgagtccac   3000
tttccacctc tggatcggcg gttctggacg ttcatgcagg tggttcccgc agtgcgaggc   3060
cttttgtttc gggctcctct cacaagcctc acgtttccag gtacgtcgtg gtgttgtgca   3120
gacccacaat tcatcccttt tcatgggtgt gtaatagtcc accatagatt ctctacgttt   3180
taaagcatgt tttatgtgcc tgaaatgtct ctgcactcga gactatagct tgctttcttt   3240
cttttctttt ttttttttta atttgagacg gagtcttgct ctgttttcag gctggagtgc   3300
agtggtgcga tctcggctca ctataacctc tgcctcccag gttcaactga ttcttttgcc   3360
tcagcctccc gagtagctgg gactataggc gcgccacccc acccggccaa tttttttgta   3420
tttttagtag agatggggtt tcatcatgtt ggccaggatg gtctcgatct tccgaccttg   3480
tgatctgccc gcctcggcct cccaaattgt tgggattaca ggcgtgagcc accgcgccca   3540
gccgagacta cagctttctt taactgcatc cctggaggga tctgagagtc tctttccctg   3600
tctcctttcc tttggaaaac atttcagcca gggctcccca agatgaaagg ccagagtccc   3660
aggcatgggc gttgcaggtg cacagttgcc acggggagct gtgggtgatg gtcgctgtca   3720
gcgatggctg ctgcaggtcc ctgtgaggaa ggggcagtgc cacagcagga ggagagggag   3780
tcagcggacg ttgattggca gtgcccgccc attccatcat tcagtcaccc actgtgcacc   3840
cagcacccag gctcggctgc atagaacatg gcccaggaag gctccacttc ctgtctcctc   3900
ttctcccctc tccagtctca tgatggggct ggaggcatct tctagttttg agttctgagc   3960
taatgaacat gctcatgagc aggcggcagg atcccaggac ggtggagctg ggagcctgac   4020
tgcgggtgac ggacaggctc tggcagcccc tgtcagcatc ctctccaggg catgtgaaag   4080
ccagtgtgtc ctcagctgcc agtgccccct ccccacctcc tctgggccca tgtgcacggg   4140
acctgggctc ccccaaccaa gcctgcccgc cttggttcag cagaacggct cctgtctcta   4200
cagcggtgcc aggccaggag tgctgtgtct gtgaagcggg gtcatggttt tggggccctc   4260
atctccctcg cgccctctca ttggggaccc cccgtctccc tagcgccctc tcgtcctctc   4320
ctgcatgtgc tgtgtctgtg aagcggggtc atggttttgg ggccccccgt ctccctagcg   4380
ttctctcgcc ctctccagca tgtgaagtgg ggtcatggtt tgggggcccc catctcccta   4440
gcgccctctc gttggggacc ccccgtctcc ctagcgccct ctcgccctcg cctgcatgtg   4500
ctgtgtccat gaagtggggt catggtttgg gggcccccta tctttctagc accctctcgc   4560
cctctcctgt atgtgaagtg gggtcatggt ttgggggccg ccatctttct agcgccctct   4620
cgccttctcc tgagcgtgtg gaactctgtg gtggtcagag ctaaggttct gaataggtcg   4680
aagcacctcc ccggtgcctc tcaccctgaa tgctctggga ggacacagcc ttttcatagg   4740
ctacgactga catggcagga ggggcctgcc tgccacccgg gtcctctgct gcctgctgct   4800
tgctggggag ggggctcgag actgggatcc tgggcttctg ctccagctgt gcccaaggga   4860
gctgctgagg agggaccggg tggggcatcc actctgggca ggttcagggt cattcttggt   4920
gaccccgggt ccggttacaa aggctgatgg agcgcgtggg tggctgccta agtctctgga   4980
agcccaagaa tgtggagatg gcgcgtctcg gcccggggtc tcgtggctgg tctgggagaa   5040
```

-continued

```
cttgccttta tttctaggca ggaggctgca ctgcaaggga gcgtcagtgg cccggctggc   5100
tttccccggc cctcagcccg cactcgtcca ccaaagcaag ctcctttgtg gggctgccct   5160
gggaagccgg gatcacgagg ctctgccggc cgtggtcacc ccatgaggca gggtcagctc   5220
gggagcaagg cggatcagat ggaacagaac acgtagacca cctcgcccgc ccttagtcag   5280
ctgggccatt gaaaatcaag tccgtagaaa gacctagaaa taagtcccgg ggtgcccttg   5340
cctgttgacg ggcgggccga gcaggactgt tctcaggcag gcactggtct cttggcttcc   5400
aggtggtttg tttgctggtt tgaggctggg ggtgacgctc ctgtgcggga ggaggtcgca   5460
ttccattcat agcggcttat ctgggctgtc aggcaggcct gggagggagc ctgcctctgt   5520
gctctccaag ggtgggcgac ggacagacag ggtgtcccac cccttctggg ccaaggacag   5580
agggtcagtg tttgcagaga cctggggagg cccaggtgac ctccaccgag cacctgctgt   5640
gtgcagggcc agtgctggct gcagagacag cggagcgtgt gtggacccgg cggcccaggg   5700
gagggggca ggcaggaccc ggcggcccag gggaggggg caggcaggac ccggcggccc   5760
aggggaggtg ggcaggcagg acccggcggc ccaggggagg ggggcaggca ggacccggcg   5820
gcccagggga gggggcaggc aggacccggc ggcccagggg agggggcag gcaggactcg   5880
gcggcccagg ggaggggggc aggcaggacc aggcggccct gggggtcagg ggtggaggcc   5940
aggcctagac ggcccacagg agggtggact cattctgacc gattcctgga agcccccgga   6000
aagtggtgat gttctggagg gcccagcaga ccccaaggcc cccaagacaa tcccagctgg   6060
ctctctgcgg ctctcggtgt ctgccatttg agacaatttg ggcacaggca gggcaggccg   6120
tcgcggacgg tctaagccgc gcgcattggt gggggcagca gagcccctgc tctcagctcc   6180
tcggggtaca gcgggggtac caggcgggtg agtgggtggg tggtcactgc tcctgccaag   6240
ggcagccctg gtttggtttg cacttgctgc cctggtgacg gctgctctca ttcctgcccc   6300
attgctaaca agggtgtcat aagctacttt cccggcccac atcctattaa gcccatggag   6360
accctcccac agctgagcct gctgtgggct gcaggccctg ggcggtgccc acctcggtcc   6420
ccactggcct ccttccagca ctttagagca gacacaggtt ggagataagg aaagttccag   6480
agcacagact ggaacaagcc ccaggcctct ccctgcccca gcagggcctc cctggatttg   6540
ggggacaggt gccctcatgg ggggtcctga aggtcagagc tggggctggg gctgggctgg   6600
cggaggtggc cttggcggag gccacattcc agggtctcag tgagagtctg tggcaggcag   6660
ccttgcagat gccgctgagg gaccccccac ttcatgttgt gggtgatgtg gtccattgat   6720
tgcctccagg tttaaatcag gtggatattt acctagcggc ctcctctccc tctgcacagg   6780
gcctggagtg ggatggactg gggtgctcag ctggaggctc tgcagacaca gccccctggg   6840
ctatgcaggc cctgctggga gccacattgc catttttcat cacccacttt ttgggtgaga   6900
acccctcga gtcctaacat ctgccgcatc tcagagcctg tggctccagt cagagcatct   6960
ggaccatact gctggggtca gagcgcggca ggacaatggc                        7000
```

<210> SEQ ID NO 246
<211> LENGTH: 1500
<212> TYPE: DNA
<213> ORGANISM: Homo sapiens

<400> SEQUENCE: 246

```
tgccaccacc atcttcaggt agagcttctc tctcctcctt gctgggcggg gcccctccct     60
ggggaagcct gcaggaccca gacagccaag gactctcgcc cgccgcagcc gctcccagcc    120
```

-continued

```
agcagctcca acgccctgac gtccgcctgc gcacgccact tctgcacccc ctggtgatgg    180
gctccctggg caagcacgcg gccccctccg ccttctcctc tgggctcccg ggcgcactgt    240
ctcaggtcgc agtcaccact ttaaccaggg acagcggtgc ttgggtctcc cacgtggcta    300
actctgtggg gccgggtctt gctaataact ctgccctgct cggggctgac cccgaggccc    360
ccgccggtcg ctgcctgccc ctgccaccct ccctgccagt ctgcggccac ctgggcatct    420
cacgcttctg gctgcccaac cacctccacc acgagagcgg cgagcaggtg cgggccgggg    480
cacgggcgtg ggggggcctg ctgcagacgc actgccaccc cttcctcgcc tggttcttct    540
gcctgctgct ggtcccccca tgcggcagcg tcccgccgcc cgccccgcca ccctgctgcc    600
agttctgcga ggccctgcag gatgcgtgtt ggagccgcct gggcgggggc cggctgcccg    660
tcgcctgtgc ctcgctcccg acccaggagg atgggtactg tgtgctcatt gggccggctg    720
caggtaactg gccggccccg atctccccac cctttccttt ttgccttgcc aggtaagtgt    780
gggcggggct gacgtgagcc tggtacaggt tccccccaca tcgaatctct acgttcaggg    840
gcccgtggcc ctcgggaggt gggagagctg ggagtgaggc ctcctgtgtg gggaggaggc    900
cggcgtctgg acaggaagag ggctggatga accgcagccg atgtgtccag gtgccacctg    960
ggcctggagc tccctgagca ttttagcgca tttagtcctc agcacggtcc cgagataccc   1020
tgccatgccc cgagtcacag aggggaaact gaggcgtggg gcagtggcgt gactcacccc   1080
agggagccga gattcccgct caggtgtggc tgcatcgacc ttgctccggt cactaagctg   1140
cacggttcga tgcgcttcct gggagcccca gcgtgctcgg gccaagggtg ctgccgcgtg   1200
ggcagtgcag agaccctacc agcgtgggga ccagggaggt ctgcagggcc cgtcctgaga   1260
gggagccttt catgtccccc tccccatcct gaagcacaca gcctccctgc cacagtgggg   1320
gccgcttctg ggcccagggg acgttgcccc atcaccgtgt ggcctggcct tgttgctggc   1380
tggacagttg gggcaggaa gaggagggaa agggggactc tttaacctcc tgggggcagg   1440
ggcagcccag aaaggacccc agcagatccc tcctctgtgt ccgggagtag acggggcccc   1500
```

<210> SEQ ID NO 247
<211> LENGTH: 2000
<212> TYPE: DNA
<213> ORGANISM: Homo sapiens

<400> SEQUENCE: 247

```
gggctccaca gcggcctgtc tcctcacagg gttcagccca gtctgctctc actcatttgc     60
tgattcattc tttcattcag ccagtcaata gtcatggccc ctcctgtgtg ccgggtggcc    120
atggatattg ccctgggtaa cacacagcct ggccctgtgg agcagacagt ggggacagcc    180
atgtggacag ggtgcaggtg gatggcaatg gcagctgggt caggaggggc tgagggccgt    240
ggggaaaggt gcagaatcaa taggggcatc cggactgggg tgcaggcctg ggggctggga    300
tttctagggt ggaggtcacc tctgagggag acagagcaag gccctgggag attagaaggt    360
cgaaggtcgc cgtgttgagg tcaggggccc tgaattggag ccgcggcaaa ggagagggca    420
ggtcagggca cgtggtgagt gattgctgcg gcttctgagc acggctgggt ctgtggggcc    480
tgagcagagg tgacccgcga tccggcgcca cggcaggcag gactccccac ccttgctgct    540
gcctacaccc ccagggcagc cccagagtcg ggggcgcagc tccctgcttg ccagttcaga    600
gcccagcccc tctcacccag cccagaggag gacacagatg gaggaggggc acccggaggg    660
tccccccgcc gacaggcccc acgtctccca cctgcaggac aatgaagtgg ccgccttgca    720
gccccccgtg gtgcagctgc acgacagcaa cccctacccg cggcgggagc acccccaccc    780
```

caccgcgcgg ccctggcggg cagatgacat cctggccagc ccccctcgcc tgcccgagcc 840
ccagccctac cccggagccc cgcaccacag ctcctacgtg cacctgcggc cggcgcgacc 900
cacaagccca cccgcccaca gccaccgcga cttccagccg gtggtgagtg cccccccaaa 960
gtgggcttgg ctccatctag cccctcggct ctcggcagca gaagagggcc cagcccctgc 1020
agagctgctg gggtcccag gcttcggcca tgggtggggg tctggcggct cagggccact 1080
cagggcggct tggctggccc tgggacttgc cctctggtgg ccaagcagtg gtcatgaaag 1140
tccagccgct gtcacatcct tgaggaaccg gcgtacctcc gcctacagcg gcagctgggg 1200
gcacccacgt ggcccggggc tgctctgacc tggcagcgta tgggggctgc tgcctgggcc 1260
cctcagtgtg tcacttgcgc gcctcccgct cagcgcccct cggccgtgcc tgtccacaca 1320
ggtgcggggc cggggtggtg cgcccggggc ctgggtgcag ggggcagcgt gggacacagc 1380
ccgtgacgcg cccctctccc cgcagctcca cctggttgcg ctcaacagcc ccctgtcagg 1440
cggcatgcgg ggcatccgcg gggccgactt ccagtgcttc cagcaggcgc gggccgtggg 1500
gctggcgggc accttccgcg ccttcctgtc ctcgcgcctg caggacctgt acagcatcgt 1560
gcgccgtgcc gaccgcgcag ccgtgcccat cgtcaacctc aaggtgggtc agtccagtcc 1620
tgagggcgcg ggctcctcgg cccccacttg acctctgggg tgaactccca gcggggagct 1680
cccctctagg gcctctggag gccaccatgt tacagacact ggcgcctagg ctggcgactt 1740
cagggcaggc tccgggtggg tcacacccct ccaggctcag gccaggcctc tgcatccctg 1800
ggcactgcca cgtcccccag ggcatcccat gaggcccccc cgtggccccc tgaccccccg 1860
ctcccccggc agtgcccctc agagggtccc atgctgctgg accaagtgtc cacacaggtg 1920
atagggctca catacaagcc tggaatcagg aaccgtcctt tgggcctcta gtgccatgcg 1980
ggctggtggc ccctctgcca 2000

<210> SEQ ID NO 248
<211> LENGTH: 2000
<212> TYPE: DNA
<213> ORGANISM: Homo sapiens

<400> SEQUENCE: 248
gcctggagtg tagtcctgct gaaggccaga gaccacacac tccacccaga ctccggatct 60
ccctccccag caggggggatg gaggccctgc cgctgggagt gctggtgtta tgtggaaggg 120
ctgggcttct ccagggctcc tgggaggcct aaacatcttg caaggttttg acgttaatta 180
ctattatgat tgctttctgt gtgttactgt tttccccaca ctttagccag ctaatgtgga 240
gctacagaag gccctcgccc ctacccctcc agatgtccca gcccatgaca agcaggaagg 300
ccgggtgctg ggagacttcc tggggctgga tctgacatca ttccaagcag atgataacct 360
gccttcccga tttccaaacc cacagcaaga caccctggag ttatttataa atgcgagccc 420
ctgggtgcac ttctgacggg accagcaccc tgacggccat gagagggtgg agacagcgca 480
ccccgagctc agggaggcag gaaactctgg acctggaggc cgggcaccat gagggacacg 540
ctgcaggccc agctgctgcc gcctggggcg gggctgccct gcaggctccg ggaaaaccca 600
gaaccaggcc ggatcagcgt gtgtcaagag gcggggcgtg agagatgagc tgcttttttt 660
cttcacaggg ttggcaggaa ctgcaaataa tagaaagtct ttagggtcta acacgctgcc 720
ctgaaaacac tatcattact ttcctaatga ctaactgtgt ctttcagccg gcggggcagg 780
cagctgaggc cgcaggctcc cgcagaggac cgggggaggc tggcagcctg taatctgggg 840

-continued

```
gcgctgacag tgctctgccc agaccctcgc gccagctcca gctccagcac agcagccctg    900
ggtccctctg gccccctgcc cgcagagtcc aggtgtggca gaggccgccc agtatccctt    960
ctcctcctcc ttttctaaaa acagagtctc acgatgtttc ccatgcgggt ctccaacgcc   1020
tgggctcaag cgatccttct gcctcggcct cccaaagcgt tgggattaag ggcgagccca   1080
ccgcgcccgg cccaccttcc cttctggttc atttccagta aggtcctgtc cacagcgtcc   1140
ttcccagcat tcccaccagg ctgcaggcct tggcctccct cccctccatt ctcattctcc   1200
ccgaaaccgc caagcgcgtc caaagcacgg gttcgccaag cgcccccccc gccccactcc   1260
acattccctt ccccgccgac tcagcctccg tagctcgcgg acggcccctc ctcacgccag   1320
cccaggcttt tttttttttt ttttcttcta ttttaaggtt gtcttttaat gacacaagcg   1380
acatttggag acaaaaggac acatctcttc ctgacccacc tccaacccca gctgacggcc   1440
gccctgagcc tggcgtagac ggcccggaac gttccctgcg tgggttccgt ccatcccgaa   1500
cccctgtccc cgcgccggct ccgggggtgc tcgggggggcc gcgtggggtc tgtgacgtcg   1560
cctcgaggct gcatcccggt gacccggcag cccctggcgc tcgcgggagg cgggcgggcg   1620
cggaccccag gctttagggc gcgattcctg cagctggctg ccggcccgag gttctggggt   1680
gtctgaggtc tcgggcgggg cgaggacgtt tctccggctc agccccccca cctcctgccc   1740
tgccgccccc cacacccagc tccccacgga cgccaagagg cgcctcccac cccggcgagg   1800
acccgcgggg aaacggggcc caggcgcggc gactgcggag gacgcgcctc ggccccagcg   1860
ccctggtcct cggggcgtcc ggctgccctt gcccgaggcc ggggcgggcg ctcagcgccg   1920
cggaagaaac gcccgggcgg ggacgcacag cgaggcgggc tccgcgggaa gtaccgggaa   1980
aacggcgcgg agcggaacag                                               2000
```

<210> SEQ ID NO 249
<211> LENGTH: 3000
<212> TYPE: DNA
<213> ORGANISM: Homo sapiens

<400> SEQUENCE: 249

```
tggagcaatc ccagagaggc tgaggtgttc aggctggccc cagatgcaca cgagcgtgaa     60
gcctgttcag aagccagctc ctcacaccct ctcccctgcc agaggctcca gcacccctc    120
ccctctcctc tcccctccct tccctgtggt cctcctgccc accccacccc cgtctgcatg    180
tgcaccgtca cggagatgcg tgtactaggg cggaggtcgg ggacagtcgt cagaaggaca    240
caggaaagaa gggaacagga atcccataac agaacattat ccggcaggag taattaacac    300
aggcaggact ggaggctttg ttttgttttg cttaaaaaac agtggtattt aaattaatgg    360
gcatgggaag actattcagt gaaagacatc ggtcattgag gtatctattc aaaaacacgg    420
tttagtactc tgccacacac cgaacgcaac gccacagcag ccatagaagc gtgtgtggct    480
gtttaacgtg gtctttttgg ggagggcatc ctaggcagag caggcgtgga agggaaggcg    540
gcggacggaa caaaacgcgg gcacgcaacg gctgctgcgc cggatctgag gcagggccag    600
cctgtgggag cagcaacatc gctcgcagga cagcgatgga gcccccacga atccgcgtga    660
aagcagcaac cacctagaaa tgaacgtaca gctgcttaga aacagaatac ggatgacccg    720
aaagacttcc cgatggtagt caccagcata caggacctga cacgggcgtg cgggcagggt    780
gtgccgctac ggggtccctg gcgcacctgc taccccctgct acccgcattc accgcacgcg    840
gagggtgcgg gccgtgaagg ttatacatgc aaatatcctt ccaccagcca gttctccttc    900
caggaatctg ccacccgacc cttgtgttgt gcacagacat ggtccaggtg tttgcgacgt    960
```

gattgtttat cagagagaga gaagggaaat ctccaggctc gctgtagctg caggagctct 1020
gggggctgcg cccatcgtgg agacggatag ctgtctctca tgaacacagg acagcaagtc 1080
cggctgcggc cacagaagac tcgccctcct ggacgcagcg tcttccttcc tcagccccac 1140
actggaggtg gccagtgcca tccacagcag aaggggccag ccgggaccag gctcacgccg 1200
tggaattctg ctctgtggta agaggaagag cgatagctgg aacccagcgc cgtcgcacac 1260
acagcgggga agagtctcag aaatgttact ttgagtcaaa aagctggaca aaaaaaggcg 1320
caagccagat ggtgctgaag aggccacagg aggctggcag ccagggggtc tggcacctca 1380
ctcggaggcg cagtgggccc gtccggaatt agtggccata cggcaagtgc cgagtggaca 1440
tcaaaccgtc acttcagact cctgcgcttc actgcctgtc ggttatgcct gggttttgaa 1500
atcaagtcac agaacacctg gaatgtggtg tttacgcaga acaaagcggg tgcctcggag 1560
gagagagcct agggacaggg gcacctcccg gtgtgggtgc ccagggttgc agggtggctt 1620
cctctgtctg cgcggttttc agagccccag ggtcctgcct gcccggctgc ctggaggcgg 1680
cccacatcct gctctgcgcc gccgaatctc agcctgaaca gcttcgctgg tgtttgtgtt 1740
gacttatttg ttcttttttt tttttttttt ttttaaataa aggattccga tgctgttaca 1800
gtcaataaaa gccacaggtc tgggtgacct acaaatgtgt gtgtctgact ttctgcagtt 1860
taaatcgcca ctgagcctta aggcgtctgg cccgcgcatt gaggaatcca cgtgggtctc 1920
ggggtcccca tgcctgccca gctccctgct tcagcctggg cgggtctggc gggcatttct 1980
gcgagcctgt ccctgggccc gcctcctggc cagacttcca gaaacattgt ccacatcccc 2040
gttgcacgtc cccccgtcac cggaaactgc agcccacagc actgggaaga acccgggagg 2100
caggcgttag gacggggtgg ccgagacagg gaagggagcc atggcggacg tcctcaccca 2160
agccagggct tcctgcccct gtggtactga caggagcccc gcaggacgtg gggttggctt 2220
tgggcagctc ggtggacact tctctttcag atcctgccac agcaaagctc acgagactca 2280
cttcttccca ttggaattca ctaagaacaa attcaacaat tcagacgccc cagctggagg 2340
tttattttat ggattttacc tgtgcggtat ttagggttgt gtttatgaat aaaggtgtgc 2400
gttctggcaa gtagaaatac agagcttgtc tttcacccaa gtatctgtaa ctttctccaa 2460
tgcagacact aaaatgcaat aaaaacaaac caaacccatt aaacatgaat tagatgaggc 2520
aggctgatgg gaggttgtgg gattaacagg ccgtcagcgg attgaagctg cgcacatcgc 2580
tgggatgctg ctgcgggagg attcggtcta atccgggagc atctggctgg gcagtgggca 2640
gcgtctgcag tcgtggctgc ttgaaggtat gaaggttgtg gcctttgctt ccccccatca 2700
ggctgcccca ccctggaccc cacccagacc cctcgggcac cctggggtca tcttcagctc 2760
ccccttctct tccttccttc tcttccgcct gggcccctac tgtgacccga ggtcagcaga 2820
ggaccctggc aggtggctgc tccctgggac tcgactgtgc aggtgaggct tggggtgacc 2880
gctgctcctg ctcctgctcc tctcgccgtc cccaccctcc tccatcatgc tgtcaacatg 2940
catgtgggct gcagccctca gcctgcagga cgctgtcagt gcagctcctc agtggccagg 3000

<210> SEQ ID NO 250
<211> LENGTH: 2500
<212> TYPE: DNA
<213> ORGANISM: Homo sapiens

<400> SEQUENCE: 250
atcttgtctt ccttgtccca gtcctggaac cagccactgc cccagcagct cctgtgtgtg 60

-continued

```
gtggcatgtt ctggaagcca ggatgcatgg tgctcctggg ctgctgtggg tcctgggctg    120
ctgtgggtcc cgagctgctg tgggtcctgg gctgcacccc tgcagaacac ttccttccat    180
gttcagctcc ctatatggaa ccccagttcc agccccacag cacagggtcc cccagttctt    240
cctgcctcag gtgtgcacca cgaggaatcc aactgccagt atctgtgcgt ggcctcccgc    300
cgggaggagg ctgccggagg ctctgagctc tagccccaca gcactggcac atcctagatt    360
tccgggaaga cacggcctcc tccccagggg aaggtggtgg tgcccacacc cagagcattc    420
attcctgcag tggagacaga gggacctgcc tctccaactg tgggtgtcag gagccaaggc    480
gcatggtaaa tggggctctc tgtgaggcca ggtgcacggc cccatctcca gcagcagcgg    540
ccatgccacc cagctgcact ctgtggggga ggtgccatga ttgacggggg cccctccctg    600
tgtccagtgt cctcctccct ccacgggccc ctctgcacac cgtcctcaca gtctccctct    660
gcacaccgtc ctcacagcct ccctctgcac accatcctca tggtctccct ctgcacaccg    720
tcctcacagc ctccctctgc acaccgtcct cacagcctcc ctctgcacac cgtcctcaca    780
gcctccctct gcacaccatc ctcatggtct ccctctcctt ccacagaccc ctctgctcgc    840
catcctgacg gcctccctct ccctccacgg acccctctac acactgtcct cccagcctcc    900
ctctacacgc catcctcaca gcctccctct ccctccacgg gcccctctac acaccgtcct    960
cacggcctcc ctctccctcc acgggcccct ctgcacaccg tcctcacagc ctccctctcc   1020
ctccacgggc ccctctgcac gccgtcctca cggcctccct ctgcctccac gggcccctct   1080
gcacgccgtc ctcacggcct ccctctgcct ccacgggccc ctctgcatgc cgtcctcacg   1140
gcctccctct ctctccacgg gcccctctgc acgccgtcct cacggcctcc ctctctctcc   1200
acgggcccct ctgcacgccg tcctcacagc cttcctcttt ttccacagac ccctctgcac   1260
gccgtcctca cggcctccct ctccctccac gggcccctct gcatgccgtc ctcacagcct   1320
caccgacgtc accattgctg gccccgcttc aggtgacagg ccacagtagc acctgtcagc   1380
tctgtcccgc tgctggacag ggagatactg ggccactcag cccagcgggg aacgtgtgtc   1440
ccgaaactgc cttgggctcg ccatcagaac tgtggcagca tcttccagcg ttccttttaa   1500
caggctgccg ttggaatagg agtcacggag caattgcagt gctaagtttt ctttaagtca   1560
cacaattgaa ggaggcttta tttttcacac atttcttcca gagtttcctg gtagcctgag   1620
tgcatgggtg atgccccctg agttatttat caggggcagc cagctgccct cccccggggc   1680
acttacagtc agcccatctc tgtcctggtc aggtgggcgc caaggaagac ccggctcagg   1740
gcctctgtat gggcagcctg gcttgtacac acacccctcc ccaccagcag attctgaatt   1800
ctcccttctt catgcacacc gggaaggtcc cttctgcact cataccggga aggtaggcag   1860
gtttcggtag tgtctgcctc cagtgttttc ctcctcctgc tctatgacat catctttctg   1920
tgattttttt tttcttgcag gaagttggaa gcatcatcgg gaaggtaatt attgattgaa   1980
tctctgcctc tcctggggtc tctgtaaggg gatggtgagg atggcagcct ccctgggtac   2040
taggtggcac ccagtaggtg cgcctttccc agttggtggg tggtctgtgt tccatgaaga   2100
caggaccca gaggtgtcgc ctttatgctg tatgacattg aagctggtcc ctggctctgc    2160
gtggcctgag gggaaggggt tcactccagc tggtcacctc gctgccccct gcccgtggcc   2220
ttggtggcca gtccttcttt cccggttgaa gaccccacga agaatgattt ctcacgcctt   2280
cttcagccgg ctgtgtagtc tgggtggtct ccaggagtgc cagtggaggc agcagccccc   2340
agacaattcc tttccaaatc agggctggcc cgggggaagt aaggcccagt ttggaagcct   2400
gctgccccgg gaggccgagc agtgagggcc acctccctgt cttcatcaca ttttcaccgc   2460
```

ttccgggggt ccttcccctc agtcccacca tgggggcgcc 2500

<210> SEQ ID NO 251
<211> LENGTH: 6000
<212> TYPE: DNA
<213> ORGANISM: Homo sapiens

<400> SEQUENCE: 251
gctggacacc tctgagagcg tggccctgag gctgaagccc tacggggccc tcgtggacaa 60
agtcaagtcc ttcaccaagc gcttcatcga caacctgagg gacaggtagg agggacgccc 120
cgtgaccttc ctcctgtgct tctgggcctc ttggagggag gggtgggggc ccaggggaac 180
acgggtgcga cggcctcaac ctcctaaggt tgggcgagcg ttgccctgac cggggcccct 240
cccggcgccc tccagagtga ggccggggcc ctttccggcg ccctccagag tgagctggtc 300
tgagcctctc ccagcgcctt ccagagtgag ctggtttgag accctgctcg cgggggtggc 360
acctgttcag cagggccgag gtgacagtga ggctgagatg tagggaagag aggctcccgc 420
aggctgaccg agagggctca gcgcactggc ccagacacgc agtcctgcct ggtgcgcggg 480
agcccctcac taaccacctg gaccctggtt tgttccgtgg gcagtgagag cctctacctg 540
ggtcctggat cccacgttct gaaggtcccc gactcgggag ccaggagggg tgtcgctctg 600
cagccccagg gcccccaggc ttggttctgg gcttgggaca cggcaccctc tgctccacgt 660
tcctccatct gtgcgtgtgg ctgaggacag accgggggga gaggggagtc ggtcctgtgg 720
gtgcacaggg ccgctgaggg gggggcatgt agaacggggc tcccccactg agacgggtcc 780
tggcagtggg gacacagctt agccggcgta ggaacccccg tcctccttga ccctgctgac 840
tggccgctgg gccggagcct cccgccacca gaaggggcac agtcagaggc tgccggtaac 900
agcagggtgg accttccagc ccacaccgtg cccagcagga gccattggta ccaggaaccc 960
tgagcttagt ggacatggcc aggcccgtgc ggcagtgttt gggggggggt ctggctgtgg 1020
atggcaccgg ggaggggcgg ccgcgtggcc cagcgtcccc cgagtcgccc ttgttgcctt 1080
tactcagtct ccccatgact cagtttccca cctgtgaaat ggggcggagt catccccatg 1140
tcgctgccac tggattcctg caggcgccgt ggtcactctg ctgaatggat gggagggtgg 1200
gtggggcaga ggtgggccca ccccaggctg gggcagagca gacccctgag agcctcaggc 1260
tcaggtgctc agagggcagc gagggggctg ctcagatccc cggggtgcct ccttccccca 1320
ctgtcatgct gccccactgc aggcccaagg accccacccc agcagggcca cacactcagg 1380
gctcctggtc tgagggcctg agggatcggg gcgcaggtcg cttgctggcc acacccgcct 1440
gcacagcctt ccaggagggc cggcctcagg gccacagggc aagtccagct gtgtgtcagc 1500
cacggccagg gtggggcagc ctgtccatct gggtgacgtc gcgccctggg acgggtagcg 1560
atggcgccag gggccgcccg cctcacgccc gccgtgcctg ttcctggcag gtactaccgc 1620
tgtgaccgaa acctggtgtg gaacgcaggc gcgctgcact acagtgacga ggtggagatc 1680
atccaaggcc tcacgcgcat gcctggcggc cgcgacgcac tcaaaagcag cgtggacgcg 1740
gtcaagtact ttgggaaggg cacctacacc gactgcgcta tcaagaaggg gctggagcag 1800
ctcctcgtgg ggtgagtggc ccccagcctc ctgcccacgc cagttctcac gcgtggtacc 1860
cagcctgggc tggggttggc ctggggtccc tgtgcggctt cagctgcagc ctccctgttc 1920
tcttggaggc tgcacggcct ccctgaccca ctttgtgggc aggaaagaga cggagacaga 1980
cagagacaga gagaaacaga aacagggaga aacagacaca gagagagaca gagacagaga 2040

-continued

```
gagatagaga cagagacaga gagagacaga gacaaagagt gacagaggga ccaagacagg   2100
cagacagaga caaacagaga cagagacaga gacacagaga gagacacaga gagacagaga   2160
cgggaacaga gacaggcaga cagagacaga gagagacaga gacagaaaca gagacagagg   2220
gacagagaca ggcagagaga gacagagaga cagagacaga gacagacaaa cagagacaga   2280
gagacagaaa cagggacaga gacagaaaga gagagagaca gagggaaaca gagagagaca   2340
gagacagata gaaaaagaca gaggcagaga gaagcagaga cagagaaaca aagacagtca   2400
gagacagaca gagacagaga cagaaacaga gacagagaga cagagacaga ggggcagaga   2460
caggcagaca gagagacaga gacagagaca gcgaaacaga gacagaaaca tacagagaca   2520
gagagacaga gagaagcaga gacagacaga ggcagagaga cagagagaag cagagacagg   2580
gacagagaca gagacagaaa tagagagata gagacagagg gacagagaca gagagataga   2640
gacagagagg gagacagaga gatagaagca gagagagaga gacaaagaca gaggcagaga   2700
gacagagaga gaagcacaga cagagacaga cagagagaca gggacagaca gagacagaga   2760
gaccggaaac agaggcagag agactgagag actgagagag acggggtggt tttccccaca   2820
gcatcaacac caagcagggc taggatcact gaaacagact catcagaccc gaagcatgcg   2880
ctttctcggg gtttttctgg actgaggggt ttcctctcat cccagtgtcc agctgtgggg   2940
acgcaggggc cgcaagcccc ggagtgtcca gaggggaacg tggcctcccc acacccagcc   3000
cttcacgagg cctcaggatc ccagtggggg tacccgaggc tgccctgtcc agccaggcgg   3060
tgcgggggt ttggggagag cctctccccg aggtcggtct cagagggcca catggccggt   3120
gtgggccgga cattcccttt ccaatggttg tgcccacttc cctccagagt tggtgccaag   3180
ctgggacctg gggacttgg agtctcagga agtcgtccgc tgtctgcagg gggtgcatgg   3240
gggatgtggc cacacacgtc agagtgcggc cccctgtgga agccacagac agacacgact   3300
cccctaaatg agctcgccct tctggccgag atgctcagcg tccccagcag gctgcccgac   3360
tgccctgcga tactgccctc cttcctgctg ctcccacttt ccctttcggg gggttggatt   3420
tggggcattc agggatcgcc ctgttgtttg ctcatcacac ccatttcctg caagagccac   3480
ggtgaccgag cagccttgag ttgaggcagc ttgtgggtag acgcggcggg catctcggag   3540
gggcacgctc cctgccaccc tcagcctcca ctcactggtc aggggctttg cgccccaggg   3600
caccccagga accgagcctc ctttggggtc atgggtgcct ctcctgggag ggcgtggatt   3660
ttccaaagca gtttagagaa atgagaccca caggcgttat ttcccatggt gaggttcttt   3720
tcagtaaccc ccaccgtata gccaggatca gcaaagagag gcggctcctc ccggtgagac   3780
agggaccagc acctcccgga caggcttggg tctccctcca gttcccccac ctagtctcga   3840
ggtctcacgc tgccctctcc tgtccagggg ctcccacctg aaggagaata agtacctgat   3900
tgtggtgacc gacgggcacc ccctggaggg ctacaaggaa ccctgtgggg ggctggagga   3960
tgctgtgaac gaggccaagc acctgggcgt caaagtcttc tcggtggcca tcacacccga   4020
ccacctggta ggcaccggcc ccccccggca gatgccccca accacaggga gtggcggctg   4080
caaggccccc ggcagctggg accgtctttt ggtcctcggg agggtgtggg ttctccagcc   4140
ggccaccctt gcccctgaga ggccagcccc tcctgctgag gagcctggag cgccccagcc   4200
cagcctcccc tctggccctg tgggaagcgg ccccggccgt caggggtccc agccctgctc   4260
agcccaccct gaacactgcc cccaggagcc gcgtctgagc atcatcgcca cggaccacac   4320
gtaccggcgc aacttcacgg cggctgactg gggccagagc cgcgacgcag aggaggccat   4380
cagccagacc atcgacacca tcgtggacat gatcgtgagg cccctgccca ggagacgggg   4440
```

```
aggcccgcgg cggccgcagg tggaaagtaa ttctgcgttt ccatttctct ttccagaaaa   4500
ataacgtgga gcaagtggta agagccctcc ccaccacccc cagccgtgag tctgcacacg   4560
tccacccaca cgtccacctg tgtgttcagg acgcatgtcc ctatgcatat ccgcccatgt   4620
gcccgggaca catgtcccct gcgtgtctgc ccgtgtgccc gggatgtgtg tccccctgcg   4680
tgtccacctg tgtgtctgcc catgtgcctg ggacatgtgt ccgcctgtgc gtccatccgt   4740
gtgtccgtct gcccatgtgc ctgggtcgca tgtcaccctg tgtcccagcc gtatgtccgt   4800
ggctttccca ctgactcgtc tccatgcttt ccccccacag tgctgctcct tcgaatgcca   4860
ggtgagtgtg ccccccgacc cctgaccccg cgccctgcac cctgggaacc tgagtctggg   4920
gtcctggctg accgtcccct ctgccttgca gcctgcaaga ggacctccgg ggctccgggg   4980
cgaccccggc tttgaggtga gtggtgactc ctgctcctcc catgtgttgt ggggcctggg   5040
agtgggggtg gcaggaccaa agcctcctgg gcacccaagt ccaccatgag gatccagagg   5100
ggacggcggg ggtccagatg gaggggacgg cgggggtcca gatggagggg acggcgggag   5160
tccagatgga ggggatggcg gggtccagat ggaggggacg gcggggtcca gatggagggg   5220
acggcggggt ccagatggag gggatggcgg ggtccagatg gaggggacgg cggggtccag   5280
atggagggga cggcggggtc cagatggagg ggacgtcggg gctccagatg gaggggacgg   5340
cgggagtcca gatggagggg acggcggggt ccagatggag gggacggcgg ggtccagatg   5400
gaggggacgg cggggtccag atggagggga cgtcggggct ccagatggag gggacggcgg   5460
gagtccagat ggaggggacg gcgtggtcca gatggagggg acggcggggt ccagatggag   5520
gggacgtcgg ggctccagat ggaggggacg gcgggggtcc agatggaggg gacggcgggg   5580
tccagatgga ggggacggcg gggtccagat ggaggggacg gcggggtcca gatggagggg   5640
acggcggggt ccagatggag gggacggcgg ggtccagatg gaggggacgg cgggagtcca   5700
gatggagggg acggcgtggt ccagatggag gggacggcgg ggtccagatg gaggggacgt   5760
cggggctcca gatggagggg acggcggggt ccagatggag gggatgtcgg ggtccagatg   5820
gaagggacgg cggggtccag caggcaggct ccggccgtgc agggtgtgga ctgtcccggg   5880
ggcgctgggg gcttctgagg gtgtctctgt ccgccctgcc ctcagccgca ctctgttcag   5940
aaggaccttt ctggaggtag gagggtgaga atgtgggtcc cctgcttctg tgtggctcac   6000
```

<210> SEQ ID NO 252
<211> LENGTH: 7000
<212> TYPE: DNA
<213> ORGANISM: Homo sapiens

<400> SEQUENCE: 252

```
ggccggggag gcggggaggc tgccccaaga gtaaaagcct ttctgacgtg cgcaggacgc     60
ggccctgact ggtctaactg actctttctc ttctcctcag cttgctgtgg tgagacccag    120
gctctagctc ctgagagaat ggatcccggg ggtcggggag cgaggcctgg gtcccacaca    180
tgtcacagga cagcacatgg cactctggtc cccgcccgca gctccctgca cctgcccgcc    240
ccctctgggg cctgctccaa gccagcaggg ttcccgggtg ttgggctggg ccccgccctc    300
tttcacccat aactgaaata accaggagca ggcttggggg ggtccctgct ccatcattct    360
ggcccacagg ccccacccta gcctggctga gcaacgccag ccctgaccag ccgccggaca    420
gagcagcctt tacggggcca tgggaggggg tgggcttttc tggggctgag acggggggac    480
cccaacgtgt caggtgagga tgtggcagcc aaggaggggc cagggcggtg gaggggaggg    540
```

-continued

```
gccagggcac tggaggggag gggcgtgctc tgctgacacc gcccccgcct gcagaatgca    600
agtgcggccc catcgacctc ctgttcgtgc tggacagctc agagagcatt ggcctgcaga    660
acttcgagat tgccaaggac ttcgtcgtca aggtcatcga ccggctgagc cgggacgagc    720
tggtcaaggt gaggcctcgc cccgcccggc tttctcaagc ccaggtgcac cccgaccctg    780
ccggccgccc ctgcccgcgc cagacctcag cctcccgagg ccaccgctgc atccctgtga    840
cttccctact catgacaagg atgccaggca cgcgccagcc cgtccaggcc tccagctcca    900
cctggcgagg ctggcccatt gtacacaggc gccccagatg agggagggtc tccccctctc    960
cttgaagggc ggtagtctgg ggtcctgagt gctgggtgtg ggcttgtccc tcgtggacag   1020
aacccaggag ggcttcatcc accaaggaag attgctttgc agggtaccca ggtcccgggg   1080
gctgtgccac cctctgggca cccggagcca atcgcagggt acccaggtcc cgggggctgt   1140
gccaccctct gtgcacccag agccaatcgc aggggaccca ggtcctgagg tcctgggggc   1200
catgccaccc tctgggcacc cgcagccaat agagtcaccc ttgggaagct tatgcggacc   1260
tggggcagca ctcgcgtcct gaccccggtg ccggtcccac agttcgagcc agggcagtcg   1320
tacgcgggtg tggtgcagta cagccacagc cagatgcagg agcacgtgag cctgcgcagc   1380
cccagcatcc ggaacgtgca ggagctcaag gagtgagtgc ccccacgcggc caggaccctc   1440
ccacccctcg ccccgaccgc tgttcccacg gcaggtcggc cctgacccct gatcccaggt   1500
gggctcggcc ccgcggcagg cctggcccca accggccctt cctgcccttt gctatgcaga   1560
gccatcaaga gcctgcagtg gatggcgggc ggcaccttca cgggggaggc cctgcagtac   1620
acgcgggacc agctgctgcc gcccagcccg aacaaccgca tcgccctggt catcactgac   1680
gggcgctcag acactcagag ggacaccaca ccgctcaacg tgctctgcag ccccggcatc   1740
caggtggggt ggccaccccc aggctgcacc tgccccgcct agggcgcccc gccagccagg   1800
gtggccttgt ccccagaaag acgagggcag agcaggctgc gccacaccga tactgtctgt   1860
ccccacaggt ggtctccgtg ggcatcaaag acgtgtttga cttcatccca ggctcagacc   1920
agctcaatgt catttcttgc caaggcctgg caccatccca gggccggccc ggcctctcgc   1980
tggtcaagga gaactatgca gagctgctgg aggatgcctt cctgaagaat gtcaccgccc   2040
agatctgcat aggtgcgcat ggggccaccc gggcagtccc agatctgcgt aggtgcgcgc   2100
ggggccgccc gggcagtccc agatctgcgt aggtgcacgc ggggccgccc gggcagtccc   2160
agatctgcgt aggtgcacgc ggggccgccc agggccgtcc cagatctgtg taggtgcgcg   2220
caggcgccca gggctgtccc agaggcctcc tcccagctca ctgttacctc caggggcacg   2280
gccaccctgt aggtgcgcac ggggccgcct ggggctgtcc cacaggcatc ctcctcccgg   2340
ctcgctgtga cttccggggg cacggccacc cctgtgctcg gccgggaggt cctgtgacat   2400
ctccttgcgg ggttataggt ggagcagtgg gctcacactg cacggctttt ctcttttaca   2460
gacaagaagt gtccagatta cacctgcccc agtgagtacc tcggcggccg ggacacgtgg   2520
ggaggagggc accgtggttg gggcgagggc tctgagagga cggggctctg ggaggagggc   2580
ctggcggtca cgagagtagg tgcatggctc actccggtgg ctgagcacca ccgtgccgtg   2640
ccctctctgg ggagcttaga cgctctctgg ccggcccact gcggctgcat caccagggcc   2700
tcatgctaac ggctgcccac cccgccccgc agtcacgttc tcctccccgg ctgacatcac   2760
catcctgctg gacggctccg ccagcgtggg cagccacaac tttgacacca ccaagcgctt   2820
cgccaagcgc ctggccgagc gcttcctcac agcgggcagg acggaccccg cccacgacgt   2880
gcgggtggcg gtggtgcagt acagcggcac gggccagcag cgcccagagc gggcgtcgct   2940
```

-continued

```
gcagttcctg cagaactaca cggccctggc cagtgccgtc gatgccatgg actttatcaa   3000
cgacgccacc gacgtcaacg atgccctggg ctatgtgacc cgcttctacc gcgaggcctc   3060
gtccggcgct gccaagaaga ggctgctgct cttctcagat ggcaactcgc agggcgccac   3120
gcccgctgcc atcgagaagg ccgtgcagga agcccagcgg gcaggcatcg agatcttcgt   3180
ggtggtcgtg ggccgccagg tgaatgagcc ccacatccgc gtcctggtca ccggcaagac   3240
ggccgagtac gacgtggcct acggcgagag ccacctgttc cgtgtcccca gctaccaggc   3300
cctgctccgc ggtgtcttcc accagacagt ctccaggaag gtggcgctgg gctagcccac   3360
cctgcacgcc ggcaccaaac cctgtcctcc cacccctccc cactcatcac taaacagagt   3420
aaaatgtgat gcgaattttc ccgaccaacc tgattcgcta gattttttttt aaggaaaagc   3480
ttggaaagcc aggacacaac gctgctgcct gctttgtgca gggtcctccg gggctcagcc   3540
ctgagttggc atcacctgcg cagggccctc tggggctcag ccctgagcta gtgtcacctg   3600
cacagggccc tctgaggctc agccctgagc tggcgtcacc tgtgcagggc cctctggggc   3660
tcagccctga gctggcctca cctgggttcc ccaccccggg ctctcctgcc ctgccctcct   3720
gcccgccctc cctcctgcct gcgcagctcc ttccctaggc acctctgtgc tgcatcccac   3780
cagcctgagc aagacgccct ctcggggcct gtgccgcact agcctccctc tcctctgtcc   3840
ccatagctgg tttttcccac caatcctcac ctaacagtta ctttacaatt aaactcaaag   3900
caagctcttc tcctcagctt ggggcagcca ttggcctctg tctcgttttg ggaaaccaag   3960
gtcaggaggc cgttgcagac ataaatctcg gcgactcggc cccgtctcct gagggtcctg   4020
ctggtgaccg gcctggacct tggccctaca gccctggagg ccgctgctga ccagcactga   4080
ccccgacctc agagagtact cgcaggggcg ctggctgcac tcaagaccct cgagattaac   4140
ggtgctaacc ccgtctgctc ctccctcccg cagagactgg ggcctggact ggacatgaga   4200
gccccttggt gccacagagg gctgtgtctt actagaaaca acgcaaacct ctccttcctc   4260
agaatagtga tgtgttcgac gttttatcaa aggccccctt tctatgttca tgttagtttt   4320
gctccttctg tgtttttttc tgaaccatat ccatgttgct gacttttcca aataaaggtt   4380
ttcactcctc tccctgtggt tatcttcccc acaaagtaaa atcctgccgt gtgccccaaa   4440
ggagcagtca caggaggttg gggggcgtgt gcgtgcgtgc tcactcccaa cccccatcac   4500
caccagtccc aggccagaac cagggctgcc cttggctaca gctgtccatc catgcccctt   4560
atctgcgtct gcgtcggtga catggagacc atgctgcacc tgtggacaga gaggagctga   4620
gaaggcaaca ccctgggctt tggggtcggg agcagatcag gcctcagtgg gctggggccg   4680
gccacatcca ccgaggtcaa ccacagaggc cggccacagg ttctaggctt ggtactgaaa   4740
taccccctggg agctcggaag gggagttgag atactgcagg gcccatagga agaagtcttg   4800
ggaggctcca cctttggggc agaggaagaa gtcttgggag gctccacctt tggggcagag   4860
caagaagagg gcggagggca gaggcagcga gggctcatcc tcaaaagaaa gaagttagtg   4920
gcccctgaat cccagaatcc ggggtgcacg gctgttctgg gggccgctag gggactaaga   4980
ggatcggccg agggctgggc tggaggaggg cagcagggat gggcggcgag ggtgagggtg   5040
gggcttcctg aaggccttca cctgcgggga ccccggcgag cccctcaggt gccacaggca   5100
gggacacgcc tcgctcgatg cgtcacacca tgtggccacc agagctgcgg gaaaatgctg   5160
gggaccctgc atttccgttt caggtggcga acaagcgccc ctcacagaac tgcaggtaga   5220
gacgggcccg gggcagacgc agtgaggcgg tgggcggggc ccggggcaga tgcagtgagg   5280
```

-continued

```
cggtgggcgg ggcccggggc agaggcagcg agcggtgggc ggggcccggg gcagacgcag   5340
tgaggcggtg ggcggggccc ggggcagagg cagcgggtgg tggccggggc ccggggcaga   5400
cgcagtgagg cggtgggcgg ggcccggggt agtcgcagta ggtggtgggc ggggcccggg   5460
gcagacgcag tgaggtggtg ggcggggccc ggggcagacg cagtgaggcg gtgggagggg   5520
cccggggcag acgcagtgag gcggtgggcg gggcccgggt cagaggcaac gggtggtggg   5580
cggggcccgg ggcagacgca gtgaggcggt gggcggggcc cggggcagat gcagtgaggc   5640
ggtgggcggg gcccggggca gatgcagtga ggcggtggga ggggcccggg gcagacgcag   5700
tgaggcggtg ggcggggccc ggggcagacg cagtgaggcg gtgggcgggg cccggggcag   5760
acgcagtgag gcagttgcca gcctctctca gctgcctcat gggattcgca ctgcagctgc   5820
ggccctggcg cgacaagggc tggacttggc cagcgggacg gtccctcacg gcgctgaggc   5880
ccacactctg cgtggagcct ccccgtgccc aggctaccct gcaaggtcct cggagaggct   5940
tcctccagcc ccagccccca cacagctccg gcccaggccc gctcttcccc atcccagttg   6000
ctttgcgctg tatacggcca ggtgacccg agccggccct gagccctcgt cccggcttcc   6060
tcccctgtaa gctgggtgaa ggactccatg gcacccacct gagagggttg tggcgaggcc   6120
caggcccctc gtgcccacac ggccggcggc ccatgcctgg caggggctgg gaggaggctg   6180
gggcgaccag aggggagcgg cctgtcctgg aggaggccca gggaccctgg tgagagggtc   6240
tctcccaagt gctctctatg ggaccccctt cctctgcgcc cgtccttcac ggacctctcc   6300
gggtcacccc tgggctgcac actgggttca ggggggcctt gaggtggggc ccctgttccc   6360
aagtcccggc ggggtttctc ctgaacctca acccatcctc acctgcgggc attcccatcc   6420
cccaacgcct gggtcaccag gattccaggc aggaggggcg gtgggggtta ccaaggcccg   6480
ggttgccatg cagaaccccc agccaccacg cagaccccca cggggcccag ggaagctcct   6540
ggtctcacac tgcacctcac acttcctgtg ggggcagact ccaaggtccc ggcctctcat   6600
cttgtagaaa ctgaggcaca ggagggacac acactcccac ggccggtcac cgtggccccc   6660
acacctccca ctggactgac acctggccag gctccggaca cccgtggcac agcctcagcc   6720
cctgcggccc ctgctccgtg gcccccaggc cccagctccc atgtgcacgt cctgcctcag   6780
gcctggaggc ccctcggccc caaataatca gacaattcaa cagcaaaact actttttttca   6840
ggctggcagg actctgggca accccctgca acagcccccct gccctatcac agccacccctt   6900
gcctcccagg cacggagacc ccaccatcag gtcccagcct tggttcatcc ccaagcaccc   6960
tgtgtgttgg gatggcgatg ctggctgagc ccctgcatcc                         7000
```

<210> SEQ ID NO 253
<211> LENGTH: 2500
<212> TYPE: DNA
<213> ORGANISM: Homo sapiens

<400> SEQUENCE: 253

```
agggcgtttg ggaacacccc tcccggaggg gtgaggcggc ccagcctgcg gctgccagag     60
gacacaggtt ctgctgcgga acctgcagac atggccataa caggccacag tgctcgggcc    120
cacacagcct ggacccacat ggccctgtgt cacctcctca ggggcaggct tcagggcctc    180
gaccctagag gctgcccctc ggttctgctc catggacggc gcaggcaggc ccaggcctgt    240
gacgagttca cggaagctcc aggatgaccc ccgctctgcg ccctcctcca gcattccaga    300
ccacaaacca ctctgggcta aaacgaggca tcgccagagc atcccacttc ctcggaaagc    360
tgcggtctgg ggacgcgtct tggccctgaa gaggctccag atggctccca tcaggcctct    420
```

```
ccgcctacgt gcggccgaca tggagtgaca gagcgtcggg gacacagaat tcagagctgg    480
gcctggggct gctttgagat actgatggct gccagggggc acagagaccc gtcctgcaga    540
cagggctgtg agggccacag gggcctcgg ggagaggcag tgggagggag gacagtgggg    600
gcctccagct gggtgagcag ctggagcgag gggggcccgg ggcttgtgat ggtgctgccg    660
accctagagg tgccggcccc acgatggaga gcacgtagtg ccccccggga gtcaggaggc    720
cgggcctgac ctcgggggct gcagccaggg gaggccggca ccccagataa cccccaaaga    780
actgcaggcc ctgaggcgag gccagagtgg gggcgggggc aggtcccagc cgaggaggtg    840
ctccgtgctg cctcagcaga acccatgatg ggctggccca aggctctgaa ggtggaaagg    900
cctcacacat tctgccccgg ctgacgcctt ccttgggcca gtgctcgggg gtgtgtaaca    960
aacgccaaga cgcattgtaa agaaggaagc ctgcgtttcc atcaccggct taatatcaaa   1020
caaaagtgca attttgaaaa tgtagtccaa ggttttctgt ggtgcggaaa tggccaggcc   1080
agacctccgt gggtggtcct tcgtgtccac gtcagcgccc tacatccaca ctgtgggcac   1140
catgacctca catgcggagc ggagcagggc cggcgcccgg agagccaggc tggtcacgaa   1200
cgaggcctag agggcgtcag gccccaaagc actcacaggc ttctcctctg tcctcggggc   1260
cttcagacac ctgcatgcgc cgattcagcc acccgcgcgc gccgattccc ctggccatgg   1320
ggtttccaaa gtgtgtgctc agaggacagt ttcctccagg atgacctgtc agtggctctc   1380
tgtgccgggg acgtcgcgtg ctgggtcccg gtctgaatgc ttcctaacga tttacccagt   1440
tccttttctc cactcaggag gcgtttgctg agaggcacag gctgagcccc cgtgctgatg   1500
ccacgaccga gggaacgggt ctccctgtcg gcgtgaactg acccggccag gcgtccactg   1560
ccactcggac tgtctcccag gcacgtggcg cccacacggg cagaacacgc cctccacaca   1620
cgcggcttcg ggcagaacac gaggcgccct ccacacacgc ggcttcgggg cttgtcatga   1680
aaaaagctga atgctggggg tgcagctttc accaacagaa tcccgtttgg aagggacgcg   1740
gtgagacatg atccacccta agttgtgatc ctgggtgagc cgccgtccac accctgctga   1800
gggtcccttc acccacttta ttctccagaa aaccctgccc atcagggctg agtcccacgc   1860
cttccctctc cgtccaggcc tggctttgac ctctggggtc gtgtggggca caggggacac   1920
cctatccagg cagaggccct acggctatct ggaggaagtg gtgggagctg ggcttctgcc   1980
tggaggatgc acccagaggg gtcacagtcc acacagagac acacgggtgc cttccagatg   2040
gctgagccag tccagcccag aagggcctgg gggttggggg ctgcacctgg cctgtcccca   2100
ccagcagggc tcagggcttc ccaaggtgtg tgggggacgg ggcagcacct ctcaaccagg   2160
tcacctgaaa cccgaactga aaggcatcct aagttaagac attaactccc attgtcaagg   2220
tgccatcgtc aattctgtct ccaaatcctt ctttgttatt tcatgtattc acagagtgac   2280
gctccgtgtt tcgttcagcc tgcaggcctg cagaagctgc atctcgggat ggccaagagc   2340
ccggccaggc cccacggctg cacccaggac gggattcatg ccccatgcct ggcttctcac   2400
gaccacagag tgcctttccc gggactggat ggaggcagag tgagagaaga gcctggagca   2460
agtgttttgg accacagtga tcaaacacgg agcccgtggg                         2500
```

<210> SEQ ID NO 254
<211> LENGTH: 700
<212> TYPE: DNA
<213> ORGANISM: Homo sapiens

<400> SEQUENCE: 254

-continued

```
aagaaaggcc agaccgggca cggtggctca cgcctgtaat cccaacactt ggggaggccg      60
aggcgggcag atcacctgag gtcaggagtt cgagaccagc ctggccaaca gggtgaaacc     120
ccgtctctac taaaaataca aaaaaaaatt agccgggcgt ggtggcaggc acctgtaatc     180
ccagctaatc gggaggctga ggcaggagaa aatcacttga acctgggagg cggaggctgc     240
agtgagctga gatcgcgcca ctgcactcca gcctgggtga gggagcgaga ctgtctcaaa     300
aaaaaaaaaa aaaaaaaaaa aaaaggaaag aaaggcccgg tgagatgctt tctcttaaac     360
acggccctgc acgttgagtt gctgcctcct gtggcctatt tcacgtttat gcaaagtcgg     420
gcgcctgatg cggggctcac ccgccacaag caggggtcct ggtgctgctc atggaagggg     480
ccctacccag cccgcggggc actggctggg acggggctgc ccaggtccgc ccaggatcca     540
aacacccagc cccgcccagc ggcccttcct ggcctgcagt ggaggctgta atgggcaggg     600
gtggtgggaa tcccagctca cagggcgcct gctcttagaa gggcggcatc tgggtccaga     660
ggtcagaaac gtcagatgcc catcccagaa gtggcgggga                           700
```

<210> SEQ ID NO 255
<211> LENGTH: 10000
<212> TYPE: DNA
<213> ORGANISM: Homo sapiens

<400> SEQUENCE: 255

```
gggtgaatga gtagatgtat gggtgagtag gtgggtaggt gggtagatgg atgggtgggt      60
gggcgagtgt gtggttagat gatggatggc tgaatggatg agtgggggga tggatgggtg     120
agtgggtgta tgtatggatg ggttagtggg tgggtggatg aatggatggg tgcataaagg     180
atggatggat gaatgagtta gtgggttggc agatggatgg atgggtgagt cagtggatag     240
atggatgggt gggtggatag aggatggatg gttgggtagg tgatgggtgg atgagtggat     300
agatgggtat gtgagtgagt ggggggatgg gtaggtgggt ggatggatgg ttaggtgaat     360
gagtggatgg acagacggac agtgggtgga tggatgagtg aacggatgga ccgatggatg     420
aatgggtggg tgggtagagg atggacggac aggtgagtgg gtgggtggat ggatagatgg     480
gtaagtgagt ggatagatag atgggtgggt ggacagagga tgggtggatg aatggatggg     540
ttagtgggtg gctgggtgga tggatgatgg atgggtgact gggtggatgg atggatgggt     600
tagtgggtgg ctgggtggat agatggatgg gtgattgggc gaatgggcga atgggtggat     660
gggtgggcgt ggagttggtg ggtacatgat aatggggtgg aatacccatg gattggaatg     720
agctgttttg gctgctattt ctgggacacc cagctctgcc aggcccctac ccctctggtg     780
ggccaggctc tgacggtggc cactcatggc ctttctagct ctggtgccag catagggaag     840
gaggaggcac agccttgtct tactccttgc acctgttagc cccccccccc gccaagggag     900
gacccgtggt tggggacagc acagggggcc ctgctgtgtg cagggactgt ccctggggcc     960
actgaagccc acctgttctt gttccttctc aggcggatcc tggtccccct ggtgagccag    1020
gccctcgggg gccaagagga gtcccaggac ccgaggtagg ttggtggcca gtccccatgc    1080
cctcccccca acctgccagg ccaacacaca cccaagcctc gtggttctgc ccacggtgga    1140
cccacgtatc agtgggcagt ggcctgggag agactcagcc acccagcctt ggccccagag    1200
tctcagcctc atccttcctt ccccagggtg agcccggccc ccctggagac cccggtctca    1260
cggtaggtgt cacatggggc agaaccagtg tccttctcct gccaaaacta gacaccaaga    1320
gcagcagggg tgggggaagg tcagctggca cggtcagaga gcaagatcag tggaggaggt    1380
cagagggcaa ggtcagagag caagcttggt tggggaaggt cacagggcaa ggttggtggg    1440
```

-continued

```
gggaggaggg tggcagcgag gttggtaggg acaggacccg ccagcctccc cgcatggctg   1500
cctccacacg tgggctggaa tgtcccggga cccccaggcc aggaccttgc tgtggaaact   1560
cttctggggc cccgggggga ctaccctgcc tgccgtgtgc attgcaggag tgtgacgtca   1620
tgacctacgt gagggagacc tgcgggtgct gcggtgaggc actgcccacg gcagggtcgg   1680
ggcccatgca ccgggtggag ggcgggagtg cagcagggct gggtcatcgc tgggtcctgc   1740
atgtgcacgt gaccctaggg tctgaggtct ccccggtacc ccccgatgac cctgccaccc   1800
ccccagactg tgagaagcgc tgtggcgccc tggacgtggt cttcgtcatc gacagctccg   1860
agagcattgg gtacaccaac ttcacactgg agaagaactt cgtcatcaac gtggtcaaca   1920
ggctgggtgc catcgctaag gaccccaagt ccgagacagg tcagcggggc aggggcgggt   1980
gcagcattgc ggggggccgg gcggggcgtg ggaggcgatg agatgggaga agtccagacg   2040
cgtccctcca acgagggcct ctgcatggct ggggatgccc cagaccccga ggcctctggc   2100
aacgacctca cgcgtgcggc ttgcagggac gcgtgtgggc gtggtgcagt acagccacga   2160
gggcaccttt gaggccatcc agctggacga cgaacgtatc gactccctgt cgagcttcaa   2220
ggaggctgtc aagaacctcg agtggattgc gggcggcacc tggacaccct cagccctcaa   2280
gtttgcctac gaccgcctca tcaaggagag ccggcgccag aagacacgtg tgtttgcggt   2340
ggtcatcacg gacgggcgcc acgaccctcg ggacgatgac ctcaacttgc gggcgctgtg   2400
cgaccgcgac gtcacagtga cggccatcgg catcggggac atgttccacg agaagcacga   2460
gagtgaaaac ctctactcca tcgcctgcga caagccacag caggtgcgca acatgacgct   2520
gttctccgac ctggtcgctg agaagttcat cgatgacatg gaggacgtcc tctgcccggg   2580
tgagcgtgtg ggcgcggggc agtcggccga ggagcagcag gccccagccg ctgtctagcg   2640
tgagccccag ggacacccct cacctgaggg atgaatgtgc agcccaggat cttgggctgt   2700
gggtgggaag gggtcgggcc ctctcggggc tgcagggcag aggccagctg caccctgagc   2760
ctgtctaggc agatcagtga acggccgctg agggttcgct agggactgac cctggcctgg   2820
cccggcctct ctcctctctt ccagaccctc agatcgtgtg cccagacctt ccctgccaaa   2880
caggtaatgc agggcaccct gagccaccac cccagactag caaagcagcc ctggtgtcct   2940
tcctcctcga gggccgggct gggggagggg ccgtgcaggg acccgggggg cggcggagcc   3000
actgcggagg ctgctcctta gggagatggc cccaggatgg cagcacaggg gaggaggggc   3060
ttggggaagg caggctccca ggaacgcagg aacagcatca cgaggccatg aggtgggtgc   3120
tgctagcctg gcgctgtgct cggcatgtgg ccactggtct tgaaggccca ccatgggcct   3180
tgcagtctcc ctcagctgcc gcccagctcc catgggctgg ccgtgcatgt gccactcgga   3240
ggaagccctg gattcagtga gtgaaaccat cccggggtgg aagcactgac accccccagc   3300
accagcaggt cttgctccaa ccctggcctg cctcggagct gcagctgcgg ctctcacatc   3360
tctgggagtg ggggagccca tgtcccggat gtggcccacg tgggtgtgaa gctggagctg   3420
ggggtgccgt ccaggctctg ctggacgtgg tgctgccccc atggtgcact gctgcaccgt   3480
acctgggccc acaggaggtc cccgggggcg ttaggagctg agtccccctc agtgagccgt   3540
cccctccagg agtgtgaggg tagggatgcc atggagacag ggtgggaggg tccgacctgg   3600
aggaccacag ggaggaaacc tcagggtctg cggtacgaag tcagcgcttc ctcagcacgc   3660
gggtcgcggt gtgcgttcgg gcgttccatg gggagctccc ggtgggtgag ctgggccact   3720
gagcacattc acaggccctg aggctgcccc aggggaggag ccgtggactc agagccgagg   3780
```

-continued

```
ttccccatac gtgctgcgac agagaaccta gggcttgcac ctgggtctgg ctgcccttca   3840
gcaggcgggc agcctctggc cccacaacag tgggctgtgc ttctgccgcc aaggtgcagg   3900
cgtcctcccc cagggtccac atcagcagca ggggcacctg gaccctgagg gcaggaacca   3960
gaccttggct cctccaccca ccccctcgtt cctgatgggg cagggaagtc tcgggacccc   4020
atgatgggcg acatggcgat ggtcactgtg ggtgctttgc tatcaggtgg ggggccttcc   4080
tctccactct gggtccagtg tgagtggccg ctatggcttc ccctccactc caggttctat   4140
cgtgagtggg tgggtgctgc gtctgtggat gtcacgtgac ctttcctctt tagcctatca   4200
ttgtagttgg gagttagtta gcccgttgag cgtcattgaa tttccagtgt tgagccagcc   4260
ctgcgtgccc gggataaacc cacctggccg tggtgtgtgg ccctgtttat gcacgtgggc   4320
cctgattcgc tgatgcctgc ctgagggttt gcgcttatcg gcgacatcag cctgcacttt   4380
tcttttctcg tgatctctct ggttctggcc tcagggtgac gtgggcctcg tagggtcctg   4440
tggtggctcc tccccagacg gtgacatgga gtgagcccat tctccctcct gggagtgggt   4500
cactcaggcc accagagcac cacagggaaa gcagccaggg aggacacgga ggcccttgaa   4560
gctctggcct cttctgaggc ctccaggacc tgacagtgag tgggagcagc cctggcagaa   4620
cccctcccct cctctcggcc gccctgacac ctcatccccg acactcagag ctcatcctcc   4680
ttcccagctg tttccaattt caaagtgaac tcgaccttgt ggctccagga gatgcagcag   4740
ggacagtgtt aaatcggctt tcaccagccc acacggccag gcatcctcct cggccctcct   4800
gggcactggg tggacaccac tggctgtggc ctggccctgg ccttctccag acagccctgt   4860
ccaccccaaa gcccagccac cctgggcctg cagcaggcct gtggagttct cagttgcgtg   4920
gggaccagag ggtgctggag aaacaaacca gacgcagctg aaggcagtca gggcagggcg   4980
caatcagcga taagagctgc ataggggcca cagcgtaacc tgagctccag tcggtggaaa   5040
gaaaaggcag agacgttgca gaggccaggt ctgctcaggg gaagacagtt ctgggtgtag   5100
aggactcaca tcccagagag gctgaggaag ggtttaccac cgcaagcttt ctcaggcggg   5160
ctcttgaggg gtggctgggg tcttcctggc gacgggcctg cggcactgga agccctactg   5220
gagtttggcc tgtctccggc acaggtttgg acggagctgt tttgtgctga aaggttttct   5280
cggggtccgt ggtgtccccc aaaggtgcca ccgtgcgggt ctcctagctc cctgccagct   5340
tcctgtccct gtgctcactg cccccacgcc tcctgccaag gccgagccac acacccgctc   5400
cacctgcatt tcctctaccg actcgccagc ccaaatgccg ctcttcactc tggcctcgct   5460
gagcggctgc ccgaggagga gctctaggcc gacgcccacc gcaggcctta cagtcttctc   5520
tggacgctcc cttgcagatg caccgtggcc tggcggcgag cccccggtca ccttcctccg   5580
cacggaagag gggccggacg ccaccttccc caggaccatt cccctgatcc aacagttgct   5640
aaacgccacg gagctcacgc aggacccggc cgcctactcc cagctggtgg ccgtgctggt   5700
ctacaccgcc gagcgggcca agttcgccac cggggtagag cggcaggact ggatggagct   5760
gttcattgac acctttaagc tggtgcacag ggacatcgtg ggggaccccg agaccgcgct   5820
ggccctctgc taaagcccgg gcacccgccc agccgggctg ggccctccct gccacactag   5880
cttcccaggg ctgcccccga caggctggct ctcagtggag gccagagatc tggaatcggg   5940
gtcagcgggg ctacagtcct tccaggggct ctggggcagc tcccagcctc ttcccatgct   6000
ggtggccacc gtgtcccttg ctgcggctgc atcttccagt ctctcctccg tcttcctgtg   6060
gccgctctct ttataagaac cctggtcatt gaatttaagg cccaccccaa gtccagaatg   6120
acctcgcaag acccttaact cactcccgtc tgcagagtcc ttctttgctg catcaggtca   6180
```

-continued

```
ccctcacagg ctccagggtt tgggtgtgga agtctttgga ggcccttact tagcggccca   6240
gctgggctgc cgtgcgtctg ggatggggct gagggagggt gctgcccagg tgctggagga   6300
tgttccagca ccaggttcca gcggagcctc ggaaacaggc cccagaggct ggtgagcctc   6360
gctgggtgtg ggcactaatc ccgtgcatgg tgactcgtgg gcgctcacgg cccacctggt   6420
ggcaggtgaa ggcttccggt tgggcagcag atagtcctgg gggaagctgg cagtcctggc   6480
accatgacgt atctgggctg gtgtcatgca cagtagggcg aatggccaca gctgcctgcc   6540
agcagccctg atcccggggt gtctgcaccc ttccagccca acctctgggt ctccaaaagc   6600
acagtcgggg gagcatccac caggcacaac ctctgcggtc ctcagaggac tgagcagaga   6660
atcccagggt ccacaatgtt ggggagcggc agggatcacc atccaaaggg agcggccccc   6720
acggcgagct gaccccgacg ttctgactgc aggagccctc atccaggctg ggctcctgcc   6780
gggcacggct gtgaccattt ctcagggcca ggttctcgtc cccacaccca ctgcacaggg   6840
caggccaggc tggtcttccc actgtgggga tgaaggatcc tccacaggag gaggagagca   6900
gagtccacag acatcccaac agcctcagcc tccctgtgcc tggccggccc ccacagcttc   6960
cccgtctcct ccaggcccca cagacactga tgaatggaca gagaccccca aaaccagctg   7020
ccccttgcat gtctgtctcc atatgtttgg tgacagcagt gaaaatgtta ttagttttga   7080
gggggtttgg gaagcccagc ggtacctgag gagtttctgg acatttaagc cggttcctag   7140
gtgtggcctt aacagggagg ctgcccttcc tttcactgaa tgagctgcgt cactcataag   7200
ctcactgagg gaaccccatc tgccagctcg tgcgtgctca gacggcgtcc atgtctcaag   7260
cgttctgtga aggctgcggt gcagcgtgag gtcaccctgc tgtgttcaga gctttgctca   7320
ctgcctgcgg ggctggaccg ttgcacctcc agggccccca gaaaccgagt ttcgggtcag   7380
ggtcctctgt gtgcattcct gggggtccat gtaccagctg tgacgacgtc caggggttgg   7440
gctgagaagc agacaccctt ggggaaactg gctctgtccc tcccctcccc catcccagga   7500
gctgaggtct tggtgaggcc acagggccag gtccacgcaa ggactgtccg tgtcctgtcc   7560
tgtggtctct ggccccacgt gacacccaca cgtgtggtag gcagcctggc ctgggttgtg   7620
gctatggcca ggcccccaag ctgtccccga tgcccagggc tggtgaccac ccaggcaggt   7680
gggggcccca cttggtaaca gagtcatagg gcagaaccca cctgggctgc cacagaaggt   7740
ctggctgccc ctgtgcccac tgctccccac catggccaat cagaagagtc aggggctcct   7800
ggtctttccg ggagggacgt ggcccagcca gctctaggtg ttctgagcag ctctgggacc   7860
cagcgattga ggggtcaggc tgggggtgtc agagccaggg tcctccttaa gtacctccca   7920
cactacacag acagtggccc ttttgtgggc agcaaattct tgagccatga aaggatgctt   7980
tgggcccctt ccctcccagg agggcagcct gtgcagggat ggtgctcagc aggtggacag   8040
ggcctggggc ctgtgtcagg gtctcaggcc tgggagcacc agcagaggag atggcggctc   8100
ccagcagtgc cgcctgaaag tgtcttgggc taaggaccca cacccagggc tgccctgcag   8160
aaacgccccc gcagagccca gtggtctgtg aggttgcagg cagggtgcga atggaagggc   8220
acaggtgcgg ggctggcacc tgcccggtcc tgcccacctc ccctccgccc agcccgcacc   8280
tgcgtctccc cacagagctg tccgtggcac agtgcacgca gcggcccgtg gacatcgtct   8340
tcctgctgga cggctccgag cggctgggtg agcagaactt ccacaaggcc cggcgcttcg   8400
tggagcaggt ggcgcggcgg ctgacgctgg cccggaggga cgacgaccct ctcaacgcac   8460
gcgtggcgct gctgcagttt ggtggccccg gcgagcagca ggtggccttc ccgctgagcc   8520
```

-continued

```
acaacctcac ggccatccac gaggcgctgg agaccacaca atacctgaac tccttctcgc   8580

acgtgggcgc aggcgtggtg cacgccatca atgccatcgt gcgcagcccg cgtggcgggg   8640

cccggaggca cgcagagctg tccttcgtgt tcctcacgga cggcgtcacg ggcaacgaca   8700

gtctgcacga gtcggcgcac tccatgcgca agcagaacgt ggtacccacc gtgctggcct   8760

tgggcagcga cgtggacatg gacgtgctca ccacgctcag cctgggtgac cgcgccgccg   8820

tgttccacga gaaggactat gacagcctgg cgcaacccgg cttcttcgac cgcttcatcc   8880

gctggatctg ctagcgccgc cgcccgggcc ccgcagtcga gggtcgtgag cccaccccgt   8940

ccatggtgct aagcgggccc gggtcccaca cggccagcac cgctgctcac tcggacgacg   9000

ccctgggcct gcacctctcc agctcctccc acggggtccc cgtagccccg gcccccgccc   9060

agccccaggt ctccccaggc cctccgcagg ctgcccggcc tccctccccc tgcagccatc   9120

ccaaggctcc tgacctacct ggcccctgag ctctggagca agccctgacc caataaaggc   9180

tttgaaccca ttgcgtgcct gcttgcgagc ttctgtgcgc aggagagacc tcaaaggtgt   9240

cttgtggcca ggagggaaac actgcagctg tcgctcgccc accagggtca atggctcccc   9300

cgggcccagc cctgacctcc taggacatca actgcaggtg ctggctgacc ccgcctgtgc   9360

agaccccaca gccttgatca gcaaactctc cctccagccc cagccaggcc caaagtgctc   9420

taagaagtgt caccatggct gagggtcttc tgtgggtgga cgcatgatta acactagacg   9480

gggagacagc aggtgctgag cctgttgtgt tctgtgtgga gatctcagtg agtttttgct   9540

gttcagaccc cagggtcctt caggctcagc tcaggagccc cacagtgaac cagaggctcc   9600

acaggcaggt gctgacctga caggagtggg cttggtggcc atcacagggc accacagaca   9660

cagcttgaac aactaccagt atcggccaca ggcctggagg catcagccgg gccatgcttc   9720

ctctggaggg ctagaggagg actagagaag ggcctgcccc ggcctctccc cagcatccca   9780

gggttcctga tctcctggat aaggatacaa gtcaccacac tggactgggg ctcagcctgc   9840

tctagaatac ctcacctaag tcacagtgga ccaggctcag cctgctctaa ggtgagctta   9900

cccgagacac tggaccagag atcagcctat cctgggataa gctcacccga gtcacactgg   9960

accagggctc agcctattcc gggatgagct cacccgagtc                         10000
```

<210> SEQ ID NO 256
<211> LENGTH: 800
<212> TYPE: DNA
<213> ORGANISM: Homo sapiens

<400> SEQUENCE: 256

```
gacacttcca tgactgcagc tgaccagtcc acctgccagc ggttgaccac tcccacttcg     60

ccagcgaccg aaggggaggg gaggggcctc acctgagggc aacagcagaa cccaccacct    120

ggtcttgctt tactcagacc tgagggtgtg aaaggtgccc gtgacctccc gcatcaggga    180

gctggccgcc accctcgact cccggggagc aggcgtcccg cgacccccctc atctaccagg    240

ccatctgagc tgggcggcgc ctcacctccg ctcccggggg agccggcctc agggtaggca    300

tgcgccctgg gtgggagcag gtcgtggccg ccgccctcct ggcagctctg gctgagcagc    360

cgccgcagca tctgattctc cttcaggagg cgcacctgct tcttcaggtc cgcgttctcg    420

ctcaggagcc ggctcatcag ctcgccgcct tcagccatgg cgggtgcgtc cctccttgtc    480

cctcacggct cctgcagccc catggaggtg ggagcccaga gcccgcaggc accacagaaa    540

cagcccaggc acggagttcc gtagccacca ccgccttcca cgccttgtga tgtcactgcc    600

ctagtgatga ggtgcccagc accctgcctg cccccgcgat ggctcatggc cccgttgagg    660
```

cagtgaagct ggaggcccgt ggcgtgcaca ggcagccact cccacattat gaccagggcc 720
cgagaatgcc aaggacatta ggcagctacg ggatgtagcg actgtactcc aagaggggcg 780
tccaagccac tccccattga 800

<210> SEQ ID NO 257
<211> LENGTH: 293
<212> TYPE: DNA
<213> ORGANISM: Homo sapiens

<400> SEQUENCE: 257
aggtggaggt tgcagtgagc cctcctcccc tcctcccccct tcccttccca cctcccatgc 60
ccccctttct tcctcccact cccctcccga ggccccgctt attctcccgg cctgtggcgg 120
ttcgtgcact cgctgagctc aggttctggt gaaggtgccc ggagccgggt cccgccttcg 180
gcctgagcta gagccgcgcg ggcggccggc ttcccccaaa ccctgtggga ggggcatccc 240
gaggaggcga ccccagagag tggggcgcgg acaccttccc tggggagggc cag 293

<210> SEQ ID NO 258
<211> LENGTH: 474
<212> TYPE: DNA
<213> ORGANISM: Homo sapiens

<400> SEQUENCE: 258
ccttccagat gttccagaag gagaaggcgg tgctggacga gctgggccga cgcacgggga 60
cccggctgca gcccctgacc cggggcctct tcggagggag ctgagggccg cgttccttct 120
gaaagcggga cgcgggaggg gtggaggctg cggggagccg gggtcgcaca cgaataaata 180
acgaatgaac gtacgagggg aacctcctct tatttccttc acgttgcatc gggtattttt 240
cgttattgta aataaaacgg ttccgagccg tggcatcgag agggcgtctg gagttcaggg 300
aacgcgtggc ccccgcccgg gagcaccgcg cagcgctcgc ctctcgccct tcaagggggt 360
ccctgcccgg agcctgcgcc cccggagagg aaggggctcg aggggcttgg gtgccgcagc 420
gcgtccttcc gtagaaaagg cttgcgtcag tatttcctgc ttttacctcc tgag 474

<210> SEQ ID NO 259
<211> LENGTH: 346
<212> TYPE: DNA
<213> ORGANISM: Homo sapiens

<400> SEQUENCE: 259
cagtatttcc tgcttttacc tcctgagtat tggaatattc gagtaaaccc tggagtttca 60
gcgccagcgc acgcctcttc atcagggcag cgcgtcgcga gcgcgctggt tccccggggc 120
ctcccggcca cggacaccgc tctagccagg gccacggcga ggccgccgag cagcacctca 180
gagacctgcg tgagttctaa agcctggggc tactacaatt ctgctcatct gtttgtcctg 240
tgaaatgatt cagggacatg aaaatgcctt cccactgact tgcgtcctgt cttagcctgg 300
acttgtcccc ttgggaacac gggccaggcc cctctgttcc tgaagt 346

<210> SEQ ID NO 260
<211> LENGTH: 490
<212> TYPE: DNA
<213> ORGANISM: Homo sapiens

<400> SEQUENCE: 260
atgtctgcag ggaagaagca gggggaccct gaataaagtt tccgtttttc ctatttgtta 60

```
aagtgataga gcattatagg accagagaac aggtgtgtct gtacactgtg caggtccccg    120

gggcaggctc tgagtccgtc tgcacacggt gcgggtcccc ggggcgcgcc ctgagcccgt    180

ctgcacacgg tgcgggtccc cggggcgcgc cctgagcccg tctgcacacg gtgcgggtcc    240

ccggggcgcg ccctgagccc gtctgcacac ggtgcgggtc cccggggcgc gccctgagcc    300

cgtctgcaca cggtgcgggt ccccggggcg cgccctgagc ccgtctgcac acggtgcggg    360

tccccggggc gcgccctgag cccgtctgta cacggtgcgg gtccccgggg cgcgccctga    420

gtctctacta aaaatacaaa aattagccag gcgtggtggt tcaagcctgt aatcccagct    480

ccttgggagg                                                             490


<210> SEQ ID NO 261
<211> LENGTH: 2000
<212> TYPE: DNA
<213> ORGANISM: Homo sapiens

<400> SEQUENCE: 261

catacatggt tattagaaaa ggcatctcat ccaaatgtgg tggctcgtgc ttgtaatccc     60

agtgcttcag gaggccaagg gaggaggatt acttgagcct aagagtttga gaccagcctg    120

ggcaacacaa caagaccttg cctctacaaa aaacttaaaa actagctggg tatgatggtg    180

cacacctgta gtcccagcta cttgggaggc ggaggcgggc agatcgcctg aggtcaggag    240

ttcgagacca gcctggccaa catgatgaaa ccccgtctct actaaaaata caaaaattag    300

ccgagtgtgg tggtgcatgc ctgtaatccc agctactcag gaggctgagg caggagaatc    360

acttgaaccc gggaggcgga ggttgccatg agccgagatc acgtcactgc actccagcct    420

gggtgacaga gcacaaaaga caggcatgac tttgtactta actgctcagc tttgtaatca    480

ctgggggccc agatgctcac ttggattcta actttgttgg catctgggcc taaaagccgt    540

gatgcaggtg agcaatgatg cagagggctc tgtgcgcctg gcgggctctg tttgcctgct    600

gggctctgtg cgcctgctgg gctctgtgcg cccgggaagg tgcggccacc ctcacgcgga    660

aggcggccag cggatcccgg tgcgcgcagc tcccagcgct ggggttccag cgccccgcct    720

cttcctatag caaccagcgg gacctgccgt cccccggggc accccgaggg gtctgcgccc    780

gcttctttcc gaaacgggaa ggcgctgggg gctcggcagc cagagggacg ggttcaggga    840

gcgtccggtg agcctaagac gcgcctttgc cggggttgcc gggtgtctgc ctctcactta    900

ggtattagga accgtggcac aaatctgtag gttttcctct gggggtgggc ggaggctcca    960

aaccggacgg ttttctcctg gaggactgtg ttcagacaga tactggtttc cttatccgca   1020

ggtgtgcgcg gcgctcgcaa gtggtcagca taacgccggg cgaattcgga aagcccgtgc   1080

gtccgtggac gacccacttg gaaggagttg ggagaagtcc ttgttcccac gcgcggacgc   1140

ttccctccgt gtgtccttcg agccacaaaa agcccagacc ctaacccgct cctttctccc   1200

gccgcgtcca tgcagaactc cgccgttcct gggaggggaa gcccgcgagg cgtcgggaga   1260

ggcacgtcct ccgtgagcaa agagctcctc cgagcgcgcg gcggggacgc tgggccgaca   1320

ggggaccgcg gggcagggc ggagaggacc cgccctcgag tcggcccagc cctaacactc   1380

aggaccgcct ccagccggag gtctgcgccc ttctgaggac cctgcctggg ggagcttatt   1440

gcggttcttt tgcaaatacc cgctgcgctt ggacggagga agcgcccacg cgtcgacccc   1500

ggaaacgaag gcctccctga tgggaacgca tgcgtccagg agcctttatt tactcttaat   1560

tctgcccgat gcttgtacgt gtgtgaaatg cttcagatgc ttttgggagc gaggtgttac   1620

ataaatcatg gaaatgcctc ctggtctcac cacacccagg gtgacagctg agatgcggct   1680
```

tctccagggt ggagcctcct cgttttccag agctgcttgt tgaagtcttc ccagggcccc 1740
tgacttgcac tggaaactgc tcaccttggc atcgggatgt ggagcaagaa atgcttttgt 1800
tttcattcat cctagtgttc ataaaatgga aaacaaataa ggacatacaa aaacattaat 1860
aaaataaatt aatggaacta gatttttcag aaagcacaac aaacacaaaa tccaagtatt 1920
gccatgtcag caacacattc ctactttaag ttttatgaag ttaattggag tagtggagaa 1980
caaaagtgga tgtggggcag 2000

<210> SEQ ID NO 262
<211> LENGTH: 88
<212> TYPE: DNA
<213> ORGANISM: Homo sapiens

<400> SEQUENCE: 262
gattgacagt ttctccttcc ccagactggc caatcacagg caggaagatg aaggttctgt 60
gggctgcgtt gctggtcaca ttcctggc 88

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 263
acgttggatg ttgacagttt ctccttcccc 30

<210> SEQ ID NO 264
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 264
acgttggatg gaatgtgacc agcaacgcag 30

<210> SEQ ID NO 265
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 265
gcaggaagat gaaggtty 18

<210> SEQ ID NO 266
<211> LENGTH: 88
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 266
gattgacagt ttctccttcc ccagactggc caatcacagg caggaagatg aaggttttgt 60
gggctgcgtt gctggtcaca ttcctggc 88

<210> SEQ ID NO 267
<211> LENGTH: 90
<212> TYPE: DNA
<213> ORGANISM: Homo sapiens

<400> SEQUENCE: 267
gagttttgga tagtaaaata agtttcgaac tctggcacct ttcaattttg tcgcactctc 60
cttgtttttg acaatgcaat catatgcttc 90

<210> SEQ ID NO 268
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 268
acgtggatag taaaataagt ttcgaactct g 31

<210> SEQ ID NO 269
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 269
gaagcatatg attgcattgt caaaaac 27

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 270
atttcaattt tgtcgcacty 20

<210> SEQ ID NO 271
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 271
gagttttgga tagtaaaata agtttcgaac tctggcacct ttcaattttg tcgcactttc 60
cttgtttttg acaatgcaat catatgcttc 90

<210> SEQ ID NO 272
<211> LENGTH: 97
<212> TYPE: DNA
<213> ORGANISM: Homo sapiens

<400> SEQUENCE: 272
gaactcctct ttgtctctgc gtgcccggcg cgcccccctc ccggtgggtg ataaacccac 60
tctggcgccg gccatgcgct gggtgattaa tttgcga 97

<210> SEQ ID NO 273
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 273
acgttggatg tctttgtctc tgcgtgccc 29

<210> SEQ ID NO 274
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 274
acgttggatg ttaatcaccc agcgcatggc 30

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 275
cccctcccgg tgggtgataa ay 22

<210> SEQ ID NO 276
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 276
gaactcctct ttgtctctgc gtgcccggcg cgcccccctc ccggtgggtg ataaatccac 60
tctggcgccg gccatgcgct gggtgattaa tttgcga 97

<210> SEQ ID NO 277
<211> LENGTH: 86
<212> TYPE: DNA
<213> ORGANISM: Homo sapiens

<400> SEQUENCE: 277
ccattggccg tccgccgtgg cagtgcgggc gggagcgcag ggagagaacc acagctggaa 60
tccgattccc accccaaaac ccagga 86

<210> SEQ ID NO 278
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 278
acgttggatg ccattggccg tccgccgtg 29

<210> SEQ ID NO 279
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
acgttggatg tcctgggttt tggggtggga a 31

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ttccagctgt ggttctctc 19

<210> SEQ ID NO 281
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ccattggccg tccgccgtgg cagtgcgggc gggagcgcag agagagaacc acagctggaa 60
tccgattccc accccaaaac ccagga 86

<210> SEQ ID NO 282
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
acgttggatg acatggtcgg ccccacggaa t 31

<210> SEQ ID NO 283
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
acgttggatg acccattggc cgtccgccgt 30

<210> SEQ ID NO 284
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
acgttggatg gaactcctct ttgtctctgc g 31

<210> SEQ ID NO 285
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 285
acgttggatg cgcagcaacg ggaccgctac a 31

<210> SEQ ID NO 286
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 286
acgttgcgta gcaacctgtt acatattaa 29

<210> SEQ ID NO 287
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 287
acgttggatg catagaggcc catgatggtg g 31

<210> SEQ ID NO 288
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 288
acgttggatg gtgtggtcag ctcttccctt cat 33

<210> SEQ ID NO 289
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 289
acgttggatg ctccttccta gtgtgagaac cg 32

<210> SEQ ID NO 290
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 290
acgttggatg ttttggggtg ggaatcggat t 31

<210> SEQ ID NO 291
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
acgttggatg tggcatggcc ggcgccaga 29

<210> SEQ ID NO 292
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
acgttggcat ctaggtaggt ctttgtagcc aa 32

<210> SEQ ID NO 293
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 293
acgttggatc tgagcaaagg caatcaacac cc 32

<210> SEQ ID NO 294
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
acgttggatg accttctgcc cctctactcc aa 32

<210> SEQ ID NO 295
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 295
acgttggccc acatgtaatg tgttgaaaaa gca 33

<210> SEQ ID NO 296
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 296
caggttccgg ggcttggg 18

<210> SEQ ID NO 297

<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
cgcagggaga gaaccacag 19

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
cccctcccgg tgggtgataa a 21

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
aaagctgtag gacaatcggg t 21

<210> SEQ ID NO 300
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
catttttcta catcctttgt tt 22

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
agaagatcac caggcagaag agg 23

<210> SEQ ID NO 302
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
acttggagaa caaaggacac cgtta 25

<210> SEQ ID NO 303
<211> LENGTH: 81

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 303
ggtcggcccc acggaatccc ggctctgtgt gcgcccaggt tccggggctt gggtgttgcc 60
ggttctcaca ctaggaagga g 81

<210> SEQ ID NO 304
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 304
ccattggccg tccgccgtgg cagtgcgggc gggagcgcag agagagaacc acagctggaa 60
tccgattccc accccaaaa 79

<210> SEQ ID NO 305
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 305
gaactcctct ttgtctctgc gtgcccggcg cgccccccctc ccggtgggtg ataaatccac 60
tctggcgccg gccatgc 77

<210> SEQ ID NO 306
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 306
gcagcaacgg gaccgctaca gccactggac aaagccgtag gacaatcggg taacattggc 60
tacaaagacc tacctagatg c 81

<210> SEQ ID NO 307
<211> LENGTH: 95
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 307
gcgtagcaac ctgttacata ttaaagtttt attatactac atttttctac atcctttgtt 60
tcagagtgtt gattgccttt gctcagtatc ttcag 95

<210> SEQ ID NO 308
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 308
ccttctgccc ctctactcca agcgctacac cctcttctgc ctggtgatct ttgccggcgt 60
cctggccacc atcatgggcc tctatg 86

<210> SEQ ID NO 309
<211> LENGTH: 83
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 309
gtgtggtcag ctcttccctt catcacatac ttggagaaca aaggacaccg ttatccatgc 60
tttttcaaca cattacatgt ggg 83

<210> SEQ ID NO 310
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 310
acgttggatg ttctgcccct ctactccaag 30

<210> SEQ ID NO 311
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 311
acgttggatg tcagctcttc ccttcatcac 30

<210> SEQ ID NO 312
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 312
acgttggatg ttgacagttt ctccttcccc 30

<210> SEQ ID NO 313
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 313
acgttggatg cggtcggccc cacggaat 28

<210> SEQ ID NO 314
<211> LENGTH: 31
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 314
acgtggatag taaaataagt ttcgaactct g 31

<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
acgttggatg cacagctcac cgcagcaacg 30

<210> SEQ ID NO 316
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
acgttggatg tctttgtctc tgcgtgccc 29

<210> SEQ ID NO 317
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
acgttggatg gactgagccc cagaactcg 29

<210> SEQ ID NO 318
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
acgttggatg aagccaagtt tccctccgc 29

<210> SEQ ID NO 319
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
acgttagcgt agcaacctgt tacatattaa 30

<210> SEQ ID NO 320
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 320
acgttggatg catagaggcc catgatggtg 30

<210> SEQ ID NO 321
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 321
acgttggatg cctacctccc acatgtaatg t 31

<210> SEQ ID NO 322
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 322
acgttggatg gaatgtgacc agcaacgcag 30

<210> SEQ ID NO 323
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 323
acgttggatg ctccttccta gtgtgagaac cg 32

<210> SEQ ID NO 324
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 324
gaagcatatg attgcattgt caaaaac 27

<210> SEQ ID NO 325
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 325
acgttggatg ctaggtaggt ctttgtagcc aa 32

<210> SEQ ID NO 326
<211> LENGTH: 30
<212> TYPE: DNA
<213> ORGANISM: Artificial Sequence
<220> FEATURE:

<223> OTHER INFORMATION: Description of Artificial Sequence: Synthetic
primer

<400> SEQUENCE: 326
acgttggatg ttaatcaccc agcgcatggc 30

<210> SEQ ID NO 327
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 327
acgttggatg gtgggtttgt gctttccacg 30

<210> SEQ ID NO 328
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 328
acgttggatg cttttgcttt cccagccagg 30

<210> SEQ ID NO 329
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 329
acgttggatg ctgagcaaag gcaatcaaca 30

<210> SEQ ID NO 330
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 330
ttctgcctgg tgatctt 17

<210> SEQ ID NO 331
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 331
aacaaaggac accgtta 17

<210> SEQ ID NO 332
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 332
gcaggaagat gaaggtt 17

<210> SEQ ID NO 333
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 333
aaggttccgg ggcttggg 18

<210> SEQ ID NO 334
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 334
atttcaattt tgtcgcact 19

<210> SEQ ID NO 335
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 335
agctgtagga caatcgggt 19

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 336
ccctcccggt gggtgataaa 20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 337
agggccgggg tctgcgcgtg 20

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 338
gaggcactgc ccggacaaac c 21

<210> SEQ ID NO 339
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 339
catttttcta catcctttgt tt 22

<210> SEQ ID NO 340
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 340
ccttctgccc ctctactcca agcgctacac cctcttctgc ctggtgatct ttgccggcgt 60
cctggccacc atcatgggcc tctatg 86

<210> SEQ ID NO 341
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 341
gtgtggtcag ctcttccctt catcacatac ttggagaaca aaggacaccg ttatccatgc 60
tttttcaaca cattacatgt gggaggtagg 90

<210> SEQ ID NO 342
<211> LENGTH: 88
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 342
gattgacagt ttctccttcc ccagactggc caatcacagg caggaagatg aaggttttgt 60
gggctgcgtt gctggtcaca ttcctggc 88

<210> SEQ ID NO 343
<211> LENGTH: 98
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 343
aaaaccagag attcgcggtc ggccccacgg aatcccggct ctgtgtgcgc ccaggttccg 60
gggcttgggt gttgccggtt ctcacactag gaaggagc 98

<210> SEQ ID NO 344
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 344
gagttttgga tagtaaaata agtttcgaac tctggcacct ttcaattttg tcgcactttc 60
cttgtttttg acaatgcaat catatgcttc 90

<210> SEQ ID NO 345
<211> LENGTH: 95
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 345
gcagccagct caccgcagca acgggaccgc tacagccact ggacaaagct gtaggacaat 60
cgggtgacat tggctacaaa gacctaccta gatgc 95

<210> SEQ ID NO 346
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 346
gaactcctct ttgtctctgc gtgcccggcg cgcccccctc ccggtgggtg ataaatccac 60
tctggcgccg gccatgcgct gggtgattaa tttgcga 97

<210> SEQ ID NO 347
<211> LENGTH: 86
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 347
gtgggtttgt gctttccacg cgtgcacaca cacgcgcaga ccccggccct tgccccgcct 60
acctccccga gttctggggc tcagtc 86

<210> SEQ ID NO 348
<211> LENGTH: 89
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 348
gcgccagctt ttgctttccc agccagggcg cggtgaggtt tgtccgggca gtgcctcgag 60
caactgggaa ggccaaggcg gagggaaac 89

<210> SEQ ID NO 349
<211> LENGTH: 96
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 349

gcgtagcaac ctgttacata ttaaagtttt attatactac atttttctac atcctttgtt     60

ttagggtgtt gattgccttt gctcagtatc ttcagc                               96


<210> SEQ ID NO 350
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350

cgcaaccact                                                            10


<210> SEQ ID NO 351
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351

cgcgaccact                                                            10
```